US008389511B2

(12) United States Patent
Nakahira et al.

(10) Patent No.: US 8,389,511 B2
(45) Date of Patent: Mar. 5, 2013

(54) BICYCLIC HETEROCYCLIC DERIVATIVE

(75) Inventors: Hiroyuki Nakahira, Osaka (JP); Yohei Ikuma, Osaka (JP); Nobuhisa Fukuda, Osaka (JP); Kozo Yoshida, Osaka (JP); Hidenori Kimura, Osaka (JP); Satoshi Suetsugu, Osaka (JP); Akira Fusano, Osaka (JP); Kiyoto Sawamura, Osaka (JP); Junya Ikeda, Osaka (JP); Yoshio Nakai, Osaka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 33 days.

(21) Appl. No.: 12/809,489

(22) PCT Filed: Dec. 19, 2008

(86) PCT No.: PCT/JP2008/073184

§ 371 (c)(1), (2), (4) Date: Jun. 18, 2010

(87) PCT Pub. No.: WO2009/078481

PCT Pub. Date: Jun. 25, 2009

(65) Prior Publication Data

US 2011/0190278 A1 Aug. 4, 2011

(30) Foreign Application Priority Data

Dec. 19, 2007 (JP) ................................ 2007-328087
Aug. 6, 2008 (JP) ................................ 2008-202960

(51) Int. Cl.

| | |
|---|---|
| *A61K 31/5415* | (2006.01) |
| *A61K 31/538* | (2006.01) |
| *A61K 31/454* | (2006.01) |
| *A61K 31/4709* | (2006.01) |
| *A61K 31/547* | (2006.01) |
| *C07D 413/12* | (2006.01) |
| *C07D 413/14* | (2006.01) |
| *C07D 401/12* | (2006.01) |
| *C07D 417/12* | (2006.01) |
| *A61P 9/12* | (2006.01) |

(52) U.S. Cl. ......... 514/224.2; 544/105; 544/73; 544/52; 544/6; 514/230.5; 514/323; 514/312; 514/224.5; 514/322; 546/201; 546/157; 546/199

(58) Field of Classification Search ........................ None
See application file for complete search history.

(56) References Cited

U.S. PATENT DOCUMENTS

| | | | | |
|---|---|---|---|---|
| 5,908,824 | A * | 6/1999 | Yanagawa .................... | 424/94.1 |
| 2004/0204455 | A1 | 10/2004 | Cody et al. | |
| 2005/0137229 | A1 | 6/2005 | Fish et al. | |
| 2010/0056497 | A1 * | 3/2010 | Nakahira et al. ......... | 514/217.11 |
| 2010/0087427 | A1 | 4/2010 | Breitenstein et al. | |

FOREIGN PATENT DOCUMENTS

| | | | |
|---|---|---|---|
| EP | 1908761 | A1 | 4/2008 |
| JP | 2010-037276 | A | 2/2010 |
| JP | 2010-064982 | A | 3/2010 |
| JP | 2011-026301 | A | 2/2011 |
| WO | 2004/089903 | A1 | 10/2004 |
| WO | 2004/110995 | A1 | 12/2004 |
| WO | 2005/053663 | A2 | 6/2005 |
| WO | 2006/020598 | A2 | 2/2006 |
| WO | 2006/064336 | A2 | 6/2006 |
| WO | 2006/066133 | A2 | 6/2006 |
| WO | 2006/066896 | A2 | 6/2006 |
| WO | WO2006/069788 | * | 6/2006 |
| WO | 2006/069788 | A1 | 7/2006 |
| WO | 2006/094763 | A1 | 9/2006 |
| WO | 2006/103273 | A1 | 10/2006 |
| WO | 2006/103275 | A1 | 10/2006 |
| WO | 2006/103277 | A2 | 10/2006 |
| WO | 2007/006534 | A2 | 1/2007 |
| WO | 2007/038138 | A2 | 4/2007 |
| WO | 2007/077005 | A1 | 7/2007 |
| WO | 2007/082907 | A1 | 7/2007 |

(Continued)

OTHER PUBLICATIONS

'Troxipide' (in www.chemical book.com/Chemical ProductProperty_EN_CB7188765.htm).*

U.S. Appl. No. 13/380,376, filed Dec. 22, 2011, Satoshi Suetsugu et al.

Kawakita, Takeshi et al., "Synthesis and Pharmacology of 3,4-Dihydro-3-oxo-1,4-benzoxazine-8-carboxamide Derivatives, a New Class of Potent Serotonin-3 (5-HT3)Receptor Antagonists", Chem. Pharm. Bull., 1992, pp. 624-630, vol. 40, No. 3.

*Primary Examiner* — Dennis Heyer
(74) *Attorney, Agent, or Firm* — Sughrue Mion, PLLC

(57) ABSTRACT

The present invention relates to a compound of the following formula (I) or a pharmaceutically acceptable salt thereof, being useful as a renin inhibitor.

(I)

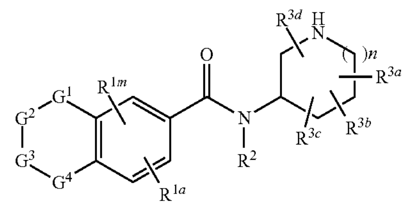

[wherein $R^{1a}$ is halogen, etc.; $R^{1m}$ is H, etc.; $G^1$ is —N($R^{1b}$)—, etc.; $G^2$ is —CO—, etc.; $G^3$ is —C($R^{1c}$)($R^{1d}$)—, etc.; $G^4$ is oxygen, etc.; $R^{1b}$ is optionally substituted $C_{1-6}$ alkyl, etc.; $R^{1c}$ and $R^{1d}$ are independently the same or different, H, etc.; $R^3$ is H, optionally substituted $C_{1-6}$ alkyl, etc.; $R^{3a}$, $R^{3b}$, $R^3$c and $R^{3d}$ are independently the same or different, and a group: -A-B (said A is single bond, etc., and said B is H, etc.), etc.; and n is 1, etc.]

38 Claims, No Drawings

FOREIGN PATENT DOCUMENTS

| | | | |
|---|---|---|---|
| WO | 2007/141318 | A1 | 12/2007 |
| WO | 2008/017685 | A1 | 2/2008 |
| WO | 2008/040764 | A1 | 4/2008 |
| WO | 2008/093737 | A1 | 8/2008 |
| WO | WO 2008/093737 | * | 8/2008 |
| WO | 2008/136444 | A1 | 11/2008 |
| WO | 2008/136457 | A1 | 11/2008 |
| WO | 2008/153135 | A1 | 12/2008 |
| WO | 2008/153182 | A1 | 12/2008 |
| WO | 2009/005002 | A1 | 1/2009 |
| WO | 2009/014217 | A1 | 1/2009 |
| WO | 2009/050253 | A1 | 4/2009 |
| WO | 2009/051112 | A1 | 4/2009 |
| WO | 2009/053452 | A1 | 4/2009 |
| WO | 2009/056617 | A2 | 5/2009 |
| WO | 2009/070869 | A1 | 6/2009 |
| WO | 2009/071606 | A1 | 6/2009 |
| WO | 2009/072469 | A1 | 6/2009 |
| WO | 2009/072649 | A1 | 6/2009 |
| WO | 2009/074674 | A2 | 6/2009 |
| WO | 2009/078481 | A1 | 6/2009 |
| WO | 2009/154300 | A2 | 12/2009 |

* cited by examiner

BICYCLIC HETEROCYCLIC DERIVATIVE

CROSS REFERENCE TO RELATED APPLICATIONS

This application is a National Stage of International Application No. PCT/JP2008/073184, filed Dec. 19, 2008, claiming priority from Japanese Patent Application Nos. 2007-328087 and 2008-202960, filed Dec. 19, 2007 and Aug. 6, 2008, respectively, the contents of all of which are incorporated herein by reference in their entirety.

TECHNICAL FIELD

The present invention relates to derivatives being useful as a medicament. More particularly, the present invention relates to a bicyclic heterocyclic derivative being effective as a renin inhibitor. Further, the present invention relates to a remedy for treatment of hypertension comprising as the active ingredient bicyclic heterocyclic derivatives being effective as a renin inhibitor.

BACKGROUND ART

Renin-angiotensin (RA) system is a hormone system being important to the maintenance of blood pressure or electrocyte balance in the living body, and plays an important role in the onset or exacerbation of circulatory system diseases such as hypertension, congestive heart failure, kidney damage, etc.

Renin, that is an important component of the RA system, is an aspartic protease secreted mainly from the kidney into the blood, and specifically decomposes angiotensinogen produced in the liver to produce angiotensin I. Angiotensin I is converted into angiotensin II by angiotensin-converting enzyme (ACE) being present at the lung or the vascular endothelial cells. Angiotensin II constricts the blood vessel as well as stimulates the adrenal gland to promote the secretion of aldosteron. Aldosteron acts on the kidney and let it pool sodium and excrete potassium. Such a cascade leads to the elevated blood pressure (Non-patent Document 1).

Recently, it is suggested that a component of the RA system exists locally in peripheral tissues such as heart, blood vessel, kidney, adrenal grand, adipose, etc. or the central tissues, and that a (pro)renin receptor may possibly play an important role as a novel component in the activation of the local RA system (Non-patent Document 2), and hence, the importance of the local (tissue) RA system is being recognized. It is suggested that the tissue RA system may possibly cause organ damages such as heart enlargement, arterioscrelosis, kidney damage, etc. by promoting in the long-term the remodeling of various organs such as heart, kidney, blood vessel, etc., while the circulatory RA system anticipates in the control of the short-term circulation (Non-patent Document 3).

As a medicament inhibiting the RA system, ACE inhibitors and angiotensin II receptor blockers (ARB) may be exemplified, and these medicaments (especially the former ones) have been proved to be useful as a remedy for the treatment of not only hypertension but also cardiovascular diseases and renal diseases such as heart failure, diabetic nephropathy, etc. and have been widely used in the clinical field (Non-patent Document 4, Non-patent Document 5).

Several steps for inhibiting the RA system exist, and among them, since renin is located on the most upper stream of the RA system and controls the rate of this cascade, it is theoretically quite appealing approach to inhibit renin (Non-patent Document 6, Non-patent Document 7). In fact, it has been confirmed that aliskiren, which is a renin inhibitor being developed recently, prominently inhibits the serum renin activity, and exhibits an excellent hypotensive activity as comparable to other RA system inhibitors in the clinical trial of hypertension patients (Non-patent Document 8, Non-patent Document 9, Non-patent Document 10).

Various renin inhibitors have been reported. For example, Patent Document 1 and Patent Document 2 reported that derivatives having a piperidine ring are useful as a renin inhibitor. Patent Document 3 reported that derivatives having a pyrrolidine ring are useful as a renin inhibitor. The compounds disclosed in these literatures are characteristic in that these compounds have a partial structure where a piperidine ring or a pyrrolidine ring binds to an amino group at the 3-position thereof via a carbonyl group or a methylene group. However, it has not been known until now that compounds having a basic structure of 3-(substituted-(benzoxazinon-6-yl)carbonylamino)piperidine, etc. are useful as a renin inhibitor.

[Non-patent Document 1] Nat Rev Drug Discov. 1(8): p. 621-36 (2002)

[Non-patent Document 2] Curr Hypertens Rep. 6(2): p. 129-32 (2004)

[Non-patent Document 3] Physiol. Rev. 86: p. 747-803 (2006)

[Non-patent Document 4] Curr Diab Rep. 6(1): p. 8-16 (2006)

[Non-patent Document 5] J Hypertens Suppl. 23(1): S9-17 (2005)

[Non-patent Document 6] J Exp Med. 106 (3): p. 439-53 (1957)

[Non-patent Document 7] J Am Soc Nephrol 16: p. 592-599 (2005)

[Non-patent Document 8] Hypertension 42 (6): p. 1137-43 (2003)

[Non-patent Document 9] Circulation 111 (8): p. 1012-8 (2005)

[Non-patent Document 10] J Hypertens. 24 (Suppl 4): S82. Abstract P4.269 (2006)

[Patent Document 1] WO 06/069788 pamphlet

[Patent Document 2] WO 06/094763 pamphlet

[Patent Document 3] WO 06/066896 pamphlet

DISCLOSURE OF INVENTION

Problems to be Solved by Invention

An object of the present invention is to provide a novel compound having an excellent renin inhibitory activity.

Means for Solving the Problems

The present inventors have intensively studied in order to achieve the above object, and have found that the following compounds or a pharmaceutically acceptable salt thereof (hereinafter, referred to as the present compound(s) when necessary) have an excellent renin inhibitory activity and finally have accomplished the present invention.

Namely, the present invention relates to the following:

Item 1: A compound of the formula (I) or a pharmaceutically acceptable salt thereof.

[Chemical formula 1]

(I)

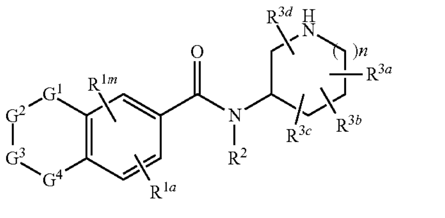

[wherein $R^{1a}$ is a halogen atom, a hydroxy group, a formyl group, a carboxyl group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-6}$ cycloalkyl group, an optionally substituted $C_{5-6}$ cycloalkenyl group, an optionally substituted $C_{1-6}$ alkylthio group, an optionally substituted $C_{6-10}$ arylthio group, an optionally substituted $C_{1-6}$ alkylsulfonyl group, an optionally substituted $C_{1-6}$ alkoxy group, an optionally substituted $C_{3-6}$ cycloalkoxy group, an optionally substituted $C_{5-6}$ cycloalkenyloxy group, an optionally substituted amino group, an optionally substituted aminocarbonyl group, an optionally substituted $C_{1-4}$ alkoxycarbonyl group, an optionally substituted $C_{1-4}$ alkylcarbonyl group, an optionally substituted $C_{6-10}$ arylcarbonyl group, an optionally substituted $C_{6-10}$ aryl group, an optionally substituted $C_{6-10}$ aryloxy group, an optionally substituted $C_{7-14}$ aralkyloxy group, or an optionally substituted 5- to 10-membered monocyclic or polycyclic heteroaryl group;

$R^{1m}$ is a hydrogen atom, a halogen atom, a $C_{1-6}$ alkyl group, a $C_{3-6}$ cycloalkyl group, a $C_{1-6}$ alkoxy group, or a $C_{3-6}$ cycloalkoxy group;

$G^1$, $G^2$, $G^3$ and $G^4$ are one of the following (i) to (iv) (wherein (i) $G^1$ is —N($R^{1b}$)—, $G^2$ is —CO—, $G^3$ is —C($R^{1c}$)($R^{1d}$)—, and $G^4$ is —C($R^{1x}$)($R^{1y}$)—, —$SO_2$—, an oxygen atom, a sulfur atom, or does not exist at all, (ii) $G^1$ is —N($R^{1b}$)—, $G^2$ is —CO—, $G^3$ is —N($R^{1b}$)—, and $G^4$ does not exist at all ($R^{1b}$ for $G^1$ and $G^3$ are independent each other), (iii) $G^1$ is an oxygen atom, $G^2$ is —$CH_2$—, $G^3$ is an oxygen atom, and $G^4$ does not exist at all, or (iv) $G^1$ is an oxygen atom, $G^2$ is —$CH_2$—, $G^3$ is —$CH_2$—, and $G^4$ is an oxygen atom);

$R^{1b}$ is an optionally substituted $C_{1-6}$ alkyl group, an optionally substituted $C_{2-6}$ alkenyl group, an optionally substituted $C_{2-6}$ alkynyl group, or an optionally substituted 5- to 10-membered monocyclic or polycyclic heteroaryl-$C_{1-4}$ alkyl group;

$R^{1c}$ and $R^{1d}$ are independently the same or different, and each is a hydrogen atom, a halogen atom, a hydroxy group, a carboxyl group, an optionally substituted $C_{2-6}$ alkenyl group, an optionally substituted $C_{5-6}$ cycloalkenyl group, an optionally substituted $C_{2-6}$ alkynyl group, an optionally substituted $C_{1-6}$ alkyl group, an optionally substituted $C_{3-6}$ cycloalkyl group, an optionally substituted aminocarbonyl group, an optionally substituted saturated heterocyclic group, an optionally substituted $C_{1-6}$ alkoxy group, an optionally substituted $C_{3-6}$ cycloalkoxy group, an optionally substituted aminocarbonyl group, an optionally substituted $C_{1-4}$ alkoxycarbonyl group, an optionally substituted $C_{1-4}$ alkylcarbonyl group, an optionally substituted $C_{6-10}$ arylcarbonyl group, an optionally substituted 5- to 10-membered monocyclic or polycyclic heteroaryl group, a cyano group, an optionally substituted $C_{6-10}$ aryloxy group, an optionally substituted 5- to 10-membered monocyclic or polycyclic heteroaryloxy, an optionally substituted $C_{7-14}$ aralkyloxy group, an optionally substituted $C_{7-14}$ aralkyl group, an optionally substituted amino group, an optionally substituted saturated heterocyclyl-oxy group, an optionally substituted 5- to 10-membered monocyclic or polycyclic heteroaryl-$C_{1-4}$ alkyl group, or a group of the following formula:

[Chemical formula 2]

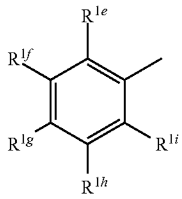

(in which $R^{1e}$, $R^{1f}$, $R^{1g}$, $R^{1h}$ and $R^{1i}$ are independently the same or different, and each is a hydrogen atom, a halogen atom, a cyano group, a $C_{1-4}$ alkyl group (said group being optionally substituted with a 5- or 6-membered saturated heterocyclyloxy, a $C_{1-4}$ alkoxy (being optionally substituted with $C_{1-4}$ alkoxy or $C_{3-6}$ alkoxy), or 1 to 3 fluorine atom(s)), a $C_{1-4}$ alkoxy group (said group being optionally substituted with 1 to 3 halogen atom(s), $C_{1-4}$ alkoxy or $C_{1-6}$ alkylaminocarbonyl), a $C_{3-6}$ cycloalkoxy group (being optionally substituted with $C_{1-4}$ alkoxy), 5- or 6-membered saturated heterocyclyloxy group, a $C_{1-6}$ alkylaminocarbonyl group, a hydroxy group, or a $C_{1-4}$ alkoxysulfonyl group, or $R^{1e}$, $R^{1h}$ and $R^{1i}$ are independently a hydrogen atom, $R^{1f}$ and $R^{1g}$, combine each other to form a condensed ring), or $R^{1c}$ and $R^{1d}$ combine each other to form a group of the following formula:

[Chemical formula 3]

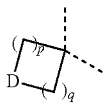

(wherein D is an oxygen atom, a sulfur atom, —$SO_2$—, —$NR^5$—, —$NR^5CO$—, —$NR^5SO_2$—, —$NR^5CONR^5$—, —CH($R^6$)—, or —CH($R^6$)$CH_2$—, $R^5$ is a hydrogen atom, an optionally substituted $C_{1-6}$ alkyl group, an optionally substituted $C_{1-4}$ alkoxycarbonyl group, an optionally substituted $C_{1-4}$ alkylsulfonyl group, or an optionally substituted $C_{6-10}$ arylsulfonyl group, $R^6$ is a hydrogen atom, a halogen atom, an optionally substituted $C_{1-6}$ alkoxy group, an optionally substituted $C_{3-6}$ cycloalkoxy group, an optionally substituted $C_{7-14}$ aralkyloxy group, or an optionally substituted aminocarbonyloxy group, p and q are independently the same or different and each is 0, 1 or 2);

$R^{1x}$ and $R^{1y}$ are independently the same or different and each is a hydrogen atom, a halogen atom, or a $C_{1-4}$ alkyl group, or $R^{1x}$ and $R^{1y}$ combine each other to form a group of the following formula:

[Chemical formula 4]

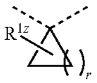

(in which $R^{1z}$ is a hydrogen atom, a halogen atom, a $C_{1-4}$ alkyl group or a $C_{1-4}$ alkoxy group, r is 1, 2, 3 or 4);

$R^2$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, or an optionally substituted 5- to 10-membered monocyclic or polycyclic heteroaryl group;

$R^{3a}$, $R^{3b}$, $R^{3c}$ and $R^{3d}$ are independently the same or different and each is a halogen atom, a hydroxy group, a formyl group, a carboxyl group, a cyano group, or a group: -A-B (in which A is a single bond, $—(CH_2)_sO—$, $—(CH_2)_sN(R^4)—$, $—(CH_2)_sSO_2—$, $—(CH_2)_sCO—$, $—(CH_2)_sCOO—$, $—(CH_2)_sN(R^4)CO—$, $—(CH_2)_sN(R^4)SO_2—$, $—(CH_2)_sN(R^4)COO—$, $—(CH_2)_sOCON(R^4)—$, $—(CH_2)_sOCO—$, $—(CH_2)_sCON(R^4)—$, $—(CH_2)_sN(R^4)CON(R^4)—$, or $—(CH_2)_sSO_2N(R^4)—$, B is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5- to 10-membered monocyclic or polycyclic heteroaryl group, an optionally substituted 5- to 10-membered monocyclic or polycyclic heteroaryl-$C_{1-4}$ alkyl group, or an optionally substituted saturated heterocyclic group (when A is $—(CH_2)_sN(R^4)—$, $—(CH_2)_sOCON(R^4)—$, $—(CH_2)_sCON(R^4)—$, $—(CH_2)_sN(R^4)CON(R^4)—$, or $—(CH_2)_sSO_2N(R^4)—$, then $R^4$ and B may combine each other to form a ring)), or two of $R^{3a}$, $R^{3b}$, $R^{3c}$ and $R^{3d}$ are a hydrogen atom, and the remaining 2 groups may combine each other to form a fused ring with a heterocyclic ring;

$R^4$ is a hydrogen atom, an optionally substituted $C_{1-6}$ alkyl group, an optionally substituted $C_{3-10}$ cycloalkyl group, an optionally substituted $C_{6-10}$ aryl group, an optionally substituted $C_{7-14}$ aralkyl group, or an optionally substituted 5- to 10-membered monocyclic or polycyclic heteroaryl group;

s is 0, 1 or 2 (when A is $—(CH_2)_sN(R^4)—$, then s is 0 or 2, and when A is $—(CH_2)_sCON(R^4)—$, then s is 1 or 2);

n is 0, 1 or 2]

Item 2: The compound according to Item 1 or a pharmaceutically acceptable salt thereof, wherein $G^1$, $G^2$, $G^3$ and $G^4$ are the following (i) or (ii) (wherein (i) $G^1$ is $—N(R^{1b})—$, $G^2$ is —CO—, $G^3$ is $—C(R^{1c})(R^{1d})—$, and $G^4$ is $—C(R^{1x})(R^{1y})—$, $—SO_2—$, an oxygen atom, a sulfur atom, or does not exist at all, or (ii) $G^1$ is $—N(R^{1b})—$, $G^2$ is —CO—, $G^3$ is $—N(R^{1b})—$, and $G^4$ does not exist at all).

Item 3: The compound according to Item 1 or a pharmaceutically acceptable salt thereof, wherein $G^1$ is $—N(R^{1b})—$, $G^2$ is —CO—, $G^3$ is $—C(R^{1c})(R^{1d})—$, and $G^4$ is $—CH_2—$, $—C(CH_3)(CH_3)—$, $—SO_2—$, an oxygen atom, or a sulfur atom.

Item 4: The compound according to Item 3 or a pharmaceutically acceptable salt thereof, wherein $G^4$ is an oxygen atom.

Item 5: The compound according to Item 3 or a pharmaceutically acceptable salt thereof, wherein $G^4$ is a sulfur atom.

Item 6: The compound according to Item 3 or a pharmaceutically acceptable salt thereof, wherein $G^4$ is $—CH_2—$.

Item 7: The compound according to Item 2 or a pharmaceutically acceptable salt thereof, wherein $G^4$ does not exist at all.

Item 8: The compound according to Item 2 or a pharmaceutically acceptable salt thereof, wherein $G^1$ is $—N(R^{1b})—$, $G^2$ is —CO—, $G^3$ is $—N(R^{1b})—$, and $G^4$ does not exist at all.

Item 9: The compound according to any one of Items 1 to 8 or a pharmaceutically acceptable salt thereof, wherein $R^{1a}$ and $R^{1m}$ are located on any position selected from the following formulae (A) to (C):

[Chemical formula 5]

(A)

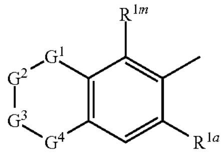

(B)

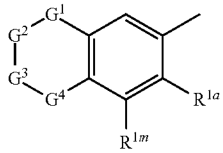

(C)

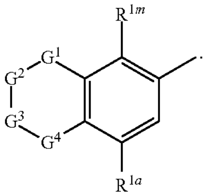

Item 10: The compound according to any one of Items 1 to 9 or a pharmaceutically acceptable salt thereof, wherein $R^{1a}$ is one group selected from a group consisting of 1: a halogen atom;

2: a cyano group;

3: a $C_{1-6}$ alkyl group (said group being optionally substituted with (a) 1 to 3 fluorine atom(s), (b) $C_{1-4}$ alkoxy, or (c) $C_{3-6}$ cycloalkoxy);

4: a $C_{1-6}$ alkoxy group (said group being optionally substituted with (a) 1 to 3 fluorine atom(s), or (b) $C_{3-6}$ cycloalkoxy);

5: a $C_{3-6}$ cycloalkyl group;

6: a $C_{3-6}$ cycloalkoxy group (said group being optionally substituted with (a) 1 to 3 fluorine atom(s), or (b) $C_{1-4}$ alkoxy); and 7: a 5- or 6-membered heteroaryl group (said group being optionally substituted with $C_{1-4}$ alkyl).

Item 11: The compound according to any one of Items 1 to 10 or a pharmaceutically acceptable salt thereof, wherein $R^{1a}$ is a halogen atom, a cyano group, a $C_{1-6}$ alkyl group being optionally substituted with 1 to 3 fluorine atom(s), or a $C_{1-6}$ alkoxy group.

Item 12: The compound according to Item 11 or a pharmaceutically acceptable salt thereof, wherein $R^{1a}$ is a $C_{1-6}$ alkyl group being optionally substituted with 1 to 3 fluorine atom(s).

Item 13: The compound according to one of Items 1 to 12 or a pharmaceutically acceptable salt thereof, wherein $R^{1m}$ is a hydrogen atom, a halogen atom, or a $C_{1-6}$ alkoxy group.

Item 14: The compound according to Item 13 or a pharmaceutically acceptable salt thereof, wherein $R^{1m}$ is a hydrogen atom.

Item 15: The compound according to one of Items 1 to 14 or a pharmaceutically acceptable salt thereof, wherein $R^{1b}$ is 1: a $C_{1-6}$ alkyl group (said group being optionally substituted with one group selected from a group consisting of (a) hydroxy, (b) $C_{1-4}$ alkoxy (being optionally substituted with 1 to 3 fluorine atom(s) or $C_{1-4}$ alkoxy), (c) cyano, (d) trifluoromethyl, (e) trifluoromethoxy, (f) $C_{3-6}$ cycloalkyl (being optionally substituted with 1 to 2 fluorine atom(s), $C_{1-4}$ alkyl being optionally substituted with $C_{1-4}$ alkoxy, or $C_{1-4}$ alkoxy), (g) $C_{3-6}$ cycloalkoxy, (h) formylamino, (i) $C_{1-4}$ alkylcarbonylamino (being optionally substituted with 1 to 3 fluorine atom(s)), (j) N—($C_{1-4}$ alkylcarbonyl)-N—($C_{1-6}$ alkyl)-amino, (k) $C_{3-6}$ cycloalkylcarbonylamino, (l) ($C_{3-6}$ cycloalkyl-$C_{1-4}$ alkyl)carbonylamino, (m) $C_{1-4}$ alkylthiocarbonyl-amino, (n) $C_{1-4}$ alkoxycarbonylamino (being optionally substituted with 1 to 3 fluorine atom(s)), (O)N—($C_{1-4}$ alkoxycarbonyl)-N—($C_{1-6}$ alkyl)-amino, (p) mono- or di-($C_{1-6}$ alkyl)aminocarbonyloxy, (q) $C_{1-6}$ alkylaminocarbonyl (being optionally substituted with 1 to 3 fluorine atom(s)), (r) di-($C_{1-6}$ alkyl)-aminocarbonyl, (s) $C_{3-6}$ cycloalkylaminocarbonyl, (t) $C_{1-6}$ alkylaminocarbonylamino, (u) $C_{1-6}$ alkyl-aminothiocarbonylamino, (v) $C_{1-4}$ alkylcarbonyl (being optionally substituted with $C_{1-4}$ alkoxy), (w) $C_{1-4}$ alkylcarbonyloxy, (x) $C_{1-4}$ alkoxycarbonyl, (y) $C_{1-6}$ alkylsulfonyl, (z) $C_{1-4}$ alkylsulfonylamino, (aa) 5- or 6-membered saturated heterocyclic group, (ab) carboxyl, and (ac) $C_{1-6}$ alkylamino (said alkyl being optionally substituted with 1 to 3 fluorine atom(s)));

2: a $C_{2-6}$ alkenyl group (said group being optionally substituted with a halogen atom);

3: a $C_{2-6}$ alkynyl group (said group being optionally substituted with $C_{1-4}$ alkoxy);

4: a 5- or 6-membered heteroaryl-$C_{1-4}$ alkyl group; or

5: a $C_{3-6}$ cycloalkyl group.

Item 16: The compound according to one of Items 1 to 15 or a pharmaceutically acceptable salt thereof, wherein $R^{1b}$ is a $C_{1-6}$ alkyl group being optionally substituted with $C_{1-6}$ alkoxy, $C_{1-4}$ alkylcarbonylamino (being optionally substituted with 1 to 3 fluorine atom(s)), or $C_{1-4}$ alkoxycarbonylamino; or 5- or 6-membered heteroaryl-$C_{1-4}$ alkyl group.

Item 17: The compound according to Item 16 or a pharmaceutically acceptable salt thereof, wherein $R^{1b}$ is a $C_{1-6}$ alkyl group being optionally substituted with $C_{1-6}$ alkoxy.

Item 18: The compound according to Item 17 or a pharmaceutically acceptable salt thereof, wherein $R^{1b}$ is a 3-methoxypropoxy group.

Item 19: The compound according to Item 17 or a pharmaceutically acceptable salt thereof, wherein $R^{1b}$ is a 4-methoxybutyl group.

Item 20: The compound according to Item 16 or a pharmaceutically acceptable salt thereof, wherein $R^{1b}$ is a $C_{1-6}$ alkyl group being optionally substituted with $C_{1-4}$ alkylcarbonylamino (being optionally substituted with 1 to 3 fluorine atom(s)).

Item 21: The compound according to Item 20 or a pharmaceutically acceptable salt thereof, wherein $R^{1b}$ is a 2-(ethylcarbonylamino)ethyl group.

Item 22: The compound according to Item 20 or a pharmaceutically acceptable salt thereof, wherein $R^{1b}$ is a 2-(difluororoacetylamino)ethyl group.

Item 23: The compound according to Item 16 or a pharmaceutically acceptable salt thereof, wherein $R^{1b}$ is a $C_{1-6}$ alkyl group being optionally substituted with $C_{1-4}$ alkoxycarbonylamino Item 24: The compound according to Item 23 or a pharmaceutically acceptable salt thereof, wherein $R^{1b}$ is a 2-(methoxycarbonylamino)ethyl group.

Item 25: The compound according to any one of Items 1 to 24 or a pharmaceutically acceptable salt thereof, wherein $R^{1c}$ is a hydrogen atom, a halogen atom, or a $C_{1-6}$ alkyl group being optionally substituted with $C_{1-4}$ alkoxy.

Item 26: The compound according to any one of Items 1 to 25 or a pharmaceutically acceptable salt thereof, wherein $R^{1c}$ is a hydrogen atom, or a $C_{1-6}$ alkyl group.

Item 27: The compound according to any one of Items 1 to 26 or a pharmaceutically acceptable salt thereof, wherein $R^{1c}$ is a $C_{1-6}$ alkyl group.

Item 28: The compound according to any one of Items 1 to 27 or a pharmaceutically acceptable salt thereof, wherein $R^{1d}$ is one group selected from a group consisting of 1: a hydrogen atom;

2: a halogen atom;

3: a cyano group;

4: a $C_{2-6}$ alkenyl group (being optionally substituted with $C_{6-10}$ aryl having optionally $C_{1-4}$ alkoxy substituent);

5: alkynyl group (being optionally substituted with $C_{6-10}$ aryl having optionally $C_{1-4}$ alkoxy a $C_{2-6}$ substituent);

6: a $C_{1-6}$ alkyl group (said group being optionally substituted with the same or different 1 to 2 group(s) selected from a group consisting of (a) 1 to 3 halogen atom(s), (b) cyano, (c) $C_{3-6}$ cycloalkyl (said group being optionally substituted with a halogen atom, $C_{1-4}$ alkyl or $C_{1-4}$ alkoxy), (d) hydroxy, (e) $C_{1-4}$ alkoxy (said group being optionally substituted with the same or different 1 to 3 group(s) selected from a group consisting of a halogen atom, cyano, $C_{3-6}$ cycloalkoxy (having optionally mono- or di-($C_{1-6}$ alkyl)aminocarbonyl substituent), mono- or di-($C_{1-6}$ alkyl)aminosulfonyl, $C_{1-6}$ alkylsulfonyl, aminocarbonyl having optionally mono- or di-($C_{1-6}$ alkyl) substituent, $C_{1-4}$ alkylcarbonyl, 5- to 7-membered cyclic aminocarbonyl, hydroxy, $C_{1-4}$ alkoxy, 5- or 6-membered saturated heterocyclic group, and $C_{1-4}$ alkoxycarbonyl), (f) $C_{3-6}$ cycloalkoxy (said group being optionally substituted with $C_{1-4}$ alkyl (having optionally $C_{1-4}$ alkoxy substituent)), (g) $C_{6-10}$ aryloxy (said group being optionally substituted with the same or different 1 to 3 group(s) selected from a group consisting of a halogen atom, cyano, and $C_{1-4}$ alkoxy), (h) mono- or di-substituted amino (said group being substituted with 1 to 2 group(s) selected from a group consisting of $C_{1-6}$ alkyl, $C_{3-6}$ cycloalkyl, $C_{3-6}$ cycloalkyl-$C_{1-4}$ alkyl (having optionally aminocarbonyl substituent), $C_{3-6}$ cycloalkyl-$C_{1-4}$ alkoxycarbonyl, $C_{1-4}$ alkylcarbonyl, $C_{3-6}$ cycloalkylcarbonyl (having optionally $C_{1-4}$ alkylsulfonylamino substituent), 5- or 6-membered saturated heterocyclyl-$C_{1-4}$ alkyl (having optionally $C_{1-4}$ alkyl substituent), 5- or 6-membered saturated heterocyclyl-carbonyl, 5- or 6-membered saturated heterocyclyl-oxycarbonyl, 5- or 6-membered saturated heterocyclyl-$C_{1-4}$ alkylcarbonyl, and $C_{1-4}$ alkylsulfonyl), (i) 5- to 7-membered cyclic amino (being optionally substituted with the same or different 1 to 4 group(s) selected from a group consisting of $C_{1-4}$ alkyl, $C_{7-14}$ aralkyl, and oxo), (i) mono- or di-($C_{1-6}$ alkyl)aminocarbonyl, (k) 4- to 7-membered cyclic aminocarbonyl (being optionally substituted with $C_{1-4}$ alkyl), (l) mono- or di-substituted aminocarbonyloxy (said amino being substituted with the same or different 1 to 2 group(s) selected from a group consisting of $C_{1-6}$ alkyl (having optionally 5- or 6-membered saturated heterocyclic substituent), $C_{3-6}$ cycloalkyl (having optionally hydroxy substituent), and 5- or 6-membered saturated heterocyclic group), (m) 5- to 7-membered cyclic aminocarbonyloxy (being optionally substituted with 1 to 2 fluorine atom(s)), (n) 5- to 7-membered cyclic aminocarbonyl-$C_{1-4}$ alkoxy, (o) mono- or di-($C_{1-6}$ alkyl)aminocarbonyl-$C_{1-4}$ alkoxy, (p) 5- or 6-membered saturated heterocyclic group (being substituted with the same or different group selected from a group consisting of $C_{1-4}$ alkyl and oxo), (q) 5- or 6-membered saturated heterocyclyl-$C_{1-4}$ alkoxy (having optionally $C_{1-4}$ alkyl substituent), (r) 5- or 6-membered saturated heterocyclyl-oxy (having optionally the same or different 1 to 2 substituents selected from a group consisting of $C_{1-4}$ alkyl and oxo), (s) mono- or di-$C_{1-4}$ alkylaminosulfonyl, (t) carboxy, (u) $C_{1-4}$ alkoxycarbonyl, (v) $C_{6-10}$ arylcarbonyl (said group having optionally $C_{1-4}$ alkoxy substituent), (w) $C_{1-4}$ alkoxycarbonylamino, (x) $C_{6-10}$ aryloxycarbonylamino (having optionally a halogen substituent), (y) 5- or 6-membered monocyclic aryloxycarbonylamino, and (z) N—($C_{1-4}$ alkylaminocarbonyl)-N—($C_{1-6}$ alkyl) amino);

7: a $C_{3-10}$ cycloalkyl group (said group being optionally substituted with (a) a halogen atom, (b) hydroxy, or (c) $C_{1-4}$ alkoxy);

8: a $C_{7-14}$ aralkyl group (said group being optionally substituted with the same or different 1 to 3 group(s) selected from a group consisting of (a) a halogen atom, (b) cyano, (c) hydroxy, (d) $C_{1-4}$ alkoxy, and (e) $C_{1-4}$ alkyl having optionally $C_{1-4}$ alkoxy substituent);

9: a $C_{1-6}$ alkoxy group (said group being optionally substituted with (a) $C_{1-4}$ alkoxycarbonylamino, (b) N—($C_{1-6}$ alkylsulfonyl)-N—($C_{1-6}$ alkyl)aminocarbonyl, (c) mono- or di-($C_{1-6}$ alkyl)aminocarbonyl, or (d) 5- to 7-membered cyclic aminocarbonyl);

10: a $C_{3-6}$ cycloalkoxy group;

11: a $C_{7-14}$ aralkyloxy group (having optionally $C_{1-4}$ alkoxy substituent);

12: mono- or di-substituted aminocarbonyl group (said amino being optionally substituted with $C_{1-6}$ alkyl having optionally 5- or 6-membered saturated heterocyclic substituent);

13: 5- to 7-membered cyclic aminocarbonyl group (said group being optionally substituted with a group selected from a group consisting of (a) a halogen atom, (b) $C_{1-4}$ alkoxy, and (c) $C_{6-10}$ aryl having optionally a halogen substituent);

14: a saturated heterocyclic group (said group being optionally substituted with the same or different 1 to 4 group(s) selected from a group consisting of (a) $C_{1-4}$ alkyl, (b) $C_{6-10}$ aryl having optionally 1 to 3 halogen substituent(s), and (c) oxo);

15: a saturated heterocyclyl-oxy group (said group being optionally substituted with $C_{1-4}$ alkoxycarbonyl or $C_{1-4}$ alkylcarbonyl);

16: 5- to 10-membered monocyclic or polycyclic heteroaryl group (said group being optionally substituted with the same or different 1 to 2 group(s) selected from a group consisting of (a) a halogen atom, (b) $C_{1-4}$ alkyl having optionally 1 to 3 fluorine substituent(s), and (c) $C_{1-4}$ alkoxy (having optionally mono- or di-($C_{1-6}$ alkyl) aminocarbonyl substituent));

17: 5- to 10-membered monocyclic or polycyclic heteroaryl-$C_{1-4}$ alkyl group;

18: an amino group (said amino being optionally substituted with (a) $C_{3-6}$ cycloalkyl-$C_{1-4}$ alkyl (having optionally aminocarbonyl substituent), (b) $C_{1-4}$ alkylcarbonyl (having optionally $C_{1-4}$ alkoxy substituent), (c) $C_{3-6}$ cycloalkylcarbonyl (having optionally $C_{1-4}$ alkylsulfonylamino substituent) or (d) 5- or 6-membered saturated heterocyclyl-oxycarbonyl);

19: a hydroxy group, and

20: a group of the following formula:

[Chemical formula 6]

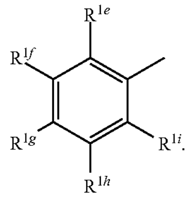

Item 29: The compound according to any one of Items 1 to 28 or a pharmaceutically acceptable salt thereof, wherein $R^{1d}$ is one group selected from a group consisting of 1: a hydrogen atom;

2: a halogen atom;

3: a $C_{1-6}$ alkyl group (said group being optionally substituted with (a) 1 to 3 halogen atom(s), (b) hydroxy, (c) a $C_{1-4}$ alkoxy (said group having optionally 1 to 2 substituent(s) selected from a group consisting of hydroxy, $C_{1-4}$ alkoxy, 5- or 6-membered saturated heterocyclic group, and $C_{1-4}$ alkoxycarbonyl), (d) aryloxy (said group having optionally the same or different 1 to 3 substituent(s) a $C_{6-10}$ selected from a group consisting of cyano and $C_{1-4}$ alkoxy), (e) a $C_{1-6}$ alkylaminocarbonyloxy, (f) (5- or 6-membered saturated heterocyclyl-$C_{1-4}$ alkyl) aminocarbonyloxy, or (g) 5- to 7-membered cyclic aminocarbonyloxy);

4: an aminocarbonyl group;

5: a mono- or di-($C_{1-6}$ alkyl)aminocarbonyl group;

6: an N-(5- or 6-membered saturated heterocyclyl-$C_{1-4}$ alkyl)-N—($C_{1-6}$ alkyl)-aminocarbonyl group;

7: a 5- to 7-membered cyclic aminocarbonyl group;

8: a $C_{7-14}$ aralkyl group being optionally substituted with $C_{1-4}$ alkoxy;

9: a 5- or 6-membered saturated heterocyclic group;

10: a $C_{3-6}$ cycloalkyl group;

11: a $C_{3-6}$ cycloalkoxy group; and

12: a group of the following formula:

[Chemical formula 7]

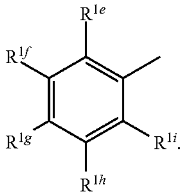

Item 30: The compound according to any one of Items 1 to 29 or a pharmaceutically acceptable salt thereof, wherein $R^{1d}$ is a $C_{1-6}$ alkyl group being substituted with one group selected from a group consisting of 1: halogen, 2: hydroxy, 3: $C_{1-4}$ alkoxy (said group having optionally 1 to 2 substituent(s) selected from a group consisting of (a) hydroxy, (b) $C_{1-4}$ alkoxy, (c) 5- or 6-membered saturated heterocyclic group, and (d) $C_{1-4}$ alkoxycarbonyl), 4: $C_{6-10}$ aryloxy (said group having optionally the same or different 1 to 3 substituent(s) selected from a group consisting of cyano and $C_{1-4}$ alkoxy), 5: $C_{1-6}$ alkylaminocarbonyloxy, 6: (5- or 6-membered saturated heterocyclyl-$C_{1-4}$ alkyl)aminocarbonyloxy, and 7: 5- to 7-membered cyclic aminocarbonyloxy.

Item 31: The compound according to any one of Items 1 to 29 or a pharmaceutically acceptable salt thereof, wherein $R^{1d}$ is a group of the following formula:

[Chemical formula 8]

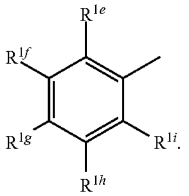

Item 32: The compound according to any one of Items 1 to 31 or a pharmaceutically acceptable salt thereof, wherein $R^{1e}$, $R^{1f}$, $R^{1g}$, $R^{1h}$ and $R^{1i}$ are independently the same or different, and each is 1: a hydrogen atom, 2: a halogen atom, 3: a cyano group, 4: a $C_{1-4}$ alkyl group (said group being optionally substituted with (a) 5- or 6-membered saturated heterocyclyl-oxy, (b) $C_{1-4}$ alkoxy (having optionally $C_{1-4}$ alkoxy or $C_{3-6}$ cycloalkoxy substituent), or (c) 1 to 3 fluorine atom(s)), 5: a $C_{1-4}$ alkoxy group (said group being optionally substituted with (a) 1 to 3 halogen atom(s), (b) $C_{1-4}$ alkoxy, or (c) $C_{1-6}$ alkylaminocarbonyl), 6: a $C_{3-6}$ cycloalkoxy group (said group being optionally substituted with $C_{1-4}$ alkoxy), 7: a 5- or 6-membered saturated heterocyclyl-oxy group, 8: a $C_{1-6}$ alkylaminocarbonyl group, 9: a hydroxy group, or 10: a $C_{1-4}$ alkoxysulfonyl group.

Item 33: The compound according to any one of Items 1 to 32 or a pharmaceutically acceptable salt thereof, wherein $R^{1e}$, $R^{1f}$, $R^{1g}$, $R^{1h}$ and $R^{1i}$ are independently the same or different, and each is the same or different 1 to 3 group(s) selected from a group consisting of a hydrogen atom, a halogen atom, a cyano group, a $C_{1-4}$ alkyl group having optionally 1 to 3 fluorine substituent(s), a $C_{1-4}$ alkoxy group, a hydroxy group, and a $C_{1-4}$ alkoxysulfonyl group.

Item 34: The compound according to any one of Items 1 to 33 or a pharmaceutically acceptable salt thereof, wherein $R^{1e}$, $R^{1f}$, $R^{1g}$, $R^{1h}$ and $R^{1i}$ are independently the same or different and each is a hydrogen atom, a halogen atom, or a $C_{1-4}$ alkoxy group.

Item 35: The compound according to any one of Items 1 to 33 or a pharmaceutically acceptable salt thereof, wherein $R^{1d}$ is a group selected from the groups of the following formulae:

[Chemical formula 9]

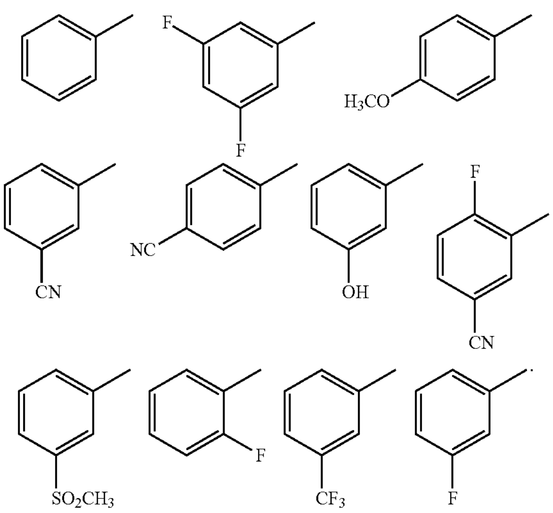

Item 36: The compound according to any one of Items 1 to 24 or a pharmaceutically acceptable salt thereof, wherein $R^{1c}$ and $R^{1d}$ combine each other to form a group of the following formula:

[Chemical formula 10]

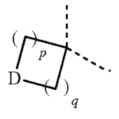

Item 37: The compound according to Item 36 or a pharmaceutically acceptable salt thereof, wherein $R^5$ is a hydrogen atom, a $C_{1-6}$ alkyl group, a $C_{1-4}$ alkoxycarbonyl group, a $C_{1-4}$ alkylsulfonyl group, or a $C_{6-10}$ arylsulfonyl group.

Item 38: The compound according to Item 36 or a pharmaceutically acceptable salt thereof, wherein $R^6$ is a hydrogen atom, a halogen atom, a $C_{1-4}$ alkoxy group being optionally substituted with $C_{1-4}$ alkoxy, a $C_{7-14}$ aralkyloxy group having optionally 1 to 3 substituent(s) selected from a group consisting of fluorine atom and cyano, or an aminocarbonyloxy group being optionally substituted with mono- or di-($C_{1-6}$ alkyl).

Item 39: The compound according to any one of Items 36 to 38 or a pharmaceutically acceptable salt thereof, wherein D, p and q are one of the following combinations:

(i) D is an oxygen atom, and p and q are the same and each is 2, (ii) D is —$CH_2$—, and p and q are the same and each is 1 or 2, or (iii) D is —$CH_2CH_2$—, and p and q are the same and each is 0 or 1.

Item 40: The compound according to any one of Items 1 to 39 or a pharmaceutically acceptable salt thereof, wherein $R^2$ is one group selected from a group consisting of a $C_{1-6}$ alkyl group being optionally substituted with $C_{3-6}$ cycloalkyl (said $C_{1-6}$ alkyl having optionally 1 to 3 halogen substituent(s), and said $C_{3-6}$ cycloalkyl having optionally halogen substituent, $C_{1-4}$ alkyl substituent or $C_{1-4}$ alkoxy substituent); a $C_{3-6}$ cycloalkyl group being optionally substituted with halogen atom or $C_{1-4}$ alkyl, a $C_{2-6}$ alkenyl group, and a $C_{7-10}$ aralkyl group having optionally halogen substituent.

Item 41: The compound according to Item 40 or a pharmaceutically acceptable salt thereof, wherein $R^2$ is $C_{1-6}$ alkyl.

Item 42: The compound according to Item 41 or a pharmaceutically acceptable salt thereof, wherein $R^2$ is an isopropyl group.

Item 43: The compound according to any one of Items 1 to 42 or a pharmaceutically acceptable salt thereof, wherein $R^{3a}$, $R^{3b}$, $R^{3c}$ and $R^{3d}$ are independently a group: -A-B (wherein A is a single bond, —$(CH_2)_sO$—, —$(CH_2)_sN(R^4)$—, —$(CH_2)_sCOO$—, —$(CH_2)_sN(R^4)CO$—, —$(CH_2)_sN(R^4)SO_2$—, —$(CH_2)_sN(R^4)COO$—, —$(CH_2)_sOCON(R^4)$—, —$(CH_2)_sCON(R^4)$—, or —$(CH_2)_sN(R^4)CON(R^4)$—, B is one group selected from a group consisting of 1: a hydrogen atom;

2: a $C_{1-6}$ alkyl group (said group being optionally substituted with 1 to 3 group(s) selected from a group consisting of (a) a halogen atom, (b) $C_{3-6}$ cycloalkyl (said group having optionally the same or different 1 to 2 substituent(s) selected from a group consisting of a halogen atom, hydroxy, $C_{1-4}$ alkoxy and $C_{3-6}$ cycloalkylcarbonyl-amino), (c) hydroxy, (d) $C_{1-4}$ alkoxy, (e) carboxy, (f) $C_{1-4}$ alkoxycarbonyl, (g) saturated heterocyclic group (said ring having optionally the same or different 1 to 3 substituent(s) selected from a group consisting of $C_{1-4}$ alkyl, $C_{1-4}$ alkoxy, $C_{1-4}$ alkylcarbonylamino, and oxo), (h) aminocarbonyl (amino having optionally $C_{1-4}$ alkyl, $C_{3-6}$ cycloalkyl, or $C_{3-6}$ cycloalkyl-$C_{1-4}$ alkyl substituent), and (i) 5- to 7-membered cyclic amino group (said group having optionally the same or different 1 to 3 substituent(s) selected from a group consisting of a halogen atom, $C_{1-4}$ alkyl, $C_6$ aryl having optionally $C_{1-4}$ alkoxy substituent, $C_6$ aryloxy having optionally 1 to 3 halogen substituent(s), and oxo));

3: a $C_{2-6}$ alkenyl group (said group being optionally substituted with (a) fluorine substituent, or (b) $C_{1-6}$ alkyl substituent);

4: a $C_{3-10}$ cycloalkyl group (said group being optionally substituted with (a) a halogen atom, (b) $C_{1-4}$ alkyl having optionally $C_{1-4}$ alkoxy substituent, (c) hydroxy, or (d) $C_{1-4}$ alkoxy);

5: a $C_6$ aryl group (said group being optionally substituted with the same or different 1 to 4 group(s) selected from a group consisting of (a) a halogen atom, (b) $C_{1-4}$ alkyl (said $C_{1-4}$ alkyl having optionally one substituent selected from a group consisting of 5- to 7-membered cyclic amino (being optionally substituted with a $C_6$ aryl having optionally 1 to 3 halogen substituent(s)), mono-$C_{1-6}$ alkylamino (said $C_{1-6}$ alkyl being optionally substituted with a $C_6$ aryloxy having optionally 1 to 3 halogen substituent(s)), 5- or 6-membered saturated heterocyclic amino (said saturated heterocycle having optionally $C_6$ aryl substituent), 5- or 6-membered saturated heterocyclyl-oxy (said saturated heterocycle having optionally $C_6$ aryl or 5- to 10-membered monocyclic or polycyclic heteroaryl substituent), $C_6$ aryloxy (being optionally substituted with the same or different 1 to 3 group(s) selected from a group consisting of a halogen atom and $C_{1-4}$ alkyl), $C_{1-4}$ alkoxy, and $C_{3-6}$ cycloalkoxy), (c) $C_{1-4}$ alkoxy (said $C_{1-4}$ alkoxy being optionally substituted with one group selected from a group consisting of $C_{1-4}$ alkoxy, $C_6$ aryloxy (being optionally substituted with $C_{1-4}$ alkyl or 1 to 3 halogen atom(s)), $C_{3-6}$ cycloalkyloxy (being optionally substituted with $C_{1-4}$ alkyl), phenylamino (said phenyl being optionally substituted with 1 to 3 halogen atom(s)), and $C_{7-10}$ aralkyloxy (being optionally substituted with 1 to 3 halogen atom(s))), (d) $C_6$ aryloxy (said group being optionally substituted with 1 to 3 group(s) selected from a group consisting of a halogen atom, cyano, $C_{1-4}$ alkyl, and $C_{1-4}$ alkoxy), (e) $C_{7-10}$ aralkyloxy (being optionally substituted with 1 to 3 group(s) selected from a group consisting of a halogen atom and $C_{1-4}$ alkoxy), (f) 5- to 7-membered cyclic amino (said ring being optionally substituted with ($C_{1-6}$ alkyl)(phenylcarbonyl)amino, or $C_6$ aryloxy (being optionally substituted with the same or different 1 to 3 group(s) selected from a group consisting of a halogen atom and $C_{1-4}$ alkyl having optionally hydroxy substituent)), (g) 5- or 6-membered saturated heterocyclyl-oxy (said ring being optionally substituted with $C_6$ aryl having optionally 1 to 3 halogen substituent(s), 5- to 10-membered monocyclic or poly cyclic heteroaryl, 5- or 6-membered saturated heterocyclyl-carbonyl, or oxo), (h) 5- or 6-membered monocyclic heteroaryloxy (being optionally substituted with $C_{1-4}$ alkyl), (i) 5- to 7-membered cyclic aminocarbonyl (being optionally substituted with $C_6$ aryloxy having optionally 1 to 3 halogen substituent(s)), (j) 5- to 7-membered cyclic aminocarbonyloxy (being optionally substituted with $C_6$ aryl), and (k) $C_6$ aryl);

6: $C_{7-14}$ aralkyl group (said group being optionally substituted with the same or different 1 to 3 group(s) selected from a group consisting of (a) a halogen atom, (b) cyano, (c) $C_{1-4}$ alkyl, (d) hydroxy, (e) $C_{1-4}$ alkoxy (being optionally substituted with 1 to 3 fluorine atom(s)), (f) $C_{3-6}$ cycloalkoxy (being optionally substituted with 1 to 2 halogen atom(s)), (g) $C_{1-4}$ alkoxycarbonyl,
(h) aminocarbonyl,
(i) $C_{6-10}$ aryl (being optionally substituted with 1 to 3 halogen atom(s)) and
(i) $C_{1-4}$ alkylsulfonyl);

7: 5- to 10-membered monocyclic or polycyclic heteroaryl group (said group being optionally substituted with a halogen atom);

8: 5- to 10-membered monocyclic or polycyclic heteroaryl-$C_{1-4}$ alkyl group (said group being optionally substituted with a halogen atom, or $C_{1-4}$ alkyl (having optionally 1 to 3 fluorine substituent(s))); and 9: saturated heterocyclic group (said group being optionally substituted with $C_{1-4}$ alkyl (having optionally $C_{1-4}$ alkoxy substituent)) (provided that when A is $—(CH_2)_sN(R^4)—$, $—(CH_2)_sOCON(R^4)—$, $—(CH_2)_sCON(R^4)—$, or $—(CH_2)_sN(R^4)CON(R^4)—$, then $R^4$ and B combine each other to form a ring)).

Item 44: The compound according to any one of Items 1 to 42, wherein $R^{3a}$, $R^{3b}$, $R^{3c}$ and $R^{3d}$ attach to the piperidine ring at a substitution position shown in the following formula:

[Chemical formula 11]

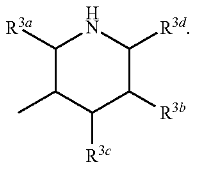

Item 45: The compound according to Item 44 or a pharmaceutically acceptable salt thereof, wherein $R^{3a}$, $R^{3b}$ and $R^{3d}$ are each a group: -A-B (in which A is a single bond, and B is a hydrogen atom); $R^{3c}$ is a group: -A-B (in which A is a single bond or $—(CH_2)_sO—$, and B is a hydrogen atom, an optionally substituted $C_{6-10}$ aryl group, an optionally substituted $C_{7-14}$ aralkyl group, or an optionally substituted 5- to 10-membered monocyclic or polycyclic heteroaryl group).

Item 46: The compound according to Item 45 or a pharmaceutically acceptable salt thereof, wherein $R^{3c}$ is a group: -A-B (in which A is a single bond, and B is an optionally substituted $C_{6-10}$ aryl group).

Item 47: The compound according to Item 46 or a pharmaceutically acceptable salt thereof, wherein B is an optionally substituted $C_{6-10}$ aryl group, or an optionally substituted $C_{7-14}$ aralkyl group.

Item 48: The compound according to Item 45 or a pharmaceutically acceptable salt thereof, wherein $R^{3c}$ is a group: -A-B (in which A is $—(CH_2)_sO—$, B is a hydrogen atom, an optionally substituted $C_{6-10}$ aryl group, or an optionally substituted $C_{7-14}$ aralkyl group).

Item 49: The compound according to Item 44 or a pharmaceutically acceptable salt thereof, wherein $R^{3a}$, $R^{3c}$ and $R^{3d}$ are each a group: -A-B (in which A is a single bond, B is a hydrogen atom); $R^{3b}$ is a group: -A-B (in which A is a single bond, $—(CH_2)_sO—$, $—(CH_2)_sN(R^4)—$, $—(CH_2)_sCOO—$, $—(CH_2)_sN(R^4)CO—$, $—(CH_2)_sN(R^4)SO_2—$, $—(CH_2)_sN(R^4)COO—$, $—(CH_2)_sOCON(R^4)—$, $—(CH_2)_sCON(R^4)—$, $—(CH_2)_sN(R^4)CON(R^4)—$, or $—(CH_2)_sSO_2N(R^4)—$, B is a hydrogen atom, an optionally substituted $C_{1-6}$ alkyl group, an optionally substituted $C_{3-6}$ cycloalkyl group, an optionally substituted $C_{6-10}$ aryl group, an optionally substituted $C_{7-14}$ aralkyl group, an optionally substituted 5- to 10-membered monocyclic or polycyclic heteroaryl group, or an optionally substituted 5- or 6-membered saturated heterocyclic group).

Item 50: The compound according to Item 44 or a pharmaceutically acceptable salt thereof, wherein $R^{3a}$, $R^{3b}$, and $R^{3c}$ are independently a group: -A-B (in which A is a single bond, B is a hydrogen atom); $R^{3d}$ is a group: -A-B (in which A is a single bond, $—(CH_2)_sO—$, $—(CH_2)_sN(R^4)—$, $—(CH_2)_sCOO—$, $—(CH_2)_sN(R^4)CO—$, $—(CH_2)_sN(R^4)SO_2—$, $—(CH_2)_sN(R^4)COO—$, $—(CH_2)_sOCON(R^4)—$, or $—(CH_2)_sN(R^4)CON(R^4)—$, B is a hydrogen atom, an optionally substituted $C_{1-6}$ alkyl group, an optionally substituted $C_{2-6}$ alkenyl group, an optionally substituted $C_{3-10}$ cycloalkyl group, an optionally substituted $C_{6-10}$ aryl group, an optionally substituted $C_{7-14}$ aralkyl group, an optionally substituted 5- to 10-membered monocyclic or polycyclic heteroaryl group, an optionally substituted 5- to 10-membered monocyclic or polycyclic heteroaryl-$C_{1-4}$ alkyl group or an optionally substituted 5- or 6-membered saturated heterocyclic group).

Item 51: The compound according to Item 50 or a pharmaceutically acceptable salt thereof, wherein A for $R^{3d}$ is $—(CH_2)_sN(R^4)CO—$.

Item 52: The compound according to Item 50 or Item 51 or a pharmaceutically acceptable salt thereof, wherein B for $R^{3d}$ is an optionally substituted $C_{1-6}$ alkyl group.

Item 53: The compound according to Item 51 or a pharmaceutically acceptable salt thereof, wherein B for $R^{3d}$ is a $C_{7-14}$ aralkyl group being optionally substituted with 1 to 3 halogen atom(s).

Item 54: The compound according to any one of Items 50 to 53 or a pharmaceutically acceptable salt thereof, wherein s is 2.

Item 55: The compound according to any one of Items 1 to 54 or a pharmaceutically acceptable salt thereof, wherein $R^4$ is a hydrogen atom, a $C_{1-6}$ alkyl group being substituted with 1 to 3 halogen atom(s) or $C_{3-6}$ cycloalkyl, a $C_{3-6}$ cycloalkyl group being optionally substituted with 1 to 2 halogen atom(s), or a $C_7$ aralkyl group.

Item 56: The compound according to Item 55 or a pharmaceutically acceptable salt thereof, wherein $R^4$ is a $C_{1-6}$ alkyl group being substituted with 1 to 3 halogen atom(s), or a $C_{3-6}$ cycloalkyl group.

Item 57: The compound according to Item 56 or a pharmaceutically acceptable salt thereof, wherein $R^4$ is a $C_{3-6}$ cycloalkyl group.

Item 58: The compound according to any one of Items 1 to 40 or a pharmaceutically acceptable salt thereof, wherein $R^{3a}$, $R^{3b}$, $R^{3c}$ and $R^{3d}$ are each a group: -A-B (in which A is a single bond, B is a hydrogen atom).

Item 59: The compound according to any one of Items 1 to 43 or a pharmaceutically acceptable salt thereof, wherein n is 1.

Item 60: A pharmaceutical composition, which comprises as the active ingredient a compound as set forth in any one of Items 1 to 59 or a pharmaceutically acceptable salt thereof Item 61: A renin inhibitor, which comprises as the active ingredient a compound as set forth in any one of Items 1 to 59 or a pharmaceutically acceptable salt thereof Item 62: A drug for treatment of hypertension, which comprises as the active ingredient a compound as set forth in any one of Items 1 to 59 or a pharmaceutically acceptable salt thereof Item 63: Use of a compound as set forth in any one of Items 1 to 59 or a pharmaceutically acceptable salt thereof in the preparation of a renin inhibitor.

Item 64: Use of a compound as set forth in any one of Items 1 to 59 or a pharmaceutically acceptable salt thereof in the preparation of a drug for treatment of hypertension.

Item 65: A method for treatment of hypertension, which comprises administering an effective amount of a compound as set forth in any one of Items 1 to 59 or a pharmaceutically acceptable salt thereof to a patient in need.

Hereinafter, the compound of the formula (I) or a pharmaceutically acceptable salt thereof is occasionally referred to as "the compound of the present invention".

EFFECTS OF INVENTION

The compound of the present invention shows an excellent renin inhibitory activity and is useful as a therapeutic agent for hypertension.

BEST MODE FOR CARRYING OUT THE INVENTION

Hereinafter, the present invention will be illustrated in more detail. In the present specification, the number of the carbon atom in definitions for substituents may be expressed, for example, as "$C_{1-6}$". For example, the expression of "$C_{1-6}$ alkyl" is the same as the expression of an alkyl group having 1 to 6 carbon atoms. In addition, in the present specification, any group without a term of "an optionally substituted" or "substituted" means an "unsubstituted" group. For example, "$C_{1-6}$ alkyl" means an "unsubstituted" one.

The term "group" in the present specification means a monovalent group. For example, the "alkyl group" means a monovalent saturated hydrocarbon group. In addition, in the explanation of each group in the present specification, the term "group" may be occasionally omitted. Further, the number of the substituents as defined with "an optionally substituted" or "substituted" is not necessarily limited, and it can be either one or more as long as the substitution can be possible. The definition for each group is also applied to cases where said group is a part of other groups, unless indicated specifically.

The "halogen atom" is, for example, fluorine atom, chlorine atom, bromine atom or iodine atom.

The "$C_{1-6}$ alkyl group" means a straight or branched chain saturated hydrocarbon group having 1 to 6 carbon atoms, and preferable one is a $C_{1-4}$ alkyl group. Examples of the $C_{1-6}$ alkyl group are methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, etc.

The "$C_{1-6}$ alkyl group" for "B" includes a group where a $C_{2-4}$ ring is formed on one carbon atom of the saturated hydrocarbon group, for example, groups of the following formulae are exemplified. In addition, the alkyl moiety of $C_{7-14}$ aralkyl includes likewise.

[Chemical formula 12]

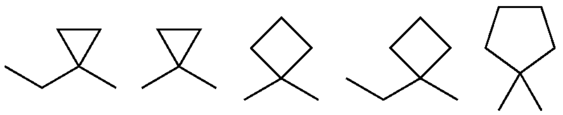

The "$C_{2-6}$ alkenyl group" means a straight or branched chain unsaturated hydrocarbon group having 2 to 10 carbon atoms and one double bond, and includes, for example, vinyl, propenyl, methylpropenyl, butenyl or methylbutenyl, etc.

The "$C_{2-6}$ alkenyl group" for "B" includes the groups of the following formula.

[Chemical formula 13]

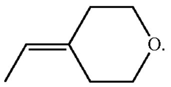

The "$C_{2-6}$ alkynyl group" means a straight chain or branched chain unsaturated hydrocarbon group having 2 to 6 carbon atoms and one triple bond, and includes, for example, ethynyl, 1-propinyl, 2-propinyl, 2-butynyl, pentynyl or hexynyl, etc.

The "$C_{3-10}$ cycloalkyl group" means a saturated cyclic hydrocarbon group having 3 to 10 carbon atoms, and a preferable one is "$C_{3-6}$ cycloalkyl group", etc. Examples of the "$C_{3-10}$ cycloalkyl group" are cyclopropyl, cyclobutyl, cyclopentyl, cyclohexyl, cycloheptyl, adamantyl or norbornyl, etc.

The "$C_{3-10}$ cycloalkyl group" for "B" also includes a saturated bicyclic group. Examples thereof are the groups of the following formulae:

[Chemical formula 14]

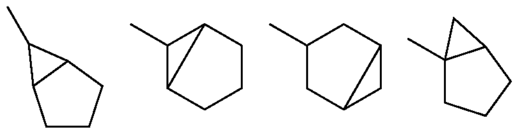

The "$C_{3-10}$ cycloalkyl group" for "B" includes a compound wherein an aromatic ring is condensed, and examples thereof are a group of the following formulae:

[Chemical formula 15]

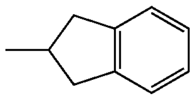

The "$C_{3-6}$ cycloalkyl-$C_{1-4}$ alkyl group" means a group where a "$C_{3-6}$ cycloalkyl" is attached to a "$C_{1-4}$ alkyl". Examples thereof are cyclopropylmethyl, cyclobutylmethyl, cyclopentylmethyl, cyclohexylmethyl, etc.

The "$C_{5-6}$ cycloalkenyl group" means a cyclic unsaturated hydrocarbon group having a double bond, and includes, for example, 1-cyclopentenyl, 1-cyclohexenyl, etc.

The "$C_{6-10}$ aryl group" means an aromatic hydrocarbon group having 6 to 10 carbon atoms.

Preferable one is a $C_6$ aryl group (phenyl). Examples of the "$C_{6-10}$ aryl group" are phenyl, 1-naphthyl or 2-naphthyl, etc.

The "$C_{7-14}$ aralkyl group" means a "$C_{6-10}$ aryl-$C_{1-4}$ alkyl group", which is a group where the above-mentioned "alkyl group" is attached to the above-mentioned "aryl group". Preferable one is a "$C_{7-10}$ aralkyl group" (a $C_6$ aryl-$C_{1-4}$ alkyl group). Examples of the "$C_{7-14}$ aralkyl group" are benzyl, 2-phenyl, 2-phenylethyl, 1-phenylpropyl or 1-naphthylmethyl, etc.

The $C_{1-4}$ alkyl moiety of "$C_{7-14}$ aralkyl group" for "B" includes a group which forms a $C_2$-$C_4$ ring on one carbon atom of the $C_{1-4}$ alkyl group.

The "heteroaryl group" includes, for example, a 5- to 10-membered monocyclic or polycyclic group, etc., and said group contains the same or different one or more heteroatoms (e.g., 1 to 4 heteroatoms) selected from nitrogen atom, sulfur atom and oxygen atom. Preferable one is, for example, a 5- or 6-membered monocyclic group containing one heteroatom selected from nitrogen atom, sulfur atom and oxygen atom. Examples of the "heteroaryl group" are pyrrolyl, thienyl, benzothienyl, benzofuranyl, benzoxazolyl, benzothiazolyl, furyl, oxazolyl, thiazolyl, isoxazolyl, imidazolyl, pyrazolyl, pyridyl, pyrazyl, pyrimidyl, pyridazinyl, quinolyl, isoquinolyl, triazolyl, triazinyl, tetrazolyl, indolyl, imidazo[1,2-a]pyridyl, dibenzofuranyl, benzimidazolyl, quinoxalyl, cinnolyl, quinazolyl, indazolyl, naphthyridyl, quinolinoly, or isoquinolinolyl, etc.

The "heteroaryl-$C_{1-4}$ alkyl group" means a group where the above-mentioned "alkyl group" is substituted with the above-mentioned "heteroaryl group". The heteroaryl moiety of said group includes the same ones as exemplified as the above-mentioned heteroaryl group such as "heteroaryl-$C_{1-4}$ alkyl". Examples thereof are 2-pyridylmethyl, etc.

The "$C_{1-6}$ alkyl moiety" of the "$C_{1-6}$ alkoxy group" is the same as the above-mentioned "$C_{1-6}$ alkyl". Preferable one is a "$C_{1-4}$ alkoxy group". Examples of the "$C_{1-6}$ alkoxy group" are methoxy, ethoxy, propoxy, isopropoxy, butoxy, isobutoxy, sec-butoxy, tert-butoxy, etc.

The "$C_{1-6}$ alkyl moiety" of the "$C_{1-6}$ alkylthio group" is the same as the above-mentioned "$C_{1-6}$ alkyl". Preferable one is a "$C_{1-4}$ alkylthio group". Examples of the "$C_{1-6}$ alkylthio group" are methylthio, ethylthio, propylthio, isopropylthio, butylthio, sec-butylthio, tert-butylthio, pentylthio or hexylthio, etc.

The "$C_{1-6}$ alkyl moiety" of the "$C_{1-6}$ alkylsulfonyl group" is the same as the above-mentioned "$C_{1-6}$ alkyl". Preferable one is a "$C_{1-4}$ alkylsulfonyl group". Examples of the "$C_{1-6}$ alkylsulfonyl group" are methylsulfonyl, ethylsulfonyl, propylsulfonyl, isopropylsulfonyl, butylsulfonyl, pentylsulfonyl or hexylsulfonyl, etc.

The "$C_{6-10}$ aryl moiety" of the "$C_{6-10}$ arylthio group" is the same as the above-mentioned "$C_{6-10}$ aryl". Examples of the "$C_{6-10}$ arylthio group" are phenylthio, 1-naphthylthio or 2-naphthylthio, etc.

The "$C_{3-10}$ cycloalkyl moiety" of the "$C_{3-10}$ cycloalkoxy group" is the same as the above-mentioned "$C_{3-10}$ cycloalkyl". Preferable one is a "$C_{3-6}$ cycloalkoxy group", etc. Examples of the "$C_{3-10}$ cycloalkoxy group" are cyclopropyloxy, cyclobutyloxy, cyclopentyloxy, cyclohexyloxy, cycloheptyloxy, adamantyloxy or norbornyloxy, etc.

The "$C_{5-6}$ cycloalkenyloxy moiety" of the "$C_{5-6}$ cycloalkenyloxy group" is the same as the above-mentioned "$C_{5-6}$ cycloalkenyloxy". Examples thereof are 1-cyclopentenyloxy, etc.

The "$C_{6-10}$ aryl moiety" of the "$C_{6-10}$ aryloxy group" is the same as the above-mentioned $C_{6-10}$ aryl, and the preferable one is a "$C_6$ aryloxy" (phenyloxy). Example of the "$C_{6-10}$ aryloxy group" is phenoxy, 1-naphthyloxy or 2-naphthyloxy, etc.

The "$C_{7-14}$ aralkyl moiety" of the "$C_{7-14}$ aralkyloxy group" ($C_{6-10}$ aryl-$C_{1-4}$ alkyloxy group) is the same as the above-mentioned "$C_{7-14}$ aralkyl", and preferable one is a "$C_{7-10}$ aralky group" (phenyl-$C_{1-4}$ alkyl group), etc. Examples of the "$C_{7-14}$ aralkyloxy group" is benzyloxy, phenethyloxy, naphthylmethyloxy, etc.

The "heteroaryloxy group" is a group where the "aralkyl moiety" of the above-mentioned "aralkyloxy group" is replaced by a "heteroaryl". Examples thereof are a "5- to 10-membered monocyclic or polycyclic heteroaryloxy group", etc.

The "$C_{1-4}$ alkoxy moiety" of the "$C_{1-4}$ alkoxysulfonyl group" is the same as the above-mentioned "$C_{1-4}$ alkoxy group". Examples thereof are methoxysulfonyl, etc.

The "$C_{3-6}$ cycloalkoxy moiety" of the "$C_{3-6}$ cycloalkoxysulfonyl group" is the same as the above-mentioned "$C_{3-6}$ cycloalkoxy group". Examples thereof are cyclopropyloxysulfonyl, etc.

The "$C_{6-10}$ aryl moiety" of the "$C_{6-10}$ aryloxysulfonyl group" is the same as the above-mentioned "$C_{6-10}$ aryl group". Examples thereof are phenoxysulfonyl, etc.

The "$C_{1-4}$ alkoxycarbonyl group" means a group where the above-mentioned "$C_{1-4}$ alkoxy group" is attached to a carbonyl group. Examples thereof are methoxycarbonyl, ethoxycarbonyl, propoxycarbonyl, 2-propoxycarbonyl or tert-butoxycarbonyl, etc.

The "$C_{3-6}$ cycloalkoxycarbonyl group" means a group where the above-mentioned "$C_{3-6}$ cycloalkoxy group" is attached to a carbonyl group. Examples of the $C_{3-6}$ cycloalkoxy moiety are ones as exemplified as the above-mentioned cycloalkoxy group The "$C_{1-4}$ alkylcarbonyl group" means a group where the above-mentioned "$C_{1-4}$ alkyl group" is attached to a carbonyl group. Examples thereof are acetyl, propionyl, or butynyl, etc.

The "$C_{3-10}$ cycloalkylcarbonyl group" means a group where the above-mentioned "$C_{3-10}$ cycloalkyl group" is attached to a carbonyl group. Preferable one includes a $C_{3-6}$ cycloalkylcarbonyl group. Examples of the "$C_{3-10}$ cycloalkylcarbony group" are cyclopropylcarbonyl, cyclobutylcarbonyl, cyclopentylcarbonyl, cyclohexylcarbonyl, adamantylcarbonyl or norbornylcarbonyl, etc.

The "$C_{3-6}$ cycloalkyl-$C_{1-4}$ alkylcarbonyl group" means a group wherein the above-mentioned "$C_{3-10}$ cycloalkyl-$C_{1-4}$ alkyl group" is attached to a carbonyl group. Examples thereof are cyclopropylmethylcarbonyl, etc.

The "$C_{6-10}$ arylcarbonyl group" means a group where the above-mentioned "$C_{6-10}$ aryl group" is attached to a carbonyl group. The "$C_{6-10}$ aryl moiety" is the same as the above-mentioned "$C_{6-10}$ aryl group". Preferable one is a "$C_6$ arylcarbonyl group" (phenylcarbonyl group). Examples of the "$C_{6-10}$ arylcarbonyl group" are benzoyl, 1-naphthoyl, or 2-naphthoyl, etc.

The "$C_{1-4}$ alkyl moiety" of the "$C_{1-4}$ alkylcarbonyloxy group" is the same as the above-mentioned "$C_{1-4}$ alkyl group". Examples thereof are methylcarbonyloxy, ethylcarbonyloxy, isopropylcarbonyloxy, etc.

The "$C_{3-6}$ cycloalkyl" moiety of the "$C_{3-6}$ cycloalkylcarbonyloxy group" is the same as the above-mentioned "$C_{3-6}$ cycloalkyl group". Examples thereof are cyclopropylcarbonyloxy, cyclobutylcarbonyloxy, cyclopentylcarbonyloxy, etc.

The "$C_{3-6}$ cycloalkyl-$C_{1-4}$ alkoxy group" means a group where a "$C_{1-4}$ alkoxy group" is substituted with the above-mentioned "$C_{3-6}$ cycloalkyl group". Examples thereof are cyclopropylmethoxy, etc.

The "$C_{3-6}$ cycloalkyl-$C_{1-4}$ alkoxy moiety" of the "$C_{3-6}$ cycloalkyl-$C_{1-4}$ alkoxycarbonyl group" is the same as mentioned above. Examples thereof are cyclopropylmethoxycarbonyl, etc.

The "$C_{1-4}$ alkylcarbonylamino group" means a group where one of the above-mentioned "$C_{1-4}$ alkylcarbonyl group"s is attached to an amino group. Examples thereof are methylcarbonylamino, etc. In addition, the "$C_{1-4}$ alkyl" may optionally be substituted by 1 to 3 fluorine atom(s).

The "$C_{1-4}$ alkylthiocarbonylamino group" means a group where the carbonyl of the above-mentioned "$C_{1-4}$ alkylcarbonyl group" is replaced with a thiocarbonyl. Examples thereof are methylthiocarbonylamino, etc.

The "N—($C_{1-4}$ alkylcarbonyl)-N—($C_{1-6}$ alkyl)amino group" means a group where the amino of the above-mentioned "$C_{1-4}$ alkyl carbonylamino group" is substituted with the above-mentioned "$C_{1-6}$ alkyl group". Examples thereof are N-methyl-N-ethylcarbonylamino, etc.

The "$C_{3-6}$ cycloalkylcarbonylamino group" means a group where one of the above-mentioned "$C_{3-6}$ cycloalkylcarbonyl group" is attached to an amino group. Examples thereof are cyclopropyl-carbonylamino, etc.

The "$C_{3-6}$ cycloalkyl-$C_{1-4}$ alkylcarbonylamino group" means a group where one of the above-mentioned "$C_{3-6}$ cycloalkyl-$C_{1-4}$ alkylcarbonyl group" is attached to an amino group. Examples thereof are cyclopropylmethylcarbonylamino, etc.

The "$C_{1-4}$ alkoxycarbonylamino group" means a group where one of the above-mentioned "$C_{1-4}$ alkoxycarbonyl group" is attached to an amino group. Examples thereof are methoxycarbonylamino, ethoxycarbonylamino, etc. In addition, the "$C_{1-4}$ alkyl" may optionally be substituted with 1 to 3 fluorine atom(s).

The "N—($C_{1-6}$ alkyl)-N—($C_{1-4}$ alkoxycarbonyl)-amino group" means a group where a "$C_{1-6}$ alkyl group" substitutes to the amino group of the above-mentioned "$C_{1-4}$ alkoxycarbonylamino group", and examples thereof are N-methyl-methoxycarbonylamino, etc.

The "$C_{1-4}$ alkylsulfonylamino group" means a group where one of the above-mentioned "$C_{1-4}$ alkylsulfonyl group" is attached to an amino group. Examples thereof are methylsulfonylamino, ethylsulfonylamino, etc.

The "$C_{1-4}$ alkylsulfonylaminocarbonyl group" means a group where the above-mentioned "$C_{1-4}$ alkylsulfonylamino group" is attached to a carbonyl group. Examples thereof are methylsulfonylamino, etc.

The "saturated heterocyclic group" includes, for example, a 5- or 6-membered saturated heterocyclic group having the same or different 1 to 3 heteroatom(s) selected from nitrogen atom, oxygen atom and sulfur atom, where the above-mentioned nitrogen, oxygen and sulfur atom are all a ring-forming atom. Examples thereof are pyranyl, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, imidazolidinyl, oxoimidazolidinyl, dioxoimidazolidinyl, oxooxazolidinyl, dioxooxazolidinyl, dioxothiazolidinyl, tetrahydrofuranyl, or tetrahydropyridinyl, etc. Said group does not bind at the ring-forming nitrogen atom. Namely, said group does not include a concept such as pyrrolidino group.

The "5- or 6-membered saturated heterocyclic group" includes a saturated bicyclic group and saturated spirocyclic group having a "5- or 6-membered saturated heterocyclic group" as a basic skeleton. Examples thereof are group of the following group.

[Chemical formula 16]

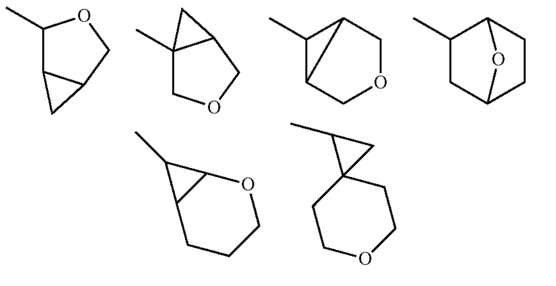

The above-mentioned "saturated heterocyclic group" may form a condensed ring with a 6-membered aromatic hydrocarbon or a 6-membered unsaturated heterocycle. For example, said "saturated heterocyclic group" includes a bicyclic 11- or 12-membered "saturated heterocyclic group" wherein the above mentioned 5- or 6-membered saturated heterocyclic group is condensed with a 6-membered aromatic hydrocarbon group or a 6-membered unsaturated heterocyclic group. The 6-membered aromatic hydrocarbon group includes benzene, etc. The 6-membered unsaturated heterocyclic group includes pyridine, pyrimidine, or pyridazine, etc. Examples thereof are dihydroindolyl, dihydroisoindolyl, dihydropurinyl, dihydrothiazolopyrimidinyl, dihydrobenzodioxanyl, isoindolinyl, indazolyl, pyrrolidinyl, tetrahydroquinolinyl, decahydroquinolinyl, tetrahydroisoquinolinyl, decahydroisoquinolinyl, tetrahydronaphthyridinyl or tetrahydropyridoazepinyl, etc.

The "saturated heterocyclic ring moiety" of the "saturated heterocyclyl-oxy group" is the same as the above-mentioned "saturated heterocyclic group". Examples thereof are 4-pyranyloxy, etc.

The "saturated heterocyclyl-carbonyl group" means a group where the above-mentioned "saturated heterocyclic group" is attached to a carbonyl group. Examples thereof are 4-pyranylcarbonyl, etc.

The "saturated heterocyclyl-$C_{1-4}$ alkyl group" means a group where the above-mentioned "saturated heterocyclic group" is attached to a "$C_{1-4}$ alkyl group". Examples thereof are 4-pyranylmethyl, etc.

The "saturated heterocyclyl-$C_{1-4}$ alkoxy group" means a group where the above-mentioned "saturated heterocyclic group" is attached to a "$C_{1-4}$ alkoxy group". Examples thereof are 4-pyranylmethoxy, etc.

The "saturated heterocyclyl-oxy moiety" of the "saturated heterocyclyl-oxycarbonyl group" is the same as mentioned above. Examples thereof are 4-pyranyloxycarbonyl, etc.

The "saturated heterocyclyl-$C_{1-4}$ alkyl moiety" of the "saturated heterocyclyl-$C_{1-4}$ alkylcarbonyl group" is the same. Examples thereof are 4-pyranylmethylcarbonyl, etc.

The "optionally substituted amino group" includes an amino group, a mono- or di-substituted amino group, and a 5- to 7-membered cyclic amino group.

The "mono- or di-substituted amino group" means an amino group which is substituted with the same or different 1 to 2 group(s) selected from "$C_{1-6}$ alkyl", "$C_{3-6}$ cycloalkyl", "$C_{3-6}$ cycloalkyl-$C_{1-4}$ alkyl", "$C_{3-6}$ cycloalkyl-$C_{1-4}$ alkoxy-carbonyl", "$C_{1-4}$ alkylcarbonyl", "saturated heterocycle", "saturated heterocyclyl-$C_{1-4}$ alkyl", "saturated heterocyclyl-carbonyl", "saturated heterocyclyl-oxycarbonyl", "saturated heterocyclyl-$C_{1-4}$ alkylcarbonyl", and "benzyl".

Examples of the "mono- or di-substituted amino group" are "mono- or di-($C_{1-6}$ alkyl)-substituted amino group" (e.g., methylamino, ethyl amino, dimethylamino, diethylamino, etc.), "mono- or di-($C_{3-6}$ cycloalkyl)-substituted amino group" (e.g., cyclopropylamino, cyclobutylamino, cyclopentylamino, dicyclopropylamino, dicyclobutylamino, cyclodipentylamino, etc.), "mono-($C_{3-6}$ cycloalkyl-$C_{1-4}$ alkyl)-substituted amino group" (e.g., cyclopropylmethylamino, cyclobutylmethylamino, cyclopentylmethylamino, etc.), "($C_{1-4}$ alkyl)(benzyl)-substituted amino group" (e.g., N-methyl-N-benzylamino, N-ethyl-N-benzylamino, etc.), "($C_{3-6}$ cycloalkyl)(benzyl)-substituted amino group" (e.g., N-cyclopropyl-N-benzylamino, N-cyclopentyl-N-benzylamino, N-cyclohexyl-N-benzylamino, etc.), "$C_{3-6}$ cycloalkyl-$C_{1-4}$ alkoxycarbonylamino" (e.g., cyclopropylmethoxycarbonylamino, etc.), "5- or 6-membered saturated heterocyclyl-amino group" (e.g., 3-pyrrolidinylamino, etc.), "saturated heterocyclyl-$C_{1-4}$ alkylcarbonylamino group" (e.g., (4-pyranylmethylcarbonyl)amino, etc.), "N—($C_{1-6}$ alkyl)-N-(saturated heterocyclyl-$C_{1-4}$ alkyl carbonyl)-amino group" (e.g., N-methyl-N-(4-pyranyl-methylcarbonyl)amino, etc.), "saturated heterocyclyl-carbonylamino group" (e.g., 4-pyranyl-carbonyl-amino, etc.), "N—($C_{1-6}$ alkyl)-N-(saturated heterocyclyl-carbonyl)-amino group" (e.g., N-methyl-N-(4-pyranylcarbonyl)amino, etc.), "N—($C_{1-4}$ alkylcarbonyl)-N—($C_{1-6}$ alkyl)-amino group" (e.g., N-methyl-N-methylcarbonylamino, etc.), "(saturated heterocyclyl-oxycarbonyl)amino group" (e.g., 3-tetrahydro-furyloxycarbonylamino, etc.), "N-(saturated heterocyclyl-$C_{1-4}$ alkyl)-N—($C_{1-6}$ alkyl)-amino group" (e.g., N-methyl-N-(4-pyranylmethyl)amino, etc.), "N-(saturated heterocyclyl-carbonyl)-N—($C_{1-6}$ alkyl)-amino group" (e.g., N-methyl-N-(4-pyranylcarbonyl)amino, etc.), "N-(saturated heterocyclyl-$C_{1-4}$ alkyl-carbonyl)-N—($C_{1-6}$ alkyl)-amino group" (e.g., N-methyl-N-(4-pyranylmethylcarbonyl)amino, etc.), "N-(saturated heterocyclyl-oxycarbonyl)-N—($C_{3-6}$ cycloalkyl)-amino group" (e.g., N-cyclopropyl-N-(4-pyranyloxycarbonyl)amino, etc.), "N-(saturated heterocyclyl-$C_{1-4}$ alkylcarbonyl)-N—($C_{3-6}$ cycloalkyl)-amino group" (e.g., N-cyclopropyl-N-(4-pyranylmethylcarbonyl)amino, etc.), etc.

In addition, the "$C_{1-6}$ alkyl moiety" of the "mono- or di-($C_{1-6}$ alkyl)-substituted amino group" may optionally be substituted with $C_{1-6}$ alkoxy, mono-$C_{1-6}$ alkylcarbonylamino (said $C_{1-6}$ alkyl being optionally substituted with 1 to 3 fluorine atom(s)), or mono-$C_{1-6}$ alkoxycarbonylamino.

The "4- to 7-membered cyclic amino group" means a cyclic amino group having 4 to 7 members, where the nitrogen atom of said ring is a direct bond to said group. Preferable one is 5- to 7-membered ones, and more preferable one is 5- or 6-membered ones. Examples thereof are pyrrolidino, piperidino, morpholino, thiomorpholino, thiomorpholino oxide, thiomorpholino dioxide, piperazino, 2-pyrrolidon-1-yl, etc. Said ring may optionally be substituted with a halogen atom, $C_{1-4}$ alkyl, or a $C_6$ aryl having optionally a $C_{1-4}$ alkoxy substituent.

The "5- to 7-membered cyclic amino group" may form a condensed ring with a 6-membered aromatic hydrocarbon or a 6-membered unsaturated heterocycle. Example thereof is a group of the following formula.

[Chemical formula 17]

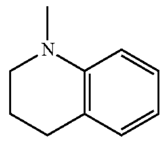

The substituent of the "optionally substituted $C_{1-6}$ alkyl group" includes, for example, (a) a halogen atom, (b) a cyano group, (c) a $C_{3-6}$ cycloalkyl group (said group being optionally substituted by halogen, hydroxy or $C_{1-4}$ alkoxy), (d) a hydroxy group, (e) a $C_{1-4}$ alkoxy group (being optionally substituted by fluorine, $C_{1-4}$ alkoxy, or $C_{3-6}$ cycloalkyl), (f) a $C_{3-6}$ cycloalkyloxy group, (g) a $C_6$ aryloxy group (said group being optionally substituted by the same or different groups selected from a group consisting of halogen, cyano and $C_{1-4}$ alkoxy), (h) a benzyloxy group, (i) a formyl group, (j) a $C_{1-4}$ alkylcarbonyl group, (k) a $C_{3-6}$ cycloalkylcarbonyl group, (l) a phenylcarbonyl group, (m) a benzylcarbonyl group, (n) a formylcarbonyloxy group, (o) a $C_{1-4}$ alkylcarbonyloxy group, (p) a $C_{3-6}$ cycloalkylcarbonyloxy group, (q) a carboxyl group, (r) a $C_{1-4}$ alkoxycarbonyl group, (s) a $C_{3-6}$ cycloalkoxycarbonyl group, (t) an amino group, (u) a mono-substituted amino group (said group being substituted by (u1) $C_{1-6}$ alkyl, (u2) $C_{3-6}$ cycloalkyl, (u3) $C_{3-6}$ cycloalkyl-$C_{1-4}$ alkyl, (u4) benzyl, (u5) $C_{3-6}$ cycloalkyl-$C_{1-4}$ alkoxycarbonyl, (u6) $C_{1-4}$ alkylcarbonyl, (u7) $C_{3-6}$ cycloalkylcarbonyl, (u8) saturated heterocyclyl-$C_{1-4}$ alkyl, (u9) saturated heterocyclyl-carbonyl, (u10) saturated heterocyclyl-oxycarbonyl, (u11) saturated heterocyclyl-$C_{1-4}$ alkylcarbonyl, or (u12) $C_{1-4}$ alkyl sulfonyl), (v) a di-substituted amino group (said group being substituted by the same or different 2 groups selected from the above-mentioned (u1)~(u12)), (w) a 5- or 7-membered cyclic amino group, (x) an optionally substituted aminocarbonyl group, (y) an optionally substituted aminocarbonyloxy group, or (z) a saturated heterocyclic group (said ring being optionally substituted with $C_{1-4}$ alkyl having optionally $C_{1-4}$ alkoxy substituent, $C_{1-4}$ alkoxy, or $C_{1-4}$ alkylcarbonylamino).

In addition, the substituent of the "optionally substituted $C_{1-6}$ alkyl group" should not be limited to those listed above. That is, in addition to the above substituents' list, the groups (f801) to (f826) and (b120) to (b128) as explained below are also included in the substituents' list.

The above-mentioned "optionally substituted aminocarbonyl group" means a group where the "optionally substituted amino" is attached to a carbonyl. The "substituted amino" includes mono-substituted amino group, di-substituted amino group or 5- to 7-membered cyclic amino.

Examples of the "mono- or di-substituted aminocarbonyl group" are ones where the "mono- or di-aminocarbonyl moiety" thereof is the same ones as exemplified as the above-mentioned "mono- or di-substituted amino"

The "5- to 7-membered cyclic aminocarbonyl group" may optionally be substituted with a $C_{6-10}$ aryloxy. Examples thereof are 3-phenyloxypyrrolidinocarbonyl, etc.

The "$C_{1-6}$ alkyl-aminocarbonylamino group" means an amino group which is substituted with one the above-mentioned "mono-($C_{1-6}$ alkyl)-substituted aminocarbonyl group", and examples thereof are methylaminocarbonylamino, etc.

The "N—($C_{1-6}$ alkylaminocarbonyl)-N—($C_{1-6}$ alkyl)-amino group" means a group where a "$C_{1-6}$ alkyl group" substitutes on the amino group of the above-mentioned "$C_{1-6}$ alkylaminocarbonylamino group", and examples thereof are N-methylaminocarbonyl-N-methylamino, etc.

The "$C_{1-6}$ alkylaminothiocarbonylamino group" means a group where the carbonyl of the above-mentioned "$C_{1-6}$ alkylaminocarbonylamino group" is replaced with a thiocarbonyl, and examples thereof are methylaminothiocarbonylamino.

The optionally substituted aminocarbonyl moiety of the above-mentioned "optionally substituted aminocarbonyloxy group" is the same as the above-mentioned "optionally substituted aminocarbonyl group", and examples thereof are aminocarbonyloxy, etc.

The"5- to 7-membered cyclic aminocarbonyl moiety" of the "5- to 7-membered cyclic amino-carbonyloxy" is the same as mentioned above. Examples thereof are pyrrolidinocarbonyloxy, etc.

The "5- to 7-membered cyclic aminocarbonyl-$C_{1-4}$ alkoxy" means a group where the above-mentioned "5- to 7-membered cyclic aminocarbonyl" is attached to the above-mentioned "$C_{1-4}$ alkoxy group". Examples thereof are 1-morpholinocarbonyl-1,1-dimethylmethoxy, etc.

The substituent of the "optionally substituted $C_{1-6}$ alkyl group" for B is preferably the following groups selected from a group consisting of:

(a2) a halogen atom, (b2) a $C_{3-6}$ cycloalkyl (being optionally substituted by the same or different 1 to 2 group(s) selected from a group consisting of (b21) a halogen atom, (b22) hydroxy, (b23) $C_{1-4}$ alkoxy, and (b24) $C_{3-6}$ cycloalkylcarbonylamino, (c2) a hydroxy group, (d2) a $C_{1-4}$ alkoxy, (e2) a $C_{3-6}$ cycloalkoxy, (f2) a $C_6$ aryloxy (being optionally substituted by $C_{1-4}$ alkyl), (g2) a carboxy, (h2) a $C_{1-4}$ alkoxycarbonyl, (i2) an amino (being optionally substituted by $C_{1-6}$ alkyl or benzyl), (j2) an aminocarbonyl (the amino moiety being optionally substituted by (j21) $C_{1-6}$ alkyl, (j22) $C_{3-6}$ cycloalkyl, or (j23) $C_{3-6}$ cycloalkyl-$C_{1-4}$ alkyl), (k2) a $C_{3-6}$ cycloalkyl carbonylamino, (l2) a saturated heterocycle (said ring being optionally substituted by the same or different 1 to 2 group(s) selected from a group consisting of (l21) $C_{1-4}$ alkyl, (l22) $C_{1-4}$ alkoxy, (l23) $C_{1-4}$ alkylcarbonylamino, and (l24) oxo), and (m2) a 5- to 7-membered cyclic amino group (said group being optionally substituted by the same or different 1 to 3 group(s) selected from a group consisting of (m21) a halogen atom, (m22) a $C_{1-4}$ alkyl, (m23) $C_6$ aryl having optionally $C_{1-4}$ alkoxy substituent, (m24) a $C_6$ aryloxy having optionally 1 to 3 halogen substituent(s), and (m25) oxo).

When "B" is a $C_{1-6}$ alkyl group being substituted with "mono-($C_{1-6}$ alkyl)-substituted amino", then the "$C_{1-6}$ alkyl" of the amino moiety may be optionally substituted with aminocarbonyl, mono- or di-($C_{1-6}$ alkyl)aminocarbonyl, or 5- or 6-membered cyclic aminocarbonyl (provided that when "A" should be a single bond, and "B" should be an optionally substituted $C_{1-6}$ alkyl group. The ($C_{1-6}$ alkyl)amino and the cyclic amino moiety are the same as mentioned above). Examples of the "$C_{1-6}$ alkyl" of the above-mentioned amino moiety are the following groups.

[Chemical formula 18]

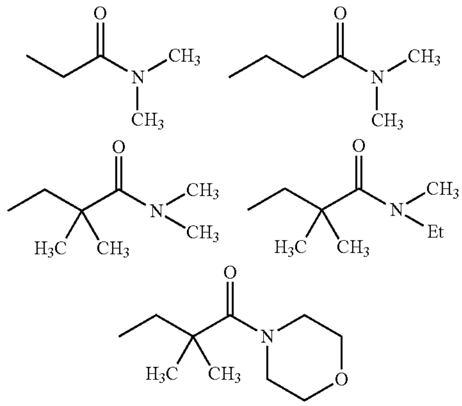

The substituent of the "optionally substituted $C_{1-6}$ alkyl group" for "B" may optionally be substituted with the same or different 1 to 3 group(s) selected from the above-mentioned groups. For example, when "A" is a single bond, then it may be substituted simultaneously with 2 substituents of the above-mentioned (b2) and (j2). In addition, when "A" is a group other than a single bond, said group may be substituted simultaneously with 2 groups of the above-mentioned (b2) and (d2).

Examples of the above-mentioned group include the following "groups".

[Chemical formula 19]

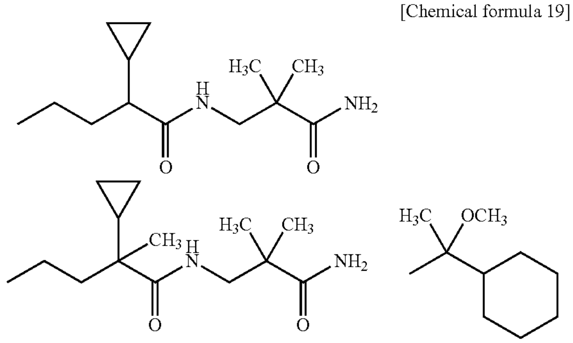

The substituent of the "optionally substituted $C_{1-6}$ alkoxy group" includes, for example, one group selected from a group consisting of the above-mentioned (a) to (z) (in which the substituent of (u) mono-substituted amino group should be $C_{1-4}$ alkyl group or $C_{3-6}$ alkyl group, and as for (v), (x) and (y), the same).

The substituent of the "optionally substituted $C_{2-6}$ alkenyl group" and the "optionally substituted $C_{2-6}$ alkynyl group" includes, for example, one group selected from a group consisting of the above-mentioned (a) to (s) and $C_{1-4}$ alkyl (in which the above-mentioned $C_{1-4}$ alkyl group being optionally substituted with hydroxy).

The substituent of the "optionally substituted $C_{3-10}$ cycloalkyl group" and the "optionally substituted $C_{3-10}$ cycloalkyloxy group" includes, for example, one group selected from a group consisting of the above-mentioned (x), a halogen atom, $C_{1-4}$ alkyl group being optionally substituted with $C_{1-4}$ alkoxy and a $C_{6-10}$ aryl group (said aryl group being optionally substituted with a halogen atom, $C_{1-4}$ alkyl, a hydroxy group, or $C_{1-4}$ alkoxy).

The substituent of the "optionally substituted $C_{5-6}$ cycloalkenyl group" and the "optionally substituted $C_{5-6}$ cycloalkenyloxy group" includes, for example, one group selected from a group consisting of the above-mentioned (a) to (s) and nitro group.

The substituent of the "optionally substituted $C_{1-4}$ alkylcarbonyl" and the "optionally substituted $C_{3-10}$ cycloalkylcarbonyl group" includes, for example, one group selected from a group consisting of the above-mentioned (a) to (h), nitro group, $C_{1-4}$ alkylcarbonylamino group and $C_{1-4}$ alkoxycarbonylamino group.

The substituent of the "optionally substituted $C_{1-6}$ alkylthio group", "optionally substituted $C_{1-6}$ alkylsulfonyl group", and the "optionally substituted $C_{1-4}$ alkoxycarbonyl group" includes, for example, one group selected from a group consisting of a halogen atom, a hydroxy group, nitro group, a cyano group, and the above-mentioned (d) to (h).

The substituent of the "optionally substituted $C_{6-10}$ aryl group", the "optionally substituted $C_{6-10}$ aryloxy group", the "optionally substituted $C_{6-10}$ arylcarbonyl group", the "optionally substituted 5- to 10-membered monocyclic or polycyclic heteroaryl group" and the "optionally substituted 5- to 10-membered monocyclic or polycyclic heteroaryloxy" includes, for example, the following groups selected from a group consisting of (a3) a halogen atom, (b3) a nitro group, (c3) a cyano group, (d3) a $C_{1-4}$ alkyl group (said group being optionally substituted with a halogen atom, a hydroxy group, or amino), (e3) a hydroxy group, (f3) a $C_{1-4}$ alkoxy group (said group being optionally substituted with (f31) $C_{1-4}$ alkoxy, (f32) $C_{3-6}$ cycloalkyl having optionally $C_{1-4}$ alkyl substituent, or (f33) a $C_6$ aryloxy having optionally halogen substituent), (g3) a $C_{3-6}$ cycloalkyloxy group, (h3) a $C_{6-10}$ aryloxy group (said group being optionally substituted with the same or different group selected from a group consisting of a halogen atom, cyano and $C_{1-4}$ alkoxy), (i3) a $C_{6-10}$ aryl group (said group being optionally substituted with (i31) a halogen atom, (i32) $C_{1-4}$ alkyl having optionally carboxy substituent, (i33) $C_{1-4}$ alkoxy having optionally a substituent selected from fluorine atom, a hydroxy group, and carboxy), (j3) a sulfonyl group, (k3) a $C_{1-4}$ alkoxysulfonyl group, (l3) a $C_{3-6}$ cycloalkoxysulfonyl group, (m3) a $C_{6-10}$ aryloxysulfonyl group (said phenyl being optionally substituted with the same or different group selected from a group consisting of a halogen atom, cyano and a $C_{1-4}$ alkoxy), (n3) benzyloxysulfonyl group, (o3) 5- or 6-membered monocyclic heteroaryloxy group (said group being optionally substituted with $C_{1-4}$ alkyl), (p3) a saturated heterocyclyl-oxy group (said group being optionally substituted with the same or different 1 to 2 group(s) selected from (p31) a $C_6$ aryl optionally having a halogen substituent, or (p32) saturated heterocyclyl-carbonyl), (q3) an amino group (said group being optionally substituted with the same or different 1 to 2 group(s) selected from the above-mentioned u1 to u12), (r3) 5- to 7-membered cyclic amino group (being optionally substituted with $C_6$ aryl), (s3) an optionally substituted aminocarbonyl group, and (t3) an optionally substituted aminocarbonyloxy group.

In addition, the substituents should not be limited thereto, and may include, in addition to the ones as listed above, the substituents of (e1201) to (e1211) as explained below.

The substituent of the aryl moiety of the "optionally substituted $C_{7-14}$ aralkyl group" and the "optionally substituted $C_{7-14}$ aralkyloxy group" includes, for example, the following groups selected from a group consisting of (a4) a halogen atom, (b4) a cyano group, (c4) a $C_{1-4}$ alkyl group (being optionally substituted with 1 to 3 halogen atom(s)), (d4) a hydroxy group, (e4) a $C_{1-4}$ alkoxy group (being optionally substituted with 1 to 3 halogen atom(s)), (f4) a $C_{3-6}$ cycloalkoxy group (being optionally substituted with 1 to 2 halogen atom(s)), (g4) carboxy group, (h4) a $C_{1-4}$ alkoxycarbonyl group, (i4) a $C_{6-10}$ aryl group (being optionally substituted with 1 to 3 halogen atom(s) or $C_{1-4}$ alkoxy), (j4) a $C_{6-10}$ aryloxy group, (k4) a $C_{7-10}$ aralkyloxy group, (l4) an aminocarbonyl group (the amino moiety having optionally a $C_{1-6}$ alkyl substituent), (m4) a $C_{1-4}$ alkylsulfonylamino group, and (n4) a $C_{1-4}$ alkylsulfonyl group.

The substituent of the above-mentioned (a4) to (n4) may substitute on the $C_{1-4}$ alkyl moiety of the $C_{7-14}$ aralkyl group ($C_{6-10}$ aryl-$C_{1-4}$ alkyl group).

The substituent of the heteroaryl moiety of the "optionally substituted 5- to 10-membered monocyclic or polycyclic heteroaryl-$C_{1-4}$ alkyl group" includes ones as exemplified as a substituent for the "optionally substituted 5- to 10-membered monocyclic or polycyclic heteroaryl group".

The substituent of the "saturated heterocyclic group" and the "saturated heterocycle" includes, for example, (a5) a halogen atom, (b5) a hydroxy group, (c5) a nitro group, (d5) a cyano group, (e5) a $C_{1-4}$ alkyl group (being optionally substituted with 1 to 3 halogen atom(s) or $C_{1-4}$ alkoxy), (f5) a $C_{1-4}$ alkoxy group (being optionally substituted with 1 to 3 halogen atom(s)), (g5) a carboxyl group, (h5) a $C_{1-4}$ alkoxycarbonyl group, (i5) a $C_{3-6}$ cycloalkoxycarbonyl group, (j5) an amino group (being optionally substituted with $C_{1-4}$ alkyl), (k5) a $C_6$ aryl group (being optionally substituted with $C_{1-4}$ alkoxy), (l5) an aminocarbonyl group, (m5) a $C_{1-4}$ alkylcarbonylamino group, (n5) an oxo group, or (o5) a thioxo group.

Said "saturated heterocyclic group" or "saturated heterocycle" may be substituted with the same or different 2 groups selected from the above substituents.

The "optionally substituted saturated heterocyclic group" for "B" is preferably a 5- or 6-membered saturated heterocyclic group having the same or different 1 to 3 atom(s) selected from "nitrogen atom, an oxygen atom and sulfur atom.

The definitions of "$G^1$", "$G^2$", "$G^3$" and "$G^4$" of the compound of the formula (I) are explained below. The compound where $G^1$ is —N($R^{1b}$)—, $G^2$ is —CO—, $G^3$ is —C($R^{1c}$)($R^{1d}$)— and $G^4$ does not exist at all means a compound of the following formula:

[Chemical formula 20]

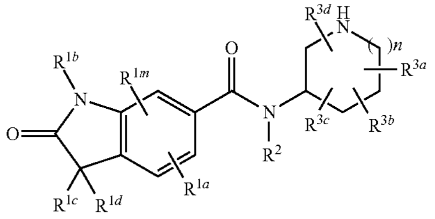

(wherein the definitions are the same as defined in Item 1).

The compound where $G^1$ is —N($R^{1b}$)—, $G^2$ is —CO—, $G^3$ is —N($R^{1b}$)—, and $G^4$ does not exist at all means a compound of the following formula:

[Chemical formula 21]

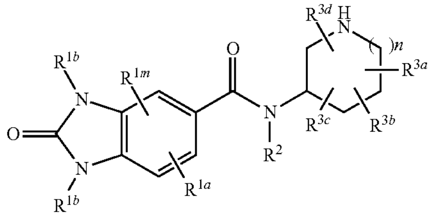

(wherein the definitions are the same as defined in Item 1).

The compound where $G^1$ is —N($R^{1b}$)—, $G^2$ is —CO—, $G^3$ is —C($R^{1c}$)($R^{1d}$)—, and $G^4$ is —C($R^{1x}$)($R^{1y}$)— means a compound of the following formula:

[Chemical formula 22]

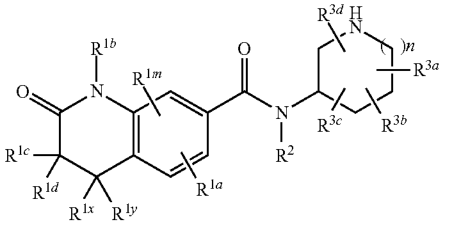

(wherein the definitions are the same as defined in Item 1). In this case, "$R^{1c}$" and "$R^{1x}$" may combine each other. That is, the compound of the above definition also includes a compound of the following formula:

[Chemical formula 23]

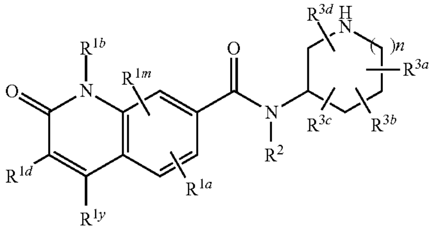

The definition of a group of the following formula where "$R^{1x}$ and $R^{1y}$ combine each other is explained below.

[Chemical formula 24]

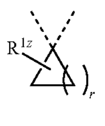

Said definition means a spiro ing of the following formulae (the part expressed with a solid line means a part formed by $R^{1x}$ and $R^{1y}$, and the part expressed with a broken line means a skeleton formed by $G^1$ to $G^4$).

[Chemical formula 25]

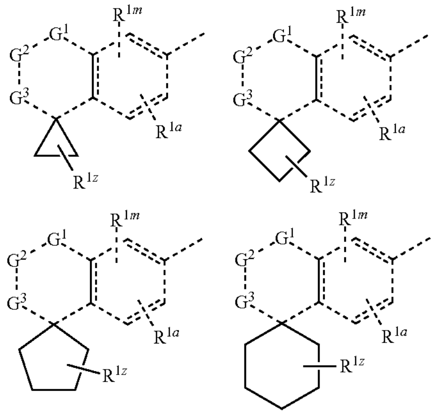

The binding position of "A" of "a group: -A-B" is explained below. When A is —$(CH_2)_s$O— and B is a hydrogen atom, then the "group: -A-B" means a "group: —$(CH_2)_s$O—H".

In case that "A is —$(CH_2)_s$N($R^4$)—, —$(CH_2)_s$OCON($R^4$)—, —$(CH_2)_s$CON($R^4$)—, —$(CH_2)_s$N($R^4$)CO—N($R^4$)— or —$(CH_2)_s$$SO_2$N($R^4$)—, $R^4$ and B combine each other to form a ring" means that "N($R^4$)—" moiety forms a "5- or 6-membered cyclic amino group". Examples thereof are groups of the following formulae.

[Chemical formula 26]

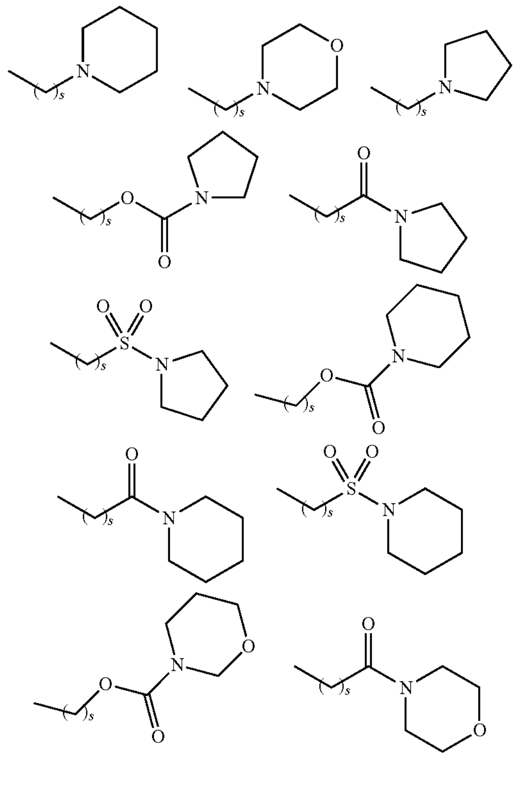

-continued

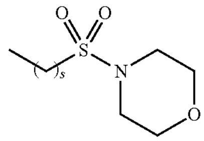

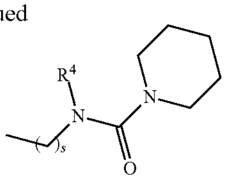

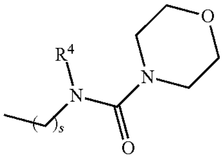

The above-mentioned ring formed by combining $R^4$ and B includes, for example, a condensed ring with a $C_6$ aryl, a 5- or 6-membered heteroaryl or a 5- or 6-membered saturated heterocycle. Examples thereof are groups of the following formulae.

[Chemical formula 27]

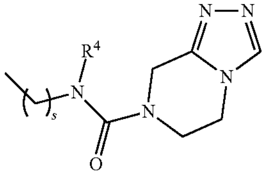

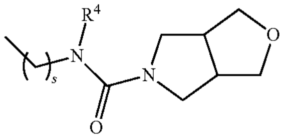

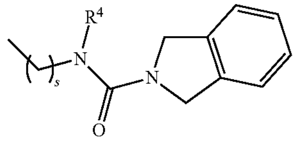

The above-mentioned cyclic amino group may optionally be substituted with the same substituents as ones for the above-mentioned "saturated heterocyclic group". Examples thereof are 4-hydroxypiperidino; 2-methoxymorpholino; 4-formyl-piperidino; 4-methoxycarbonylpiperidino; 4-aminocarbonylpiperidino; 4-N-methylaminopiperidino; 3-phenylpyrrolidino; 4-dimethylaminopiperidino, etc.

In the compounds of the formula (I), when A is —$(CH_2)_s$ $N(R^4)CON(R^4)$—, then each $R^4$ may independently be different. Examples thereof are A being "—$(CH_2)_s$NHCON $(CH_3)$—", and the like.

The "any two groups of $R^{3a}$, $R^{3b}$, $R^{3c}$ and $R^{3d}$ are a hydrogen atom, and the remaining 2 groups combine each other to form a fused ring with a heterocyclic ring" means that the remaining two groups as defined above form a fused ring with a hetero ring (pyrrolidine ring, piperidine ring, etc.) to which said definition substitutes. Examples of said definition are groups of the following structures.

[Chemical formula 28]

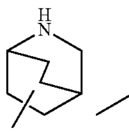

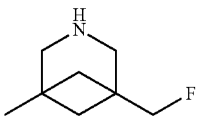

Preferable embodiments of the compounds of the formula (I) are explained. The definitions for the following partial structure:

[Chemical formula 29]

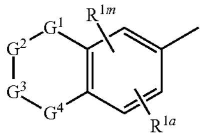

(wherein the definitions are the same as defined above) are explained.

The "$G^1$", "$G^2$", "$G^3$" and "$G^4$" are preferably, (i) $G^1$ is —$N(R^{1b})$—, $G^2$ is —CO—, $G^3$ is —$C(R^{1c})(R^{1d})$—, and $G^4$ is —$C(R^{1x})(R^{1y})$—, —$SO_2$—, an oxygen atom, a sulfur atom, or does not exist at all, or (ii) $G^1$ is —$N(R^{1b})$—, $G^2$ is —CO—, $G^3$ is —$N(R^{1b})$—, and $G^4$ does not exist at all.

The "$G^1$", "$G^2$", "$G^3$" and "$G^4$" are preferably, $G^1$ is —$N(R^{1b})$—, $G^2$ is —CO—, $G^3$ is —$N(R^{1b})$—, and $G^4$ does not exist at all.

The "$G^1$", "$G^2$", "$G^3$" and "$G^4$" are more preferably, $G^1$ is —$N(R^{1b})$—, $G^2$ is —CO—, $G^3$ is —$C(R^{1c})(R^{1d})$—, and $G^4$ is —$C(R^{1x})(R^{1y})$—, an oxygen atom, or a sulfur atom.

The "$G^4$" is preferably —$C(R^{1x})(R^{1y})$—, and $R^{1x}$ and $R^{1y}$ are preferably a hydrogen atom or a $C_{1-4}$ alkyl group.

The "$G^4$" is preferably an oxygen atom or a sulfur atom.

The "$R^{1a}$" is one group selected from a group consisting of (a6) a halogen atom, (b6) a cyano group, (c6) a $C_{1-6}$ alkyl group (being optionally substituted with 1 to 3 fluorine atom(s), $C_{1-4}$ alkoxy, or $C_{3-6}$ cycloalkoxy), (d6) a $C_{1-6}$ alkoxy group (being optionally substituted with 1 to 3 fluorine atom(s), or $C_{3-6}$ cycloalkyl), (e6) a $C_{3-6}$ cycloalkyl group, (f6) a $C_{3-6}$ cycloalkoxy group (being optionally substituted with 1 to 2 fluorine atom(s), or $C_{1-4}$ alkoxy), and (g6) a 5-membered to 6-membered heteroaryl group (being optionally substituted with a halogen atom or $C_{1-4}$ alkyl).

The "$R^{1a}$" is preferably a group selected from a group consisting of a halogen atom, a cyano group, a $C_{1-6}$ alkyl group having optionally 1 to 3 fluorine substituent(s), and a $C_{1-6}$ alkoxy group.

The "$R^{1a}$" preferably substitutes on the following position.

[Chemical formula 30]

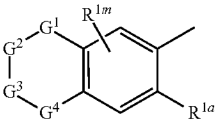

The "$R^{1b}$" is preferably (a7) a $C_{1-6}$ alkyl group (said group being optionally substituted with one group selected from the following groups selected from a group consisting of (a700) hydroxy, (a702) cyano, (a703) $C_{1-4}$ alkoxy (being optionally substituted with 1 to 3 fluorine atom(s) or $C_{1-4}$ alkoxy), (a704) trifluoromethyl, (a705) trifluoromethoxy, (a706) $C_{3-6}$ cycloalkyl (being optionally substituted with 1 to 2 fluorine atom(s), or $C_{1-4}$ alkoxy), (a707) $C_{3-6}$ cycloalkoxy, (a708) formylamino, (a709) $C_{1-4}$ alkylcarbonylamino (having optionally 1 to 3 fluorine substituent(s)), (a710) N—($C_{1-4}$ alkylcarbonyl)-N—($C_{1-6}$ alkyl)-amino,
(a711) $C_{3-6}$ cycloalkylcarbonylamino,
(a712) ($C_{3-6}$ cycloalkyl-$C_{1-4}$ alkyl)carbonylamino,
(a713) $C_{1-6}$ alkylthiocarbonylamino,
(a714) $C_{1-4}$ alkoxycarbonylamino (having optionally 1 to 3 fluorine substituent(s)),
(a715) N—($C_{1-4}$ alkoxycarbonyl)-N—($C_{1-6}$ alkyl)-amino,
(a716) mono- or di-($C_{1-6}$ alkyl)aminocarbonyloxy,
(a717) $C_{1-6}$ alkylaminocarbonyl (having optionally 1 to 3 fluorine atom(s)),
(a718) di-($C_{1-6}$ alkyl)aminocarbonyl,
(a719) $C_{3-6}$ cycloalkylaminocarbonyl,
(a720) $C_{1-6}$ alkylaminocarbonylamino,
(a721) $C_{1-6}$ alkylaminothiocarbonylamino,
(a722) $C_{1-4}$ alkylcarbonyl,
(a723) $C_{1-4}$ alkyl carbonyloxy,
(a724) $C_{1-4}$ alkoxycarbonyl,
(a725) $C_{1-6}$ alkylsulfonyl,
(a726) $C_{1-4}$ alkylsulfonylamino,
(a727) 5- or 6-membered saturated heterocycle,
(a728) carboxy, and
(a729) $C_{1-6}$ alkylamino, (b7) a $C_{2-6}$ alkenyl group (being optionally substituted with a halogen atom), (c7) a $C_{2-6}$ alkynyl group (being optionally substituted with $C_{1-4}$ alkoxy), or (d7) a 5-membered to 6-membered heteroaryl-$C_{1-4}$ alkyl group.

The above-mentioned $C_{1-6}$ alkyl group(a7) may optionally be substituted with the same or different substituent(s).

The "$R^{1b}$" is preferably a $C_{1-6}$ alkyl group substituted with a $C_{1-4}$ alkoxy-, and more preferably 3-methoxypropyl group or 4-methoxybutyl group.

The "$R^{1b}$" is preferably a $C_{1-6}$ alkyl group substituted with a $C_{1-6}$ alkylcarbonylamino, and more preferably 2-(ethylcarbonylamino)ethyl group.

The "$R^{1b}$" is preferably a $C_{1-6}$ alkyl group substituted with a $C_{1-4}$ alkoxycarbonylamino, and more preferably 2-(methoxycarbonylamino)ethyl group.

The "$R^{1c}$" and "$R^{1d}$" are independently the same or different, and each is a group selected from the following group consisting of (a8) a hydrogen atom, (b8) a halogen atom, (c8) a cyano group, (d8) a $C_{2-6}$ alkenyl group (being optionally substituted with $C_{6-10}$ aryl having optionally $C_{1-4}$ alkoxy substituent), (e8) a $C_{2-6}$ alkynyl group (being optionally substituted with $C_{6-10}$ aryl having optionally $C_{1-4}$ alkoxy substituent), (f8) a $C_{1-6}$ alkyl group (said group being optionally substituted with the same or different 1 to 2 group(s) selected from a group consisting of (f801) 1 to 3 halogen atom(s),
(f802) cyano,
(f803) $C_{3-6}$ cycloalkyl (being optionally substituted with a halogen atom, $C_{1-4}$ alkyl, or $C_{1-4}$ alkoxy),
(f804) hydroxy,
(f805) $C_{1-4}$ alkoxy (said group being optionally substituted with the same or different 1 to 3 substituent(s) selected from a group consisting of (f80511) a halogen atom, (f80512) cyano, (f80513) $C_{3-6}$ cycloalkoxy (being optionally substituted with mono- or di-($C_{1-6}$ alkyl)aminocarbonyl), (f80514) mono- or di-($C_{1-6}$ alkyl)aminosulfonyl, (f80515) $C_{1-6}$ alkylsulfonyl, (f80516) aminocarbonyl having optionally mono- or di-($C_{1-6}$ alkyl), (f80517) $C_{1-4}$ alkylcarbonyl, and (f80518) 5- to 7-membered cyclic aminocarbonyl,
(f806) $C_{3-6}$ cycloalkoxy (said group being optionally substituted with (f8061) $C_{1-4}$ alkyl (optionally having $C_{1-4}$ alkoxy substituent)),
(f807) $C_{6-10}$ aryloxy (said group being optionally substituted with the same or different 1 to 3 substituents selected from a group consisting of (f8071) a halogen atom, (f8072) cyano, and (f8073) $C_{1-4}$ alkoxy)
(f808) mono- or di-substituted amino (said group being substituent with the same or different 1 to 2 group(s) selected from a group consisting of (f80811) $C_{1-6}$ alkyl, (f80812) $C_{3-6}$ cycloalkyl, (f80813) $C_{3-6}$ cycloalkyl-$C_{1-4}$ alkyl (being optionally substituted with aminocarbonyl), (f80814) $C_{3-6}$ cycloalkyl-$C_{1-4}$ alkoxycarbonyl, (f80815) $C_{1-4}$ alkylcarbonyl, (f80816) $C_{3-6}$ cycloalkylcarbonyl (being optionally substituted with $C_{1-4}$ alkylsulfonylamino), (f80817) 5- or 6-membered saturated heterocyclyl-$C_{1-4}$ alkyl (being optionally substituted with $C_{1-4}$ alkyl), (f80818) 5- or 6-membered saturated heterocyclyl-carbonyl, (f80819) 5- or 6-membered saturated heterocyclyl-oxycarbonyl, (f80820) 5- or 6-membered saturated heterocyclyl-$C_{1-4}$ alkylcarbonyl, and (f80821) $C_{1-4}$ alkylsulfonyl),
(f809) 5- to 7-membered cyclic amino (being optionally substituted with 1 to 4 group(s) selected from a group consisting of $C_{1-4}$ alkyl, and $C_{7-14}$ aralkyl),
(f810) mono- or di-($C_{1-6}$ alkyl)aminocarbonyl,
(f811) 4- to 7-membered cyclic aminocarbonyl (being optionally substituted with $C_{1-4}$ alkyl),
(f812) mono- or di-substituted aminocarbonyloxy (said amino being substituted with the same or different 1 to 2 group(s) selected from a group consisting of (f8121) $C_{1-6}$ alkyl (being optionally substituted with 5- or 6-membered saturated heterocycle), (f8122) $C_{3-6}$ cycloalkyl (being optionally substituted with hydroxy), and (f8123) 5- or 6-membered saturated heterocycle),
(f813) 5- to 7-membered cyclic aminocarbonyloxy (being optionally substituted with 1 to 2 fluorine atom(s)),
(f814) 5- to 7-membered cyclic aminocarbonyl-$C_{1-4}$ alkoxy,
(f815) mono- or di-($C_{1-6}$ alkyl)aminocarbonyl-$C_{1-4}$ alkoxy,
(f816) 5- or 6-membered saturated heterocycle (being optionally substituted with the same or different 1 to 2 group(s) selected from a group consisting of $C_{1-4}$ alkyl),
(f817) 5- or 6-membered saturated heterocyclyl-$C_{1-4}$ alkoxy (being optionally substituted with $C_{1-4}$ alkyl),
(f818) 5- or 6-membered saturated heterocyclyl-oxy(being optionally substituted with the same or different 1 to 2 group(s) selected from a group consisting of $C_{1-4}$ alkyl),
(f819) mono- or di-$C_{1-4}$ alkylaminosulfonyl,
(f820) carboxy,
(f821) $C_{1-4}$ alkoxycarbonyl,
(f822) $C_{6-10}$ arylcarbonyl (said group being optionally substituted with $C_{1-4}$ alkoxy),
(f823) $C_{1-4}$ alkoxycarbonylamino,
(f824) $C_{6-10}$ aryloxycarbonylamino (being optionally substituted with a halogen atom),
(f825) 5- or 6-membered monocyclic aryloxycarbonylamino, and
(f826) N—($C_{1-4}$ alkylaminocarbonyl)-N—($C_{1-6}$ alkyl) amino), (g8) a $C_{3-10}$ cycloalkyl group (said group being optionally substituted with (g81) a halogen atom,
(g82) hydroxy, or
(g83) $C_{1-4}$ alkoxy), (h8) a $C_{7-14}$ aralkyl group (said group being optionally substituted with the same or different 1 to 3 group(s) selected from a group consisting of (h81) a halogen atom, (h82) cyano, (h83) hydroxy, (h84) $C_{1-4}$ alkoxy, and (h85) $C_{1-4}$ alkyl being optionally substituted with $C_{1-4}$ alkoxy), (i8) a $C_{1-6}$ alkoxy group (said group being optionally substituted with $C_{1-4}$ alkoxycarbonylamino), (j8) a $C_{3-6}$ cycloalkoxy group, (k8) a $C_{7-14}$ aralkyloxy group (being optionally substituted with $C_{1-4}$ alkoxy), (l8) mono- or di-substituted aminocarbonyl group (said amino being optionally substituted with $C_{1-6}$ alkyl having optionally 5- or 6-membered saturated heterocycle substituent), (m8) 5- to 7-membered cyclic aminocarbonyl group (being optionally substituted with a group selected from a group consisting of a halogen atom, $C_{1-4}$ alkoxy and $C_{6-10}$ aryl having optionally halogen substituent), (n8) a saturated heterocyclic group (said group being optionally substituted with the same or different 1 to 4 group(s) selected from a group consisting of (n81) $C_{1-4}$ alkyl, (n82) $C_{6-10}$ aryl having optionally 1 to 3 halogen substituent(s)

(o8) a saturated heterocyclyl-oxy group (being optionally substituted with $C_{1-4}$ alkoxycarbonyl or $C_{1-4}$ alkylcarbonyl)

(p8) a 5- to 10-membered monocyclic or polycyclic heteroaryl group (said group being optionally substituted with the same or different 1 to 2 group(s) selected from a group consisting of (p81) a halogen atom, (p82) $C_{1-4}$ alkyl having optionally 1 to 3 fluorine atom(s), and (p83) $C_{1-4}$ alkoxy (being optionally substituted with mono- or di-($C_{1-6}$ alkyl)aminocarbonyl)), (q8) a 5- to 10-membered monocyclic or polycyclic heteroaryl-$C_{1-4}$ alkyl group, (t8) a group of the following formula:

[Chemical formula 31]

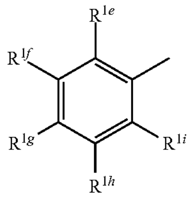

(wherein $R^{1e}$, $R^{1f}$, $R^{1g}$, $R^{1h}$ and $R^{1i}$ are the same as defined above).

The "$R^{1c}$" is preferably a group selected from a group consisting of (a9) a hydrogen atom, (b9) a halogen atom, (c9) a hydroxy group, and (d9) a $C_{1-6}$ alkyl group being optionally substituted with $C_{1-4}$ alkoxy.

The "$R^{1d}$" is preferably a group selected from a group consisting of (a8) to (t8).

The $R^{1d}$" is more preferably one group selected a group consisting of (a10) a hydrogen atom, (b10) a halogen atom, (c10) a $C_{1-6}$ alkyl group (said group being optionally substituted with a group selected from (c101) 1 to 3 halogen atom(s), (c102) hydroxy, (c103) $C_{1-4}$ alkoxy, (c104) $C_{6-10}$ aryloxy (said group being optionally substituted with the same or different 1 to 3 group(s) selected from cyano and $C_{1-4}$ alkoxy), (c105) $C_{1-6}$ alkylaminocarbonyloxy, (c106) (5- or 6-membered saturated heterocyclyl-$C_{1-4}$ alkyl)aminocarbonyloxy, or (c107) 5- to 7-membered cyclic aminocarbonyloxy), (e10) mono- or di-($C_{1-6}$ alkyl)aminocarbonyl group, (f10) N-(5- or 6-membered saturated heterocyclyl-$C_{1-4}$ alkyl)-N—(C alkyl)-aminocarbonyl group, (g10) 5- to 7-membered cyclic aminocarbonyl group, (h10) $C_{7-14}$ aralkyl group (being optionally substituted with $C_{1-4}$ alkoxy), (i10) 5- or 6-membered saturated heterocyclic group, (j10) $C_{3-6}$ cycloalkyl group, (k10) $C_{3-6}$ cycloalkoxy group, and (l10) a group of the following formula:

The "$R^{1e}$", "$R^{1f}$", "$R^{1g}$", "$R^{1h}$" and "$R^{1i}$" are independently the same or different, and each is preferably (a11) a hydrogen atom, (b11) a halogen atom, (c11) a cyano group, (d11) a $C_{1\cdot 4}$ alkyl group (said group being optionally substituted with (d111) 5- or 6-membered saturated heterocyclyl-oxy, (d112) $C_{1-4}$ alkoxy (said group being optionally substituted with $C_{1-4}$ alkoxy or $C_{3-6}$ alkoxy)), (e11) a $C_{1-4}$ alkoxy group (said group being optionally substituted with (e111) 1 to 3 halogen atom(s), (e112) $C_{1-4}$ alkoxy, or (e113) $C_{1-6}$ alkylaminocarbonyl), (f11) a $C_{3-6}$ cycloalkoxy group (said group being optionally substituted with (f111) $C_{1-4}$ alkoxy), (g11) 5- or 6-membered saturated heterocyclyl-oxy group, (h11) a $C_{1-6}$ alkylaminocarbonyl group.

[Chemical formula 32]

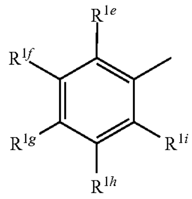

($R^{1e}$, $R^{1f}$, $R^{1g}$, $R^{1h}$ and $R^{1i}$ are the same as defined above).

The "$R^{1e}$", "$R^{1f}$", "$R^{1g}$,", "$R^{1h}$" and "$R^{1i}$" are independently the same or different, and each is preferably (a11) a hydrogen atom, (b11) a halogen atom, (c11) a cyano group, (d11) a $C_{1-4}$ alkyl group (said group being optionally substituted with (d111) 5- or 6-membered saturated heterocyclyl-oxy, (d112) $C_{1-4}$ alkoxy (said group being optionally substituted with $C_{1-4}$ alkoxy or $C_{3-6}$ alkoxy) or (d113) 1 to 3 fluorine atom(s)), (e11) a $C_{1-4}$ alkoxy group (said group being optionally substituted with (e111) 1 to 3 halogen atom(s), (e112) $C_{1-4}$ alkoxy, or (e113) $C_{1-6}$ alkylaminocarbonyl), (f11) a $C_{3-6}$ cycloalkoxy group (said group being optionally substituted with (f111) $C_{1-4}$ alkoxy), (g11) 5- or 6-membered saturated heterocyclyl-oxy group, (h11) a $C_{1-6}$ alkylaminocarbonyl group, (h12) a hydroxy group, or (h13) a $C_{1-4}$ alkoxysulfonyl group.

The "$R^{1e}$", "$R^{1f}$", "$R^{1g}$", "$R^{1h}$" and "$R^{1i}$" are independently the same or different, and each is preferably a hydrogen atom, a halogen atom, or a $C_{1-4}$ alkoxy group.

The "$R^{1e}$, $R^{1h}$ and $R^{1i}$ are a hydrogen atom, and $R^{1f}$ and $R^{1g}$ combine each other to form a condensed ring" means that forming a bicyclic or tricyclic condensed ring with a phenyl group to which $R^{1f}$ and $R^{1g}$ attach. Said condensed ring may be any 5- or 6-membered saturated ring or unsaturated ring, and said ring contains at least one atom selected from nitrogen atom, oxygen atom, and sulfur atom. Said ring may optionally be substituted with $C_{1-4}$ alkyl group, a hydroxy group, or oxo group.

Examples of the group where "$R^{1e}$, $R^{1h}$ and $R^{1i}$ are a hydrogen atom, and $R^{1f}$ and $R^{1g}$ combine each other to form a condensed ring" are one group selected from the following formulae.

[Chemical formula 33]

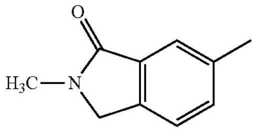
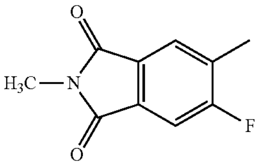
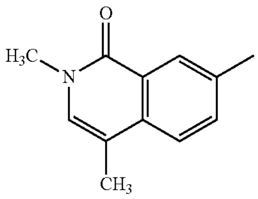
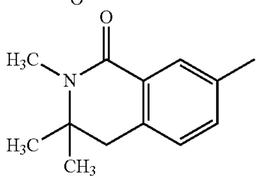
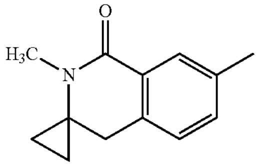
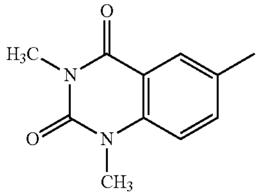
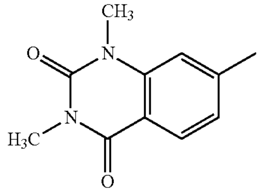
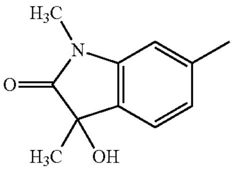

-continued

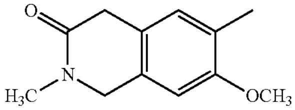
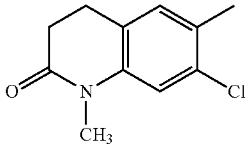
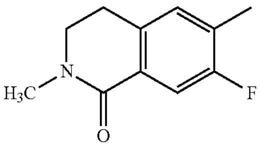
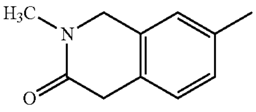
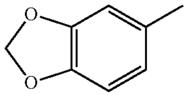
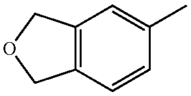
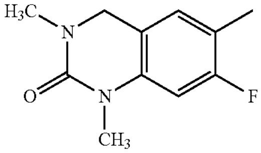
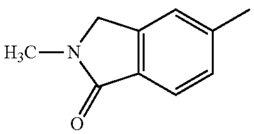
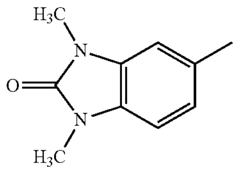
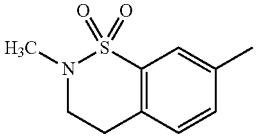
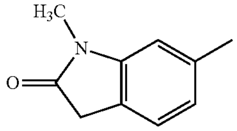
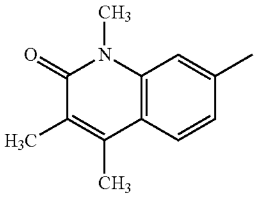
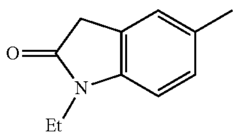
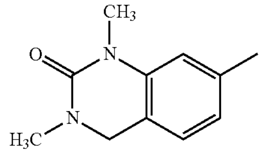
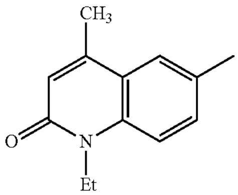
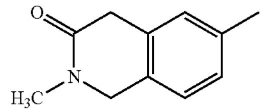
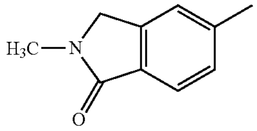
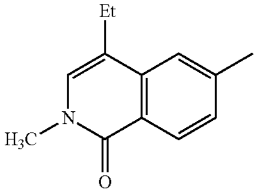
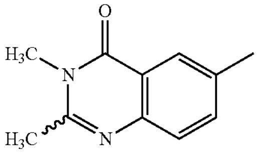
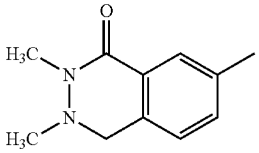

-continued
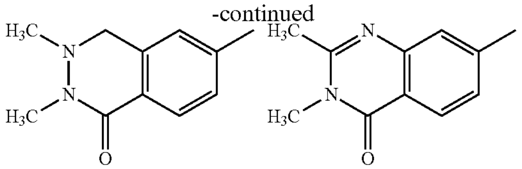
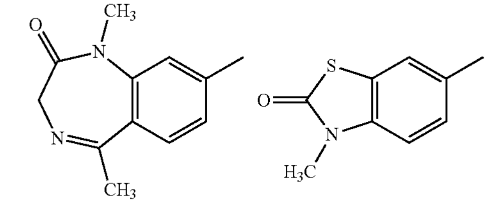
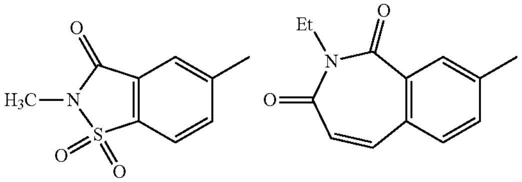
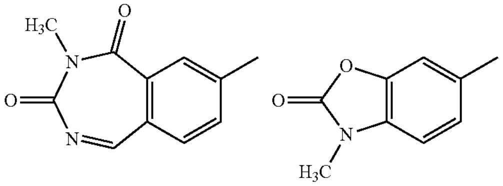
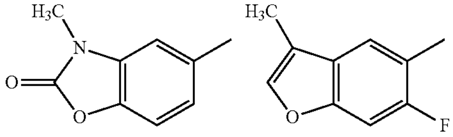
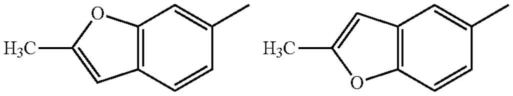
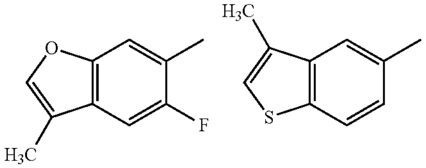
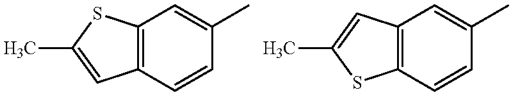
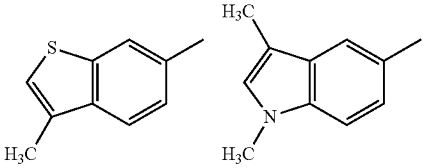
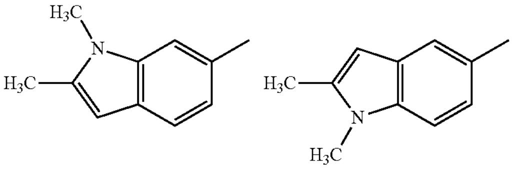
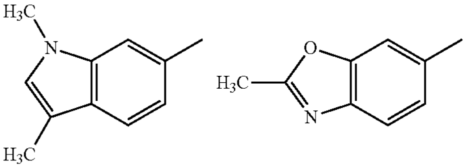
-continued
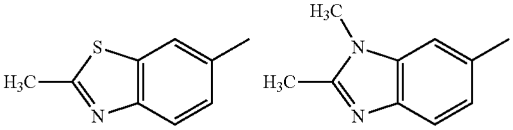
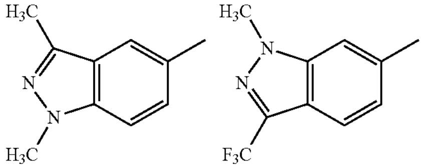
[Chemical formula 34]
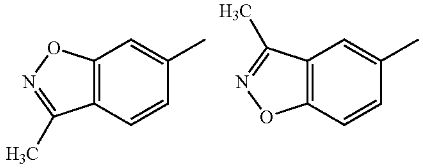
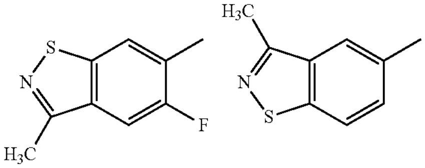
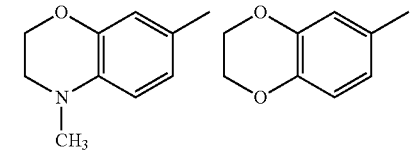
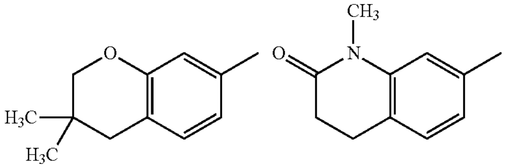
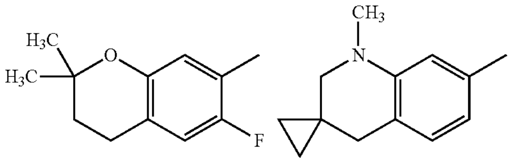
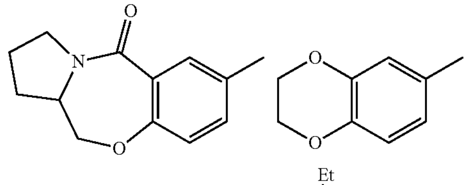
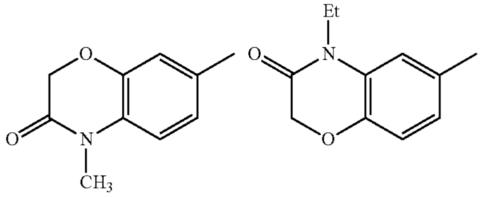
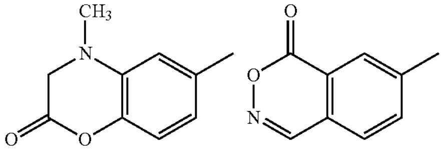

-continued

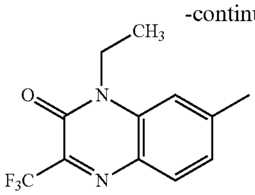
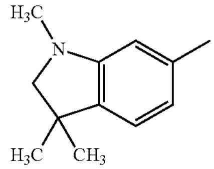
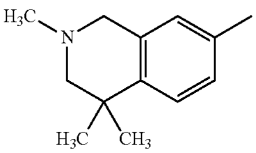
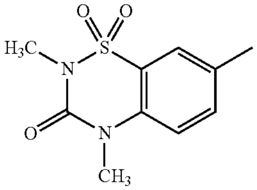
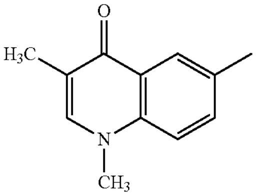
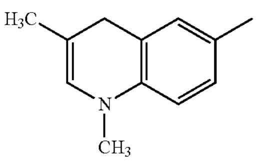
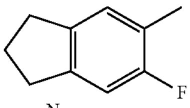
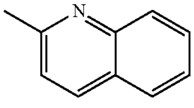
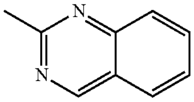
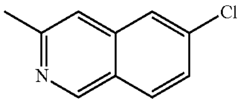
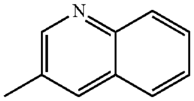
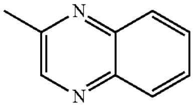
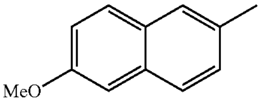
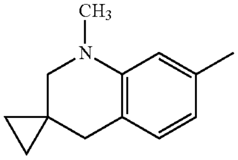

The group of the following formula is preferable when $R^{1c}$ and $R^{1d}$ combine each other.

[Chemical formula 35]

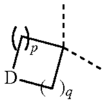

(the part expressed with a solid line is a moiety formed with $R^{1c}$ and $R^{1d}$, and the part expressed with a broken line is a skeleton formed by $G^1$ to $G^4$).

When "D" is an oxygen atom or a sulfur atom, and p and q are 0, then $R^{1c}$ and $R^{1d}$ combine each other to form an oxo group or a thioxo group.

In "—$NR^5CONR^5$—" for "D", each $R^5$ is independent each other.

The "—$CH(R^6)CH_2$—" for "D" may be "—$CH_2CH(R^6)$—". In addition, when "D" is —$SO_2$—, —$NR^5CO$—, —$NR^5SO_2$—, —$NR^5CONR^5$—, then "p" and "q" are not simultaneously 0. When "D" is "—$CH(R^6)$—", and "$R^6$" is a halogen atom, then the hydrogen atom of "—$CH(R^6)$—" may be replaced with a halogen atom.

Examples of the groups as mentioned above are structures of the following formulae.

[Chemical formula 36]

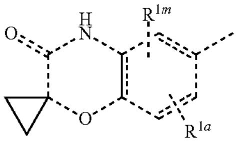
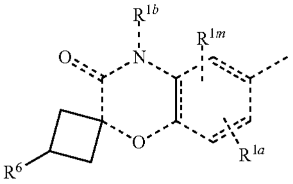
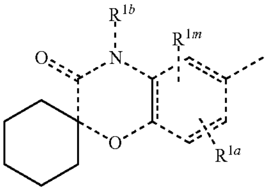
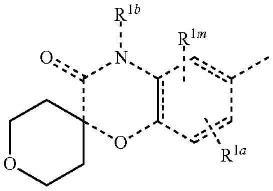
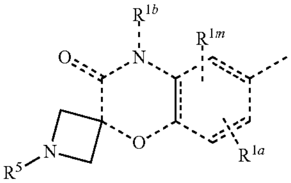
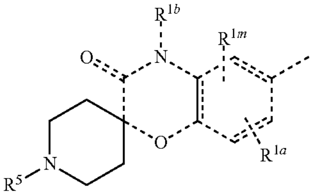
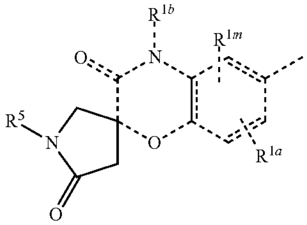

Preferable $R^5$ is a group selected from a group consisting of a hydrogen atom, a $C_{1-6}$ alkyl group, a $C_{1-4}$ alkoxycarbonyl group, a $C_{1-4}$ alkylsulfonyl group, and a $C_{6-10}$ arylsulfonyl group.

Preferable $R^6$ is a group selected from a group consisting of a hydrogen atom; a halogen atom; a $C_{1-4}$ alkoxy group being optionally substituted with $C_{1-4}$ alkoxy; a $C_{7-14}$ aralkyloxy group being optionally substituted with 1 to 3 group(s) selected from a group consisting of a fluorine atom and cyano; and an aminocarbonyloxy group being optionally substituted with mono- or di-($C_{1-6}$ alkyl), and a hydrogen atom is more preferable.

As to "D", "p" and "q", preferable combinations are (i) D is an oxygen atom, "p" and "q" are 2, (ii) D is —$CH_2$—, "p" and "q" are 1 or 2, or (iii) D is —$CH_2CH_2$—, and "p" and "q" are 0 or 1.

The above-mentioned partial structure of the compound of the formula (I) includes, for example, a partial structure selected from the following group.

[Chemical formula 37]
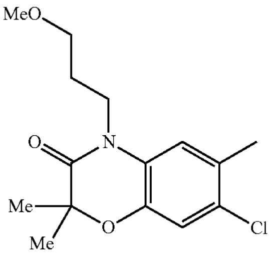
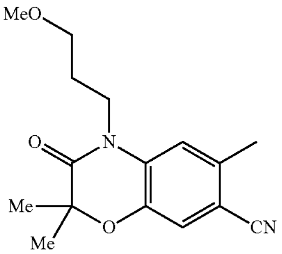
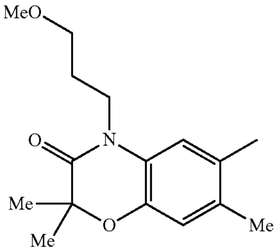
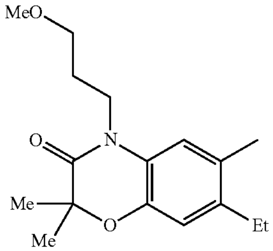
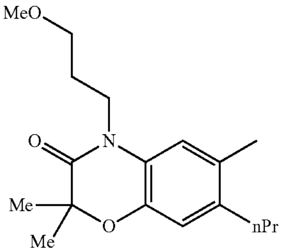
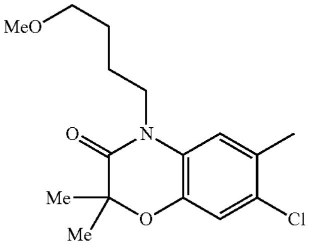
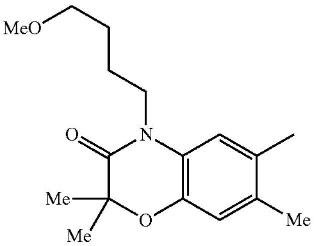
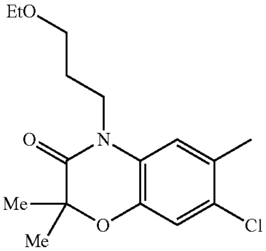
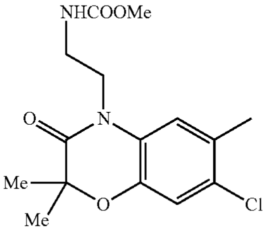
-continued
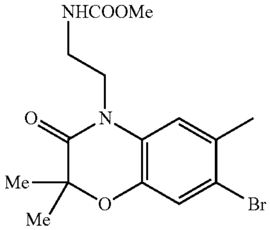
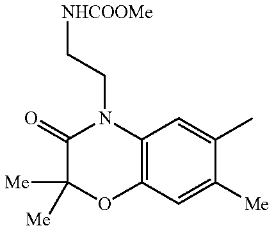
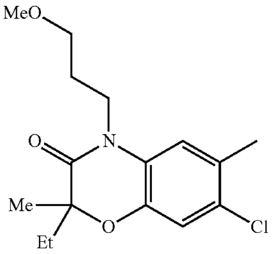
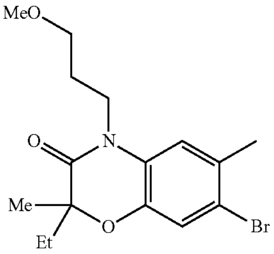
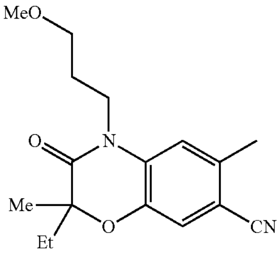
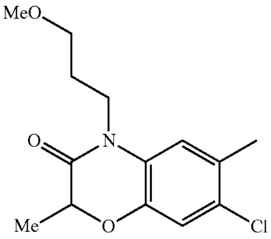
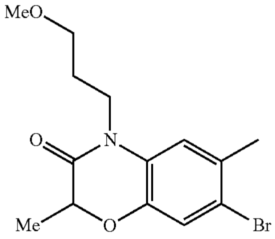
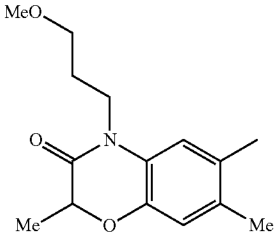
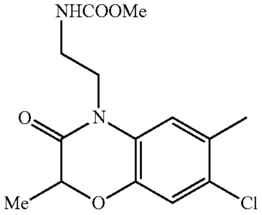
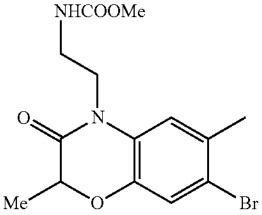
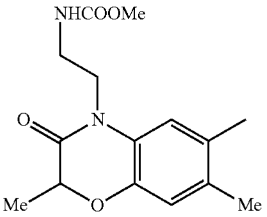
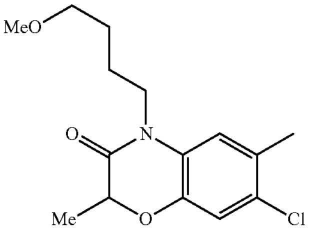
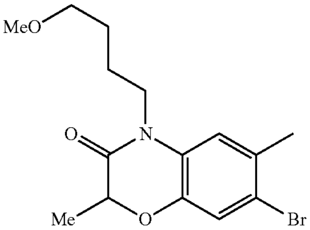

-continued
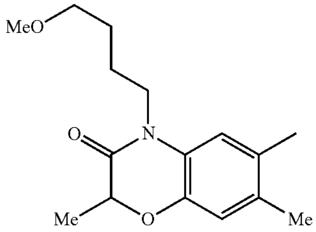
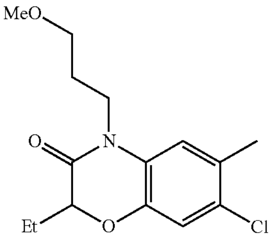
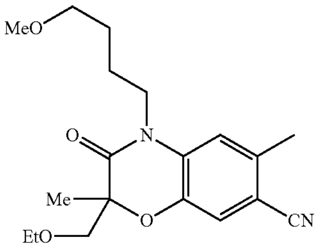
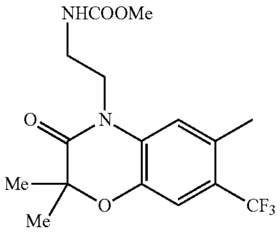
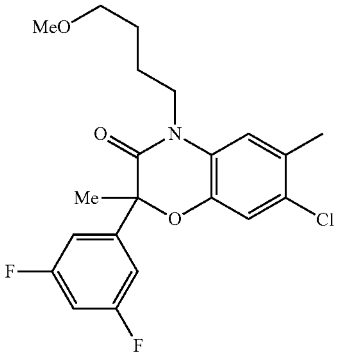
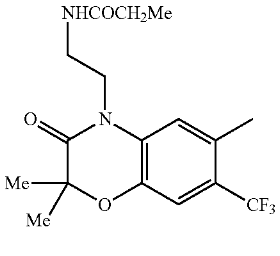
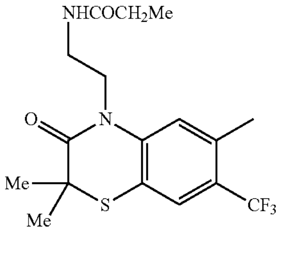
-continued
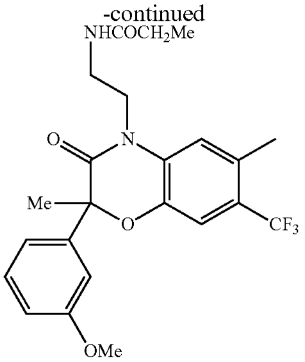
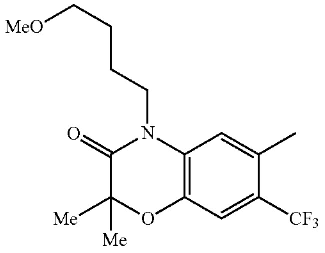
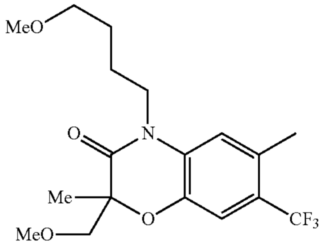
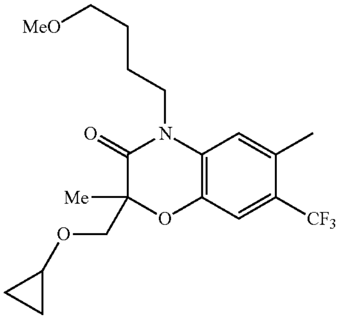
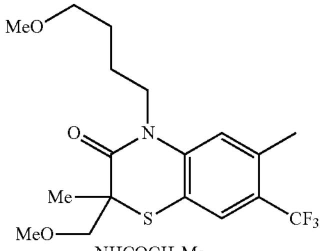
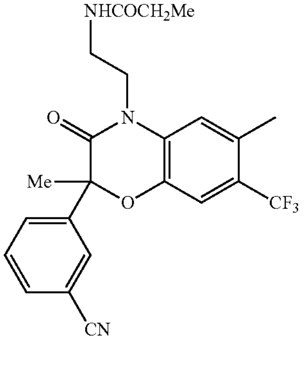

The "$R^2$" is one group selected from (a100) a hydrogen atom, (b100) a $C_{1-6}$ alkyl group (being optionally substituted with a halogen atom; $C_{3-6}$ cycloalkyl having optionally a substituent selected from a halogen atom, $C_{1-4}$ alkyl and $C_{1-4}$ alkoxy), (c100) a $C_{3-6}$ cycloalkyl group (being optionally substituted with a halogen atom or $C_{1-4}$ alkyl), (d100) a $C_{2-6}$ alkenyl group, and (e100) a $C_{7-10}$ aralkyl group (being optionally substituted with a halogen atom).

Preferable "$R^2$" is a $C_{1-6}$ alkyl group, and more preferable one is isopropyl group.

Preferable "B" is one group selected from (a12) a hydrogen atom, (b12) a $C_{1-6}$ alkyl group (said group being optionally substituted with 1 to 3 group(s) selected from (b120) a halogen atom, (b121) a $C_{3-6}$ cycloalkyl (said group being optionally substituted with the same or different 1 to 2 group(s) selected from (i) a halogen atom, (ii) hydroxy, (iii) $C_{1-4}$ alkoxy, and (iv) $C_{3-6}$ cycloalkylcarbonylamino), (b122) a hydroxy group, (b123) $C_{1-4}$ alkoxy, (b124) carboxy, (b125) $C_{1-4}$ alkoxycarbonyl, (b126) saturated heterocycle (said ring being optionally substituted with the same or different 1 to 3 group(s) selected from (i) $C_{1-4}$ alkyl, (ii) $C_{1-4}$ alkoxy, (iii) $C_{1-4}$ alkylcarbonylamino, and (iv) oxo), (b127) aminocarbonyl (amino being optionally substituted with (i) $C_{1-4}$ alkyl, (ii) $C_{3-6}$ cycloalkyl, or (iii) $C_{3-6}$ cycloalkyl-$C_{1-4}$ alkyl), and (b128) 5- to 7-membered cyclic amino group (said group being optionally substituted with the same or different 1 to 3 group(s) selected from (i) a halogen atom, (ii) $C_{1-4}$ alkyl, (iii) $C_6$ aryl having optionally $C_{1-4}$ alkoxy substituent, (iv) $C_6$ aryloxy having optionally 1 to 3 halogen substituent(s), and (iv) oxo)), (c12) a $C_{2-6}$ alkenyl group (being optionally substituted with 1 to 2 group(s) selected from fluorine atom and $C_{1-6}$ alkyl), (d12) a $C_{3-10}$ cycloalkyl group (said group being optionally substituted with (d121) a halogen atom, (d122) $C_{1-4}$ alkyl being optionally substituted with $C_{1-4}$ alkoxy, (d123) hydroxy, or (d124) $C_{1-4}$ alkoxy), (e12) a $C_6$ aryl group (said group being optionally substituted with the same or different 1 to 3 group(s) selected from (e1201) a halogen atom, (e1202) $C_{1-4}$ alkyl (said $C_{1-4}$ alkyl being optionally substituted with one group selected from (i) 5- to 7-membered cyclic amino (being optionally substituted with $C_6$ aryl having optionally 1 to 3 halogen substituent(s)), (ii) mono-$C_{1-6}$ alkylamino (said $C_{1-6}$ alkyl being optionally substituted with $C_6$ aryloxy having optionally 1 to 3 halogen substituent(s)), (iii) 5- or 6-membered saturated heterocyclyl-amino (said saturated heterocycle being optionally substituted with $C_6$ aryl), (iv) 5- or 6-membered saturated heterocyclyl-oxy (said saturated heterocycle being optionally substituted with $C_6$ aryl or 5- to 10-membered monocyclic or polycyclic heteroaryl), (v) $C_6$ aryloxy (being optionally substituted with the same or different 1 to 3 group(s) selected from a halogen atom and $C_{1-4}$ alkyl), (vi) $C_{1-4}$ alkoxy, and (vii) $C_{3-6}$ cycloalkoxy), (e1203) $C_{1-4}$ alkoxy (said $C_{1-4}$ alkoxy being optionally substituted with one group selected from (i) $C_{1-4}$ alkoxy, (ii) $C_6$ aryloxy (being optionally substituted with 1 to 3 group(s) selected from $C_{1-4}$ alkyl and a halogen atom), (iii) $C_{3-6}$ cycloalkyloxy (being optionally substituted with $C_{1-4}$ alkyl), (iv) phenylamino (said phenyl being optionally substituted with 1 to 3 halogen atom(s)), and (v) $C_{7-10}$ aralkyloxy (being optionally substituted with 1 to 3 halogen atom(s))), (e1204) $C_6$ aryloxy (said aryl being optionally substituted with 1 to 3 group(s) selected from (i) a halogen atom, (ii) cyano, (iii) $C_{1-4}$ alkyl, and (iv) $C_{1-4}$ alkoxy), (e1205) $C_{7-10}$ aralkyloxy (being optionally substituted with 1 to 3 group(s) selected from a halogen atom and a $C_{1-4}$ alkoxy), (e1206) 5- to 7-membered cyclic amino (said ring being optionally substituted with (i) ($C_{1-6}$ alkyl)(phenylcarbonyl)amino, or (ii) $C_6$ aryloxy (being optionally substituted with the same or different 1 to 3 group(s) selected from a halogen atom and $C_{1-4}$ alkyl having optionally hydroxy substituent)), (e1207) 5- or 6-membered saturated heterocyclyl-oxy (said ring being optionally substituted with (i) $C_6$ aryl having optionally 1 to 3 halogen substituent(s), (ii) 5- to 10-membered monocyclic or polycyclic heteroaryl, (iii) 5- or 6-membered saturated heterocyclyl-carbonyl, (iv) oxo), (e1208) 5- or 6-membered monocyclic heteroaryloxy (being optionally substituted with $C_{1-4}$ alkyl)

(e1209) 5- to 7-membered cyclic aminocarbonyl (being optionally substituted with $C_6$ aryloxy having optionally 1 to 3 halogen substituent(s)), (e1210) 5- to 7-membered cyclic aminocarbonyloxy (being optionally substituted with $C_6$ aryl), and (e1211) $C_6$ aryl), (f12) a $C_{7-14}$ aralkyl group (said group being optionally substituted with the same or different 1 to 3 group(s) selected from (f120) a halogen atom, (f121) cyano, (f122) $C_{1-4}$ alkyl, (f123) hydroxy, (f124) $C_{1-4}$ alkoxy (being optionally substituted with 1 to 3 fluorine atom(s)), (f125) $C_{3-6}$ cycloalkoxy (being optionally substituted with 1 to 2 halogen atom(s)), (f126) $C_{1-4}$ alkoxycarbonyl, (f127) aminocarbonyl, (f128) $C_{6-10}$ aryl (being optionally substituted with 1 to 3 halogen atom(s)) and (f129) $C_{1-4}$ alkylsulfonyl), (g12) a 5- to 10-membered monocyclic or polycyclic heteroaryl group (said group being optionally substituted with a halogen atom), (h12) a 5- to 10-membered monocyclic or polycyclic heteroaryl-$C_{1-4}$ alkyl group (said group being optionally substituted with (h121) a halogen atom, or (h122) $C_{1-4}$ alkyl (being optionally substituted with 1 to 3 fluorine atom(s))), and (i12) a saturated heterocyclic group (said group being optionally substituted with $C_{1-4}$ alkyl having optionally $C_{1-4}$ alkoxy substituent).

The "$C_{1-6}$ alkoxy group substituted with a $C_{1-4}$ alkoxy", which is a substituent (e1203) for "B" includes the following group.

[Chemical formula 38]

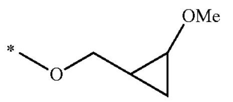

The "$R^4$" is preferably one group selected from a group consisting of a hydrogen atom, 1 to 3 halogen atom(s), a $C_{1-6}$ alkyl group substituted with a $C_{3-6}$ cycloalkyl, a $C_{3-6}$ cycloalkyl group and a $C_7$ aralkyl group, and a hydrogen atom and a $C_{3-6}$ cycloalkyl group are more preferable.

The compound of the present invention in more preferable embodiments includes the compounds of the following formulae.

Namely, the present invention relates to the following.

(1) A compound of the following formula (Ia) or a pharmaceutically acceptable salt thereof

[Chemical formula 39]

(Ia)

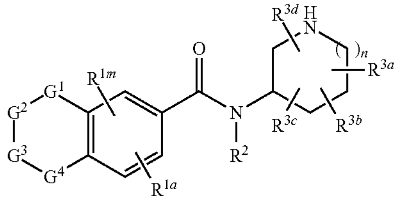

[wherein $R^{1a}$, $R^{1m}$, $G^1$, $G^2$, $G^3$, $G^4$, $R^2$, $R^{3a}$, $R^{3b}$, $R^{3e}$, $R^{3d}$ and n are the same as defined in Item 1, provided that among the compounds of the formula (I), the compound of the following formula:

[Chemical formula 40]

(Ib)

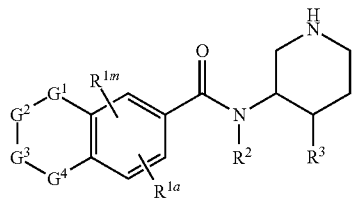

should be restricted to compounds wherein $R^{1a}$, $R^{1m}$, $G^1$, $G^2$, $G^3$, $G^4$ and $R^2$ are the same as defined above; $R^3$ is one of the above-mentioned $R^{3a}$, $R^{3b}$, $R^{3e}$, or $R^{3d}$ (wherein $R^{3a}$, $R^{3b}$, $R^{3e}$ and $R^{3d}$ are the same as defined above, provided that when $R^3$ is a group: -A-B, then A is a single bond, B is an optionally substituted $C_{7-14}$ aralkyl group or an optionally substituted 5- to 10-membered monocyclic or polycyclic heteroaryl group, or A is $-(CH_2)_sO-$, B is a hydrogen atom, an optionally substituted $C_{6-10}$ aryl group, or an optionally substituted $C_{7-14}$ aralkyl group)].

The present invention also includes the compound according to any one of Items 2 to Items 65, or a pharmaceutically acceptable salt thereof, wherein the compound of the formula (I) is replaced by the compound of the formula (Ia).

(2) A compound of the formula (Ic), or a pharmaceutically acceptable salt thereof.

[Chemical formula 41]

(Ic)

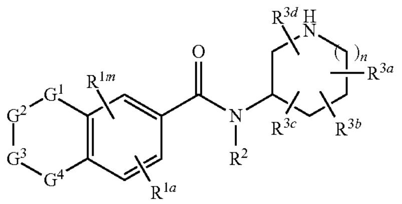

[wherein $R^{1a}$, $R^{1m}$, $G^1$, $G^2$, $G^3$, $G^4$, $R^2$, $R^{3a}$, $R^{3b}$, $R^{3c}$, $R^{3d}$ and n are the same as defined above, provided that among the compounds of the formula (I), the compound of the following formula:

[Chemical formula 42]

(Id)

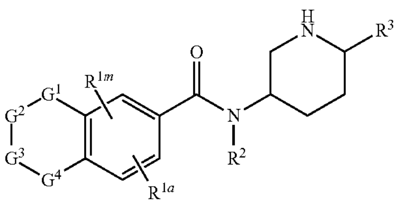

should be restricted to compounds wherein $R^3$ is one of the above-mentioned $R^{3a}$, $R^{3b}$, $R^{3c}$ and $R^{3d}$ (wherein when $R^3$ is a group: -A-B, then (i) A is $-(CH_2)_sN(R^4)CO-$, or $-(CH_2)_sN(R^4)COO-$; B is the same as defined in Item 1; $R^4$ is an optionally substituted $C_{3-10}$ cycloalkyl group, an optionally substituted $C_{6-10}$ aryl group, or an optionally substituted 5- to 10-membered monocyclic or polycyclic heteroaryl group, (ii) A is $-(CH_2)_sN(R^4)-$; B is the same as defined in Item 1; $R^4$ is an optionally substituted $C_{3-10}$ cycloalkyl group, or an optionally substituted 5- to 10-membered monocyclic or polycyclic heteroaryl group, (iii) A is $-(CH_2)_sN(R^4)SO_2-$, $-(CH_2)_sOCON(R^4)-$, or $-(CH_2)_sSO_2N(R^4)-$; B is the same as defined in Item 1; $R^4$ is an optionally substituted $C_{3-10}$ cycloalkyl group, or an optionally substituted 5- to 10-membered monocyclic or polycyclic heteroaryl group, (iv) A is $-(CH_2)_sN(R^4)CON(H)-$; B is the same as defined in Item 1; $R^4$ is an optionally substituted $C_{3-10}$ cycloalkyl group, or an optionally substituted 5- to 10-membered monocyclic or polycyclic heteroaryl group, (v) A is $-(CH_2)_sCON(R^4)-$; B is the same as defined in Item 1; $R^4$ is a $C_{1-6}$ alkyl group, an optionally substituted $C_{6-10}$ aryl group, or an optionally substituted $C_{7-14}$ aralkyl group, (vi) A is $-(CH_2)_sSO_2-$, $-(CH_2)_sCO-$, or $-(CH_2)_sCOO-$; B is a hydrogen atom, an optionally substituted $C_{3-10}$ cycloalkyl group, an optionally substituted $C_{5-6}$ cycloalkenyl group, or an optionally substituted $C_{6-10}$ aryl group, or (vii) A is a single bond; B is a hydrogen atom, an optionally substituted $C_{3-10}$ cycloalkyl group, an optionally substituted $C_{5-6}$ cycloalkenyl group, an optionally substituted $C_{6-10}$ aryl group, an optionally substituted 5- to 10-membered monocyclic or polycyclic heteroaryl group, or an optionally substituted saturated heterocyclic group)].

The present invention also includes the compound according to any one of Item 2 to Item 65, or a pharmaceutically acceptable salt thereof, wherein the compound of the formula (I) is replaced by the compound of the formula (Ic).

(3) A compound of the following formula (Ie), or a pharmaceutically acceptable salt thereof.

[Chemical formula 43]

(Ie)

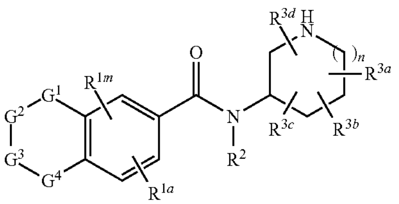

[wherein $R^{1a}$, $R^{1m}$, $G^1$, $G^2$, $G^3$, $G^4$, $R^2$, $R^{3a}$, $R^{3b}$, $R^{3c}$, $R^{3d}$ and n are the same as defined in Item 1, provided that the compounds of the formula (Ib) and the compound (Id) in the formula (Ie) should be restricted to ones as mentioned above]

The present invention also includes the compound according to any one of Item 2 to Item 65, or a pharmaceutically acceptable salt thereof, wherein the compound of the formula (I) is replaced by the compound of the formula (Ie).

(4) A compound of the formula (II), or a pharmaceutically acceptable salt thereof.

[Chemical formula 44]

(II)

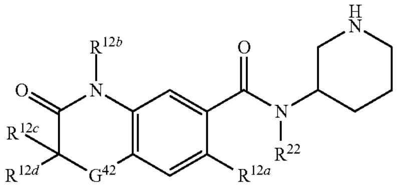

[wherein $R^{12a}$ is a halogen atom, a cyano group, or a $C_{1-6}$ alkyl group being optionally substituted with a fluorine atom;

$G^{42}$ is an oxygen atom, or a sulfur atom;

$R^{12b}$ is a $C_{1-6}$ alkyl group being optionally substituted with $C_{1-4}$ alkoxy, $C_{1-4}$ alkylcarbonylamino (said alkyl being optionally substituted with 1 to 3 fluorine atom(s)), or a $C_{1-4}$ alkoxycarbonylamino; or a 5-membered to 6-membered heteroaryl-$C_{1-4}$ alkyl group;

$R^{12c}$ is a hydrogen atom, a halogen atom, or a $C_{1-6}$ alkyl group being optionally substituted with $C_{1-4}$ alkoxy;

$R^{12d}$ is one group selected from a group consisting of a hydrogen atom; a halogen atom; a $C_{1-6}$ alkyl group (said group being optionally substituted with 1 to 3 halogen atom(s), hydroxy, $C_{1-4}$ alkoxy (said group being optionally substituted with 1 to 2 group(s) selected from hydroxy, $C_{1-4}$ alkoxy, 5- or 6-membered saturated heterocycle, and $C_{1-4}$ alkoxycarbonyl), $C_{6-10}$ aryloxy (said group being optionally substituted with the same or different 1 to 3 group(s) selected from cyano and $C_{1-4}$ alkoxy), $C_{1-6}$ alkylaminocarbonyloxy (which may optionally be substituted with 5- or 6-membered saturated heterocyclyl-$C_{1-4}$ alkyl)aminocarbonyloxy, or a 5- to 7-membered cyclic aminocarbonyloxy); an aminocarbonyl group; a mono- or di-($C_{1-6}$ alkyl)aminocarbonyl group; an N-(5- or 6-membered saturated heterocyclyl-$C_{1-4}$ alkyl)-N—($C_{1-6}$ alkyl)-aminocarbonyl group; a 5- to 7-membered cyclic aminocarbonyl group; a $C_{7-14}$ aralkyl group being optionally substituted with $C_{1-4}$ alkoxy; and a group of the following formula

[Chemical formula 45]

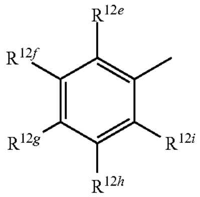

(wherein $R^{12e}$, $R^{12f}$, $R^{12g}$, $R^{12h}$ and $R^{12i}$ are independently the same or different, and each is a hydrogen atom, a halogen atom, a cyano group, a $C_{1-4}$ alkyl group being optionally substituted with 1 to 3 fluorine atom(s), a $C_{1-4}$ alkoxy group, a hydroxy group, or a $C_{1-4}$ alkoxysulfonyl group), or $R^{12c}$ and $R^{12d}$ combine each other to form a group of the following formula:

[Chemical formula 46]

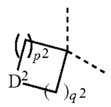

($D^2$ is an oxygen atom, a carbon atom, $—CH_2—$, or $—CH_2CH_2—$, $p^2$ and $q^2$ are 0, 1 or 2);

$R^{22}$ is a hydrogen atom, or a $C_{1-6}$ alkyl group]

(5) A compound of the formula (III), or a pharmaceutically acceptable salt thereof.

[Chemical formula 47]

(III)

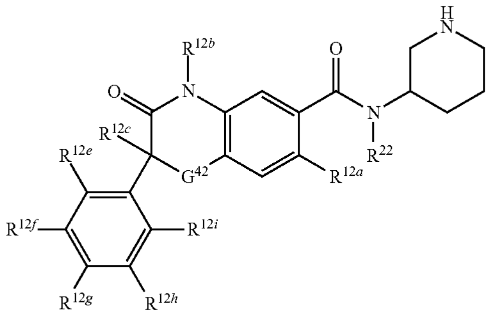

[wherein $R^{12a}$, $G^{42}$, $R^{12b}$, $R^{12c}$, $R^{12e}$, $R^{12f}$, $R^{12g}$, $R^{12h}$, $R^{12i}$ and $R^{22}$ are the same as defined above]

(6) A compound of the formula (IVa), or a pharmaceutically acceptable salt thereof.

[Chemical formula 48]

(IVa)

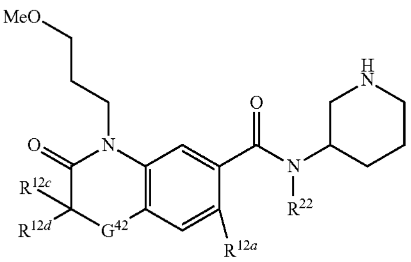

[wherein $G^{42}$, $R^{12a}$, $R^{12c}$, $R^{12d}$ and $R^{22}$ are the same as defined above]

(7) A compound of the formula (IVb), or a pharmaceutically acceptable salt thereof.

[Chemical formula 49]

(IVb)

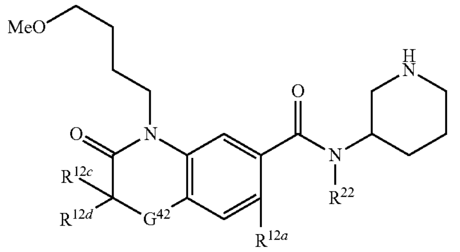

[wherein $G^{42}$, $R^{12a}$, $R^{12c}$, $R^{12d}$ and $R^{22}$ are the same as defined above]

(8) A compound of the formula (Va), or a pharmaceutically acceptable salt thereof.

[Chemical formula 50]

(Va)

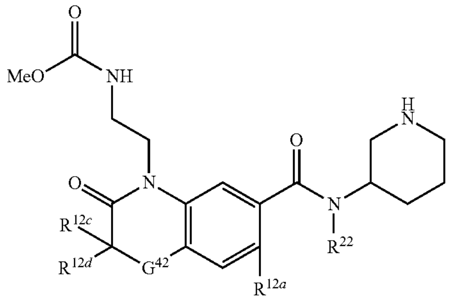

[wherein $G^{42}$, $R^{12a}$, $R^{12c}$, $R^{12d}$ and $R^{22}$ are the same as defined above]

(9) A compound of the formula (Vb), or a pharmaceutically acceptable salt thereof.

[Chemical formula 51]

(Vb)

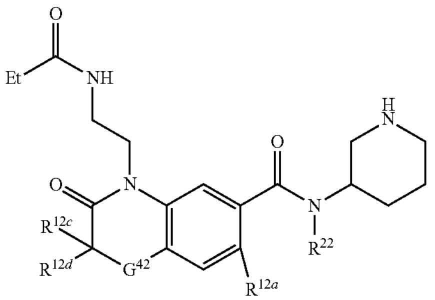

[wherein $G^{42}$, $R^{12a}$, $R^{12c}$, $R^{12d}$ and $R^{22}$ are the same as defined above]

(10) A compound of the formula (Vc), or a pharmaceutically acceptable salt thereof.

[Chemical formula 52]

(Vc)

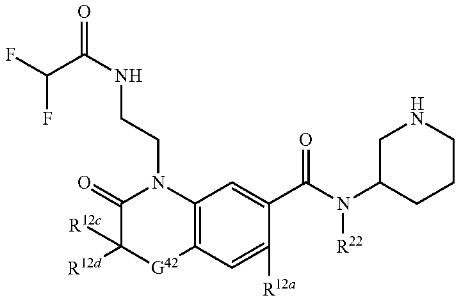

[wherein $G^{42}$, $R^{12a}$, $R^{12c}$, $R^{12d}$ and $R^{22}$ are the same as defined above]

The preferable embodiments for the substituents of the compounds of the above-mentioned (1) to (10) (the formula (Ia) to the formula (Vc)) are the same ones as defined in the preferable embodiments for the substituents of the compound of the formula (I).

The "pharmaceutically acceptable salt" includes a salt with an inorganic acid such as hydrochloride, hydrobromide, sulfate, phosphate, or nitrate, or a salt with an organic acid such as acetate, propionate, oxalate, succinate, lactate, malate, tartrate, citrate, maleate, fumarate, methanesulfonate, benzenesulfonate, p-toluenesulfonate, or ascorbate, etc.

In addition, the present invention includes the compound of the formula (I) or a prodrug thereof, or a pharmaceutically acceptable salt thereof. Further, the present invention also includes a hydrate thereof or a solvate thereof such as ethanolate. Further, the present invention includes a crystalline form of every embodiment.

The term "prodrug of the compound of the formula (I)" used in the present specification means a compound which is converted into the compound of the formula (I) in the living body by reaction by an enzyme or gastric acid under physiological conditions, namely, a compound which is converted into the compound of the formula (I) by oxidization, reduction, hydrolysis, etc. enzymatically, or by hydrolysis by gastric acid.

The compound of the formula (I) may exist in the form of a tautomer. Accordingly, the present invention also includes a tautomer of the compound of the formula (I).

The compound of the present invention may contain at least one asymmetric carbon atom. Accordingly, the present invention includes not only the racemic mixture of the present compound but also optically active compounds of the present compound. When the compound of the present invention has two or more asymmetric carbon atoms, then steric isomerism may occasionally occur. Accordingly, the present invention also includes these stereoisomers and a mixture thereof The compound of the present invention may have an axial isomerism due to rotational hindrance at a phenyl group and a carbonyl group. Because of this axial isomerism, the present invention includes the stereoisomers of the following formulae.

[Chemical formula 53]

(I)

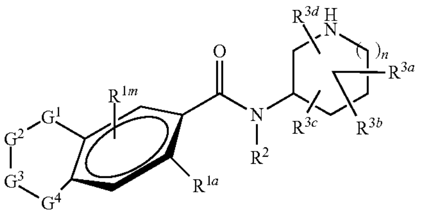

(I)

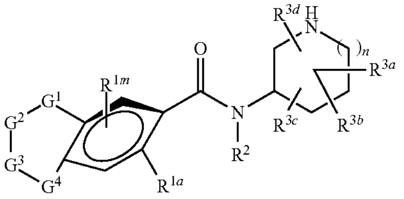

The present compound can be exemplified by the following compounds. In the following Tables, the compounds as expressed, for example, by No. 1 (T1:Q144;T2:Q144;T3:Q182;T4:Q263) indicates the following compound.

[Chemical formula 54]

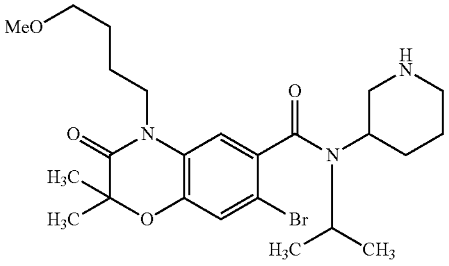

[Chemical formula 55]

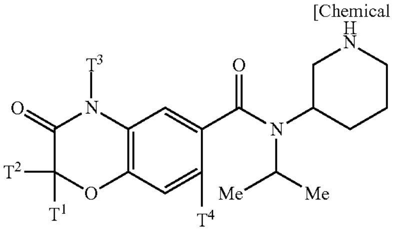

| No. | $T^1$ | $T^2$ | $T^3$ | $T^4$ |
|---|---|---|---|---|
| 1 | Q144 | Q144 | Q182 | Q263 |
| 2 | Q144 | Q144 | Q182 | Q262 |
| 3 | Q144 | Q144 | Q182 | Q143 |
| 4 | Q144 | Q144 | Q182 | Q144 |
| 5 | Q144 | Q144 | Q182 | Q145 |
| 6 | Q144 | Q144 | Q182 | Q261 |
| 7 | Q144 | Q144 | Q183 | Q262 |
| 8 | Q144 | Q144 | Q183 | Q144 |
| 9 | Q144 | Q144 | Q284 | Q262 |
| 10 | Q144 | Q144 | Q186 | Q263 |
| 11 | Q144 | Q144 | Q186 | Q262 |
| 12 | Q144 | Q144 | Q186 | Q144 |
| 13 | Q145 | Q144 | Q182 | Q262 |
| 14 | Q145 | Q144 | Q182 | Q144 |
| 15 | Q145 | Q144 | Q182 | Q143 |

-continued

[Chemical formula 55]

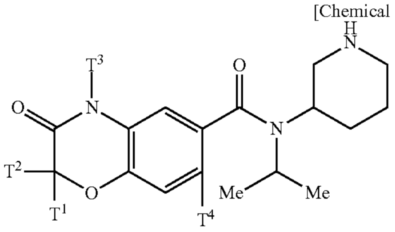

| No. | $T^1$ | $T^2$ | $T^3$ | $T^4$ |
|---|---|---|---|---|
| 16 | H | Q144 | Q182 | Q262 |
| 17 | H | Q144 | Q182 | Q263 |
| 18 | H | Q144 | Q182 | Q144 |
| 19 | H | Q144 | Q183 | Q262 |
| 20 | H | Q144 | Q183 | Q263 |
| 21 | H | Q144 | Q183 | Q144 |
| 22 | H | Q144 | Q186 | Q262 |
| 23 | H | Q144 | Q186 | Q263 |
| 24 | H | Q144 | Q186 | Q144 |
| 25 | H | Q145 | Q182 | Q262 |
| 26 | Q285 | Q144 | Q183 | Q262 |

[Chemical formula 56]

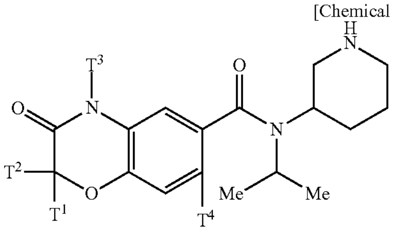

| No. | $T^1$ | $T^2$ | $T^3$ | $T^4$ |
|---|---|---|---|---|
| 27 | Q1 | H | Q183 | Q262 |
| 28 | Q2 | Q144 | Q183 | Q144 |
| 29 | Q3 | Q145 | Q183 | Q262 |
| 30 | Q4 | H | Q183 | Q144 |
| 31 | Q5 | Q144 | Q183 | Q143 |
| 32 | Q6 | Q145 | Q182 | Q262 |
| 33 | Q7 | H | Q183 | Q144 |
| 34 | Q8 | Q144 | Q183 | Q262 |
| 35 | Q9 | Q145 | Q183 | Q144 |
| 36 | Q10 | H | Q183 | Q143 |
| 37 | Q11 | Q144 | Q183 | Q262 |
| 38 | Q12 | Q145 | Q182 | Q144 |
| 39 | Q13 | H | Q183 | Q262 |
| 40 | Q14 | Q144 | Q183 | Q144 |
| 41 | Q15 | Q145 | Q183 | Q143 |
| 42 | Q16 | H | Q183 | Q262 |
| 43 | Q17 | Q144 | Q183 | Q144 |
| 44 | Q18 | Q145 | Q182 | Q262 |
| 45 | Q19 | H | Q183 | Q144 |
| 46 | Q20 | Q144 | Q183 | Q143 |
| 47 | Q21 | Q145 | Q183 | Q262 |
| 48 | Q22 | H | Q183 | Q144 |
| 49 | Q23 | Q144 | Q183 | Q262 |
| 50 | Q24 | Q145 | Q182 | Q144 |
| 51 | Q25 | H | Q183 | Q143 |
| 52 | Q26 | H | Q183 | Q262 |
| 53 | Q27 | Q144 | Q183 | Q144 |
| 54 | Q28 | Q145 | Q183 | Q262 |
| 55 | Q29 | H | Q183 | Q144 |
| 56 | Q30 | Q144 | Q183 | Q143 |
| 57 | Q31 | Q145 | Q182 | Q262 |
| 58 | Q32 | H | Q183 | Q144 |
| 59 | Q33 | Q144 | Q183 | Q262 |
| 60 | Q34 | Q145 | Q183 | Q144 |
| 61 | Q35 | H | Q183 | Q143 |

-continued

[Chemical formula 56]

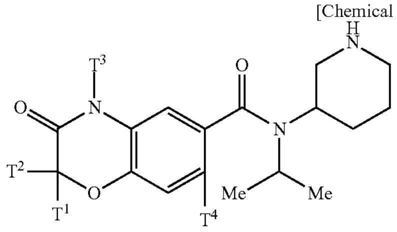

| No. | $T^1$ | $T^2$ | $T^3$ | $T^4$ |
|---|---|---|---|---|
| 62 | Q36 | Q144 | Q183 | Q262 |
| 63 | Q37 | Q145 | Q182 | Q144 |
| 64 | Q38 | H | Q183 | Q262 |
| 65 | Q39 | Q144 | Q183 | Q144 |
| 66 | Q40 | Q145 | Q183 | Q143 |
| 67 | Q41 | H | Q183 | Q262 |
| 68 | Q42 | Q144 | Q183 | Q144 |
| 69 | Q43 | Q145 | Q182 | Q262 |
| 70 | Q44 | H | Q183 | Q144 |
| 71 | Q45 | Q144 | Q183 | Q143 |
| 72 | Q46 | Q145 | Q183 | Q262 |
| 73 | Q47 | H | Q183 | Q144 |
| 74 | Q48 | Q144 | Q183 | Q262 |
| 75 | Q49 | Q145 | Q182 | Q144 |
| 76 | Q50 | H | Q183 | Q143 |

[Chemical formula 57]

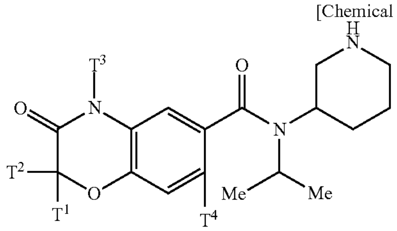

| No. | $T^1$ | $T^2$ | $T^3$ | $T^4$ |
|---|---|---|---|---|
| 77 | Q51 | H | Q183 | Q262 |
| 78 | Q52 | Q144 | Q183 | Q144 |
| 79 | Q53 | Q145 | Q183 | Q262 |
| 80 | Q54 | H | Q183 | Q144 |
| 81 | Q55 | Q144 | Q183 | Q143 |
| 82 | Q56 | Q145 | Q182 | Q262 |
| 83 | Q57 | H | Q183 | Q144 |
| 84 | Q58 | Q144 | Q183 | Q262 |
| 85 | Q59 | Q145 | Q183 | Q144 |
| 86 | Q60 | H | Q183 | Q143 |
| 87 | Q61 | Q144 | Q183 | Q262 |
| 88 | Q62 | Q145 | Q182 | Q144 |
| 89 | Q63 | H | Q183 | Q262 |
| 90 | Q64 | Q144 | Q183 | Q144 |
| 91 | Q65 | Q145 | Q183 | Q143 |
| 92 | Q66 | H | Q183 | Q262 |
| 93 | Q67 | Q144 | Q183 | Q144 |
| 94 | Q68 | Q145 | Q182 | Q262 |
| 95 | Q69 | H | Q183 | Q144 |
| 96 | Q70 | Q144 | Q183 | Q143 |
| 97 | Q71 | Q145 | Q183 | Q262 |
| 98 | Q72 | H | Q183 | Q144 |
| 99 | Q73 | Q144 | Q183 | Q262 |
| 100 | Q74 | Q145 | Q182 | Q144 |
| 101 | Q75 | H | Q183 | Q143 |
| 102 | Q76 | H | Q183 | Q262 |
| 103 | Q77 | Q144 | Q183 | Q144 |
| 104 | Q78 | Q145 | Q183 | Q262 |
| 105 | Q79 | H | Q183 | Q144 |
| 106 | Q80 | Q144 | Q183 | Q143 |
| 107 | Q81 | Q145 | Q182 | Q262 |

-continued

[Chemical formula 57]

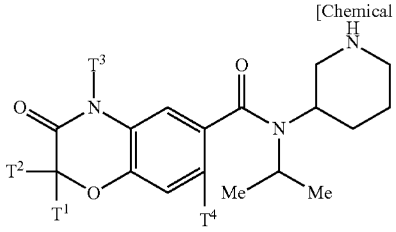

| No. | $T^1$ | $T^2$ | $T^3$ | $T^4$ |
|---|---|---|---|---|
| 108 | Q82 | H | Q183 | Q144 |
| 109 | Q83 | Q144 | Q183 | Q262 |
| 110 | Q84 | Q145 | Q183 | Q144 |
| 111 | Q85 | H | Q183 | Q143 |
| 112 | Q86 | Q144 | Q183 | Q262 |
| 113 | Q87 | Q145 | Q182 | Q144 |
| 114 | Q88 | H | Q183 | Q262 |
| 115 | Q89 | Q144 | Q183 | Q144 |
| 116 | Q90 | Q145 | Q183 | Q143 |
| 117 | Q91 | H | Q183 | Q262 |
| 118 | Q92 | Q144 | Q183 | Q144 |
| 119 | Q93 | Q145 | Q182 | Q262 |
| 120 | Q94 | H | Q183 | Q144 |
| 121 | Q95 | Q144 | Q183 | Q143 |
| 122 | Q96 | Q145 | Q183 | Q262 |
| 123 | Q97 | H | Q183 | Q144 |
| 124 | Q98 | Q144 | Q183 | Q262 |
| 125 | Q99 | Q145 | Q182 | Q144 |
| 126 | Q100 | H | Q183 | Q143 |

[Chemical formula 58]

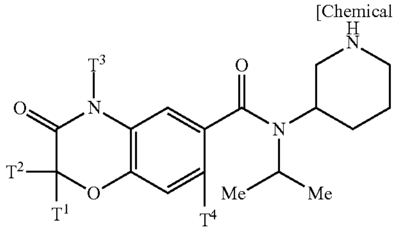

| No. | $T^1$ | $T^2$ | $T^3$ | $T^4$ |
|---|---|---|---|---|
| 127 | Q101 | H | Q183 | Q262 |
| 128 | Q102 | Q144 | Q183 | Q144 |
| 129 | Q103 | Q145 | Q183 | Q262 |
| 130 | Q104 | H | Q183 | Q144 |
| 131 | Q105 | Q144 | Q183 | Q143 |
| 132 | Q106 | Q145 | Q182 | Q262 |
| 135 | Q107 | H | Q183 | Q144 |
| 136 | Q108 | Q144 | Q183 | Q262 |
| 137 | Q109 | Q145 | Q183 | Q144 |
| 138 | Q110 | H | Q183 | Q143 |
| 139 | Q111 | Q144 | Q183 | Q262 |
| 140 | Q112 | Q145 | Q182 | Q144 |
| 141 | Q113 | H | Q183 | Q262 |
| 142 | Q114 | Q144 | Q183 | Q144 |
| 143 | Q115 | Q145 | Q183 | Q143 |
| 144 | Q116 | H | Q183 | Q262 |
| 145 | Q117 | Q144 | Q183 | Q144 |
| 146 | Q118 | Q145 | Q182 | Q262 |
| 147 | Q119 | H | Q183 | Q144 |
| 148 | Q120 | Q144 | Q183 | Q143 |
| 149 | Q121 | Q145 | Q183 | Q262 |
| 150 | Q122 | H | Q183 | Q144 |
| 151 | Q123 | Q144 | Q183 | Q262 |
| 152 | Q124 | Q145 | Q182 | Q144 |
| 153 | Q125 | H | Q183 | Q143 |
| 154 | Q126 | H | Q183 | Q262 |
| 155 | Q127 | Q144 | Q183 | Q144 |

-continued

[Chemical formula 58]

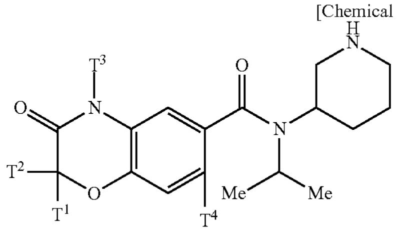

| No. | T¹ | T² | T³ | T⁴ |
|---|---|---|---|---|
| 156 | Q128 | Q145 | Q183 | Q262 |
| 157 | Q129 | H | Q183 | Q144 |
| 158 | Q130 | Q144 | Q183 | Q143 |
| 159 | Q131 | Q145 | Q182 | Q262 |
| 160 | Q132 | H | Q183 | Q144 |
| 161 | Q133 | Q144 | Q183 | Q262 |
| 162 | Q134 | Q145 | Q183 | Q144 |
| 163 | Q135 | H | Q183 | Q143 |
| 164 | Q136 | Q144 | Q183 | Q262 |
| 165 | Q10 | Q145 | Q186 | Q148 |
| 166 | Q138 | H | Q183 | Q262 |
| 167 | Q139 | Q144 | Q183 | Q144 |
| 168 | Q140 | Q145 | Q183 | Q143 |
| 169 | Q141 | H | Q183 | Q262 |
| 170 | Q142 | Q144 | Q183 | Q144 |
| 171 | Q144 | Q145 | Q182 | Q262 |
| 172 | Q145 | H | Q183 | Q144 |
| 173 | Q146 | H | Q183 | Q143 |
| 174 | Q147 | H | Q183 | Q262 |
| 175 | Q148 | H | Q183 | Q144 |
| 176 | Q149 | Q144 | Q183 | Q262 |
| 177 | Q150 | Q145 | Q182 | Q144 |
| 178 | Q151 | H | Q183 | Q143 |

[Chemical formula 59]

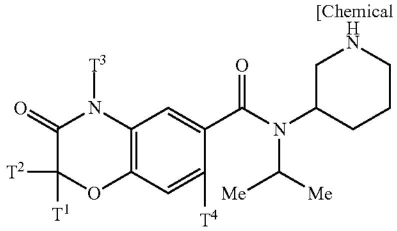

| No. | T¹ | T² | T³ | T⁴ |
|---|---|---|---|---|
| 179 | Q152 | H | Q183 | Q262 |
| 180 | Q153 | Q144 | Q183 | Q144 |
| 181 | Q154 | Q145 | Q183 | Q262 |
| 182 | Q155 | H | Q183 | Q144 |
| 183 | Q156 | Q144 | Q183 | Q143 |
| 184 | Q157 | Q145 | Q182 | Q262 |
| 185 | Q158 | H | Q183 | Q144 |
| 186 | Q159 | Q144 | Q183 | Q262 |
| 187 | Q160 | Q145 | Q183 | Q144 |
| 188 | Q161 | H | Q183 | Q143 |
| 189 | Q162 | Q144 | Q183 | Q262 |
| 190 | Q163 | Q145 | Q182 | Q144 |
| 191 | Q164 | H | Q183 | Q262 |
| 192 | Q165 | Q144 | Q183 | Q144 |
| 193 | Q166 | Q145 | Q183 | Q143 |
| 194 | Q167 | H | Q183 | Q262 |
| 195 | Q168 | Q144 | Q183 | Q144 |
| 196 | Q169 | Q145 | Q182 | Q262 |
| 197 | Q170 | H | Q183 | Q144 |
| 198 | Q171 | Q144 | Q183 | Q143 |
| 199 | Q172 | Q145 | Q183 | Q262 |
| 200 | Q173 | H | Q183 | Q144 |
| 201 | Q174 | Q144 | Q183 | Q262 |
| 202 | Q175 | Q145 | Q182 | Q144 |

-continued

[Chemical formula 59]

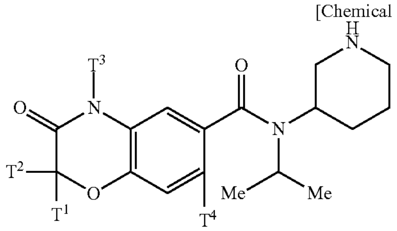

| No. | T¹ | T² | T³ | T⁴ |
|---|---|---|---|---|
| 203 | Q176 | H | Q183 | Q143 |
| 204 | Q177 | H | Q183 | Q262 |
| 205 | Q178 | Q144 | Q183 | Q144 |
| 206 | Q179 | Q145 | Q183 | Q262 |
| 207 | Q180 | H | Q183 | Q144 |
| 208 | Q181 | Q144 | Q183 | Q143 |
| 209 | Q182 | Q145 | Q182 | Q262 |
| 210 | Q183 | H | Q183 | Q144 |
| 211 | Q184 | Q144 | Q183 | Q262 |
| 212 | Q185 | Q145 | Q183 | Q144 |
| 213 | Q210 | H | Q183 | Q143 |
| 214 | Q223 | Q144 | Q183 | Q262 |
| 215 | Q137 | Q145 | Q182 | Q144 |
| 216 | Q236 | H | Q183 | Q262 |
| 217 | Q244 | H | Q183 | Q144 |
| 218 | Q238 | H | Q183 | Q143 |
| 219 | Q144 | Q144 | Q138 | Q262 |
| 220 | Q144 | Q144 | Q184 | Q144 |
| 221 | Q144 | Q144 | Q185 | Q262 |
| 222 | Q144 | Q144 | Q186 | Q144 |
| 223 | Q144 | H | Q183 | Q145 |
| 224 | Q144 | H | Q183 | Q148 |
| 225 | Q145 | H | Q183 | Q263 |
| 226 | Q144 | Q144 | Q183 | Q261 |
| 227 | Q144 | Q144 | Q182 | Q180 |
| 228 | Q182 | R144 | Q183 | Q149 |

[Chemical formula 60]

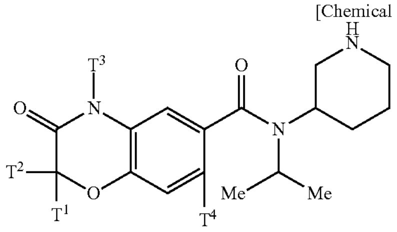

| No. | T¹ | T² | T³ | T⁴ | T⁵ |
|---|---|---|---|---|---|
| 229 | Q144 | Q144 | Q183 | Q262 | Q191 |
| 230 | Q144 | H | Q183 | Q144 | Q192 |
| 231 | Q144 | Q144 | Q183 | Q143 | Q193 |
| 232 | Q145 | H | Q183 | Q143 | Q194 |
| 233 | Q144 | Q144 | Q183 | Q262 | Q195 |
| 234 | Q144 | H | Q183 | Q144 | Q196 |
| 235 | Q144 | Q144 | Q183 | Q143 | Q197 |
| 236 | Q145 | H | Q183 | Q143 | Q198 |
| 237 | Q144 | Q144 | Q183 | Q262 | Q199 |
| 238 | Q144 | H | Q183 | Q144 | Q200 |
| 239 | Q144 | Q144 | Q183 | Q143 | Q201 |
| 240 | Q145 | H | Q183 | Q143 | Q202 |
| 241 | Q144 | Q144 | Q183 | Q262 | Q203 |
| 242 | Q144 | H | Q183 | Q144 | Q204 |
| 243 | Q144 | Q144 | Q183 | Q143 | Q205 |
| 244 | Q145 | H | Q183 | Q143 | Q206 |
| 245 | Q144 | Q144 | Q183 | Q262 | Q207 |
| 246 | Q144 | H | Q183 | Q144 | Q208 |
| 247 | Q144 | Q144 | Q183 | Q143 | Q209 |
| 248 | Q145 | H | Q183 | Q143 | Q210 |
| 249 | Q144 | Q144 | Q183 | Q262 | Q211 |

-continued

[Chemical formula 60]

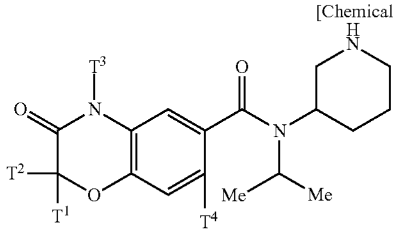

| No. | $T^1$ | $T^2$ | $T^3$ | $T^4$ | $T^5$ |
|---|---|---|---|---|---|
| 250 | Q144 | H | Q183 | Q144 | Q212 |
| 251 | Q144 | Q144 | Q183 | Q143 | Q213 |
| 252 | Q145 | H | Q183 | Q143 | Q214 |
| 253 | Q145 | H | Q183 | Q143 | Q215 |

[Chemical formula 61]

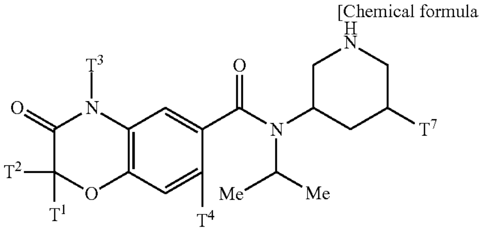

| No. | $T^1$ | $T^2$ | $T^3$ | $T^4$ | $T^7$ |
|---|---|---|---|---|---|
| 254 | Q144 | Q144 | Q183 | Q262 | Q216 |
| 255 | Q144 | H | Q183 | Q144 | Q217 |
| 256 | Q144 | Q144 | Q183 | Q143 | Q218 |
| 257 | Q145 | H | Q183 | Q143 | Q219 |
| 258 | Q144 | Q144 | Q183 | Q262 | Q220 |
| 259 | Q144 | H | Q183 | Q144 | Q221 |
| 260 | Q144 | Q144 | Q182 | Q143 | Q222 |
| 261 | Q145 | H | Q183 | Q143 | Q223 |
| 262 | Q144 | Q144 | Q183 | Q262 | Q224 |
| 263 | Q144 | H | Q183 | Q144 | Q225 |
| 264 | Q144 | Q144 | Q183 | Q143 | Q226 |
| 265 | Q145 | H | Q183 | Q143 | Q227 |
| 266 | Q144 | Q144 | Q182 | Q262 | Q228 |
| 267 | Q144 | H | Q183 | Q144 | Q229 |
| 268 | Q144 | Q144 | Q183 | Q143 | Q230 |
| 269 | Q145 | H | Q183 | Q143 | Q231 |
| 270 | Q144 | Q144 | Q183 | Q262 | Q232 |
| 271 | Q144 | H | Q183 | Q144 | Q233 |
| 272 | Q144 | Q144 | Q183 | Q143 | Q234 |
| 273 | Q145 | H | Q183 | Q143 | Q235 |

[Chemical formula 62]

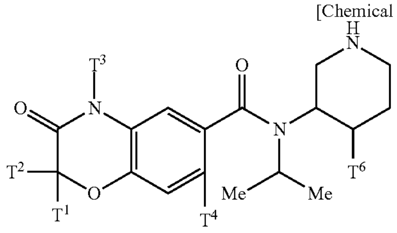

| No. | $T^1$ | $T^2$ | $T^3$ | $T^4$ | $T^6$ |
|---|---|---|---|---|---|
| 274 | Q144 | Q144 | Q183 | Q262 | Q247 |
| 275 | Q144 | H | Q183 | Q144 | Q248 |
| 276 | Q144 | Q144 | Q183 | Q143 | Q249 |

-continued

[Chemical formula 62]

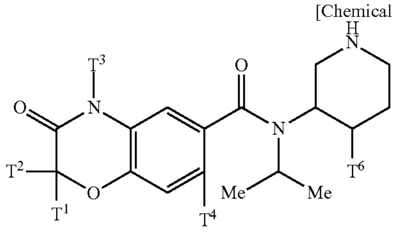

| No. | $T^1$ | $T^2$ | $T^3$ | $T^4$ | $T^6$ |
|---|---|---|---|---|---|
| 277 | Q145 | H | Q183 | Q143 | Q250 |
| 278 | Q144 | Q144 | Q183 | Q262 | Q251 |
| 279 | Q144 | H | Q183 | Q144 | Q252 |
| 280 | Q144 | Q144 | Q182 | Q143 | Q253 |
| 281 | Q145 | H | Q183 | Q143 | Q254 |
| 282 | Q144 | Q144 | Q183 | Q262 | Q255 |
| 283 | Q144 | H | Q183 | Q144 | Q256 |
| 284 | Q144 | Q144 | Q183 | Q143 | Q257 |
| 285 | Q145 | H | Q183 | Q143 | Q258 |
| 286 | Q144 | Q144 | Q183 | Q262 | Q259 |
| 287 | Q144 | H | Q182 | Q144 | Q260 |
| 288 | Q144 | Q144 | Q183 | Q143 | Q187 |

[Chemical formula 63]

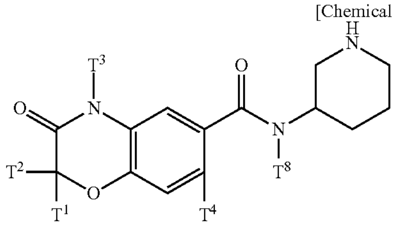

| No. | $T^1$ | $T^2$ | $T^3$ | $T^4$ | $T^8$ |
|---|---|---|---|---|---|
| 289 | Q144 | Q144 | Q183 | Q262 | Q237 |
| 290 | Q144 | H | Q183 | Q144 | Q238 |
| 291 | Q144 | Q144 | Q183 | Q143 | Q115 |
| 292 | Q145 | H | Q183 | Q143 | Q116 |
| 293 | Q144 | Q144 | Q183 | Q262 | Q117 |
| 294 | Q144 | H | Q182 | Q144 | Q118 |
| 295 | Q144 | Q144 | Q183 | Q143 | Q119 |
| 296 | Q145 | H | Q183 | Q143 | Q180 |
| 297 | Q138 | H | Q183 | Q262 | Q180 |
| 298 | Q139 | H | Q183 | Q144 | Q180 |

[Chemical formula 64]

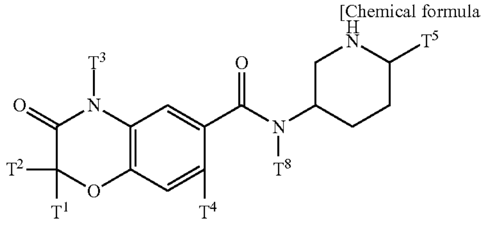

| No. | $T^1$ | $T^2$ | $T^3$ | $T^4$ | $T^8$ | $T^5$ |
|---|---|---|---|---|---|---|
| 299 | Q144 | Q144 | Q183 | Q262 | Q237 | Q210 |
| 300 | Q144 | H | Q182 | Q144 | Q238 | Q223 |
| 301 | Q144 | Q144 | Q183 | Q143 | Q115 | Q192 |
| 302 | Q145 | H | Q183 | Q143 | Q116 | Q193 |
| 303 | Q144 | Q144 | Q183 | Q262 | Q117 | Q194 |
| 304 | Q144 | H | Q183 | Q144 | Q118 | Q195 |

-continued

[Chemical formula 64]

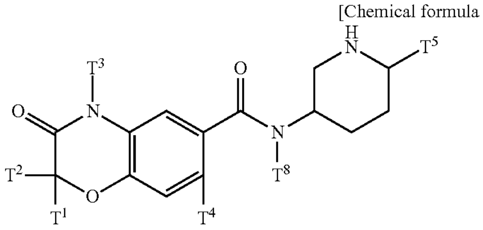

| No. | $T^1$ | $T^2$ | $T^3$ | $T^4$ | $T^8$ | $T^5$ |
|---|---|---|---|---|---|---|
| 305 | Q144 | Q144 | Q183 | Q143 | Q119 | Q196 |
| 306 | Q145 | H | Q182 | Q143 | Q180 | Q197 |
| 307 | Q138 | H | Q183 | Q262 | Q180 | Q199 |
| 308 | Q139 | H | Q183 | Q144 | Q180 | Q200 |

[Chemical formula 65]

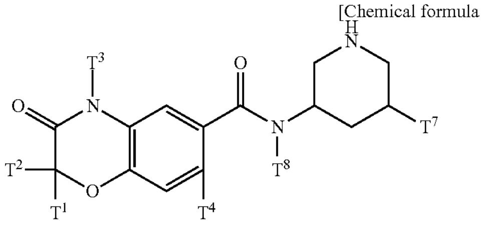

| No. | $T^1$ | $T^2$ | $T^3$ | $T^4$ | $T^8$ | $T^7$ |
|---|---|---|---|---|---|---|
| 309 | Q144 | Q144 | Q183 | Q262 | Q237 | Q210 |
| 310 | Q144 | H | Q183 | Q144 | Q238 | Q223 |
| 311 | Q144 | Q144 | Q182 | Q143 | Q115 | Q192 |
| 312 | Q145 | H | Q183 | Q143 | Q116 | Q193 |
| 313 | Q144 | Q144 | Q183 | Q262 | Q117 | Q194 |
| 314 | Q144 | H | Q183 | Q144 | Q118 | Q195 |
| 315 | Q144 | Q144 | Q183 | Q143 | Q119 | Q196 |
| 316 | Q145 | H | Q182 | Q143 | Q180 | Q197 |
| 317 | Q138 | H | Q183 | Q262 | Q180 | Q199 |
| 318 | Q139 | H | Q183 | Q144 | Q180 | Q200 |

[Chemical formula 66]

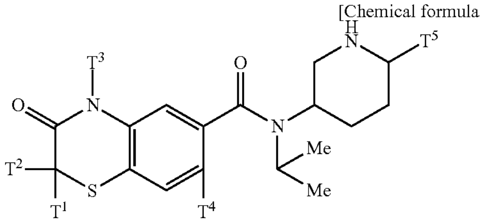

| No. | $T^1$ | $T^2$ | $T^3$ | $T^4$ | $T^5$ |
|---|---|---|---|---|---|
| 319 | Q144 | Q144 | Q183 | Q262 | H |
| 320 | Q144 | H | Q183 | Q144 | H |
| 321 | Q179 | Q144 | Q183 | Q143 | H |
| 322 | Q138 | H | Q183 | Q143 | H |
| 323 | Q139 | Q144 | Q182 | Q262 | H |
| 324 | Q144 | H | Q183 | Q144 | Q223 |
| 325 | Q144 | Q144 | Q183 | Q143 | Q210 |
| 326 | Q145 | Q144 | Q183 | Q143 | Q215 |
| 327 | Q144 | H | Q182 | Q262 | Q216 |
| 328 | Q144 | H | Q183 | Q144 | Q203 |

[Chemical formula 67]

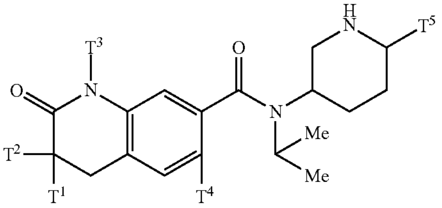

| No. | $T^1$ | $T^2$ | $T^3$ | $T^4$ | $T^5$ |
|---|---|---|---|---|---|
| 329 | Q144 | Q144 | Q183 | Q262 | H |
| 330 | Q144 | H | Q183 | Q144 | H |
| 331 | Q179 | Q144 | Q183 | Q143 | H |
| 332 | Q138 | Q144 | Q183 | Q143 | H |
| 333 | Q139 | Q144 | Q182 | Q262 | H |
| 334 | Q144 | H | Q183 | Q144 | Q223 |
| 335 | Q144 | Q144 | Q183 | Q143 | Q210 |
| 336 | Q145 | Q144 | Q183 | Q143 | Q215 |
| 337 | Q144 | H | Q182 | Q262 | Q216 |
| 338 | Q144 | H | Q183 | Q144 | Q203 |

[Chemical formula 68]

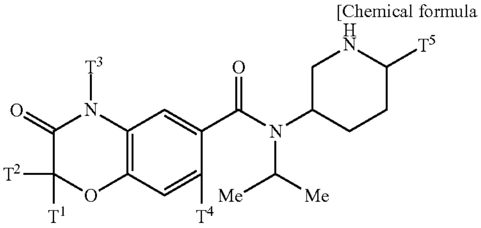

| No. | $T^1$ | $T^2$ | $T^3$ | $T^4$ | $T^5$ |
|---|---|---|---|---|---|
| 339 | Q144 | Q144 | Q183 | Q262 | Q264 |
| 340 | Q144 | H | Q183 | Q144 | Q265 |
| 341 | Q144 | Q144 | Q183 | Q143 | Q266 |
| 342 | Q145 | H | Q182 | Q143 | Q267 |
| 343 | Q144 | Q144 | Q183 | Q262 | Q268 |

[Chemical formula 69]

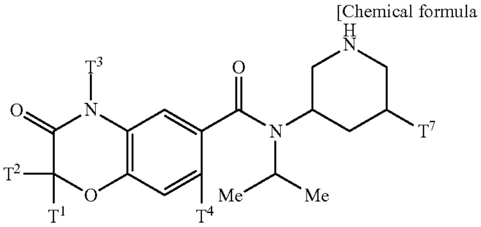

| No. | $T^1$ | $T^2$ | $T^3$ | $T^4$ | $T^7$ |
|---|---|---|---|---|---|
| 344 | Q144 | Q144 | Q183 | Q262 | Q264 |
| 345 | Q144 | H | Q183 | Q144 | Q265 |
| 346 | Q144 | Q144 | Q183 | Q143 | Q266 |
| 347 | Q145 | H | Q183 | Q143 | Q267 |
| 348 | Q144 | Q144 | Q183 | Q262 | Q268 |

[Chemical formula 70]
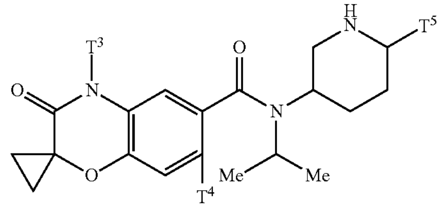
| No. | T3 | T4 | T5 |
|---|---|---|---|
| 349 | Q183 | Q262 | Q223 |
| 350 | Q183 | Q144 | Q210 |
| 351 | Q183 | Q143 | Q268 |
| 352 | Q183 | Q143 | H |
[Chemical formula 71]
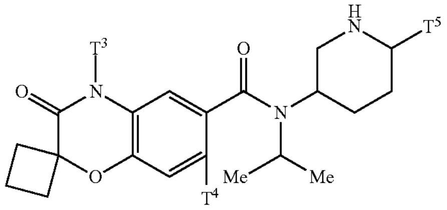
| No. | T3 | T4 | T5 |
|---|---|---|---|
| 353 | Q183 | Q262 | Q223 |
| 354 | Q183 | Q262 | Q210 |
| 355 | Q183 | Q143 | H |
[Chemical formula 72]
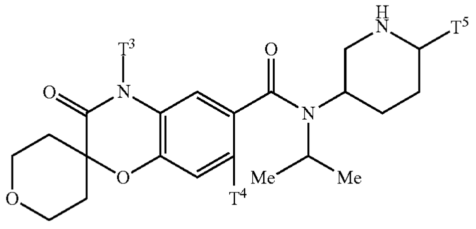
| No. | T3 | T4 | T5 |
|---|---|---|---|
| 356 | Q183 | Q262 | Q223 |
| 357 | Q183 | Q144 | Q210 |
| 358 | Q183 | Q143 | Q268 |
| 359 | Q183 | Q262 | Q223 |
| 360 | Q183 | Q262 | Q210 |
| 361 | Q183 | Q143 | H |
[Chemical formula 73]
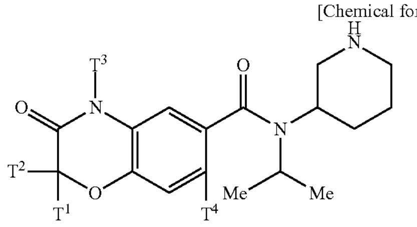
| No. | T1 | T2 | T3 | T4 |
|---|---|---|---|---|
| 362 | Q10 | Q144 | Q186 | Q148 |
| 363 | Q10 | Q144 | Q183 | Q144 |
| 364 | Q10 | Q144 | Q183 | Q143 |
| 365 | Q78 | Q144 | Q183 | Q144 |
| 366 | Q80 | Q144 | Q183 | Q144 |
| 367 | Q82 | Q144 | Q183 | Q143 |
| 368 | Q83 | Q144 | Q186 | Q262 |
| 369 | Q91 | Q144 | Q183 | Q262 |
| 370 | Q144 | Q144 | Q186 | Q274 |
| 371 | Q144 | Q144 | Q186 | Q275 |
| 372 | Q277 | H | Q183 | Q262 |
| 373 | Q144 | Q144 | Q183 | Q272 |
| 374 | Q144 | Q144 | Q183 | Q273 |
| 375 | Q144 | Q144 | Q281 | Q262 |
| 376 | Q144 | Q144 | Q282 | Q262 |
| 377 | Q283 | Q144 | Q183 | Q262 |
| 378 | Q144 | Q144 | Q186 | Q148 |
| 379 | Q10 | Q144 | Q186 | Q147 |
| 380 | Q10 | Q144 | Q186 | Q146 |
| 381 | Q145 | Q144 | Q183 | Q262 |
| 382 | Q278 | H | Q183 | Q262 |
| 383 | Q143 | H | Q183 | Q262 |
[Chemical formula 74]
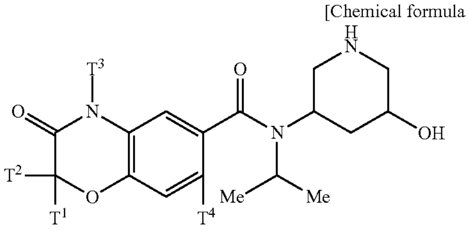
| No. | T1 | T2 | T3 | T4 |
|---|---|---|---|---|
| 384 | Q10 | Q144 | Q183 | Q148 |
| 385 | Q10 | Q144 | Q183 | Q144 |
| 386 | Q10 | Q144 | Q183 | Q262 |
| 387 | Q144 | Q144 | Q183 | Q263 |
| 388 | Q10 | Q144 | Q183 | Q147 |
[Chemical formula 75]
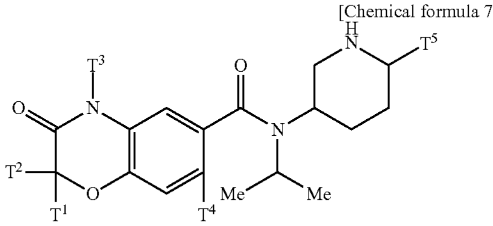
| No. | T1 | T2 | T3 | T4 | T5 |
|---|---|---|---|---|---|
| 389 | Q144 | Q144 | Q183 | Q148 | Q286 |
| 390 | Q144 | Q144 | Q183 | Q148 | Q287 |

-continued

[Chemical formula 75]

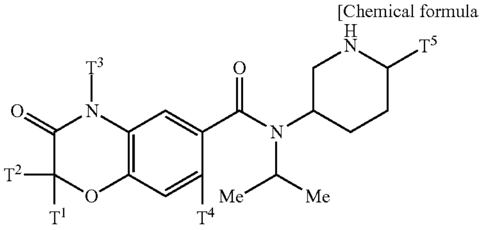

| No. | $T^1$ | $T^2$ | $T^3$ | $T^4$ | $T^5$ |
|---|---|---|---|---|---|
| 391 | Q144 | Q144 | Q183 | Q148 | 0288 |
| 392 | Q144 | Q144 | Q183 | Q148 | Q289 |
| 393 | Q144 | Q144 | Q183 | Q148 | Q290 |
| 394 | Q144 | Q144 | Q183 | Q148 | Q291 |
| 395 | Q144 | Q144 | Q183 | Q148 | Q296 |
| 396 | Q144 | Q144 | Q183 | Q148 | Q300 |
| 397 | Q144 | Q144 | Q183 | Q148 | Q301 |
| 398 | Q144 | Q144 | Q183 | Q148 | Q302 |
| 399 | Q144 | Q144 | Q183 | Q148 | Q303 |
| 400 | Q144 | Q144 | Q183 | Q148 | Q304 |
| 401 | Q144 | Q144 | Q183 | Q148 | Q305 |
| 402 | Q144 | Q144 | Q183 | Q148 | Q306 |
| 403 | Q144 | Q144 | Q183 | Q148 | Q307 |
| 404 | Q144 | Q144 | Q183 | Q148 | Q308 |
| 405 | Q144 | Q144 | Q183 | Q148 | Q309 |
| 406 | Q144 | Q144 | Q183 | Q148 | Q310 |
| 407 | Q144 | Q144 | Q183 | Q148 | Q311 |
| 408 | Q144 | Q144 | Q183 | Q148 | Q312 |
| 409 | Q144 | Q144 | Q183 | Q148 | Q313 |
| 410 | Q144 | Q144 | Q183 | Q148 | Q314 |
| 411 | Q144 | Q144 | Q183 | Q148 | Q315 |
| 412 | Q144 | Q144 | Q183 | Q148 | Q316 |
| 413 | Q144 | Q144 | Q183 | Q148 | Q317 |
| 414 | Q144 | Q144 | Q183 | Q148 | Q318 |
| 415 | Q144 | Q144 | Q183 | Q148 | Q319 |
| 416 | Q144 | Q144 | Q183 | Q148 | Q320 |
| 417 | Q144 | Q144 | Q183 | Q148 | Q321 |
| 418 | Q144 | Q144 | Q183 | Q148 | Q322 |
| 419 | Q144 | Q144 | Q183 | Q148 | Q323 |
| 420 | Q144 | Q144 | Q183 | Q148 | Q324 |
| 421 | Q144 | Q144 | Q183 | Q148 | Q325 |
| 422 | Q144 | Q144 | Q183 | Q148 | Q326 |
| 423 | Q144 | Q144 | Q183 | Q148 | Q327 |
| 424 | Q144 | Q144 | Q183 | Q148 | Q328 |
| 425 | Q144 | Q144 | Q183 | Q148 | Q329 |
| 426 | Q144 | Q144 | Q183 | Q148 | Q334 |
| 427 | Q144 | Q144 | Q183 | Q148 | Q338 |
| 428 | Q144 | Q144 | Q183 | Q148 | Q339 |
| 429 | Q144 | Q144 | Q183 | Q148 | Q340 |
| 430 | Q144 | Q144 | Q183 | Q148 | Q341 |
| 431 | Q144 | Q144 | Q183 | Q148 | Q342 |
| 432 | Q144 | Q144 | Q183 | Q148 | Q343 |
| 433 | Q144 | Q144 | Q183 | Q148 | Q344 |
| 434 | Q144 | Q144 | Q183 | Q148 | Q345 |
| 435 | Q144 | Q144 | Q183 | Q148 | Q346 |
| 436 | Q144 | Q144 | Q183 | Q148 | Q347 |
| 437 | Q144 | Q144 | Q183 | Q148 | Q348 |
| 438 | Q144 | Q144 | Q183 | Q148 | Q349 |
| 439 | Q144 | Q144 | Q183 | Q148 | Q350 |
| 440 | Q144 | Q144 | Q183 | Q148 | Q351 |
| 441 | Q144 | Q144 | Q183 | Q148 | Q352 |
| 442 | Q144 | Q144 | Q183 | Q148 | Q353 |
| 443 | Q144 | Q144 | Q183 | Q148 | Q354 |
| 444 | Q144 | Q144 | Q183 | Q148 | Q355 |
| 445 | Q144 | Q144 | Q183 | Q148 | Q356 |
| 446 | Q144 | Q144 | Q183 | Q148 | Q357 |

[Chemical formula 76]

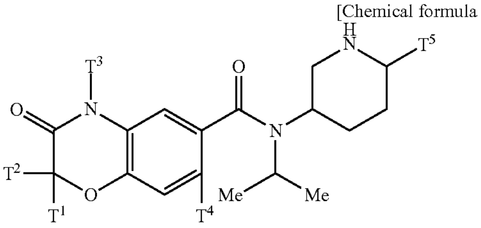

| No. | $T^1$ | $T^2$ | $T^3$ | $T^4$ | $T^5$ |
|---|---|---|---|---|---|
| 447 | Q144 | Q144 | Q183 | Q148 | Q358 |
| 448 | Q465 | Q144 | Q183 | Q148 | Q359 |
| 449 | Q14 | Q144 | Q183 | Q148 | Q360 |
| 450 | Q2 | H | Q183 | Q148 | Q361 |
| 451 | Q11 | Q144 | Q183 | Q148 | Q362 |
| 452 | Q468 | | Q183 | Q148 | Q363 |
| 453 | Q285 | Q144 | Q183 | Q148 | Q364 |
| 454 | Q181 | Q144 | Q183 | Q148 | Q365 |
| 455 | Q149 | Q144 | Q183 | Q148 | Q366 |
| 456 | Q103 | Q144 | Q183 | Q148 | Q367 |
| 457 | Q149 | Q144 | Q183 | Q148 | Q368 |
| 458 | Q182 | Q144 | Q183 | Q148 | Q369 |
| 459 | Q176 | Q144 | Q183 | Q148 | Q370 |
| 460 | Q116 | Q144 | Q183 | Q148 | Q371 |
| 461 | Q149 | Q144 | Q183 | Q148 | Q372 |
| 462 | Q547 | | Q183 | Q148 | Q373 |
| 463 | Q144 | Q144 | Q183 | Q148 | Q374 |
| 464 | Q465 | Q144 | Q183 | Q148 | Q375 |
| 465 | Q14 | Q144 | Q183 | Q148 | Q376 |
| 466 | Q2 | H | Q183 | Q148 | Q377 |
| 467 | Q11 | Q144 | Q183 | Q144 | Q288 |
| 468 | Q468 | | Q183 | Q262 | Q308 |
| 469 | Q285 | Q144 | Q183 | Q143 | Q288 |
| 470 | Q181 | Q144 | Q183 | Q147 | Q308 |
| 471 | Q149 | Q144 | Q183 | Q145 | Q288 |
| 472 | Q103 | Q144 | Q183 | Q277 | Q308 |
| 473 | Q149 | Q144 | Q183 | Q280 | Q288 |
| 474 | Q182 | Q144 | Q183 | Q478 | Q308 |
| 475 | Q176 | Q144 | Q183 | Q479 | Q288 |
| 476 | Q116 | Q144 | Q183 | Q480 | Q308 |
| 477 | Q149 | Q144 | Q183 | Q481 | Q288 |
| 478 | Q547 | | Q183 | Q482 | Q308 |
| 479 | Q144 | Q144 | Q427 | Q148 | Q353 |
| 480 | Q465 | Q144 | Q186 | Q148 | Q264 |
| 481 | Q14 | Q144 | Q445 | Q148 | Q223 |
| 482 | Q2 | H | Q427 | Q148 | Q353 |
| 483 | Q11 | Q144 | Q427 | Q148 | Q264 |
| 484 | Q468 | | Q186 | Q148 | Q223 |
| 485 | Q285 | Q144 | Q427 | Q148 | Q353 |
| 486 | Q181 | Q144 | Q186 | Q148 | Q264 |
| 487 | Q149 | Q144 | Q445 | Q148 | Q223 |
| 488 | Q103 | Q144 | Q427 | Q148 | Q353 |
| 489 | Q149 | Q144 | Q427 | Q148 | Q264 |
| 490 | Q182 | Q144 | Q186 | Q148 | Q223 |
| 491 | Q176 | Q144 | Q427 | Q148 | Q353 |
| 492 | Q116 | Q144 | Q186 | Q148 | Q264 |
| 493 | Q149 | Q144 | Q445 | Q148 | Q353 |
| 494 | Q547 | | Q427 | Q262 | Q353 |
| 495 | Q144 | Q144 | Q445 | Q144 | Q264 |
| 496 | Q465 | Q144 | Q186 | Q143 | Q223 |
| 497 | Q14 | Q144 | Q427 | Q145 | Q353 |
| 498 | Q2 | H | Q445 | Q147 | Q264 |
| 499 | Q11 | Q144 | Q186 | Q277 | Q223 |
| 500 | Q468 | | Q427 | Q280 | Q353 |
| 501 | Q285 | Q144 | Q445 | Q279 | Q264 |
| 502 | Q181 | Q144 | Q186 | Q261 | Q223 |
| 503 | Q149 | Q144 | Q445 | Q263 | Q353 |
| 504 | Q103 | Q144 | Q186 | Q180 | Q264 |

[Chemical formula 77]

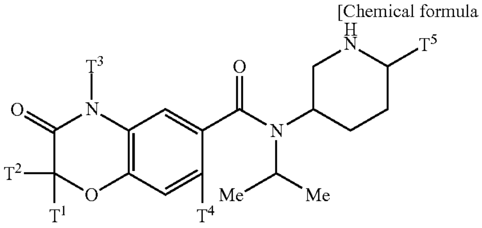

| No. | $T^1$ | $T^2$ | $T^3$ | $T^4$ | $T^5$ |
|---|---|---|---|---|---|
| 505 | Q269 | Q144 | Q183 | Q148 | Q358 |
| 506 | Q270 | Q144 | Q183 | Q148 | Q359 |
| 507 | Q271 | Q145 | Q183 | Q148 | Q360 |
| 508 | Q272 | H | Q183 | Q148 | Q361 |
| 509 | Q273 | Q144 | Q183 | Q148 | Q362 |
| 510 | Q274 | Q144 | Q183 | Q148 | Q363 |
| 511 | Q283 | Q144 | Q183 | Q148 | Q364 |
| 512 | Q390 | Q144 | Q183 | Q148 | Q365 |
| 513 | Q404 | H | Q183 | Q148 | Q366 |
| 514 | Q405 | Q144 | Q183 | Q148 | Q367 |
| 515 | Q408 | Q145 | Q183 | Q148 | Q368 |
| 516 | Q410 | Q144 | Q183 | Q148 | Q369 |
| 517 | Q411 | H | Q183 | Q148 | Q370 |
| 518 | Q412 | Q144 | Q183 | Q148 | Q371 |
| 519 | Q413 | Q144 | Q183 | Q148 | Q372 |
| 520 | Q414 | Q144 | Q183 | Q148 | Q373 |
| 521 | Q415 | Q145 | Q183 | Q148 | Q374 |
| 522 | Q447 | Q144 | Q183 | Q148 | Q375 |
| 523 | Q448 | Q144 | Q183 | Q148 | Q376 |
| 524 | Q449 | H | Q183 | Q148 | Q377 |
| 525 | Q450 | Q144 | Q183 | Q144 | Q288 |
| 526 | Q451 | Q144 | Q183 | Q262 | Q308 |
| 527 | Q452 | Q145 | Q183 | Q143 | Q288 |
| 528 | Q453 | Q144 | Q183 | Q147 | Q308 |
| 529 | Q454 | H | Q183 | Q145 | Q288 |
| 530 | Q455 | Q144 | Q183 | Q277 | Q308 |
| 531 | Q456 | Q145 | Q183 | Q280 | Q288 |
| 532 | Q457 | Q144 | Q183 | Q478 | Q308 |
| 533 | Q458 | Q144 | Q183 | Q479 | Q288 |
| 534 | Q459 | Q145 | Q183 | Q480 | Q308 |
| 535 | Q460 | Q144 | Q183 | Q481 | Q288 |
| 536 | Q461 | Q144 | Q183 | Q482 | Q308 |
| 537 | Q462 | Q144 | Q427 | Q148 | Q353 |
| 538 | Q463 | Q145 | Q186 | Q148 | Q264 |
| 539 | Q464 | Q144 | Q445 | Q148 | Q223 |
| 540 | Q465 | H | Q427 | Q148 | Q353 |
| 541 | Q466 | | Q427 | Q148 | Q264 |
| 542 | Q467 | | Q186 | Q148 | Q223 |
| 543 | Q468 | | Q427 | Q148 | Q353 |
| 544 | Q469 | | Q186 | Q148 | Q264 |
| 545 | Q470 | | Q445 | Q148 | Q223 |
| 546 | Q471 | Q145 | Q427 | Q148 | Q353 |
| 547 | Q472 | Q144 | Q427 | Q148 | Q264 |
| 548 | Q473 | | Q186 | Q148 | Q223 |
| 549 | Q474 | Q144 | Q427 | Q148 | Q353 |
| 550 | Q475 | Q144 | Q186 | Q148 | Q264 |
| 551 | Q476 | Q144 | Q445 | Q148 | Q353 |
| 552 | Q477 | Q144 | Q427 | Q262 | Q353 |
| 553 | Q483 | Q144 | Q445 | Q144 | Q264 |
| 554 | Q484 | Q144 | Q186 | Q143 | Q223 |
| 555 | Q485 | Q145 | Q427 | Q145 | Q353 |
| 556 | Q486 | H | Q445 | Q147 | Q264 |
| 557 | Q487 | Q144 | Q186 | Q277 | Q223 |
| 558 | Q488 | Q144 | Q427 | Q280 | Q353 |
| 559 | Q489 | Q144 | Q445 | Q279 | Q264 |
| 560 | Q490 | Q144 | Q186 | Q261 | Q223 |
| 561 | Q491 | Q144 | Q445 | Q263 | Q353 |
| 562 | Q492 | Q145 | Q186 | Q180 | Q264 |

[Chemical formula 78]

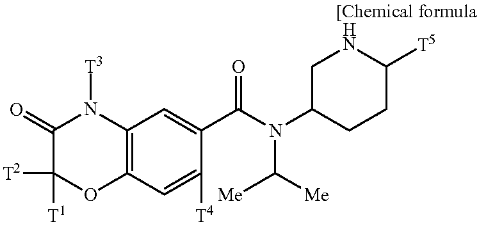

| No. | $T^1$ | $T^2$ | $T^3$ | $T^4$ | $T^5$ |
|---|---|---|---|---|---|
| 563 | Q493 | Q144 | Q183 | Q148 | Q358 |
| 564 | Q494 | Q144 | Q183 | Q148 | Q359 |
| 565 | Q495 | Q145 | Q183 | Q148 | Q360 |
| 566 | Q496 | | Q183 | Q148 | Q361 |
| 567 | Q497 | | Q183 | Q148 | Q362 |
| 568 | Q498 | | Q183 | Q148 | Q363 |
| 569 | Q499 | | Q183 | Q148 | Q364 |
| 570 | Q500 | Q144 | Q183 | Q148 | Q365 |
| 571 | Q501 | H | Q183 | Q148 | Q366 |
| 572 | Q502 | Q144 | Q183 | Q148 | Q367 |
| 573 | Q503 | Q145 | Q183 | Q148 | Q368 |
| 574 | Q504 | Q144 | Q183 | Q148 | Q369 |
| 575 | Q505 | H | Q183 | Q148 | Q370 |
| 576 | Q506 | Q144 | Q183 | Q148 | Q371 |
| 577 | Q507 | | Q183 | Q148 | Q372 |
| 578 | Q508 | | Q183 | Q148 | Q373 |
| 579 | Q509 | | Q183 | Q148 | Q374 |
| 580 | Q510 | Q144 | Q183 | Q148 | Q375 |
| 581 | Q511 | Q144 | Q183 | Q148 | Q376 |
| 582 | Q512 | H | Q183 | Q148 | Q377 |
| 583 | Q513 | Q144 | Q183 | Q144 | Q288 |
| 584 | Q514 | Q144 | Q183 | Q262 | Q308 |
| 585 | Q515 | Q145 | Q183 | Q143 | Q288 |
| 586 | Q516 | | Q183 | Q147 | Q308 |
| 587 | Q517 | | Q183 | Q145 | Q288 |
| 588 | Q518 | | Q183 | Q277 | Q308 |
| 589 | Q519 | | Q183 | Q280 | Q288 |
| 590 | Q520 | | Q183 | Q478 | Q308 |
| 591 | Q521 | | Q183 | Q479 | Q288 |
| 592 | Q522 | | Q183 | Q480 | Q308 |
| 593 | Q523 | | Q183 | Q481 | Q288 |
| 594 | Q524 | | Q183 | Q482 | Q308 |
| 595 | Q525 | Q144 | Q427 | Q148 | Q353 |
| 596 | Q526 | Q145 | Q186 | Q148 | Q264 |
| 597 | Q527 | Q144 | Q445 | Q148 | Q223 |
| 598 | Q528 | H | Q427 | Q148 | Q353 |
| 599 | Q529 | | Q427 | Q148 | Q264 |
| 600 | Q530 | | Q186 | Q148 | Q223 |
| 601 | Q531 | Q144 | Q427 | Q148 | Q353 |
| 602 | Q532 | Q144 | Q186 | Q148 | Q264 |
| 603 | Q533 | Q144 | Q445 | Q148 | Q223 |
| 604 | Q534 | Q145 | Q427 | Q148 | Q353 |
| 605 | Q535 | Q144 | Q427 | Q148 | Q264 |
| 606 | Q536 | Q144 | Q186 | Q148 | Q223 |
| 607 | Q537 | Q144 | Q427 | Q148 | Q353 |
| 608 | Q538 | Q144 | Q186 | Q148 | Q264 |
| 609 | Q539 | Q144 | Q445 | Q148 | Q353 |
| 610 | Q540 | Q144 | Q427 | Q262 | Q353 |
| 611 | Q541 | Q144 | Q445 | Q144 | Q264 |
| 612 | Q542 | Q144 | Q186 | Q143 | Q223 |
| 613 | Q543 | Q145 | Q427 | Q145 | Q353 |
| 614 | Q544 | H | Q445 | Q147 | Q264 |
| 615 | Q545 | Q144 | Q186 | Q277 | Q223 |
| 616 | Q546 | Q144 | Q427 | Q280 | Q353 |
| 617 | Q547 | | Q445 | Q279 | Q264 |
| 618 | Q269 | Q144 | Q183 | Q148 | H |
| 619 | Q270 | Q144 | Q183 | Q148 | H |
| 620 | Q271 | Q145 | Q183 | Q148 | H |

[Chemical formula 79]

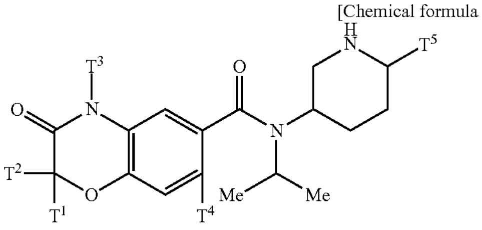

| No. | $T^1$ | $T^2$ | $T^3$ | $T^4$ | $T^5$ |
|---|---|---|---|---|---|
| 621 | Q272 | H | Q183 | Q148 | H |
| 622 | Q273 | Q144 | Q183 | Q148 | H |
| 623 | Q274 | Q144 | Q183 | Q148 | H |
| 624 | Q283 | Q144 | Q183 | Q148 | H |
| 625 | Q390 | Q144 | Q183 | Q148 | H |
| 626 | Q404 | H | Q183 | Q148 | H |
| 627 | Q405 | Q144 | Q183 | Q148 | H |
| 628 | Q408 | Q145 | Q183 | Q148 | H |
| 629 | Q410 | Q144 | Q183 | Q148 | H |
| 630 | Q411 | H | Q183 | Q148 | H |
| 631 | Q412 | Q144 | Q183 | Q148 | H |
| 632 | Q413 | Q144 | Q183 | Q148 | H |
| 633 | Q414 | Q144 | Q183 | Q148 | H |
| 634 | Q415 | Q145 | Q183 | Q148 | H |
| 635 | Q447 | Q144 | Q183 | Q148 | H |
| 636 | Q448 | Q144 | Q183 | Q148 | H |
| 637 | Q449 | H | Q183 | Q148 | H |
| 638 | Q450 | Q144 | Q183 | Q144 | H |
| 639 | Q451 | Q144 | Q183 | Q262 | H |
| 640 | Q452 | Q145 | Q183 | Q143 | H |
| 641 | Q453 | Q144 | Q183 | Q147 | H |
| 642 | Q454 | H | Q183 | Q145 | H |
| 643 | Q455 | Q144 | Q183 | Q277 | H |
| 644 | Q456 | Q145 | Q183 | Q280 | H |
| 645 | Q457 | Q144 | Q183 | Q478 | H |
| 646 | Q458 | Q144 | Q183 | Q479 | H |
| 647 | Q459 | Q145 | Q183 | Q480 | H |
| 648 | Q460 | Q144 | Q183 | Q481 | H |
| 649 | Q461 | Q144 | Q183 | Q482 | H |
| 650 | Q462 | Q144 | Q427 | Q148 | H |
| 651 | Q463 | Q145 | Q186 | Q148 | H |
| 652 | Q464 | Q144 | Q445 | Q148 | H |
| 653 | Q465 | H | Q427 | Q148 | H |
| 654 | Q466 | | Q427 | Q148 | H |
| 655 | Q467 | | Q186 | Q148 | H |
| 656 | Q468 | | Q427 | Q148 | H |
| 657 | Q469 | | Q186 | Q148 | H |
| 658 | Q470 | | Q445 | Q148 | H |
| 659 | Q471 | Q145 | Q427 | Q148 | H |
| 660 | Q472 | Q144 | Q427 | Q148 | H |
| 661 | Q473 | | Q186 | Q148 | H |
| 662 | Q474 | Q144 | Q427 | Q148 | H |
| 663 | Q475 | Q144 | Q186 | Q148 | H |
| 664 | Q476 | Q144 | Q445 | Q148 | H |
| 665 | Q477 | Q144 | Q427 | Q262 | H |
| 666 | Q483 | Q144 | Q445 | Q144 | H |
| 667 | Q484 | Q144 | Q186 | Q143 | H |
| 668 | Q485 | Q145 | Q427 | Q145 | H |
| 669 | Q486 | H | Q445 | Q147 | H |
| 670 | Q487 | Q144 | Q186 | Q277 | H |
| 671 | Q488 | Q144 | Q427 | Q280 | H |
| 672 | Q489 | Q144 | Q445 | Q279 | H |
| 673 | Q490 | Q144 | Q186 | Q261 | H |
| 674 | Q491 | Q144 | Q445 | Q263 | H |
| 675 | Q492 | Q145 | Q186 | Q180 | H |
| 676 | Q490 | Q144 | Q186 | Q148 | H |
| 677 | Q491 | Q144 | Q445 | Q148 | H |
| 678 | Q492 | Q145 | Q186 | Q148 | H |

[Chemical formula 80]

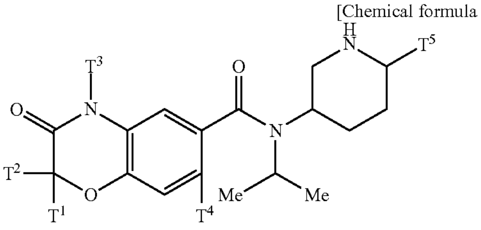

| No. | $T^1$ | $T^2$ | $T^3$ | $T^4$ | $T^5$ |
|---|---|---|---|---|---|
| 679 | Q493 | Q144 | Q183 | Q148 | H |
| 680 | Q494 | Q144 | Q183 | Q148 | H |
| 681 | Q495 | Q145 | Q183 | Q148 | H |
| 682 | Q496 | | Q183 | Q148 | H |
| 683 | Q497 | | Q183 | Q148 | H |
| 684 | Q498 | | Q183 | Q148 | H |
| 685 | Q499 | | Q183 | Q148 | H |
| 686 | Q500 | Q144 | Q183 | Q148 | H |
| 687 | Q501 | H | Q183 | Q148 | H |
| 688 | Q502 | Q144 | Q183 | Q148 | H |
| 689 | Q503 | Q145 | Q183 | Q148 | H |
| 690 | Q504 | Q144 | Q183 | Q148 | H |
| 691 | Q505 | H | Q183 | Q148 | H |
| 692 | Q506 | Q144 | Q183 | Q148 | H |
| 693 | Q507 | | Q183 | Q148 | H |
| 694 | Q508 | | Q183 | Q148 | H |
| 695 | Q509 | | Q183 | Q148 | H |
| 696 | Q510 | Q144 | Q183 | Q148 | H |
| 697 | Q511 | Q144 | Q183 | Q148 | H |
| 698 | Q512 | H | Q183 | Q148 | H |
| 699 | Q513 | Q144 | Q183 | Q144 | H |
| 700 | Q514 | Q144 | Q183 | Q262 | H |
| 701 | Q515 | Q145 | Q183 | Q143 | H |
| 702 | Q516 | | Q183 | Q147 | H |
| 703 | Q517 | | Q183 | Q145 | H |
| 704 | Q518 | | Q183 | Q277 | H |
| 705 | Q519 | | Q183 | Q280 | H |
| 706 | Q520 | | Q183 | Q478 | H |
| 707 | Q521 | | Q183 | Q479 | H |
| 708 | Q522 | | Q183 | Q480 | H |
| 709 | Q523 | | Q183 | Q481 | H |
| 710 | Q524 | | Q183 | Q482 | H |
| 711 | Q525 | Q144 | Q427 | Q148 | H |
| 712 | Q526 | Q145 | Q186 | Q148 | H |
| 713 | Q527 | Q144 | Q445 | Q148 | H |
| 714 | Q528 | H | Q427 | Q148 | H |
| 715 | Q529 | | Q427 | Q148 | H |
| 716 | Q530 | | Q186 | Q148 | H |
| 717 | Q531 | Q144 | Q427 | Q148 | H |
| 718 | Q532 | Q144 | Q186 | Q148 | H |
| 719 | Q533 | Q144 | Q445 | Q148 | H |
| 720 | Q534 | Q145 | Q427 | Q148 | H |
| 721 | Q535 | Q144 | Q427 | Q148 | H |
| 722 | Q536 | Q144 | Q186 | Q148 | H |
| 723 | Q537 | Q144 | Q427 | Q148 | H |
| 724 | Q538 | Q144 | Q186 | Q148 | H |
| 725 | Q539 | Q144 | Q445 | Q148 | H |
| 726 | Q540 | Q144 | Q427 | Q262 | H |
| 727 | Q541 | Q144 | Q445 | Q144 | H |
| 728 | Q542 | Q144 | Q186 | Q143 | H |
| 729 | Q543 | Q145 | Q427 | Q145 | H |
| 730 | Q544 | H | Q445 | Q147 | H |
| 731 | Q545 | Q144 | Q186 | Q277 | H |
| 732 | Q546 | Q144 | Q427 | Q280 | H |
| 733 | Q547 | | Q445 | Q279 | H |
| 734 | Q149 | Q144 | Q445 | Q148 | H |
| 735 | Q149 | Q144 | Q186 | Q148 | H |
| 736 | Q149 | Q144 | Q186 | Q144 | H |

[Chemical formula 81]

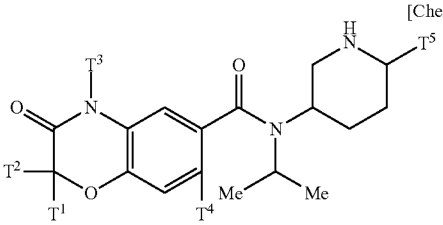

| No. | T1 | T2 | T3 | T4 | T5 |
|---|---|---|---|---|---|
| 737 | Q103 | Q144 | Q186 | Q148 | H |
| 738 | Q103 | Q144 | Q183 | Q148 | H |
| 739 | Q103 | Q144 | Q427 | Q148 | H |
| 740 | Q116 | Q144 | Q186 | Q148 | H |
| 741 | Q116 | Q144 | Q183 | Q148 | H |
| 742 | Q116 | Q144 | Q427 | Q148 | H |
| 743 | Q176 | Q144 | Q186 | Q148 | H |
| 744 | Q176 | Q144 | Q183 | Q148 | H |
| 745 | Q176 | Q144 | Q427 | Q148 | H |
| 746 | Q181 | Q144 | Q186 | Q148 | H |
| 747 | Q181 | Q144 | Q183 | Q148 | H |
| 748 | Q181 | Q144 | Q427 | Q148 | H |
| 749 | Q182 | Q144 | Q186 | Q148 | H |
| 750 | Q182 | Q144 | Q183 | Q148 | H |
| 751 | Q182 | Q144 | Q427 | Q148 | H |

[Chemical formula 82]

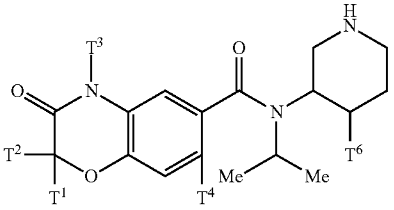

| No. | T1 | T2 | T3 | T4 | T6 |
|---|---|---|---|---|---|
| 752 | Q468 | | Q427 | Q148 | Q292 |
| 753 | Q144 | Q144 | Q427 | Q148 | Q293 |
| 754 | Q149 | Q144 | Q183 | Q148 | Q294 |
| 755 | Q144 | Q144 | Q427 | Q143 | Q295 |
| 756 | Q149 | Q144 | Q186 | Q148 | Q297 |
| 757 | Q144 | Q144 | Q183 | Q148 | Q298 |
| 758 | Q547 | | Q427 | Q148 | Q299 |
| 759 | Q144 | Q144 | Q427 | Q148 | Q330 |
| 760 | Q144 | Q144 | Q427 | Q144 | Q331 |
| 761 | Q2 | Q144 | Q183 | Q148 | Q332 |
| 762 | Q182 | Q144 | Q427 | Q148 | Q333 |
| 763 | Q144 | Q144 | Q186 | Q148 | Q335 |
| 764 | Q103 | Q144 | Q183 | Q262 | Q336 |
| 765 | Q2 | Q144 | Q427 | Q148 | Q337 |
| 766 | Q144 | Q144 | Q427 | Q148 | Q387 |
| 767 | Q547 | | Q186 | Q147 | Q388 |
| 768 | Q144 | Q144 | Q183 | Q148 | Q389 |
| 769 | Q285 | Q144 | Q427 | Q148 | Q391 |
| 770 | Q144 | Q144 | Q427 | Q148 | Q392 |
| 771 | Q144 | Q144 | Q183 | Q148 | Q393 |
| 772 | Q11 | Q144 | Q427 | Q148 | Q394 |
| 773 | Q468 | | Q186 | Q148 | Q395 |
| 774 | Q144 | Q144 | Q183 | Q147 | Q396 |
| 775 | Q144 | Q145 | Q427 | Q148 | Q397 |
| 776 | Q144 | Q144 | Q427 | Q148 | Q398 |
| 777 | Q468 | | Q183 | Q148 | Q399 |
| 778 | Q144 | Q144 | Q427 | Q148 | Q400 |
| 779 | Q176 | Q144 | Q186 | Q148 | Q401 |
| 780 | Q11 | Q144 | Q183 | Q148 | Q402 |
| 781 | Q144 | Q144 | Q427 | Q148 | Q403 |

[Chemical formula 83]

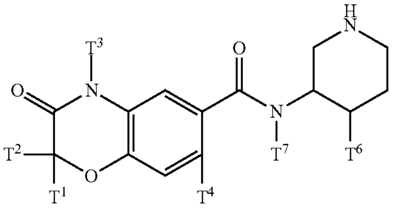

| No. | T1 | T2 | T3 | T4 | T6 | T7 |
|---|---|---|---|---|---|---|
| 782 | Q468 | | Q427 | Q148 | Q250 | Q144 |
| 783 | Q144 | Q144 | Q427 | Q148 | Q257 | Q145 |
| 784 | Q149 | Q144 | Q183 | Q148 | Q294 | Q180 |
| 785 | Q144 | Q144 | Q427 | Q143 | Q295 | Q261 |
| 786 | Q149 | Q144 | Q186 | Q148 | Q297 | Q115 |
| 787 | Q144 | Q144 | Q183 | Q148 | Q298 | Q144 |
| 788 | Q547 | | Q427 | Q148 | Q335 | Q145 |
| 789 | Q144 | Q144 | Q427 | Q148 | Q336 | Q145 |
| 790 | Q144 | Q144 | Q427 | Q144 | Q388 | Q180 |
| 791 | Q2 | Q144 | Q183 | Q148 | Q397 | Q261 |
| 792 | Q182 | Q144 | Q427 | Q148 | Q402 | Q115 |

[Chemical formula 84]

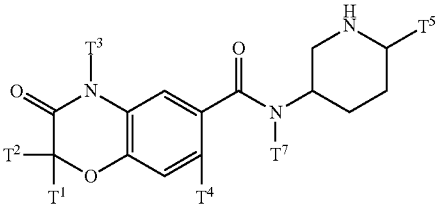

| No. | T1 | T2 | T3 | T4 | T5 | T7 |
|---|---|---|---|---|---|---|
| 793 | Q468 | | Q427 | Q148 | Q223 | Q406 |
| 794 | Q149 | Q144 | Q427 | Q148 | Q264 | Q407 |
| 795 | Q11 | Q144 | Q183 | Q148 | Q353 | Q409 |
| 796 | Q14 | Q145 | Q427 | Q143 | Q215 | Q416 |
| 797 | Q149 | Q144 | Q186 | Q148 | Q307 | Q417 |
| 798 | Q144 | Q144 | Q183 | Q148 | Q339 | Q418 |
| 799 | Q547 | | Q427 | Q148 | Q223 | Q419 |
| 800 | Q144 | Q144 | Q427 | Q148 | Q264 | Q180 |
| 801 | Q144 | Q145 | Q427 | Q144 | Q353 | Q406 |
| 802 | Q2 | Q144 | Q445 | Q148 | Q215 | Q416 |
| 803 | Q182 | Q144 | Q427 | Q148 | Q307 | Q416 |
| 804 | Q468 | | Q427 | Q148 | H | Q406 |
| 805 | Q149 | Q144 | Q427 | Q148 | H | Q407 |
| 806 | Q11 | Q144 | Q183 | Q148 | H | Q409 |
| 807 | Q14 | Q145 | Q427 | Q143 | H | Q416 |
| 808 | Q149 | Q144 | Q186 | Q148 | H | Q417 |
| 809 | Q144 | Q144 | Q183 | Q148 | H | Q418 |
| 810 | Q547 | | Q427 | Q148 | H | Q419 |
| 811 | Q144 | Q144 | Q427 | Q148 | H | Q180 |
| 812 | Q144 | Q145 | Q427 | Q144 | H | Q406 |
| 813 | Q2 | Q144 | Q445 | Q148 | H | Q416 |
| 814 | Q182 | Q144 | Q427 | Q148 | H | Q416 |

[Chemical formula 85]

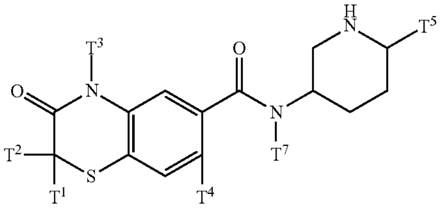

| No. | $T^1$ | $T^2$ | $T^3$ | $T^4$ | $T^5$ | $T^7$ |
|---|---|---|---|---|---|---|
| 815 | Q468 | | Q427 | Q148 | Q223 | Q236 |
| 816 | Q149 | Q144 | Q427 | Q148 | Q264 | Q236 |
| 817 | Q11 | Q144 | Q183 | Q148 | Q353 | Q236 |
| 818 | Q14 | Q145 | Q427 | Q143 | Q215 | Q237 |
| 819 | Q149 | Q144 | Q186 | Q148 | Q307 | Q416 |
| 820 | Q144 | Q144 | Q183 | Q148 | Q339 | Q180 |
| 821 | Q547 | | Q427 | Q148 | Q223 | Q236 |
| 822 | Q144 | Q144 | Q427 | Q148 | Q264 | Q236 |
| 823 | Q144 | Q145 | Q427 | Q144 | Q353 | Q236 |
| 824 | Q2 | Q144 | Q445 | Q148 | Q215 | Q236 |
| 825 | Q182 | Q144 | Q427 | Q148 | Q307 | Q236 |
| 826 | Q473 | | Q427 | Q148 | Q223 | Q236 |
| 827 | Q469 | | Q427 | Q148 | Q264 | Q236 |
| 828 | Q467 | | Q183 | Q148 | Q353 | Q236 |
| 829 | Q496 | | Q427 | Q143 | Q215 | Q237 |
| 830 | Q461 | Q144 | Q186 | Q148 | Q307 | Q416 |
| 831 | Q465 | Q144 | Q183 | Q148 | Q339 | Q180 |
| 832 | Q466 | | Q427 | Q148 | Q223 | Q236 |
| 833 | Q493 | Q144 | Q427 | Q148 | Q264 | Q236 |
| 834 | Q500 | Q145 | Q427 | Q144 | Q353 | Q236 |
| 835 | Q135 | Q144 | Q445 | Q148 | Q215 | Q236 |
| 836 | Q138 | Q144 | Q427 | Q148 | Q307 | Q236 |
| 837 | Q468 | | Q427 | Q148 | H | Q236 |
| 838 | Q149 | Q144 | Q427 | Q148 | H | Q236 |
| 839 | Q11 | Q144 | Q183 | Q148 | H | Q236 |
| 840 | Q14 | Q145 | Q427 | Q143 | H | Q237 |
| 841 | Q149 | Q144 | Q186 | Q148 | H | Q416 |
| 842 | Q144 | Q144 | Q183 | Q148 | H | Q180 |
| 843 | Q547 | | Q427 | Q148 | H | Q236 |
| 844 | Q548 | Q144 | Q183 | Q148 | H | Q236 |
| 845 | Q144 | Q145 | Q427 | Q144 | H | Q236 |
| 846 | Q2 | Q144 | Q445 | Q148 | H | Q236 |
| 847 | Q182 | Q144 | Q427 | Q148 | H | Q236 |
| 848 | Q473 | | Q427 | Q148 | H | Q236 |
| 849 | Q469 | | Q427 | Q148 | H | Q236 |
| 850 | Q467 | | Q183 | Q148 | H | Q236 |
| 851 | Q496 | | Q427 | Q143 | H | Q237 |
| 852 | Q461 | Q144 | Q186 | Q148 | H | Q416 |
| 853 | Q465 | Q144 | Q183 | Q148 | H | Q180 |
| 854 | Q466 | | Q427 | Q148 | H | Q236 |
| 855 | Q493 | Q144 | Q427 | Q148 | H | Q236 |
| 856 | Q500 | Q145 | Q427 | Q144 | H | Q236 |
| 857 | Q135 | Q144 | Q445 | Q148 | H | Q236 |
| 858 | Q138 | Q144 | Q427 | Q148 | H | Q236 |

[Chemical formula 86]

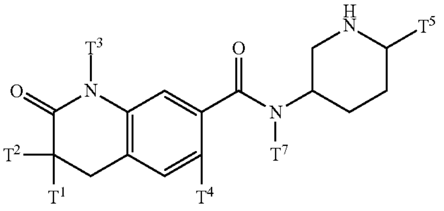

| No. | $T^1$ | $T^2$ | $T^3$ | $T^4$ | $T^5$ | $T^7$ |
|---|---|---|---|---|---|---|
| 859 | Q468 | | Q427 | Q148 | Q223 | Q236 |
| 860 | Q149 | Q144 | Q427 | Q148 | Q264 | Q236 |
| 861 | Q11 | Q144 | Q183 | Q148 | Q353 | Q236 |
| 862 | Q14 | Q145 | Q427 | Q143 | Q215 | Q237 |
| 863 | Q149 | Q144 | Q186 | Q148 | Q307 | Q416 |
| 864 | Q144 | Q144 | Q183 | Q148 | Q339 | Q180 |
| 865 | Q547 | | Q427 | Q148 | Q223 | Q236 |
| 866 | Q144 | Q144 | Q427 | Q148 | Q264 | Q236 |
| 867 | Q144 | Q145 | Q427 | Q144 | Q353 | Q236 |
| 868 | Q2 | Q144 | Q445 | Q148 | Q215 | Q236 |
| 869 | Q182 | Q144 | Q427 | Q148 | Q307 | Q236 |
| 870 | Q473 | | Q427 | Q148 | Q223 | Q236 |
| 871 | Q469 | | Q427 | Q148 | Q264 | Q236 |
| 872 | Q467 | | Q183 | Q148 | Q353 | Q236 |
| 873 | Q496 | | Q427 | Q143 | Q215 | Q237 |
| 874 | Q461 | Q144 | Q186 | Q148 | Q307 | Q416 |
| 875 | Q465 | Q144 | Q183 | Q148 | Q339 | Q180 |
| 876 | Q466 | | Q427 | Q148 | Q223 | Q236 |
| 877 | Q493 | Q144 | Q427 | Q148 | Q264 | Q236 |
| 878 | Q500 | Q145 | Q427 | Q144 | Q353 | Q236 |
| 879 | Q135 | Q144 | Q445 | Q148 | Q215 | Q236 |
| 880 | Q138 | Q144 | Q427 | Q148 | Q307 | Q236 |
| 881 | Q468 | | Q427 | Q148 | H | Q236 |
| 882 | Q149 | Q144 | Q427 | Q148 | H | Q236 |
| 883 | Q11 | Q144 | Q183 | Q148 | H | Q236 |
| 884 | Q14 | Q145 | Q427 | Q143 | H | Q237 |
| 885 | Q149 | Q144 | Q186 | Q148 | H | Q416 |
| 886 | Q144 | Q144 | Q183 | Q148 | H | Q180 |
| 887 | Q547 | | Q427 | Q148 | H | Q236 |
| 888 | Q144 | Q144 | Q427 | Q148 | H | Q236 |
| 889 | Q144 | Q145 | Q427 | Q144 | H | Q236 |
| 890 | Q2 | Q144 | Q445 | Q148 | H | Q236 |
| 891 | Q182 | Q144 | Q427 | Q148 | H | Q236 |
| 892 | Q473 | | Q427 | Q148 | H | Q236 |
| 893 | Q469 | | Q427 | Q148 | H | Q236 |
| 894 | Q467 | | Q183 | Q148 | H | Q236 |
| 895 | Q496 | | Q427 | Q143 | H | Q237 |
| 896 | Q461 | Q144 | Q186 | Q148 | H | Q416 |
| 897 | Q465 | Q144 | Q183 | Q148 | H | Q180 |
| 898 | Q466 | | Q427 | Q148 | H | Q236 |
| 899 | Q493 | Q144 | Q427 | Q148 | H | Q236 |
| 900 | Q500 | Q145 | Q427 | Q144 | H | Q236 |
| 901 | Q135 | Q144 | Q445 | Q148 | H | Q236 |
| 902 | Q138 | Q144 | Q427 | Q148 | H | Q236 |

[Chemical formula 87]

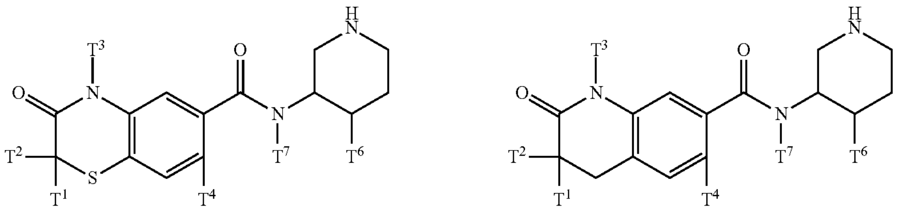

| No. | $T^1$ | $T^2$ | $T^3$ | $T^4$ | $T^6$ | $T^7$ | No. | $T^1$ | $T^2$ | $T^3$ | $T^4$ | $T^6$ | $T^7$ |
|---|---|---|---|---|---|---|---|---|---|---|---|---|---|
| 903 | Q468 | | Q427 | Q148 | Q292 | Q236 | 918 | Q468 | | Q427 | Q148 | Q292 | Q236 |
| 904 | Q149 | Q144 | Q427 | Q148 | Q293 | Q236 | 919 | Q149 | Q144 | Q427 | Q148 | Q293 | Q236 |

-continued

[Chemical formula 87]

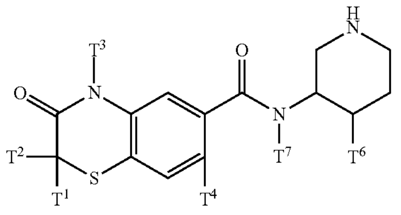

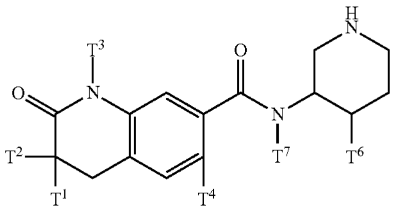

| No. | $T^1$ | $T^2$ | $T^3$ | $T^4$ | $T^6$ | $T^7$ | No. | $T^1$ | $T^2$ | $T^3$ | $T^4$ | $T^6$ | $T^7$ |
|---|---|---|---|---|---|---|---|---|---|---|---|---|---|
| 905 | Q11 | Q144 | Q183 | Q148 | Q294 | Q144 | 920 | Q11 | Q144 | Q183 | Q148 | Q294 | Q144 |
| 906 | Q14 | Q145 | Q427 | Q143 | Q295 | Q145 | 921 | Q14 | Q145 | Q427 | Q143 | Q295 | Q145 |
| 907 | Q149 | Q144 | Q186 | Q148 | Q297 | Q145 | 922 | Q149 | Q144 | Q186 | Q148 | Q297 | Q145 |
| 908 | Q144 | Q144 | Q183 | Q148 | Q298 | Q180 | 923 | Q144 | Q144 | Q183 | Q148 | Q298 | Q180 |
| 909 | Q547 | | Q427 | Q148 | Q299 | Q180 | 924 | Q547 | | Q427 | Q148 | Q299 | Q180 |
| 910 | Q144 | Q144 | Q427 | Q148 | Q330 | Q419 | 925 | Q144 | Q144 | Q427 | Q148 | Q330 | Q419 |
| 911 | Q144 | Q145 | Q427 | Q144 | Q331 | Q236 | 926 | Q144 | Q145 | Q427 | Q144 | Q331 | Q236 |
| 912 | Q2 | Q144 | Q445 | Q148 | Q332 | Q236 | 927 | Q2 | Q144 | Q445 | Q148 | Q332 | Q236 |
| 913 | Q182 | Q144 | Q427 | Q148 | Q333 | Q144 | 928 | Q182 | Q144 | Q427 | Q148 | Q333 | Q144 |
| 914 | Q473 | | Q427 | Q148 | Q335 | Q145 | 929 | Q473 | | Q427 | Q148 | Q335 | Q145 |
| 915 | Q469 | | Q427 | Q148 | Q336 | Q145 | 930 | Q469 | | Q427 | Q148 | Q336 | Q145 |
| 916 | Q467 | | Q183 | Q148 | Q337 | Q180 | 931 | Q467 | | Q183 | Q148 | Q337 | Q180 |
| 917 | Q496 | | Q427 | Q143 | Q387 | Q180 | 932 | Q496 | | Q427 | Q143 | Q387 | Q180 |

[Chemical formula 88]

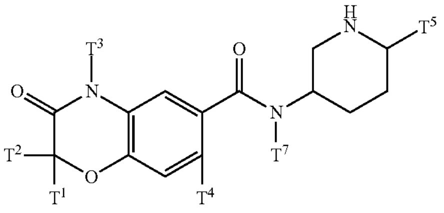

| No. | $T^1$ | $T^2$ | $T^3$ | $T^4$ | $T^5$ | $T^7$ |
|---|---|---|---|---|---|---|
| 933 | Q468 | | Q281 | Q148 | Q223 | Q236 |
| 934 | Q149 | Q144 | Q282 | Q148 | Q264 | Q236 |
| 935 | Q11 | Q144 | Q284 | Q148 | Q353 | Q236 |
| 936 | Q14 | Q145 | Q378 | Q143 | Q215 | Q236 |
| 937 | Q149 | Q144 | Q379 | Q148 | Q307 | Q236 |
| 938 | Q144 | Q144 | Q380 | Q148 | Q339 | Q236 |
| 939 | Q547 | | Q381 | Q148 | Q223 | Q236 |
| 940 | Q144 | Q144 | Q382 | Q148 | Q264 | Q180 |
| 941 | Q144 | Q145 | Q383 | Q144 | Q353 | Q236 |
| 942 | Q2 | Q144 | Q384 | Q148 | Q215 | Q236 |
| 943 | Q182 | Q144 | Q385 | Q148 | Q307 | Q236 |
| 944 | Q468 | | Q386 | Q148 | Q223 | Q416 |
| 945 | Q149 | Q144 | Q420 | Q148 | Q264 | Q236 |
| 946 | Q11 | Q144 | Q421 | Q148 | Q353 | Q236 |
| 947 | Q14 | Q145 | Q422 | Q143 | Q215 | Q236 |
| 948 | Q149 | Q144 | Q423 | Q148 | Q307 | Q236 |
| 949 | Q144 | Q144 | Q424 | Q148 | Q339 | Q416 |
| 950 | Q547 | | Q425 | Q148 | Q223 | Q180 |
| 951 | Q144 | Q144 | Q426 | Q148 | Q264 | Q236 |
| 952 | Q144 | Q145 | Q428 | Q144 | Q353 | Q236 |
| 953 | Q2 | Q144 | Q429 | Q148 | Q215 | Q236 |
| 954 | Q182 | Q144 | Q430 | Q148 | Q307 | Q236 |
| 955 | Q468 | | Q431 | Q148 | Q223 | Q236 |
| 956 | Q149 | Q144 | Q432 | Q148 | Q264 | Q236 |
| 957 | Q11 | Q144 | Q433 | Q148 | Q353 | Q236 |
| 958 | Q14 | Q145 | Q434 | Q143 | Q215 | Q236 |
| 959 | Q149 | Q144 | Q435 | Q148 | Q307 | Q236 |
| 960 | Q144 | Q144 | Q436 | Q148 | Q339 | Q180 |
| 961 | Q11 | Q144 | Q437 | Q148 | Q353 | Q236 |
| 962 | Q14 | Q145 | Q438 | Q143 | Q215 | Q236 |
| 963 | Q149 | Q144 | Q439 | Q148 | Q307 | Q236 |
| 964 | Q144 | Q144 | Q440 | Q148 | Q339 | Q416 |

-continued

[Chemical formula 88]

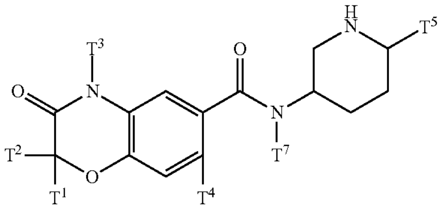

| No. | $T^1$ | $T^2$ | $T^3$ | $T^4$ | $T^5$ | $T^7$ |
|---|---|---|---|---|---|---|
| 965 | Q547 | | Q441 | Q148 | Q223 | Q236 |
| 966 | Q144 | Q144 | Q442 | Q148 | Q264 | Q236 |
| 967 | Q144 | Q145 | Q443 | Q144 | Q353 | Q416 |
| 968 | Q2 | Q144 | Q444 | Q148 | Q215 | Q236 |
| 969 | Q182 | Q144 | Q446 | Q148 | Q307 | Q416 |
| 970 | Q468 | | Q281 | Q148 | H | Q236 |
| 971 | Q149 | Q144 | Q282 | Q148 | H | Q236 |
| 972 | Q11 | Q144 | Q284 | Q148 | H | Q236 |
| 973 | Q14 | Q145 | Q378 | Q143 | H | Q236 |
| 974 | Q149 | Q144 | Q379 | Q148 | H | Q236 |
| 975 | Q144 | Q144 | Q380 | Q148 | H | Q236 |
| 976 | Q547 | | Q381 | Q148 | H | Q236 |
| 977 | Q144 | Q144 | Q382 | Q148 | H | Q180 |
| 978 | Q144 | Q145 | Q383 | Q144 | H | Q236 |
| 979 | Q2 | Q144 | Q384 | Q148 | H | Q236 |
| 980 | Q182 | Q144 | Q385 | Q148 | H | Q236 |
| 981 | Q468 | | Q386 | Q148 | H | Q416 |
| 982 | Q149 | Q144 | Q420 | Q148 | H | Q236 |
| 983 | Q11 | Q144 | Q421 | Q148 | H | Q236 |
| 984 | Q14 | Q145 | Q422 | Q143 | H | Q236 |
| 985 | Q149 | Q144 | Q423 | Q148 | H | Q236 |
| 986 | Q144 | Q144 | Q424 | Q148 | H | Q416 |
| 987 | Q547 | | Q425 | Q148 | H | Q180 |
| 988 | Q144 | Q144 | Q426 | Q148 | H | Q236 |
| 989 | Q144 | Q145 | Q428 | Q144 | H | Q236 |
| 990 | Q2 | Q144 | Q429 | Q148 | H | Q236 |
| 991 | Q182 | Q144 | Q430 | Q148 | H | Q236 |
| 992 | Q468 | | Q431 | Q148 | H | Q236 |
| 993 | Q149 | Q144 | Q432 | Q148 | H | Q236 |
| 994 | Q11 | Q144 | Q433 | Q148 | H | Q236 |
| 995 | Q14 | Q145 | Q434 | Q143 | H | Q236 |
| 996 | Q149 | Q144 | Q435 | Q148 | H | Q236 |

-continued

[Chemical formula 88]

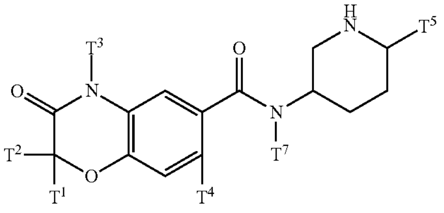

| No. | $T^1$ | $T^2$ | $T^3$ | $T^4$ | $T^5$ | $T^7$ |
|---|---|---|---|---|---|---|
| 997 | Q144 | Q144 | Q436 | Q148 | H | Q180 |
| 998 | Q11 | Q144 | Q437 | Q148 | H | Q236 |
| 999 | Q14 | Q145 | Q438 | Q143 | H | Q236 |
| 1000 | Q149 | Q144 | Q439 | Q148 | H | Q236 |
| 1001 | Q144 | Q144 | Q440 | Q148 | H | Q416 |
| 1002 | Q547 | | Q441 | Q148 | H | Q236 |
| 1003 | Q144 | Q144 | Q442 | Q148 | H | Q236 |
| 1004 | Q144 | Q145 | Q443 | Q144 | H | Q416 |
| 1005 | Q2 | Q144 | Q444 | Q148 | H | Q236 |
| 1006 | Q182 | Q144 | Q446 | Q148 | H | Q416 |

[Chemical formula 89]

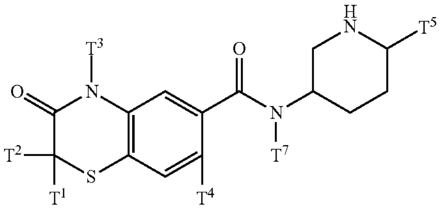

| No. | $T^1$ | $T^2$ | $T^3$ | $T^4$ | $T^5$ | $T^7$ |
|---|---|---|---|---|---|---|
| 1007 | Q468 | | Q281 | Q148 | Q223 | Q236 |
| 1008 | Q149 | Q144 | Q282 | Q148 | Q264 | Q236 |
| 1009 | Q11 | Q144 | Q284 | Q148 | Q353 | Q236 |
| 1010 | Q14 | Q145 | Q378 | Q143 | Q215 | Q236 |
| 1011 | Q149 | Q144 | Q379 | Q148 | Q307 | Q236 |
| 1012 | Q144 | Q144 | Q380 | Q148 | Q339 | Q236 |
| 1013 | Q547 | | Q381 | Q148 | Q223 | Q236 |
| 1014 | Q144 | Q144 | Q382 | Q148 | Q264 | Q180 |
| 1015 | Q144 | Q145 | Q383 | Q144 | Q353 | Q236 |
| 1016 | Q2 | Q144 | Q384 | Q148 | Q215 | Q236 |
| 1017 | Q182 | Q144 | Q385 | Q148 | Q307 | Q236 |
| 1018 | Q468 | | Q386 | Q148 | Q223 | Q416 |
| 1019 | Q149 | Q144 | Q420 | Q148 | Q264 | Q236 |
| 1020 | Q11 | Q144 | Q421 | Q148 | Q353 | Q236 |
| 1021 | Q14 | Q145 | Q422 | Q143 | Q215 | Q236 |
| 1022 | Q149 | Q144 | Q423 | Q148 | Q307 | Q236 |
| 1023 | Q144 | Q144 | Q424 | Q148 | Q339 | Q416 |
| 1024 | Q547 | | Q425 | Q148 | Q223 | Q180 |
| 1025 | Q144 | Q144 | Q426 | Q148 | Q264 | Q236 |
| 1026 | Q144 | Q145 | Q428 | Q144 | Q353 | Q236 |
| 1027 | Q2 | Q144 | Q429 | Q148 | Q215 | Q236 |
| 1028 | Q182 | Q144 | Q430 | Q148 | Q307 | Q236 |
| 1029 | Q468 | | Q431 | Q148 | Q223 | Q236 |
| 1030 | Q149 | Q144 | Q432 | Q148 | Q264 | Q236 |
| 1031 | Q11 | Q144 | Q433 | Q148 | Q353 | Q236 |
| 1032 | Q14 | Q145 | Q434 | Q143 | Q215 | Q236 |
| 1033 | Q149 | Q144 | Q435 | Q148 | Q307 | Q236 |
| 1034 | Q144 | Q144 | Q436 | Q148 | Q339 | Q180 |
| 1035 | Q11 | Q144 | Q437 | Q148 | Q353 | Q236 |
| 1036 | Q14 | Q145 | Q438 | Q143 | Q215 | Q236 |
| 1037 | Q149 | Q144 | Q439 | Q148 | Q307 | Q236 |
| 1038 | Q144 | Q144 | Q440 | Q148 | Q339 | Q416 |
| 1039 | Q547 | | Q441 | Q148 | Q223 | Q236 |
| 1040 | Q144 | Q144 | Q442 | Q148 | Q264 | Q236 |
| 1041 | Q144 | Q145 | Q443 | Q144 | Q353 | Q416 |

-continued

[Chemical formula 89]

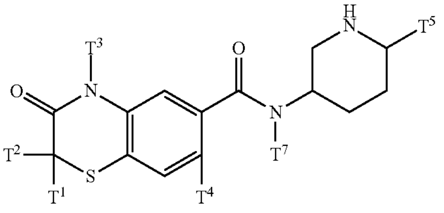

| No. | $T^1$ | $T^2$ | $T^3$ | $T^4$ | $T^5$ | $T^7$ |
|---|---|---|---|---|---|---|
| 1042 | Q2 | Q144 | Q444 | Q148 | Q215 | Q236 |
| 1043 | Q182 | Q144 | Q446 | Q148 | Q307 | Q416 |
| 1044 | Q468 | | Q281 | Q148 | H | Q236 |
| 1045 | Q149 | Q144 | Q282 | Q148 | H | Q236 |
| 1046 | Q11 | Q144 | Q284 | Q148 | H | Q236 |
| 1047 | Q14 | Q145 | Q378 | Q143 | H | Q236 |
| 1048 | Q149 | Q144 | Q379 | Q148 | H | Q236 |
| 1049 | Q144 | Q144 | Q380 | Q148 | H | Q236 |
| 1050 | Q547 | | Q381 | Q148 | H | Q236 |
| 1051 | Q144 | Q144 | Q382 | Q148 | H | Q180 |
| 1052 | Q144 | Q145 | Q383 | Q144 | H | Q236 |
| 1053 | Q2 | Q144 | Q384 | Q148 | H | Q236 |
| 1054 | Q182 | Q144 | Q385 | Q148 | H | Q236 |
| 1055 | Q468 | | Q386 | Q148 | H | Q416 |
| 1056 | Q149 | Q144 | Q420 | Q148 | H | Q236 |
| 1057 | Q11 | Q144 | Q421 | Q148 | H | Q236 |
| 1058 | Q14 | Q145 | Q422 | Q143 | H | Q236 |
| 1059 | Q149 | Q144 | Q423 | Q148 | H | Q236 |
| 1060 | Q144 | Q144 | Q424 | Q148 | H | Q416 |
| 1061 | Q547 | | Q425 | Q148 | H | Q180 |
| 1062 | Q144 | Q144 | Q426 | Q148 | H | Q236 |
| 1063 | Q144 | Q145 | Q428 | Q144 | H | Q236 |
| 1064 | Q2 | Q144 | Q429 | Q148 | H | Q236 |
| 1065 | Q182 | Q144 | Q430 | Q148 | H | Q236 |
| 1066 | Q468 | | Q431 | Q148 | H | Q236 |
| 1067 | Q149 | Q144 | Q432 | Q148 | H | Q236 |
| 1068 | Q11 | Q144 | Q433 | Q148 | H | Q236 |
| 1069 | Q14 | Q145 | Q434 | Q143 | H | Q236 |
| 1070 | Q149 | Q144 | Q435 | Q148 | H | Q236 |
| 1071 | Q144 | Q144 | Q436 | Q148 | H | Q180 |
| 1072 | Q11 | Q144 | Q437 | Q148 | H | Q236 |
| 1073 | Q14 | Q145 | Q438 | Q143 | H | Q236 |
| 1074 | Q149 | Q144 | Q439 | Q148 | H | Q236 |
| 1075 | Q144 | Q144 | Q440 | Q148 | H | Q416 |
| 1076 | Q547 | | Q441 | Q148 | H | Q236 |
| 1077 | Q144 | Q144 | Q442 | Q148 | H | Q236 |
| 1078 | Q144 | Q145 | Q443 | Q144 | H | Q416 |
| 1079 | Q2 | Q144 | Q444 | Q148 | H | Q236 |
| 1080 | Q182 | Q144 | Q446 | Q148 | H | Q416 |

[Chemical formula 90]

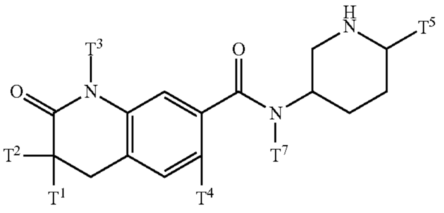

| No. | $T^1$ | $T^2$ | $T^3$ | $T^4$ | $T^5$ | $T^7$ |
|---|---|---|---|---|---|---|
| 1081 | Q468 | | Q281 | Q148 | Q223 | Q236 |
| 1082 | Q149 | Q144 | Q282 | Q148 | Q264 | Q236 |
| 1083 | Q11 | Q144 | Q284 | Q148 | Q353 | Q236 |
| 1084 | Q14 | Q145 | Q378 | Q143 | Q215 | Q236 |
| 1085 | Q149 | Q144 | Q379 | Q148 | Q307 | Q236 |
| 1086 | Q144 | Q144 | Q380 | Q148 | Q339 | Q236 |

-continued

[Chemical formula 90]

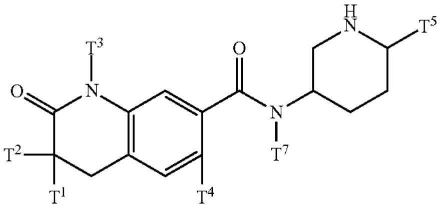

| No. | $T^1$ | $T^2$ | $T^3$ | $T^4$ | $T^5$ | $T^7$ |
|---|---|---|---|---|---|---|
| 1087 | Q547 | | Q381 | Q148 | Q223 | Q236 |
| 1088 | Q144 | Q144 | Q382 | Q148 | Q264 | Q180 |
| 1089 | Q144 | Q145 | Q383 | Q144 | Q353 | Q236 |
| 1090 | Q2 | Q144 | Q384 | Q148 | Q215 | Q236 |
| 1091 | Q182 | Q144 | Q385 | Q148 | Q307 | Q236 |
| 1092 | Q468 | | Q386 | Q148 | Q223 | Q416 |
| 1093 | Q149 | Q144 | Q420 | Q148 | Q264 | Q236 |
| 1094 | Q11 | Q144 | Q421 | Q148 | Q353 | Q236 |
| 1095 | Q14 | Q145 | Q422 | Q143 | Q215 | Q236 |
| 1096 | Q149 | Q144 | Q423 | Q148 | Q307 | Q236 |
| 1097 | Q144 | Q144 | Q424 | Q148 | Q339 | Q416 |
| 1098 | Q547 | | Q425 | Q148 | Q223 | Q180 |
| 1099 | Q144 | Q144 | Q426 | Q148 | Q264 | Q236 |
| 1100 | Q144 | Q145 | Q428 | Q144 | Q353 | Q236 |
| 1101 | Q2 | Q144 | Q429 | Q148 | Q215 | Q236 |
| 1102 | Q182 | Q144 | Q430 | Q148 | Q307 | Q236 |
| 1103 | Q468 | | Q431 | Q148 | Q223 | Q236 |
| 1104 | Q149 | Q144 | Q432 | Q148 | Q264 | Q236 |
| 1105 | Q11 | Q144 | Q433 | Q148 | Q353 | Q236 |
| 1106 | Q14 | Q145 | Q434 | Q143 | Q215 | Q236 |
| 1107 | Q149 | Q144 | Q435 | Q148 | Q307 | Q236 |
| 1108 | Q144 | Q144 | Q436 | Q148 | Q339 | Q180 |
| 1109 | Q11 | Q144 | Q437 | Q148 | Q353 | Q236 |
| 1110 | Q14 | Q145 | Q438 | Q143 | Q215 | Q236 |
| 1111 | Q149 | Q144 | Q439 | Q148 | Q307 | Q236 |
| 1112 | Q144 | Q144 | Q440 | Q148 | Q339 | Q416 |
| 1113 | Q547 | | Q441 | Q148 | Q223 | Q236 |
| 1114 | Q144 | Q144 | Q442 | Q148 | Q264 | Q236 |
| 1115 | Q144 | Q145 | Q443 | Q144 | Q353 | Q416 |
| 1116 | Q2 | Q144 | Q444 | Q148 | Q215 | Q236 |
| 1117 | Q182 | Q144 | Q446 | Q148 | Q307 | Q416 |
| 1118 | Q468 | | Q281 | Q148 | H | Q236 |
| 1119 | Q149 | Q144 | Q282 | Q148 | H | Q236 |
| 1120 | Q11 | Q144 | Q284 | Q148 | H | Q236 |
| 1121 | Q14 | Q145 | Q378 | Q143 | H | Q236 |
| 1122 | Q149 | Q144 | Q379 | Q148 | H | Q236 |
| 1123 | Q144 | Q144 | Q380 | Q148 | H | Q236 |
| 1124 | Q547 | | Q381 | Q148 | H | Q236 |
| 1125 | Q144 | Q144 | Q382 | Q148 | H | Q180 |
| 1126 | Q144 | Q145 | Q383 | Q144 | H | Q236 |
| 1127 | Q2 | Q144 | Q384 | Q148 | H | Q236 |
| 1128 | Q182 | Q144 | Q385 | Q148 | H | Q236 |
| 1129 | Q468 | | Q386 | Q148 | H | Q416 |
| 1130 | Q149 | Q144 | Q420 | Q148 | H | Q236 |
| 1131 | Q11 | Q144 | Q421 | Q148 | H | Q236 |
| 1132 | Q14 | Q145 | Q422 | Q143 | H | Q236 |
| 1133 | Q149 | Q144 | Q423 | Q148 | H | Q236 |
| 1134 | Q144 | Q144 | Q424 | Q148 | H | Q416 |
| 1135 | Q547 | | Q425 | Q148 | H | Q180 |
| 1136 | Q144 | Q144 | Q426 | Q148 | H | Q236 |
| 1137 | Q144 | Q145 | Q428 | Q144 | H | Q236 |
| 1138 | Q2 | Q144 | Q429 | Q148 | H | Q236 |
| 1139 | Q182 | Q144 | Q430 | Q148 | H | Q236 |
| 1140 | Q468 | | Q431 | Q148 | H | Q236 |
| 1141 | Q149 | Q144 | Q432 | Q148 | H | Q236 |
| 1142 | Q11 | Q144 | Q433 | Q148 | H | Q236 |
| 1143 | Q14 | Q145 | Q434 | Q143 | H | Q236 |
| 1144 | Q149 | Q144 | Q435 | Q148 | H | Q236 |
| 1145 | Q144 | Q144 | Q436 | Q148 | H | Q180 |
| 1146 | Q11 | Q144 | Q437 | Q148 | H | Q236 |
| 1147 | Q14 | Q145 | Q438 | Q143 | H | Q236 |
| 1148 | Q149 | Q144 | Q439 | Q148 | H | Q236 |
| 1149 | Q144 | Q144 | Q440 | Q148 | H | Q416 |
| 1150 | Q547 | | Q441 | Q148 | H | Q236 |
| 1151 | Q144 | Q144 | Q442 | Q148 | H | Q236 |

-continued

[Chemical formula 90]

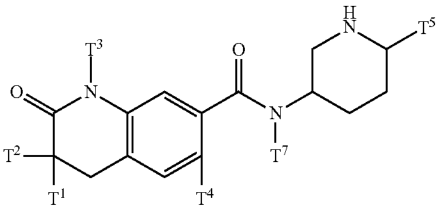

| No. | $T^1$ | $T^2$ | $T^3$ | $T^4$ | $T^5$ | $T^7$ |
|---|---|---|---|---|---|---|
| 1152 | Q144 | Q145 | Q443 | Q144 | H | Q416 |
| 1153 | Q2 | Q144 | Q444 | Q148 | H | Q236 |
| 1154 | Q182 | Q144 | Q446 | Q148 | H | Q416 |

[Chemical formula 91]

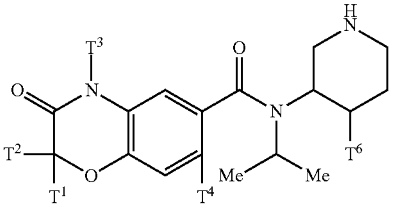

| No. | $T^1$ | $T^2$ | $T^3$ | $T^4$ | $T^6$ |
|---|---|---|---|---|---|
| 1155 | Q468 | | Q428 | Q148 | Q292 |
| 1156 | Q144 | Q144 | Q428 | Q148 | Q293 |
| 1157 | Q149 | Q144 | Q428 | Q148 | Q294 |
| 1158 | Q144 | Q144 | Q428 | Q143 | Q295 |
| 1159 | Q149 | Q144 | Q430 | Q148 | Q297 |
| 1160 | Q144 | Q144 | Q430 | Q148 | Q298 |
| 1161 | Q547 | | Q430 | Q148 | Q299 |
| 1162 | Q144 | Q144 | Q425 | Q148 | Q330 |
| 1163 | Q144 | Q144 | Q425 | Q144 | Q331 |
| 1164 | Q2 | Q144 | Q425 | Q148 | Q332 |
| 1165 | Q182 | Q144 | Q437 | Q148 | Q333 |
| 1166 | Q144 | Q144 | Q437 | Q148 | Q335 |
| 1167 | Q103 | Q144 | Q437 | Q262 | Q336 |
| 1168 | Q2 | Q144 | Q428 | Q148 | Q337 |
| 1169 | Q144 | Q144 | Q428 | Q148 | Q387 |
| 1170 | Q547 | | Q428 | Q147 | Q388 |
| 1171 | Q144 | Q144 | Q428 | Q148 | Q389 |
| 1172 | Q285 | Q144 | Q428 | Q148 | Q391 |
| 1173 | Q144 | Q144 | Q428 | Q148 | Q392 |
| 1174 | Q144 | Q144 | Q430 | Q148 | Q393 |
| 1175 | Q11 | Q144 | Q430 | Q148 | Q394 |
| 1176 | Q468 | | Q430 | Q148 | Q395 |
| 1177 | Q144 | Q144 | Q425 | Q147 | Q396 |
| 1178 | Q144 | Q145 | Q425 | Q148 | Q397 |
| 1179 | Q144 | Q144 | Q425 | Q148 | Q398 |
| 1180 | Q468 | | Q437 | Q148 | Q399 |
| 1181 | Q144 | Q144 | Q437 | Q148 | Q400 |
| 1182 | Q176 | Q144 | Q437 | Q148 | Q401 |
| 1183 | Q11 | Q144 | Q428 | Q148 | Q402 |
| 1184 | Q144 | Q144 | Q428 | Q148 | Q403 |

[Chemical formula 92]

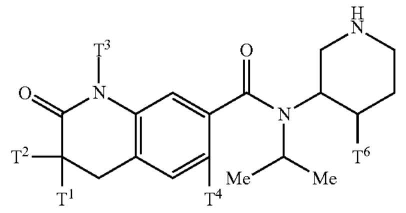

| No. | T¹ | T² | T³ | T⁴ | T⁶ |
|---|---|---|---|---|---|
| 1185 | Q468 | | Q428 | Q148 | Q292 |
| 1186 | Q144 | Q144 | Q428 | Q148 | Q293 |
| 1187 | Q149 | Q144 | Q428 | Q148 | Q294 |
| 1188 | Q144 | Q144 | Q428 | Q143 | Q295 |
| 1189 | Q149 | Q144 | Q430 | Q148 | Q297 |
| 1190 | Q144 | Q144 | Q430 | Q148 | Q298 |
| 1191 | Q547 | | Q430 | Q148 | Q299 |
| 1192 | Q144 | Q144 | Q425 | Q148 | Q330 |
| 1193 | Q144 | Q144 | Q425 | Q144 | Q331 |
| 1194 | Q2 | Q144 | Q425 | Q148 | Q332 |
| 1195 | Q182 | Q144 | Q437 | Q148 | Q333 |
| 1196 | Q144 | Q144 | Q437 | Q148 | Q335 |
| 1197 | Q103 | Q144 | Q437 | Q262 | Q336 |
| 1198 | Q2 | Q144 | Q428 | Q148 | Q337 |
| 1199 | Q144 | Q144 | Q428 | Q148 | Q387 |
| 1200 | Q547 | | Q428 | Q147 | Q388 |
| 1201 | Q144 | Q144 | Q428 | Q148 | Q389 |
| 1202 | Q285 | Q144 | Q428 | Q148 | Q391 |
| 1203 | Q144 | Q144 | Q428 | Q148 | Q392 |
| 1204 | Q144 | Q144 | Q430 | Q148 | Q393 |
| 1205 | Q11 | Q144 | Q430 | Q148 | Q394 |
| 1206 | Q468 | | Q430 | Q148 | Q395 |
| 1207 | Q144 | Q144 | Q425 | Q147 | Q396 |
| 1208 | Q144 | Q145 | Q425 | Q148 | Q397 |
| 1209 | Q144 | Q144 | Q425 | Q148 | Q398 |
| 1210 | Q468 | | Q437 | Q148 | Q399 |
| 1211 | Q144 | Q144 | Q437 | Q148 | Q400 |
| 1212 | Q176 | Q144 | Q437 | Q148 | Q401 |
| 1213 | Q11 | Q144 | Q428 | Q148 | Q402 |
| 1214 | Q144 | Q144 | Q428 | Q148 | Q403 |

[Chemical formula 93]

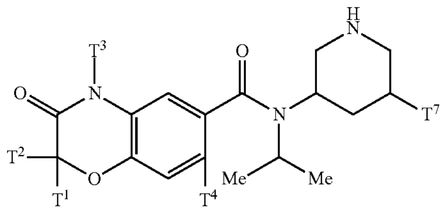

| No. | T¹ | T² | T³ | T⁴ | T⁷ |
|---|---|---|---|---|---|
| 1215 | Q468 | | Q183 | Q148 | Q223 |
| 1216 | Q144 | Q144 | Q186 | Q148 | Q204 |
| 1217 | Q149 | Q144 | Q183 | Q148 | Q210 |
| 1218 | Q144 | Q144 | Q183 | Q143 | Q212 |
| 1219 | Q149 | Q144 | Q186 | Q148 | Q227 |
| 1220 | Q144 | Q144 | Q183 | Q148 | Q228 |
| 1221 | Q547 | | Q427 | Q148 | Q219 |
| 1222 | Q144 | Q144 | Q445 | Q148 | Q220 |
| 1223 | Q144 | Q144 | Q427 | Q144 | Q219 |
| 1224 | Q2 | Q144 | Q445 | Q148 | Q221 |
| 1225 | Q182 | Q144 | Q427 | Q148 | Q205 |
| 1226 | Q144 | Q144 | Q427 | Q148 | Q195 |
| 1227 | Q103 | Q144 | Q427 | Q262 | Q234 |
| 1228 | Q2 | Q144 | Q186 | Q148 | Q235 |
| 1229 | Q144 | Q144 | Q186 | Q148 | Q200 |
| 1230 | Q547 | | Q183 | Q147 | Q314 |
| 1231 | Q144 | Q144 | Q186 | Q148 | Q307 |
| 1232 | Q285 | Q144 | Q183 | Q148 | Q322 |

-continued

[Chemical formula 93]

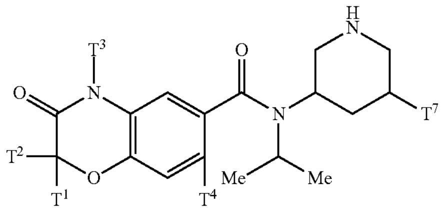

| No. | T¹ | T² | T³ | T⁴ | T⁷ |
|---|---|---|---|---|---|
| 1233 | Q144 | Q144 | Q183 | Q148 | Q327 |
| 1234 | Q144 | Q144 | Q186 | Q148 | Q344 |
| 1235 | Q11 | Q144 | Q183 | Q148 | Q368 |
| 1236 | Q468 | | Q427 | Q148 | Q376 |
| 1237 | Q144 | Q144 | Q445 | Q147 | Q353 |
| 1238 | Q144 | Q145 | Q427 | Q148 | Q361 |
| 1239 | Q144 | Q144 | Q445 | Q148 | Q338 |
| 1240 | Q468 | | Q427 | Q148 | Q349 |
| 1241 | Q144 | Q144 | Q427 | Q148 | Q318 |
| 1242 | Q176 | Q144 | Q427 | Q148 | Q366 |
| 1243 | Q11 | Q144 | Q186 | Q148 | Q123 |
| 1244 | Q144 | Q144 | Q186 | Q148 | Q323 |

[Chemical formula 94]

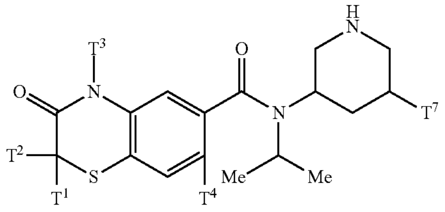

| No. | T¹ | T² | T³ | T⁴ | T⁷ |
|---|---|---|---|---|---|
| 1245 | Q468 | | Q183 | Q148 | Q223 |
| 1246 | Q144 | Q144 | Q186 | Q148 | Q204 |
| 1247 | Q149 | Q144 | Q183 | Q148 | Q210 |
| 1248 | Q144 | Q144 | Q183 | Q143 | Q212 |
| 1249 | Q149 | Q144 | Q186 | Q148 | Q227 |
| 1250 | Q144 | Q144 | Q183 | Q148 | Q228 |
| 1251 | Q547 | | Q427 | Q148 | Q219 |
| 1252 | Q144 | Q144 | Q445 | Q148 | Q220 |
| 1253 | Q144 | Q144 | Q427 | Q144 | Q219 |
| 1254 | Q2 | Q144 | Q445 | Q148 | Q221 |
| 1255 | Q182 | Q144 | Q427 | Q148 | Q205 |
| 1256 | Q144 | Q144 | Q427 | Q148 | Q195 |
| 1257 | Q103 | Q144 | Q427 | Q262 | Q234 |
| 1258 | Q2 | Q144 | Q186 | Q148 | Q235 |
| 1259 | Q144 | Q144 | Q186 | Q148 | Q200 |
| 1260 | Q547 | | Q183 | Q147 | Q314 |
| 1261 | Q144 | Q144 | Q186 | Q148 | Q307 |
| 1262 | Q285 | Q144 | Q183 | Q148 | Q322 |
| 1263 | Q144 | Q144 | Q183 | Q148 | Q327 |
| 1264 | Q144 | Q144 | Q186 | Q148 | Q344 |
| 1265 | Q11 | Q144 | Q183 | Q148 | Q368 |
| 1266 | Q468 | | Q427 | Q148 | Q376 |
| 1267 | Q144 | Q144 | Q445 | Q147 | Q353 |
| 1268 | Q144 | Q145 | Q427 | Q148 | Q361 |
| 1269 | Q144 | Q144 | Q445 | Q148 | Q338 |
| 1270 | Q468 | | Q427 | Q148 | Q349 |
| 1271 | Q144 | Q144 | Q427 | Q148 | Q318 |
| 1272 | Q176 | Q144 | Q427 | Q148 | Q366 |
| 1273 | Q11 | Q144 | Q186 | Q148 | Q123 |
| 1274 | Q144 | Q144 | Q186 | Q148 | Q323 |

[Chemical formula 95]

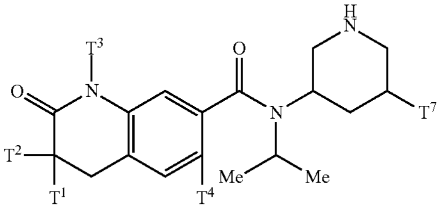

| No | $T^1$ | $T^2$ | $T^3$ | $T^4$ | $T^7$ |
|---|---|---|---|---|---|
| 1275 | Q468 | | Q183 | Q148 | Q223 |
| 1276 | Q144 | Q144 | Q186 | Q148 | Q204 |
| 1277 | Q149 | Q144 | Q183 | Q148 | Q210 |
| 1278 | Q144 | Q144 | Q183 | Q143 | Q212 |
| 1279 | Q149 | Q144 | Q186 | Q148 | Q227 |
| 1280 | Q144 | Q144 | Q183 | Q148 | Q228 |
| 1281 | Q547 | | Q427 | Q148 | Q219 |
| 1282 | Q144 | Q144 | Q445 | Q148 | Q220 |
| 1283 | Q144 | Q144 | Q427 | Q144 | Q219 |
| 1284 | Q2 | Q144 | Q445 | Q148 | Q221 |
| 1285 | Q182 | Q144 | Q427 | Q148 | Q205 |
| 1286 | Q144 | Q144 | Q427 | Q148 | Q195 |
| 1287 | Q103 | Q144 | Q427 | Q262 | Q234 |
| 1288 | Q2 | Q144 | Q186 | Q148 | Q235 |
| 1289 | Q144 | Q144 | Q186 | Q148 | Q200 |
| 1290 | Q547 | | Q183 | Q147 | Q314 |
| 1291 | Q144 | Q144 | Q186 | Q148 | Q307 |
| 1292 | Q285 | Q144 | Q183 | Q148 | Q322 |
| 1293 | Q144 | Q144 | Q183 | Q148 | Q327 |
| 1294 | Q144 | Q144 | Q186 | Q148 | Q344 |
| 1295 | Q11 | Q144 | Q183 | Q148 | Q368 |
| 1296 | Q468 | | Q427 | Q148 | Q376 |
| 1297 | Q144 | Q144 | Q445 | Q147 | Q353 |
| 1298 | Q144 | Q145 | Q427 | Q148 | Q361 |
| 1299 | Q144 | Q144 | Q445 | Q148 | Q338 |
| 1300 | Q468 | | Q427 | Q148 | Q349 |
| 1301 | Q144 | Q144 | Q427 | Q148 | Q318 |
| 1302 | Q176 | Q144 | Q427 | Q148 | Q366 |
| 1303 | Q11 | Q144 | Q186 | Q148 | Q123 |
| 1304 | Q144 | Q144 | Q186 | Q148 | Q323 |

In the above-mentioned Tables, the mnemonic symbols mean respectively a partial structure of the following partial formulae:

Q1:

[Chemical formula 96]

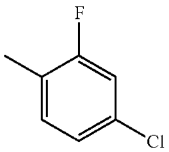

Q2:

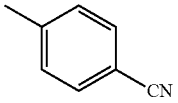

Q3:

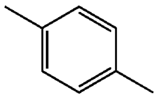

-continued

Q4:

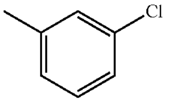

Q5:

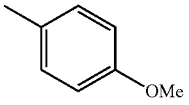

Q6:

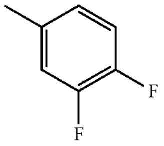

Q7:

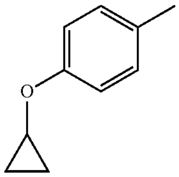

Q8:

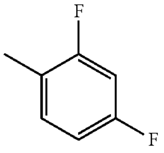

Q9:

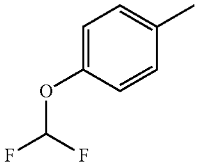

Q10:

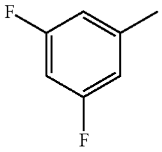

Q11:

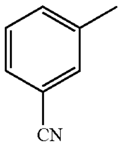

Q12:

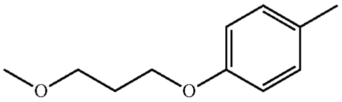

-continued
Q13:
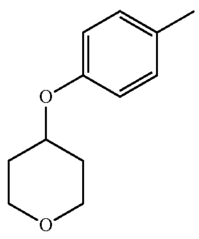
Q14:
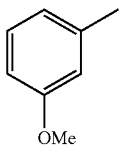
Q15:
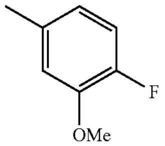
Q16:
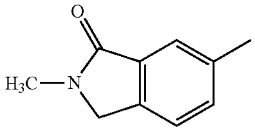
Q17:
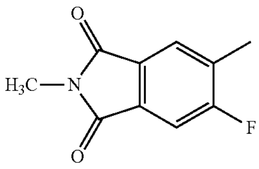
Q18:
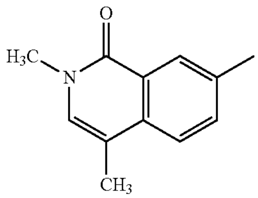
Q19:
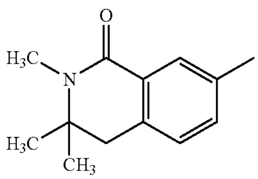
Q20:
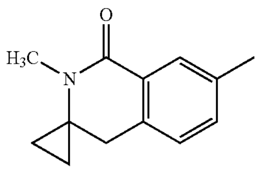
-continued
Q21:
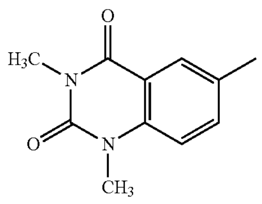
Q22:
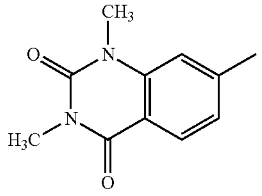
Q23:
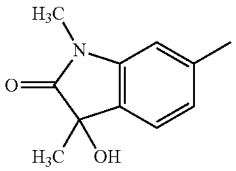
Q24:
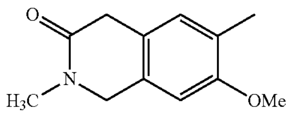
Q25:
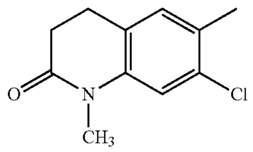
Q26:
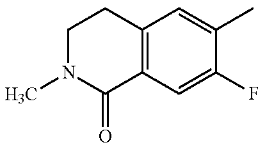
Q27:
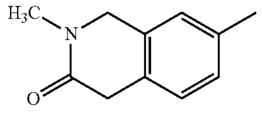
Q28:
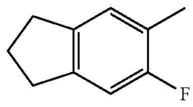
Q29:
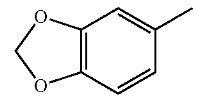

-continued
Q30:
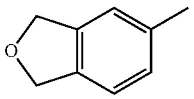
Q31:
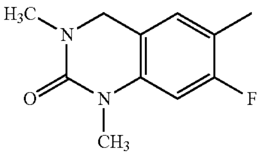
Q32:
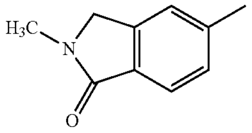
Q33:
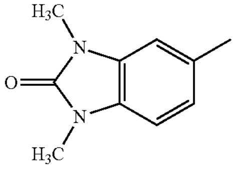
Q34:
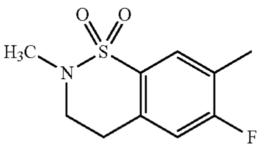
Q35:
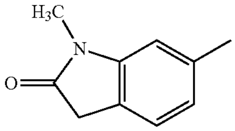
Q36:
[Chemical formula 97]
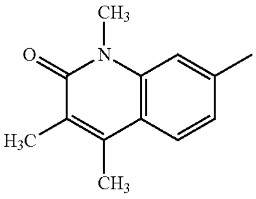
Q37:
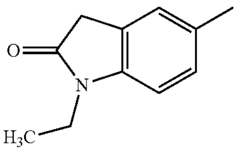
Q38:
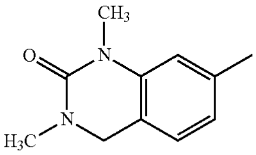
-continued
Q39:
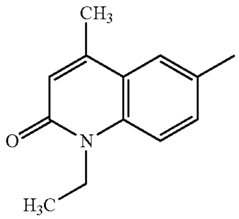
Q40:
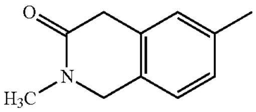
Q41:
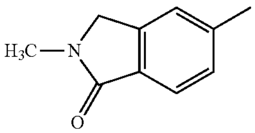
Q42:
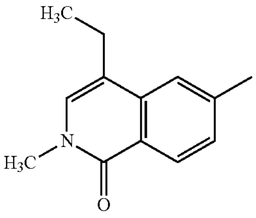
Q43:
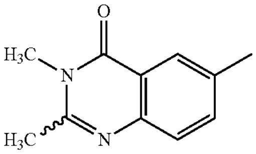
Q44:
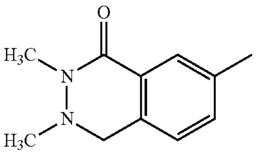
Q45:
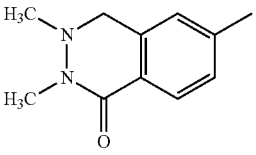
Q46:
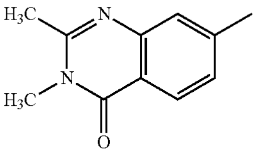

-continued
Q47:
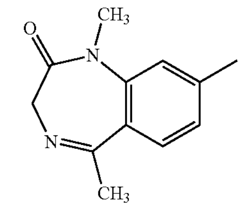
Q48:
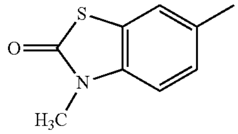
Q49:
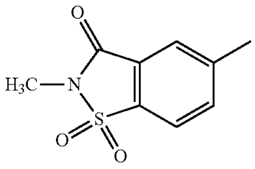
Q50:
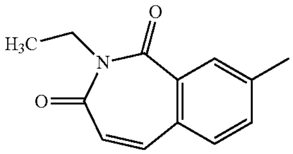
Q51:
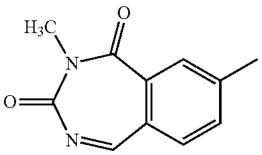
Q52:
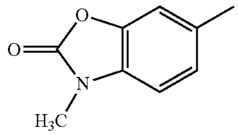
Q53:
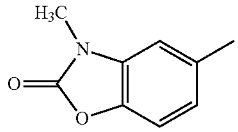
Q54:
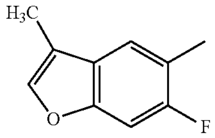
Q55:
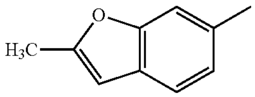
-continued
Q56:
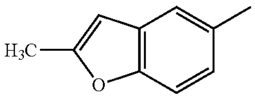
Q57:
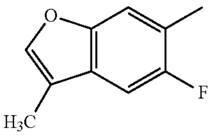
Q58:
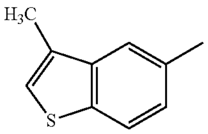
Q59:
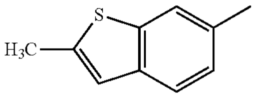
Q60:
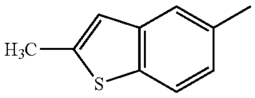
Q61:
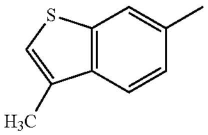
Q62:
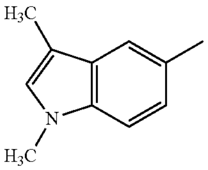
Q63:
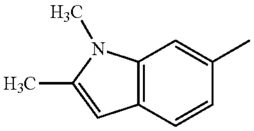
Q64:
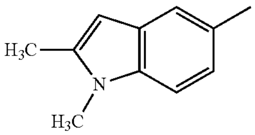
Q65:
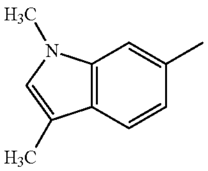

-continued
Q66:
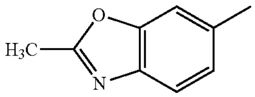
Q67:
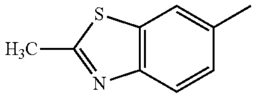
Q68:
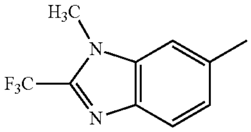
Q69:
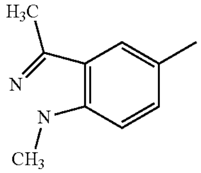
Q70:
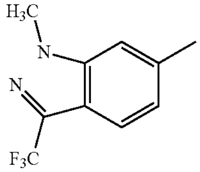
Q71:
[Chemical formula 98]
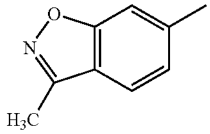
Q72:
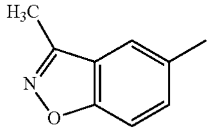
Q73:
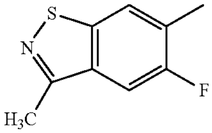
Q74:
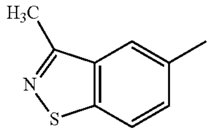
-continued
Q75:
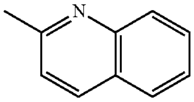
Q76:
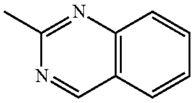
Q77:
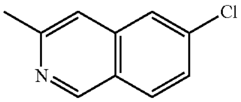
Q78:
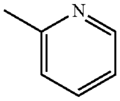
Q79:
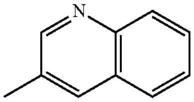
Q80:
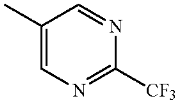
Q81:
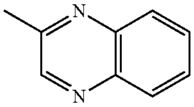
Q82:
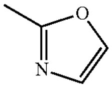
Q83:
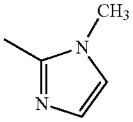
Q84:
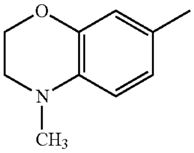
Q85:
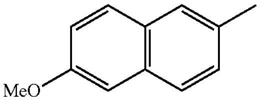

Q86:
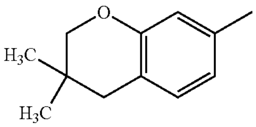
Q87:
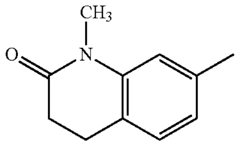
Q88:
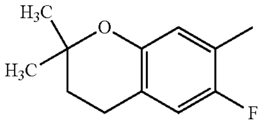
Q89:
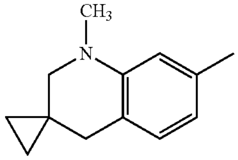
Q90:
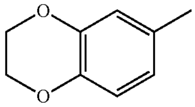
Q91:
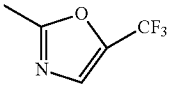
Q92:
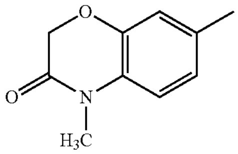
Q93:
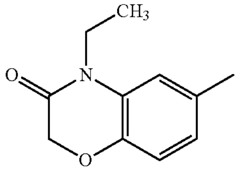
Q94:
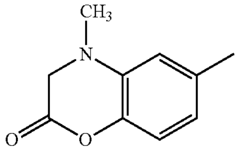
Q95:
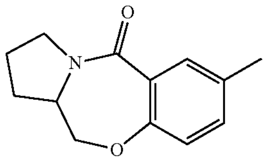
Q96:
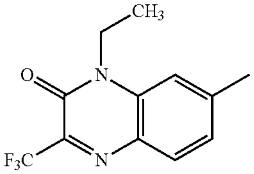
Q97:
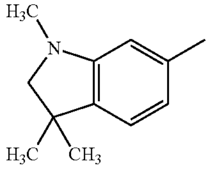
Q98:
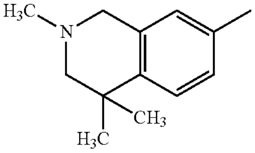
Q99:
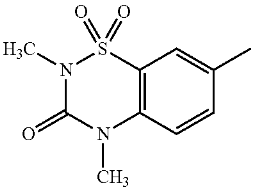
Q100:
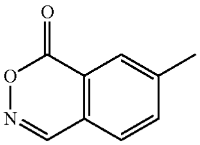
Q101:
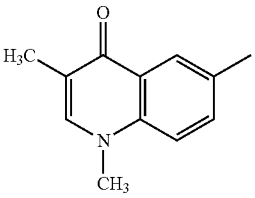
Q102:
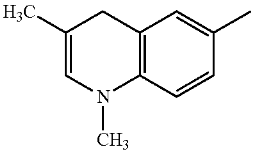

-continued
Q103:
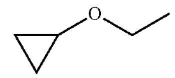
Q104:
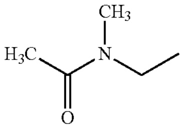
Q105:
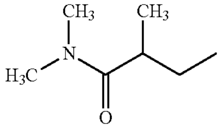
Q106:
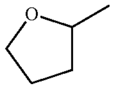
Q107:
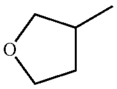
Q108:
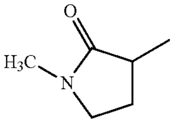
Q109:
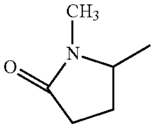
Q110:
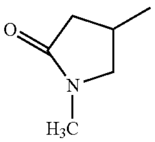
Q111:
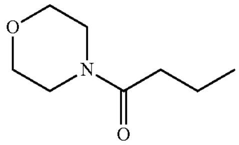
Q112:
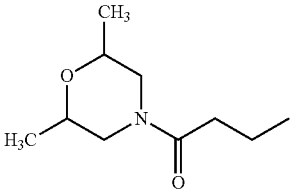
-continued
Q113:
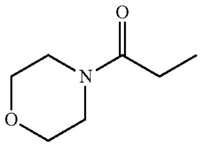
Q114:
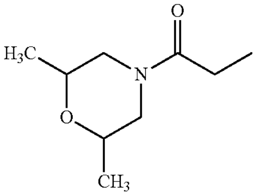
Q115:
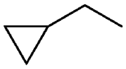
[Chemical formula 99]
Q116:
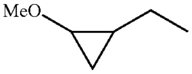
Q117:
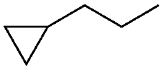
Q118:
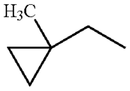
Q119:
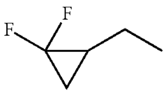
Q120:
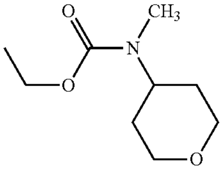
Q121:
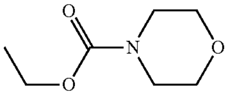
Q122:
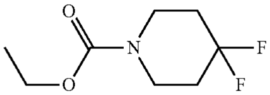
Q123:
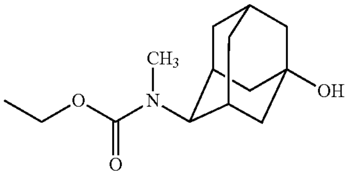

-continued
Q124:
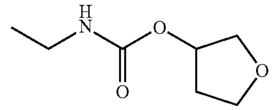
Q125:
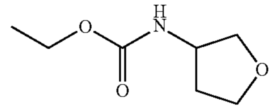
Q126:
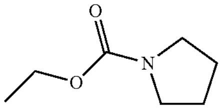
Q127:
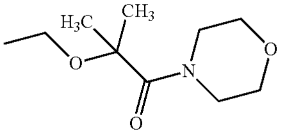
Q128:
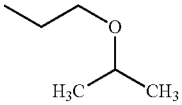
Q129:
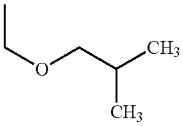
Q130:
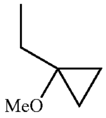
Q131:
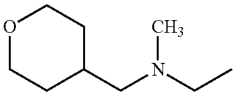
Q132:
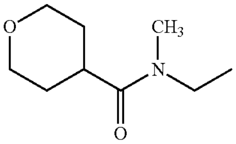
Q133:
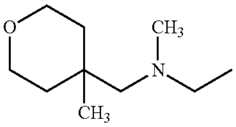
Q134:
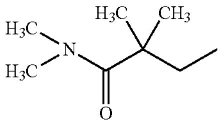
-continued
Q135:
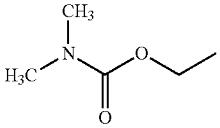
Q136:
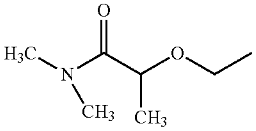
Q137:
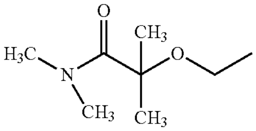
Q138:
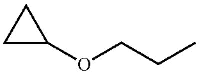
Q139:
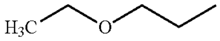
Q140:
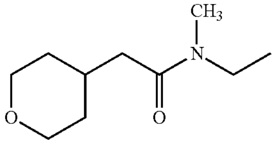
Q141:
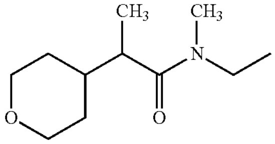
Q142:
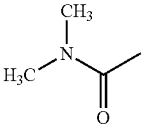
Q143:
CN
Q144:
Me
Q145:
Et
Q146:
[Chemical formula 100]
$FH_2C$
Q147:
$F_2HC$
Q148:
$F_3C$ -continued
Q149:
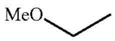
Q150:
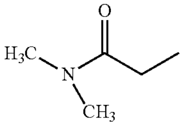
Q151:
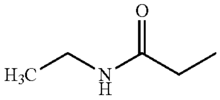
Q152:
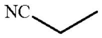
Q153:
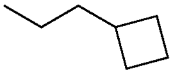
Q154:
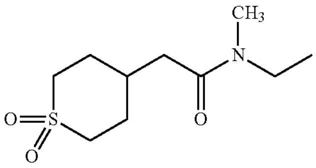
Q155:
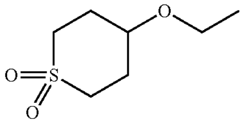
Q156:
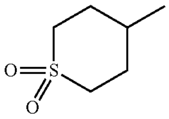
Q157:
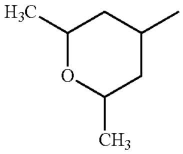
Q158:
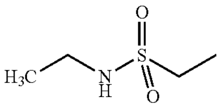
Q159:
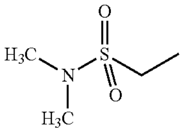
-continued
Q160:
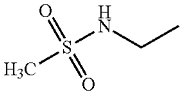
Q161:
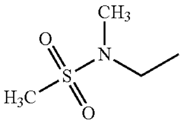
Q162:
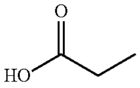
Q163:
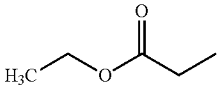
Q164:
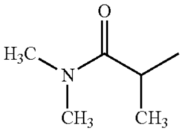
Q165:
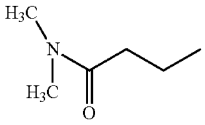
Q166:
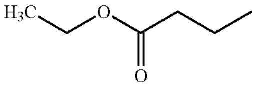
Q167:
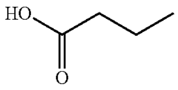
Q168:
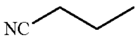
Q169:
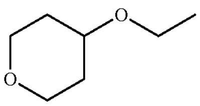
Q170:
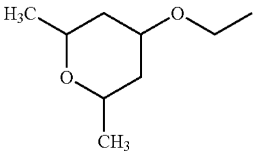

-continued
Q171:
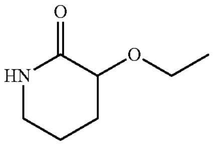
Q172:
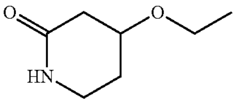
Q173:
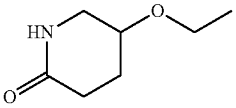
Q174:
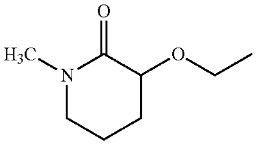
Q175:
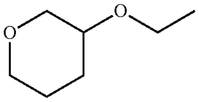
Q176:
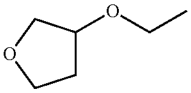
Q177:
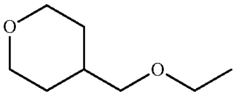
Q178:
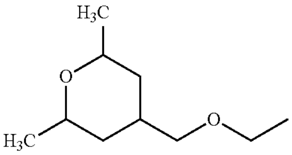
Q179:
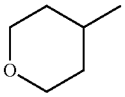
Q180:
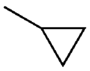
Q181:
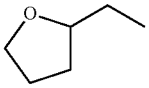
Q182:
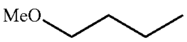
-continued
Q183:
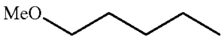
Q184:
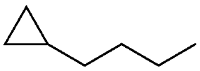
Q185:
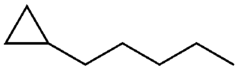
Q186:
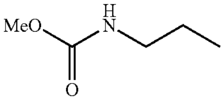
[Chemical formula 101]
Q187:
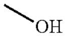
Q188:
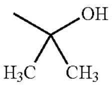
Q189:
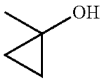
Q190:
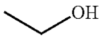
Q191:
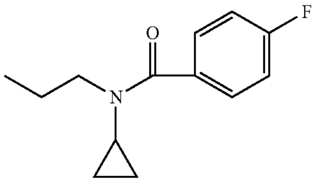
Q192:
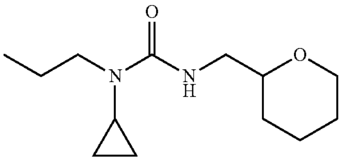
Q193:
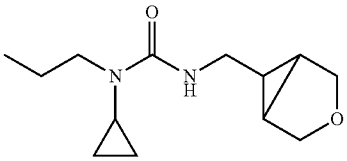
Q194:
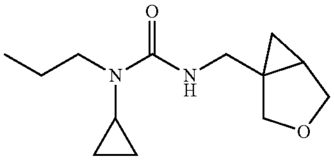

-continued
Q195:
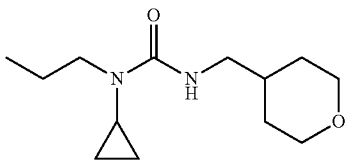
Q196:
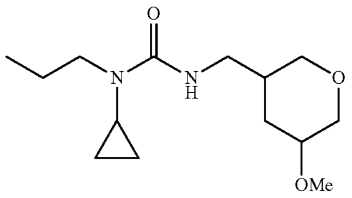
Q197:
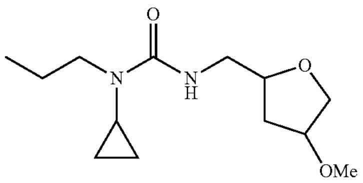
Q198:
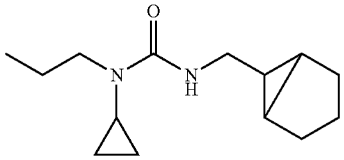
Q199:
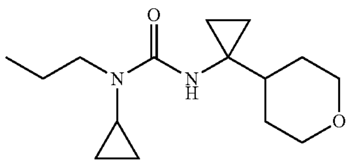
Q200:
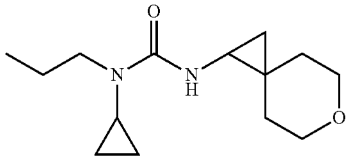
Q201:
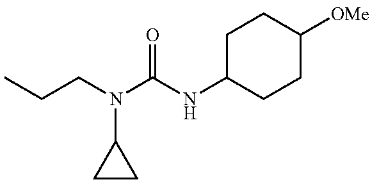
Q202:
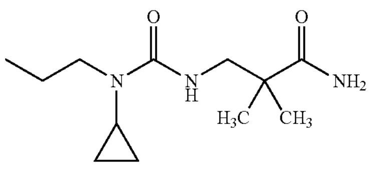
-continued
Q203:
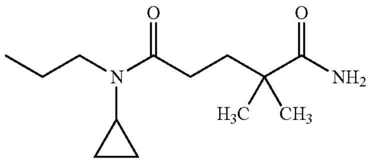
Q204:
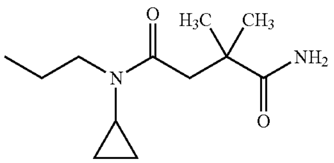
Q205:
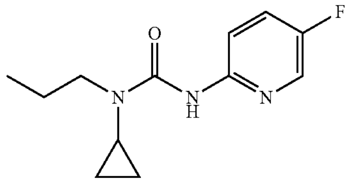
Q206:
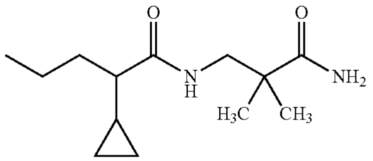
Q207:
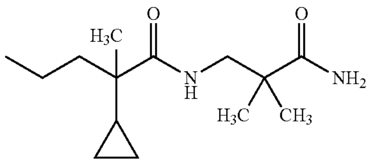
Q208:
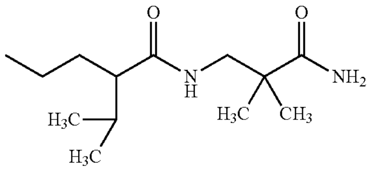
Q209:
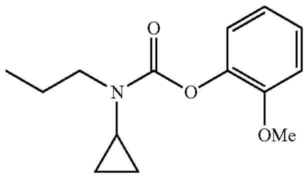
Q210:
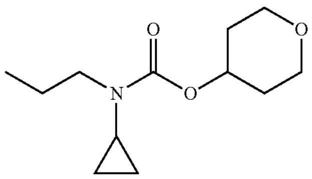

-continued
Q211:
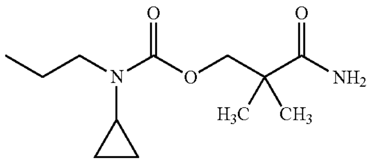
Q212:
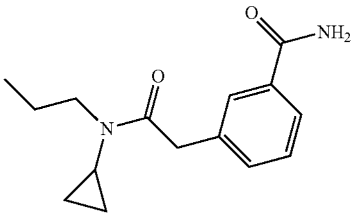
Q213:
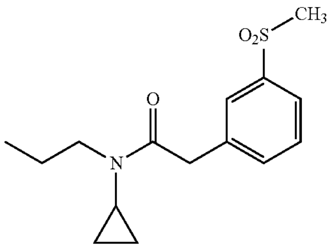
Q214:
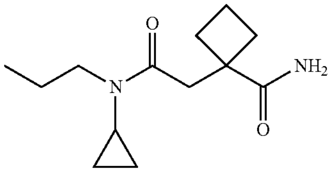
Q215:
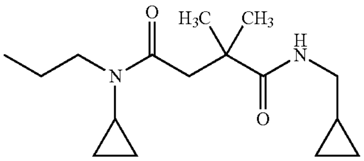
Q216:
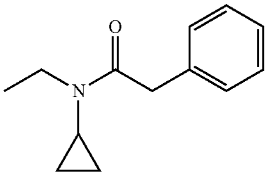
Q217:
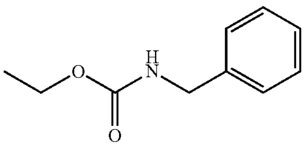
Q218:
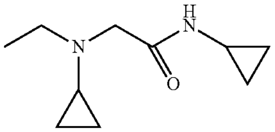
-continued
Q219:
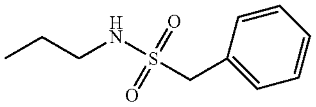
Q220:
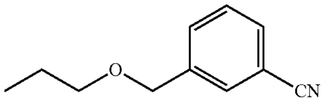
Q221:
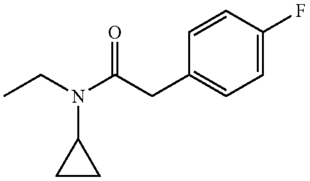
Q222:
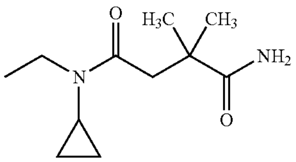
Q223:
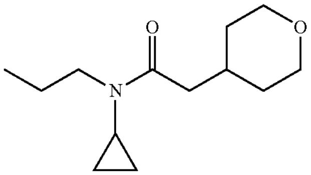
Q224:
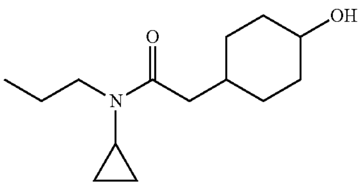
Q225:
[Chemical formula 102]
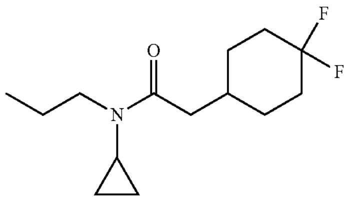
Q226:
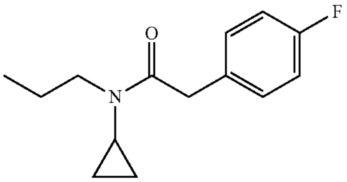

-continued
Q227:
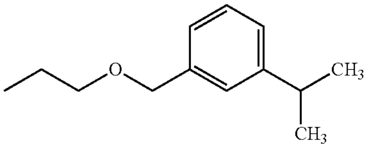
Q228:
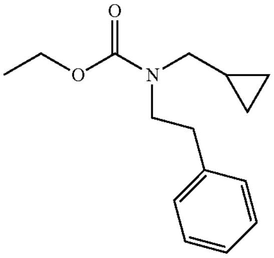
Q229:
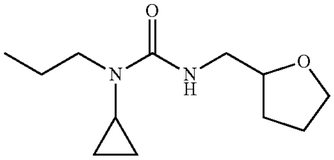
Q230:
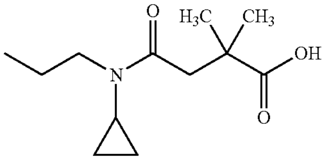
Q231:
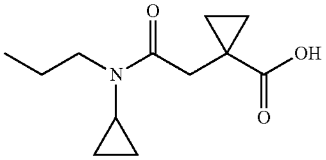
Q232:
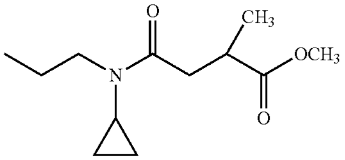
Q233:
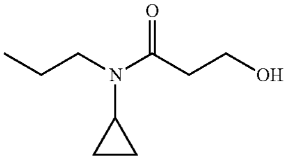
Q234:
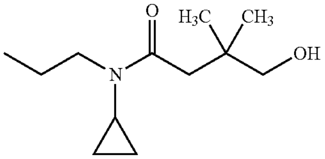
-continued
Q235:
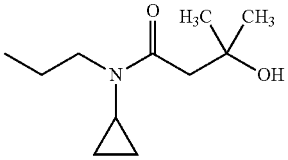
Q236:
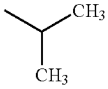
Q237:
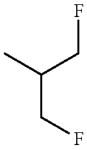
Q238:
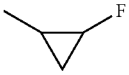
Q239:
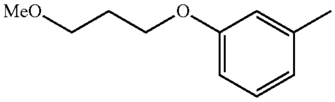
Q240:
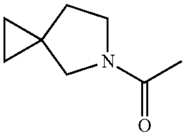
Q241:
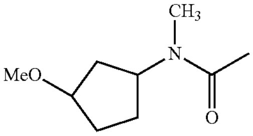
Q242:
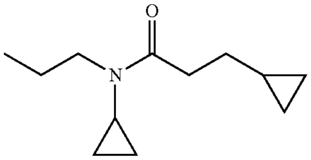
Q243:
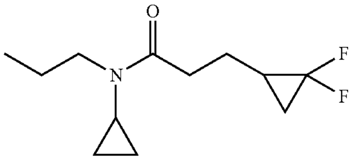
Q244:
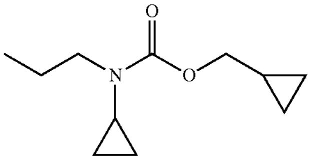

-continued
Q245:
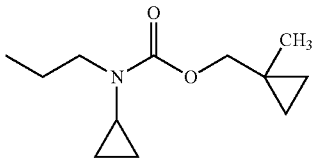
Q246:
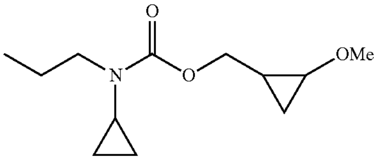
Q247:
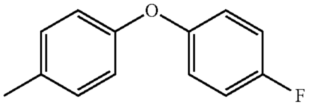
Q248:
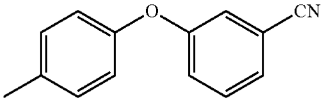
Q249:
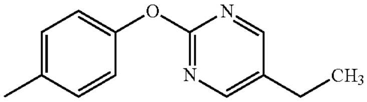
Q250:
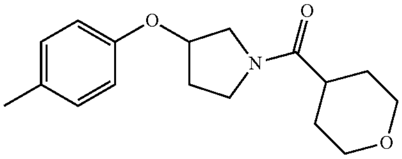
Q251:
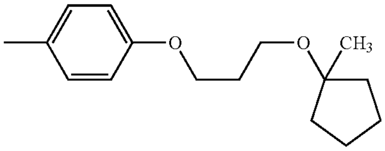
Q252:
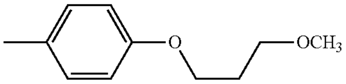
Q253:
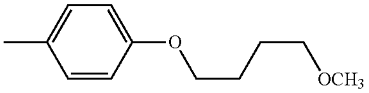
Q254:
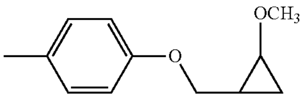
-continued
Q255:
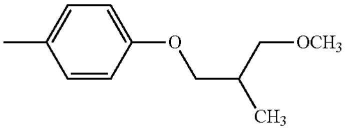
Q256:
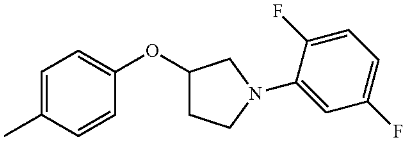
Q257:
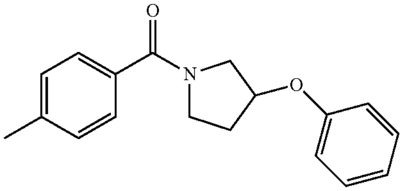
Q258:
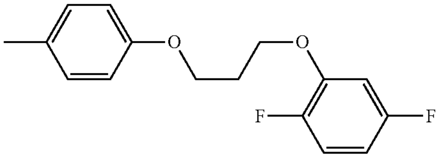
Q259:
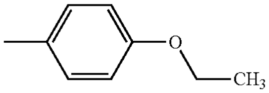
Q260:
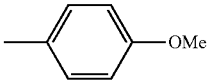
Q261:
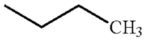
Q262:
Cl
Q263:
Br
Q264:
[Chemical formula 103]
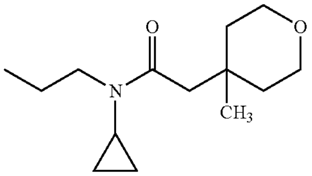
Q265:
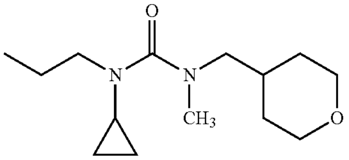

-continued
Q266:
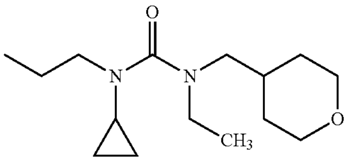
Q267:
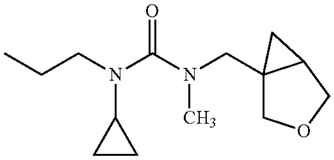
Q268:
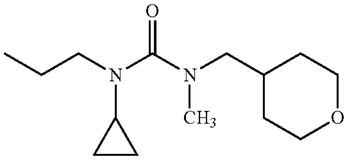
Q269:
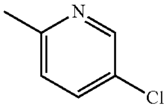
Q270:
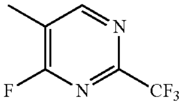
Q271:
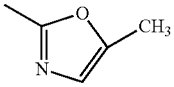
Q272:
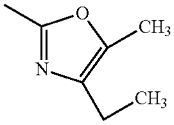
Q273:
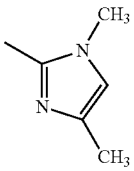
Q274:
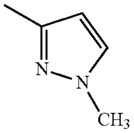
-continued
Q275:
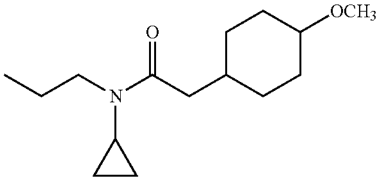
Q276:
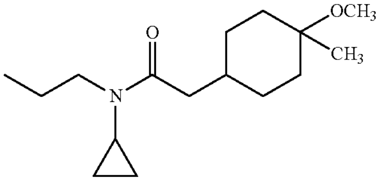
Q277:
OMe
Q278:
OEt
Q279:
$OCHF_2$
Q280:
$OCF_3$
Q281:
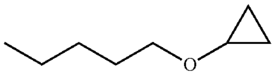
Q282:
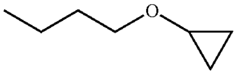
Q283:
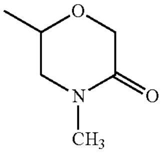
Q284:
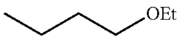
Q285:
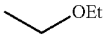
Q286:
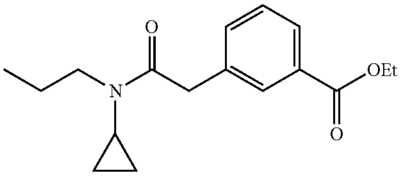

-continued
Q287:
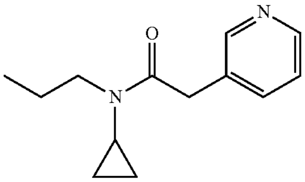
Q288:
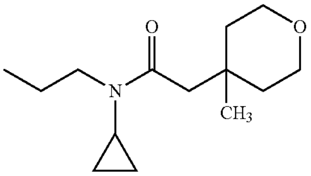
Q289:
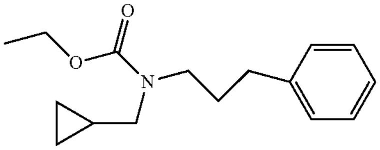
Q290:
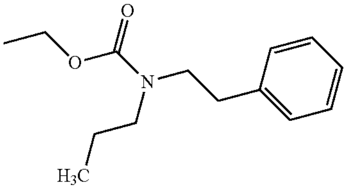
Q291:
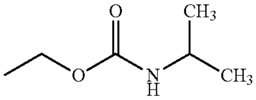
Q292:
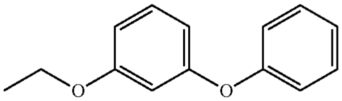
Q293:
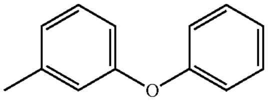
Q294:
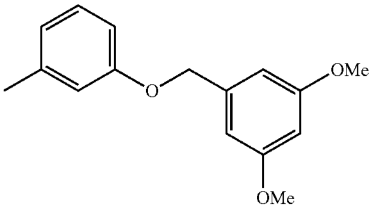
Q295:
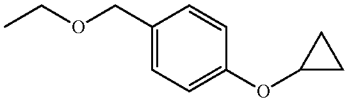
-continued
Q296:
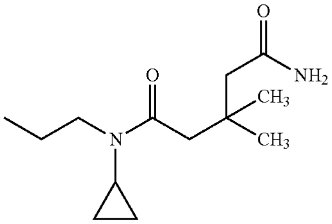
Q297:
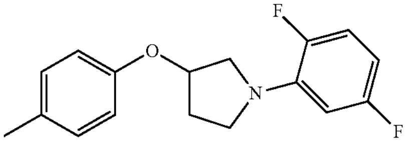
Q298:
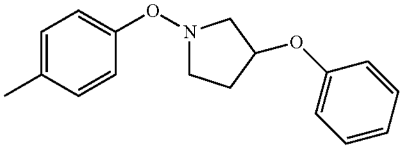
Q299:
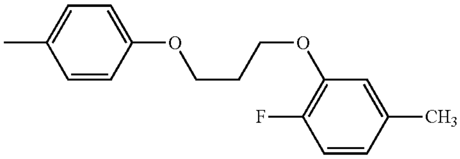
Q300:
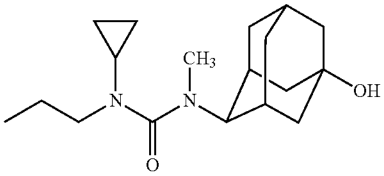
Q301:
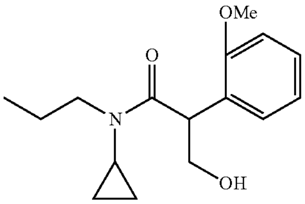
Q302:
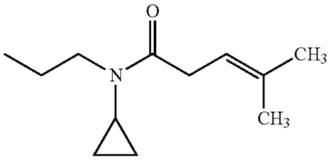

-continued
Q303:
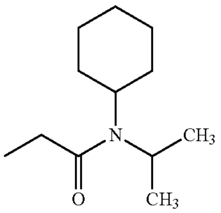
Q304:
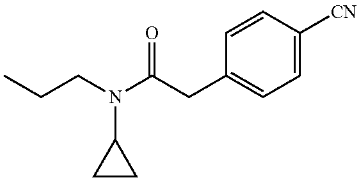
Q305:
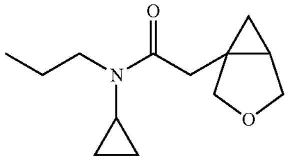
Q306:
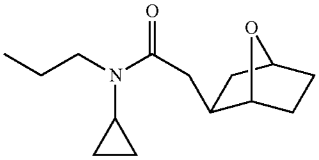
Q307:
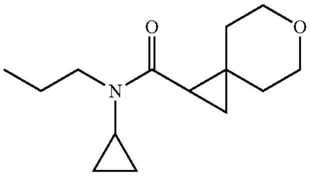
Q308:
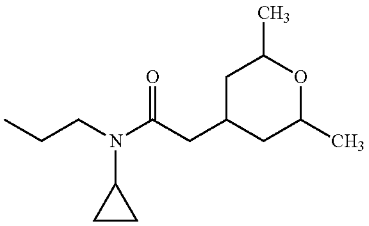
Q309:
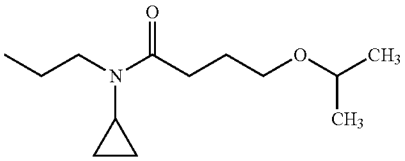
Q310:
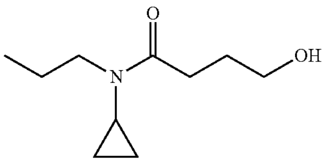
-continued
Q311:
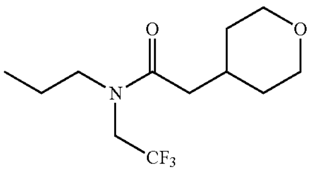
Q312:
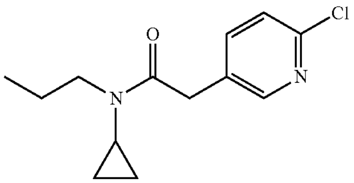
Q313:
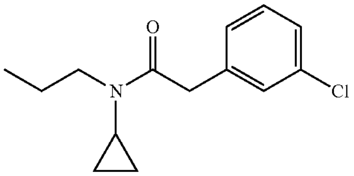
Q314:
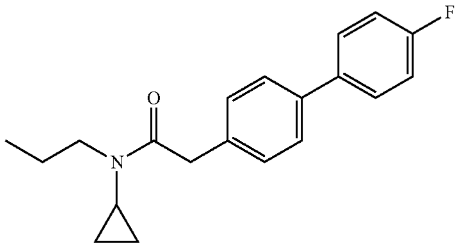
Q315:
[Chemical formula 104]
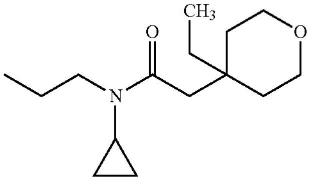
Q316:
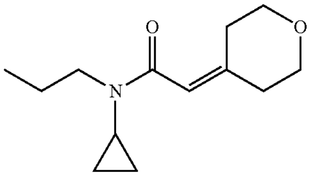
Q317:
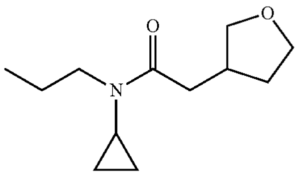

-continued
Q318:
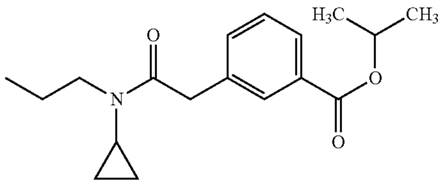
Q319:
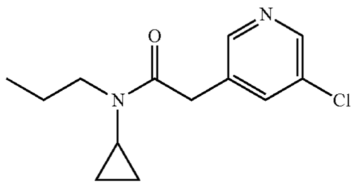
Q320:
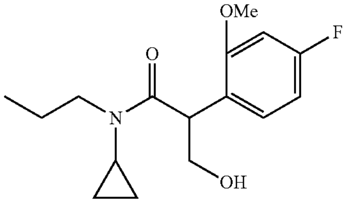
Q321:
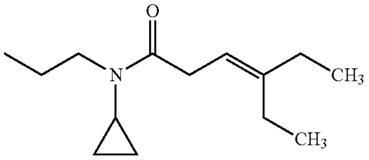
Q322:
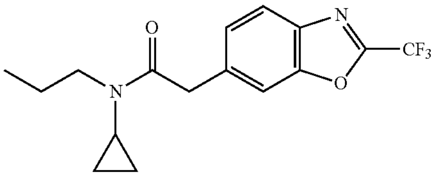
Q323:
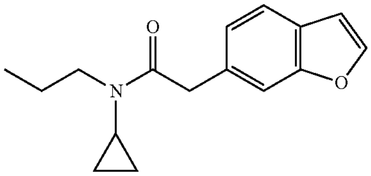
Q324:
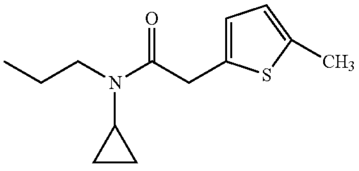
Q325:
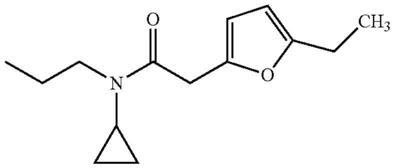
-continued
Q326:
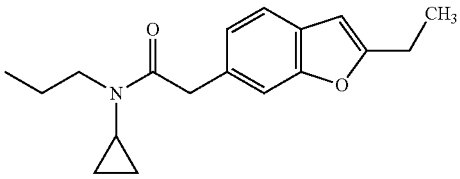
Q327:
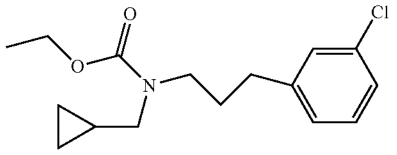
Q328:
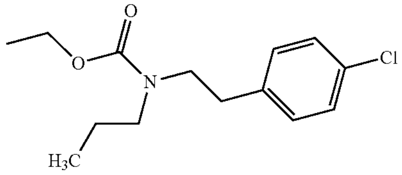
Q329:
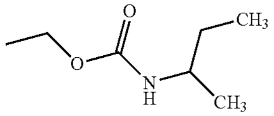
Q330:
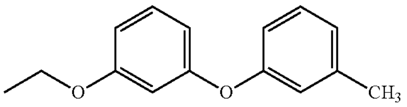
Q331:
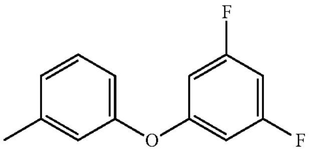
Q332:
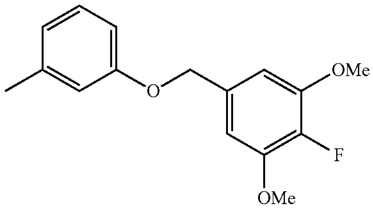
Q333:
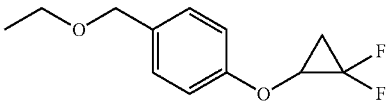

-continued
Q334:
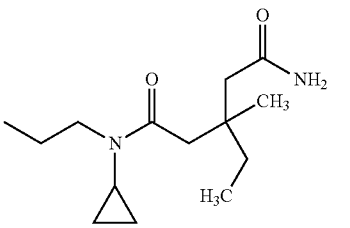
Q335:
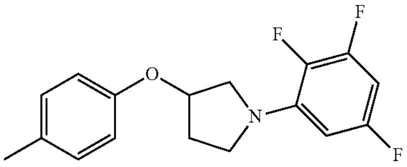
Q336:
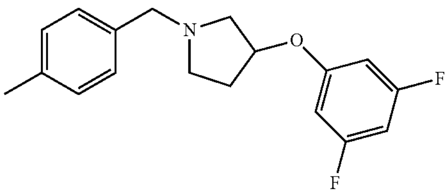
Q337:
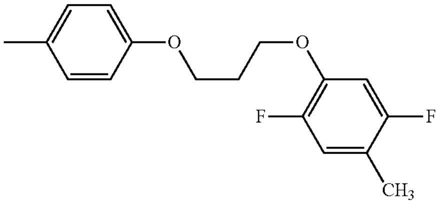
Q338:
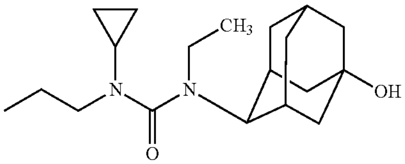
Q339:
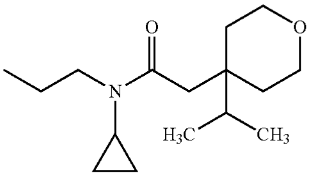
Q340:
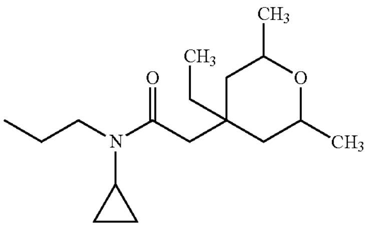
-continued
Q341:
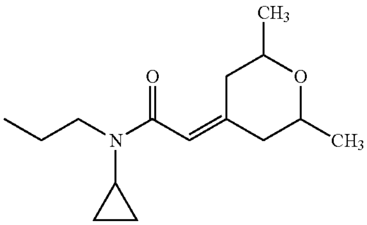
Q342:
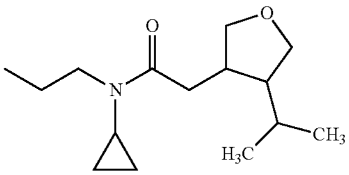
Q343:
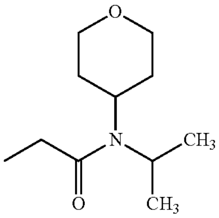
Q344:
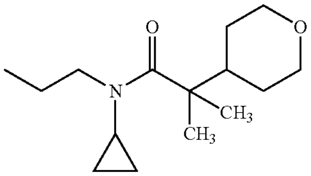
Q345:
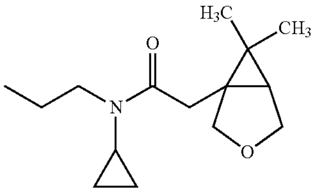
Q346:
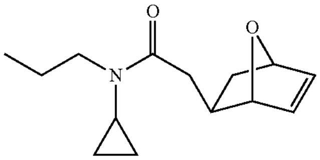
Q347:
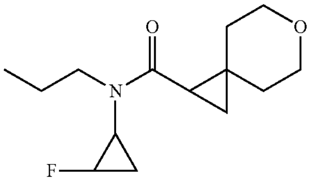

-continued
Q348:
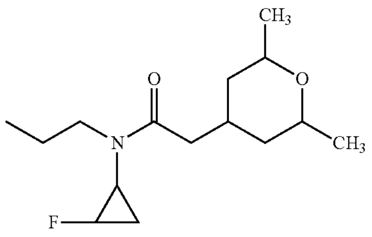
Q349:
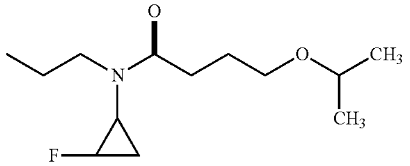
Q350:
[Chemical formula 105]
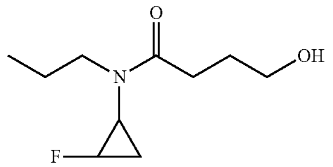
Q351:
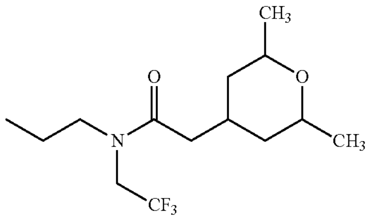
Q352:
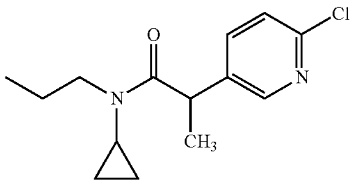
Q353:
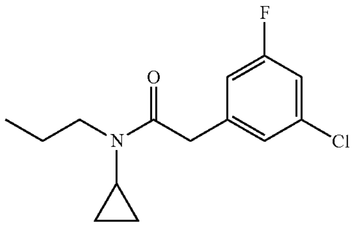
-continued
Q354:
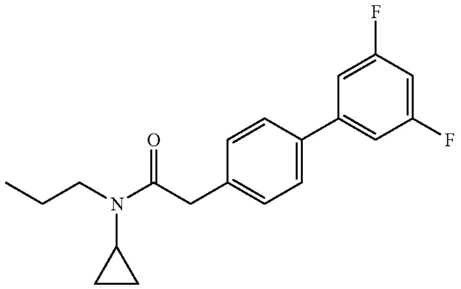
Q355:
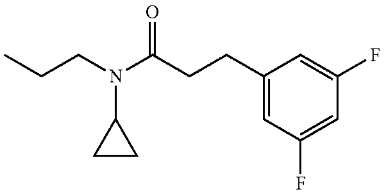
Q356:
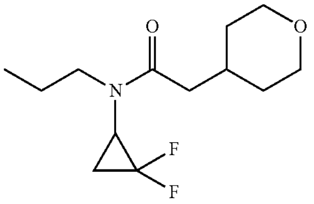
Q357:
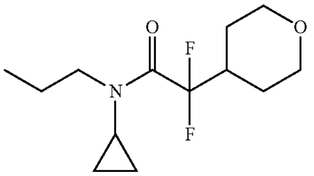
Q358:
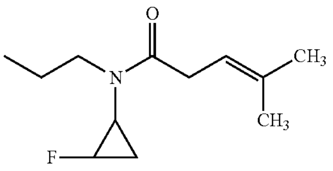
Q359:
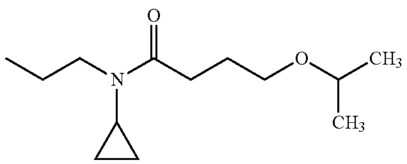
Q360:
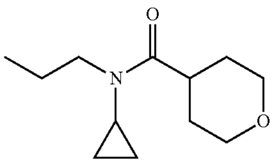

-continued
Q361:
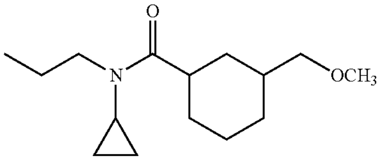
Q362:
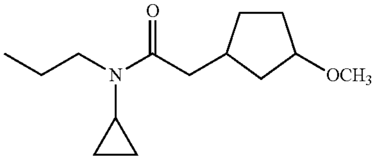
Q363:
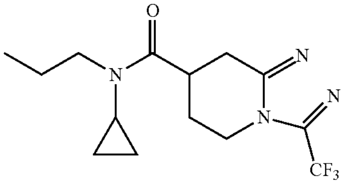
Q364:
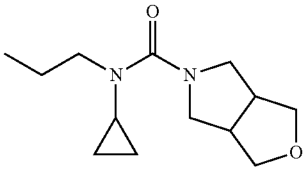
Q365:
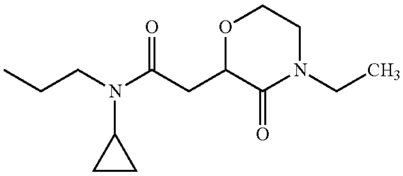
Q366:
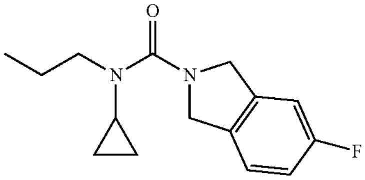
Q367:
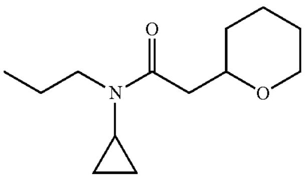
Q368:
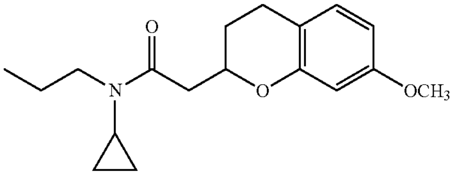
-continued
Q369:
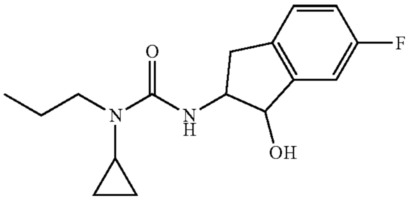
Q370:
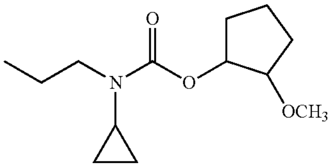
Q371:
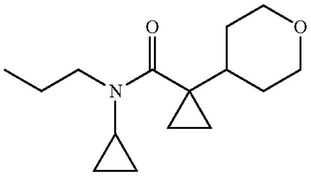
Q372:
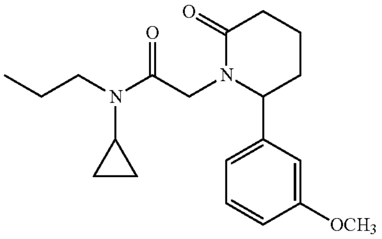
Q373:
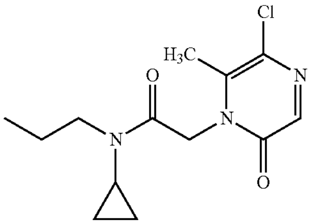
Q374:
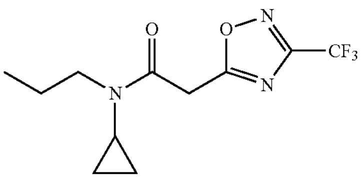
Q375:
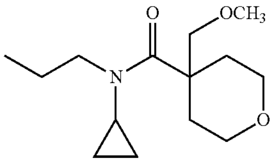

Q376:
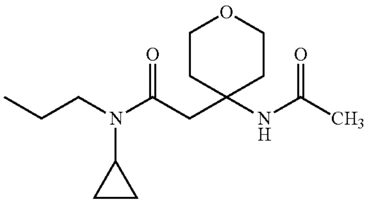
Q377:
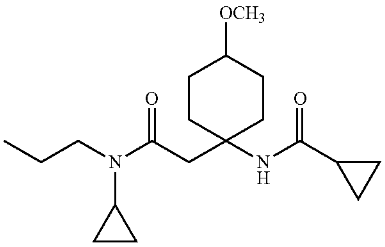
Q378:
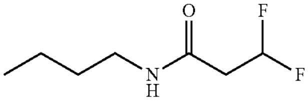
Q379:
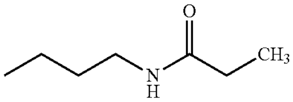
Q380:
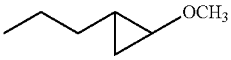
Q381:
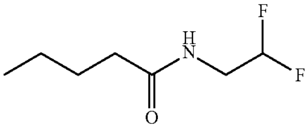
Q382:
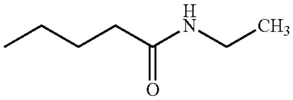
Q383:
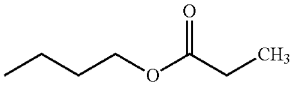
Q384:
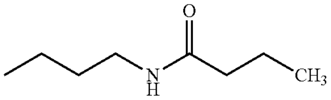
Q385:
[Chemical formula 106]
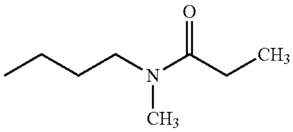
Q386:
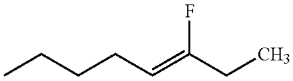
Q387:
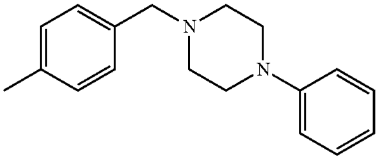
Q388:
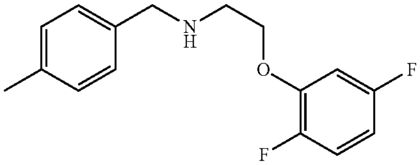
Q389:
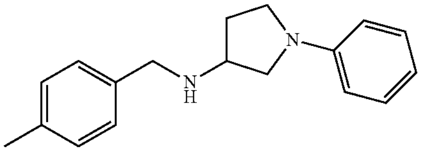
Q390:
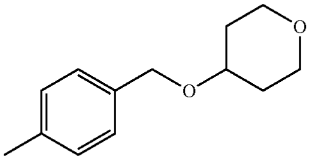
Q391:
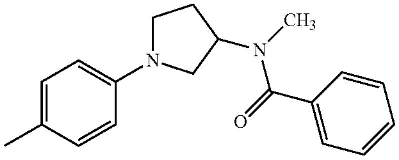
Q392:
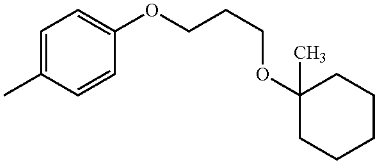
Q393:
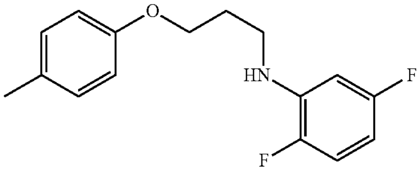
Q394:
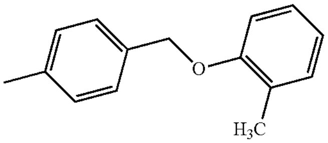

-continued
Q395:
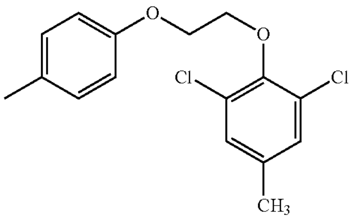
Q396:
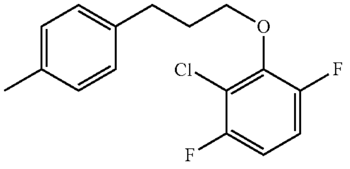
Q397:
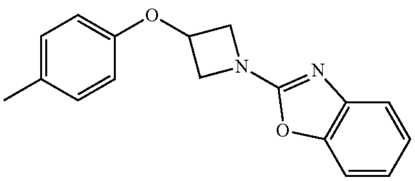
Q398:
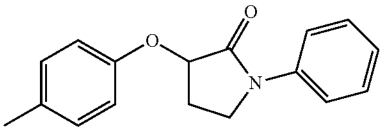
Q399:
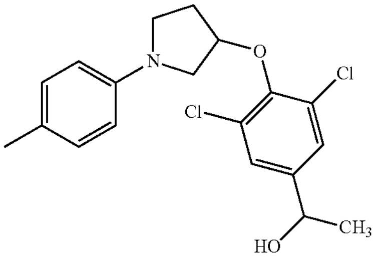
Q400:
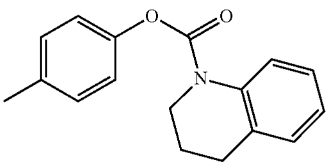
Q401:
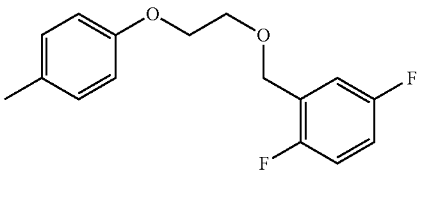
-continued
Q402:
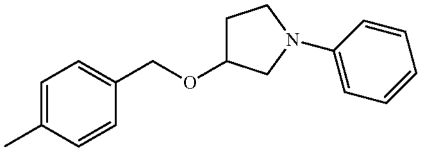
Q403:
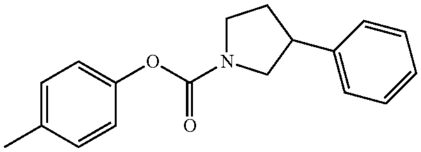
Q404:
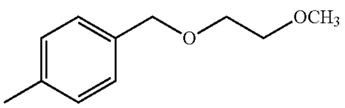
Q405:
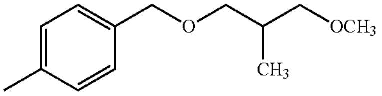
Q406:
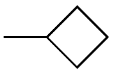
Q407:
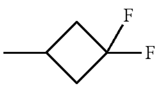
Q408:
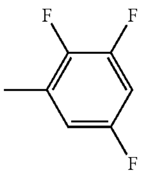
Q409:
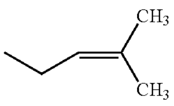
Q410:
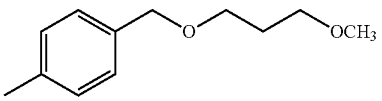
Q411:
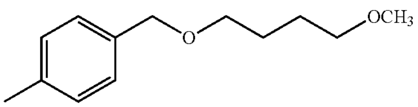
Q412:
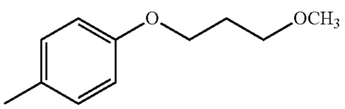

-continued
Q413:
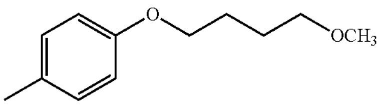
Q414:
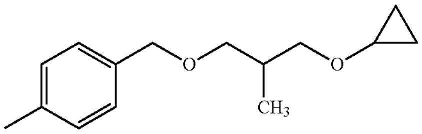
Q415:
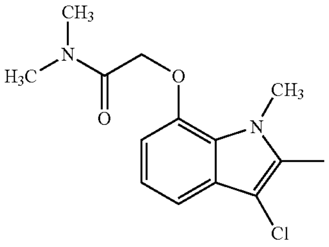
Q416:
[Chemical formula 107]
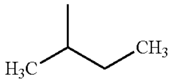
Q417:
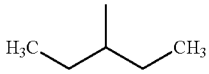
Q418:
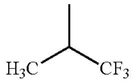
Q419:
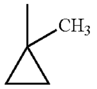
Q420:
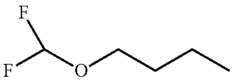
Q421:
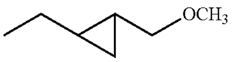
Q422:
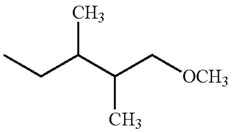
Q423:
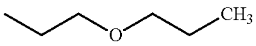
Q424:
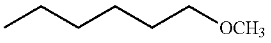
-continued
Q425:
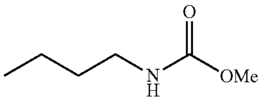
Q426:
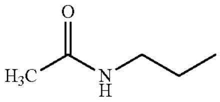
Q427:
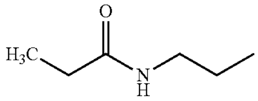
Q428:
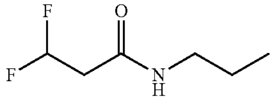
Q429:
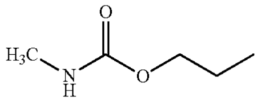
Q430:
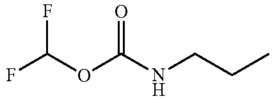
Q431:
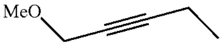
Q432:
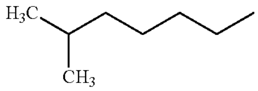
Q433:
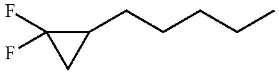
Q434:
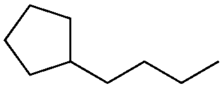
Q435:
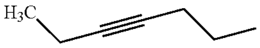
Q436:
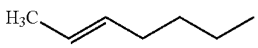
Q437:
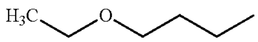
Q438:
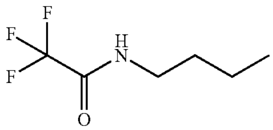

-continued
Q439:
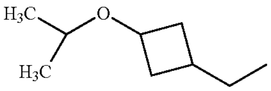
Q440:
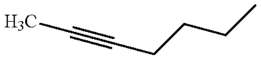
Q441:
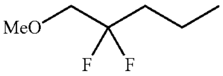
Q442:
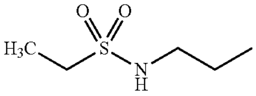
Q443:
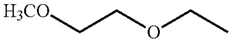
Q444:
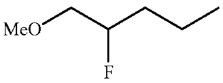
Q445:
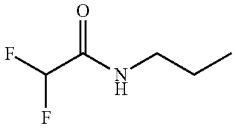
Q446:
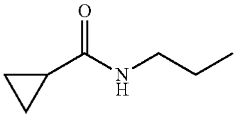
Q447:
[Chemical formula 108]
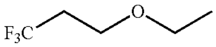
Q448:
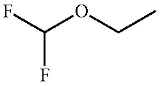
Q449:
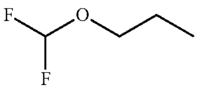
Q450:
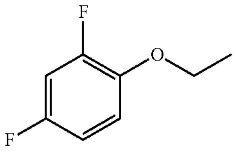
Q451:
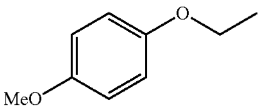
-continued
Q452:
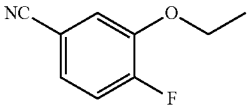
Q453:
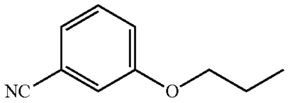
Q454:
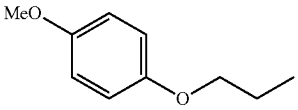
Q455:
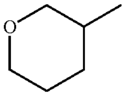
Q456:
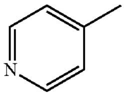
Q457:
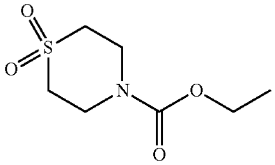
Q458:
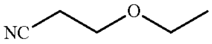
Q459:
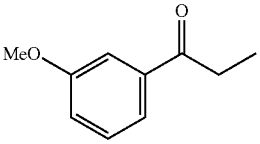
Q460:
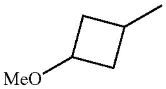
Q461:
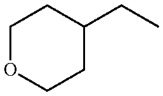
Q462:
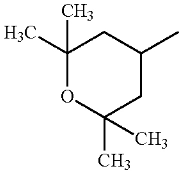

-continued
Q463:
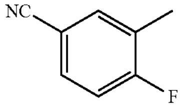
Q464:
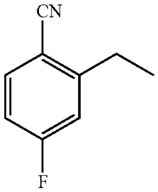
Q465:
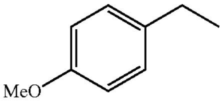
Q466:
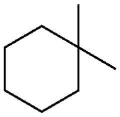
Q467:
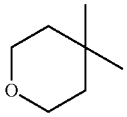
Q468:
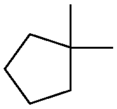
Q469:
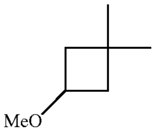
Q470:
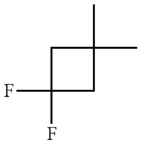
Q471:
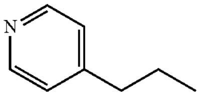
Q472:
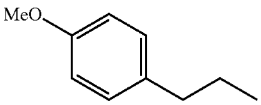
Q473:
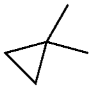
-continued
Q474:
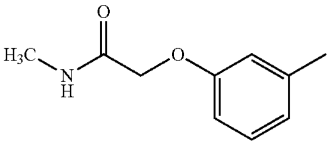
Q475:
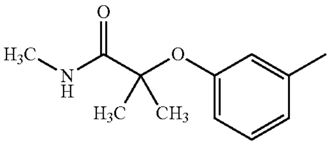
Q476:
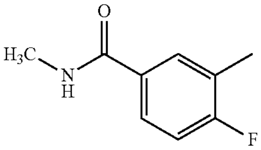
Q477:
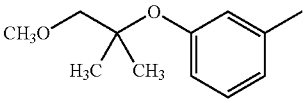
Q478:
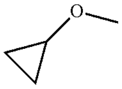
Q479:
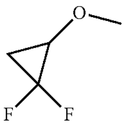
Q480:
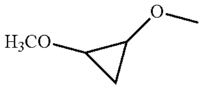
Q481:
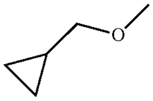
Q482:
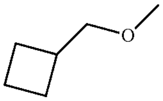
[Chemical formula 109]
Q483:
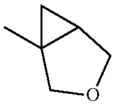
Q484:
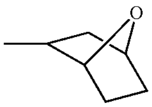

-continued
Q485:
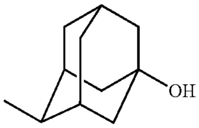
Q486:
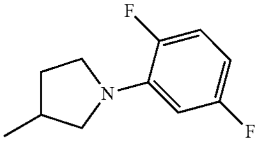
Q487:
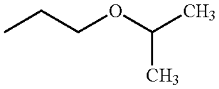
Q488:
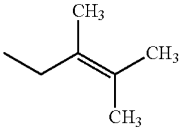
Q489:
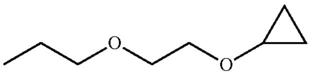
Q490:
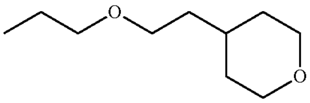
Q491:
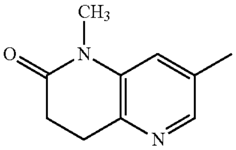
Q492:
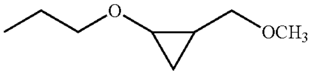
Q493:
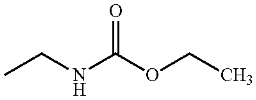
Q494:
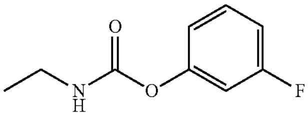
Q495:
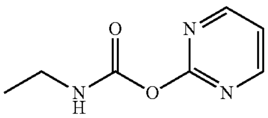
-continued
Q496:
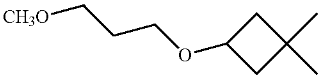
Q497:
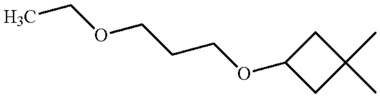
Q498:
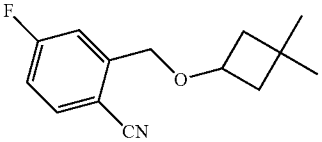
Q499:
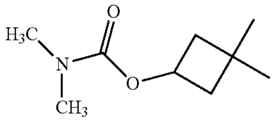
Q500:
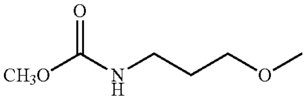
Q501:
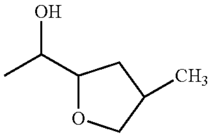
Q502:
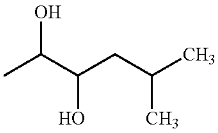
Q503:
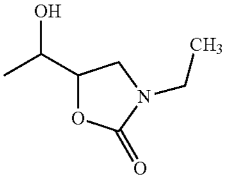
Q504:
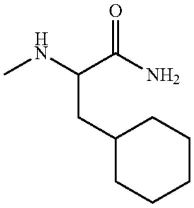

-continued
Q505:
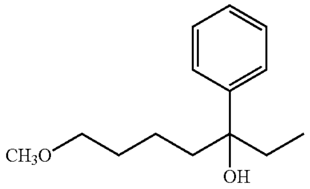
Q506:
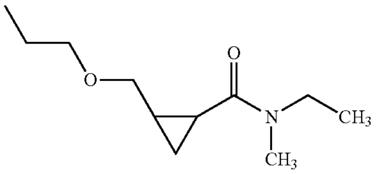
Q507:
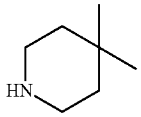
Q508:
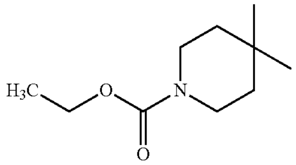
Q509:
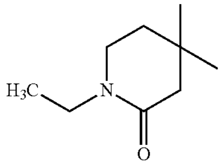
Q510:
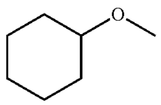
Q511:
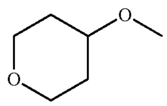
Q512:
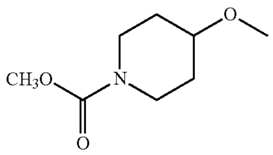
Q513:
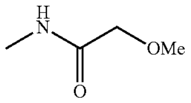
-continued
Q514:
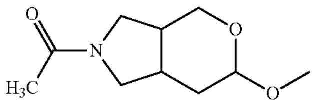
Q515:
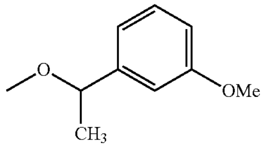
Q516:
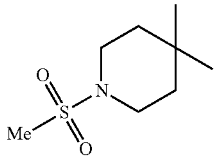
Q517:
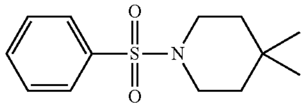
Q518:
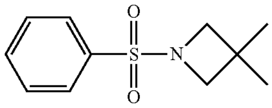
Q519:
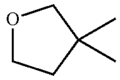
Q520:
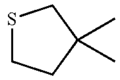
Q521:
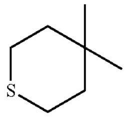
Q522:
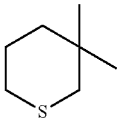
Q523:
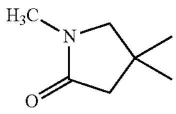
Q524:
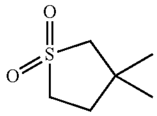

-continued
Q525:
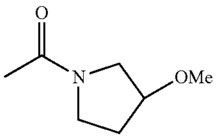
Q526:
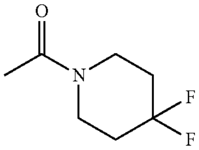
Q527:
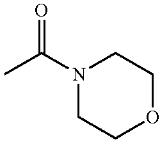
Q528:
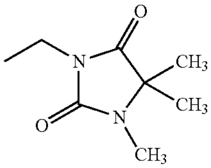
[Chemical formula 110]
Q529:
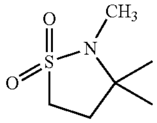
Q530:
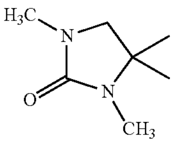
Q531:
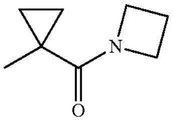
Q532:
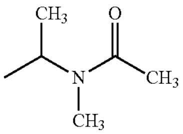
Q533:
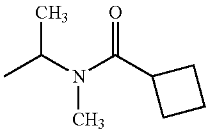
-continued
Q534:
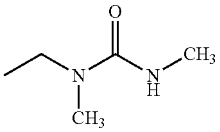
Q535:
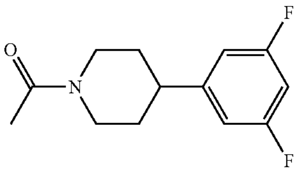
Q536:
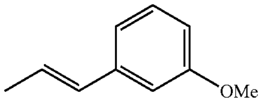
Q537:
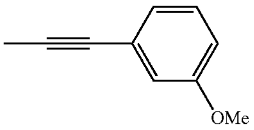
Q538:
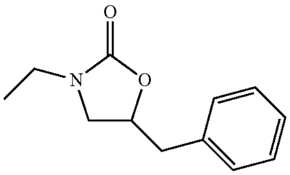
Q539:
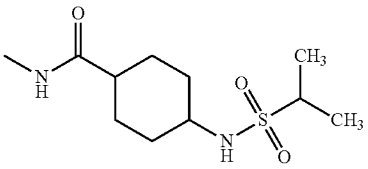
Q540:
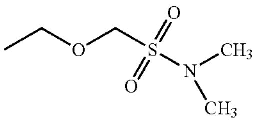
Q541:
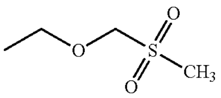
Q542:
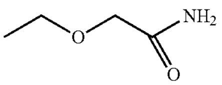
Q543:
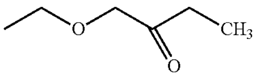

-continued

Q544:

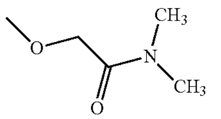

Q545:

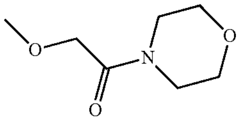

Q546:

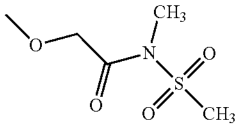

Q547:

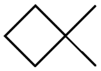

Q548:

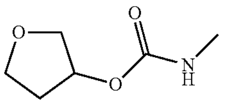

The process for preparing the compound of the formula (I) of the present invention will be illustrated herein below by Examples, but the present invention should not be construed to be limited thereto. In addition, in order to simplify the description of the present invention, the following abbreviations may be used in the present specification.

Boc: tert-butoxycarbonyl group
Cbz: benzyloxycarbonyl group
TMS: trimethylsilyl group
TBS: tert-butyldimethylsilyl group
SEM: 2-[(trimethylsilyl)ethoxy]methyl group
Ac: acetyl group
Me: methyl group
Et: ethyl group
Pr: propyl group
i-Pr: isopropyl group
Bu: butyl group
i-Bu: isobutyl group
t-Bu: tert-butyl group
Ph: phenyl group
Bn: benzyl group
Ms: methanesulfonyl group
TFA: trifluoroacetic acid
Alloc: allyloxycarbonyl group
Tf: trifluoromethanesulfonate The compound of the formula (I) may be synthesized from the well-known compound by a combination of the well-known methods, for example, by the following Methods. In addition, the compound of the formula (I) may be synthesized by suitably combining the following Methods depending on the kinds of the starting compounds.

Method 1

The compound of the formula (I) or a salt thereof may be prepared, for example, by the following method.

[Chemical formula 111]

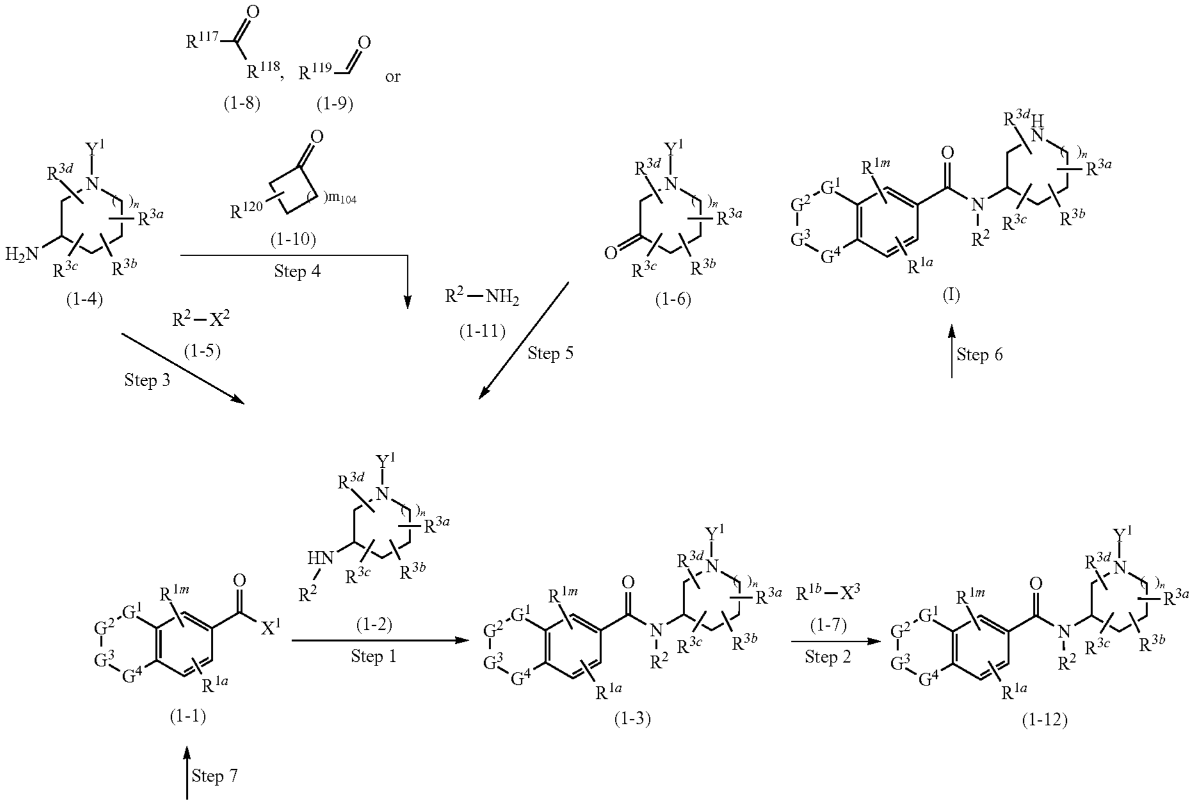

-continued

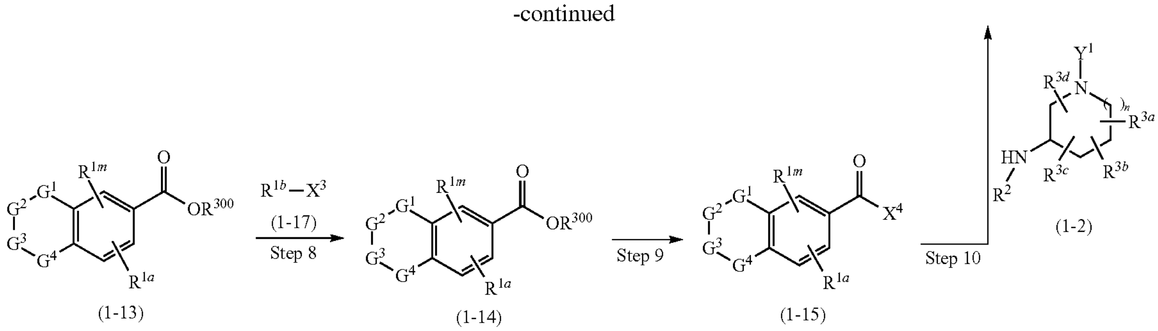

(1-13) (1-14) (1-15) (1-2)

[wherein n, $G^1$, $G^2$, $G^3$, $G^4$, $R^{1a}$, $R^{1m}$, $R^{3a}$, $R^{3b}$, $R^{3c}$, $R^{3d}$ and $R^2$ are the same as defined in the above-mentioned Item 1, $R^{300}$ is a $C_{1-6}$ alkyl group, $X^1$ is a hydroxy group or a chlorine atom, $X^2$ is an iodine atom, a bromine atom, a chlorine atom, a methanesulfonyloxy group, a trifluoromethanesulfonyloxy group or a p-toluenesulfonyloxy group, $X^3$ is an iodine atom, a methanesulfonyloxy group, a bromine atom or a trifluoromethanesulfonyloxy group, $X^4$ is a hydroxy group or a chlorine atom, $R^{120}$ is a fluorine atom or a $C_{1-3}$ alkoxy group, $m^{104}$ is an integer of 0, 1, 2, or 3, $Y^1$ is Cbz, Boc or Alloc]

1) Step 1

When $X^1$ is a hydroxy group, then the compound of the formula (1-3) may be synthesized by reacting the compound of the formula (1-1) in an inert solvent with the compound of the formula (1-2) in the presence of a condensing agent and, if necessary, in the presence of a base. In this reaction, a phase-transfer catalyst may occasionally be used.

The base may be any conventional ones which are usually used as a base in conventional reactions and is not necessarily defined, and includes, for example, organic bases such as N-methylmorpholine, triethylamine, diisopropylethylamine, tributylamine, 1,8-diazabicyclo[5.4.0]undec-7-ene, 1,5-diazabicyclo[4.3.0]nona-5-ene, 1,4-diazabicyclo[5.4.0]undec-7-ene, pyridine, dimethylaminopyridine, or picoline, etc., or inorganic bases such as sodium hydrogen carbonate, potassium hydrogen carbonate, sodium carbonate, potassium carbonate, sodium hydroxide, or sodium hydride, etc. The phase-transfer catalyst includes, for example, quaternary ammonium salts such as tetrabutylammonium bromide or benzyltriethylammonium bromide, etc. or crown ethers such as 18-crown-6-ether, etc.

The condensing agent may be ones as described in Jikken-Kagaku-Koza (edited by Chemical Society of Japan, Maruzen), vol. 22.

The inert solvent includes, for example, ethers such as tetrahydrofuran, diethyl ether, 1,4-dioxane, or 1,2-dimethoxyethane, etc., hydrocarbons such as hexane, heptane, toluene, benzene, or xylene, etc., halogenated hydrocarbons such as dichloromethane, chloroform, or 1,2-dichloroethane, etc., ketones such as acetone, etc., aprotic solvents such as acetonitrile, N,N'-dimethylformamide, dimethylsulfoxide, or hexamethylenephosphamide, etc., or a mixture of these solvents. The reaction temperature may be selected from the range of about −70° C. to about 80° C.

When $X^1$ is a chlorine atom, the compound of the formula (1-3) may be synthesized by reacting the compound of the formula (1-2) with the compound of the formula (1-1) in an inert solvent, and if necessary, in the presence of a base. The base includes, for example, organic bases such as N-methylmorpholine, triethylamine, diisopropylethylamine, tributylamine, 1,8-diazabicyclo[5.4.0]undec-7-ene, 1,5-diazabicyclo[4.3.0]non-5-ene, 1,4-diazabicyclo[5.4.0]undec-7-ene, pyridine, dimethylamino-pyridine, or picoline, etc. The base is usually used in an amount of 1 to 20 equivalents to 1 equivalent of the compound of the formula (1-1) wherein $X^1$ is a chlorine atom. The inert solvent includes, for example, halogenated hydrocarbons such as dichloromethane, chloroform, or 1,2-dichloroethane. The reaction temperature may be selected from the range of about −10° C. to about 50° C.

The compound of the formula (1-1) wherein $X^1$ is a chlorine atom may be synthesized by reacting the compound of the formula (1-1) wherein $X^1$ is a hydroxy group with oxalyl chloride or thionyl chloride in an inert solvent in the presence or absence of an additive. The additive includes, for example, dimethylformamide, diethylformamide, etc. The inert solvent includes, for example, halogenated hydrocarbons such as dichloromethane, dichloroethane, or chloroform, etc. The reaction temperature may be selected from the range of about −10° C. to about 50° C. After the reaction is completed, the reaction solution is concentrated under reduced pressure in the presence of a hydrocarbon solvent such as benzene or toluene to give the compound of the formula (1-1) wherein $X^1$ is a hydroxy group.

This Step may also be referred to a method disclosed in a literature (e.g., Tetrahedron 61, 10827 (2005), etc.). The $R^{3a}$, $R^{3b}$, $R^{3c}$, and $R^{3d}$, which are the substituent of the compound (1-3), can be converted into substituents disclosed in Method 2 to Method 18 by processes disclosed in Method 2 to Method 18, Method 21, Method 31 and Method 32.

2) Step 2

The compound (1-12) may be synthesized from the compound (1-3) by a similar method to Step 8 of Method 1.

3) Step 3

The compound (1-2) may be synthesized from the compound (1-4) by a similar method to Step 8 of Method 1. In addition, when $R^2$ of the compound (1-5) is an optionally substituted aryl group or an optionally substituted heteroaryl group, the compound (1-2) may be synthesized from the compound (1-4) by a similar method to ones disclosed in the literature (J. Org. Chem. 71, 6522 (2006), etc.).

4) Step 4

The compound (1-2) may be synthesized from the compound (1-4) by a similar method to ones disclosed in the literature (e.g., J. Org. Chem. 61, 3849 (1996), J. Org. Chem. 68, 4120 (2003), J. Org. Chem. 63, 370 (1998), J. Org. Chem. 70, 2195 (2005), etc.). For instance, the following Methods are exemplified.

The compound (1-2) can be prepared by reacting a compound selected from the compound (1-8), the compound (1-9), and the compound (1-10) with the compound (1-4) in an inert solvent in the presence or absence of acetic acid by a reductive amination reaction using a boron hydride compound such as sodium triacetoxyborohydride, or sodium cyanoborohydride, etc. The inert solvent includes, for example, halogenated hydrocarbons such as dichloromethane, or dichloroethane, etc.; alcohols such as methanol or ethanol, etc.; ether solvents such as tetrahydrofuran, or 1,4-dioxane, or 1,2-dimethoxyethane, etc. The boron hydride compound may be usually used in an amount of 1 to 3 equivalents to 1 equivalent of the compound (1-4). The reaction temperature may be selected from the range of about −10° C. to about 40° C.

5) Step 5

The compound (1-2) may be synthesized from the compound (1-6) by a similar method to Step 4 of Method 1.

6) Step 6

The compound (1) may be synthesized from the compound (1-12) by a similar method to ones disclosed in the literature (e.g., Protective Groups in Organic Synthesis 2nd Edition (John Wiley & Sons, Inc.), etc.).

7) Step 7

The compound (1-1) wherein $X^1$ is a hydroxy group may be prepared from the compound (1-13) by a similar method to Step 1 of Method 1.

8) Step 8

The compound (1-14) may be prepared by reacting the compound (1-7) with the compound (1-13) in an inert solvent in the presence of a base. The base includes, for example, alkali metal salts such as sodium hydrogen carbonate, potassium carbonate, or sodium hydroxide, etc.; organic bases such as triethylamine or 1,8-diazabicyclo[5.4.0]undec-7-ene (DBU), etc.; alkali metal hydrides such as sodium hydride or potassium hydride, etc.; alkali metal alkoxides such as potassium t-butoxide, etc. When $X^3$ is a chlorine atom or a bromine atom, additives such as sodium iodide or potassium iodide, etc. may be used. The inert solvent includes, for example, ether solvents such as tetrahydrofuran or 1,4-dioxane, etc.; aprotic solvents such as dimethylformamide or dimethylsulfoxide, etc.; halogenated hydrocarbons such as dichloromethane or dichloroethane, etc., or a mixture of these solvents. The reaction temperature may be selected from the range of about 0° C. to about 150° C.

9) Step 9

The compound (1-15) may be prepared from the compound (1-14) in a similar method to Step 1 of Method 1.

10) Step 10

The compound (1-12) may be prepared from the compound (1-15) in a similar method to Step 1 of Method 1.

Method 2

Among the compounds of the formula (1-4), the compound of the formula (2-3) or a pharmaceutically acceptable salt thereof may be prepared, for example, by the following method.

[Chemical formula 112]

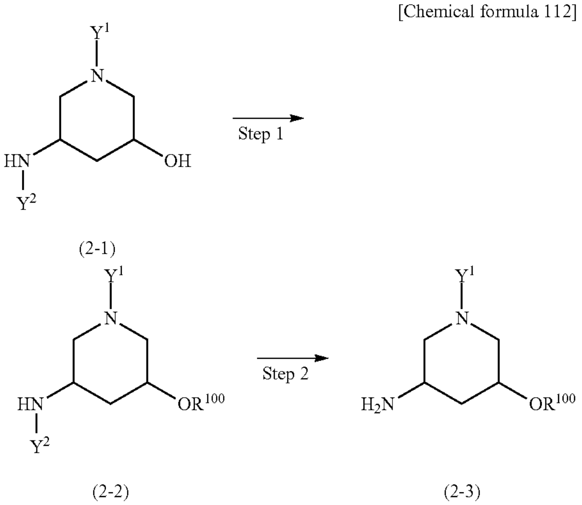

(2-1) (2-2) (2-3)

[wherein $Y^1$ is as defined in the above; $Y^2$ is Cbz, Boc or Alloc; $R^{100}$ is the same as defined for B of the above-mentioned Item 1]

1) Step 1

The compound (2-2) may be prepared from the compound (2-1) by a similar method to ones disclosed in the literatures (e.g., Comprehensive Organic transformation, R. C. Laroque, VCH publisher Inc., 1989, etc.). The compound (2-1) may be prepared by a similar method to ones disclosed in the literatures (e.g., WO 05/028467, etc.).

2) Step 2

The compound (2-3) may be prepared from the compound (2-2) in a similar method to ones disclosed in the literatures (e.g., Protective Groups in Organic Synthesis 2nd Edition (John Wiley & Sons, Inc.), etc.).

Method 3

Among the compounds of the formula (1-4), the compound of the formula (3-6) or a salt thereof may be prepared, for example, by the following method.

[Chemical formula 113]

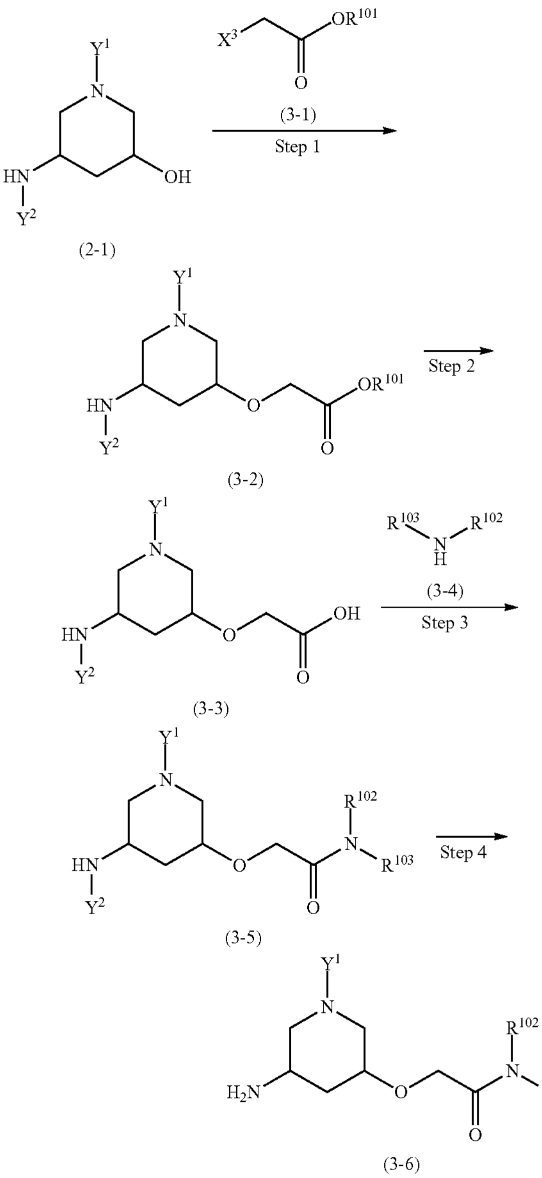

(3-1) (2-1) (3-2) (3-4) (3-3) (3-5) (3-6)

[wherein $Y^1$ and $Y^2$ are as defined in the above; $X^3$ is a chlorine atom or a bromine atom; $R^{101}$ is a $C_{1-4}$ alkyl group; $R^{102}$ and $R^{103}$ are the same or different, and each is a hydrogen atom, a $C_{1-4}$ alkyl, a $C_{3-6}$ cycloalkyl, or a $C_{3-6}$ cycloalkyl-$C_{1-4}$ alkyl]

1) Step 1

The compound (3-2) may be prepared from the compound (2-1) in a similar method to ones disclosed in the literatures (e.g., Comprehensive Organic transformation, R. C. Laroque, VCH publisher Inc., 1989, etc.). The compound (2-1) may be prepared by a similar method to ones disclosed in the literatures (e.g., WO 05/028467, etc.).

2) Step 2 to Step 3

The compound (3-5) may be prepared from the compound (3-2) by a similar method to ones disclosed in the literatures (e.g., Comprehensive Organic transformation, R. C. Laroque, VCH publisher Inc., 1989, etc.).

3) Step 4

The compound (3-6) may be prepared from the compound (3-5) by a similar method disclosed in the literatures (e.g., Protective Groups in Organic Synthesis 2nd Edition (John Wiley & Sons, Inc.), etc.).

Method 4

Among the compounds of the formula (1-4), the compound of the formula (4-3) and the compound of the formula (4-6), or a salt thereof, may be prepared, for example, by the following method.

VCH publisher Inc., 1989, etc.). The compound (2-1) may be prepared by a similar method to ones disclosed in the literatures (e.g., WO 05/028467, etc.).

2) Step 2

The compound (4-3) may be prepared from the compound (4-2) by a similar method to ones disclosed in the literatures (e.g. Protective Groups in Organic Synthesis 2nd Edition (John Wiley & Sons, Inc.), etc.).

3) Step 3

The compound (4-5) may be prepared from the compound (4-2) by a similar method to ones disclosed in the literatures (e.g., Comprehensive Organic transformation, R. C. Laroque, VCH publisher Inc., 1989, etc.).

4) Step 4

The compound (4-6) may be prepared from the compound (4-5) by a similar method to ones disclosed in the literatures (e.g., Protective Groups in Organic Synthesis 2nd Edition (John Wiley & Sons, Inc.), etc.).

Method 5

Among the compounds of the formula (1-4), the compound of the formula (5-4) or a salt thereof may be prepared, for example, by the following method.

[Chemical formula 114]

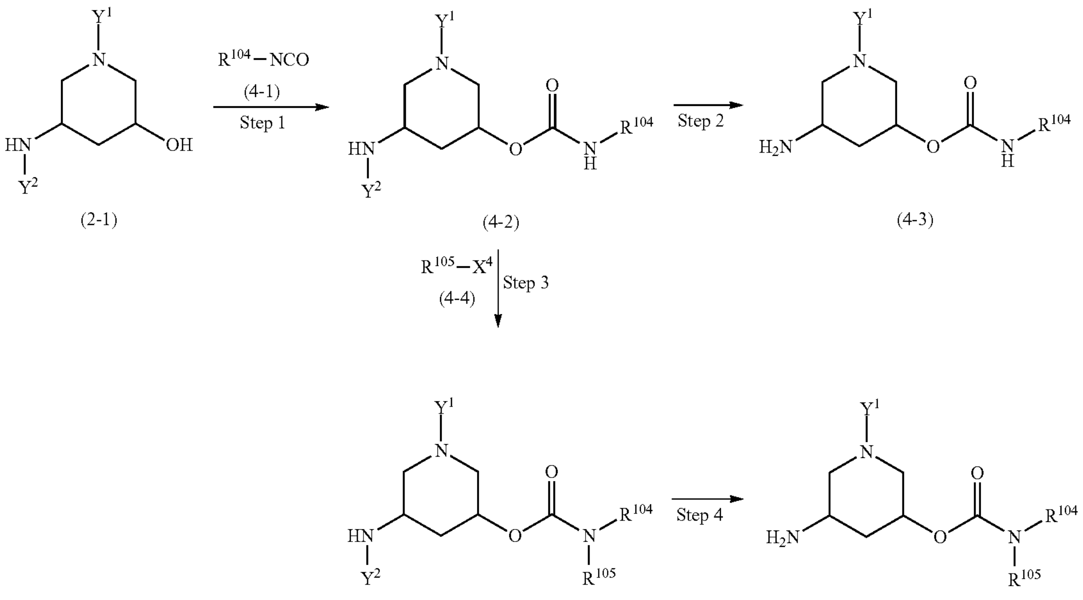

(2-1) (4-2) (4-3) (4-5) (4-6)

[wherein $Y^1$ and $Y^2$ are as defined in the above; $R^{104}$ is the same as defined for B of the above-mentioned Item 1; $R^{105}$ is the same as defined for $R^4$ of the above-mentioned Item 1; or $R^{104}$ and $R^{105}$ may combine each other to form a ring; $X^4$ is an iodine atom, a bromine atom, a chlorine atom, a methanesulfonyloxy group, a trifluoromethanesulfonyloxy group, or a p-toluenesulfonyloxy group]

1) Step 1

The compound (4-2) may be prepared from the compound (2-1) by a similar method to ones disclosed in the literatures (e.g., Comprehensive Organic transformation, R. C. Laroque,

[Chemical formula 115]

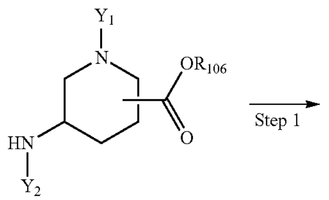

(5-1)

-continued

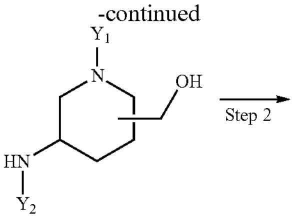

(5-2)

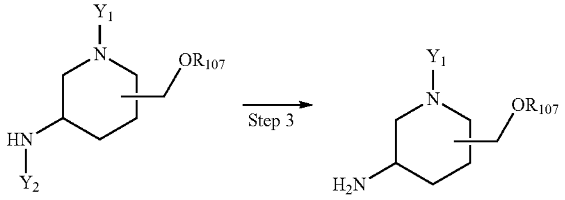

(5-3) (5-4)

[wherein $Y^1$ and $Y^2$ are as defined in the above; $R^{106}$ is a $C_{1-4}$ alkyl group; $R^{107}$ is the same as defined for B of the above-mentioned Item 1. In addition, the substituent crossing the bond indicates that such a substituent bonds to one of the positions of $R^{3a}$, $R^{3b}$, $R^{3c}$, $R^{3d}$ in Item 20. The same applies to the following formulae]

1) Step 1

The compound (5-2) may be prepared from the compound (5-1) by a similar method to ones disclosed in the literatures (e.g., Comprehensive Organic transformation, R. C. Laroque, VCH publisher Inc., 1989, etc.). The compound (5-1) may be prepared by a similar method to ones disclosed in the literatures (e.g., WO 97/18813, WO 02/10172, Tetrahedron Letters 46, 7495 (2005), WO 02/02525, etc.).

2) Step 2

The compound (5-3) may be prepared from the compound (5-2) by a similar method to ones disclosed in the literatures (e.g. Comprehensive Organic transformation, R. C. Laroque, VCH publisher Inc., 1989, etc.).

3) Step 3

The compound (5-4) may be prepared from the compound (5-3) by a similar method to ones disclosed in the literatures (e.g., Protective groups in Organic Synthesis 2nd Edition (John Wiley & Sons, Inc.), etc.).

Method 6

Among the compounds of the formula (1-4), the compound of the formula (6-5) or a salt thereof may be prepared, for example, by the following method.

[Chemical formula 116]

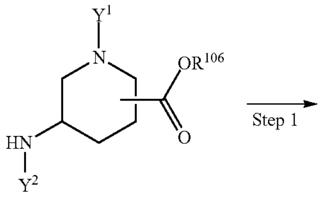

(5-1)

-continued

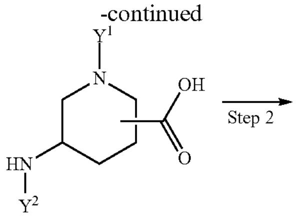

(6-1)

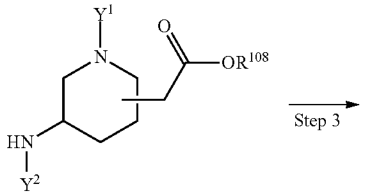

(6-2)

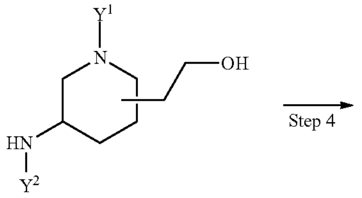

(6-3)

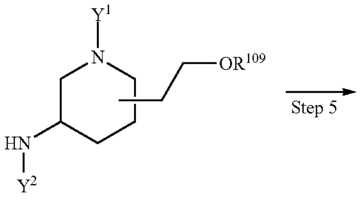

(6-4)

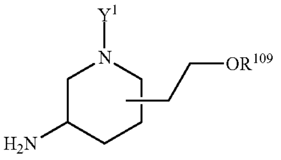

(6-5)

[wherein $Y^1$, $Y^2$ and $R^{106}$ are as defined in the above; $R^{108}$ is a $C_{1-4}$ alkyl group; $R^{109}$ is the same as defined for B of the above-mentioned Item 1]

1) Step 1

The compound (6-1) may be prepared from the compound (5-1) by a similar method to ones disclosed in the literatures (e.g., Comprehensive Organic transformation, R. C. Laroque, VCH publisher Inc., 1989, etc.). The compound (5-1) may be prepared by a similar method to ones disclosed in the literatures (e.g., WO 97/18813, WO 02/10172, Tetrahedron Letters 46, 7495 (2005), WO02/02525, J. Org. Chem. 70, 6956 (2005), etc.).

2) Step 2

The compound (6-2) may be prepared from the compound (6-1) by a similar method to ones disclosed in the literatures (e.g., Comprehensive Organic transformation, R. C. Laroque, VCH publisher Inc., 1989, J. Org. Chem. 57, 7194 (1992), etc.).

3) Step 3 to Step 4

The compound (6-4) may be prepared from the compound (6-2) by a similar method to ones disclosed in the literatures (e.g., Comprehensive Organic transformation, R. C. Laroque, VCH publisher Inc., 1989, etc.).

4) Step 5

The compound (6-5) may be prepared from the compound (6-4) by a similar method to ones disclosed in the literatures (e.g., Protective Groups in Organic Synthesis 2nd Edition (John Wiley & Sons, Inc.), etc.).

Method 7

Among the compounds of the formula (1-4), the compound of the formula (7-4), the compound of the formula (7-6), and the compound of the formula (7-8) or a salt thereof may be prepared, for example, by the following method.

3) Step 3

The compound (7-5) may be prepared from the compound (7-3) by a similar method to ones disclosed in the literatures (e.g., Comprehensive Organic transformation, R. C. Laroque, VCH publisher Inc., 1989, etc.).

4) Step 4

The compound (7-6) may be prepared from the compound (7-5) by a similar method to ones disclosed in the literatures (e.g., Protective Groups in Organic Synthesis 2nd Edition (John Wiley & Sons, Inc.), etc.).

[Chemical formula 117]

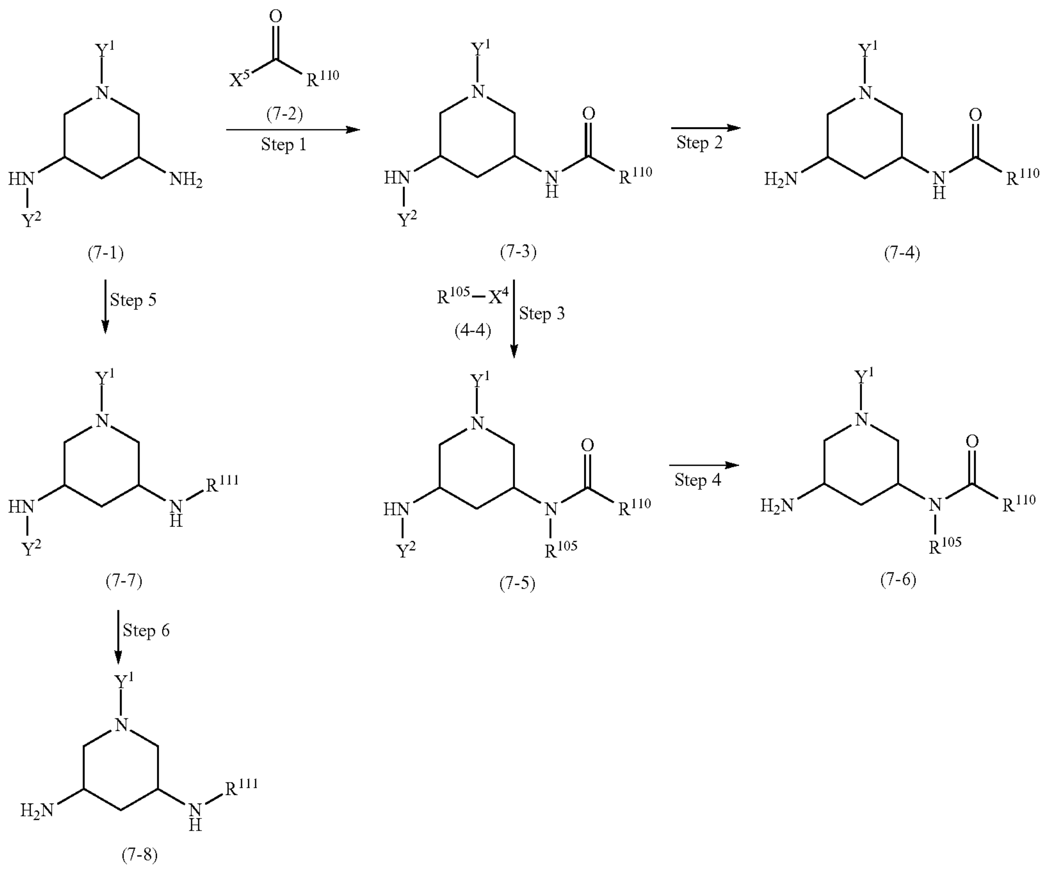

[wherein $R^{105}$, $X^4$, $Y^1$ and $Y^2$ are as defined in the above; X' is a hydroxy group or a chlorine atom; and $R^{110}$ and $R^{111}$ are independent, and they are the same as B of the above-mentioned Item 1]

1) Step 1

The compound (7-3) may be prepared from the compound (7-1) by a similar method to ones disclosed in the literatures (e.g., Comprehensive Organic transformation, R. C. Laroque, VCH publisher Inc., 1989; Chem. Pharm. Bull. 40, 102 (1992); J. Med. Chem. 26, 507 (1983), etc.). The compound (7-1) may be prepared by a similar method to ones disclosed in the literatures (e.g., WO 05/028467, etc.).

2) Step 2

The compound (7-4) may be prepared from the compound (7-3) by a similar method to ones disclosed in the literatures (e.g., Protective Groups in Organic Synthesis 2nd Edition (John Wiley & Sons, Inc.), etc.).

5) Step 5

The compound (7-7) may be prepared from the compound (7-1) by a similar method to ones disclosed in the literatures (e.g., Comprehensive Organic transformation, R. C. Laroque, VCH publisher Inc., 1989; J. Org. Chem. 61, 3849 (1996); J. Org. Chem. 68, 4120 (2003); J. Org. Chem. 63, 370 (1998); J. Org. Chem. 70, 2195 (2005), etc.).

6) Step 6

The compound (7-8) may be prepared from the compound (7-7) by a similar method to ones disclosed in the literatures (e.g., Protective Groups in Organic Synthesis 2nd Edition (John Wiley & Sons, Inc.), etc.).

Method 8

Among the compounds of the formula (1-4), the compound of the formula (8-4) or a salt thereof may be prepared, for example, by the following method.

[Chemical formula 118]

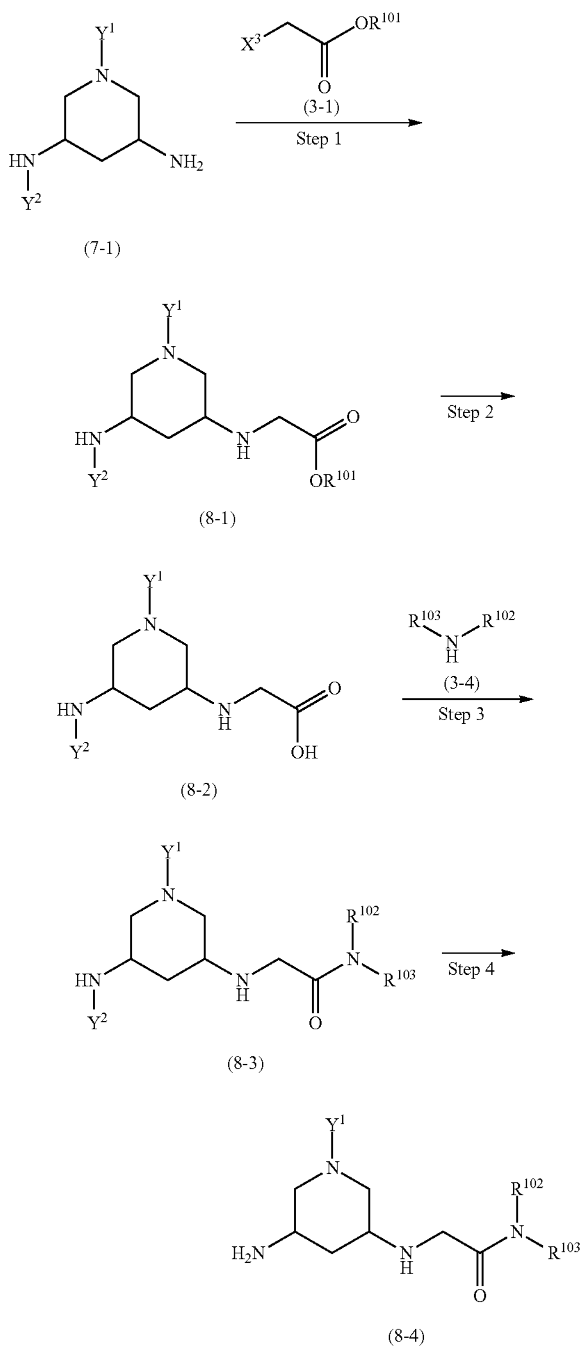

[wherein $R^{101}$, $R^{102}$, $R^{103}$, $X^3$, $Y^1$ and $Y^2$ are as defined in the above]

1) Step 1

The compound (8-1) may be prepared from the compound (7-1) by a similar method to ones disclosed in the literatures (e.g., Comprehensive Organic transformation, R. C. Laroque, VCH publisher Inc., 1989; Synthetic Communications 34, 219 (2004); etc.). The compound (7-1) may be prepared by a similar method to ones disclosed in the literatures (e.g., WO 05/028467, etc.).

2) Step 2 to Step 3

The compound (8-3) may be prepared from the compound (8-1) by a similar method to ones disclosed in the literatures (e.g., Comprehensive Organic transformation, R. C. Laroque, VCH publisher Inc., 1989, etc.).

3) Step 4

The compound (8-4) may be prepared from the compound (8-3) by a similar method to ones disclosed in the literatures (e.g., Protective Groups in Organic Synthesis 2nd Edition (John Wiley & Sons, Inc.), etc.).

Method 9

Among the compounds of the formula (1-4), the compound of the formula (9-4) or a salt thereof may be prepared, for example by the following method.

[Chemical formula 119]

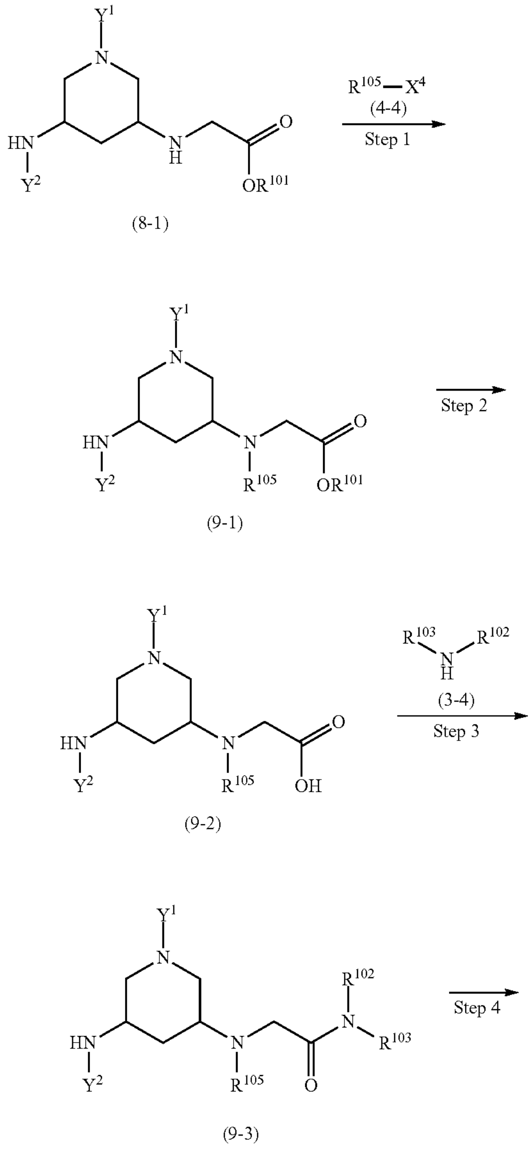

-continued

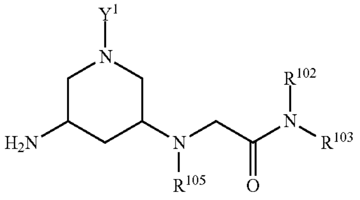

(9-4)

[wherein $R^{101}$, $R^{102}$, $R^{103}$, R105, $X^4$, $Y^1$ and $Y^2$ are as defined in the above]

1) Step 1 to Step 3

The compound (9-3) may be prepared from the compound (8-1) by a similar method to ones disclosed in the literatures (e.g., Comprehensive Organic transformation, R. C. Laroque, VCH publisher Inc., 1989, etc.).

2) Step 4

The compound (9-4) may be prepared from the compound (9-3) by a similar method to ones disclosed in the literatures (e.g., Protective Groups in Organic Synthesis 2nd Edition (John Wiley & Sons, Inc.), etc.).

Method 10

Among the compounds of the formula (1-4), the compound of the formula (10-4) and the compound of the formula (10-6) or a salt thereof may be prepared, for example, by the following method.

[wherein $R^{102}$, $R^{103}$, R105, $X^4$, $Y^1$ and $Y^2$ are as defined in the above]

1) Step 1

The compound (10-2) may be prepared from the compound (7-1) by a similar method to ones disclosed in the literatures (e.g., Tetrahedron: Asymmetry 16, 2599 (2005), etc.). The compound (7-1) may be prepared by a similar method to ones disclosed in the literatures (e.g., WO 05/028467, etc.).

2) Step 2

The compound (10-3) may be prepared from the compound (10-2) by a similar method to ones disclosed in the literatures (e.g., Tetrahedron: Asymmetry 16, 2599 (2005), etc.).

3) Step 3

The compound (10-4) may be prepared from the compound (10-3) by a similar method to ones disclosed in the literatures (e.g., Protective Groups in Organic Synthesis 2nd Edition (John Wiley & Sons, Inc.), etc.).

4) Step 4

The compound (10-5) may be prepared from the compound (10-3) by a similar method to ones disclosed in the literatures (e.g., Comprehensive Organic transformation, R. C. Laroque, VCH publisher Inc., 1989, etc.).

5) Step 5

The compound (10-6) may be prepared from the compound (10-5) by a similar method to ones disclosed in the literatures (e.g., Protective Groups in Organic Synthesis 2nd Edition (John Wiley & Sons, Inc.), etc.).

Method 11

Among the compounds of the formula (1-4), the compound of the formula (11-3) and the compound of the formula (11-5) or a salt thereof may be prepared, for example, by the following method.

[Chemical formula 120]

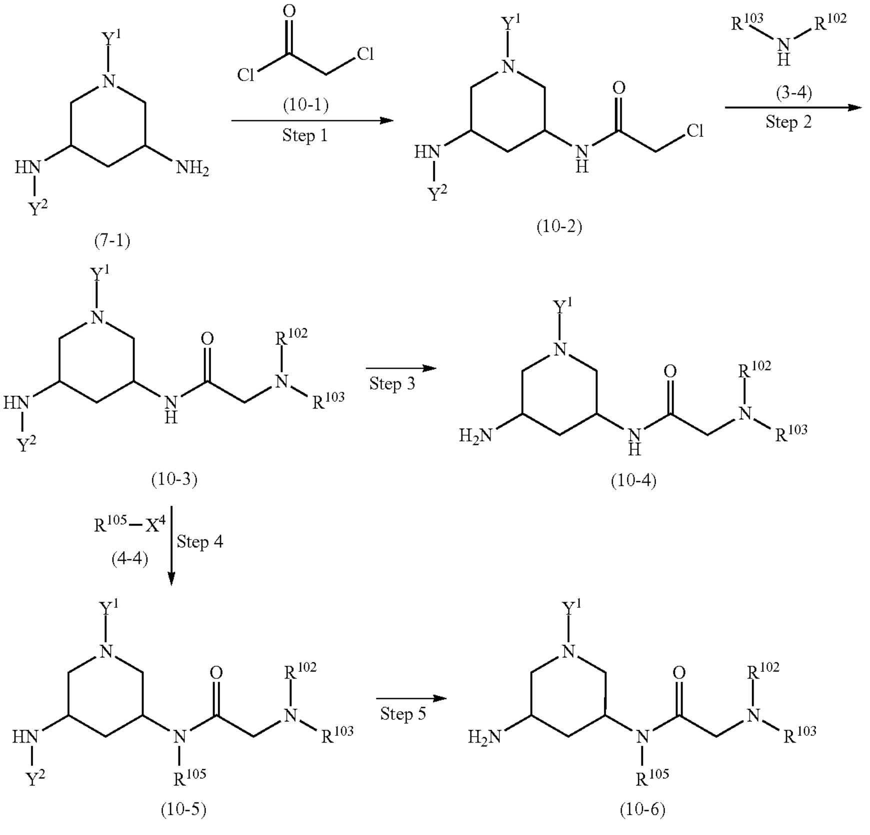

(7-1) (10-2) (10-3) (10-4) (10-5) (10-6)

[Chemical formula 121]

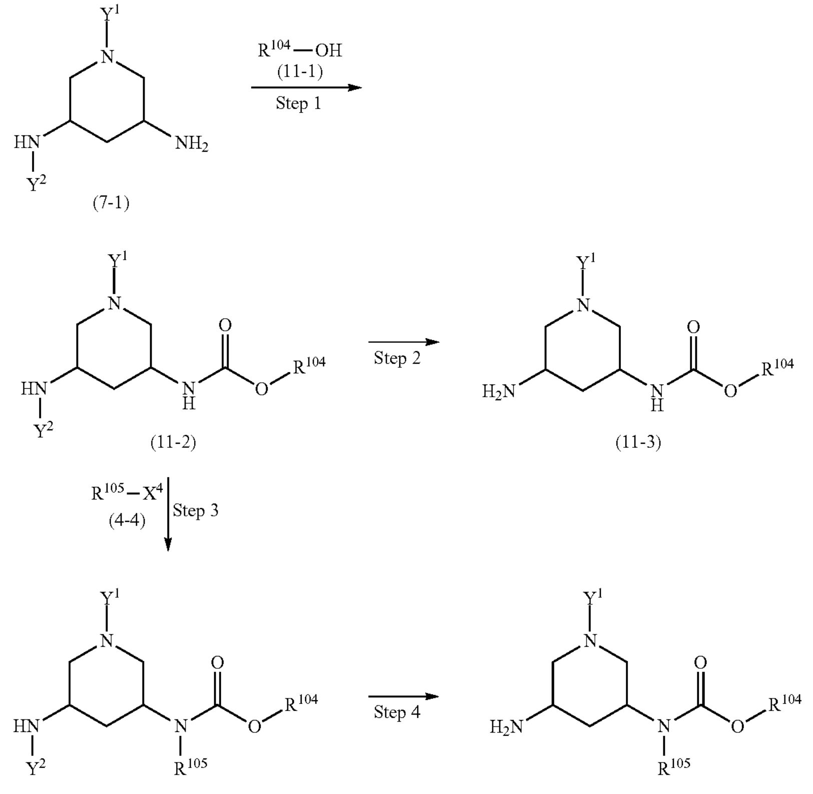

(7-1) (11-2) (11-3) (11-4) (11-5)

[wherein $R^{104}$, R105, $X^4$, $Y^1$ and $Y^2$ are as defined in the above]

1) Step 1

The compound (11-2) may be prepared by reacting the compound (7-1) and the compound (11-1) by a similar method to ones disclosed in the literatures (e.g., WO01/057044; etc.).

2) Step 2

The compound (11-3) may be prepared from the compound (11-2) by a similar method to ones disclosed in the literatures (e.g., Protective Groups in Organic Synthesis 2nd Edition (John Wiley & Sons, Inc.), etc.).

3) Step 3

The compound (11-4) may be prepared from the compound (11-2) by a similar method to ones disclosed in the literatures (e.g., Comprehensive Organic transformation, R. C. Laroque, VCH publisher Inc., 1989, etc.).

4) Step 4

The compound (11-5) may be prepared from the compound (11-4) by a similar method to ones disclosed in the literatures (e.g., Protective Groups in Organic Synthesis 2nd Edition (John Wiley & Sons, Inc.), etc.).

Method 12

Among the compounds of the formula (1-4), the compound of the formula (12-3) or a salt thereof may be prepared, for example, by the following method.

[Chemical formula 122]

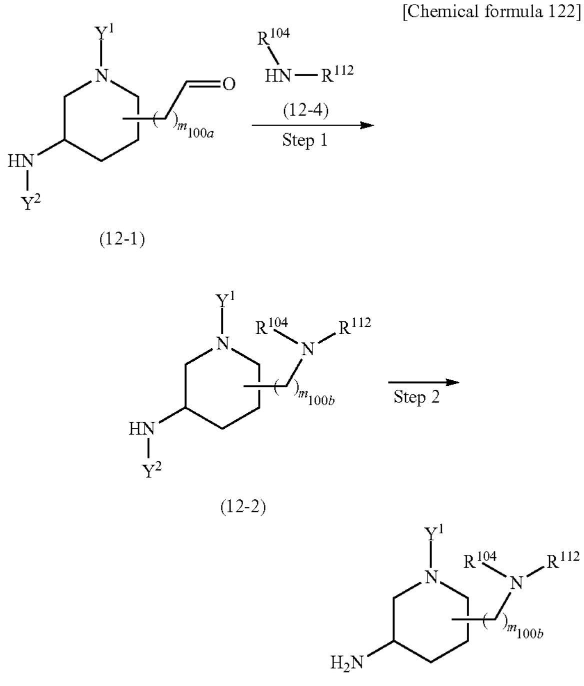

(12-1) (12-2) (12-3)

[wherein $R^{104}$, $Y^1$ and $Y^2$ are as defined in the above; $R^{112}$ is the same as defined for $R^4$ of the above-mentioned Item 1;

$R^{104}$ and $R^{112}$ may combine each other to form a ring; and $m_{100a}$ is 0 or 1, $m_{100b}$ is 1 or 2.]

1) Step 1

The compound (12-2) may be prepared from the compound (12-1) by a similar method to ones disclosed in the literatures (e.g., Comprehensive Organic transformation, R. C. Laroque, VCH publisher Inc., 1989, etc.).

2) Step 2

The compound (12-3) may be prepared from the compound (12-2) by a similar method to ones disclosed in the literatures (e.g., Protective Groups in Organic Synthesis 2nd Edition (John Wiley & Sons, Inc.), etc.).

Method 13

Among the compounds of the formula (1-4), the compound of the formula (13-4) and the compound of the formula (13-6) or a salt thereof may be prepared, for example, by the following method.

[Chemical formula 123]

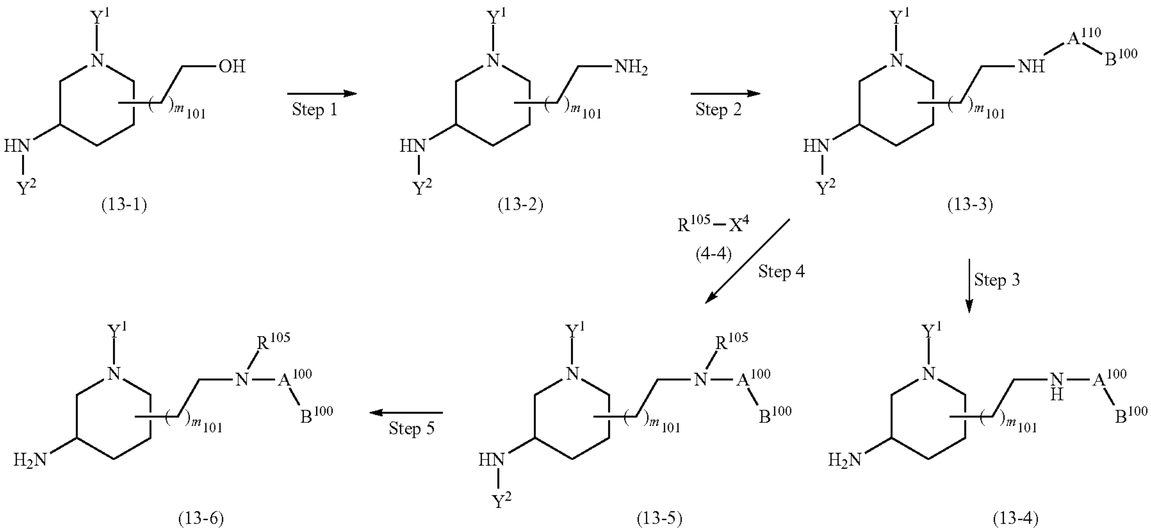

[wherein $R^{105}$, $X^4$, $Y^1$ and $Y^2$ are as defined in the above; $A^{100}$ is —$SO_2$—, or —CO—; $B^{100}$ is the same as defined in B of the above-mentioned Item 1; $m_{101}$ is an integer of 0 or 1]

1) Step 1 to Step 2

The compound (13-3) may be prepared from the compound (13-1) by a similar method to ones disclosed in the literatures (e.g., Comprehensive Organic transformation, R. C. Laroque, VCH publisher Inc., 1989, etc.).

2) Step 3

The compound (13-4) may be prepared from the compound (13-3) by a similar method to ones disclosed in the literatures (e.g., Protective Groups in Organic Synthesis 2nd Edition (John Wiley & Sons, Inc.), etc.).

3) Step 4

The compound (13-5) may be prepared from the compound (13-3) by a similar method to ones disclosed in the literatures (e.g., Comprehensive Organic transformation, R. C. Laroque, VCH publisher Inc., 1989, etc.).

4) Step 5

The compound (13-6) may be prepared from the compound (13-5) by a similar method to ones disclosed in the literatures (e.g., Protective Groups in Organic Synthesis 2nd Edition (John Wiley & Sons, Inc.), etc.).

Method 14

Among the compounds of the formula (1-4), the compound of the formula (14-2) or a salt thereof may be prepared, for example, by the following method.

[Chemical formula 124]

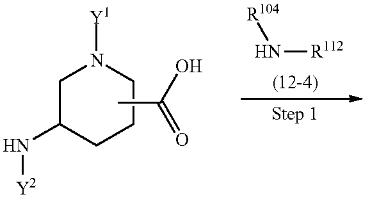

(6-1)

-continued

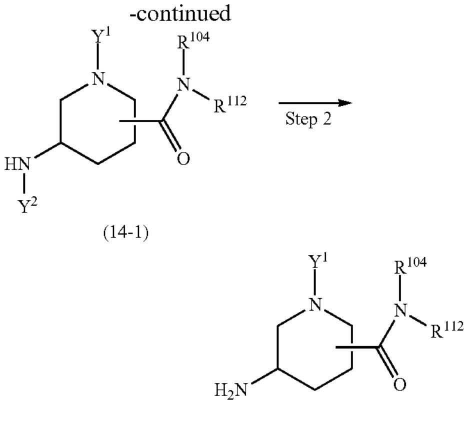

[wherein $R^{104}$, $R^{112}$, $Y^1$ and $Y^2$ are as defined in the above]

1) Step 1

The compound (14-1) may be prepared from the compound (6-1) by a similar method to ones disclosed in the literatures (e.g., Comprehensive Organic transformation, R. C. Laroque, VCH publisher Inc., 1989, etc.).

2) Step 2

The compound (14-2) may be prepared from the compound (14-1) by a similar method to ones disclosed in the literatures (e.g., Protective Groups in Organic Synthesis 2nd Edition (John Wiley & Sons, Inc.), etc.).

Method 15

Among the compounds of the formula (1-4), the compound of the formula (15-3) or a pharmaceutically acceptable salt thereof may be prepared, for example, by the following method.

[Chemical formula 125]

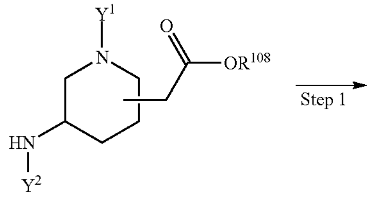

(6-2)

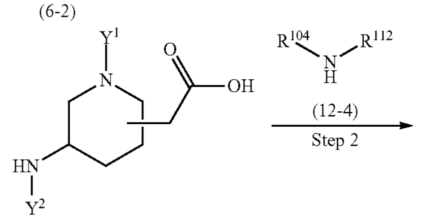

(15-1)

-continued

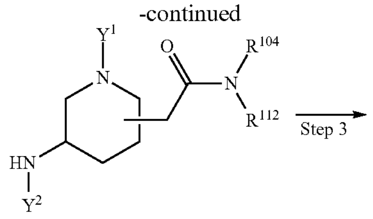

(15-2)

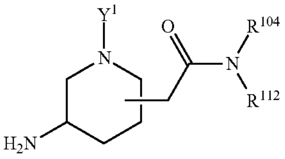

(15-3)

[wherein $R^{104}$, $R^{112}$, $R^{108}$, $Y^1$ and $Y^2$ are as defined in the above]

1) Step 1 to Step 2

The compound (15-2) may be prepared from the compound (6-2) by a similar method to ones disclosed in the literatures (e.g., Comprehensive Organic transformation, R. C. Laroque, VCH publisher Inc., 1989, etc.).

2) Step 3

The compound (15-3) may be prepared from the compound (15-2) by a similar method to ones disclosed in the literatures (e.g., Protective Groups in Organic Synthesis 2nd Edition (John Wiley & Sons, Inc.), etc.).

Method 16

Among the compounds of the formula (1-4), the compound of the formula (16-4) and the compound of the formula (16-6) or a pharmaceutically acceptable salt thereof may be prepared, for example, by the following method.

[Chemical formula 126]

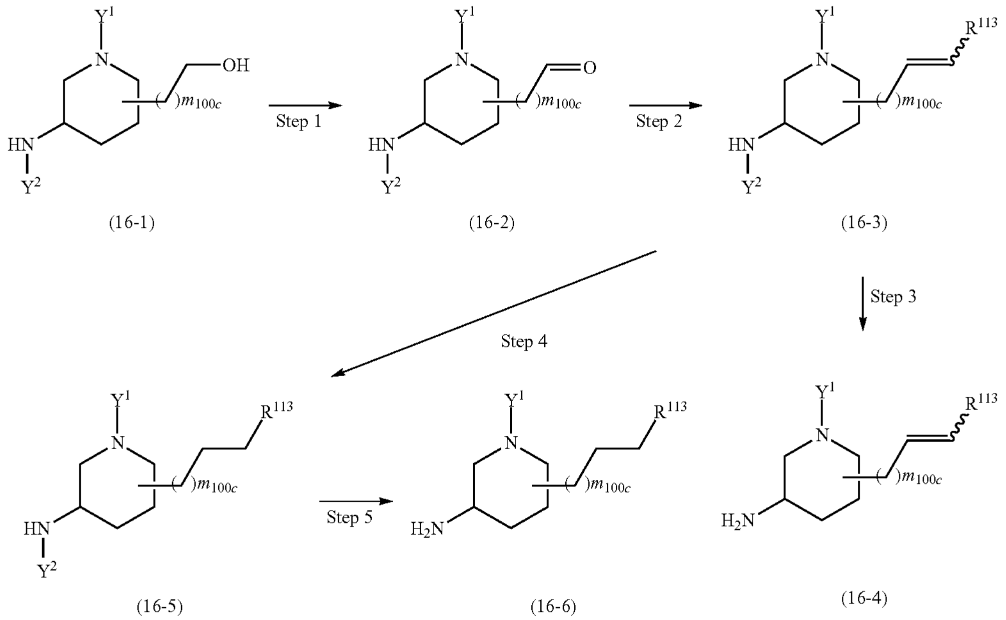

[wherein $Y^1$ and $Y^2$ are as defined in the above; $m_{100b}$ is an integer of 0 to 4; $R^{113}$ is one of the above-mentioned (a) to (z), provided that in the compound (16-4), $R^{113}$ is one of the above-mentioned (a) to (s)]

1) Step 1

The compound (16-2) may be prepared from the compound (16-1) by a similar method to ones disclosed in the literatures (e.g., Tetrahedron: Asymmetry 17, 993 (2006), Comprehensive Organic transformation, R. C. Laroque, VCH publisher Inc., 1989, etc.).

2) Step 2

The compound (16-3) may be prepared from the compound (16-2) by a similar method to ones disclosed in the literatures (e.g., Tetrahedron: Asymmetry 8, 3685 (1997); J. Org. Chem. 61, 6033 (1996); JP-A-8-12605; Comprehensive Organic transformation, R. C. Laroque, VCH publisher Inc., 1989, etc.).

3) Step 3

The compound (16-4) may be prepared from the compound (16-3) by a similar method to ones disclosed in the literatures (e.g., Protective Groups in Organic Synthesis 2nd Edition (John Wiley & Sons, Inc.), etc.).

4) Step 4

The compound (16-5) may be prepared from the compound (16-3) by a similar method to ones disclosed in the literatures (e.g., Comprehensive Organic transformation, R. C. Laroque, VCH publisher Inc., 1989, etc.).

5) Step 5

The compound (16-6) may be prepared from the compound (16-5) by a similar method to ones disclosed in the literatures (e.g., Protective Groups in Organic Synthesis 2nd Edition (John Wiley & Sons, Inc.), etc.).

Method 17

Among the compounds of the formula (1-4), the compound of the formula (17-3) and the compound of the formula (17-5) or a salt thereof may be prepared, for example, by the following method.

[wherein $R^{104}$, $R^{105}$, $X^4$, $Y^1$ and $Y^2$ are as defined in the above; $m_{102}$ is an integer of 0 or 1]

1) Step 1

The compound (17-2) may be prepared by reacting the compound (17-1) and the compound (11-1) by a similar method to ones disclosed in the literatures (e.g., WO 01/057044, etc.).

2) Step 2

The compound (17-3) may be prepared from the compound (17-2) by a similar method to ones disclosed in the literatures (e.g., Protective Groups in Organic Synthesis 2nd Edition (John Wiley & Sons, Inc.), etc.).

3) Step 3

The compound (17-4) may be prepared from the compound (17-2) by a similar method to ones disclosed in the literatures (e.g., Comprehensive Organic transformation, R. C. Laroque, VCH publisher Inc., 1989, etc.).

4) Step 4

The compound (17-5) may be prepared from the compound (17-4) by a similar method to ones disclosed in the literatures (e.g., Protective Groups in Organic Synthesis 2nd Edition (John Wiley & Sons, Inc.), etc.).

Method 18

Among the compounds of the formula (1-4), the compound of the formula (18-5) and the compound of the formula (18-7) or a salt thereof may be prepared, for example, by the following method.

[Chemical formula 127]

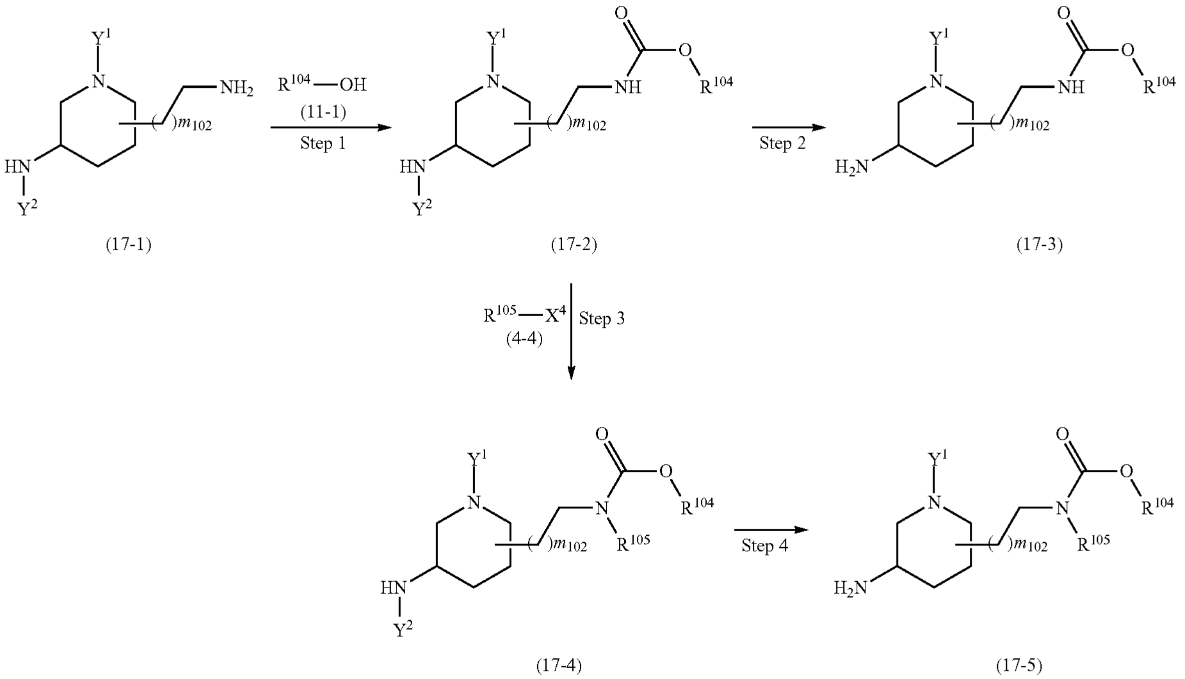

(17-1) (17-2) (17-3) (17-4) (17-5)

[Chemical formula 128]

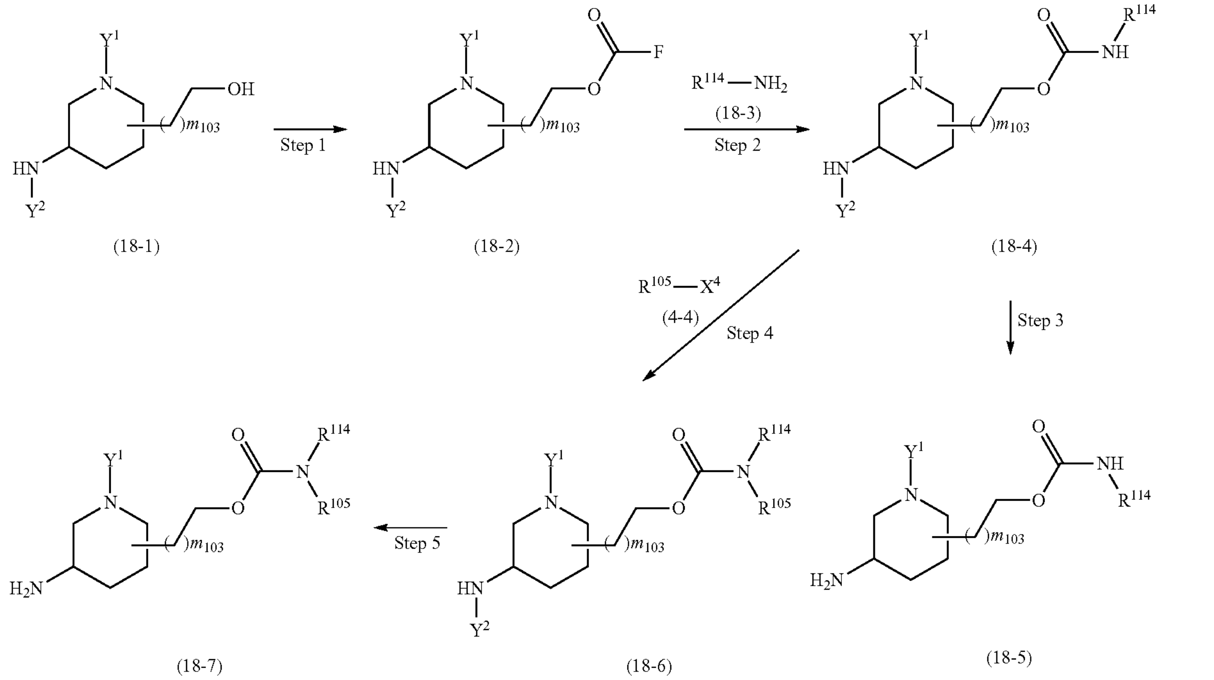

[wherein $R^{105}$, $X^4$, $Y^1$ and $Y^2$ are as defined in the above; $m_{103}$ is an integer of 0 or 1; $R^{114}$ is the same as defined for B of the above-mentioned Item 1]

1) Step 1

The compound (18-2) may be prepared from the compound (18-1) by a similar method to ones disclosed in the literatures (e.g., Tetrahedron Letters 43, 4275 (2002), etc.).

2) Step 2

The compound (18-4) may be prepared from the compound (18-2) by a similar method to ones disclosed in the literatures (e.g., Comprehensive Organic transformation, R. C. Laroque, VCH publisher Inc., 1989, etc.).

3) Step 3

The compound (18-5) may be prepared from the compound (18-4) by a similar method to ones disclosed in the literatures (e.g., Protective Groups in Organic Synthesis 2nd Edition (John Wiley & Sons, Inc.), etc.).

4) Step 4

The compound (18-6) may be prepared from the compound (18-4) by a similar method to ones disclosed in the literatures (e.g., Comprehensive Organic transformation, R. C. Laroque, VCH publisher Inc., 1989, etc.).

5) Step 5

The compound (18-7) may be prepared from the compound (18-6) by a similar method to ones disclosed in the literatures (e.g., Protective Groups in Organic Synthesis 2nd Edition (John Wiley & Sons, Inc.), etc.).

Method 19

Among the compounds of the formula (1-4), the compound of the formula (19-13) or a salt thereof may be prepared, for example, by the following method.

[Chemical formula 129]

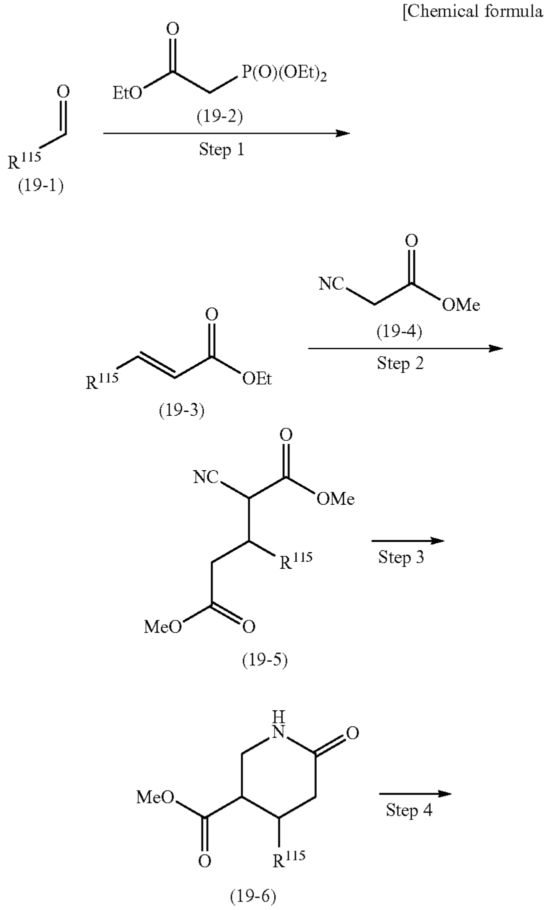

-continued

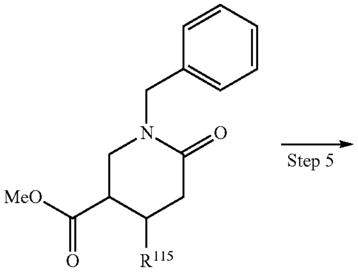

(19-7)

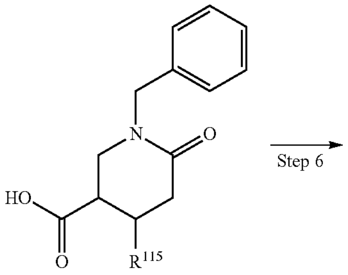

(19-8)

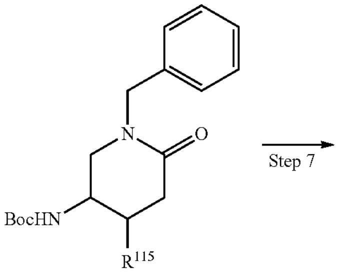

(19-9)

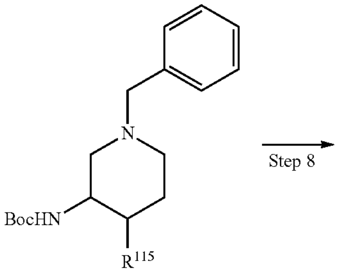

(19-10)

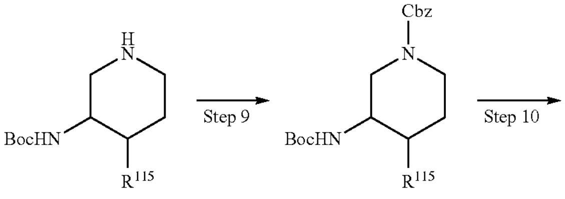

(19-11) (19-12)

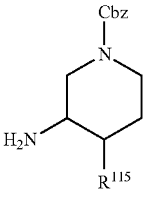

(19-13)

[wherein $R^{115}$ is the same as defined for B of the above-mentioned Item 1]

1) Step 1 to Step 8

The compound (19-11) may be prepared from the compound (19-1) by a similar method to ones disclosed in the literatures (e.g., WO 06/039325, etc.).

2) Step 9 to Step 10

The compound (19-13) may be prepared from the compound (19-11) by a similar method to ones disclosed in the literatures (e.g., Protective Groups in Organic Synthesis 2nd Edition (John Wiley & Sons, Inc.), etc.).

Method 20

Among the compounds of the formula (1-4), the compound of the formula (20-8) a salt thereof may be prepared, for example, by the following method.

[Chemical formula 130]

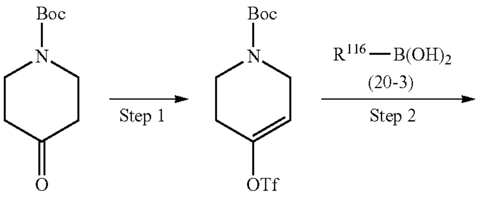

(20-1) (20-2)

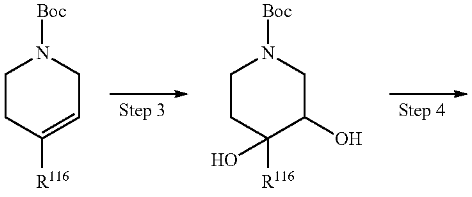

(20-4) (20-5)

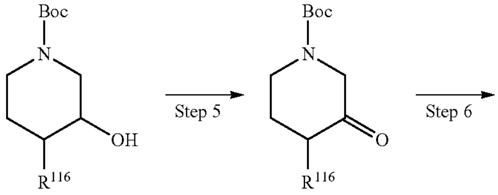

(20-6) (20-7)

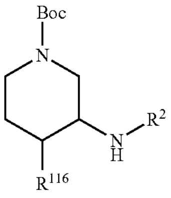

(20-8)

[wherein $R^2$ is the same as defined in the above Item 1; $R^{116}$ is an optionally substituted $C_{6-10}$ aryl group, or an optionally substituted 5- to 10-membered monocyclic or polycyclic heteroaryl group.]

1) Step 1 to Step 5

The compound (20-7) may be prepared from the compound (20-1) by a similar method to ones disclosed in the literatures (e.g., Bioorganic & Medicinal Chemistry 13, 59 (2005), etc.).

2) Step 6

The compound (20-8) may be prepared from the compound (20-7) by a similar method to ones disclosed in the literatures (e.g., Protective Groups in Organic Synthesis 2nd Edition (John Wiley & Sons, Inc.), etc.).

Method 21

Among the compounds of the formula (1-4), the compound of the formula (21-3) or a salt thereof may be prepared, for example, by the following method.

[Chemical formula 131]

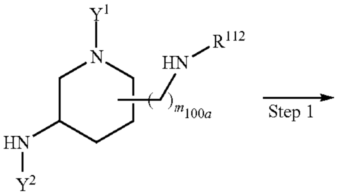

(21-1)

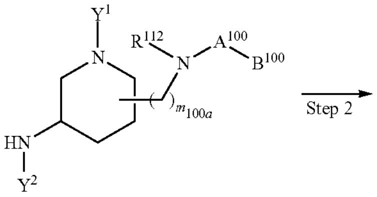

(21-2)

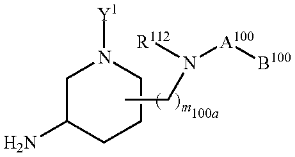

(21-3)

[wherein $m_{100a}$, $R^{112}$, $A^{100}$, $B^{100}$, $Y^1$ and $Y^2$ are the same as defined in the above.]

1) Step 1

The compound (21-2) may be prepared from the compound (21-1) by a similar method to Step 2 of Method 13. The compound (21-1) may be prepared by a similar method to Steps of Method 12.

2) Step 2

The compound (21-3) may be prepared from the compound (21-2) by a similar method to ones disclosed in the literatures (e.g., Protective Groups in Organic Synthesis 2nd Edition (John Wiley & Sons, Inc.), etc.).

Method 22

Among the compounds of the formula (1-14), the compound of formula (22-2) or a salt thereof may be prepared, for example, by the following method.

[Chemical formula 132]

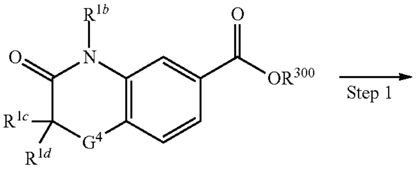

(22-1)

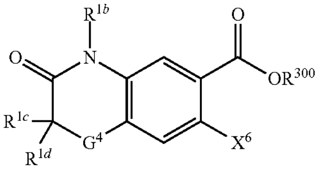

(22-2)

[wherein $G^4$, $R^{1b}$, $R^{1c}$, $R^{1d}$ and $R^{300}$ are the same as defined in the above, and $X^6$ is a halogen atom]

1) Step 1

The compound (22-2) may be prepared by reacting the compound (22-1) in an inert solvent in the presence of sodium acetate with one compound selected from N-chlorosuccinimide, N-bromosuccinimide, and N-iodosuccinimide. The inert solvent includes, for example, an organic acid such as acetic acid, propionic acid, etc. The reaction temperature is suitably selected from the range of from about 20° C. to about 50° C.

Method 23

Among the compounds of the formula (1-14), the compound of the formula (23-3) and the compound of the formula (23-6) or a salt thereof may be prepared, for example, by the following method.

[Chemical formula 133]

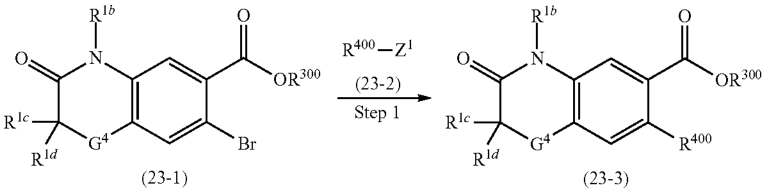

(23-1) (23-3)

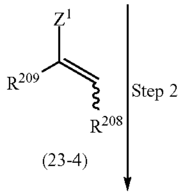

(23-4)

-continued

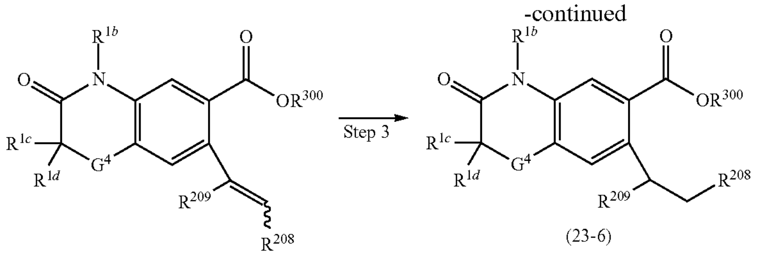

(23-5) (23-6)

[wherein $G^4$, $R^{1b}$, $R^{1c}$, $R^{1d}$ and $R^{300}$ are the same as defined in the above; $R^{208}$ and $R^{209}$ are a hydrogen atom or an alkyl group; $R^{400}$ is an alkyl group; and $Z^1$ is a group of the formula:

[Chemical formula 134]

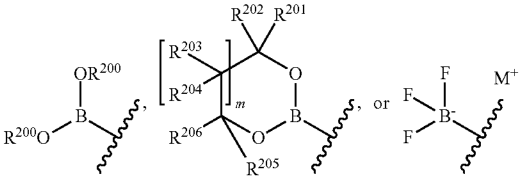

, or (wherein $R^{200}$ is a hydrogen atom or a $C_{1-4}$ alkyl group, or two $R^{200}$s combine each other to form a 1,2-pheneylene, $R^{201}$, $R^{202}$, $R^{203}$, $R^{204}$, $R^{205}$ and $R^{206}$ are independent, and each is a hydrogen atom or a $C_{1-2}$ alkyl group, m is an integer of 0 or 1, $M^+$ is potassium ion, sodium ion or ammonium ion)]

1) Step 1

The compound (23-3) may be prepared by reacting the compound (23-1) and the compound (23-2) in an inert solvent in the presence of a Pd catalyst and an inorganic base. The inorganic base includes, for example, sodium hydrogen carbonate, potassium hydrogen carbonate, sodium carbonate, or potassium carbonate, etc. The Pd catalyst includes, for example, [1,1'-bis(diphenylphosphino) ferrocene]palladium dichloride, [1,1'-bis(diphenylphosphino)ferrocene]palladium dichloride dichloromethane complex, etc. The inert solvent includes, for example, water, tetrahydrofuran, or ethers such as 1,4-dioxane, or 1,2-dimethoxyethane, etc. Usually, a mixture of water and an ether solvent is used. The reaction temperature is selected from the range of from about 50° C. to about 120° C.

2) Step 2

The compound (23-5) may be prepared from the compound (23-1) by a similar method to ones disclosed in the literatures (e.g., Eur. J. Org. Chem. EN 5, 1075 (2004), WO 07/39142, J. Org. Chem. 67, 8424 (2002), Organic Letters 4, 107 (2002), Organic Letters 3, 393 (2001), Tetrahedron 58, 465 (2002), etc.). Examples thereof are illustrated below.

The compound (23-5) may be prepared by reacting the compound (23-1) with the compound (23-4) wherein $Z^1$ is $B(OH)_2$ in inert solvent in the presence of a Pd catalyst and a base. The inert solvent includes, for example, water, or ether solvents such as tetrahydrofuran, 1,4-dioxane, or 1,2-dimethoxyethane, etc. Usually, a mixture of water and an ether solvent is used. The base includes, for example, sodium carbonate, sodium hydrogen carbonate, potassium carbonate, or potassium hydrogen carbonate, etc. The Pd catalyst includes, for example, palladium diphenylphosphino dichloride, or tetrakis(triphenylphosphine)palladium, etc. The reaction temperature is selected from the range of from about 50° C. to about 150° C.

3) Step 3

The compound (23-6) may be prepared by subjecting the compound (23-5) to hydrogenation in the presence of palladium carbon or palladium hydroxide in an inert solvent. The inert solvent includes, for example, alcohols such as methanol, ethanol, or 2-propanol, etc. The reaction temperature is selected from the range of from about 0° C. to about 50° C.

Method 24

Among the compounds of the formula (1-14), the compound of the formula (24-1) or a salt thereof may be prepared, for example, by the following method.

[Chemical formula 135]

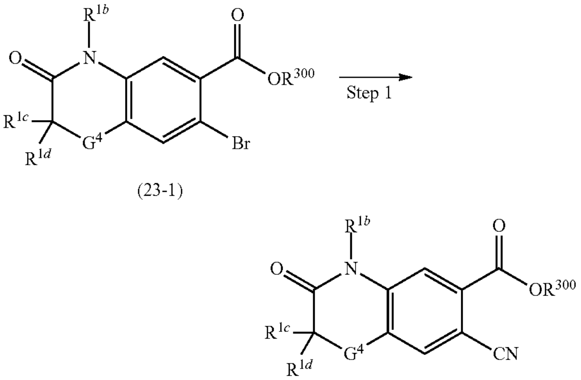

(23-1) (24-1)

[wherein $G^4$, $R^{1b}$, $R^{1c}$, $R^{1d}$ and $R^{300}$ are the same as defined in the above]

1) Step 1

The compound (24-1) may be prepared from the compound (23-1) by a similar method to ones disclosed in the literatures (e.g., Synth. Commun. 24, 887 (1994), Organic Letters 9, 1711 (2007), Tetrahedron Lett. 40, 8193 (1999), Tetrahedron Lett. 45, 1441 (2004), etc.).

Method 25

Among the compounds of the formula (1-13), the compound of the formula (25-4) or a salt thereof may be prepared, for example, by the following method.

[Chemical formula 136]

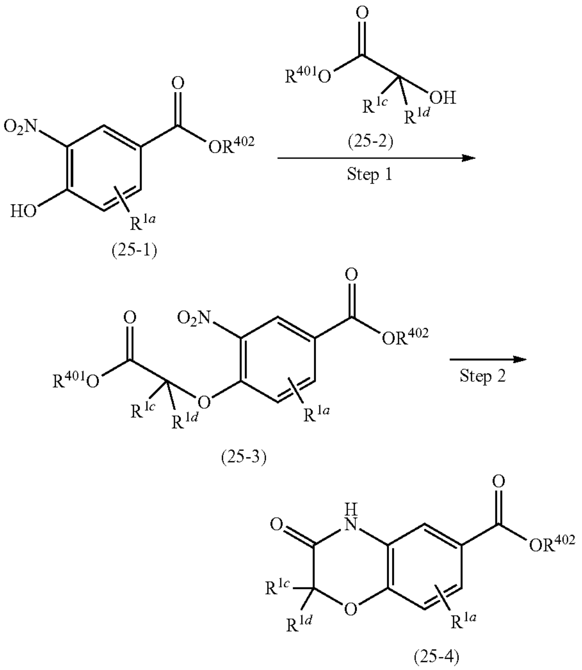

(25-1) (25-3) (25-4)

[wherein $R^{1a}$, $R^{1c}$ and $R^{1d}$ are the same as defined in the above, $R^{401}$ is a $C_{1-6}$ alkyl group, $R^{402}$ is a $C_{1-2}$ alkyl group]

1) Step 1

The compound (25-3) may be prepared by reacting the compound (25-1) and the compound (25-2) in the presence of a phosphine and a condensing agent in an inert solvent. The phosphine includes, for example, triphenylphosphine, etc., and the inert solvent includes, for example, ethers such as tetrahydrofuran, diethyl ether, 1,4-dioxane, 1,2-dimethoxyethane, etc. The condensing agent includes, for example, azodicarboxylic acid diisopropyl ester, etc. The reaction temperature may be selected from the range of from about 0° C. to about 80° C.

2) Step 2

Step 2 may by carried out, for example, by the following method (i. or ii.).

i. The compound (25-4) may be prepared by reacting an iron and the compound (25-3) in an inert solvent. The inert solvent includes, for example, water, acetic acid, or alcohols such as methanol, ethanol, 2-propanol, etc., or a mixture of these solvents. The reaction temperature may be selected from the range of about 30° C. to about 100° C.

ii. The compound (25-4) may be prepared by subjecting the compound (25-3) to hydrogenation in the presence of palladium carbon or palladium hydroxide in an inert solvent. The inert solvent includes, for example, alcohols such as methanol, ethanol, 2-propanol, etc. or ethers such as tetrahydrofuran, diethyl ether, 1,4-dioxane, 1,2-dimethoxyethane, etc. The reaction temperature may be selected from the range of about 0° C. to about 50° C.

Method 26

Among the compounds of the formula (1-14), the compound of the formula (26-5) may be prepared, for example, by the following method.

[Chemical formula 137]

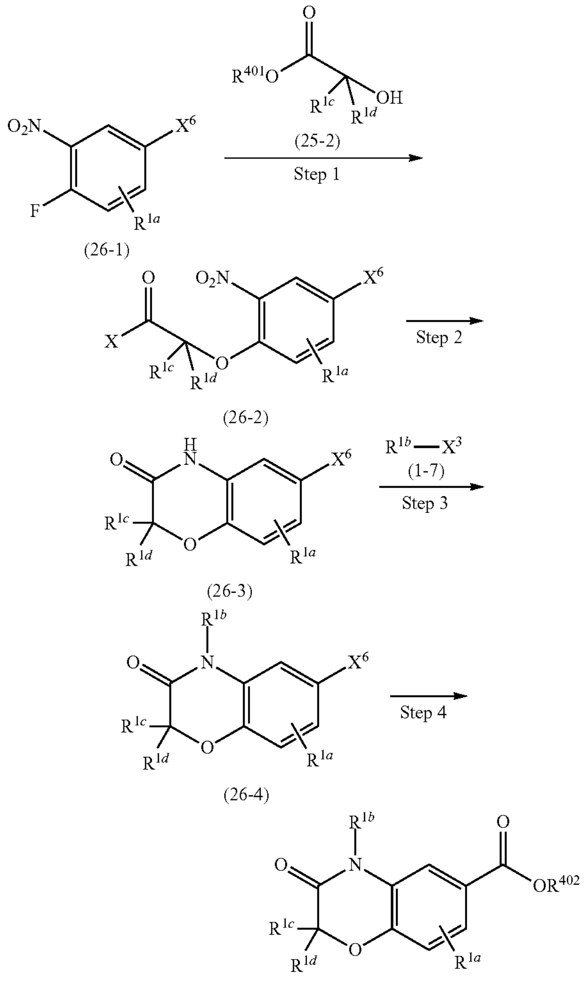

(26-1) (26-2) (26-3) (26-4) (26-5)

[wherein $X^3$, $R^{1a}$, $R^{1b}$, $R^{1c}$, $R^{1d}$, $R^{401}$ and $R^{402}$ are the same as defined in the above, and $X^6$ is a bromine atom or an iodine atom]

1) Step 1

The compound (26-2) may be prepared by reacting the compound (26-1) with the compound (25-2) in the presence or absence of a crown ether and in the presence of sodium hydride in an inert solvent. The crown ether includes, for example, 15-crown, etc. The inert solvent includes, for example, ethers such as tetrahydrofuran, diethyl ether, 1,4-dioxane, or 1,2-dimethoxyethane, etc. The reaction temperature may be selected from the range of from about 0° C. to about 50° C.

2) Step 2

The compound (26-3) may be prepared from the compound (26-2) by a similar method to Step 2 of Method 25.

3) Step 3

The compound (26-4) may be prepared by reacting the compound (26-3) with the compound (1-7) in the presence of an inorganic base in an inert solvent. The inorganic base includes, for example, potassium carbonate, sodium hydride, etc. The inert solvent includes, for example, ethers such as tetrahydrofuran, diethyl ether, 1,4-dioxane, or 1,2-dimethoxyethane, etc., or nitrile solvents such as acetonitrile, or propionitrile, etc. The reaction temperature may be selected from the range of from about 30° C. to about 100° C.

4) Step 4

The compound (26-5) may be prepared by reacting the compound (26-4) under carbon oxide atmosphere in the presence of methanol or ethanol, an organic base, an auxiliary ligand and palladium acetate in an inert solvent. The auxiliary ligand includes diphenylphosphinopropane, etc. The organic base includes N,N-diisopropylethylamine, etc. The inert solvent includes, for example, acetamide solvents such as dimethylacetamide, etc. The reaction temperature may be selected from the range of from about 70° C. to about 150° C.

Method 27

Among the compounds of the formula (1-3), the compound of the formula (27-7) or a salt thereof may be prepared, for example, by the following method.

[Chemical formula 138]

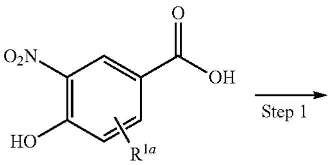

(27-1)

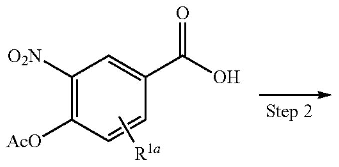

(27-2)

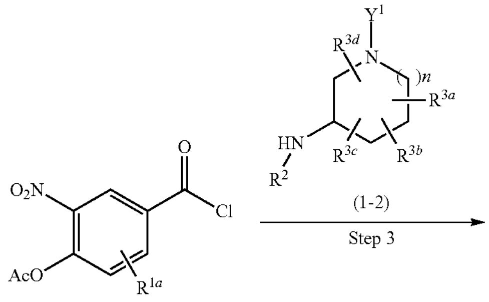

(27-3)

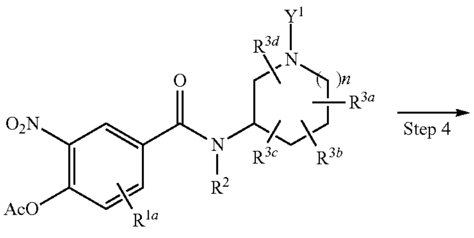

(27-4)

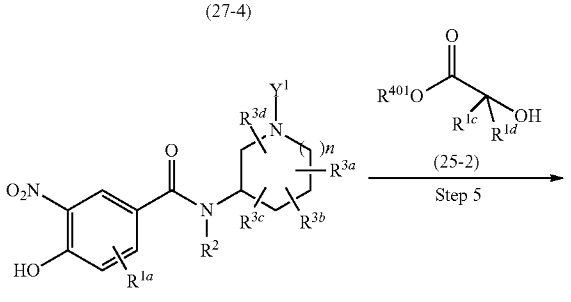

(27-5)

-continued

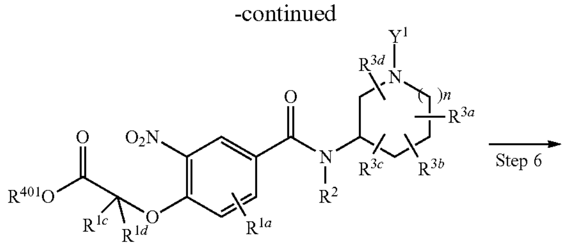

(27-6)

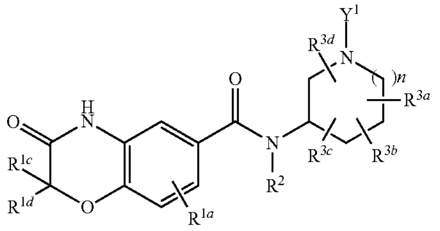

(27-7)

[wherein n, $R^{401}$, $Y^1$, $R^{1a}$, $R^{1c}$, $R^{1d}$, $R^{3a}$, $R^{3c}$, $R^{3d}$ and $R^2$ are the same as defined in the above.]

1) Step 1

The compound (27-2) may be prepared, for example, by reacting the compound (27-1) with acetic anhydride in a pyridine solvent. The reaction temperature may be selected from the range of from about 10° C. to about 40° C.

2) Step 2

The compound (27-3) may be prepared from the compound (27-2) in a similar manner to Step 1 of Method 1.

3) Step 3

The compound (27-4) may be prepared from the compound (27-3) in a similar manner to Step 1 of Method 1.

4) Step 4

The compound (27-5) may be prepared by reacting the compound (27-4) with a base in the presence or absence of Amberlite (registered trade name) in an inert solvent. The base includes inorganic bases such as sodium hydrogen carbonate, potassium hydrogen carbonate, sodium carbonate, potassium carbonate, sodium hydroxide, or sodium hydride, etc. The inert solvent includes, for example, alcohols such as methanol, ethanol, or 2-propanol, etc. The reaction temperature may be selected from the range of from about 10° C. to about 40° C.

5) Step 5

The compound (27-6) may be prepared from the compound (27-5) in a similar manner to Step 1 of Method 1.

6) Step 6

The compound (27-7) may be prepared from the compound (27-6) in a similar manner to Step 6 of Method 1.

Method 28

Among the compounds of the formula (1-13), the compound (28-3) or a salt thereof may be prepared, for example, by the following method.

[Chemical formula 139]

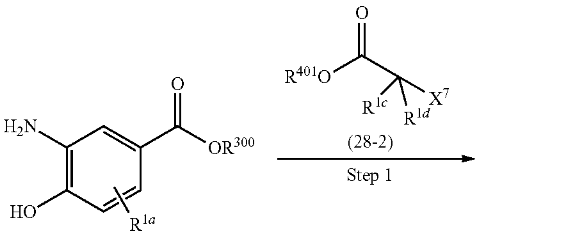

(28-1)

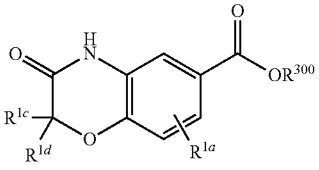

(28-3)

[wherein $R^{1a}$, $R^{1c}$, $R^{1d}$, $R^{401}$ and $R^{300}$ are the same as defined in the above, and $X^7$ is a bromine atom or a chlorine atom]

1) Step 1

The compound (28-3) may be prepared from the compound (28-1) by a similar method to ones disclosed in the literatures (e.g., Chem. Pharm. Bull. 46, 1716 (1998), etc.).

Method 29

Among the compounds of the formula (1-13), the compound of the formula (29-4) or a salt thereof may be prepared, for example, by the following method.

[Chemical formula 140]

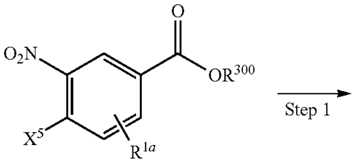

(29-1)

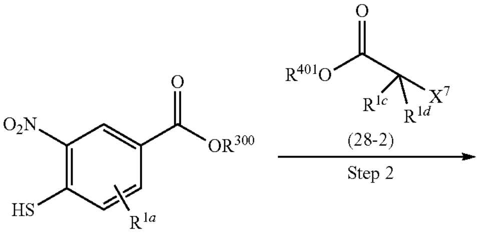

(29-2)

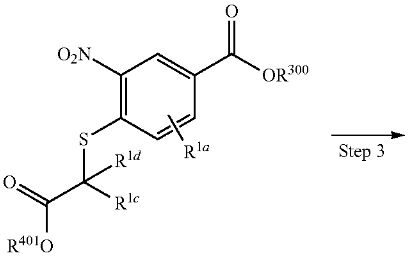

(29-3)

-continued

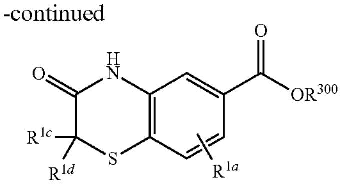

(29-4)

[wherein $X^5$, $X^7$, $R^{1a}$, $R^{1c}$, $R^{1d}$, $R^{401}$, and $R^{300}$ are the same as defined in the above.]

1) Step 1

The compound (29-2) may be prepared from the compound (29-1) by a similar method to ones disclosed in the literatures (e.g., Synth. Commun. 27, 2943 (1997), J. Chem. Soc. Perkin Trans 2, 691 (1988), etc.).

2) Step 2 to Step 3

The compound (29-4) may be prepared from the compound (29-2) by a similar method to ones disclosed in the literatures (e.g., WO 2005/082872, etc.).

Method 30

Among the compounds of the formula (1-13), the compound of the formula (30-5) or a salt thereof may be prepared, for example, by the following method.

[Chemical formula 141]

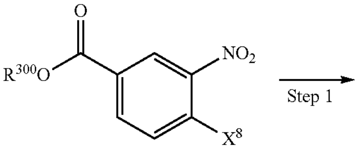

(30-1)

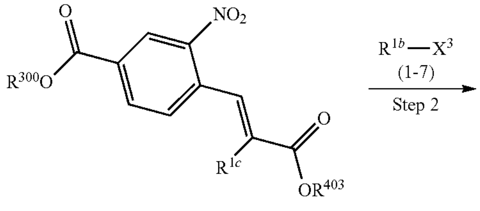

(30-2)

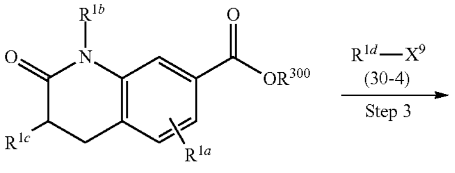

(30-3)

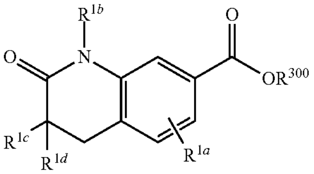

(30-5)

[wherein $X^3$, $R^{1a}$, $R^{1b}$, $R^{1c}$, $X^{1d}$, and $R^{300}$ are the same as defined in the above; $R^{403}$ is a $C_{1-6}$ alkyl group; $X^8$ is an iodine atom, a bromine atom, a chlorine atom or a trifluoromethanesulfonyloxy group; $X^9$ is an iodine atom, a bromine atom, a chlorine atom, a methanesulfonyloxy group, a trifluoromethanesulfonyl-oxy group or a p-toluenesulfonyloxy group.]

1) Step 1

The compound (30-2) may be prepared from the compound (30-1) by a similar method to ones disclosed in the literatures (e.g., J. Am. Chem. Soc. 123, 6989 (2001), J. Org. Chem. 70, 4360 (2005), Synth. Commun. 29, 591 (1999), etc.).

2) Step 2

The compound (30-3) may be prepared from the compound (30-2) by a similar method to Step 8 of Method 1.

3) Step 3

The compound (30-5) may be prepared from the compound (30-3) by a similar method to ones disclosed in the literatures (e.g., WO 2004/096773, etc.).

Method 31

Among the compounds of the formula (1-2), the compound of the formula (31-3) or a salt thereof may be prepared, for example, by the following method.

[Chemical formula 142]

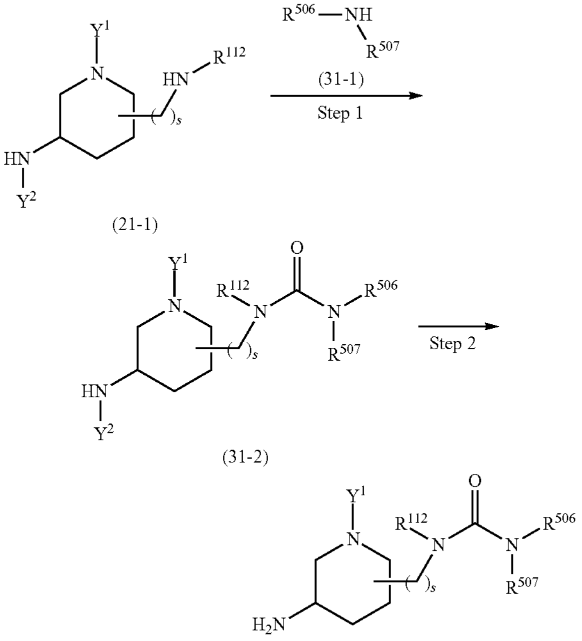

(31-1)

(21-1)

(31-2)

(31-3)

[wherein $R^{112}$, s, $Y^1$ and $Y^2$ are the same as defined in the above; $R^{506}$ is the same as B as defined in the above; and $R^{507}$ is the same as $R^4$ as defined in the above.]

1) Step 1

The compound (31-2) may be prepared from the compound (21-1) by a similar method to ones disclosed in the literatures (e.g., Bioorganic & Medicinal Chemistry Letters 1621, 16 (2006), WO 99/054321, etc.).

2) Step 2

The compound (31-3) may be prepared from the compound (31-2) by a similar method to ones disclosed in the literatures (e.g., Protective Groups in Organic Synthesis 2nd Edition (John Wiley & Sons, Inc.), etc.).

Method 32

Among the compounds of the formula (I), the compound of the formula (32-17) or a salt thereof may be prepared, for example, by the following method.

[Chemical formula 143]

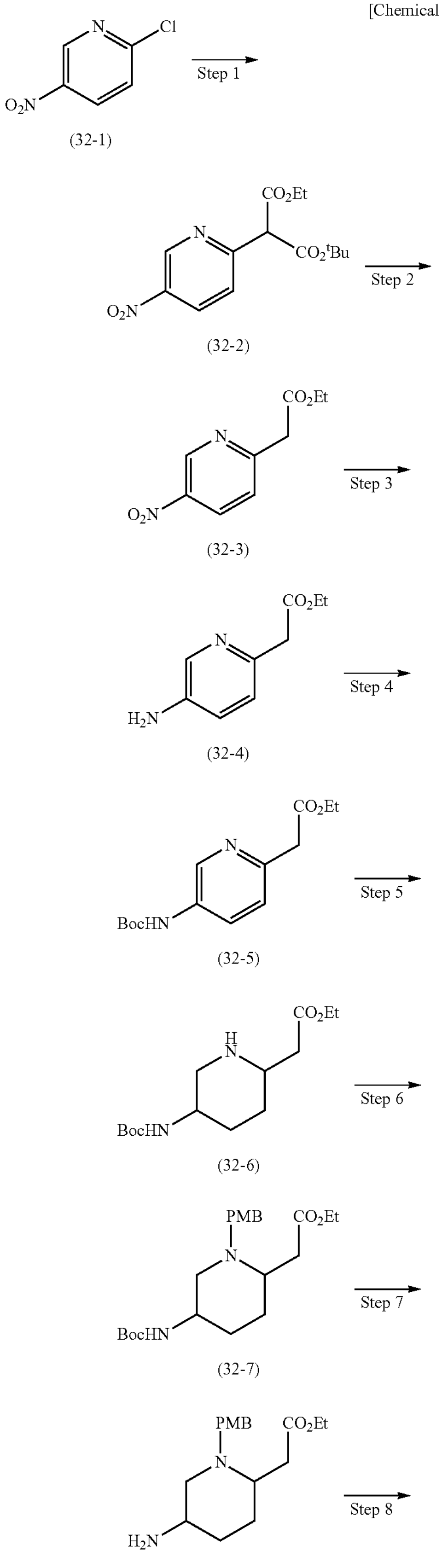

(32-1)

(32-2)

(32-3)

(32-4)

(32-5)

(32-6)

(32-7)

(32-8)

-continued

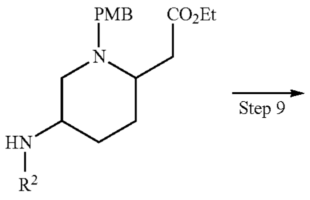

(32-9)

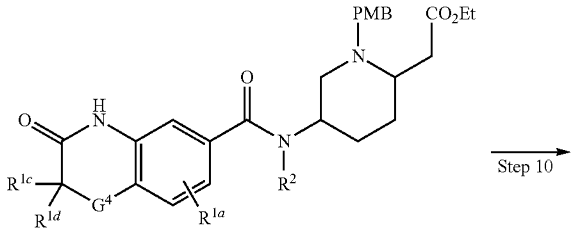

(32-10)

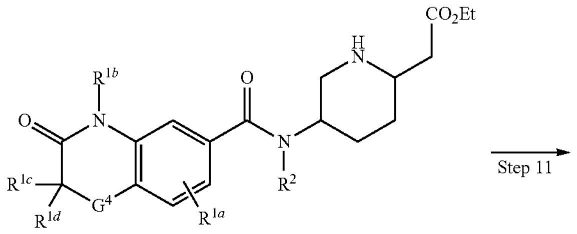

(32-11)

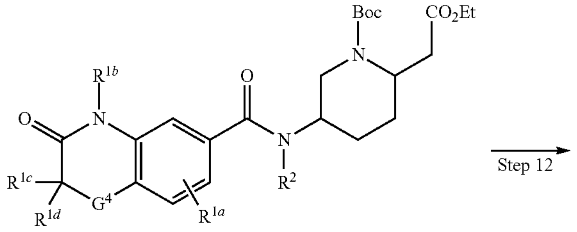

(32-12)

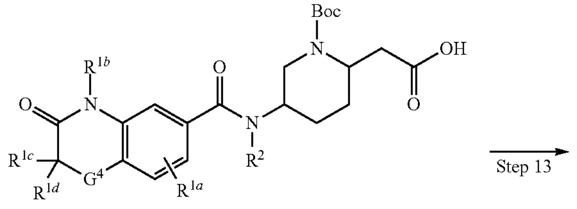

(32-13)

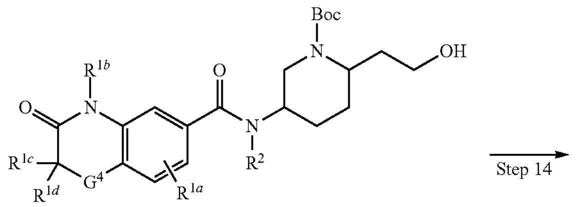

(32-14)

-continued

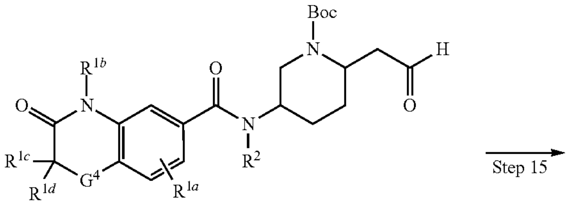

(32-15)

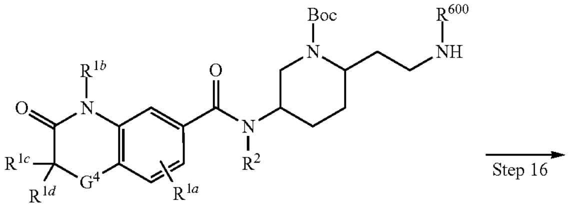

(32-16)

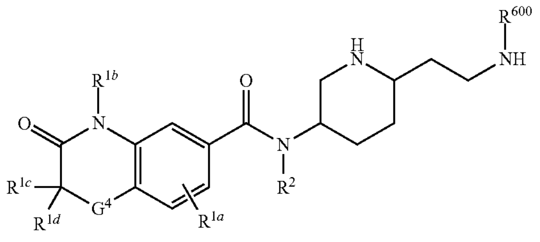

(32-17)

[wherein $G^4$, $R^{1a}$, $R^{1b}$, $R^{1c}$, $X^{1d}$, and $R^2$ are the same as defined in the above, and $R^{600}$ is the same as B as defined in Item 1.]

1) Step 1

The compound (32-2) may be prepared by reacting the compound (32-1) with a base in an inert solvent, followed by reacting the resultant with tert-butyl ethyl malonate. The base includes inorganic bases such as potassium hydride, or sodium hydride, etc. The inert solvent includes, for example, aprotic solvents such as N,N'-dimethylformamide, dimethylsulfoxide, or hexamethylenephosphoamide, etc. The reaction temperature may be selected from the range of from about 10° C. to about 40° C.

2) Step 2

The compound (32-3) may be prepared by reacting the compound (32-2) with trifluoroacetic acid in an inert solvent. The inert solvent includes, for example, halogenated hydrocarbon solvents such as dichloromethane, chloroform, or 1,2-dichloroethane, etc. The reaction temperature may be selected from the range of from about 10° C. to about 40° C.

3) Step 3

The compound (32-4) may be prepared by subjecting the compound (32-3) to reduction under hydrogen atmosphere in the presence of palladium carbon in an inert solvent. The inert solvent includes, for example, alcohols such as methanol, or ethanol, etc. The reaction temperature may be selected from the range of from about 10° C. to about 40° C.

4) Step 4

The compound (32-5) may be prepared by reacting the compound (32-4) with di-tert-butyl dicarbonate in an inert solvent. The inert solvent includes, for example, ethers such as dioxane, tetrahydrofuran, etc. The reaction temperature may be selected from the range of from about 10° C. to about 40° C.

5) Step 5

The compound (32-6) may be prepared by subjecting the compound (32-5) to reduction under hydrogen atmosphere in the presence of platinum oxide in an inert solvent. The inert solvent includes alcohols such as methanol, or ethanol, etc. The reaction temperature may be selected from the range of from about 10° C. to about 40° C.

6) Step 6

The compound (32-7) may be prepared by reacting the compound (32-6) with p-methoxybenzyl chloride in an inert solvent in the presence of an inorganic base. The inorganic base includes potassium carbonate, or cesium carbonate, etc. The inert solvent includes, for example, aprotic solvents such as N,N'-dimethylformamide, dimethylsulfoxide, or hexamethylenephosphoamide, etc. The reaction temperature may be selected from the range of from about 10° C. to about 40° C. In addition, in this Step, sodium iodide or potassium iodide may be added.

7) Step 7

The compound (32-8) may be prepared from the compound (32-7) by a similar method to Step 6 of Method 1.

8) Step 8

The compound (32-9) may be prepared from the compound (32-8) by a similar method to Step 4 of Method 1.

9) Step 9

The compound (32-10) may be prepared from the compound (32-9) by a similar method to Step 10 of Method 1.

10) Step 10

The compound (32-11) may be prepared by subjecting the compound (32-10) to reduction under hydrogen atmosphere in the presence of palladium carbon in an inert solvent. The inert solvent includes, for example, alcohols such as methanol, or ethanol, etc. The reaction temperature may be selected from the range of from about 10° C. to about 40° C.

11) Step 11

The compound (32-12) may be prepared from the compound (32-11) by a similar method to Step 4 of Method 32.

12) Step 12

The compound (32-13) may be prepared from the compound (32-12) by a similar method to Step 2 of Method 3.

13) Step 13

The compound (32-14) may be prepared from the compound (32-13) by carrying out the following reactions (i. to ii.) continuously in an inert solvent. The inert solvent may be, for example, ethers such as dioxane, or tetrahydrofuran, etc.

i. the compound (32-13) is reacted with ethyl chloroformate in the presence of triethylamine. The reaction temperature may be selected from the range from about −10° C. to about 20° C.

ii. sodium borohydride is added to the reaction mixture of the above i., and the mixture is reacted. The reaction temperature may be selected from the range of from about 0° C. to about 20° C.

14) Step 14

The compound (32-15) may be prepared by subjecting the compound (32-14) to Swern oxidation. For instance, dimethylsulfoxide was added to oxalyl chloride in a halogenated hydrocarbon solvent such as dichloromethane, chloroform, or 1,2-dichloroethane, etc., and then, the compound (30-14) is added thereto, and further, diisopropylethylamine is added. The reaction temperature may be selected from the range of from about −80° C. to about −30° C.

15) Step 15

The compound (32-16) may be prepared from the compound (32-15) by a similar method to Step 4 of Method 1.

16) Step 16

The compound (32-17) may be prepared from the compound (32-16) by a similar method to Step 6 of Method 1.

Method 33

Among the compounds of the formula (I), the compound of the formula (33-2) or a salt thereof may be prepared, for example, by the following method.

[Chemical formula 144]

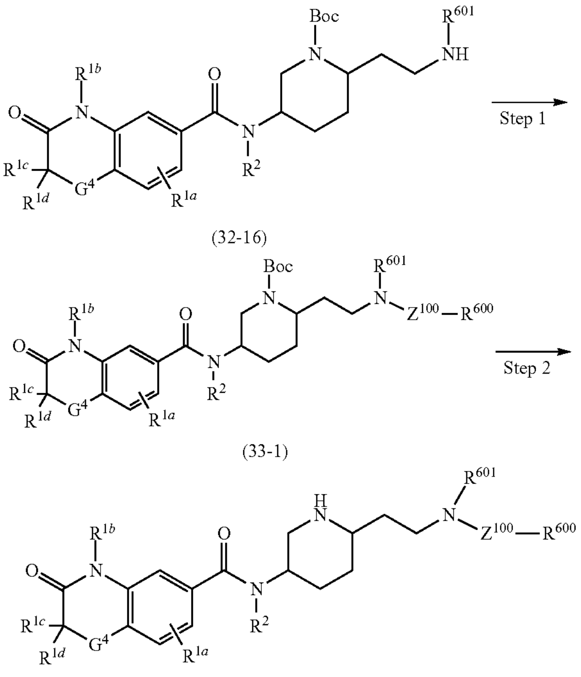

(32-16)

(33-1)

(33-2)

[wherein $G^4$, $R^{1a}$, $R^{1b}$, $R^{1c}$, $X^{1d}$, $R^2$ are the same as defined in the above; $Z^{100}$ is C(O), $S(O)_2$, or $C(O)N(R^{601})$; $R^{601}$ is the same as $R^4$ as defined in Item 1.]

1) Step 1

The compound (33-1) may be prepared from the compound (33-16) by a similar method to ones disclosed in the literatures (e.g., Comprehensive Organic transformation, R. C. Laroque, VCH publisher Inc., 1989, etc.).

2) Step 2

The compound (33-2) may be prepared from the compound (33-1) by a similar method of Step 6 of Method 1.

In the above-mentioned each step, when the starting compounds used in each reaction has reactive groups such as a hydroxy group, an amino group or a carboxyl group, then these groups at sites other than the sites to be reacted can be protected by a suitable protecting group prior to the reaction, if necessary, and such protecting groups can be removed after each reaction is completed or after some reactions are done, to give the desired compound. The protecting groups for protecting a hydroxy group, an amino group, a carboxyl group, etc. may be any conventional protecting groups usually used in the organic chemistry field, and the introduction and the removal of these protecting groups may be carried out by a conventional method (e.g., the methods disclosed in Protective Groups in Organic Synthesis, T. W. Greene, co-written by G. M. Wuts, 2nd edition, John Wiley & Sons, Inc. (1991)).

For instance, a protecting group for a hydroxy group may be a tert-butyldimethylsilyl group, a methoxymethyl group, a tetrahydropyranyl group, etc. A protecting group for an amino group may be a tert-butyloxycarbonyl group, a benzyloxycarbonyl group, etc. A protecting group for a hydroxy group may be removed by reacting in the presence of acids such as hydrochloric acid, sulfuric acid, acetic acid, etc. in a solvent such as aqueous methanol, aqueous ethanol, aqueous tetrahydrofuran, etc. In addition, a tert-butyldimethylsilyl group may be removed, for example, in the presence of tetrabutylammonium fluoride in a solvent such as tetrahydrofuran. As for the protecting group for an amino group, tert-butyloxycarbonyl group may be removed, for example, by reacting in the presence of acids such as hydrochloric acid, trifluoroacetic acid, etc. in a solvent such as aqueous tetrahydrofuran, methylene chloride, chloroform, aqueous methanol, etc. A benzyloxycarbonyl group may be removed, for example, by reacting in the presence of an acid such as hydrobromic acid in a solvent such as acetic acid.

tert-Butyl ester, ortho ester, acid amide, etc. may be exemplified as a protecting group for a carboxyl group. These protecting groups may be removed, for example, when such a protecting group is a tert-butyl ester, then it can be removed by reacting in the presence of hydrochloric acid in an aqueous solvent. When an ortho ester is used, it can be removed, for example, by treating with an acid in a solvent such as aqueous methanol, aqueous tetrahydrofuran, aqueous 1,2-dimethoxyethane, followed by treatment with an alkali such as sodium hydroxide, etc. When an acid amide is used, then it may be removed, for example, by reacting in the presence of an acid such as hydrochloric acid, sulfuric acid, etc. in a solvent such as water, aqueous methanol, aqueous tetrahydrofuran, etc.

The compound of the formula (I) includes compounds having an optically-active center, and such compounds may be obtained in a mixture of racemic compounds, or in the form of an optically active compound when an optically active starting compound is used. If necessary, the obtained racemic mixture may be resolved physically or chemically by a conventional method into optical enantiomers thereof, or preferably resolved into diastereomers thereof by a reaction using an optically active resolving agent. Diastereomers in a different form may be resolved by a conventional method such as fractional crystallization.

The compound of the present invention may be converted into a salt thereof, for example, by mixing with a pharmaceutically acceptable acid in solvents such as water, methanol, ethanol, acetone, etc. The pharmaceutically acceptable acid includes, for example, inorganic acids such as hydrochloric acid, hydrobromic acid, sulfuric acid, phosphoric acid, nitric acid, etc. or organic acids such as acetic acid, propionic acid, oxalic acid, succinic acid, lactic acid, malic acid, tartaric acid, citric acid, maleic acid, fumaric acid, methanesulfonic acid, p-toluenesulfonic acid, ascorbic acid, etc.

The compound of the present invention may possibly be applied to the treatment of various diseases because of its renin inhibitory activity. The compounds disclosed in the present specification are useful as a therapeutic agent for hypertension. These compounds are also useful in the control of acute and chronic congestive heart failure. These compounds can be expected to be useful in the treatment of primary or secondary pulmonary hypertension, secondary hyperaldosteronism, primary and secondary pulmonary hyperaldosteronism, kidney failure (such as glomerulonephritis, diabetic nephropathy, glomerulosclerosis, primary renal disease, end-stage renal disease, renovascular hypertension), left ventricular failure, diabetic retinopathy, and for the minimization of vascular diseases such as migraine, Raynaud's disease and atherosclerosis process. In addition, these compounds are also useful in the treatment of diseases relating to elevated intraocular pressure such as glaucoma.

When the present compound is used in the therapy, it may be administered orally or parenterally (e.g., intravenously, subcutaneously or intramuscularly, locally, rectally, percutaneously, or transnasally) in the form of a pharmaceutical composition. The composition for oral administration may be, for example, tablets, capsules, pills, granules, powders, solutions, suspensions, etc. The composition for parenteral administration may be, for example, aqueous solutions for injection, or oils, ointments, creams, lotions, aerosols, suppositories, adhesive preparations, etc. These preparations may be prepared by a conventional method, and may additionally contain a nontoxic and nonactive carrier or excipient, that is usually used in the pharmaceutical field.

The dosage may vary depending on each compound, or diseases, ages, body weights, sexes, conditions of each patient, or administration route, etc., and the present compound or a pharmaceutically acceptable salt thereof may usually be administered at a dose of 0.1 to 1000 mg/day, preferably at a dose of 1 to 300 mg/day in an adult (body weight: 50 kg), which is administered once a day or divided into 2 or 3 dosage forms. In addition, the present compound can be administered once in several days to once in several weeks.

Aiming at the enhancement of the pharmacological activity, the present compound may be used in a combination with a medicament such as an antidiabetic agent, an agent for antidiabetic complications, an antilipedemic agent, a hypotensive agent, an antiobesity agent, a diuretic agent (hereinafter referred to as combined medicine). The administration timing of the present compound and a combined medicine is not necessarily defined, and they can be administered to a subject simultaneously or administered with time-interval.

In addition, the present compound and a combined medicine may be used in the form of a combination drug. The dosage of a combined medicine may be suitably selected based on the dosage thereof which is clinical used. In addition, the mixing ratio of the present compound and a combined medicine may suitably be determined depending on the subject to be administered, administration route, the disease to be treated, the conditions of a patient, and a kind of combination. For example, when the subject to be administered is human, then a combined medicine is used in an amount of 0.01 to 100 parts by weight to one part by weight of the present compound.

The antidiabetic agent includes insulin preparations (e.g., animal insulin preparations extracted from the bovine pancreas or swine pancreas; genetically-engineered human insulin preparations using *Escherichia coli* or yeast, etc.), insulin sensitizers (e.g., pioglitazone or hydrochloride thereof, troglitazone, rosiglitazone or a maleate thereof, GI-262570, JTT-501, CC-555, YM-440, KRP-297, CS-011, etc.), α-glucosidase inhibitors (e.g., voglibose, acarbose, miglitol, emiglitate, etc.), biguanides (e.g., metformine, etc.), insulin secretagogues (e.g., sulfonylureas such as tolbutamide, glibenclamide, gliclazide, chlorpropamide, tolazamide, acetohexamide, glyclopyramide, glimepiride, etc.; repaglinide, senaglinide, nateglinide, mitiglinide, etc.), GLP-1, GLP-1 analogues (exenatide, liraglutide, SUN-E7001, AVE010, BIM-51077, CJC1131, etc.), protein tyrosine phosphatase inhibitors (e.g., vanadic acid, etc.), β3 agonists (e.g., GW-427353B, N-5984, etc.), DPPIV inhibitors (e.g., sitagliptin, vildagliptin, saxagliptin, SYR-322, etc.).

The therapeutic agents for diabetic complications include aldose reductase inhibitors (e.g., tolrestat, epalrestat, zenarestat, zopolrestat, minarestat, fidarestat, SK-860, CT-112, etc.), neurotrophic factors (e.g., NGF, NT-3, BDNF, etc.), PKC inhibitors (e.g., LY-333531, etc.), AGE inhibitors (e.g., ALT946, pimagedine, pyratoxatin, N-phenacylthiazolium bromide (ALT766), etc.), active oxygen scavenger (e.g., thioctic acid, etc.), cerebral vasodilators (e.g., tiapride, mexiletine, etc.). A antilipidemic agent includes HMG-CoA reductase inhibitors (e.g., pravastatin, simvastatin, lovastatin, atorvastatin, fluvastatin, itavastatin or sodium salt thereof, etc.), squalene synthetase inhibitors, ACAT inhibitors, etc. The hypotensive agent includes angiotensin-converting enzyme inhibitors (e.g., captopril, enalapril, alacepril, delapril, lisinopril, imidapril, benazepril, cilazapril, temocapril, trandolapril, etc.), angiotensin II antagonists (e.g., olmesartan medoxomil, candesartan cilexetil, losartan, eprosartan, valsartan, telmisartan, irbesartan, tasosartan, etc.), calcium antagonists (e.g., nicardipine hydrochloride, manidipine hydrochloride, nisoldipine, nitrendipine, nilvadipine, amlodipine, etc.), ACE/NEP inhibitors (e.g., omapatrilat, fasidotril, etc.), beta blockers (e.g., atenolol, bisoprolol, betaxolol, metoprolol, etc.), alpha blockers (e.g., urapidil, terazosin, doxazosin, bunazosin, etc.), alpha beta blockers (e.g., amosulalol, arotinolol, labetalol, carvedilol, etc.).

The antiobesity agent includes, for example, central antiobesity agents (e.g., phentermine, sibutramine, amfepramone, dexamphetamine, Mazindol, SR-141716A, etc.), pancreatic lipase inhibitors (e.g., Orlistat, etc.), peptidic appetite suppressors (e.g., leptin, CNTF (ciliary neurotrophic factor), etc.), cholecystokinin agonists (e.g., lintitript, FPL-15849, etc.). The diuretic agent includes, for example, xanthine derivatives (e.g., theobromine sodium salicylate, theobromine calcium salicylate. etc.), thiazide preparations (e.g., Ethiazide, cyclopenthiazide, trichloromethiazide, hydrochlorotiazide, hydroflumethiazide, bentylhydrochlorothiazide, penflutizide, polythiazide, methychlothiazide, etc.), antialdosterone preparations (e.g., spironolactone, triamterene, etc.), carbonate dehydratase inhibitors (e.g., acetazolamide, etc.), chlorbenzenesulfonamide preparations (e.g., chlorthalidone, mefruside, indapamide, etc.), azosemide, isosorbide, ethacrynic acid, piretanide, bumetanide, furosemide, etc.

The above mentioned combined medicines may be used in a mixture of two or more of these drugs.

When the present compound is used in a combination of a combined medicine, the dosage of these drugs can be lessened within the safe range, in view of the side effects of the drugs. Accordingly, any possible side effect caused by these drugs may safely be inhibited.

EXAMPLES

The present invention is illustrated in more detail by Reference Examples, Examples and Experiments, but the present invention should not be construed to be limited thereto. In addition, the compound names used in the following Reference Examples and Examples are not necessarily based on IUPAC nomenclature. Further, in order to simplify the description, some abbreviations may be used, and these abbreviations are as defined in the above-mentioned.

Reference Example 1

Methyl 4-(2-ethoxy-1,1-dimethyl-2-oxoethoxy)-3-nitrobenzoate

[Chemical formula 145]

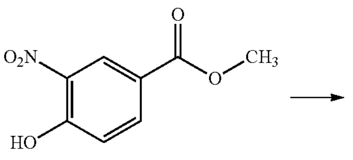

-continued

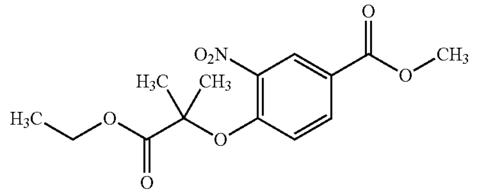

To a solution of methyl 4-hydroxy-3-nitrobenzoate (18.0 g) in N,N-dimethylformamide (70 ml) were added potassium carbonate (25.1 g) and ethyl 2-bromoisobutyrate (20.0 g), and the mixture was heated at 80° C. with stirring. Ten hours later, the reaction solution was cooled to 25° C., and water was added to the reaction solution. The mixture was extracted with ethyl acetate, and the organic layer was washed with a saturated aqueous sodium chloride solution, dried over magnesium sulfate, filtered and concentrated under reduced pressure. The obtained residue was purified by silica gel column chromatography (hexane/ethyl acetate=5/1) to give the title compound (11.8 g).

MS (ESI+) 312 ($M^+$+1, 100%).

Reference Example 2

Methyl 2,2-dimethyl-3-oxo-3,4-dihydro-2H-1,4-benzoxazine-6-carboxylate

[Chemical formula 146]

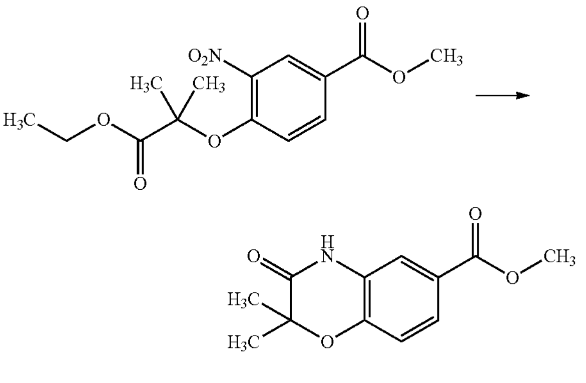

To a suspension of iron (12.0 g) in acetic acid (30 ml) was gradually added dropwise a solution of the compound of Reference Example 1 (11.8 g) in acetic acid (50 ml)/ethanol (50 ml) at 80° C., and after the addition, the mixture was heated at 80° C. with stirring. Three hours later, the reaction solution was cooled to 25° C., and the insoluble materials were removed by filtration on celite. The filtrate was concentrated under reduced pressure. To the obtained residue was added water, and the mixture was extracted with ethyl acetate. The organic layer was washed with a saturated aqueous sodium chloride solution, dried over magnesium sulfate, filtered and concentrated under reduced pressure. The obtained residue was washed by repulping with ethyl acetate, and collected by filtration to give the title compound (6.8 g) as a white solid.

MS (ESI+) 236 ($M^+$+1, 100%).

Reference Example 3

Methyl 4-(3-methoxypropyl)-2,2-dimethyl-3-oxo-3,4-dihydro-2H-1,4-benzoxazine-6-carboxylate

[Chemical formula 147]

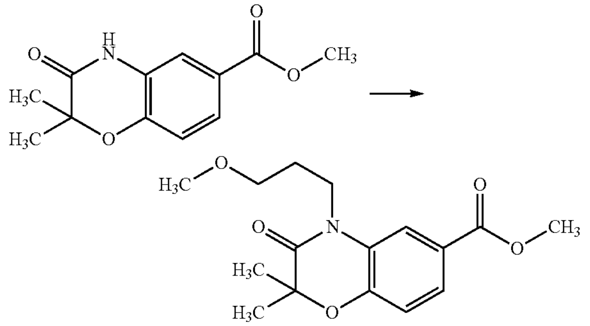

To a solution of the compound of Reference Example 2 (1.80 g) in N,N-dimethylformamide (20 ml) were added sodium hydride (55% wg, 0.40 g) and 1-bromo-3-methoxypropane (1.40 g), and the mixture was heated at 80° C. with stirring. Six hours later, the reaction solution was cooled to 25° C., and water was added thereto. The mixture was extracted with ethyl acetate, and the organic layer was washed with a saturated aqueous sodium chloride solution, dried over magnesium sulfate, filtered and concentrated under reduced pressure. The obtained residue was purified by silica gel column chromatography (hexane/ethyl acetate=5/1) to give the title compound (1.85 g).

MS (ESI+) 308 ($M^{+}$+1, 100%).

Reference Example 4

4-(3-Methoxypropyl)-2,2-dimethyl-3-oxo-3,4-dihydro-2H-1,4-benzoxazine-6-carboxylic acid

[Chemical formula 148]

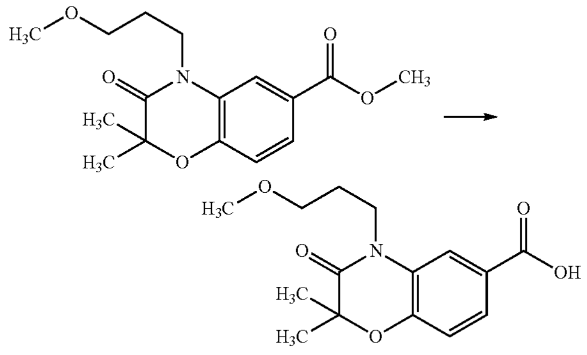

The compound of Reference Example 3 (2.0 g) was dissolved in tetrahydrofuran (5 ml) and methanol (5 ml), and thereto was added a 2N aqueous sodium hydroxide solution (5 ml), and the mixture was heated at 60° C. with stirring for 5 hours. The reaction solution was concentrated under reduced pressure, and thereto was added a 5% potassium hydrogen sulfate, and the mixture was extracted with ethyl acetate. The organic layer was washed with a saturated aqueous sodium chloride solution, dried over magnesium sulfate, filtered and concentrated under reduced pressure to give the title compound (1.81 g).

MS (ESI+) 294 ($M^{+}$+1, 100%).

Reference Example 5 tert-Butyl (3R)-3-(isopropyl{[4-(3-methoxypropyl)-2,2-dimethyl-3-oxo-3,4-dihydro-2H-1,4-benzoxazin-6-yl]carbonyl}amino)piperidine-1-carboxylate

[Chemical formula 149]

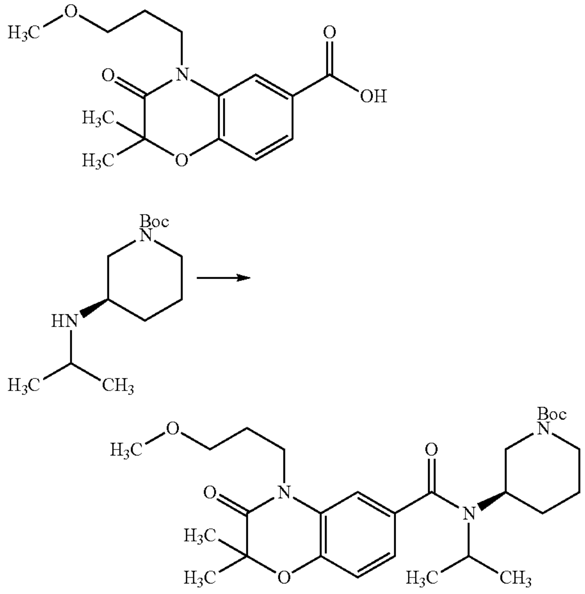

To a solution of the compound of Reference Example 4 (1.47 g) in dichloromethane (20 ml) were added oxalyl chloride (0.66 ml) and dimethylformamide (10 μl), and the mixture was stirred at room temperature for one hour. The solvent was removed by evaporation, and to the residue was added toluene, and the mixture was concentrated under reduced pressure. The obtained residue was dissolved in dichloromethane (10 ml), and thereto was added dropwise a solution of tert-butyl (3R)-3-(isopropylamino)piperidine-1-carboxylate (1.51 g), triethylamine (1.2 ml) in dichloromethane (20 ml), and the mixture was stirred at room temperature for 2 hours. To the reaction mixture was added water, and the mixture was extracted with ethyl acetate. The organic layer was washed with a saturated aqueous sodium chloride solution, dried over magnesium sulfate, filtered and concentrated under reduced pressure. The obtained residue was purified by silica gel column chromatography (the developing solvent: hexane/ethyl acetate=2/1) to give the title compound (2.0 g).

MS (ESI+) 518 ($M^{+}$+1, 100%).

Reference Example 6 tert-Butyl (3R)-3-[{[7-bromo-4-(3-methoxypropyl)-2,2-dimethyl-3-oxo-3,4-dihydro-2H-1,4-benzoxazin-6-yl]carbonyl}(isopropyl)amino]piperidine-1-carboxylate

[Chemical formula 150]

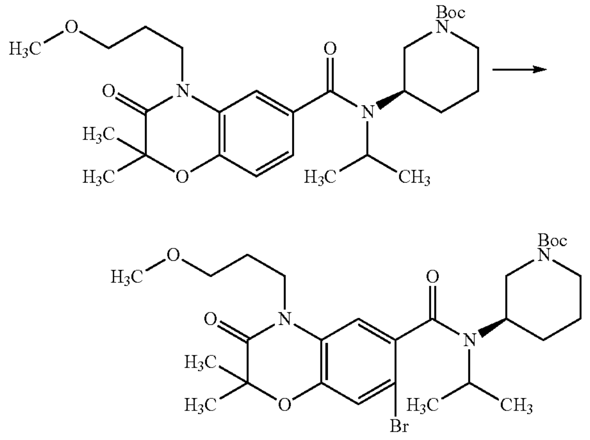

The compound of Reference Example 5 (280 mg) was dissolved in N,N-dimethylformamide (3 ml), and thereto was added N-bromosuccinimide (200 mg), and the mixture was stirred at 70° C. for 3 hours. To the reaction mixture was added water, and the mixture was extracted with ethyl acetate. The organic layer was washed with a saturated aqueous sodium hydrogen carbonate solution, dried over magnesium sulfate, filtered and concentrated under reduced pressure. The obtained residue was purified by silica gel column chromatography (hexane/ethyl acetate=2/1) to give the title compound (300 mg).

MS (ESI+) 595 ($M^+$+1, 100%), 597 ($M^+$+1, 100%).

Reference Example 7 tert-Butyl (3R)-3-[isopropyl({4-(3-methoxypropyl)-2,2-dimethyl-3-oxo-7-[(1E)-prop-1-en-1-yl]-3,4-dihydro-2H-1,4-benzoxazin-6-yl}carbonyl)amino]piperidine-1-carboxylate

[Chemical formula 151]

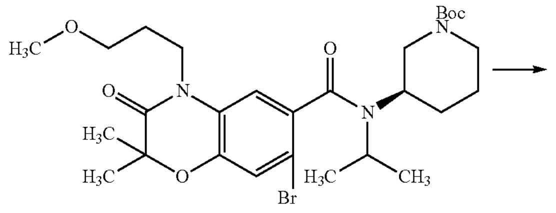

-continued

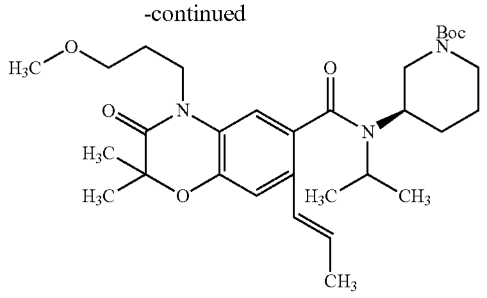

The compound of Reference Example 6 (300 mg) was dissolved in dimethoxyethane (3 ml) and water (1.5 ml), and thereto were added trans-propenylboronic acid (170 mg), sodium carbonate (106 mg), palladium diphenylphosphino dichloride.dichloromethane complex (7.8 mg), and the mixture was refluxed for 8 hours. To the reaction mixture was added a saturated aqueous sodium hydrogen carbonate solution, and the mixture was extracted with ethyl acetate. The organic layer was washed with a saturated aqueous sodium chloride solution, dried over sodium sulfate, and filtered and concentrated under reduced pressure. The obtained residue was purified by silica gel column chromatography (hexane/ethyl acetate=2/1) to give the title compound (260 mg).

MS (ESI+) 558 ($M^+$+1, 100%).

Reference Example 8 tert-Butyl (3R)-3-(isopropyl{[4-(3-methoxypropyl)-2,2-dimethyl-3-oxo-7-propyl-3,4-dihydro-2H-1,4-benzoxazin-6-yl]carbonyl)amino]piperidine-1-carboxylate

[Chemical formula 152]

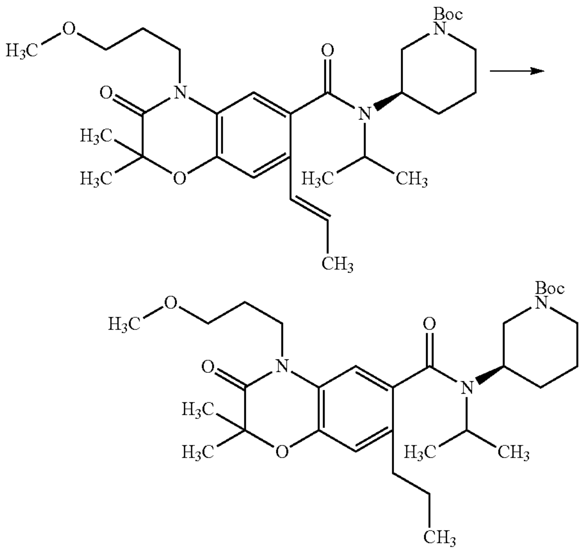

The compound of Reference Example 7 (90.1 mg) was dissolved in ethyl acetate (10 ml), and thereto was added palladium-carbon (100 mg), and the mixture was stirred under hydrogen atmosphere for 5 hours. The reaction solution was filtered on celite, and the filtrate was concentrated under reduced pressure. The obtained residue was purified by silica gel column chromatography (hexane/ethyl acetate=2/1) to give the title compound (60.0 mg).

MS (ESI+) 560 ($M^+$+1, 100%).

Reference Example 9 tert-Butyl (3R)-3-[{[7-ethyl-4-(3-methoxypropyl)-2,2-dimethyl-3-oxo-3,4-dihydro-2H-1,4-benzoxazin-6-yl]carbonyl}(isopropyl)amino]piperidine-1-carboxylate

[Chemical formula 153]

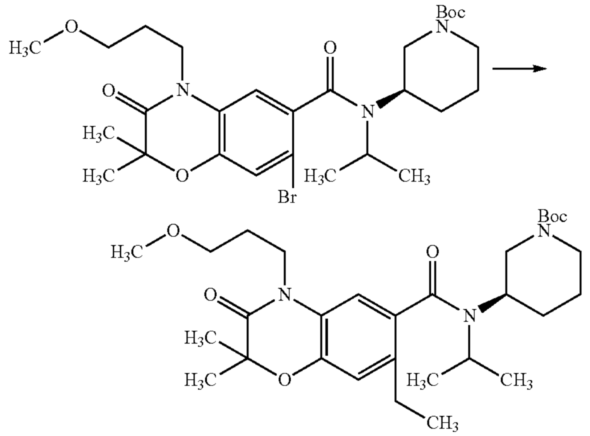

Using the compound of Reference Example 6 and vinylboronic acid pinacol ester, the title compound was obtained in a similar manner to Reference Examples 7 and 8.

MS (ESI+) 546 ($M^+$+1, 100%).

Reference Example 10 tert-Butyl (3R)-3-(isopropyl{[4-(3-methoxypropyl)-2,2,7-trimethyl-3-oxo-3,4-dihydro-2H-1,4-benzoxazin-6-yl]carbonyl}amino)piperidine-1-carboxylate

[Chemical formula 154]

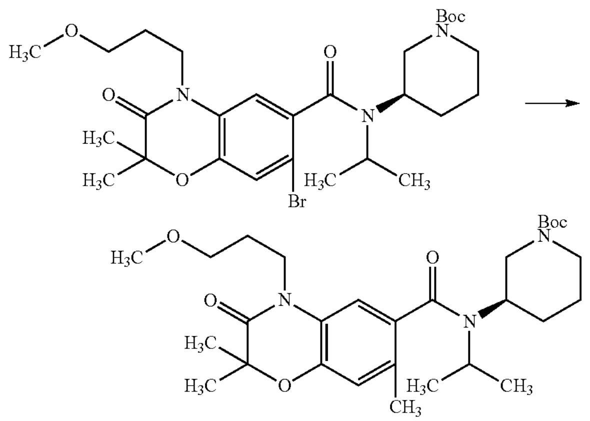

To a solution of the compound of Reference Example 6 (275 mg), bis(tributylphosphine)-palladium (25 mg) in tetrahydrofuran (4 ml) was added a 2.0 M solution of methylzinc chloride in tetrahydrofuran (0.3 ml) at room temperature, and the mixture was stirred at room temperature for 4 hours. To the reaction mixture was added water, and the mixture was extracted with ethyl acetate. The organic layer was washed with a saturated aqueous sodium chloride solution, dried over sodium sulfate, filtered and concentrated under reduced pressure. The obtained residue was purified by silica gel column chromatography (hexane/ethyl acetate=2/1) to give the title compound (170 mg).

MS (ESI+) 532 ($M^+$+1, 100%).

Reference Example 11 tert-Butyl (3R)-3-[{[7-cyano-4-(3-methoxypropyl)-2,2-dimethyl-3-oxo-3,4-dihydro-2H-1,4-benzoxazin-6-yl]carbonyl}(isopropyl)amino]piperidine-1-carboxylate

[Chemical formula 155]

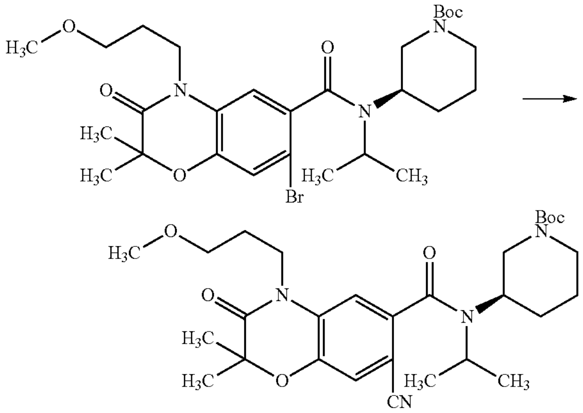

To a solution of Reference Example 6 (130 mg) in N,N-dimethylformamide (3 ml) were added zinc cyanide (100 mg) and ditributylphosphine palladium (38.2 mg), and the mixture was heated at 100° C. with stirring for 6 hours. The mixture was cooled to room temperature, and then, a saturated aqueous sodium hydrogen carbonate solution was added thereto, and the mixture was extracted with ethyl acetate. The organic layer was washed with water and a saturated aqueous sodium chloride solution, dried over sodium sulfate, filtered and concentrated under reduced pressure. The obtained residue was purified by silica gel column chromatography (hexane/ethyl acetate=1/1) to give the title compound (90.4 mg).

MS (ESI+) 543 ($M^+$+1, 100%).

Reference Example 12 tert-Butyl (3R)-3-[{[7-chloro-4-(3-methoxypropyl)-2,2-dimethyl-3-oxo-3,4-dihydro-2H-1,4-benzoxazin-6-yl]carbonyl}(isopropyl)amino]piperidine-1-carboxylate

[Chemical formula 156]

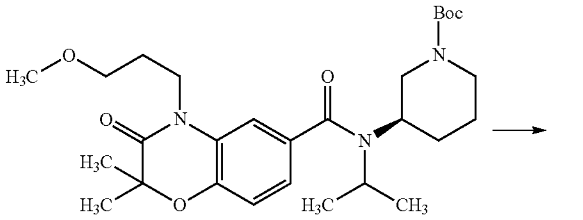

-continued

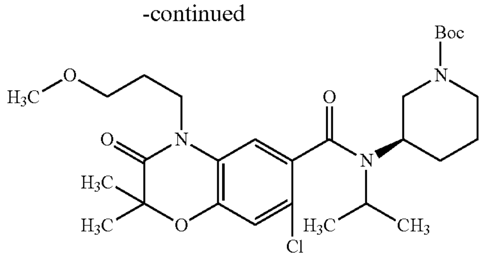

The compound of Reference Example 5 (200 mg) was dissolved in N,N-dimethylformamide (3 ml), and thereto was added N-chlorosuccinimide (100 mg), and the mixture was stirred at 80° C. for 3 hours. The mixture was cooled to room temperature, and thereto was added water. The mixture was extracted with ethyl acetate, and the organic layer was washed with a saturated aqueous sodium hydrogen carbonate solution, dried over magnesium sulfate, filtered and concentrated under reduced pressure. The obtained residue was purified by silica gel column chromatography (hexane/ethyl acetate=2/1) to give the title compound (150 mg).

MS (ESI+) 552 ($M^{+}$+1, 100%).

Reference Example 13

Methyl 4-{2-[(methoxycarbonyl)amino]ethyl}-2,2-dimethyl-3-oxo-3,4-dihydro-2H-1,4-benzoxazine-6-carboxylate

[Chemical formula 157]

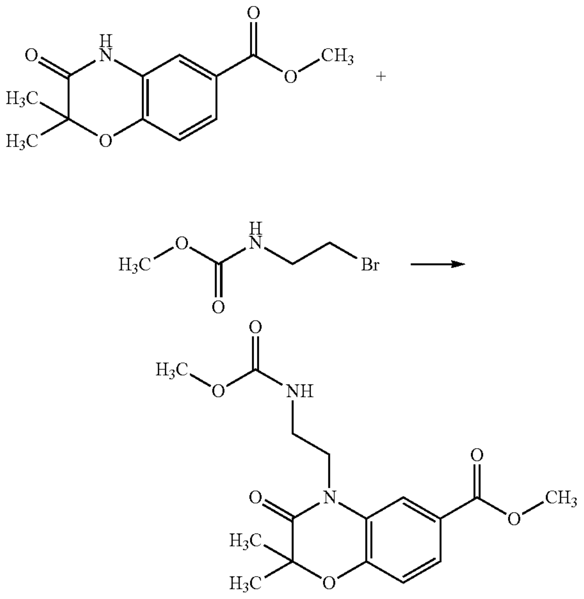

Using the compound of Reference Example 2 and methyl (2-bromoethyl)carbamate, the title compound was obtained in a similar manner to Reference Example 3.

MS (ESI+) 546 ($M^{+}$+1, 100%).

Reference Example 14 tert-Butyl (3R)-3-[[(7-bromo-4-{2-[(methoxycarbonyl)amino]ethyl}-2,2-dimethyl-3-oxo-3,4-dihydro-2H-1,4-benzoxazin-6-yl)carbonyl](isopropyl)amino]piperidine-1-carboxylate

[Chemical formula 158]

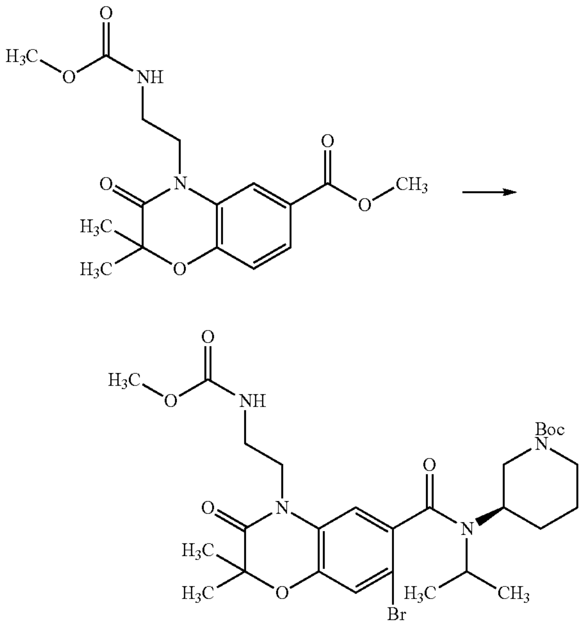

Using the compound of Reference Example 13, the title compound was obtained in a similar manner to Reference Example 6.

MS (ESI+) 624 ($M^{+}$+1, 100%), 626 ($M^{+}$+1, 100%).

Reference Example 15 tert-Butyl (3R)-3-{isopropyl[(4-{2-[(methoxycarbonyl)amino]ethyl}-2,2,7-trimethyl-3-oxo-3,4-dihydro-2H-1,4-benzoxazin-6-yl)carbonyl]amino}piperidine-1-carboxylate

[Chemical formula 159]

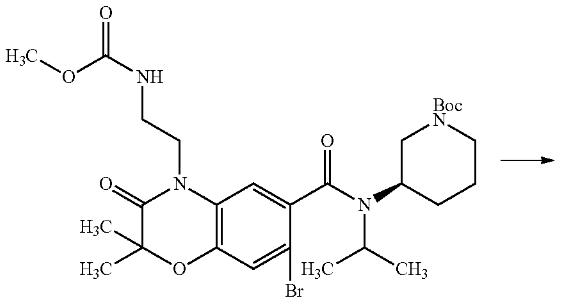

-continued

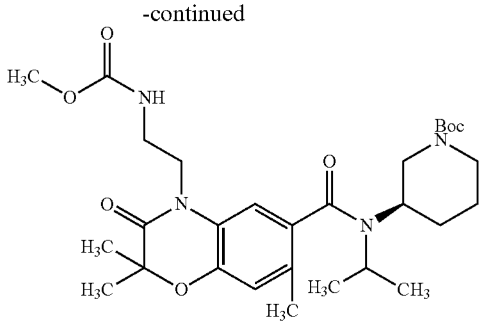

Using the compound of Reference Example 14, the title compound was obtained in a similar manner to Reference Example 10.

MS (ESI+) 561 ($M^{+}$+1, 100%).

Reference Example 16 tert-Butyl (3R)-3-[[(7-chloro-4-{2-[(methoxycarbonyl)amino]ethyl}-2,2-dimethyl-3-oxo-3,4-dihydro-2H-1,4-benzoxazin-6-yl)carbonyl](isopropyl)amino]piperidine-1-carboxylate

[Chemical formula 160]

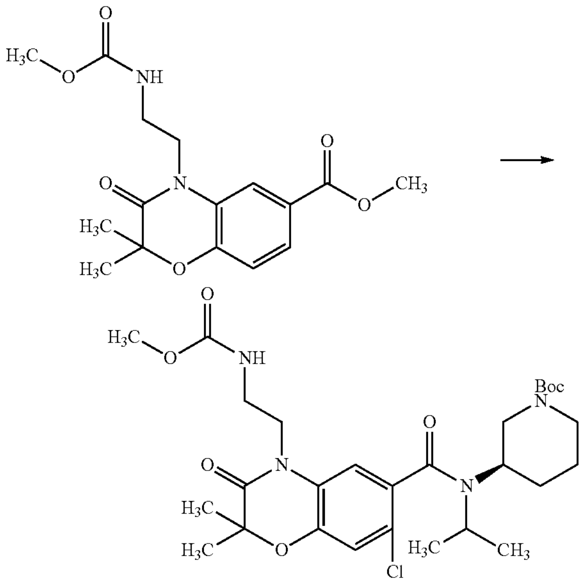

Using the compound of Reference Example 13, the title compound was obtained in a similar manner to Reference Example 12.

MS (ESI+) 581 ($M^{+}$+1, 100%).

Reference Example 17

Methyl 4-(4-methoxybutyl)-2,2-dimethyl-3-oxo-3,4-dihydro-2H-1,4-benzoxazine-6-carboxylate

[Chemical formula 161]

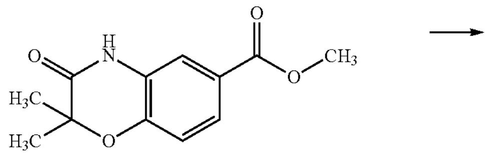

-continued

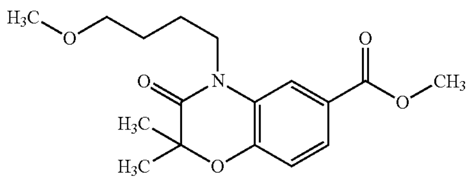

Using the compound of Reference Example 2 and 1-chloro-4-methoxybutane, the title compound was obtained in a similar manner to Reference Example 3.

MS (ESI+) 322 ($M^{+}$+1, 100%).

Reference Example 18 tert-Butyl (3R)-3-[{[7-chloro-4-(4-methoxybutyl)-2,2-dimethyl-3-oxo-3,4-dihydro-2H-1,4-benzoxazin-6-yl]carbonyl}(isopropyl)amino]piperidine-1-carboxylate

[Chemical formula 162]

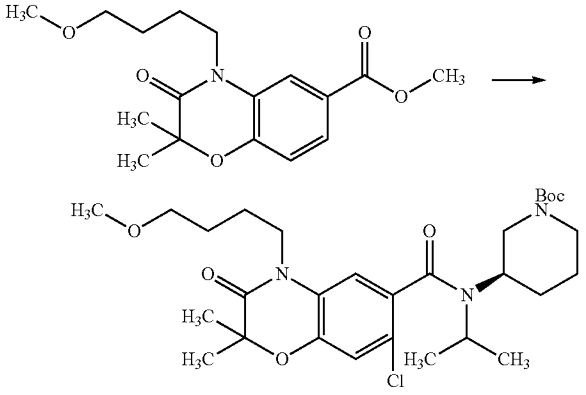

Using the compound of Reference Example 17, the title compound was obtained in a similar manner to Reference Example 12.

MS (ESI+) 566 ($M^{+}$+1, 100%).

Reference Example 19

Methyl 4-(3-ethoxypropyl)-2,2-dimethyl-3-oxo-3,4-dihydro-2H-1,4-benzoxazine-6-carboxylate

[Chemical formula 163]

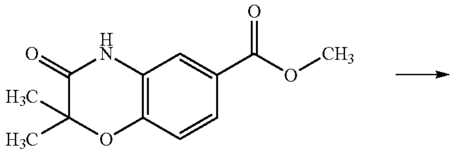

-continued

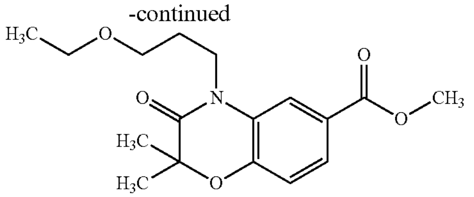

Using the compound of Reference Example 2 and 1-bromo-3-ethoxypropane, the title compound was obtained in a similar manner to Reference Example 3.

MS (ESI+) 322 ($M^{+}$+1, 100%).

Reference Example 20 tert-Butyl (3R)-3-[{[7-chloro-4-(3-ethoxypropyl)-2,2-dimethyl-3-oxo-3,4-dihydro-2H-1,4-benzoxazin-6-yl]carbonyl}(isopropyl)amino]piperidine-1-carboxylate

[Chemical formula 164]

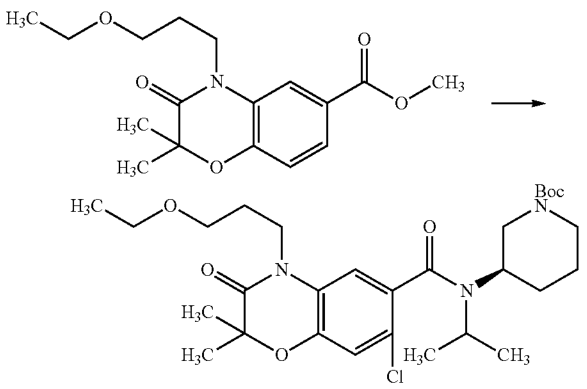

Using the compound of Reference Example 19, the title compound was obtained in a similar manner to Reference Example 12.

MS (ESI+) 566 ($M^{+}$+1, 100%).

Reference Example 21 tert-Butyl (3R)-3-(isopropyl{[4-(4-methoxybutyl)-2,2,7-trimethyl-3-oxo-3,4-dihydro-2H-1,4-benzoxazin-6-yl]carbonyl}amino)piperidine-1-carboxylate

[Chemical formula 165]

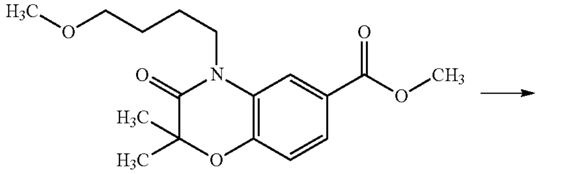

-continued

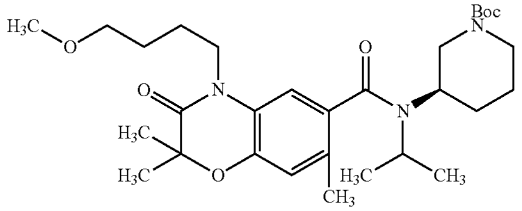

Using the compound of Reference Example 17, the title compound was obtained in a similar manner to Reference Example 10.

MS (ESI+) 546 ($M^{+}$+1, 100%).

Reference Example 22

Ethyl 2-(4-bromo-2-nitrophenoxy)-2-methylbutanoate

[Chemical formula 166]

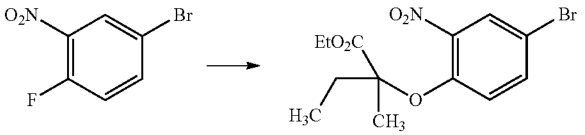

To a solution of ethyl 2-hydroxy-2-methylbutyrate (3.5 g) in tetrahydrofuran (80 ml) was added under ice-cooling sodium hydride (1.2 g), and the mixture was stirred at room temperature for 10 minutes. To the mixture was added a drop of 15-crown-5, and further thereto was added dropwise 5-bromo-2-fluoronitrobenzene (2.8 ml), and the mixture was stirred at room temperature for 14 hours. To the reaction solution was added a saturated aqueous ammonium chloride solution, and the mixture was extracted with ethyl acetate. The organic layer was washed with a saturated aqueous sodium chloride solution, dried over sodium sulfate, filtered and concentrated under reduced pressure. The obtained residue was purified by silica gel column chromatography (hexane/ethyl acetate=15/1) to give the title compound (5.5 g).

MS (ESI+) 346 ($M^{+}$+1, 100%), 348 ($M^{+}$+1, 98%).

Reference Example 23

6-Bromo-2-ethyl-2-methyl-2H-1,4-benzoxazin-3(4H)-one

[Chemical formula 167]

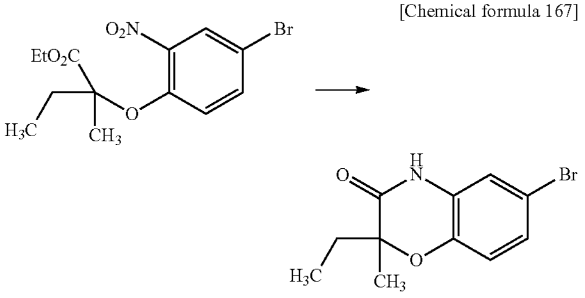

The title compound was synthesized from the corresponding compound in a similar manner to Reference Example 2.

MS (ESI+) 270 ($M^+$+1, 100%), 272 ($M^+$+1, 100%).

Reference Example 24

6-Bromo-2-ethyl-4-(3-methoxypropyl)-2-methyl-2H-1,4-benzoxazin-3(4H)-one

[Chemical formula 168]

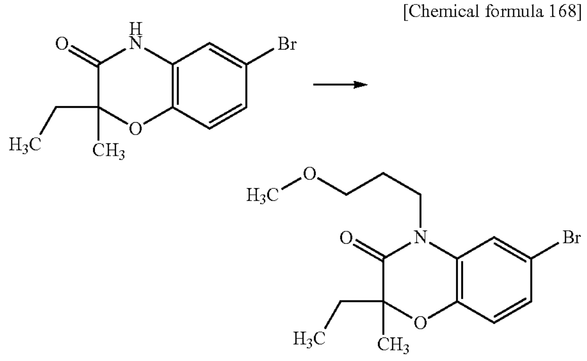

The title compound was synthesized from the corresponding compound in a similar manner to Reference Example 3.

MS (ESI+) 611 ($M^+$+1, 100%), 613 ($M^+$+1, 100%).

Reference Example 25

Methyl 2-ethyl-4-(3-methoxypropyl)-2-methyl-3-oxo-3,4-dihydro-2H-1,4-benzoxazine-6-carboxylate

[Chemical formula 169]

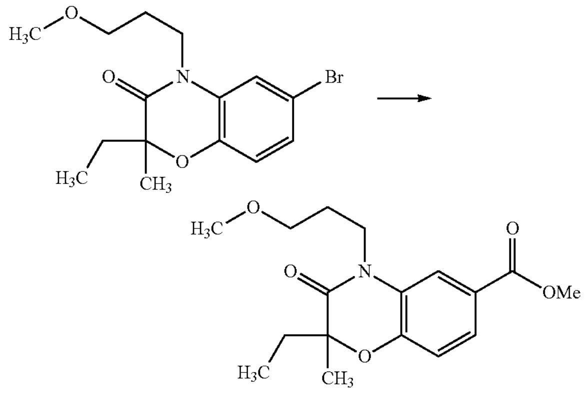

To a solution of the compound of Reference Example 24 (4.3 g) in N,N-dimethylacetamide (50 ml)/methanol (20 ml) were added palladium acetate (849 mg), 1,3-bis(diphenylphosphino)propane (1.56 g), and N,N-diisopropylethylamine (4.4 ml), and the mixture was stirred at 100° C. for 4 hours under carbon monoxide atmosphere. The reaction solution was cooled to room temperature, filtered on celite, and water was added to the filtrate. The mixture was extracted with ethyl acetate, and the organic layer was washed with water and a saturated aqueous sodium chloride solution, dried over sodium sulfate, filtered and concentrated under reduced pressure. The obtained residue was purified by silica gel column chromatography (hexane/ethyl acetate=3/1) to give the title compound (2.4 g).

MS (ESI+) 322 ($M^+$+1, 100%).

Reference Example 26

Methyl 4-[(1R)-2-ethoxy-1-methyl-2-oxoethoxy]-3-nitrobenzoate

[Chemical formula 170]

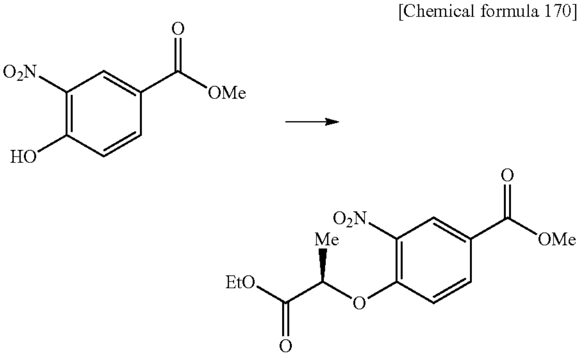

To a solution of methyl 4-hydroxy-3-nitrobenzoate (5.0 g) and ethyl L-lactate (2.9 ml) in tetrahydrofuran (120 ml) was added triphenylphosphine (10 g), and the mixture was stirred at room temperature for 10 minutes. To the mixture was added under ice-cooling diisopropyl azodicarboxylate (20 ml), and the mixture was stirred at 60° C. for 4 hours. The reaction solution was cooled to room temperature, and water was added thereto, and the mixture was extracted with ethyl acetate. The organic layer was washed with a saturated aqueous sodium chloride solution, dried over sodium sulfate, filtered and concentrated under reduced pressure. The obtained residue was purified by silica gel column chromatography (hexane/ethyl acetate=5/1) to give the title compound (9.5 g).

MS (ESI+) 298 ($M^+$+1, 100%).

Reference Example 27

Methyl (2R)-4-(4-methoxybutyl)-2-methyl-3-oxo-3,4-dihydro-2H-1,4-benzoxazine-6-carboxylate

[Chemical formual 171]

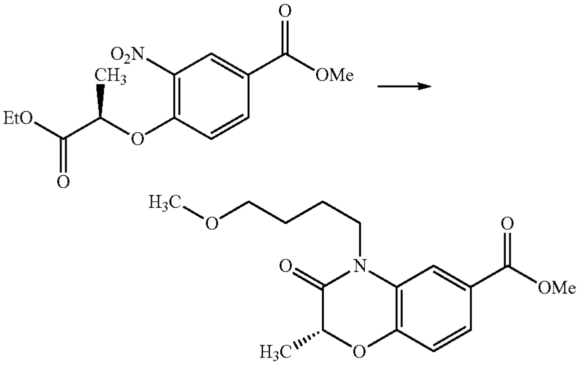

Using the compound of Reference Example 26, the title compound was synthesized in a similar manner to Reference Example 17.

MS (ESI+) 308 ($M^+$+1, 100%).

Reference Example 28

Methyl 4-[1-(methoxycarbonyl)propoxy]-3-nitrobenzoate

[Chemical formula 172]

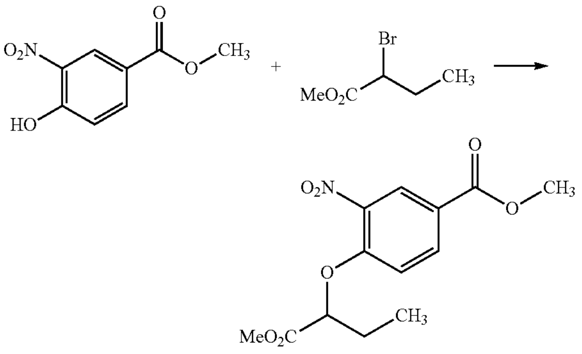

Using methyl 4-hydroxy-3-nitrobenzoate and methyl 2-bromobutyrate, the title compound was synthesized in a similar manner to Reference Example 1.

MS (ESI+) 298 ($M^{+}$+1, 100%).

Reference Example 29

4-(Acetyloxy)-3-nitrobenzoic acid

[Chemical formula 173]

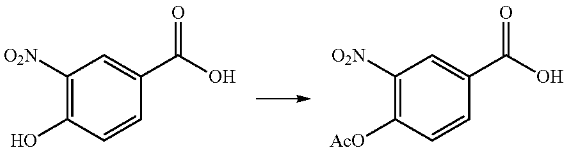

To 4-hydroxy-3-nitrobenzoic acid (10 g) were added pyridine (12 ml) and acetic anhydride (55 ml), and the mixture was stirred at room temperature for 65 hours. The reaction solution was concentrated under reduced pressure, and thereto was added a 5% aqueous sodium hydrogen sulfate solution, and the mixture was extracted with ethyl acetate. The organic layer was washed with a saturated aqueous sodium chloride solution, dried over sodium sulfate, filtered and concentrated under reduced pressure to give the title compound (11.7 g).

MS (ESI+) 226 ($M^{+}$+1, 100%).

Reference Example 30 tert-Butyl (3R)-3-[[4-(acetyloxy)-3-nitrobenzoyl](isopropyl)amino]piperidine-1-carboxylate

[Chemical formula 174]

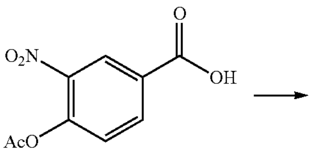

-continued

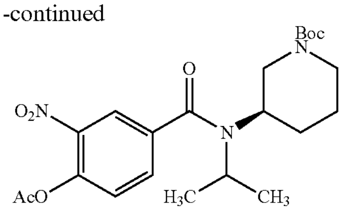

The title compound was synthesized from the corresponding compound in a similar manner to Reference Example 5.

MS (ESI+) 450 ($M^{+}$+1, 100%).

Reference Example 31 tert-Butyl (3R)-3-[(4-hydroxy-3-nitrobenzoyl)(isopropyl)amino]piperidine-1-carboxylate

[Chemical formula 175]

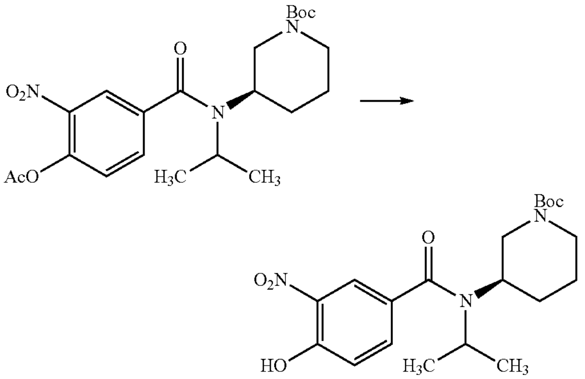

To a solution of the compound of Reference Example 30 (4.4 g) in methanol (60 ml) was added sodium methoxide (1 M methanol solution, 12.7 ml), and the mixture was stirred at room temperature for 2 hours. To the reaction solution was added Amberlite (registered trade mark), and the mixture was stirred at room temperature for 30 minutes, filtered, and washed with methanol. The filtrate was concentrated under reduced pressure to give the title compound (4.1 g).

MS (ESI+) 408 ($M^{+}$+1, 86%).

Reference Example 32

Diethyl (4-{[[(3R)-1-(tert-butoxycarbonyl)piperidin-3-yl](isopropyl)amino]carbonyl}-2-nitrophenyl-oxy)(methyl)malonate

[Chemical formula 176]

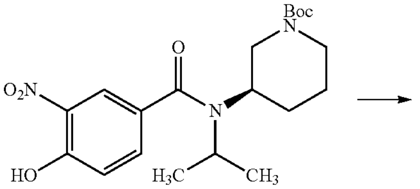

-continued

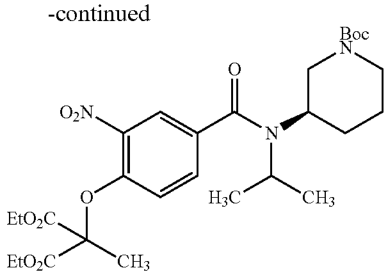

Using the compound of Reference Example 31 and diethyl 2-bromo-2-methylmalonate, the title compound was synthesized in a similar manner to Reference Example 1.

MS (ESI+) 580 ($M^{+}$+1, 84%).

Reference Example 33

Ethyl 6-{[[(3R)-1-(tert-butoxycarbonyl)piperidin-3-yl](isopropyl)amino]carbonyl}-4-(4-methoxybutyl)-2-methyl-3-oxo-3,4-dihydro-2H-1,4-benzoxazine-2-carboxylate

[Chemical formula 177]

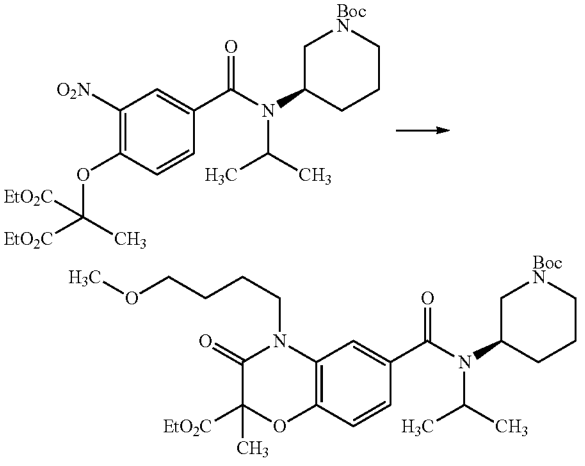

Using the compound of Reference Example 32, the title compound was obtained in a similar manner to Reference Example 2 and Reference Example 3.

MS (ESI+) 590 ($M^{+}$+1, 100%).

Reference Example 34

6-{[[(3R)-1-(tert-Butoxycarbonyl)piperidin-3-yl](isopropyl)amino]carbonyl}-4-(4-methoxybutyl)-2-methyl-3-oxo-3,4-dihydro-2H-1,4-benzoxazine-2-carboxylic acid

[Chemical formula 178]

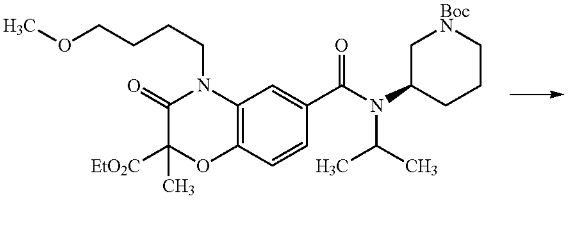

-continued

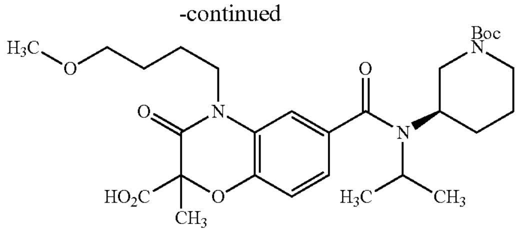

To the compound of Reference Example 33 (1.8 g) were added methanol (20 ml) and a 1N aqueous sodium hydroxide solution (6 ml), and the mixture was stirred at 60° C. for 3 hours. The reaction solution was cooled to room temperature, and thereto was added a 5% aqueous sodium hydrogen sulfate solution. The mixture was extracted with chloroform, and the organic layer was washed with a saturated aqueous sodium chloride solution, dried over sodium sulfate, filtered and concentrated under reduced pressure to give the title compound (1.7 g).

MS (ESI+) 562 ($M^{+}$+1, 100%).

Reference Example 35 tert-Butyl (3R)-3-[{[2-(hydroxymethyl)-4-(4-methoxybutyl)-2-methyl-3-oxo-3,4-dihydro-2H-1,4-benzoxazin-6-yl]carbonyl}(isopropyl)amino]piperidine-1-carboxylate

[Chemical formula 179]

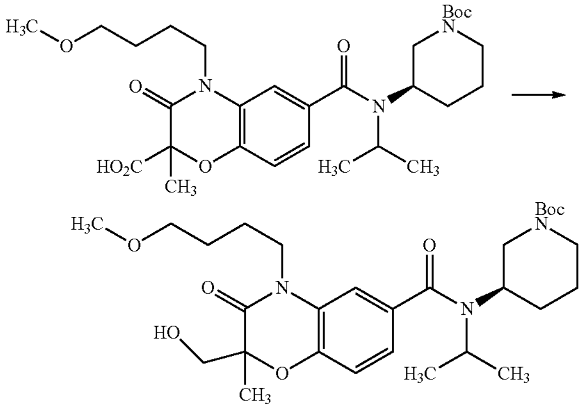

To a solution of the compound of Reference Example 34 (1.68 g) and triethylamine (500 μl) in tetrahydrofuran (10 ml) wad added dropwise isopropyl chloroformate (495 μl) under ice-cooling, and the mixture was stirred in an ice bath for one hour. The precipitates were removed by filtration, and to the filtrate was added dropwise a solution of sodium borohydride (228 mg) in water (2 ml) under ice-cooling. The mixture was stirred in an ice-bath for one hour. To the reaction solution was added a saturated aqueous ammonium chloride solution, and the mixture was extracted with ethyl acetate. The organic layer was washed with a saturated aqueous sodium chloride solution, dried over sodium sulfate, filtered and concentrated under reduced pressure. The obtained residue was purified by silica gel column chromatography (hexane/ethyl acetate=1/5) to give the title compound (510 mg).

MS (ESI+) 548 ($M^{+}$+1, 100%).

Reference Example 36 tert-Butyl (3R)-3-[{[2-(ethoxymethyl)-4-(4-methoxybutyl)-2-methyl-3-oxo-3,4-dihydro-2H-1,4-benzoxazin-6-yl]carbonyl}(isopropyl)amino]piperidine-1-carboxylate

[Chemical formula 180]

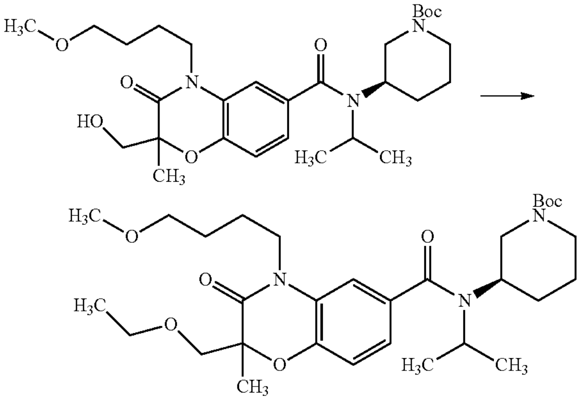

To a solution of the compound of Reference Example 35 (20 mg) in N,N-dimethylformamide (1 ml) were added sodium hydride (10 mg) and ethyl iodide (50 μl), the mixture was stirred at room temperature for 2 hours. To the reaction solution was added a saturated aqueous ammonium chloride solution, and the mixture was extracted with ethyl acetate. The organic layer was washed with a saturated aqueous sodium chloride solution, dried over sodium sulfate, filtered and concentrated under reduced pressure. The obtained residue was purified by silica gel column chromatography (hexane/ethyl acetate=1/1) to give the title compound (19 mg).

MS (ESI+) 576 ($M^{+}$+1, 100%).

Reference Example 37 tert-Butyl (3R)-3-[{[7-chloro-2-ethyl-4-(3-methoxypropyl)-2-methyl-3-oxo-3,4-dihydro-2H-1,4-benzoxazin-6-yl]carbonyl}(isopropyl)amino]piperidine-1-carboxylate

[Chemical formula 181]

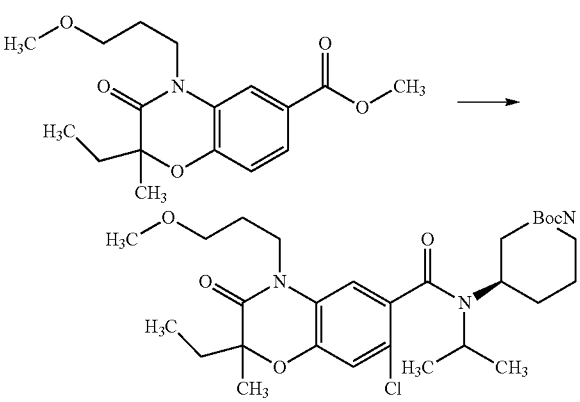

Using the compound of Reference Example 25, the title compound was synthesized in a similar manner to Reference Example 12.

MS (ESI+) 566 ($M^{+}$+1, 100%).

Reference Example 38 tert-Butyl (3R)-3-[{[7-bromo-2-ethyl-4-(3-methoxypropyl)-2-methyl-3-oxo-3,4-dihydro-2H-1,4-benzoxazin-6-yl]carbonyl}(isopropyl)amino]piperidine-1-carboxylate

[Chemical formula 182]

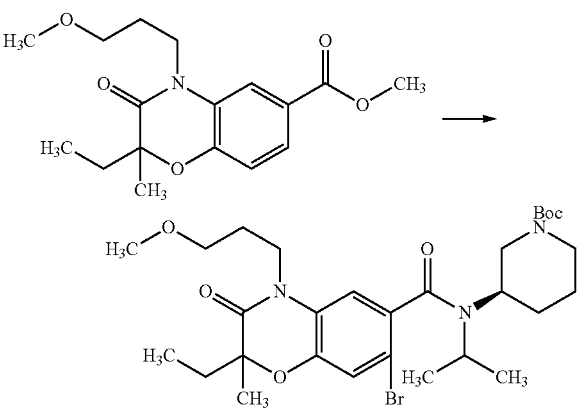

Using the compound of Reference Example 25, the title compound was synthesized in a similar manner to Reference Example 6.

MS (ESI+) 610 ($M^{+}$+1, 100%) 612 ($M^{+}$+1, 100%).

Reference Example 39 tert-Butyl (3R)-3-[{[7-cyano-2-ethyl-4-(3-methoxypropyl)-2-methyl-3-oxo-3,4-dihydro-2H-1,4-benzoxazin-6-yl]carbonyl}(isopropyl)amino]piperidine-1-carboxylate

[Chemical formula 183]

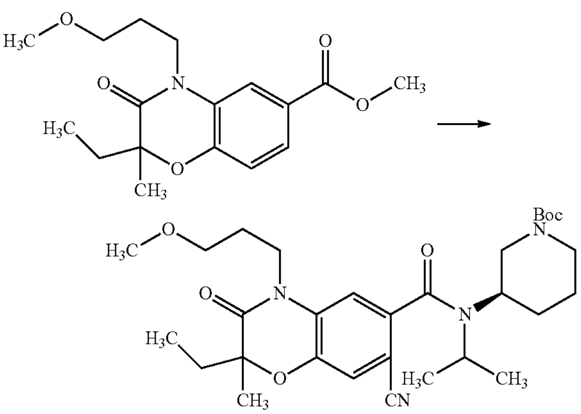

Using the compound of Reference Example 25, the title compound was synthesized in a similar manner to Reference Example 11.

MS (ESI+) 557 ($M^{+}$+1, 100%).

Reference Example 40 tert-Butyl (3R)-3-[{[(2R)-7-chloro-4-(3-methoxypropyl)-2-methyl-3-oxo-3,4-dihydro-2H-1,4-benzoxazin-6-yl]carbonyl}(isopropyl)amino]piperidine-1-carboxylate

[Chemical formula 184]

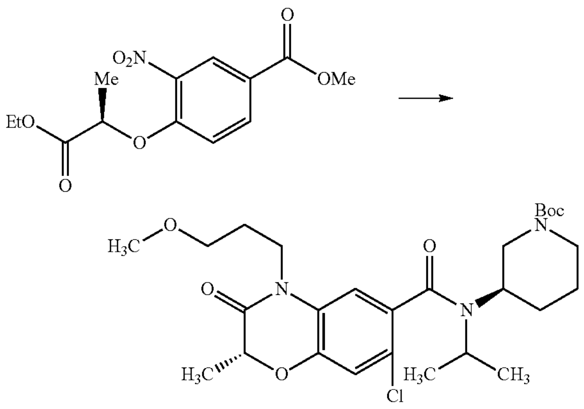

Using the compound of Reference Example 26, the title compound was synthesized in a similar manner to Reference Example 12.

MS (ESI+) 538 ($M^{+}$+1, 100%).

Reference Example 41 tert-Butyl (3R)-3-[{[(2R)-7-bromo-4-(3-methoxypropyl)-2-methyl-3-oxo-3,4-dihydro-2H-1,4-benzoxazin-6-yl]carbonyl}(isopropyl)amino]piperidine-1-carboxylate

[Chemical formula 185]

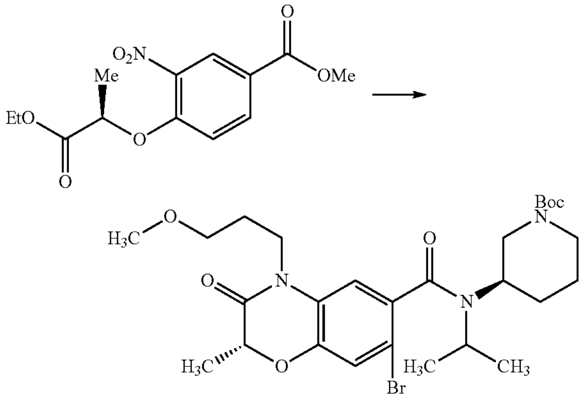

Using the compound of Reference Example 26, the title compound was synthesized in a similar manner to Reference Example 6.

MS (ESI+) 582 ($M^{+}$+1, 100%) 584 ($M^{+}$+1, 100%).

Reference Example 42 tert-Butyl (3R)-3-(isopropyl{[(2R)-4-(3-methoxypropyl)-2,7-dimethyl-3-oxo-3,4-dihydro-2H-1,4-benzoxazin-6-yl]carbonyl}amino)piperidine-1-carboxylate

[Chemical formula 186]

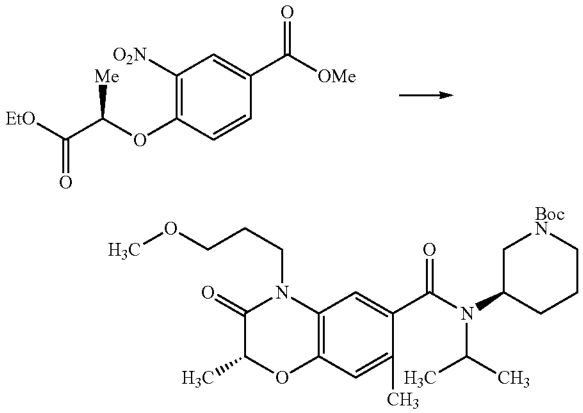

Using the compound of Reference Example 26, the title compound was synthesized in a similar manner to Reference Example 10.

MS (ESI+) 518 ($M^{+}$+1, 100%).

Reference Example 43 tert-Butyl (3R)-3-[{[(2R)-7-chloro-4-(4-methoxybutyl)-2-methyl-3-oxo-3,4-dihydro-2H-1,4-benzoxazin-6-yl]carbonyl}(isopropyl)amino]piperidine-1-carboxylate

[Chemical formula 187]

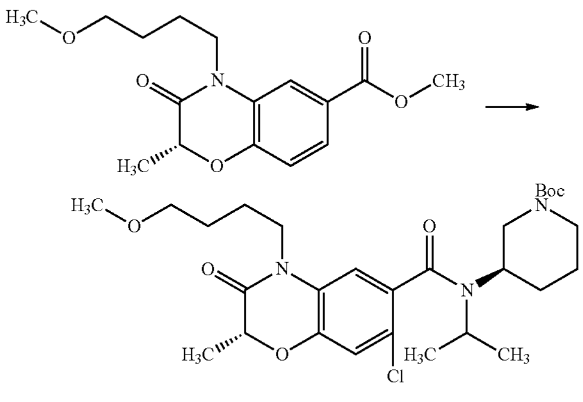

Using the compound of Reference Example 27, the title compound was synthesized in a similar manner to Reference Example 18.

MS (ESI+) 552 ($M^{+}$+1, 100%).

Reference Example 44 tert-Butyl (3R)-3-[{[(2R)-7-bromo-4-(4-methoxybutyl)-2-methyl-3-oxo-3,4-dihydro-2H-1,4-benzoxazin-6-yl]carbonyl}(isopropyl)amino]piperidine-1-carboxylate

[Chemical formula 188]

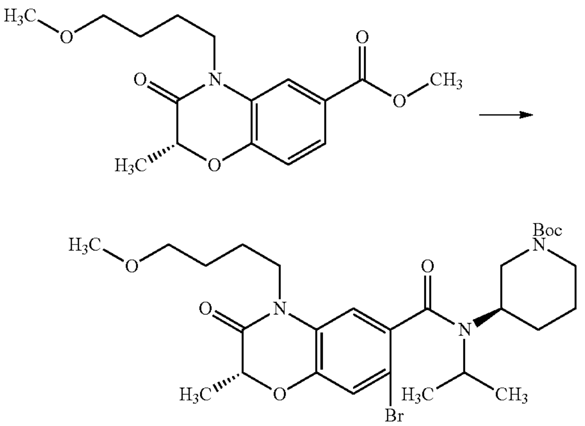

Using the compound of Reference Example 27, the title compound was synthesized in a similar manner to Reference Example 6.

MS (ESI+) 596 ($M^+$+1, 100%) 598 ($M^+$+1, 100%).

Reference Example 45 tert-Butyl (3R)-3-(isopropyl{[(2R)-4-(4-methoxybutyl)-2,7-dimethyl-3-oxo-3,4-dihydro-2H-1,4-benzoxazin-6-yl]carbonyl}amino)piperidine-1-carboxylate

[Chemical formula 189]

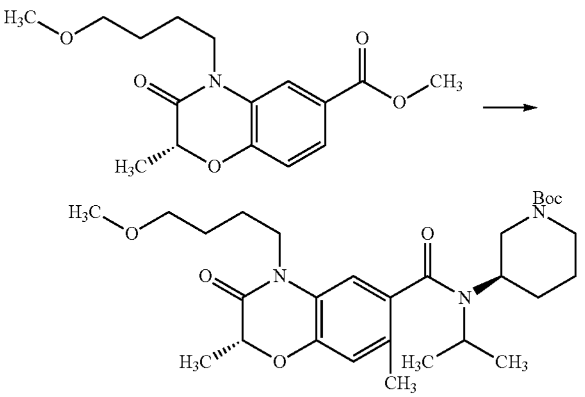

Using the compound of Reference Example 27, the title compound was synthesized in a similar manner to Reference Example 21.

MS (ESI+) 532 ($M^+$+1, 100%).

Reference Example 46 tert-Butyl (3R)-3-[[((2R)-7-chloro-4-{2-[(methoxycarbonyl)amino]ethyl}-2-methyl-3-oxo-3,4-dihydro-2H-1,4-benzoxazin-6-yl)carbonyl](isopropyl)amino]piperidine-1-carboxylate

[Chemical formula 190]

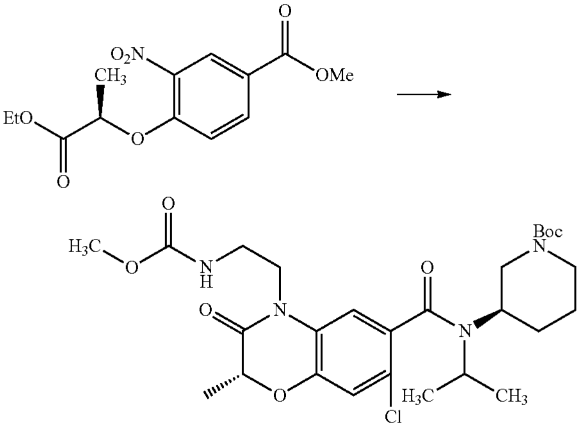

Using the compound of Reference Example 26, the title compound was synthesized in a similar manner to Reference Example 16.

MS (ESI+) 567 ($M^+$+1, 100%).

Reference Example 47 tert-Butyl (3R)-3-[[((2R)-7-bromo-4-{2-[(methoxycarbonyl)amino]ethyl}-2-methyl-3-oxo-3,4-dihydro-2H-1,4-benzoxazin-6-yl)carbonyl](isopropyl)amino]piperidine-1-carboxylate

[Chemical formula 191]

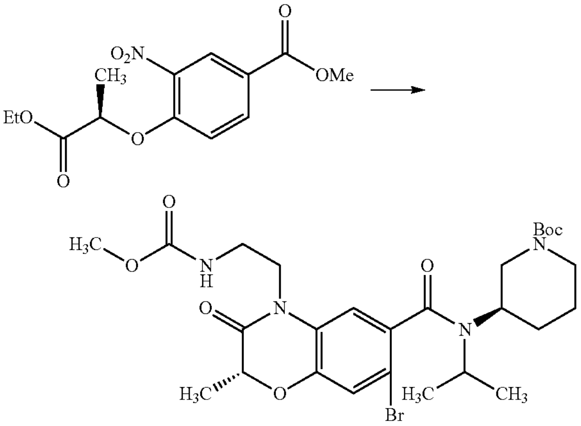

Using the compound of Reference Example 26, the title compound was synthesized in a similar manner to Reference Example 14.

MS (ESI+) 611 ($M^+$+1, 100%) 613($M^+$+1, 100%).

Reference Example 48 tert-Butyl (3R)-3-{isopropyl[((2R)-4-{2-[(methoxy-carbonyl)amino]ethyl}-2,7-dimethyl-3-oxo-3,4-dihydro-2H-1,4-benzoxazin-6-yl)carbonyl]amino}piperidine-1-carboxylate

[Chemical formula 192]

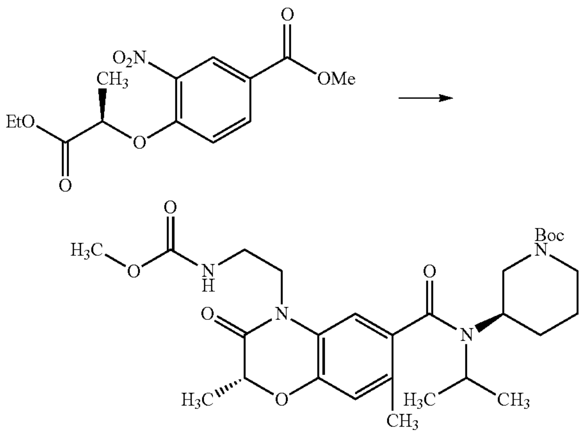

Using the compound of Reference Example 26, the title compound was synthesized in a similar manner to Reference Example 15.

MS (ESI+) 547 ($M^+$+1, 100%).

Reference Example 49 tert-Butyl (3R)-3-[{[7-chloro-2-ethyl-4-(3-methoxypropyl)-3-oxo-3,4-dihydro-2H-1,4-benzoxazin-6-yl]carbonyl}(isopropyl)amino]piperidine-1-carboxylate

[Chemical formula 193]

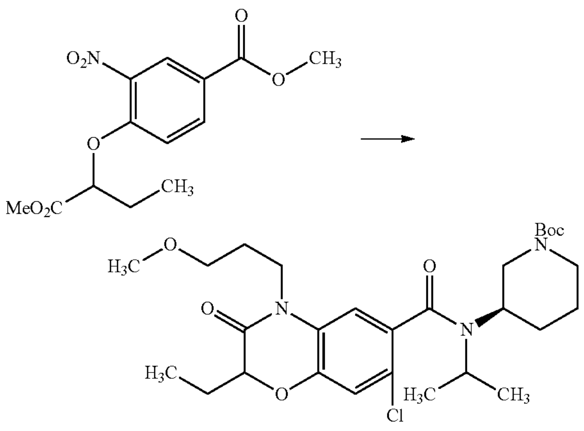

Using the compound of Reference Example 28, the title compound was synthesized in a similar manner to Reference Example 12.

MS (ESI+) 552 ($M^+$+1, 100%).

Reference Example 50 tert-Butyl (3R)-3-[{[7-chloro-2-(ethoxymethyl)-4-(4-methoxybutyl)-2-methyl-3-oxo-3,4-dihydro-2H-1,4-benzoxazin-6-yl]carbonyl}(isopropyl)amino]piperidine-1-carboxylate

[Chemical formula 194]

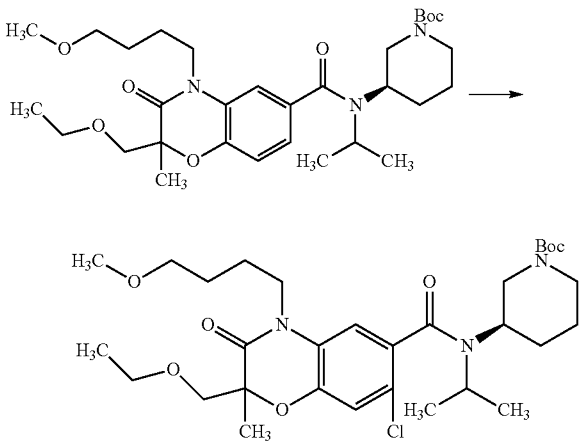

Using the compound of Reference Example 36, the title compound was synthesized in a similar manner to Reference Example 12.

MS (ESI+) 610 ($M^+$+1, 100%).

Reference Example 51

Methyl 4-hydroxy-2-(trifluoromethyl)benzoate

[Chemical formula 195]

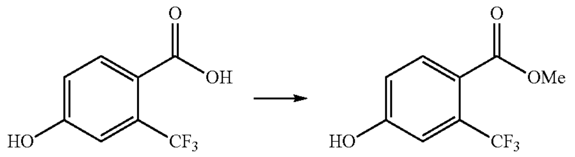

4-Hydroxy-2-(trifluoromethyl)benzoic acid (30.0 g) was dissolved in methanol (600 ml), thereto was added dropwise conc. sulfuric acid (10 ml). Then, the mixture was refluxed with stirring for 20 hours. The mixture was cooled to room temperature, and to the reaction mixture was added water (200 ml), and methanol was removed by evaporation, and the resultant was extracted twice with ethyl acetate (300 ml). The organic layer was washed with water, a saturated aqueous sodium hydrogen carbonate solution and a saturated aqueous sodium chloride solution, dried over sodium sulfate, filtered and concentrated under reduced pressure to give the title compound (32.0 g).

$^1$H NMR (400 MHz, $CDCl_3$) δ 9.77 (s, 1H), 7.79-7.76 (m, 1H), 7.28-7.22 (m, 1H), 7.03-6.99 (m, 1H), 3.88 (s, 3H).

Reference Example 52

Methyl 4-hydroxy-5-nitro-2-(trifluoromethyl)benzoate

[Chemical formula 196]

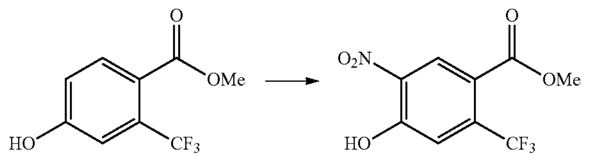

Methyl 4-hydroxy-2-(trifluoromethyl)benzoate (32.0 g) was dissolved in acetic acid (180 ml), and thereto was added conc. sulfuric acid (0.45 ml), and the mixture was heated to 65° C. Then, thereto was slowly added a 70% solution of conc. nitric acid (12.4 g) in acetic acid (60 ml) dropwise, and the mixture was stirred at 65° C. for one hour. The reaction mixture was cooled to room temperature, and poured into ice-water (500 ml), and the mixture was extracted twice with toluene (800 ml). The organic layer was washed with water and a saturated aqueous sodium chloride solution, dried over sodium sulfate, filtered and concentrated under reduced pressure. The obtained residue was purified by silica gel column chromatography (hexane/ethyl acetate) to give the title compound (15.0 g).

$^1$H NMR (400 MHz, $CDCl_3$) δ 10.8 (s, 1H), 8.72 (s, 1H), 7.61 (s, 1H), 3.96 (s, 3H).

Reference Example 53

Methyl 5-amino-4-hydroxy-2-(trifluoromethyl)benzoate

[Chemical formula 197]

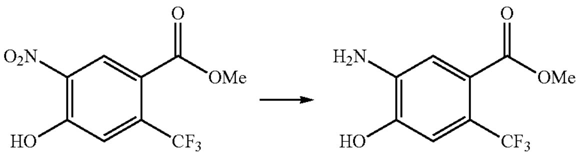

Methyl 4-hydroxy-5-nitro-2-(trifluoromethyl)benzoate (58.0 g) was dissolved in methanol (600 ml), and thereto was added 10% palladium carbon (50% wet.: 11.60 g). The mixture was vigorously stirred under hydrogen atmosphere at 25° C. for 8 hours. After the reaction was complete, the mixture was filtered on celite, washed with methanol, and the filtrate was concentrated under reduced pressure to give the title compound (53.0 g).

MS (ESI+) 236 ($M^+$+1, 100%).

Reference Example 54

Methyl 5-amino-4-hydroxy-2-methylbenzoate

[Chemical formula 198]

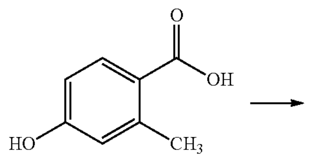

-continued

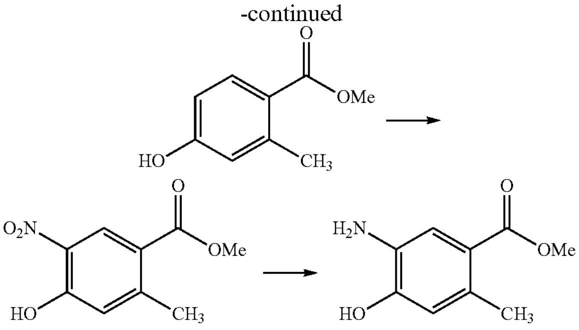

Using 4-hydroxy-2-methylbenzoic acid, the title compound was obtained in a similar manner to Reference Example 53.

MS (ESI+) 182 ($M^+$+1, 100%).

Reference Example 55

Methyl 2,2-dimethyl-3-oxo-7-(trifluoromethyl)-3,4-dihydro-2H-1,4-benzoxazine-6-carboxylate

[Chemical formula 199]

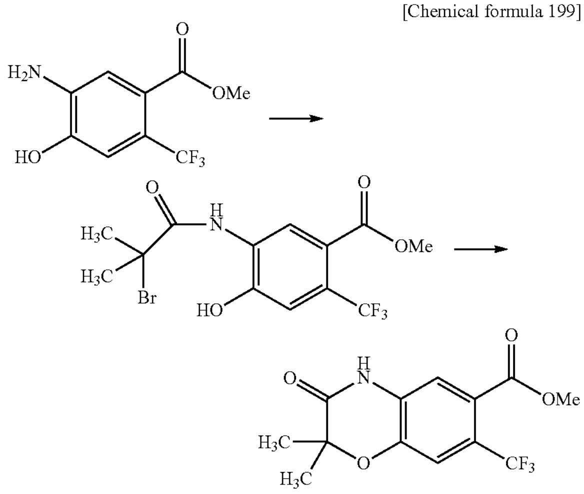

Methyl 5-amino-4-hydroxy-2-(trifluoromethyl)benzoate (53.0 g) was dissolved in chloroform (200 ml) and tetrahydrofuran (200 ml), and thereto was added an aqueous sodium hydrogen carbonate solution (27.60 g/240 ml), and the mixture was vigorously stirred. The mixture was cooled in an ice-bath, and thereto was slowly added dropwise 2-bromoisobutyryl bromide (65.5 g), and the mixture was stirred for 30 minutes. The mixture was warmed to room temperature, and further stirred for 2.5 hours. After the reaction was complete, the mixture was extracted twice with chloroform (300 ml). The organic layer was dried over sodium sulfate, filtered and concentrated under reduced pressure to give methyl 5-[(2-bromo-2-methylpropanoyl)amino]-4-hydroxy-2-(trifluoromethyl)benzoate. This crude product was diluted in N,N-dimethylformamide (500 ml), and thereto was added potassium carbonate (60.53 g), and the mixture was stirred at 50° C. for 5 hours. After the reaction was complete, the mixture was cooled to room temperature, and the obtained solid was removed by filtration. To the filtrate was added ethyl acetate (500 ml), and the mixture was washed with a 1N hydrochloric acid (500 ml) and a saturated aqueous sodium chloride solution. The organic layer was dried over sodium sulfate, filtered, and concentrated under reduced pressure to give the crude product, which was crystallized from ethyl acetate/hexane (5/1, 200 ml) to give the title compound (48.5 g).

MS (ESI+) 304 ($M^{+}$+1, 31%).

Reference Example 56

Methyl 2,2,7-trimethyl-3-oxo-3,4-dihydro-2H-1,4-benzoxazine-6-carboxylate

[Chemical formula 200]

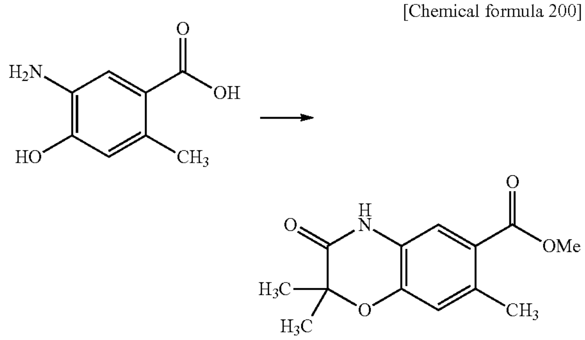

Using methyl 5-amino-4-hydroxy-2-methylbenzoate, the title compound was obtained in a similar manner to Reference Example 55.

MS (ESI+) 250 ($M^{+}$+1, 35%).

Reference Example 57

Methyl 4-(4-methoxybutyl)-2,2-dimethyl-3-oxo-7-(trifluoromethyl)-3,4-dihydro-2H-1,4-benzoxazine-6-carboxylate

[Chemical formula 201]

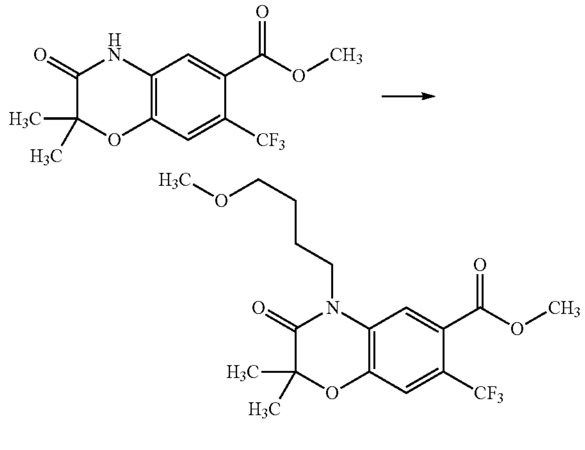

Using the compound of Reference Example 55, the title compound was obtained in a similar manner to Reference Example 3.

MS (ESI+) 390 ($M^{+}$+1, 100%).

Reference Example 58 tert-Butyl (3R)-3-(isopropyl{[4-(4-methoxybutyl)-2,2-dimethyl-3-oxo-7-(trifluoromethyl)-3,4-dihydro-2H-1,4-benzoxazin-6-yl]carbonyl}amino)piperidine-1-carboxylate

[Chemical formula 202]

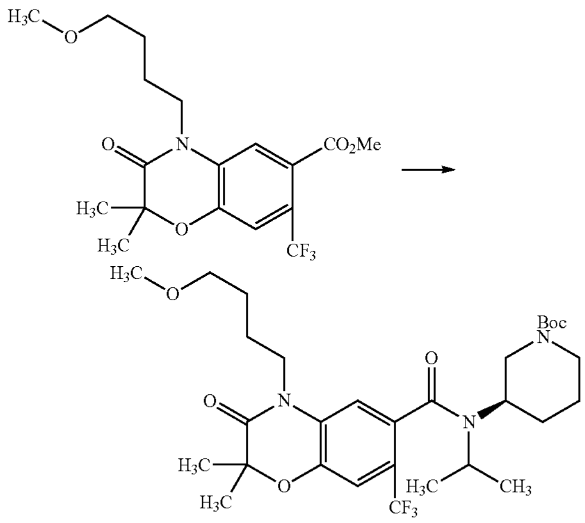

Using the compound of Reference Example 57, the title compound was obtained in a similar manner to Reference Example 5.

MS (ESI+) 600 ($M^{+}$+1, 100%).

Reference Example 59 tert-Butyl (3R)-3-(isopropyl{[4-(3-methoxypropyl)-2,2-dimethyl-3-oxo-7-(trifluoromethyl)-3,4-dihydro-2H-1,4-benzoxazin-6-yl]carbonyl}amino)piperidine-1-carboxylate

[Chemical formula 203]

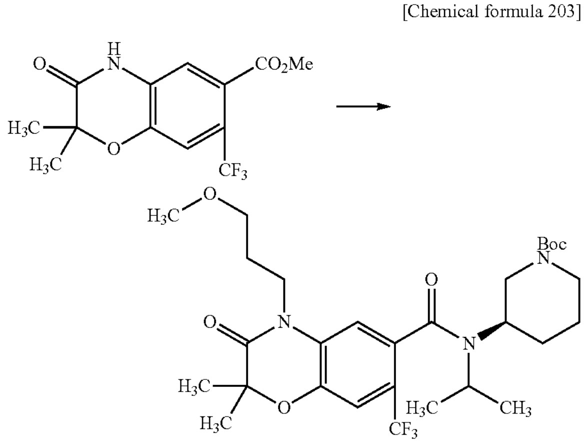

Using the compound of Reference Example 55, the title compound was obtained in a similar manner to Reference Example 3 and Reference Example 5.

MS (ESI+) 586 ($M^{+}$+1, 100%).

Reference Example 60 tert-Butyl (3R)-3-(isopropyl{[4-{2-[(methoxycarbonyl)amino]ethyl}-2,2-dimethyl-3-oxo-7-(trifluoromethyl)-3,4-dihydro-2H-1,4-benzoxazin-6-yl]carbonyl}amino)piperidine-1-carboxylate

[Chemical formula 204]

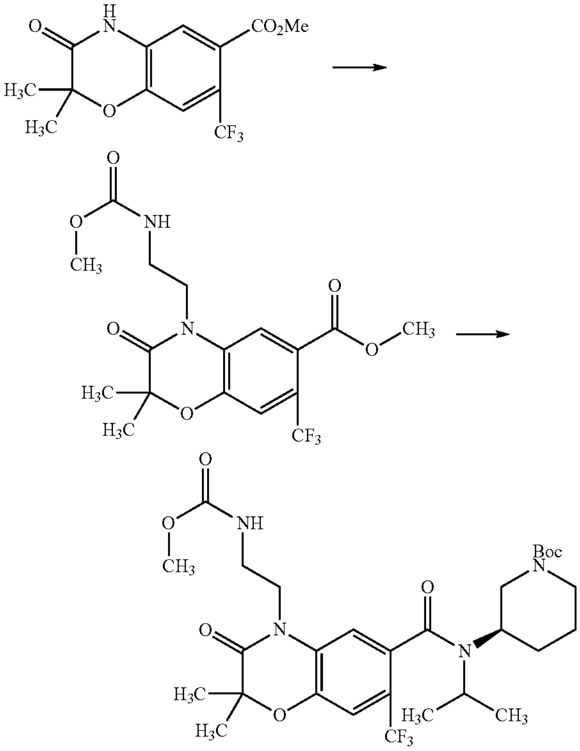

Using the compound of Reference Example 55, the title compound was obtained in a similar manner to Reference Example 13 and Reference Example 5.

MS (ESI+) 615 ($M^+$+1, 100%).

Reference Example 61 tert-Butyl (3R)-3-[{[7-bromo-4-(4-methoxybutyl)-2,2-dimethyl-3-oxo-3,4-dihydro-2H-1,4-benzoxazin-6-yl]carbonyl}(isopropyl)amino]piperidine-1-carboxylate

[Chemical formula 205]

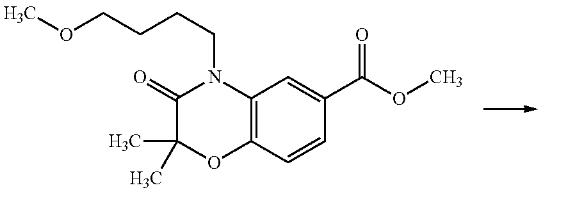

-continued

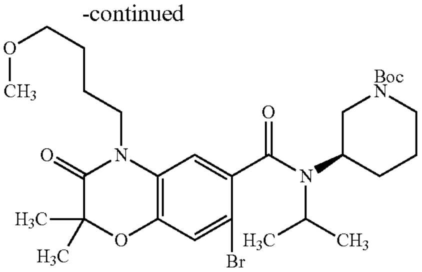

Using the compound of Reference Example 17, the title compound was obtained in a similar manner to Reference Example 6.

MS (ESI+) 610 ($M^+$+1, 100%).

Reference Example 62 tert-Butyl (3R)-3-[{[7-cyano-4-(4-methoxybutyl)-2,2-dimethyl-3-oxo-3,4-dihydro-2H-1,4-benzoxazin-6-yl]carbonyl}(isopropyl)amino]piperidine-1-carboxylate

[Chemical formula 206]

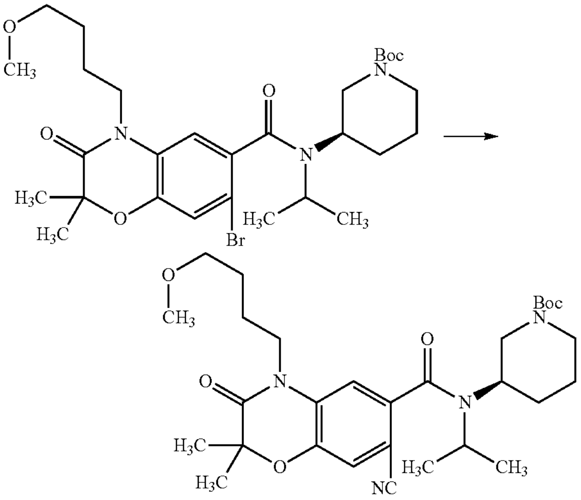

Using the compound of Reference Example 61, the title compound was obtained in a similar manner to Reference Example 11.

MS (ESI+) 557 ($M^+$+1, 100%).

Reference Example 63

Methyl (2R)-4-(4-methoxybutyl)-2-methyl-3-oxo-7-(trifluoromethyl)-3,4-dihydro-2H-1,4-benzoxazine-6-carboxylate

[Chemical formula 207]

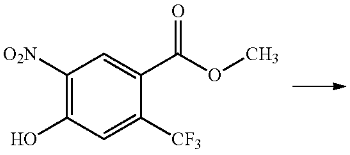

-continued

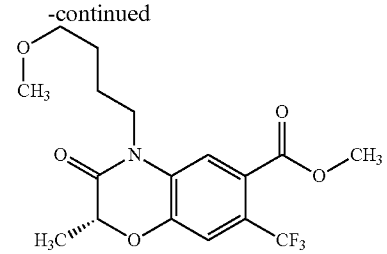

Using the compound of Reference Example 52, the title compound was obtained in a similar manner to Reference Example 27.

MS (ESI+) 376 ($M^{+}$+1, 100%).

Reference Example 64 tert-Butyl (3R)-3-(isopropyl{[(2R)-4-(4-methoxybutyl)-2-methyl-3-oxo-7-(trifluoromethyl)-3,4-dihydro-2H-1,4-benzoxazin-6-yl]carbonyl}amino)piperidine-1-carboxylate

[Chemical formula 208]

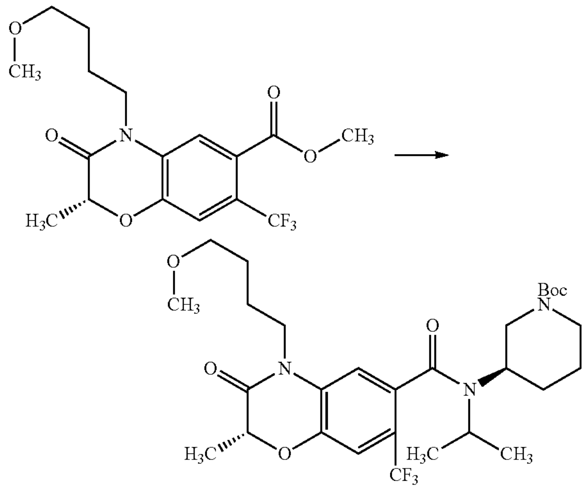

Using the compound of Reference Example 63, the title compound was obtained in a similar manner to Reference Example 5.

MS (ESI+) 586 ($M^{+}$+1, 100%).

Reference Example 65

2,2-Dimethyl-3-oxo-7-(trifluoromethyl)-3,4-dihydro-2H-1,4-benzoxazine-6-carboxylic acid

[Chemical formula 209]

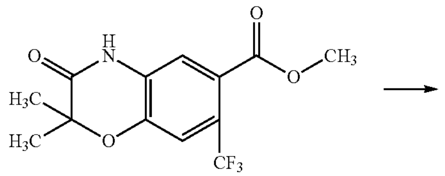

-continued

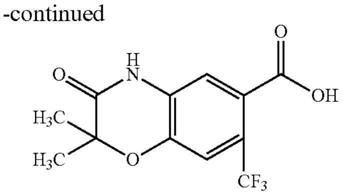

Using the compound of Reference Example 55, the title compound was obtained in a similar manner to Reference Example 4.

MS (ESI+) 289 ($M^{+}$+1, 13%).

Reference Example 66 tert-Butyl (3R)-3-[{[2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 210]

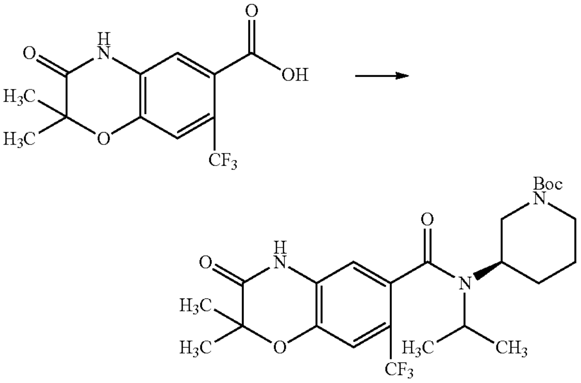

Using the compound of Reference Example 65, the title compound was obtained in a similar manner to Reference Example 5.

MS (ESI+) 514 ($M^{+}$+1, 27%).

Reference Example 67 tert-Butyl (3R)-3-(isopropyl{[7-methoxy-4-(4-methoxybutyl)-2,2-dimethyl-3-oxo-3,4-dihydro-2H-1,4-benzoxazin-6-yl]carbonyl}amino)piperidine-1-carboxylate

[Chemical formula 211]

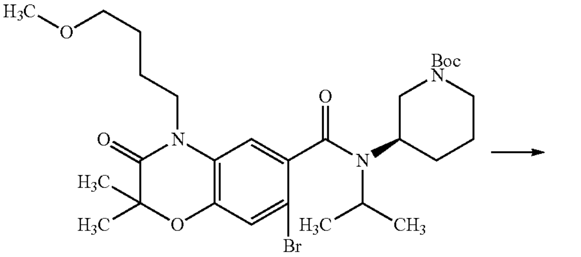

-continued

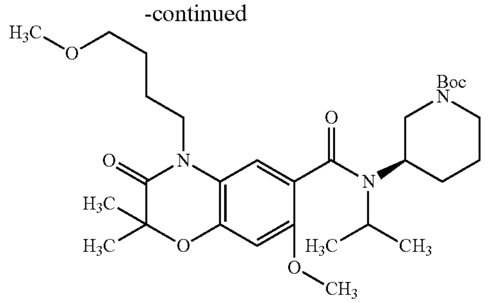

To tert-Butyl (3R)-3-[{[7-bromo-4-(4-methoxybutyl)-2,2-dimethyl-3-oxo-3,4-dihydro-2H-1,4-benzoxazin-6-yl]carbonyl}(isopropyl)amino]piperidine-1-carboxylate (500 mg) were added CuBr (59 mg), NaOMe (1M methanol solution) (16.4 ml) and DMF (5.5 ml), and the mixture was stirred at 100° C. for 15 hours. After the reaction was complete, water was added to the reaction solution, and the mixture was extracted with ethyl acetate solution. The obtained ethyl acetate solution was washed with water and a saturated aqueous sodium chloride solution, dried over magnesium sulfate, filtered and concentrated. The obtained residue was purified by silica gel column chromatography (hexane/ethyl acetate=1/2) to give the title compound (240 mg) as a colorless liquid.

MS (ESI+) 562 ($M^{+}$+1, 30%).

Reference Example 68

Methyl 4-(4-cyanobutyl)-2,2,7-trimethyl-3-oxo-3,4-dihydro-2H-1,4-benzoxazine-6-carboxylate

[Chemical formula 212]

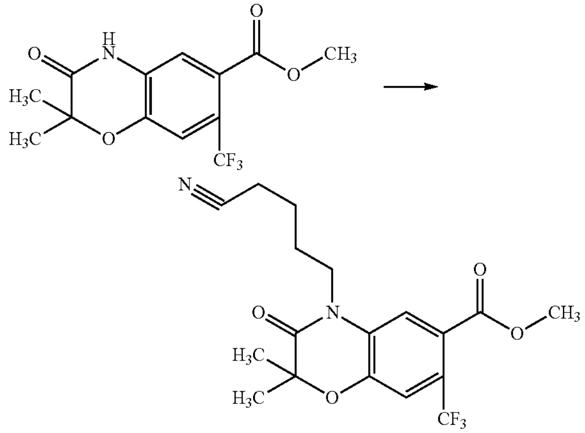

To the compound of Reference Example 56 (700 mg) were added sodium hydride (155 mg), 5-chloropentanenitrile (1.0 ml), potassium iodide (100 mg) and N,N-dimethylformamide (9 ml), and the mixture was stirred at 100° C. for 5 hours. After the reaction was complete, water was added to the reaction solution, and the mixture was extracted with ethyl acetate solution. The obtained ethyl acetate solution was washed with water and an aqueous sodium chloride solution, dried over magnesium sulfate, filtered and concentrated. The obtained residue was purified by silica gel column chromatography (hexane/ethyl acetate=2/1) to give the title compound (250 mg) as a colorless liquid.

MS (ESI+) 331 ($M^{+}$+1, 72%).

Reference Example 69

Methyl 4-(2-{[(dimethylamino)carbonyl]oxy}ethyl)-2,2,7-trimethyl-3-oxo-3,4-dihydro-2H-1,4-benzoxazine-6-carboxylate

[Chemical formula 213]

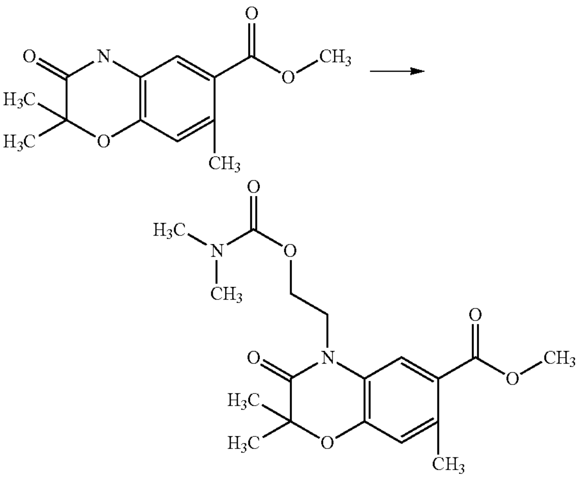

Using the compound of Reference Example 56, the title compound was obtained in a similar manner to Reference Example 3.

MS (ESI+) 365 ($M^{+}$+1, 26%).

Reference Example 70

Methyl 4-hex-5-en-1-yl-2,2,7-trimethyl-3-oxo-3,4-dihydro-2H-1,4-benzoxazine-6-carboxylate

[Chemical formula 214]

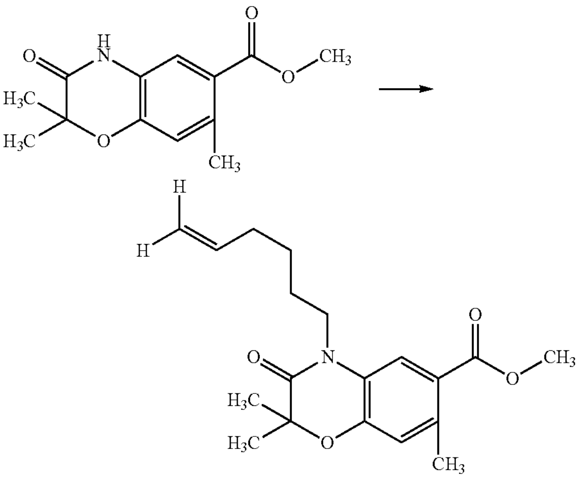

Using the compound of Reference Example 56, the title compound was obtained in a similar manner to Reference Example 3.

MS (ESI+) 332 ($M^{+}$+1, 81%).

Reference Example 71

Methyl 4-(4-{[tert-butyl(dimethyl)silyl]oxy}butyl)-2,2,7-trimethyl-3-oxo-3,4-dihydro-2H-1,4-benzoxazine-6-carboxylate

[Chemical formula 215]

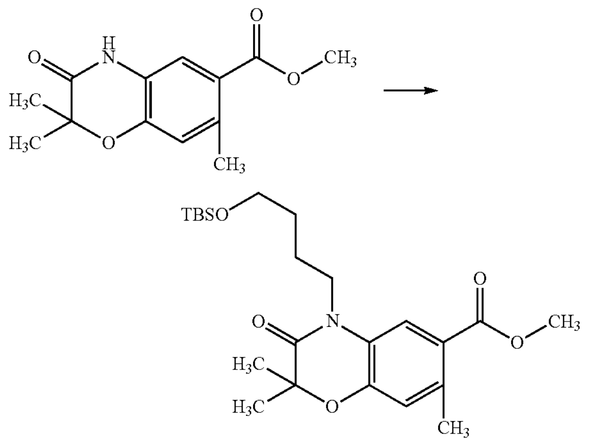

Using the compound of Reference Example 56, the title compound was obtained in a similar manner to Reference Example 3.

MS (ESI+) 436 ($M^{+}$+1, 51%).

Reference Example 72

Methyl 4-(2-{[(benzyloxy)carbonyl]amino}ethyl)-2,2-dimethyl-3-oxo-3,4-dihydro-2H-1,4-benzoxazine-6-carboxylate

[Chemical formula 216]

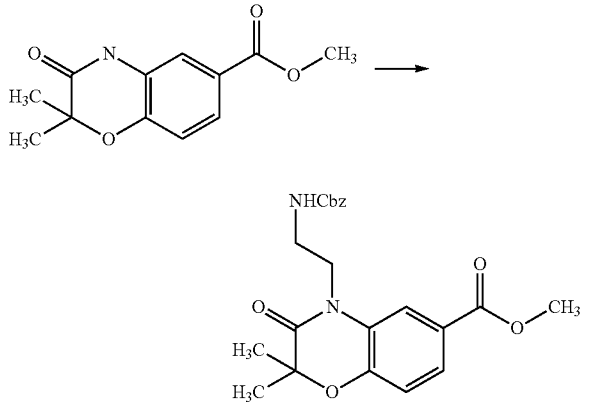

Using the compound of Reference Example 56, the title compound was obtained in a similar manner to Reference Example 3.

MS (ESI+) 413 ($M^{+}$+1, 30%).

Reference Example 73

Methyl 4-(2-{[(benzyloxy)carbonyl]amino}ethyl)-2,2,7-trimethyl-3-oxo-3,4-dihydro-2H-1,4-benzoxazine-6-carboxylate

[Chemical formula 217]

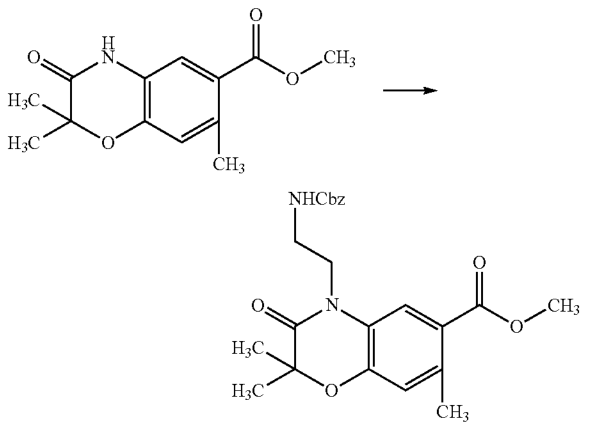

Using the compound of Reference Example 56, the title compound was obtained in a similar manner to Reference Example 3.

MS (ESI+) 427 ($M^{+}$+1, 37%).

Reference Example 74

Methyl 4-(2-{[(benzyloxy)carbonyl]amino}ethyl)-2,2-dimethyl-3-oxo-7-(trifluoromethyl)-3,4-dihydro-2H-1,4-benzoxazine-6-carboxylate

[Chemical formula 218]

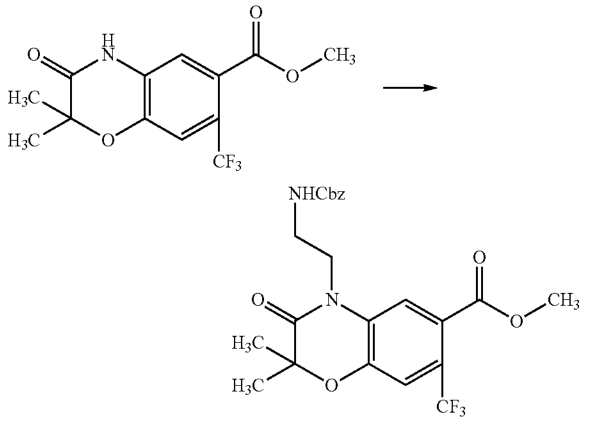

Using the compound of Reference Example 55, the title compound was obtained in a similar manner to Reference Example 3.

MS (ESI+) 427 ($M^{+}$+1, 42%).

Reference Example 75

Methyl 4-(3-{[(benzyloxy)carbonyl]amino}propyl)-2,2,7-trimethyl-3-oxo-3,4-dihydro-2H-1,4-benzoxazine-6-carboxylate

[Chemical formula 219]

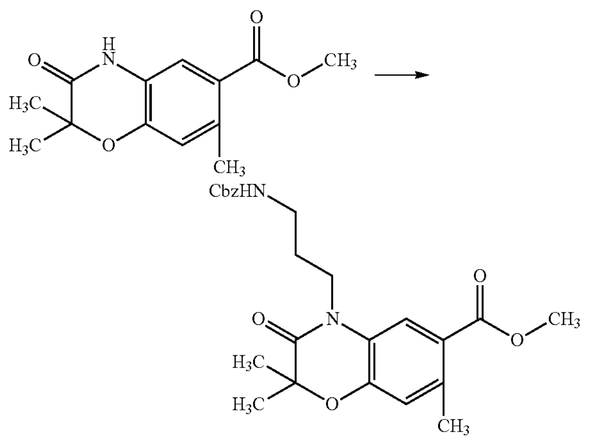

Using the compound of Reference Example 56, the title compound was obtained in a similar manner to Reference Example 3.

MS (ESI+) 441 ($M^{+}$+1, 24%).

Reference Example 76

Methyl 2-ethyl 4-{2-[(methoxycarbonyl)amino]ethyl}-2-methyl-3-oxo-7-(trifluoromethyl)-3,4-dihydro-2H-1,4-benzoxazine-6-carboxylate

[Chemical formula 220]

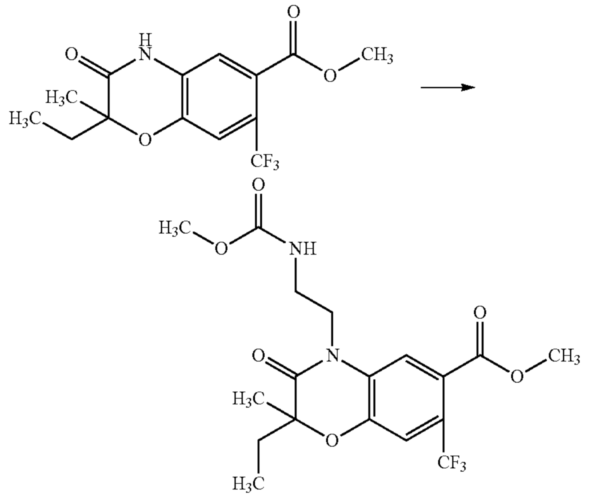

Using methyl 2-ethyl-2-methyl-3-oxo-7-(trifluoromethyl)-3,4-dihydro-2H-1,4-benzoxazine-6-carboxylate, the title compound was obtained in a similar manner to Reference Example 13.

MS (ESI+) 419 ($M^{+}$+1, 20%).

Reference Example 77

Methyl 2,2,7-trimethyl-3-oxo-4-(tetrahydro-2H-pyran-4-ylmethyl)-3,4-dihydro-2H-1,4-benzoxazine-6-carboxylate

[Chemical formula 221]

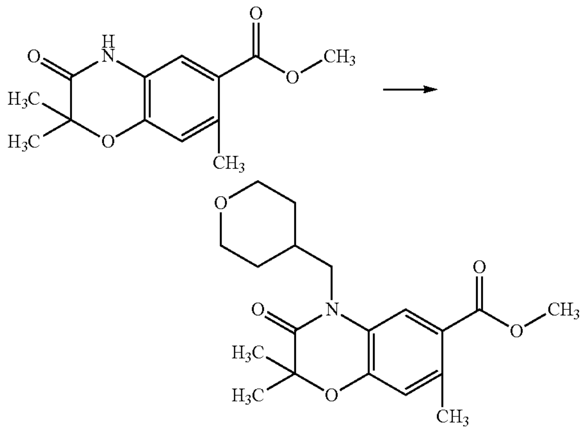

Using the compound of Reference Example 56, the title compound was obtained in a similar manner to Reference Example 3.

MS (ESI+) 348 ($M^{+}$+1, 26%).

Reference Example 78

Methyl 4-[3-(2-ethyl-1,3-dioxolan-2-yl)propyl]-2,2,7-trimethyl-3-oxo-3,4-dihydro-2H-1,4-benzoxazine-6-carboxylate

[Chemical formula 222]

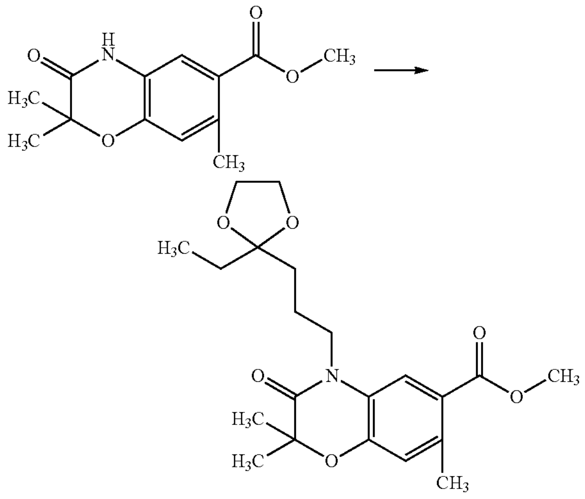

Using the compound of Reference Example 56, the title compound was obtained in a similar manner to Reference Example 3.

MS (ESI+) 392 ($M^{+}$+1, 30%).

Reference Example 79

Methyl 4-[4-(benzyloxy)butyl]-2,2,7-trimethyl-3-oxo-3,4-dihydro-2H-1,4-benzoxazine-6-carboxylate

[Chemical formula 223]

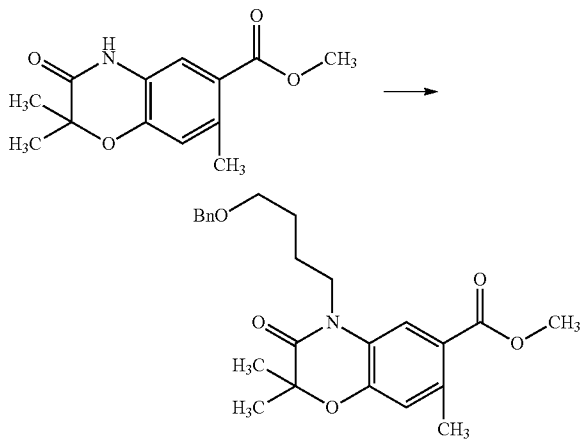

Using the compound of Reference Example 56, the title compound was obtained in a similar manner to Reference Example 3.

MS (ESI+) 412 ($M^{+}$+1, 35%).

Reference Example 80

Methyl 4-[2-(benzyloxy)ethyl]-2,2,7-trimethyl-3-oxo-3,4-dihydro-2H-1,4-benzoxazine-6-carboxylate

[Chemical formula 224]

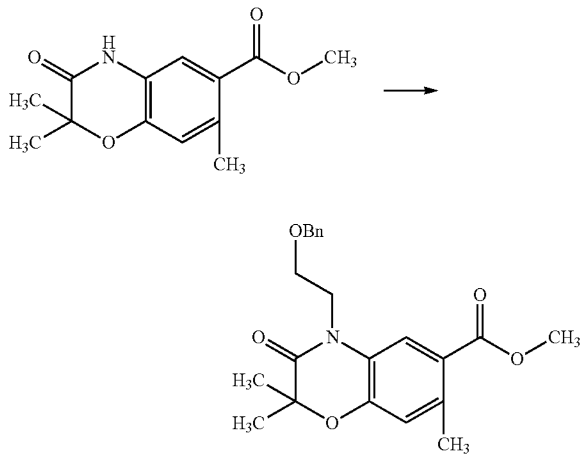

Using the compound of Reference Example 56, the title compound was obtained in a similar manner to Reference Example 3.

MS (ESI+) 384 ($M^{+}$+1, 24%).

Reference Example 81

Methyl 2,2,7-trimethyl-3-oxo-4-(4,4,4-trifluorobutyl)-3,4-dihydro-2H-1,4-benzoxazine-6-carboxylate

[Chemical formula 225]

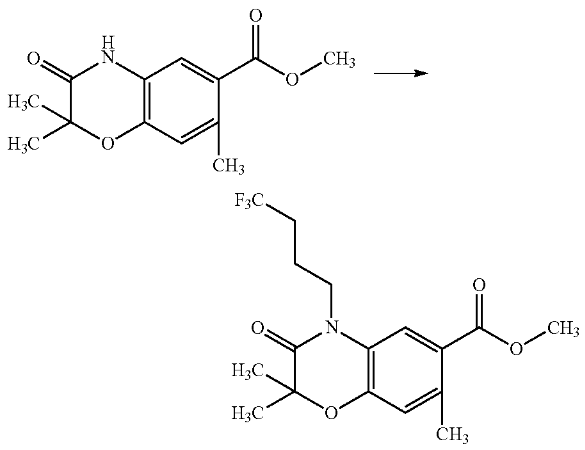

Using the compound of Reference Example 56, the title compound was obtained in a similar manner to Reference Example 3.

MS (ESI+) 360 ($M^{+}$+1, 23%).

Reference Example 82

Methyl 2,2,7-trimethyl-3-oxo-4-(5,5,5-trifluoropentyl)-3,4-dihydro-2H-1,4-benzoxazine-6-carboxylate

[Chemical formula 226]

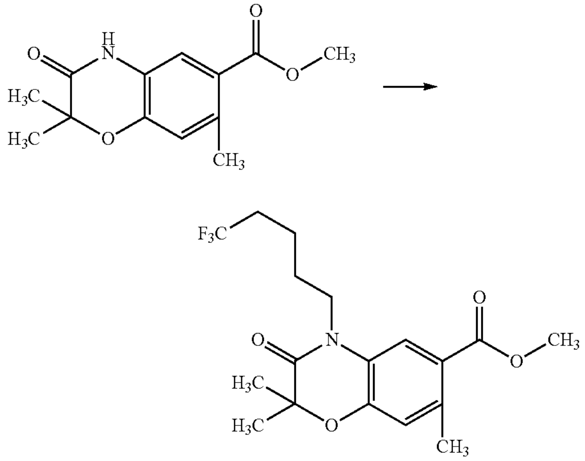

Using the compound of Reference Example 56, the title compound was obtained in a similar manner to Reference Example 3.

MS (ESI+) 374 ($M^{+}$+1, 26%).

Reference Example 83

Methyl 4-(4-tert-butoxy-4-oxobutyl)-2,2,7-trimethyl-3-oxo-3,4-dihydro-2H-1,4-benzoxazine-6-carboxylate

[Chemical formula 227]

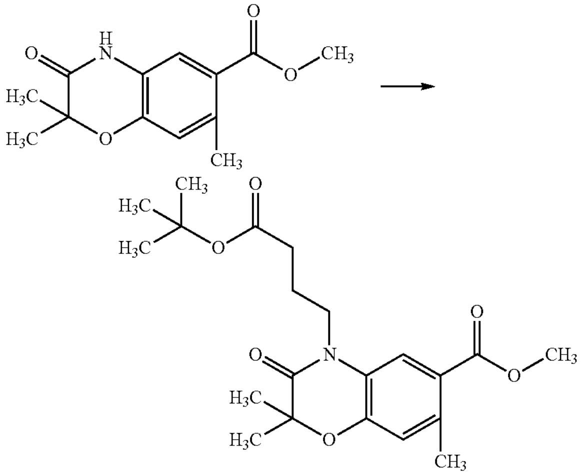

Using the compound of Reference Example 56, the title compound was obtained in a similar manner to Reference Example 3.

MS (ESI+) 392 ($M^{+}$+1, 22%).

Reference Example 84

Methyl 4-(2-tert-butoxy-2-oxoethyl)-2,2,7-trimethyl-3-oxo-3,4-dihydro-2H-1,4-benzoxazine-6-carboxylate

[Chemical formula 228]

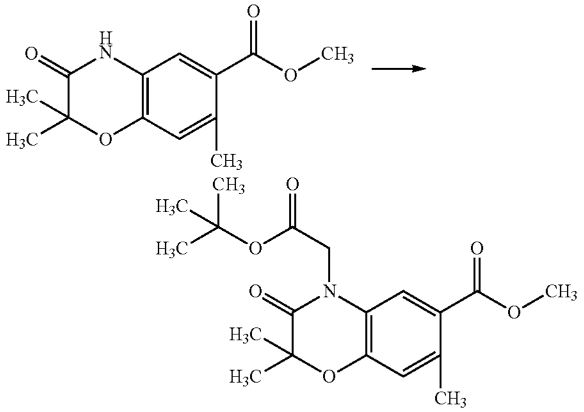

Using the compound of Reference Example 56, the title compound was obtained in a similar manner to Reference Example 3.

MS (ESI+) 364 ($M^{+}$+1, 21%).

Reference Example 85 tert-Butyl (3R)-3-[{[4-((2S)-2-{[(benzyloxy)carbonyl]amino}propyl)-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 229]

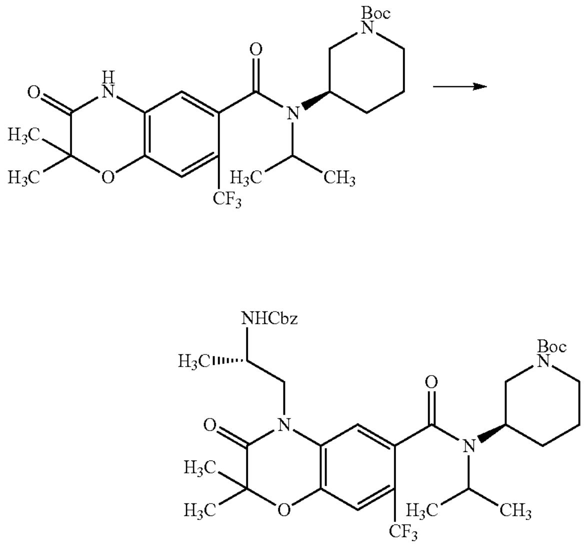

To tert-butyl (3R)-3-[{[2,2-dimethyl-3-oxo-7-(trifluoromethyl)-3,4-dihydro-2H-1,4-benzoxazin-6-yl]carbonyl}(isopropyl)amino]piperidine-1-carboxylate (100 mg) were added 2-hydroxycarbamic acid benzyl ester (49 mg), diisopropyl azodicarboxylate (0.26 ml), triphenylphosphine (122 mg) and tetrahydrofuran (3 ml), and the mixture was stirred at room temperature overnight. After the reaction was complete, the mixture was concentrated, and the obtained residue was purified by silica gel column chromatography (hexane/ethyl acetate=1/1) to give the title compound (120 mg).

MS (ESI+) 705 ($M^{+}$+1, 39%).

Reference Example 86 tert-Butyl (3R)-3-[{[4-(3-ethoxy-3-oxopropyl)-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 230]

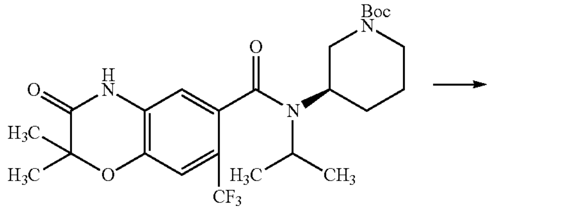

-continued

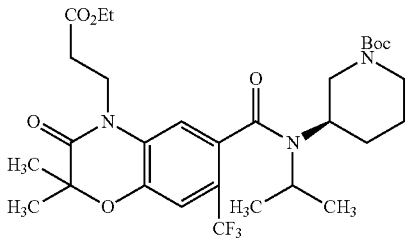

To tert-Butyl (3R)-3-[{[2,2-dimethyl-3-oxo-7-(trifluoromethyl)-3,4-dihydro-2H-1,4-benzoxazin-6-yl]carbonyl}(isopropyl)amino]piperidine-1-carboxylate (460 mg) were added 3-bromopropionic acid ethyl ester (0.19 ml), potassium carbonate (298 mg) and acetonitrile (5 ml), and the mixture was refluxed for 5 hours. After the reaction was complete, water was added to the reaction solution, and the mixture was extracted with ethyl acetate solution. The obtained ethyl acetate solution was washed with water and an aqueous sodium chloride solution, dried over magnesium sulfate, filtered and concentrated. The obtained residue was purified by silica gel column chromatography (hexane/ethyl acetate=1/1) to give the title compound (350 mg) as a colorless liquid.

MS (ESI+) 614 ($M^{+}$+1, 32%).

Reference Example 87 tert-Butyl (3R)-3-(isopropyl{[4-[(2S)-3-methoxy-2-methyl-3-oxopropyl]-2,2-dimethyl-3-oxo-7-(trifluoromethyl)-3,4-dihydro-2H-1,4-benzoxazin-6-yl]carbonyl}amino)piperidine-1-carboxylate

[Chemical formula 231]

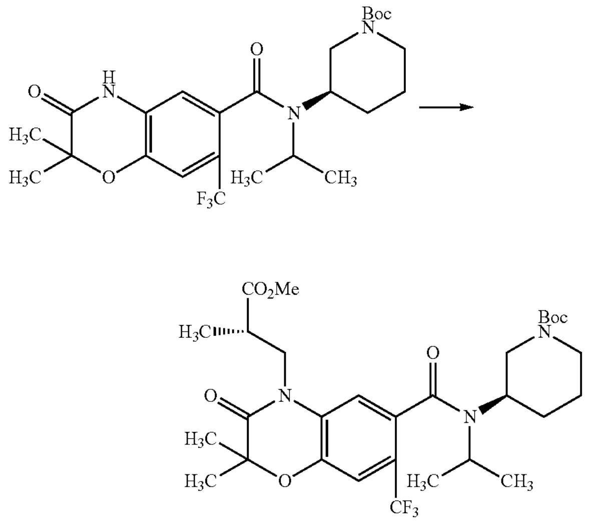

Using the compound of Reference Example 66, the title compound was obtained in a similar manner to Reference Example 3.

MS (ESI+) 614 ($M^{+}$+1, 32%).

Reference Example 88 tert-Butyl (3R)-3-[{[4-(1H-imidazol-5-ylmethyl)-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 232]

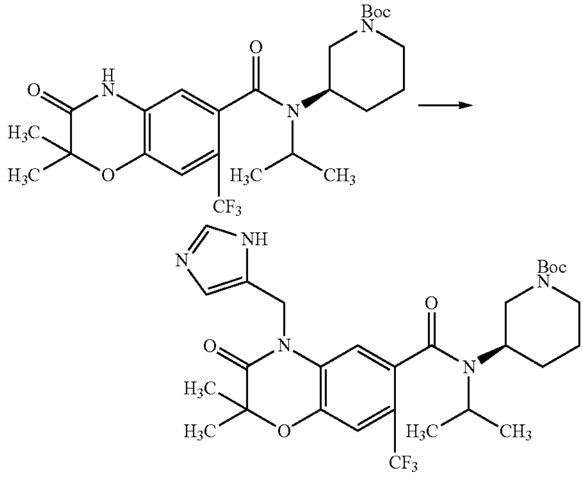

Using the compound of Reference Example 66, the title compound was obtained in a similar manner to Reference Example 3.

MS (ESI+) 594 ($M^{+}$+1, 31%).

Reference Example 89 tert-Butyl (3R)-3-[{[4-(2-{[(dimethylamino)carbonyl]oxy}ethyl)-2,2,7-trimethyl-3-oxo-3,4-dihydro-2H-1,4-benzoxazin-6-yl]carbonyl}(isopropyl)amino]piperidine-1-carboxylate

[Chemical formula 233]

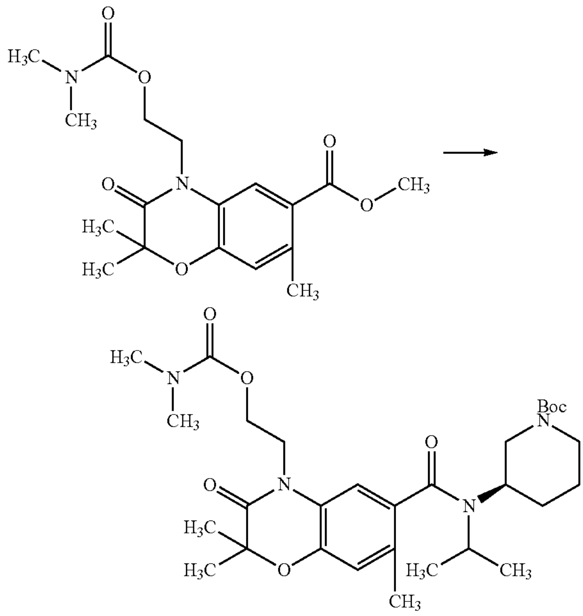

Using the compound of Reference Example 69, the title compound was obtained in a similar manner to Reference Example 5.

MS (ESI+) 575 ($M^{+}$+1, 32%).

Reference Example 90 tert-Butyl (3R)-3-[{[4-(4-cyanobutyl)-2,2,7-trimethyl-3-oxo-3,4-dihydro-2H-1,4-benzoxazin-6-yl]-carbonyl}(isopropyl)amino]piperidine-1-carboxylate

[Chemical formula 234]

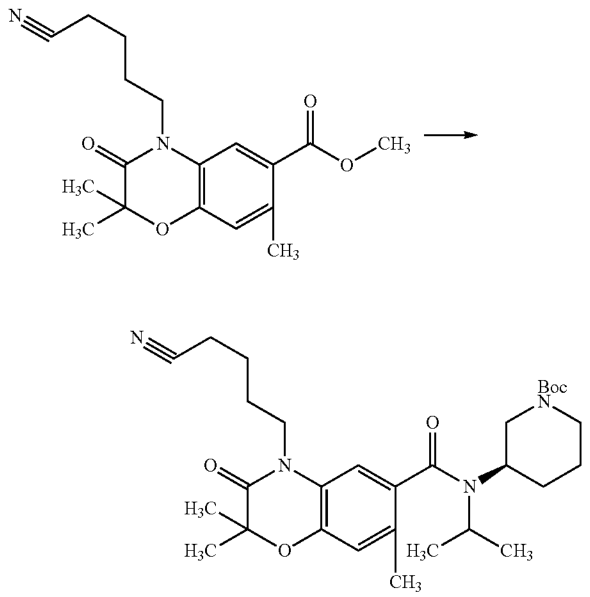

Using the compound of Reference Example 68, the title compound was obtained in a similar manner to Reference Example 5.

MS (ESI+) 541 ($M^{+}$+1, 32%).

Reference Example 91 tert-Butyl (3R)-3-[[(4-hex-5-en-1-yl-2,2,7-trimethyl-3-oxo-3,4-dihydro-2H-1,4-benzoxazin-6-yl)-carbonyl](isopropyl)amino]piperidine-1-carboxylate

[Chemical formula 235]

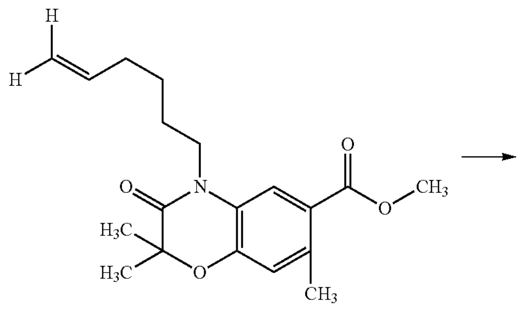

-continued

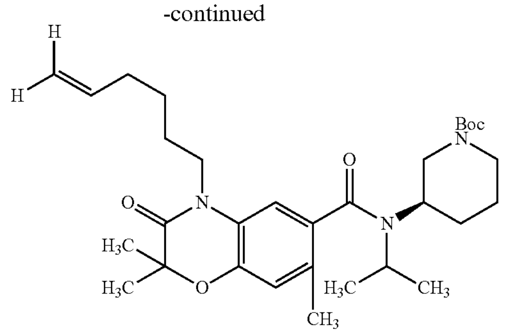

Using the compound of Reference Example 70, the title compound was obtained in a similar manner to Reference Example 5.

MS (ESI+) 542 ($M^{+}$+1, 34%).

Reference Example 92 tert-Butyl (3R)-3-[{[4-(4-{[tert-butyl(dimethyl)silyl]oxy}butyl)-2,2,7-trimethyl-3-oxo-3,4-dihydro-2H-1,4-benzoxazin-6-yl]carbonyl}(isopropyl)amino]piperidine-1-carboxylate

[Chemical formula 236]

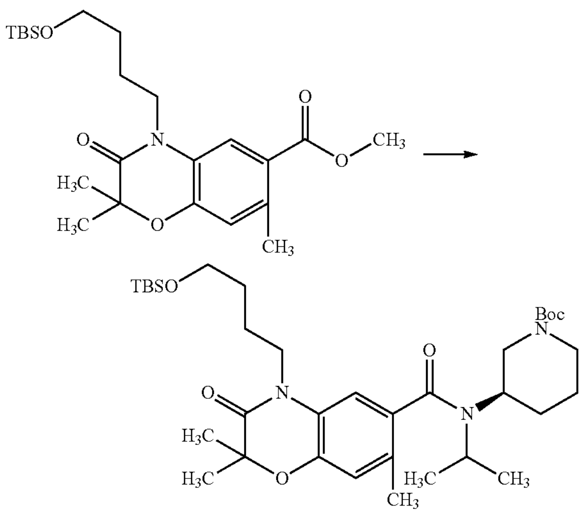

Using the compound of Reference Example 71, the title compound was obtained in a similar manner to Reference Example 5.

MS (ESI+) 646 ($M^{+}$+1, 38%).

Reference Example 93 tert-Butyl (3R)-3-[{[4-(2-{[(benzyloxy)carbonyl]amino}ethyl)-2,2-dimethyl-3-oxo-3,4-dihydro-2H-1,4-benzoxazin-6-yl]carbonyl}(isopropyl)amino]piperidine-1-carboxylate

[Chemical formula 237]

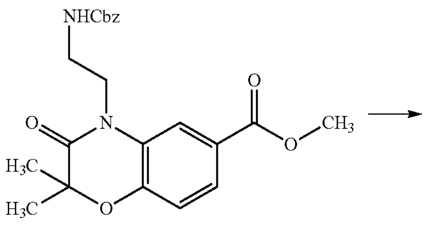

-continued

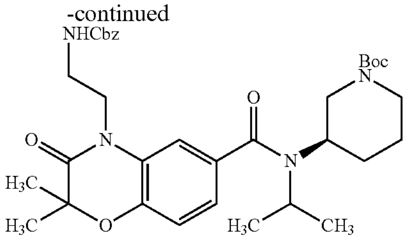

Using the compound of Reference Example 72, the title compound was obtained in a similar manner to Reference Example 5.

MS (ESI+) 623 ($M^{+}$+1, 37%).

Reference Example 94 tert-Butyl (3R)-3-[{[4-(2-{[(benzyloxy)carbonyl]amino}ethyl)-2,2,7-trimethyl-3-oxo-3,4-dihydro-2H-1,4-benzoxazin-6-yl]carbonyl}(isopropyl)amino]piperidine-1-carboxylate

[Chemical formula 238]

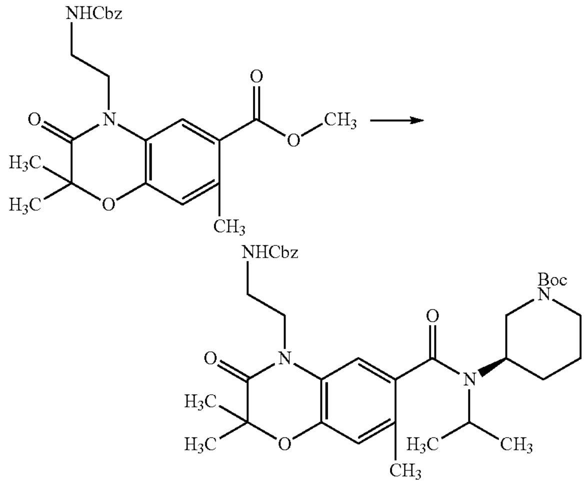

Using the compound of Reference Example 73, the title compound was obtained in a similar manner to Reference Example 5.

MS (ESI+) 637 ($M^{+}$+1, 38%).

Reference Example 95 tert-Butyl (3R)-3-[{[4-(3-{[(benzyloxy)carbonyl]amino}propyl)-2,2,7-trimethyl-3-oxo-3,4-dihydro-2H-1,4-benzoxazin-6-yl]carbonyl}(isopropyl)amino]piperidine-1-carboxylate

[Chemical formula 239]

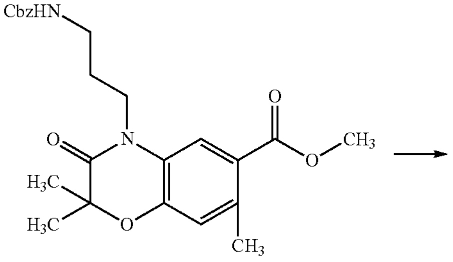

-continued

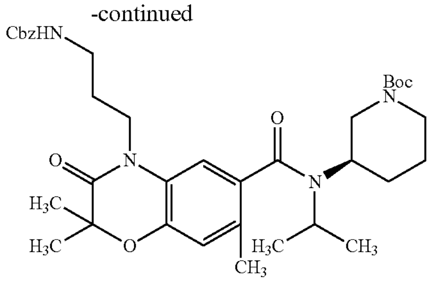

Using the compound of Reference Example 75, the title compound was obtained in a similar manner to Reference Example 5.

MS (ESI+) 651 ($M^{+}$+1, 39%).

Reference Example 96 tert-Butyl (3R)-3-(isopropyl{[2,2,7-trimethyl-3-oxo-4-(tetrahydro-2H-pyran-4-ylmethyl)-3,4-dihydro-2H-1,4-benzoxazin-6-yl]carbonyl}amino)piperidine-1-carboxylate

[Chemical formula 240]

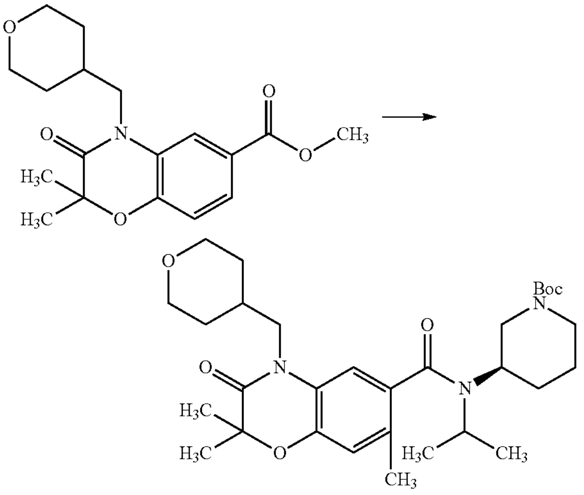

Using the compound of Reference Example 77, the title compound was obtained in a similar manner to Reference Example 5.

MS (ESI+) 558 ($M^{+}$+1, 34%).

Reference Example 97 tert-Butyl (3R)-3-(isopropyl{[2,2,7-trimethyl-3-oxo-4-(4-oxohexyl)-3,4-dihydro-2H-1,4-benzoxazin-6-yl]carbonyl}amino)piperidine-1-carboxylate

[Chemical formula 241]

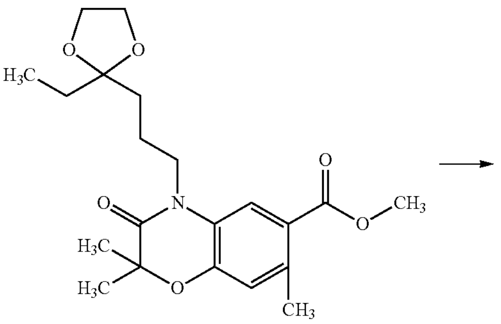

-continued

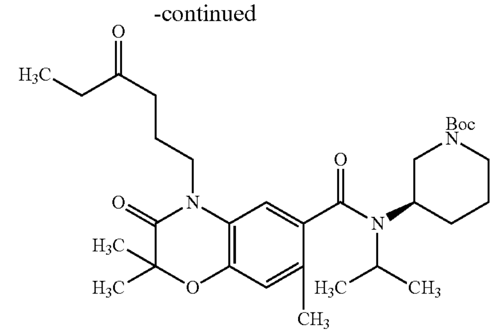

Using the compound of Reference Example 78, the title compound was obtained in a similar manner to Reference Example 5.

MS (ESI+) 558 ($M^{+}$+1, 34%).

Reference Example 98 tert-Butyl (3R)-3-[({4-[4-(benzyloxy)butyl]-2,2,7-trimethyl-3-oxo-3,4-dihydro-2H-1,4-benzoxazin-6-yl}carbonyl)(isopropyl)amino]piperidine-1-carboxylate

[Chemical formula 242]

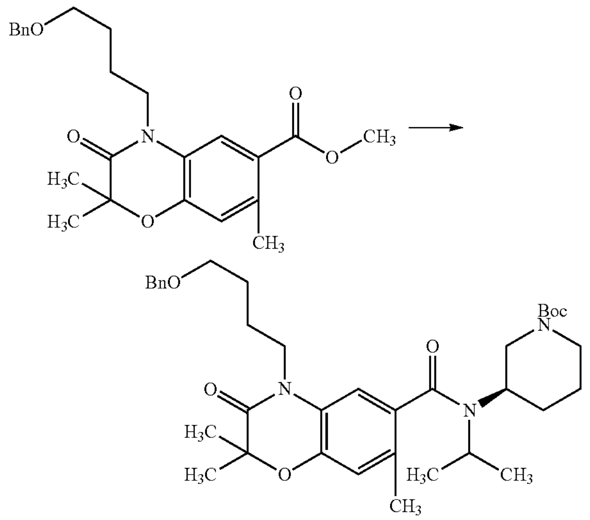

Using the compound of Reference Example 79, the title compound was obtained in a similar manner to Reference Example 5.

MS (ESI+) 622 ($M^{+}$+1, 39%).

Reference Example 99 tert-Butyl (3R)-3-[({442-(benzyloxy)ethyl]-2,2,7-trimethyl-3-oxy-3,4-dihydro-2H-1,4-benzoxazin-6-yl}carbonyl)(isopropyl)amino]piperidine-1-carboxylate

[Chemical formula 243]

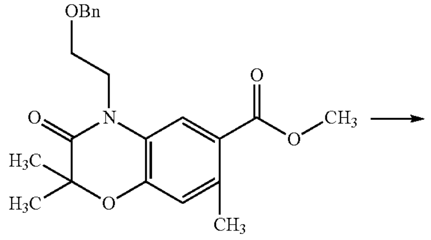

-continued

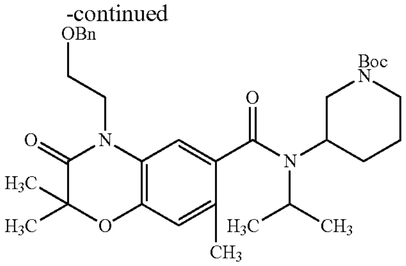

Using the compound of Reference Example 80, the title compound was obtained in a similar manner to Reference Example 5.

MS (ESI+) 594 ($M^{+}$+1, 37%).

Reference Example 100 tert-Butyl (3R)-3-(isopropyl{[2,2,7-trimethyl-3-oxo-4-(4,4,4-trifluorobutyl)-3,4-dihydro-2H-1,4-benzoxazin-6-yl]carbonyl}amino)piperidine-1-carboxylate

[Chemical formula 244]

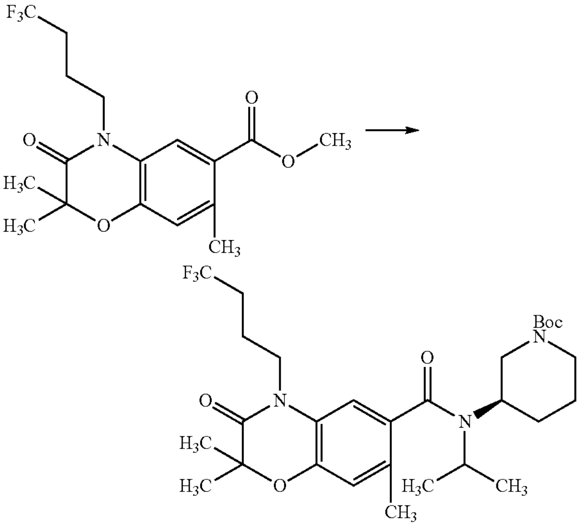

Using the compound of Reference Example 81, the title compound was obtained in a similar manner to Reference Example 5.

MS (ESI+) 570 ($M^{+}$+1, 31%).

Reference Example 101 tert-Butyl (3R)-3-(isopropyl{[2,2,7-trimethyl-3-oxo-4-(5,5,5-trifluoropentyl)-3,4-dihydro-2H-1,4-benzoxazin-6-yl]carbonyl}amino)piperidine-1-carboxylate

[Chemical formula 245]

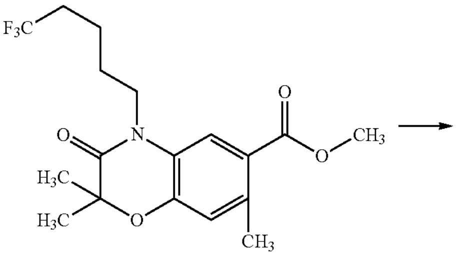

-continued

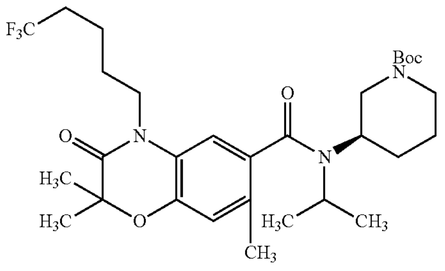

Using the compound of Reference Example 82, the title compound was obtained in a similar manner to Reference Example 5.

MS (ESI+) 584 ($M^{+}$+1, 32%).

Reference Example 102 tert-Butyl (3R)-3-[{[2-ethyl-4-{3-[(methoxycarbonyl)amino]propyl}-2-methyl-3-oxo-7-(trifluoro-methyl)-3,4-dihydro-2H-1,4-benzoxazin-6-yl]carbonyl}(isopropyl)amino]piperidine-1-carboxylate

[Chemical formula 246]

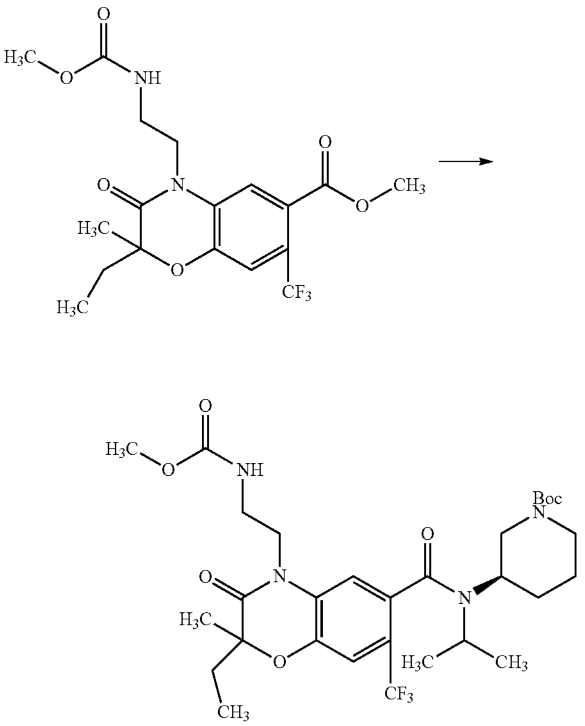

Using the compound of Reference Example 76, the title compound was obtained in a similar manner to Reference Example 5.

MS (ESI+) 629 ($M^{+}$+1, 32%).

Reference Example 103 tert-Butyl (3R)-3-[isopropyl({2,2,7-trimethyl-4-[4-(methylamino)-4-oxobutyl]-3-oxo-3,4-dihydro-2H-1,4-benzoxazin-6-yl}carbonyl)amino]piperidine-1-carboxylate

[Chemical formula 247]

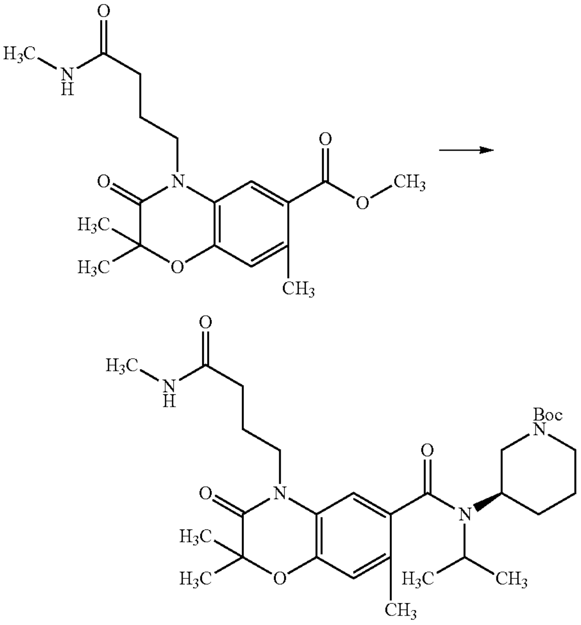

Using the compound of Reference Example 112, the title compound was obtained in a similar manner to Reference Example 5.

MS (ESI+) 559 ($M^{+}$+1, 32%).

Reference Example 104 tert-Butyl (3R)-3-[({4-[4-(ethylamino)-4-oxobutyl]-2,2,7-trimethyl-3-oxo-3,4-dihydro-2H-1,4-benzoxazin-6-yl}carbonyl)(isopropyl)amino]piperidine-1-carboxylate

[Chemical formula 248]

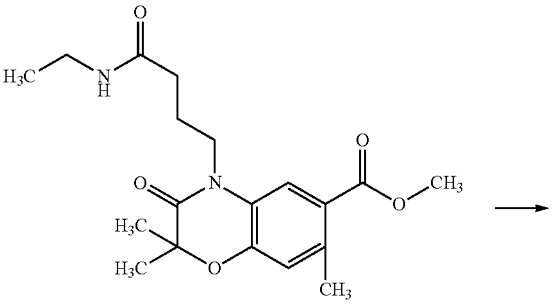

-continued

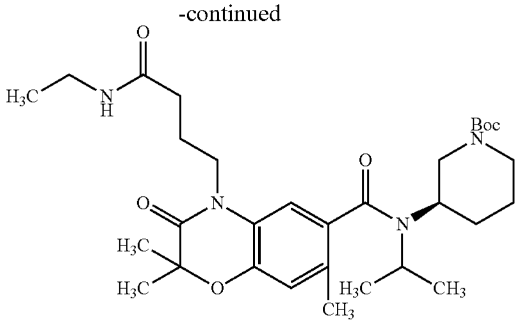

Using the compound of Reference Example 113, the title compound was obtained in a similar manner to Reference Example 5.

MS (ESI+) 573 ($M^{+}$+1, 34%).

Reference Example 105 tert-Butyl (3R)-3-[[(4-{2-[(2,2-difluoroethyl)amino]-2-oxoethyl}-2,2,7-trimethyl-3-oxo-3,4-dihydro-2H-1,4-benzoxazin-6-yl)carbonyl](isopropyl)amino]piperidine-1-carboxylate

[Chemical formula 249]

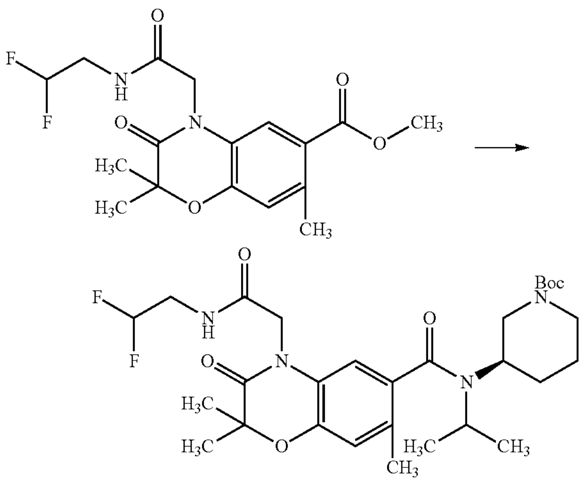

Using the compound of Reference Example 128, the title compound was obtained in a similar manner to Reference Example 5.

MS (ESI+) 581 ($M^{+}$+1, 31%).

Reference Example 106 tert-Butyl (3R)-3-[{[4-(4-tert-butoxy-4-oxobutyl)-2,2,7-trimethyl-3-oxo-3,4-dihydro-2H-1,4-benzoxazin-6-yl]carbonyl}(isopropyl)amino]piperidine-1-carboxylate

[Chemical formula 250]

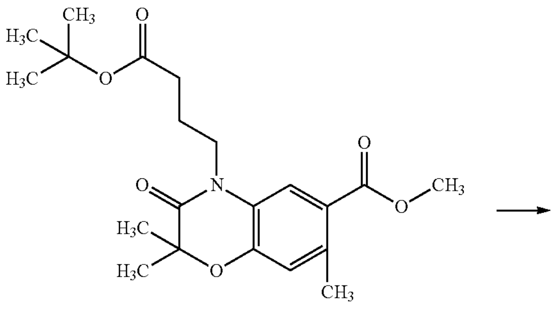

-continued

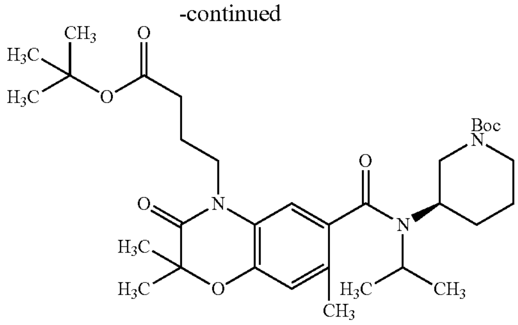

Using the compound of Reference Example 83, the title compound was obtained in a similar manner to Reference Example 5.

MS (ESI+) 602 ($M^{+}$+1, 36%).

Reference Example 107

3-[6-{[[(3R)-1-(tert-Butoxycarbonyl)piperidin-3-yl](isopropyl)amino]carbonyl}-2,2-dimethyl-3-oxo-7-(trifluoromethyl)-2,3-dihydro-4H-1,4-benzoxazin-4-yl]propanoic acid

[Chemical formula 251]

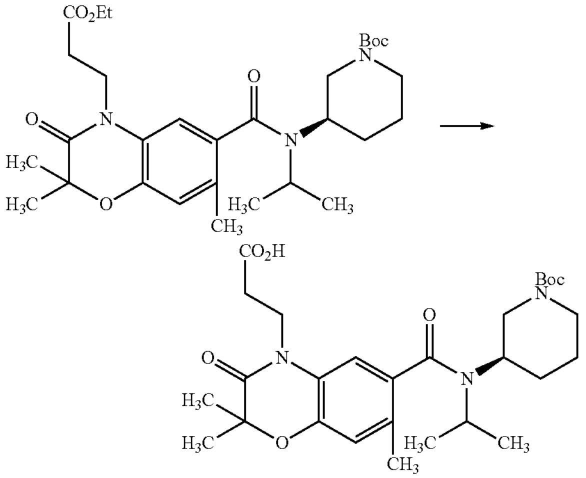

To tert-butyl (3R)-3-[{[4-(3-ethoxy-3-oxopropyl)-2,2-dimethyl-3-oxo-7-(trifluoromethyl)-3,4-dihydro-2H-1,4-benzoxazin-6-yl]carbonyl}(isopropyl)amino]piperidine-1-carboxylate (350 mg) were added a 2N NaOH aqueous solution (5 ml), MeOH (5 ml) and THF (5 ml), and the mixture was stirred at room temperature for 2 hours. After the reaction was complete, the solvent was concentrated, and thereto was added dropwise a 2N aqueous hydrochloric acid solution. The precipitated crystals were extracted with ethyl acetate. The obtained ethyl acetate solution was washed with water and an aqueous sodium chloride solution, dried over magnesium sulfate, filtered and concentrated. The obtained residue (260 mg) was used in the subsequent reaction without a further treatment.

MS (ESI+) 586 ($M^{+}$+1, 30%).

Reference Example 108

(2S)-3-[6-{[[(3R)-1-(tert-Butoxycarbonyl)piperidine-3-yl](isopropyl)amino]carbonyl}-2,2-dimethyl-3-oxo-7-(trifluoromethyl)-2,3-dihydro-4H-1,4-benzoxazin-4-yl]-2-methylpropionic acid

[Chemical formula 252]

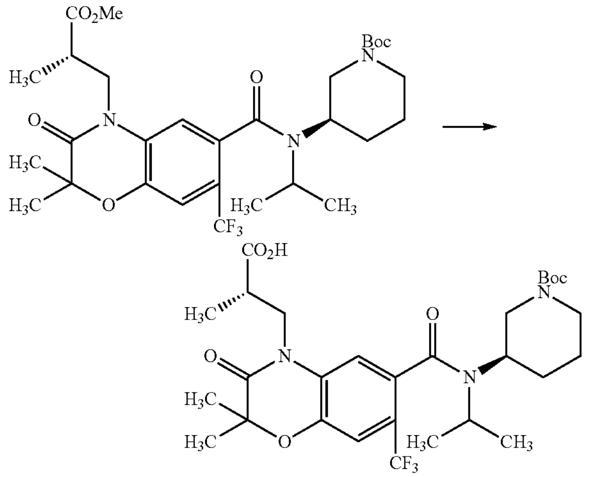

Using the compound of Reference Example 87, the title compound was obtained in a similar manner to Reference Example 107.

MS (ESI+) 600 ($M^{+}$+1, 31%).

Reference Example 109

4-[6-(Methoxycarbonyl)-2,2,7-trimethyl-3-oxo-2,3-dihydro-4H-1,4-benzoxazin-4-yl]butanoic acid

[Chemical formula 253]

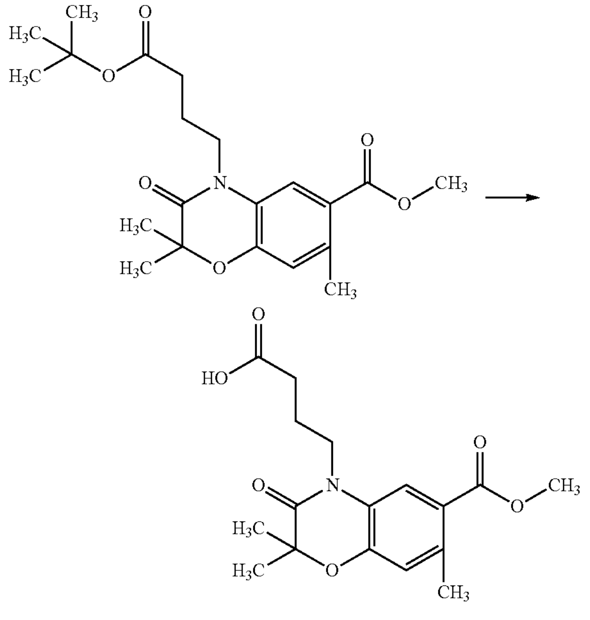

To methyl 4-(4-tert-butoxy-4-oxobutyl)-2,2,7-trimethyl-3-oxo-3,4-dihydro-2H-1,4-benzoxazine-6-carboxylate (2.7 g) was added TFA (5 ml), and the mixture was stirred at room temperature for 2 hours. After the reaction was complete, the mixture was neutralized with a saturated aqueous sodium hydrogen carbonate solution, and the precipitated compound was extracted with ethyl acetate. The obtained ethyl acetate solution was washed with water and an aqueous sodium chloride solution, dried over magnesium sulfate, filtered and concentrated. The obtained residue (950 mg) was used in the subsequent reaction without further treatment.

MS (ESI+) 336 ($M^{+}$+1, 18%).

Reference Example 110

[6-(Methoxycarbonyl)-2,2,7-trimethyl-3-oxo-2,3-dihydro-4H-1,4-benzoxazin-4-yl]acetic acid

[Chemical formula 254]

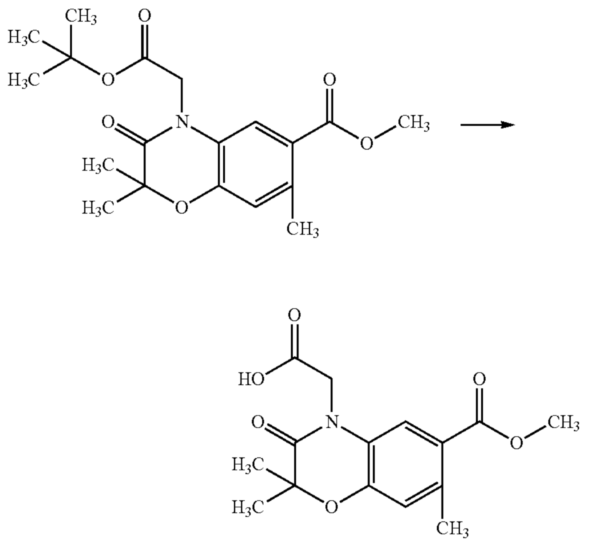

Using the compound of Reference Example 84, the title compound was obtained in a similar manner to Reference Example 109.

MS (ESI+) 308 ($M^{+}$+1, 16%).

Reference Example 111 tert-Butyl (3R)-3-[{[4-(2-{[(benzyloxy)carbonyl]amino}ethyl)-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 255]

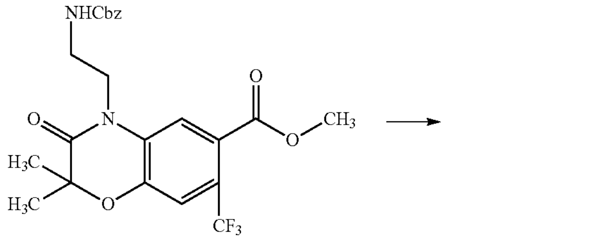

-continued

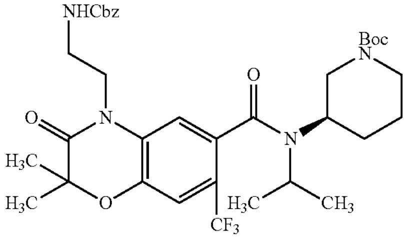

Using the compound of Reference Example 74, the title compound was obtained in a similar manner to Reference Example 5.

MS (ESI+) 691 ($M^{+}$+1, 38%).

Reference Example 112 tert-Butyl (3R)-3-[isopropyl({2,2,7-trimethyl-4-[4-(methylamino)-4-oxobutyl]-3-oxo-3,4-dihydro-2H-1,4-benzoxazin-6-yl}carbonyl)amino]piperidine-1-carboxylate

[Chemical formula 256]

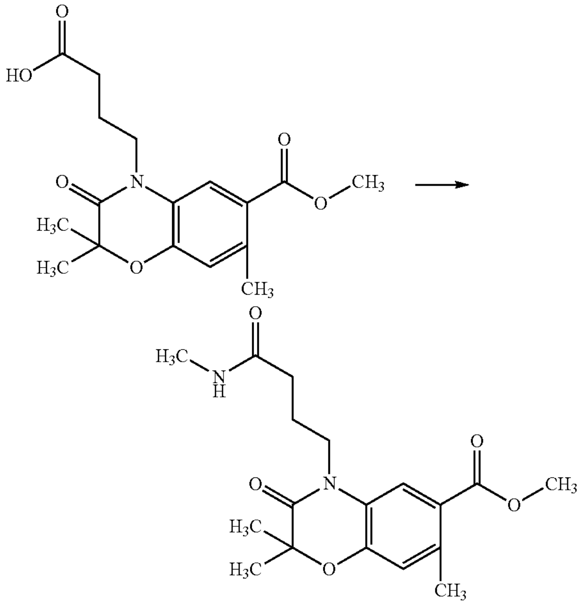

To 4-[6-(methoxycarbonyl)-2,2,7-trimethyl-3-oxo-2,3-dihydro-4H-1,4-benzoxazin-4-yl]-butanoic acid (500 mg) were added 1-(3-dimethylaminopropyl)-3-ethylcarbodiimide hydrochloride (372 mg), 1-hydroxybenzotriazole (262 mg), triethylamine (0.27 ml), chloroform (10 ml), methylamine (0.20 ml), and the mixture was stirred at room temperature overnight. After the reaction was complete, the mixture was concentrated, and the obtained residue was purified by silica gel column chromatography (chloroform/methanol=9/1) to give the title compound (420 mg) as colorless amorphous.

MS (ESI+) 349 ($M^{+}$+1, 20%).

Reference Example 113 tert-Butyl (3R)-3-[({4-[4-(ethylamino)-4-oxobutyl]-2,2,7-trimethyl-3-oxo-3,4-dihydro-2H-1,4-benzoxazin-6-yl}carbonyl)(isopropyl)amino]piperidine-1-carboxylate

[Chemical formula 257]

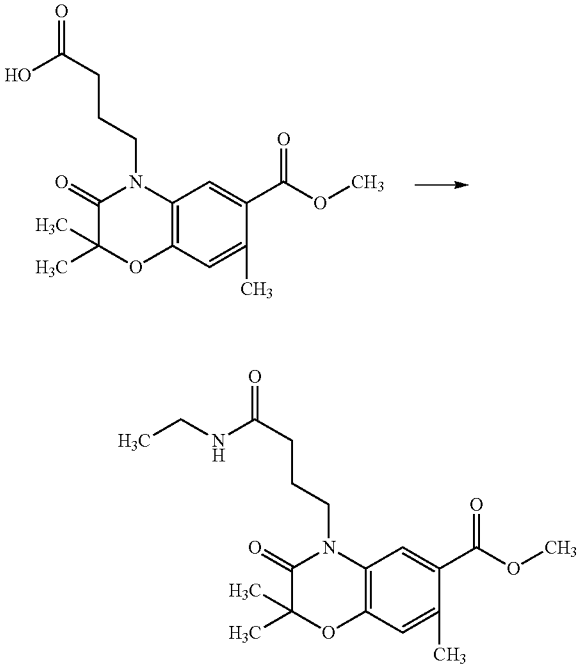

Using the compound of Reference Example 109, the title compound was obtained in a similar manner to Reference Example 112.

MS (ESI+) 363 ($M^{+}$+1, 21%).

Reference Example 114 tert-Butyl (3R)-3-[{[2,2-dimethyl-4-[3-(methylamino)-3-oxopropyl]-3-oxo-7-(trifluoromethyl)-3,4-dihydro-2H-1,4-benzoxazin-6-yl]carbonyl}(isopropyl)amino]piperidine-1-carboxylate

[Chemical formula 258]

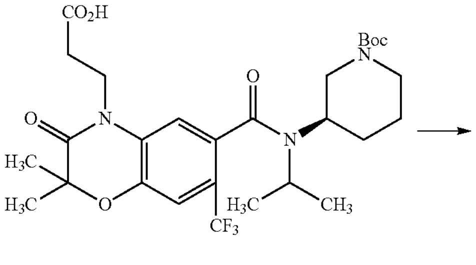

-continued

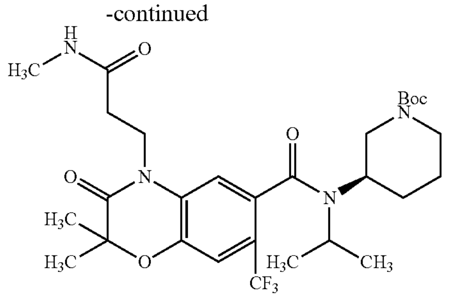

Using the compound of Reference Example 107, the title compound was obtained in a similar manner to Reference Example 112.

MS (ESI+) 599 ($M^{+}$+1, 31%).

Reference Example 115 tert-Butyl (3R)-3-[{[4-[3-(ethylamino)-3-oxopropyl]-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 259]

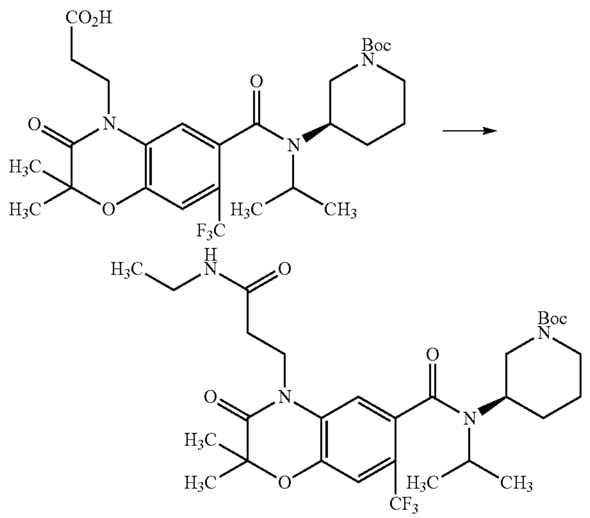

Using the compound of Reference Example 107, the title compound was obtained in a similar manner to Reference Example 112.

MS (ESI+) 613 ($M^{+}$+1, 32%).

Reference Example 116 tert-Butyl (3R)-3-[{[4-{3-[(2-fluoroethyl)amino]-3-oxopropyl}-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 260]

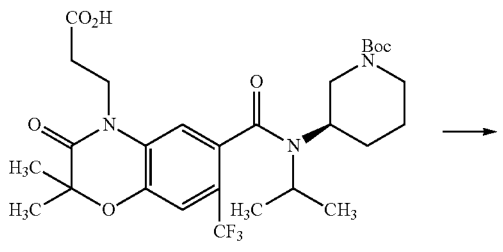

-continued

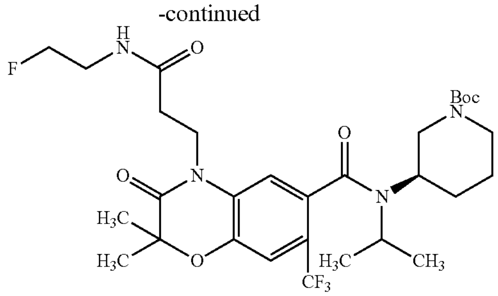

Using the compound of Reference Example 107, the title compound was obtained in a similar manner to Reference Example 112.

MS (ESI+) 631 ($M^{+}$+1, 32%).

Reference Example 117 tert-Butyl (3R)-3-[{[4-{3-[(2,2-difluoroethyl)amino]-3-oxopropyl}-2,2-dimethyl-3-oxo-7-(trifluoro-methyl)-3,4-dihydro-2H-1,4-benzoxazin-6-yl]carbonyl}(isopropyl)amino]piperidine-1-carboxylate

[Chemical formula 261]

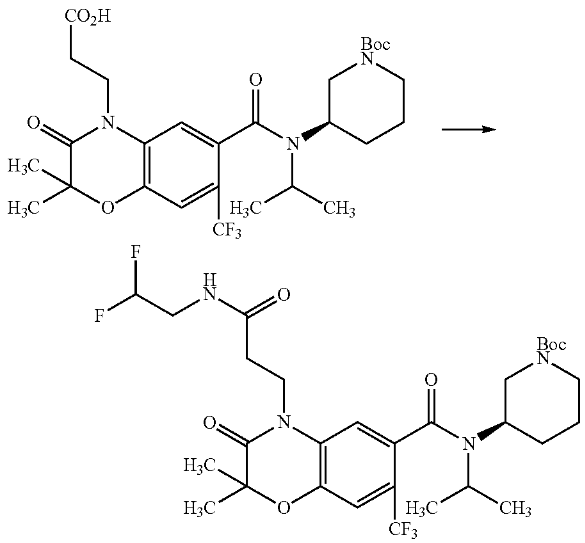

Using the compound of Reference Example 107, the title compound was obtained in a similar manner to Reference Example 112.

MS (ESI+) 649 ($M^{+}$+1, 32%).

Reference Example 118 tert-Butyl (3R)-3-[{[4-[3-(cyclopropylamino)-3-oxopropyl]-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 262]

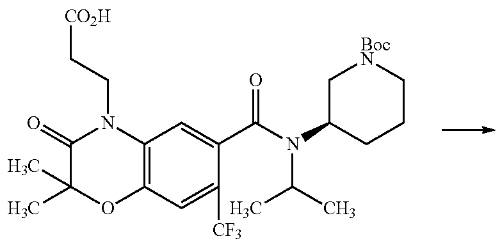

-continued

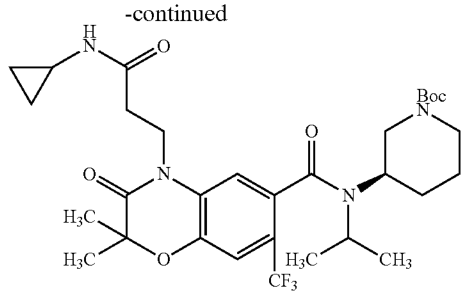

Using the compound of Reference Example 107, the title compound was obtained in a similar manner to Reference Example 112.

MS (ESI+) 625 ($M^{+}$+1, 34%).

Reference Example 119 tert-Butyl (3R)-3-[{[4-[(2S)-3-(ethylamino)-2-methyl-3-oxopropyl]-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 263]

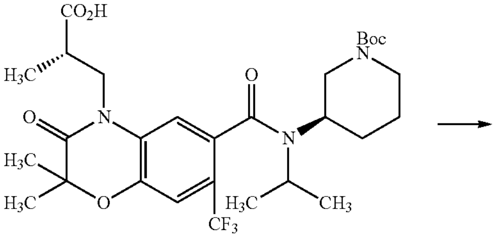

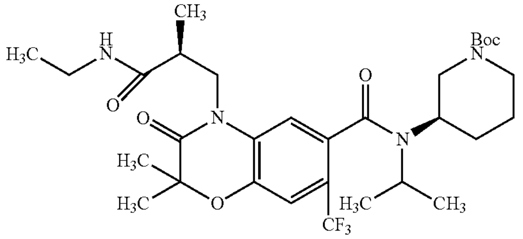

Using the compound of Reference Example 108, the title compound was obtained in a similar manner to Reference Example 112.

MS (ESI+) 627 ($M^{+}$+1, 34%).

Reference Example 120 tert-Butyl (3R)-3-[[(4-{2-[(cyclopropylcarbonyl)amino]ethyl}-2,2,7-trimethyl)-3-oxy-3,4-dihydro-2H-1,4-benzoxazin-6-yl)carbonyl](isopropyl)]piperidine-1-carboxylate

[Chemical formula 264]

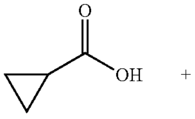

+

-continued

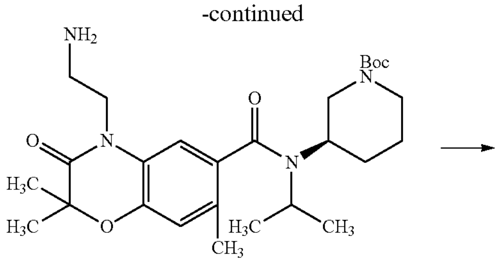

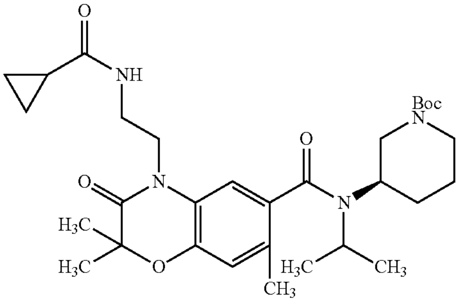

Using the compound of Reference Example 139, the title compound was obtained in a similar manner to Reference Example 112.

MS (ESI+) 571 ($M^{+}$+1, 34%).

Reference Example 121 tert-Butyl (3R)-3-[[(4-{2-[(difluoroacetyl)amino]ethyl}-2,2,7-trimethyl-3-oxo-3,4-dihydro-2H-1,4-benzoxazin-6-yl)carbonyl](isopropyl)amino]piperidine-1-carboxylate

[Chemical formula 265]

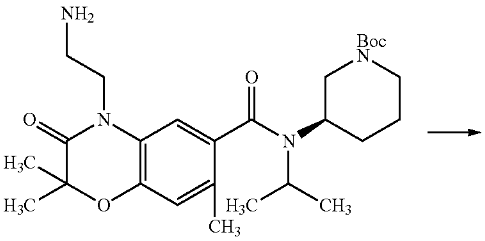

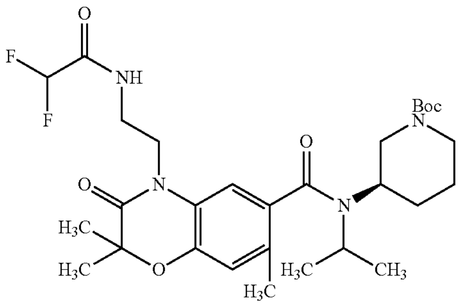

Using the compound of Reference Example 139, the title compound was obtained in a similar manner to Reference Example 120.

MS (ESI+) 581 ($M^{+}$+1, 31%).

Reference Example 122 tert-Butyl (3R)-3-[[(4-{2-[(difluoroacetyl)amino]ethyl}-2,2-dimethyl-3-oxo-3,4-dihydro-2H-1,4-benzoxazin-6-yl)carbonyl](isopropyl)amino]piperidine-1-carboxylate

[Chemical formula 266]

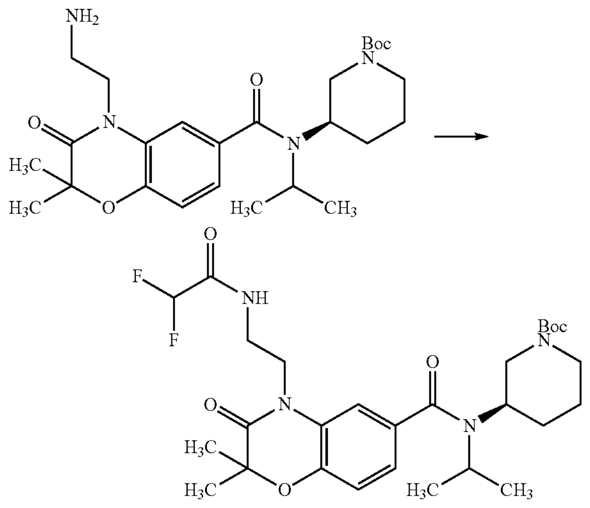

Using the compound of Reference Example 141, the title compound was obtained in a similar manner to Reference Example 120.

MS (ESI+) 567 ($M^+$+1, 30%).

Reference Example 123 tert-Butyl (3R)-3-[[(2,2-dimethyl-3-oxo-4-{2-[(3,3,3-trifluoropropanyl)amino]ethyl}-3,4-dihydro-2H-1,4-benzoxazin-6-yl)carbonyl](isopropyl)amino]piperidine-1-carboxylate

[Chemical formula 267]

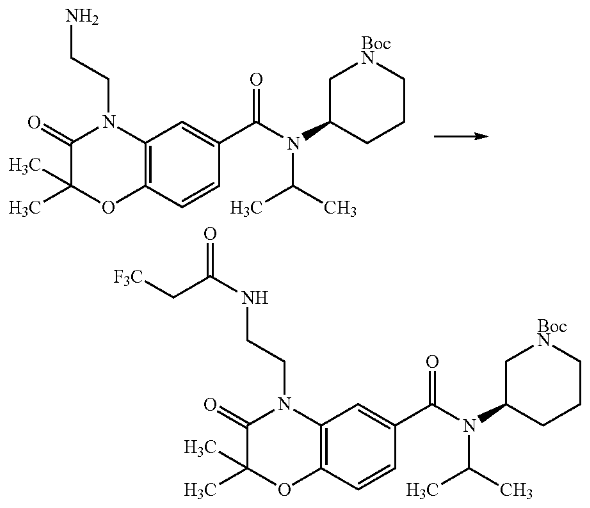

Using the compound of Reference Example 141, the title compound was obtained in a similar manner to Reference Example 120

MS (ESI+) 599 ($M^+$+1, 31%).

Reference Example 124 tert-Butyl (3R)-3-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 268]

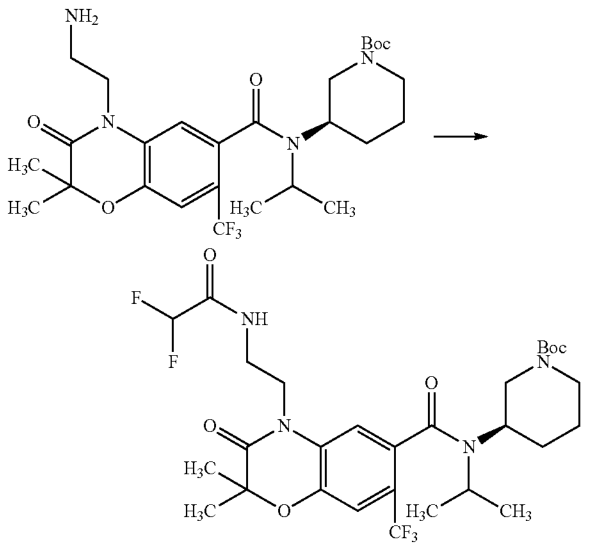

Using the compound of Reference Example 142, the title compound was obtained in a similar manner to Reference Example 120.

MS (ESI+) 599 ($M^+$+1, 31%).

Reference Example 125 tert-Butyl (3R)-3-[[(4-{2-[(cyclopropylacetyl)amino]ethyl}-2,2,7-trimethyl-3-oxo-3,4-dihydro-2H-1,4-benzoxazin-6-yl)carbonyl](isopropyl)amino]piperidine-1-carboxylate

[Chemical formula 269]

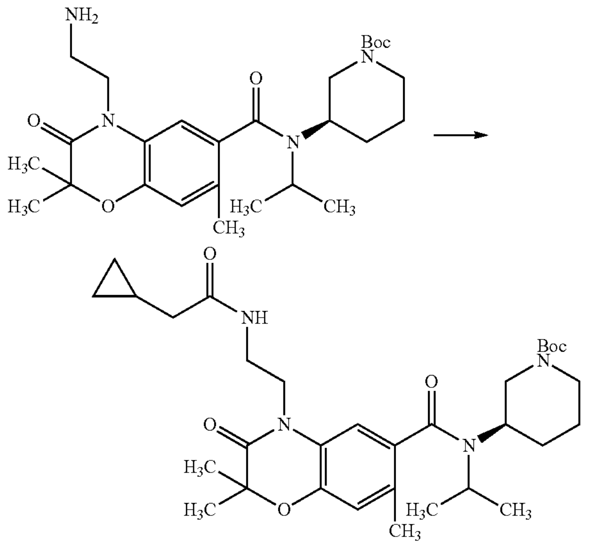

Using the compound of Reference Example 139, the title compound was obtained in a similar manner to Reference Example 120.

MS (ESI+) 599 ($M^+$+1, 31%).

Reference Example 126 tert-Butyl (3R)-3-[({4-[2-(butyrylamino)ethyl]-2,2,7-trimethyl-3-oxo-3,4-dihydro-2H-1,4-benzoxazin-6-yl}carbonyl)(isopropyl)amino]piperidine-1-carboxylate

[Chemical formula 270]

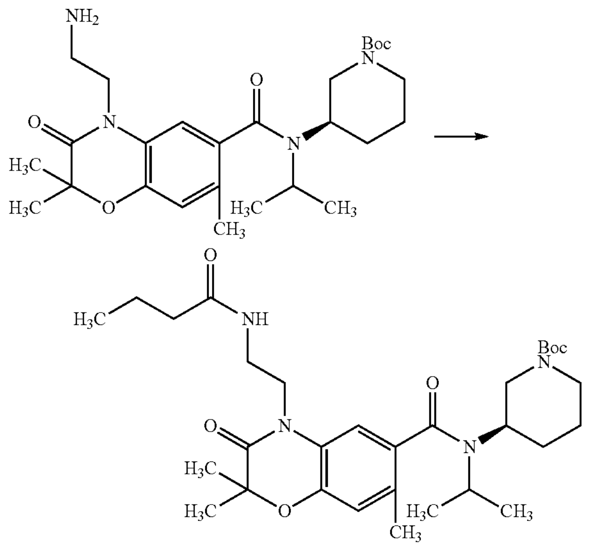

Using the compound of Reference Example 139, the title compound was obtained in a similar manner to Reference Example 120.

MS (ESI+) 573 ($M^{+}$+1, 34%).

Reference Example 127 tert-Butyl (3R)-3-[[(4-{2-[(2,2-difluoropropanoyl)amino]ethyl}-2,2,7-trimethyl-3-oxo-3,4-dihydro-2H-1,4-benzoxazin-6-yl)carbonyl](isopropyl)amino]piperidine-1-carboxylate

[Chemical formula 271]

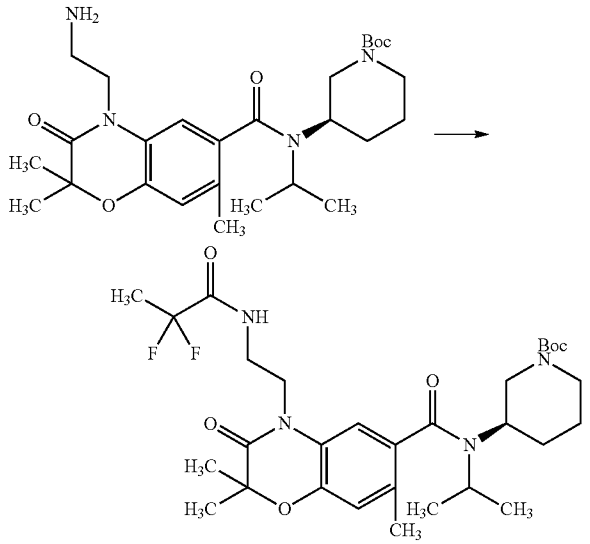

Using the compound of Reference Example 139, the title compound was obtained in a similar manner to Reference Example 120.

MS (ESI+) 595 ($M^{+}$+1, 32%).

Reference Example 128

Methyl 4-{2-[(2,2-difluoroethyl)amino]-2-oxoethyl}-2,2,7-trimethyl-3-oxo-3,4-dihydro-2H-1,4-benzoxazine-6-carboxylate

[Chemical formula 272]

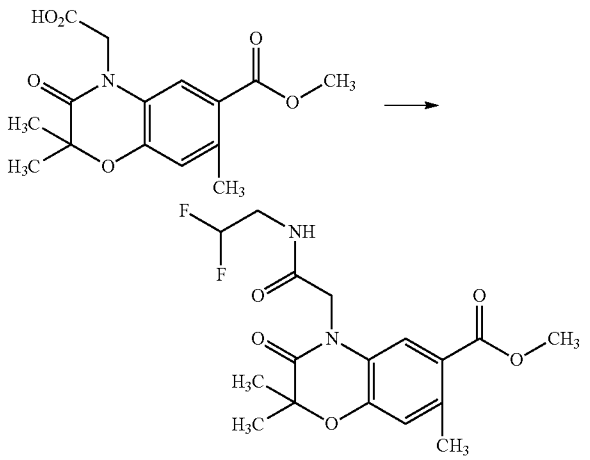

Using the compound of Reference Example 110, the title compound was obtained in a similar manner to Reference Example 112.

MS (ESI+) 371 ($M^{+}$+1, 18%).

Reference Example 129 tert-Butyl (3R)-3-[{[2,2-dimethyl-3-oxo-4-{2-[(trifluoroacetyl)amino]ethyl}-7-(trifluoromethyl)-3,4-dihydro-2H-1,4-benzoxazin-6-yl]carbonyl}(isopropyl)amino]piperidine-1-carboxylate

[Chemical formula 273]

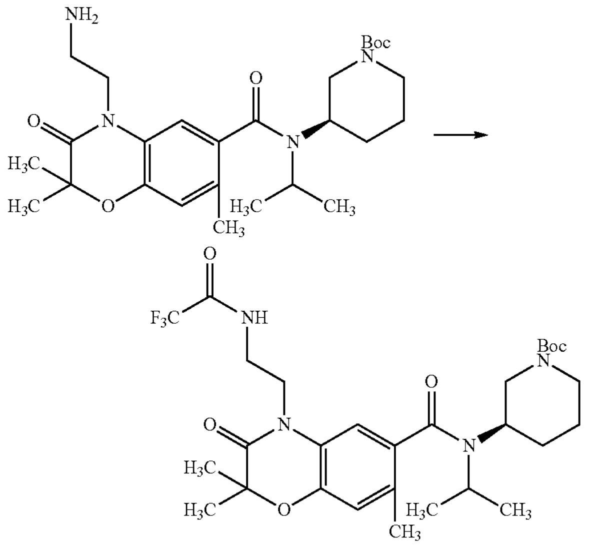

Using the compound of Reference Example 142, the title compound was obtained in a similar manner to Reference Example 120.

MS (ESI+) 653 ($M^{+}$+1, 31%).

Reference Example 130 tert-Butyl (3R)-3-[[(4-{3-[(difluoroacetyl)amino]propyl}-2,2,7-trimethyl-3-oxo-3,4-dihydro-2H-1,4-benzoxazin-6-yl)carbonyl](isopropyl)amino]piperidine-1-carboxylate

[Chemical formula 274]

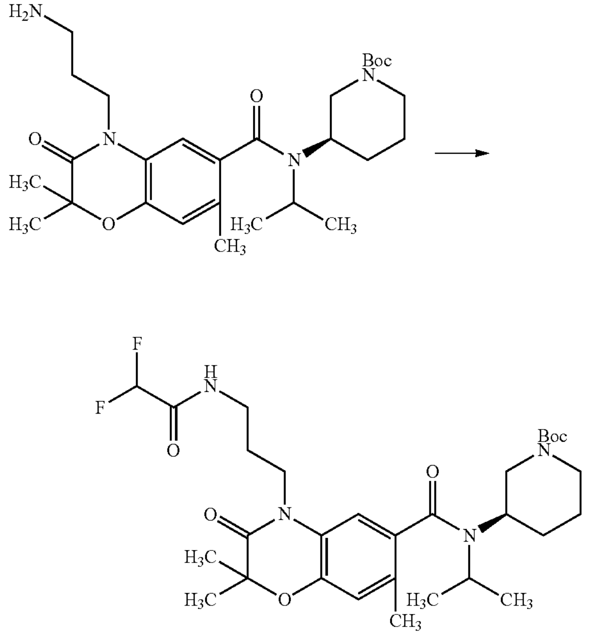

Using the compound of Reference Example 145, the title compound was obtained in a similar manner to Reference Example 120.

MS (ESI+) 595 ($M^{+}$+1, 32%).

Reference Example 131 tert-Butyl (3R)-3-[({4-[3-(acetylamino)propyl]-2,2,7-trimethyl-3-oxo-3,4-dihydro-2H-1,4-benzoxazin-6-yl}carbonyl)(isopropyl)amino]piperidine-1-carboxylate

[Chemical formula 275]

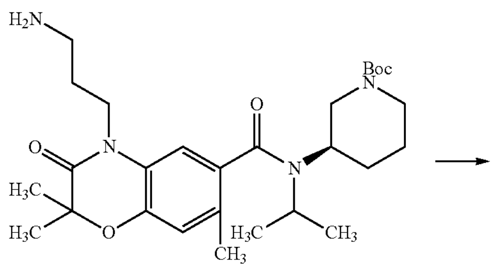

-continued

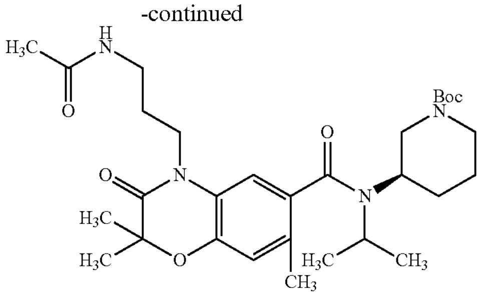

Using the compound of Reference Example 145, the title compound was obtained in a similar manner to Reference Example 120.

MS (ESI+) 559 ($M^{+}$+1, 32%).

Reference Example 132 tert-Butyl (3R)-3-[({4-[2-(acetylamino)ethyl]-2,2,7-trimethyl-3-oxo-3,4-dihydro-2H-1,4-benzoxazin-6-yl}carbonyl)(isopropyl)amino]piperidine-1-carboxylate

[Chemical formula 276]

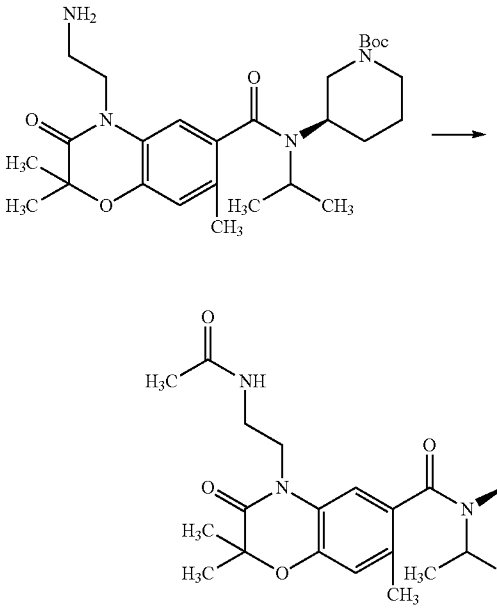

To tert-butyl (3R)-3-[{[4-(2-aminoethyl)-2,2,7-trimethyl-3-oxo-3,4-dihydro-2H-1,4-benzoxazin-6-yl]carbonyl}(isopropyl)amino]piperidine-1-carboxylate (200 mg) were added triethyl-amine (0.040 ml), tetrahydrofuran (3 ml), acetyl chloride (0.04 ml) under ice-cooling, and the mixture was stirred at room temperature for one hour. After the reaction was complete, the mixture was concentrated, and the obtained residue was purified by silica gel column chromatography (chloroform/methanol=9/1) to give the title compound (80 mg) as colorless amorphous.

MS (ESI+) 545 ($M^{+}$+1, 31%).

Reference Example 133 tert-Butyl (3R)-3-[{[2,2-dimethyl-3-oxo-4-[(2S)-2-(propionylamino)propyl]-7-(trifluoromethyl)-3,4-dihydro-2H-1,4-benzoxazin-6-yl]carbonyl}(isopropyl)amino]piperidine-1-carboxylate

[Chemical formula 277]

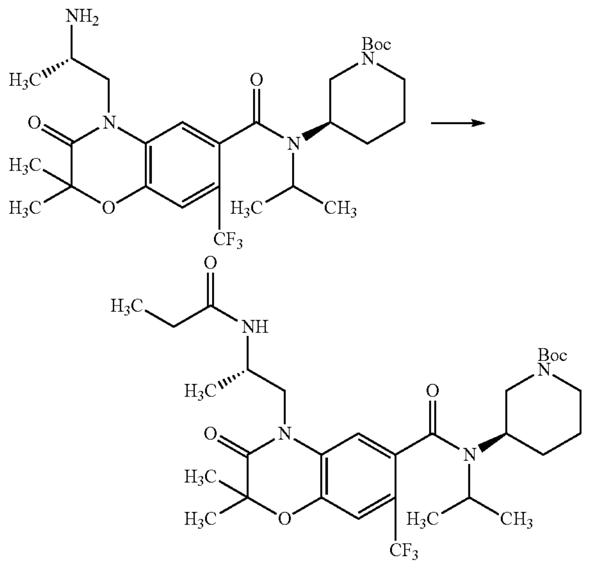

Using the compound of Reference Example 146, the title compound was obtained in a similar manner to Reference Example 132.

MS (ESI+) 627 ($M^{+}$+1, 34%).

Reference Example 134 tert-Butyl (3R)-3-{isopropyl[(2,2,7-trimethyl-4-{2-[(methylsulfonyl)amino]ethyl}-3-oxo-3,4-dihydro-2H-1,4-benzoxazin-6-yl)carbonyl]amino}piperidine-1-carboxylate

[Chemical formula 278]

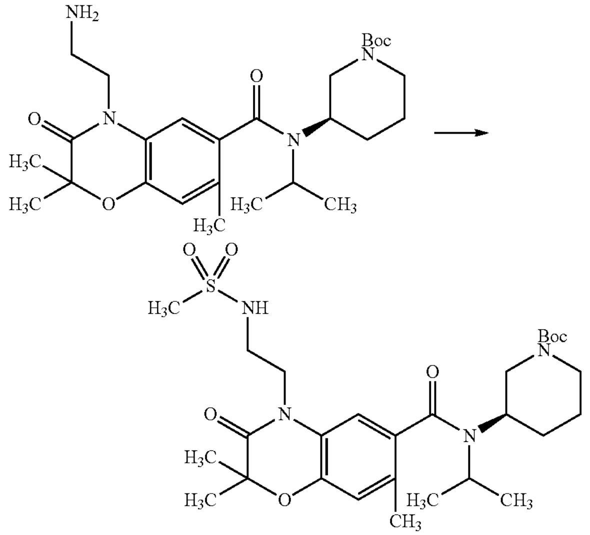

Using the compound of Reference Example 139, the title compound was obtained in a similar manner to Reference Example 132.

MS (ESI+) 581 ($M^{+}$+1, 30%).

Reference Example 135 tert-Butyl (3R)-3-[isopropyl({2,2,7-trimethyl-3-oxo-4-[2-(propionylamino)ethyl]-3,4-dihydro-2H-1,4-benzoxazin-6-yl}carbonyl)amino]piperidine-1-carboxylate

[Chemical formula 279]

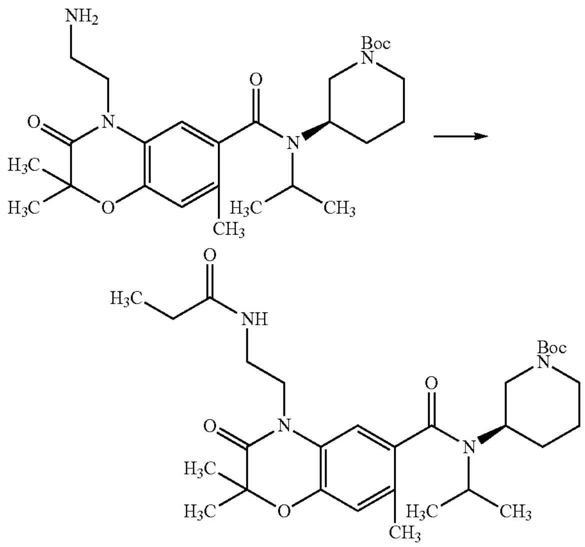

Using the compound of Reference Example 139, the title compound was obtained in a similar manner to Reference Example 132.

MS (ESI+) 559 ($M^{+}$+1, 32%).

Reference Example 136 tert-Butyl (3R)-3-[({2,2-dimethyl-3-oxo-4-[2-(propionylamino)ethyl]-3,4-dihydro-2H-1,4-benzoxazin-6-yl}carbonyl)(isopropyl)amino]piperidine-1-carboxylate

[Chemical formula 280]

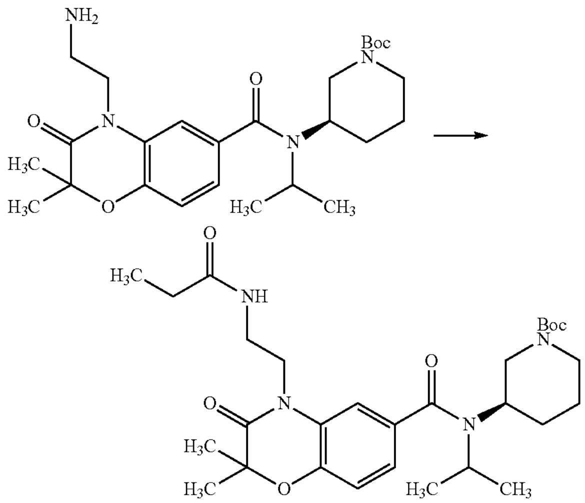

Using the compound of Reference Example 141, the title compound was obtained in a similar manner to Reference Example 132.

MS (ESI+) 545 ($M^{+}$+1, 31%).

Reference Example 137 tert-Butyl (3R)-3-[{[2,2-dimethyl-3-oxo-4-[2-(propionylamino)ethyl]-7-(trifluoromethyl)-3,4-dihydro-2H-1,4-benzoxazin-6-yl]carbonyl}(isopropyl)amino] piperidine-1-carboxylate

[Chemical formula 281]

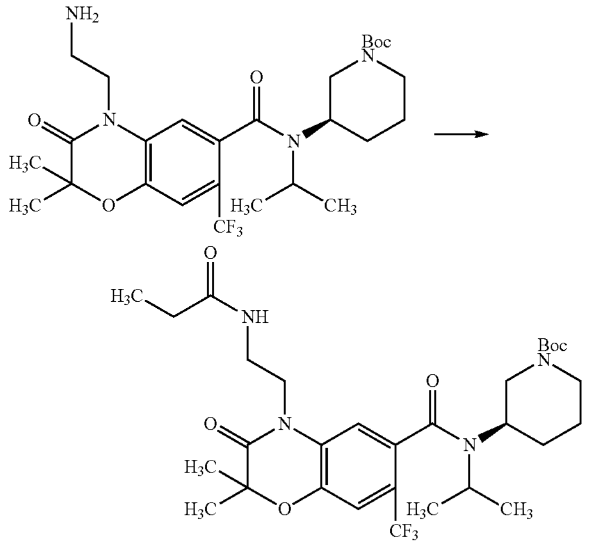

Using the compound of Reference Example 142, the title compound was obtained in a similar manner to Reference Example 132.

MS (ESI+) 613 ($M^+$+1, 32%).

Reference Example 138 tert-Butyl (3R)-3-[{[4-{2-[(fluoroacetyl)amino] ethyl}-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 282]

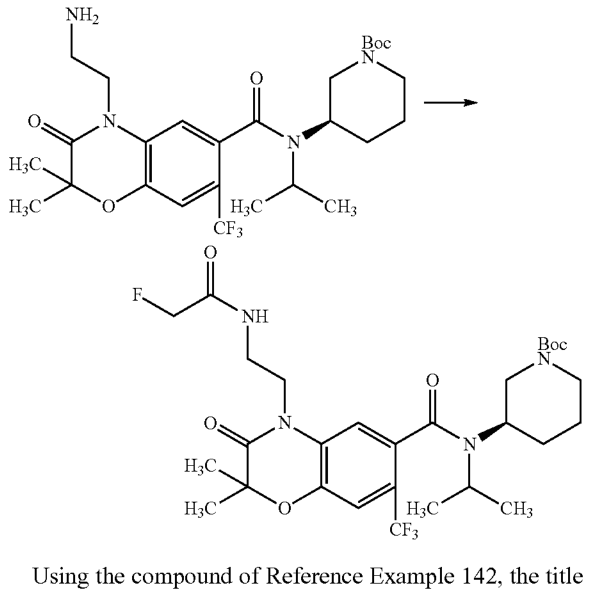

Using the compound of Reference Example 142, the title compound was obtained in a similar manner to Reference Example 132.

MS (ESI+) 617 ($M^+$+1, 31%).

Reference Example 139 tert-Butyl (3R)-3-[{[4-(2-aminoethyl)-2,2,7-trimethyl-3-oxo-3,4-dihydro-2H-1,4-benzoxazin-6-yl]-carbonyl}(isopropyl)amino]piperidine-1-carboxylate

[Chemical formula 283]

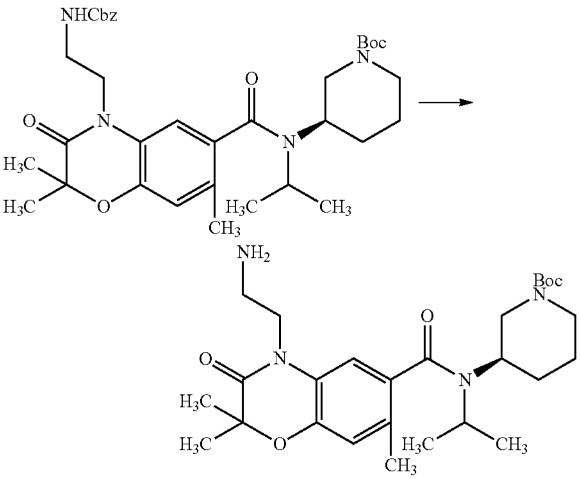

To tert-butyl (3R)-3-[{[4-(2-{[(benzyloxy)carbonyl] amino}ethyl)-2,2,7-trimethyl-3-oxo-3,4-dihydro-2H-1,4-benzoxazin-6-yl]carbonyl}(isopropyl)amino]piperidine-1-carboxylate (1.14 g) were added a 10% palladium carbon (500 mg) and methanol (30 ml), and the mixture was stirred at room temperature under hydrogen atmosphere for 2 hours. After the reaction was complete, the mixture was filtered and concentrated. The obtained residue (900 mg) was used in the subsequent reaction without further treatment.

MS (ESI+) 503 ($M^+$+1, 29%).

Reference Example 140 tert-Butyl (3R)-3-[[(4-hexyl-2,2,7-trimethyl-3-oxo-3,4-dihydro-2H-1,4-benzoxazin-6-yl)carbonyl](isopropyl)amino]piperidine-1-carboxylate

[Chemical formula 284]

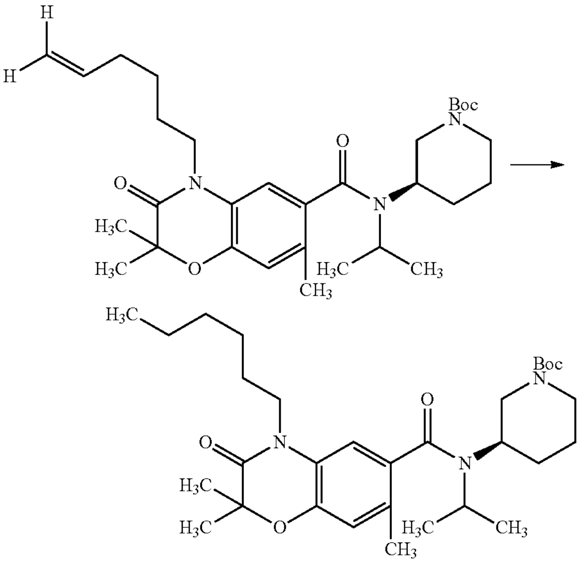

Using the compound of Reference Example 91, the title compound was obtained in a similar manner to Reference Example 139.

MS (ESI+) 544 ($M^+$+1, 34%).

Reference Example 141 tert-Butyl (3R)-3-[{[4-(2-aminoethyl)-2,2-dimethyl-3-oxo-3,4-dihydro-2H-1,4-benzoxazin-6-yl]-carbonyl}(isopropyl)amino]piperidine-1-carboxylate

[Chemical formula 285]

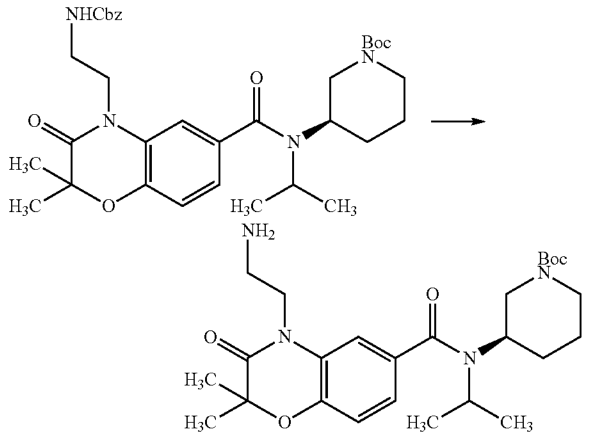

Using the compound of Reference Example 93, the title compound was obtained in a similar manner to Reference Example 139.

MS (ESI+) 489 ($M^{+}$+1, 28%).

Reference Example 142 tert-Butyl (3R)-3-[{[4-(2-aminoethyl)-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 286]

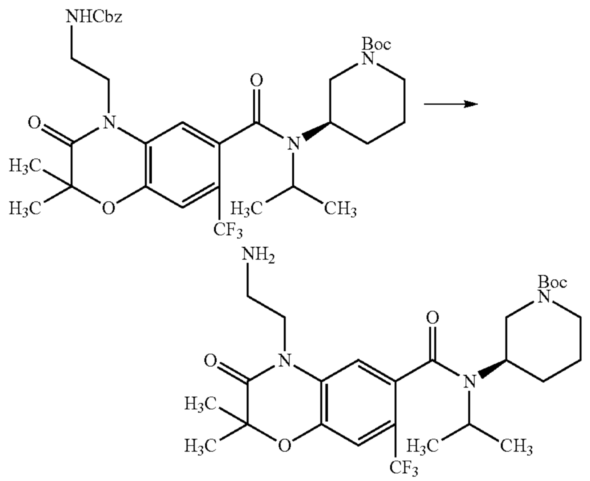

Using the compound of Reference Example 111, the title compound was obtained in a similar manner to Reference Example 139.

MS (ESI+) 557 ($M^{+}$+1, 29%).

Reference Example 143 tert-Butyl (3R)-3-[{[4-(4-hydroxybutyl)-2,2,7-trimethyl-3-oxo-3,4-dihydro-2H-1,4-benzoxazin-6-yl]-carbonyl}(isopropyl)amino]piperidine-1-carboxylate

[Chemical formula 287]

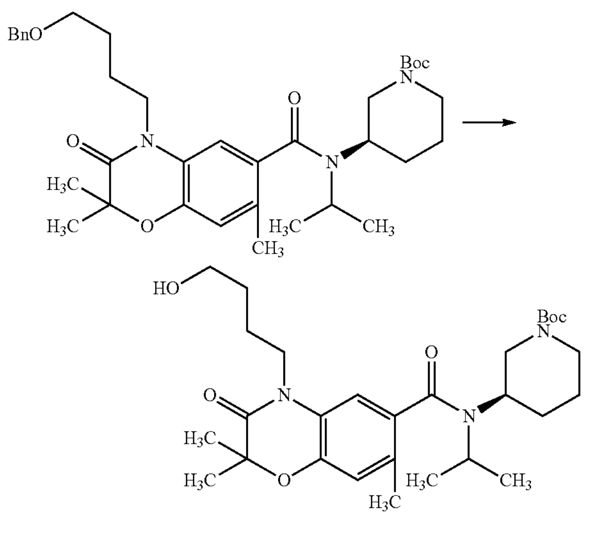

Using the compound of Reference Example 98, the title compound was obtained in a similar manner to Reference Example 139.

MS (ESI+) 532 ($M^{+}$+1, 31%).

Reference Example 144 tert-Butyl (3R)-3-[{[4-(2-hydroxyethyl)-2,2,7-trimethyl-3-oxo-3,4-dihydro-2H-1,4-benzoxazin-6-yl]-carbonyl}(isopropyl)amino]piperidine-1-carboxylate

[Chemical formula 288]

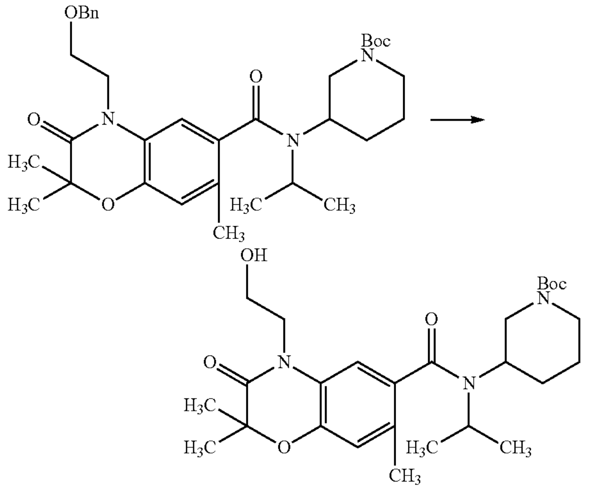

Using the compound of Reference Example 98, the title compound was obtained in a similar manner to Reference Example 139.

MS (ESI+) 504 ($M^{+}$+1, 29%).

Reference Example 145 tert-Butyl (3R)-3-[{[4-(3-amino)-2,2,7-trimethyl-3-oxo-3,4-dihydro-2H-1,4-benzoxazin-6-yl]-carbonyl}(isopropyl)amino]piperidine-1-carboxylate

[Chemical formula 289]

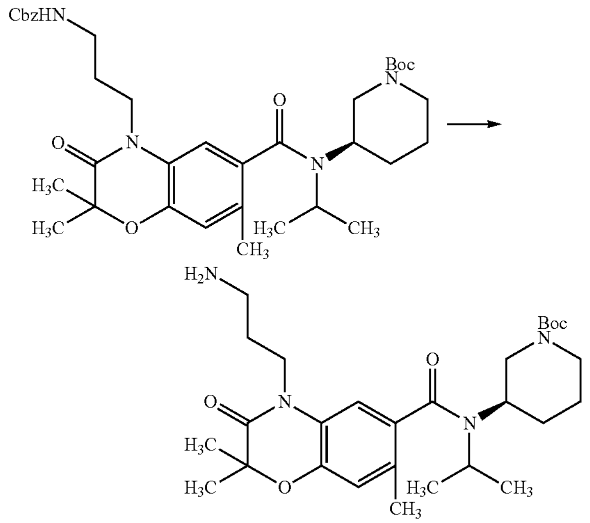

Using the compound of Reference Example 95, the title compound was obtained in a similar manner to Reference Example 139.

MS (ESI+) 517 ($M^+$+1, 30%).

Reference Example 146 tert-Butyl (3R)-3-[{[4-[(2S)-2-aminopropyl]-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 290]

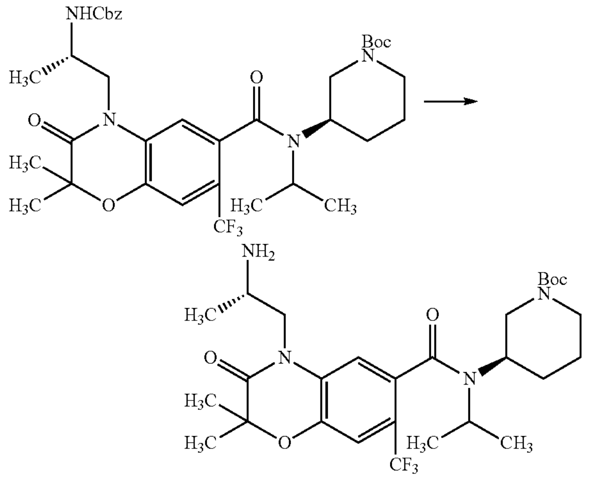

Using the compound of Reference Example 85, the title compound was obtained in a similar manner to Reference Example 139.

MS (ESI+) 571 ($M^+$+1, 30%).

Reference Example 147 tert-Butyl (3R)-3-[({7-chloro-2,2-dimethyl-3-oxo-4-[2-(propionylamino)ethyl]-3,4-dihydro-2H-1,4-benzoxazin-6-yl}carbonyl)(isopropyl)amino]piperidine-1-carboxylate

[Chemical formula 291]

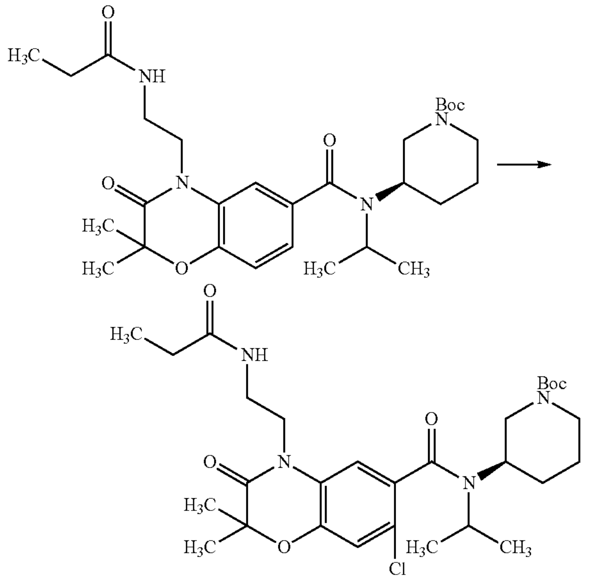

Using the compound of Reference Example 136, the title compound was obtained in a similar manner to Reference Example 12.

MS (ESI+) 580 ($M^+$+1, 32%).

Reference Example 148 tert-Butyl (3R)-3-[[(7-chloro-4-{2-[(difluoroacetyl)amino]ethyl}-2,2-dimethyl-3-oxo-3,4-dihydro-2H-1,4-benzoxazin-6-yl)carbonyl](isopropyl)amino]piperidine-1-carboxylate

[Chemical formula 292]

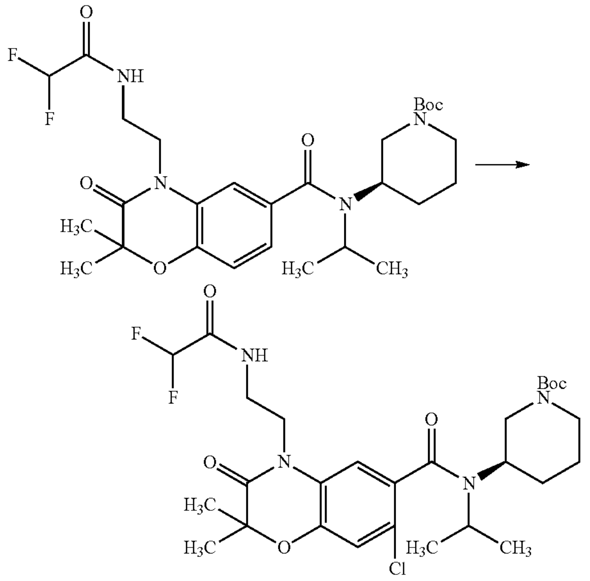

Using the compound of Reference Example 122, the title compound was obtained in a similar manner to Reference Example 12.

MS (ESI+) 602 ($M^{+}$+1, 32%).

Reference Example 149 tert-Butyl (3R)-3-[[(7-chloro-2,2-dimethyl-3-oxo-4-{2-[(3,3,3-trifluoropropanoyl)amino]ethyl}-3,4-dihydro-2H-1,4-benzoxazin-6-yl)carbonyl](isopropyl)amino]piperidine-1-carboxylate

[Chemical formula 293]

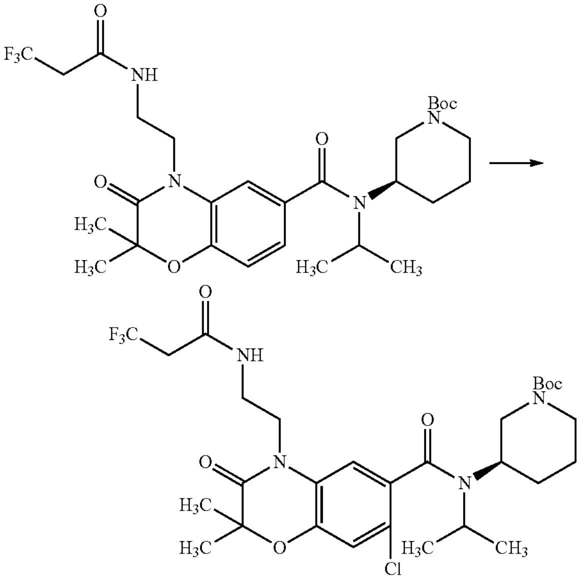

Using the compound of Reference Example 123, the title compound was obtained in a similar manner to Reference Example 12.

MS (ESI+) 634 ($M^{+}$+1, 32%).

Reference Example 150 tert-Butyl (3R)-3-[{[4-(4-cyclopropylbutyl)-2,2,7-trimethyl-3-oxo-3,4-dihydro-2H-1,4-benzoxazin-6-yl]carbonyl}(isopropyl)amino]piperidine-1-carboxylate

[Chemical formula 294]

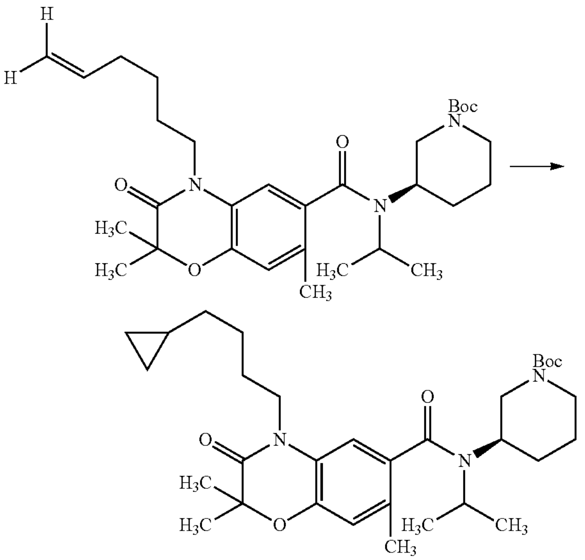

N-Nitroso-N-methylurea (2.62 g) was dissolved in diethyl ether (34 ml), and the mixture was added dropwise into a solution of potassium hydroxide (1.53 g) in water (9 ml) under ice-cooling, and the mixture was stirred at 0° C. for 15 minutes. Then, the obtained supernatant was added dropwise to a solution of tert-butyl (3R)-3-[[(4-hex-5-en-1-yl-2,2,7-trimethyl-3-oxo-3,4-dihydro-2H-1,4-benzoxazin-6-yl)carbonyl](isopropyl)amino]piperidine-1-carboxylate (300 mg) with palladium acetate (15 mg) in a mixed solvent of chloroform/diethyl ether. The mixture was stirred at room temperature for one hour. After the reaction was complete, the mixture was filtered and concentrated. The obtained residue was purified by silica gel column chromatography (hexane/ethyl acetate=4/1) to give the title compound (250 mg) as a colorless liquid.

MS (ESI+) 556 ($M^{+}$+1, 35%).

Reference Example 151 tert-Butyl (3R)-3-(isopropyl{[4-{2-[(methoxycarbonyl)(methyl)amino]ethyl}-2,2-dimethyl-3-oxo-7-(trifluoromethyl)-3,4-dihydro-2H-1,4-benzoxazin-6-yl]carbonyl}amino)piperidine-1-carboxylate

[Chemical formula 295]

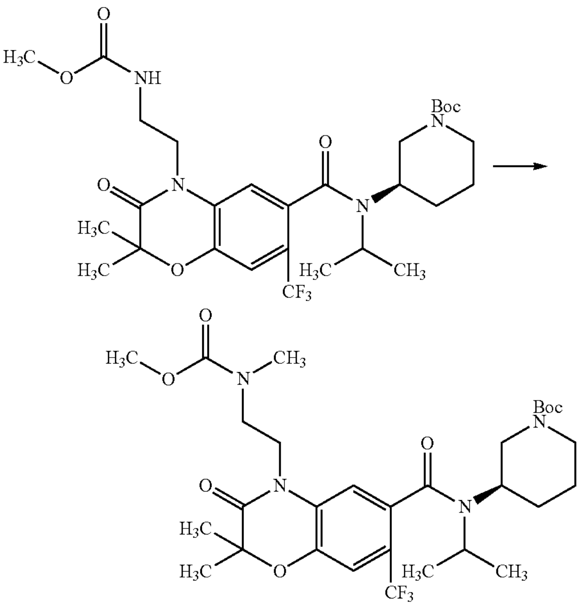

To tert-butyl (3R)-3-(isopropyl{[4-{2-[(methoxycarbonyl)amino]ethyl}-2,2-dimethyl-3-oxo-7-(trifluoromethyl)-3,4-dihydro-2H-1,4-benzoxazin-6-yl]carbonyl}amino)piperidine-1-carboxylate (110 mg) were added sodium hydride (9.3 mg) and N,N-dimethylformamide (9 ml) under ice-cooling, and the mixture was stirred at room temperature for 30 minutes. Then, to the mixture was added methyl iodide (0.02 ml), and the mixture was stirred at room temperature for 2 hours. After the reaction was complete, water was added to the reaction solution, and the mixture was extracted with ethyl acetate solution. The obtained ethyl acetate solution was washed with water and an aqueous sodium chloride solution, dried over magnesium sulfate, filtered and concentrated. The obtained residue was purified by silica gel column chromatography (hexane/ethyl acetate=1/2) to give the title compound (110 mg) as a colorless liquid.

MS (ESI+) 629 ($M^{+}$+1, 32%).

Reference Example 152 tert-Butyl (3R)-3-{isopropyl[(2,2,7-trimethyl-4-{2-[methyl(propionyl)amino]ethyl}-3-oxo-3,4-dihydro-2H-1,4-benzoxazin-6-yl)carbonyl]amino}piperidine-1-carboxylate

[Chemical formula 296]

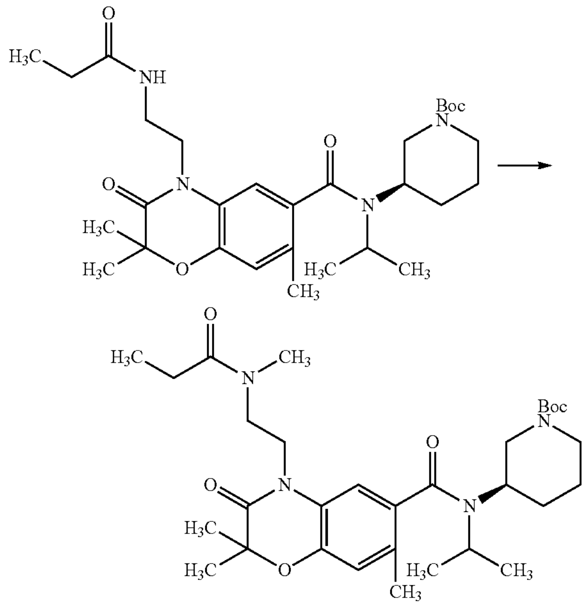

Using the compound of Reference Example 135, the title compound was obtained in a similar manner to Reference Example 151.

MS (ESI+) 573 ($M^{+}$+1, 34%).

Reference Example 153 tert-Butyl (3R)-3-[isopropyl({2,2,7-trimethyl-3-oxo-4-[2-(propionyloxy)ethyl]-3,4-dihydro-2H-1,4-benzoxazin-6-yl}carbonyl)amino]piperidine-1-carboxylate

[Chemical formula 297]

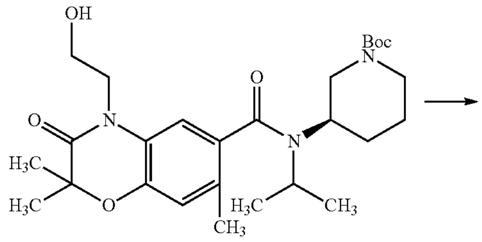

-continued

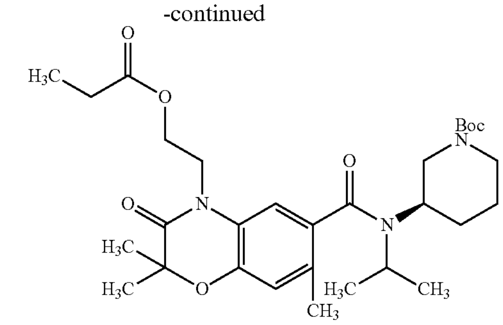

To tert-butyl (3R)-3-[{[4-(2-hydroxyethyl)-2,2,7-trimethyl-3-oxo-3,4-dihydro-2H-1,4-benzoxazin-6-yl]carbonyl}(isopropyl)amino]piperidine-1-carboxylate (150 mg) were added sodium hydride (16 mg) and N,N-dimethylformamide (9 ml) under ice-cooling, and the mixture was stirred at room temperature for 30 minutes. Then, to the mixture was added propionic chloride (0.03 ml), and the mixture was further stirred at room temperature for 2 hours. After the reaction was complete, water was added to the reaction solution, and the mixture was extracted with ethyl acetate solution. The obtained ethyl acetate solution was washed with water and an aqueous sodium chloride solution, dried over magnesium sulfate, filtered and concentrated. The obtained residue was purified by silica gel column chromatography (hexane/ethyl acetate=1/2) to give the title compound (110 mg) as a colorless liquid.

MS (ESI+) 560 ($M^{+}$+1, 32%).

Reference Example 154 tert-Butyl (3R)-3-[({4-[4-(cyclopropyloxy)butyl]-2,2,7-trimethyl-3-oxo-3,4-dihydro-2H-1,4-benzoxazin-6-yl}carbonyl)(isopropyl)amino]piperidine-1-carboxylate

[Chemical formula 298]

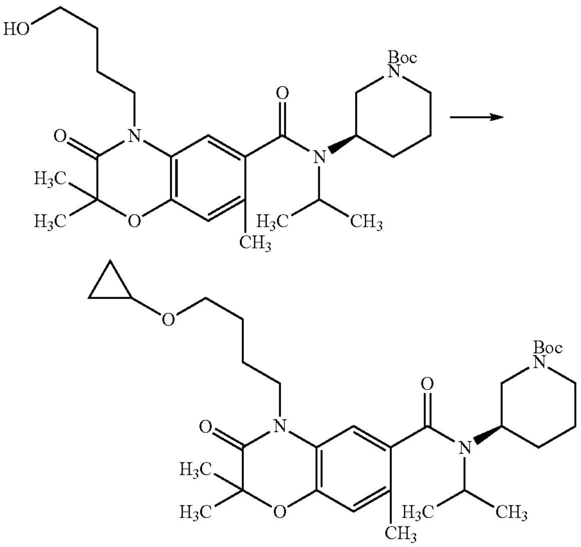

To tert-butyl (3R)-3-[{[4-(4-hydroxybutyl)-2,2,7-trimethyl-3-oxo-3,4-dihydro-2H-1,4-benzoxazin-6-yl]carbonyl}

(isopropyl)amino]piperidine-1-carboxylate (200 mg) were added sodium hydride (60 mg) and N,N-dimethylformamide (3 ml) under ice-cooling, and the mixture was stirred at room temperature for 30 minutes. Then, to the mixture was added bromocyclopropane (0.30 ml), and the mixture was stirred at 150° C. for 6 hours. After the reaction was complete, water was added to the reaction solution, and the mixture was extracted with ethyl acetate solution. The obtained ethyl acetate solution was washed with water and an aqueous sodium chloride solution, dried over magnesium sulfate, filtered and concentrated. The obtained residue was purified by silica gel column chromatography (hexane/ethyl acetate=1/2) to give the title compound (30 mg) as a colorless liquid.

MS (ESI+) 572 ($M^{+}$+1, 32%).

Reference Example 155 tert-Butyl (3R)-3-(isopropyl{[2,2,7-trimethyl-3-oxo-4-(2-propoxyethyl)-3,4-dihydro-2H-1,4-benzoxazin-6-yl]carbonyl}amino)piperidine-1-carboxylate

[Chemical formula 299]

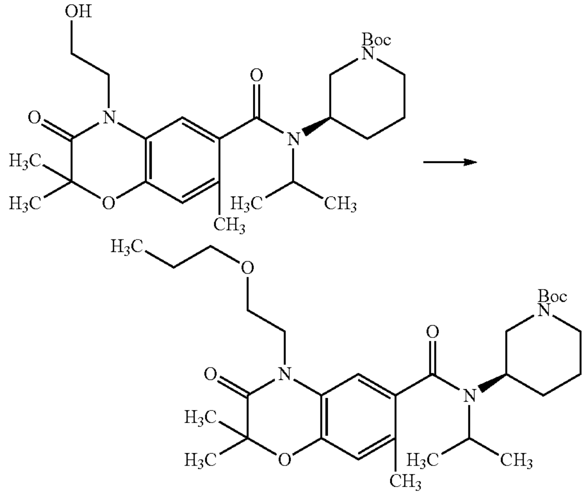

Using the compound of Reference Example 144, the title compound was obtained in a similar manner to Reference Example 154.

MS (ESI+) 546 ($M^{+}$+1, 31%).

Reference Example 156 tert-Butyl (3R)-3-[{[2,2-dimethyl-3-oxo-4-[2-(propanethioylamino)ethyl]-7-(trifluoromethyl)-3,4-dihydro-2H-1,4-benzoxazin-6-yl]carbonyl}(isopropyl)amino]piperidine-1-carboxylate

[Chemical formula 300]

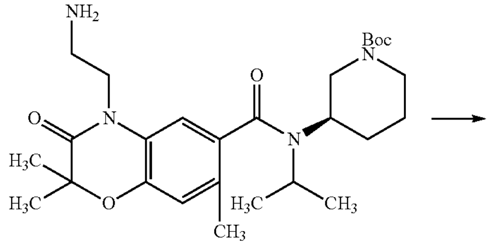

-continued

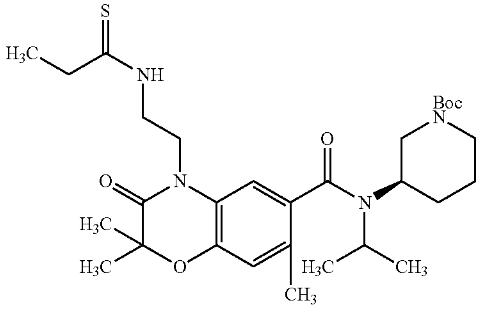

To tert-butyl (3R)-3-[{[4-(2-aminoethyl)-2,2-dimethyl-3-oxo-7-(trifluoromethyl)-3,4-dihydro-2H-1,4-benzoxazin-6-yl]carbonyl}(isopropyl)amino]piperidine-1-carboxylate (100 mg) were added methylpropane dithionate (23 mg), triethylamine (0.050 ml) and MeOH (3 ml), and the mixture was stirred at room temperature for 3 hours. After the reaction was complete, water was added to the reaction solution, and the mixture was extracted with ethyl acetate solution. The obtained ethyl acetate solution was washed with water and an aqueous sodium chloride solution, dried over magnesium sulfate, filtered and concentrated. The obtained residue was purified by silica gel column chromatography (hexane/ethyl acetate=1/2) to give the title compound (90 mg) as a colorless liquid.

MS (ESI+) 629 ($M^{+}$+1, 32%).

Reference Example 157 tert-Butyl (3R)-3-(isopropyl{[2,2,7-trimethyl-4-(2-{[(methylamino)carbonyl]amino}ethyl)-3-oxo-3,4-dihydro-2H-1,4-benzoxazin-6-yl]carbonyl}amino)piperidine-1-carboxylate

[Chemical formula 301]

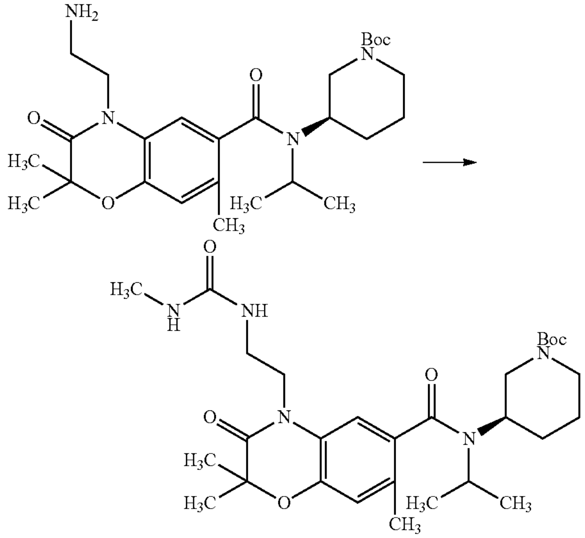

To tert-butyl (3R)-3-[{[4-(2-aminoethyl)-2,2,7-trimethyl-3-oxo-3,4-dihydro-2H-1,4-benzoxazin-6-yl]carbonyl}(isopropyl)amino]piperidine-1-carboxylate (200 mg) were added triphosgene (47 mg), triethylamine (0.12 ml) and chloroform (5 ml) under ice-cooling, and the mixture was stirred at room temperature for 2 hours. After the reaction was complete, the reaction solution was concentrated, and thereto were added methylamine (0.17 ml) and chloroform (5 ml) under ice-cooling, and the mixture was stirred at room temperature for 2 hours. After the reaction was complete, water was added to the reaction solution, and the mixture was extracted with ethyl acetate solution. The obtained ethyl acetate solution was washed with water and an aqueous sodium chloride solution, dried over magnesium sulfate, filtered and concentrated. The obtained residue was purified by silica gel column chromatography (chloroform /methanol=9/1) to give the title compound (70 mg) as colorless amorphous.

MS (ESI+) 560 ($M^+$+1, 31%).

Reference Example 158

Methyl 7-iodo-2,2-dimethyl-3-oxo-3,4-dihydro-2H-1,4-benzoxazine-6-carboxylate

[Chemical formula 302]

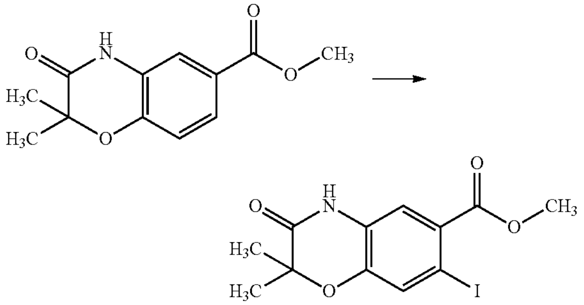

The compound of Reference Example 2 (1.2 g) was dissolved in chloroform (25 ml), and thereto were added silver trifluoromethanesulfonate (1.38 g) and iodine (1.36 g) under ice-cooling, and the mixture was stirred at room temperature for 14 hours. The reaction mixture was filtered on celite, and the organic layer was washed twice with an aqueous sodium thiosulfate solution, dried over magnesium sulfate, filtered and concentrated under reduced pressure to give the title compound (1.2 g) as a pale yellow solid.

MS (ESI+) 362 ($M^+$+1, 100%).

Reference Example 159

Methyl (2R)-7-iodo-2-methyl-3-oxo-3,4-dihydro-2H-1,4-benzoxazine-6-carboxylate

[Chemical formula 303]

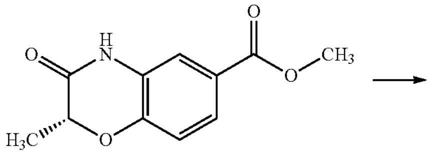

-continued

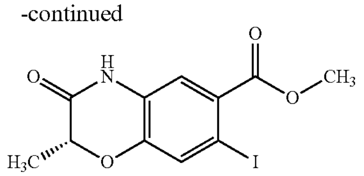

Using methyl (2R)-2-methyl-3-oxo-3,4-dihydro-2H-1,4-benzoxazine-6-carboxylate, the title compound (1.3 g) was obtained in a similar manner to Reference Example 158.

MS (ESI+) 348 ($M^+$+1, 100%).

Reference Example 160

Methyl 7-Iodo-4-(4-methoxybutyl)-2,2-dimethyl-3-oxo-3,4-dihydro-2H-1,4-benzoxazine-6-carboxylate

[Chemical formula 304]

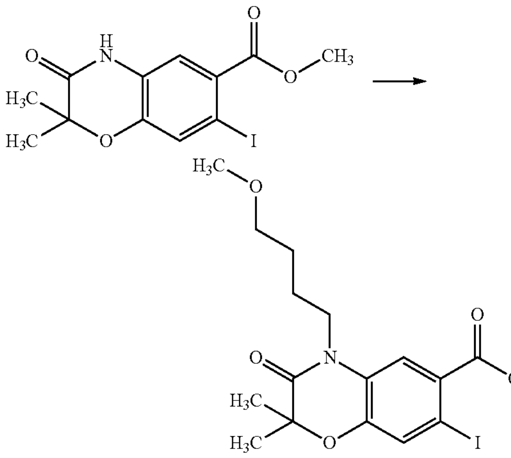

The compound of Reference Example 158 (1.2 g) was dissolved in N,N-dimethylformamide (20 ml), and thereto were added 1-chloro-4-methoxybutane (815 mg), potassium carbonate (919 mg), cesium carbonate (218 mg) and potassium iodide (111 mg), and the mixture was stirred at 90° C. for 8 hours. The reaction mixture was cooled, and water was added thereto, and the mixture was extracted with ethyl acetate. The organic layer was washed twice with water, dried over magnesium sulfate, filtered and concentrated under reduced pressure.

The obtained residue was purified by silica gel column chromatography (the developing solvent: hexane/ethyl acetate =5:1→4:1) to give the title compound (1.1 g) as a colorless clear oil.

MS (ESI+) 448 ($M^+$+1, 83%).

Reference Example 161

Methyl (2R)-7-Iodo-4-(4-methoxybutyl)-2-methyl-3-oxo-3,4-dihydro-2H-1,4-benzoxazine-6-carboxylate

[Chemical formula 305]

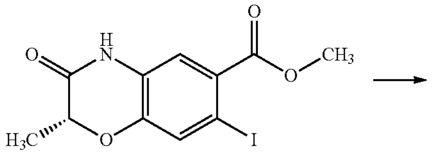

-continued

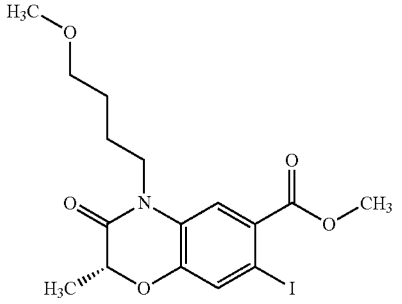

Using the compound of Reference Example 159, the title compound (1.2 g) was obtained in a similar manner to Reference Example 160.

MS (ESI+) 434 ($M^{+}$+1, 40%).

Reference Example 162

Methyl 7-Iodo-4-{2-[(methoxycarbonyl)amino]ethyl}-2,2-dimethyl-3-oxo-3,4-dihydro-2H-1,4-benzoxazine-6-carboxylate

[Chemical formula 306]

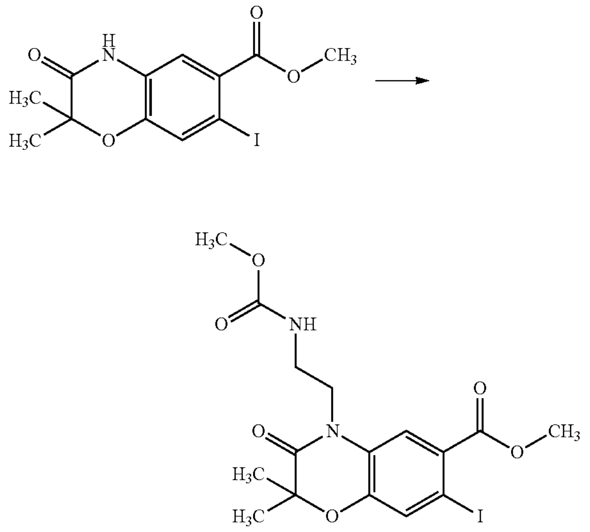

The compound of Reference Example 158 (1.1 g) was dissolved in N,N-dimethylformamide (20 ml), and thereto were added methyl (2-bromoethyl)carbamate (1.1 g) and potassium carbonate (1.05 g), and the mixture was stirred at 90° C. for 8 hours. The reaction mixture was cooled, and water was added thereto. The mixture was extracted with ethyl acetate, and the organic layer was washed twice with water, dried over magnesium sulfate, filtered and concentrated under reduced pressure. The obtained residue was purified by silica gel column chromatography (the developing solvent: hexane/acetone =4:1→3:1) to give the title compound (1.1 g) as a pale yellow oil.

MS (ESI+) 463 ($M^{+}$+1, 51%).

Reference Example 163

Methyl (2R)-7-Iodo-4-{2-[(methoxycarbonyl)amino]ethyl}-2-methyl-3-oxo-3,4-dihydro-2H-1,4-benzoxazine-6-carboxylate

[Chemical formula 307]

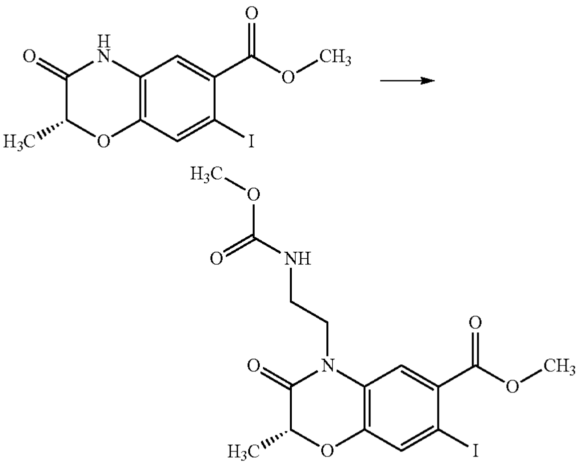

Using the compound of Reference Example 159, the title compound (1.2 g) was obtained in a similar manner to Reference Example 162.

MS (ESI+) 449 ($M^{+}$+1, 33%).

Reference Example 164

Methyl 4-{2-{[(benzyloxy)carbonyl]amino}ethyl}-7-iodo-2,2-dimethyl-3-oxo-3,4-dihydro-2H-1,4-benzoxazine-6-carboxylate

[Chemical formula 308]

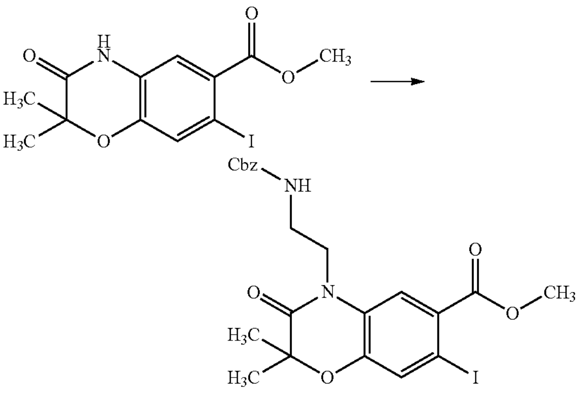

Using the compound of Reference Example 158, the title compound (1.4 g) was obtained in a similar manner to Reference Example 3.

MS (ESI+) 539 ($M^{+}$+1, 100%).

Reference Example 165

Methyl (2R)-4-{2-{[(Benzyloxy)carbonyl] amino}ethyl}-7-iodo-2-methyl-3-oxo-3,4-dihydro-2H-1,4-benzoxazine-6-carboxylate

[Chemical formula 309]

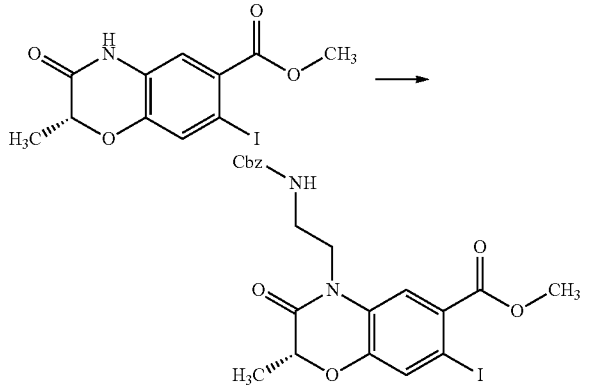

Using the compound of Reference Example 159, the title compound (1.7 g) was obtained in a similar manner to Reference Example 3.

MS (ESI+) 525 ($M^+$+1, 100%).

Reference Example 166

Methyl 4-(4-methoxybutyl)-2,2-dimethyl-3-oxo-7-[(trimethylsilyl)ethynyl-3,4-dihydro-2H-1,4-benzoxazine-6-carboxylate

[Chemical formula 310]

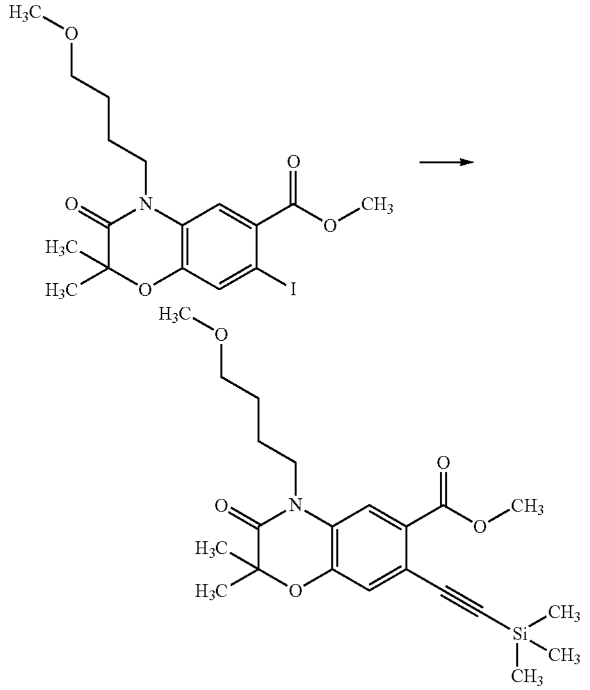

The compound of Reference Example 160 (1.1 g) was dissolved in triethylamine (20 ml), and thereto were added dichlorobis(triphenylphosphine)palladium (II) (86 mg), copper iodide (23 mg) and trimethylsilylacetylene (1.2 g) under ice-cooling. Then, the mixture was stirred at room temperature for 6 hours. The reaction solvent was evaporated under reduced pressure to some extent, and the resulting residue was diluted with ethyl acetate. The mixture was filtered on celite, and the organic layer was washed twice with a 10% aqueous citric acid solution, dried over magnesium sulfate, filtered and concentrated under reduced pressure. The obtained residue was purified by silica gel column chromatography (the developing solvent: hexane/acetone=5:1→4:1) to give the title compound (730 mg) as a colorless clear oil.

MS (ESI+) 418 ($M^+$+1, 100%).

Reference Example 167

Methyl (2R)-4-(4-methoxybutyl)-2-methyl-3-oxo-7-[(trimethylsilyl)ethynyl-3,4-dihydro-2H-1,4-benzoxazine-6-carboxylate

[Chemical formula 311]

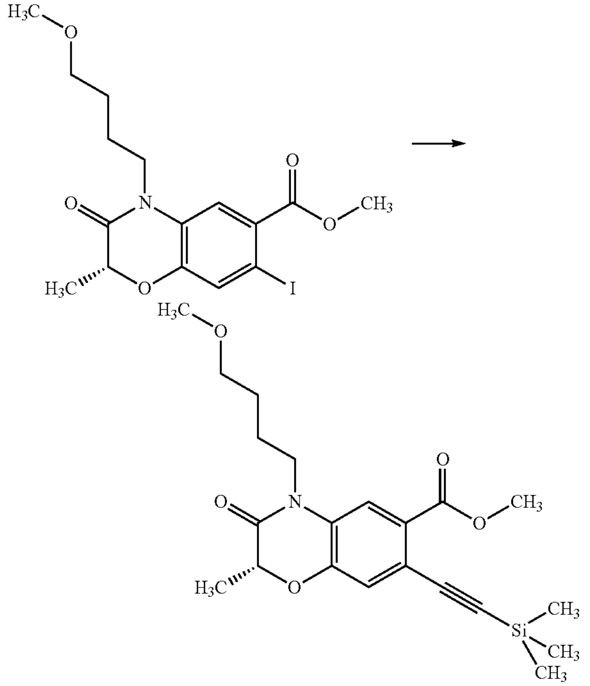

Using the compound of Reference Example 161, the title compound (850 mg) was obtained in a similar manner to Reference Example 166.

MS (ESI+) 404 ($M^+$+1, 100%).

Reference Example 168

Methyl 4-{2-[(methoxycarbonyl)amino]ethyl}-2,2-dimethyl-3-oxo-7-[(trimethylsilyl)ethynyl-3,4-dihydro-2H-1,4-benzoxazine-6-carboxylate

[Chemical formula 312]

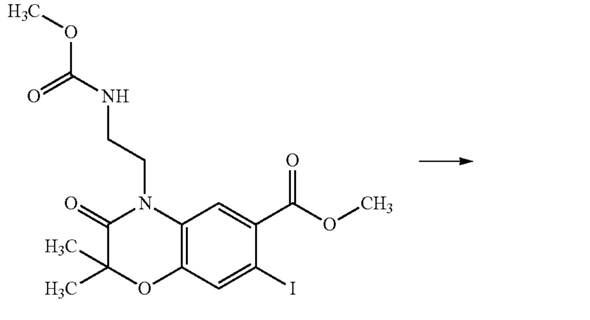

-continued

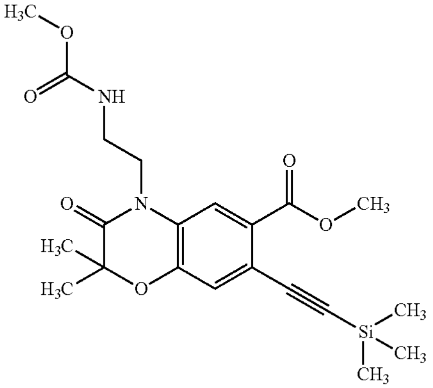

Using the compound of Reference Example 162, the title compound (800 mg) was obtained in a similar manner to Reference Example 166.

MS (ESI+) 433 ($M^{+}$+1, 100%).

Reference Example 169

Methyl (2R)-4-{2-[(methoxycarbonyl)amino]ethyl}-2-methyl-3-oxo-7-[(trimethylsilyl)ethynyl-3,4-dihydro-2H-1,4-benzoxazine-6-carboxylate

[Chemical formula 313]

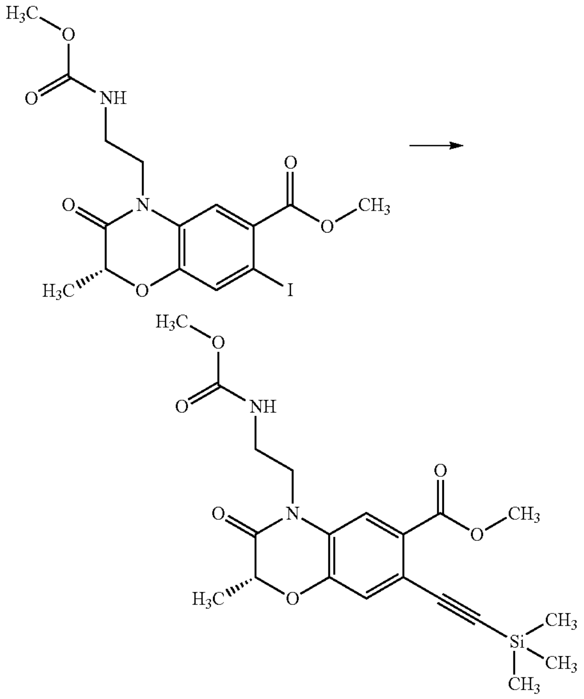

Using the compound of Reference Example 163, the title compound (850 mg) was obtained in a similar manner to Reference Example 166.

MS (ESI+) 419 ($M^{+}$+1, 65%).

Reference Example 170

Methyl 4-(2-{[(benzyloxy)carbonyl]amino}ethyl)-2,2-dimethyl-3-oxo-7-[(trimethylsilyl)ethynyl-3,4-dihydro-2H-1,4-benzoxazine-6-carboxylate

[Chemical formula 314]

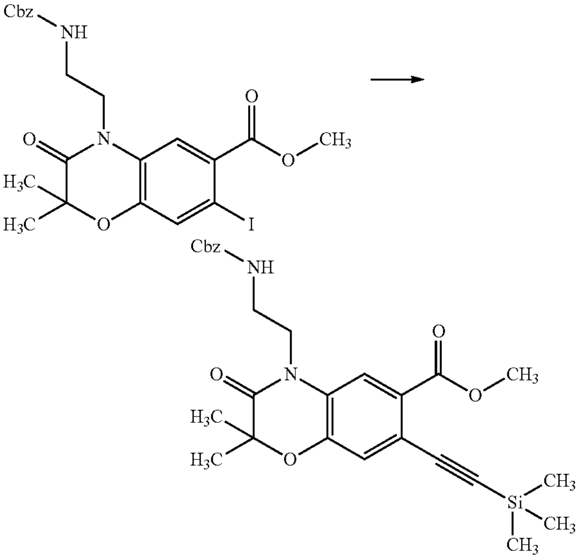

Using the compound of Reference Example 164, the title compound (1.9 g) was obtained in a similar manner to Reference Example 166.

MS (ESI+) 509 ($M^{+}$+1, 100%).

Reference Example 171

Methyl (2R)-4-(2-{[(benzyloxy)carbonyl]amino}ethyl)-2-methyl-3-oxo-7-[(trimethylsilyl)ethynyl-3,4-dihydro-2H-1,4-benzoxazine-6-carboxylate

[Chemical formula 315]

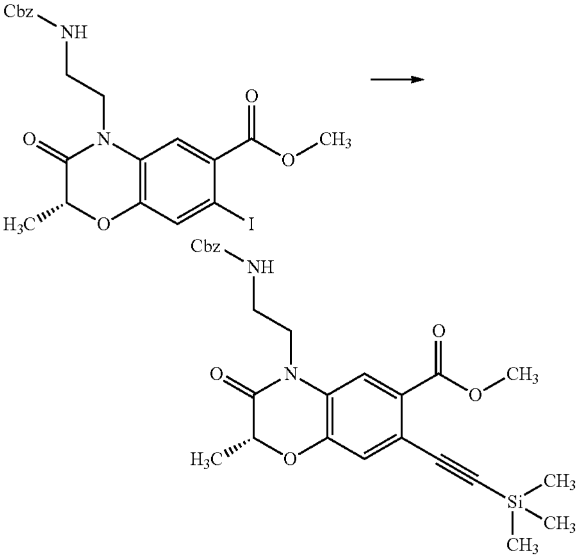

Using the compound of Reference Example 165, the title compound (1.2 g) was obtained in a similar manner to Reference Example 166.

MS (ESI+) 495 ($M^{+}$+1, 100%).

Reference Example 172

Methyl 7-ethynyl-4-(4-methoxybutyl)-2,2-dimethyl-3-oxo-3,4-dihydro-2H-1,4-benzoxazine-6-carboxylate

[Chemical formula 316]

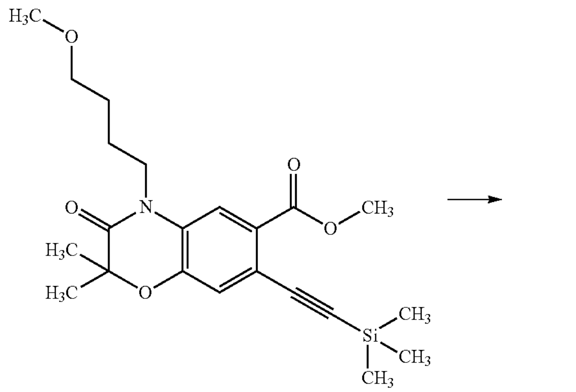

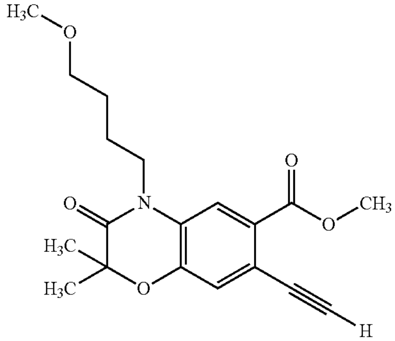

The compound of Reference Example 166 (730 mg) was dissolved in tetrahydrofuran (10 ml), and thereto was slowly added a 1 mol/L solution of tetrabutylammonium fluoride in tetrahydrofuran (1.8 ml) dropwise under ice-cooling. Then, the mixture was stirred under ice-cooling for one hour. The reaction solvent was evaporated under reduced pressure to some extent, and the resulting residue was diluted with ethyl acetate. The organic layer was washed twice with water, dried over magnesium sulfate, filtered and concentrated under reduced pressure. The obtained residue was purified by silica gel column chromatography (the developing solvent: hexane/acetone=4:1→3:1) to give the title compound (430 mg) as a colorless clear oil.

MS (ESI+) 346 ($M^{+}$+1, 90%).

Reference Example 173

Methyl (2R)-7-ethynyl-4-(4-methoxybutyl)-2-methyl-3-oxo-3,4-dihydro-2H-1,4-benzoxazine-6-carboxylate

[Chemical formula 317]

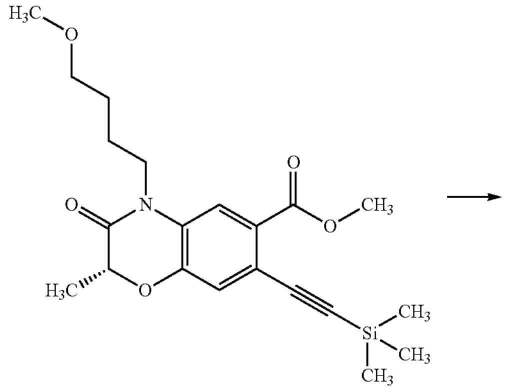

-continued

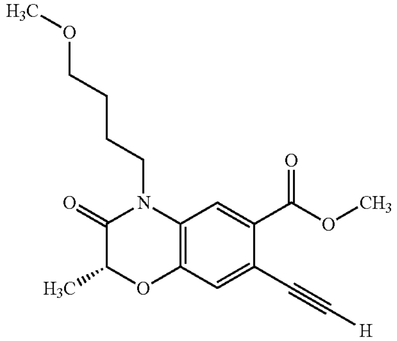

Using the compound of Reference Example 167, the title compound (530 mg) was obtained in a similar manner to Reference Example 172.

MS (ESI+) 332 ($M^{+}$+1, 66%).

Reference Example 174

Methyl 7-ethynyl-4-{2-[(methoxycarbonyl)amino]ethyl}-2,2-dimethyl-3-oxo-3,4-dihydro-2H-1,4-benzoxazine-6-carboxylate

[Chemical formula 318]

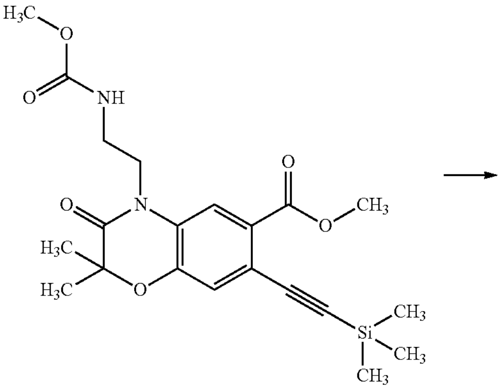

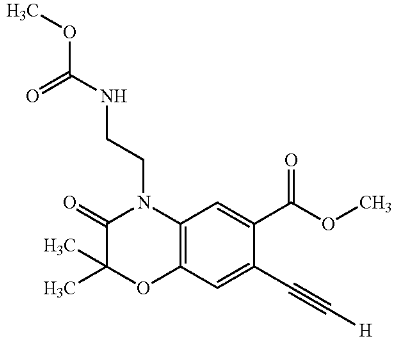

Using the compound of Reference Example 168, the title compound (530 mg) was obtained in a similar manner to Reference Example 172.

MS (ESI+) 361 ($M^{+}$+1, 50%).

Reference Example 175

Methyl (2R)-7-ethynyl-4-{2-[(methoxycarbonyl)amino]ethyl}-2-methyl-3-oxo-3,4-dihydro-2H-1,4-benzoxazine-6-carboxylate

[Chemical formula 319]

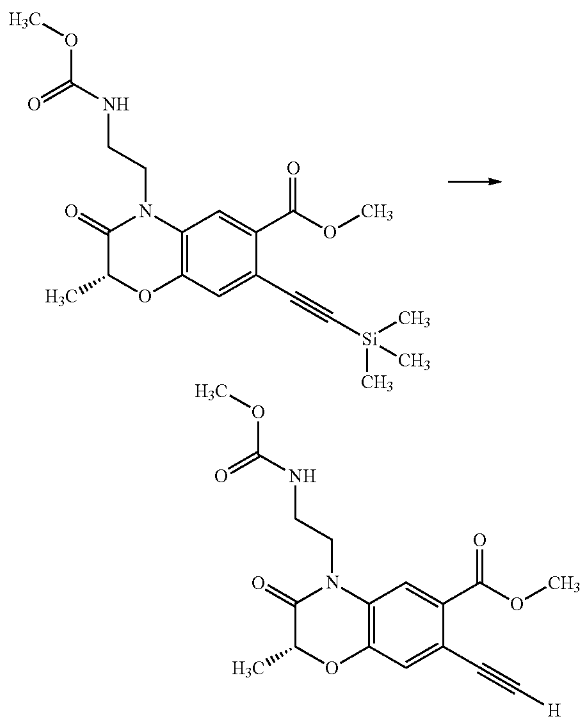

Using the compound of Reference Example 169, the title compound (530 mg) was obtained in a similar manner to Reference Example 172.

MS (ESI+) 347 ($M^{+}$+1, 37%).

Reference Example 176

Methyl 4-(2-{[(benzyloxy)carbonyl]amino}ethyl)-7-ethynyl-2,2-dimethyl-3-oxo-3,4-dihydro-2H-1,4-benzoxazine-6-carboxylate

[Chemical formula 320]

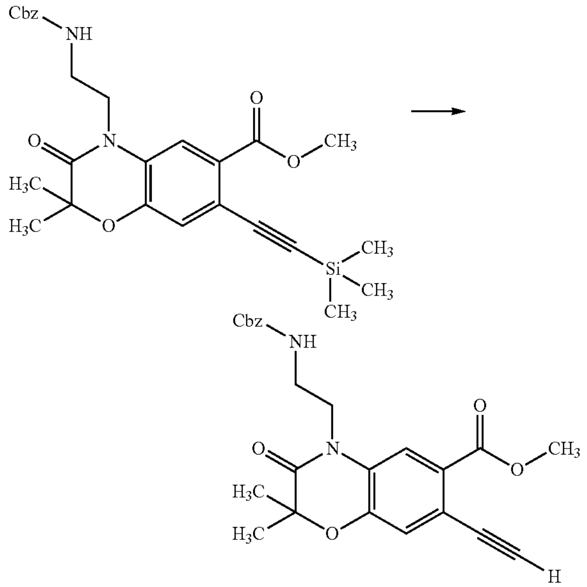

Using the compound of Reference Example 170, the title compound (700 mg) was obtained in a similar manner to Reference Example 172.

MS (ESI+) 437 ($M^{+}$+1, 100%).

Reference Example 177

Methyl (2R)-4-(2-{[(benzyloxy)carbonyl]amino}ethyl)-7-ethynyl-2-methyl-3-oxo-3,4-dihydro-2H-1,4-benzoxazine-6-carboxylate

[Chemical formula 321]

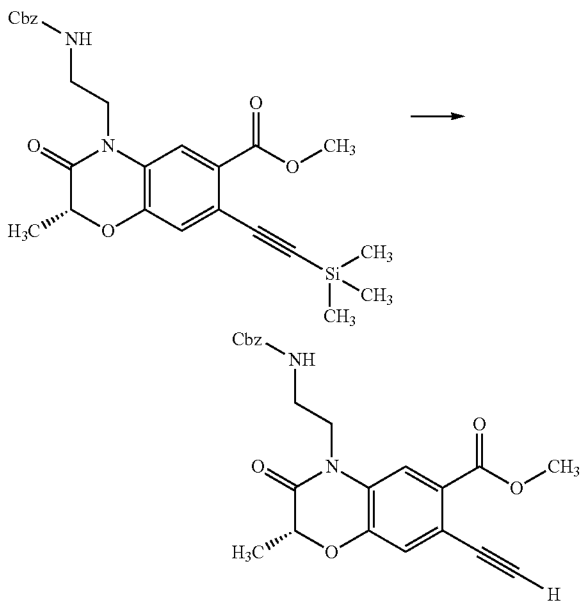

Using the compound of Reference Example 171, the title compound (750 mg) was obtained in a similar manner to Reference Example 172.

MS (ESI+) 423 ($M^{+}$+1, 100%).

Reference Example 178

Methyl 7-ethyl-4-(4-methoxybutyl)-2,2-dimethyl-3-oxo-3,4-dihydro-2H-1,4-benzoxazine-6-carboxylate

[Chemical formula 322]

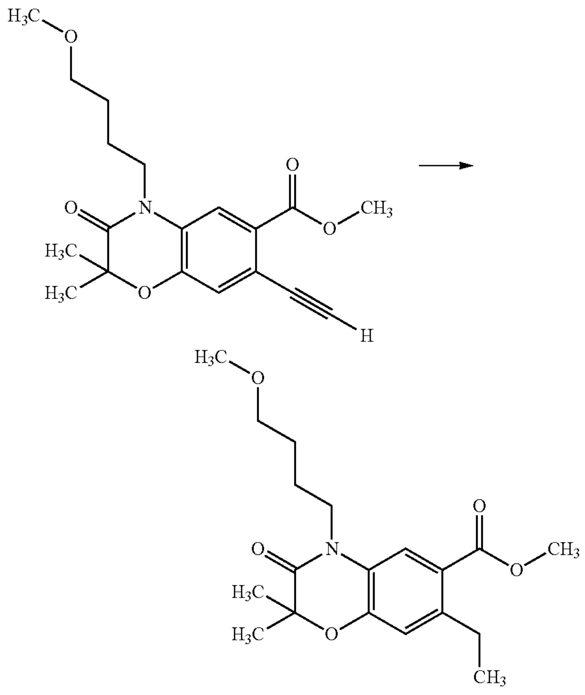

The compound of Reference Example 172 (500 mg) was dissolved in methanol (15 ml), and to the mixture was added a 20% palladium hydroxide carbon (150 mg) under ice-cooling. Then, the mixture was stirred at room temperature for 6 hours under hydrogen atmosphere. The reaction mixture was filtered on celite, and the reaction solvent was evaporated under reduced pressure. The obtained residue was purified by silica gel column chromatography (the developing solvent: hexane/acetone=5:1→4:1) to give the title compound (400 mg) as a colorless clear oil.

MS (ESI+) 350 ($M^+$+1, 78%).

Reference Example 179

Methyl (2R)-7-ethyl-4-(4-methoxybutyl)-2-methyl-3-oxo-3,4-dihydro-2H-1,4-benzoxazine-6-carboxylate

[Chemical formula 323]

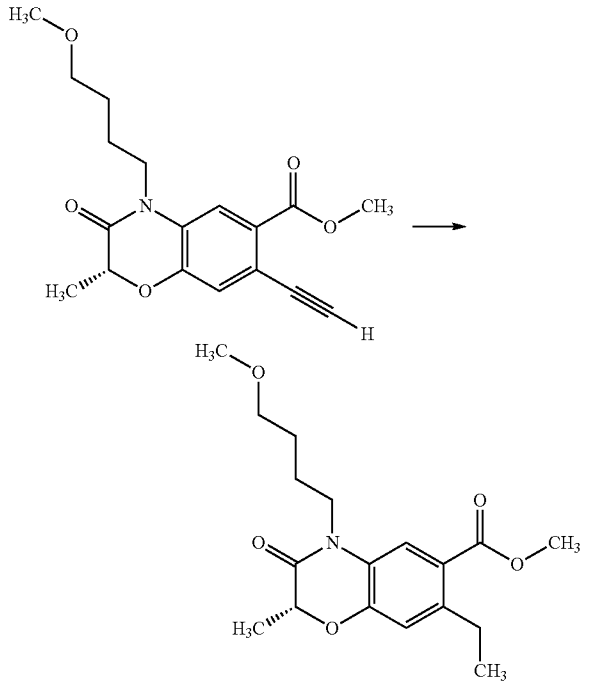

Using the compound of Reference Example 173, the title compound (450 mg) was obtained in a similar manner to Reference Example 178.

MS (ESI+) 336 ($M^+$+1, 38%).

Reference Example 180

Methyl 7-ethyl-4-{2-[(methoxycarbonyl)amino]ethyl}-2,2-dimethyl-3-oxo-3,4-dihydro-2H-1,4-benzoxazine-6-carboxylate

[Chemical formula 324]

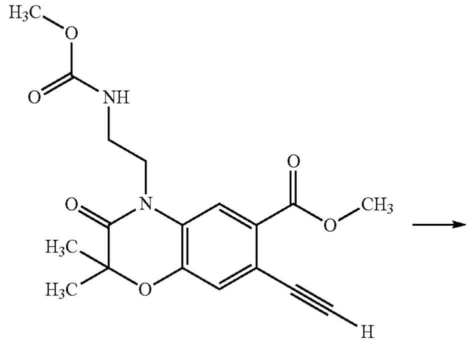

-continued

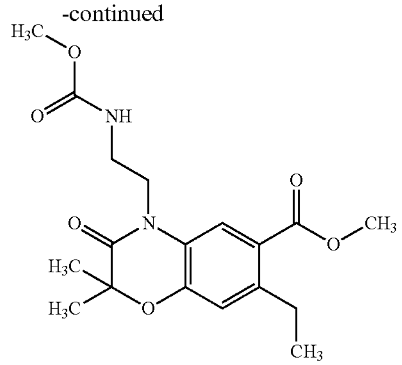

Using the compound of Reference Example 174, the title compound (520 mg) was obtained in a similar manner to Reference Example 178.

MS (ESI+) 365 ($M^+$+1, 36%).

Reference Example 181

Methyl (2R)-7-ethyl-4-{2-[(methoxycarbonyl)amino]ethyl}-2-methyl-3-oxo-3,4-dihydro-2H-1,4-benzoxazine-6-carboxylate

[Chemical formula 325]

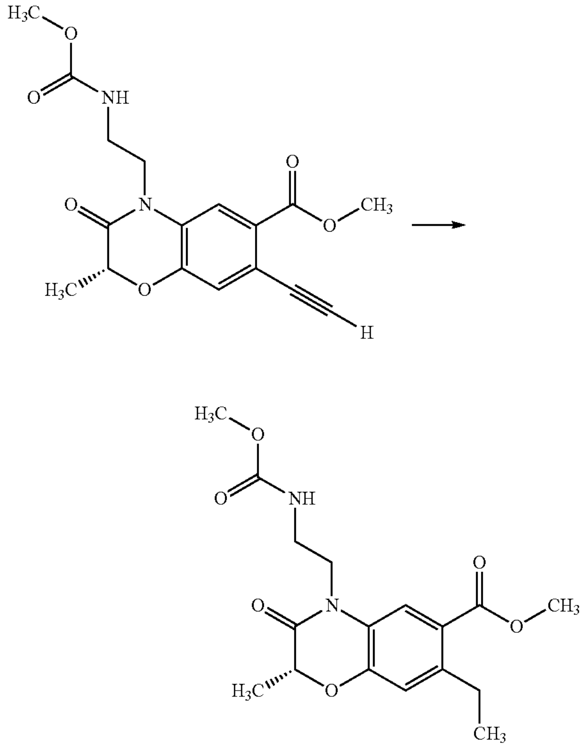

Using the compound of Reference Example 175, the title compound (480 mg) was obtained in a similar manner to Reference Example 178.

MS (ESI+) 351 ($M^+$+1, 36%).

Reference Example 182 tert-Butyl (3R)-3-[{[7-ethyl-4-(4-methoxybutyl)-2,2-dimethyl-3-oxo-3,4-dihydro-2H-1,4-benzoxazin-6-yl]carbonyl}(isopropyl)amino]piperidine-1-carboxylate

[Chemical formula 326]

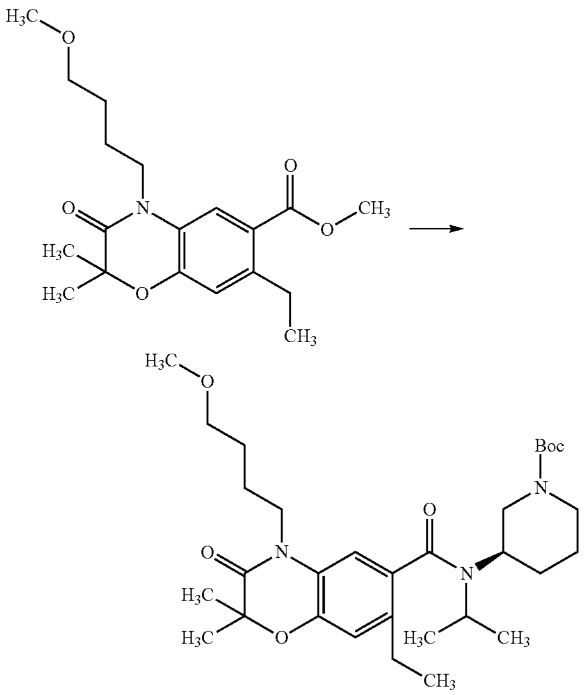

Using the compound of Reference Example 178, the title compound (450 mg) was obtained in a similar manner to Reference Example 5.

MS (ESI+) 560 ($M^{+}$+1, 56%).

Reference Example 183 tert-Butyl (3R)-3-[{[(2R)-7-ethyl-4-(4-methoxybutyl)-2-methyl-3-oxo-3,4-dihydro-2H-1,4-benzoxazin-6-yl]carbonyl}(isopropyl)amino]piperidine-1-carboxylate

[Chemical formula 327]

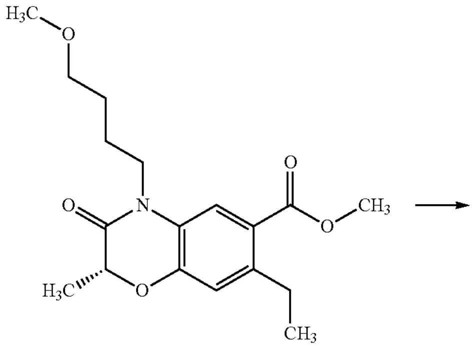

-continued

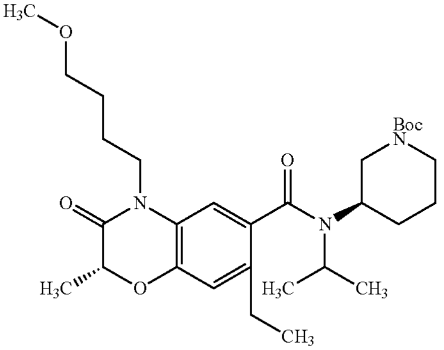

Using the compound of Reference Example 179, the title compound (410 mg) was obtained in a similar manner to Reference Example 5.

MS (ESI+) 546 ($M^{+}$+1, 50%).

Reference Example 184 tert-Butyl (3R)-3-[[(7-ethyl-4-{2-[(methoxycarbonyl)amino]ethyl}-2,2-dimethyl-3-oxo-3,4-dihydro-2H-1,4-benzoxazin-6-yl)carbonyl](isopropyl)amino]piperidine-1-carboxylate

[Chemical formula 328]

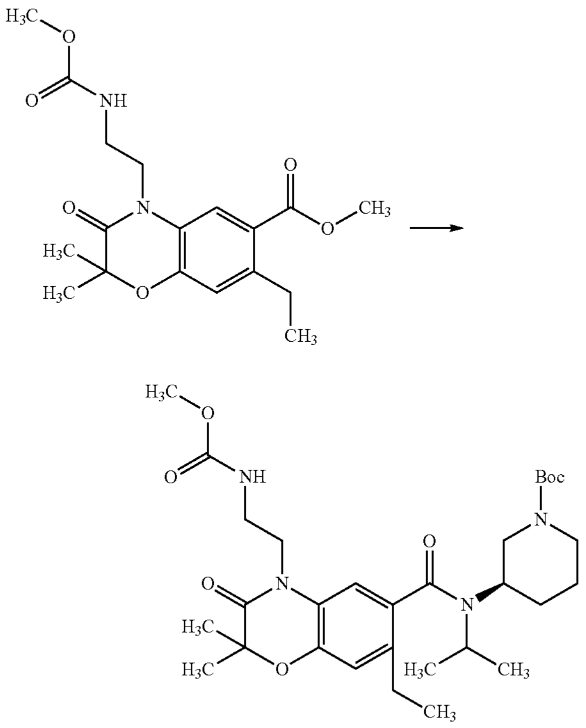

Using the compound of Reference Example 180, the title compound (460 mg) was obtained in a similar manner to Reference Example 5.

MS (ESI+) 575 ($M^{+}$+1, 46%).

Reference Example 185 tert-Butyl (3R)-3-[[((2R)-7-ethyl-4-{2-[(methoxycarbonyl)amino]ethyl}-2-methyl-3-oxo-3,4-dihydro-2H-1,4-benzoxazin-6-yl)carbonyl](isopropyl)amino]piperidine-1-carboxylate

[Chemical formula 329]

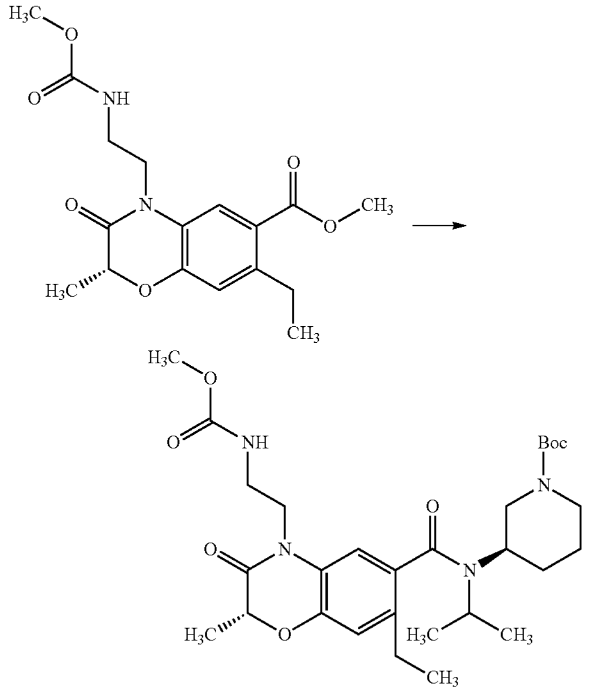

Using the compound of Reference Example 181, the title compound (440 mg) was obtained in a similar manner to Reference Example 5.

MS (ESI+) 561 ($M^{+}$+1, 26%).

Reference Example 186 tert-Butyl (3R)-3-[{[4-(2-{[(benzyloxy)carbonyl]amino}ethyl}-7-ethynyl-2,2-dimethyl-3-oxo-3,4-dihydro-2H-1,4-benzoxazin-6-yl)carbonyl](isopropyl)amino]piperidine-1-carboxylate

[Chemical formula 330]

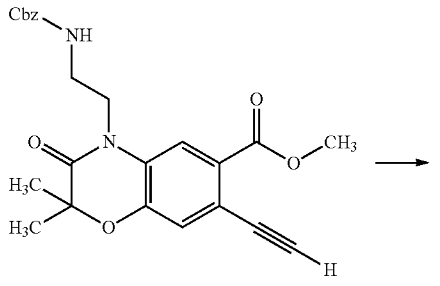

-continued

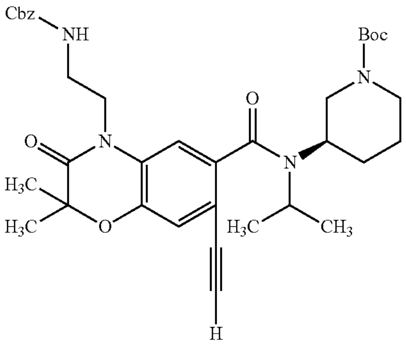

Using the compound of Reference Example 176, the title compound was obtained in a similar manner to Reference Example 5.

MS (ESI+) 647 ($M^{+}$+1, 22%).

Reference Example 187 tert-Butyl (3R)-3-[{[(2R)-4-(2-{[(benzyloxy)carbonyl]amino}ethyl}-7-ethynyl-2-methyl-3-oxo-3,4-dihydro-2H-1,4-benzoxazin-6-yl)carbonyl](isopropyl)amino]piperidine-1-carboxylate

[Chemical formula 331]

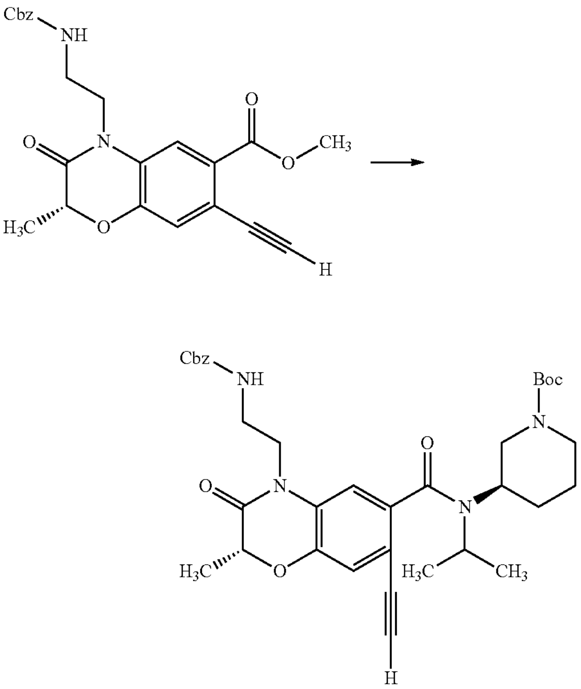

Using the compound of Reference Example 177, the title compound (610 mg) was obtained in a similar manner to Reference Example 5.

MS (ESI+) 633 ($M^{+}$+1, 19%).

Reference Example 188 tert-Butyl (3R)-3-[{[4-(2-aminoethyl)-7-ethyl-2,2-dimethyl-3-oxo-3,4-dihydro-2H-1,4-benzoxazin-6-yl]carbonyl}(isopropyl)amino]piperidine-1-carboxylate

[Chemical formula 332]

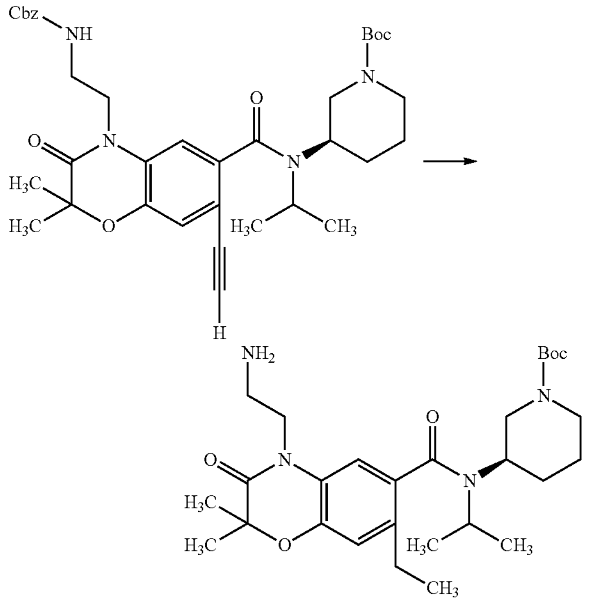

Using the compound of Reference Example 186, the title compound (430 mg) was obtained in a similar manner to Reference Example 139.

MS (ESI+) 517 ($M^+$+1, 97%).

Reference Example 189 tert-Butyl (3R)-3-[{[(2R)-4-(2-aminoethyl)-7-ethyl-2-methyl-3-oxo-3,4-dihydro-2H-1,4-benzoxazin-6-yl]carbonyl}(isopropyl)amino]piperidine-1-carboxylate

[Chemical formula 333]

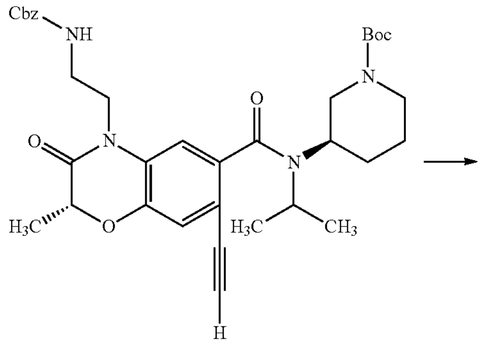

-continued

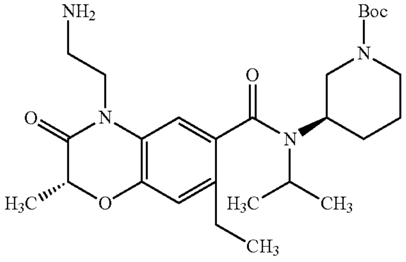

Using the compound of Reference Example 187, the title compound (485 mg) was obtained in a similar manner to Reference Example 139.

MS (ESI+) 503 ($M^+$+1, 73%).

Reference Example 190 tert-Butyl (3R)-3-[({7-ethyl-2,2-dimethyl-3-oxo-4-[2-(propylamino)ethyl]-3,4-dihydro-2H-1,4-benzoxazin-6-yl}carbonyl)(isopropyl)amino]piperidine-1-carboxylate

[Chemical formula 334]

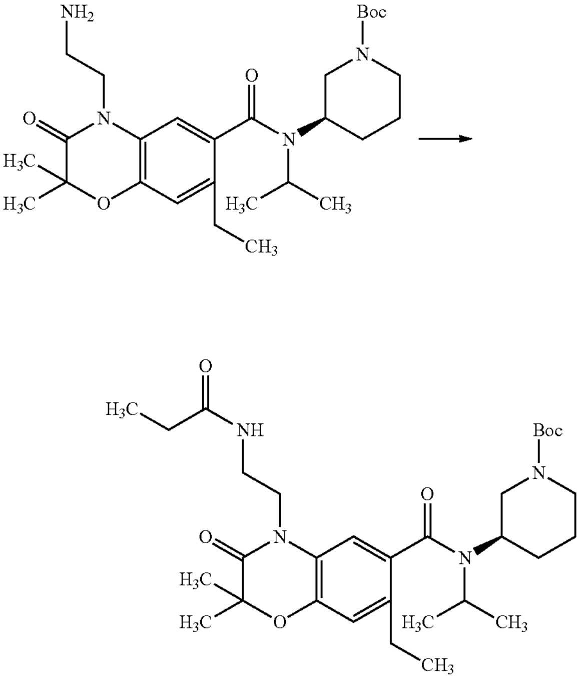

Using the compound of Reference Example 188, the title compound (180 mg) was obtained in a similar manner to Reference Example 132.

MS (ESI+) 573 ($M^+$+1, 44%).

Reference Example 191 tert-Butyl (3R)-3-[[(4-{2-[(difluoroacetyl)amino] ethyl}-7-ethyl-2,2-dimethyl-3-oxo-3,4-dihydro-2H-1,4-benzoxazin-6-yl)carbonyl](isopropyl)amino] piperidine-1-carboxylate

[Chemical formula 335]

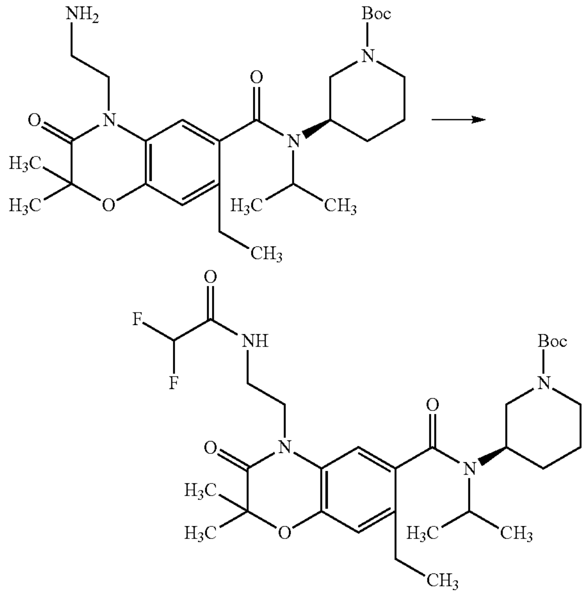

Using the compound of Reference Example 188, the title compound (180 mg) was obtained in a similar manner to Reference Example 120.

MS (ESI+) 595 ($M^{+}$+1, 39%).

Reference Example 192 tert-Butyl (3R)-3-[[(4-{2-[(ethoxycarbonyl)amino] ethyl}-7-ethyl-2,2-dimethyl-3-oxo-3,4-dihydro-2H-1,4-benzoxazin-6-yl)carbonyl](isopropyl)amino] piperidine-1-carboxylate

[Chemical formula 336]

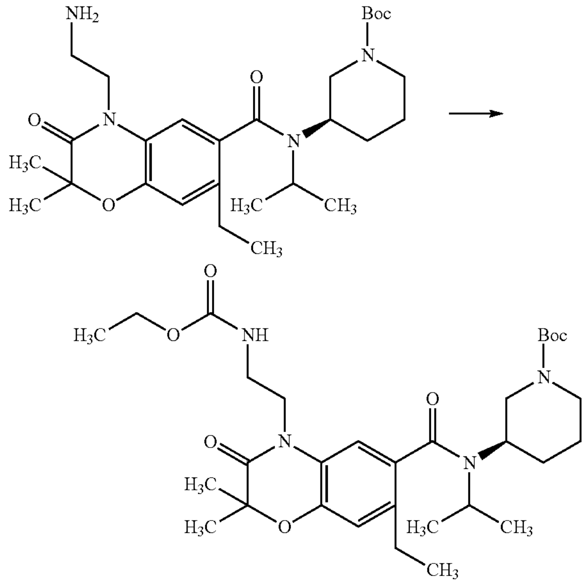

Using the compound of Reference Example 188, the title compound (210 mg) was obtained in a similar manner to Reference Example 132.

MS (ESI+) 589 ($M^{+}$+1, 41%).

Reference Example 193 tert-Butyl (3R)-3-[({4-[2-(butyrylamino)ethyl]-7-ethyl-2,2-dimethyl-3-oxo-3,4-dihydro-2H-1,4-benzoxazin-6-yl}carbonyl)(isopropyl)amino]piperidine-1-carboxylate

[Chemical formula 337]

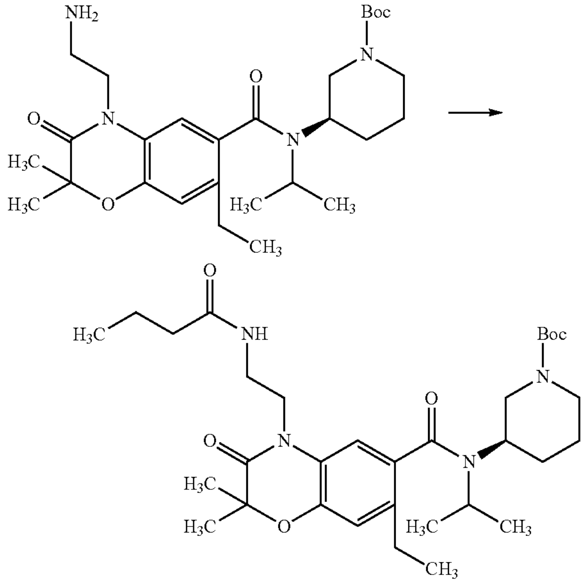

Using the compound of Reference Example 188, the title compound (210 mg) was obtained in a similar manner to Reference Example 132.

MS (ESI+) 587 ($M^{+}$+1, 40%).

Reference Example 194 tert-Butyl (3R)-3-[({(2R)-7-ethyl-2-methyl-3-oxo-4-[2-(propylamino)ethyl]-3,4-dihydro-2H-1,4-benzoxazin-6-yl}carbonyl)(isopropyl)amino]piperidine-1-carboxylate

[Chemical formula 338]

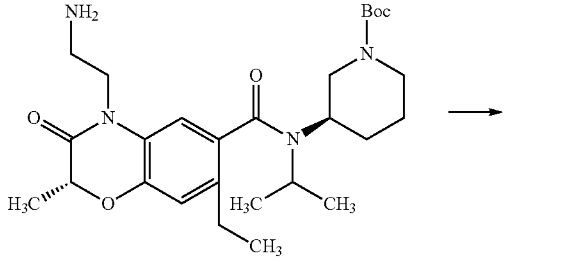

-continued

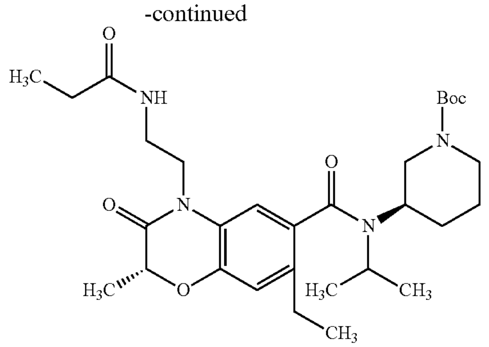

Using the compound of Reference Example 189, the title compound (120 mg) was obtained in a similar manner to Reference Example 132.

MS (ESI+) 559 ($M^{+}$+1, 21%).

Reference Example 195 tert-Butyl (3R)-3-[({(2R)-4-[2-(acetylamino)ethyl]-7-ethyl-2-methyl-3-oxo-3,4-dihydro-2H-1,4-benzoxazin-6-yl}carbonyl)(isopropyl)amino]piperidine-1-carboxylate

[Chemical formula 339]

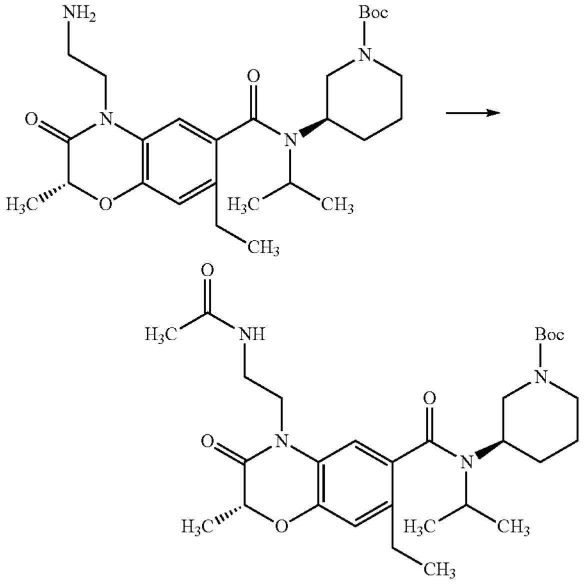

Using the compound of Reference Example 189, the title compound (120 mg) was obtained in a similar manner to Reference Example 132.

MS (ESI+) 545 ($M^{+}$+1, 16%).

Reference Example 196 tert-Butyl (3R)-3-[({(2R)-7-ethyl-4-[2-(formylamino)ethyl]-2-methyl-3-oxo-3,4-dihydro-2H-1,4-benzoxazin-6-yl}carbonyl)(isopropyl)amino]piperidine-1-carboxylate

[Chemical formula 340]

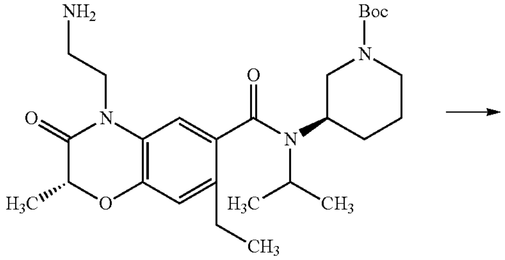

-continued

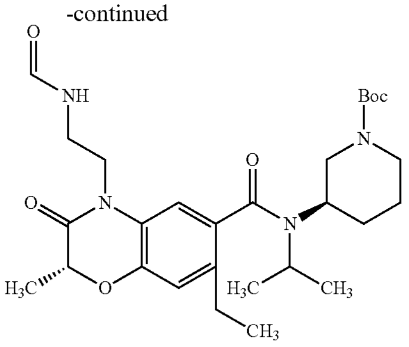

The compound of Reference Example 189 (150 mg) was dissolved in dichloromethane (5 ml), and thereto was added under ice-cooling a solution which had been previously prepared by stirring acetic anhydride (91 mg) and formic acid (82 mg) at 45° C. for one hour. Then, the mixture was stirred at room temperature for 6 hours. To the reaction mixture was added an aqueous sodium hydrogen carbonate solution, and the mixture was extracted with chloroform. The organic layer was dried over magnesium sulfate, filtered and concentrated under reduced pressure. The obtained residue was purified by silica gel column chromatography (the developing solvent: chloroform /methanol=30:1→15:1) to give the title compound (110 mg) as amorphous.

MS (ESI+) 531 ($M^{+}$+1, 22%).

Reference Example 197 tert-Butyl (3R)-3-({[4-(4-methoxybutyl)-2,2-dimethyl-3-oxo-7-(trifluoromethyl)-3,4-dihydro-2H-1,4-benzoxazin-6-yl]carbonyl}amino)piperidine-1-carboxylate

[Chemical formula 341]

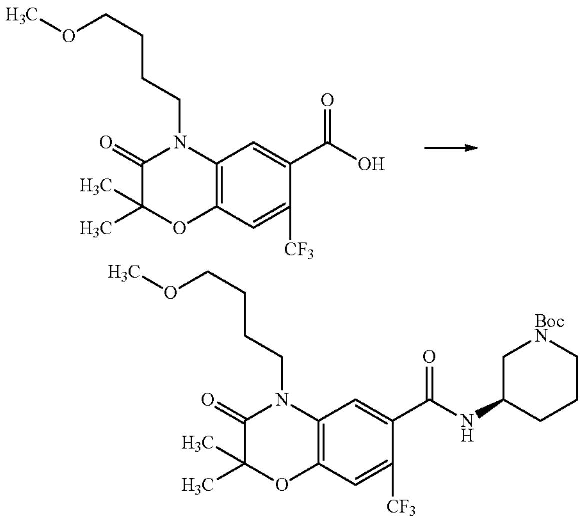

4-(4-Methoxybutyl)-2,2-dimethyl-3-oxo-7-(trifluoromethyl)-3,4-dihydro-2H-1,4-benzoxazine-6-carboxylic acid (100 mg) was dissolved in dimethylformamide (2 ml), and thereto were added 1-hydroxybenzotriazole (61.1 mg), 1-ethyl-3-(dimethylaminopropyl)carbodiimide hydrochloride (76.5 mg), triethylamine (55.6 μl) and tert-butyl (3R)-3-aminopiperidine-1-carboxylate (64.0 mg), and the mixture was stirred at room temperature for 2 hours. To the reaction mixture was added a 5% aqueous sodium hydrogen sulfate solution, and the mixture was extracted with ethyl acetate. The organic layer was washed with a 5% aqueous sodium hydrogen sulfate solution, a saturated aqueous sodium hydrogen carbonate solution, and a saturated aqueous sodium chloride solution, dried over sodium sulfate, filtered and concentrated under reduced pressure. The obtained residue was purified by silica gel column chromatography (hexane/ethyl acetate=1/1) to give the title compound (1136 mg) as a white solid.

MS (ESI+) 558 ($M^{+}$+1, 100%).

Reference Example 198 tert-Butyl (rac.)-(3R,4R)-4-benzyl-3-({[4-(4-methoxybutyl)-2,2-dimethyl-3-oxo-7-(trifluoromethyl)-3,4-dihydro-2H-1,4-benzoxazin-6-yl]carbonyl}amino)piperidine-1-carboxylate

[Chemical formula 342]

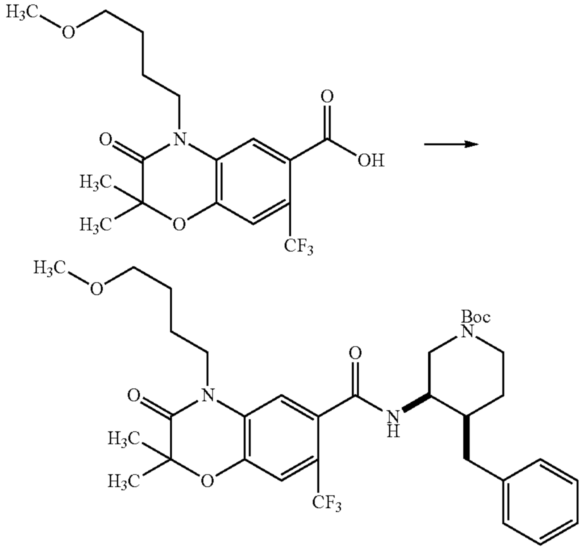

Using 4-(4-methoxybutyl)-2,2-dimethyl-3-oxo-7-(trifluoromethyl)-3,4-dihydro-2H-1,4-benzoxazine-6-carboxylic acid and tert-butyl (rac.)-(3R,4R)-3-amino-4-benzylpiperidine-1-carboxylate (US 2005/182095), the title compound was obtained in a similar manner to Reference Example 197.

MS (ESI+) 648 ($M^{+}$+1, 100%).

Reference Example 199 tert-Butyl (rac.)-(3R,4S)-4-benzyl-3-({[4-(4-methoxybutyl)-2,2-dimethyl-3-oxo-7-(trifluoromethyl)-3,4-dihydro-2H-1,4-benzoxazin-6-yl]carbonyl}amino)piperidine-1-carboxylate

[Chemical formula 343]

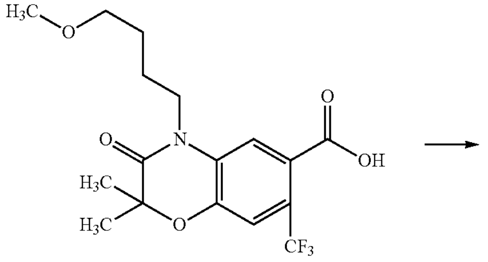

-continued

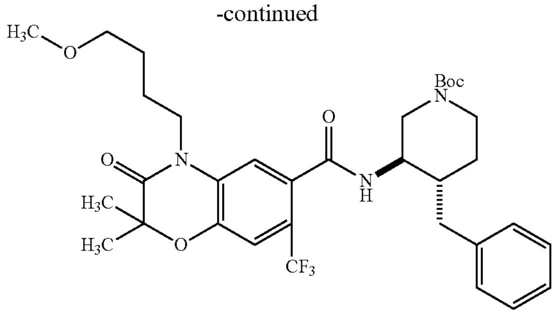

Using 4-(4-methoxybutyl)-2,2-dimethyl-3-oxo-7-(trifluoromethyl)-3,4-dihydro-2H-1,4-benzoxazine-6-carboxylic acid, tert-butyl (rac.)-(3R,4S)-3-amino-4-benzylpiperidine-1-carboxylate (US 2005/182095), the title compound was obtained in a similar manner to Reference Example 197.

MS (ESI+) 648 ($M^{+}$+1, 100%).

Reference Example 200 tert-Butyl (3R)-3-[{[4-(4-methoxybutyl)-2,2-dimethyl-3-oxo-7-(trifluoromethyl)-3,4-dihydro-2H-1,4-benzoxazin-6-yl]carbonyl}(methyl)amino]piperidine-1-carboxylate

[Chemical formula 344]

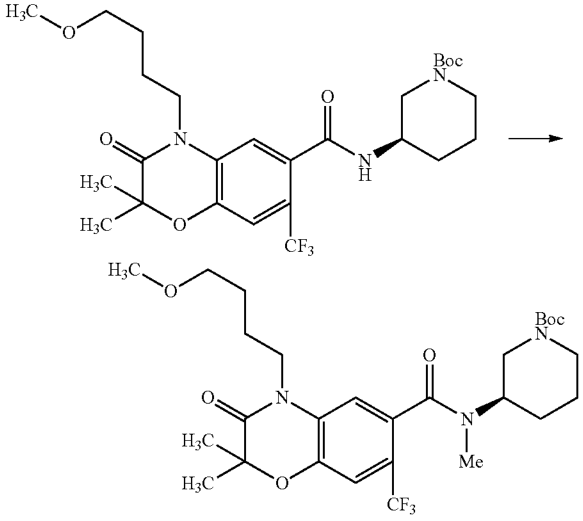

The compound of Reference Example 197 (71.6 mg) was dissolved in dimethylformamide (2 ml), and thereto was added at 0° C. sodium hydride (15.4 mg), and the mixture was stirred. Five minutes later, to the mixture was added methyl iodide (23.9 μl), and the mixture was stirred at room temperature for 4 hours. To the reaction mixture was added a saturated aqueous sodium thiosulfate solution, and the mixture was extracted with ethyl acetate. The organic layer was washed twice with a saturated aqueous ammonium chloride solution, and washed with a saturated aqueous sodium chloride solution. The organic layer was dried over sodium sulfate, filtered and concentrated under reduced pressure. The obtained residue was purified by silica gel column chromatography (the developing solvent: hexane/ethyl acetate=1/1) to give the title compound (53.9 mg) as a colorless oil.

MS (ESI+) 572 ($M^{+}$+1, 100%).

Reference Example 201 tert-Butyl (rac.)-(3R,4R)-4-benzyl-3-[{[4-(4-methoxybutyl)-2,2-dimethyl-3-oxo-7-(trifluoromethyl)-3,4-dihydro-2H-1,4-benzoxazin-6-yl]carbonyl}(methyl)amino]piperidine-1-carboxylate

[Chemical formula 345]

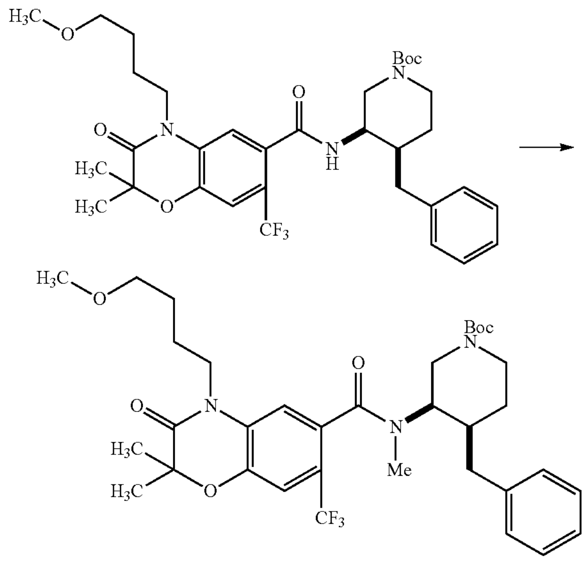

Using the compound of Reference Example 198, the title compound was obtained in a similar manner to Reference Example 200.

MS (ESI+) 662 ($M^{+}$+1, 100%).

Reference Example 202 tert-Butyl (rac.)-(3R,4S)-4-benzyl-3-[{[4-(4-methoxybutyl)-2,2-dimethyl-3-oxo-7-(trifluoromethyl)-3,4-dihydro-2H-1,4-benzoxazin-6-yl]carbonyl}(methyl)amino]piperidine-1-carboxylate

[Chemical formula 346]

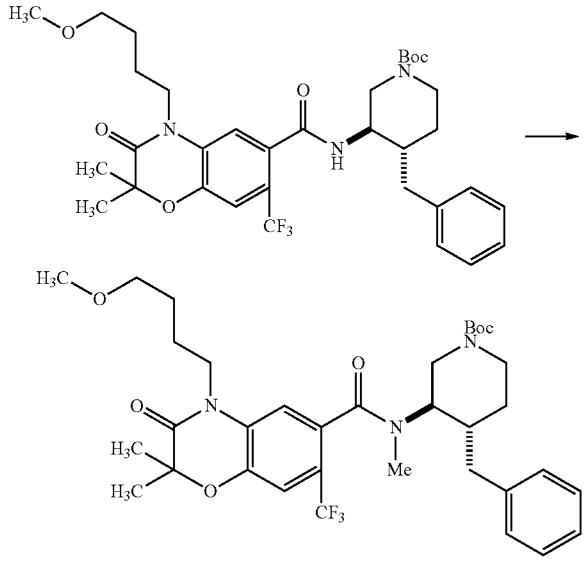

Using the compound of Reference Example 199, the title compound was obtained in a similar manner to Reference Example 200.

MS (ESI+) 662 ($M^{+}$+1, 100%).

Reference Example 203 tert-Butyl 3-(isopropyl{[4-(4-methoxybutyl)-2,2-dimethyl-3-oxo-7-(trifluoromethyl)-3,4-dihydro-2H-1,4-benzoxazin-6-yl]carbonyl}amino)azepane-1-carboxylate

[Chemical formula 347]

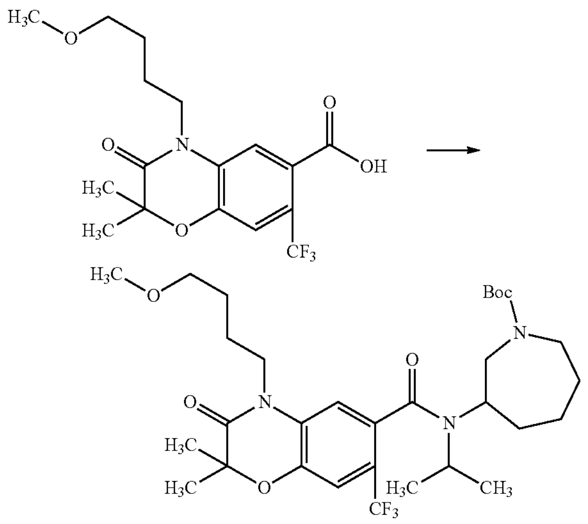

Using 4-(4-methoxybutyl)-2,2-dimethyl-3-oxo-7-(trifluoromethyl)-3,4-dihydro-2H-1,4-benzoxazine-6-carboxylic acid and tert-butyl 3-(isopropylamino)azepane-1-carboxylate, the title compound was obtained in a similar manner to Reference Example 5.

MS (ESI+) 614 ($M^{+}$+1, 100%).

Reference Example 204

Benzyl 3-(isopropyl{[4-(4-methoxybutyl)-2,2-dimethyl-3-oxo-7-(trifluoromethyl)-3,4-dihydro-2H-1,4-benzoxazin-6-yl]carbonyl}amino)pyrrolidine-1-carboxylate

[Chemical formula 348]

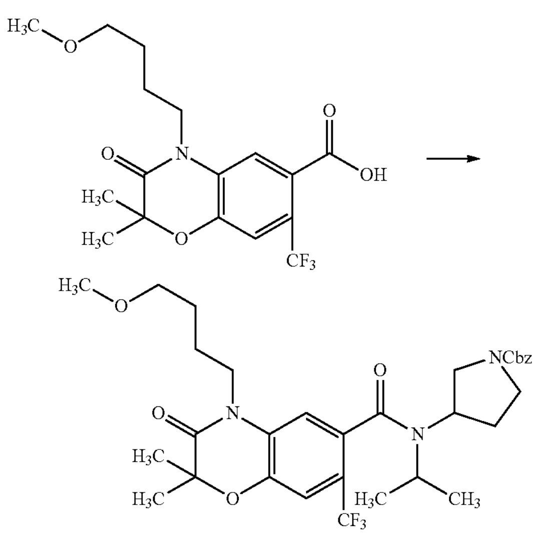

Using 4-(4-methoxybutyl)-2,2-dimethyl-3-oxo-7-(trifluoromethyl)-3,4-dihydro-2H-1,4-benzoxazine-6-carboxylic acid and benzyl 3-(isopropylamino)pyrrolidine-1-carboxylate, the title compound was obtained in a similar manner to Reference Example 5.

MS (ESI+) 620 ($M^{+}$+1, 100%).

Reference Example 205

Methyl 4-{[(1R)-1-(methoxycarbonyl)-2-methylpropyl]oxy}-2-methyl-5-nitrobenzoate

[Chemical formula 349]

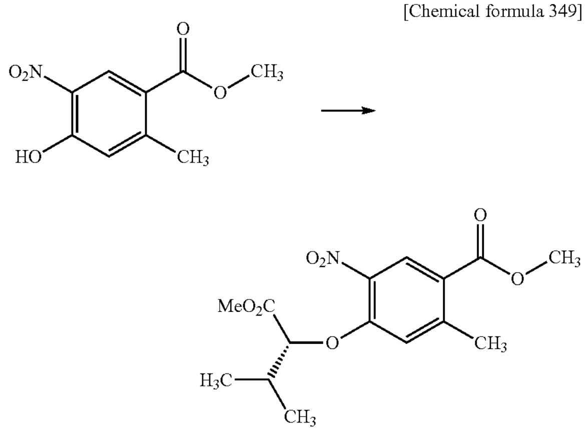

Using methyl 4-hydroxy-2-methyl-5-nitrobenzoate, the title compound was obtained in a similar manner to Reference Example 26.

MS (ESI+) 326 ($M^{+}$+1, 65%).

Reference Example 206

Methyl (2R)-2-isopropyl-4-(4-methoxybutyl)-7-methyl-3-oxo-3,4-dihydro-2H-1,4-benzoxazine-6-carboxylate

[Chemical formula 350]

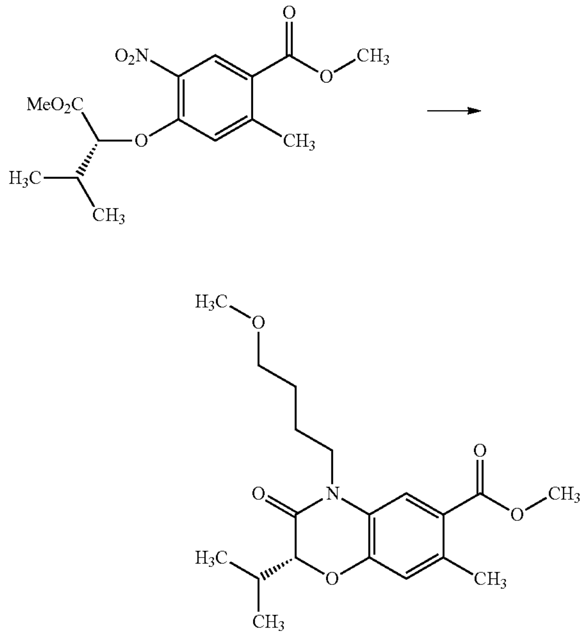

Using the compound of Reference Example 205, the title compound was obtained in a similar manner to Reference Example 17.

MS (ESI+) 350 ($M^{+}$+1, 100%).

Reference Example 207 tert-Butyl (3R)-3-(isobutyl {[(2R)-2-isopropyl-4-(4-methoxybutyl)-7-methyl-3-oxo-3,4-dihydro-2H-1,4-benzoxazin-6-yl]carbonyl}amino)piperidine-1-carboxylate

[Chemical formula 351]

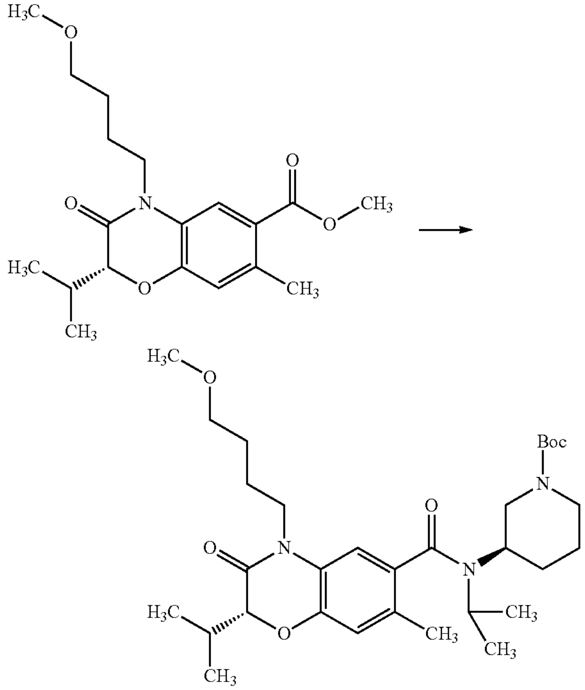

Using the compound of Reference Example 206, the title compound was obtained in a similar manner to Reference Example 5.

MS (ESI+) 560 ($M^{+}$+1, 30%).

Reference Example 208

Methyl 2,2-difluoro-7-methyl-3-oxo-3,4-dihydro-2H-1,4-benzoxazine-6-carboxylate

[Chemical formula 352]

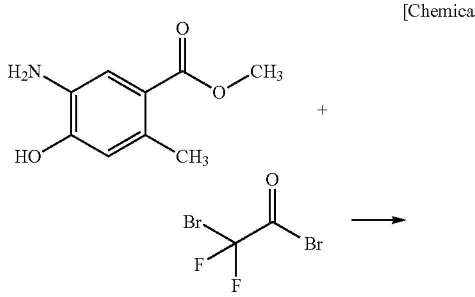

-continued

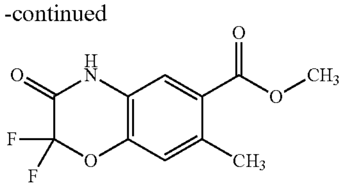

Using the compound of Reference Example 54 and bromodifluoroacetyl bromide, the title compound was obtained in a similar manner to Reference Example 55.

MS (ESI+) 258 ($M^{+}$+1, 100%).

Reference Example 209

Methyl 4-(2-{[(benzyloxy)carbonyl]amino}ethyl)-2,2-difluoro-7-methyl-3-oxo-3,4-dihydro-2H-1,4-benzoxazine-6-carboxylate

[Chemical formula 353]

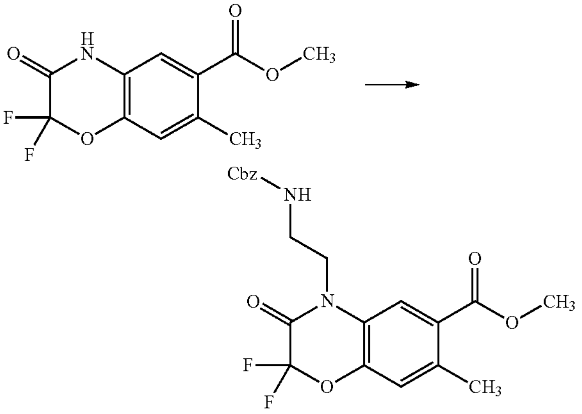

Using the compound of Reference Example 208, the title compound was obtained in a similar manner to Reference Example 3.

MS (ESI+) 435 ($M^{+}$+1, 26%).

Reference Example 210 tert-Butyl 3-[{[4-(2-{[(benzyloxy)carbonyl]amino}ethyl)-2,2-difluoro-7-methyl-3-oxo-3,4-dihydro-2H-1,4-benzoxazin-6-yl]carbonyl}(isopropyl)amino]piperidine-1-carboxylate

[Chemical formula 354]

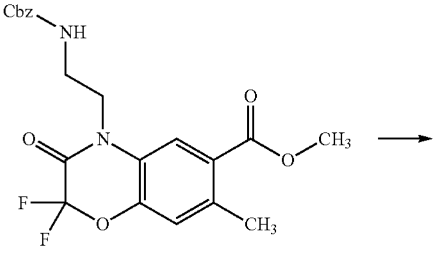

-continued

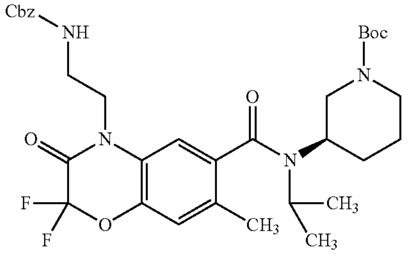

Using the compound of Reference Example 209, the title compound was obtained in a similar manner to Reference Example 5.

MS (ESI+) 645 ($M^{+}$+1, 28%).

Reference Example 211 tert-Butyl 3-[{[4-(2-aminoethyl)-2,2-difluoro-7-methyl-3-oxo-3,4-dihydro-2H-1,4-benzoxazin-6-yl]carbonyl}(isopropyl)amino]piperidine-1-carboxylate

[Chemical formula 355]

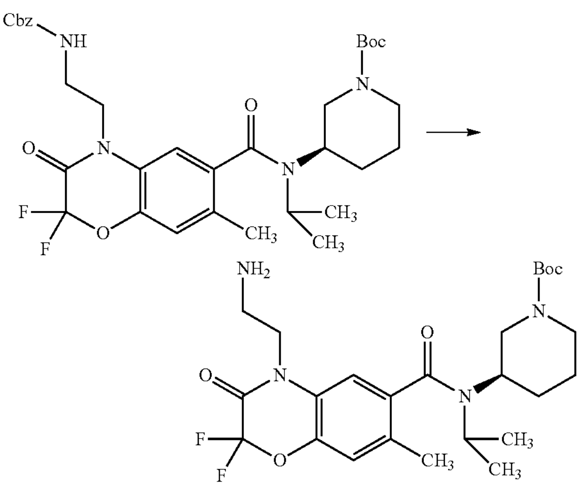

Using the compound of Reference Example 210, the title compound was obtained in a similar manner to Reference Example 139.

MS (ESI+) 511 ($M^{+}$+1, 34%).

Reference Example 212 tert-Butyl 3-[({2,2-difluoro-7-methyl-3-oxo-4-[2-(propionylamino)ethyl]-3,4-dihydro-2H-1,4-benzoxazin-6-yl}carbonyl)(isopropyl)amino]piperidine-1-carboxylate

[Chemical formula 356]

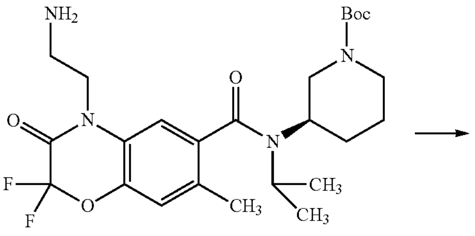

-continued

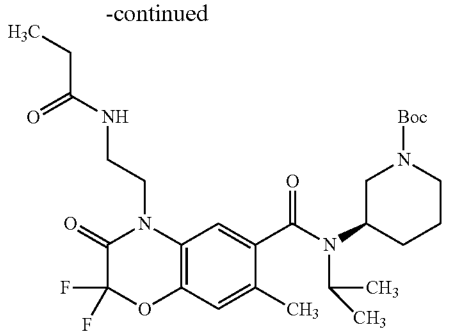

Using the compound of Reference Example 211, the title compound was obtained in a similar manner to Reference Example 132.

MS (ESI+) 567 ($M^{+}$+1, 13%).

Reference Example 213

Methyl 4-fluoro-2-(trifluoromethyl)benzoate

[Chemical formula 357]

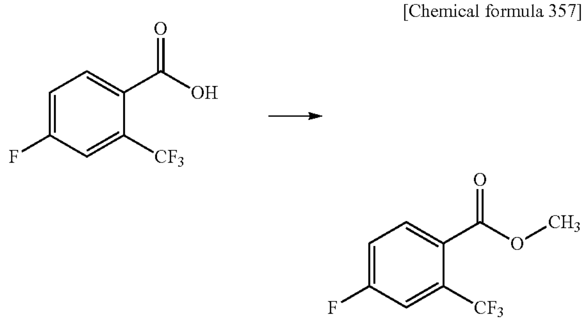

Using the compound of 4-fluoro-2-(trifluoromethyl)benzoic acid, the title compound was obtained in a similar manner to Reference Example 51.

MS (ESI+) 223 ($M^{+}$+1, 100%).

Reference Example 214

Methyl 4-fluoro-5-nitro-2-(trifluoromethyl)benzoate

[Chemical formula 358]

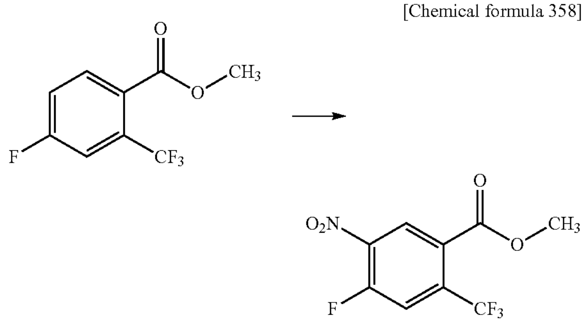

Methyl 4-fluoro-5-nitro-2-(trifluoromethyl)benzoate (8.31 g) was dissolved in con. sulfuric acid (8.5 ml), and thereto was added dropwise fuming nitric acid (15.7 ml) under ice-cooling, and the mixture was stirred at room temperature for 30 minutes. Then, the mixture was warmed to 45° C., and stirred with heating. Ten hours later, the reaction solution was slowly added dropwise into ice-water (50 ml), and thereto was added ethyl acetate (50 ml), and stirred for 30 minutes. The mixture was extracted with ethyl acetate, and the organic layer was washed successively with water, a saturated aqueous sodium hydrogen carbonate solution, a saturated aqueous sodium chloride solution, dried over sodium sulfate, filtered and concentrated under reduced pressure. The obtained residue was purified by silica gel column chromatography (the developing solvent: hexane/ethyl acetate=6/1, 4/1) to give the title compound (1.98 g) as a colorless liquid.

MS (ESI+) 268 ($M^{+}$+1, 100%).

Reference Example 215

Benzyl (2R)-3,3,3-trifluoro-2-hydroxy-2-methylpropanoate

[Chemical formula 359]

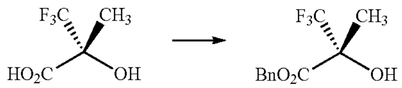

(S)-3,3,3-Trifluoro-2-hydroxy-2-methylpropionic acid (1.00 g) was dissolved in tetrahydro-furan (10.0 ml), and thereto were added successively benzotriazol-1-yl-oxy-tris-pyrrolidino-phosphonium hexafluorophosphate (3.64 g) and triethylamine (1.80 ml) under ice-cooling, and the mixture was stirred at room temperature. Ten hours later, to the reaction solution was added a 1N aqueous hydrochloric acid solution under ice-cooling, and the mixture was extracted with ethyl acetate. The organic layer was washed successively with a saturated aqueous sodium hydrogen carbonate solution and a saturated aqueous sodium chloride solution, dried over sodium sulfate, filtered and concentrated under reduced pressure. The obtained residue was purified by silica gel column chromatography (the developing solvent: hexane/ethyl acetate=10/1, 5/1) to give the title compound (1.10 g) as a colorless liquid.

$^{1}$H NMR (400 MHz, $CDCl_3$) δ 7.43-7.27 (m, 5H), 5.32 (s, 2H), 3.82 (s, 1H), 1.61 (s, 3H).

Reference Example 216

Methyl 4-{(1R)-1-[(benzyloxy)carbonyl]-2,2,2-trifluoro-1-methylethoxy}-5-nitro-2-(trifluoromethyl) benzoate

[Chemical formula 360]

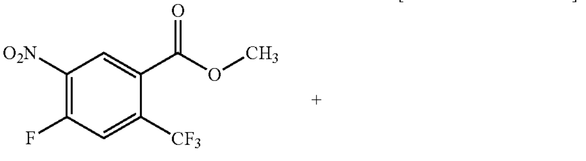

-continued

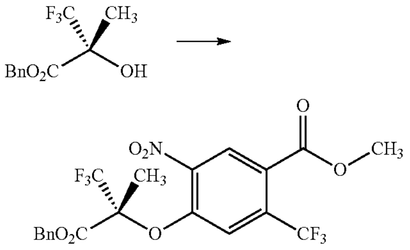

Using the compounds of Reference Example 214 and Reference Example 215, the title compound was obtained in a similar manner to Reference Example 22.

MS (ESI+) 496 ($M^+$+1, 8%).

Reference Example 217

Methyl (2R)-2-methyl-3-oxo-2,7-bis(trifluoromethyl)-3,4-dihydro-2H-1,4-benzoxazine-6-carboxylate

[Chemical formula 361]

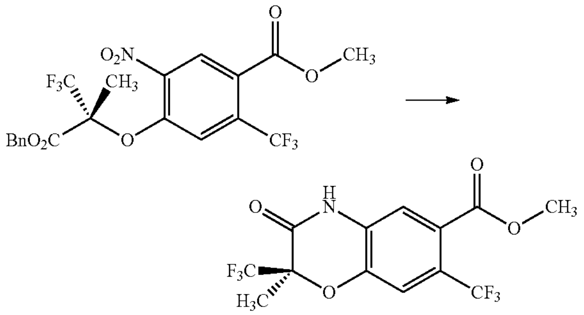

Using the compound of Reference Example 216, the title compound was obtained in a similar manner to Reference Example 2.

MS (ESI−) 356 ($M^+$−1, 100%).

Reference Example 218

Methyl (2R)-4-(2-{[(benzyloxy)carbonyl]amino}ethyl)-2-methyl-3-oxo-2,7-bis(trifluoromethyl)-3,4-dihydro-2H-1,4-benzoxazine-6-carboxylate

[Chemical formula 362]

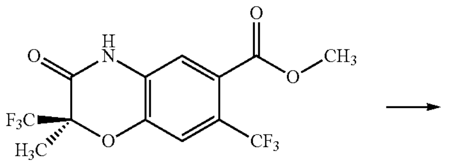

-continued

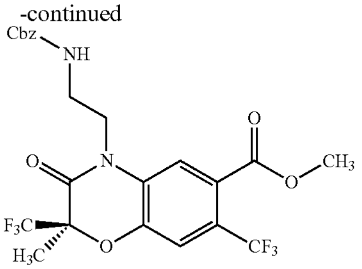

Using the compound of Reference Example 217, the title compound was obtained in a similar manner to Reference Example 3.

MS (ESI+) 535 ($M^+$+1, 60%).

Reference Example 219 tert-Butyl 3-[{[(2R)-4-(2-{[(benzyloxy)carbonyl]amino}ethyl)-2-methyl-3-oxo-2,7-bis(trifluoro-methyl)-3,4-dihydro-2H-1,4-benzoxazin-6-yl]carbonyl}(isopropyl)amino]piperidine-1-carboxylate

[Chemical formula 363]

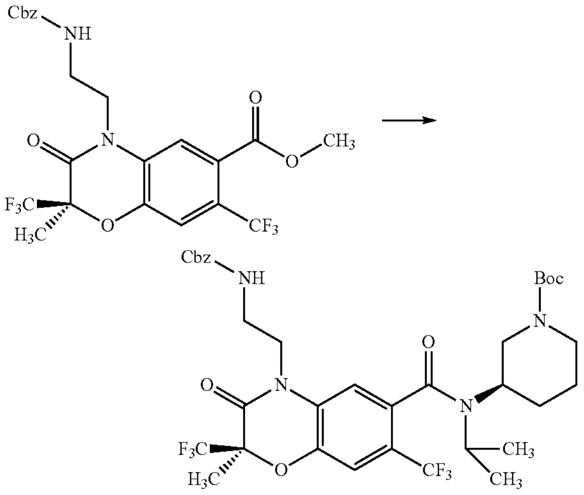

Using the compound of Reference Example 218, the title compound was obtained in a similar manner to Reference Example 5.

MS (ESI+) 745 ($M^+$+1, 22%).

Reference Example 220 tert-Butyl 3-[{[(2R)-4-(2-aminoethyl)-2-methyl-3-oxo-2,7-bis(trifluoromethyl)-3,4-dihydro-2H-1,4-benzoxazin-6-yl]carbonyl}(isopropyl)amino]piperidine-1-carboxylate

[Chemical formula 364]

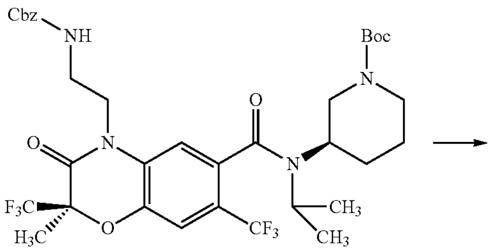

-continued

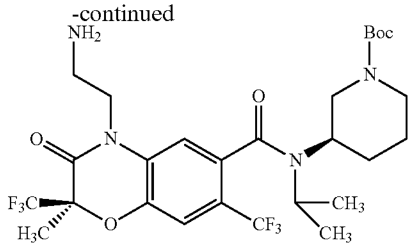

Using the compound of Reference Example 219, the title compound was obtained in a similar manner to Reference Example 139.

MS (ESI+) 611 ($M^{+}$+1, 100%).

Reference Example 221 tert-Butyl 3-(isopropyl{[(2R)-2-methyl-3-oxo-4-[2-(propionylamino)ethyl]-2,7-bis(trifluoromethyl)-3,4-dihydro-2H-1,4-benzoxazin-6-yl]carbonyl}amino)piperidine-1-carboxylate

[Chemical formula 365]

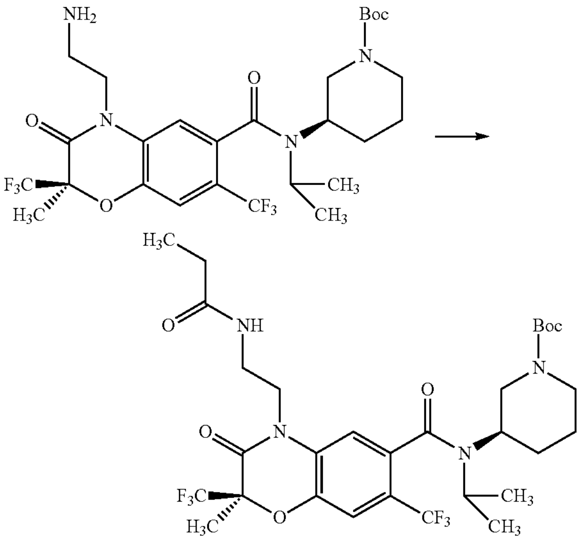

Using the compound of Reference Example 220, the title compound was obtained in a similar manner to Reference Example 132.

MS (ESI+) 667 ($M^{+}$+1, 68%).

Reference Example 222

Ethyl (2R)-2-hydroxy-3-(4-methoxyphenyl)propanoate

[Chemical formula 366]

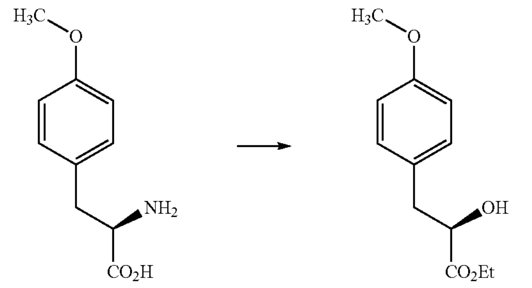

Commercially available O-methyl-D-tyrosine (5.00 g) was dissolved in 1,4-dioxane (62.5 ml), and thereto were added successively dropwise an aqueous sulfuric acid solution (5.4 g/17.5 ml of water) and an aqueous sodium nitrite solution (6.3 g/15.0 ml of water) under ice-cooling, and the mixture was stirred at room temperature. Ten hours later, to the reaction solution was added a saturated aqueous sodium hydrogen carbonate solution, and the mixture was extracted with ethyl acetate. The organic layer was washed with a saturated aqueous sodium chloride solution, dried over sodium hydrogen sulfate, filtered, and concentrated under reduced pressure. The resultant was duly dried, and then, the obtained residue was dissolved in ethanol (50 ml), and further thereto was added conc. sulfuric acid (200 μL). The mixture was refluxed for 15 hours, and the reaction solution was added dropwise into ice-water (50 ml), and the mixture was extracted with ethyl acetate (50 ml). The organic layer was washed successively with a saturated aqueous sodium hydrogen carbonate solution and a saturated aqueous sodium chloride solution, dried over sodium sulfate, filtered, and concentrated under reduced pressure. The obtained residue was purified by silica gel column chromatography (the developing solvent: hexane/ethyl acetate=5/1) to give the title compound (3.40 g) as a colorless liquid.

MS (ESI+) 225 ($M^{+}$+1, 33%).

Reference Example 223

Methyl 4-[(1S)-2-(benzyloxy)-1-(4-methoxybenzyl)-2-oxoethoxy]-5-nitro-2-(trifluoromethyl)benzoate

[Chemical formula 367]

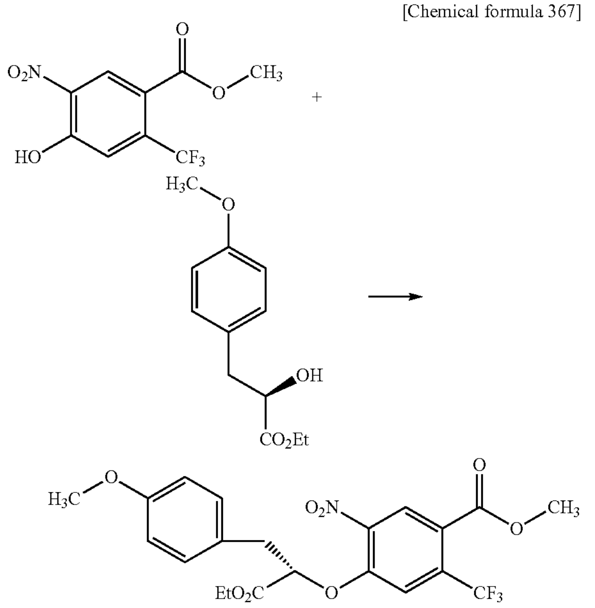

Using the compound of Reference Example 52, the title compound was obtained in a similar manner to Reference Example 26.

MS (ESI+) 472 ($M^{+}$+1, 47%).

Reference Example 224

Methyl (2S)-2-(4-methoxybenzyl)-3-oxo-7-(trifluoromethyl)-3,4-dihydro-2H-1,4-benzoxazine-6-carboxylate

[Chemicla formula 368]

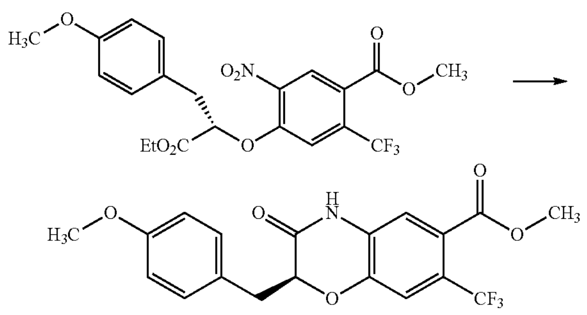

Using the compound of Reference Example 223, the title compound was obtained in a similar manner to Reference Example 2.

MS (ESI+) 396 ($M^+$+1, 100%).

Reference Example 225 tert-Butyl 3-(isopropyl{[(2S)-2-(4-methoxybenzyl)-3-oxo-4-[2-(propionylamino)ethyl]-7-(trifluoro-methyl)-3,4-dihydro-2H-1,4-benzoxazin-6-yl] carbonyl}amino)piperidine-1-carboxylate

[Chemical formula 369]

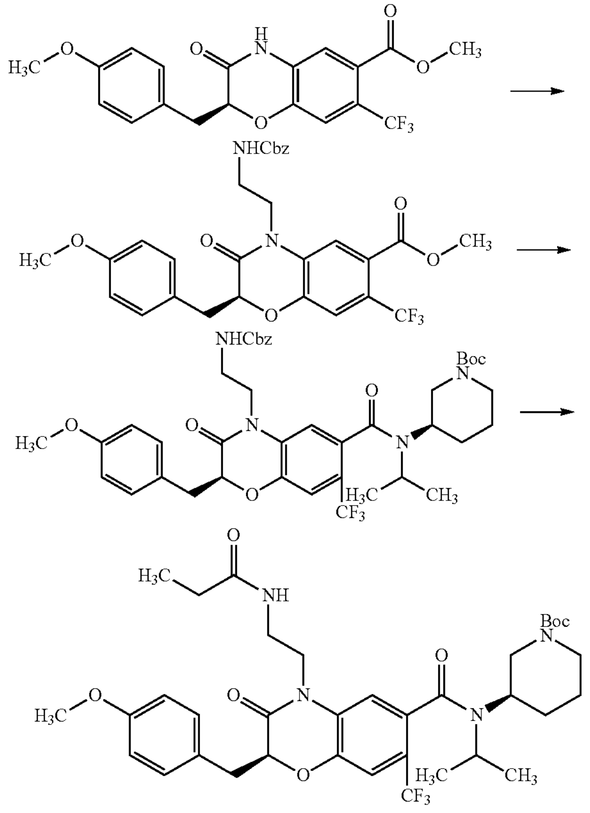

Using the compound of Reference Example 224, the title compound was obtained in a similar manner to Reference Example 137.

MS (ESI+) 705 ($M^+$+1, 15%).

Reference Example 226

Methyl 3-amino-5-chloro-4-hydroxybenzoate

[Chemical formula 370]

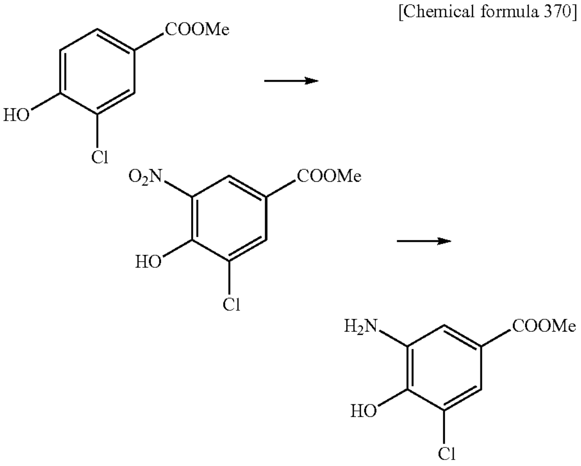

Using methyl 3-chloro-4-hydroxybenzoate, the title compound was obtained in a similar manner to Reference Example 53.

MS (ESI+) 202 ($M^+$+1, 100%).

Reference Example 227

Methyl 8-chloro-2,2-dimethyl-3-oxo-3,4-dihydro-2H-1,4-benzoxazine-6-carboxylate

[Chemical formula 371]

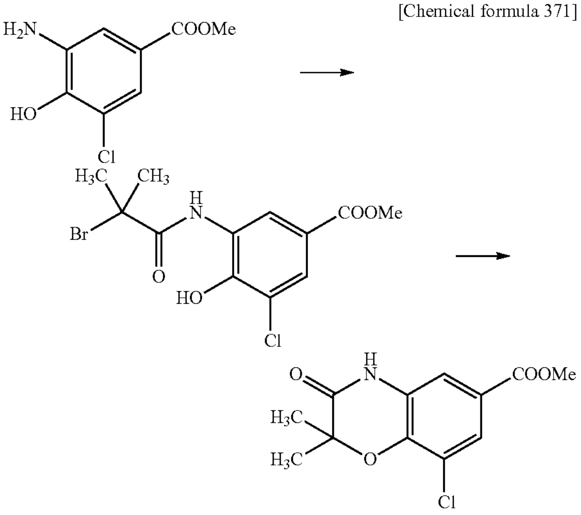

Using the compound of Reference Example 226, the title compound was obtained in a similar manner to Reference Example 55.

MS (ESI+) 270 ($M^+$+1, 100%).

Reference Example 228

Methyl 8-chloro-4-(4-methoxybutyl)-2,2-dimethyl-3-oxo-3,4-dihydro-2H-1,4-benzoxazine-6-carboxylate

[Chemical formula 372]

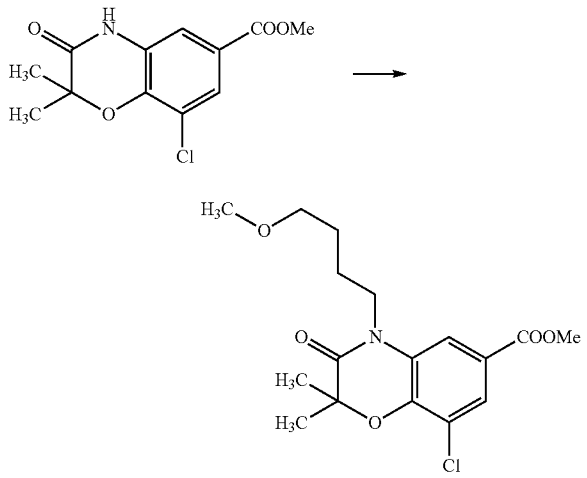

Using the compound of Reference Example 227, the title compound was obtained in a similar manner to Reference Example 3.

MS (ESI+) 356 ($M^{+}$+1, 100%).

Reference Example 229 tert-Butyl (3R)-3-[{[8-chloro-4-(4-methoxybutyl)-2,2-dimethyl-3-oxo-3,4-dihydro-2H-1,4-benzoxazin-6-yl]carbonyl}(isopropyl)amino]piperidine-1-carboxylate

[Chemical formula 373]

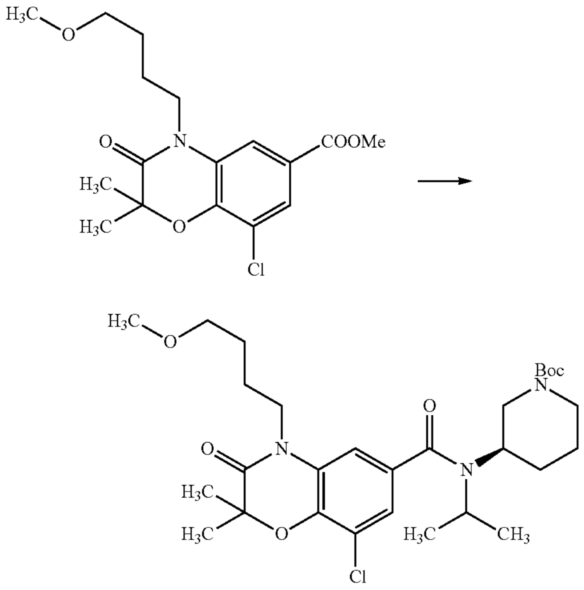

Using the compound of Reference Example 228, the title compound was obtained in a similar manner to Reference Example 5.

MS (ESI+) 566 ($M^{+}$+1, 100%).

Reference Example 230 tert-Butyl (3R)-3-[{[7,8-dichloro-4-(4-methoxybutyl)-2,2-dimethyl-3-oxo-3,4-dihydro-2H-1,4-benzoxazin-6-yl]carbonyl}(isopropyl)amino]piperidine-1-carboxylate

[Chemical formula 374]

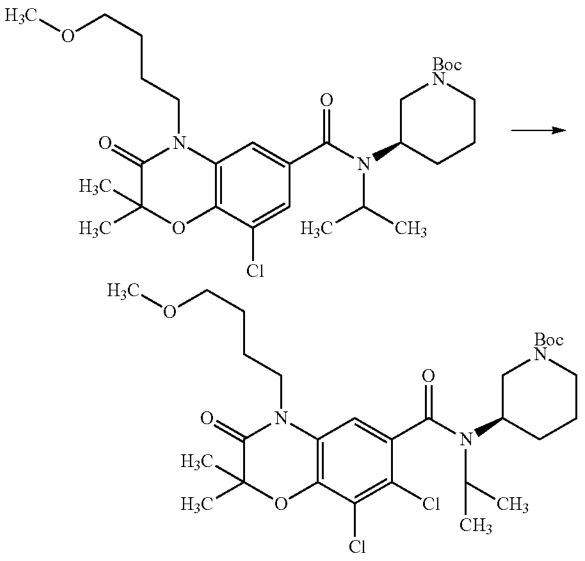

Using the compound of Reference Example 229, the title compound was obtained in a similar manner to Reference Example 12.

MS (ESI+) 600 ($M^{+}$+1, 100%).

Reference Example 231 tert-Butyl (3R)-3-[{[7-bromo-8-chloro-4-(4-methoxybutyl)-2,2-dimethyl-3-oxo-3,4-dihydro-2H-1,4-benzoxazin-6-yl]carbonyl}(isopropyl)amino]piperidine-1-carboxylate

[Chemical formula 375]

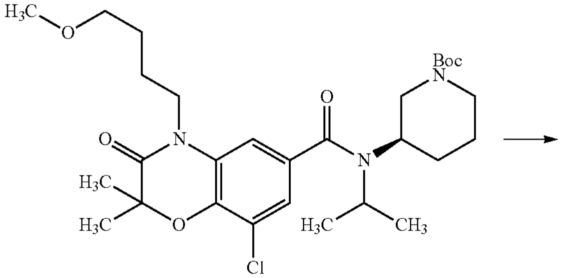

-continued

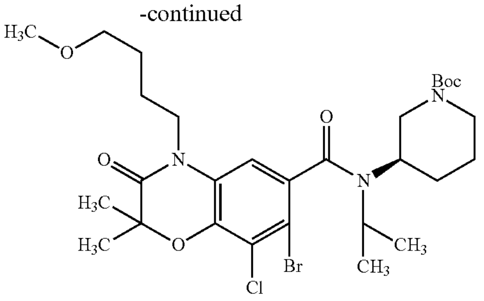

Using the compound of Reference Example 230, the title compound was obtained in a similar manner to Reference Example 6.

MS (ESI+) 644 ($M^{+}$+1, 100%).

Reference Example 232

2-Amino-4-bromo-6-fluorophenol

[Chemical formula 376]

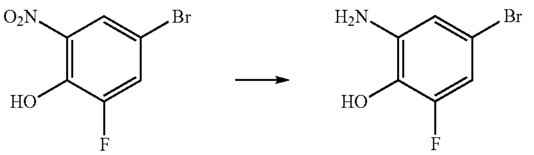

Using the compound of 4-bromo-2-fluoro-6-nitrophenol, the title compound was obtained in a similar manner to Reference Example 53.

MS (ESI+) 205 ($M^{+}$+1, 100%).

Reference Example 233

6-Bromo-8-fluoro-2,2-dimethyl-2H-1,4-benzoxazin-3(4H)-one

[Chemical formula 377]

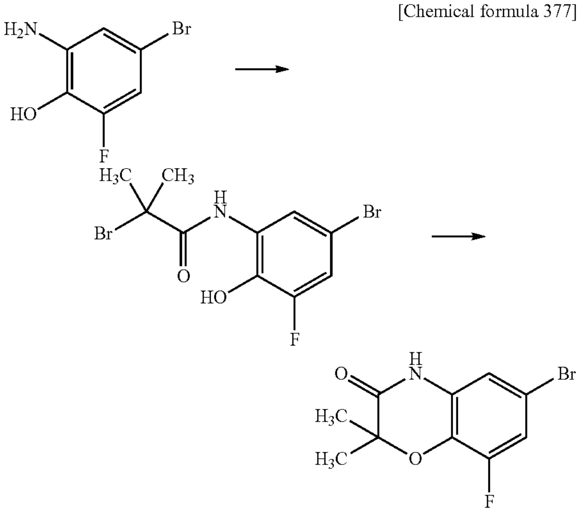

Using the compound of Reference Example 232, the title compound was obtained in a similar manner to Reference Example 55.

MS (ESI+) 273 ($M^{+}$+1, 100%).

Reference Example 234

6-Bromo-8-fluoro-4-(4-methoxybutyl)-2,2-dimethyl-2H-1,4-benzoxazin-3(4H)-one

[Chemical formula 378]

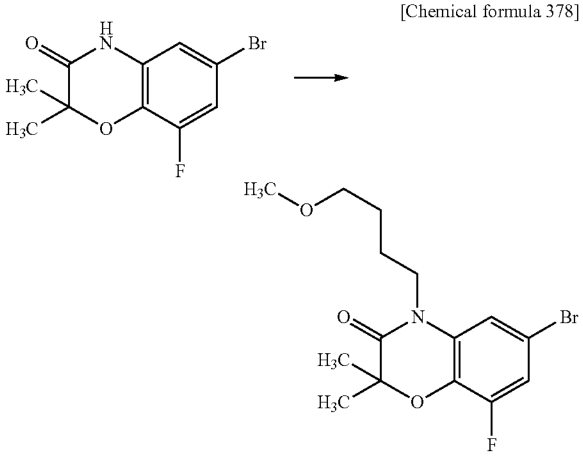

Using the compound of Reference Example 233, the title compound was obtained in a similar manner to Reference Example 3.

MS (ESI+) 360 ($M^{+}$+1, 100%).

Reference Example 235

Methyl 8-fluoro-4-(4-methoxybutyl)-2,2-dimethyl-3-oxo-3,4-dihydro-2H-1,4-benzoxazine-6-carboxylate

[Chemical formula [379]

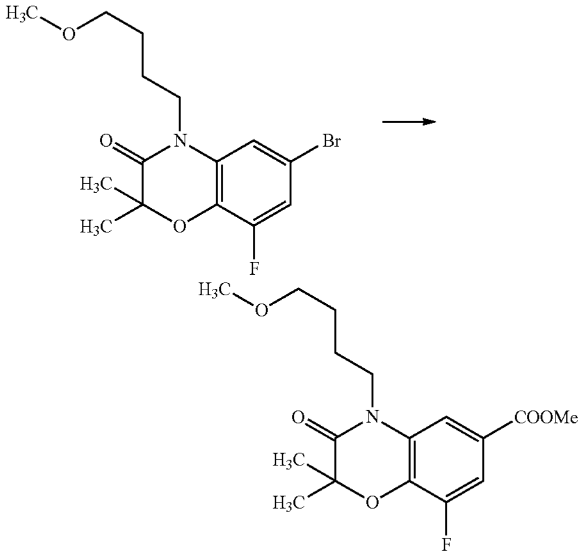

Using the compound of Reference Example 234, the title compound was obtained in a similar manner to Reference Example 25.

MS (ESI+) 340 ($M^{+}$+1, 100%).

Reference Example 236 tert-Butyl (3R)-3-[{[8-fluoro-4-(4-methoxybutyl)-2,2-dimethyl-3-oxo-3,4-dihydro-2H-1,4-benzoxazin-6-yl]carbonyl}(isopropyl)amino]piperidine-1-carboxylate

[Chemical formula 380]

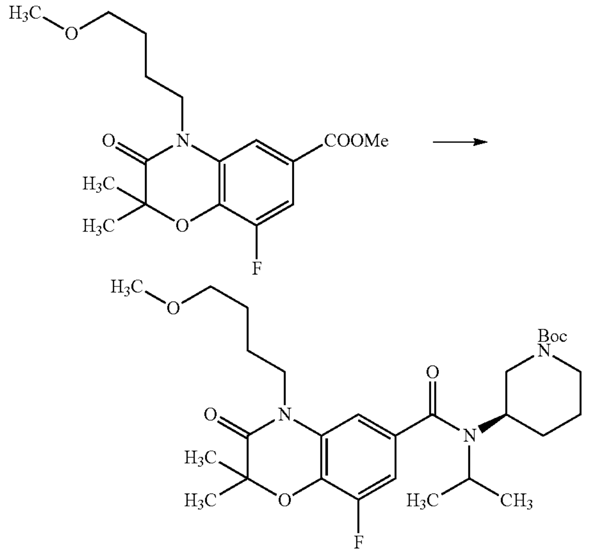

Using the compound of Reference Example 235, the title compound was obtained in a similar manner to Reference Example 5.

MS (ESI+) 550 ($M^+$+1, 100%).

Reference Example 237

Methyl 2-(4-bromo-3-methyl-2-nitrophenoxy)-2-methylpropanoate

[Chemical formula 381]

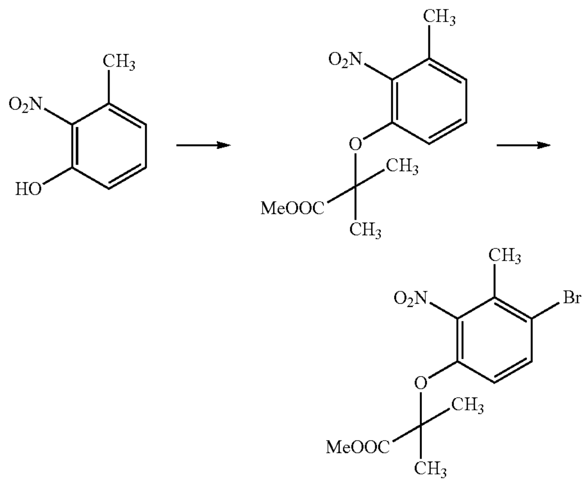

Using the compound of 3-methyl-2-nitrophenol, the title compound was obtained in a similar manner to Reference Example 1 and Reference Example 6.

MS (ESI+) 332 ($M^+$+1, 100%).

Reference Example 238 tert-Butyl (3R)-3-[{[2-[(dimethylamino)carbonyl]-4-(4-methoxybutyl)-2-methyl-3-oxo-3,4-dihydro-2H-1,4-benzoxazin-6-yl]carbonyl}(isopropyl)amino]piperidine-1-carboxylate

[Chemical formula 382]

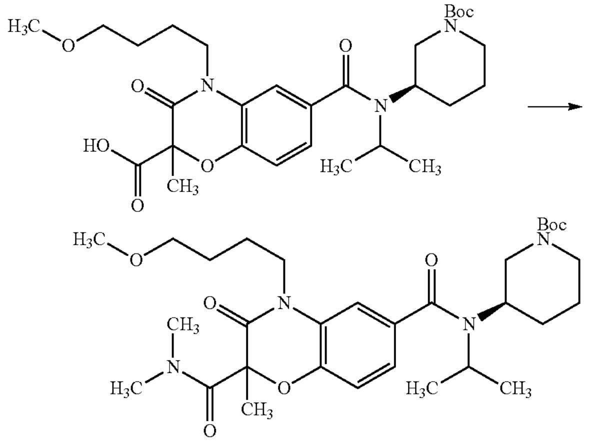

Using the compound of Reference Example 34, the title compound was obtained in a similar manner to Reference Example 197.

MS (ESI+) 589 ($M^+$+1, 34%).

Reference Example 239 tert-Butyl (3R)-3-(isopropyl{[4-(4-methoxybutyl)-2-methyl-2-(morpholin-4-ylcarbonyl)-3-oxo-3,4-dihydro-2H-1,4-benzoxazin-6-yl]carbonyl}amino)piperidine-1-carboxylate

[Chemical formula 383]

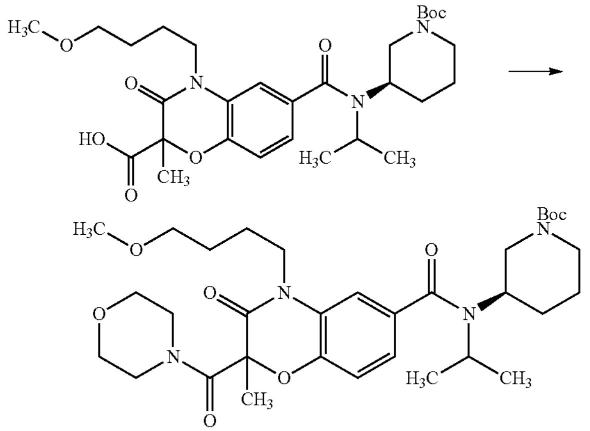

Using the compound of Reference Example 34, the title compound was obtained in a similar manner to Reference Example 197.

MS (ESI+) 631 ($M^{+}$+1, 32%).

Reference Example 240 tert-Butyl (3R)-3-{isopropyl[(4-(4-methoxybutyl)-2-methyl-2-{[methyl(tetrahydro-2H-pyran-4-ylmethyl) amino]carbonyl}-3-oxo-3,4-dihydro-2H-1,4-benzoxazin-6-yl)carbonyl]amino}piperidine-1-carboxylate

[Chemical formula 384]

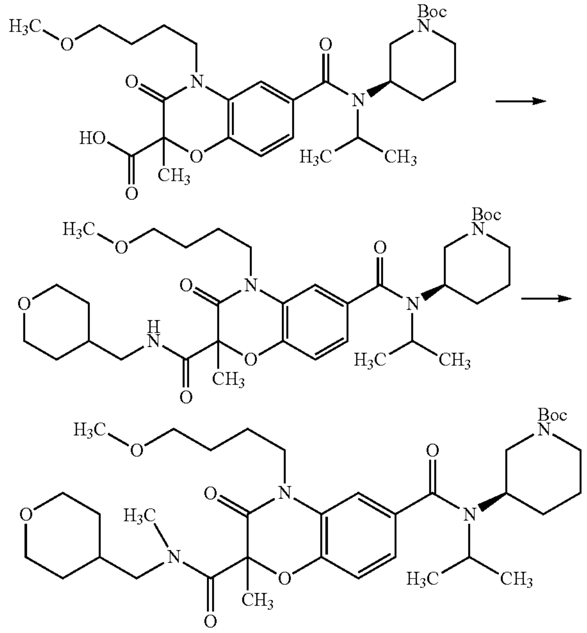

Using the compound of Reference Example 34, the title compound was obtained in a similar manner to Reference Example 197 and Reference Example 200.

MS (ESI+) 673 ($M^{+}$+1, 32%).

Reference Example 241 tert-Butyl (3R)-3-[{[7-chloro-2-[(dimethylamino) carbonyl]-4-(4-methoxybutyl)-2-methyl-3-oxo-3,4-dihydro-2H-1,4-benzoxazin-6-yl]carbonyl}(isopropyl)amino]piperidine-1-carboxylate

[Chemical formula 385]

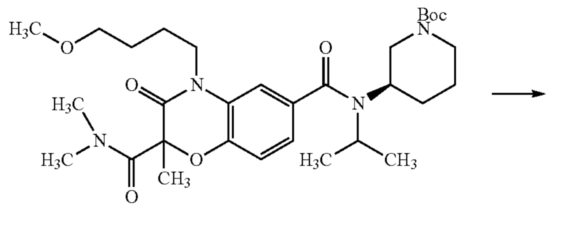

-continued

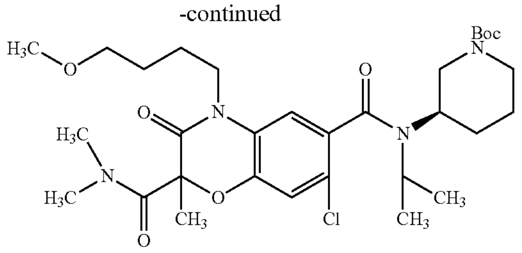

Using the compound of Reference Example 238, the title compound was obtained in a similar manner to Reference Example 12.

MS (ESI+) 623 ($M^{+}$+1, 35%).

Reference Example 242 tert-Butyl (3R)-3-[{[7-chloro-4-(4-methoxybutyl)-2-methyl-2-(morpholin-4-ylcarbonyl)-3-oxo-3,4-dihydro-2H-1,4-benzoxazin-6-yl]carbonyl}(isopropyl) amino]piperidine-1-carboxylate

[Chemical formula 386]

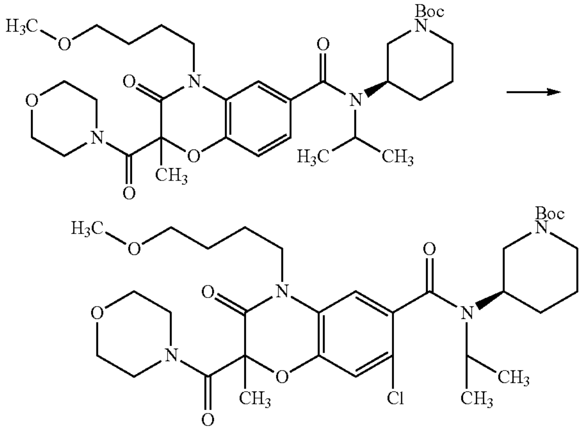

Using the compound of Reference Example 239, the title compound was obtained in a similar manner to Reference Example 12.

MS (ESI+) 665 ($M^{+}$+1, 40%).

Reference Example 243 tert-Butyl (3R)-3-[[(7-chloro-4-(4-methoxybutyl)-2-methyl-2-{[methyl (tetrahydro-2H-pyran-4-ylmethyl)amino]carbonyl}-3-oxo-3,4-dihydro-2H-1,4-benzoxazin-6-yl)carbonyl](isopropyl)amino]-piperidine-1-carboxylate

[Chemical formula 387]

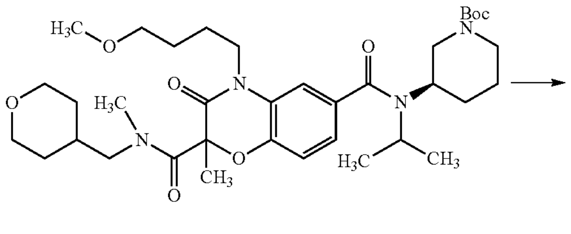

-continued

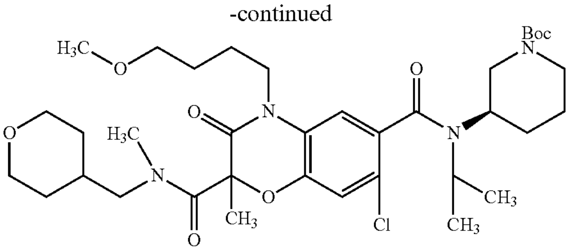

Using the compound of Reference Example 240, the title compound was obtained in a similar manner to Reference Example 12.

MS (ESI+) 707 ($M^{+}$+1, 39%).

Reference Example 244 tert-Butyl (3R)-3-[{[7-chloro-4-(4-methoxybutyl)-2-(methoxymethyl)-2-methyl-3-oxo-3,4-dihydro-2H-1,4-benzoxazin-6-yl]carbonyl}(isopropyl)amino]piperidine-1-carboxylate

[Chemical formula 388]

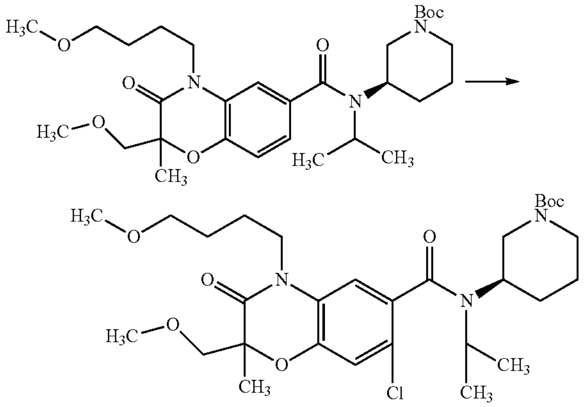

Using the compound of Reference Example 245, the title compound was obtained in a similar manner to Reference Example 12.

MS (ESI+) 596 ($M^{+}$+1, 33%).

Reference Example 245 tert-Butyl (3R)-3-(isopropyl{[4-(4-methoxybutyl)-2-(methoxymethyl)-2-methyl-3-oxo-3,4-dihydro-2H-1,4-benzoxazin-6-yl]carbonyl}amino)piperidine-1-carboxylate

[Chemical formula 389]

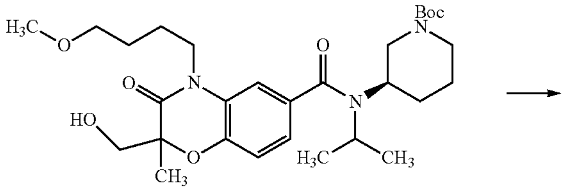

-continued

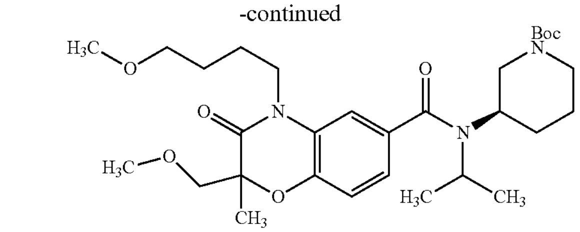

Using the compound of Reference Example 35, the title compound was obtained in a similar manner to Reference Example 36.

MS (ESI+) 562 ($M^{+}$+1, 42%).

Reference Example 246 tert-Butyl (3R)-3-[{[7-bromo-2-(ethoxymethyl)-4-(4-methoxybutyl)-2-methyl-3-oxo-3,4-dihydro-2H-1,4-benzoxazin-6-yl]carbonyl}(isopropyl)amino]piperidine-1-carboxylate

[Chemical formula 390]

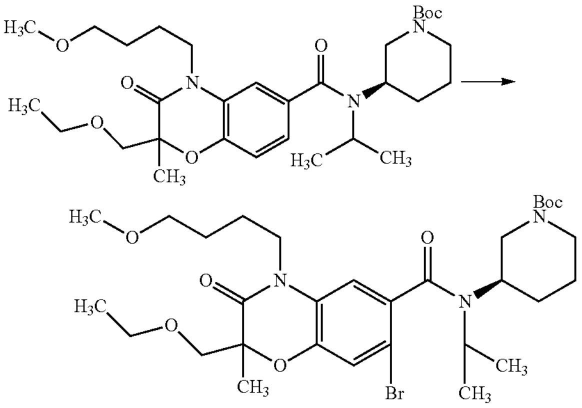

Using the compound of Reference Example 36, the title compound was obtained in a similar manner to Reference Example 6.

MS (ESI+) 654 ($M^{+}$+1, 43%).

Reference Example 247 tert-Butyl (3R)-3-[{[2-(ethoxymethyl)-4-(4-methoxybutyl)-2,7-dimethyl-3-oxo-3,4-dihydro-2H-1,4-benzoxazin-6-yl]carbonyl}(isopropyl)amino]piperidine-1-carboxylate

[Chemical formula 391]

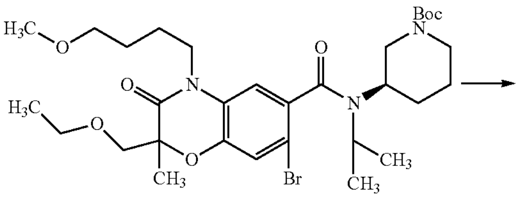

-continued

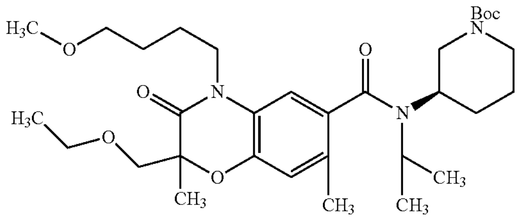

Using the compound of Reference Example 246, the title compound was obtained in a similar manner to Reference Example 10.

MS (ESI+) 590 ($M^{+}$+1, 43%).

Reference Example 248

Ethyl 6-bromo-2-methyl-3-oxo-3,4-dihydro-2H-1,4-benzoxazine-2-carboxylate

[Chemicla formula 392]

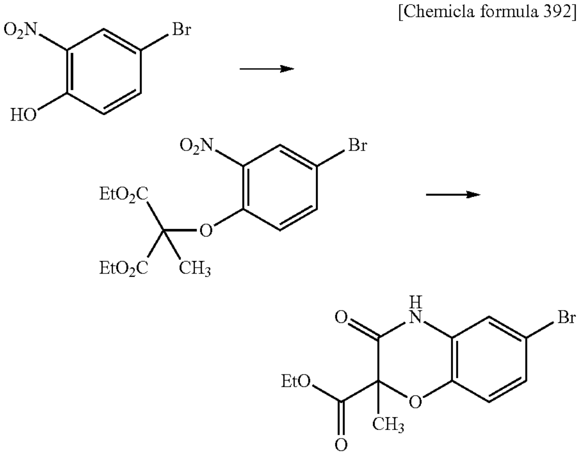

Using 4-bromo-2-nitrophenol, the title compound was obtained in a similar manner to Reference Example 33.

MS (ESI+) 313 ($M^{+}$+1, 76%).

Reference Example 249

Ethyl 6-bromo-4-(3-methoxyl)propyl)-2-methyl-3-oxo-3,4-dihydro-2H-1,4-benzoxazine-2-carboxylate

[Chemical formula 393]

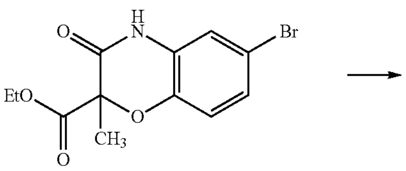

-continued

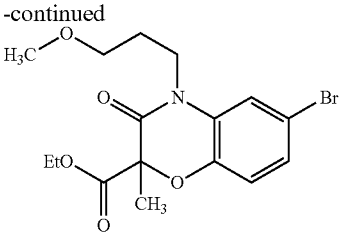

Using the compound of Reference Example 248, the title compound was obtained in a similar manner to Reference Example 5.

MS (ESI+) 386 ($M^{+}$+1, 87%).

Reference Example 250

6-Bromo-4-(3-methoxypropyl)-N,N,2-trimethyl-3-oxo-3,4-dihydro-2H-1,4-benzoxazine-2-carboxamide

[Chemical formula 394]

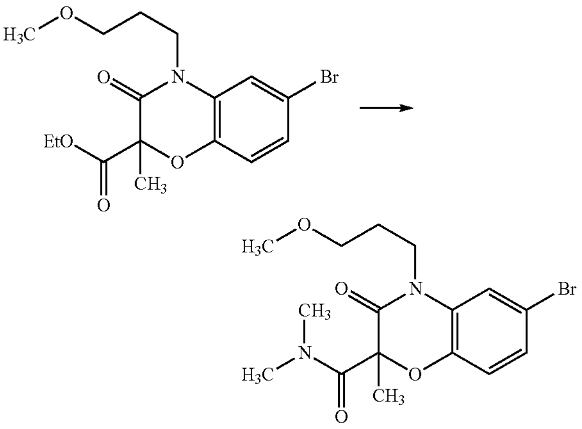

Using the compound of Reference Example 249, the title compound was obtained in a similar manner to Reference Example 34 and Reference Example 197.

MS (ESI+) 385 ($M^{+}$+1, 72%).

Reference Example 251

Methyl 2-[(dimethylamino)carbonyl]-4-(3-methoxypropyl)-2-methyl-3-oxo-3,4-dihydro-2H-1,4-benzoxazine-6-carboxylate

[Chemical formula 395]

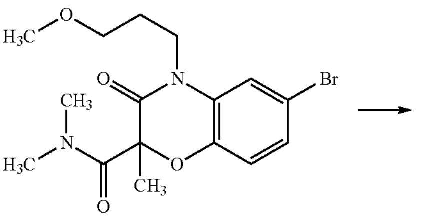

-continued

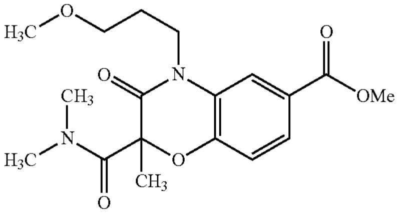

Using the compound of Reference Example 250, the title compound was obtained in a similar manner to Reference Example 25.

MS (ESI+) 365 ($M^+$+1, 76%).

Reference Example 252 tert-Butyl (3R)-3-[{[2-[(dimethylamino)carbonyl]-4-(3-methoxypropyl)-2-methyl-3-oxo-3,4-dihydro-2H-1,4-benzoxazin-6-yl]carbonyl}(isopropyl)amino]piperidine-1-carboxylate

[Chemical formula 396]

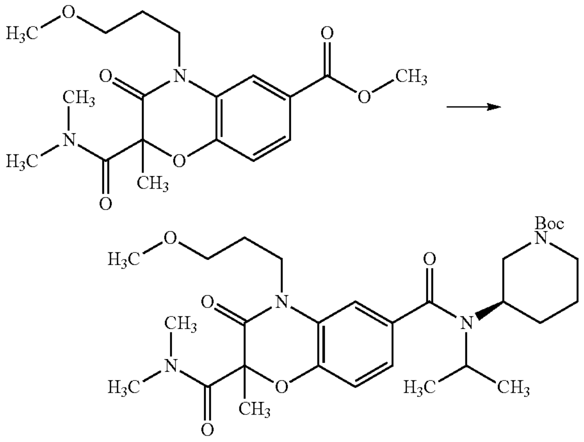

Using the compound of Reference Example 251, the title compound was obtained in a similar manner to Reference Example 5.

MS (ESI+) 575 ($M^+$+1, 38%).

Reference Example 253

6-Bromo-2',3',5',6'-tetrahydrospiro[1,4-benzoxazine-2,4'-pyran]-3(4H)-one

[Chemical formula 397]

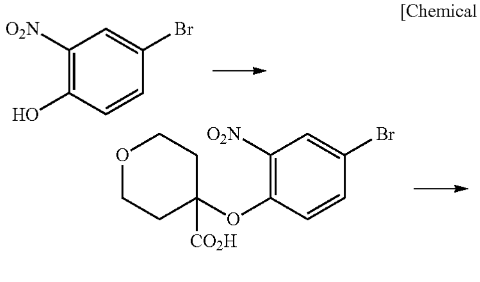

-continued

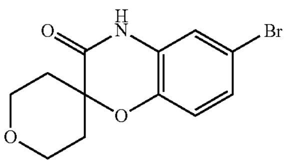

To a solution of 4-bromo-2-nitrophenol (5.0 g) in tetrahydrofuran (80 ml) was added sodium hydroxide powder (7.8 g), and the mixture was stirred at room temperature for 15 minutes, and further thereto was added tetrahydro-4H-pyran-4-one (180 ml). Under ice-cooling, chloroform (7.3 ml) was added thereto dropwise, and the mixture was stirred for one hour. Then, the mixture was further stirred at room temperature overnight. To the reaction mixture was added 2N hydrochloric acid, and the mixture was extracted with chloroform. The organic layer was washed with a saturated aqueous sodium chloride solution, dried over sodium sulfate, filtered, and concentrated under reduced pressure. Using the obtained residue, the title compound (1.6 g) was obtained in a similar manner to Reference Example 2.

MS (ESI+) 298 ($M^+$+1, 85%).

Reference Example 254

Methyl 4-(4-methoxybutyl)-3-oxo-2',3,3',4,5',6'-hexahydrospiro[1,4-benzoxazine-2,4'-pyran]-6-carboxylate

[Chemicla formula 398]

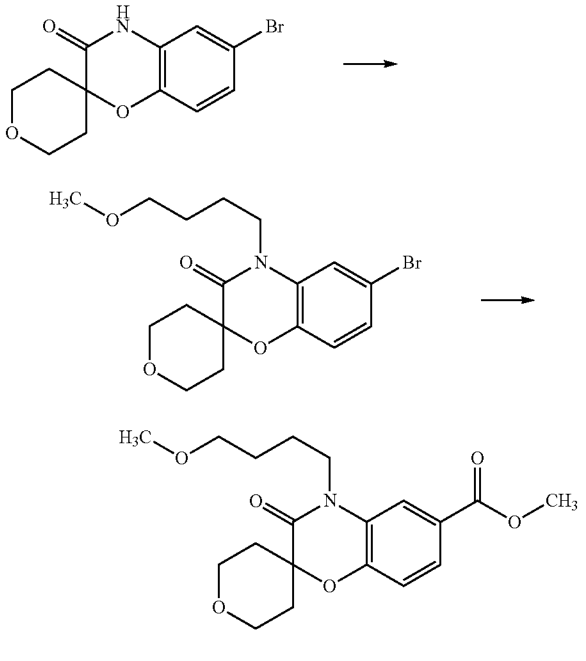

Using the compound of Reference Example 253, the title compound was obtained in a similar manner to Reference Example 25.

MS (ESI+) 364 ($M^+$+1, 86%).

Reference Example 255 tert-Butyl (3R)-3-(isopropyl{[4-(4-methoxybutyl)-3-oxo-2',3,3',4,5',6'-hexahydrospiro[1,4-benzoxazine-2,4'-pyran]-6-yl]carbonyl}amino)piperidine-1-carboxylate

[Chemical formula 399]

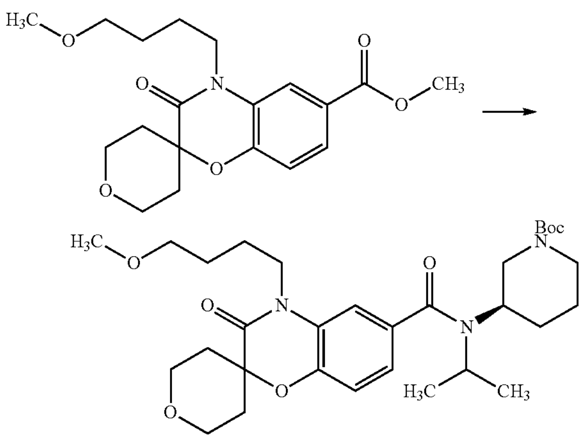

Using the compound of Reference Example 254, the title compound was obtained in a similar manner to Reference Example 5.

MS (ESI+) 574 ($M^{+}$+1, 34%).

Reference Example 256 tert-Butyl (3R)-3-[{[7-bromo-4-(4-methoxybutyl)-3-oxo-2',3,3',4,5',6'-hexahydrospiro[1,4-benzoxazine-2,4'-pyran]-6-yl]carbonyl}(isopropyl)amino]piperidine-1-carboxylate

[Chemical formula 400]

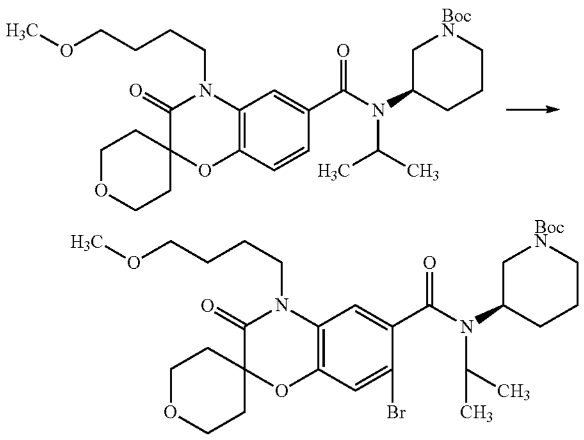

Using the compound of Reference Example 255, the title compound was obtained in a similar manner to Reference Example 6.

MS (ESI+) 652 ($M^{+}$+1, 33%).

Reference Example 257 tert-Butyl (3R)-3-(isopropyl{[4-(4-methoxybutyl)-7-methyl-3-oxo-2',3,3',4,5',6'-hexahydrospiro[1,4-benzoxazine-2,4'-pyran]-6-yl]carbonyl}amino)piperidine-1-carboxylate

[Chemical formula 401]

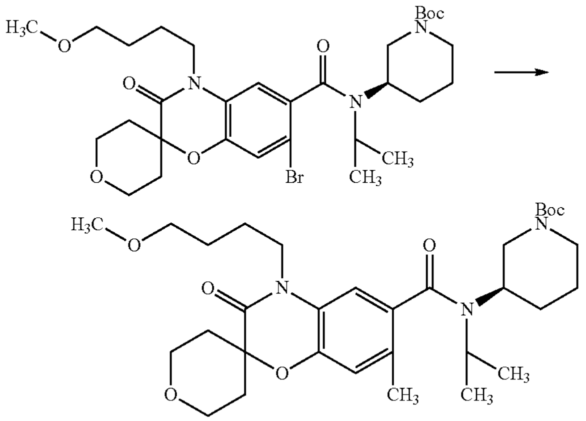

Using the compound of Reference Example 256, the title compound was obtained in a similar manner to Reference Example 10.

MS (ESI+) 588 ($M^{+}$+1, 100%).

Reference Example 258 tert-Butyl (3R)-3-[{[7-chloro-4-(4-methoxybutyl)-3-oxo-2',3,3',4,5',6'-hexahydrospiro[1,4-benzoxazine-2,4'-pyran]-6-yl]carbonyl}(isopropyl)amino]piperidine-1-carboxylate

[Chemical formula 402]

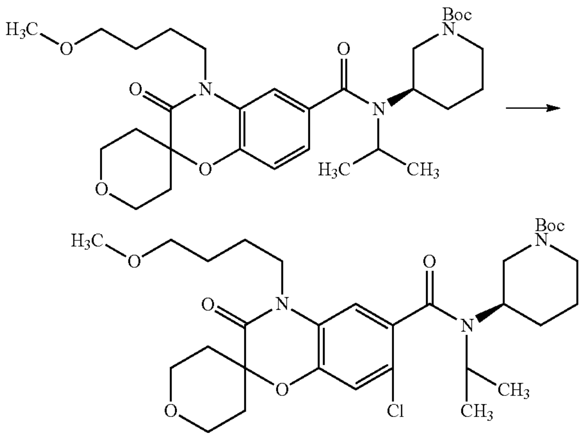

Using the compound of Reference Example 255, the title compound was obtained in a similar manner to Reference Example 12.

MS (ESI+) 608 ($M^{+}$+1, 100%).

Reference Example 259

Methyl [2-(6-bromo-3-oxo-2',3',5',6'-tetrahydrospiro[1,4-benzoxazine-2,4'-pyran]-4(3H)-yl)ethyl]-carbamate

[Chemical formula 403]

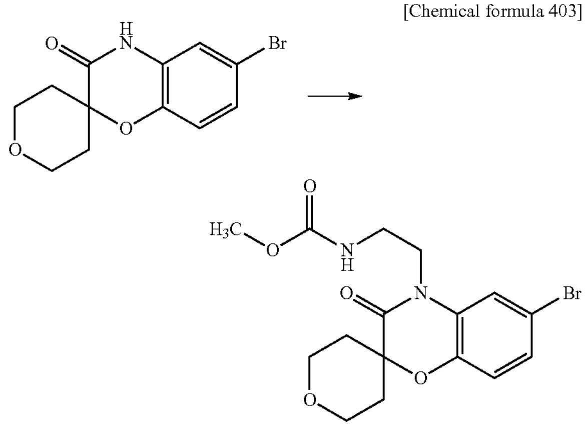

Using the compound of Reference Example 253, the title compound was obtained in a similar manner to Reference Example 162.

MS (ESI+) 399 ($M^{+}$+1, 65%).

Reference Example 260

Methyl 4-{2-[(methoxycarbonyl)amino]ethyl}-3-oxo-2',3,3',4,5',6'-hexahydrospiro[1,4-benzoxazine-2,4'-pyran]-6-carboxylate

[Chemical formula 404]

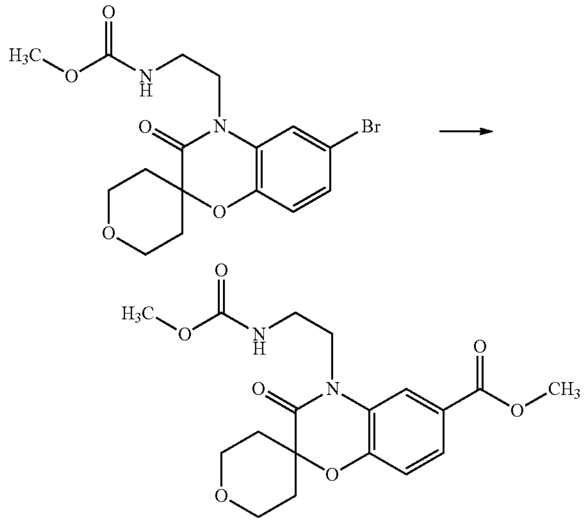

Using the compound of Reference Example 259, the title compound was obtained in a similar manner to Reference Example 25.

MS (ESI+) 379 ($M^{+}$+1, 67%).

Reference Example 261 tert-Butyl (3R)-3-{isopropyl[(4-{2-[(methoxycarbonyl)amino]ethyl}-3-oxo-2',3,3',4,5',6'-hexahydrospiro[1,4-benzoxazine-2,4'-pyran]-6-yl)carbonyl]amino}piperidine-1-carboxylate

[Chemical formula 405]

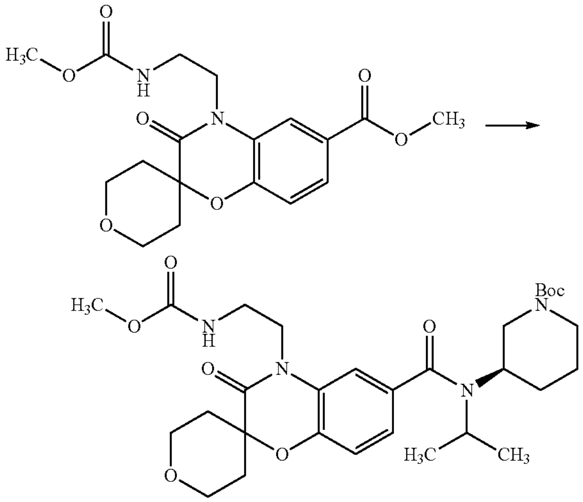

Using the compound of Reference Example 260, the title compound was obtained in a similar manner to Reference Example 5.

MS (ESI+) 589 ($M^{+}$+1, 33%).

Reference Example 262 tert-Butyl (3R)-3-[[(7-bromo-4-{2-[(methoxycarbonyl)amino]ethyl}-3-oxo-2',3,3',4,5',6'-hexahydrospiro[1,4-benzoxazine-2,4'-pyran]-6-yl)carbonyl](isopropyl)amino]piperidine-1-carboxylate

[Chemical formula 406]

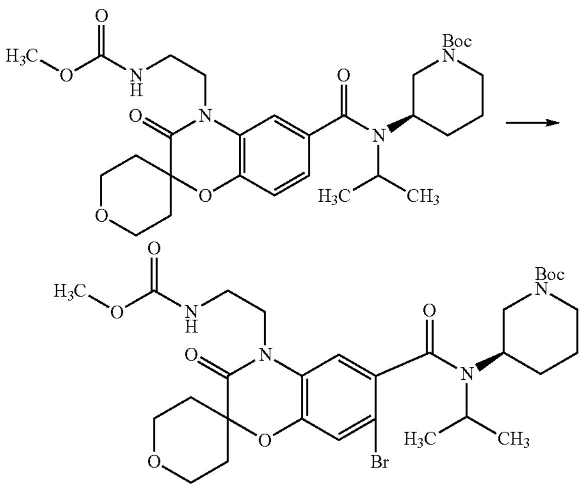

Using the compound of Reference Example 261, the title compound was obtained in a similar manner to Reference Example 6.

MS (ESI+) 667 ($M^{+}$+1, 42%).

Reference Example 263 tert-Butyl (3R)-3-{isopropyl[(4-{2-[(methoxycarbonyl)amino]ethyl}-7-methyl-3-oxo-2',3,3',4,5',6'-hexahydrospiro[1,4-benzoxazine-2,4'-pyran]-6-yl)carbonyl]amino}piperidine-1-carboxylate

[Chemical formula 407]

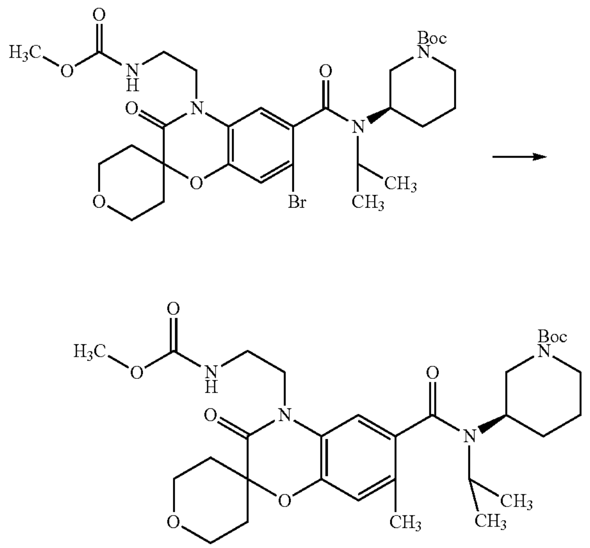

Using the compound of Reference Example 262, the title compound was obtained in a similar manner to Reference Example 10.

MS (ESI+) 603 ($M^{+}$+1, 46%).

Reference Example 264 tert-Butyl (3R)-3-[(4-acetoxy-2-methyl-5-nitrobenzoyl)(isopropyl)amino]piperidine-1-carboxylate

[Chemical formula 408]

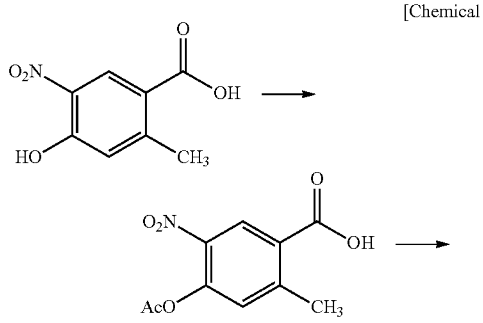

-continued

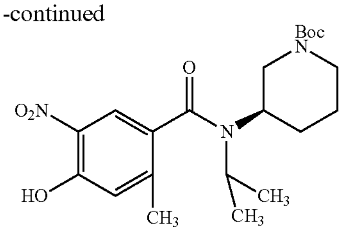

Using 4-hydroxy-2-methyl-5-nitrobenzoic acid, the title compound was obtained in a similar manner to Reference Example 31.

MS (ESI+) 422 ($M^{+}$+1, 12%).

Reference Example 265

Diethyl (4-{[[(3R)-1-(tert-butoxycarbonyl)piperidin-3-yl](isopropyl)amino]carbonyl}-5-methyl-2-nitrophenoxy)(methyl)malonate

[Chemical formula 409]

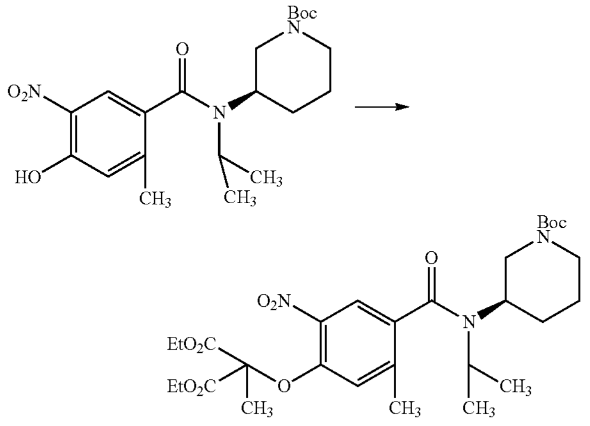

Using the compound of Reference Example 264, the title compound was obtained in a similar manner to Reference Example 32.

MS (ESI+) 594 ($M^{+}$+1, 25%).

Reference Example 266

Ethyl 6-{[[(3R)-1-(tert-butoxycarbonyl)piperidin-3-yl](isopropyl)amino]carbonyl}-4-(4-methoxybutyl)-2,7-dimethyl-3-oxo-3,4-dihydro-2H-1,4-benzoxazine-2-carboxylate

[Chemical Formula 410]

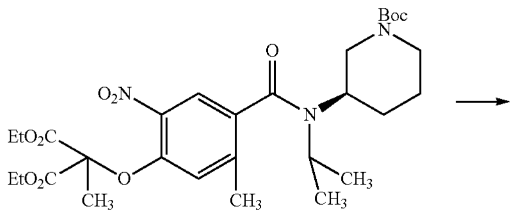

-continued

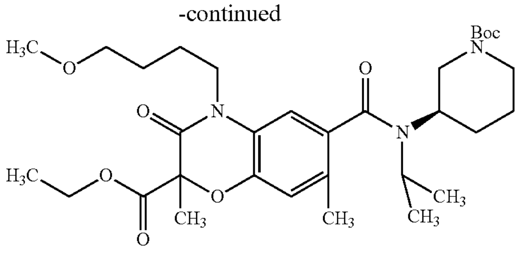

Using the compound of Reference Example 265, the title compound was obtained in a similar manner to Reference Example 33.

MS (ESI+) 604 ($M^{+}$+1, 32%).

Reference Example 267

6-{[[(3R)-1-(tert-Butoxycarbonyl)piperidin-3-yl](isopropyl)amino]carbonyl}-4-(4-methoxybutyl)-2,7-dimethyl-3-oxo-3,4-dihydro-2H-1,4-benzoxazine-2-carboxylic acid

[Chemical formula 411]

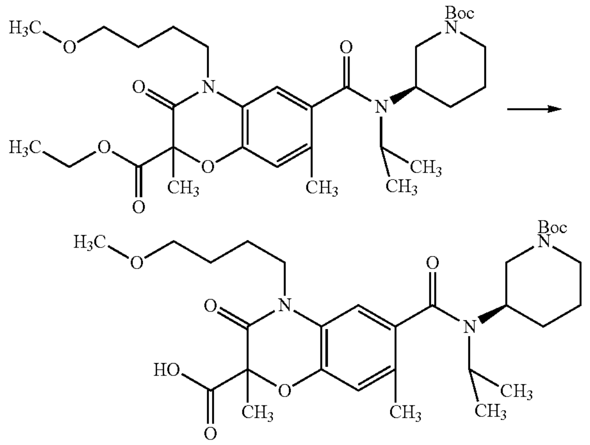

Using the compound of Reference Example 266, the title compound was obtained in a similar manner to Reference Example 34.

MS (ESI+) 576 ($M^{+}$+1, 46%).

Reference Example 268 tert-Butyl (3R)-3-[{[2-(hydroxymethyl)-4-(4-methoxybutyl)-2,7-dimethyl-3-oxo-3,4-dihydro-2H-1,4-benzoxazin-6-yl]carbonyl}(isopropyl)amino]piperidine-1-carboxylate

[Chemical formula 412]

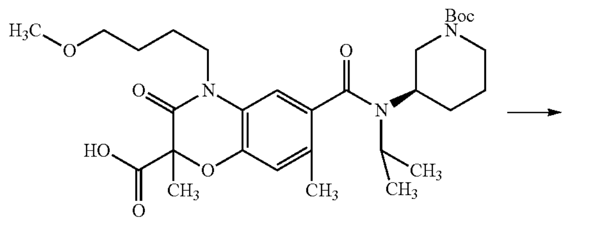

-continued

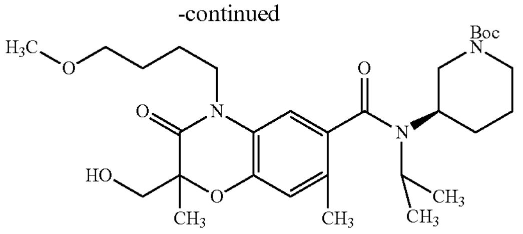

Using the compound of Reference Example 267, the title compound was obtained in a similar manner to Reference Example 35.

MS (ESI+) 562 ($M^{+}$+1, 43%).

Reference Example 269 tert-Butyl (3R)-3-(isopropyl{[4-(4-methoxybutyl)-2-(methoxymethyl)-2,7-dimethyl-3-oxo-3,4-dihydro-2H-1,4-benzoxazin-6-yl]carbonyl}amino)piperidine-1-carboxylate

[Chemical formula 413]

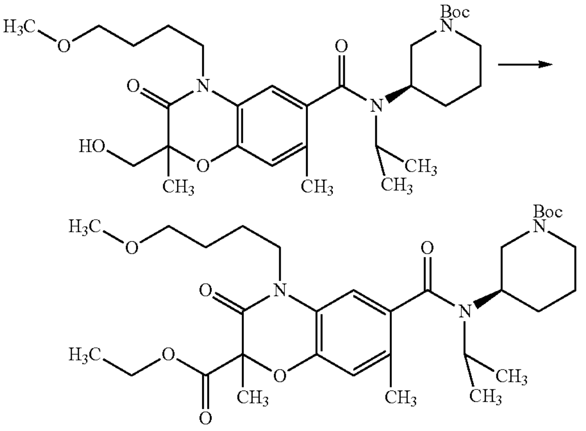

Using the compound of Reference Example 268, the title compound was obtained in a similar manner to Reference Example 36.

MS (ESI+) 576 ($M^{+}$+1, 28%).

Reference Example 270 tert-Butyl (3R)-3-[{[2-({[(ethylamino)carbonyl]oxy}methyl)-4-(4-methoxybutyl)-2,7-dimethyl-3-oxo-3,4-dihydro-2H-1,4-benzoxazin-6-yl]carbonyl}(isopropyl)amino]piperidine-1-carboxylate

[Chemical formula 414]

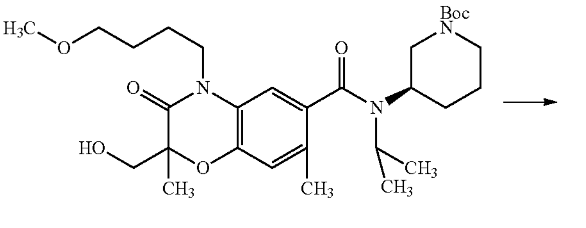

-continued

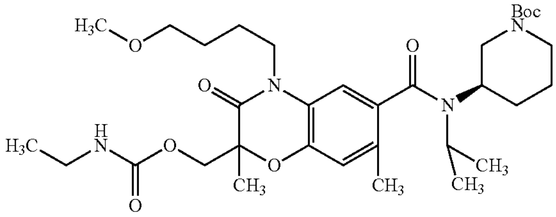

To a solution of tert-butyl (3R)-3-[{[2-(hydroxymethyl)-4-(4-methoxybutyl)-2,7-dimethyl-3-oxo-3,4-dihydro-2H-1,4-benzoxazin-6-yl]carbonyl}(isopropyl)amino]piperidine-1-carboxylate (66 mg) in tetrahydrofuran (1 ml) was added ethyl isocyanate (83 mg), and the mixture was stirred at 60° C. for 4 hours. The reaction mixture was cooled to room temperature, concentrated under reduced pressure, and the obtained residue was purified by silica gel column chromatography (hexane/ethyl acetate) to give the title compound (65 mg).

MS (ESI+) 633 ($M^{+}$+1, 29%).

Reference Example 271 tert-Butyl (3R)-3-{isopropyl[(4-(4-methoxybutyl)-2,7-dimethyl-3-oxo-2-{[(pyrrolidin-1-ylcarbonyl)oxy]methyl}-3,4-dihydro-2H-1,4-benzoxazin-6-yl)carbonyl]amino}piperidine-1-carboxylate

[Chemical formula 415]

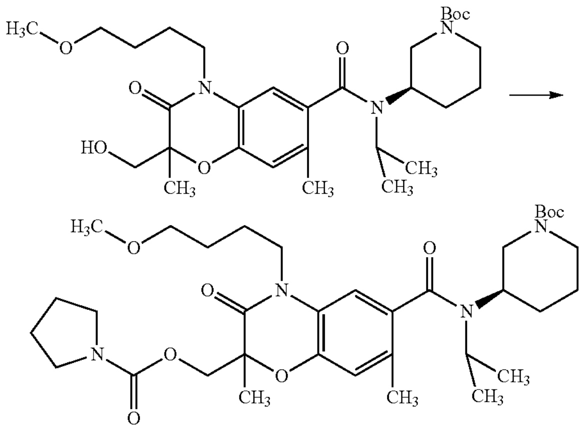

To a solution of tert-butyl (3R)-3-[{[2-(hydroxymethyl)-4-(4-methoxybutyl)-2,7-dimethyl-3-oxo-3,4-dihydro-2H-1,4-benzoxazin-6-yl]carbonyl}(isopropyl)amino]piperidine-1-carboxylate (60 mg), N,N'-carbonyldiimidazole (20 mg) in tetrahydrofuran (1 ml) was added diisopropylethylamine (95 μl), and the mixture was stirred at room temperature for one hour. To the reaction mixture was added pyrrolidine (10 μl), and the mixture was stirred at room temperature overnight. Water was added to the reaction mixture, and extracted with chloroform. The organic layer was washed with a saturated aqueous sodium chloride solution, dried over sodium sulfate, filtered, and concentrated under reduced pressure. The obtained residue was purified by silica gel column chromatography (hexane/ethyl acetate) to give the title compound (59 mg).

MS (ESI+) 659 ($M^{+}$+1, 31%).

Reference Example 272 tert-Butyl (3R)-3-[isopropyl({4-(4-methoxybutyl)-2,7-dimethyl-3-oxo-2-[({[(tetrahydro-2H-pyran-4-ylmethyl)amino]carbonyl}oxy)methyl]-3,4-dihydro-2H-1,4-benzoxazin-6-yl}carbonyl)amino]-piperidine-1-carboxylate

[Chemical formula 416]

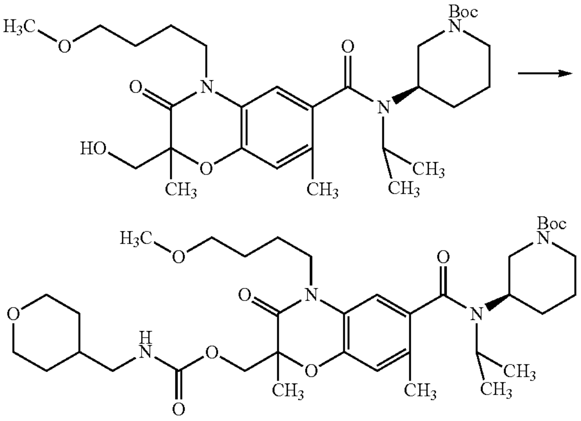

Using the compound of Reference Example 268, the title compound was obtained in a similar manner to Reference Example 271.

MS (ESI+) 703 ($M^{+}$+1, 28%).

Reference Example 273 tert-Butyl (3R)-3-(isopropyl{[4-(4-methoxybutyl)-2-(methoxymethyl)-2-methyl-3-oxo-7-(trifluoro-methyl)-3,4-dihydro-2H-1,4-benzoxazin-6-yl]carbonyl}amino)piperidine-1-carboxylate

[Chemical formula 417]

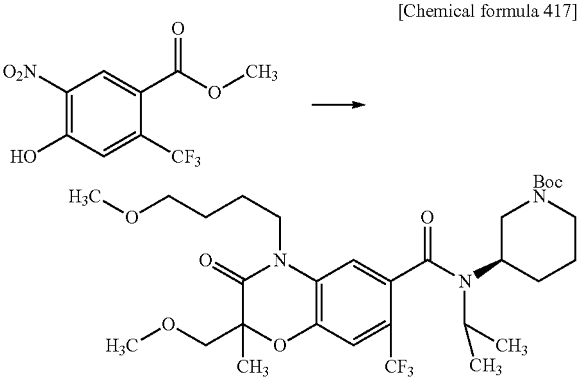

Using the compound of Reference Example 52, the title compound was obtained in a similar manner to Reference Example 36.

MS (ESI+) 630 ($M^{+}$+1, 30%).

Reference Example 274

2-Bromo-5-(methoxymethoxy)benzaldehyde

[Chemical formula 418]

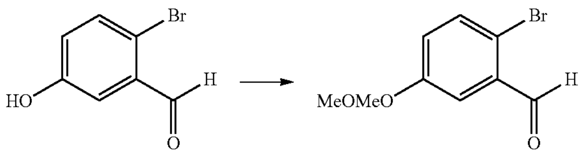

To a solution of 2-bromo-5-hydroxybenzaldehyde (4.4 g) in tetrahydrofuran (100 ml) were added sodium hydride (1.2 g) and chloromethyl methyl ether (2.1 ml), and the mixture was stirred at room temperature overnight. To the reaction mixture was added a saturated aqueous ammonium chloride solution, and extracted with ethyl acetate. The organic layer was washed with a saturated aqueous sodium chloride solution, dried over sodium sulfate, filtered, and concentrated under reduced pressure. The obtained residue was purified by silica gel column chromatography (hexane/ethyl acetate) to give the title compound (1.84 g).

MS (ESI+) 265 ($M^+$+1, 31%).

Reference Example 275

6-Bromo-2-fluoro-3-(methoxymethoxy)benzaldehyde

[Chemical formula 419]

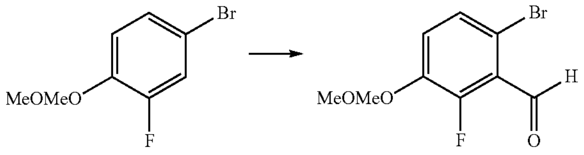

A solution of diisopropylamine (364 μl) in tetrahydrofuran (1 ml) was cooled to −78° C., and thereto was added dropwise n-butyl lithium (0.86 ml, 2.77M hexane solution), and the mixture was stirred at 0° C. for 10 minutes. The reaction mixture was cooled to −78° C., and thereto was added dropwise a solution of 1-bromo-3-fluoro-4-(methoxymethoxy) benzene (470 mg) in tetrahydrofuran (1 ml), and the mixture was stirred for 30 minutes. To the mixture was added dropwise N,N-dimethyl-formamide (210 μl), and the mixture was stirred at room temperature for one hour. To the reaction mixture was added a saturated aqueous ammonium chloride solution, and the mixture was extracted with ethyl acetate, washed with a saturated aqueous sodium chloride solution, dried over sodium sulfate, filtered, and concentrated under reduced pressure. The obtained residue was purified by silica gel column chromatography (hexane/ethyl acetate) to give the title compound (48 mg).

MS (ESI+) 265 ($M^+$+1, 35%).

Reference Example 276

1-Bromo-2-(difluoromethyl)-4-(methoxymethoxy) benzene

[Chemical formula 420]

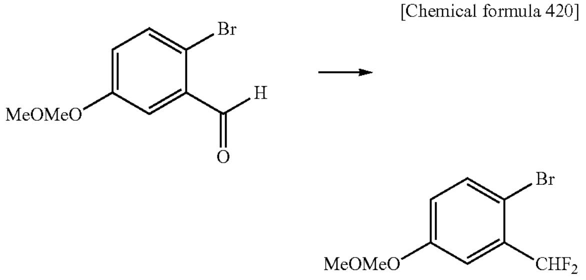

To a solution of 2-bromo-5-(methoxymethoxy)benzaldehyde (450 mg) in dichloromethane (5 ml) was added under ice-cooling diethylaminosulfur trifluoride (485 μl), and the mixture was stirred at room temperature overnight. To the reaction mixture was added a saturated aqueous sodium hydrogen carbonate solution, and the mixture was extracted with chloroform. The organic layer was washed with a saturated aqueous sodium chloride solution, dried over sodium sulfate, filtered, and concentrated under reduced pressure. The obtained residue was purified by silica gel column chromatography (hexane/ethyl acetate) to give the title compound (370 mg).

MS (ESI+) 265 ($M^+$+1, 78%).

Reference Example 277

1-Bromo-2-(difluoromethyl)-3-fluoro-4-(methoxymethoxy)benzene

[Chemical formula 421]

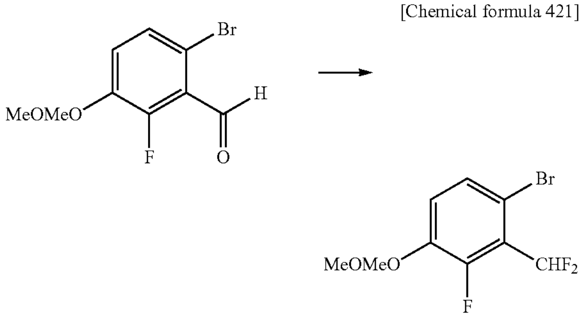

Using the compound of Reference Example 275, the title compound was obtained in a similar manner to Reference Example 276.

MS (ESI+) 265 ($M^+$+1, 89%).

Reference Example 278

Methyl 2-(difluoromethyl)-4-(methoxymethoxy)benzoate

[Chemical formula 422]

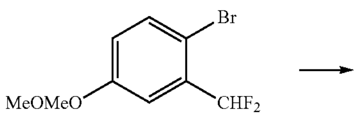

-continued

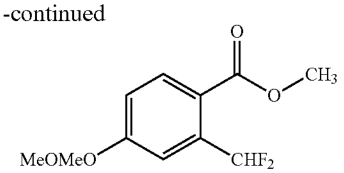

Using the compound of Reference Example 276, the title compound was obtained in a similar manner to Reference Example 25.

MS (ESI+) 247 ($M^{+}$+1, 79%).

Reference Example 279

Methyl 2-(difluoromethyl)-3-fluoro-4-(methoxymethoxy)benzoate

[Chemical formula 423]

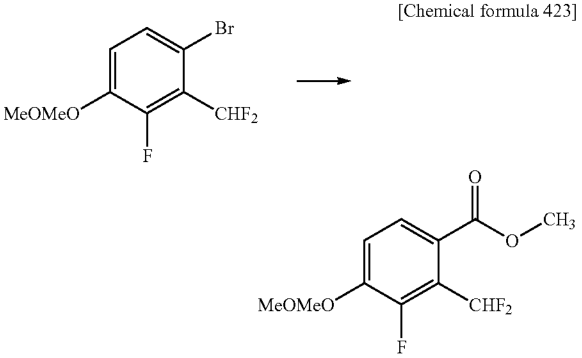

Using the compound of Reference Example 277, the title compound was obtained in a similar manner to Reference Example 25.

MS (ESI+) 265 ($M^{+}$+1, 78%).

Reference Example 280

Methyl 2-(difluoromethyl)-4-hydroxybenzoate

[Chemical formula 424]

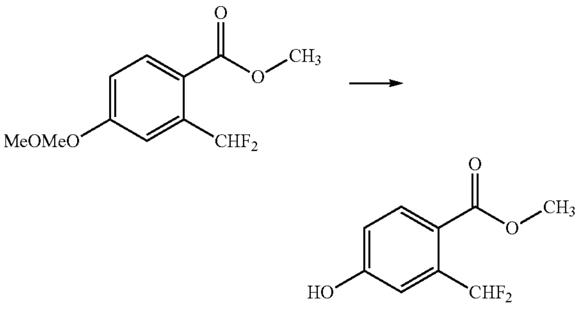

To methyl 2-(difluoromethyl)-4-(methoxymethoxy)benzoate (720 mg) were added 2N hydrochloric acid (6 ml) and ethanol (6 ml), and the mixture was stirred at 80° C. for 3 hours. The mixture was cooled to room temperature, and water was added thereto, and extracted with ethyl acetate. To the extract was added a saturated aqueous sodium chloride solution, and the mixture was dried over sodium sulfate, filtered, and concentrated under reduced pressure. The obtained residue was purified by silica gel column chromatography (hexane/ethyl acetate) to give the title compound (500 mg).

MS (ESI+) 203 ($M^{+}$+1, 22%).

Reference Example 281

Methyl 2-(difluoromethyl)-3-fluoro-4-hydroxybenzoate

[Chemical formula 425]

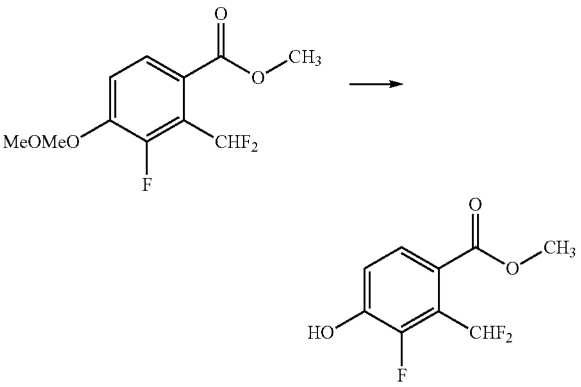

Using the compound of Reference Example 279, the title compound was obtained in a similar manner to Reference Example 280.

MS (ESI+) 221 ($M^{+}$+1, 18%).

Reference Example 282 tert-Butyl (3R)-3-[{[7-(difluoromethyl)-4-(4-methoxybutyl)-2,2-dimethyl-3-oxo-3,4-dihydro-2H-1,4-benzoxazin-6-yl]carbonyl}(isopropyl)amino]piperidine-1-carboxylate

[Chemical formula 426]

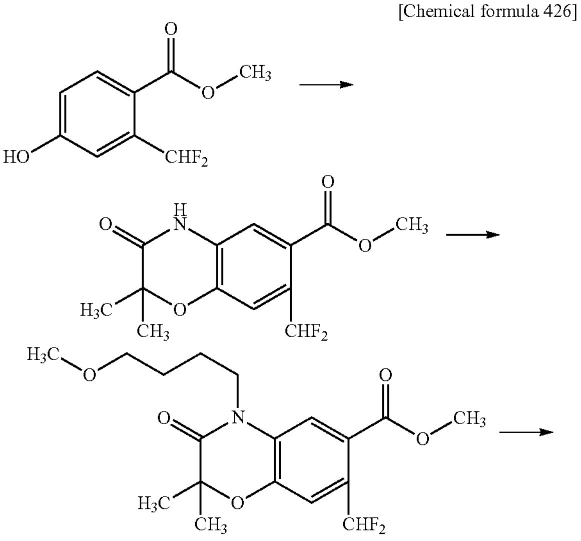

-continued

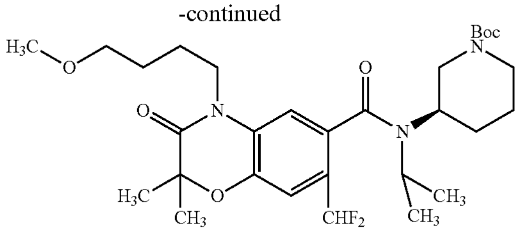

Using the compound of Reference Example 280, the title compound was obtained in a similar manner to Reference Example 55, Reference Example 3 and Reference Example 5.

MS (ESI+) 582 ($M^+$+1, 35%).

Reference Example 283 tert-Butyl (3R)-3-[{[7-(difluoromethyl)-8-fluoro-4-(4-methoxybutyl)-2,2-dimethyl-3-oxo-3,4-dihydro-2H-1,4-benzoxazin-6-yl]carbonyl}(isopropyl)amino]piperidine-1-carboxylate

[Chemical formula 427]

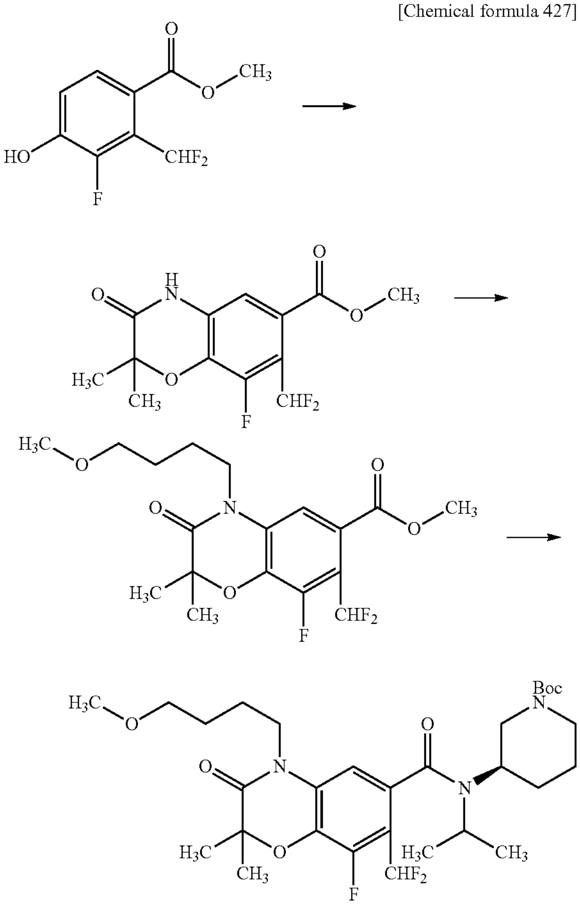

Using the compound of Reference Example 281, the title compound was obtained in a similar manner to Reference Example 55, Reference Example 3 and Reference Example 5.

MS (ESI+) 600 ($M^+$+1, 34%).

Reference Example 284 tert-Butyl (3R)-3-[[4-(benzyloxy)-5-nitro-2-(trifluoromethyl)benzoyl](isopropyl)amino]piperidine-1-carboxylate

[Chemical formula 428]

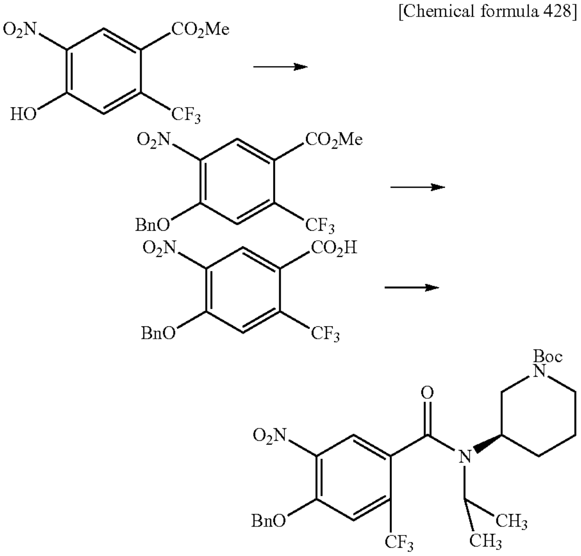

Methyl 4-hydroxy-5-nitro-2-(trifluoromethyl)benzoate (3.0 g) was dissolved in N,N-dimethyl-formamide (50 ml), and thereto were added benzyl bromide (2.3 g) and potassium carbonate (2.3 g), and the mixture was stirred at 80° C. for 6 hours. The reaction mixture was cooled, and water was added thereto. The mixture was extracted with ethyl acetate, and the organic layer was washed twice with water, dried over magnesium sulfate, filtered, and concentrated under reduced pressure. The residue was purified by silica gel column chromatography (the developing solvent: hexane/ethyl acetate=8:1→5:1→3:1) to give methyl 4-(benzyloxy)-5-nitro-2-(trifluoromethyl)benzoate (2.1 g), which was treated in a similar manner to Reference Example 5 to give the title compound (1.9 g).

MS (ESI+) 566 ($M^+$+1, 37%).

Reference Example 285 tert-Butyl (3R)-3-[[5-amino-4-hydroxy-2-(trifluoromethyl)benzoyl](isopropyl)amino]piperidine-1-carboxylate

[Chemical formula 429]

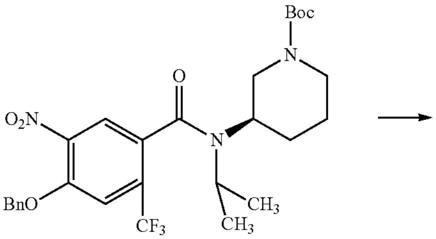

-continued

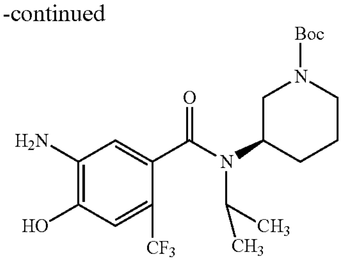

The compound of Reference Example 284 (1.9 g) was dissolved in methanol (30 ml), and thereto was added a 20% palladium hydroxide carbon (600 mg) under ice-cooling. Then, the mixture was stirred at room temperature for 8 hours under hydrogen atmosphere. The reaction mixture was filtered on celite, and the filtrate was concentrated under reduced pressure to give the title compound (1.3 g) as amorphous.

MS (ESI+) 446 ($M^{+}$+1, 34%).

Reference Example 286 tert-Butyl (3R)-3-[(5-amino-4-hydroxy-2-methylbenzoyl)(isopropyl)amino]piperidine-1-carboxylate

[Chemical formula 430]

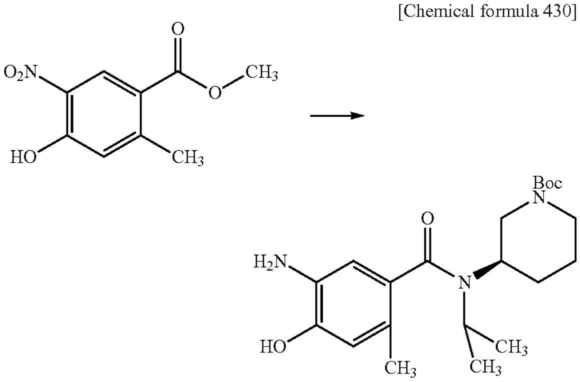

Using methyl 4-hydroxy-2-methyl-5-nitrobenzoate, the title compound was obtained in a similar manner to Reference Example 284.

MS (ESI+) 392 ($M^{+}$+1, 93%).

Reference Example 287

Methyl 7-methyl-3-oxo-3,4-dihydrospiro[1,4-benzoxazine-2,1'-cyclohexane]-6-carboxylate

[Chemical formula 431]

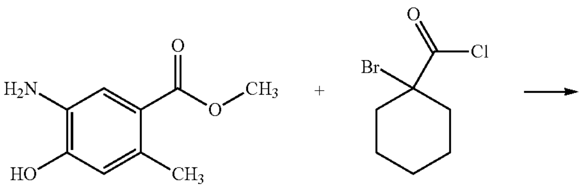

-continued

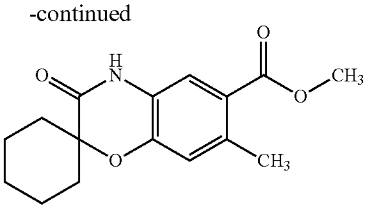

Using the compound of Reference Example 54 and 1-bromocyclohexanecarbonyl chloride, the title compound was obtained in a similar manner to Reference Example 55.

MS (ESI+) 290 ($M^{+}$+1, 100%).

Reference Example 288

Methyl 4-(2-{[(benzoyloxy)carbonyl]amino}ethyl)-7-methyl-3-oxo-3,4-dihydrospiro[1,4-benzoxazine-2,1'-cyclohexane]-6-carboxylate

[Chemical formula 432]

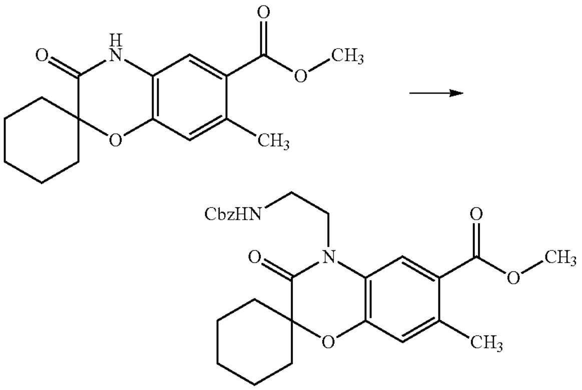

Using the compound of Reference Example 287, the title compound was obtained in a similar manner to Reference Example 3.

MS (ESI+) 467 ($M^{+}$+1, 100%).

Reference Example 289 tert-Butyl (3R)-3-[{[4-(2-{[(benzoyloxy)carbonyl]amino}ethyl)-7-methyl-3-oxo-3,4-dihydrospiro[1,4-benzoxazine-2,1'-cyclohexan]-6-yl]carbonyl}(isopropyl)amino]piperidine-1-carboxylate

[Chemical formula 433]

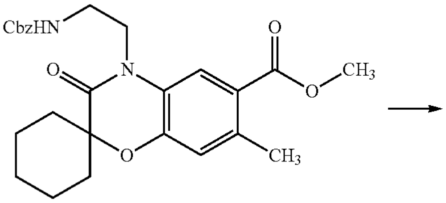

-continued

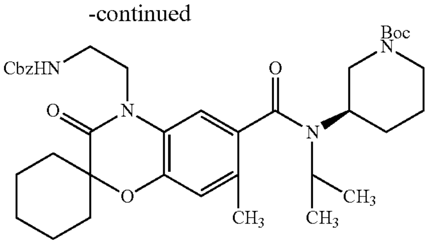

Using the compound of Reference Example 288, the title compound was obtained in a similar manner to Reference Example 5.

MS (ESI+) 677 ($M^+$+1, 43%).

Reference Example 290 tert-Butyl (3R)-3-[isopropyl({7-methyl-3-oxo-4-[2-(propionylamino)ethyl]-3,4-dihydrospiro[1,4-benzoxazine-2,1'-cyclohexan]-6-yl}carbonyl)amino]piperidine-1-carboxylate

[Chemical formula 434]

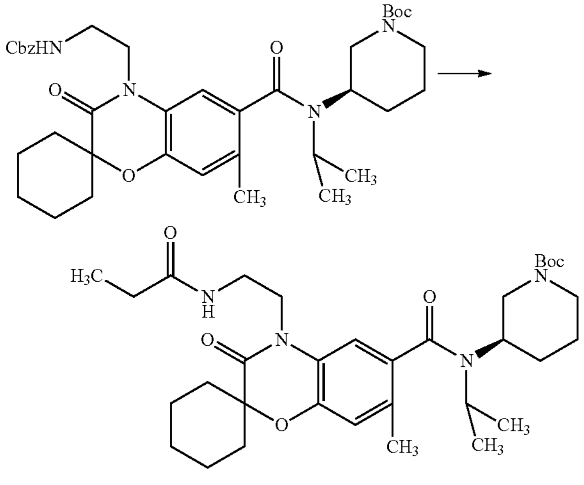

Using the compound of Reference Example 289, the title compound was obtained in a similar manner to Reference Example 132.

MS (ESI+) 599 ($M^+$+1, 30%).

Reference Example 291 tert-Butyl (3R)-3-{isopropyl[(7-methyl-3-oxo-3,4-dihydrospiro[1,4-benzoxazine-2,1'-cyclobutan]-6-yl)carbonyl]amino}piperidine-1-carboxylate

[Chemical formula 435]

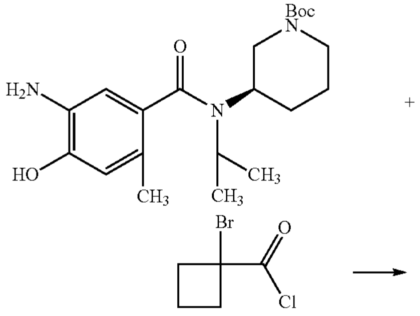

-continued

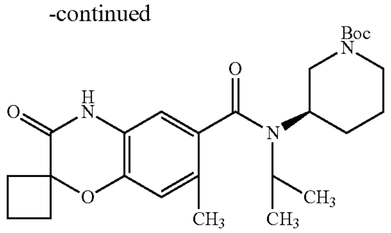

Using the compound of Reference Example 286 and 1-bromocyclobutanecarbonyl chloride, the title compound was obtained in a similar manner to Reference Example 55.

MS (ESI+) 472 ($M^+$+1, 30%).

Reference Example 292 tert-Butyl (3R)-3-(isopropyl{[3-oxo-7-(trifluoromethyl)-3,4-dihydrospiro[1,4-benzoxazine-2,1'-cyclobutan]-6-yl]carbonyl}amino)piperidine-1-carboxylate

[Chemical formula 436]

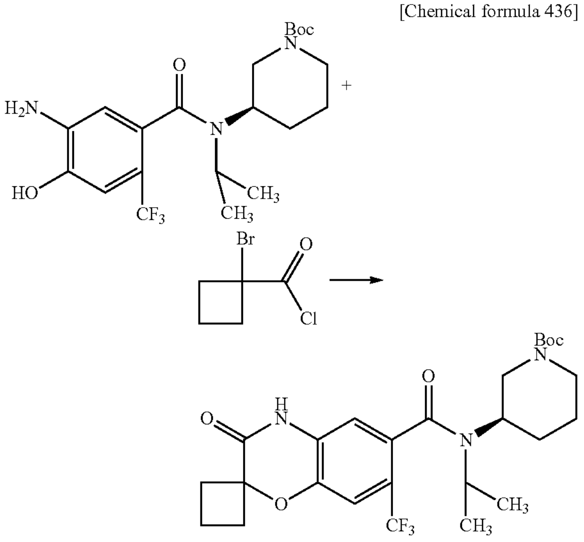

Using the compound of Reference Example 285 and 1-bromocyclobutanecarbonyl chloride, the title compound was obtained in a similar manner to Reference Example 55.

MS (ESI+) 526 ($M^+$+1, 31%).

Reference Example 293 tert-Butyl (3R)-3-(isopropyl{[3-oxo-7-(trifluoromethyl)-3,4-dihydrospiro[1,4-benzoxazine-2,1'-cyclopentan]-6-yl]carbonyl}amino)piperidine-1-carboxylate

[Chemical formula 437]

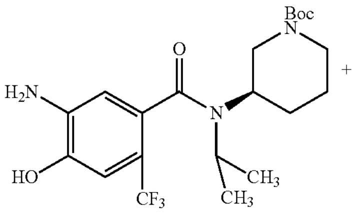

-continued

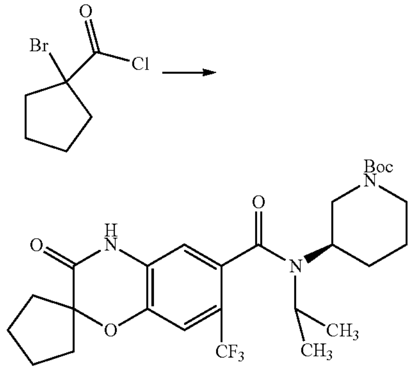

Using the compound of Reference Example 285 and 1-bromocyclopentanecarbonyl chloride, the title compound was obtained in a similar manner to Reference Example 55.

MS (ESI+) 540 ($M^{+}$+1, 31%).

Reference Example 294 tert-Butyl (3R)-3-[{[4-(2-{[(benzyloxy)carbonyl]amino}ethyl)-7-methyl-3-oxo-3,4-dihydrospiro[1,4-benzoxazine-2,1'-cyclobutan]-6-yl]carbonyl}(isopropyl)amino]piperidine-1-carboxylate

[Chemical formula 438]

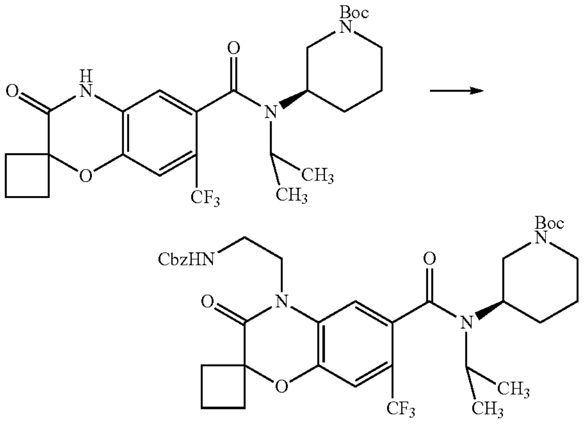

Using the compound of Reference Example 291, the title compound was obtained in a similar manner to Reference Example 3.

MS (ESI+) 649 ($M^{+}$+1, 40%).

Reference Example 295 tert-Butyl (3R)-3-[{[4-(2-{[(benzyloxy)carbonyl]amino}ethyl)-3-oxo-7-(trifluoromethyl)-3,4-dihydrospiro[1,4-benzoxazine-2,1'-cyclobutan]-6-yl]carbonyl}(isopropyl)amino]piperidine-1-carboxylate

[Chemical formula 439]

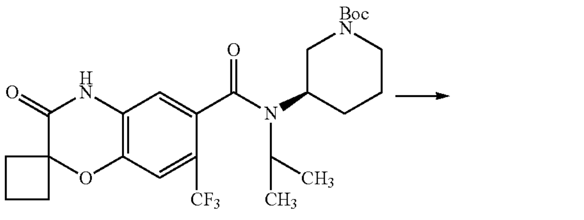

-continued

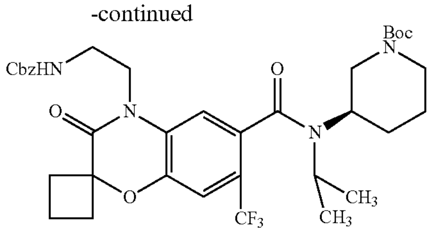

Using the compound of Reference Example 292, the title compound was obtained in a similar manner to Reference Example 3.

MS (ESI+) 703 ($M^{+}$+1, 39%).

Reference Example 296 tert-Butyl (3R)-3-[{[4-(2-{[(benzyloxy)carbonyl]amino}ethyl)-7-methyl-3-oxo-3,4-dihydrospiro[1,4-benzoxazine-2,1'-cyclopentan]-6-yl]carbonyl}(isopropyl)amino]piperidine-1-carboxylate

[Chemical formula 440]

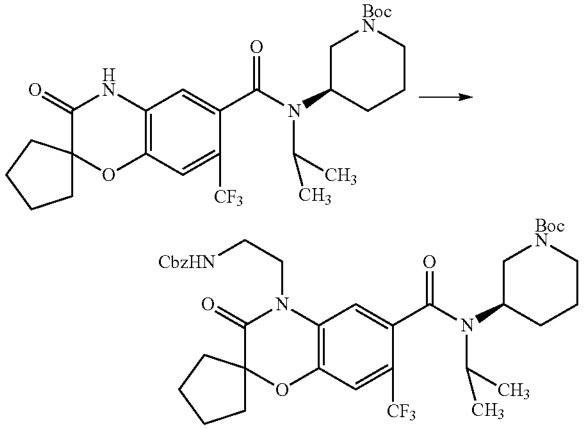

Using the compound of Reference Example 293, the title compound was obtained in a similar manner to Reference Example 3.

MS (ESI+) 717 ($M^{+}$+1, 30%).

Reference Example 297 tert-Butyl (3R)-3-(isopropyl{[4-{2-[(methoxycarbonyl)amino]ethyl}-3-oxo-7-(trifluoromethyl)-3,4-dihydrospiro[1,4-benzoxazine-2,1'-cyclobutan]-6-yl]carbonyl}amino)piperidine-1-carboxylate

[Chemical formula 441]

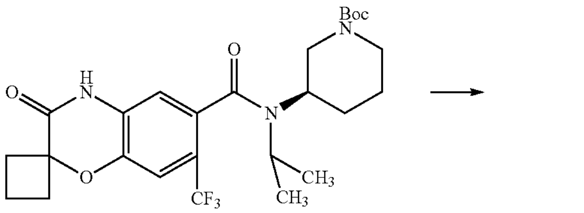

-continued

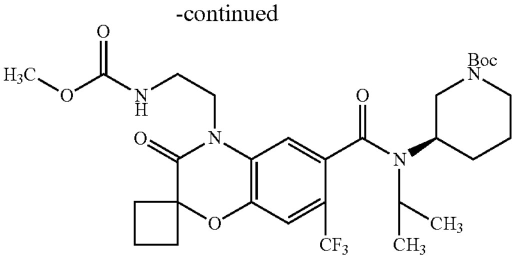

Using the compound of Reference Example 292, the title compound was obtained in a similar manner to Reference Example 162.

MS (ESI+) 627 ($M^{+}$+1, 30%).

Reference Example 298 tert-Butyl (3R)-3-[isopropyl({7-methyl-3-oxo-4-[2-(propionylamino)ethyl]-3,4-dihydrospiro[1,4-benzoxazine-2,1'-cyclobutan]-6-yl}carbonyl)amino]piperidine-1-carboxylate

[Chemical formula 442]

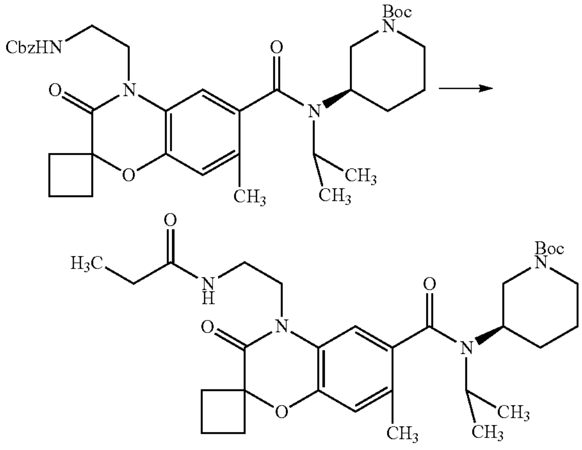

Using the compound of Reference Example 294, the title compound was obtained in a similar manner to Reference Example 132.

MS (ESI+) 571 ($M^{+}$+1, 31%).

Reference Example 299 tert-Butyl (3R)-3-(isopropyl{[3-oxo-4-[2-(propionylamino)ethyl]-7-(trifluoromethyl)-3,4-dihydro-spiro[1,4-benzoxazine-2,1'-cyclobutan]-6-yl]carbonyl}amino)piperidine-1-carboxylate

[Chemical formula 443]

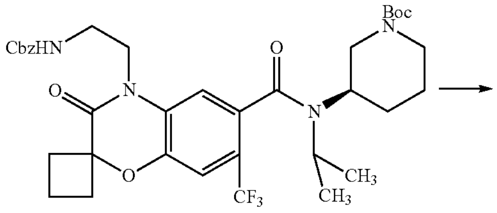

-continued

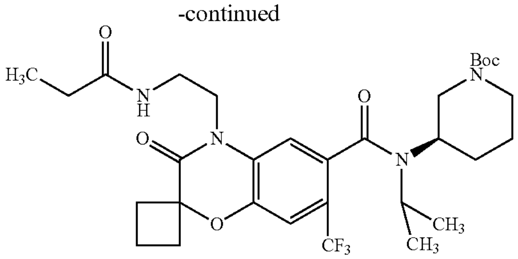

Using the compound of Reference Example 295, the title compound was obtained in a similar manner to Reference Example 132.

MS (ESI+) 625 ($M^{+}$+1, 32%).

Reference Example 300 tert-Butyl (3R)-3-(isopropyl{[3-oxo-4-[2-(propionylamino)ethyl]-7-(trifluoromethyl)-3,4-dihydro-spiro[1,4-benzoxazine-2,1'-cyclopentan]-6-yl]carbonyl}amino)piperidine-1-carboxylate

[Chemical formula 444]

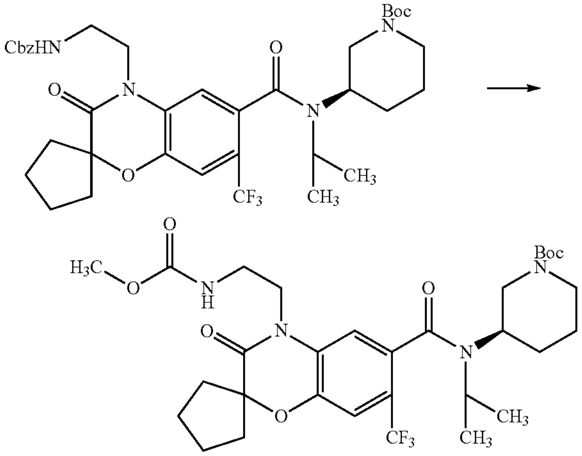

Using the compound of Reference Example 296, the title compound was obtained in a similar manner to Reference Example 132.

MS (ESI+) 639 ($M^{+}$+1, 43%).

Reference Example 301 tert-Butyl (3R)-3-({[2,2-dimethyl-3-oxo-4-[2-(propionylamino)ethyl]-7-(trifluoromethyl)-3,4-dihydro-2H-1,4-benzoxazin-6-yl]carbonyl}amino)piperidine-1-carboxylate

[Chemical formula 445]

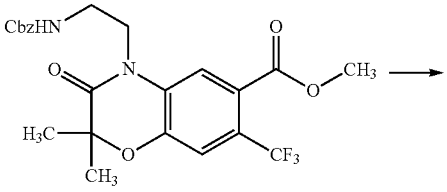

-continued

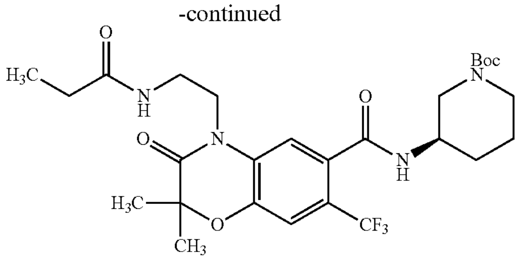

Using the compound of Reference Example 74, the title compound was obtained in a similar manner to Reference Example 5 and Reference Example 132.

MS (ESI+) 571 ($M^{+}$+1, 38%).

Reference Example 302 tert-Butyl (3R)-3-[{[2,2-dimethyl-3-oxo-4-[2-(propionylamino)ethyl]-7-(trifluoromethyl)-3,4-dihydro-2H-1,4-benzoxazin-6-yl]carbonyl}(ethyl)amino]piperidine-1-carboxylate

[Chemical formula 446]

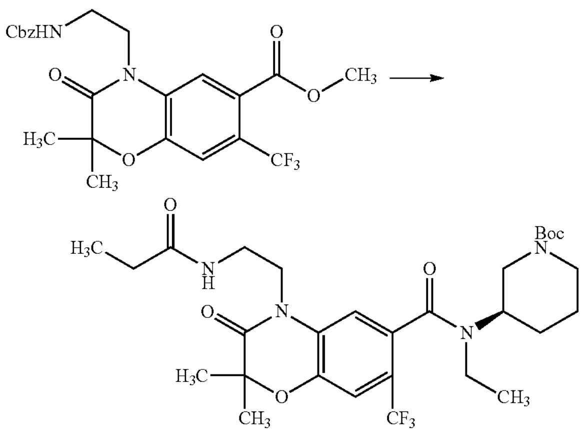

Using the compound of Reference Example 74, the title compound was obtained in a similar manner to Reference Example 5 and Reference Example 132.

MS (ESI+) 599 ($M^{+}$+1, 38%).

Reference Example 303 tert-Butyl (3R)-3-(sec-butyl {[2,2-dimethyl-3-oxo-4-[2-(propionylamino)ethyl]-7-(trifluoromethyl)-3,4-dihydro-2H-1,4-benzoxazin-6-yl]carbonyl}amino)piperidine-1-carboxylate

[Chemical formula 447]

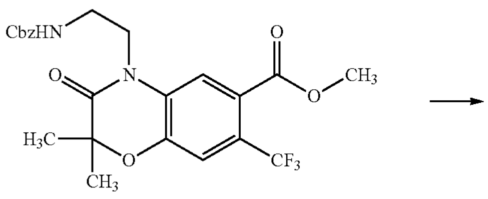

-continued

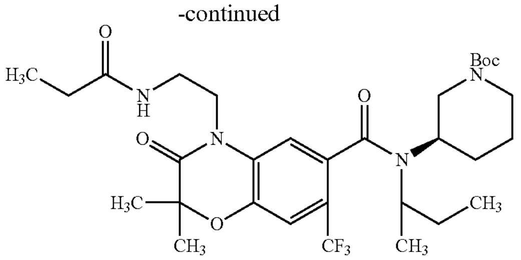

Using the compound of Reference Example 74, the title compound was obtained in a similar manner to Reference Example 5 and Reference Example 132.

MS (ESI+) 627 ($M^{+}$+1, 40%).

Reference Example 304 tert-Butyl (3R)-3-(benzyl{[2,2-dimethyl-3-oxo-4-[2-(propionylamino)ethyl]-7-(trifluoromethyl)-3,4-dihydro-2H-1,4-benzoxazin-6-yl]carbonyl}amino)piperidine-1-carboxylate

[Chemical formula 448]

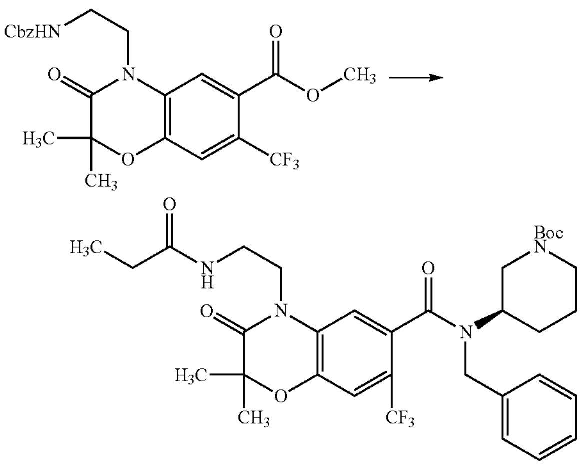

Using the compound of Reference Example 74, the title compound was obtained in a similar manner to Reference Example 5 and Reference Example 132.

MS (ESI+) 661 ($M^{+}$+1, 31%).

Reference Example 305

Ethyl [(2R,5R)-5-(isopropylamino)-1-(4-methoxybenzyl)piperidin-2-yl]acetate

[Chemical formula 449]

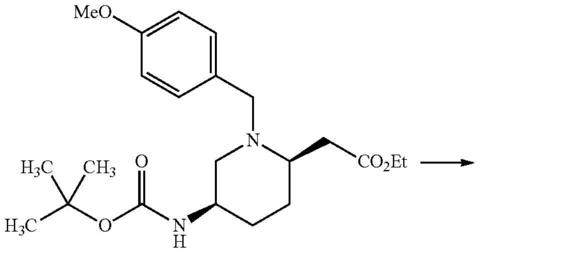

-continued

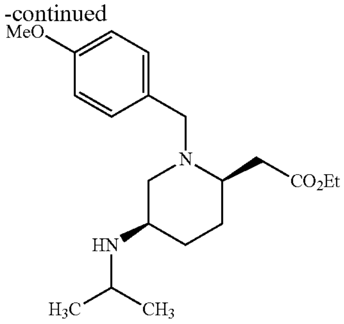

Ethyl [(2R,5R)-5-(tert-butoxycarbonyl)amino]-1-(4-methoxybenzyl)piperidin-2-yl]acetate (20.0 g) and 4N hydrochloric acid-dioxane solution (200 ml) were mixed, and the mixture was stirred at room temperature for 14 hours. The reaction solution was concentrated under reduced pressure, and to the obtained residue was poured diluted aqueous sodium hydroxide solution in order to adjust the pH value to pH 10, and then the mixture was extracted with chloroform. The organic layer was dried over anhydrous magnesium sulfate, and the solvent was concentrated under reduced pressure to give ethyl [(2R,5R)-5-amino]-(4-methoxybenzyl)piperidin-2-yl]acetate (16.3 g) as a pale brown oil. This compound was dissolved in chloroform (100 ml), and thereto were added acetone (14.4 mL), acetic acid (8.5 mL) and molecular sieve 4 Å (16 g), and the mixture was stirred at room temperature for one hour. To this reaction mixture was added sodium triacetoxyborohydride (20.9 g), and the mixture was stirred at room temperature for 14 hours. To this reaction mixture was added ice-cold diluted aqueous sodium hydroxide solution, and the insoluble materials were removed by filtration, and the filtrate was extracted with chloroform. The organic layer was dried over magnesium sulfate, and the solvent was concentrated under reduced pressure to give the title compound (16.2 g) as a pale yellow oil.

MS (ESI+) 349($M^+$+1, 85%).

Reference Example 306 tert-Butyl (2R,5R)-2-(2-ethoxy-2-oxoethyl)-5-(isopropylamino)piperidine-1-carboxylate

[Chemical formula 450]

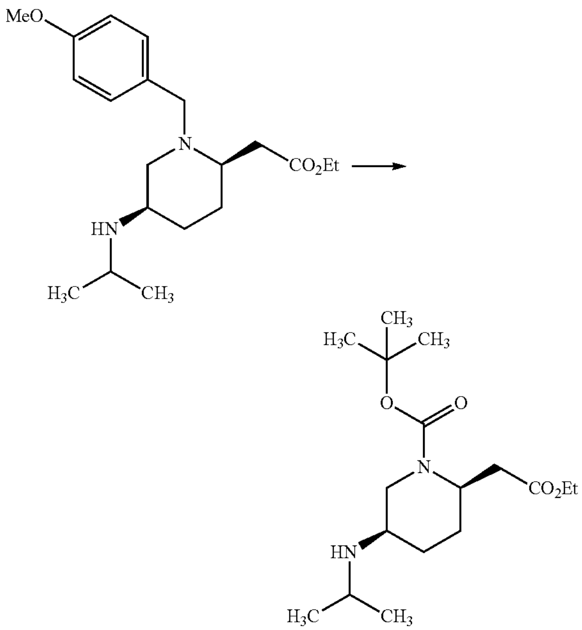

To a solution of ethyl [(2R,5R)-5-(isopropylamino)-1-(4-methoxybenzyl)piperidin-2-yl]acetate (10.0 g) in ethanol (200 mL) were added $Boc_2O$ (14.2 g) and 10% palladium carbon (20 g), and the mixture was stirred at room temperature for 3 hours under hydrogen atmosphere. $Boc_2O$ (7.1 g) was added thereto, and the mixture was further stirred for 3 hours. The insoluble materials were removed by filtration, and the filtrate was concentrated under reduced pressure. The obtained residue was purified by silica gel chromatography to give the title compound (6.4 g) as a colorless oil.

MS (ESI+) 329($M^+$+1, 40%).

Reference Example 307 tert-Butyl (2R,5R)-5-[[(benzyloxy)carbonyl](isopropyl)amino]-2-(2-ethoxy-2-oxoethyl)piperidine-1-carboxylate

[Chemical formula 451]

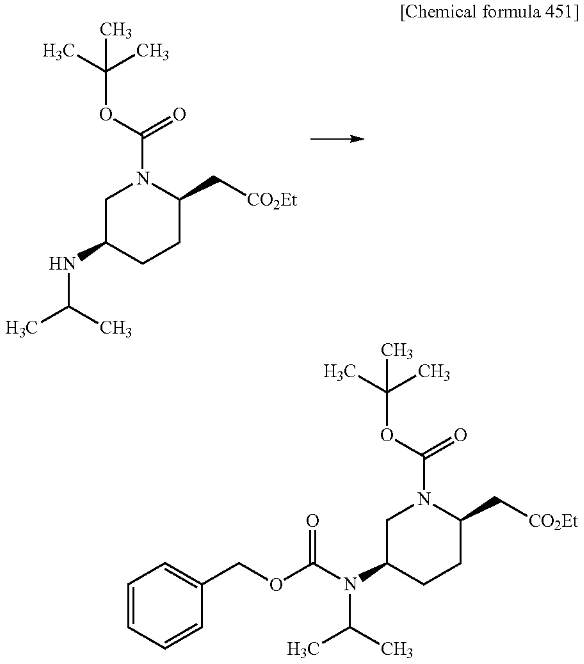

To a solution of tert-butyl (2R,5R)-2-(2-ethoxy-2-oxoethyl)-5-(isopropylamino)piperidine-1-carboxylate (6.0 g) in dichloromethane (200 mL) was added diisopropylethylamine (19.1 mL), and thereto was further added dropwise under ice-cooling Z—Cl (13.0 mL) over a period of one hour. The mixture was stirred at room temperature for one hour, and then, the reaction solution was diluted with chloroform. The mixture was washed successively with an ice-cold aqueous potassium hydrogen sulfate solution and a saturated aqueous sodium chloride solution. The organic layer was dried over anhydrous magnesium sulfate, and the solvent was evaporated under reduced pressure. The obtained residue was purified by silica gel chromatography to give the title compound (8.9 g) as a pale brown oil.

MS (ESI+) 463 ($M^+$+1, 50%).

Reference Example 308

[(2R,5R)-5-[[(Benzyloxy)carbonyl](isopropyl)amino]-1-(tert-butoxycarbonyl)piperidin-2-yl]acetic acid

[Chemical formula 452]

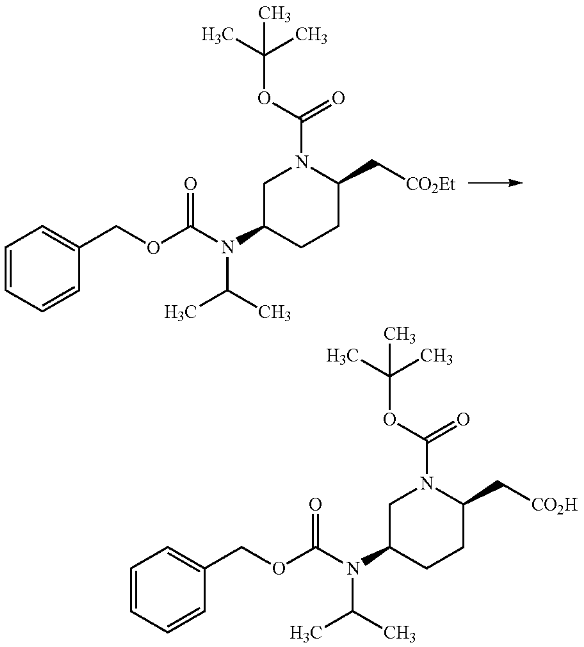

To a solution of tert-butyl (2R,5R)-5-[[(benzyloxy)carbonyl](isopropyl)amino]-2-(2-ethoxy-2-oxoethyl)piperidine-1-carboxylate (8.5 g) in ethanol (100 mL) was added a 2N aqueous sodium hydroxide solution (50 mL), and the mixture was stirred at 50° C. for one hour. The reaction solution was cooled with ice, and thereto was added an aqueous potassium hydrogen sulfate solution in order to adjust the pH value to pH 3. The mixture was extracted with chloroform, and the organic layer was dried over anhydrous magnesium sulfate, and the solvent was evaporated under reduced pressure to give the title compound (6.0 g) as a colorless solid.

MS (ESI+) 435 ($M^{+}$+1, 7%).

Reference Example 309 tert-Butyl (2R,5R)-5-[[(benzyloxy)carbonyl](isopropyl)amino]-2-(hydroxyethyl)piperidine-1-carboxylate

[Chemical formula 453]

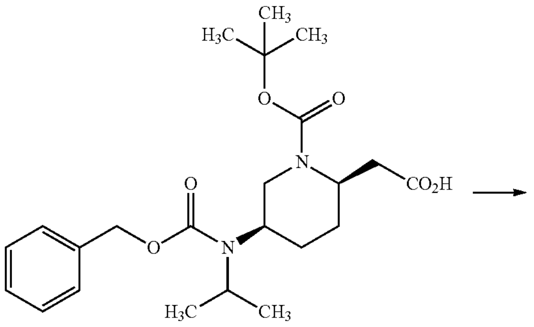

-continued

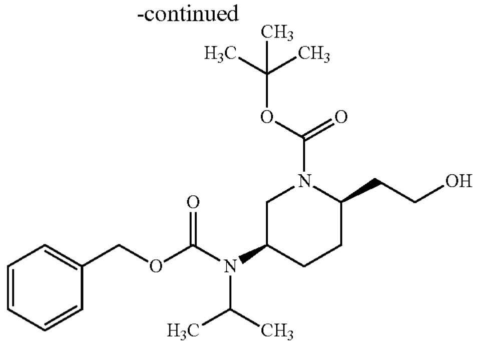

To a solution of [(2R,5R)-5-[[(benzyloxy)carbonyl](isopropyl)amino]-1-(tert-butoxycarbonyl)-piperidin-2-yl]acetic acid (8.0 g) in tetrahydrofuran (100 mL) was added triethylamine (7.7 mL), and thereto was added ethyl chloroformate (3.5 mL) under ice-cooling. After the mixture was stirred under ice-cooling for one hour, the insoluble materials were removed by filtration. To the filtrate was added dropwise a solution of sodium borohydride (3.5 g) in water (30 mL) under ice-cooling with stirring. Then, the mixture was stirred at room temperature for one hour. To the mixture was added an aqueous potassium hydrogen sulfate solution under ice-cooling, the mixture was extracted with ethyl acetate. The organic layer was washed with a saturated aqueous sodium chloride solution, dried over anhydrous magnesium sulfate, and the solvent was evaporated under reduced pressure. The obtained residue was purified by silica gel chromatography to give the title compound (6.7 g) as a colorless oil.

MS (ESI+) 421 ($M^{+}$+1, 32%).

Reference Example 310 tert-Butyl (2R,5R)-5-[[(benzyloxy)carbonyl](isopropyl)amino]-2-(methoxyethyl)piperidine-1-carboxylate

[Chemical formula 454]

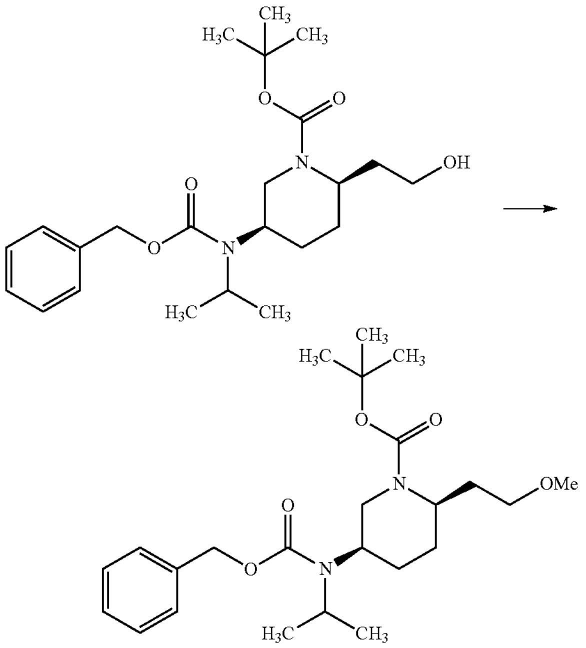

To a solution of tert-butyl (2R,5R)-5-[[(benzyloxy)carbonyl](isopropyl)amino]-2-(hydroxy-ethyl)piperidine-1-carboxylate (2.10 g) in tetrahydrofuran (10 mL) was added methyl iodide (1.42 g), and the mixture was stirred. To the mixture was added 55% sodium hydride (300 mg) under ice-cooling, and the mixture was stirred at room temperature for 19 hours. To the reaction solution was added a saturated aqueous ammonium chloride solution (5 ml), and the mixture was extracted with ethyl acetate (50 ml). The organic layer was washed with water and a saturated aqueous sodium chloride solution, dried over sodium sulfate, filtered and concentrated under reduced pressure. The obtained residue was purified by silica gel column chromatography (the developing solvent: hexane/ethyl acetate=4/1) to give the title compound (2.15 g).

MS (ESI+) 435 ($M^{+}$+1, 100%).

Reference Example 311 tert-Butyl (2R,5R)-5-[[(benzyloxy)carbonyl](isopropyl)amino]-2-(2-{[tert-butyl(diphenyl)silyl]oxy}-ethyl)piperidine-1-carboxylate

[Chemical formula 455]

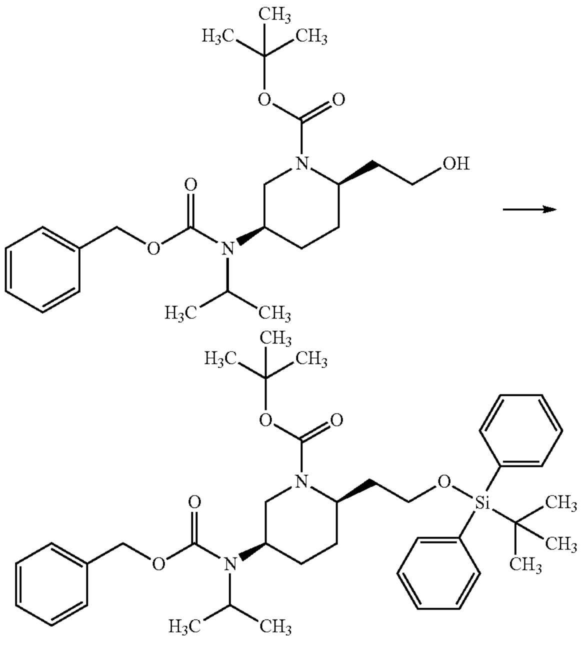

To a solution of tert-butyl (2R,5R)-5-[[(benzyloxy)carbonyl](isopropyl)amino]-2-(hydroxy-ethyl)piperidine-1-carboxylate (2.93 g) in methylene chloride (35 ml) were added tert-butyl diphenyl-chlorosilane (2.30 g) and imidazole (569 mg), and the mixture was stirred at room temperature for 4 hours. To the mixture was added a saturated aqueous sodium hydrogen carbonate solution (10 ml), and the mixture was extracted with chloroform (100 ml). The organic layer was dried over sodium sulfate, filtered, and concentrated under reduced pressure. The obtained residue was purified by silica gel column chromatography (the developing solvent: hexane/ethyl acetate=12/1) to give the title compound (4.42 g).

MS (ESI+) 659 ($M^{+}$+1, 100%).

Reference Example 312 tert-Butyl (2R,5R)-5-[[(benzyloxy)carbonyl](isopropyl)amino]-2-(2-{[tert-butyl(diphenyl)silyl]oxy}ethyl)piperidine-1-carboxylate

[Chemical formula 456]

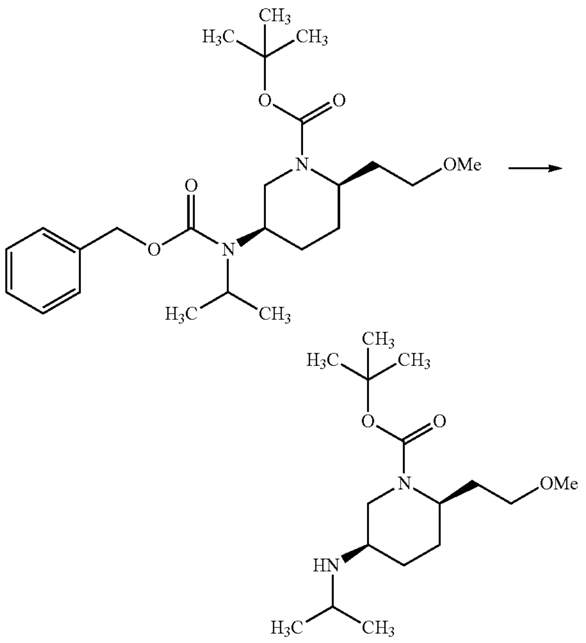

To a solution of tert-butyl (2R,5R)-5-[[(benzyloxy)carbonyl](isopropyl)amino]-2-(methoxy-ethyl)piperidine-1-carboxylate (2.15 g) in methanol (25 ml) was added 10% palladium carbon (1.05 g), and the mixture was stirred at room temperature for 3 hours under hydrogen atmosphere. The insoluble materials were removed by filtration, and the filtrate was concentrated under reduced pressure to give the title compound (1.35 g) as a pale yellow oil.

MS (ESI+) 301 ($M^{+}$+1, 100%).

Reference Example 313 tert-Butyl (2R,5R)-2-(2-{[tert-butyl(diphenyl)silyl]oxy}ethyl)-5-(isopropylamino)piperidine-1-carboxylate

[Chemical formula 457]

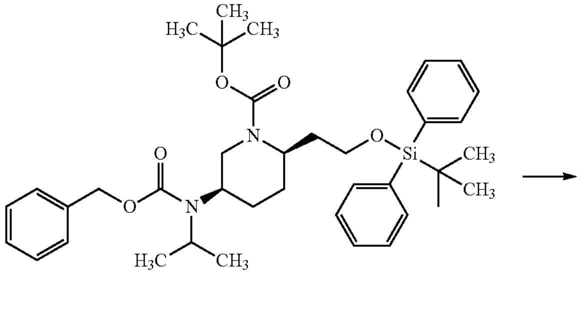

-continued

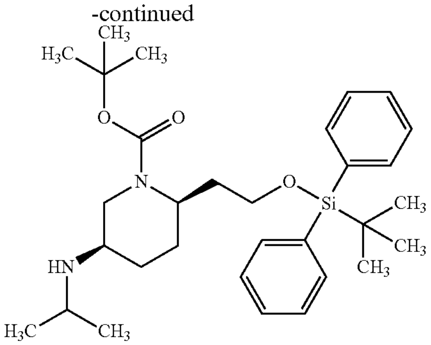

Using the compound of Reference Example 311, the title compound was obtained in a similar manner to Reference Example 312.

MS (ESI+) 525 ($M^{+}$+1, 100%).

Reference Example 314 tert-Butyl (2R,5R)-5-[{[4-(2-{[(benzyloxy)carbonyl] amino}ethyl)-2,2-dimethyl-3-oxo-7-(trifluoro-methyl)-3,4-dihydro-2H-1,4-benzoxazin-6-yl]carbonyl}(isopropylamino)-2-(2-methoxyethyl)-piperidine-1-carboxylate

[Chemical formula 458]

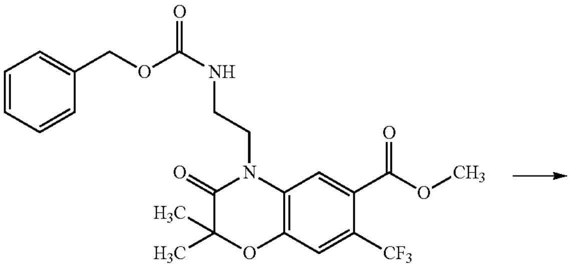

-continued

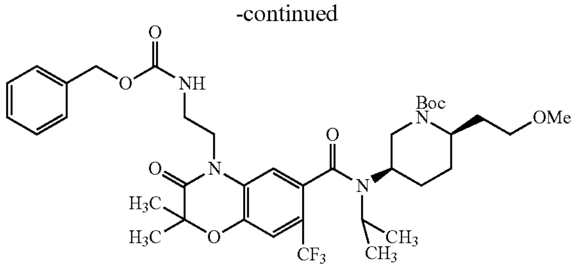

Using the compound of Reference Example 74, the title compound was obtained in a similar manner to Reference Example 5.

MS (ESI+) 749 ($M^{+}$+1, 100%).

Reference Example 315 tert-Butyl (2R,5R)-5-[{[4-(2-{[(benzyloxy)carbonyl] amino}ethyl)-2,2-dimethyl-3-oxo-7-(trifluoro-methyl)-3,4-dihydro-2H-1,4-benzoxazin-6-yl]carbonyl}(isopropylamino)-2-(2-{[tert-butyl(diphenyl)-silyl] oxy}ethyl)-piperidine-1-carboxylate

[Chemical formula 459]

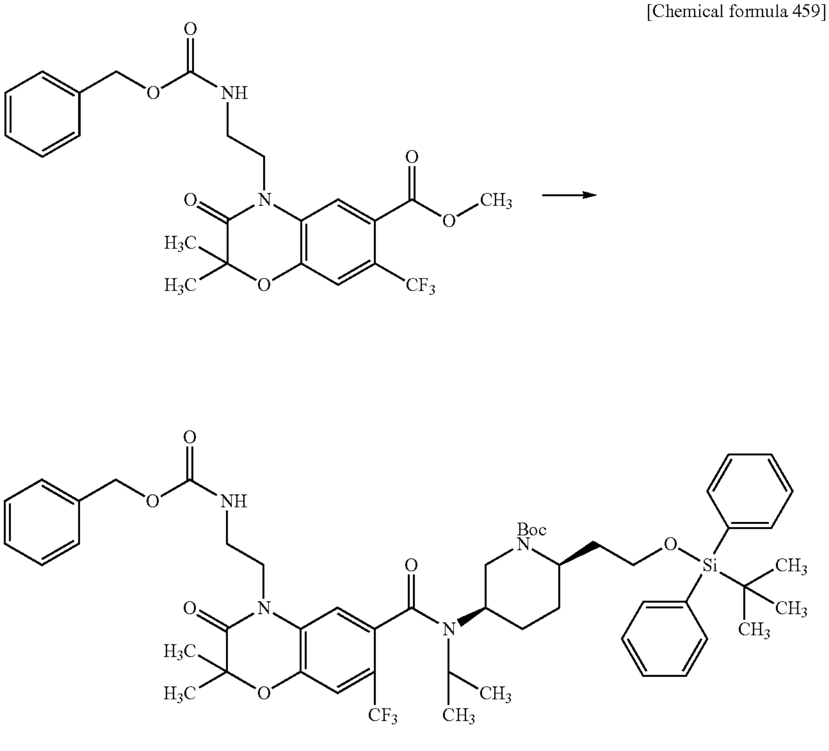

Using the compound of Reference Example 74, the title compound was obtained in a similar manner to Reference Example 5.

MS (ESI+) 974 ($M^{+}$+1, 100%).

Reference Example 316 tert-Butyl (2R,5R)-5-[{[4-(2-{[(benzyloxy)carbonyl]amino}ethyl)-2,2,7-trimethyl-3-oxo-3,4-dihydro-2H-1,4-benzoxazin-6-yl]carbonyl}(isopropylamino)-2-(2-{[tert-butyl(diphenyl)silyl]oxy}ethyl)-piperidine-1-carboxylate

[Chemical formula 460]

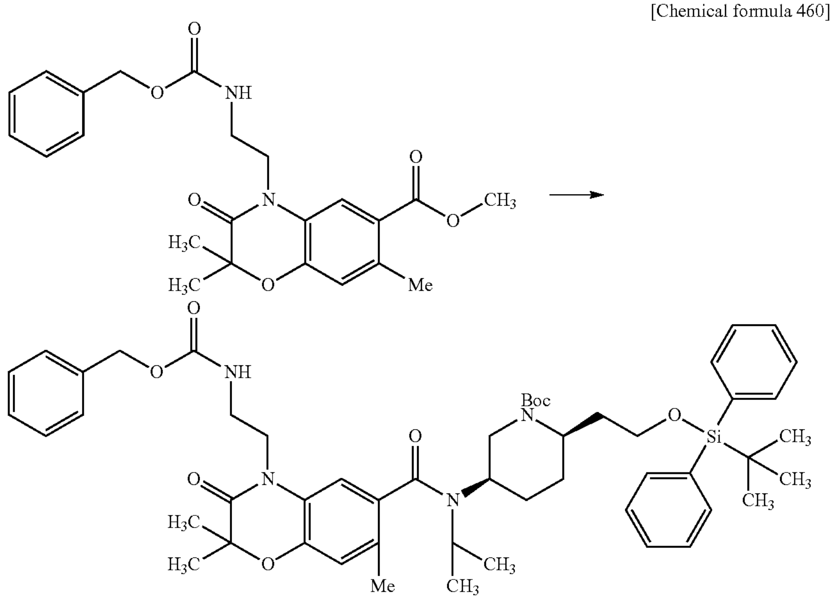

Using the compound of Reference Example 73, the title compound was obtained in a similar manner to Reference Example 5.

MS (ESI+) 920 ($M^{+}$+1, 61%).

Reference Example 317 tert-Butyl (2R,5R)-5-[{[4-(2-aminoethyl)-2,2-dimethyl-3-oxo-7-(trifluoromethyl)-3,4-dihydro-2H-1,4-benzoxazin-6-yl]carbonyl}(isopropylamino)-2-(2-methoxyethyl)-piperidine-1-carboxylate

[Chemical formula 461]

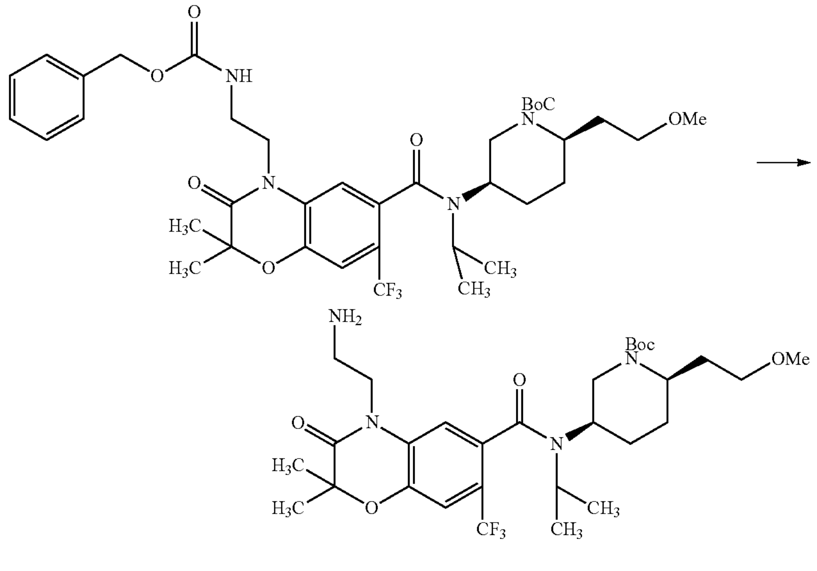

Using the compound of Reference Example 314, the title compound was obtained in a similar manner to Reference Example 139.

MS (ESI+) 615 ($M^{+}$+1, 100%).

Reference Example 318 tert-Butyl (2R,5R)-5-[{[4-(2-aminoethyl)-2,2-dimethyl-3-oxo-7-(trifluoromethyl)-3,4-dihydro-2H-1,4-benzoxazin-6-yl]carbonyl}(isopropylamino)-2-(2-{[tert-butyl (diphenyl)silyl]oxy}ethyl)-piperidine-1-carboxylate

[Chemical formula 462]

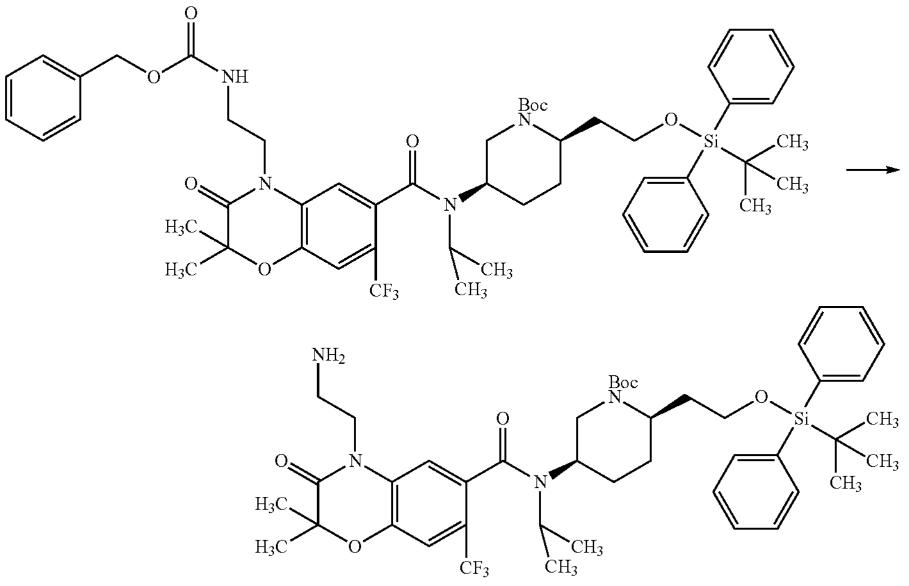

Using the compound of Reference Example 315, the title compound was obtained in a similar manner to Reference Example 139.

MS (ESI+) 840 ($M^{+}$+1, 100%).

Reference Example 319 tert-Butyl (2R,5R)-5-[{[(4-(2-aminoethyl)-2,2,7-trimethyl-3-oxo-3,4-dihydro-2H-1,4-benzoxazin-6-yl]carbonyl}(isopropylamino)-2-(2-{[tert-butyl (diphenyl)silyl]oxy}ethyl)-piperidine-1-carboxylate

[Chemical formula 463]

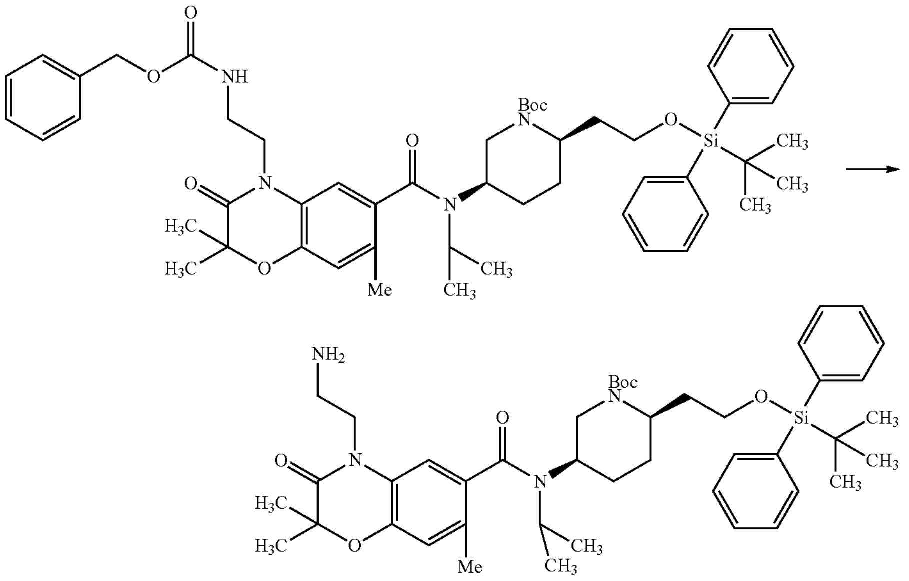

Using the compound of Reference Example 316, the title compound was obtained in a similar manner to Reference Example 139.

MS (ESI+) 786 ($M^{+}$+1, 100%).

Reference Example 320 tert-Butyl (2R,5R)-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropylamino)-2-(2-methoxyethyl)-piperidine-1-carboxylate

[Chemical formula 464]

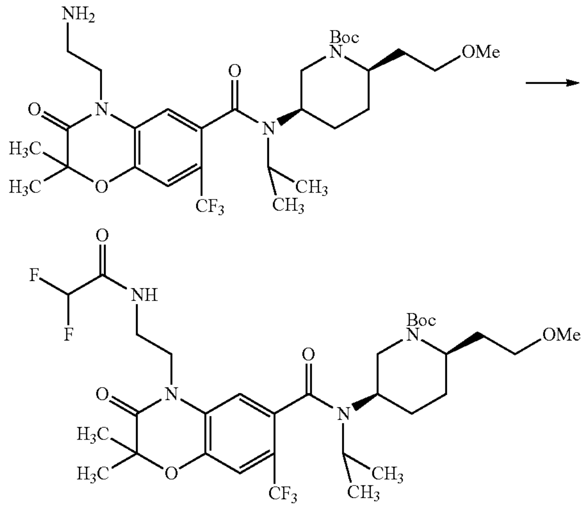

Using the compound of Reference Example 317, the title compound was obtained in a similar manner to Reference Example 120.

MS (ESI+) 693 ($M^{+}$+1, 100%).

Reference Example 321 tert-Butyl (2R,5R)-2-(2-{[tert-butyl(diphenyl)silyl]oxy}ethyl)-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropylamino)-piperidine-1-carboxylate

[Chemical formula 465]

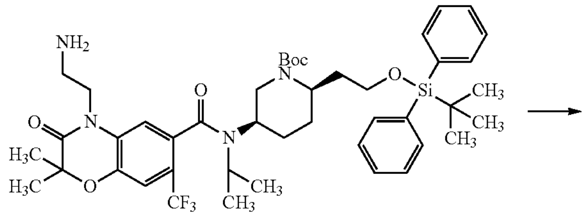

-continued

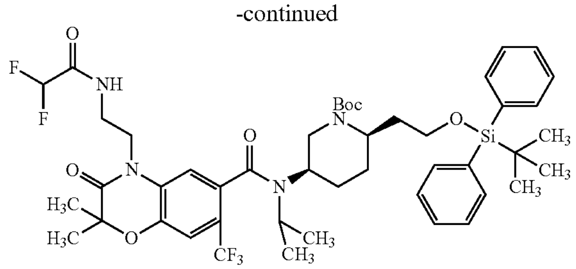

Using the compound of Reference Example 318, the title compound was obtained in a similar manner to Reference Example 120.

MS (ESI+) 918 ($M^{+}$+1, 68%).

Reference Example 322 tert-Butyl (2R,5R)-2-(2-{[tert-butyl (diphenyl)silyl]oxy}ethyl)-5-[[(4-{2-[(difluoroacetyl)amino]ethyl}-2,2,7-trimethyl-3-oxo-3,4-dihydro-2H-1,4-benzoxazin-6-yl)carbonyl](isopropyl)amino]piperidine-1-carboxylate

[Chemical formula 466]

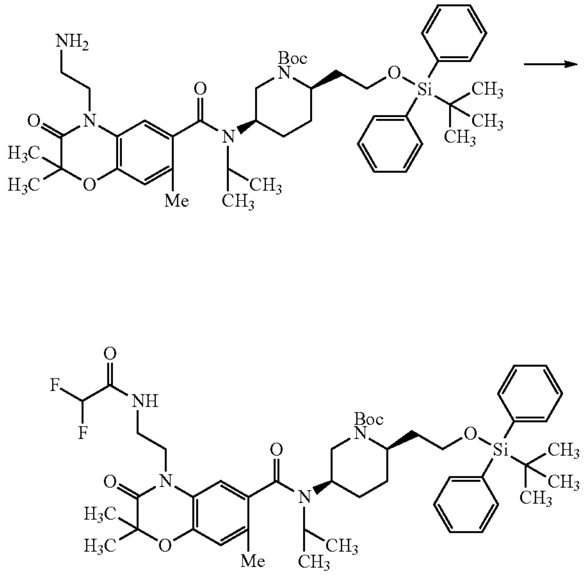

Using the compound of Reference Example 319, the title compound was obtained in a similar manner to Reference Example 120.

MS (ESI+) 864 ($M^{+}$+1, 43%).

Reference Example 323 tert-Butyl (2R,5R)-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropyl)amino]-2-(2-hydroxyethyl)piperidine-1-carboxylate

[Chemical formula 467]

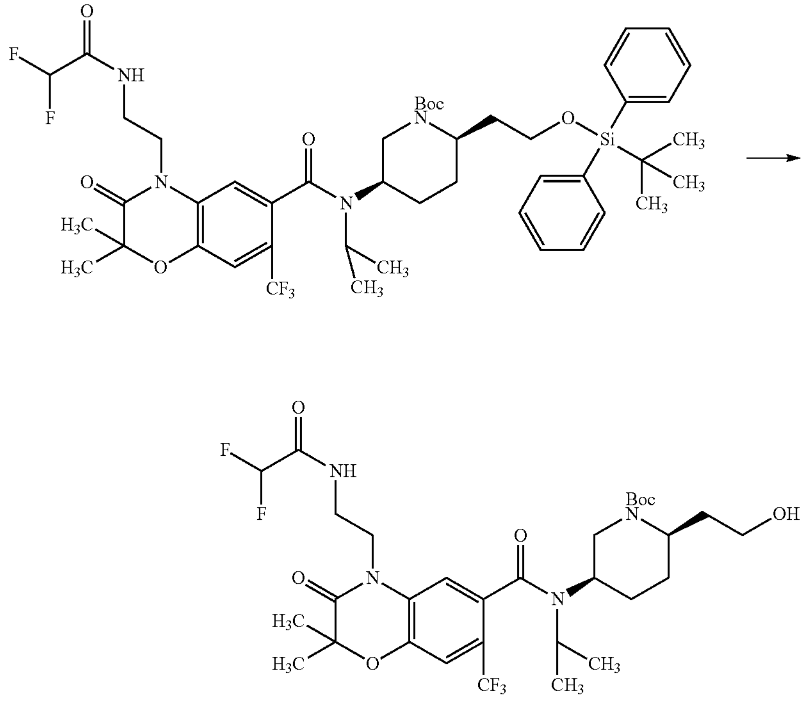

To a solution of tert-butyl (2R,5R)-2-(2-{[tert-butyl(diphenyl)silyl]oxy}ethyl)-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropylamino)-piperidine-1-carboxylate (1.48 g) in tetrahydrofuran (10 ml) was added a solution of 1N tetrabutylammonium fluoride in tetrahydrofuran (3.55 ml), and the mixture was stirred at room temperature for 2 hours. To the mixture was added a saturated aqueous sodium chloride solution (5 ml), and the mixture was extracted with ethyl acetate (50 ml). The organic layer was dried over sodium sulfate, filtered, and concentrated under reduced pressure. The obtained residue was purified by silica gel column chromatography (the developing solvent: hexane/acetone=2/1) to give the title compound (1.1 g).

MS (ESI+) 679 ($M^{+}$+1, 100%).

Reference Example 324 tert-Butyl (2R,5R)-5-[[(4-{2-[(difluoroacetyl)amino]ethyl}-2,2,7-trimethyl-3-oxo-3,4-dihydro-2H-1,4-benzoxazin-6-yl)carbonyl](isopropyl)amino]-2-(2-hydroxyethyl)piperidine-1-carboxylate

[Chemical formula 468]

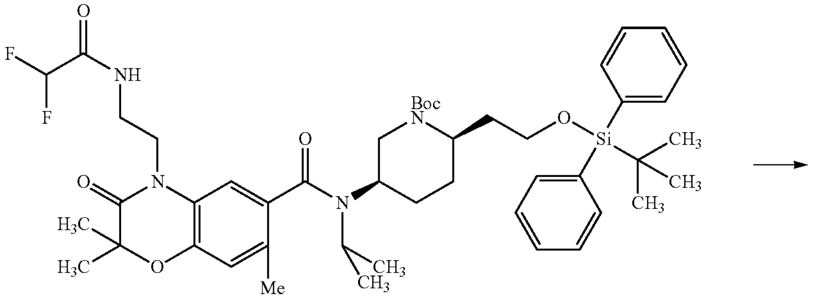

-continued

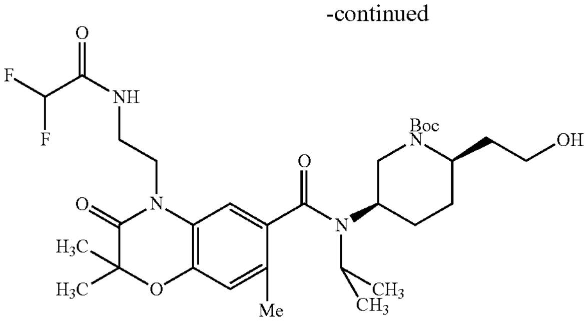

Using the compound of Reference Example 322, the title compound was obtained in a similar manner to Reference Example 323.

MS (ESI+) 626 ($M^{+}$+1, 48%).

Reference Example 325 tert-Butyl (2R,5R)-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropyl)amino]-2-(2-oxoethyl)piperidine-1-carboxylate

[Chemical formula 469]

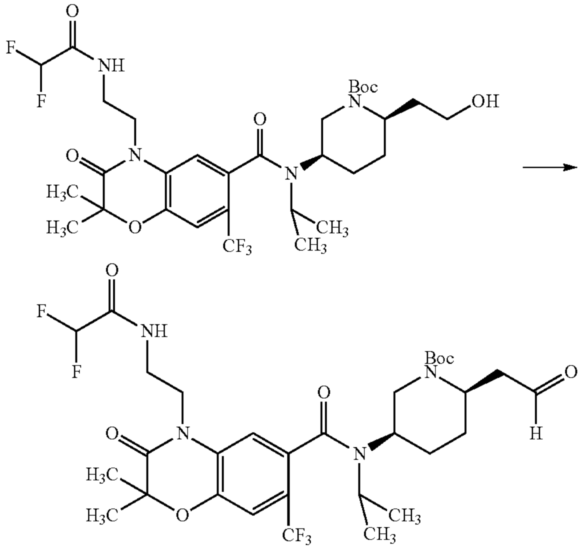

Under the nitrogen atmosphere, to a solution of tert-butyl (2R,5R)-5-[{[4-{2-[(difluoroacetyl)-amino]ethyl}-2,2-dimethyl-3-oxo-7-(trifluoromethyl)-3,4-dihydro-2H-1,4-benzoxazin-6-yl]carbonyl}-(isopropyl)amino]-2-(2-hydroxyethyl)piperidine-1-carboxylate (1.1 g) in methylene chloride-acetonitrile (5 ml, 5 ml) were added N-methylmorpholine oxide (283 mg) and molecular sieve 4 Å (750 mg), and the mixture was stirred at room temperature for a while. Then, tetrapropylammonium perruthenate (56 mg) was added thereto, and the mixture was stirred at room temperature for 3 hours. Then, the insoluble materials were removed by filtration, and the filtrate was concentrated under reduced pressure. The obtained residue was purified by silica gel column chromatography (the developing solvent: hexane/acetone=2/1) to give the title compound (757 mg).

MS (ESI+) 677 ($M^{+}$+1, 100%).

Reference Example 326 tert-Butyl (2R,5R)-5-[[(4-{2-[(difluoroacetyl)amino]ethyl}-2,2,7-trimethyl-3-oxo-3,4-dihydro-2H-1,4-benzoxazin-6-yl)carbonyl](isopropyl)amino]-2-(2-oxoethyl)piperidine-1-carboxylate

[Chemical formula 470]

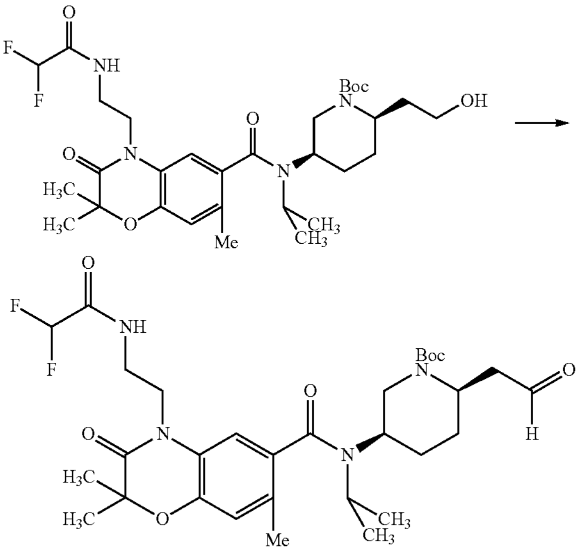

Using the compound of Reference Example 324, the title compound was obtained in a similar manner to Reference Example 325.

MS (ESI+) 624 ($M^{+}$+1, 11%).

Reference Example 327 tert-Butyl (2R,5R)-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropyl)amino]-2-{2-[(2,2,2-trifluoroethyl)-amino]ethyl}piperidine-1-carboxylate

[Chemical formula 471]

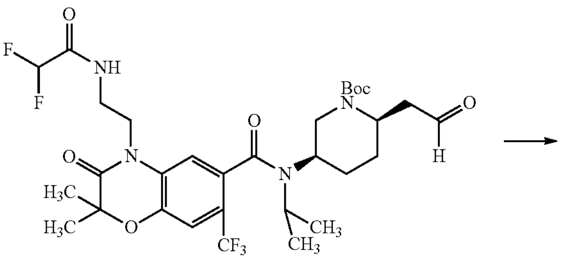

-continued

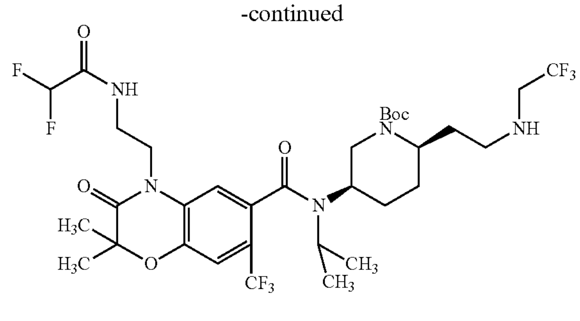

To a solution of tert-butyl (2R,5R)-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropyl)amino]-2-(2-oxoethyl)piperidine-1-carboxylate (377 mg) in ethanol (3 ml) were added 2,2,2-trifluoroethylamine hydrochloride (227 mg), acetic acid (128 μl), sodium triacetoxyborohydride (367 mg), and the mixture was stirred at room temperature for 19 hours. To the reaction solution was added a saturated aqueous sodium hydrogen carbonate solution (2 ml), and the mixture was extracted with ethyl acetate (50 ml). The organic layer was dried over sodium sulfate, filtered, and concentrated under reduced pressure. The obtained residue was purified by silica gel column chromatography (the developing solvent: chloroform/methanol=99/1) to give the title compound (425 mg).

MS (ESI+) 761 ($M^{+}$+1, 100%).

Reference Example 328 tert-Butyl (2R,5R)-5-[[(4-{2-[(difluoroacetyl)amino]ethyl}-2,2,7-trimethyl-3-oxo-3,4-dihydro-2H-1,4-benzoxazin-6-yl)carbonyl](isopropyl)amino]-2-{2-[(2,2,2-trifluoroethyl)amino]ethyl}piperidine-1-carboxylate

[Chemical formula 472]

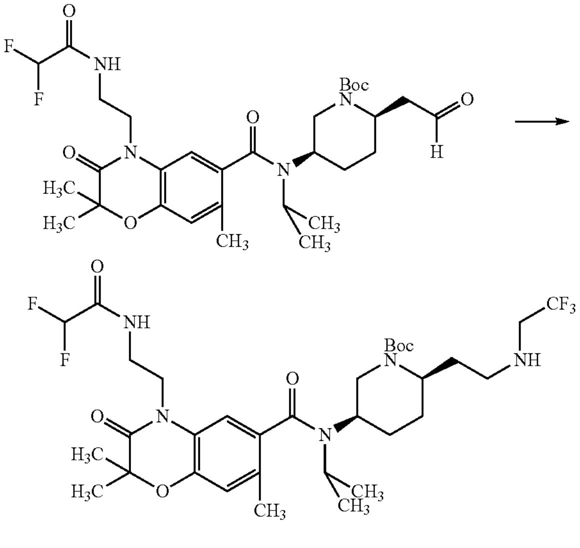

Using the compound of Reference Example 326, the title compound was obtained in a similar manner to Reference Example 327.

MS (ESI+) 707 ($M^{+}$+1, 100%).

Reference Example 329 tert-Butyl (2R,5R)-2-[2-(cyclopropylamino)ethyl]-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropyl)-amino]piperidine-1-carboxylate

[Chemical formula 473]

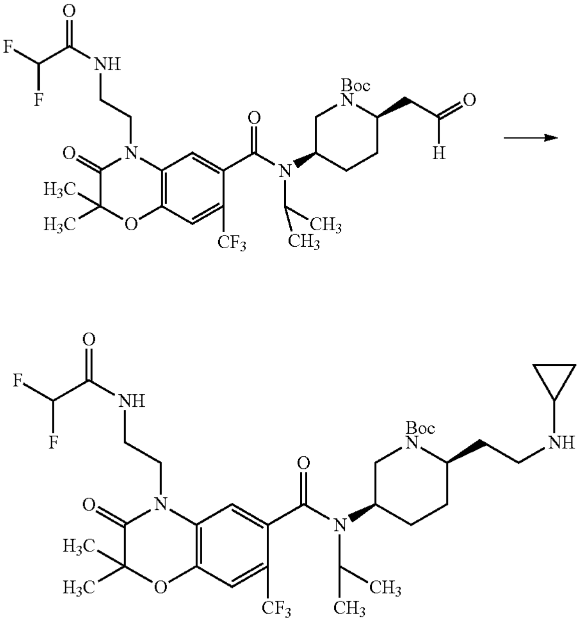

Using the compound of Reference Example 325, the title compound was obtained in a similar manner to Reference Example 327.

MS (ESI+) 719 ($M^{+}$+1, 100%).

Reference Example 330 tert-Butyl (2R,5R)-2-[2-(cyclopropylamino)ethyl]-5-[[(4-{2-[(difluoroacetyl)amino]ethyl}-2,2,7-trimethyl-3-oxo-3,4-dihydro-2H-1,4-benzoxazin-6-yl)carbonyl](isopropyl)amino]piperidine-1-carboxylate

[Chemical formula 474]

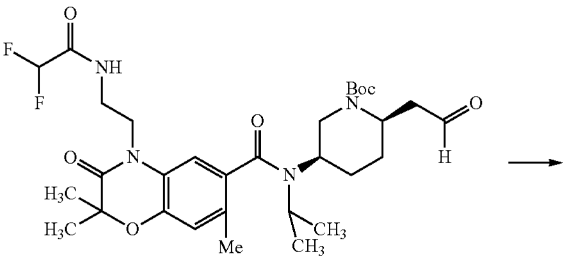

-continued

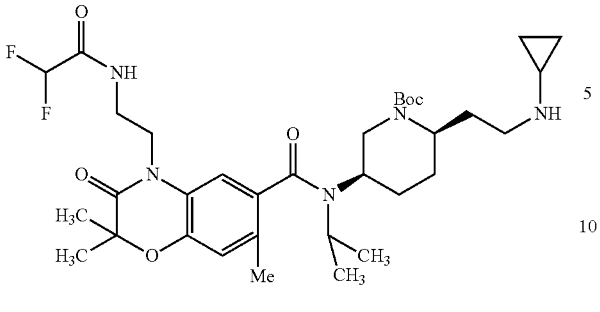

Using the compound of Reference Example 326, the title compound was obtained in a similar manner to Reference Example 327.

MS (ESI+) 665 ($M^{+}$+1, 100%).

Reference Example 331 tert-Butyl (2R,5R)-2-{2-[[(4-chlorophenyl)acetyl](cyclopropyl)amino]ethyl}-5-[{[4-{2-[(difluoroacetyl)amino]ethyl}-2,2-dimethyl-3-oxo-7-(trifluoromethyl)-3,4-dihydro-2H-1,4-benzoxazin-6-yl)carbonyl](isopropyl)amino]piperidine-1-carboxylate

[Chemical formula 475]

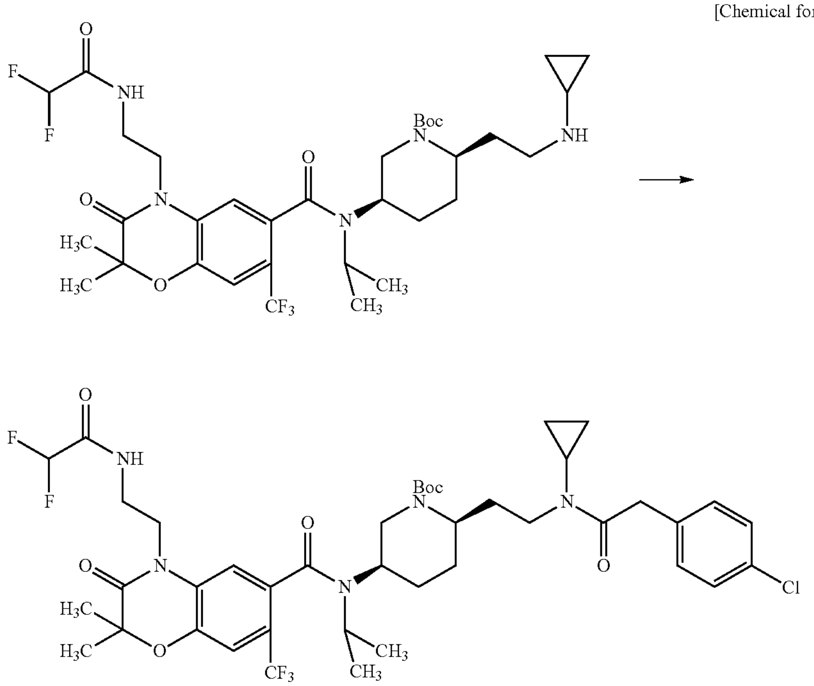

To a solution of tert-butyl (2R,5R)-2-[2-(cyclopropylamino)ethyl]-5-[{[4-{2-[(difluoroacetyl)-amino]ethyl}-2,2-dimethyl-3-oxo-7-(trifluoromethyl)-3,4-dihydro-2H-1,4-benzoxazin-6-yl]carbonyl}-(isopropyl)amino]piperidine-1-carboxylate (86 mg) in N,N-dimethylformamide (1 ml) were added 4-chlorophenylacetic acid (22 mg), 1-(3-dimethylaminopropyl)-3-ethylcarbodiimide hydrochloride (34 mg), 1-hydroxybenzotriazole monohydrate (24 mg) and triethylamine (50 μl), and the mixture was stirred at room temperature overnight. To the reaction solution was added water, and the mixture was extracted with ethyl acetate (50 ml). The organic layer was washed with water and a saturated aqueous sodium chloride solution. Then, the mixture was dried over sodium sulfate, filtered, and concentrated under reduced pressure. The obtained residue was purified by silica gel column chromatography (the developing solvent: hexane/acetone=2/1) to give the title compound (90 mg).

MS (ESI+) 870 ($M^{+}$+1, 100%).

Reference Example 332 tert-Butyl (2R,5R)-2-{2-[[(4-chlorophenyl)acetyl](cyclopropyl)amino]ethyl}-5-[[(4-{2-[(difluoroacetyl)amino]ethyl}-2,2,7-trimethyl-3-oxo-3,4-dihydro-2H-1,4-benzoxazin-6-yl)carbonyl](isopropyl)amino]piperidine-1-carboxylate

[Chemical formula 476]

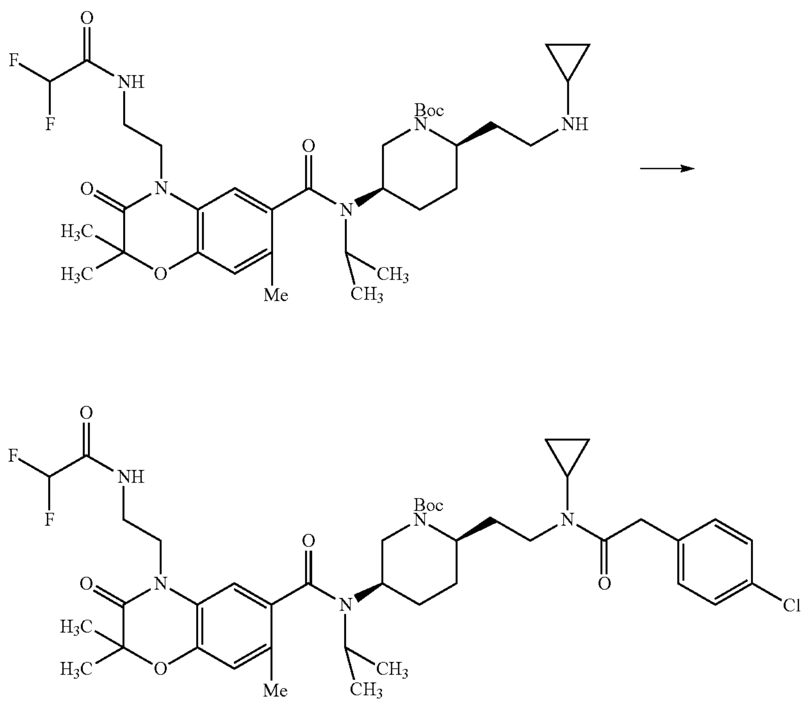

Using the compound of Reference Example 330, the title compound was obtained in a similar manner to Reference Example 331.

MS (ESI+) 817 ($M^{+}$+2, 42%).

Reference Example 333 tert-Butyl (2R,5R)-2-{2-[[(4-chlorophenyl)acetyl](2,2,2-trifluoroethyl)amino]ethyl}-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 477]

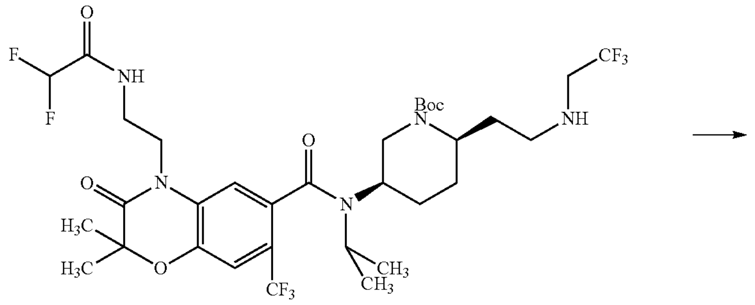

-continued

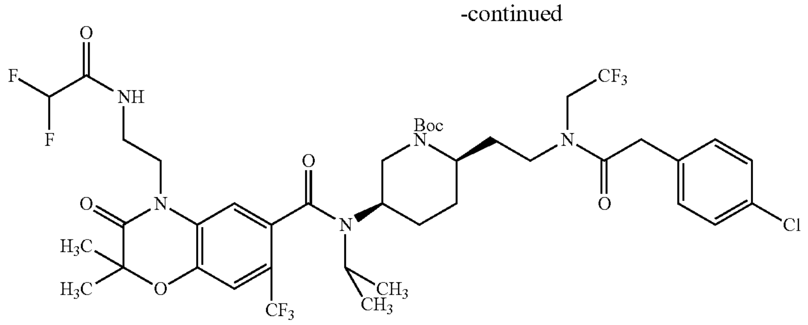

Using the compound of Reference Example 327, the title compound was obtained in a similar manner to Reference Example 331.

MS (ESI+) 913 ($M^{+}$+1, 50%).

Reference Example 334 tert-Butyl (2R,5R)-2-{2-[[(4-chlorophenyl)acetyl](2,2,2-trifluoroethyl)amino]ethyl}-5-[[(4-{2-[(difluoroacetyl)amino]ethyl}-2,2,7-trimethyl-3-oxo-3,4-dihydro-2H-1,4-benzoxazin-6-yl)carbonyl]-(isopropyl)amino]piperidine-1-carboxylate

[Chemical formula 478]

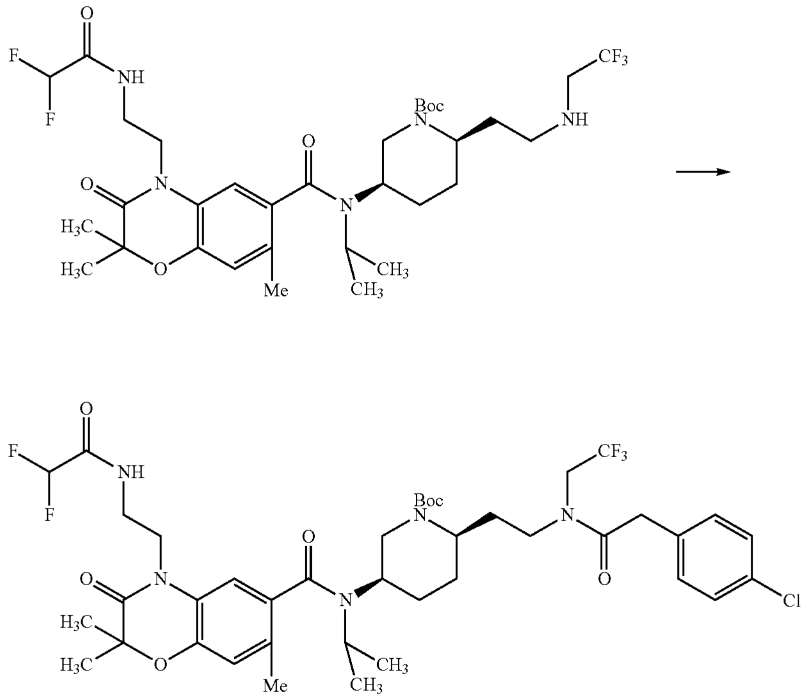

Using the compound of Reference Example 328, the title compound was obtained in a similar manner to Reference Example 331.

MS (ESI+) 859 ($M^{+}$+2, 11%).

Reference Example 335 tert-Butyl (2R,5R)-2-(2-{cyclopropyl[(3,4-dichlorophenyl)acetyl]amino}ethyl)-5-[{[4-{2-[(difluoroacetyl)amino]ethyl}-2,2-dimethyl-3-oxo-7-(trifluoromethyl)-3,4-dihydro-2H-1,4-benzoxazin-6-yl]-carbonyl}(isopropyl)amino]piperidine-1-carboxylate

[Chemical formula 479]

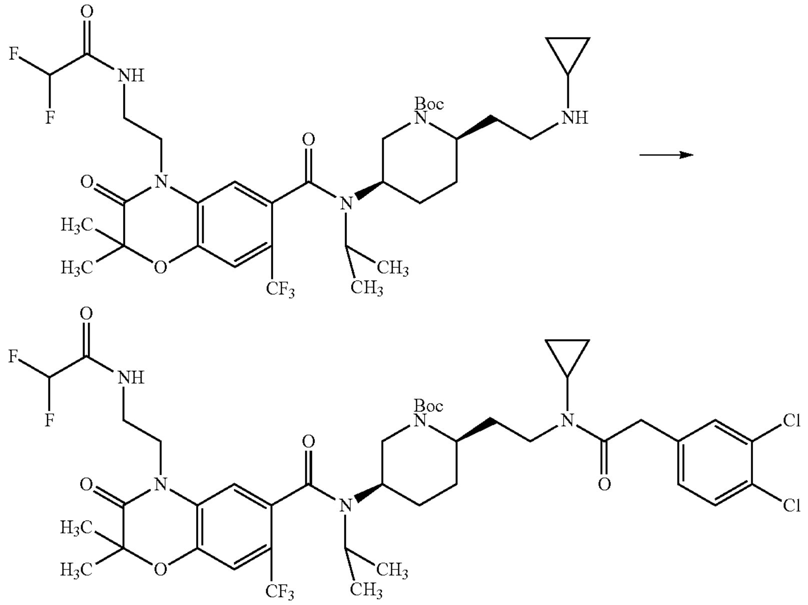

Using the compound of Reference Example 329, the title compound was obtained in a similar manner to Reference Example 331.

MS (ESI+) 904 ($M^{+}$+1, 100%).

Reference Example 336 tert-Butyl (2R,5R)-2-(2-{cyclopropyl[(3,4-dichlorophenyl)acetyl]amino}ethyl)-5-[[(4-{2-[(difluoroacetyl)amino]ethyl}-2,2,7-trimethyl-3-oxo-3,4-dihydro-2H-1,4-benzoxazin-6-yl)carbonyl](isopropyl)-amino]piperidine-1-carboxylate

[Chemical formula 480]

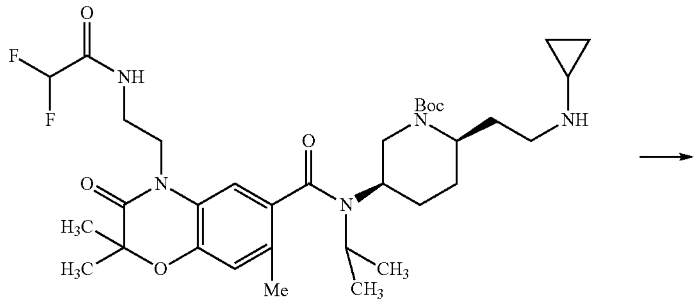

-continued

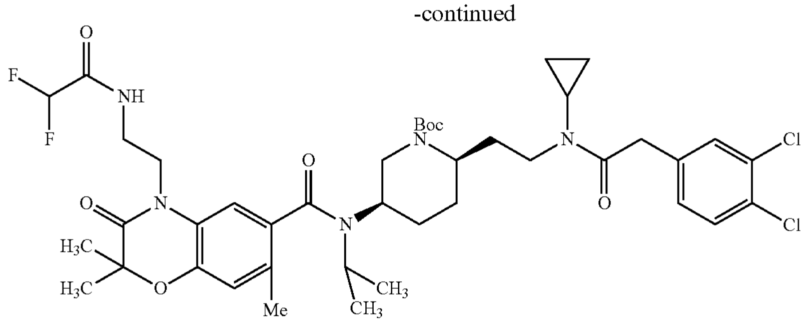

Using the compound of Reference Example 330, the title compound was obtained in a similar manner to Reference Example 331.

MS (ESI+) 851 ($M^{+}$+2, 22%).

Reference Example 337 tert-Butyl (2R,5R)-2-{2-[[(3,4-dichlorophenyl) acetyl](2,2,2-trifluoroethyl)amino]ethyl}-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 481]

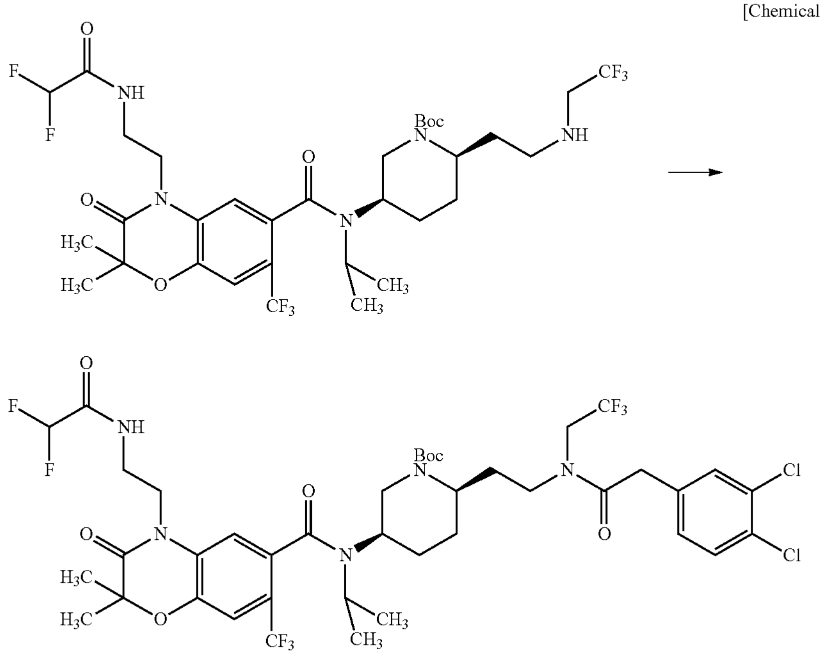

Using the compound of Reference Example 327, the title compound was obtained in a similar manner to Reference Example 331.

MS (ESI+) 946 ($M^{+}$+1, 100%).

Reference Example 338 tert-Butyl (2R,5R)-2-{2-[[2-(4-chlorophenyl)-2-methyl propanoyl](cyclopropyl)amino]ethyl}-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 482]

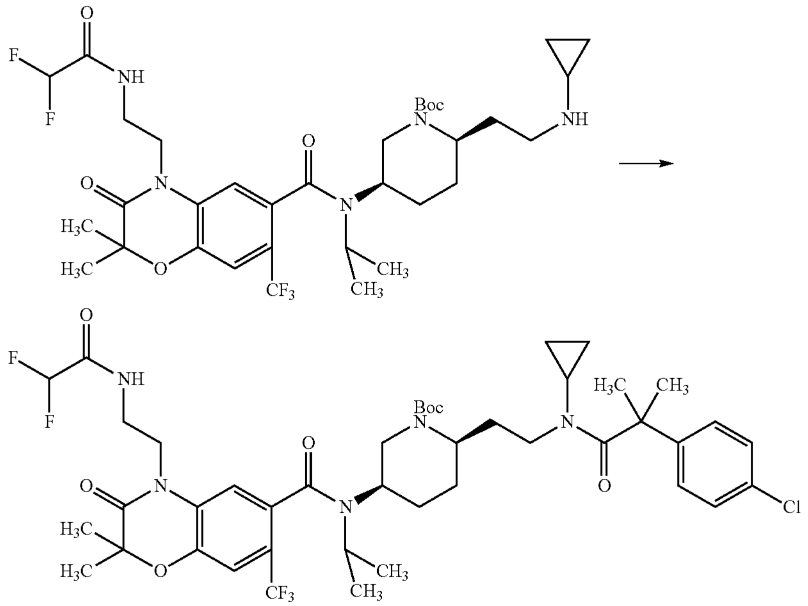

Using the compound of Reference Example 329, the title compound was obtained in a similar manner to Reference Example 331.

MS (ESI+) 898 ($M^{+}$+1, 100%).

Reference Example 339 tert-Butyl (2R,5R)-2-{2-[{[1-(4-chlorophenyl)cyclopropyl]carbonyl}(cyclopropyl)amino]ethyl}-5-[{[4-{2-[(difluoroacetyl)amino]ethyl}-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 483]

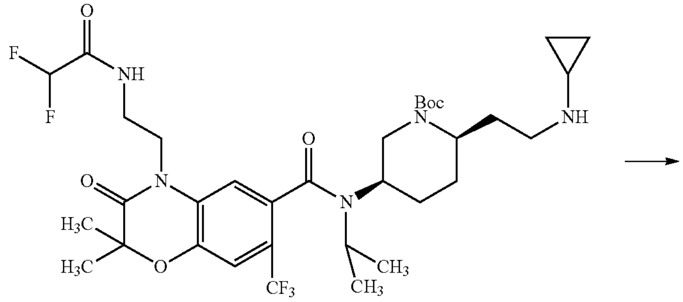

-continued

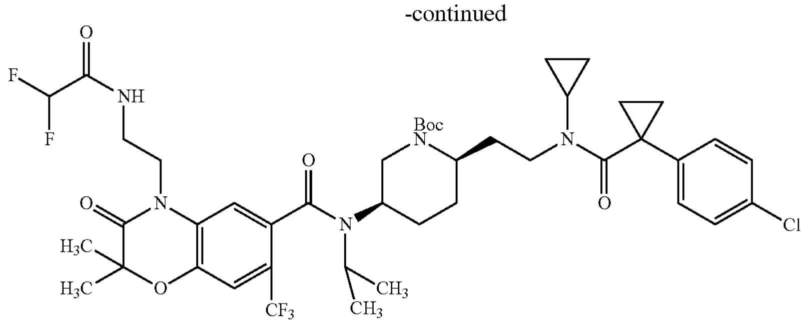

Using the compound of Reference Example 329, the title compound was obtained in a similar manner to Reference Example 331.

MS (ESI+) 896 ($M^{+}$+1, 100%).

Reference Example 340 tert-Butyl (2R,5R)-5-[{[2,2-dimethyl-4-(2-{[(methylamino)carbonothioyl]amino}ethyl)-3-oxo-7-(trifluoromethyl)-3,4-dihydro-2H-1,4-benzoxazin-6-yl]carbonyl}(isopropyl)amino]-2-(2-methoxyethyl) piperidine-1-carboxylate

[Chemical formula 484]

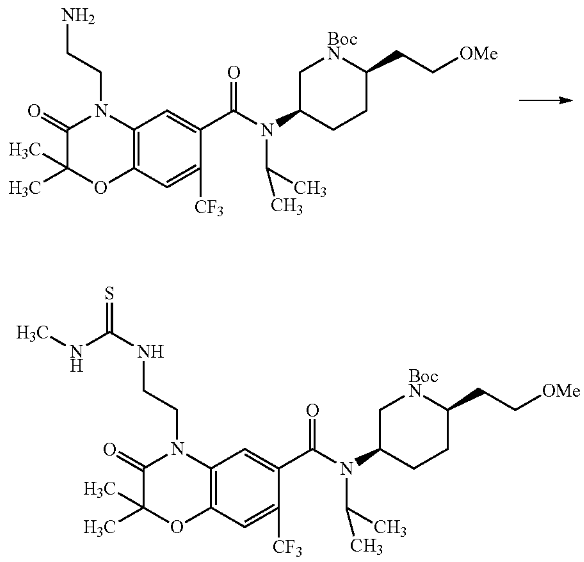

Under ice-cooling, to a solution of tert-butyl (2R,5R)-5-[{[4-(2-aminoethyl)-2,2-dimethyl-3-oxo-7-(trifluoromethyl)-3,4-dihydro-2H-1,4-benzoxazin-6-yl]carbonyl}(isopropylamino)-2-(2-methoxyethyl)-piperidine-1-carboxylate (246 mg) in tetrahydrofuran (3 ml) were added triethylamine (169 μl) and thiophosgene (32 μl), and the mixture was stirred for one hour. Then, to the mixture was added a 40% aqueous methylamine solution (200 μl), and the mixture was stirred overnight. Water was added thereto, and the mixture was extracted with ethyl acetate (50 ml). The organic layer was washed with water and a saturated aqueous sodium chloride solution. Then, the mixture was dried over sodium sulfate, filtered, and concentrated under reduced pressure. The obtained residue was purified by silica gel column chromatography (the developing solvent: hexane/acetone=2/1) to give the title compound (90 mg).

MS (ESI+) 688 ($M^{+}$+1, 100%).

Reference Example 341

(rac)-tert-Butyl (2S,5R)-5-[{[4-{2-[(difluoroacetyl) amino]ethyl}-2,2-dimethyl-3-oxo-7-(trifluoromethyl)-3,4-dihydro-2H-1,4-benzoxazin-6-yl]carbonyl}(isopropyl)amino]-2-methylpiperidine-1-carboxylate

[Chemical formula 485]

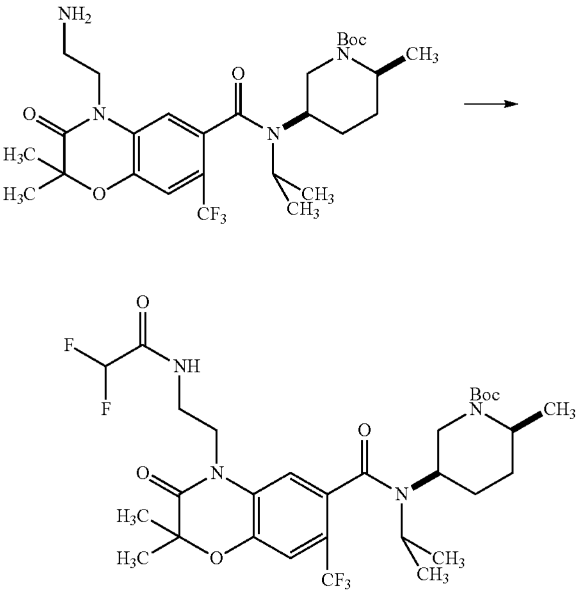

Using the compound of Reference Example 343, the title compound was obtained in a similar manner to Reference Example 120.

MS (ESI+) 649 ($M^{+}$+1, 29%).

Reference Example 342 tert-Butyl (2S ,5R)-5- [{[4-{2-[(difluoroacetyl) amino]ethyl }-2,2-dimethyl-3-oxo-7-(trifluoromethyl)-3,4-dihydro-2H-1,4-benzoxazin-6-yl]carbonyl}(isopropyl)amino] -2-(2-methoxyethyl) piperidine-1-carboxylate

[Chemical formula 486]

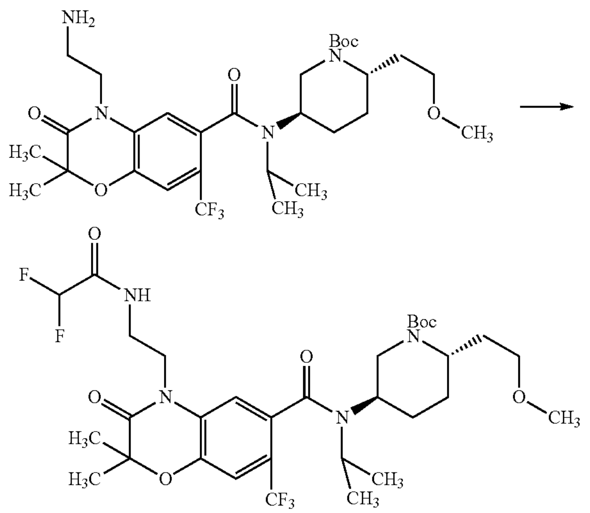

Using the compound of Reference Example 344, the title compound was obtained in a similar manner to Reference Example 120.

MS (ESI+) 693 ($M^{+}$+1, 11%).

Reference Example 343

(rac)-tert-Butyl (2S,5R)-5-[{[4-(2-aminoethyl)-2,2-dimethyl-3-oxo-7-(trifluoromethyl)-3,4-dihydro-2H-1,4-benzoxazin-6-yl]carbonyl}(isopropyl)amino]-2-methylpiperidine-1-carboxylate

[Chemical formula 487]

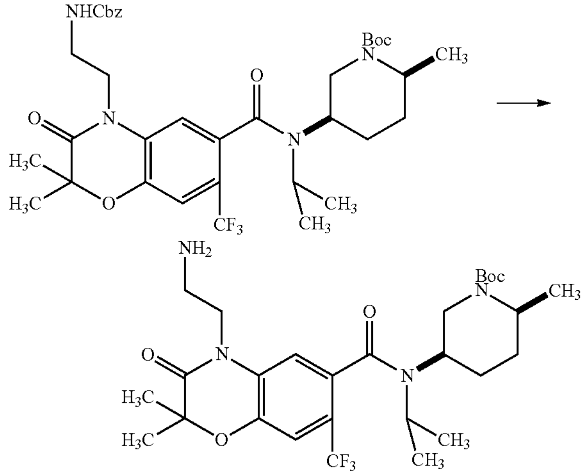

Using the compound of Reference Example 345, the title compound was obtained in a similar manner to Reference Example 139.

MS (ESI+) 571 ($M^{+}$+1, 77%).

Reference Example 344 tert-Butyl (2S,5R)-5-[{[4-(2-aminoethyl)-2,2-dimethyl-3-oxo-7-(trifluoromethyl)-3,4-dihydro-2H-1,4-benzoxazin-6-yl]carbonyl}(isopropyl)amino]-2-(2-methoxyethyl)piperidine-1-carboxylate

[Chemical formula 488]

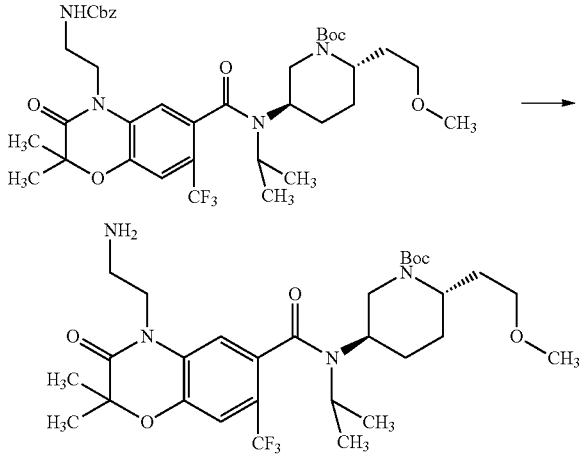

Using the compound of Reference Example 346, the title compound was obtained in a similar manner to Reference Example 139.

MS (ESI+) 615 ($M^{+}$+1, 27%).

Reference Example 345

(rac)-tert-Butyl (2S ,5R)-5- [{[4-(2-{[(benzyloxy) carbonyl]amino{ethyl)-2,2-dimethyl-3-oxo-7-(trifluoromethyl)-3,4-dihydro-2H-1,4-benzoxazin-6-yl] carbonyl }(isopropyl)amino]-2-methylpiperidine-1-carboxylate

[Chemical formula 489]

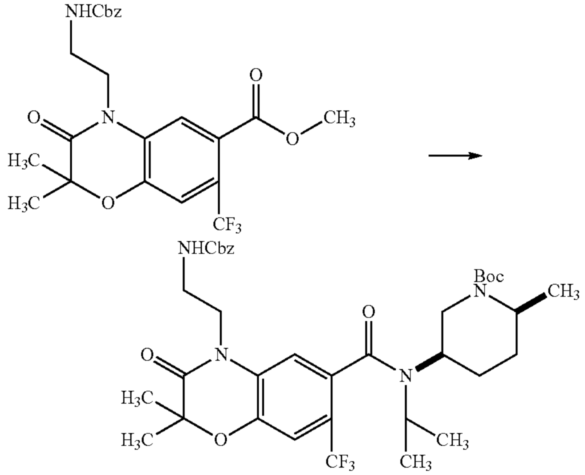

Using the compound of Reference Example 74, the title compound was obtained in a similar manner to Reference Example 5.

MS (ESI+) 705 ($M^{+}$+1, 31%).

Reference Example 346 tert-Butyl (2S,5R)-5-[{[4-(2-{[(benzyloxy)carbonyl] amino}ethyl)-2,2-dimethyl-3-oxo-7-(trifluoromethyl)-3,4-dihydro-2H-1,4-benzoxazin-6-yl]carbonyl}(isopropyl)amino]-2-(2-methoxyethyl) piperidine-1-carboxylate

[Chemical formula 490)

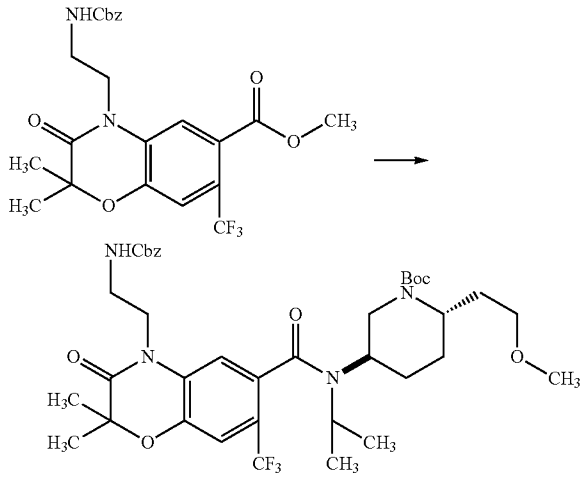

Using the compound of Reference Example 74, the title compound was obtained in a similar manner to Reference Example 5.

MS (ESI+) 749 ($M^{+}$+1, 10%).

Reference Example 347 tert-Butyl (2S,5R)-5-(isopropylamino)-2-(2-methoxyethyl)piperidine-1-carboxylate

[Chemical formula 491]

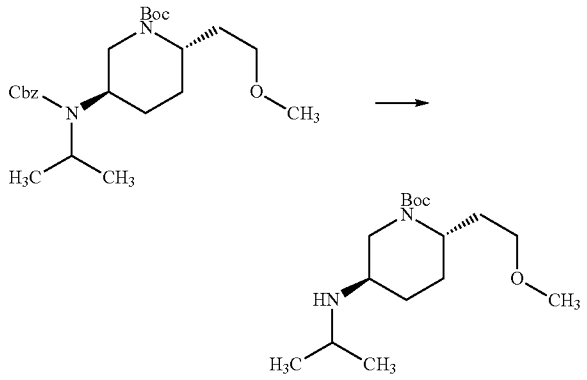

Using the compound of Reference Example 348, the title compound was obtained in a similar manner to Reference Example 312.

MS (ESI+) 301 ($M^{+}$+1, 52%).

Reference Example 348 tert-Butyl (2S,5R)-5-[[(benzyloxy)carbonyl](isopropyl)amino]-2-(2-methoxyethyl)piperidine-1-carboxylate

[Chemical formula 492]

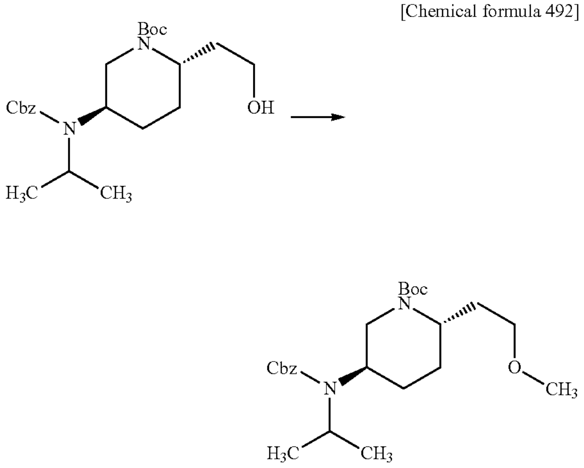 [SMILES: CC(C)N(C(=O)OCc1ccccc1)[C@@H]1CC[C@@H](CCO)N(C(=O)OC(C)(C)C)C1 ; COCC[C@@H]1CC[C@@H](N(C(=O)OCc2ccccc2)C(C)C)CN1C(=O)OC(C)(C)C]

Using the compound of Reference Example 349, the title compound was obtained in a similar manner to Reference Example 310.

MS (ESI+) 435 ($M^{+}$+1, 11%).

Reference Example 349 tert-Butyl (2S,5R)-5-[[(benzyloxy)carbonyl](isopropyl)amino]-2-(2-hydroxyethyl)piperidine-1-carboxylate

[Chemical formula 493]

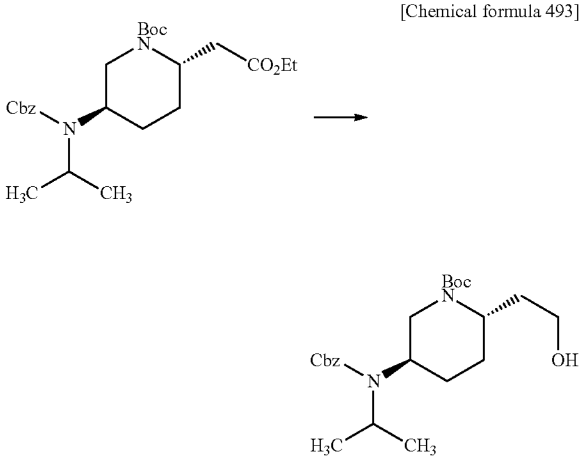 [SMILES: CCOC(=O)C[C@@H]1CC[C@@H](N(C(=O)OCc2ccccc2)C(C)C)CN1C(=O)OC(C)(C)C ; CC(C)N(C(=O)OCc1ccccc1)[C@@H]1CC[C@@H](CCO)N(C(=O)OC(C)(C)C)C1]

Using the compound of Reference Example 350, the title compound was obtained in a similar manner to Reference Example 309.

MS (ESI+) 421 ($M^{+}$+1, 15%).

Reference Example 350 tert-Butyl (2S,5R)-5-[[(benzyloxy)carbonyl](isopropyl)amino]-2-(2-ethoxy-2-oxoethyl)piperidine-1-carboxylate

[Chemical formula 494]

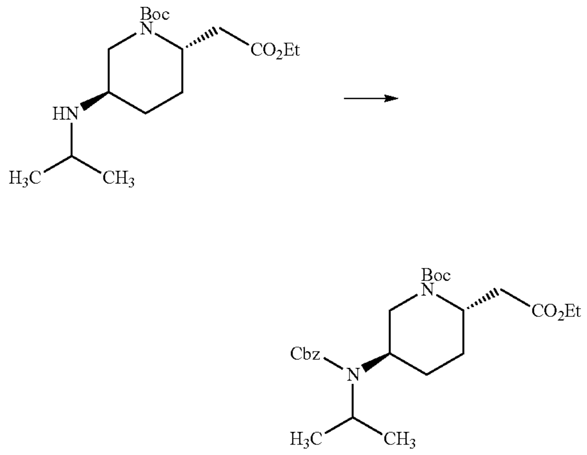

Using the compound of Reference Example 351, the title compound was obtained in a similar manner to Reference Example 307.

MS (ESI+) 463 ($M^{+}$+1, 11%).

Reference Example 351 tert-Butyl (2S,5R)-2-(2-ethoxy-2-oxoethyl)-5-(isopropylamino)piperidine-1-carboxylate

[Chemical formula 495]

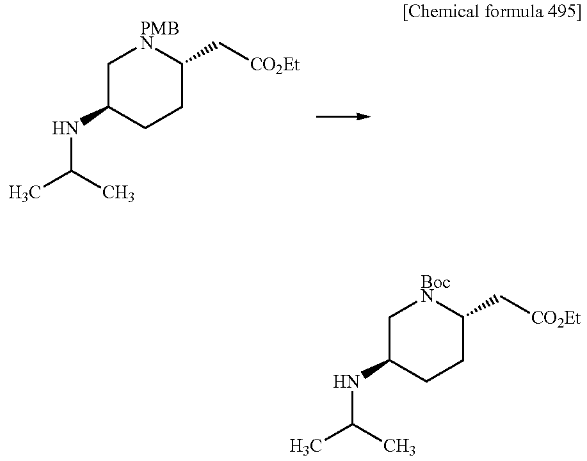

Using the compound of Reference Example 353, the title compound was obtained in a similar manner to Reference Example 306.

MS (ESI+) 329 ($M^{+}$+1, 71%).

Reference Example 352

(rac)-tert-Butyl (2S,5R)-5-(isopropylamino)-2-methylpiperidine-1-carboxylate

[Chemical formula 496]

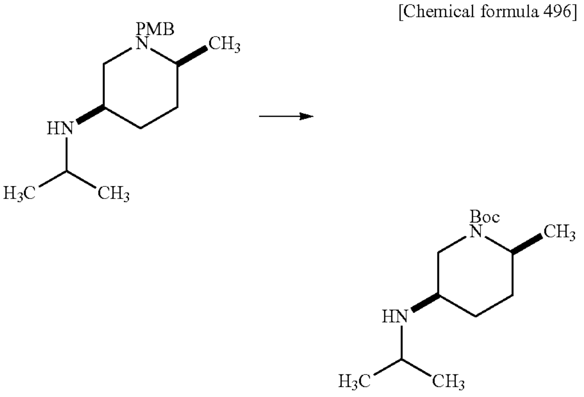

Using the compound of Reference Example 354, the title compound was obtained in a similar manner to Reference Example 306.

MS (ESI+) 257 ($M^{+}$+1, 38%).

Reference Example 353

Ethyl [(2S,5R)-5-(isopropylamino)-1-(4-methoxybenzyl)piperidin-2-yl]acetate

[Chemical formula 497]

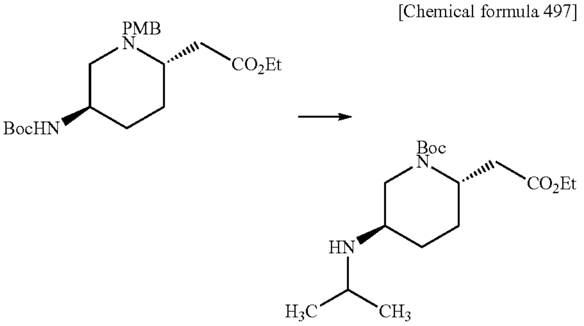

To a solution of ethyl [(2S,5R)-5-[(tert-butoxycarbonyl)amino]-1-(4-methoxybenzyl)piperidin-2-yl]acetate (25.0 g) in 1,4-dioxane (90 ml) was added a 4N solution of hydrochloric acid in 1,4-dioxane (92.2 ml), and the mixture was stirred at room temperature for 3 hours. To the reaction solution was added a saturated aqueous sodium hydrogen carbonate solution, and the mixture was extracted with ethyl acetate. The organic layer was washed with a saturated aqueous sodium chloride solution, dried over sodium sulfate, filtered, and concentrated under reduced pressure to give a crude intermediate amine compound. To a solution of the obtained intermediate in ethanol (125 ml) were added acetic acid (7.39 g) and acetone (13.5 ml), and the mixture was stirred at 60° C. for one hour. The reaction solution was cooled to room temperature, and thereto was added sodium triacetoxyborohydride (32.6 g), and the mixture was stirred for 16 hours. To the reaction solution was added a 10% aqueous potassium carbonate solution, and the mixture was extracted with ethyl acetate. The organic layer was washed with a saturated aqueous sodium chloride solution, dried over sodium sulfate, filtered, and concentrated under reduced pressure. The obtained residue was purified by silica gel column chromatography (the developing solvent: chloroform/ethanol=20/1) to give the title compound (15.5 g) as a colorless oil.

MS (ESI+) 349 ($M^+$+1, 33%).

Reference Example 354

(rac)-(3R,6S)—N-Isopropyl-1-(4-methoxybenzyl)-6-methylpiperidine-3-amine

[Chemical formula 498]

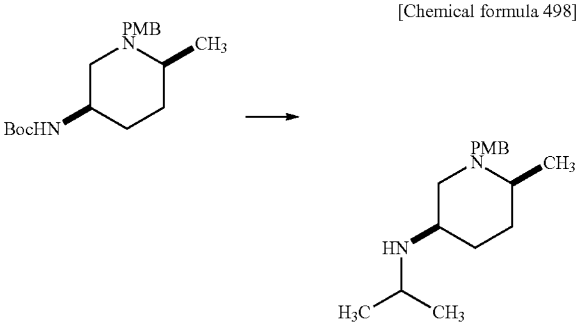

Using the compound of Reference Example 355, the title compound was obtained in a similar manner to Reference Example 353.

MS (ESI+) 277 ($M^+$+1, 59%).

Reference Example 355

(rac)-tert-Butyl [(3R,6S)-1-(4-methoxybenzyl)-6-methylpiperidin-3-yl]carbamate

[Chemical formula 499]

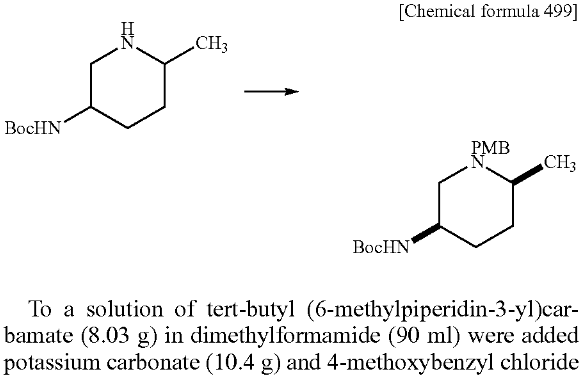

To a solution of tert-butyl (6-methylpiperidin-3-yl)carbamate (8.03 g) in dimethylformamide (90 ml) were added potassium carbonate (10.4 g) and 4-methoxybenzyl chloride (5.34 ml), and the mixture was stirred at room temperature for 6 hours. Water was added to the reaction solution, and the mixture was extracted with ethyl acetate. The organic layer was washed with a saturated aqueous sodium chloride solution, dried over sodium sulfate, filtered, and concentrated under reduced pressure. The obtained residue was purified by silica gel column chromatography (the developing solvent: chloroform/methanol=100/3) to give the title compound (8.87 g) as a colorless oil.

MS (ESI+) 335 ($M^+$+1, 100%).

Reference Example 356 tert-Butyl (6-methylpiperidin-3-yl)carbamate

[Chemical formula 500]

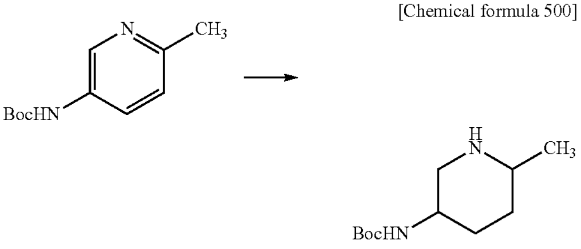

To a solution of tert-butyl (6-methylpyridin-3-yl)carbamate (9.00 g) in a mixture of acetic acid-ethanol (1:1, 100 ml) was added platinum (IV) oxide (900 mg), and the mixture was stirred under hydrogen pressure (0.4 MPa) at room temperature for 9 hours. To the mixture was further added platinum (IV) oxide (2.0 g), and the mixture was stirred for 10 hours. The reaction mixture was filtered on celite, and thereto was added toluene. The mixture was concentrated under reduced pressure, and to the residue was added a 5% aqueous potassium carbonates solution. The mixture was extracted with chloroform, and the organic layer was washed with a saturated aqueous sodium chloride solution, dried over sodium sulfate, filtered and concentrated under reduced pressure to give a crude product (8.03 g) of the title compound as a colorless oil.

MS (ESI+) 215 ($M^+$+1, 9%).

Reference Example 357 tert-Butyl (6-methylpyridin-3-yl)carbamate

[Chemical formula 501]

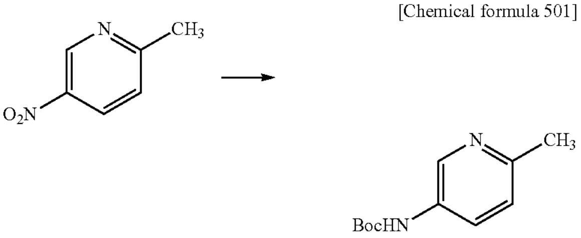

To a solution of 2-methyl-5-nitropyridine (13.5 g) (Synth. Commun. 1990, 20(19), 2965) in methanol (200 ml) was added 10% palladium-C (50% wet) (2.7 g), and the mixture was stirred at room temperature under hydrogen atmosphere for 4 hours. The reaction mixture was filtered on celite, and concentrated under reduced pressure. To a solution of the obtained residue in 1,4-dioxane (135 ml) was added di-tert-butyl dicarbonate (23.3 g), and the mixture was refluxed for one hour. The reaction solution was cooled to room temperature, and thereto was added a 5% aqueous potassium carbonate solution, and the mixture was extracted with ethyl acetate. The organic layer was washed with a saturated aqueous sodium chloride solution, dried over sodium sulfate, filtered and concentrated under reduced pressure. The obtained residue was purified by silica gel column chromatography (the developing solvent: hexane/ethyl acetate=1/1) to give the title compound (9.06 g) as a colorless oil.

MS (ESI+) 209 ($M^+$+1, 4%).

Reference Example 358

Methyl 4-mercapto-2-methyl-5-nitrobenzoate

[Chemical formula 502]

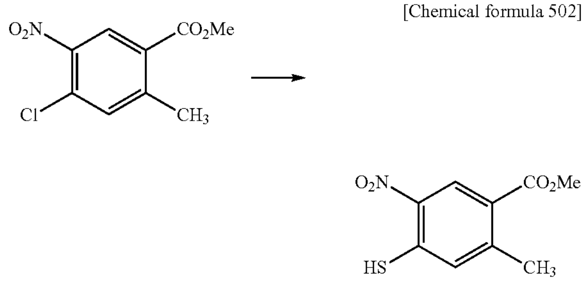

To a solution of methyl 4-chloro-2-methyl-5-nitrobenzoate (1.21 g) in methanol (20 ml) was added sodium hydrosulfide (561 mg), and the mixture was refluxed with stirring for 2 hours. After the reaction was complete, the reaction solution was concentrated, and methanol was concentrated under reduced pressure. Then, to the resultant were added water and 2N hydrochloric acid, and the mixture was extracted with ethyl acetate. The organic layer was dried over sodium sulfate, filtered, concentrated under reduced pressure. The obtained residue was purified by column chromatography to give the title compound (1.17 g).

MS (ESI+) 228 ($M^{+}$+1, 100%).

Reference Example 359

Methyl 4-[(2-ethoxy-1,1-dimethyl-2-oxoethyl)thio]-2-methyl-5-nitrobenzoate

[Chemical formula 503]

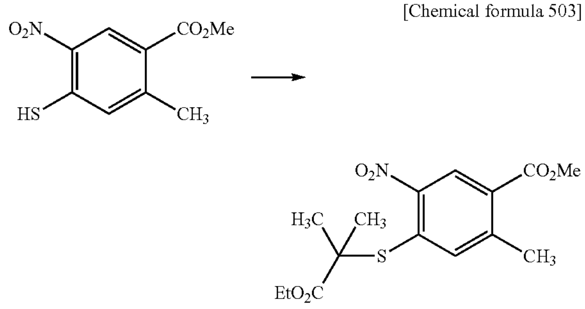

To a solution of methyl 4-mercapto-2-methyl-5-nitrobenzoate (1.17 g) in N,N-dimethyl-formamide (20 ml) were added potassium carbonate (1.42 g), ethyl 2-bromoisobutyrate, and the mixture was stirred at 80° C. for 4 hours. After the reaction was complete, water and 2N hydrochloric acid were added thereto, and the mixture was extracted with ethyl acetate. The organic layer was dried over sodium sulfate, filtered, concentrated under reduced pressure. The obtained residue was purified by column chromatography to give a crude product of the title compound (3.56 g).

MS (ESI+) 342 ($M^{+}$+1, 100%).

Reference Example 360

Methyl 2,7-dimethyl-3-oxo-3,4-dihydro-2H-1,4-benzothiazine-6-carboxylate

[Chemical formula 504]

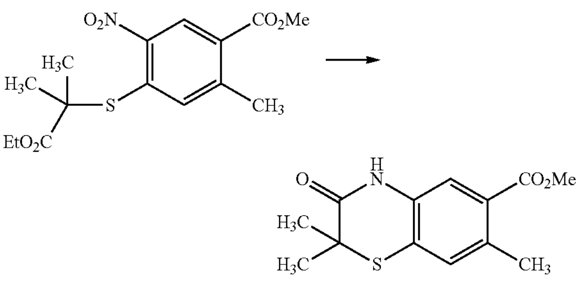

Iron powder (1.4 g) was suspended in acetic acid (5 ml) and warmed to 100° C., and thereto was added dropwise a solution of the above crude product (methyl 4-[(2-ethoxy-1,1-dimethyl-2-oxoethyl)-thio]-2-methyl-5-nitrobenzoate) in acetic acid (20 ml), and the mixture was heated with stirring for 4 hours. After the reaction was complete, the mixture was cooled to room temperature, and filtered on celite to remove the iron powder. Acetic acid was evaporated under reduced pressure, and water was added to the residue. The mixture was extracted with ethyl acetate, and the organic layer was dried over sodium sulfate, filtered, and concentrated under reduced pressure to give a crude product of the title compound. The obtained residue was purified by silica gel column chromatography to give the title compound (410 mg).

MS (ESI+) 266 ($M^{+}$+1, 100%).

Reference Example 361

Methyl 4-{2-[(methoxycarbonyl)amino]ethyl}-2,7-dimethyl-3-oxo-3,4-dihydro-2H-1,4-benzothiadine-6-carboxylate

[Chemical formula 505]

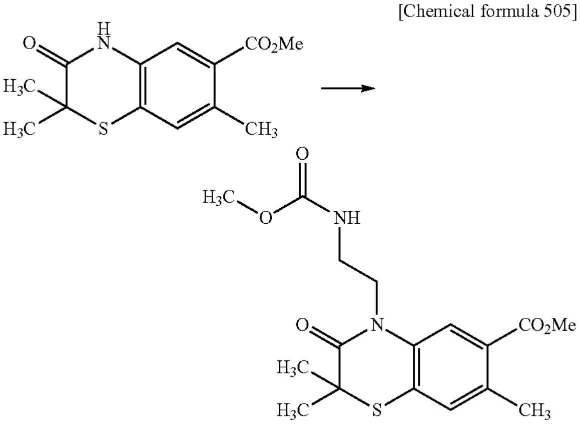

To a solution of methyl 2,7-dimethyl-3-oxo-3,4-dihydro-2H-1,4-benzothiazine-6-carboxylate (410 mg) in N,N-dimethylformamide (10 ml) solution were added potassium carbonate (590 mg, 4.3 mmol), methyl (2-bromoethyl) carbamate (422 mg), and the mixture was warmed to 80° C., and heated with stirring for 5 hours. Methyl (2-bromoethyl) carbamate (422 mg) was added thereto, and the mixture was stirred for 4 hours. Then, methyl (2-bromoethyl)carbamate (422 mg) was additionally added again, and the mixture was stirred for 6 hours. The reaction solution was cooled to room temperature, and the reaction solvent was evaporated under reduced pressure. Water was added to the residue, and the mixture was extracted with ethyl acetate. The organic layer was washed with a saturated aqueous sodium chloride solution, dried over sodium sulfate, filtered and concentrated under reduced pressure. The obtained residue was purified by silica gel column chromatography to give the title compound (200 mg).

MS (ESI+) 366 ($M^+$+1, 13%).

Reference Example 362 tert-Butyl (3R)-3-{isopropyl[(4-{2-[(methoxycarbonyl)amino]ethyl}-2,2,7-trimethyl-3-oxo-3,4-dihydro-2H-1,4-benzothiazin-6-yl)carbonyl]amino}piperidine-1-carboxylate

[Chemical formula 506]

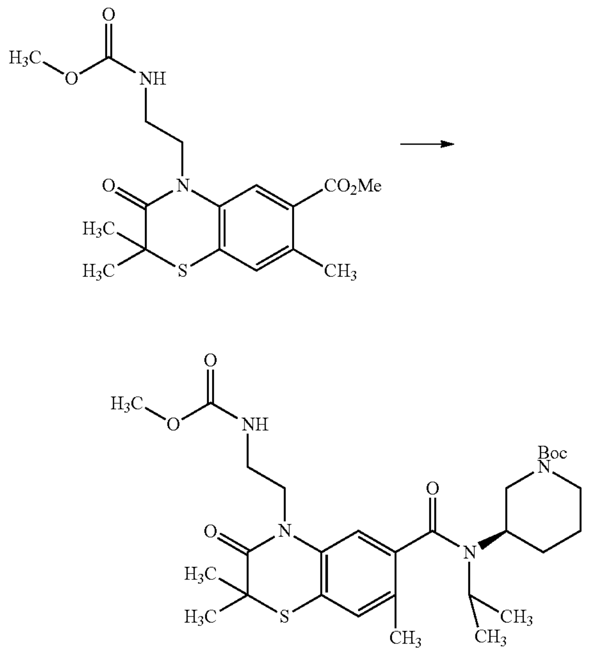

Methyl 4-{2-[(methoxycarbonyl)amino]ethyl}-2,7-dimethyl-3-oxo-3,4-dihydro-2H-1,4-benzothiazine-6-carboxylate (210 mg) was dissolved in 1M aqueous sodium hydroxide solution/tetrahydrofuran/ethanol=(2:1:1), and the mixture was stirred at 80° C. for one hour. The reaction solution was concentrated under reduced pressure to remove ethanol. To the concentrated residue was added 2N hydrochloric acid, and the mixture was extracted with ethyl acetate. The organic layer was dried over sodium sulfate, filtered, concentrated under reduced pressure. The obtained residue was purified by silica gel column chromatography to give 4-{2-[(methoxycarbonyl)amino]-ethyl}-2,2,7-trimethyl-3-oxo-3,4-dihydro-2H-1,4-benzothiazine-6-carboxylic acid (200 mg).

4-{2-[(Methoxycarbonyl)amino]ethyl}-2,2,7-trimethyl-3-oxo-3,4-dihydro-2H-1,4-benzo-thiazine-6-carboxylic acid (200 mg) was dissolved in dichloromethane (4 ml), and thereto were slowly added dropwise DMF (1 drop) and oxalyl chloride (74 μl), and the mixture was stirred at 25° C. for one hour. The solvent was evaporated under reduced pressure, and thereto was added toluene, and the mixture was concentrated under reduced pressure. This procedure was repeated twice so that the resultant was duly dried under reduced pressure.

The above crude product was dissolved in dichloromethane (4 ml), and thereto was slowly added dropwise triethylamine (158 μl), and further thereto was slowly added a solution of tert-butyl (3R)-3-(isopropylamino)piperidine-1-carboxylate (151 mg) in dichloromethane (1 ml) over a period of one hour. Then, the mixture was warmed to room temperature and stirred overnight. After the reaction was complete, to the mixture was added a 5% aqueous potassium hydrogen sulfate solution, and the mixture was extracted with ethyl acetate. The organic layer was dried over sodium sulfate, filtered, concentrated under reduced pressure. The obtained residue was purified by silica gel column chromatography to give the title compound (56 mg).

MS (ESI+) 577 ($M^+$+1, 16%).

Reference Example 363

Methyl 2,7-dimethyl-3-oxo-3,4-dihydro-2H-1,4-benzothiazine-6-carboxylate

[Chemical formula 507]

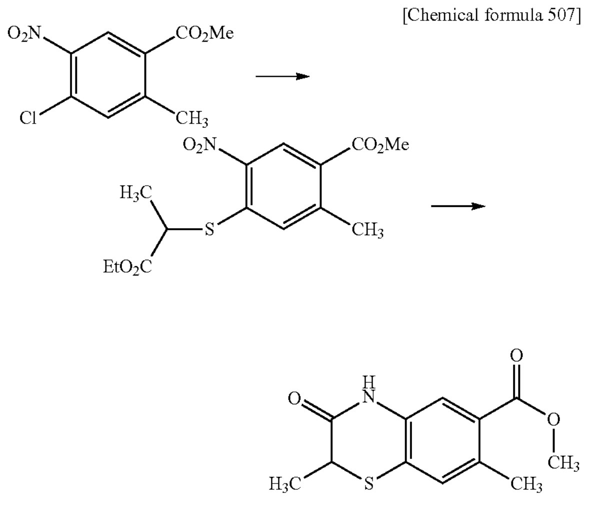

To a solution of methyl 4-chloro-2-methyl-5-nitrobenzoate (2.52 g) in N,N-dimethylformamide (20 ml) were added potassium carbonate (3.04 g) and ethyl 2-mercaptopropionate (2.2 g), and the mixture was stirred at 80° C. for 4 hours. After the reaction was complete, to the mixture was added a saturated aqueous sodium chloride solution, and the mixture was extracted with ethyl acetate. The organic layer was dried over sodium sulfate, filtered, concentrated under reduced pressure to give methyl 4-[(2-ethoxy-1-methyl-2-oxoethyl) thio]-2-methyl-5-nitrobenzoate (4.0 g). Subsequently, the title compound was obtained in a similar manner to Reference Example 2.

MS (ESI+) 252 ($M^+$+1, 100%).

Reference Example 364

Methyl 4-{2-[(methoxycarbonyl)amino]ethyl}-2,7-dimethyl-3-oxo-3,4-dihydro-2H-1,4-benzothiazine-6-carboxylate

[Chemical formula 508]

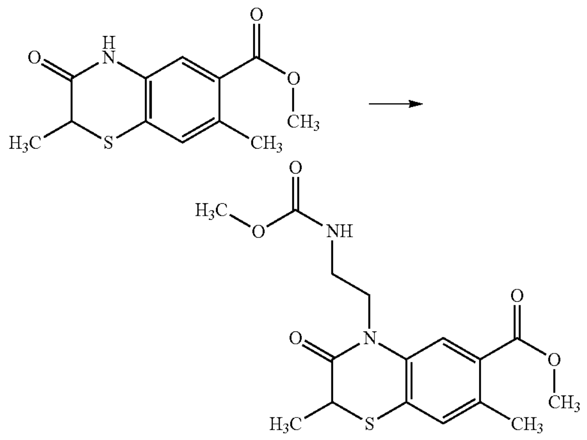

Using the compound of Reference Example 363, the title compound was obtained in a similar manner to Reference Example 361.

MS (ESI+) 353 ($M^{+}$+1, 100%).

Reference Example 365 tert-Butyl (3R)-3-{isopropyl[(4-{2-[(methoxycarbonyl)amino]ethyl}-2,7-dimethyl-3-oxo-3,4-dihydro-2H-1,4-benzothiazin-6-yl)carbonyl]amino}piperidine-1-carboxylate

[Chemical formula 509]

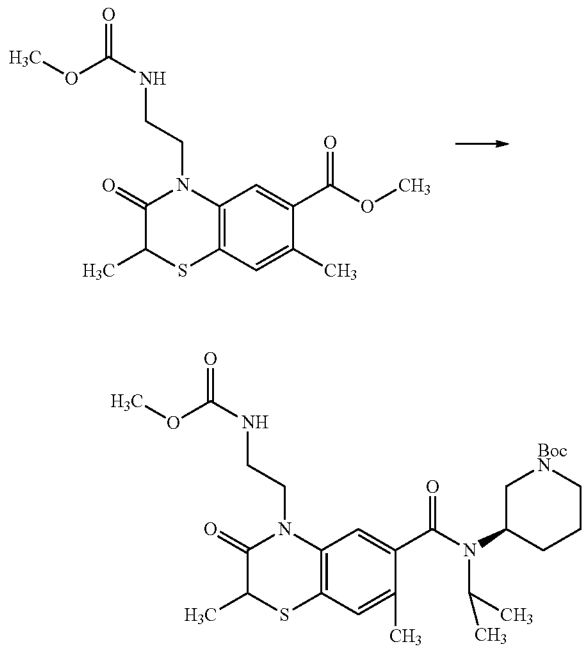

Using methyl 4-{2-[(methoxycarbonyl)amino]ethyl}-2,7-dimethyl-3-oxo-3,4-dihydro-2H-1,4-benzothiazine-6-carboxylate, 4-{2-[(methoxycarbonyl)amino]ethyl}-2,7-dimethyl-3-oxo-3,4-dihydro-2H-1,4-benzothiazine-6-carboxylic acid was obtained in a similar manner to Reference Example 4.

To a solution of 4-{2-[(methoxycarbonyl)amino]ethyl}-2,7-dimethyl-3-oxo-3,4-dihydro-2H-1,4-benzothiazine-6-carboxylic acid (460 mg) in N,N-dimethylformamide (4 ml) were added CIP reagent, N-ethyldiisopropylamine, tert-butyl (3R)-3-(isopropylamino)piperidine-1-carboxylate, and the mixture was stirred overnight. After the reaction was complete, to the mixture was added a saturated aqueous sodium chloride solution, and the mixture was extracted with ethyl acetate. The organic layer was dried over sodium sulfate, filtered, concentrated under reduced pressure. The obtained residue was purified by silica gel column chromatography to give the title compound (284 mg).

MS (ESI+) 563 ($M^{+}$+1, 41%).

Reference Example 366 tert-Butyl (3R)-3-[(4-chloro-2-methyl-5-nitrobenzoyl)(isopropyl)amino]piperidine-1-carboxylate

[Chemical formula 510]

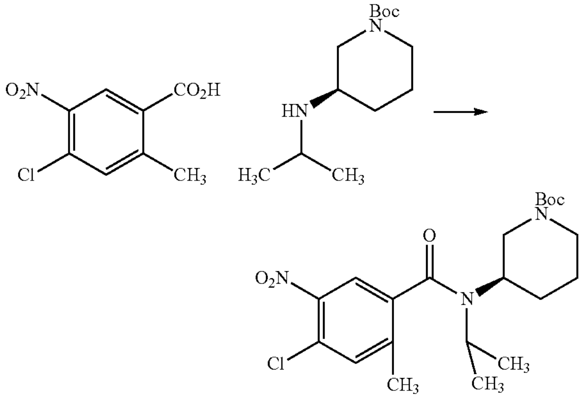

Using methyl 4-chloro-2-methyl-5-nitrobenzoate, the title compound was obtained in a similar manner to Reference Example 5.

MS (ESI+) 440 ($M^{+}$+1, 100%).

Reference Example 367 tert-Butyl (3R)-3-[[(2,7-dimethyl-3-oxo-3,4-dihydro-2H-1,4-benzothiazin-6-yl)carbonyl](isopropyl)amino]piperidine-1-carboxylate

[Chemical formula 511]

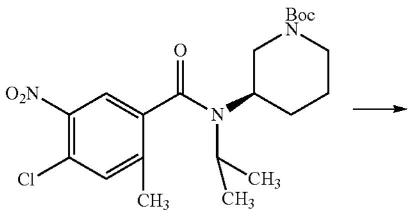

-continued

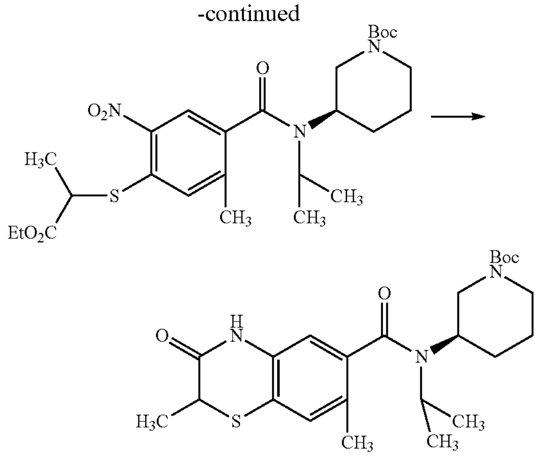

Using the compound of Reference Example 366, the title compound was obtained in a similar manner to Reference Example 363

MS (ESI+) 462 ($M^{+}$+1, 61%).

Reference Example 368 tert-Butyl (3R)-3-(isopropyl{[4-(4-methoxybutyl)-2,7-dimethyl-3-oxo-3,4-dihydro-2H-1,4-benzothiazin-6-yl]carbonyl}amino)piperidine-1-carboxylate

[Chemical formula 512]

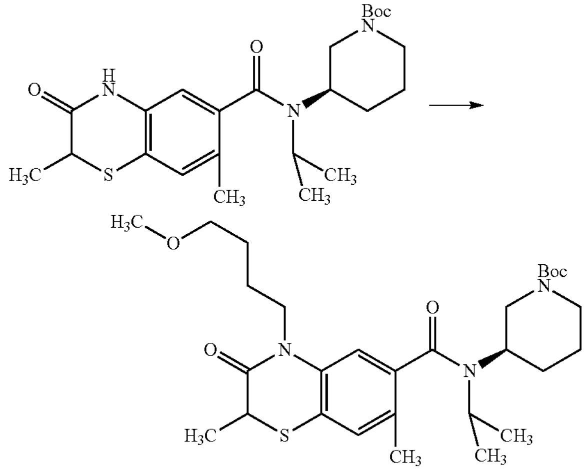

Using the compound of Reference Example 367, the title compound was obtained in a similar manner to Reference Example 3.

MS (ESI+) 548 ($M^{+}$+1, 32%).

Reference Example 369

Methyl 2,2,7-trimethyl-3-oxo-3,4-dihydro-2H-1,4-benzothiazine-6-carboxylate 1,1-dioxide

[Chemical formula 513]

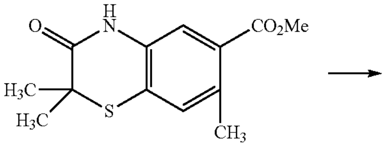

-continued

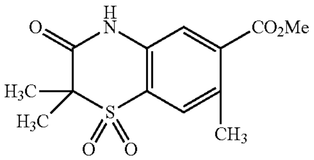

To a solution of methyl 2,7-dimethyl-3-oxo-3,4-dihydro-2H-1,4-benzothiazine-6-carboxylate (1.1 g) in acetic acid (10 ml) was added a 35% aqueous hydrogen peroxide solution (1.4 ml), and the mixture was stirred at 60° C. for 4 hours. Then, to the mixture was added aqueous hydrogen peroxide solution (1.4 ml) again, and the mixture was stirred for 4 hours. After the reaction was complete, to the mixture was added a saturated aqueous sodium chloride solution, and the mixture was extracted with ethyl acetate. The organic layer was dried over sodium sulfate, filtered, and concentrated under reduced pressure. The obtained residue was purified by silica gel column chromatography to give the title compound (238 mg).

MS (ESI+) 298 ($M^{+}$+1, 100%).

Reference Example 370

Methyl 4-(4-methoxybutyl)-2,2,7-trimethyl-3-oxo-3,4-dihydro-2H-1,4-benzothiazine-6-carboxylate 1,1-dioxide

[Chemical formula 514]

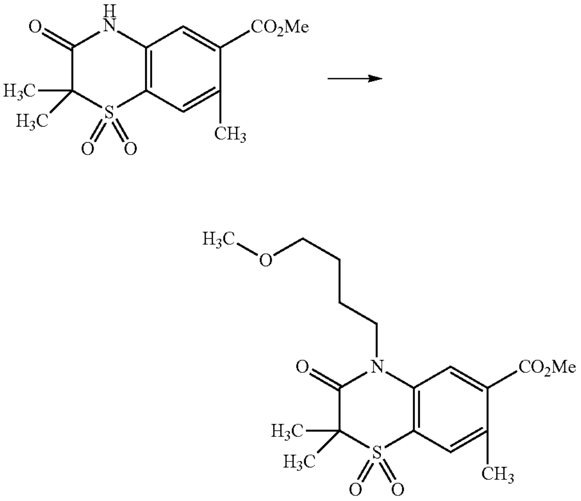

Using the compound of Reference Example 369, the title compound was obtained in a similar manner to Reference Example 3.

MS (ESI+) 384 ($M^{+}$+1, 100%).

Reference Example 371 tert-Butyl (3R)-3-(isopropyl{[4-(4-methoxybutyl)-2,2,7-trimethyl-1,1-dioxide-3-oxo-3,4-dihydro-2H-1,4-benzothiazin-6-yl]carbonyl}amino)piperidine-1-carboxylate

[Chemical formula 515]

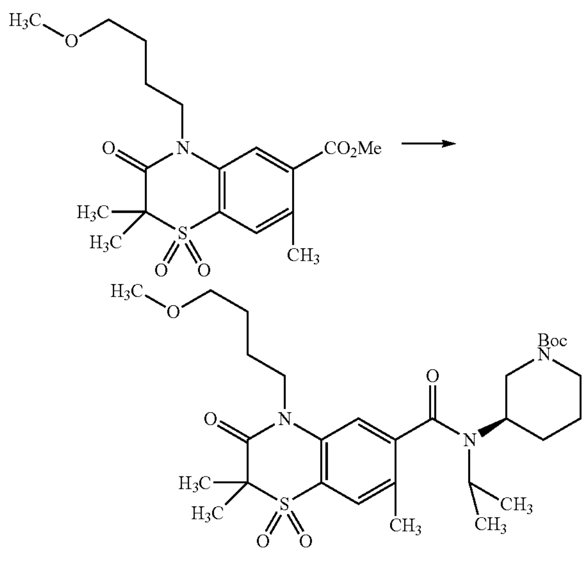

Using the compound of Reference Example 370, the title compound was obtained in a similar manner to Reference Example 5.

MS (ESI+) 594 ($M^{+}$+1, 41%).

Reference Example 372 tert-Butyl (3R)-3-[{[4-(2-{[(benzyloxy)carbonyl]amino}ethyl)-2,7-dimethyl-3-oxo-3,4-dihydro-2H-1,4-benzothiazin-6-yl]carbonyl}(isopropyl)amino]piperidine-1-carboxylate

[Chemical formula 516]

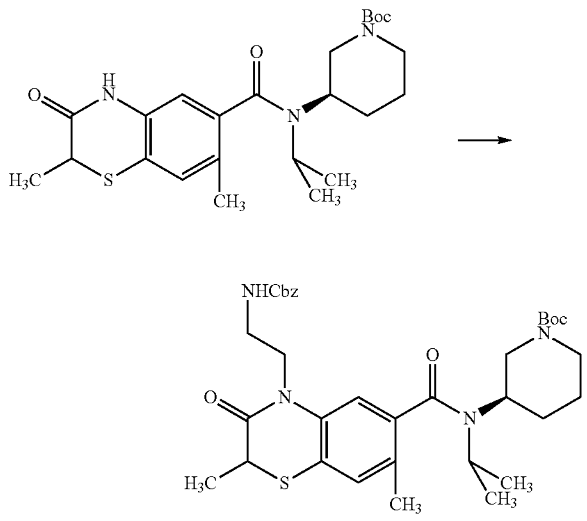

Using the compound of Reference Example 367, the title compound was obtained in a similar manner to Reference Example 378.

MS (ESI+) 638 ($M^{+}$+1, 65%).

Reference Example 373 tert-Butyl (3R)-3-[{[4-(2-aminoethyl)-2,7-dimethyl-3-oxo-3,4-dihydro-2H-1,4-benzothiazin-6-yl]carbonyl}(isopropyl)amino]piperidine-1-carboxylate

[Chemical formula 517]

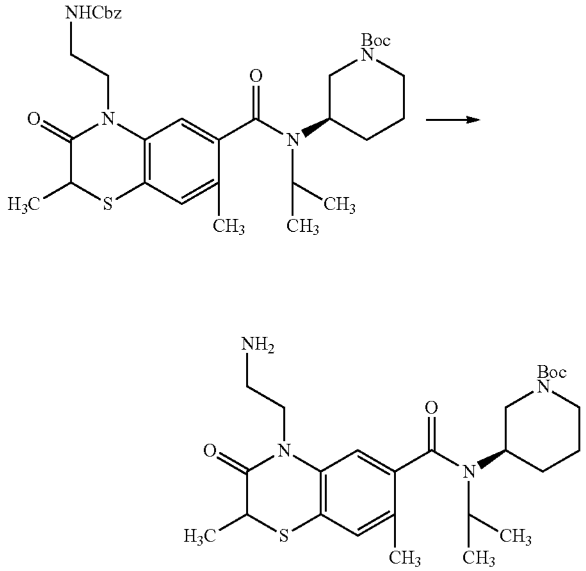

Using the compound of Reference Example 372, the title compound was obtained in a similar manner to Reference Example 139.

MS (ESI+) 505 ($M^{+}$+1, 100%).

Reference Example 374 tert-Butyl (3R)-3-[({2,7-dimethyl-3-oxo-4-[2-(propionylamide)ethyl]-3,4-dihydro-2H-1,4-benzothiazin-6-yl}carbonyl)(isopropyl)amino]piperidine-1-carboxylate

[Chemical formula 518]

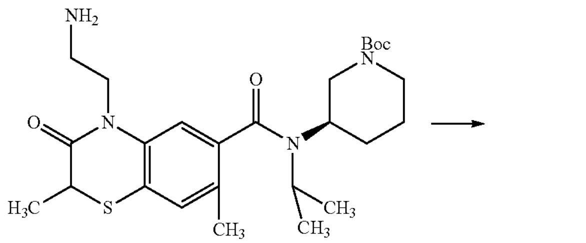

-continued

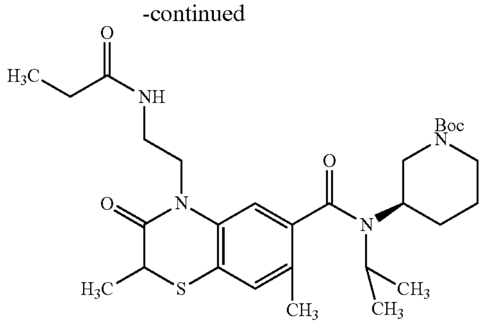

Using the compound of Reference Example 373, the title compound was obtained in a similar manner to Reference Example 132.

MS (ESI+) 561 ($M^{+}$+1, 15%).

Reference Example 375 tert-Butyl (3R)-3-[[4-chloro-5-nitro-2-(trifluoromethyl)benzoyl](isopropyl)amino]piperidine-1-carboxylate

[Chemical formula 519]

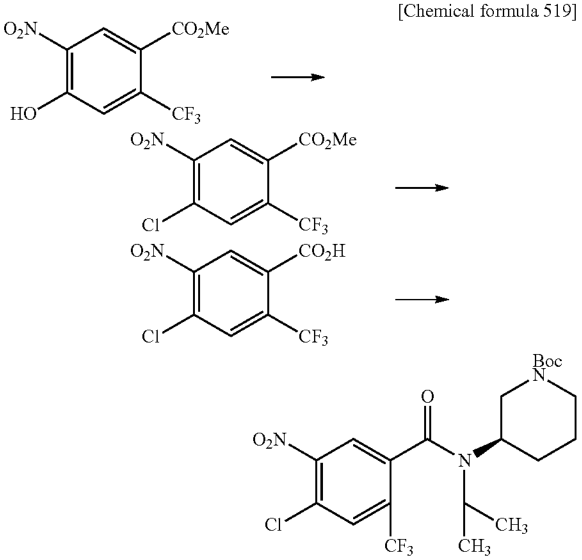

To a solution of methyl 4-hydroxy-5-nitro-2-(trifluoromethyl)benzoate (15 g) in dimethyl-formamide (170 ml) was added dropwise phosphorus oxychloride (7.4 ml) under ice-cooling. The reaction solution was heated at 100° C., and stirred for 2 hours. After the reaction was complete, water was added to the reaction mixture, and the mixture was extracted with ethyl acetate. The organic layer was washed with water, a saturated aqueous sodium chloride solution, dried over sodium sulfate, filtered, concentrated under reduced pressure. The obtained residue was purified by silica gel column chromatography to give methyl 4-chloro-5-nitro-2-(trifluoromethyl)benzoate (14.78 g).

Using methyl 4-chloro-5-nitro-2-(trifluoromethyl)benzoate, 4-chloro-5-nitro-2-(trifluoromethyl)benzoic acid was obtained in a similar manner to Reference Example 4.

Using 4-chloro-5-nitro-2-(trifluoromethyl)benzoic acid, the title compound was obtained in a similar manner to Reference Example 5.

MS (ESI+) 494 ($M^{+}$+1, 17%).

Reference Example 376 tert-Butyl (3R)-3-[[4-[(2-ethoxy-1,1-dimethyl-2-oxoethyl)thio]-5-nitro-2-(trifluoromethyl)benzoyl](isopropyl)amino]piperidine-1-carboxylate

[Chemical formula 520]

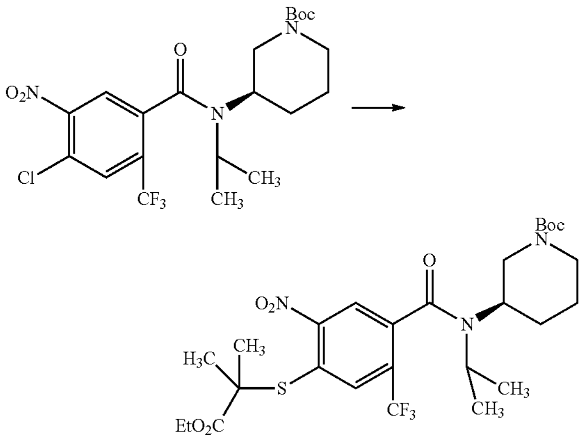

The compound of Reference Example 375 (2.20 g) was dissolved in dimethylsulfoxide (45 ml), and thereto was added sodium sulfide 9 hydrate (1.28 g), and the mixture was stirred at room temperature for 2 hours. Then, potassium carbonate (1.80 g) and ethyl 2-bromoisobutyrate (1.33 ml) were added to the mixture, and the mixture was warmed to 50° C., and stirred for 2 hours. After the reaction was complete, water was added to the mixture, and the mixture was extracted with ethyl acetate. The organic layer was dried over sodium sulfate, filtered, and concentrated under reduced pressure to give a crude product of the title compound. The obtained residue was purified by silica gel column chromatography to give the crude title compound.

MS (ESI+) 606 ($M^{+}$+1, 74%).

Reference Example 377 tert-Butyl (3R)-3-[{[2,2-dimethyl-3-oxo-7-(trifluoromethyl)-3,4-dihydro-2H-1,4-benzothiazin-6-yl]carbonyl}(isopropyl)amino]piperidine-1-carboxylate

[Chemical formula 521]

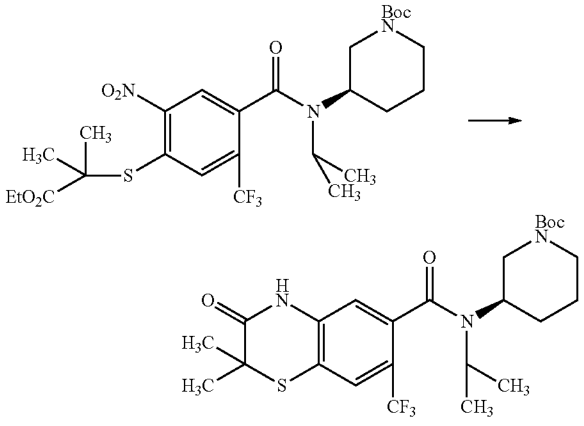

Using the compound of Reference Example 376, the title compound was obtained in a similar manner to Reference Example 2.

MS (ESI+) 530 ($M^{+}$+1, 20%).

Reference Example 378 tert-Butyl (3R)-3-[{[4-(2-{[(benzyloxy)carbonyl]amino}ethyl)-2,2-dimethyl-3-oxo-7-(trifluoromethyl)-3,4-dihydro-2H-1,4-benzothiazin-6-yl]carbonyl}(isopropyl)amino]piperidine-1-carboxylate

[Chemical formula 522]

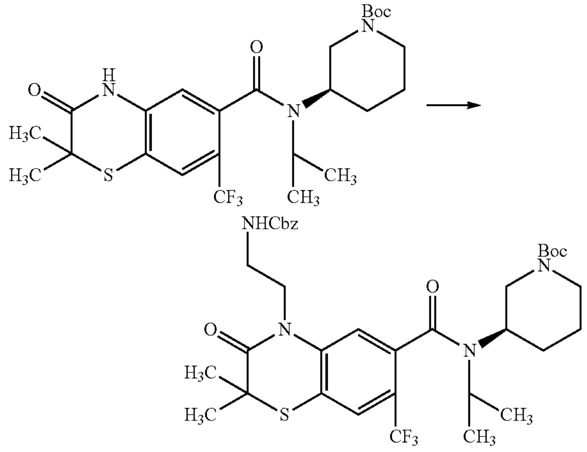

To a solution of BR-3925 (1.51 g) in acetonitrile (20 ml) were added potassium carbonate (590 mg), 18-crown-6 (75 mg), BR-3519 (883 mg), and the mixture was warmed to 80° C., and the mixture was heated with stirring for 7 hours. The reaction solution was cooled to room temperature, and the reaction solvent was evaporated under reduced pressure. Water was added to the residue, and the mixture was extracted with ethyl acetate. The organic layer was washed with a saturated aqueous sodium chloride solution, dried over sodium sulfate, filtered, concentrated under reduced pressure. The obtained residue was purified by silica gel column chromatography to give the title compound (2.11 g).

MS (ESI+) 707 ($M^{+}$+1, 76%).

Reference Example 379 tert-Butyl (3R)-3-[{[2,2-dimethyl-3-oxo-4-[2-(propionylamino)ethyl]-7-(trifluoromethyl)-3,4-dihydro-2H-1,4-benzothiazin-6-yl]carbonyl}(isopropyl)amino]piperidine-1-carboxylate

[Chemical formula 523]

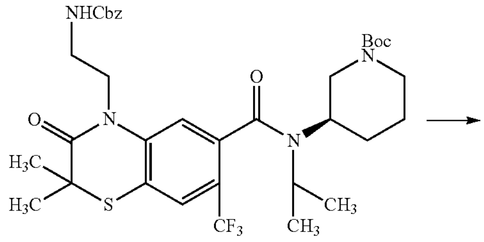

-continued

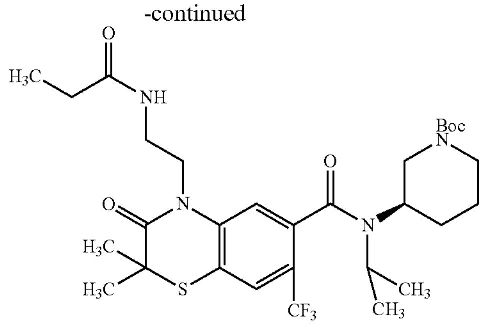

The compound of Reference Example 378 (2.07 g) was dissolved in methanol (100 ml), and thereto were added 20% palladium hydroxide/carbon (50% wet.), propionic anhydride (0.42 ml, 5.86 mmol), and the mixture was vigorously stirred under hydrogen atmosphere at room temperature for 12 hours. Further, 20% palladium hydroxide/carbon (50% wet.: 1.0 g), propionic anhydride (0.21 ml, 2.93 mmol) were added again, and the mixture was vigorously stirred under hydrogen atmosphere at room temperature for 10 hours.

After the reaction was complete, the mixture was filtered on celite, and washed with methanol, and the filtrate was concentrated under reduced pressure. The crude product was dissolved in tetrahydrofuran (200 ml), dried over sodium sulfate, filtered, concentrated under reduced pressure. The obtained residue was purified by silica gel column chromatography (the developing solvent: hexane/acetone=20/1-2/1) to give the title compound (1.06 g).

MS (ESI+) 629 ($M^{+}$+1, 100%).

Reference Example 380 tert-Butyl (3R)-3-[[(7-chloro-4-{2-[(methoxycarbonyl)amino]ethyl}-2,2-dimethyl-3-oxo-3,4-dihydro-2H-1,4-benzoxazin-6-yl)carbonyl](isopropyl)amino]piperidine-1-carboxylate

[Chemical formula 524]

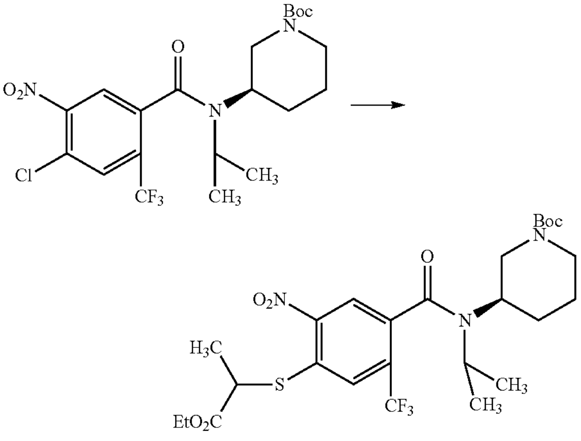

Using the compound of Reference Example 375, the title compound was obtained in a similar manner to Reference Example 363.

MS (ESI+) 592 ($M^{+}$+1, 74%).

Reference Example 381 tert-Butyl (3R)-3-[[(7-chloro-4-{2-[(methoxycarbonyl)amino]ethyl}-2,2-dimethyl-3-oxo-3,4-dihydro-2H-1,4-benzoxazin-6-yl)carbonyl](isopropyl)amino] piperidine-1-carboxylate

[Chemical formula 525]

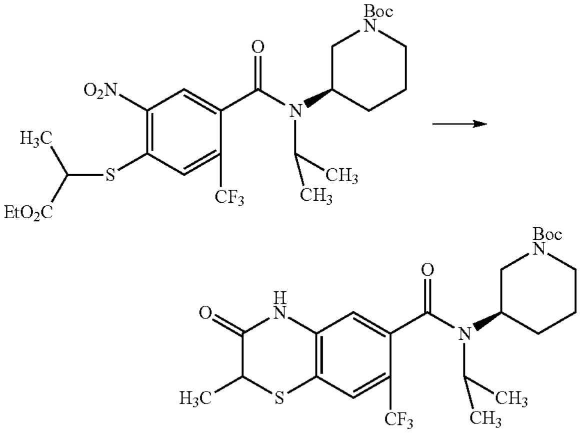

Using the compound of Reference Example 380, the title compound was obtained in a similar manner to Reference Example 2.

MS (ESI+) 516 ($M^{+}$+1, 22%).

Reference Example 382 tert-Butyl (3R)-3-[[(7-chloro-4-{2-[(methoxycarbonyl)amino]ethyl}-2,2-dimethyl-3-oxo-3,4-dihydro-2H-1,4-benzoxazin-6-yl)carbonyl](isopropyl)amino] piperidine-1-carboxylate

[Chemical formula 526]

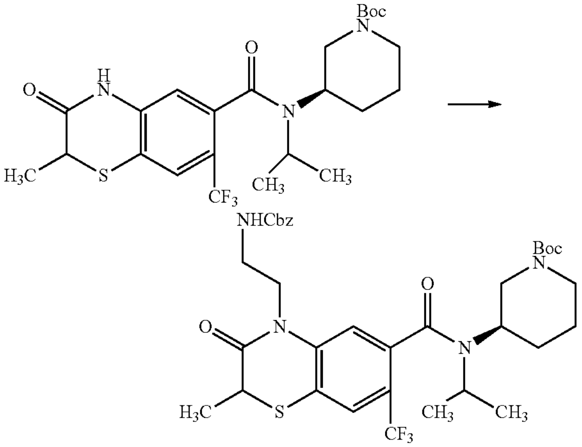

Using the compound of Reference Example 381, the title compound was obtained in a similar manner to Reference Example 378.

MS (ESI+) 693 ($M^{+}$+1, 96%).

Reference Example 383 tert-Butyl (3R)-3-(isopropyl{[2-methyl-3-oxo-4-[2-(propionylamine)ethyl]-7-(trifluoromethyl)-3,4-dihydro-2H-1,4-benzothiazin-6-yl]carbonyl}amino)piperidine-1-carboxylate

[Chemical formula 527]

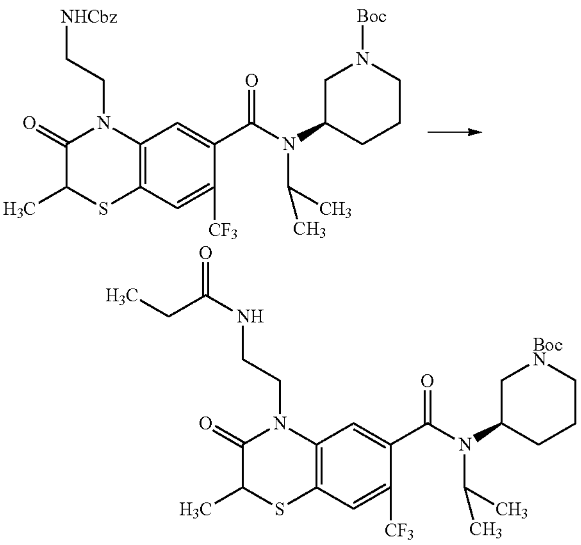

Using the compound of Reference Example 382, the title compound was obtained in a similar manner to Reference Example 379.

MS (ESI+) 629 ($M^{+}$+1, 100%).

Reference Example 384 tert-Butyl (3R)-3-[{[7-ethyl-4-(4-methoxybutyl)-3-oxo-2',3,3',4,5',6'-hexahydrospiro[1,4-benzoxazine-2,4'-pyran]-6-yl]carbonyl}(isopropyl)amino]piperidine-1-carboxylate

[Chemical formula 528]

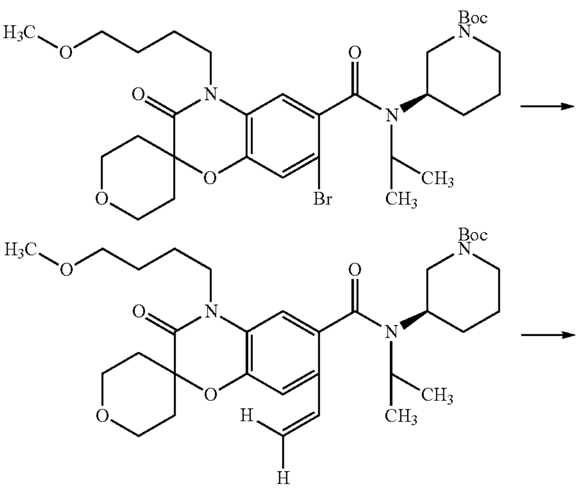

-continued

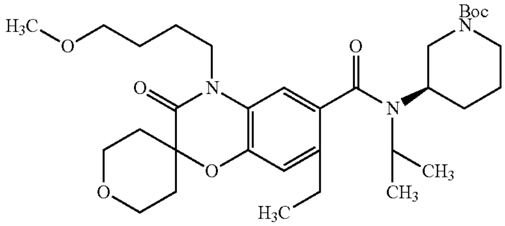

Using the compound of Reference Example 256, the title compound was obtained in a similar manner to Reference Example 9.

MS (ESI+) 602 ($M^{+}$+1, 45%).

Reference Example 385

Methyl 4-{[1-(methoxycarbonyl)cyclopropyl]oxy}-5-nitro-2-(trifluoromethyl)benzoate

[Chemical formula 529]

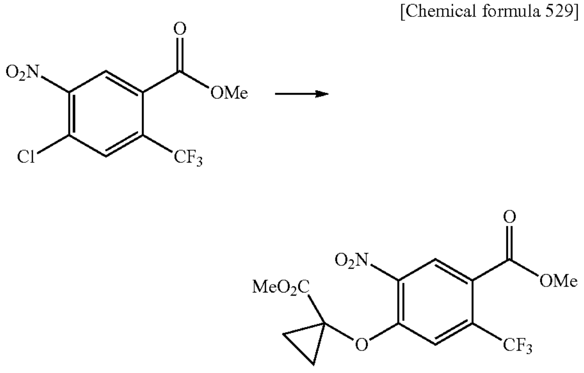

Using methyl 4-chloro-5-nitro-2-(trifluoromethyl)benzoate, the title compound was obtained in a similar manner to Reference Example 22.

MS (ESI+) 364 ($M^{+}$+1, 100%).

Reference Example 386 tert-Butyl (3R)-3-[[4-{[1-(ethoxycarbonyl)cyclobutyl]thio}-5-nitro-2-(trifluoromethyl)benzoyl]-(isopropyl)amino]piperidine-1-carboxylate

[Chemical formula 530]

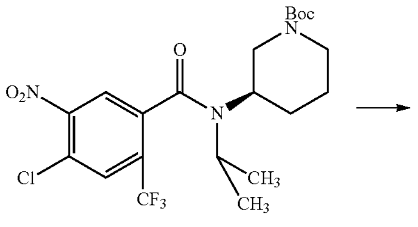

-continued

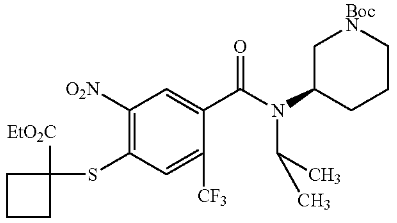

Using the compound of Reference Example 375, the title compound was obtained in a similar manner to Reference Example 376.

MS (ESI+) 618 ($M^{+}$+1, 100%).

Reference Example 387 tert-Butyl (3R)-3-{isopropyl[4-{[1-(methoxycarbonyl)cyclopentyl]thio}-5-nitro-2-(trifluoromethyl)benzoyl]amino}piperidine-1-carboxylate

[Chemical formula 531]

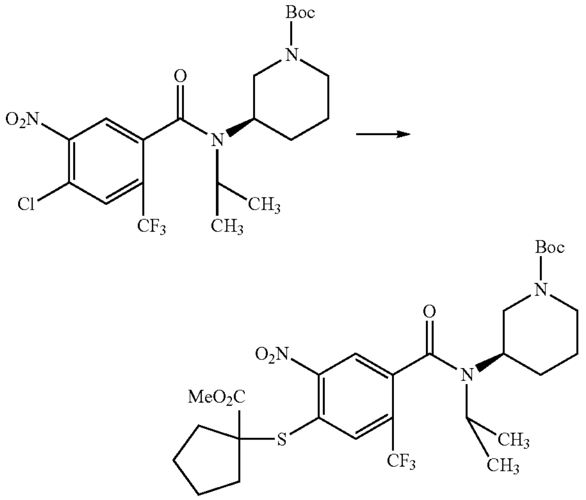

Using the compound of Reference Example 375, the title compound was obtained in a similar manner to Reference Example 376.

MS (ESI+) 618 ($M^{+}$+1, 15%).

Reference Example 388

Diethyl {[4-{[[(3R)-1-(tert-butoxycarbonyl)piperidin-3-yl](isopropyl)amino]carbonyl}-2-nitro-5-(trifluoromethyl)phenyl]thio}(methyl)malonate

[Chemical formula 532]

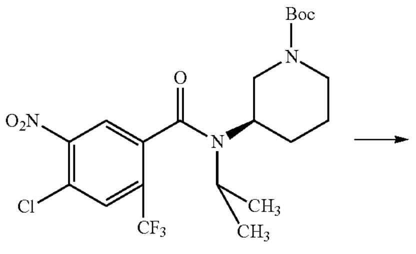

-continued

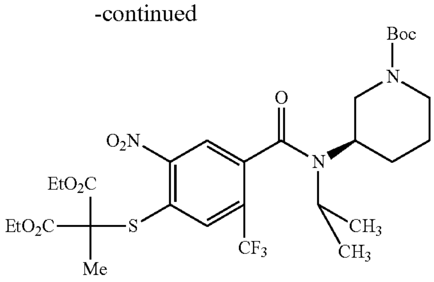

Using the compound of Reference Example 375, the title compound was obtained in a similar manner to Reference Example 376.

MS (ESI+) 664 ($M^+$+1, 20%).

Reference Example 389

Methyl 4-{[1-(methoxycarbonyl)cyclopentyl]thio}-2-methyl-5-nitrobenzoate

[Chemical formula 533]

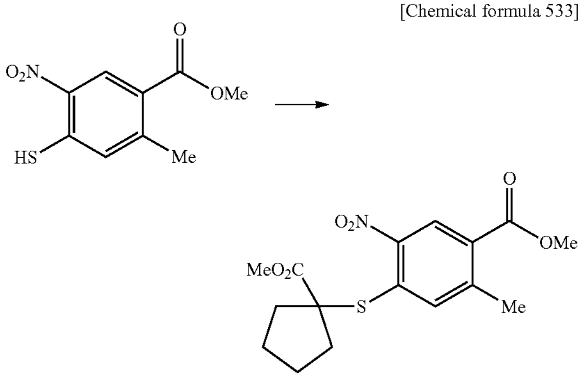

Using the compound of Reference Example 358, the title compound was obtained in a similar manner to Reference Example 359.

MS (ESI+) 354 ($M^+$+1, 30%).

Reference Example 390

Methyl 3-oxo-7-(trifluoromethyl)-3,4-dihydrospiro[1,4-benzoxazine-2,1'-cyclopropane]-6-carboxylate

[Chemical formula 534]

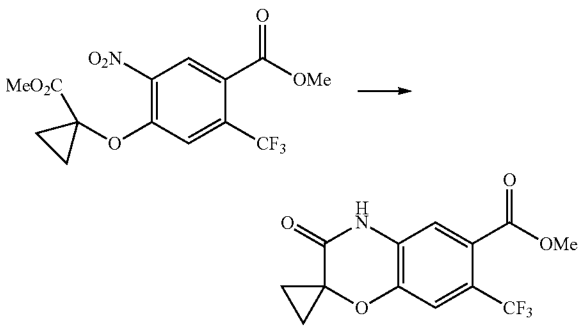

Using the compound of Reference Example 385, the title compound was obtained in a similar manner to Reference Example 2.

MS (ESI+) 302 ($M^+$+1, 100%).

Reference Example 391

Methyl 7-methyl-3-oxo-3,4-dihydrospiro[1,4-benzothiazine-2,1'-cyclopentane]-6-carboxylate

[Chemical formula 535]

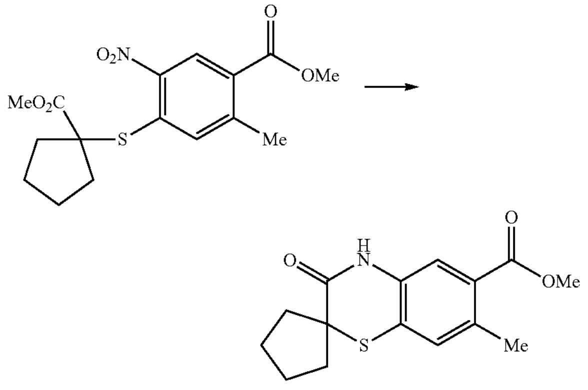

Using the compound of Reference Example 389, the title compound was obtained in a similar manner to Reference Example 2.

MS (ESI+) 292 ($M^+$+1, 100%).

Reference Example 392 tert-Butyl (3R)-3-(isopropyl{[3-oxo-7-(trifluoromethyl)-3,4-dihydrospiro[1,4-benzothiazine-2,1'-cyclobutan]-6-yl]carbonyl}amino)piperidine-1-carboxylate

[Chemical formula 536]

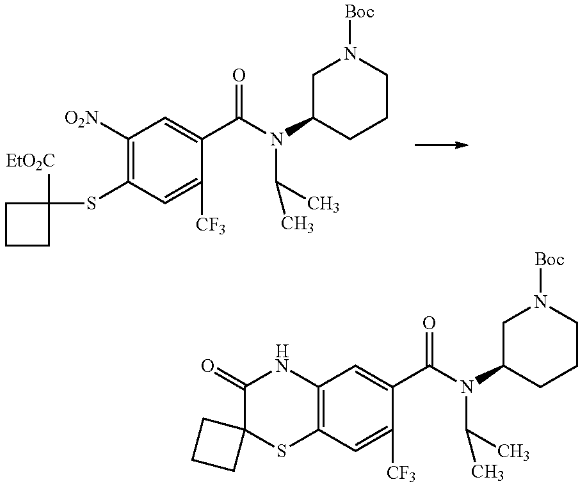

Using the compound of Reference Example 386, the title compound was obtained in a similar manner to Reference Example 2.

MS (ESI+) 542 ($M^+$+1, 20%).

Reference Example 393 tert-Butyl (3R)-3-(isopropyl{[3-oxo-7-(trifluoromethyl)-3,4-dihydrospiro[1,4-benzothiazine-2,1'-cyclopentan]-6-yl]carbonyl}amino)piperidine-1-carboxylate

[Chemical formula 537]

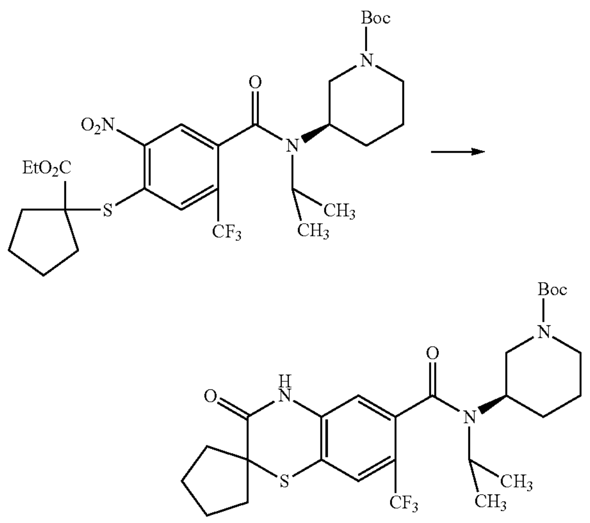

Using the compound of Reference Example 387, the title compound was obtained in a similar manner to Reference Example 2.

MS (ESI+) 556 ($M^{+}$+1, 20%).

Reference Example 394

Ethyl 6-{[[(3R)-1-(tert-butoxycarbonyl)piperidin-3-yl](isopropyl)amino]carbonyl}-2-methyl-3-oxo-7-[(trifluoromethyl)-3,4-dihydro-2H-1,4-benzothiazine-2-carboxylate

[Chemical formula 538]

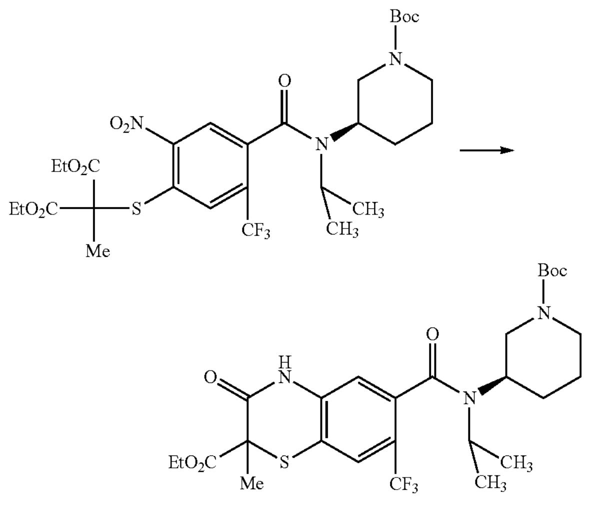

Using the compound of Reference Example 388, the title compound was obtained in a similar manner to Reference Example 2.

MS (ESI+) 588 ($M^{+}$+1, 30%).

Reference Example 395

Methyl 4-(4-methoxybutyl)-3-oxo-7-(trifluoromethyl)-3,4-dihydrospiro[1,4-benzoxazine-2,1'-cyclopropane]-6-carboxylate

[Chemical formula 539]

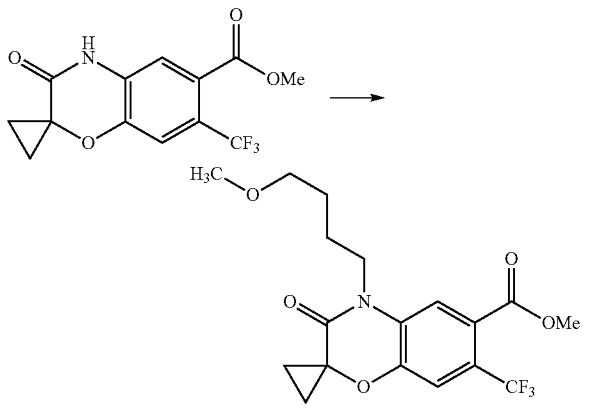

Using the compound of Reference Example 390, the title compound was obtained in a similar manner to Reference Example 3.

MS (ESI+) 388 ($M^{+}$+1, 100%).

Reference Example 396

Methyl 4-{2-[(methoxycarbonyl)amino]ethyl}-3-oxo-7-(trifluoromethyl)-3,4-dihydrospiro[1,4-benzoxazine-2,1'-cyclopropane]-6-carboxylate

[Chemical formula 540]

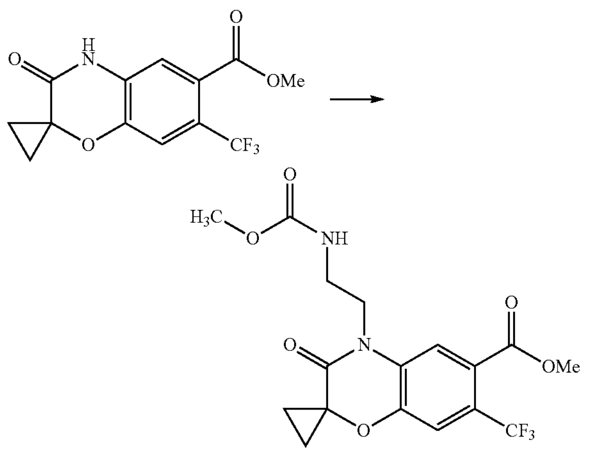

Using the compound of Reference Example 390, the title compound was obtained in a similar manner to Reference Example 361.

MS (ESI+) 403 ($M^{+}$+1, 36%).

Reference Example 397

Methyl 4-{2-[(methoxycarbonyl)amino]ethyl}-7-methyl-3-oxo-3,4-dihydrospiro[1,4-benzothiazine-2,1'-cyclopentane]-6-carboxylate

[Chemical formula 541]

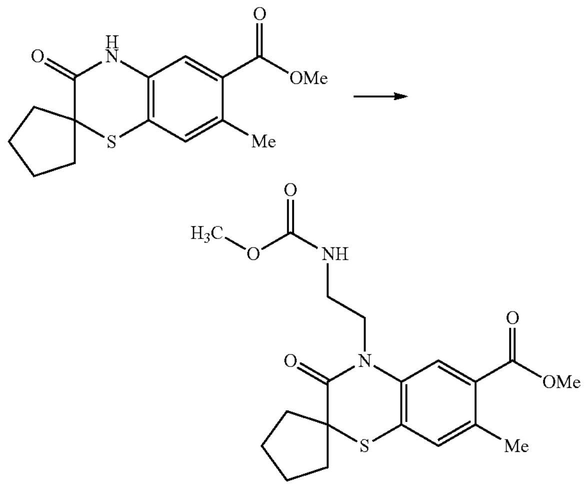

Using the compound of Reference Example 391, the title compound was obtained in a similar manner to Reference Example 361.

MS (ESI+) 393 ($M^{+}$+1, 30%).

Reference Example 398 tert-Butyl (3R)-3-(isopropyl{[4-{2-[(methoxycarbonyl)amino]ethyl}-3-oxo-7-(trifluoromethyl)-3,4-dihydrospiro[1,4-benzothiazine-2,1'-cyclobutan]-6-yl]carbonyl}amino)piperidine-1-carboxylate

[Chemical formula 542]

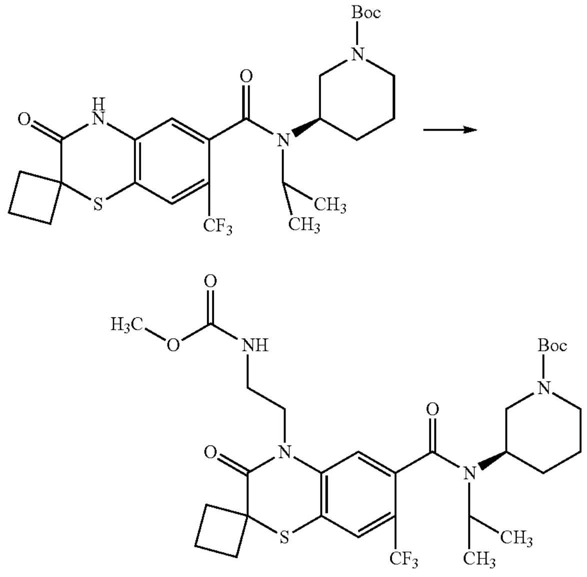

Using the compound of Reference Example 392, the title compound was obtained in a similar manner to Reference Example 361.

MS (ESI+) 643 ($M^{+}$+1, 100%).

Reference Example 399 tert-Butyl (3R)-3-(isopropyl{[4-{2-[(methoxycarbonyl)amino]ethyl}-3-oxo-7-(trifluoromethyl)-3,4-dihydrospiro[1,4-benzothiazine-2,1'-cyclopentan]-6-yl]carbonyl}amino)piperidine-1-carboxylate

[Chemical formula 543]

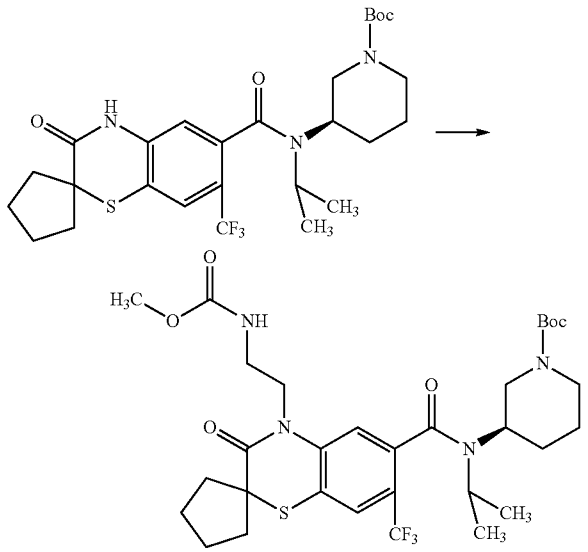

Using the compound of Reference Example 393, the title compound was obtained in a similar manner to Reference Example 361.

MS (ESI+) 657 ($M^{+}$+1, 100%).

Reference Example 400 tert-Butyl (3R)-3-(isopropyl{[4-{2-[(methoxycarbonyl)amino]ethyl}-3-oxo-7-(trifluoromethyl)-3,4-dihydrospiro[1,4-benzothiazine-2,1'-cyclopentyl]-6-yl]carbonyl}amino)piperidine-1-carboxylate

[Chemical formula 544]

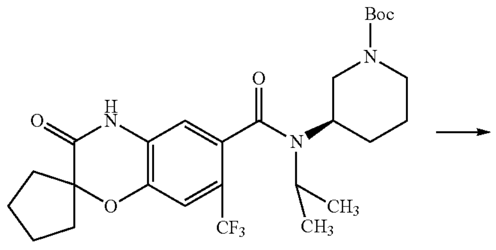

-continued

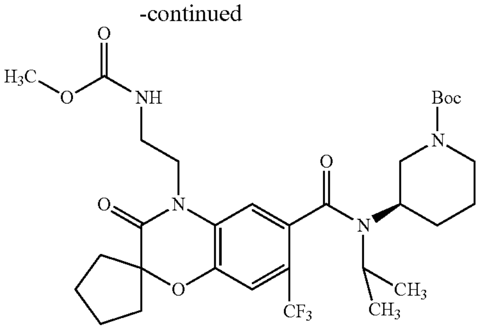

Using the compound of Reference Example 293, the title compound was obtained in a similar manner to Reference Example 13.

MS (ESI+) 641 ($M^+$+1, 20%).

Reference Example 401

Ethyl 6-{[[(3R)-1-(tert-butoxycarbonyl)piperidin-3-yl](isopropyl)amino]carbonyl}-4-(4-methoxybutyl)-2-methyl-3-oxo-7-(trifluoromethyl)-3,4-dihydro-2H-1,4-benzothiazine-2-carboxylate

[Chemical formula 545]

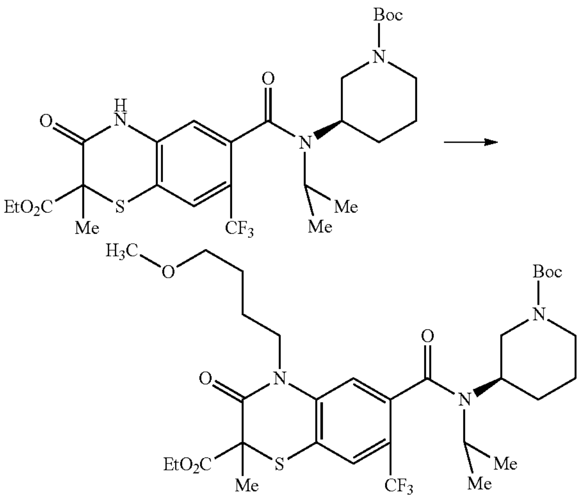

Using the compound of Reference Example 394, the title compound was obtained in a similar manner to Reference Example 3.

MS (ESI+) 674 ($M^+$+1, 20%).

Reference Example 402

6-{[[(3R)-1-(tert-Butoxycarbonyl)piperidin-3-yl](isopropyl)amino]carbonyl}-4-(4-methoxybutyl)-2-methyl-3-oxo-7-(trifluoromethyl)-3,4-dihydro-2H-1,4-benzothiazine-2-carboxylic acid

[Chemical formula 546]

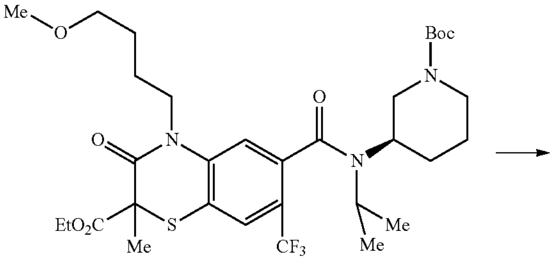

-continued

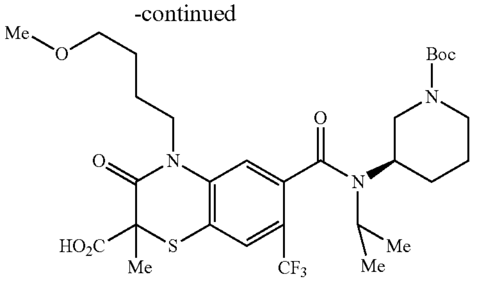

Using the compound of Reference Example 394, the title compound was obtained in a similar manner to Reference Example 34.

MS (ESI+) 646 ($M^+$+1, 30%).

Reference Example 403

A: tert-Butyl (3R)-3-[{[2-(hydroxymethyl)-4-(4-methoxybutyl)-2-methyl-3-oxo-7-(trifluoromethyl)-3,4-dihydro-2H-1,4-benzothiazin-6-yl]carbonyl}(isopropyl)amino]piperidine-1-carboxylate B: tert-Butyl (3R)-3-(isopropyl{[4-(4-methoxybutyl)-2-methyl-3-oxo-7-(trifluoromethyl)-3,4-dihydro-2H-1,4-benzothiazin-6-yl]carbonyl}amino)piperidine-1-carboxylate

[Chemical formula 547]

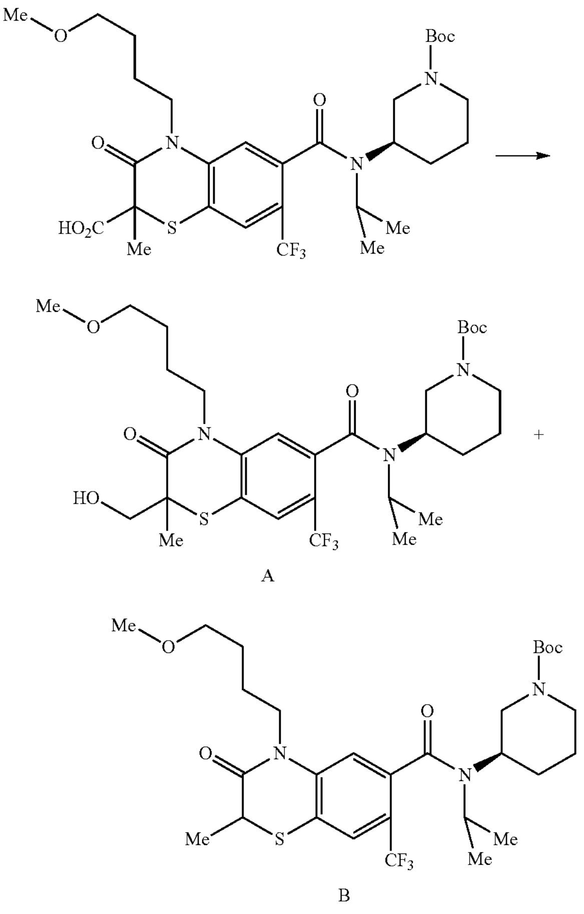

A

B

Using the compound of Reference Example 402, the title compound was obtained in a similar manner to Reference Example 35.

MS (ESI+) A: 632 ($M^{+}$+1, 11%), B: 602 ($M^{+}$+1, 17%).

Reference Example 404 tert-Butyl (3R)-3-(isopropyl{[4-(4-methoxybutyl)-2-(methoxymethyl)-2-methyl-3-oxo-7-(trifluoro-methyl)-3,4-dihydro-2H-1,4-benzothiazin-6-yl]carbonyl}amino)piperidine-1-carboxylate

[Chemical formula 548]

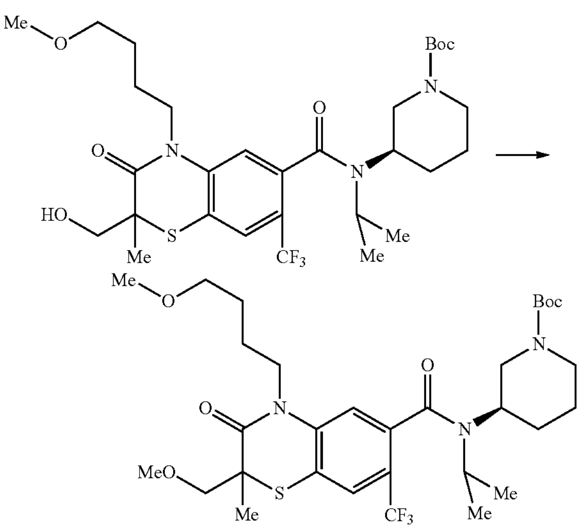

Using the compound A of Reference Example 403A, the title compound was obtained in a similar manner to Reference Example 36.

MS (ESI+) 646 ($M^{+}$+1, 30%).

Reference Example 405

Methyl 4-(2-{[(benzyloxy)carbonyl]amino}ethyl)-3-oxo-7-(trifluoromethyl)-3,4-dihydrospiro[1,4-benzoxazine-2,1'-cyclopropane]-6-carboxylate

[Chemical formula 549]

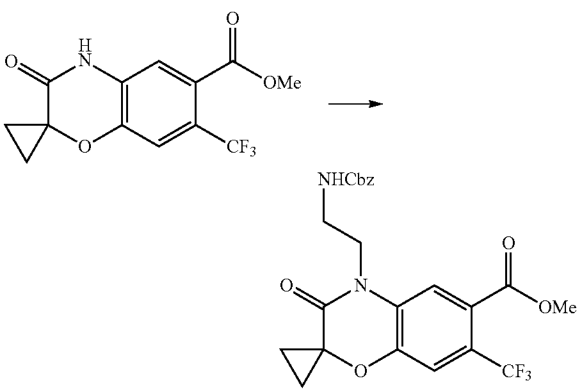

Using the compound of Reference Example 390, the title compound was obtained in a similar manner to Reference Example 378.

MS (ESI+) 479 ($M^{+}$+1, 100%).

Reference Example 406 tert-Butyl (3R)-3-[{[4-(2-{[benzyloxy)carbonyl]amino}ethyl)-3-oxo-7-(trifluoromethyl)-3,4-dihydrospiro[1,4-benzothiazine-2,1'-cyclobutan]-6-yl]carbonyl}(isopropyl)amino]piperidine-1-carboxylate

[Chemical formula 550]

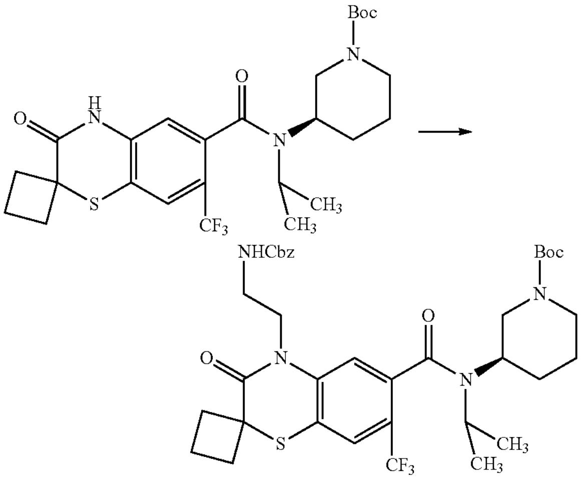

Using the compound of Reference Example 392, the title compound was obtained in a similar manner to Reference Example 378.

MS (ESI+) 719 ($M^{+}$+1, 19%).

Reference Example 407 tert-Butyl (3R)-3-[{[4-(2-{[(benzyloxy)carbonyl]amino}ethyl)-3-oxo-7-(trifluoromethyl)-3,4-dihydrospiro[1,4-benzothiazine-2,1'-cyclopentan]-6-yl]carbonyl}(isopropyl)amino]piperidine-1-carboxylate

[Chemical formula 551]

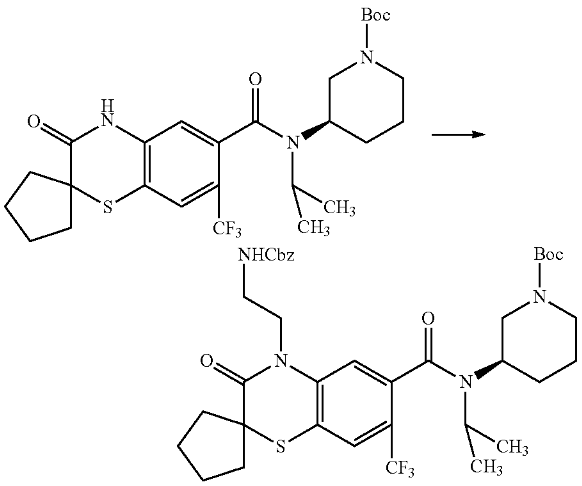

Using the compound of Reference Example 393, the title compound was obtained in a similar manner to Reference Example 378.

MS (ESI+) 733 ($M^{+}$+1, 100%).

Reference Example 408 tert-Butyl (3R)-3-(isopropyl{[4-(4-methoxybutyl)-3-oxo-7-(trifluoromethyl)-3,4-dihydrospiro[1,4-benzoxazine-2,1'-cyclopropan]-6-yl]carbonyl}amino)piperidine-1-carboxylate

[Chemical formula 552]

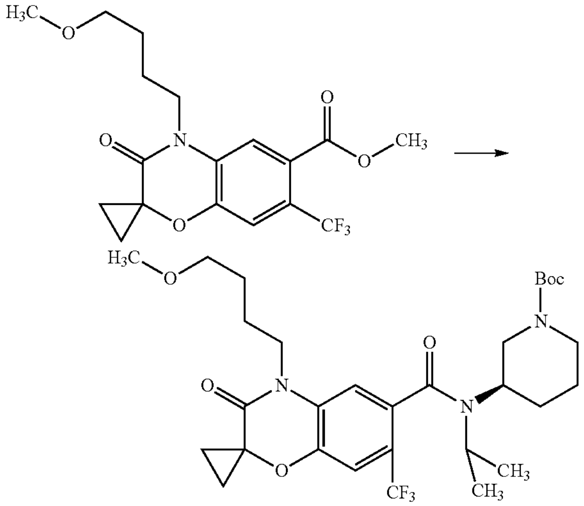

Using the compound of Reference Example 395, the title compound was obtained in a similar manner to Reference Example 5.

MS (ESI+) 598 ($M^+$+1, 20%).

Reference Example 409 tert-Butyl (3R)-3-(isopropyl{[4-{2-[(methoxycarbonyl)amino]ethyl}-3-oxo-7-(trifluoromethyl)-3,4-dihydrospiro[1,4-benzoxazine-2,1'-cyclopropan]-6-yl]carbonyl}amino)piperidine-1-carboxylate

[Chemical formula 553]

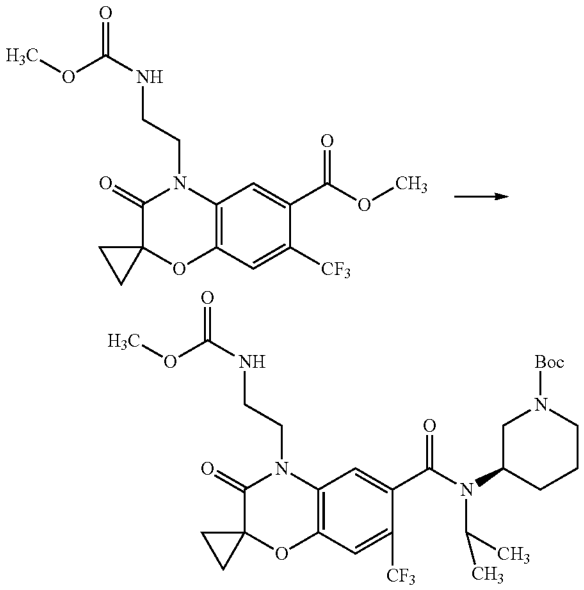

Using the compound of Reference Example 396, the title compound was obtained in a similar manner to Reference Example 5.

MS (ESI+) 613 ($M^+$+1, 20%).

Reference Example 410 tert-Butyl (3R)-3-{isopropyl[(4-{2-[(methoxycarbonyl)amino]ethyl}-7-methyl-3-oxo-3,4-dihydrospiro[1,4-benzothiazine-2,1'-cyclopentan]-6-yl)carbonyl]amino}piperidine-1-carboxylate

[Chemical formula 554]

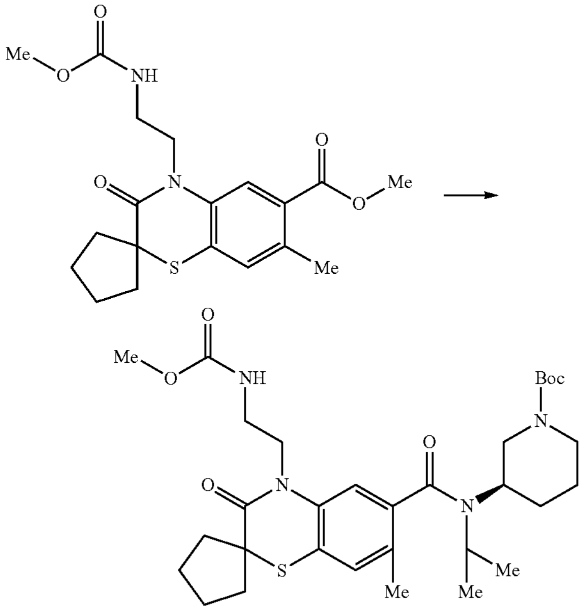

Using the compound of Reference Example 397, the title compound was obtained in a similar manner to Reference Example 5.

MS (ESI+) 603 ($M^+$+1, 12%).

Reference Example 411 tert-Butyl (3R)-3-[{[4-(2-{[(benzyloxy)carbonyl]amino}ethyl)-3-oxo-7-(trifluoromethyl)-3,4-dihydrospiro[1,4-benzoxazine-2,1'-cyclopropan]-6-yl]carbonyl}(isopropyl)amino]piperidine-1-carboxylate

[Chemical formula 555]

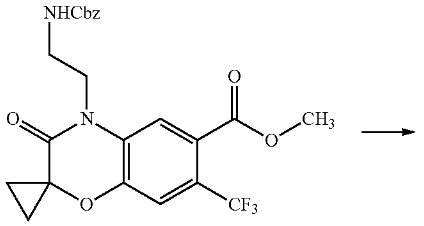

-continued

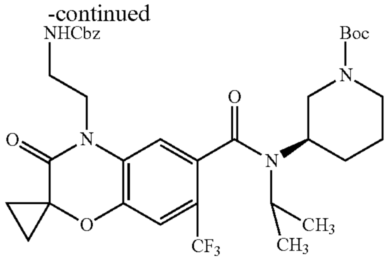

Using the compound of Reference Example 405, the title compound was obtained in a similar manner to Reference Example 5.

MS (ESI+) 689 ($M^{+}$+1, 20%).

Reference Example 412 tert-Butyl (3R)-3-[{[4-(2-aminoethyl)-3-oxo-7-(trifluoromethyl)-3,4-dihydrospiro[1,4-benzoxazine-2,1'-cyclopropan]-6-yl]carbonyl}(isopropyl)amino]piperidine-1-carboxylate

[Chemical formula 556]

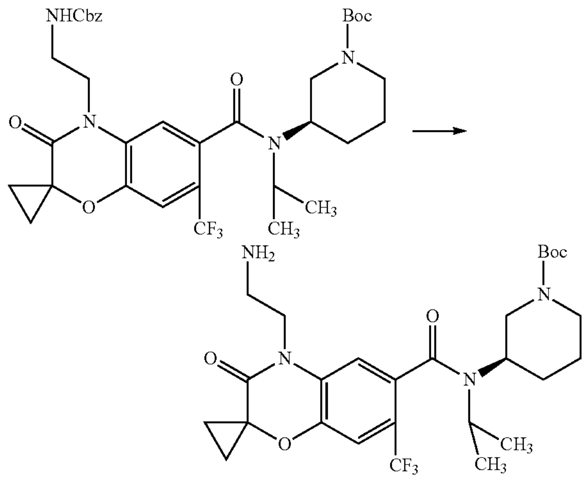

Using the compound of Reference Example 411, the title compound was obtained in a similar manner to Reference Example 139.

MS (ESI+) 555 ($M^{+}$+1, 85%).

Reference Example 413 tert-Butyl (3R)-3-[{[4-(2-aminoethyl)-3-oxo-7-(trifluoromethyl)-3,4-dihydrospiro[1,4-benzothiazine-2,1'-cyclobutan]-6-yl]carbonyl}(isopropyl)amino]piperidine-1-carboxylate

[Chemical formula 557]

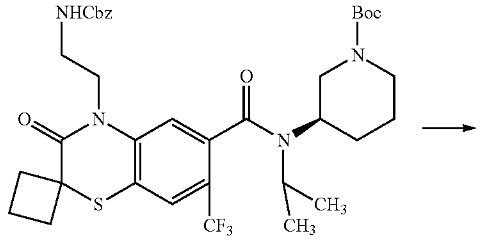

-continued

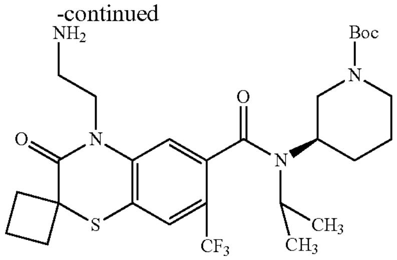

Using the compound of Reference Example 406, the title compound was obtained in a similar manner to Reference Example 139.

MS (ESI+) 585 ($M^{+}$+1, 100%).

Reference Example 414 tert-Butyl (3R)-3-[{[4-(2-aminoethyl)-3-oxo-7-(trifluoromethyl)-3,4-dihydrospiro[1,4-benzothiazine-2,1'-cyclopentan]-6-yl]carbonyl}(isopropyl)amino]piperidine-1-carboxylate

[Chemical formula 558]

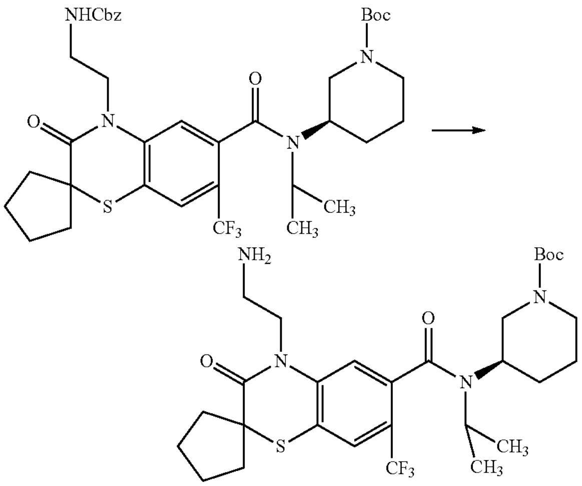

Using the compound of Reference Example 407, the title compound was obtained in a similar manner to Reference Example 139.

MS (ESI+) 599 ($M^{+}$+1, 100%).

Reference Example 415 tert-Butyl (3R)-3-(isopropyl{[3-oxo-4-[2-(propionylamino)ethyl]-7-(trifluoromethyl)-3,4-dihydrospiro[1,4-benzoxazine-2,1'-cyclopropan]-6-yl]carbonyl}amino)piperidine-1-carboxylate

[Chemical formula 559]

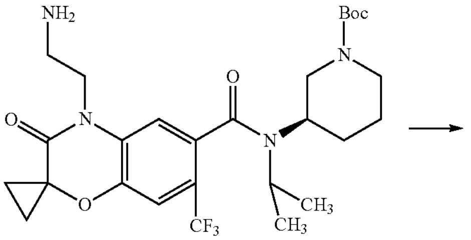

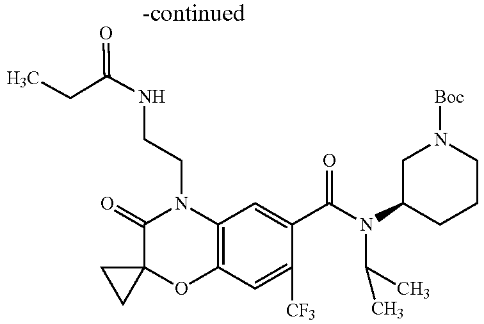

Using the compound of Reference Example 412, the title compound was obtained in a similar manner to Reference Example 132.

MS (ESI+) 611 ($M^{+}$+1, 7%).

Reference Example 416 tert-Butyl (3R)-3-(isopropyl{[3-oxo-4-[2-(propionylamino)ethyl]-7-(trifluoromethyl)-3,4-dihydrospiro[1,4-benzothiazine-2,1'-cyclobutan]-6-yl]carbonyl}amino)piperidine-1-carboxylate

[Chemical formula 560]

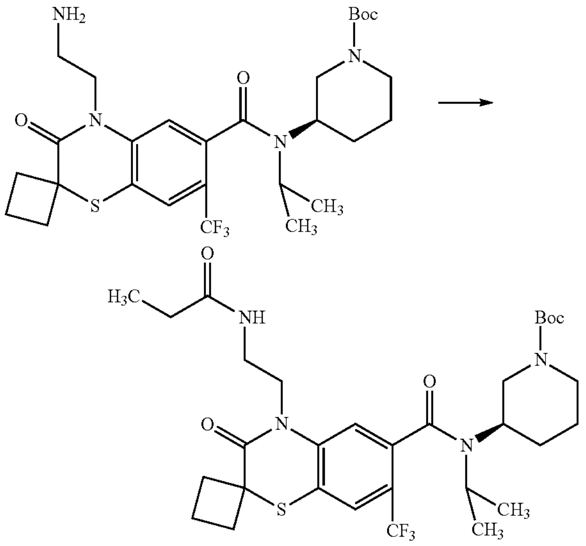

Using the compound of Reference Example 413, the title compound was obtained in a similar manner to Reference Example 132.

MS (ESI+) 641 ($M^{+}$+1, 100%).

Reference Example 417 tert-Butyl (3R)-3-(isopropyl{[3-oxo-4-[2-(propionylamino)ethyl]-7-(trifluoromethyl)-3,4-dihydrospiro[1,4-benzothiazine-2,1'-cyclopentan]-6-yl]carbonyl}amino)piperidine-1-carboxylate

[Chemical formula 561]

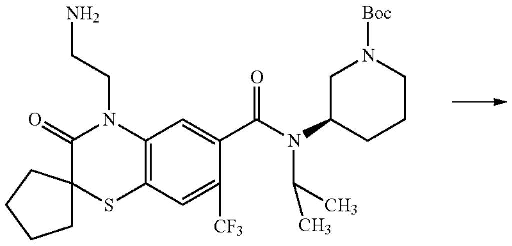

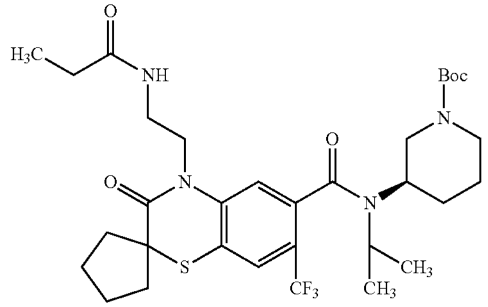

Using the compound of Reference Example 414, the title compound was obtained in a similar manner to Reference Example 132.

MS (ESI+) 655 ($M^{+}$+1, 17%).

Reference Example 418 tert-Butyl (3R)-3-[{[4-{2-[(difluoroacetyl)amino]ethyl}-3-oxo-7-(trifluoromethyl)-3,4-dihydrospiro-[1,4-benzoxazine-2,1'-cyclopropan]-6-yl]carbonyl}(isopropyl)amino]piperidine-1-carboxylate

[Chemical formula 562]

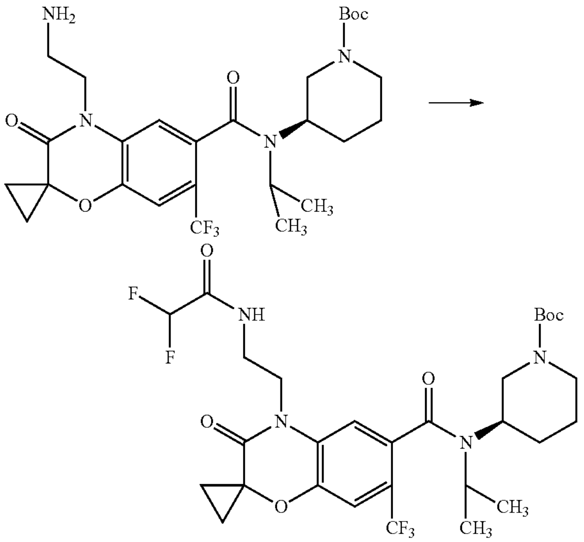

Using the compound of Reference Example 415, the title compound was obtained in a similar manner to Reference Example 132.

MS (ESI+) 633 ($M^{+}$+1, 20%).

Reference Example 419

Methyl 3,3-dimethyl-2-oxo-1,2,3,4-tetrahydroquinoline-7-carboxylate

[Chemical formula 563]

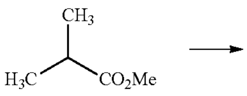

-continued

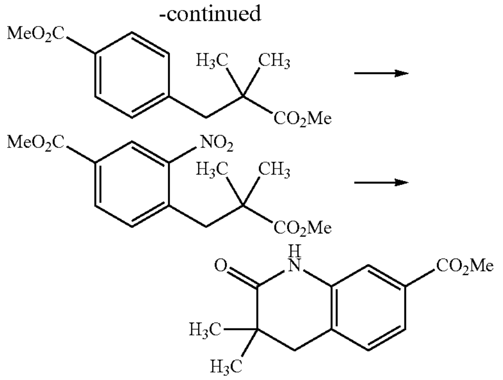

A solution of diisopropylamine (4.59 g) in THF (25 ml) was cooled to 0° C., and thereto was added dropwise a solution of n-butyl lithium (2.63 M hexane solution, 17 ml). After the addition was complete, the mixture was stirred in an ice-bath for one hour. The mixture was cooled to −78° C., and a solution of methyl 2-methylpropanoate (5.05 g) in THF (5 ml) was added dropwise thereto, and the mixture was stirred for 30 minutes as it stands. This solution was added dropwise into a solution of methyl p-(bromomethyl)benzoate (9.86 g) in THF (10 ml), which was cooled at 0° C., and the mixture was stirred at 0° C. for 2 hours, and then stirred at room temperature overnight.

After the reaction was complete, the reaction was quenched by addition of a saturated aqueous ammonium chloride solution, and the mixture was extracted with water and ethyl acetate. The organic layer was washed with water and a saturated aqueous sodium chloride solution, dried over sodium sulfate, filtered, and concentrated to give a crude product, which was purified by column chromatography to give methyl 4-(3-methoxy-2,2-dimethyl-3-oxopropyl)benzoate (10.15 g).

Then, to this product was added sulfuric acid (45 ml), and the mixture was cooled to 0° C., and thereto was slowly added dropwise fuming nitric acid (20 ml). The mixture was stirred at 0° C. for 1.5 hours. After the reaction was complete, the reaction solution was poured into ice-water, and the mixture was stirred until the temperature thereof was raised to room temperature. To the mixture was added ethyl acetate, and the mixture was extracted. The organic layer was washed with a water, an aqueous sodium hydrogen carbonate solution, and a saturated aqueous sodium chloride solution, dried over sodium sulfate, filtered to give a crude product (11.13 g) containing methyl 4-(3-methoxy-2,2-dimethyl-3-oxopropyl)-3-nitrobenzoate.

To a mixed solvent of acetic acid (50 ml) and ethanol (50 ml) was added reduced iron, and the mixture was stirred at 70° C. for 30 minutes. Then, thereto was added dropwise a solution of the above-obtained crude product in acetic acid (50 ml) and ethanol (50 ml). After the addition was complete, the mixture was stirred at 70° C. for 2 hours. After the reaction was complete, the mixture was cooled to room temperature, and filtered on celite. The filtrate was separated and extracted with ethyl acetate, and the organic layer was washed with water and a saturated aqueous sodium hydrogen carbonate solution, dried over sodium sulfate, filtered to give a crude product. This crude product was subjected to trituration with chloroform/hexane (1/9), and collected by filtration to give the title compound (7.39 g).

MS (ESI+) 234 ($M^+$+1, 100%).

Reference Example 420

Methyl 2'-oxo-1',4'-dihydro-2'H-spiro[cyclopentane-1,3'-quinoline]-7'-carboxylate

[Chemical formula 564]

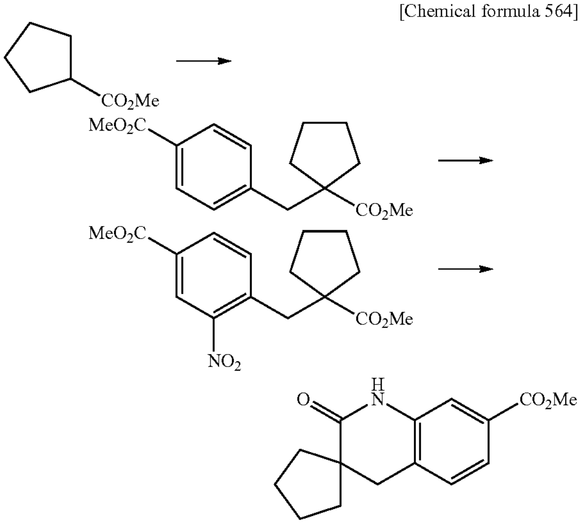

Using methyl cyclopentanecarboxylate, the title compound was obtained in a similar manner to Reference Example 419.

MS (ESI+) 260 ($M^+$+1, 100%).

Reference Example 421

Methyl 1-(4-methoxybutyl)-3,3-dimethyl-2-oxo-1,2,3,4-tetrahydroquinoline-7-carboxylate

[Chemical formula 565]

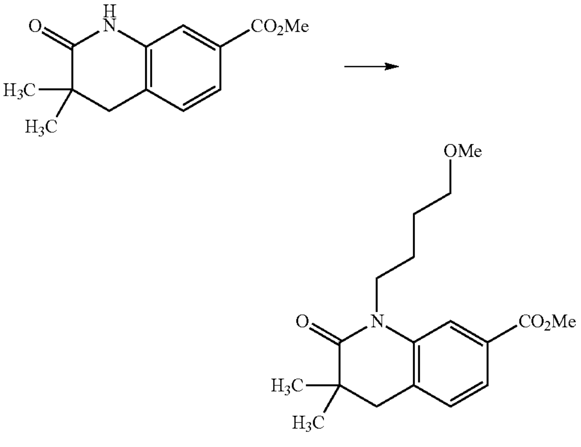

Using the compound of Reference Example 419, the title compound was obtained in a similar manner to Reference Example 3.

MS (ESI+) 320 ($M^+$+1, 75%).

Reference Example 422

Methyl 1-{2-[(methoxycarbonyl)amino]ethyl}-3,3-dimethyl-2-oxo-1,2,3,4-tetrahydroquinoline-7-carboxylate

[Chemical formula 566]

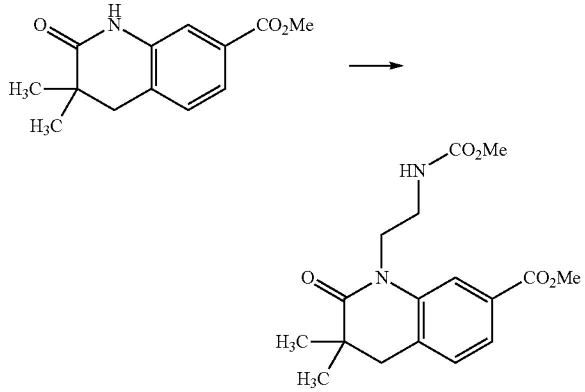

Using the compound of Reference Example 419, the title compound was obtained in a similar manner to Reference Example 162.

MS (ESI+) 335 ($M^{+}$+1, 100%).

Reference Example 423

Methyl 1-(2-{[(benzyloxy)carbonyl]amino}ethyl)-3,3-dimethyl-2-oxo-1,2,3,4-tetrahydroquinoline-7-carboxylate

[Chemical formula 567]

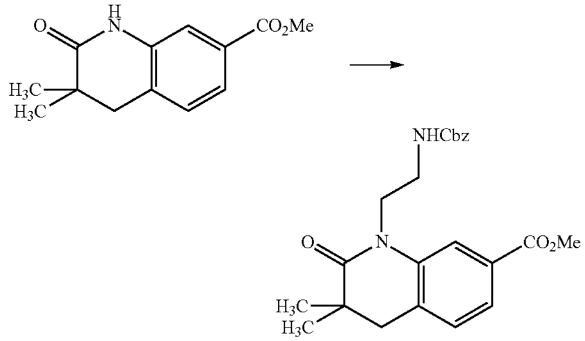

Using the compound of Reference Example 419, the title compound was obtained in a similar manner to Reference Example 164.

MS (ESI+) 411 ($M^{+}$+1, 72%).

Reference Example 424

Methyl 1-(2-{[(benzyloxy)carbonyl]amino}ethyl)-6-iodo-3,3-dimethyl-2-oxo-1,2,3,4-tetrahydro-quinoline-7-carboxylate

[Chemical formula 568]

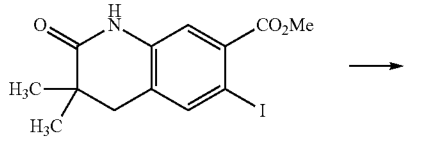

-continued

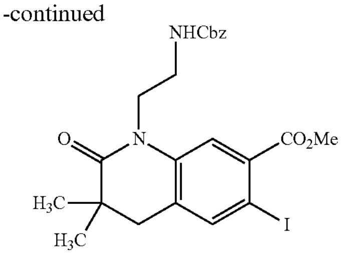

Using the compound of Reference Example 449, the title compound was obtained in a similar manner to Reference Example 164.

MS (ESI+) 537 ($M^{+}$+1, 100%).

Reference Example 425

Methyl 1'-(2-{[(benzyloxy)carbonyl]amino}ethyl)-6'-iodo-2'-oxo-1',4'-dihydro-2'H-spiro-[cyclopentane-1,3'-quinoline]-7'-carboxylate

[Chemical formula 569]

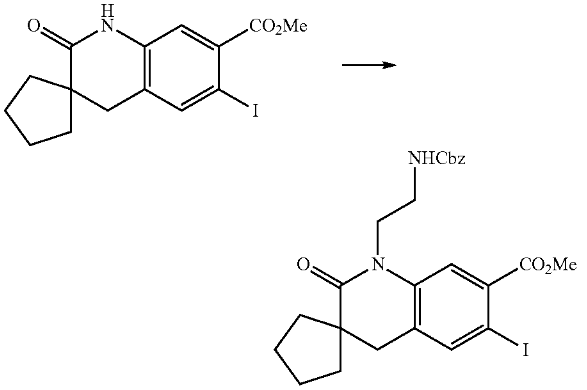

Using the compound of Reference Example 450, the title compound was obtained in a similar manner to Reference Example 164.

MS (ESI+) 563 ($M^{+}$+1, 100%).

Reference Example 426

Methyl 1-(2-{[(benzyloxy)carbonyl]amino}ethyl)-3,3-dimethyl-2-oxo-6-(trifluoromethyl)-1,2,3,4-tetrahydroquinoline-7-carboxylate

[Chemical formula 570]

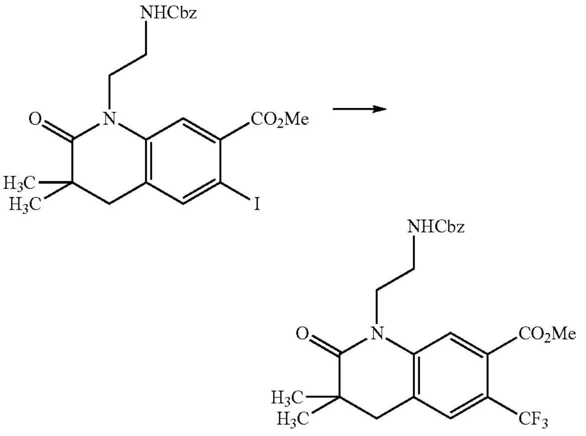

To a solution of methyl 1-(2-{[(benzyloxy)carbonyl]amino}ethyl)-6-iodo-3,3-dimethyl-2-oxo-1,2,3,4-tetrahydroquinoline-7-carboxylate (4.87 g) in NMP (10 ml) were added copper (I) bromide (0.28 g) and $FSO_2CF_2CO_2Me$ (17.43 g), and the mixture was stirred at 120~130° C. under nitrogen atmosphere for 3 hours. After the reaction was complete, the mixture was cooled to room temperature, and thereto were added water and ethyl acetate. The insoluble materials were removed by filtration on celite, and the filtrate was separated. The organic layer was washed with water and a saturated aqueous sodium chloride solution, dried over sodium sulfate, filtered and concentrated to give a crude product. This product was purified by silica gel column chromatography to give the title compound (2.50 g).

MS (ESI+) 479 ($M^+$+1, 100%).

Reference Example 427

Methyl 1'-(2-{[(benzyloxy)carbonyl]amino}ethyl)-2'-oxo-6'-(trifluoromethyl)-1',4'-dihydro-2'H-spiro[cyclopentane-1,3'-quinoline]-7'-carboxylate

[Chemical formula 571]

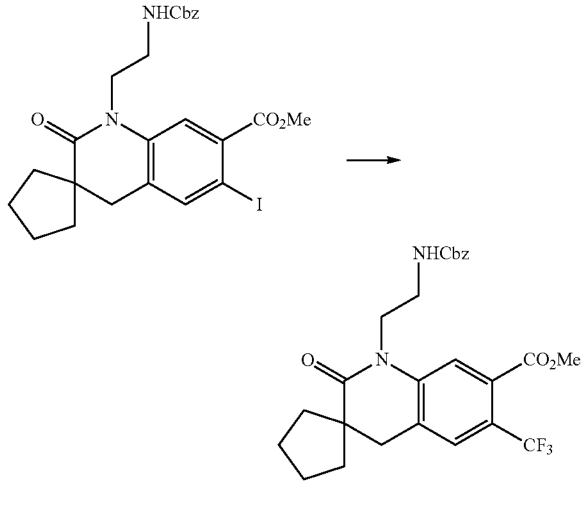

Using the compound of Reference Example 425, the title compound was obtained in a similar manner to Reference Example 426.

MS (ESI+) 505 ($M^+$+1, 100%).

Reference Example 428

1-(4-Methoxybutyl)-3,3-dimethyl-2-oxo-1,2,3,4-tetrahydroquinoline-7-carboxylic acid

[Chemical formula 572]

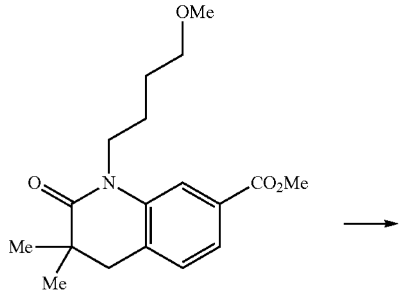

-continued

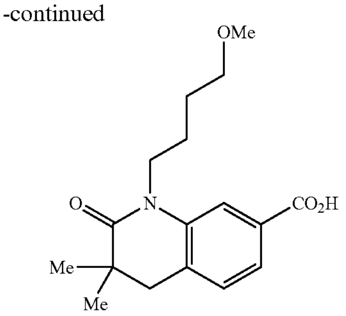

Using the compound of Reference Example 421, the title compound was obtained in a similar manner to Reference Example 4.

MS (ESI+) 306 ($M^+$+1, 100%).

Reference Example 429

1-{2-[(Methoxycarbonyl)amino]ethyl}-3,3-dimethyl-2-oxo-1,2,3,4-tetrahydroquinoline-7-carboxylic acid

[Chemical formula 573]

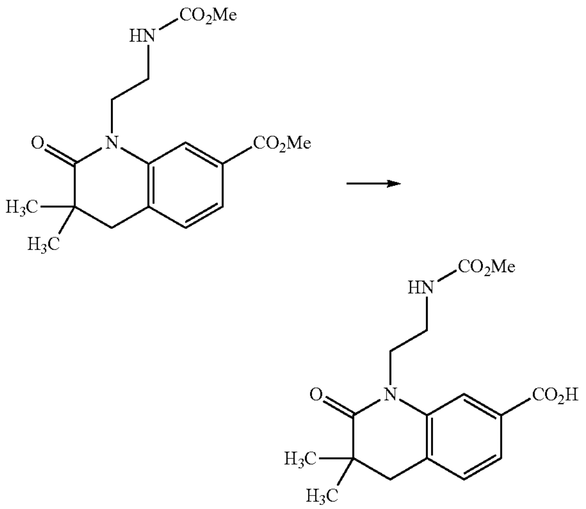

Using the compound of Reference Example 422, the title compound was obtained in a similar manner to Reference Example 4.

MS (ESI+) 321 ($M^+$+1, 100%).

Reference Example 430

1-(2-{[(Benzyloxy)carbonyl]amino}ethyl)-3,3-dimethyl-2-oxo-1,2,3,4-tetrahydroquinoline-7-carboxylic acid

[Chemical formula 574]

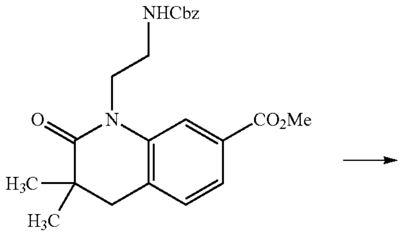

-continued

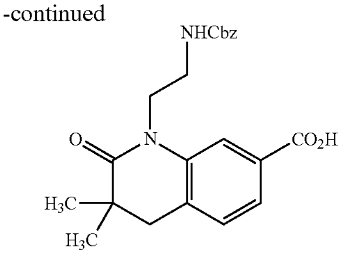

Using the compound of Reference Example 423, the title compound was obtained in a similar manner to Reference Example 4.

MS (ESI+) 397 ($M^{+}$+1, 100%).

Reference Example 431

1-(2-{[(Benzyloxy)carbonyl]amino}ethyl)-3,3-dimethyl-2-oxo-6-(trifluoromethyl)-1,2,3,4-tetrahydroquinoline-7-carboxylic acid

[Chemical formula 575]

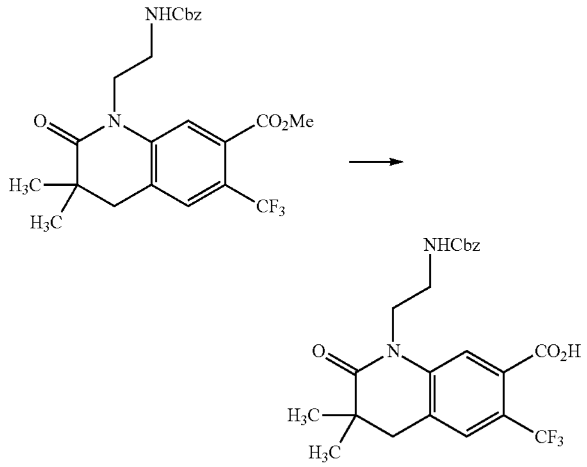

Using the compound of Reference Example 426, the title compound was obtained in a similar manner to Reference Example 4.

MS (ESI+) 465 ($M^{+}$+1, 70%).

Reference Example 432

1'-(2-{[(Benzyloxy)carbonyl]amino}ethyl)-2'-oxo-6'-(trifluoromethyl)-1',4'-dihydro-2'H-spiro[cyclopentane-1,3'-quinoline]-7'-carboxylic acid

[Chemical formula 576]

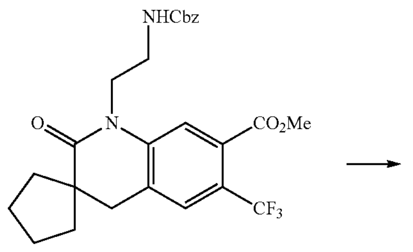

-continued

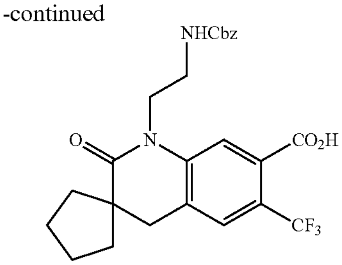

Using the compound of Reference Example 427, the title compound was obtained in a similar manner to Reference Example 4.

MS (ESI+) 491 ($M^{+}$+1, 100%).

Reference Example 433 tert-Butyl (3R)-3-(isopropyl{[1-(4-methoxybutyl)-3,3-dimethyl-2-oxo-1,2,3,4-tetrahydroquinolin-7-yl]carbonyl}amino)piperidine-1-carboxylate

[Chemical formula 577]

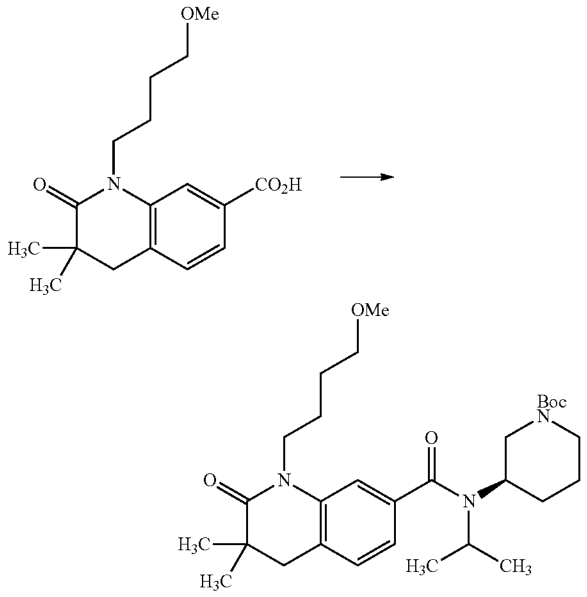

Using the compound of Reference Example 428, the title compound was obtained in a similar manner to Reference Example 5.

MS (ESI+) 530 ($M^{+}$+1, 36%).

Reference Example 434 tert-Butyl (3R)-3-{isopropyl[(1-{2-[(methoxycarbonyl)amino]ethyl}-3,3-dimethyl-2-oxo-1,2,3,4-tetrahydroquinolin-7-yl)carbonyl]amino}piperidine-1-carboxylate

[Chemical formula 578]

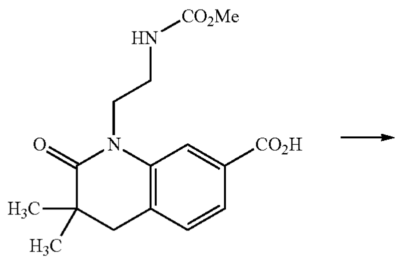

-continued

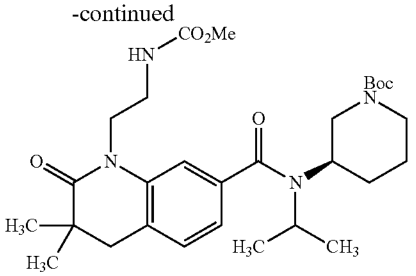

Using the compound of Reference Example 429, the title compound was obtained in a similar manner to Reference Example 5.

MS (ESI+) 545 ($M^{+}$+1, 63%).

Reference Example 435 tert-Butyl (3R)-3-[{[1-(2-{[(benzyloxy)carbonyl]amino}ethyl)-3,3-dimethyl-2-oxo-1,2,3,4-tetrahydroquinolin-7-yl]carbonyl}(isopropyl)amino]piperidine-1-carboxylate

[Chemical formula 579]

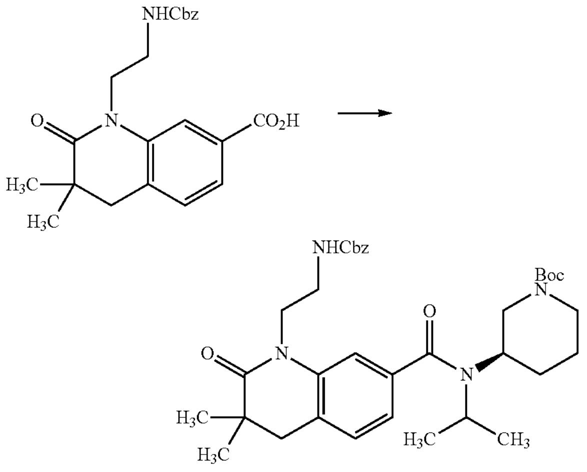

Using the compound of Reference Example 430, the title compound was obtained in a similar manner to Reference Example 5.

MS (ESI+) 621 ($M^{+}$+1, 35%).

Reference Example 436 tert-Butyl (3R)-3-[{[1-(2-{[(benzyloxy)carbonyl]amino}ethyl)-3,3-dimethyl-2-oxo-6-(trifluoromethyl)-1,2,3,4-tetrahydroquinolin-7-yl]carbonyl}(isopropyl)amino]piperidine-1-carboxylate

[Chemical formula 580]

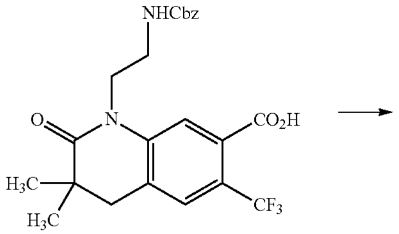

-continued

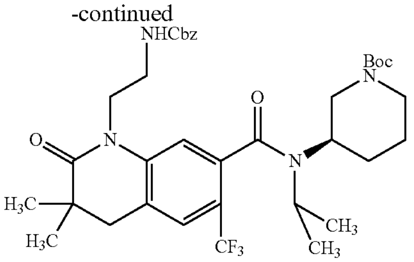

Using the compound of Reference Example 431, the title compound was obtained in a similar manner to Reference Example 5.

MS (ESI+) 689 ($M^{+}$+1, 20%).

Reference Example 437 tert-Butyl (3R)-3-[{[1'-(2-{[(benzyloxy)carbonyl]amino}ethyl)-2'-oxo-6'-(trifluoromethyl)-1',4'-dihydro-2'H-spiro[cyclopentane-1,3'-quinolin]-7'-yl]carbonyl}(isopropyl)amino]piperidine-1-carboxylate

[Chemical formula 581]

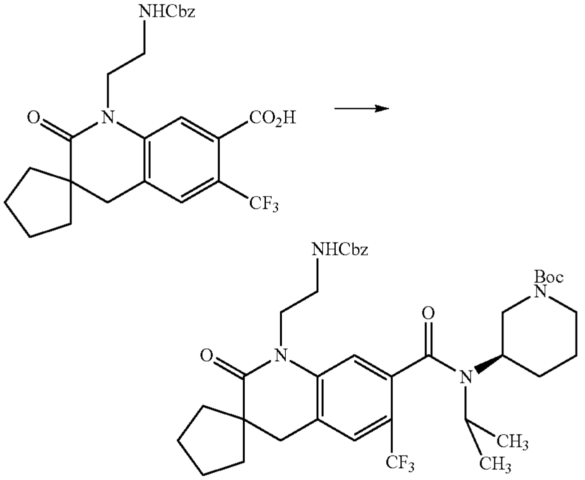

Using the compound of Reference Example 432, the title compound was obtained in a similar manner to Reference Example 5.

MS (ESI+) 715 ($M^{+}$+1, 25%).

Reference Example 438 tert-Butyl (3R)-3-[({3,3-dimethyl-2-oxo-1-[2-(propionylamino)ethyl]-1,2,3,4-tetrahydroquinolin-7-yl}carbonyl)(isopropyl)amino]piperidine-1-carboxylate

[Chemical formula 582]

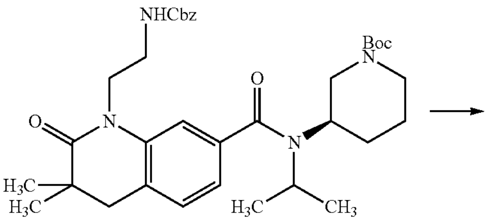

-continued

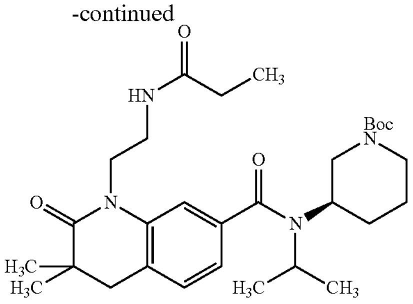

Using the compound of Reference Example 435, the title compound was obtained in a similar manner to Reference Example 132.

MS (ESI+) 543 ($M^{+}$+1, 11%).

Reference Example 439 tert-Butyl (3R)-3-[{[3,3-dimethyl-2-oxo-1-[2-(propionylamino)ethyl]-6-(trifluoromethyl)-1,2,3,4-tetrahydroquinolin-7-yl]carbonyl}(isopropyl)amino]piperidine-1-carboxylate

[Chemical formula 583]

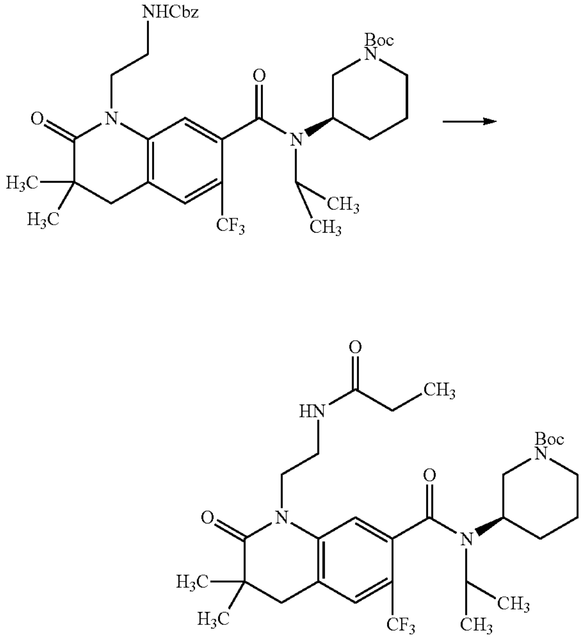

Using the compound of Reference Example 436, the title compound was obtained in a similar manner to Reference Example 132.

MS (ESI+) 611 ($M^{+}$+1, 20%).

Reference Example 440 tert-Butyl (3R)-3-(isopropyl{[2'-oxo-1'-[2-(propionylamino)ethyl]-6'-(trifluoromethyl)-1',4'-dihydro-2'H-spiro[cyclopentane-1,3'-quinolin]-7'-yl]carbonyl}amino)piperidine-1-carboxylate

[Chemical formula 584]

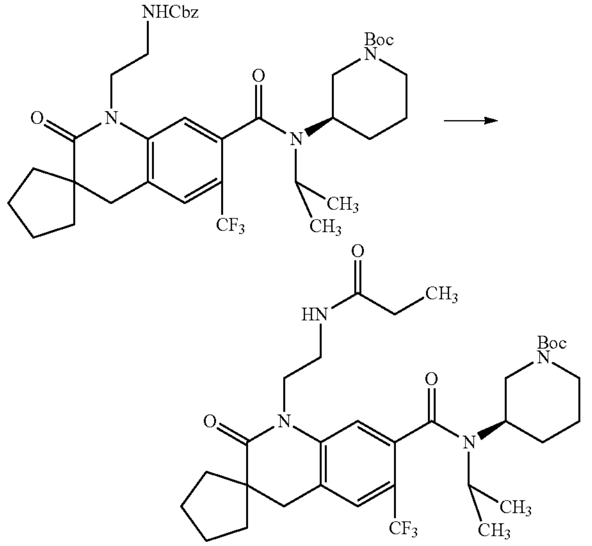

Using the compound of Reference Example 437, the title compound was obtained in a similar manner to Reference Example 132.

MS (ESI+) 637 ($M^{+}$+1, 10%).

Reference Example 441 tert-Butyl (3R)-3-[{[6-chloro-1-(4-methoxybutyl)-3,3-dimethyl-2-oxo-1,2,3,4-tetrahydroquinolin-7-yl]carbonyl}(isopropyl)amino]piperidine-1-carboxylate

[Chemical formula 585]

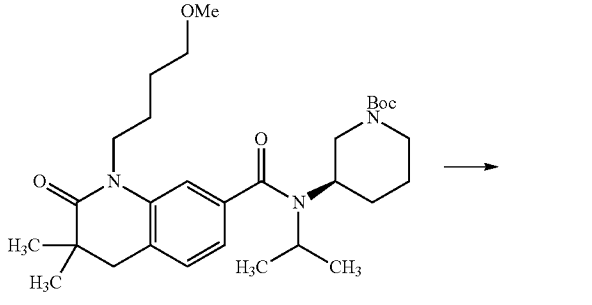

-continued

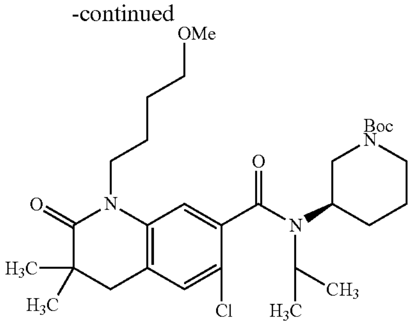

Using the compound of Reference Example 433, the title compound was obtained in a similar manner to Reference Example 12.

MS (ESI+) 564 ($M^+$+, 21%).

Reference Example 442 tert-Butyl (3R)-3-(isopropyl{[1-(4-methoxybutyl)-3,3,6-trimethyl-2-oxo-1,2,3,4-tetrahydroquinolin-7-yl]carbonyl}amino)piperidine-1-carboxylate

[Chemical formula 586]

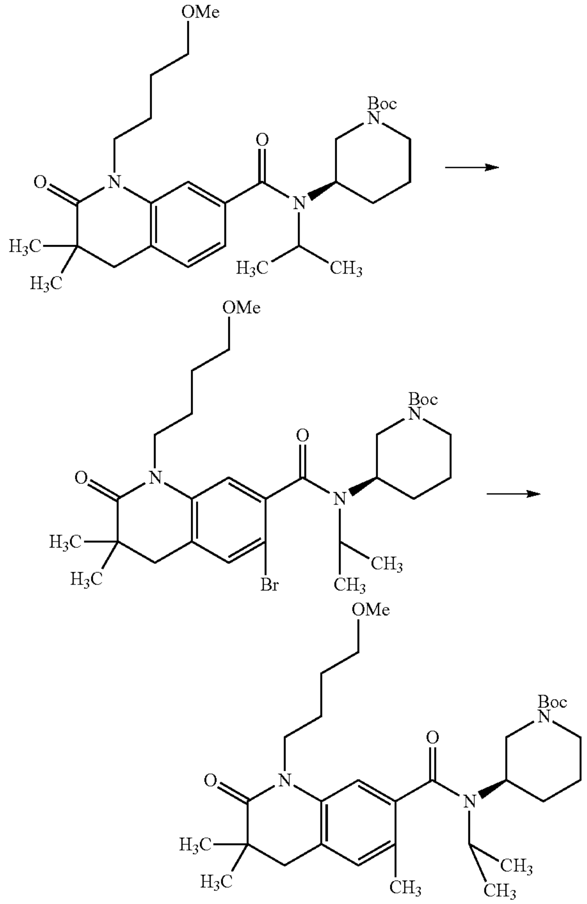

Using the compound of Reference Example 433, the title compound was obtained in a similar manner to Reference Example 10.

MS (ESI+) 544 ($M^+$+1, 21%).

Reference Example 443 tert-Butyl (3R)-3-[[(6-bromo-1-{2-[(methoxycarbonyl)amino]ethyl}-3,3-dimethyl-2-oxo-1,2,3,4-tetrahydroquinolin-7-yl)carbonyl](isopropyl)amino]piperidine-1-carboxylate

[Chemical formula 587]

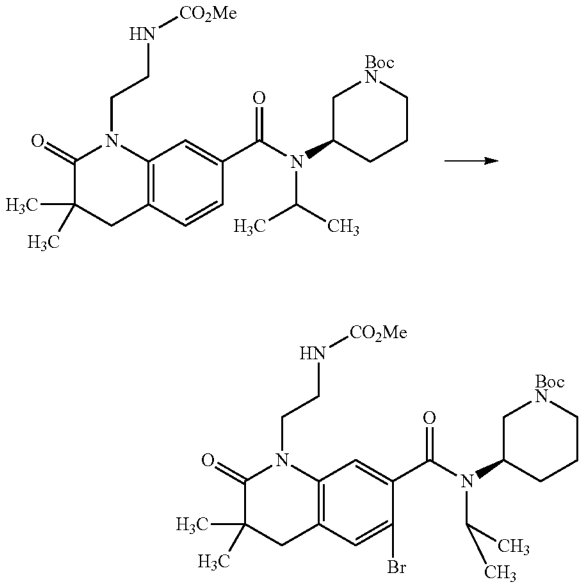

Using the compound of Reference Example 434, the title compound was obtained in a similar manner to Reference Example 6.

MS (ESI+) 625 ($M^+$+2, 10%).

Reference Example 444 tert-Butyl (3R)-3-{isopropyl [(1-{2-[(methoxycarbonyl)amino]ethyl}-3,3,6-trimethyl-2-oxo-1,2,3,4-tetrahydroquinolin-7-yl)carbonyl]amino}piperidine-1-carboxylate

[Chemical formula 588]

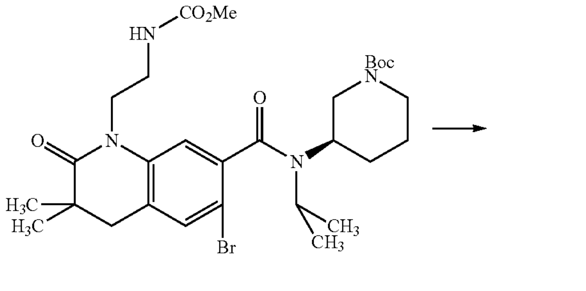

-continued

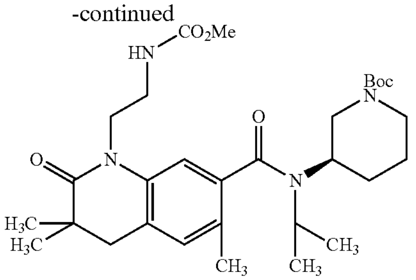

Using the compound of Reference Example 434, the title compound was obtained in a similar manner to Reference Example 10.

MS (ESI+) 559 ($M^{+}$+1, 14%).

Reference Example 445 tert-Butyl (3R)-3-[isopropyl({3,3,6-trimethyl-2-oxo-1-[2-(propionylamino)ethyl]-1,2,3,4-tetrahydroquinolin-7-yl}carbonyl)amino]piperidine-1-carboxylate

[Chemical formula 589]

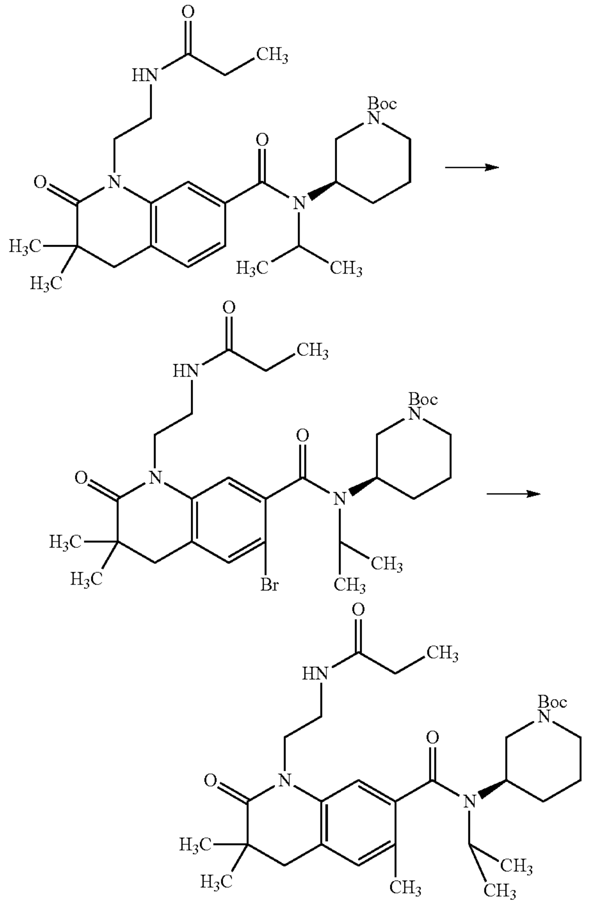

Using the compound of Reference Example 439, the title compound was obtained in a similar manner to Reference Example 10.

MS (ESI+) 557 ($M^{+}$+1, 38%).

Reference Example 446 tert-Butyl (3R)-3-[[(6-chloro-1-{2-[(methoxycarbonyl)amino]ethyl}-3,3-dimethyl-2-oxo-1,2,3,4-tetrahydroquinolin-7-yl)carbonyl](isopropyl)amino]piperidine-1-carboxylate

[Chemical formula 590]

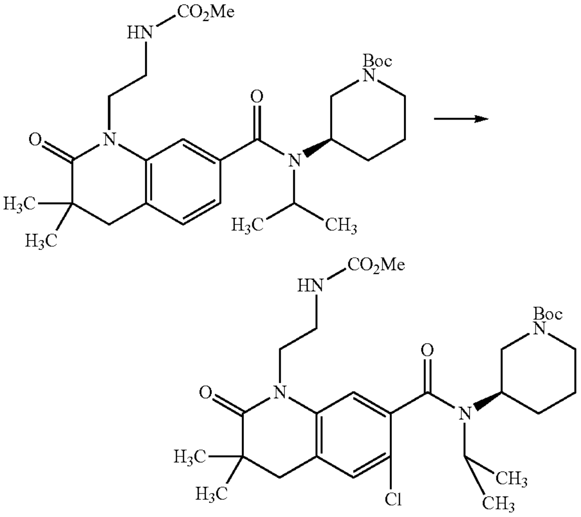

Using the compound of Reference Example 434, the title compound was obtained in a similar manner to Reference Example 12.

MS (ESI+) 579 ($M^{+}$+, 10%).

Reference Example 447 tert-Butyl (3R)-3-[({6-chloro-3,3-dimethyl-2-oxo-1-[2-(propionylamino)ethyl]-1,2,3,4-tetrahydroquinolin-7-yl}carbonyl)(isopropyl)amino]piperidine-1-carboxylate

[Chemical formula 591]

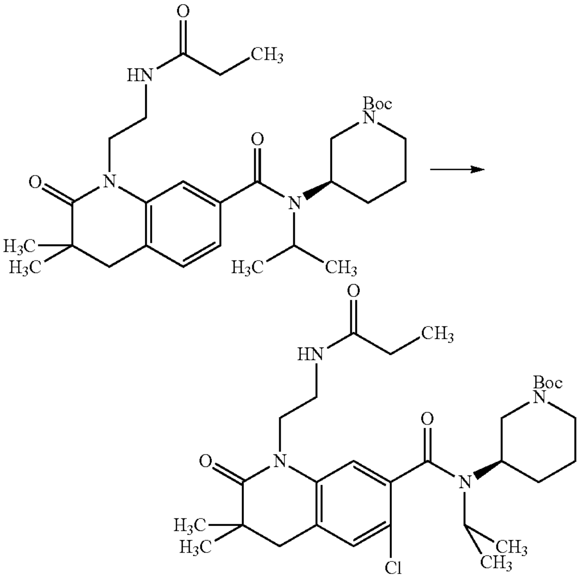

Using the compound of Reference Example 439, the title compound was obtained in a similar manner to Reference Example 12.

MS (ESI+) 577 ($M^{+}$+, 60%).

Reference Example 448 tert-Butyl (3R)-3-[[(6-ethyl-1-{2-[(methoxycarbonyl)amino]ethyl}-3,3-dimethyl-2-oxo-1,2,3,4-tetrahydroquinolin-7-yl)carbonyl](isopropyl)amino] piperidine-1-carboxylate

[Chemical formula 592]

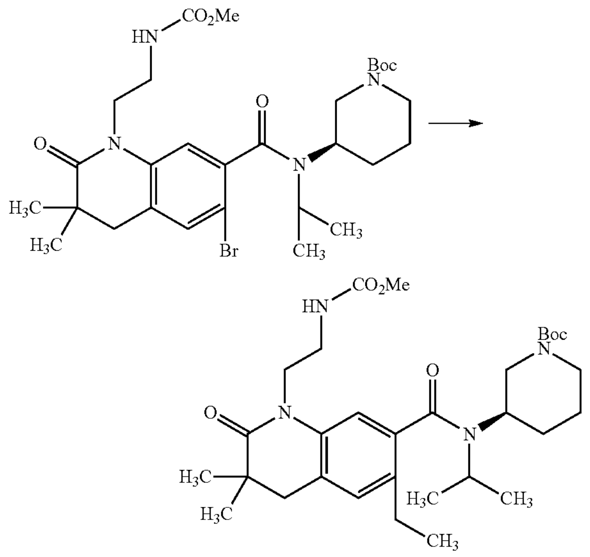

Using the compound of Reference Example 443, the title compound was obtained in a similar manner to Reference Example 9.

MS (ESI+) 573 ($M^{+}$+1, 26%).

Reference Example 449

Methyl 6-iodo-3,3-dimethyl-2-oxo-1,2,3,4-tetrahydroquinoline-7-carboxylate

[Chemical formula 593]

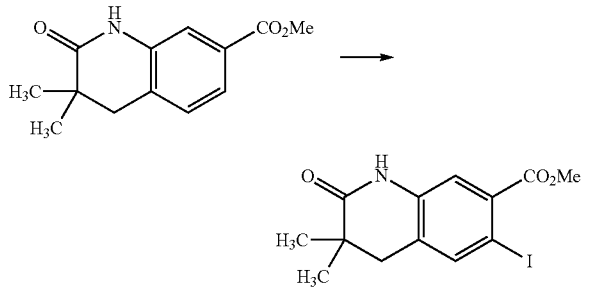

Using the compound of Reference Example 419, the title compound was obtained in a similar manner to Reference Example 158.

MS (ESI+) 360 ($M^{+}$+1, 100%).

Reference Example 450

Methyl 6'-iodo-2'-oxo-1',4'-dihydro-2'H-spiro[cyclopentane-1,3'-quinoline]-7'-carboxylate

[Chemical formula 594]

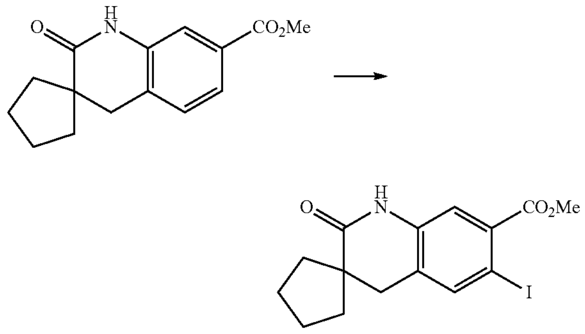

Using the compound of Reference Example 420, the title compound was obtained in a similar manner to Reference Example 158.

MS (ESI+) 386 ($M^{+}$+1, 100%).

Reference Example 451 tert-Butyl (3R)-3-{isopropyl[(2-methyl-3-oxo-2-phenyl-3,4-dihydro-2H-1,4-benzoxazin-6-yl)carbonyl]-amino}piperidine-1-carboxylate

[Chemical formula 595]

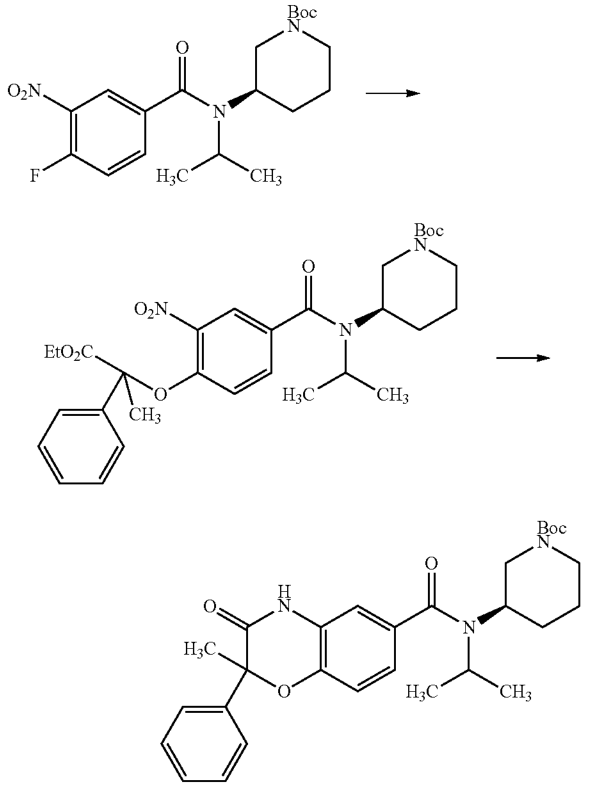

Using the compound of Reference Example 488, the title compound was obtained in a similar manner to Reference Example 22 and Reference Example 2.

MS (ESI+) 508 ($M^{+}$+1, 21%).

Reference Example 452

Methyl 2-methyl-3-oxo-2-phenyl-7-(trifluoromethyl)-3,4-dihydro-2H-1,4-benzoxazine-6-carboxylate

[Chemical formula 596]

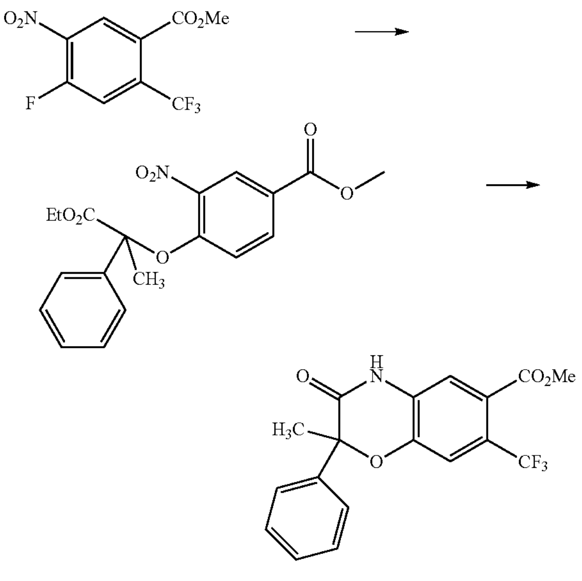

Using the compound of Reference Example 214, the title compound was obtained in a similar manner to Reference Example 22 and Reference Example 2.

MS (ESI+) 366 ($M^{+}$+1, 100%).

Reference Example 453

Methyl 2-(3-methoxyphenyl)-2-methyl-3-oxo-7-(trifluoromethyl)-3,4-dihydro-2H-1,4-benzoxazine-6-carboxylate

[Chemical formula 597]

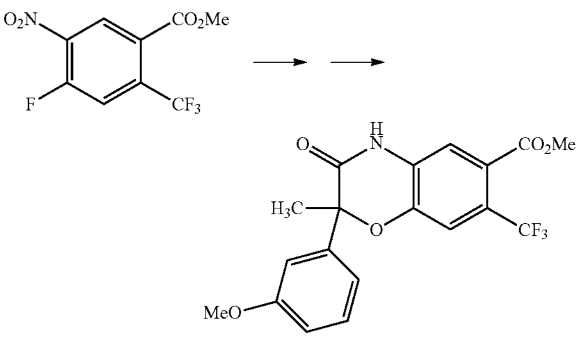

Using the compound of Reference Example 214, the title compound was obtained in a similar manner to Reference Example 22 and Reference Example 2.

MS (ESI+) 396 ($M^{+}$+1, 100%).

Reference Example 454 tert-Butyl (3R)-3-[{[4-(2-{[(benzyloxy)carbonyl]amino}ethyl)-2-methyl-3-oxo-2-phenyl-3,4-dihydro-2H-1,4-benzoxazin-6-yl]carbonyl}(isopropyl)amino]piperidine-1-carboxylate

[Chemical formula 598]

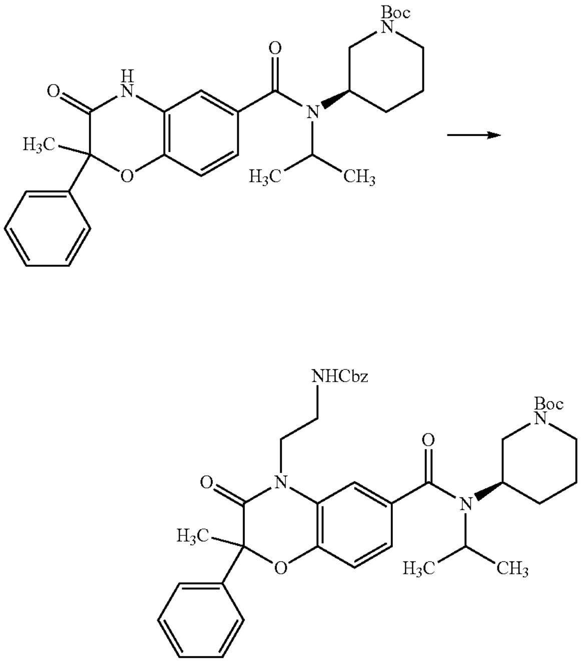

Using the compound of Reference Example 451, the title compound was obtained in a similar manner to Reference Example 164.

MS (ESI+) 685 ($M^{+}$+1, 46%).

Reference Example 455 tert-Butyl (3R)-3-[isopropyl({2-methyl-3-oxo-2-phenyl-4-[2-(propionylamino)ethyl]-3,4-dihydro-2H-1,4-benzoxazin-6-yl]carbonyl)amino]piperidine-1-carboxylate

[Chemical formula 599]

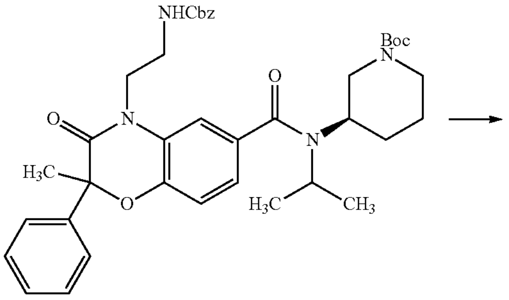

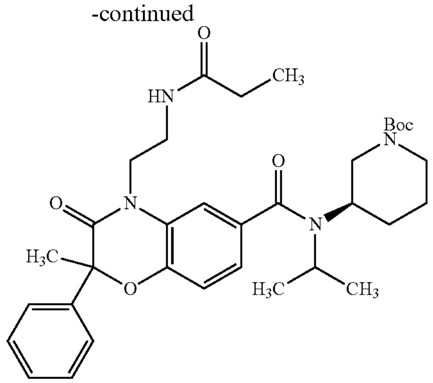

Using the compound of Reference Example 454, the title compound was obtained in a similar manner to Reference Example 132.

MS (ESI+) 607 ($M^{+}$+1, 22%).

Reference Example 456 tert-Butyl (3R)-3-[{[4-(2-{[(benzyloxy)carbonyl]amino}ethyl)-2,7-dimethyl-3-oxo-2-phenyl-3,4-dihydro-2H-1,4-benzoxazin-6-yl]carbonyl}(isopropyl)amino]piperidine-1-carboxylate

[Chemical formula 600]

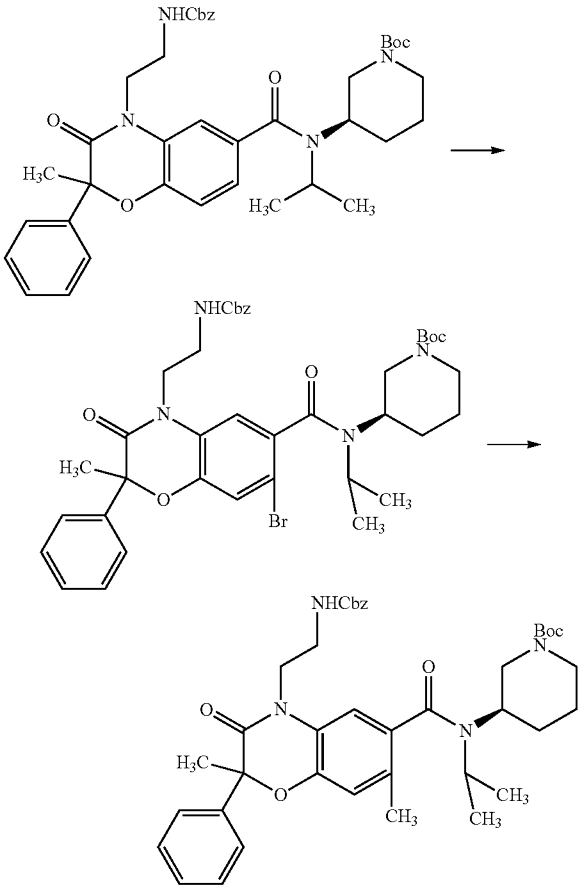

Using the compound of Reference Example 454, the title compound was obtained in a similar manner to Reference Example 10.

MS (ESI+) 699 ($M^{+}$+1, 10%).

Reference Example 457 tert-Butyl (3R)-3-[({2,7-dimethyl-3-oxo-2-phenyl-4-[2-(propionylamino)ethyl]-3,4-dihydro-2H-1,4-benzoxazin-6-yl}carbonyl)(isopropyl)amino]piperidine-1-carboxylate

[Chemical formula 601]

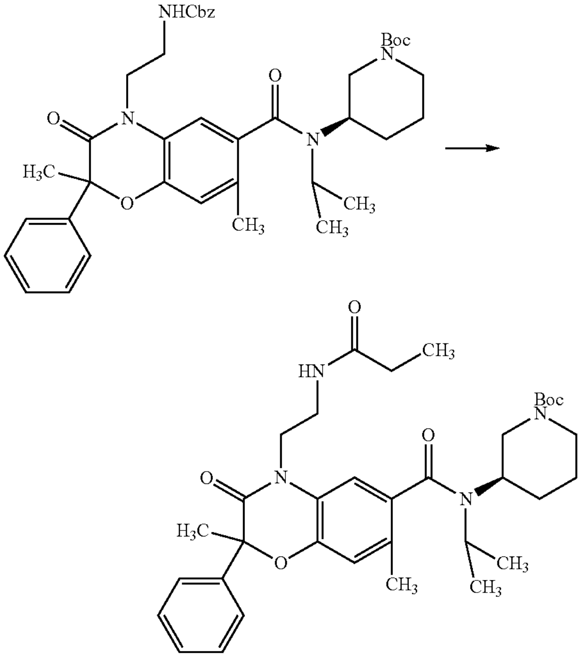

Using the compound of Reference Example 456, the title compound was obtained in a similar manner to Reference Example 132.

MS (ESI+) 621 ($M^{+}$+1, 33%).

Reference Example 458 tert-Butyl (3R)-3-[({7-chloro-2-methyl-3-oxo-2-phenyl-4-[2-(propionylamino)ethyl]-3,4-dihydro-2H-1,4-benzoxazin-6-yl}carbonyl)(isopropyl)amino]piperidine-1-carboxylate

[Chemical formula 602]

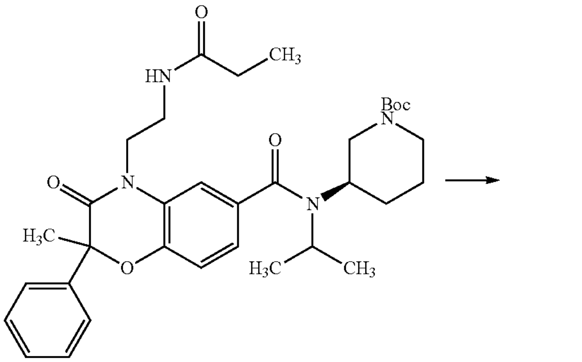

-continued

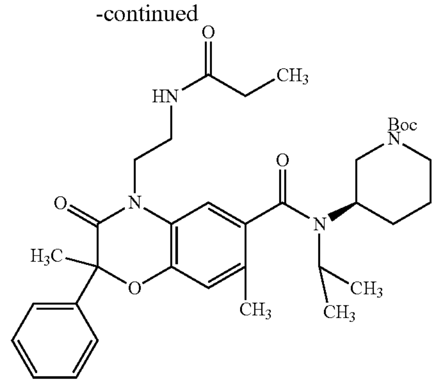

Using the compound of Reference Example 455, the title compound was obtained in a similar manner to Reference Example 12.

MS (ESI+) 641 ($M^{+}$+, 10%).

Reference Example 459

Methyl 4-(2-{[(benzyloxy)carbonyl]amino}ethyl)-2-methyl-3-oxo-2-phenyl-7-(trifluoromethyl)-3,4-dihydro-2H-1,4-benzoxazine-6-carboxylate

[Chemical formula 603]

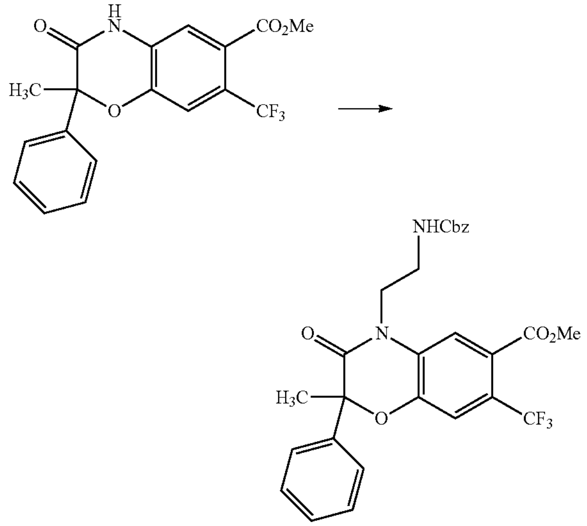

Using the compound of Reference Example 452, the title compound was obtained in a similar manner to Reference Example 164.

MS (ESI+) 543 ($M^{+}$+1, 7 0%).

Reference Example 460

Methyl 4-(2-{[(benzyloxy)carbonyl]amino}ethyl)-2-(3-methoxyphenyl)-2-methyl-3-oxo-7-(trifluoromethyl)-3,4-dihydro-2H-1,4-benzoxazine-6-carboxylate

[Chemical formula 604]

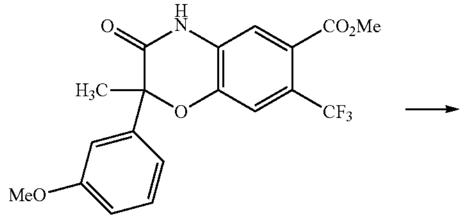

-continued

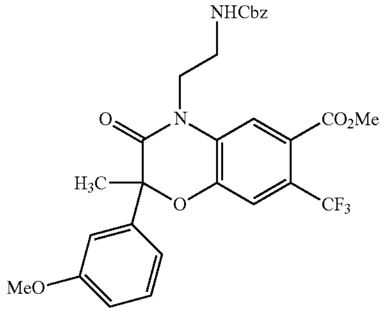

Using the compound of Reference Example 453, the title compound was obtained in a similar manner to Reference Example 164.

MS (ESI+) 573 ($M^{+}$+1, 36%).

Reference Example 461 tert-Butyl (3R)-3-[{[4-(2-{[(benzyloxy)carbonyl]amino}ethyl)-2-methyl-3-oxo-2-phenyl-7-(trifluoromethyl)-3,4-dihydro-2H-1,4-benzoxazin-6-yl]carbonyl}(isopropyl)amino]piperidine-1-carboxylate

[Chemical formula 605]

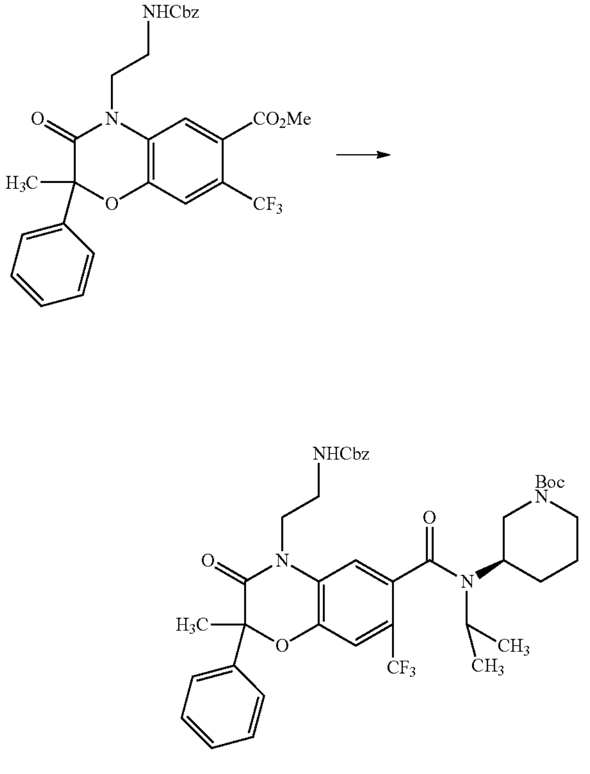

Using the compound of Reference Example 459, the title compound was obtained in a similar manner to Reference Example 5.

MS (ESI+) 753 ($M^{+}$+1, 22%).

Reference Example 462 tert-Butyl (3R)-3-[{[4-(2-{[(benzyloxy)carbonyl]amino}ethyl)-2-(3-methoxyphenyl)-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 606]

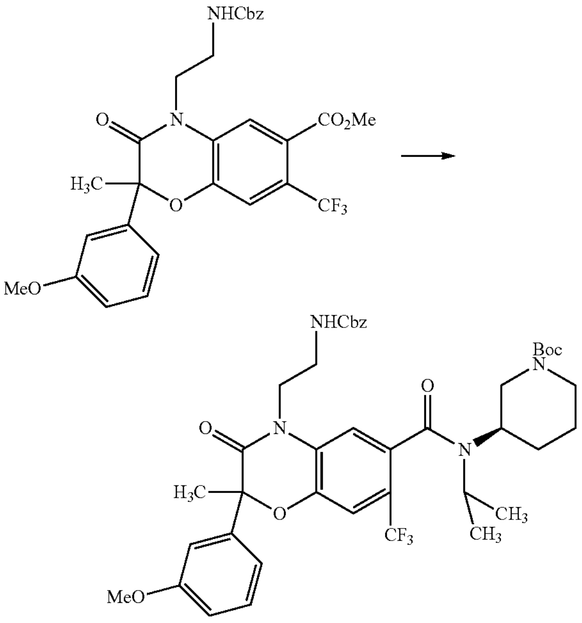

Using the compound of Reference Example 460, the title compound was obtained in a similar manner to Reference Example 5.

MS (ESI+) 783 ($M^+$+1, 19%).

Reference Example 463 tert-Butyl (3R)-3-(isopropyl{[2-methyl-3-oxo-2-phenyl-4-[2-(propionylamino)ethyl]-7-(trifluoromethyl)-3,4-dihydro-2H-1,4-benzoxazin-6-yl]carbonyl}amino)piperidine-1-carboxylate

[Chemical formula 607]

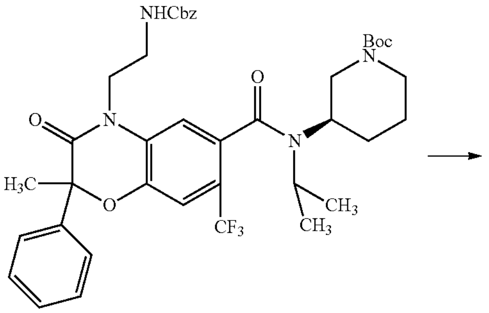

-continued

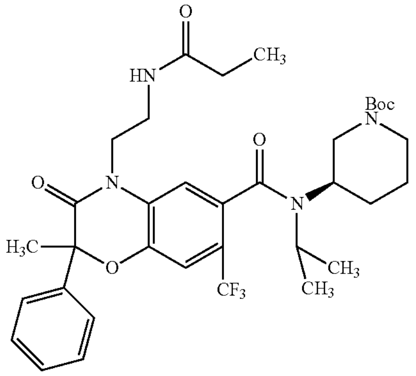

Using the compound of Reference Example 461, the title compound was obtained in a similar manner to Reference Example 132.

MS (ESI+) 675 ($M^+$+1, 31%).

Reference Example 464 tert-Butyl (3R)-3-(isopropyl{[2-(3-methoxyphenyl)-2-methyl-3-oxo-4-[2-(propionylamino)ethyl]-7-(trifluoromethyl)-3,4-dihydro-2H-1,4-benzoxazin-6-yl]carbonyl}amino)piperidine-1-carboxylate

[Chemical formula 608]

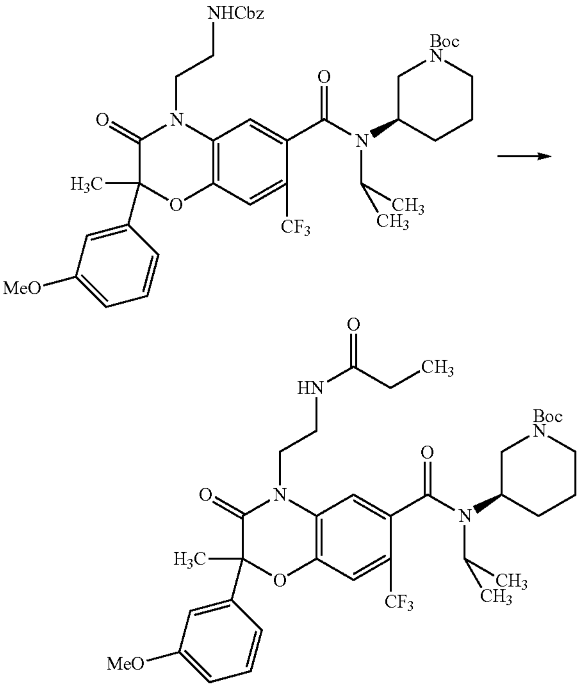

Using the compound of Reference Example 462, the title compound was obtained in a similar manner to Reference Example 132.

MS (ESI+) 705 ($M^+$+1, 14%).

Reference Example 465

4,4,6-Trimethyl-3,4-dihydroquinolin-2(1H)-one

[Chemical formula 609]

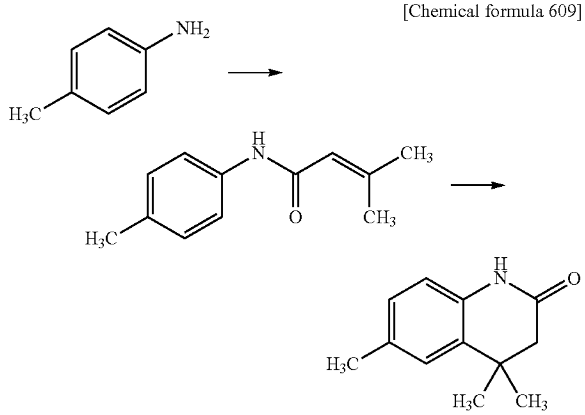

In an ice-bath, to a solution of p-toluidine (3.78 g) and triethylamine (5.5 ml) in chloroform (70 ml) was added dropwise 3,3-dimethylacryloyl chloride (3.76 g). The mixture was stirred at room temperature overnight. Water was added to the reaction solution for separation. The organic layer was dried over sodium sulfate, filtered and concentrated to give a crude product. This product was purified by silica gel column chromatography to give an intermediate (6.11 g), which was dissolved in toluene (120 ml), and thereto was added aluminum chloride (6.50 g), and the mixture was stirred at 100° C. for 5 hours. To the mixture was added aluminum chloride (2.11 g) again, and stirred again at 100° C. for 4 hours. The mixture was cooled to room temperature, and slowly poured into ice-water. The mixture was stirred for 30 minutes, and extracted with ethyl acetate. The organic layer was washed with water, a saturated aqueous sodium hydrogen carbonate solution, a saturated aqueous sodium chloride solution, dried over sodium sulfate, filtered, and concentrated to give a crude product, which was purified by silica gel column chromatography to give the title compound (4.20 g).

MS (ESI+) 190 ($M^{+}$+1, 100%).

Reference Example 466

7-Bromo-4,4,6-trimethyl-3,4-dihydroquinolin-2(1H)-one

[Chemical formula 610]

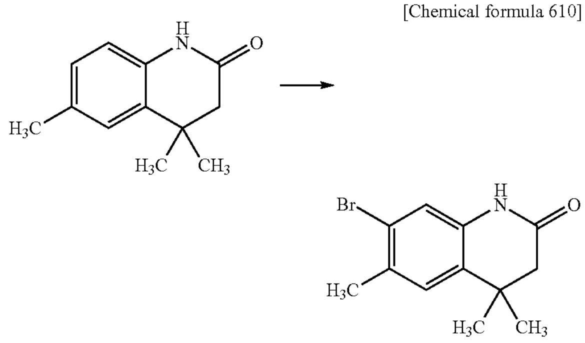

Using the compound of Reference Example 465, the title compound was obtained in a similar manner to Reference Example 6.

MS (ESI+) 270 ($M^{+}$+2, 100%).

Reference Example 467

7-Bromo-1-(4-methoxybutyl)-4,4,6-trimethyl-3,4-dihydroquinolin-2(1H)-one

[Chemical formula 611]

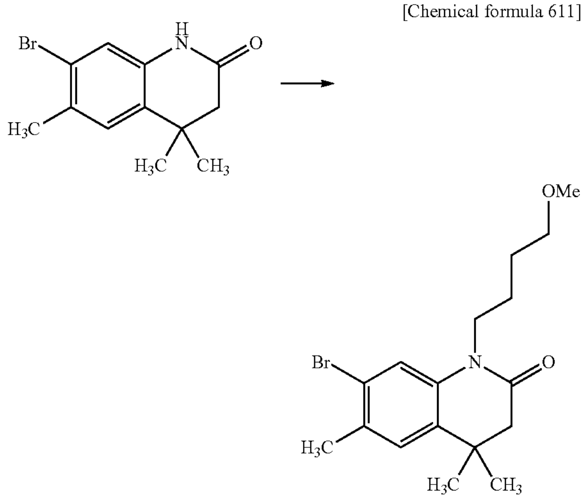 [SMILES: Cc1cc2c(cc1Br)NC(=O)CC2(C)C ; COCCCCN1C(=O)CC(C)(C)c2cc(C)c(Br)cc21]

Using the compound of Reference Example 466, the title compound was obtained in a similar manner to Reference Example 3.

MS (ESI+) 356 ($M^{+}$+2, 90%).

Reference Example 468

Methyl 1-(4-methoxybutyl)-4,4,6-trimethyl-2-oxo-1,2,3,4-tetrahydroquinoline-7-carboxylate

[Chemical formula 612]

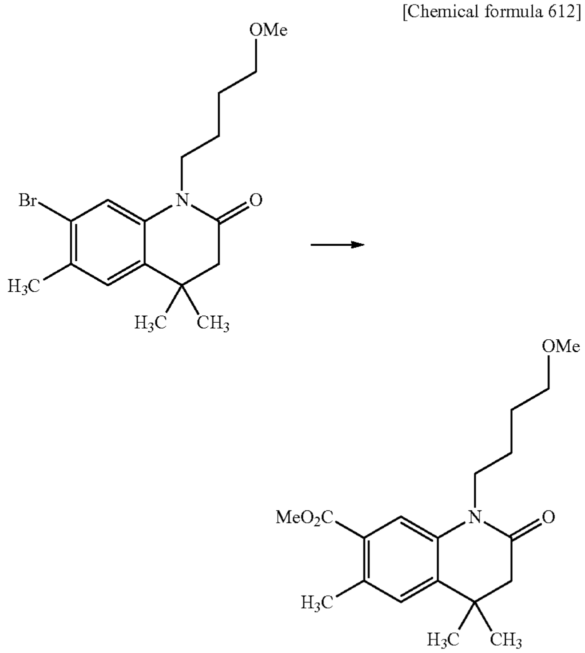

Using the compound of Reference Example 467, the title compound was obtained in a similar manner to Reference Example 25.

MS (ESI+) 334 ($M^{+}$+1, 100%).

Reference Example 469 tert-Butyl (3R)-3-(isopropyl{[1-(4-methoxybutyl)-4,4,6-trimethyl-2-oxo-1,2,3,4-tetrahydroquinolin-7-yl]carbonyl}amino)piperidine-1-carboxylate

[Chemical formula 613]

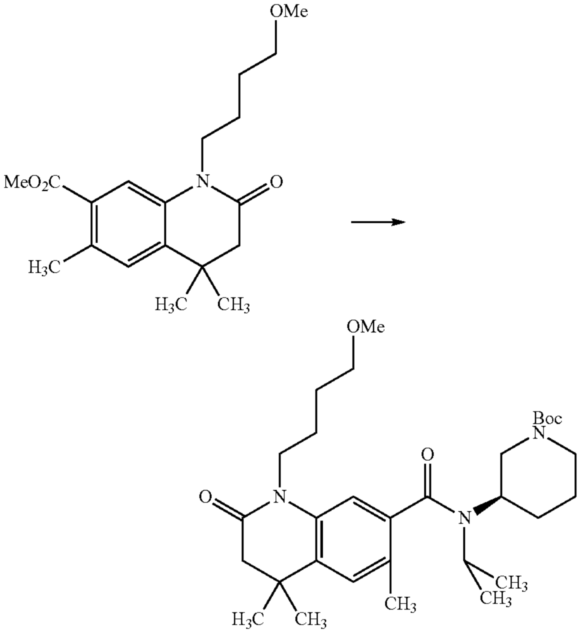

Using the compound of Reference Example 468, the title compound was obtained in a similar manner to Reference Example 5.

MS (ESI+) 544 ($M^{+}$+1, 46%).

Reference Example 470

Methyl 4-(2-{[(benzyloxy)carbonyl]amino}ethyl)-2,2,7-trimethyl-3-oxo-3,4-dihydro-2H-1,4-benzothiazine-6-carboxylate

[Chemical formula 614]

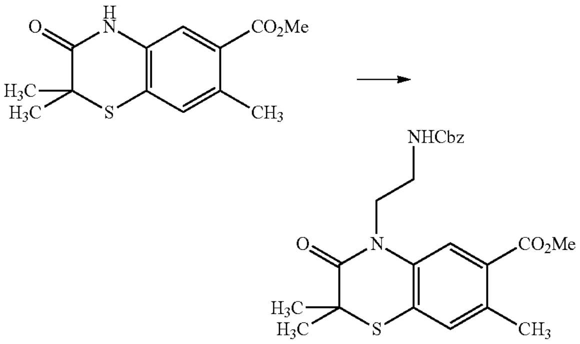

Using the compound of Reference Example 360, the title compound was obtained in a similar manner to Reference Example 378.

MS (ESI+) 443 ($M^{+}$+1, 100%).

Reference Example 471 tert-Butyl (3R)-3-[{[4-(2-{[(benzyloxy)carbonyl]amino}ethyl)-2,2,7-trimethyl-3-oxo-3,4-dihydro-2H-1,4-benzothiazin-6-yl]carbonyl}(isopropyl)amino]piperidine-1-carboxylate

[Chemical formula 615]

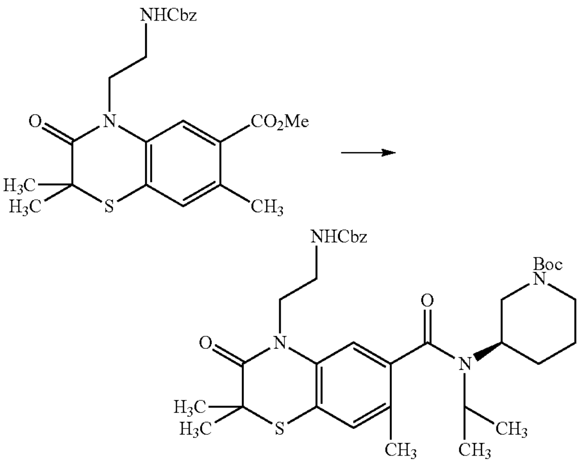

Using the compound of Reference Example 470, the title compound was obtained in a similar manner to Reference Example 5.

MS (ESI+) 653 ($M^{+}$+1, 53%).

Reference Example 472 tert-Butyl (3R)-3-[isopropyl({2,2,7-trimethyl-3-oxo-4-[2-(propionylamino)ethyl]-3,4-dihydro-2H-1,4-benzothiazin-6-yl}carbonyl)amino]piperidine-1-carboxylate

[Chemical formula 616]

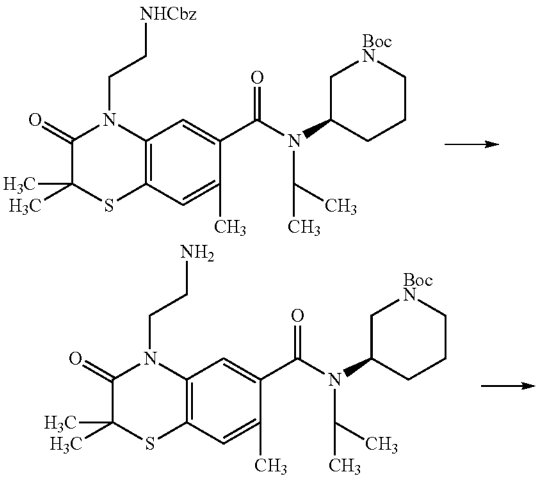

-continued

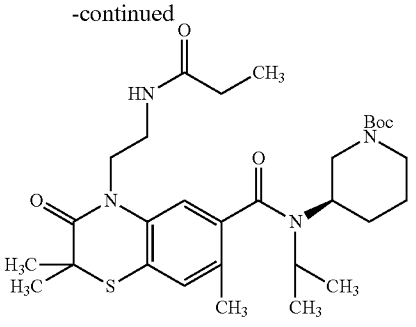

Using the compound of Reference Example 471, the title compound was obtained in a similar manner to Reference Example 132.

MS (ESI+) 575 ($M^{+}$+1, 13%).

Reference Example 473 tert-Butyl (3R)-3-[{[2-(3,5-difluorophenyl)-2-methyl-3-oxo-3,4-dihydro-2H-1,4-benzoxazin-6-yl]carbonyl}(isopropyl)amino]piperidine-1-carboxylate

[Chemical formula 617]

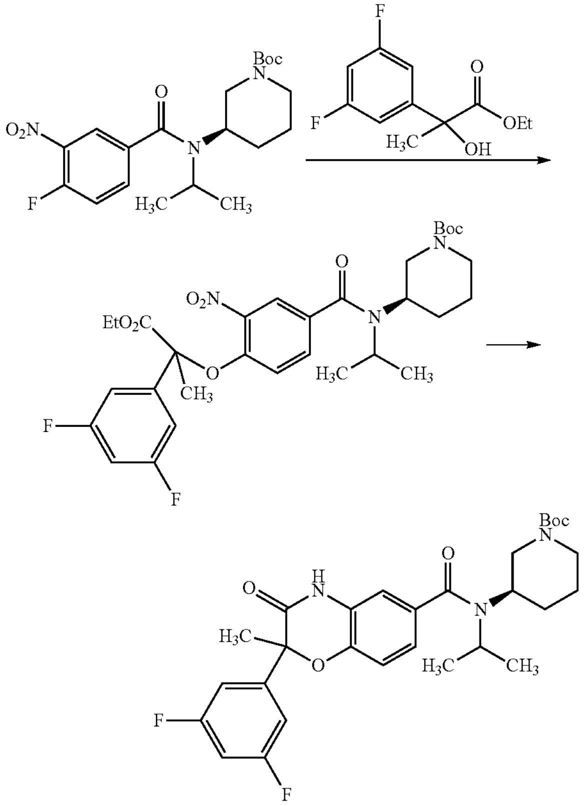

Using the compound of Reference Example 488, the title compound was obtained in a similar manner to Reference Example 22 and Reference Example 2.

MS (ESI+) 544 ($M^{+}$+1).

Reference Example 474 tert-Butyl (3R)-3-[[(2-(3,5-difluorophenyl)-4-{2-[(methoxycarbonyl)amino]ethyl}-2-methyl-3-oxo-3,4-dihydro-2H-1,4-benzoxazin-6-yl)carbonyl](isopropyl)amino]piperidine-1-carboxylate

[Chemical formula 618]

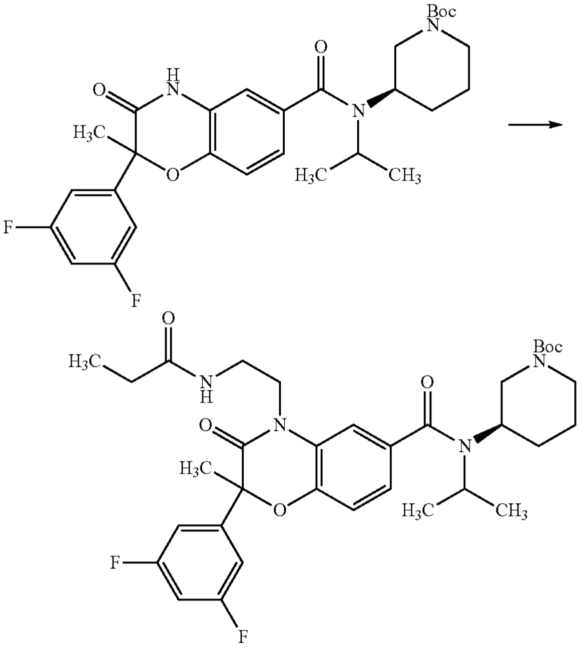

Using the compound of Reference Example 473, the title compound was obtained in a similar manner to Reference Example 13.

MS (ESI+) 645 ($M^{+}$+1).

Reference Example 475 tert-Butyl (3R)-3-[[(7-chloro-2-(3,5-difluorophenyl)-4-{2-[(methoxycarbonyl)amino]ethyl}-2-methyl-3-oxo-3,4-dihydro-2H-1,4-benzoxazin-6-yl)carbonyl](isopropyl)amino]piperidine-1-carboxylate

[Chemical formula 619]

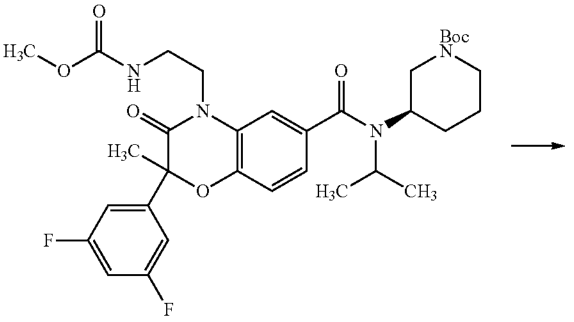

-continued

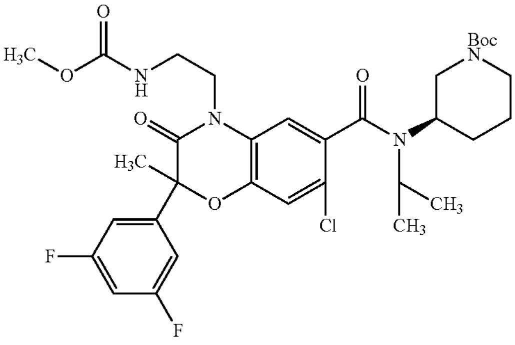

Using the compound of Reference Example 474, the title compound was obtained in a similar manner to Reference Example 12.

MS (ESI+) 679 ($M^{+}$+1).

Reference Example 476 tert-Butyl (3R)-3-[[(7-bromo-2-(3,5-difluorophenyl)-4-{2-[(methoxycarbonyl)amino]ethyl}-2-methyl-3-oxo-3,4-dihydro-2H-1,4-benzoxazin-6-yl)carbonyl](isopropyl)amino]piperidine-1-carboxylate

[Chemical formula 620]

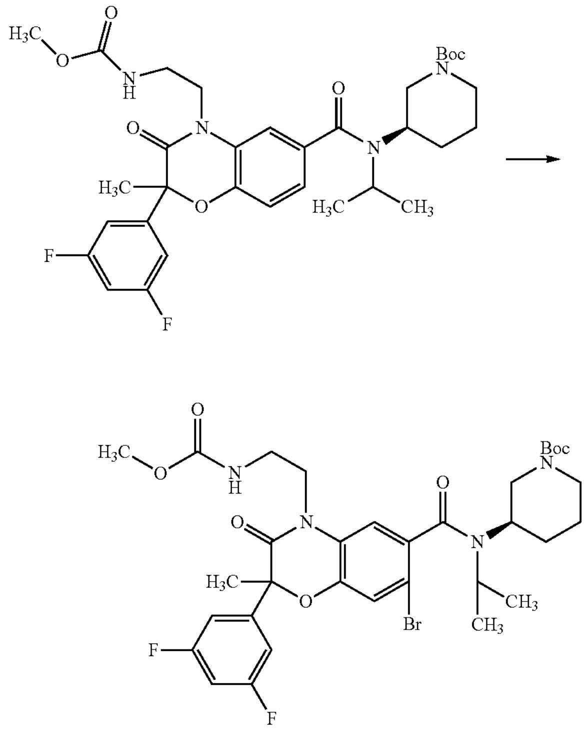

Using the compound of Reference Example 474, the title compound was obtained in a similar manner to Reference Example 6.

MS (ESI+) 723 ($M^{+}$+1).

Reference Example 477 tert-Butyl (3R)-3-[[(2-(3,5-difluorophenyl)-4-{2-[(methoxycarbonyl)amino]ethyl}-2,7-dimethyl-3-oxo-3,4-dihydro-2H-1,4-benzoxazin-6-yl)carbonyl](isopropyl)amino]piperidine-1-carboxylate

[Chemical formula 621]

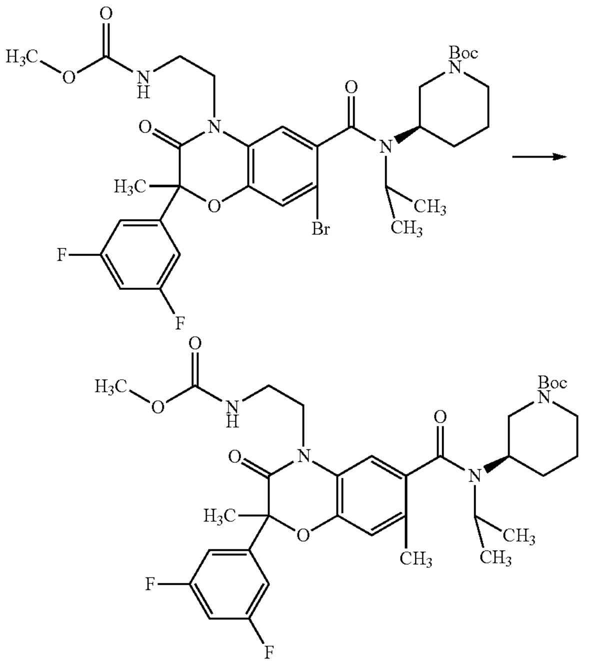

Using the compound of Reference Example 476, the title compound was obtained in a similar manner to Reference Example 10.

MS (ESI+) 659 ($M^{+}$+1).

Reference Example 478 tert-Butyl (3R)-3-[({(2S)-2-(3,5-difluorophenyl)-2-methyl-3-oxo-4-[2-(propionylamino)ethyl]-3,4-dihydro-2H-1,4-benzoxazin-6-yl}carbonyl)(isopropyl)amino]piperidine-1-carboxylate

[Chemical formula 622]

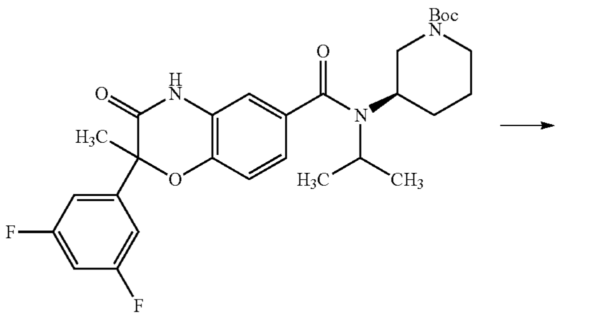

-continued

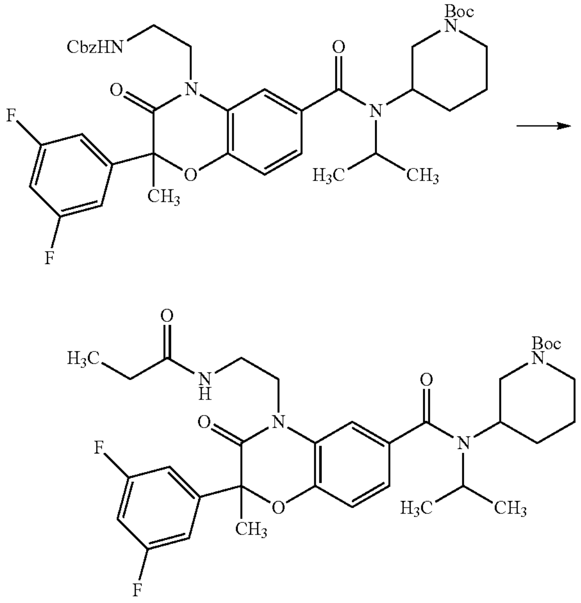

Using the compound of Reference Example 473, the title compound was obtained in a similar manner to Reference Examples 164 and 132.

MS (ESI+) 643 ($M^{+}$+1, 53%).

Reference Example 479 tert-Butyl (3R)-3-[({(2S)-2-(3,5-difluorophenyl)-2,7-dimethyl-3-oxo-4-[2-(propionylamino)ethyl]-3,4-dihydro-2H-1,4-benzoxazin-6-yl]carbonyl)(isopropyl)amino]piperidine-1-carboxylate

[Chemical formula 623]

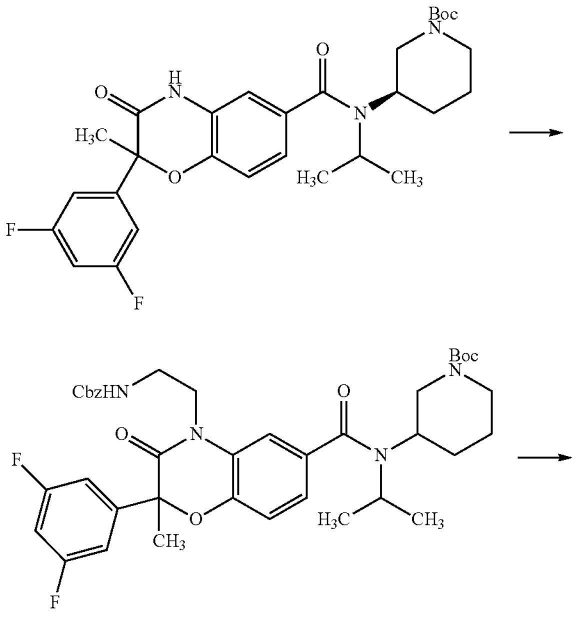

-continued

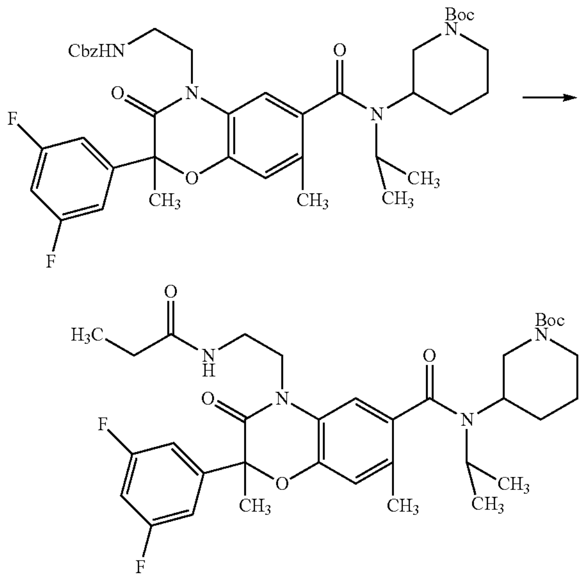

Using the compound of Reference Example 473, the title compound was obtained in a similar manner to Reference Example 164, Reference Example 10 and Reference Example 132.

MS (ESI+) 657 ($M^{+}$+1, 100%).

Reference Example 480 tert-Butyl (3R)-3-(isopropyl{[(2S)-4-(4-methoxybutyl)-2-methyl-3-oxo-7-(trifluoromethyl)-3,4-dihydro-2H-1,4-benzoxazin-6-yl]carbonyl}amino)piperidine-1-carboxylate

[Chemical formula 624]

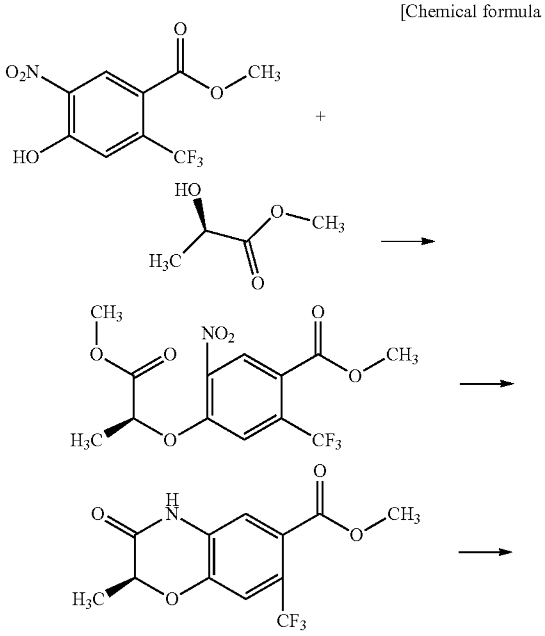

-continued

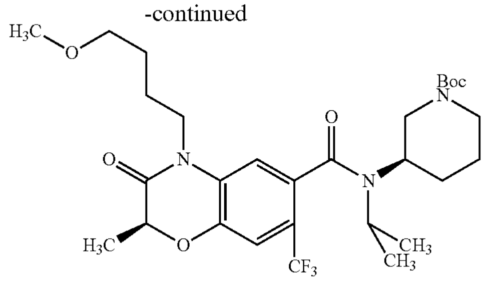

Using the compound of Reference Example 52, the title compound was obtained in a similar manner to Reference Example 64.

MS (ESI+) 586 ($M^{+}$+1, 40%).

Reference Example 481 tert-Butyl (3R)-3-(isopropyl{[(2S)-2-methyl-3-oxo-4-[2-(propionylamino)ethyl]-7-(trifluoromethyl)-3,4-dihydro-2H-1,4-benzoxazin-6-yl]carbonyl}amino) piperidine-1-carboxylate

[Chemical formula 625]

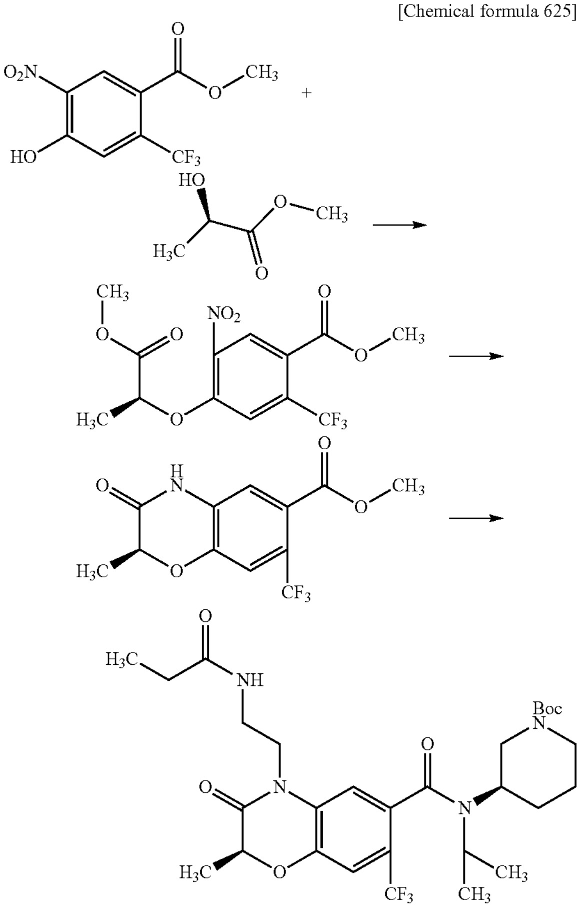

Using the compound of Reference Example 52, the title compound was obtained in a similar manner to Reference Example 26, Reference Example 2, Reference Example 164, Reference Example 132.

MS (ESI+) 599 ($M^{+}$+1, 33%).

Reference Example 482 tert-Butyl (3R)-3-(isopropylamino)piperidine-1-carboxylate

[Chemical formula 626]

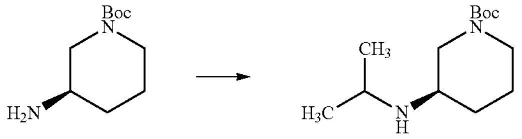

Commercially available tert-butyl (3R)-3-aminopiperidine-1-carboxylate (6.67 g) was dissolved in ethanol (100 ml), and thereto were added acetone (12.2 ml) and acetic acid (2.0 ml), and the mixture was heated at 60° C. with stirring. Seven hours later, to the mixture was added sodium triacetoxyborohydride (9.67 g), and the mixture was stirred at room temperature for 14 hours. To the reaction mixture was added a saturated aqueous sodium hydrogen carbonate solution, and the mixture was extracted with chloroform. The organic layer was washed with a saturated aqueous sodium chloride solution, dried over sodium hydrogen sulfate, filtered and concentrated under reduced pressure. The obtained residue was purified by silica gel column chromatography (the developing solvent: chloroform/methanol=30/1, 15/1, 10) to give the title compound (7.78 g) as a white solid.

MS (ESI+) 243 (M+1, 100%).

Reference Example 483 tert-Butyl 3-(isopropylamino)azepane-1-carboxylate

[Chemical formula 627]

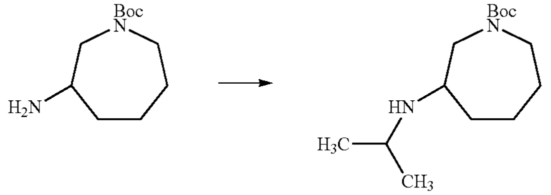

Using tert-butyl 3-aminoazepane-1-carboxylate, the title compound was obtained in a similar manner to Reference Example 482.

MS (ESI+) 257 (M++1, 100%).

Reference Example 484

Benzyl 3-(isopropylamino)pyrrolidine-1-carboxylate

[Chemical formula 628]

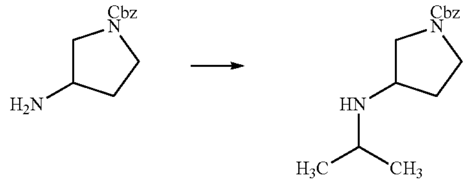

Using benzyl 3-aminopyrrolidine-1-carboxylate, the title compound was obtained in a similar manner to Reference Example 482.

MS (ESI+) 263 ($M^{+}$+1, 100%).

Reference Example 485 tert-Butyl (3R)-3-(ethylamino)piperidine-1-carboxylate

[Chemical formula 629]

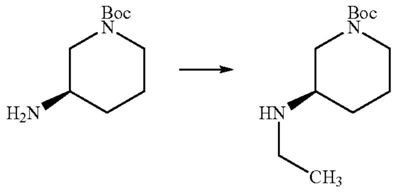

Using tert-butyl (3R)-3-aminopiperidine-1-carboxylate, the title compound was obtained in a similar manner to Reference Example 482.

MS (ESI+) 229 ($M^{+}$+1, 67%).

Reference Example 486 tert-Butyl (3R)-3-(sec-butylamino)piperidine-1-carboxylate

[Chemical formula 630]

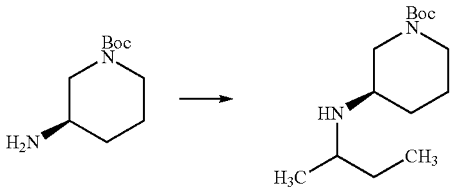

Using tert-butyl (3R)-3-aminopiperidine-1-carboxylate, the title compound was obtained in a similar manner to Reference Example 482.

MS (ESI+) 257 ($M^{+}$+1, 100%).

Reference Example 487 tert-Butyl (3R)-3-(benzylamino)piperidine-1-carboxylate

[Chemical formula 631]

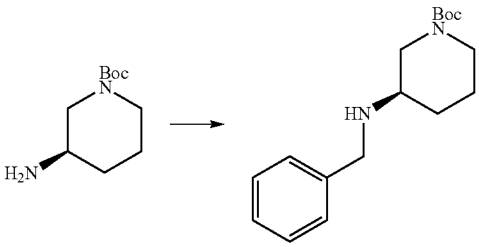

Using tert-butyl (3R)-3-aminopiperidine-1-carboxylate, the title compound was obtained in a similar manner to Reference Example 482.

MS (ESI+) 291 ($M^{+}$+1, 100%).

Reference Example 488 tert-Butyl (3R)-3-[(4-fluoro-3-nitrobenzoyl)(isopropyl)amino]piperidine-1-carboxylate

[Chemical formula 632]

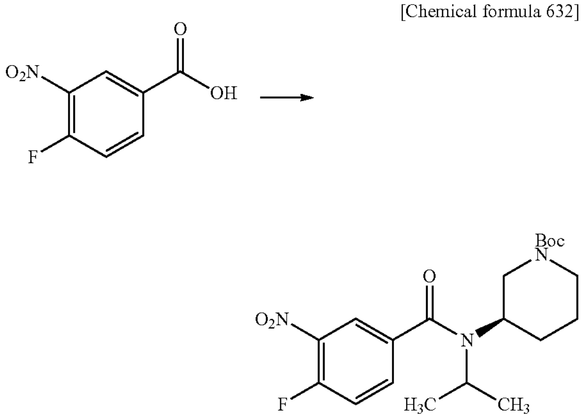

Using 4-fluoro-3-nitrobenzoic acid, the title compound was obtained in a similar manner to Reference Example 5.

MS (ESI+) 410 ($M^{+}$+1, 78%)

Reference Example 489

(2R)-2-(3,5-Difluorophenyl)-2-fluoro-N-isopropyl-3-oxo-N-[(3R)-piperidin-3-yl]-4-[2-(propionyl-amino)ethyl]-3,4-dihydro-2H-1,4-benzoxazine-6-carboxamide hydrochloride

[Chemical formula 633]

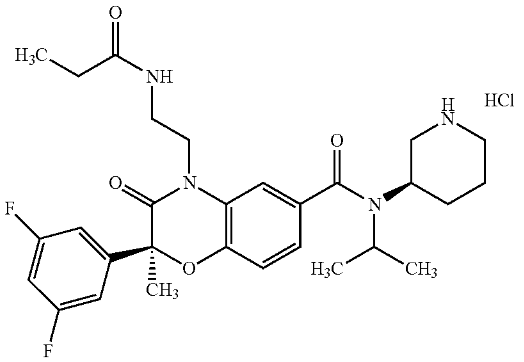

$^{1}$H NMR (400 MHz, $CDCl_3$) δ 9.91-9.39 (br, 2H), 7.12-6.55 (m, 6H), 6.79 (br, 0.5H), 6.28 (br, 0.5H), 4.21-3.24 (m, 9H), 2.87-2.49 (m, 2H), 2.22-1.80 (m, 8H), 1.37-0.97 (m, 9H).

Reference Example 490

Methyl {2-[7-({isopropyl[(3R)-piperidin-3-yl]amino}carbonyl)-3,3-dimethyl-2-oxo-3,4-dihydroquinolin-1(2H)-yl]ethyl}carbamate hydrochloride

[Chemical formula 634]

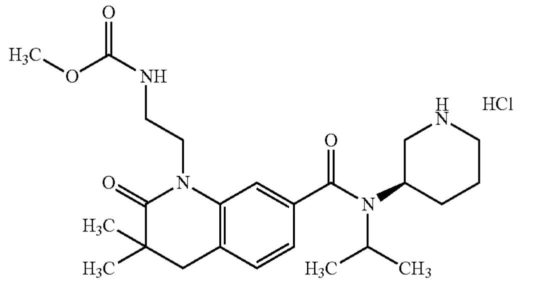

$^1$H NMR (400 MHz, $CDCl_3$) δ 9.75-9.65 (m, 2H), 7.17-7.15 (m, 2H), 6.95 (brs, 1H), 4.15-3.82 (m, 4H), 3.66-3.58 (m, 1H), 3.57 (s, 3H), 3.51-3.27 (m, 4H), 2.94-2.81 (m, 1H), 2.81-2.75 (m, 3H), 2.12-1.76 (m, 4H), 1.34-1.08 (m, 12H)

Reference Example 491

$N^6$-Isopropyl-4-(3-methoxypropyl)-$N^2$,$N^2$,2-trimethyl-3-oxo-$N^6$-[(3R)-piperidin-3-yl]-3,4-dihydro-2H-1,4-benzoxazine-2,6-dicarboxamide hydrochloride

[Chemical formula 635]

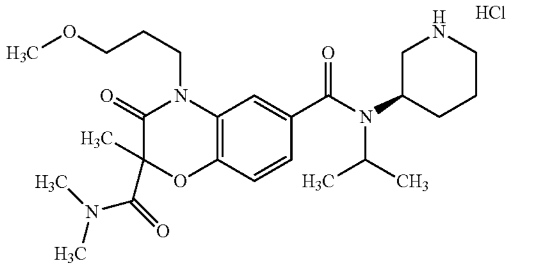

$^1$H NMR (400 MHz, $CDCl_3$) δ 9.89-9.51 (br, 2H), 7.12-6.83 (m, 3H), 4.18-3.60 (m, 5H), 3.45-3.28 (m, 4H), 3.39-3.27 (m, 3H), 3.18-3.03 (m, 3H), 2.91-2.65 (m, 5H), 2.15-1.53 (m, 8H), 1.40-1.08 (m, 6H).

Reference Example 492

N-Isopropyl-4-(4-methoxybutyl)-2-(methoxymethyl)-2-methyl-3-oxo-N-[(3R)-piperidin-3-yl]-3,4-dihydro-2H-1,4-benzoxazine-6-carboxamide hydrochloride

[Chemical formula 636]

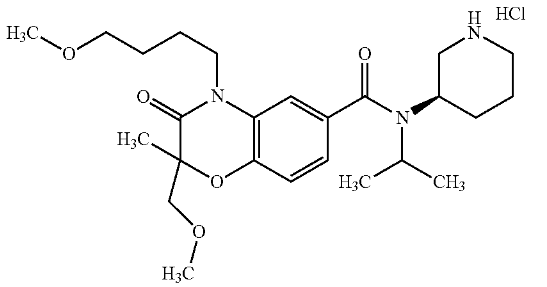

$^1$H NMR (400 MHz, $CDCl_3$) δ 9.91-9.55 (br, 2H), 6.93-6.78 (m, 3H), 4.15-3.87 (m, 4H), 3.83-3.72 (m, 2H), 3.51-3.43 (m, 2H), 3.38-3.27 (m, 2H), 3.32 (s, 3H), 3.24 (s, 3H), 2.93-2.78 (m, 2H), 2.08-1.87 (m, 2H), 1.77-1.53 (m, 6H), 1.31 (s, 3H), 1.28-1.07 (m, 6H).

Reference Example 493

N-Isopropyl-4-(4-methoxybutyl)-3-oxo-N-[(3R)-piperidin-3-yl]-2',3,3',4,5',6'-hexahydrospiro[1,4-benzoxazine-2,4'-pyran]-6-carboxamide hydrochloride

[Chemical formula 637]

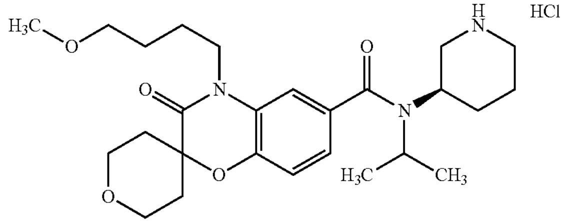

RT 2.531 min (Shim-pack XR-ODS, 0.1% trifluoroacetic acid in water/acetonitrile, acetonitrile 30-90%, 5.7 min, 1.0 ml/min).

MS (ESI+) 474 ($M^+$+1, 100%).

Reference Example 494

(2S)-2-Hydroxy-2-phenylpropanoic acid

[Chemical formula 638]

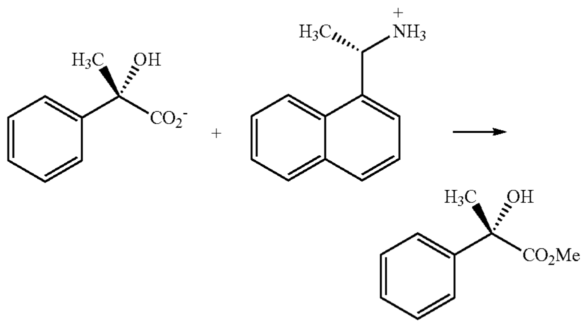

(2S)-2-Hydroxy-2-phenylpropanoic acid-(1S)-1-(1-naphthyl)ethanamine (1:1) (1.54 g) was dissolved in methanol (50 ml), and thereto was slowly added dropwise conc. sulfuric acid (5 ml). After the addition was complete, the mixture was refluxed for 10 hours. The reaction solution was cooled to room temperature, and concentrated under reduced pressure to remove methanol. The residue was dissolved in ethyl acetate, washed with water, a saturated aqueous sodium hydrogen carbonate solution, and a saturated aqueous sodium chloride solution, dried over sodium sulfate, filtered, and concentrated under reduced pressure to give the title compound (0.83 g).

$^1H$ NMR (400 MHz, $CDCl_3$) δ 7.47-7.44 (m, 2H), 7.36-7.29 (m, 2H), 7.29-7.23 (m, 1H), 6.00 (s, 1H), 3.60 (s, 1H), 1.62 (s, 3H).

Reference Example 495

Methyl (2S)-2-methyl-3-oxo-2-phenyl-7-(trifluoromethyl)-3,4-dihydro-2H-1,4-benzoxazine-6-carboxylate

[Chemical formula 639]

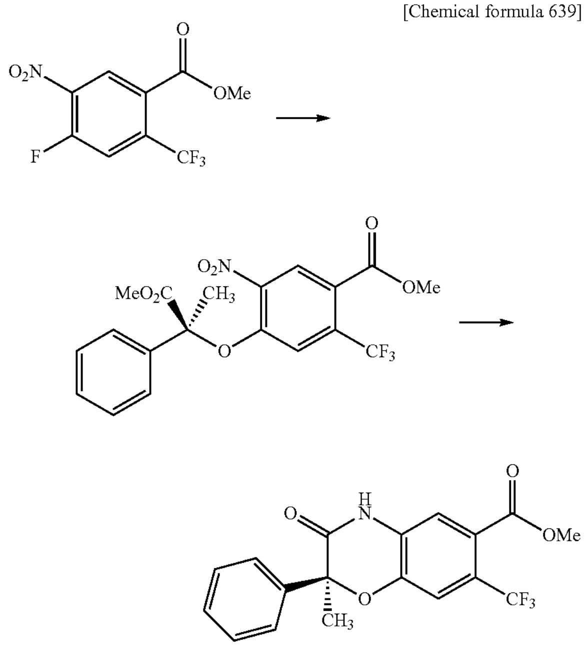

Using (2S)-2-hydroxy-2-phenylpropanoic acid and methyl 4-fluoro-5-nitro-2-(trifluoromethyl)-benzoate, the title compound was obtained in a similar manner to Reference Example 22 and Reference Example 2.

MS (ESI+) 366 ($M^+$+1, 100%).

Reference Example 496

Methyl (2S)-4-(2-{[(benzyloxy)carbonyl]amino}ethyl)-2-methyl-3-oxo-2-phenyl-7-(trifluoromethyl)-3,4-dihydro-2H-1,4-benzoxazine-6-carboxylate

[Chemical formula 640]

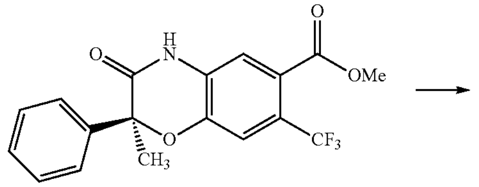

-continued

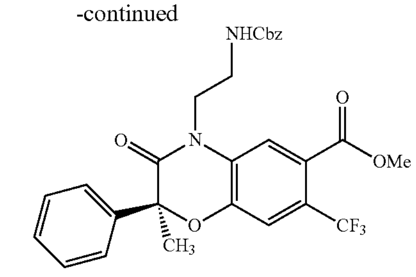

Using methyl (2S)-2-methyl-3-oxo-2-phenyl-7-(trifluoromethyl)-3,4-dihydro-2H-1,4-benzoxazine-6-carboxylate, the title compound was obtained in a similar manner to Reference Example 164.

MS (ESI+) 543 ($M^+$+1, 100%).

Reference Example 497 tert-Butyl (3R)-3-[{[(2S)-4-(2-{[(benzyloxy)carbonyl]amino}ethyl)-2-methyl-3-oxo-2-phenyl-7-(trifluoromethyl)-3,4-dihydro-2H-1,4-benzoxazin-6-yl]carbonyl}(isopropyl)amino]piperidine-1-carboxylate

[Chemical formula 641]

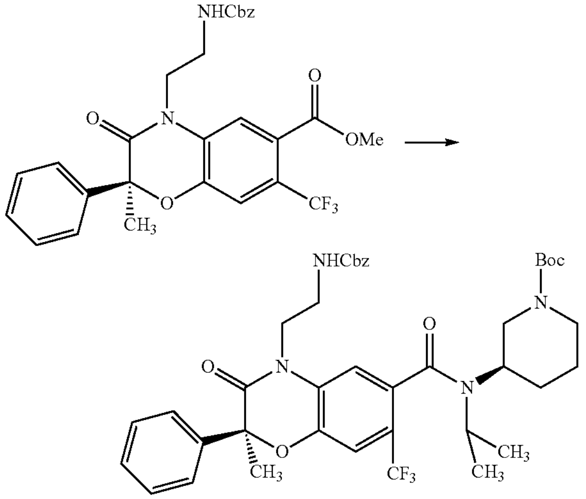

Methyl (2S)-4-(2-{[(benzyloxy)carbonyl]amino}ethyl)-2-methyl-3-oxo-2-phenyl-7-(trifluoro-methyl)-3,4-dihydro-2H-1,4-benzoxazine-6-carboxylate (1.1117 g) was dissolved in 1,4-dioxane (20 ml), and thereto was added 4N-aqueous sodium hydroxide solution (20 ml), and the mixture was stirred at 50° C. for 6 hours. The mixture was cooled to room temperature, and concentrated under reduced pressure to remove 1,4-dioxane. The residue was diluted with water, and the pH value thereof was adjusted to pH 1 with 3N-hydrochloric acid. The precipitated white solid was collected by filtration to give (2S)-4-(2-{[(benzyloxy)carbonyl]amino}ethyl)-2-methyl-3-oxo-2-phenyl-7-(trifluoromethyl)-3,4-dihydro-2H-1,4-benzoxazine-6-carboxylic acid (1.016 2 g). Thus obtained carboxylic acid (717.7 mg) was dissolved in DMF (6 ml), and thereto were added triethylamine (0.75 ml), dimethylaminopyridine (82.0 mg), tert-butyl (3R)-3-(isopropylamino)piperidine-1-carboxylate (1.3400 g), CIP reagent (1.1922 g), and the mixture was stirred at 60° C. under nitrogen atmosphere for 7 hours. To the mixture were additionally added triethylamine (0.57 ml) and CIP reagent (747.7 mg), and the mixture was further stirred at 60° C. for 4 hours. The reaction solution was cooled to room temperature, diluted with water, and extracted with ethyl acetate. The organic layer was washed with water and a saturated aqueous sodium chloride solution, dried over sodium sulfate, filtered, and concentrated under reduced pressure to give a crude product, which was purified by silica gel chromatography to give the title compound (588.4 mg).

MS (ESI+) 753 ($M^+$+1, 26%).

Reference Example 497 tert-Butyl (3R)-3-(isopropyl{[(2S)-2-methyl-3-oxo-2-phenyl-4-[2-(propionylamino)ethyl]-7-(trifluoromethyl)-3,4-dihydro-2H-1,4-benzoxazin-6-yl]carbonyl}amino)piperidine-1-carboxylate

[Chemical formula 642]

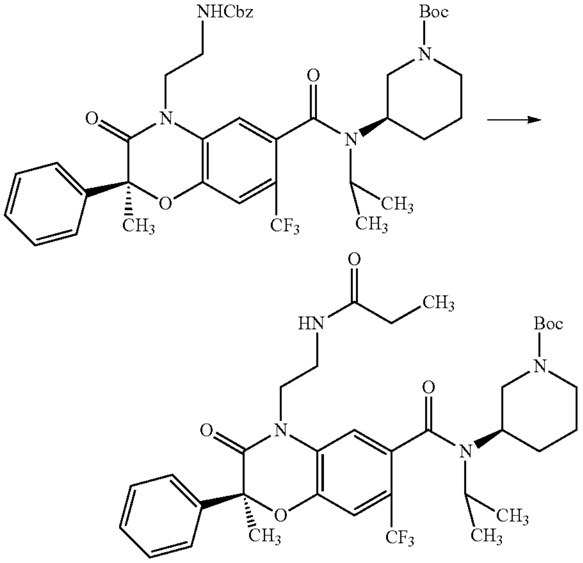

Using tert-butyl (3R)-3-[{[(2S)-4-(2-{[(benzyloxy)carbonyl]amino}ethyl)-2-methyl-3-oxo-2-phenyl-7-(trifluoromethyl)-3,4-dihydro-2H-1,4-benzoxazin-6-yl]carbonyl}(isopropyl)amino]piperidine-1-carboxylate, the title compound was obtained in a similar manner to Reference Example 132.

MS (ESI+) 675 ($M^+$+1, 40%).

Reference Example 498

Methyl 2-(5-bromo-2-fluorophenyl)-2-methyl-3-oxo-7-(trifluoromethyl)-3,4-dihydro-2H-1,4-benzoxazine-6-carboxylate

[Chemical formula 643]

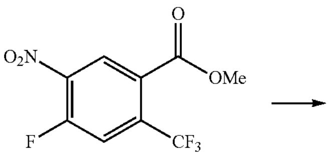

-continued

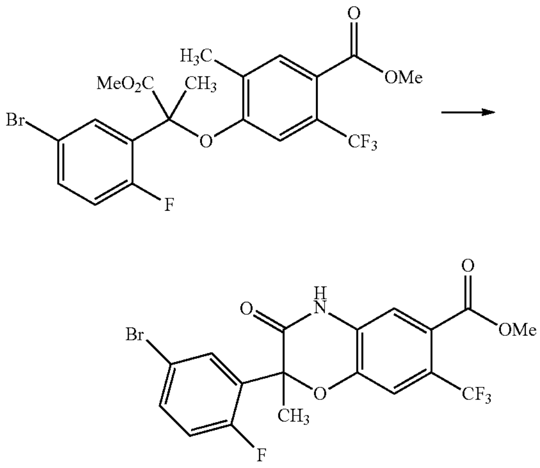

Using methyl 2-(5-bromo-2-fluorophenyl)-2-hydroxypropanoate and methyl 4-fluoro-5-nitro-2-(trifluoromethyl)benzoate, the title compound was obtained in a similar manner to Reference Example 22 and Reference Example 2.

MS (ESI+) 463 ($M^+$+2, 100%).

Reference Example 500

Methyl 4-(2-{[(benzyloxy)carbonyl]amino}ethyl)-2-(5-bromo-2-fluorophenyl)-2-methyl-3-oxo-7-(trifluoromethyl)-3,4-dihydro-2H-1,4-benzoxazine-6-carboxylate

[Chemical formula 644]

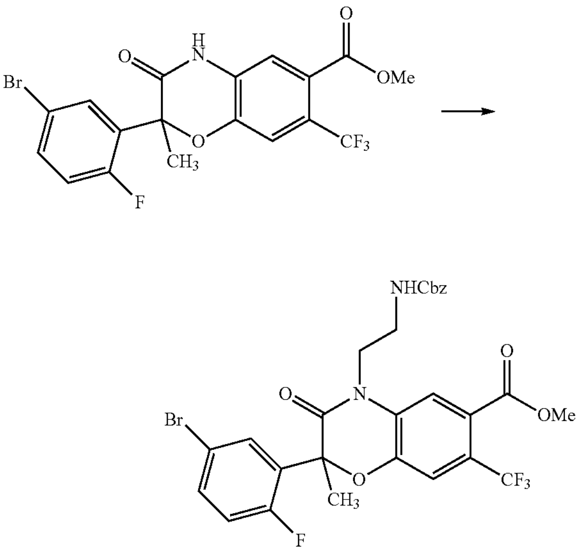

Using methyl 2-(5-bromo-2-fluorophenyl)-2-methyl-3-oxo-7-(trifluoromethyl)-3,4-dihydro-2H-1,4-benzoxazine-6-carboxylate, the title compound was obtained in a similar manner to Reference Example 164.

MS (ESI+) 641 ($M^+$+2, 100%).

Reference Example 499 tert-Butyl (3R)-3-[{[4-(2-{[(benzyloxy)carbonyl]amino}ethyl)-2-(5-bromo-2-fluorophenyl)-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 645]

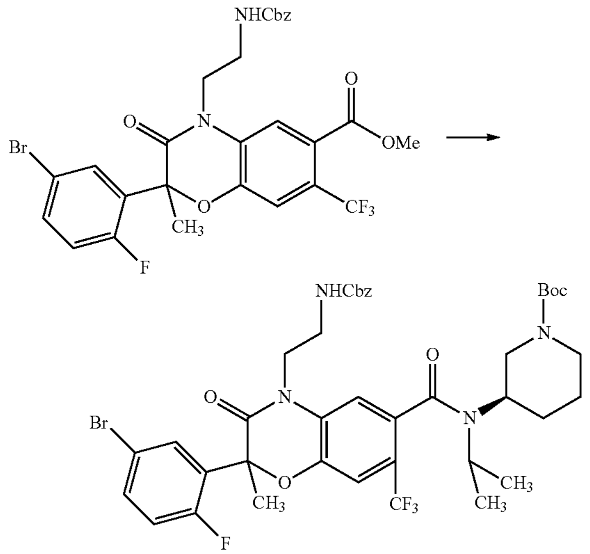

Using methyl 4-(2-{[(benzyloxy)carbonyl]amino}ethyl)-2-(5-bromo-2-fluorophenyl)-2-methyl-3-oxo-7-(trifluoromethyl)-3,4-dihydro-2H-1,4-benzoxazine-6-carboxylate, the title compound was obtained in a similar manner to Reference Example 497.

MS (ESI+) 851 ($M^+$+2, 25%).

Reference Example 500 tert-Butyl (3R)-3-[{[4-(2-{[(benzyloxy)carbonyl]amino}ethyl)-2-(5-cyano-2-fluorophenyl)-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 646]

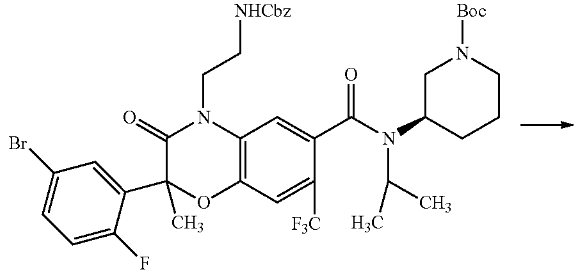

-continued

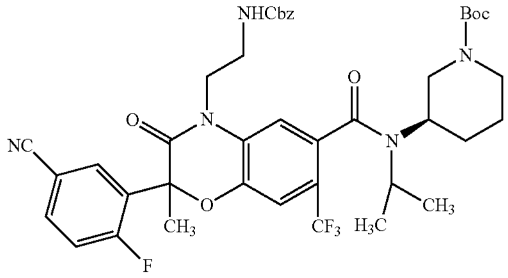

Using tert-butyl (3R)-3-[{[4-(2-{[(benzyloxy)carbonyl]amino}ethyl)-2-(5-bromo-2-fluoro-phenyl)-2-methyl-3-oxo-7-(trifluoromethyl)-3,4-dihydro-2H-1,4-benzoxazin-6-yl]carbonyl}(isopropyl)-amino]piperidine-1-carboxylate, the title compound was obtained in a similar manner to Reference Example 11.

MS (ESI+) 796 ($M^+$+1, 23%).

Reference Example 501 tert-Butyl (3R)-3-[{[2-(5-cyano-2-fluorophenyl)-2-methyl-3-oxo-4-[2-(propionylamino)ethyl]-7-(trifluoromethyl)-3,4-dihydro-2H-1,4-benzoxazin-6-yl]carbonyl}(isopropyl)amino]piperidine-1-carboxylate

[Chemical formula 647]

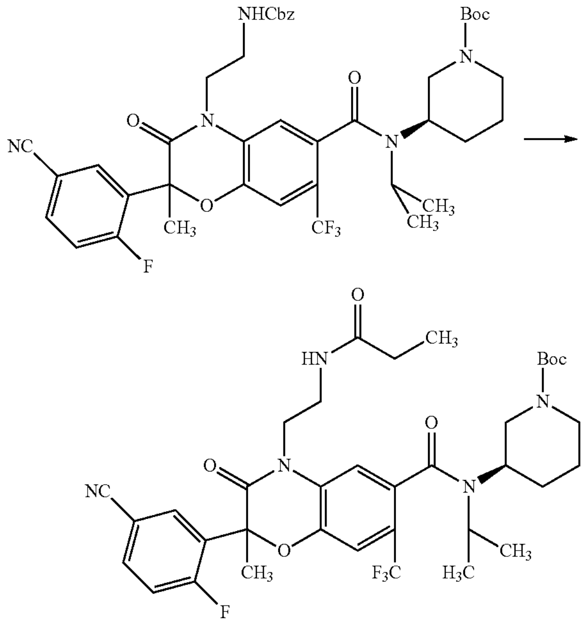

Using tert-butyl (3R)-3-[{[4-(2-{[(benzyloxy)carbonyl]amino}ethyl)-2-(5-cyano-2-fluoro-phenyl)-2-methyl-3-oxo-7-(trifluoromethyl)-3,4-dihydro-2H-1,4-benzoxazin-6-yl]carbonyl}(isopropyl)-amino]piperidine-1-carboxylate, the title compound was obtained in a similar manner to Reference Example 132.

MS (ESI+) 718 ($M^+$+1, 28%).

Reference Example 502 tert-Butyl (3R)-3-[{[2-(2-fluorophenyl)-2-methyl-3-oxo-4-[2-(propionylamino)ethyl]-7-(trifluoro-methyl)-3,4-dihydro-2H-1,4-benzoxazin-6-yl]carbonyl}(isopropyl)amino]piperidine-1-carboxylate

[Chemical formula 648]

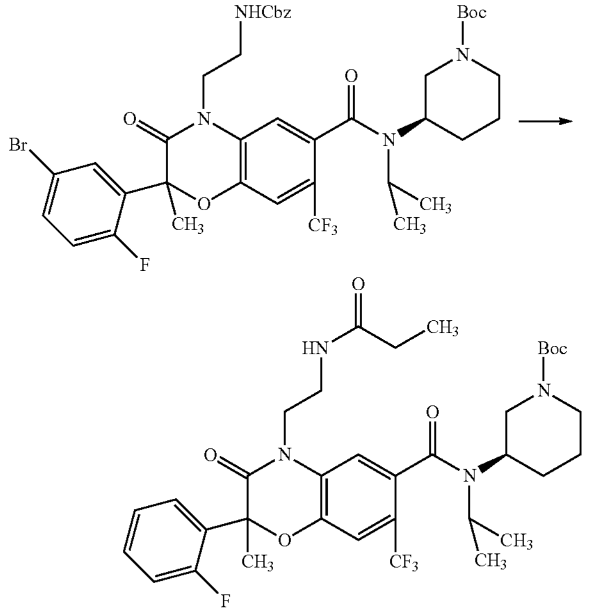

Using tert-butyl (3R)-3-[{[4-(2-{[(benzyloxy)carbonyl]amino}ethyl)-2-(5-bromo-2-fluorophenyl)-2-methyl-3-oxo-7-(trifluoromethyl)-3,4-dihydro-2H-1,4-benzoxazin-6-yl]carbonyl}(isopropyl)amino]piperidine-1-carboxylate, the title compound was obtained in a similar manner to Reference Example 132.

MS (ESI+) 693 ($M^{+}$+1, 44%).

Reference Example 503

Methyl 243-(benzyloxy)phenyl]-2-methyl-3-oxo-7-(trifluoromethyl)-3,4-dihydro-2H-1,4-benzoxazine-6-carboxylate

[Chemical formula 649]

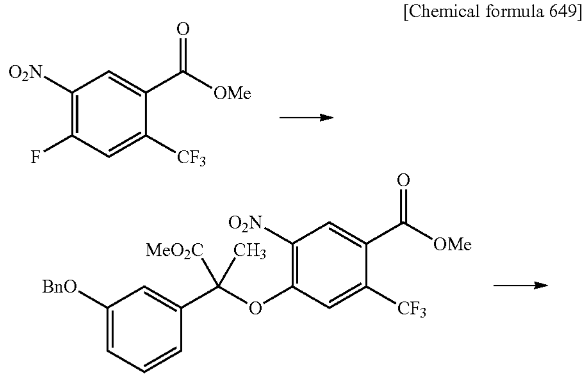

-continued

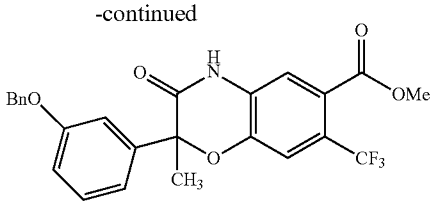

Using methyl 2-[3-(benzyloxy)phenyl]-2-hydroxypropanoate and methyl 4-fluoro-5-nitro-2-(trifluoromethyl)benzoate, the title compound was obtained in a similar manner to Reference Example 22 and Reference Example 2.

MS (ESI+) 472 ($M^{+}$+1, 100%).

Reference Example 504

Methyl 4-(2-{[(benzyloxy)carbonyl]amino}ethyl)-2-[3-(benzyloxy)phenyl]-2-methyl-3-oxo-7-(trifluoromethyl)-3,4-dihydro-2H-1,4-benzoxazine-6-carboxylate

[Chemical formula 650]

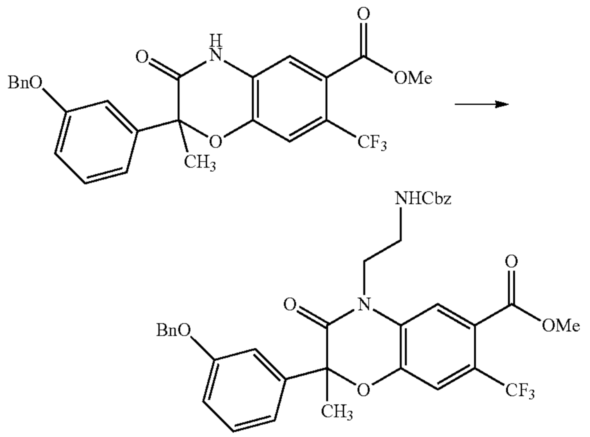

Using methyl 2-[3-(benzyloxy)phenyl]-2-methyl-3-oxo-7-(trifluoromethyl)-3,4-dihydro-2H-1,4-benzoxazine-6-carboxyalte, the title compound was obtained in a similar manner to Reference Example 164.

MS (ESI+) 635 ($M^{+}$+1, 18%).

Reference Example 505 tert-Butyl (3R)-3-[{[4-(2-{[(benzyloxy)carbonyl]amino}ethyl)-2-[3-(benzyloxy)phenyl]-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 651]

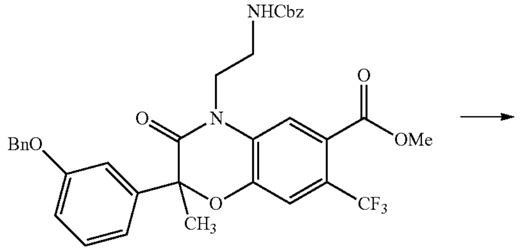

-continued

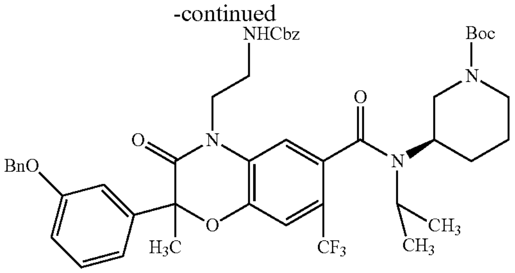

Using methyl 4-(2-{[(benzyloxy)carbonyl]amino}ethyl)-2-[3-(benzyloxy)phenyl]-2-methyl-3-oxo-7-(trifluoromethyl)-3,4-dihydro-2H-1,4-benzoxazine-6-carboxylate, the title compound was obtained in a similar manner to Reference Example 497.

MS (ESI+) 859 ($M^{+}$+1, 31%).

Reference Example 506 tert-Butyl (3R)-3-[{[2-(3-hydroxyphenyl)-2-methyl-3-oxo-4-[2-(propionylamino)ethyl]-7-(trifluoromethyl)-3,4-hydroxy-2H-1,4-benzoxazin-6-yl]carbonyl}(isopropyl)amino]piperidine-1-carboxylate

[Chemical formula 652]

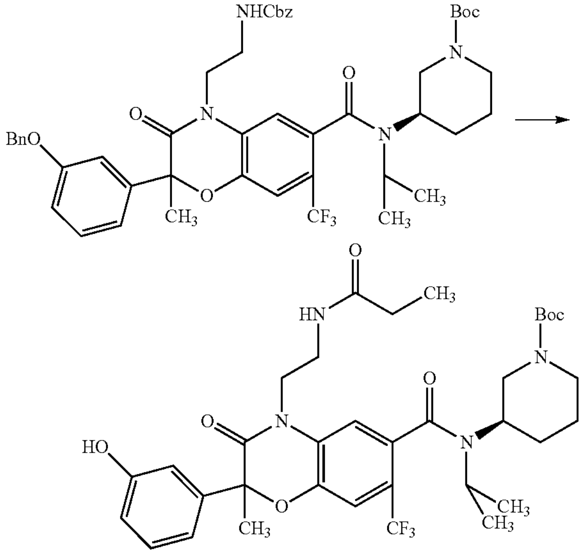

tert-Butyl (3R)-3-[{[4-(2-{[(benzyloxy)carbonyl]amino}ethyl)-2-[3-(benzyloxy)phenyl]-2-methyl-3-oxo-7-(trifluoromethyl)-3,4-dihydro-2H-1,4-benzoxazin-6-yl]carbonyl}(isopropyl)amino]-piperidine-1-carboxylate (279.7 mg) was dissolved in ethyl acetate (4 ml), and thereto were added triethylamine (0.10 ml), propionic anhydride (97.9 mg) and 10% palladium carbon (287.4 mg), and the mixture was stirred at room temperature for 6 hours under hydrogen atmosphere. The reaction solution was filtered on celite to remove palladium carbon, and the filtrate was concentrated under reduced pressure. The residue was dissolved in methanol (3 ml), and thereto was added potassium carbonate (142.6 mg), and the mixture was vigorously stirred at room temperature for 2 hours. To the reaction solution was added water, and the mixture was acidified with a saturated aqueous citric acid solution. The precipitated white solid was collected by filtration to give the title compound (196.8 mg).

MS (ESI+) 691 ($M^{+}$+1, 21%).

Reference Example 507 tert-Butyl (3R)-3-(isopropyl{[2-methyl-2-{3-[(methylsulfonyl)oxy]phenyl}-3-oxo-4-[2-(propionylamino)ethyl]-7-(trifluoromethyl)-3,4-dihydro-2H-1,4-benzoxazin-6-yl]carbonyl}amino)piperidine-1-carboxylate

[Chemical formula 653]

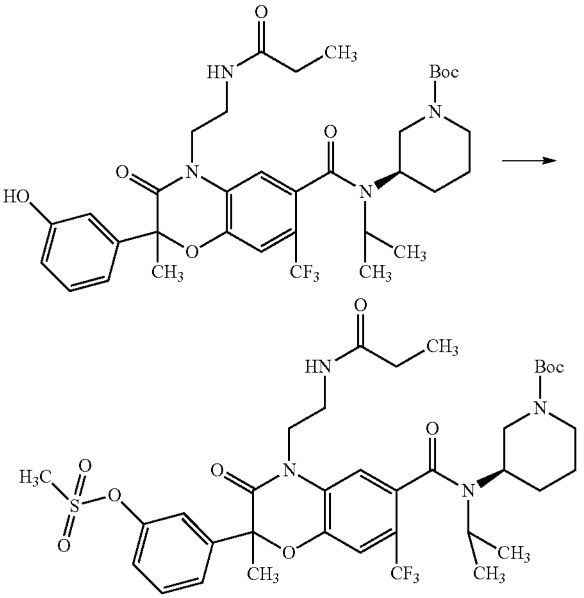

tert-Butyl (3R)-3-[{[2-(3-hydroxyphenyl)-2-methyl-3-oxo-4-[2-(propionylamino)ethyl]-7-(trifluoromethyl)-3,4-hydroxy-2H-1,4-benzoxazin-6-yl]carbonyl}(isopropyl)amino]piperidin-1-carboxylate (123.0 mg) was dissolved in chloroform (2 ml), and thereto was added triethylamine (0.05 ml), and thereto was further added dropwise a solution of methanesulfonyl chloride (34.2 mg) in chloroform (2 ml). The mixture was stirred at room temperature for 1.5 hours. The reaction solution was washed with water, dried over sodium sulfate, filtered, concentrated under reduced pressure to give a crude product, which was purified by silica gel chromatography to give the title compound (154.7 mg).

MS (ESI+) 769 ($M^{+}$+1, 63%).

Reference Example 508

Methyl 2,7-dimethyl-3-oxo-2-[3-(trifluoromethyl)phenyl]-3,4-dihydro-2H-1,4-benzoxazine-6-carboxylate

[Chemical formula 654]

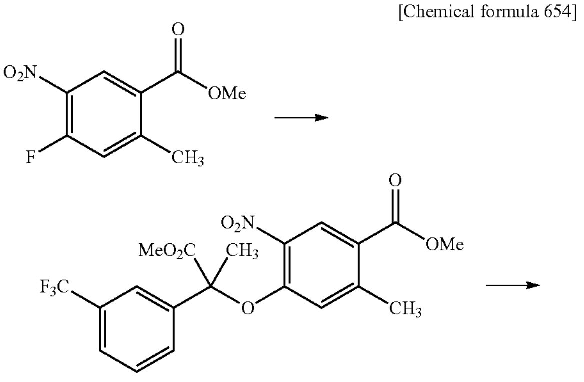

-continued

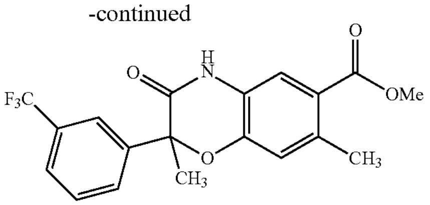

Using methyl 2-hydroxy-2-[3-(trifluoromethyl)phenyl] propanoate and methyl 4-fluoro-5-nitro-2-(trifluoromethyl) benzoate, the title compound was obtained in a similar manner to Reference Example 22 and Reference Example 2.

MS (ESI+) 380 ($M^+$+1, 100%).

Reference Example 509

Methyl 4-(2-{[(benzyloxy)carbonyl]amino}ethyl)-2,7-dimethyl-3-oxo-2-[3-(trifluoromethyl)phenyl]-3,4-dihydro-2H-1,4-benzoxazine-6-carboxylate

[Chemical formula 655]

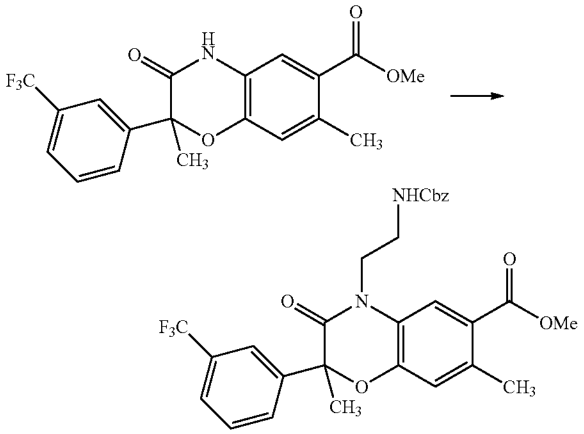

Using methyl 2,7-dimethyl-3-oxo-2-[3-(trifluoromethyl) phenyl]-3,4-dihydro-2H-1,4-benzoxazine-6-carboxylate, the title compound was obtained in a similar manner to Reference Example 164.

MS (ESI+) 557 ($M^+$+1, 61%).

Reference Example 510 tert-Butyl (3R)-3-[({2,7-dimethyl-3-oxo-4-[2-(propionylamino)ethyl]-2-[3-(trifluoromethyl)phenyl]-3,4-dihydro-2H-1,4-benzoxazin-6-yl}carbonyl)(isopropyl)amino]piperidine-1-carboxylate

[Chemical formula 656]

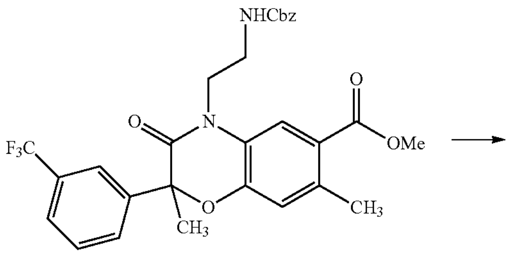

-continued

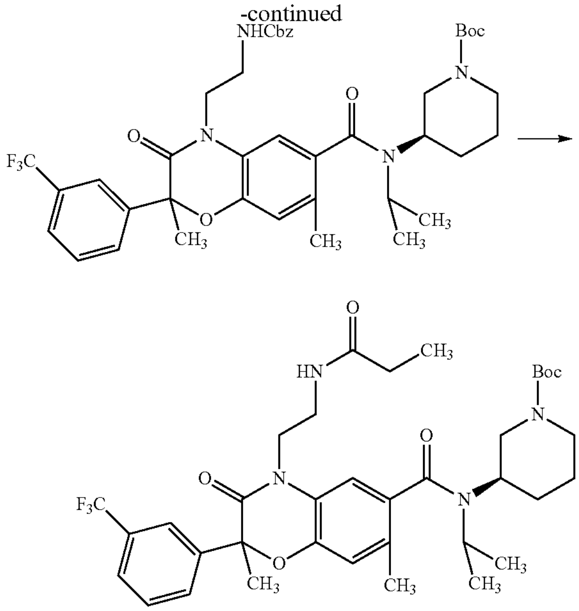

Methyl 4-(2-{[(benzyloxy)carbonyl]amino}ethyl)-2,7-dimethyl-3-oxo-2-[3-(trifluoromethyl)-phenyl]-3,4-dihydro-2H-1,4-benzoxazine-6-carboxylate (368.0 mg) was dissolved in 1,4-dioxane (5 ml), and thereto was added a 4N-aqueous sodium hydroxide solution (5 ml). The mixture was stirred at 60° C. for 2.5 hours, and cooled to room temperature. The mixture was concentrated under reduced pressure to remove 1,4-dioxane, and the residue was diluted with water, and the pH value thereof was adjusted to pH 1 with 3N-hydrochloric acid. The precipitated white solid was collected by filtration to give 4-(2-{[(benzyloxy)carbonyl] amino}ethyl)-2,7-dimethyl-3-oxo-2-[3-(trifluoromethyl) phenyl]-3,4-dihydro-2H-1,4-benzoxazine-6-carboxylic acid (340.0 mg). This carboxylic acid was dissolved in DMF (5 ml), and thereto were added triethylamine (0.35 ml), dimethylaminopyridine (45.2 mg), tert-butyl (3R)-3-(isopropylamino)piperidine-1-carboxylate (665.1 mg), CIP reagent (583.6 mg), and the mixture was stirred at 60° C. under nitrogen atmosphere for 4 hours. To the mixture were added again triethylamine (0.26 ml), CIP reagent (351.0 mg), and the mixture was further stirred at 60° C. for 5 hours. The reaction solution was cooled to room temperature, diluted with water, and the mixture was extracted with ethyl acetate. The organic layer was washed with water and a saturated aqueous sodium chloride solution, dried over sodium sulfate, filtered and concentrated under reduced pressure to give a crude product, which was purified by silica gel chromatography to give tert-butyl (3R)-3-[({4-(2-{[(benzyloxy)-carbonyl]amino}ethyl)-2,7-dimethyl-3-oxo-2-[3-(trifluoromethyl)phenyl]-3,4-dihydro-2H-1,4-benzoxazin-6-yl}carbonyl)(isopropyl)amino]piperidine-1-carboxylate (314.5 mg). Subsequently, this product was dissolved in ethyl acetate (10 ml), and thereto were added 10% palladium carbon (362.7 mg) and propionic anhydride (116.1 mg), and the mixture was vigorously stirred under hydrogen atmosphere for 4 hours. The mixture was filtered on celite to remove palladium carbon, and the filtrate was concentrated under reduced pressure. The residue was purified by silica gel chromatography to give the title compound (259.6 mg).

MS (ESI+) 689 (M+1, 6%).

Reference Example 511 tert-Butyl (3R)-3-(isopropyl{[(2S)-2-methyl-3-oxo-2-phenyl-3,4-dihydro-2H-1,4-benzoxazin-6-yl]-carbonyl}amino)piperidine-1-carboxylate

[Chemical formula 657]

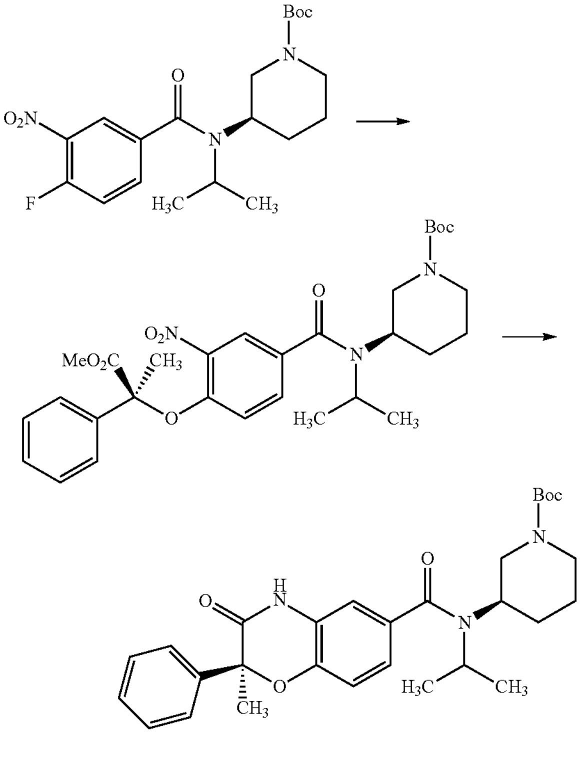

Using tert-butyl (3R)-3-[(4-fluoro-3-nitrobenzoyl)(isopropyl)amino]piperidine-1-carboxylate and (2S)-2-hydroxy-2-phenylpropanoic acid, the title compound was obtained in a similar manner to Reference Example 22 and Reference Example 2.

MS (ESI+) 508 ($M^{+}$+1, 38%).

Reference Example 512 tert-Butyl (3R)-3-[{[(2S)-4-(2-{[(benzyloxy)carbonyl]amino}ethyl)-2-methyl-3-oxo-2-phenyl-3,4-dihydro-2H-1,4-benzoxazin-6-yl]carbonyl}(isopropyl)amino]piperidine-1-carboxylate

[Chemical formula 658]

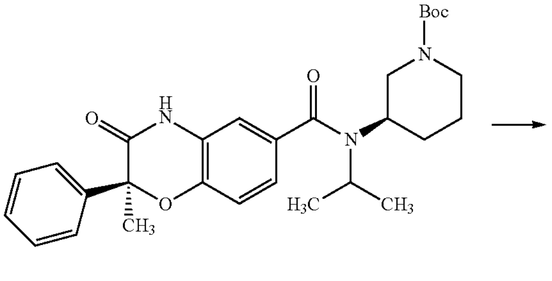

-continued

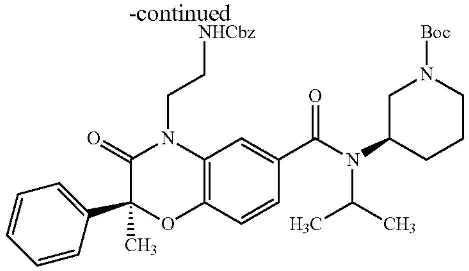

Using tert-butyl (3R)-3-(isopropyl{[(2S)-2-methyl-3-oxo-2-phenyl-3,4-dihydro-2H-1,4-benzoxazin-6-yl]carbonyl}amino)piperidine-1-carboxylate, the title compound was obtained in a similar manner to Reference Example 164.

MS (ESI+) 685 ($M^{+}$+1, 38%).

Reference Example 513 tert-Butyl (3R)-3-[({(2S)-7-chloro-2-methyl-3-oxo-2-phenyl-4-[2-(propionylamino)ethyl]-3,4-dihydro-2H-1,4-benzoxazin-6-yl}carbonyl)(isopropyl)amino]piperidine-1-carboxylate

[Chemical formula 659]

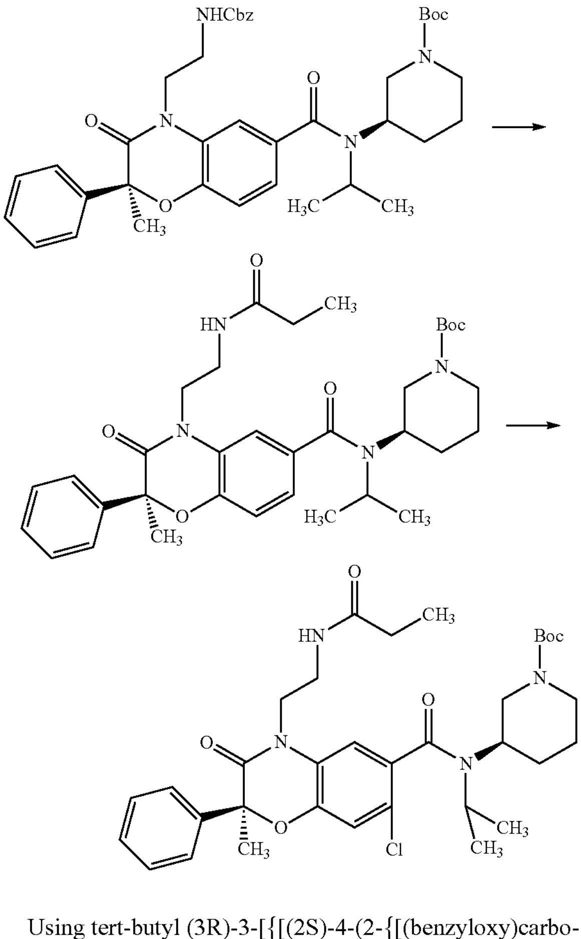

Using tert-butyl (3R)-3-[{[(2S)-4-(2-{[(benzyloxy)carbonyl]amino}ethyl)-2-methyl-3-oxo-2-phenyl-3,4-dihydro-2H-1,4-benzoxazin-6-yl]carbonyl}(isopropyl)amino]piperidine-1-carboxylate, the title compound was obtained in a similar manner to Reference Example 132 and Reference Example 12.

MS (ESI+) 641 (M+, 7%).

Reference Example 514 tert-Butyl (3R)-3-[{[(2S)-4-(2-{[(benzyloxy)carbonyl]amino}ethyl)-7-bromo-2-methyl-3-oxo-2-phenyl-3,4-dihydro-2H-1,4-benzoxazin-6-yl]carbonyl}(isopropyl)amino]piperidine-1-carboxylate

[Chemical formula 660]

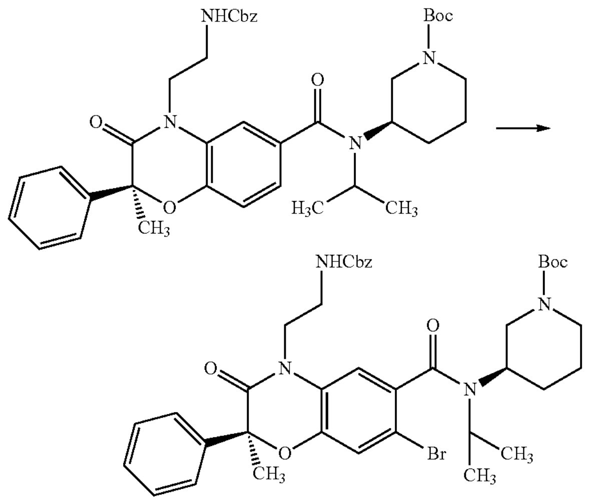

Using tert-butyl (3R)-3-[{[(2S)-4-(2-{[(benzyloxy)carbonyl]amino}ethyl)-2-methyl-3-oxo-2-phenyl-3,4-dihydro-2H-1,4-benzoxazin-6-yl]carbonyl}(isopropyl)amino]piperidine-1-carboxylate, the title compound was obtained in a similar manner to Reference Example 6.

MS (ESI+) 763 (M+, 15%).

Reference Example 515 tert-Butyl (3R)-3-[{[(2S)-4-(2-{[(benzyloxy)carbonyl]amino}ethyl)-2,7-dimethyl-3-oxo-2-phenyl-3,4-dihydro-2H-1,4-benzoxazin-6-yl]carbonyl}(isopropyl)amino]piperidine-1-carboxylate

[Chemical formula 661]

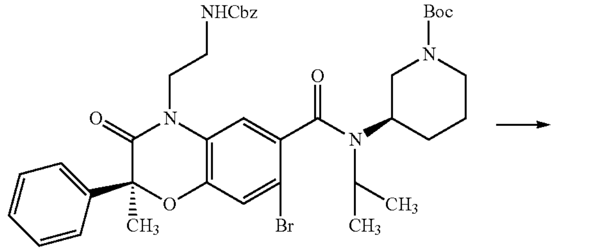

-continued

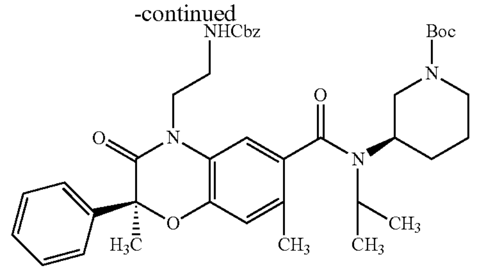

Using tert-butyl (3R)-3-[{[(2S)-4-(2-{[(benzyloxy)carbonyl]amino}ethyl)-7-bromo-2-methyl-3-oxo-2-phenyl-3,4-dihydro-2H-1,4-benzoxazin-6-yl]carbonyl}(isopropyl)amino]piperidine-1-carboxylate, the title compound was obtained in a similar manner to Reference Example 10.

MS (ESI+) 699 ($M^{+}$+1, 72%).

Reference Example 516 tert-Butyl (3R)-3-[({(2S)-2,7-dimethyl-3-oxo-2-phenyl-4-[2-(propionylamino)ethyl]-3,4-dihydro-2H-1,4-benzoxazin-6-yl}carbonyl)(isopropyl)amino]piperidine-1-carboxylate

[Chemical formula 662]

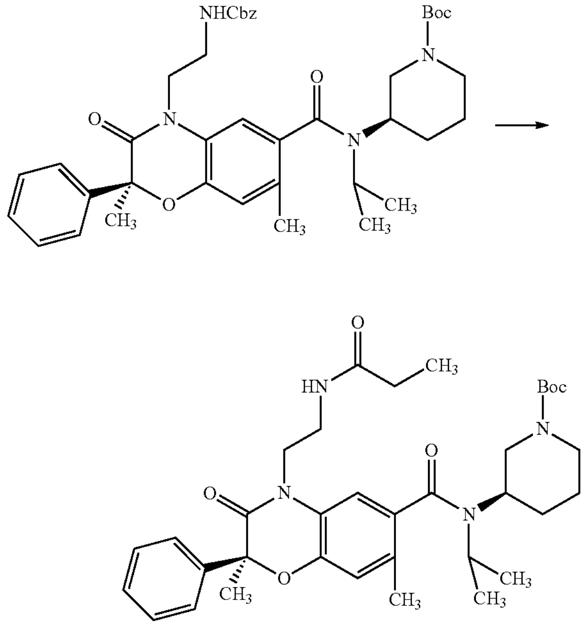

Using tert-butyl (3R)-3-[{[(2S)-4-(2-{[(benzyloxy)carbonyl]amino}ethyl)-2,7-dimethyl-3-oxo-2-phenyl-3,4-dihydro-2H-1,4-benzoxazin-6-yl]carbonyl}(isopropyl)amino]piperidine-1-carboxylate, the title compound was obtained in a similar manner to Reference Example 132.

MS (ESI+) 621 ($M^{+}$+1, 14%).

Reference Example 517

1-tert-Butyl 3-ethyl 4-oxopiperidine-1,3-dicarboxylate

[Chemical formula 663]

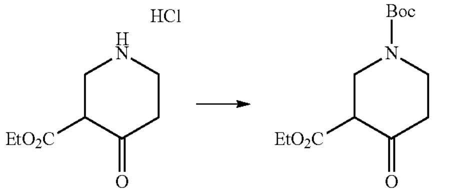

Ethyl 4-piperidone-3-carboxylate hydrochloride (5.0 g) was dissolved in tetrahydrofuran (30 ml), and thereto were added 10% aqueous potassium carbonate solution (30 ml) and di-tert-butyl dicarbonate (5.8 g) under ice-cooling. Then, the mixture was stirred at room temperature for 12 hours. The reaction mixture was concentrated under reduced pressure, and the residue was dissolved in ethyl acetate. The organic layer was washed with a 10% aqueous citric acid solution and an aqueous sodium hydrogen carbonate solution, dried over magnesium sulfate, filtered, and concentrated under reduced pressure to give the title compound (5.0 g) as a white solid.

$^1$H-NMR (300 MHz, $CDCl_3$) δ 12.03 (br, 1H), 4.25-4.18 (m, 2H), 4.04 (brs, 2H), 3.56-3.53 (m, 2H), 2.37-2.33 (m, 2H), 1.67 (brs, 2H), 1.46 (s, 9H), 1.31-1.26 (m, 3H).

Reference Example 518

1-tert-Butyl 3-ethyl 4-{[(trifluoromethyl)sulfonyl]oxy}-5,6-dihydropyridin-1,3(2H)-dicarboxylate

[Chemical formula 664]

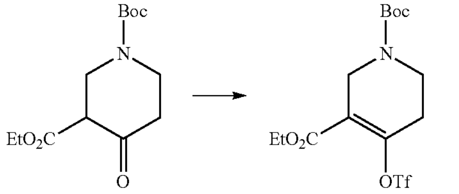

1-tert-Butyl 3-ethyl 4-oxopiperidine-1,3-dicarboxylate (7.0 g) was dissolved in methylene chloride (100 ml), and the mixture was cooled to −78° C. To the mixture were added diisopropylethylamine (6.7 ml) and trifluoromethanesulfonic anhydride (5.6 ml). Then, the mixture was stirred at room temperature for 3 days. To the reaction mixture was added an aqueous sodium hydrogen carbonate solution, and the mixture was extracted with chloroform. The organic layer was dried over magnesium sulfate, filtered, and concentrated under reduced pressure. The obtained residue was purified by silica gel column chromatography (hexane/ethyl acetate=15:1→10:1) to give the title compound (7.0 g) as a pale yellow oil.

MS (ESI+) 404 (M+1, 10%).

Reference Example 519

1-tert-Butyl 3-ethyl 4-biphenyl-3-yl-5,6-dihydropyridine-1,3(2H)-dicarboxylate

[Chemical formula 665]

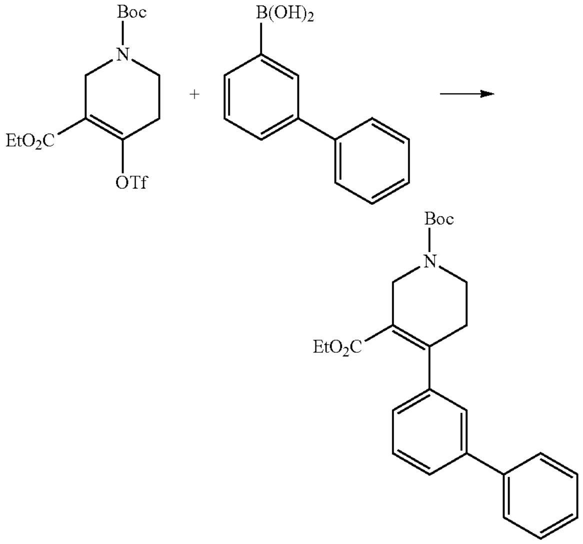

1-tert-Butyl-3-ethyl-4-{[(trifluoromethyl)sulfonyl]oxy}-5,6-dihydropyridin-1,3(2H)-dicarboxylate (500 mg) was dissolved in dimethoxyethane (10 ml), and thereto were added at room temperature 3-(N,N-dimethylaminocarbonyl)phenylboronic acid (262 mg), tetrakis(triphenylphosphine) palladium (72 mg), potassium carbonate (514 mg), and the mixture was stirred at 80° C. for 6 hours. The reaction mixture was cooled, and water was added thereto. The mixture was extracted with ethyl acetate, and the organic layer was washed with water, dried over magnesium sulfate, filtered, concentrated under reduced pressure. The obtained residue was purified by silica gel column chromatography (hexane/ethyl acetate=3:1→2:1) to give the title compound (370 mg) as a colorless clear oil.

MS (ESI+) 408 ($M^+$+1, 100%).

Reference Example 520

(3R,4S)-4-Biphenyl-3-yl-1-(tert-butoxycarbonyl)piperidine 3-carboxylic acid and (3S,4R)-4-biphenyl-3-yl-1-(tert-butoxycarbonyl)piperidine 3-carboxylic acid

[Chemical formula 666]

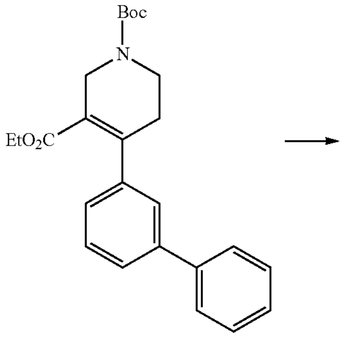

-continued

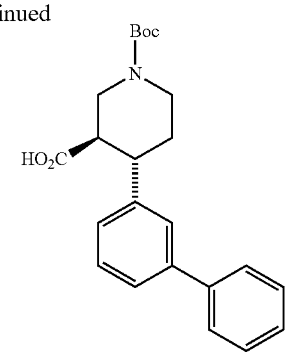

1-tert-Butyl 3-ethyl 4-biphenyl-3-yl-5,6-dihydropyridin-1,3(2H)-dicarboxylate (820 mg) was dissolved in methanol (10 ml), and thereto was added magnesium (490 mg) under ice-cooling, and the mixture was stirred at room temperature for 2 hours. The reaction mixture was filtered on celite, and concentrated under reduced pressure. The residue was diluted with ethyl acetate, and the organic layer was washed with an aqueous ammonium chloride solution and a saturated aqueous sodium chloride solution, dried over magnesium sulfate, filtered, and concentrated under reduced pressure. The obtained residue was dissolved in ethanol (10 ml), and thereto was added sodium ethoxide (20% ethanol solution, 1.2 ml) at room temperature, and the mixture was stirred at 60° C. for 4 hours. The reaction mixture was cooled, and concentrated under reduced pressure. To the residue was added a 5% aqueous sodium hydrogen sulfate solution, and the mixture was extracted with chloroform. The organic layer was dried over magnesium sulfate, filtered, and concentrated under reduced pressure. The residue was dissolved in tetrahydrofuran-ethanol-water (5 ml-3 ml-1.5 ml), and thereto was added sodium hydroxide (276 mg) at room temperature. The mixture was stirred at room temperature for 16 hours. To the reaction mixture was added a 5% aqueous sodium hydrogen sulfate solution, and extracted with chloroform. The organic layer was dried over magnesium sulfate, filtered, and concentrated under reduced pressure to give the title compound (344 mg) as amorphous.

MS (ESI+) 410 ($M^+$+1, 100%).

Reference Example 521 tert-Butyl (3R,4R)-3-{[(benzyloxy)carbonyl]amino}-4-biphenyl-3-ylpiperidine-1-carboxylate and tert-butyl (3S,4S)-3-{[(benzyloxy)carbonyl]amino}-4-biphenyl-3-ylpiperidine-1-carboxylate

[Chemical formula 667]

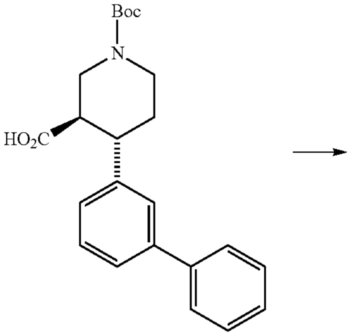

-continued

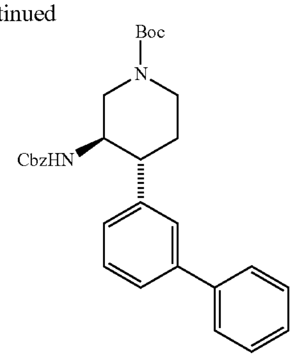

(3R,4S)-4-Biphenyl-3-yl-1-(tert-butoxycarbonyl)piperidine 3-carboxylic acid and (3S,4R)-4-biphenyl-3-yl-1-(tert-butoxycarbonyl)piperidine-3-carboxylic acid (320 mg) was dissolved in toluene (9 ml), and thereto were added triethylamine (102 mg) and diphenylphosphoryl azide (254 mg) at room temperature, and the mixture was stirred at 80° C. for one hour. The reaction mixture was cooled to 50° C., and thereto was added benzyl alcohol (273 mg), and the mixture was stirred at 80° C. for 10 hours. The reaction mixture was cooled, and water was added thereto, and the mixture was extracted with ethyl acetate. The organic layer was dried over magnesium sulfate, filtered, and concentrated under reduced pressure. The obtained residue was purified by silica gel column chromatography (hexane/ethyl acetate=1:1→1:2) to give the title compound (400 mg) as amorphous.

MS (ESI+) 487 ($M^+$+1, 100%).

Reference Example 522 tert-Butyl (3R,4R)-3-amino-4-biphenyl-3-ylpiperidine-1-carboxylate and tert-butyl (3S,4S)-3-amino-4-biphenyl-3-ylpiperidine-1-carboxylate

[Chemical formula 668]

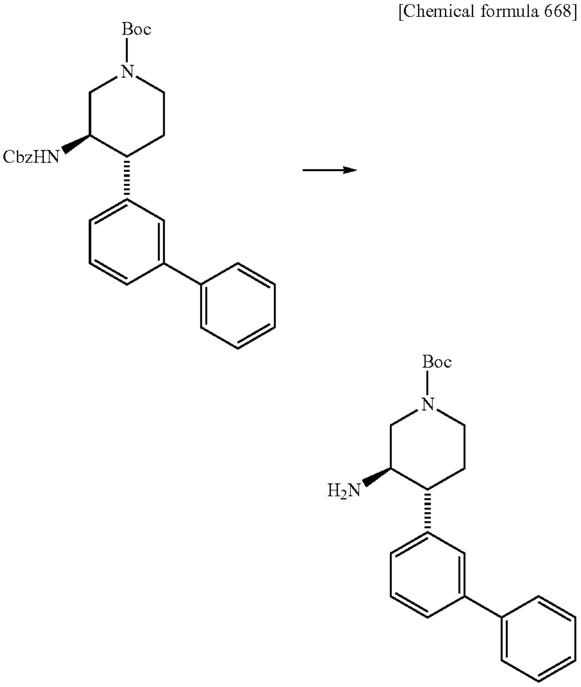

To a solution of tert-butyl (3R,4R)-3-{[(benzyloxy)carbonyl]amino}-4-biphenyl-3-ylpiperidine-1-carboxylate and tert-butyl (3S,4S)-3-{[(benzyloxy)carbonyl]amino}-4-biphenyl-3-ylpiperidine-1-carboxylate (400 mg) in methanol (10 ml) was added 10% palladium carbon (180 mg), and the mixture was stirred at room temperature under hydrogen atmosphere for 3 hours. The insoluble materials were removed by filtration, and the filtrate was concentrated under reduced pressure to give the title compound (296 mg) as pale yellow oil.

MS (ESI+) 353 ($M^+$+1, 100%).

Reference Example 523 tert-Butyl (3R,4R)-4-biphenyl-3-yl-3-(isopropylamino)piperidine-1-carboxylate and tert-butyl (3S,4S)-4-biphenyl-3-yl-3-(isopropylamino)piperidine-1-carboxylate

[Chemical formula 669]

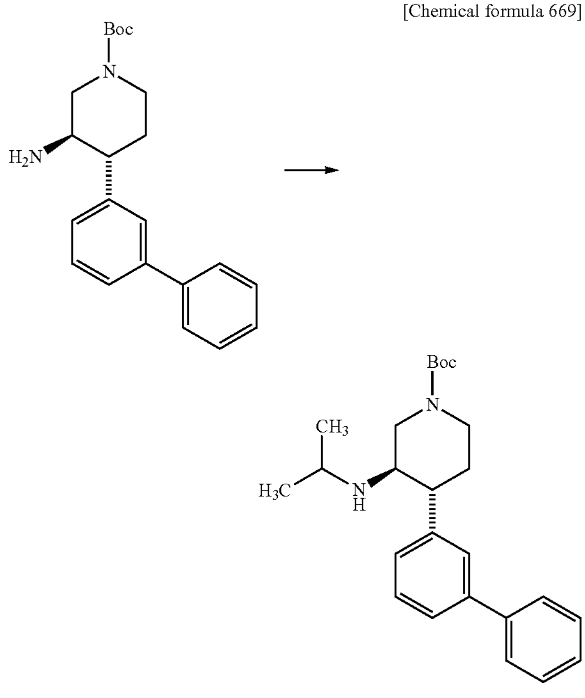

tert-Butyl (3R,4R)-3-amino-4-biphenyl-3-ylpiperidine-1-carboxylate and tert-butyl (3S,4S)-3-amino-4-biphenyl-3-ylpiperidine-1-carboxylate (296 mg) were dissolved in methanol (5 ml), and thereto were added acetone (244 mg) and acetic acid (0.048 mL), and the mixture was stirred at room temperature for one hour. To this reaction mixture was added sodium triacetoxyborohydride (534 mg), and the mixture was stirred at room temperature for 14 hours. To this reaction mixture was added ice-cooled diluted aqueous sodium hydroxide solution, and the insoluble materials were moved by filtration, and the filtrate was extracted with chloroform. The organic layer was dried over anhydrous magnesium sulfate, and the solvent was evaporated under reduced pressure to give the title compound (194 mg) as pale brown oil.

MS (ESI+) 396 ($M^+$+1, 100%).

Reference Example 524 tert-Butyl (3R,4R)-3-[{[4-(2-{[(benzyloxy)carbonyl]amino}ethyl)-2,2-dimethyl-3-oxo-7-(trifluoromethyl)-3,4-dihydro-2H-1,4-benzoxazin-6-yl]carbonyl}(isopropyl)amino]-4-biphenyl-3-ylpiperidine-1-carboxylate and tert-butyl (3S,4S)-3-[{[4-(2-{[(benzyloxy)carbonyl]amino}ethyl)-2,2-dimethyl-3-oxo-7-(trifluoromethyl)-3,4-dihydro-2H-1,4-benzoxazin-6-yl]carbonyl}(isopropyl)amino]-4-biphenyl-3-ylpiperidine-1-carboxylate

[Chemical formula 670]

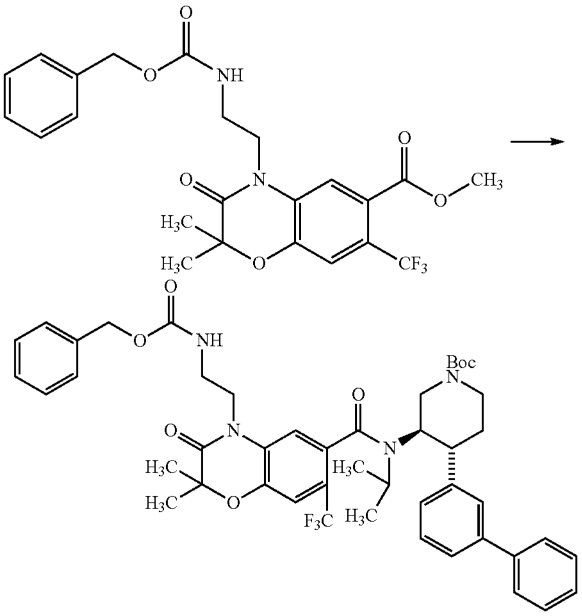

Using methyl 4-(2-{[(benzyloxy)carbonyl]amino}ethyl)-2,2-dimethyl-3-oxo-7-(trifluoro-methyl)-3,4-dihydro-2H-1,4-benzoxazine-6-carboxylate and tert-butyl (3R,4R)-4-biphenyl-3-yl-3-(isopropylamino)piperidine-1-carboxylate, and tert-butyl (3S,4S)-4-biphenyl-3-yl-3-(isopropylamino)piperidine-1-carboxylate, the title compound (98 mg) was obtained in a similar manner to Reference Example 5.

MS (ESI+) 844 ($M^+$+1, 21%).

Reference Example 525 tert-Butyl (3R,4R)-3-[{[4-(2-aminoethyl)-2,2-dimethyl-3-oxo-7-(trifluoromethyl)-3,4-dihydro-2H-1,4-benzoxazin-6-yl]carbonyl}(isopropyl)amino]-4-biphenyl-3-ylpiperidine-1-carboxylate and tert-butyl (3S,4S)-3-[{[4-(2-aminoethyl)-2,2-dimethyl-3-oxo-7-(trifluoromethyl)-3,4-dihydro-2H-1,4-benzoxazin-6-yl]carbonyl}(isopropyl)amino]-4-biphenyl-3-ylpiperidine-1-carboxylate

[Chemical formula 671]

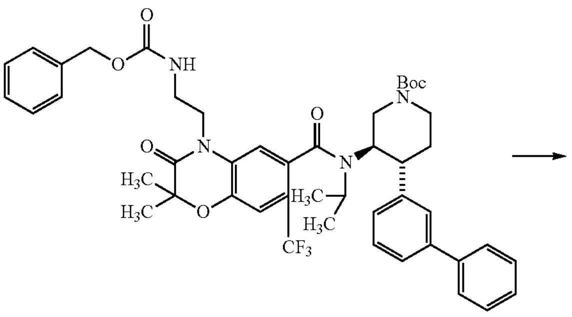

-continued

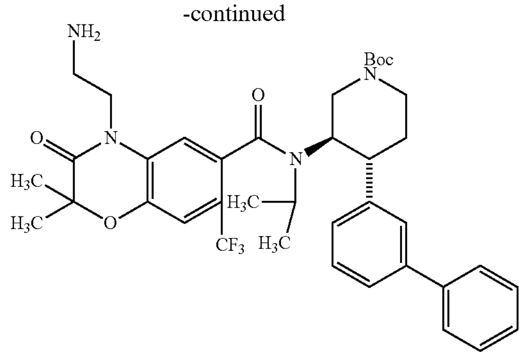

Using tert-butyl (3R,4R)-3-[{[4-(2-{[(benzyloxy)carbonyl]amino}ethyl)-2,2-dimethyl-3-oxo-7-(trifluoromethyl)-3,4-dihydro-2H-1,4-benzoxazin-6-yl]carbonyl}(isopropyl)amino]-4-biphenyl-3-ylpiperidine-1-carboxylate and tert-butyl (3S,4S)-3-[{[4-(2-{[(benzyloxy)carbonyl]amino}ethyl)-2,2-dimethyl-3-oxo-7-(trifluoromethyl)-3,4-dihydro-2H-1,4-benzoxazin-6-yl]carbonyl}(isopropyl)amino]-4-biphenyl-3-ylpiperidine-1-carboxylate, the title compound (74 mg) was obtained in a similar manner to Reference Example 139.

MS (ESI+) 710 ($M^+$+1, 46%).

Reference Example 526 tert-Butyl (3R,4R)-4-biphenyl-3-yl-3-[{[2,2-dimethyl-3-oxo-4-[2-(propionylamino)ethyl]-7-(trifluoro-methyl)-3,4-dihydro-2H-1,4-benzoxazin-6-yl]carbonyl}(isopropyl)amino]piperidine-1-carboxylate and tert-butyl (3S,4S)-4-biphenyl-3-yl-3-[{[2,2-dimethyl-3-oxo-4-[2-(propionylamino)ethyl]-7-(trifluoromethyl)-3,4-dihydro-2H-1,4-benzoxazin-6-yl]carbonyl}(isopropyl)amino]piperidine-1-carboxylate

[Chemical formula 672]

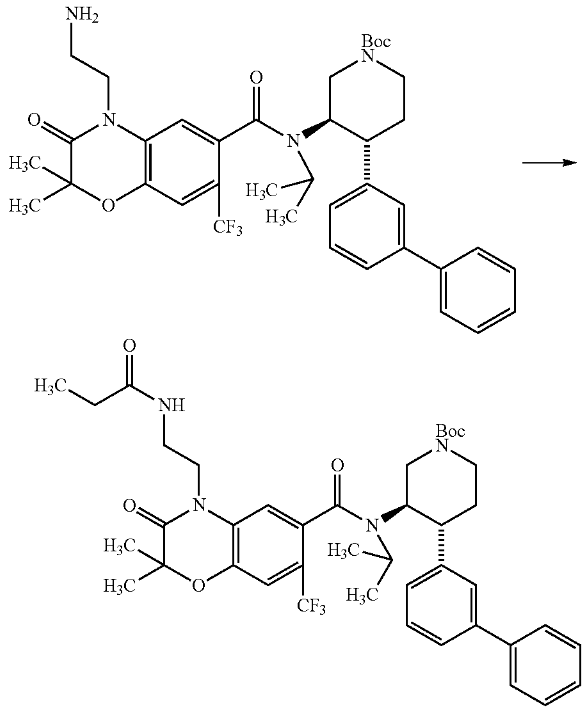

Using tert-butyl (3R,4R)-3-[{[4-(2-aminoethyl)-2,2-dimethyl-3-oxo-7-(trifluoromethyl)-3,4-dihydro-2H-1,4-benzoxazin-6-yl]carbonyl}(isopropyl)amino]-4-biphenyl-3-ylpiperidine-1-carboxylate and tert-butyl (3S,4S)-3-[{[4-(2-aminoethyl)-2,2-dimethyl-3-oxo-7-(trifluoromethyl)-3,4-dihydro-2H-1,4-benzoxazin-6-yl]carbonyl}(isopropyl)amino]-4-biphenyl-3-ylpiperidine-1-carboxylate, the title compound (50 mg) was obtained in a similar manner to Reference Example 132.

MS (ESI+) 766 ($M^+$+1, 16%).

Reference Example 527 tert-Butyl (3R)-3-[{[2,2-dimethyl-3-oxo-7-(trifluoromethyl)-4-(2-{[1-(trifluoromethyl)propyl]amino}-ethyl)-3,4-dihydro-2H-1,4-benzoxazin-6-yl]carbonyl}(isopropyl)amino]piperidine-1-carboxylate

[Chemical formula 673]

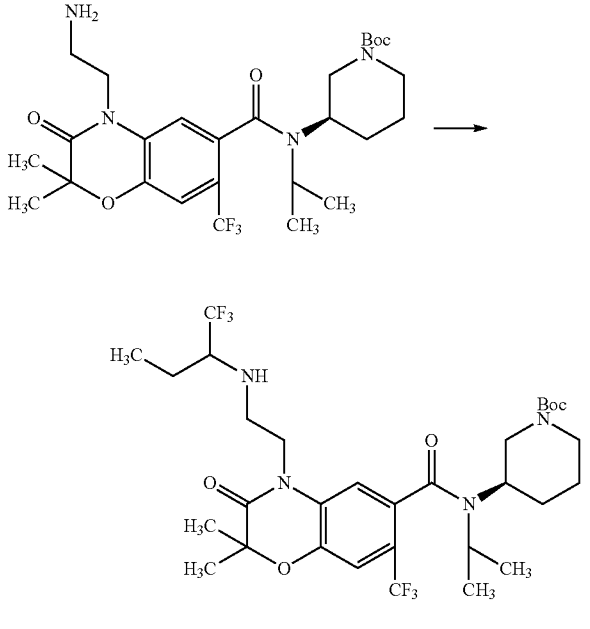

To a solution of tert-butyl (3R)-3-[{[4-(2-aminoethyl)-2,2-dimethyl-3-oxo-7-(trifluoromethyl)-3,4-dihydro-2H-1,4-benzoxazin-6-yl]carbonyl}(isopropyl)amino]piperidine-1-carboxylate (278 mg) in methylene chloride (2 ml) were added 1,1,1-trifluoro-2-butanone (0.1 ml), diisopropylethylamine (0.34 ml), and titanium tetrachloride (0.05 ml), and the mixture was stirred at room temperature for 3 hours. Then, to the reaction solution were added sodium cyanoborohydride (110 mg) and methanol (10 ml), and the mixture was stirred at room temperature for one hour. To the reaction solution was added a saturated aqueous sodium hydrogen carbonate solution (10 ml), and the mixture was extracted with ethyl acetate. The organic layer was dried over magnesium sulfate, filtered, and concentrated under reduced pressure. The obtained residue was purified by silica gel column chromatography (hexane/ethyl acetate=3:1) to give the title compound (100 mg) as amorphous.

MS (ESI+) 667 ($M^+$+1, 100%).

Reference Example 528

Ethyl 4-(2-{[(benzyloxy)carbonyl]amino}ethyl)-6-{[[(3R)-1-(tert-butoxycarbonyl)piperidin-3-yl](isopropyl)amino]carbonyl}-2-methyl-3-oxo-7-(trifluoromethyl)-3,4-dihydro-2H-1,4-benzoxazine-2-carboxylate

[Chemical formula 674]

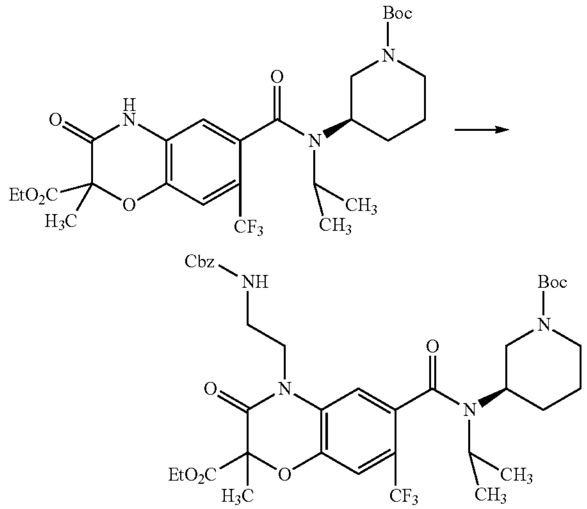

Using ethyl 6-{[[(3R)-1-(tert-butoxycarbonyl)piperidin-3-yl](isopropyl)amino]carbonyl}-2-methyl-3-oxo-7-(trifluoromethyl)-3,4-dihydro-2H-1,4-benzoxazine-2-carboxylate, the title compound was obtained in a similar manner to Reference Example 164.

MS (ESI+) 749 ($M^{+}$+1, 30%).

Reference Example 529

4-(2-{Benzyl[(benzyloxy)carbonyl]amino}ethyl)-6-{[[(3R)-1-(tert-butoxycarbonyl)piperidin-3-yl](isopropyl)amino]carbonyl}-2-methyl-3-oxo-7-(trifluoromethyl)-3,4-dihydro-2H-1,4-benzoxazine-2-carboxylic acid

[Chemical formula 675]

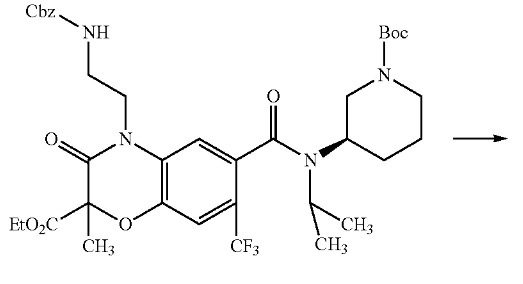

-continued

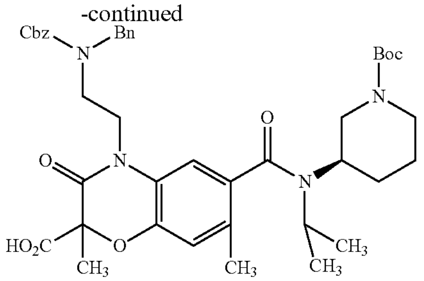

To a solution of ethyl 4-(2-{[(benzyloxy)carbonyl]amino}ethyl)-6-{[[(3R)-1-(tert-butoxycarbonyl)piperidin-3-yl](isopropyl)amino]carbonyl}-2-methyl-3-oxo-7-(trifluoromethyl)-3,4-dihydro-2H-1,4-benzoxazine-2-carboxylate (1.00 g) in N,N-dimethylacetamide (2.7 ml) was added at 0° C. benzyl bromide (0.794 ml), and sodium hydride (193 mg), and the mixture was stirred for one hour. To the reaction solution were added 2N-aqueous sodium hydroxide solution (5.36 ml) and tetrahydrofuran (5.0 ml), and the mixture was stirred at room temperature for one hour. To the reaction solution was added a 5% aqueous potassium hydrogen sulfate solution, and the mixture was extracted with ethyl acetate. The organic layer was washed with a saturated aqueous sodium chloride solution, dried over sodium sulfate, filtered and concentrated under reduced pressure. The obtained residue was purified by silica gel column chromatography (chloroform /methanol=100/3, containing 5% acetic acid) to give the title compound (0.800 g).

MS (ESI+) 811 ($M^{+}$+1, 44%).

Reference Example 530 tert-Butyl (3R)-3-[{[4-(2-{benzyl[(benzyloxy)carbonyl]amino}ethyl)-2-(hydroxymethyl)-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 676]

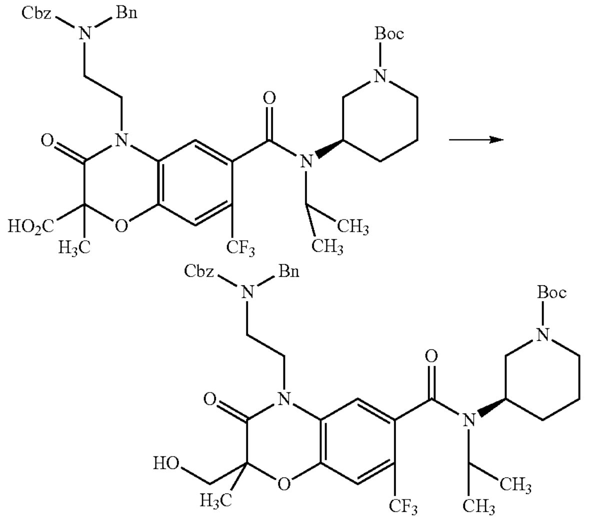

Using 4-(2-{benzyl[(benzyloxy)carbonyl]amino}ethyl)-6-{[[(3R)-1-(tert-butoxycarbonyl)-piperidin-3-yl](isopropyl)amino]carbonyl}-2-methyl-3-oxo-7-(trifluoromethyl)-3,4-dihydro-2H-1,4-benzoxazine-2-carboxylic acid, the title compound was synthesized in a similar manner to Reference Example 35.

MS (ESI+) 797 ($M^+$+1, 32%).

Reference Example 531 tert-Butyl (3R)-3-[{[4-(2-{benzyl[(benzyloxy)carbonyl]amino}ethyl)-2-(methoxymethyl)-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 677]

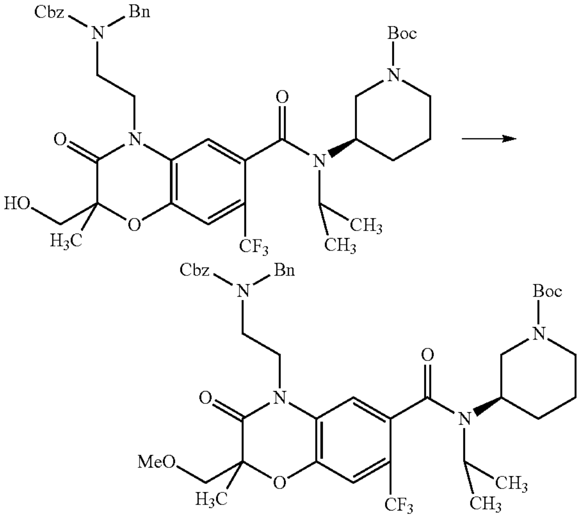

Using tert-butyl (3R)-3-[{[4-(2-{benzyl[(benzyloxy)carbonyl]amino}ethyl)-2-(hydroxy-methyl)-2-methyl-3-oxo-7-(trifluoromethyl)-3,4-dihydro-2H-1,4-benzoxazin-6-yl]carbonyl}(isopropyl)-amino]piperidine-1-carboxylate, the title compound was synthesized in a similar manner to Reference Example 36.

MS (ESI+) 811 ($M^+$+1, 44%).

Reference Example 532 tert-Butyl (3R)-3-(isopropyl{[4-{2-[(methoxycarbonyl)amino]ethyl}-2-(methoxymethyl)-2-methyl-3-oxo-7-(trifluoromethyl)-3,4-dihydro-2H-1,4-benzoxazin-6-yl]carbonyl}amino)piperidine-1-carboxylate

[Chemical formula 678]

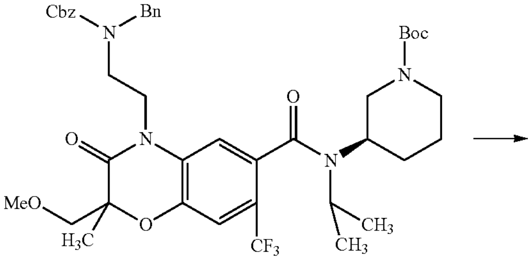

-continued

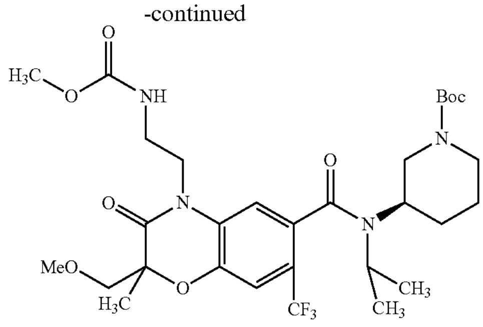

Using tert-butyl (3R)-3-[{[4-(2-{benzyl[(benzyloxy)carbonyl]amino}ethyl)-2-(methoxy-methyl)-2-methyl-3-oxo-7-(trifluoromethyl)-3,4-dihydro-2H-1,4-benzoxazin-6-yl]carbonyl}-(isopropyl)amino]piperidine-1-carboxylate, the title compound was synthesized in a similar manner to Reference Example 139, Reference Example 162.

MS (ESI+) 645 ($M^+$+1, 69%).

Reference Example 533 tert-Butyl (3R)-3-(isopropyl{[2-(methoxymethyl)-2-methyl-3-oxo-4-[2-(propionylamino)ethyl]-7-(trifluoromethyl)-3,4-dihydro-2H-1,4-benzoxazin-6-yl]carbonyl}amino)piperidine-1-carboxylate

[Chemical formula 679]

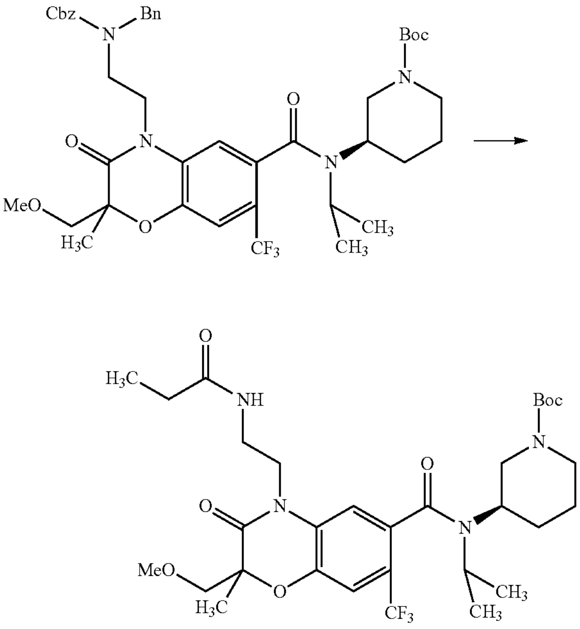

Using tert-butyl (3R)-3-[{[4-(2-{benzyl[(benzyloxy)carbonyl]amino}ethyl)-2-(methoxy-methyl)-2-methyl-3-oxo-7-(trifluoromethyl)-3,4-dihydro-2H-1,4-benzoxazin-6-yl]carbonyl}-(isopropyl)amino]piperidine-1-carboxylate, the title compound was synthesized in a similar manner to Reference Example 132.

MS (ESI+) 643 ($M^+$+1, 74%).

Reference Example 534

Methyl {2-[(2S)-6-({isopropyl[(3R)-piperidin-3-yl]amino}carbonyl)-2-(methoxymethyl)-2-methyl-3-oxo-7-(trifluoromethyl)-2,3-dihydro-4H-1,4-benzoxazin-4-yl]ethyl}carbamate hydrochloride Methyl {2-[(2R)-6-({isopropyl[(3R)-piperidin-3-yl]amino}carbonyl)-2-(methoxymethyl)-2-methyl-3-oxo-7-(trifluoromethyl)-2,3-dihydro-4H-1,4-benzoxazin-4-yl]ethyl}carbamate hydrochloride

[Chemical formula 680]

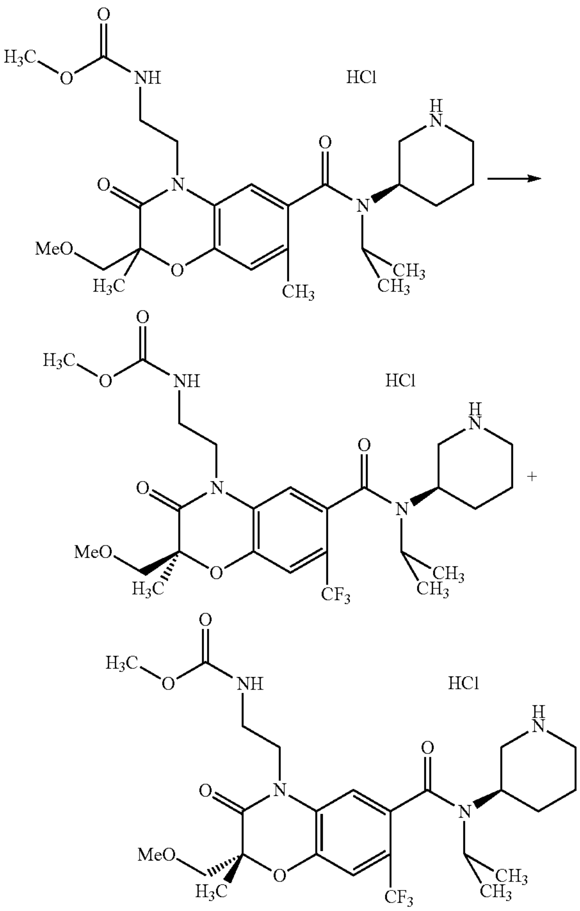

Methyl {2-[6-({isopropyl[(3R)-piperidin-3-yl]amino}carbonyl)-2-(methoxymethyl)-2-methyl-3-oxo-7-(trifluoromethyl)-2,3-dihydro-4H-1,4-benzoxazin-4-yl]ethyl}carbamate hydrochloride (10 mg) was separated by optically active column chromatography (CHIRALCEL OD-H, 2 cmϕ×25 cm, hexane:ethanol:diethylamine=80:20:0.3~50:50:0.3) to give the title compounds.

Methyl {2-[(2S)-6-({isopropyl[(3R)-piperidin-3-yl]amino}carbonyl)-2-(methoxymethyl)-2-methyl-3-oxo-7-(trifluoromethyl)-2,3-dihydro-4H-1,4-benzoxazin-4-yl]ethyl}carbamate hydrochloride Chiral column retention time: 7.26 minutes (CHIRALCEL OD-H, 0.46 cmϕ×25 cm, hexane:ethanol:diethylamine=80:20:0.3, flow rate: 1.00 ml/minute)

Methyl {2-[(2R)-6-({isopropyl[(3R)-piperidin-3-yl]amino}carbonyl)-2-(methoxymethyl)-2-methyl-3-oxo-7-(trifluoromethyl)-2,3-dihydro-4H-1,4-benzoxazin-4-yl]ethyl}carbamate hydrochloride Chiral column retention time: 27.78 minutes (CHIRALCEL OD-H, 0.46 cmϕ×25 cm, hexane:ethanol:diethylamine=80:20:0.3, flow rate: 1.00 ml/minute).

Reference Example 535 tert-Butyl 4-phenyl-3,6-dihydropyridin-1(2H)-carboxylate

[Chemical formula 681]

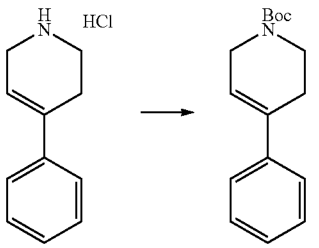

To a solution of 4-phenyl-1,2,3,6-tetrahydropyridine hydrochloride (354.6 g) in acetonitrile (12 L) was added triethylamine (366.9 g) at 20° C. in a water-bath, and the mixture was stirred for 15 minutes. To the reaction solution was added dropwise a solution of di-t-butyl carbonate (474.5 g) in acetonitrile (700 ml) at 15~19° C. in a water-bath, and further thereto was added N,N-dimethylamino-pyridine (11.06 g). The mixture was stirred at room temperature for 12 hours, and the solvent was removed by evaporation under reduced pressure. The obtained residue was diluted with methylene chloride (10 L), and washed with 1M hydrochloric acid (×3) and 5% saturated aqueous sodium hydrogen carbonate solution, dried over anhydrous sodium hydrogen sulfate, and the solvent was evaporated under reduced pressure to give a crude product (470.6 g). The obtained crude product was purified by silica gel column chromatography (methylene chloride/methanol=1/0→50/1) to give the title compound (456.8 g).

$^{1}$H NMR (400 MHz, $CDCl_3$) δ 9.77 (s, 1H), 7.79-7.76 (m, 1H), 7.28-7.22 (m, 1H), 7.03-6.99 (m, 1H), 3.88 (s, 3H).

Reference Example 536 tert-Butyl (3R,4R)-3,4-dihydroxy-4-phenylpiperidine-1-carboxylate

[Chemical formula 682]

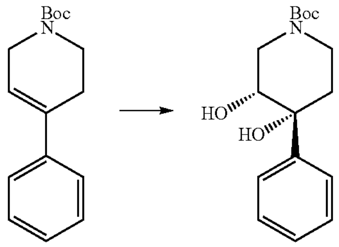

To a solution of potassium osmate (VI) 2 hydrate (8.0 g), $(DHQD)_2PHAL$ (14.2 g), potassium carbonate (379 g), potassium hexacyanoferrate (III) (903 g) in t-butanol (4.8 L) and water (4.8 L) was added methenesulfonamide (73.4 g) at room temperature. Then, tert-butyl 4-phenyl-3,6-dihydropyridine-1(2H)-carboxylate (200 g) was added thereto in an ice-bath, and the mixture was stirred for 2 hours. The mixture was further stirred at room temperature for 12 hours, and thereto was added methylene chloride (7.0 L) for separation to give the organic layer. The aqueous layer was washed twice with methylene chloride, and the obtained organic layers were combined, washed with 2M aqueous potassium hydroxide solution, dried over anhydrous sodium sulfate, and the solvent was removed by evaporation under reduced pressure. The obtained residue was purified by silica gel column chromatography (hexane/ethyl acetate=2/1) to give the title compound (215.5 g).

$^1H$ NMR (300 MHz, $CD_3OD$) δ 7.42-7.39 (m, 2H), 7.26-7.21 (m, 2H), 7.15-7.09 (m, 1H), 4.01-3.92 (m, 3H), 3.81-3.76 (m, 2H), 1.85-1.76 (m, 1H), 1.63-1.58 (m, 1H), 1.39 (s, 9H).

Reference Example 537 tert-Butyl (3S,4S)-3-hydroxy-4-phenylpiperidine-1-carboxylate

[Chemical formula 683]

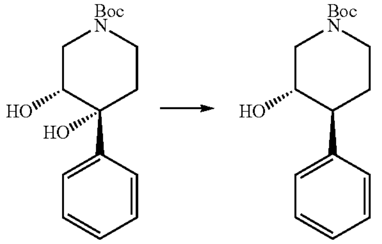

To a solution of tert-butyl (3R,4R)-3,4-dihydroxy-4-phenylpiperidine-1-carboxylate (120 g) in ethanol (4.3 L) was added Raney nickel (240 g), and the mixture was refluxed for 48 hours with bubbling of hydrogen gas. The reaction solution was cooled, and filtered on celite, and the filtrate was concentrated under reduced pressure. The obtained residue was purified by silica gel column chromatography (hexane/ethyl acetate=2/1) to give the title compound (105.1 g, 99.4% ee).

$^1H$ NMR (300 MHz, $CDCl_3$) δ 7.39-7.24 (m, 5H), 4.40 (m, 1H), 4.15-4.08 (m, 1H), 3.69 (m, 1H), 2.76-2.48 (m, 3H), 1.84-1.53 (m, 2H), 1.49 (s, 9H).

Reference Example 538 tert-Butyl (3R,4S)-3-amino-4-phenylpiperidine-1-carboxylate

[Chemical formula 684]

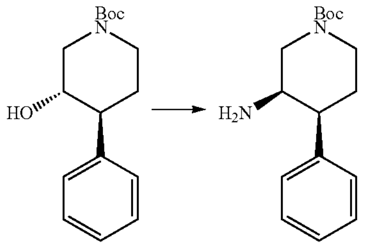

To a solution of tert-butyl (3S,4S)-3-hydroxy-4-phenylpiperidine-1-carboxylate (105.1 g), triphenylphosphine (198.8 g) and phthalimide (111.5 g) in tetrahydrofuran (2.6 L) was added dropwise a solution of diethyl azodicarboxylate (2.2M toluene solution, 345 ml) at 0° C. The reaction solution was stirred at 0° C. for 2 hours, and the temperature thereof was raised slowly, and the mixture was stirred at room temperature for 12 hours. The reaction solution was evaporated under reduced pressure to remove the solvent, and the obtained residue was separated with methylene chloride and water to give the organic layer. The aqueous layer was extracted twice with methylene chloride. The obtained organic layers were combined, and washed twice with water (×2) and a saturated aqueous sodium chloride solution, dried over sodium sulfate, filtered and concentrated under reduced pressure. The obtained residue was purified by silica gel column chromatography (hexane/ethyl acetate=6/1→4/1) to give a crude product (549.5 g).

The obtained crude product was suspended in toluene (1.4 L), and thereto were added hydrazine monohydrate (83.6 ml), and the mixture was refluxed for 12 hours. The reaction solution was cooled, filtered, and the filtrate was washed with water (×2) and a saturated aqueous sodium chloride solution, dried over anhydrous sodium sulfate, and the solvent was removed by evaporation under reduced pressure. The obtained residue was purified by silica gel column chromatography (chloroform/ethyl acetate=6/1→2/1) to give the title compound (32.4 g).

$^1H$ NMR (300 MHz, $CDCl_3$) δ 7.37-7.20 (m, 5H), 4.32-4.19 (m, 2H), 3.18-3.05 (m, 2H), 2.92-2.80 (m, 2H), 2.23-2.18 (m, 1H), 1.64-1.61 (m, 1H), 1.48 (s, 9H).

Reference Example 539 tert-Butyl (3R,4S)-3-({[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate

[Chemical formula 685]

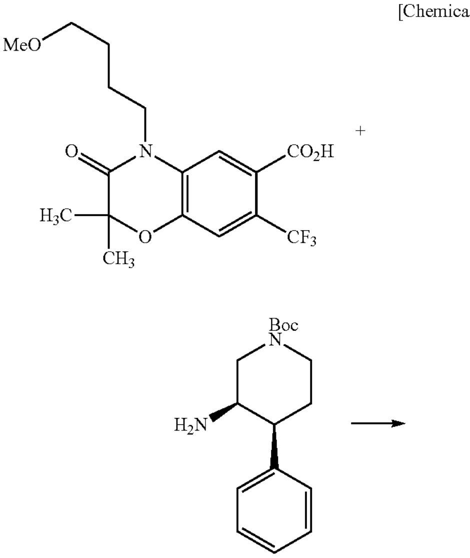

-continued

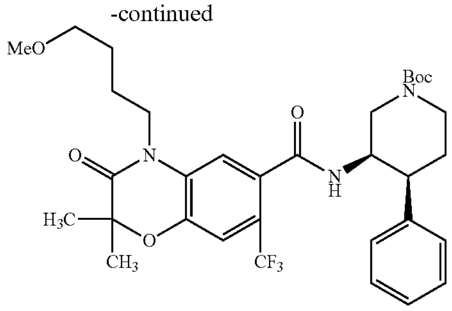

To a solution of 4-(4-methoxybutyl)-2,2-dimethyl-3-oxo-7-(trifluoromethyl)-3,4-dihydro-2H-1,4-benzoxazine-6-carboxylic acid (739 mg) in DMF (5 ml) were added 1-(3-dimethylaminopropyl)-3-ethylcarbodiimide hydrochloride (755 mg), 1-hydroxybenzotriazole (532 mg), triethylamine (549 μl), tert-butyl (3R,4S)-3-amino-4-phenylpiperidine-1-carboxylate (653 mg), and the mixture was stirred at room temperature for 3 hours. To the reaction mixture was added a saturated aqueous ammonium chloride solution, and the mixture was extracted with ethyl acetate. The organic layer was washed with a saturated aqueous ammonium chloride solution, a saturated aqueous sodium hydrogen carbonate solution and a saturated aqueous sodium chloride solution, dried over magnesium sulfate, filtered, and concentrated under reduced pressure. The obtained residue was purified by silica gel column chromatography (the developing solvent: hexane/ethyl acetate=3/1) to give the title compound (1.25 g).

MS (ESI+) 634 ($M^{+}$+1, 100%).

Reference Example 540 tert-Butyl (3R,4S)-3-(ethyl{[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate

[Chemical formula 686]

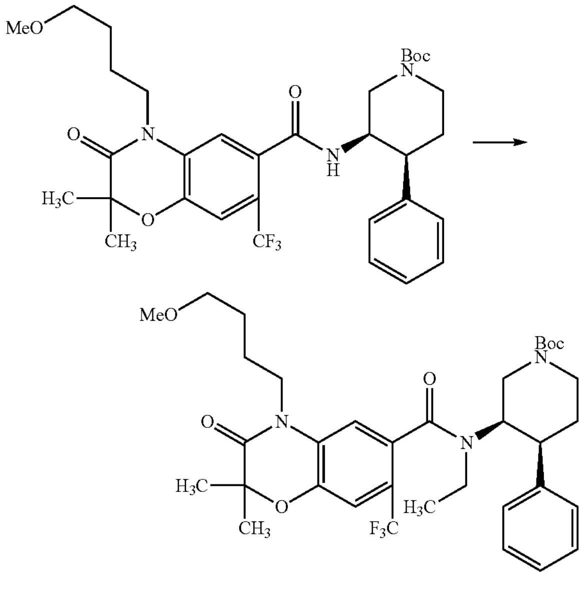

To a solution of tert-butyl (3R,4S)-3-({[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate (386 mg) in DMF (1 ml) was added sodium hydride (48.7 mg) at 0° C., and the mixture was stirred for 10 minutes. To the mixture was added ethyl iodide (126 μl), and the mixture was stirred at room temperature for 5 hours. To the reaction solution was added a saturated aqueous ammonium chloride solution, and the mixture was extracted with ethyl acetate. The organic layer was washed with water (×2) and a saturated aqueous sodium chloride solution, dried over sodium sulfate, filtered, and concentrated under reduced pressure. The obtained residue was purified by silica gel column chromatography (the developing solvent: hexane/ethyl acetate=3/1) to give the title compound (128 g).

MS (ESI+) 662 ($M^{+}$+1, 100%).

Reference Example 541 tert-Butyl (3S,4S)-3,4-dihydroxy-4-phenylpiperidine-1-carboxylate

[Chemical formula 687]

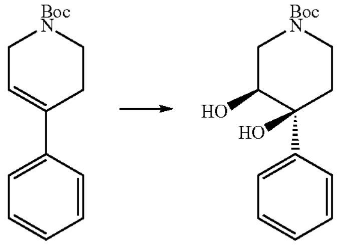

Using tert-butyl 4-phenyl-3,6-dihydropyridin-1(2H)-carboxylate and AD-mix-α, the title compound was obtained in a similar manner to Reference Example 538.

$^{1}$H NMR (300 MHz, $CD_3OD$) δ 7.42-7.39 (m, 2H), 7.26-7.21 (m, 2H), 7.15-7.09 (m, 1H), 4.01-3.92 (m, 3H), 3.81-3.76 (m, 2H), 1.85-1.76 (m, 1H), 1.63-1.58 (m, 1H), 1.39 (s, 9H).

Reference Example 542 tert-Butyl (3R,4R)-3-hydroxy-4-phenylpiperidine-1-carboxylate

[Chemical formula 688]

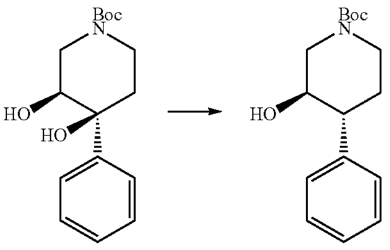

Using tert-butyl (3S,4S)-3,4-dihydroxy-4-phenylpiperidine-1-carboxylate, the title compound was obtained in a similar manner to Reference Example 539.

$^1$H NMR (300 MHz, $CDCl_3$) δ 7.39-7.24 (m, 5H), 4.40 (m, 1H), 4.15-4.08 (m, 1H), 3.69 (m, 1H), 2.76-2.48 (m, 3H), 1.84-1.53 (m, 2H), 1.49 (s, 9H).

Reference Example 543 tert-Butyl (3S,4R)-3-amino-4-phenylpiperidine-1-carboxylate

[Chemical formula 689]

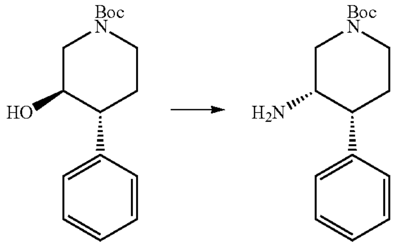

Using tert-butyl (3R,4R)-3-hydroxy-4-phenylpiperidine-1-carboxylate, the title compound was obtained in a similar manner to Reference Example 540.

$^1$H NMR (300 MHz, $CDCl_3$) δ 7.37-7.20 (m, 5H), 4.32-4.19 (m, 2H), 3.18-3.05 (m, 2H), 2.92-2.80 (m, 2H), 2.23-2.18 (m, 1H), 1.64-1.61 (m, 1H), 1.48 (s, 9H).

Reference Example 544 tert-Butyl (3S,4R)-3-({[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate

[Chemical formula 690]

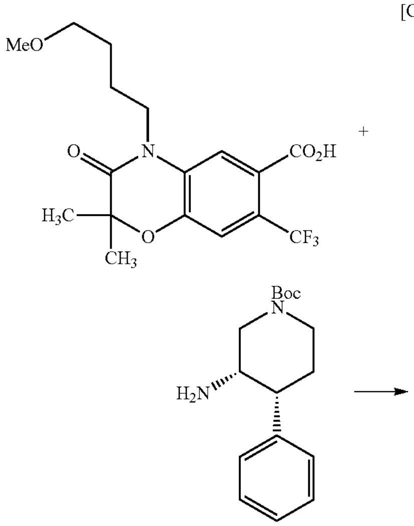

-continued

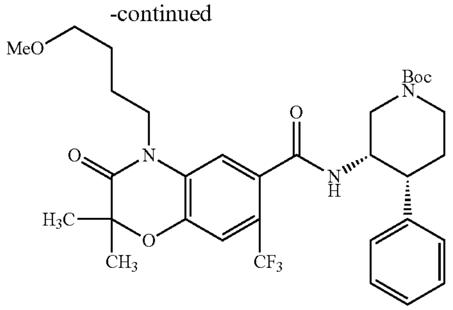

Using 4-(4-methoxybutyl)-2,2-dimethyl-3-oxo-7-(trifluoromethyl)-3,4-dihydro-2H-1,4-benzoxazine-6-carboxylic acid and tert-butyl (3S,4R)-3-amino-4-phenylpiperidine-1-carboxylate, the title compound was obtained in a similar manner to Reference Example 541.

MS (ESI+) 634 ($M^+$+1, 100%).

Reference Example 547 tert-Butyl (3S,4R)-3-(ethyl {[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate

[Chemical formula 691]

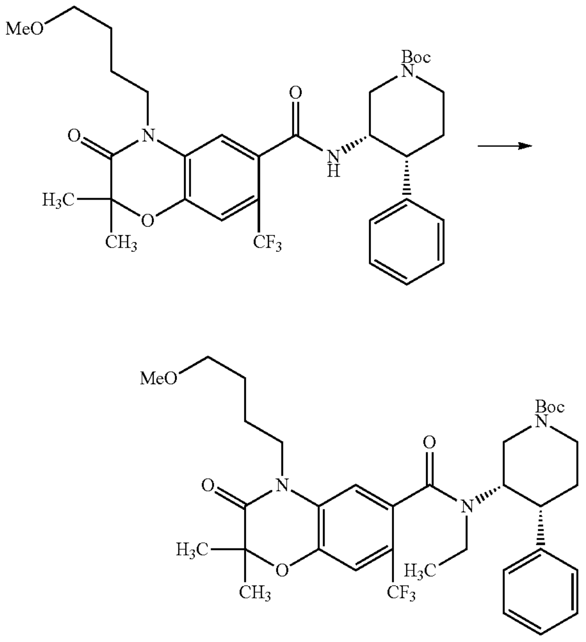

Using tert-butyl (3S,4R)-3-({[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate, the title compound was obtained in a similar manner to Reference Example 542.

MS (ESI+) 662 ($M^+$+1, 100%).

Reference Example 545 tert-Butyl (3S)-3-(isopropylamino)piperidine-1-carboxylate

[Chemical formula 692]

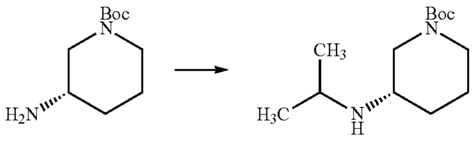

Using tert-butyl (3S)-3-aminopiperidine-1-carboxylate, the title compound was obtained in a similar manner to Reference Example 482.

MS (ESI+) 243 (M+1, 100%).

Reference Example 546 tert-Butyl (3S)-3-(isopropyl{[4-(4-methoxybutyl)-2,2-dimethyl-3-oxo-7-(trifluoromethyl)-3,4-dihydro-2H-1,4-benzoxazin-6-yl]carbonyl}amino)piperidine-1-carboxylate

[Chemical formula 693]

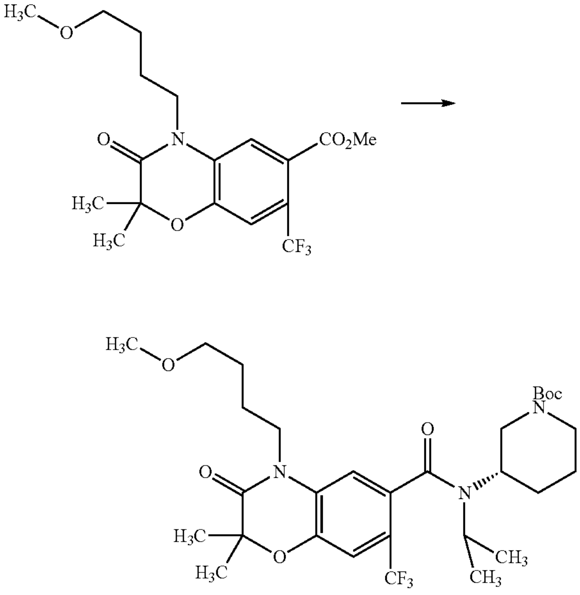

Using methyl 4-(4-methoxybutyl)-2,2-dimethyl-3-oxo-7-(trifluoromethyl)-3,4-dihydro-2H-1,4-benzoxazine-6-carboxylate and tert-butyl (3S)-3-(isopropylamino)piperidine-1-carboxylate, the title compound was obtained in a similar manner to Reference Example 5.

MS (ESI+) 600 ($M^+$+1, 100%).

Reference Example 547

1-tert-Butyl 3-ethyl 4-phenyl-5,6-dihydropyridin-1,3(2H)-dicarboxylate

[Chemical formula 694]

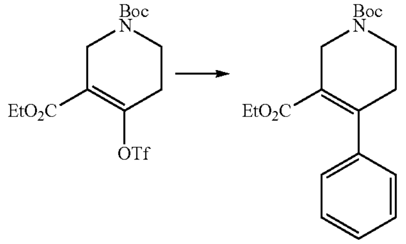

1-tert-Butyl-3-ethyl-4-{[(trifluoromethyl)sulfonyl]oxy}-5,6-dihydropyridin-1,3(2H)-dicarboxylate (8.97 g) was dissolved in dimethoxyethane (30 ml) and water (30 ml), and thereto were added phenylboronic acid (4.07 g), tetrakis (triphenylphosphine) palladium (2.57 g), and sodium carbonate (4.71 g) at room temperature, and the mixture was stirred at 80° C. for 2 hours. The reaction mixture was cooled, filtered on celite, and extracted with ethyl acetate. The organic layer was washed with water and a saturated aqueous sodium chloride solution, dried over sodium sulfate, filtered, and concentrated under reduced pressure. The obtained residue was purified by silica gel column chromatography (the developing solvent: hexane/ethyl acetate=5/1) to give the title compound (7.07 g) as pale yellow clear oil.

MS (ESI+) 332 ($M^+$+1, 100%).

Reference Example 548

1-(tert-Butoxycarbonyl)-4-phenyl-1,2,5,6-tetrahydropyridin-3-carboxylic acid

[Chemical formula 695]

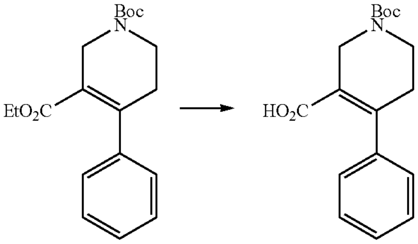

1-tert-Butyl 3-ethyl 4-phenyl-5,6-dihydropyridin-1,3(2H)-dicarboxylate (7.07 g) was dissolved in ethanol (50 ml), and thereto was added 1M aqueous sodium hydroxide solution (50 ml), and the mixture was refluxed for 2 hours. The reaction solution was concentrated under reduced pressure, and thereto was added 1M aqueous sodium hydroxide solution and ethyl acetate for separation. To the organic layer was added 1M aqueous sodium hydroxide solution for separation, and the aqueous layers were combined, and the pH value thereof was adjusted to pH<2 by the addition of 2M hydrochloric acid. The mixture was extracted with chloroform, and the organic layer was dried over sodium sulfate, filtered, and concentrated under reduced pressure to give the title compound (5.63 g).

MS (ESI+) 304 ($M^+$+1, 100%).

Reference Example 549

(rac.)-(3S,4S)-1-(tert-Butoxycarbonyl)-4-phenylpiperidine 3-carboxylic acid

[Chemical formula 696]

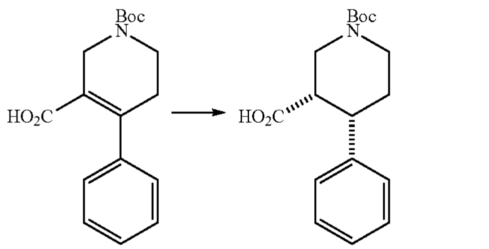

1-(tert-Butoxycarbonyl)-4-phenyl-1,2,5,6-tetrahydropyridin-3-carboxylic acid (5.63 g) was dissolved in methanol (60 ml), and thereto was added palladium-carbon (4.06 g), and the mixture was stirred under hydrogen atmosphere for 2 hours. The reaction solution was filtered on celite, and concentrated under reduced pressure to give the title compound (4.76 g).

MS (ESI+) 306 ($M^{+}$+1, 100%).

Reference Example 550

(3S,4S)-1-(tert-Butoxycarbonyl)-4-phenylpiperidine 3-carboxylic acid

[Chemical formula 697]

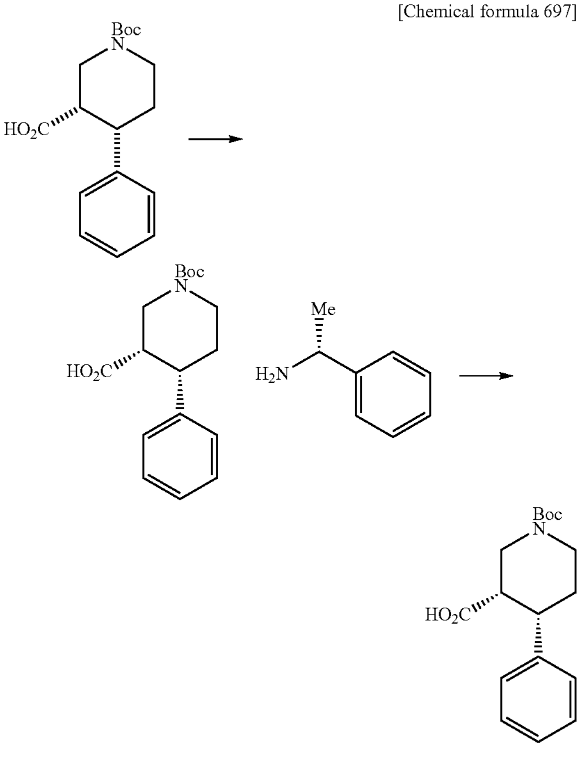

(rac.)-(3S,4S)-1-(tert-Butoxycarbonyl)-4-phenylpiperidine 3-carboxylic acid (4.76 g) was dissolved in methanol (90 ml), and thereto was added (S)-(−)-phenylethylamine (1.59 g), and the mixture was refluxed for 2 hours. The mixture was slowly cooled to room temperature, and the mixture was allowed to stand at 0° C. for 12 hours. The precipitates were collected by filtration, and recrystallized from ethyl acetate and methanol to give the crystals (1.51 g). To the obtained crystals was added 1M hydrochloric acid, and the mixture was extracted with ethyl acetate. The organic layer was washed with a saturated aqueous sodium chloride solution, dried over sodium sulfate, filtered and concentrated under reduced pressure to give the title compound (1.12 g, >99% ee).

MS (ESI+) 306 ($M^{+}$+1, 100%).

Reference Example 551

1-tert-Butyl 3-methyl (3S,4S)-4-phenylpiperidine-1,3-dicarboxylate

[Chemical formula 698]

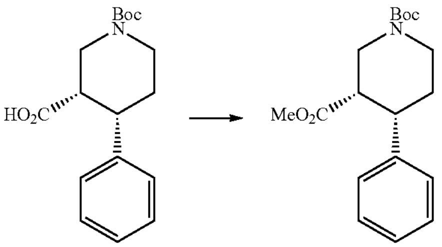

To a solution of (3S,4S)-1-(tert-butoxycarbonyl)-4-phenylpiperidine-3-carboxylic acid (1.12 g) in DMF (12 ml) were added 1-(3-dimethylaminopropyl)-3-ethylcarbodiimide hydrochloride (1.41 g), N,N-dimethylaminopyridine (992 mg), triethylamine (1.02 ml) and methanol (595 μl), and the mixture was stirred at room temperature for 3 hours. To the reaction mixture was added a saturated aqueous ammonium chloride solution, and the mixture was extracted with ethyl acetate. The organic layer was washed with a saturated aqueous ammonium chloride solution, a saturated aqueous sodium hydrogen carbonate solution, and a saturated aqueous sodium chloride solution, dried over sodium sulfate, filtered and concentrated under reduced pressure. The obtained residue was purified by silica gel column chromatography (the developing solvent: hexane/ethyl acetate=5/1) to give the title compound (1.00 g).

MS (ESI+) 320 ($M^{+}$+1, 100%).

Reference Example 552

1-tert-Butyl 3-methyl (3R,4S)-4-phenylpiperidine-1,3-dicarboxylate

[Chemical formula 699]

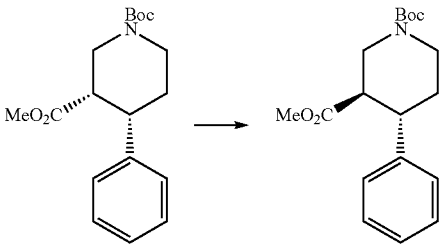

1-tert-Butyl 3-methyl (3S,4S)-4-phenylpiperidine-1,3-dicarboxylate (1.00 g) was dissolved in methanol (40 ml), and thereto was added sodium methoxide (1.0 M methanol solution, 4.70 ml), and the mixture was refluxed for 9 hours. The reaction mixture was cooled, and concentrated under reduced pressure. To the residue was added a saturated aqueous ammonium chloride solution, and the mixture was extracted with ethyl acetate. The organic layer was washed with a saturated aqueous sodium chloride solution, dried over sodium sulfate, filtered, and concentrated under reduced pressure. The obtained residue was purified by silica gel column chromatography (the developing solvent: hexane/ethyl acetate=5/1) to give the title compound (585 mg).

MS (ESI+) 320 ($M^+$+1, 100%).

Reference Example 553

(3R,4S)-1-(tert-Butoxycarbonyl)-4-phenylpiperidine 3-carboxylic acid

[Chemical formula 700]

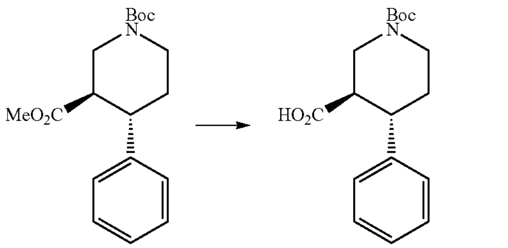

1-tert-Butyl 3-methyl (3R,4S)-4-phenylpiperidine-1,3-dicarboxylate (585 mg) was dissolved in tetrahydrofuran (5 ml) and methanol (5 ml), and thereto was added 1M aqueous sodium hydroxide solution (5.5 ml), and the mixture was stirred at room temperature for 5 hours. The reaction solution was concentrated under reduced pressure, and thereto was added a 5% potassium hydrogen sulfate, and the mixture was extracted with ethyl acetate. The organic layer was washed with a saturated aqueous sodium chloride solution, dried over sodium sulfate, filtered, and concentrated under reduced pressure to give the title compound (546 mg).

MS (ESI+) 306 ($M^+$+1, 100%).

Reference Example 554 tert-Butyl (3R,4R)-3-amino-4-phenylpiperidine-1-carboxylate

[Chemical formula 701]

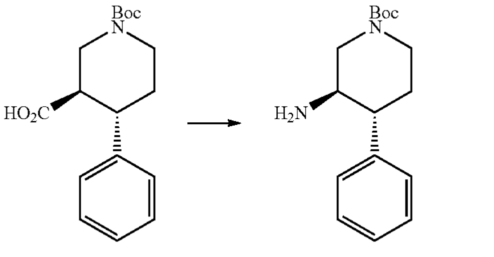

(3R,4S)-1-(tert-Butoxycarbonyl)-4-phenylpiperidine-3-carboxylic acid (546 mg) was dissolved in toluene (5 ml), and thereto were added triethylamine (374 µl) and diphenylphosphoryl azide (591 mg) at room temperature, and the mixture was stirred at 110° C. for 3 hours. The reaction mixture was cooled to 80° C., and thereto was added benzyl alcohol (556 µl), and the mixture was stirred for 3 hours. The reaction mixture was cooled, and water was added thereto. The mixture was extracted with ethyl acetate, and the organic layer was washed with a saturated aqueous sodium chloride solution, dried over sodium sulfate, filtered, and concentrated under reduced pressure. The obtained residue was purified by silica gel column chromatography (the developing solvent: hexane/ethyl acetate=2/1) to give the crude product (1.92 g).

The obtained residue was dissolved in tetrahydrofuran (8 ml), and thereto was added 10% palladium carbon (910 mg) at room temperature, and the mixture was stirred at room temperature under hydrogen atmosphere for 5 hours. The reaction mixture was filtered on celite, and concentrated under reduced pressure. The obtained residue was purified by silica gel column chromatography (hexane/ethyl acetate=1/3) to give the title compound (270 mg).

MS (ESI+) 277 ($M^+$+1, 100%).

Reference Example 555 tert-Butyl (3R,4R)-3-({[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate

[Chemical formula 702]

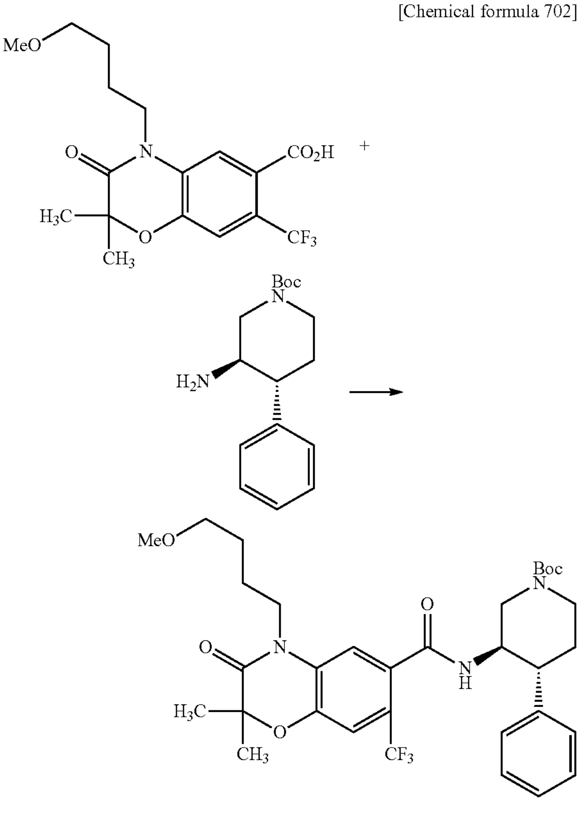

Using 4-(4-methoxybutyl)-2,2-dimethyl-3-oxo-7-(trifluoromethyl)-3,4-dihydro-2H-1,4-benzoxazine-6-carboxylic acid and tert-butyl (3R,4R)-3-amino-4-phenylpiperidine-1-carboxylate, the title compound was obtained in a similar manner to Reference Example 541.

MS (ESI+) 634 ($M^{+}$+1, 100%).

Reference Example 556 tert-Butyl (3R,4R)-3-(ethyl {[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate

[Chemical formula 703]

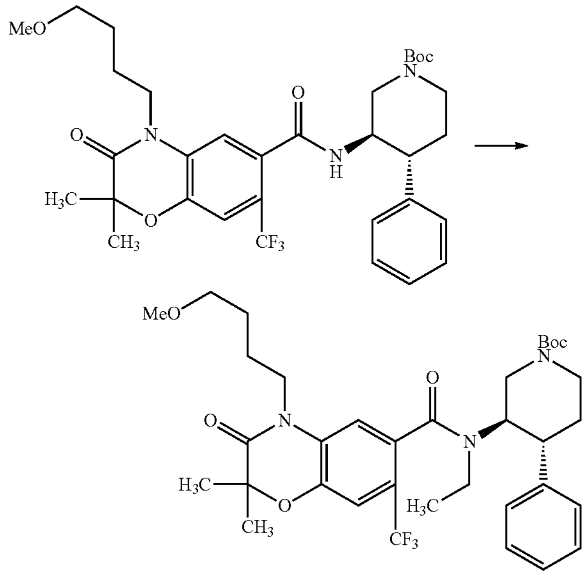

Using tert-butyl (3R,4R)-3-({[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate, the title compound was obtained in a similar manner to Reference Example 542.

MS (ESI+) 662 ($M^{+}$+1, 100%).

Reference Example 557

(3R,4R)-1-(tert-Butoxycarbonyl)-4-phenylpiperidine-3-carboxylic acid

[Chemical formula 704]

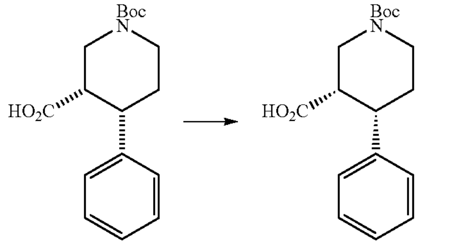

-continued

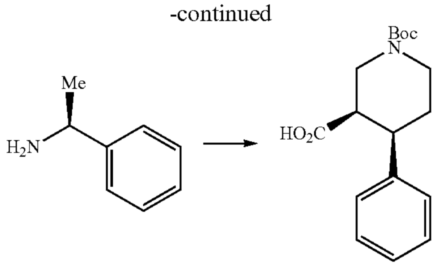

Using (rac.)-(3S,4S)-1-(tert-butoxycarbonyl)-4-phenylpiperidine-3-carboxylic acid, (R)-(+)-phenylethylamine, the title compound was obtained in a similar manner to Reference Example 553.

MS (ESI+) 306 ($M^{+}$+1, 100%).

Reference Example 558

1-tert-Butyl 3-methyl (3R,4R)-4-phenylpiperidine-1,3-dicarboxylate

[Chemical formula 705]

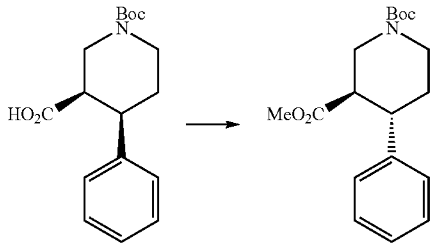

Using (3R,4R)-1-(tert-butoxycarbonyl)-4-phenylpiperidine 3-carboxylic acid, the title compound was obtained in a similar manner to Reference Example 554.

MS (ESI+) 320 ($M^{+}$+1, 100%).

Reference Example 559

1-tert-Butyl 3-methyl (3S,4R)-4-phenylpiperidine-1,3-dicarboxylate

[Chemical formula 706]

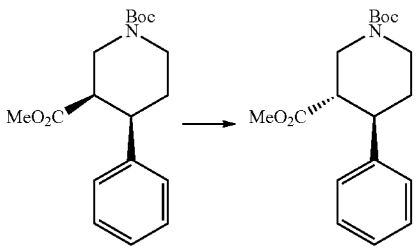

Using 1-tert-butyl 3-methyl (3R,4R)-4-phenylpiperidine-1,3-dicarboxylate, the title compound was obtained in a similar manner to Reference Example 555.

MS (ESI+) 320 ($M^{+}$+1, 100%).

Reference Example 560

(3S,4R)-1-(tert-Butoxycarbonyl)-4-phenylpiperidine-3-carboxylic acid

[Chemical formula 707]

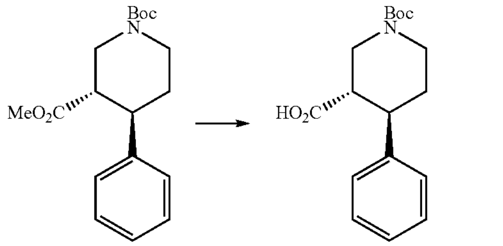

Using 1-tert-butyl 3-methyl (3S,4R)-4-phenylpiperidine 1,3-dicarboxylate, the title compound was obtained in a similar manner to Reference Example 556.

MS (ESI+) 306 ($M^{+}$+1, 100%).

Reference Example 561 tert-Butyl (3S,4S)-3-amino-4-phenylpiperidine-1-carboxylate

[Chemical formula 708]

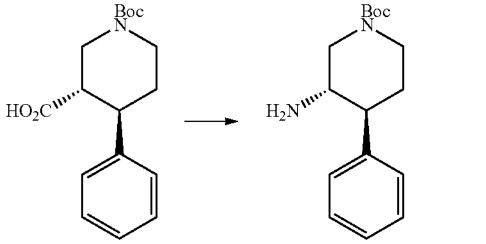

Using (3S,4R)-1-(tert-butoxycarbonyl)-4-phenylpiperidine-3-carboxylic acid, the title compound was obtained in a similar manner to Reference Example 557.

MS (ESI+) 277 ($M^{+}$+1, 100%).

Reference Example 562 tert-Butyl (3S,4S)-3-({[4-(4-methoxybutyl)-2,2-dimethyl-3-oxo-7-(trifluoromethyl)-3,4-dihydro-2H-1,4-benzoxazin-6-yl]-carbonyl]amino)-4-phenylpiperidine-1-carboxylate

[Chemical formula 709]

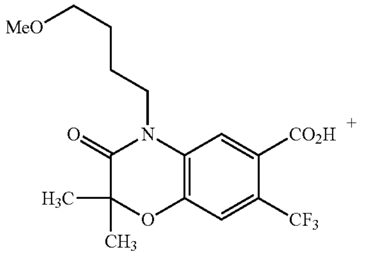

-continued

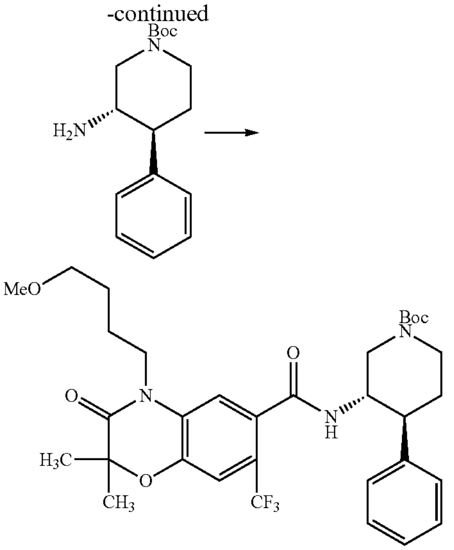

Using 4-(4-methoxybutyl)-2,2-dimethyl-3-oxo-7-(trifluoromethyl)-3,4-dihydro-2H-1,4-benzoxazine-6-carboxylic acid and tert-butyl (3S,4S)-3-amino-4-phenylpiperidine-1-carboxylate, the title compound was obtained in a similar manner to Reference Example 541.

MS (ESI+) 634 ($M^{+}$+1, 100%).

Reference Example 563 tert-Butyl (3S,4S)-3-(ethyl{[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate

[Chemical formula 710]

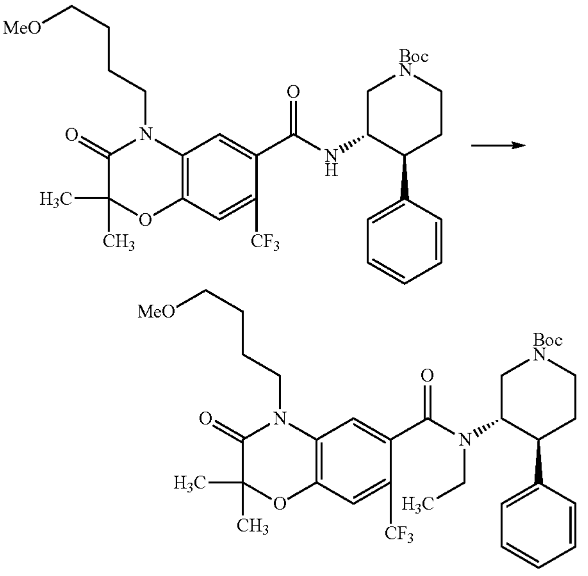

Using tert-butyl (3S,4S)-3-({[4-(4-methoxybutyl)-2,2-dimethyl-3-oxo-7-(trifluoromethyl)-3,4-dihydro-2H-1,4-benzoxazin-6-yl]carbonyl}amino)-4-phenylpiperidine-1-carboxylate, the title compound was obtained in a similar manner to Reference Example 542.

MS (ESI+) 662 ($M^{+}$+1, 100%).

Reference Example 564 tert-Butyl (3R,4R)-3-{[(2-nitrophenyl)sulfonyl]amino}-4-phenylpiperidine-1-carboxylate

[Chemical formula 711]

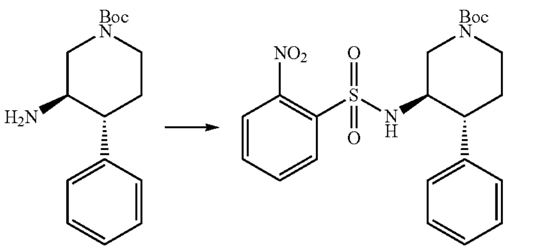

tert-Butyl (3R,4R)-3-amino-4-phenylpiperidine-1-carboxylate (124 mg) was dissolved in methylene chloride (2 ml), and thereto were added triethylamine (125 μl) and 2-nitrobenzene sulfonyl chloride (109 mg) at 0° C., and the mixture was stirred at room temperature for 3 hours. To the reaction solution was added a saturated aqueous ammonium chloride solution, and the mixture was extracted with ethyl acetate. The organic layer was washed with a saturated aqueous sodium chloride solution, dried over sodium sulfate, filtered, and concentrated under reduced pressure. The obtained residue was purified by silica gel column chromatography (the developing solvent: hexane/ethyl acetate=1/1) to give the title compound (202 mg).

MS (ESI+) 462 ($M^+$+1, 100%).

Reference Example 565 tert-Butyl (3R,4R)-3-{ethyl(2-nitrophenyl)sulfonyl]amino}-4-phenylpiperidine-1-carboxylate

[Chemical formula 712]

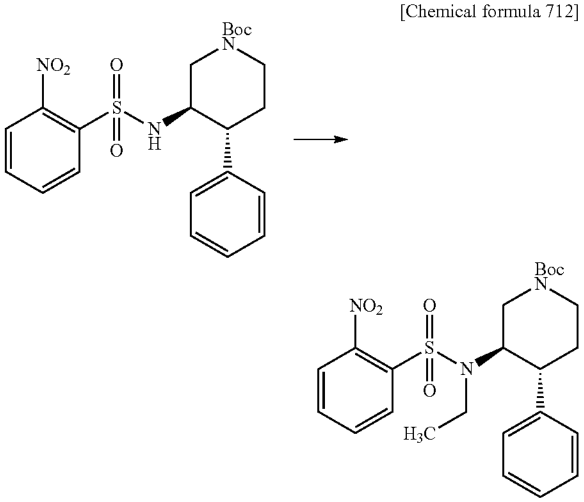

tert-Butyl (3R,4R)-3-{[(2-nitrophenyl)sulfonyl]amino}-4-phenylpiperidine-1-carboxylate (202 mg) was dissolved in N,N-dimethylformamide (2 ml), and thereto were added potassium carbonate (182 mg) and ethyl iodide (136 μl), and the mixture was stirred at 60° C. for 1.5 hour. The reaction solution was cooled, and thereto was added a saturated aqueous ammonium chloride solution, and the mixture was extracted with ethyl acetate. The organic layer was washed with a saturated aqueous ammonium chloride solution and a saturated aqueous sodium chloride solution, dried over sodium sulfate, filtered, and concentrated under reduced pressure. The obtained residue was purified by silica gel column chromatography (the developing solvent: hexane/ethyl acetate=2/1) to give the title compound (209 mg).

MS (ESI+) 490 ($M^+$+1, 100%).

Reference Example 566 tert-Butyl (3R,4R)-3-(ethylamino)-4-phenylpiperidine-1-carboxylate

[Chemical formula 713]

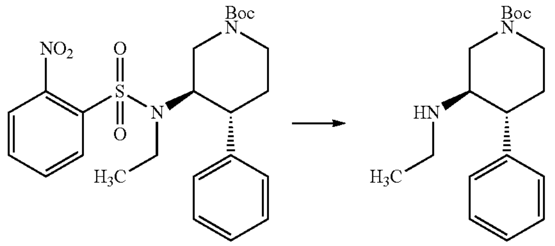

tert-Butyl (3R,4R)-3-{ethyl(2-nitrophenyl)sulfonyl]amino}-4-phenylpiperidine-1-carboxylate (209 mg) was dissolved in N,N-dimethylformamide (2 ml), and thereto were added lithium hydroxide (95.6 mg) and mercaptoacetic acid (59.0 μl), and the mixture was stirred at 45° C. for 5 hours. The reaction solution was cooled, and thereto was added a saturated aqueous sodium hydrogen carbonate solution, and the mixture was extracted with ethyl acetate. The organic layer was washed with water (×2) and a saturated aqueous sodium chloride solution, dried over sodium sulfate, filtered, and concentrated under reduced pressure. The obtained residue was purified by silica gel column chromatography (the developing solvent: hexane/ethyl acetate=1/1) to give the title compound (55.5 mg).

MS (ESI+) 305 ($M^+$+1, 100%).

Reference Example 567 tert-Butyl (3R,4R)-3-[{[4-(2-{[(benzyloxy)carbonyl]amino}ethyl)-2,2-dimethyl-3-oxo-7-(trifluoro-methyl)-3,4-dihydro-2H-1,4-benzoxazin-6-yl]carbonyl}(ethyl)amino]-4-phenylpiperidine-1-carboxylate

[Chemical formula 714]

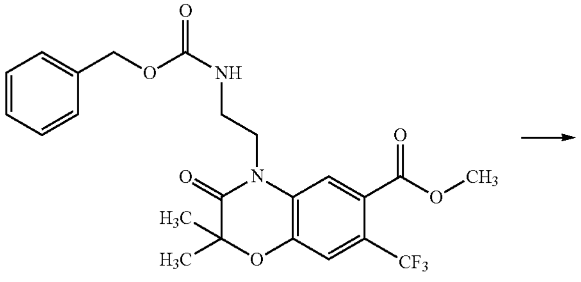

-continued

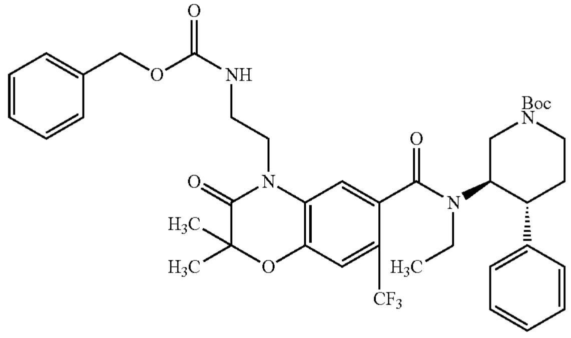

Using methyl 4-(2-{[(benzyloxy)carbonyl]amino}ethyl)-2,2-dimethyl-3-oxo-7-(trifluoro-methyl)-3,4-dihydro-2H-1,4-benzoxazine-6-carboxylate and tert-butyl (3R,4R)-3-(ethylamino)-4-phenylpiperidine-1-carboxylate, the title compound (60.4 mg) was obtained in a similar manner to Reference Example 5.

MS (ESI+) 753 ($M^{+}$+1, 100%).

Reference Example 568 tert-Butyl (3R,4R)-3-[{[4-(2-aminoethyl)-2,2-dimethyl-3-oxo-7-(trifluoromethyl)-3,4-dihydro-2H-1,4-benzoxazin-6-yl]carbonyl}(ethyl)amino]-4-phenylpiperidine-1-carboxylate

[Chemical formula 715]

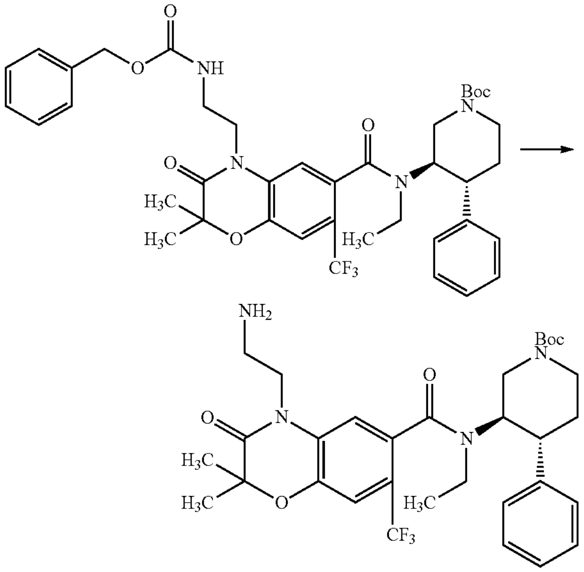

Using tert-butyl (3R,4R)-3-[{[4-(2-{[(benzyloxy)carbonyl]amino}ethyl)-2,2-dimethyl-3-oxo-7-(trifluoromethyl)-3,4-dihydro-2H-1,4-benzoxazin-6-yl]carbonyl}(ethyl)amino]-4-phenylpiperidine-1-carboxylate, the title compound (51.3 mg) was obtained in a similar manner to Reference Example 139.

MS (ESI+) 620 ($M^{+}$+1, 100%).

Reference Example 569 tert-Butyl (3R,4R)-3-[{[2,2-dimethyl-3-oxo-4-[2-(propionylamino)ethyl]-7-(trifluoromethyl)-3,4-dihydro-2H-1,4-benzoxazin-6-yl]carbonyl}(ethyl)amino]-4-phenylpiperidine-1-carboxylate

[Chemical formula 716]

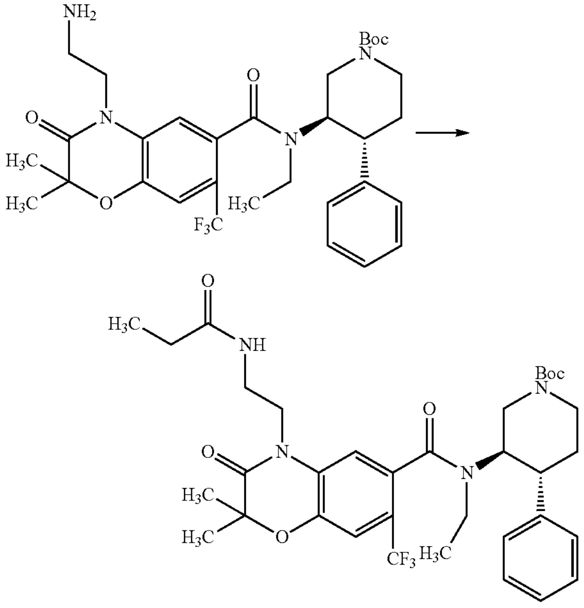

Using tert-butyl (3R,4R)-3-[{[4-(2-aminoethyl)-2,2-dimethyl-3-oxo-7-(trifluoromethyl)-3,4-dihydro-2H-1,4-benzoxazin-6-yl]carbonyl}(ethyl)amino]-4-phenylpiperidine-1-carboxylate, the title compound (41.9 mg) was obtained in a similar manner to Reference Example 132.

MS (ESI+) 675 ($M^{+}$+1, 100%).

Reference Example 570

N,N-Dibenzyl-2-bromoethaneamine

[Chemical formula 717]

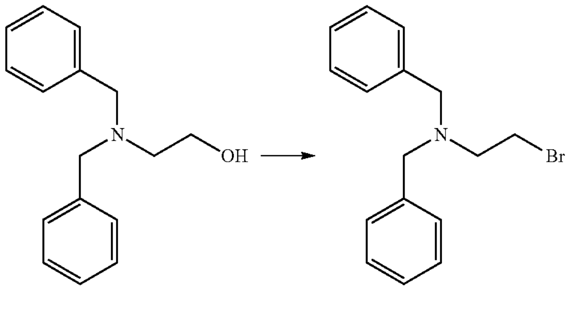

To N,N-dibenzyl-2-aminoethanol (18.47 g) was added hexane (150 ml) and DMF (0.3 ml), and thereto was added dropwise thionyl bromide (15.91 g) at 0° C. The mixture was stirred for 15 hours, and to the reaction solution was added a saturated aqueous sodium hydrogen carbonate solution in an ice-bath, and the mixture was extracted with ethyl acetate. The organic layer was washed with water (×2) and a saturated aqueous sodium chloride solution, dried over sodium sulfate, filtered, and concentrated under reduced pressure. The obtained residue was purified by silica gel column chromatography (the developing solvent: hexane) to give the title compound (12.80 g).

$^1$H NMR (400 MHz, $CDCl_3$) δ 7.48-7.39 (m, 8H), 7.36-7.33 (m, 2H), 3.74 (s, 4H), 3.43 (m, 2H), 2.97 (m, 2H).

Reference Example 571

2-Fluoro-4-hydroxy-5-nitrobenzonitrile

[Chemical formula 718]

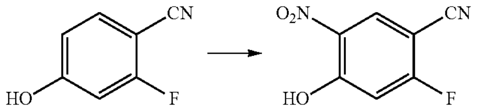

Using 2-fluoro-4-hydroxybenzonitrile, the title compound was obtained in a similar manner to Reference Example 52.

$^1$H NMR (400 MHz, $CDCl_3$) δ 11.11 (brs, 1H), 8.53 (d, J=6.5 Hz, 1H), 7.04 (d, J=9.5 Hz, 1H).

Reference Example 572

5-Amino-2-fluoro-4-hydroxybenzonitrile

[Chemical formula 719]

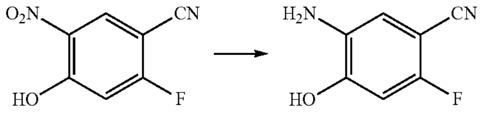

Using 2-fluoro-4-hydroxy-5-nitrobenzonitrile, the title compound was obtained in a similar manner to Reference Example 53.

MS (ESI+) 153 ($M^+$+1, 100%).

Reference Example 573

7-Fluoro-2,2-dimethyl-3-oxo-3,4-dihydro-2H-1,4-benzoxazine-6-carbonitrile

[Chemical formula 720]

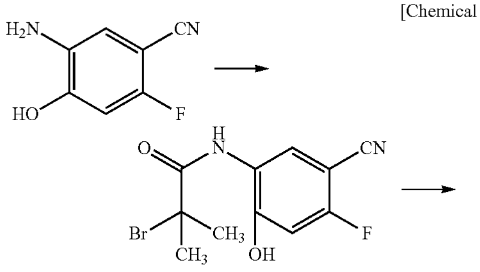

-continued

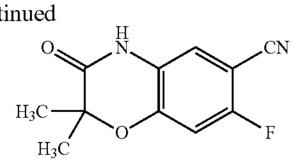

Using 5-amino-2-fluoro-4-hydroxybenzonitrile, the title compound was obtained in a similar manner to Reference Example 55.

$^1$H NMR (400 MHz, $CDCl_3$) δ 9.11 (brs, 1H), 7.06 (d, J=5.9 Hz, 1H), 6.83 (d, J=9.2 Hz, 1H), 1.60 (s, 6H).

MS (ESI+) 221 ($M^+$+1, 100%).

Reference Example 574

4-[2-(Dibenzylamino)ethyl]-7-fluoro-2,2-dimethyl-3-oxo-3,4-dihydro-2H-1,4-benzoxazine-6-carbonitrile

[Chemical formula 721]

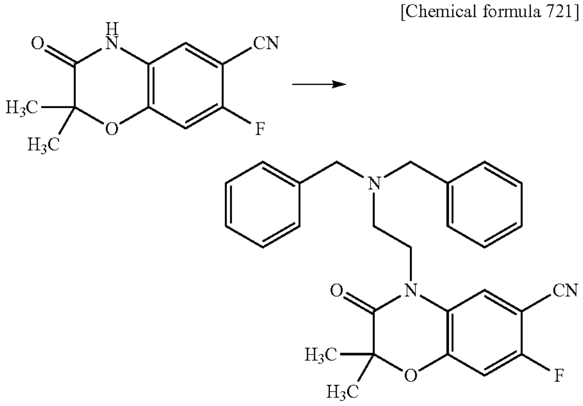

Using 7-fluoro-2,2-dimethyl-3-oxo-3,4-dihydro-2H-1,4-benzoxazine-6-carbonitrile and N,N-dibenzyl-2-bromoethanamine, the title compound was obtained in a similar manner to Reference Example 3.

MS (ESI+) 444 ($M^+$+1, 100%).

Reference Example 575

4-[2-(Dibenzylamino)ethyl]-7-fluoro-2,2-dimethyl-3-oxo-3,4-dihydro-2H-1,4-benzoxazine-6-carboxylic acid

[Chemical formula 722]

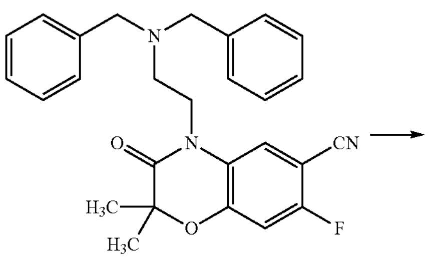

-continued

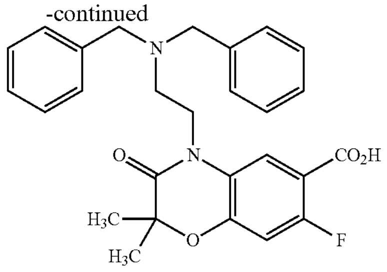

4-[2-(Dibenzylamino)ethyl]-7-fluoro-2,2-dimethyl-3-oxo-3,4-dihydro-2H-1,4-benzoxazine-6-carbonitrile (588 mg) was dissolved in acetic acid (5 ml), and thereto was added conc. hydrochloric acid (5 ml), and the mixture was refluxed for 75 hours. The reaction solution was cooled, and thereto was added water, and filtered. The solid collected by filtration was washed with water and dried at 70° C. for 18 hours to give the title compound (406 mg).

MS (ESI+) 463 ($M^+$+1, 100%).

Reference Example 576

1-tert-Butyl 3-ethyl 4-(2,4,5-trifluorophenyl)-5,6-dihydropyridine-1,3(2H)-dicarboxylate

[Chemical formula 723]

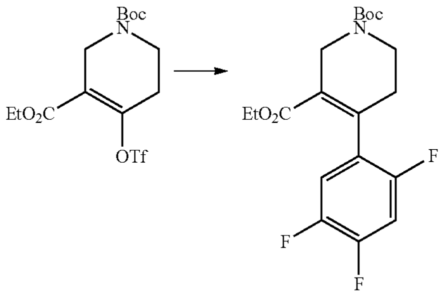

Using 1-tert-butyl-3-ethyl-4-{[(trifluoromethyl)sulfonyl]oxy}-5,6-dihydropyridin-1,3(2H)-dicarboxylate, the title compound was obtained in a similar manner to Reference Example 550.

MS (ESI+) 386 ($M^+$+1, 100%).

Reference Example 577

(3R,4S)-1-(tert-Butoxycarbonyl)-4-(2,4,5-trifluorophenyl)piperidine-3-carboxylic acid

[Chemical formula 724]

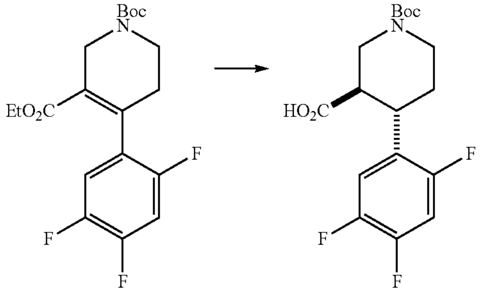

1-tert-Butyl 3-ethyl 4-(2,4,5-trifluorophenyl)-5,6-dihydropyridine-1,3(2H)-dicarboxylate (9.98 g) was dissolved in methanol (100 ml), and thereto was added magnesium (6.29 g) under ice-cooling, and the mixture was stirred at room temperature for 2 hours. In an ice-bath, to the reaction mixture was added a saturated aqueous ammonium chloride solution, and the mixture was stirred for 30 minutes. The reaction mixture was extracted with ethyl acetate, and the organic layer was washed with a saturated aqueous sodium chloride solution, dried over sodium sulfate, filtered, and concentrated under reduced pressure. The obtained residue was dissolved in ethanol (80 ml), and thereto was added sodium ethoxide (20% ethanol solution, 10.62 g) at room temperature, and the mixture was refluxed for 4 hours. The reaction mixture was cooled, and concentrated under reduced pressure. To the residue was added a 5% aqueous sodium hydrogen sulfate solution, and the mixture was extracted with ethyl acetate. The organic layer was washed with a saturated aqueous sodium chloride solution, dried over sodium sulfate, filtered, and concentrated under reduced pressure. The residue was dissolved in tetrahydrofuran (40 ml) and ethanol (40 ml), and thereto was added 1M aqueous sodium hydroxide solution (41.6 ml) at room temperature, and the mixture was stirred at 60° C. for 3 hours. The mixture was cooled, and the reaction mixture was concentrated under reduced pressure. To the residue was added a 5% aqueous sodium hydrogen sulfate solution, and the mixture was extracted with ethyl acetate. The organic layer was washed with a saturated aqueous sodium chloride solution, dried over sodium sulfate, filtered and concentrated under reduced pressure to give the title compound (7.89 g).

MS (ESI+) 360 ($M^+$+1, 100%).

Reference Example 578 tert-Butyl (3R,4R)-3-amino-4-(2,4,5-trifluorophenyl)piperidine-1-carboxylate

[Chemical formula 725]

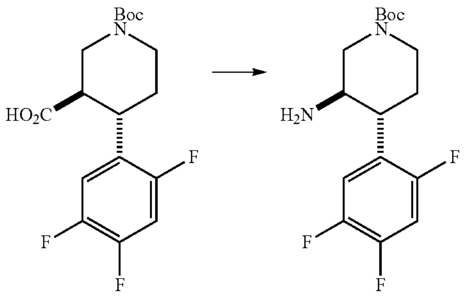

Using ((3R,4S)-1-(tert-butoxycarbonyl)-4-(2,4,5-trifluorophenyl)piperidine-3-carboxylic acid, the title compound was obtained in a similar manner to Reference Example 557.

MS (ESI+) 331 ($M^+$+1, 100%).

Reference Example 579 tert-Butyl (3R,4R)-3-[({4-[2-(dibenzylamino)ethyl]-7-fluoro-2,2-dimethyl-3-oxo-3,4-dihydro-2H-1,4-benzoxazin-6-yl}carbonyl)amino]-4-(2,4,5-trifluorophenyl)piperidine-1-carboxylate

[Chemical formula 726]

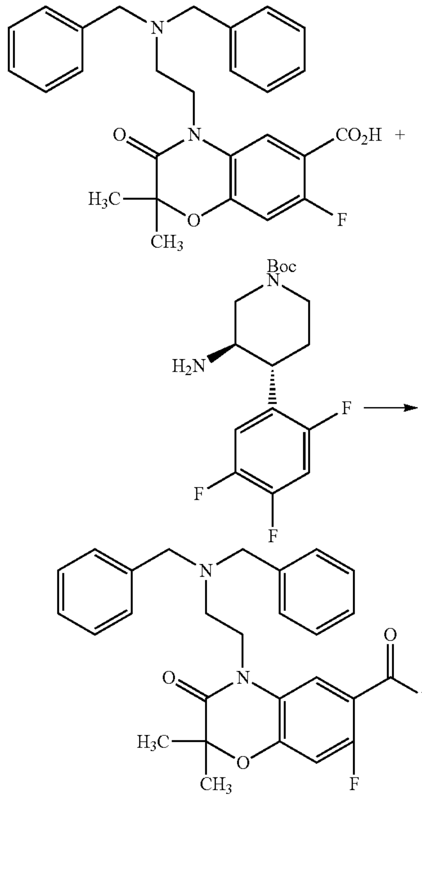

Using 4-[2-(dibenzylamino)ethyl]-7-fluoro-2,2-dimethyl-3-oxo-3,4-dihydro-2H-1,4-benzoxazine-6-carboxylic acid and tert-butyl (3R,4R)-3-amino-4-(2,4,5-trifluorophenyl)piperidine-1-carboxylate, the title compound was obtained in a similar manner to Reference Example 541.

MS (ESI+) 775 ($M^+$+1, 100%).

Reference Example 580 tert-Butyl (3R,4R)-3-[({4-[2-(dibenzylamino)ethyl]-7-fluoro-2,2-dimethyl-3-oxo-3,4-dihydro-2H-1,4-benzoxazin-6-yl}carbonyl)(ethyl)amino]-4-(2,4,5-trifluorophenyl)piperidine-1-carboxylate

[Chemical formula 727]

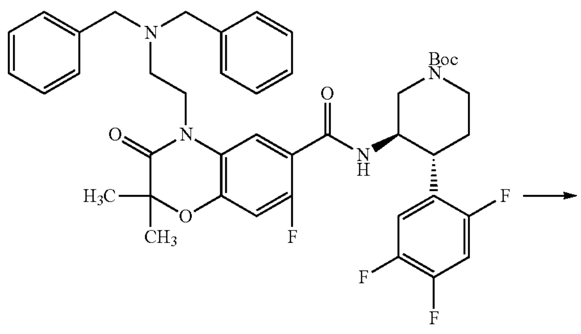

-continued

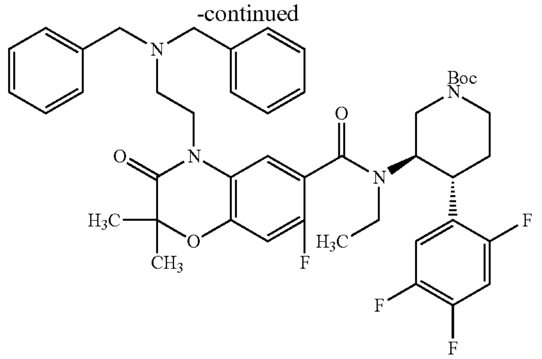

Using tert-butyl (3R,4R)-3-[({4-[2-(dibenzylamino)ethyl]-7-fluoro-2,2-dimethyl-3-oxo-3,4-dihydro-2H-1,4-benzoxazin-6-yl}carbonyl)amino]-4-(2,4,5-trifluorophenyl)piperidine-1-carboxylate, the title compound was obtained in a similar manner to Reference Example 542.

MS (ESI+) 803 ($M^+$+1, 100%).

Reference Example 581 tert-Butyl (3R,4R)-3-[{[4-(2-aminoethyl)-7-fluoro-2,2-dimethyl-3-oxo-3,4-dihydro-2H-1,4-benzoxazin-6-yl]carbonyl}(ethyl)amino]-4-(2,4,5-trifluorophenyl)piperidine-1-carboxylate

[Chemical formula 728]

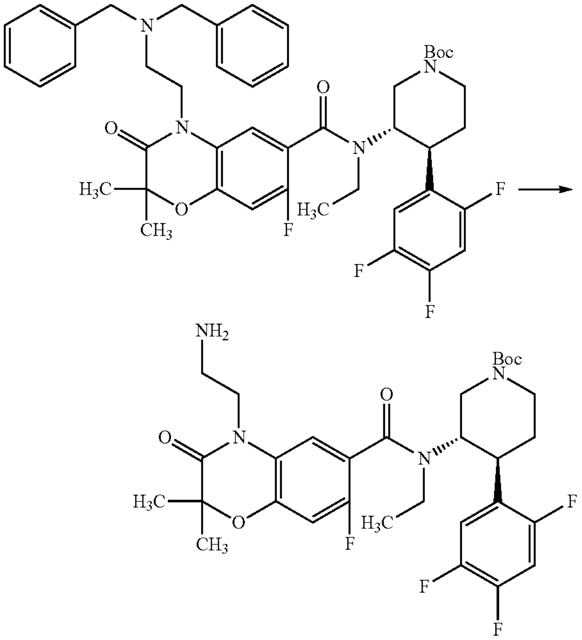

Using tert-butyl (3R,4R)-3-[({4-[2-(dibenzylamino)ethyl]-7-fluoro-2,2-dimethyl-3-oxo-3,4-dihydro-2H-1,4-benzoxazin-6-yl}carbonyl)(ethyl)amino]-4-(2,4,5-trifluorophenyl)piperidine-1-carboxylate, the title compound was obtained in a similar manner to Reference Example 139.

MS (ESI+) 623 ($M^+$+1, 100%).

Reference Example 582 tert-Butyl (3R,4R)-3-[ethyl({7-fluoro-2,2-dimethyl-3-oxo-4-[2-(propionylamino)ethyl]-3,4-dihydro-2H-1,4-benzoxazin-6-yl}carbonyl)amino]-4-(2,4,5-trifluorophenyl)piperidine-1-carboxylate

[Chemical formuula 729]

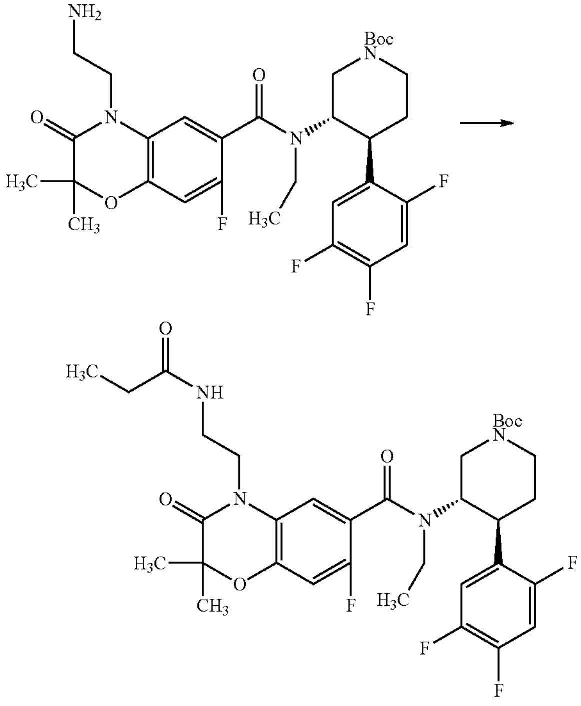

Using tert-butyl (3R,4R)-3-[{[4-(2-aminoethyl)-7-fluoro-2,2-dimethyl-3-oxo-3,4-dihydro-2H-1,4-benzoxazin-6-yl]carbonyl}(ethyl)amino]-4-(2,4,5-trifluorophenyl)piperidine-1-carboxylate, the title compound was obtained in a similar manner to Reference Example 132.

MS (ESI+) 679 ($M^+$+1, 100%).

Reference Example 583 tert-Butyl (3R)-3-[isopropyl({7-methyl-3-oxo-4-[2-(difluoroacetylamino)ethyl]-3,4-dihydrospiro[1,4-benzoxazine-2,1'-cyclobutan]-6-yl}carbonyl)amino]piperidine-1-carboxylate

[Chemical formula 730]

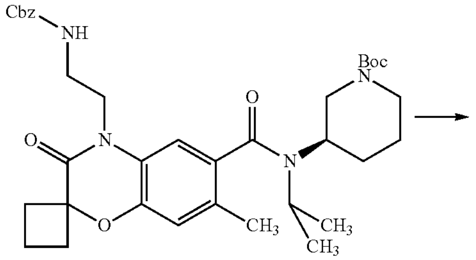

-continued

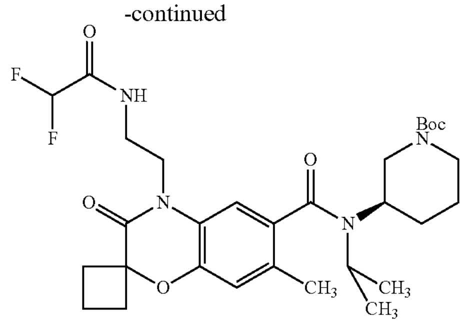

Using tert-butyl (3R)-3-[{[4-(2-{[(benzyloxy)carbonyl]amino}ethyl)-7-methyl-3-oxo-3,4-dihydrospiro[1,4-benzoxazine-2,1'-cyclobutan]-6-yl]carbonyl}(isopropyl)amino]piperidine-1-carboxylate, the title compound was obtained in a similar manner to Reference Example 139 and Reference Example 112.

MS (ESI+) 649 ($M^+$+1, 100%)

Reference Example 584 tert-Butyl (3R)-3-[(4-{[1,1-dimethyl-2-(octyloxy)-2-oxoethyl]thio}-2-methyl-5-nitrobenzoyl)(isopropyl)amino]piperidine-1-carboxylate

[Chemical formula 731]

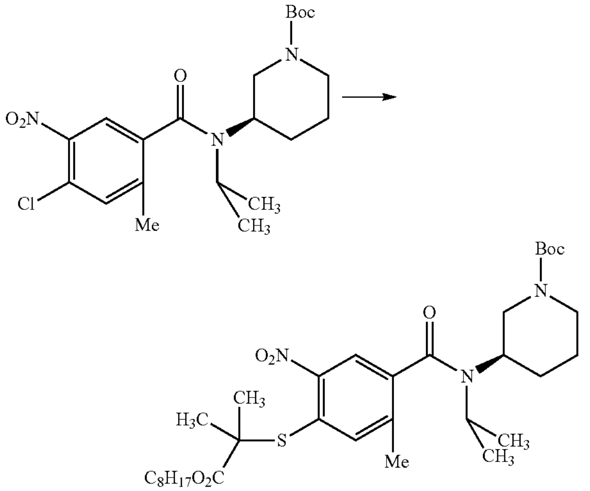

To a solution of tert-butyl (3R)-3-[(4-chloro-2-methyl-5-nitrobenzoyl)(isopropyl)amino]-piperidine-1-carboxylate (5 g) in dimethylsulfoxide (55 ml) were added potassium carbonate (4.7 g), magnesium bromide.diethyl etherate (3.5 g), lithium sulfide (0.78 g), and the mixture was stirred at room temperature. Two hours later, to the reaction solution was added octyl 2-bromoisobutyrate (4.7 g), and the mixture was stirred at 60° C. for one hour. The reaction mixture was cooled to room temperature, and filtered on celite. To the filtrate was added a saturated aqueous sodium hydrogen carbonate solution (150 ml), and the mixture was extracted twice with ethyl acetate (100 ml). The combined organic layer was washed with a saturated aqueous sodium chloride solution, dried over magnesium sulfate, filtered and concentrated under reduced pressure. The obtained residue was purified by silica gel column chromatography (the developing solvent: hexane/ethyl acetate=3/1) to give the title compound (4.9 g).

MS (ESI+) 636 ($M^+$+1, 28%).

Reference Example 585 tert-Butyl (3R)-3-[(4-{[1-(ethoxycarbonyl)cyclobutyl]thio}-2-methyl-5-nitrobenzoyl)(isopropyl)-amino]piperidine-1-carboxylate

[Chemical formula 732]

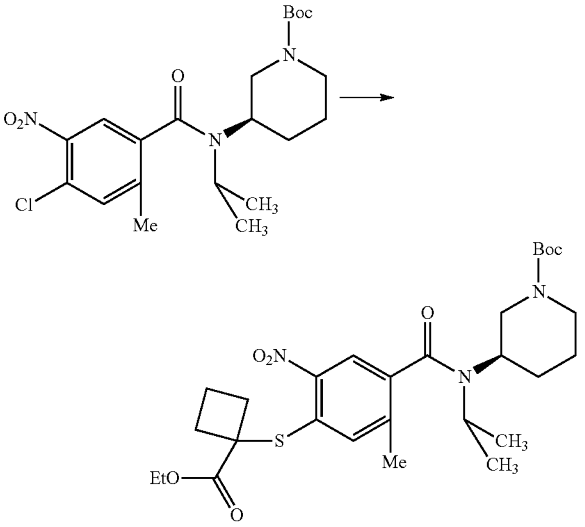

Using tert-butyl (3R)-3-[(4-chloro-2-methyl-5-nitrobenzoyl)(isopropyl)amino]piperidine-1-carboxylate, the title compound was obtained in a similar manner to Reference Example 587.

MS (ESI+) 564 ($M^+$+1, 80%).

Reference Example 586 tert-Butyl (3R)-3-{isopropyl[(2,2,7-trimethyl-3-oxo-3,4-dihydro-2H-1,4-benzothiazin-6-yl)carbonyl]-amino}piperidine-1-carboxylate

[Chemical formula 733]

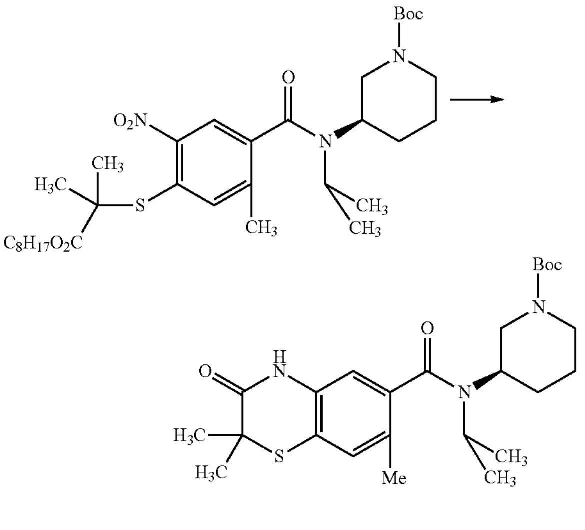

Using tert-butyl (3R)-3-[(4-{[1,1-dimethyl-2-(octyloxy)-2-oxoethyl]thio}-2-methyl-5-nitrobenzoyl)(isopropyl)amino]piperidine-1-carboxylate, the title compound was obtained in a similar manner to Reference Example 2.

MS (ESI+) 476 ($M^+$+1, 36%).

Reference Example 587 tert-Butyl (3R)-3-{isopropyl[(7-methyl-3-oxo-3,4-dihydrospiro[1,4-benzothiazine-2,1'-cyclobutan]-6-yl)carbonyl]amino}piperidine-1-carboxylate

[Chemical formula 734]

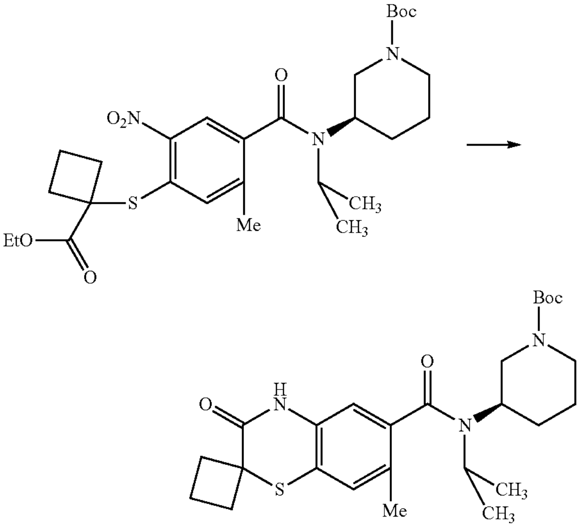

Using tert-butyl (3R)-3-[(4-{[1-(ethoxycarbonyl)cyclobutyl]thio}-2-methyl-5-nitrobenzoyl)-(isopropyl)amino]piperidine-1-carboxylate, the title compound was obtained in a similar manner to Reference Example 2.

MS (ESI+) 488 ($M^+$+1, 100%).

Reference Example 588 tert-Butyl (3R)-3-[{[4-(2-{[(benzyloxy)carbonyl]amino}ethyl)-2,2,7-trimethyl-3-oxo-3,4-dihydro-2H-1,4-benzothiazin-6-yl]carbonyl}(isopropyl)amino]piperidine-1-carboxylate

[Chemical formula 735]

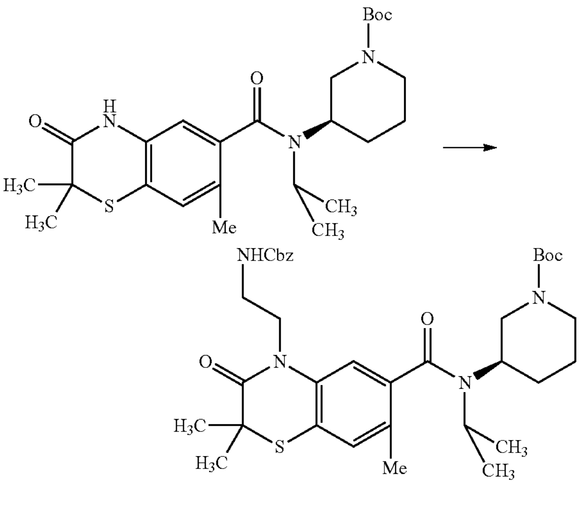

Using tert-butyl (3R)-3-{isopropyl[(2,2,7-trimethyl-3-oxo-3,4-dihydro-2H-1,4-benzothiazin-6-yl)carbonyl]amino}piperidine-1-carboxylate, the title compound was obtained in a similar manner to Reference Example 378.

MS (ESI+) 653 ($M^{+}$+1, 60%).

Reference Example 589 tert-Butyl (3R)-3-[{[4-(2-{[(benzyloxy)carbonyl]amino}ethyl)-7-methyl-3-oxo-3,4-dihydrospiro[1,4-benzothiazine-2,1'-cyclobutan]-6-yl]carbonyl}(isopropyl)amino]piperidine-1-carboxylate

[Chemical formula 736]

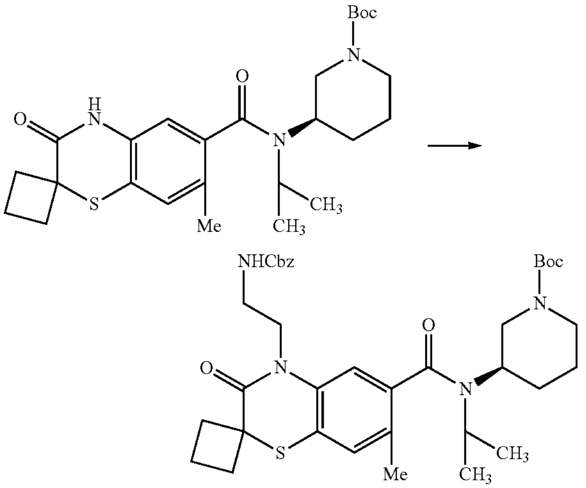

Using tert-butyl (3R)-3-{isopropyl[(7-methyl-3-oxo-3,4-dihydrospiro[1,4-benzothiazine-2,1'-cyclobutan]-6-yl)carbonyl]amino}piperidine-1-carboxylate, the title compound was obtained in a similar manner to Reference Example 3.

MS (ESI+) 665 ($M^{+}$+1, 57%).

Reference Example 590 tert-Butyl (3R)-3-[{[4-(2-aminoethyl)-2,2,7-trimethyl-3-oxo-3,4-dihydro-2H-1,4-benzothiazin-6-yl]carbonyl}(isopropyl)amino]piperidine-1-carboxylate

[Chemical formula 737]

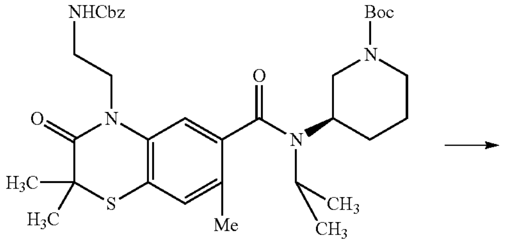

-continued

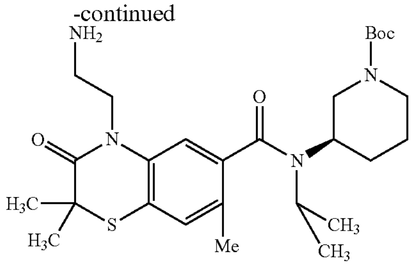

tert-Butyl (3R)-3-[{[4-(2-{[(benzyloxy)carbonyl]amino}ethyl)-2,2,7-trimethyl-3-oxo-3,4-dihydro-2H-1,4-benzothiazin-6-yl]carbonyl}(isopropyl)amino]piperidine-1-carboxylate (1.4 g) was dissolved in methanol (11 ml), and thereto was added a 20% palladium hydroxide/carbon (50% wet.) (0.7 g) under hydrogen atmosphere, and the mixture was vigorously stirred at room temperature for 3 hours. After the reaction was complete, the reaction mixture was filtered on celite, and the filtrate was concentrated under reduced pressure. The obtained residue was purified by silica gel column chromatography (the developing solvent: chloroform/methanol=98/2~92/8) to give the title compound (1.3 g).

MS (ESI+) 519 ($M^{+}$+1, 100%).

Reference Example 591 tert-Butyl (3R)-3-[[(4-{2-[(difluoroacetyl)amino]ethyl}-2,2,7-trimethyl-3-oxo-3,4-dihydro-2H-1,4-benzothiazin-6-yl)carbonyl](isopropyl)amino]piperidine-1-carboxylate

[Chemical formula 738]

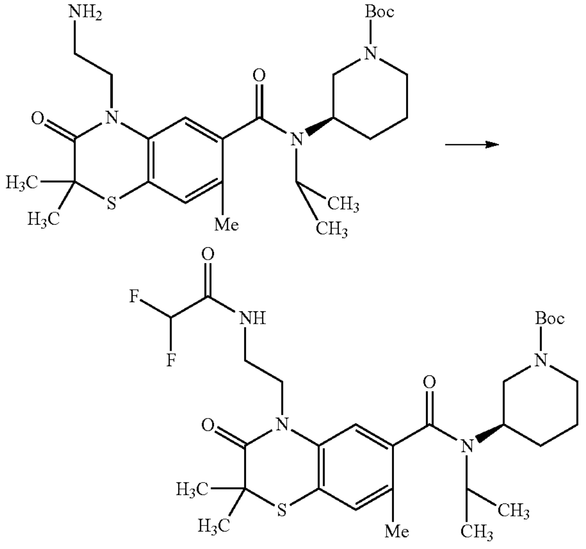

To a solution of tert-butyl (3R)-3-[{[4-(2-aminoethyl)-2,2,7-trimethyl-3-oxo-3,4-dihydro-2H-1,4-benzothiazin-6-yl]carbonyl}(isopropyl)amino]piperidine-1-carboxylate (1.3 g) in chloroform (11 ml) were added WSC (0.86 g), HOBt (0.6 g), triethylamine (0.9 mL), and the mixture was stirred at room temperature. One hour later, to the reaction solution was added a 10% aqueous potassium hydrogen sulfate solution (10 ml), and the mixture was extracted twice with ethyl acetate (10 ml). The combined organic layer was washed with a saturated aqueous sodium chloride solution, dried over magnesium sulfate, filtered, and concentrated under reduced pressure. The obtained residue was purified by silica gel column chromatography (the developing solvent: hexane/ethyl acetate=1/2~1/3) to give the title compound (1 g).

MS (ESI+) 597 ($M^+$+1, 71%).

Reference Example 592 tert-Butyl (3R)-3-[isopropyl({7-methyl-3-oxo-4-[2-(propionylamino)ethyl]-3,4-dihydrospiro[1,4-benzothiazine-2,1'-cyclobutan]-6-yl}carbonyl)amino]piperidine-1-carboxylate

[Chemical formula 739]

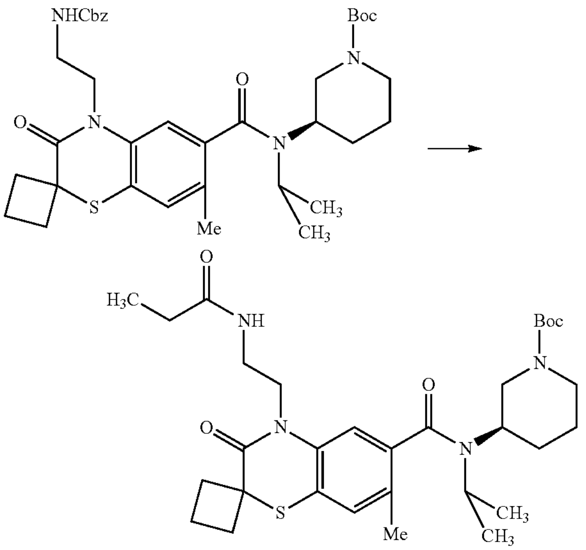

Using tert-butyl (3R)-3-[{[4-(2-{[(benzyloxy)carbonyl]amino}ethyl)-7-methyl-3-oxo-3,4-dihydrospiro[1,4-benzothiazine-2,1'-cyclobutan]-6-yl]carbonyl}(isopropyl)amino]piperidine-1-carboxylate, the title compound was obtained in a similar manner to Reference Example 379.

MS (ESI+) 587 ($M^+$+1, 29%).

Reference Example 593

2,6-Dibromo-3-methyl-1H-indole

[Chemical formula 740]

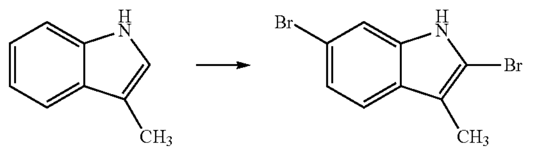

To 3-methyl-1H-indole (10 g) were added NBS (27.2 g) and $CHCl_3$ (200 ml), and the mixture was stirred at room temperature for 35 minutes. After the reaction was complete, water was added to the reaction solution, and the mixture was extracted with ethyl acetate solution. This ethyl acetate solution was washed with water and an aqueous sodium chloride solution, dried over magnesium sulfate, filtered, and concentrated. The obtained residue was purified by silica gel column chromatography (hexane/ethyl acetate=9/1) to give the title compound (15.7 g) as a brown solid.

MS (ESI+) 287 ($M^+$+1, 10%).

Reference Example 594

6-Bromo-1,3-dihydro-2H-indol-2-one

[Chemical formula 741]

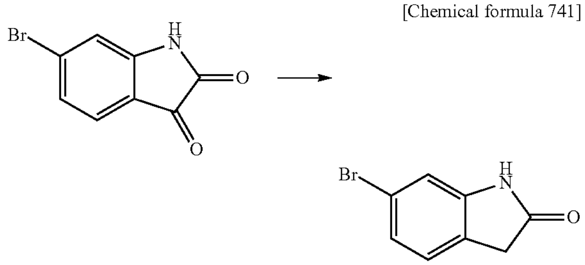

To 6-bromo-1H-indole-2,3-dione (15 g) was added hydrazine (66 ml), and the mixture was stirred at 125° C. for 2 hours. After the reaction was complete, to the mixture was added 6N aqueous HCl solution (60 ml), and the mixture was stirred at 60° C. for 2 hours. After the reaction was complete, the mixture was neutralized with 3N aqueous NaOH solution, and the mixture was extracted with ethyl acetate. This ethyl acetate solution was washed with water and an aqueous sodium chloride solution, dried over magnesium sulfate, filtered, and concentrated to give the title compound (9.1 g) as a red crystal.

MS (ESI+) 213 ($M^+$+1, 16%).

Reference Example 595

6-Bromo-3-methyl-1,3-dihydro-2H-indol-2-one

[Chemical formula 742]

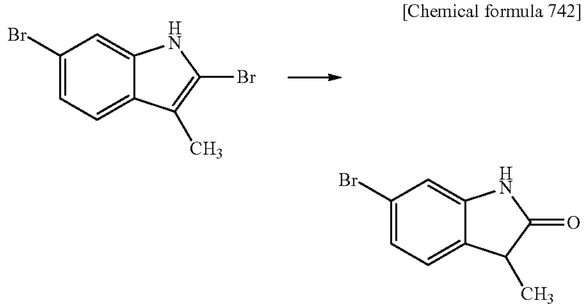

To 2,6-dibromo-3-methyl-1H-indole (15.7 g) were added 3N aqueous sulfuric acid solution (100 ml) and dioxane (100 ml), and the mixture was refluxed for 5 hours. After the reaction was complete, water was added to the reaction solution, and the mixture was extracted with ethyl acetate solution. This ethyl acetate solution was washed with water and an aqueous sodium chloride solution, dried over magnesium sulfate, filtered, and concentrated. The obtained residue was purified by silica gel column chromatography (hexane/ethyl acetate=4/1) to give the title compound (11.2 g) as a brown crystal.

MS (ESI+) 226 ($M^+$+1, 48%).

Reference Example 596

1-Acetyl-6-bromo-3-methyl-1,3-dihydro-2H-indol-2-one

[Chemical formula 743]

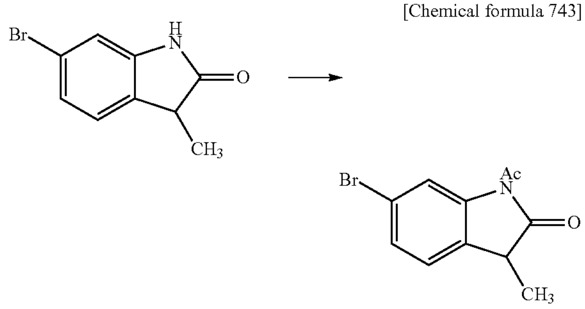

To 6-bromo-3-methyl-1,3-dihydro-2H-indol-2-one (11.2 g) were added acetic anhydride (12 ml) and xylene (120 ml), and the mixture was refluxed for 5 hours. After the reaction was complete, water was added to the reaction solution, and the mixture was extracted with ethyl acetate solution. This ethyl acetate solution was washed successively with water, a saturated aqueous sodium hydrogen carbonate solution and an aqueous sodium chloride solution, dried over magnesium sulfate, filtered, and concentrated. The obtained residue was purified by silica gel column chromatography (hexane/ethyl acetate=4/1) to give the title compound (9.5 g) as a red solid.

MS (ESI+) 228 ($M^{+}$+1, 94%).

Reference Example 597

1-Acetyl-6-bromo-1,3-dihydro-2H-indol-2-one

[Chemical formula 744]

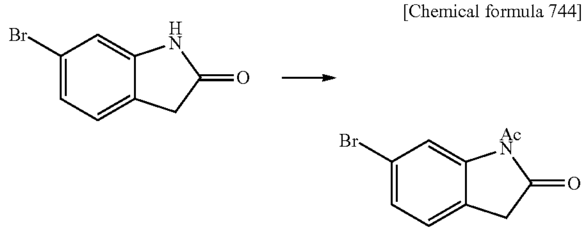

Using 6-bromo-1,3-dihydro-2H-indol-2-one, the title compound was obtained in a similar manner to Reference Example 596.

MS (ESI+) 254 ($M^{+}$+1, 27%).

Reference Example 598

1-Acetyl-6-bromo-3,3-dimethyl-1,3-dihydro-2H-indol-2-one

[Chemical formula 745]

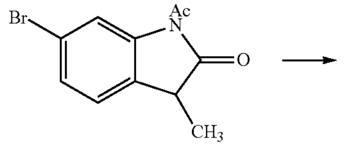

-continued

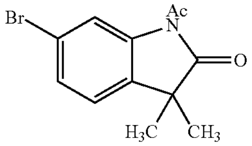

To 1-acetyl-6-bromo-3-methyl-1,3-dihydro-2H-indol-2-one (9.5 g) were added NaH (1.57 g), methyl iodide (2.45 ml) and THF (70 ml) under ice-cooling, and the mixture was stirred at room temperature for 2 hours. After the reaction was complete, water was added to the reaction solution, and the mixture was extracted with ethyl acetate solution. This ethyl acetate solution was washed with water and an aqueous sodium chloride solution, dried over magnesium sulfate, filtered, and concentrated. The obtained residue was purified by silica gel column chromatography (hexane/ethyl acetate=4/1) to give the title compound (5.2 g) as a colorless crystal.

MS (ESI+) 282 ($M^{+}$+1, 34%).

Reference Example 599

1-Acetyl-6-bromo-3,3-diethyl-1,3-dihydro-2H-indol-2-one

[Chemical formula 746]

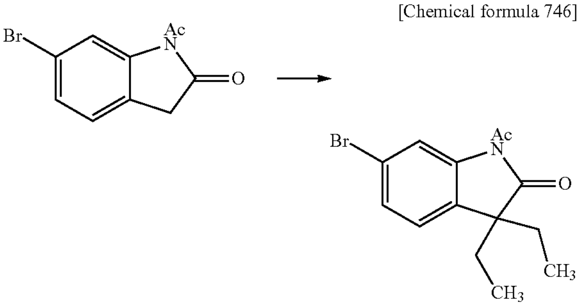

Using 1-acetyl-6-bromo-1,3-dihydro-2H-indol-2-one, the title compound was obtained in a similar manner to Reference Example 598.

MS (ESI+) 311 ($M^{+}$+1, 35%).

Reference Example 600

6-Bromo-3,3-dimethyl-1,3-dihydro-2H-indol-2-one

[Chemical formula 747]

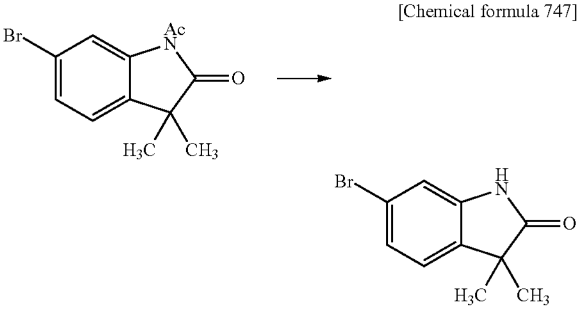

To 1-acetyl-6-bromo-3,3-dimethyl-1,3-dihydro-2H-indol-2-one (5.2 g) were added 1N aqueous NaOH solution (11 ml) and EtOH (44 ml), and the mixture was stirred at room temperature for one hour. After the reaction was complete, the solvent was concentrated, and thereto was added dropwise a 2N aqueous hydrochloric acid solution. The precipitated crystals were extracted with ethyl acetate, and this ethyl acetate solution was washed with water and an aqueous sodium chloride solution, dried over magnesium sulfate, filtered, and concentrated. The obtained residue (4.1 g) was used in the subsequent reaction without further treatment.

MS (ESI+) 326 ($M^+$+1, 62%).

Reference Example 601

6-Bromo-3,3-diethyl-1,3-dihydro-2H-indol-2-one

[Chemical formula 748]

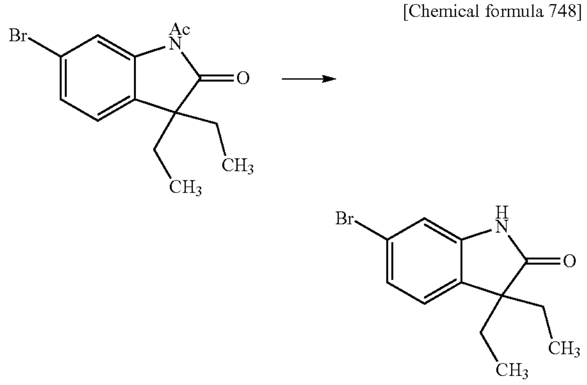

Using 1-acetyl-6-bromo-3,3-diethyl-1,3-dihydro-2H-indol-2-one, the title compound was obtained in a similar manner to Reference Example 600.

MS (ESI+) 269 ($M^+$+1, 35%).

Reference Example 602

6-Bromo-1-(4-methoxybutyl)-3,3-dimethyl-1,3-dihydro-2H-indol-2-one

[Chemical formula 749]

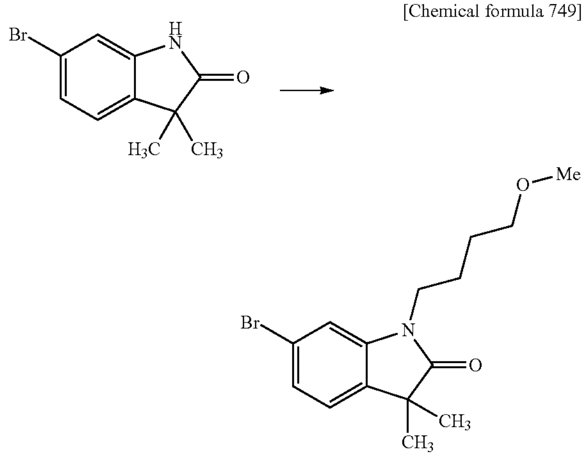

To 6-bromo-3,3-dimethyl-1,3-dihydro-2H-indol-2-one (1.5 g) were added DMF (24 mL) and NaH (326 mg) under ice-cooling, and the mixture was stirred at room temperature 15 minutes. Then, to the mixture were added 4-chloromethyl butyl ether (1.54 g) and potassium iodide (208 mg), and the mixture was stirred at 100° C. for 7 hours. After the reaction was complete, water was added to the reaction solution, and the mixture was extracted with ethyl acetate. This ethyl acetate solution was washed with water and an aqueous sodium chloride solution, dried over magnesium sulfate, filtered, and concentrated. The obtained residue was purified by silica gel column chromatography (hexane/ethyl acetate=4/1) to give the title compound (1.87 g) as a colorless liquid.

MS (ESI+) 325 ($M^+$+1, 63%).

Reference Example 603

Benzyl [2-(6-bromo-3,3-dimethyl-2-oxo-2,3-dihydro-1H-indole-1-yl)ethyl]carbamate

[Chemical formula 750]

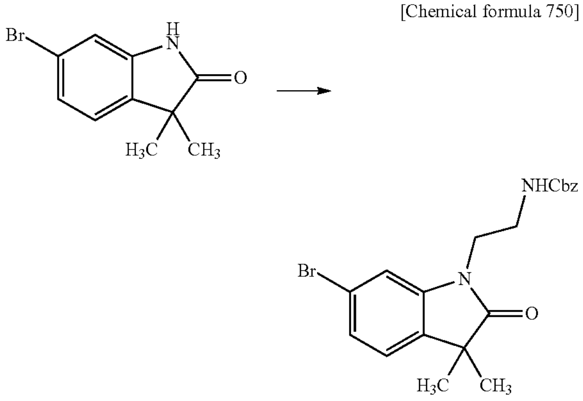

Using 6-bromo-3,3-dimethyl-1,3-dihydro-2H-indol-2-one, the title compound was obtained in a similar manner to Reference Example 602.

MS (ESI+) 417 ($M^+$+1, 24%).

Reference Example 604

Benzyl [2-(6-bromo-3,3-diethyl-2-oxo-2,3-dihydro-1H-indole-1-yl)ethyl]carbamate

[Chemical formula 751]

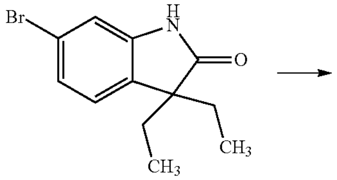

-continued

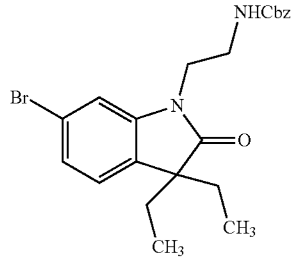

Using 6-bromo-3,3-diethyl-1,3-dihydro-2H-indol-2-one, the title compound was obtained in a similar manner to Reference Example 602.

MS (ESI+) 445 ($M^{+}$+1, 27%).

Reference Example 605

Methyl 1-(4-methoxybutyl)-3,3-dimethyl-2-oxoindoline-6-carboxylate

[Chemical formula 752]

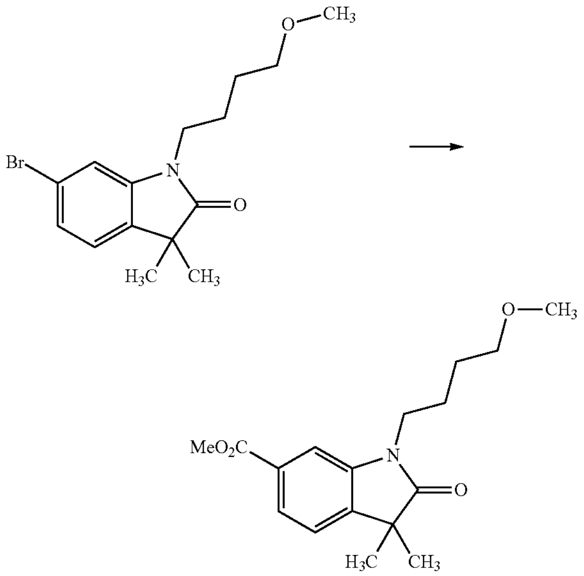

To 6-bromo-1-(4-methoxybutyl)-3,3-dimethyl-1,3-dihydro-2H-indol-2-one (1.0 g) were added palladium acetate (207 mg), triphenylphosphine (484 mg), triethylamine (0.86 ml), methanol (0.62 ml), and DMF (10 ml), and the mixture was stirred at 100° C. under carbon monoxide atmosphere for 4 hours. After the reaction was complete, water was added to the reaction solution, and the mixture was extracted with ethyl acetate solution. This ethyl acetate solution was washed with water and an aqueous sodium chloride solution, dried over magnesium sulfate, filtered, and concentrated. The obtained residue was purified by silica gel column chromatography (hexane/ethyl acetate=3/1) to give the title compound (480 mg) as a pale yellow liquid.

MS (ESI+) 307 ($M^{+}$+1, 46%).

Reference Example 606

Methyl 1-(2-{[(benzyloxy)carbonyl]amino}ethyl)-3,3-dimethyl-2-oxoindoline-6-carboxylate

[Chemical formula 753]

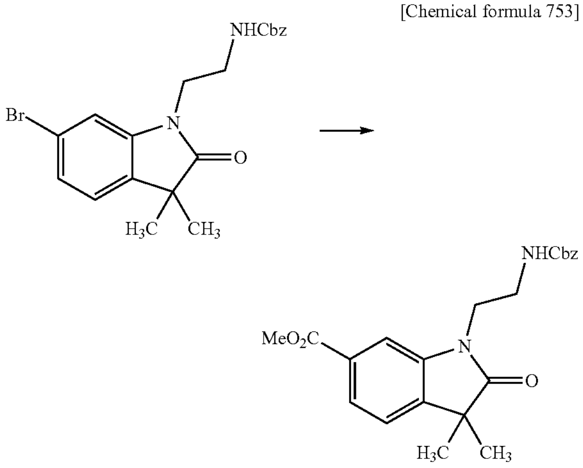

Using the compound of Reference Example 603, the title compound was obtained in a similar manner to Reference Example 605.

MS (ESI+) 397 ($M^{+}$+1, 41%).

Reference Example 607

Methyl 1-(2-{[(benzyloxy)carbonyl]amino}ethyl)-3,3-diethyl-2-oxoindoline-6-carboxylate

[Chemical formula 754]

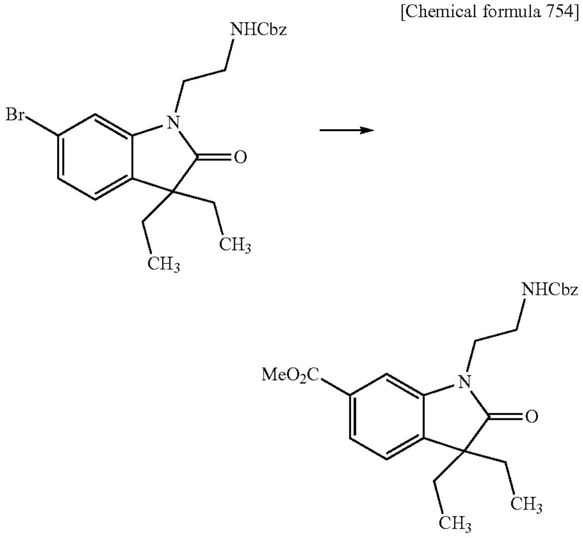

Using the compound of Reference Example 604, the title compound was obtained in a similar manner to Reference Example 605.

MS (ESI+) 425 ($M^{+}$+1, 33%).

Reference Example 608

1-(4-Methoxybutyl)-3,3-dimethyl-2-oxoindoline-6-carboxylic acid

[Chemical formula 755]

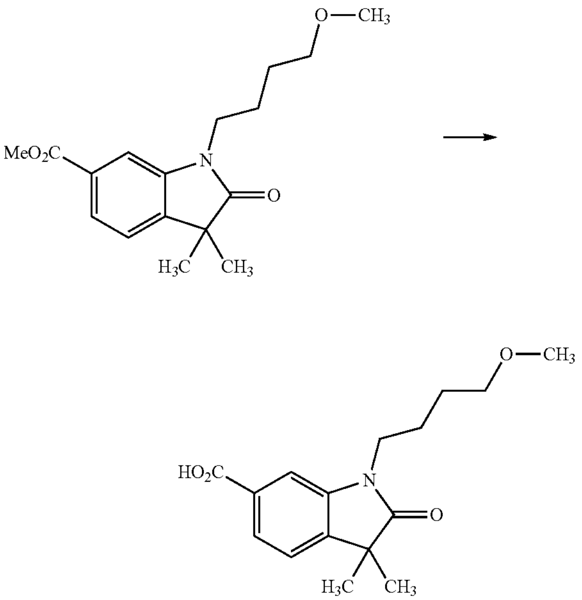

To methyl 1-(4-methoxybutyl)-3,3-dimethyl-2-oxoindoline-6-carboxylate (480 mg) were added 2N aqueous NaOH solution (5 ml), MeOH (5 ml), and THF (5 ml), and the mixture was stirred at 65° C. for one hour. After the reaction was complete, the solvent was concentrated, and to the resultant was added dropwise 2N aqueous hydrochloric acid solution. The precipitated crystals were extracted with ethyl acetate, and this ethyl acetate solution was washed with water and an aqueous sodium chloride solution, dried over magnesium sulfate, filtered, and concentrated. The obtained residue (400 mg) was used in the subsequent reaction without further treatment.

MS (ESI+) 292 ($M^+$+1, 47%).

Reference Example 609

1-(2-{[(Benzyloxy)carbonyl]amino}ethyl)-3,3-dimethyl-2-oxoindoline-6-carboxylic acid

[Chemical formula 756]

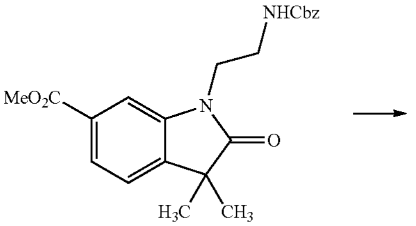

-continued

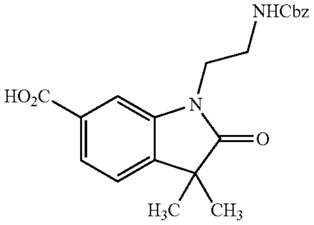

Using the compound of Reference Example 606, the title compound was obtained in a similar manner to Reference Example 608.

MS (ESI+) 383 ($M^+$+1, 22%).

Reference Example 610

1-(2-{[(Benzyloxy)carbonyl]amino}ethyl)-3,3-diethyl-2-oxoindoline-6-carboxylic acid

[Chemical formula 757]

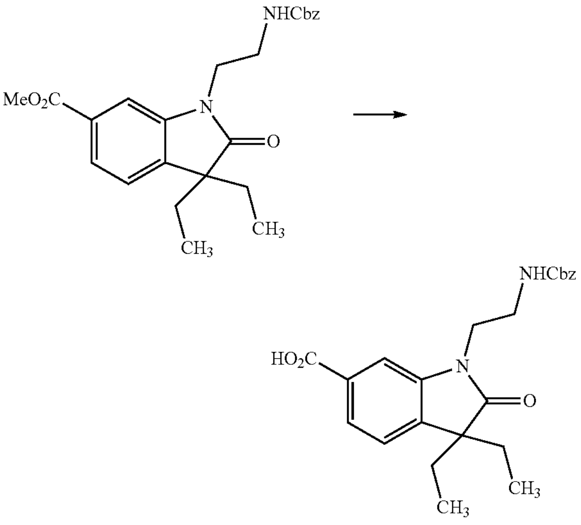

Using the compound of Reference Example 607, the title compound was obtained in a similar manner to Reference Example 608.

MS (ESI+) 411 ($M^+$+1, 21%).

Reference Example 611 tert-Butyl (3R)-3-(isopropyl{[1-(4-methoxybutyl)-3,3-dimethyl-2-oxo-2,3-dihydro-1H-indol-6-yl]carbonyl}amino)piperidine-1-carboxylate

[Chemical formula 758]

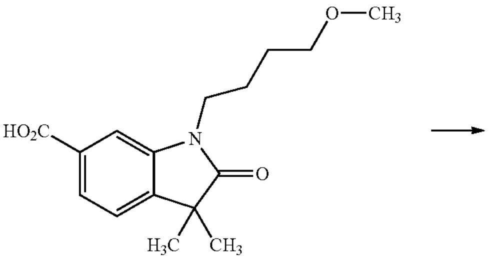

-continued

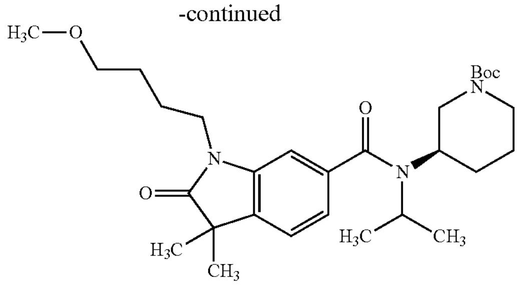

To 1-(4-methoxybutyl)-3,3-dimethyl-2-oxoindoline-6-carboxylic acid (480 mg) were added oxalyl chloride (0.28 ml), DMF (2 drops), chloroform (10 ml), and the mixture was stirred at room temperature for one hour. After the reaction was complete, the solvent was concentrated, and to the obtained residue were added 1-Boc-3R—(N-isopropyl)aminopiperidine (570 mg), triethylamine (0.44 ml), and $CHCl_3$ (10 ml), and the mixture was stirred at room temperature for 2 hours. After the reaction was complete, the mixture was concentrated, and the obtained residue was purified by silica gel column chromatography (hexane/ethyl acetate=1/1) to give the title compound (630 mg) as a colorless liquid.

MS (ESI+) 517 ($M^+$+1, 21%).

Reference Example 612 tert-Butyl (3R)-3-[{[1-(2-{[(benzyloxy)carbonyl] amino}ethyl)-3,3-dimethyl-2-oxo-2,3-dihydro-1H-indol-6-yl]carbonyl}(isopropyl)amino]piperidine-1-carboxylate

[Chemical formula 759]

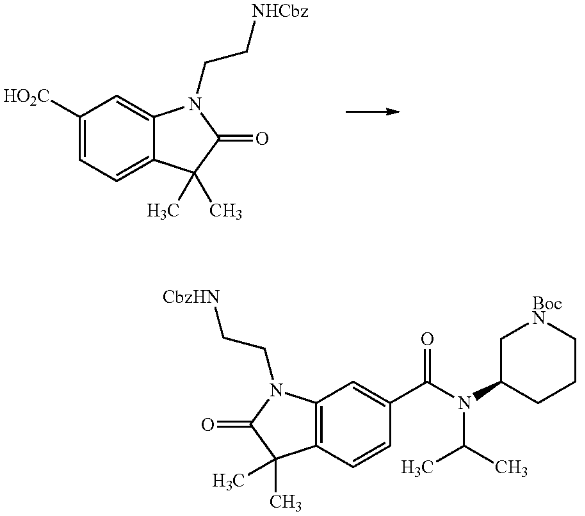

Using the compound of Reference Example 609, the title compound was obtained in a similar manner to Reference Example 611.

MS (ESI+) 607 ($M^+$+1, 56%).

Reference Example 613 tert-Butyl (3R)-3-[{[1-(2-{[(benzyloxy)carbonyl] amino}ethyl)-3,3-diethyl-2-oxo-2,3-dihydro-1H-indol-6-yl]carbonyl}(isopropyl)amino]piperidine-1-carboxylate

[Chemical formula 760]

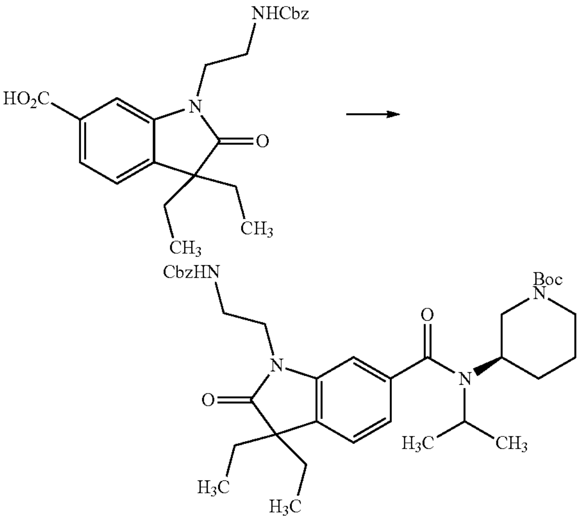

Using the compound of Reference Example 610, the title compound was obtained in a similar manner to Reference Example 611.

MS (ESI+) 635 ($M^+$+1, 19%).

Reference Example 614 tert-Butyl (3R)-3-[{[5-chloro-1-(4-methoxybutyl)-3,3-dimethyl-2-oxo-2,3-dihydro-1H-indol-6-yl]carbonyl}(isopropyl)amino]piperidine-1-carboxylate

[Chemical formula 761]

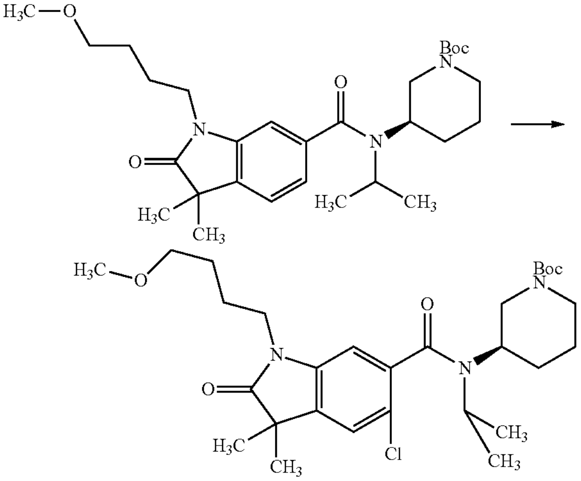

To tert-butyl (3R)-3-(isopropyl{[1-(4-methoxybutyl)-3,3-dimethyl-2-oxo-2,3-dihydro-1H-indol-6-yl]carbonyl}amino)piperidine-1-carboxylate (220 mg) were added NCS (86 mg) and DMF (5 ml), and the mixture was stirred at 65° C. for one hour. After the reaction was complete, water was added to the reaction solution, and the mixture was extracted with ethyl acetate solution. This ethyl acetate was washed with water and an aqueous sodium chloride solution, dried over magnesium sulfate, filtered and concentrated. The obtained residue was purified by silica gel column chromatography (hexane/ethyl acetate=1/1) to give the title compound (200 mg) as a colorless liquid.

MS (ESI+) 551 ($M^{+}$+1, 18%).

Reference Example 615 tert-Butyl (3R)-3-[{[1-(2-aminoethyl)-3,3-dimethyl-2-oxo-2,3-dihydro-1H-indol-6-yl]carbonyl}-(isopropyl)amino]piperidine-1-carboxylate

[Chemical formula 762]

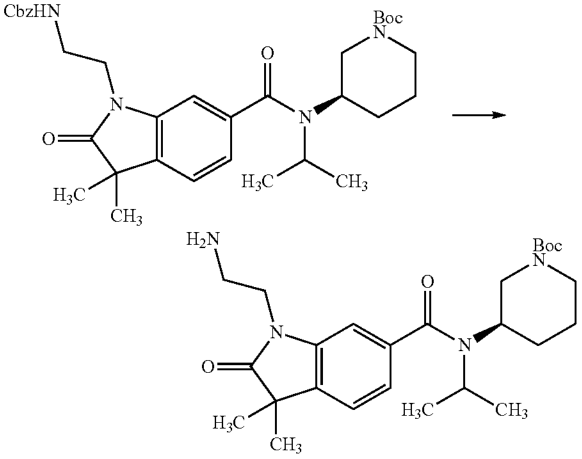

To tert-butyl (3R)-3-[{[1-(2-{[(benzyloxy)carbonyl]amino}ethyl)-3,3-dimethyl-2-oxo-2,3-dihydro-1H-indol-6-yl]carbonyl}(isopropyl)amino]piperidine-1-carboxylate (800 mg) were added 10% Pd/C (400 mg) and methanol (30 ml), and the mixture was stirred at room temperature under hydrogen atmosphere for 2 hours. After the reaction was complete, the mixture was filtered and concentrated. The obtained residue (600 mg) was used in the subsequent reaction without further treatment.

MS (ESI+) 473 ($M^{+}$+1, 29%).

Reference Example 616 tert-Butyl (3R)-3-[{[1-(2-aminoethyl)-3,3-diethyl-2-oxo-2,3-dihydro-1H-indol-6-yl]carbonyl}-(isopropyl)amino]piperidine-1-carboxylate

[Chemical formula 763]

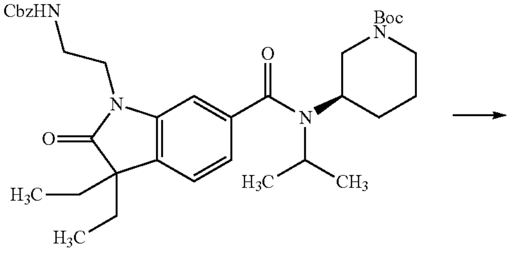

-continued

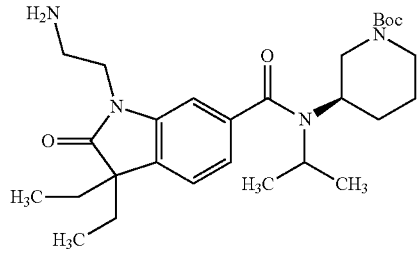

Using the compound of Reference Example 613, the title compound was obtained in a similar manner to Reference Example 615.

MS (ESI+) 501 ($M^{+}$+1, 27%).

Reference Example 617 tert-Butyl (3R)-3-[({3,3-dimethyl-2-oxo-1-[2-(propionylamino)ethyl]-2,3-dihydro-1H-indol-6-yl}carbonyl)(isopropyl)amino]piperidine-1-carboxylate

[Chemical formula 764]

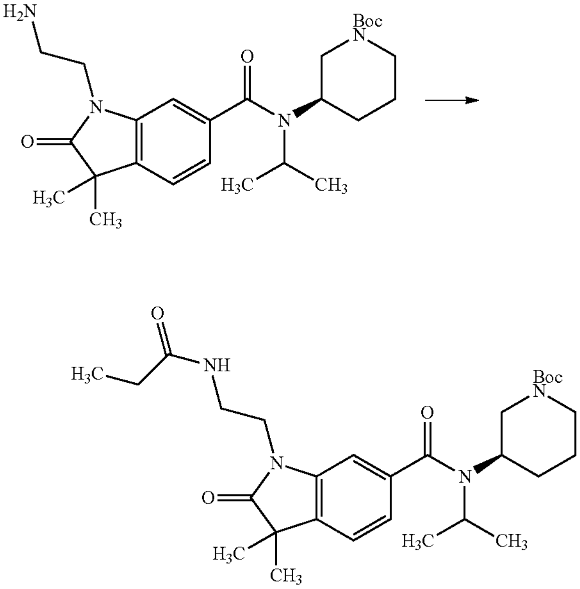

To tert-butyl (3R)-3-[{[1-(2-aminoethyl)-3,3-dimethyl-2-oxo-2,3-dihydro-1H-indol-6-yl]carbonyl}(isopropyl)amino]piperidine-1-carboxylate (300 mg) were added triethylamine (0.14 ml), THF (3 ml) and acetyl chloride (0.07 ml) under ice-cooling, and the mixture was stirred at room temperature for one hour. After the reaction was complete, the mixture was concentrated, and the obtained residue was purified by silica gel column chromatography (chloroform/methanol=9/1) to give the title compound (190 mg) as colorless amorphous.

MS (ESI+) 529 ($M^{+}$+1, 39%).

Reference Example 618 tert-Butyl (3R)-3-[({3,3-diethyl-2-oxo-1-[2-(propionylamino)ethyl]-2,3-dihydro-1H-indol-6-yl}-carbonyl)(isopropyl)amino]piperidine-1-carboxylate

[Chemical formula 765]

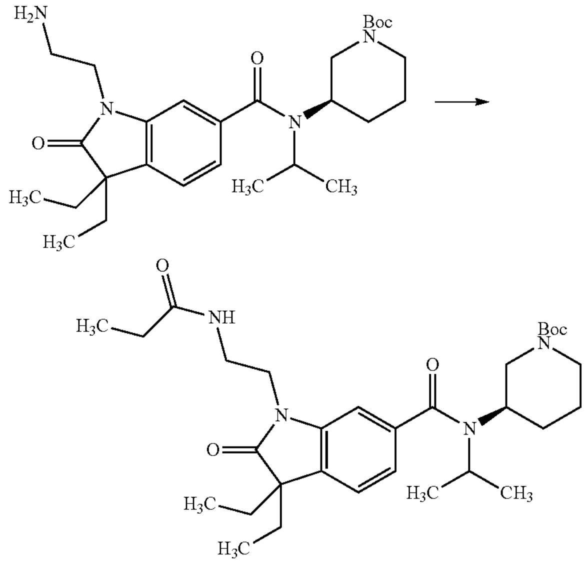

Using the compound of Reference Example 616, the title compound was obtained in a similar manner to Reference Example 617.

MS (ESI+) 557 ($M^+$+1, 34%).

Reference Example 619 tert-Butyl (3R)-3-[[(1-{2-[(difluoroacetyl)amino]ethyl}-3,3-dimethyl-2-oxo-2,3-dihydro-1H-indol-6-yl)carbonyl](isopropyl)amino]piperidine-1-carboxylate

[Chemical formula 766]

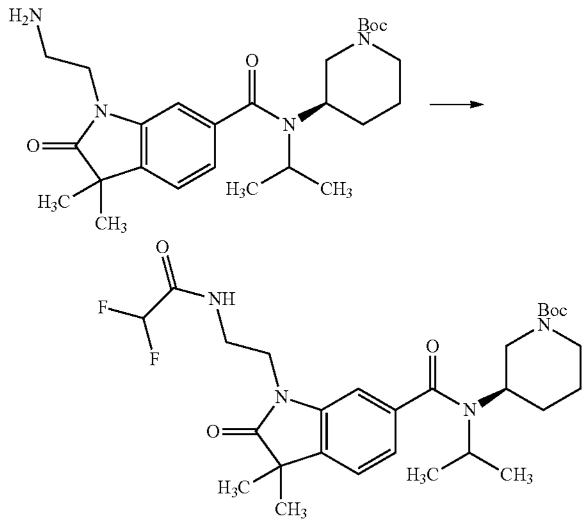

To tert-butyl (3R)-3-[{[1-(2-aminoethyl)-3,3-dimethyl-2-oxo-2,3-dihydro-1H-indol-6-yl]-carbonyl}(isopropyl)amino]piperidine-1-carboxylate (300 mg) were added WSC (210 mg), HOBt (150 mg), triethylamine (0.30 ml), chloroform (5 ml), and difluoroacetic acid (79 mg), and the mixture was stirred at room temperature overnight. After the reaction was complete, the mixture was concentrated, and the obtained residue was purified by silica gel column chromatography (chloroform/methanol=9/1) to give the title compound (170 mg) as colorless amorphous.

MS (ESI+) 551 ($M^+$+1, 35%).

Reference Example 620 tert-Butyl (3R)-3-[({5-chloro-3,3-dimethyl-2-oxo-1-[2-(propionylamino)ethyl]-2,3-dihydro-1H-indol-6-yl}carbonyl)(isopropyl)amino]piperidine-1-carboxylate

[Chemical formula 767]

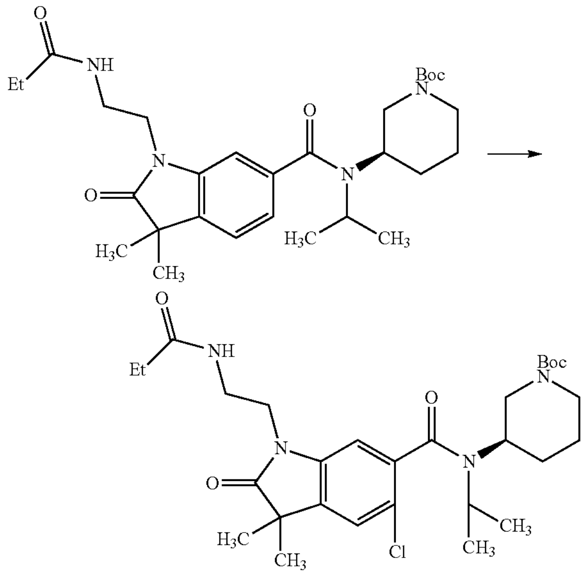

Using the compound of Reference Example 617, the title compound was obtained in a similar manner to Reference Example 614.

MS (ESI+) 563 ($M^+$+1, 30%).

Reference Example 621 tert-Butyl (3R)-3-[[(5-chloro-1-{2-[(difluoroacetyl)amino]ethyl}-3,3-dimethyl-2-oxo-2,3-dihydro-1H-indol-6-yl)carbonyl](isopropyl)amino]piperidine-1-carboxylate

[Chemical formula 768]

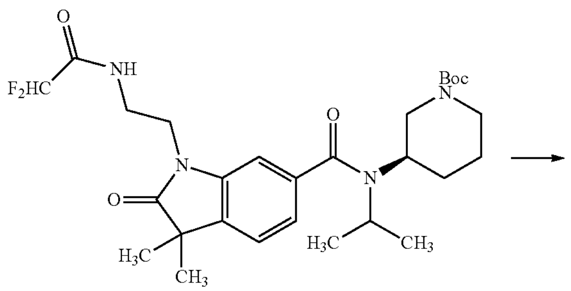

-continued

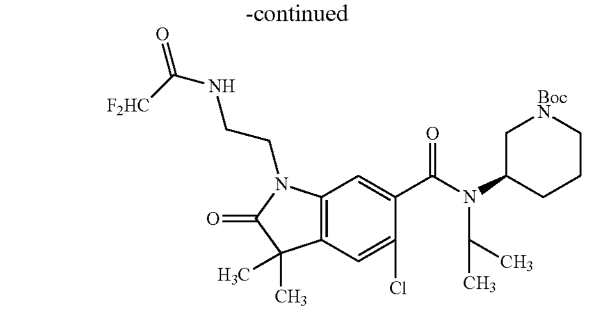

Using the compound of Reference Example 619, the title compound was obtained in a similar manner to Reference Example 614.

MS (ESI+) 585 ($M^{+}$+1, 23%).

Reference Example 622 tert-Butyl (3R)-3-[({5-chloro-3,3-diethyl-2-oxo-1-[2-(propionylamino)ethyl]-2,3-dihydro-1H-indol-6-yl]carbonyl)(isopropyl)amino]piperidine-1-carboxylate

[Chemical formula 769]

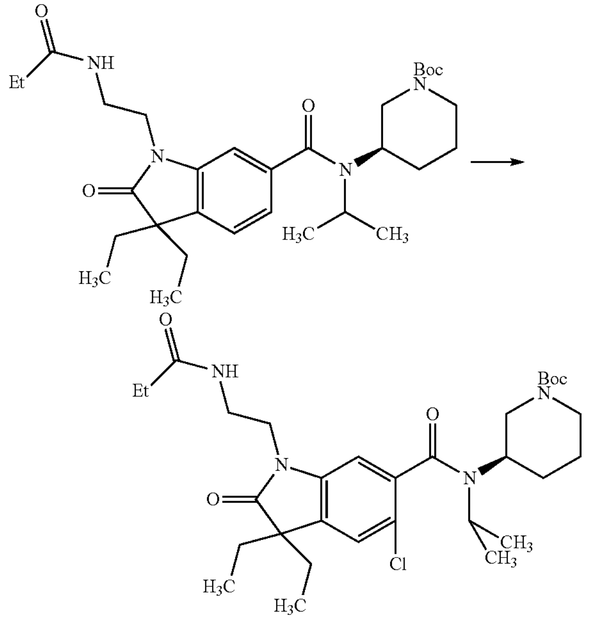

Using the compound of Reference Example 618, the title compound was obtained in a similar manner to Reference Example 614.

MS (ESI+) 591 ($M^{+}$+1, 13%).

Reference Example 623

4-Fluoro-2-methyl-5-nitrobenzoic acid

[Chemical formula 770]

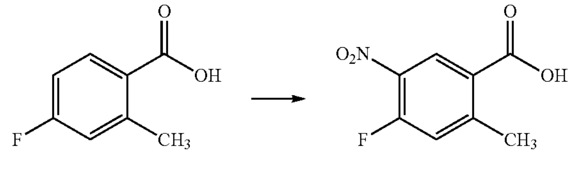

To a suspension of 4-fluoro-2-methylbenzoic acid (32.5 g) in conc. sulfuric acid (50 ml) was added dropwise conc. nitric acid (8.4 ml) at 0° C., and the mixture was stirred at room temperature for 5 hours. The reaction mixture was poured into ice-water (500 ml), and the mixture was extracted with diisopropyl ether (300 ml), and the organic layer was washed with water, and a saturated aqueous sodium chloride solution, dried over sodium sulfate, filtered, concentrated under reduced pressure to give the title compound (40.0 g).

MS (ESI+) 200 ($M^{+}$+1, 100%).

Reference Example 624

Methyl 4-fluoro-2-methyl-5-nitrobenzoate

[Chemical formula 771]

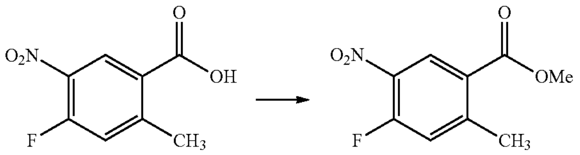

Using 4-fluoro-2-methyl-5-nitrobenzoic acid, the title compound was obtained in a similar manner to Reference Example 51.

MS (ESI+) 214 ($M^{+}$+1, 100%).

Reference Example 625

Methyl 4-{[1-(methoxycarbonyl)cyclopropyl]oxy}-2-methyl-5-nitrobenzoate

[Chemical formula 772]

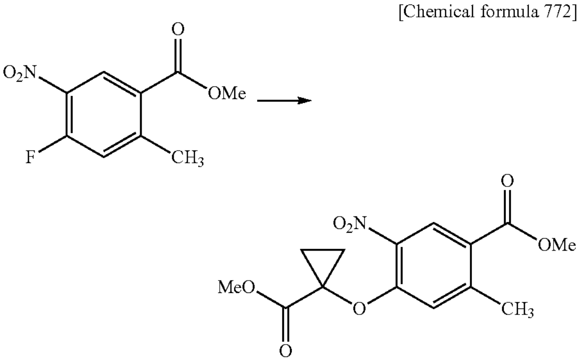

Methyl 4-fluoro-2-methyl-5-nitrobenzoate (43.0 g) was dissolved in tetrahydrofuran (300 ml), and thereto was added sodium hydride (55%, 9.60 g) at 0° C., and the mixture was stirred for 30 minutes. To the mixture was added dropwise a solution of methyl 1-hydroxy-1-cyclopropanecarboxylate (22.0 g) in tetrahydrofuran (300 ml) at 0° C., and the mixture was further stirred at room temperature for 3 hours. The mixture was cooled to room temperature, and water (100 ml) was added to the reaction mixture. The mixture was neutralized by addition of 1N aqueous hydrochloric acid solution, and extracted twice with ethyl acetate (300 ml). The organic layer was washed with water, a saturated aqueous sodium hydrogen carbonate solution, and a saturated aqueous sodium chloride solution, dried over sodium sulfate, filtered, and concentrated under reduced pressure. The resultant was purified by silica gel column (hexane/ethyl acetate=3:1) to give the title compound (58.0 g).

MS (ESI+) 310 ($M^{+}$+1, 100%).

Reference Example 626

Methyl 7-methyl-3-oxo-3,4-dihydrospiro[1,4-benzoxazine-2,1'-cyclopropane]-6-carboxylate

[Chemical formula 773]

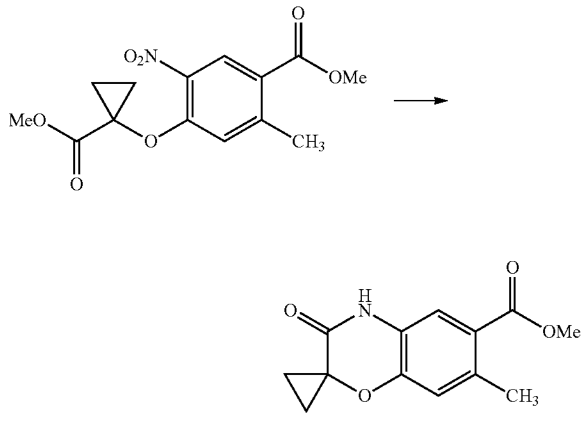

Using methyl 4-{[1-(methoxycarbonyl)cyclopropyl]oxy}-2-methyl-5-nitrobenzoate, the title compound was obtained in a similar manner to Reference Example 2.

MS (ESI+) 248 ($M^{+}$+1, 100%).

Reference Example 627

Methyl 4-(2-{[(benzyloxy)carbonyl]amino}ethyl)-7-methyl-3-oxo-3,4-dihydrospiro[1,4-benzoxazine-2,1'-cyclopropane]-6-carboxylate

[Chemical formula 774]

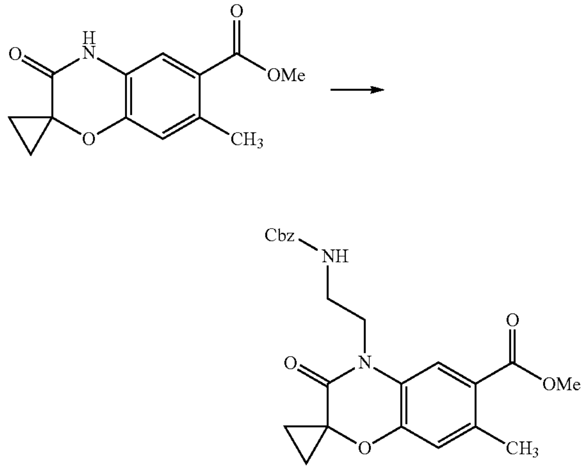

Using methyl 7-methyl-3-oxo-3,4-dihydrospiro[1,4-benzoxazine-2,1'-cyclopropane]-6-carboxylate, the title compound was obtained in a similar manner to Reference Example 3.

MS (ESI+) 425 ($M^{+}$+1, 100%).

Reference Example 628

4-(2-{[(Benzyloxy)carbonyl]amino}ethyl)-7-methyl-3-oxo-3,4-dihydrospiro[1,4-benzoxazine-2,1'-cyclopropane]-6-carboxylic acid

[Chemical formula 775]

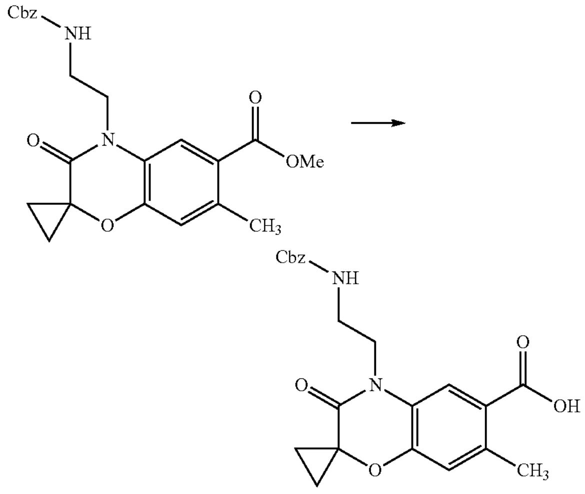

Using methyl 4-(2-{[(benzyloxy)carbonyl]amino}ethyl)-7-methyl-3-oxo-3,4-dihydrospiro[1,4-benzoxazine-2,1'-cyclopropane]-6-carboxylate, the title compound was obtained in a similar manner to Reference Example 4.

MS (ESI+) 411 ($M^{+}$+1, 100%).

Reference Example 629 tert-Butyl (3R)-3-[{[4-(2-{[(benzyloxy)carbonyl]amino}ethyl)-7-methyl-3-oxo-3,4-dihydrospiro[1,4-benzoxazine-2,1'-cyclopropan]-6-yl]carbonyl}(isopropyl)amino]piperidine-1-carboxylate

[Chemical formula 776]

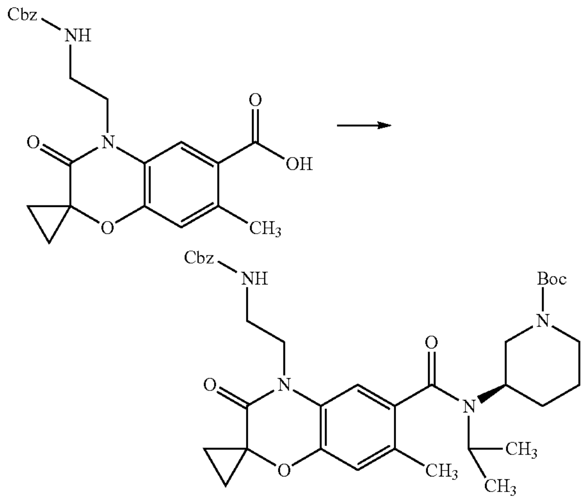

Using methyl 4-(2-{[(benzyloxy)carbonyl]amino}ethyl)-7-methyl-3-oxo-3,4-dihydrospiro[1,4-benzoxazine-2,1'-cyclopropane]-6-carboxylic acid, the title compound was obtained in a similar manner to Reference Example 5.

MS (ESI+) 635 ($M^{+}$+1, 100%).

Reference Example 630 tert-Butyl (3R)-3-[{[4-(2-aminoethyl)-7-methyl-3-oxo-3,4-dihydrospiro[1,4-benzoxazine-2,1'-cyclopropan]-6-yl]carbonyl}(isopropyl)amino]piperidine-1-carboxylate

[Chemical formula 777]

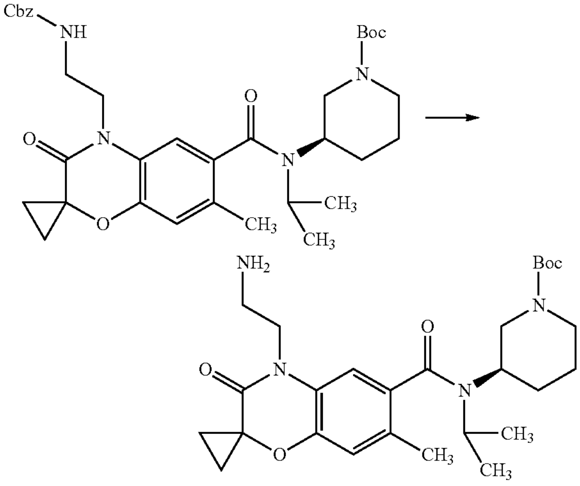

Using tert-butyl (3R)-3-[{[4-(2-{[(benzyloxy)carbonyl]amino}ethyl)-7-methyl-3-oxo-3,4-dihydrospiro[1,4-benzoxazine-2,1'-cyclopropan]-6-yl]carbonyl}(isopropyl)amino]piperidine-1-carboxylate, the title compound was obtained in a similar manner to Reference Example 139.

MS (ESI+) 501 ($M^{+}$+1, 100%).

Reference Example 631

N-Isopropyl-7-methyl-3-oxo-N-[(3R)-piperidin-3-yl]-4-[2-(propionylamino)ethyl]-3,4-dihydrospiro[1,4-benzoxazine-2,1'-cyclopropane]-6-carboxamide hydrochloride

[Chemical formula 778]

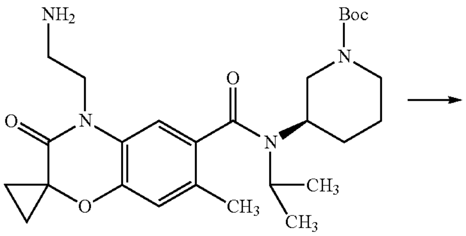

-continued

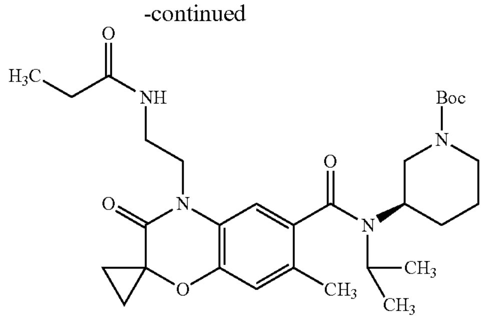

Using tert-butyl (3R)-3-[{[4-(2-aminoethyl)-7-methyl-3-oxo-3,4-dihydrospiro[1,4-benzoxazine-2,1'-cyclopropan]-6-yl]carbonyl}(isopropyl)amino]piperidine-1-carboxylate, the title compound was obtained in a similar manner to Reference Example 120.

MS (ESI+) 557 ($M^{+}$+1, 100%).

Reference Example 632

4-{2-[(Difluoroacetyl)amino]ethyl}-N-isopropyl-7-methyl-3-oxo-N-[(3R)-piperidin-3-yl]-3,4-dihydrospiro[1,4-benzoxazine-2,1'-cyclopropane]-6-carboxamide hydrochloride

[Chemical formula 779]

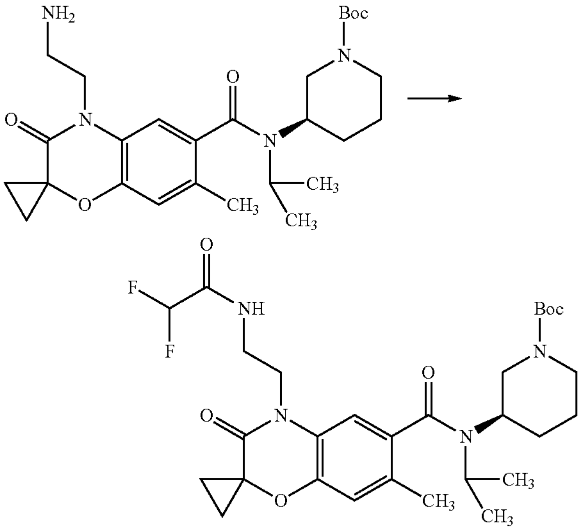

Using tert-butyl (3R)-3-[{[4-(2-aminoethyl)-7-methyl-3-oxo-3,4-dihydrospiro[1,4-benzoxazine-2,1'-cyclopropan]-6-yl]carbonyl}(isopropyl)amino]piperidine-1-carboxylate, the title compound was obtained in a similar manner to Reference Example 120.

MS (ESI+) 579 ($M^{+}$+1, 100%).

Reference Example 636 tert-Butyl (3R)-3-[[4-hydroxy-5-nitro-2-(trifluoromethyl)benzoyl](isopropyl)amino]piperidine-1-carboxylate

[Chemical formula 780]

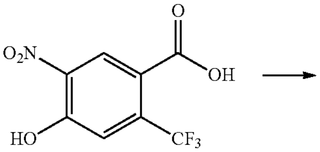

-continued

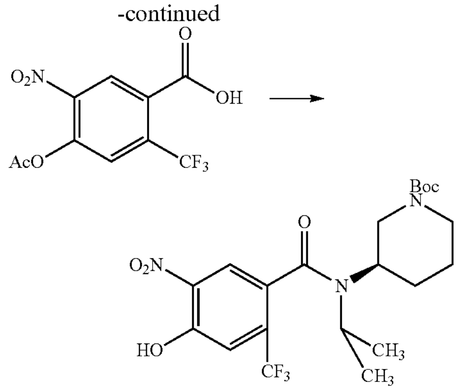

Using methyl 4-hydroxy-5-nitro-2-(trifluoromethyl)benzoate, the title compound was obtained in a similar manner to Reference Example 31.

MS (ESI+) 476 ($M^{+}$+1, 100%).

Reference Example 637

Diethyl [4-{[[(3R)-1-(tert-butoxycarbonyl)piperidin-3-yl](isopropyl)amino]carbonyl}-2-nitro-5-(trifluoromethyl)phenoxy](methyl)malonate

[Chemical formula 781]

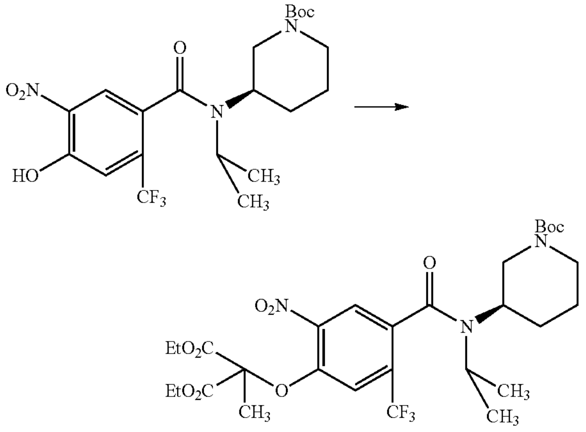

Using tert-butyl (3R)-3-[[4-hydroxy-5-nitro-2-(trifluoromethyl)benzoyl](isopropyl)amino]-piperidine-1-carboxylate, the title compound was obtained in a similar manner to Reference Example 32.

MS (ESI+) 648 ($M^{+}$+1, 100%).

Reference Example 638

Ethyl 4-(2-{[(benzyloxy)carbonyl]amino}ethyl)-6-{[[(3R)-1-(tert-butoxycarbonyl)piperidin-3-yl]-(isopropyl)amino]carbonyl}-2-methyl-3-oxo-7-(trifluoromethyl)-3,4-dihydro-2H-1,4-benzoxazine-2-carboxylate

[Chemical formula 782]

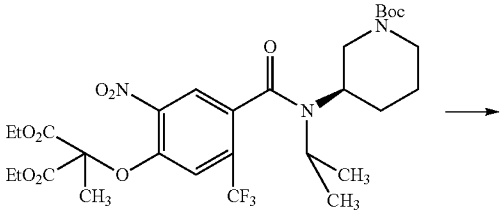

-continued

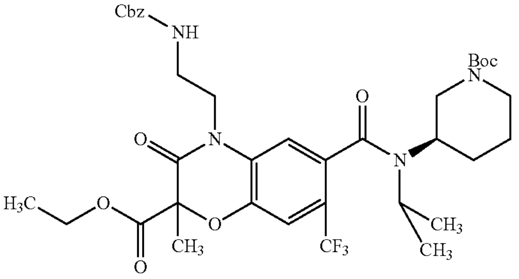

Using diethyl [4-{[[(3R)-1-(tert-butoxycarbonyl)piperidin-3-yl](isopropyl)amino]carbonyl}-2-nitro-5-(trifluoromethyl)phenoxy](methyl)malonate, the title compound was obtained in a similar manner to Reference Example 33.

MS (ESI+) 749 ($M^{+}$+1, 100%).

Reference Example 639

Ethyl 4-(2-{benzyl[(benzyloxy)carbonyl]amino}ethyl)-6-{[[(3R)-1-(tert-butoxycarbonyl)piperidin-3-yl](isopropyl)amino]carbonyl}-2-methyl-3-oxo-7-(trifluoromethyl)-3,4-dihydro-2H-1,4-benzoxazine-2-carboxylate

[Chemical formula 783]

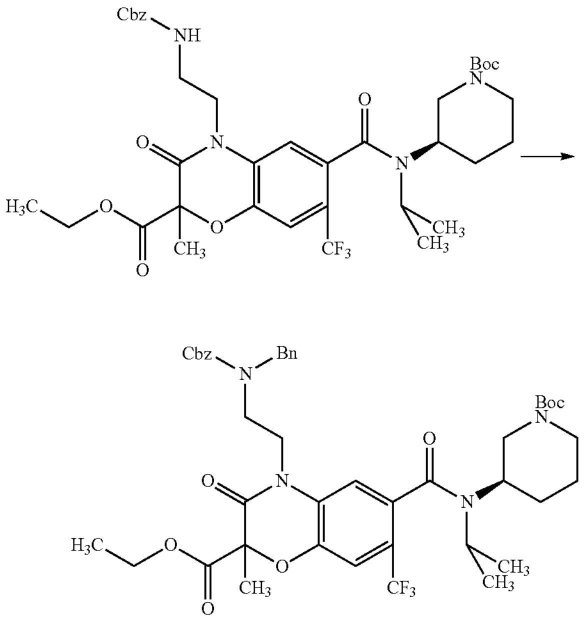

Using ethyl 4-(2-{[(benzyloxy)carbonyl]amino}ethyl)-6-{[[(3R)-1-(tert-butoxycarbonyl)-piperidin-3-yl](isopropyl)amino]carbonyl}-2-methyl-3-oxo-7-(trifluoromethyl)-3,4-dihydro-2H-1,4-benzoxazine-2-carboxylate, the title compound was obtained in a similar manner to Reference Example 34.

MS (ESI+) 839 ($M^{+}$+1, 100%).

Reference Example 640

4-(2-{Benzyl[(benzyloxy)carbonyl]amino}ethyl)-6-{[[(3R)-1-(tert-butoxycarbonyl)piperidin-3-yl](isopropyl)amino]carbonyl}-2-methyl-3-oxo-7-(trifluoromethyl)-3,4-dihydro-2H-1,4-benzoxazine-2-carboxylic acid

[Chemical formula 784]

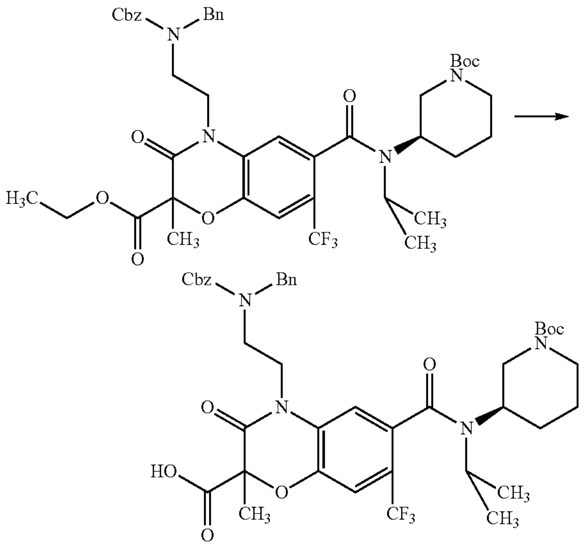

Using ethyl 4-(2-{[(benzyloxy)carbonyl]amino}ethyl)-6-{[[(3R)-1-(tert-butoxycarbonyl)-piperidin-3-yl](isopropyl)amino]carbonyl}-2-methyl-3-oxo-7-(trifluoromethyl)-3,4-dihydro-2H-1,4-benzoxazine-2-carboxylate, the title compound was obtained in a similar manner to Reference Example 34.

MS (ESI+) 811 ($M^{+}$+1, 100%).

Reference Example 641 tert-Butyl (3R)-3-[{[4-(2-{benzyl[(benzyloxy)carbonyl]amino}ethyl)-2-(hydroxymethyl)-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 785]

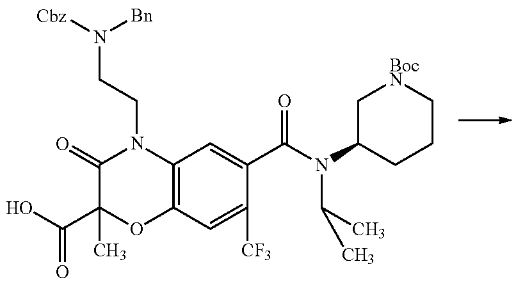

-continued

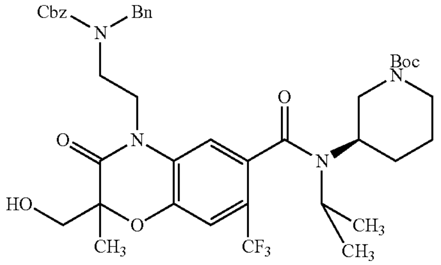

Using 4-(2-{benzyl[(benzyloxy)carbonyl]amino}ethyl)-6-{[[(3R)-1-(tert-butoxycarbonyl)-piperidin-3-yl](isopropyl)amino]carbonyl}-2-methyl-3-oxo-7-(trifluoromethyl)-3,4-dihydro-2H-1,4-benzoxazine-2-carboxylic acid, the title compound was obtained in a similar manner to Reference Example 35.

MS (ESI+) 797 ($M^{+}$+1, 100%).

Reference Example 642 tert-Butyl (3R)-3-[{[4-(2-{benzyl[(benzyloxy)carbonyl]amino}ethyl)-2-(methoxymethyl)-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 786]

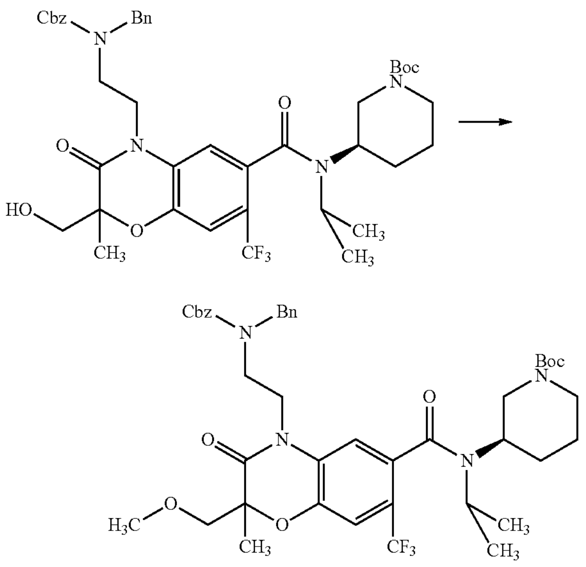

Using tert-butyl (3R)-3-[{[4-(2-{benzyl[(benzyloxy)carbonyl]amino}ethyl)-2-(hydroxy-methyl)-2-methyl-3-oxo-7-(trifluoromethyl)-3,4-dihydro-2H-1,4-benzoxazin-6-yl]carbonyl}(isopropyl)-amino]piperidine-1-carboxylate, the title compound was obtained in a similar manner to Reference Example 36.

MS (ESI+) 811 ($M^{+}$+1, 100%).

Reference Example 643 tert-Butyl (3R)-3-[{[4-(2-{benzyl[(benzyloxy)carbonyl]amino}ethyl)-2-methyl-3-oxo-2-[(tetrahydro-2H-pyran-2-yloxy)methyl]-7-(trifluoromethyl)-3,4-dihydro-2H-1,4-benzoxazin-6-yl]carbonyl}-(isopropyl) amino]piperidine-1-carboxylate

[Chemical formula 787]

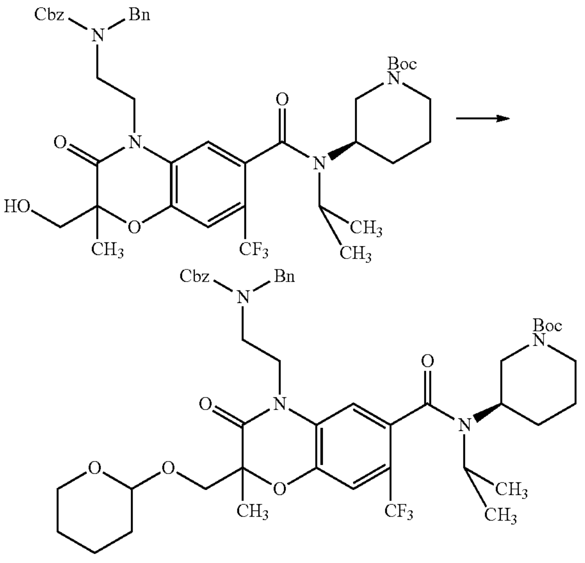

To a solution of tert-butyl (3R)-3-[{[4-(2-{benzyl[(benzyloxy)carbonyl]amino}ethyl)-2-(hydroxymethyl)-2-methyl-3-oxo-7-(trifluoromethyl)-3,4-dihydro-2H-1,4-benzoxazin-6-yl]carbonyl}(isopropyl)amino]piperidine-1-carboxylate in methylene chloride (4.0 ml) were added 3,4-dihydro-2H-pyran (86 μl) and pyridinium p-toluenesulfonate (6.3 mg), and the mixture was stirred at room temperature for 12 hours. To the reaction mixture was added water (3 ml), and the mixture was extracted with methylene chloride (5 ml). The organic layer was washed with water and a saturated aqueous sodium chloride solution, dried over sodium sulfate, filtered, concentrated under reduced pressure to give the title compound (440 mg).

MS (ESI+) 881 ($M^+$+1, 100%).

Reference Example 644 tert-Butyl (3R)-3-[{[4-(2-aminoethyl)-2-(methoxymethyl)-2-methyl-3-oxo-7-(trifluoromethyl)-3,4-dihydro-2H-1,4-benzoxazin-6-yl]carbonyl}(isopropyl) amino]piperidine-1-carboxylate

[Chemical formula 788]

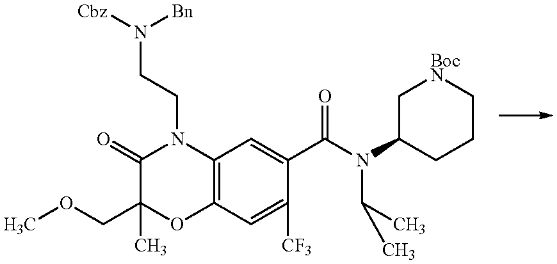

-continued

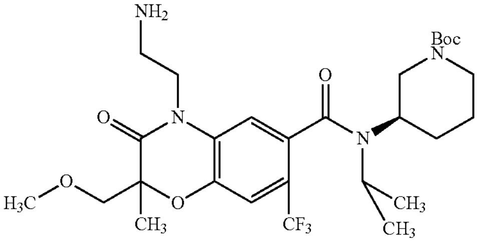

Using tert-butyl (3R)-3-[{[4-(2-{benzyl[(benzyloxy)carbonyl]amino}ethyl)-2-(methoxy-methyl)-2-methyl-3-oxo-7-(trifluoromethyl)-3,4-dihydro-2H-1,4-benzoxazin-6-yl] carbonyl}-(isopropyl)amino]piperidine-1-carboxylate, the title compound was obtained in a similar manner to Reference Example 139.

MS (ESI+) 587 ($M^+$+1, 100%).

Reference Example 645 tert-Butyl (3R)-3-[{[4-(2-aminoethyl)-2-methyl-3-oxo-2-[(tetrahydro-2H-pyran-2-yloxy)methyl]-7-(trifluoromethyl)-3,4-dihydro-2H-1,4-benzoxazin-6-yl]carbonyl}(isopropyl)amino]piperidine-1-carboxylate

[Chemical formula 789]

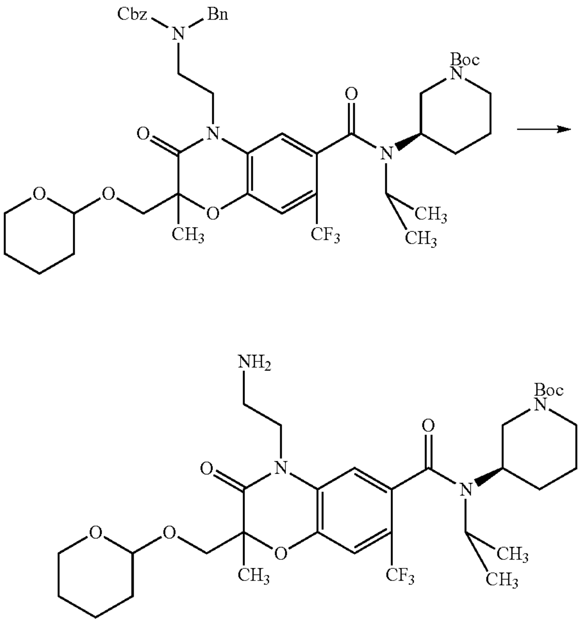

Using tert-butyl (3R)-3-[{[4-(2-{benzyl[(benzyloxy)carbonyl]amino}ethyl)-2-methyl-3-oxo-2-[(tetrahydro-2H-pyran-2-yloxy)methyl]-7-(trifluoromethyl)-3,4-dihydro-2H-1,4-benzoxazin-6-yl]carbonyl}(isopropyl)amino]piperidine-1-carboxylate, the title compound was obtained in a similar manner to Reference Example 139.

MS (ESI+) 657 ($M^+$+1, 100%).

Reference Example 646 tert-Butyl (3R)-3-[{[4-{2-[(difluoroacetyl)amino]ethyl}-2-(methoxymethyl)-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 790]

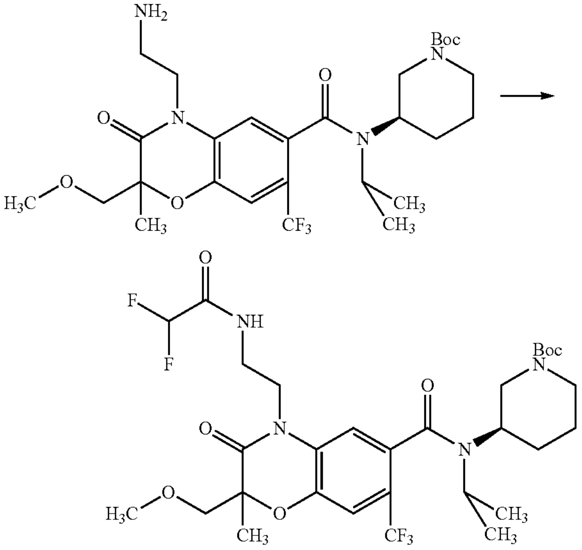

Using tert-butyl (3R)-3-[{[4-(2-aminoethyl)-2-(methoxymethyl)-2-methyl-3-oxo-7-(trifluoromethyl)-3,4-dihydro-2H-1,4-benzoxazin-6-yl]carbonyl}(isopropyl)amino]piperidine-1-carboxylate, the title compound was obtained in a similar manner to Reference Example 112.

MS (ESI+) 665 ($M^+$+1, 100%).

Reference Example 647 tert-Butyl (3R)-3-[{[4-{2-[(difluoroacetyl)amino]ethyl}-2-methyl-3-oxo-2-[(tetrahydro-2H-pyran-2-yloxy)methyl]-7-(trifluoromethyl)-3,4-dihydro-2H-1,4-benzoxazin-6-yl]carbonyl}(isopropyl)amino]-piperidine-1-carboxylate

[Chemical formula 791]

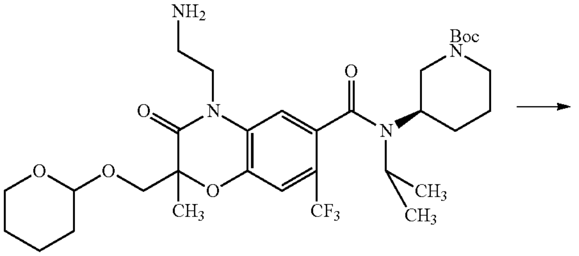

-continued

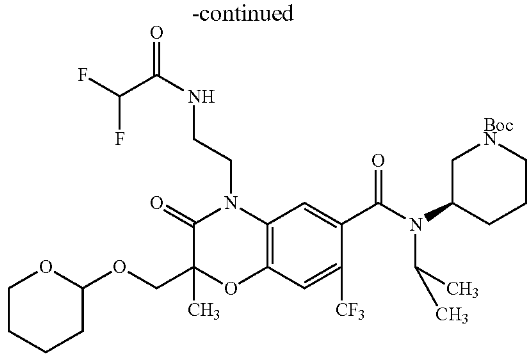

Using tert-butyl (3R)-3-[{[4-(2-aminoethyl)-2-methyl-3-oxo-2-[(tetrahydro-2H-pyran-2-yloxy)-methyl]-7-(trifluoromethyl)-3,4-dihydro-2H-1,4-benzoxazin-6-yl]carbonyl}(isopropyl)amino]-piperidine-1-carboxylate, the title compound was obtained in a similar manner to Reference Example 112.

MS (ESI+) 735 ($M^+$+1, 100%).

Reference Example 648 tert-Butyl (3R)-3-(cyclobutyl {[2,2-dimethyl-3-oxo-4-[2-(propionylamino)ethyl]-7-(trifluoromethyl)-3,4-dihydro-2H-1,4-benzoxazin-6-yl]carbonyl}amino)piperidine-1-carboxylate

[Chemical formula 792]

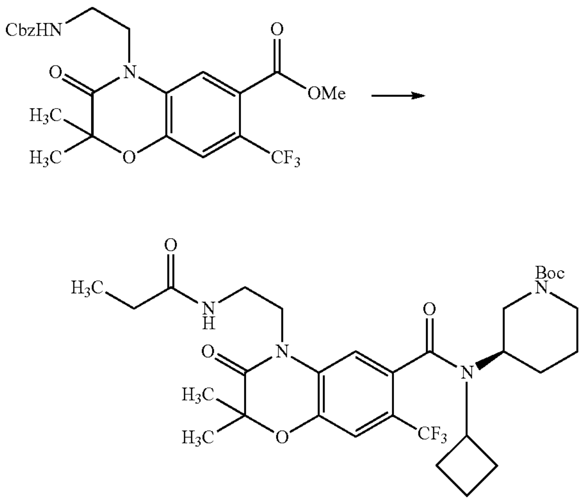

Using methyl 4-(2-{[(benzyloxy)carbonyl]amino}ethyl)-2,2-dimethyl-3-oxo-7-(trifluoromethyl)-3,4-dihydro-2H-1,4-benzoxazine-6-carboxylate, the title compound was obtained in a similar manner to Reference Examples 4, 5.

MS (ESI+) 625 (M+1, 67%).

Reference Example 649 tert-Butyl (3R)-3-((cyclopropylmethyl) {[2,2-dimethyl-3-oxo-4-[2-(propionylamino)ethyl]-7-(trifluoromethyl)-3,4-dihydro-2H-1,4-benzoxazin-6-yl]carbonyl}amino)piperidine-1-carboxylate

[Chemical formula 793]

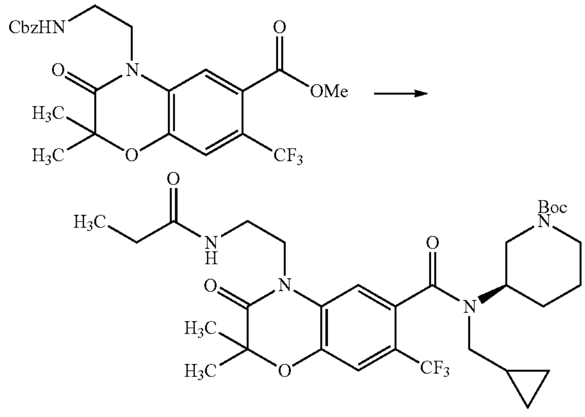

Using methyl 4-(2-{[(benzyloxy)carbonyl]amino}ethyl)-2,2-dimethyl-3-oxo-7-(trifluoro-methyl)-3,4-dihydro-2H-1,4-benzoxazine-6-carboxylate, the title compound was obtained in a similar manner to Reference Examples 4, 5.

MS (ESI+) 625 (M+1, 60%).

Reference Example 650 tert-Butyl (3R)-3-[{[2,2-dimethyl-3-oxo-4-[2-(propionylamino)ethyl]-7-(trifluoromethyl)-3,4-dihydro-2H-1,4-benzoxazin-6-yl]carbonyl}(2,2,2-trifluoroethyl)amino]piperidine-1-carboxylate

[Chemical formula 794]

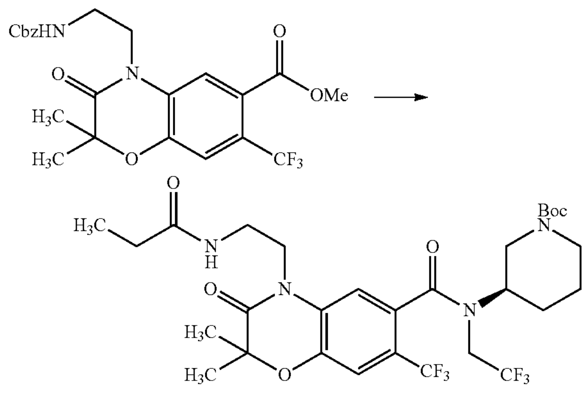

Using methyl 4-(2-{[(benzyloxy)carbonyl]amino}ethyl)-2,2-dimethyl-3-oxo-7-(trifluoro-methyl)-3,4-dihydro-2H-1,4-benzoxazine-6-carboxylate, the title compound was obtained in a similar manner to Reference Examples 4, 5.

MS (ESI+) 653 (M+1, 44%).

Reference Example 651 tert-Butyl (3R)-3-[{[4-(2-{benzyl[(benzyloxy)carbonyl]amino}ethyl)-2-methyl-2-{[(methyl-sulfonyl)oxy]methyl}-3-oxo-7-(trifluoromethyl)-3,4-dihydro-2H-1,4-benzoxazin-6-yl]-carbonyl}(isopropyl)amino]piperidine-1-carboxylate

[Chemical formula 795]

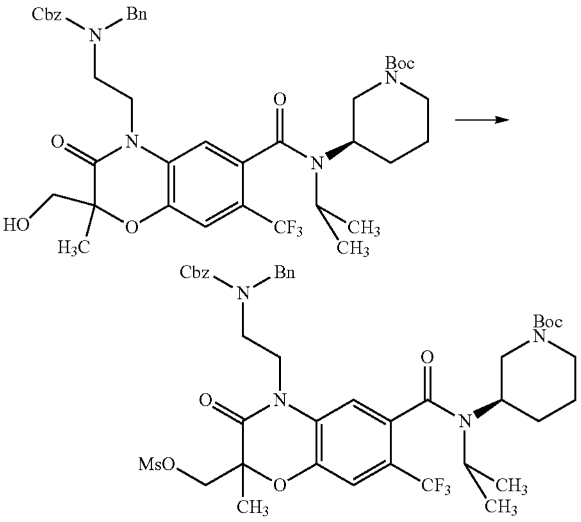

To a solution of tert-butyl (3R)-3-[{[4-(2-{benzyl[(benzyloxy)carbonyl]amino}ethyl)-2-(hydroxymethyl)-2-methyl-3-oxo-7-(trifluoromethyl)-3,4-dihydro-2H-1,4-benzoxazin-6-yl]carbonyl}-(isopropyl)amino]piperidine-1-carboxylate (700 mg) and triethylamine (0.25 ml) in tetrahydrofuran (8 ml) was added dropwise methanesulfonyl chloride (0.11 ml), and the mixture was stirred at room temperature for 2 hours. Water was added to the reaction solution, and the mixture was extracted with ethyl acetate. The extract was washed with a saturated aqueous sodium chloride solution, dried over sodium sulfate, filtered, and concentrated under reduced pressure. The obtained residue was purified by silica gel column chromatography (hexane/ethyl acetate) to give the title compound (793 mg).

MS (ESI+) 875 (M+1, 66%).

Reference Example 652 tert-Butyl (3R)-3-[{[4-(2-{benzyl[(benzyloxy)carbonyl]amino}ethyl)-2-methyl-3-oxo-2-(phenoxy-methyl)-7-(trifluoromethyl)-3,4-dihydro-2H-1,4-benzoxazin-6-yl]carbonyl}(isopropyl)amino]-piperidine-1-carboxylate

[Chemical formula 796]

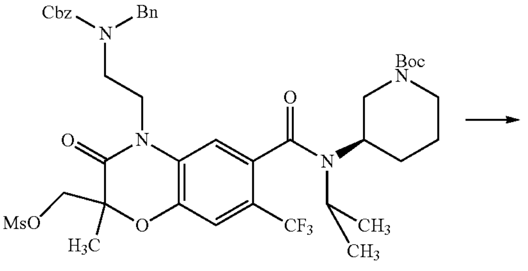

-continued

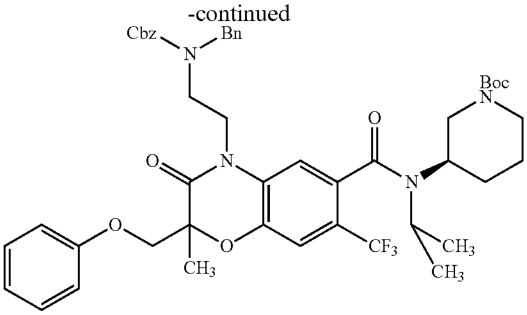

A solution of tert-butyl (3R)-3-[{[4-(2-{benzyl[(benzyloxy)carbonyl]amino}ethyl)-2-methyl-2-{[(methylsulfonyl)oxy]methyl}-3-oxo-7-(trifluoromethyl)-3,4-dihydro-2H-1,4-benzoxazin-6-yl]-carbonyl}(isopropyl)amino]piperidine-1-carboxylate (170 mg), phenol (18 mg) and cesium carbonate (186 mg) in N,N-dimethylformamide (2 ml) was stirred at 80° C. for 5 hours. Water was added to the reaction solution, and the mixture was extracted with ethyl acetate. The extract was washed with a saturated aqueous sodium chloride solution, dried over sodium sulfate, filtered, and concentrated under reduced pressure. The obtained residue was purified by silica gel column chromatography (hexane/ethyl acetate) to give the title compound (49 mg).

MS (ESI+) 873 (M+1, 89%).

Reference Example 653 tert-Butyl (3R)-3-(isopropyl{[4-{2-[(methoxycarbonyl)amino]ethyl}-2-methyl-3-oxo-2-(phenoxymethyl)-7-(trifluoromethyl)-3,4-dihydro-2H-1,4-benzoxazin-6-yl]carbonyl}amino)piperidine-1-carboxylate

[Chemical formula 797]

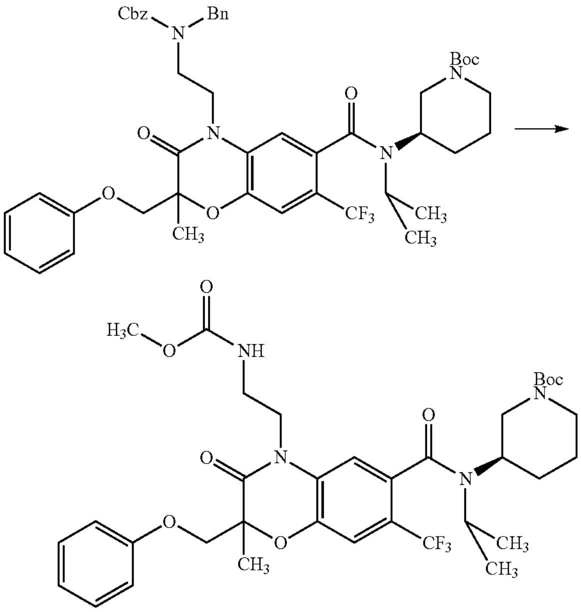

Using tert-butyl (3R)-3-[{[4-(2-{benzyl[(benzyloxy)carbonyl]amino}ethyl)-2-methyl-3-oxo-2-(phenoxymethyl)-7-(trifluoromethyl)-3,4-dihydro-2H-1,4-benzoxazin-6-yl]carbonyl}(isopropyl)amino]-piperidine-1-carboxylate, the title compound was obtained in a similar manner to Reference Example 139, Reference Example 162.

MS (ESI+) 705 (M+1, 75%).

Reference Example 654 tert-Butyl (3R)-3-(isopropyl{[4-{2-[(methoxycarbonyl)amino]ethyl}-2-[(3-methoxyphenoxy)methyl]-2-methyl-3-oxo-7-(trifluoromethyl)-3,4-dihydro-2H-1,4-benzoxazin-6-yl]carbonyl}amino)piperidine-1-carboxylate

[Chemical formula 798]

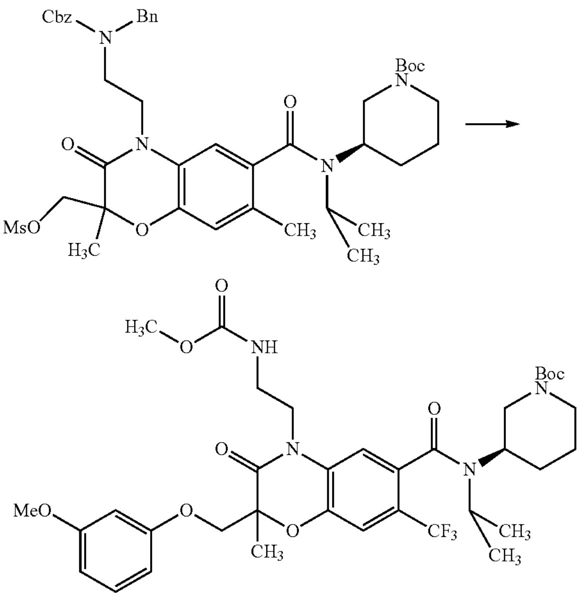

Using tert-butyl (3R)-3-[{[4-(2-{benzyl[(benzyloxy)carbonyl]amino}ethyl)-2-methyl-2-{[(methylsulfonyl)oxy]methyl}-3-oxo-7-(trifluoromethyl)-3,4-dihydro-2H-1,4-benzoxazin-6-yl]-carbonyl}(isopropyl)amino]piperidine-1-carboxylate, the title compound was obtained in a similar manner to Reference Example 652, Reference Example 139, Reference Example 162.

MS (ESI+) 737 (M+1, 72%).

Reference Example 655 tert-Butyl (3R)-3-(isopropyl{[4-{2-[(methoxycarbonyl)amino]ethyl}-2-[(4-methoxyphenoxy)methyl]-2-methyl-3-oxo-7-(trifluoromethyl)-3,4-dihydro-2H-1,4-benzoxazin-6-yl]carbonyl}amino)piperidine-1-carboxylate

[Chemical formula 799]

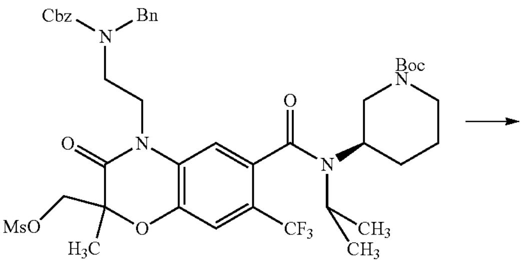

-continued

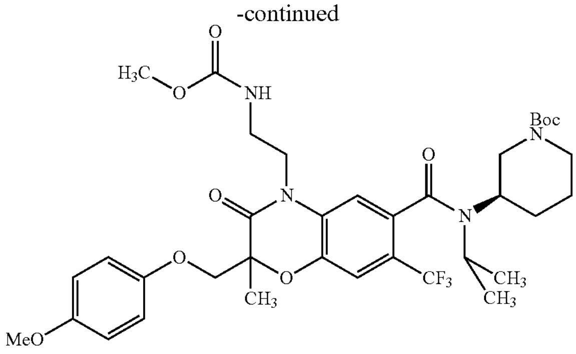

Using tert-butyl (3R)-3-[{[4-(2-{benzyl[(benzyloxy)carbonyl]amino}ethyl)-2-methyl-2-{[(methylsulfonyl)oxy]methyl}-3-oxo-7-(trifluoromethyl)-3,4-dihydro-2H-1,4-benzoxazin-6-yl]carbonyl}(isopropyl)amino]piperidine-1-carboxylate, the title compound was obtained in a similar manner to Reference Example 652, Reference Example 139, Reference Example 162.

MS (ESI+) 737 (M+1, 68%).

Reference Example 656 tert-Butyl (3R)-3-(isopropyl{[4-(4-methoxybutyl)-2-[(2-methoxyethoxy)methyl]-2-methyl-3-oxo-7-(trifluoromethyl)-3,4-dihydro-2H-1,4-benzoxazin-6-yl]carbonyl}amino)piperidine-1-carboxylate

[Chemical formula 800]

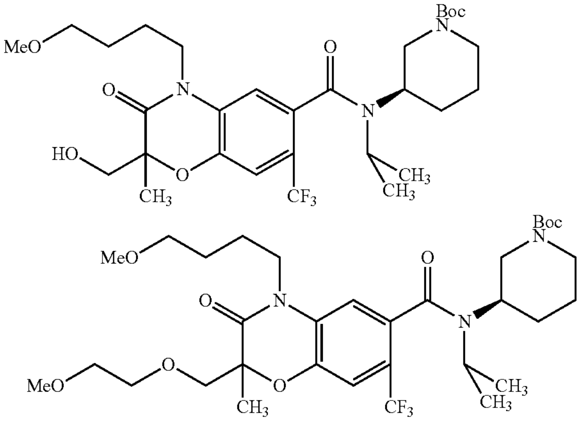

To a solution of tert-butyl (3R)-3-[{[2-(hydroxymethyl)-4-(4-methoxybutyl)-2-methyl-3-oxo-7-(trifluoromethyl)-3,4-dihydro-2H-1,4-benzoxazin-6-yl]carbonyl}(isopropyl)amino]piperidine-1-carboxylate (230 mg) in N,N-dimethylformamide (3 ml) were added sodium hydride (50 mg, 55% by weight) and 2-bromoethyl methyl ether (0.11 ml), and the mixture was stirred at 80° C. for 3 hours. To the reaction solution was added a saturated aqueous ammonium chloride solution, and the mixture was extracted with ethyl acetate. The mixture was washed with a saturated aqueous sodium chloride solution, dried over sodium sulfate, filtered, and concentrated under reduced pressure. The obtained residue was purified by silica gel column chromatography (hexane/ethyl acetate) to give the title compound (110 mg).

MS (ESI+) 674 (M+1, 81%).

Reference Example 657 tert-Butyl (3R)-3-(isopropyl{[4-(4-methoxybutyl)-2-methyl-3-oxo-2-[(tetrahydrofuran-2-ylmethoxy)-methyl]-7-(trifluoromethyl)-3,4-dihydro-2H-1,4-benzoxazin-6-yl]carbonyl}amino)piperidine-1-carboxylate

[Chemical formula 801]

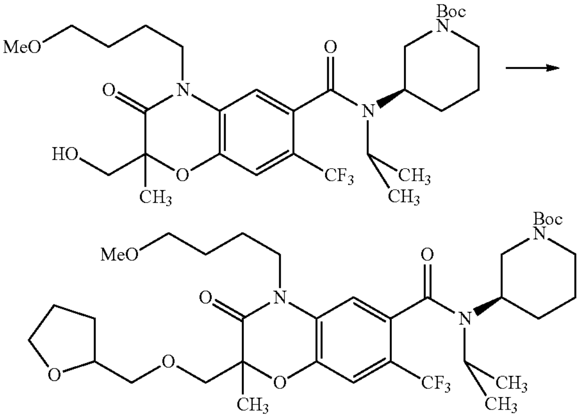

Using tert-butyl (3R)-3-[{[2-(hydroxymethyl)-4-(4-methoxybutyl)-2-methyl-3-oxo-7-(trifluoro-methyl)-3,4-dihydro-2H-1,4-benzoxazin-6-yl]carbonyl}(isopropyl)amino]piperidine-1-carboxylate, the title compound was obtained in a similar manner to Reference Example 656.

MS (ESI+) 700 (M+1, 70%).

Reference Example 658 tert-Butyl (3R)-3-[{[2-[(3-cyanophenoxy)methyl]-4-(4-methoxybutyl)-2-methyl-3-oxo-7-(trifluoro-methyl)-3,4-dihydro-2H-1,4-benzoxazin-6-yl]carbonyl}(isopropyl)amino]piperidine-1-carboxylate

[Chemical formula 802]

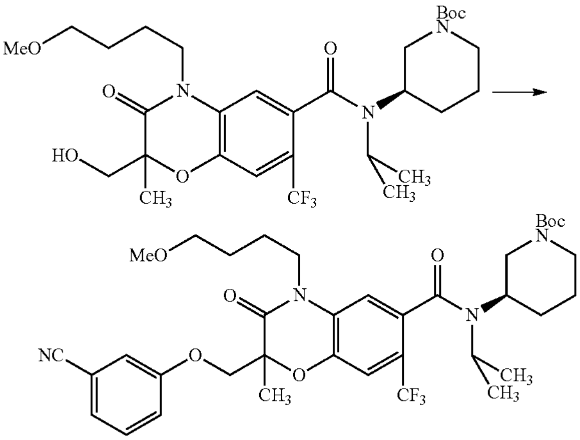

Using tert-butyl (3R)-3-[{[2-(hydroxymethyl)-4-(4-methoxybutyl)-2-methyl-3-oxo-7-(trifluoro-methyl)-3,4-dihydro-2H-1,4-benzoxazin-6-yl]carbonyl}(isopropyl)amino]piperidine-1-carboxylate, the title compound was obtained in a similar manner to Reference Example 651, Reference Example 652.

MS (ESI+) 717 (M+1, 70%).

Reference Example 659 tert-Butyl (3R)-3-[{[2-[(4-cyanophenoxy)methyl]-4-(4-methoxybutyl)-2-methyl-3-oxo-7-(trifluoro-methyl)-3,4-dihydro-2H-1,4-benzoxazin-6-yl]carbonyl}(isopropyl)amino]piperidine-1-carboxylate

[Chemical formula 803]

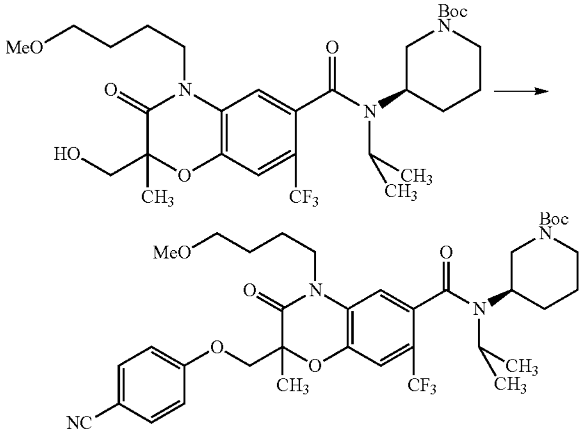

Using tert-butyl (3R)-3-[{[2-(hydroxymethyl)-4-(4-methoxybutyl)-2-methyl-3-oxo-7-(trifluoromethyl)-3,4-dihydro-2H-1,4-benzoxazin-6-yl]carbonyl}(isopropyl)amino]piperidine-1-carboxylate, the title compound was obtained in a similar manner to Reference Example 651, Reference Example 652.

MS (ESI+) 717 (M+1, 70%).

Reference Example 660 tert-Butyl (3R)-3-[{[2-[(2-ethoxy-2-oxoethoxy)methyl]-4-(4-methoxybutyl)-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 804]

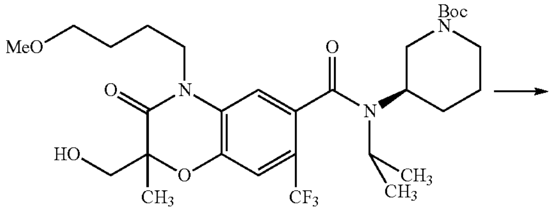

-continued

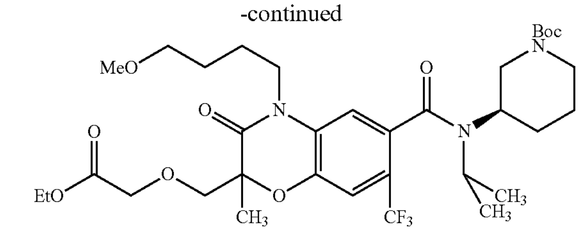

Using tert-butyl (3R)-3-[{[2-(hydroxymethyl)-4-(4-methoxybutyl)-2-methyl-3-oxo-7-(trifluoromethyl)-3,4-dihydro-2H-1,4-benzoxazin-6-yl]carbonyl}(isopropyl)amino]piperidine-1-carboxylate, the title compound was obtained in a similar manner to Reference Example 656.

MS (ESI+) 702 (M+1, 73%).

Reference Example 661 tert-Butyl (3R)-3-(isopropyl{[4-(4-methoxybutyl)-2-methyl-2-[(oxiran-2-ylmethoxy)methyl]-3-oxo-7-(trifluoromethyl)-3,4-dihydro-2H-1,4-benzoxazin-6-yl]carbonyl}amino)piperidine-1-carboxylate

[Chemical formula 805]

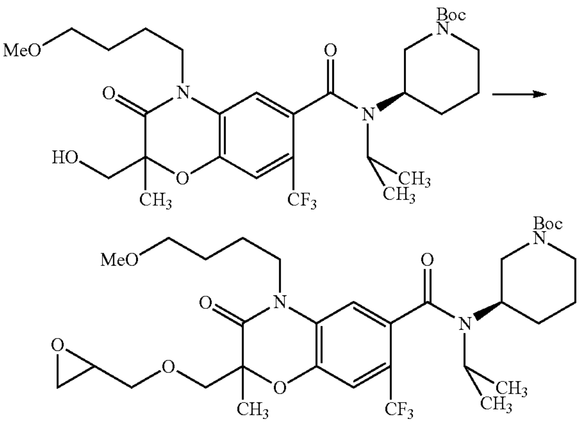

Using tert-butyl (3R)-3-[{[2-(hydroxymethyl)-4-(4-methoxybutyl)-2-methyl-3-oxo-7-(trifluoro-methyl)-3,4-dihydro-2H-1,4-benzoxazin-6-yl]carbonyl}(isopropyl)amino]piperidine-1-carboxylate, the title compound was obtained in a similar manner to Reference Example 656.

MS (ESI+) 672 (M+1, 66%).

Reference Example 662 tert-Butyl (3R)-3-[{[2-[(3-ethoxy-2-hydroxypropoxy)methyl]-4-(4-methoxybutyl)-2-methyl-3-oxo-7-(trifluoromethyl)-3,4-dihydro-2H-1,4-benzoxazin-6-yl]carbonyl}(isopropyl)amino]piperidine-1-carboxylate

[Chemical formula 806]

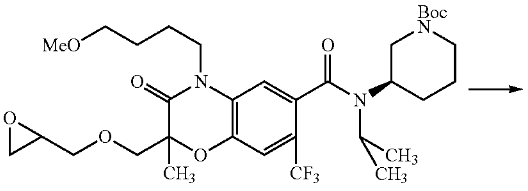

-continued

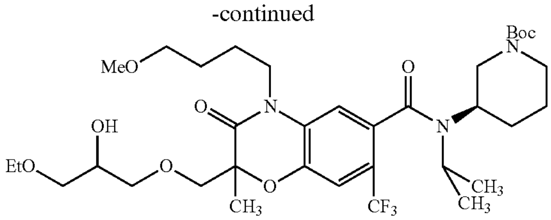

To a solution of tert-butyl (3R)-3-(isopropyl{[4-(4-methoxybutyl)-2-methyl-2-[(oxiran-2-ylmethoxy)methyl]-3-oxo-7-(trifluoromethyl)-3,4-dihydro-2H-1,4-benzoxazin-6-yl]carbonyl}-amino)piperidine-1-carboxylate (113 mg) in tetrahydrofuran (1 ml) was added sodium ethoxide (0.1 ml, 20% ethanol solution), and the mixture was stirred at 50° C. for 2 hours. The reaction solution was cooled, and thereto was added a saturated aqueous ammonium chloride solution, and the mixture was extracted with ethyl acetate. The extract was washed with a saturated aqueous sodium chloride solution, dried over sodium sulfate, filtered, and concentrated under reduced pressure. To the obtained residue was added acetic acid (1 ml), and the mixture was stirred at 50° C. for one hour. The solution was cooled to room temperature, and thereto was added ethyl acetate, and the organic layer was washed with water, dried over sodium sulfate, filtered, and concentrated under reduced pressure. The obtained residue was purified by silica gel column chromatography (hexane/ethyl acetate) to give the title compound (13 mg).

MS (ESI+) 718 (M+1, 33%).

Reference Example 663 tert-Butyl (3R)-3-(isopropyl{[4-(4-methoxybutyl)-2-[(3-methoxypropoxy)methyl]-2-methyl-3-oxo-7-(trifluoromethyl)-3,4-dihydro-2H-1,4-benzoxazin-6-yl]carbonyl}amino)piperidine-1-carboxylate

[Chemical formula 807]

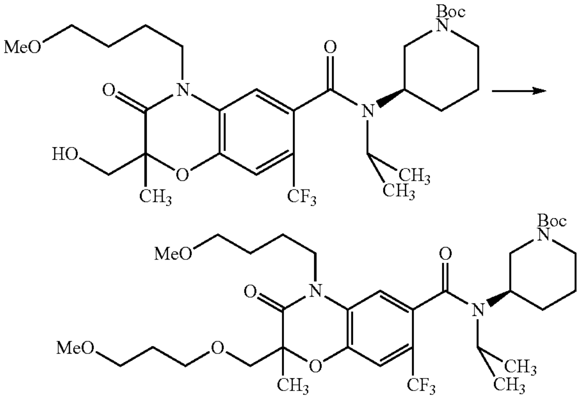

Using tert-butyl (3R)-3-[{[2-(hydroxymethyl)-4-(4-methoxybutyl)-2-methyl-3-oxo-7-(trifluoromethyl)-3,4-dihydro-2H-1,4-benzoxazin-6-yl]carbonyl}(isopropyl)amino]piperidine-1-carboxylate, the title compound was obtained in a similar manner to Reference Example 656.

MS (ESI+) 688 (M+1, 75%).

Reference Example 664 tert-Butyl (3R)-3-(isopropyl{[4-(4-methoxybutyl)-2-methyl-3-oxo-2-{[2-(tetrahydro-2H-pyran-2-yloxy)ethoxy]methyl}-7-(trifluoromethyl)-3,4-dihydro-2H-1,4-benzoxazin-6-yl]carbonyl}amino)-piperidine-1-carboxylate

[Chemical formula 808]

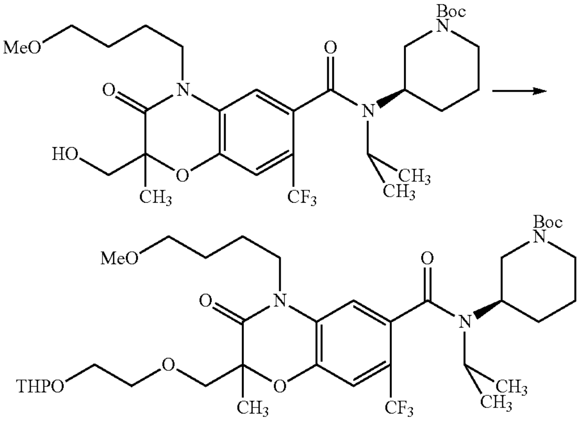

Using tert-butyl (3R)-3-[{[2-(hydroxymethyl)-4-(4-methoxybutyl)-2-methyl-3-oxo-7-(trifluoro-methyl)-3,4-dihydro-2H-1,4-benzoxazin-6-yl]carbonyl}(isopropyl)amino]piperidine-1-carboxylate, the title compound was obtained in a similar manner to Reference Example 656.

MS (ESI+) 744 (M+1, 35%).

Reference Example 665 tert-Butyl (3R)-3-[{[2-(1-hydroxy-1-methylethyl)-4-(4-methoxybutyl)-2-methyl-3-oxo-7-(trifluoro-methyl)-3,4-dihydro-2H-1,4-benzoxazin-6-yl]carbonyl}(isopropyl)amino]piperidine-1-carboxylate

[Chemical formula 809]

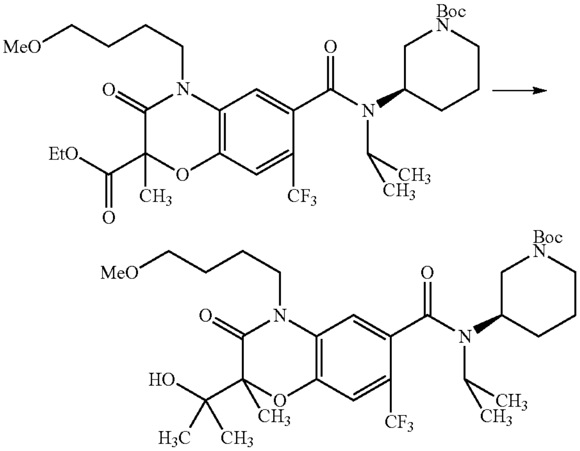

A solution of ethyl 6-{[[(3R)-1-(tert-butoxycarbonyl)piperidin-3-yl](isopropyl)amino]-carbonyl}-4-(4-methoxybutyl)-2-methyl-3-oxo-7-(trifluoromethyl)-3,4-dihydro-2H-1,4-benzoxazine-2-carboxylate (150 mg) in tetrahydrofuran (2 ml) was cooled with ice, and thereto was added dropwise methylmagnesium bromide (1M tetrahydrofuran solution, 1.2 ml), and the mixture was stirred at room temperature for 3 hours. To the reaction solution was added a saturated aqueous ammonium chloride solution, and the mixture was extracted with ethyl acetate. The extract was washed with a saturated aqueous sodium chloride solution, dried over sodium sulfate, filtered, and concentrated under reduced pressure. The obtained residue was purified by silica gel column chromatography (hexane/ethyl acetate) to give the title compound (111 mg).

MS (ESI+) 644 (M+1, 48%).

Reference Example 666

Methyl 4-but-3-en-1-yl-2,2-dimethyl-3-oxo-7-(trifluoromethyl)-3,4-dihydro-2H-1,4-benzoxazine-6-carboxylate

[Chemical formula 810]

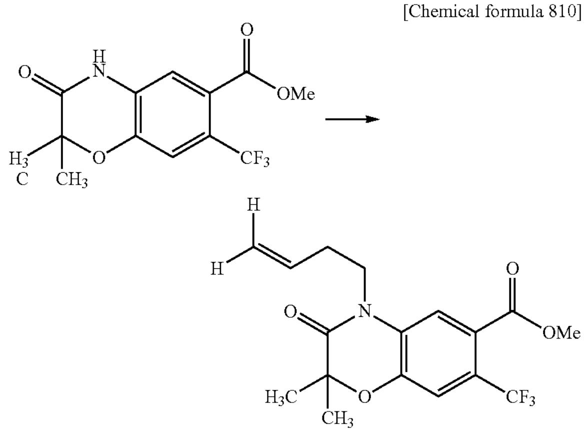

Using methyl 2,2-dimethyl-3-oxo-7-(trifluoromethyl)-3,4-dihydro-2H-1,4-benzoxazine-6-carboxylate, the title compound was obtained in a similar manner to Reference Example 3.

MS (ESI+) 358 (M+1, 100%).

Reference Example 667 tert-Butyl (3R)-3-[{[4-but-3-en-1-yl-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 811]

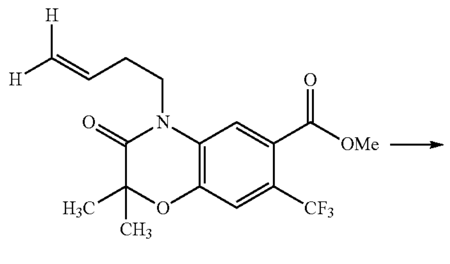

-continued

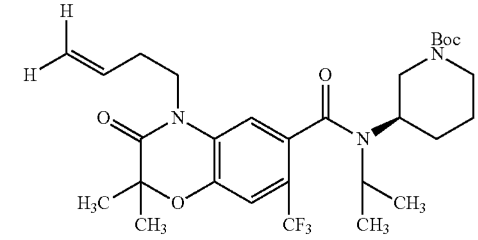

Using methyl 4-but-3-en-1-yl-2,2-dimethyl-3-oxo-7-(trifluoromethyl)-3,4-dihydro-2H-1,4-benzoxazine-6-carboxylate, the title compound was obtained in a similar manner to Reference Example 4, 5.

MS (ESI+) 568 (M+1, 67%).

Reference Example 668 tert-Butyl (3R)-3-[{[2,2-dimethyl-4-(2-oxiran-2-ylethyl)-3-oxo-7-(trifluoromethyl)-3,4-dihydro-2H-1,4-benzoxazin-6-yl]carbonyl}(isopropyl)amino]piperidine-1-carboxylate

[Chemical formula 812]

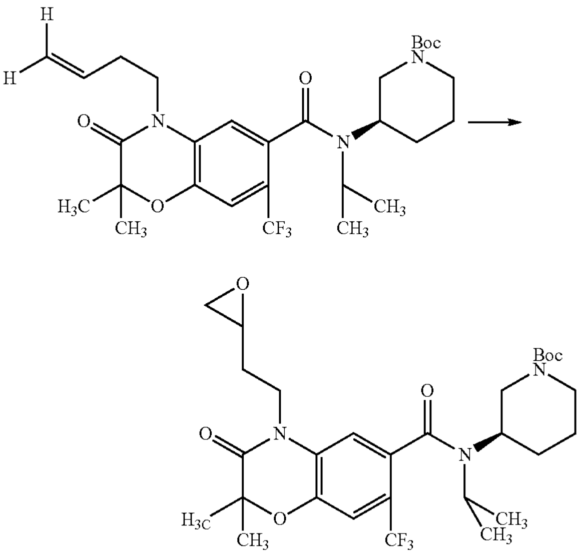

To a solution of tert-butyl (3R)-3-[{[4-but-3-en-1-yl-2,2-dimethyl-3-oxo-7-(trifluoromethyl)-3,4-dihydro-2H-1,4-benzoxazin-6-yl]carbonyl}(isopropyl)amino]piperidine-1-carboxylate (1.7 g) in dichloromethane (15 ml) was added m-chloroperbenzoic acid (775 mg), and the mixture was stirred at room temperature overnight. To the reaction solution was added water, and the mixture was extracted with chloroform. The extract was washed with a saturated aqueous sodium chloride solution, dried over sodium sulfate, filtered, and concentrated under reduced pressure. The obtained residue was purified by silica gel column chromatography (hexane/ethyl acetate) to give the title compound (780 mg).

MS (ESI+) 584 (M+1, 82%).

Reference Example 669 tert-Butyl (3R)-3-[{[4-(3-hydroxy 4-methoxybutyl)-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 813]

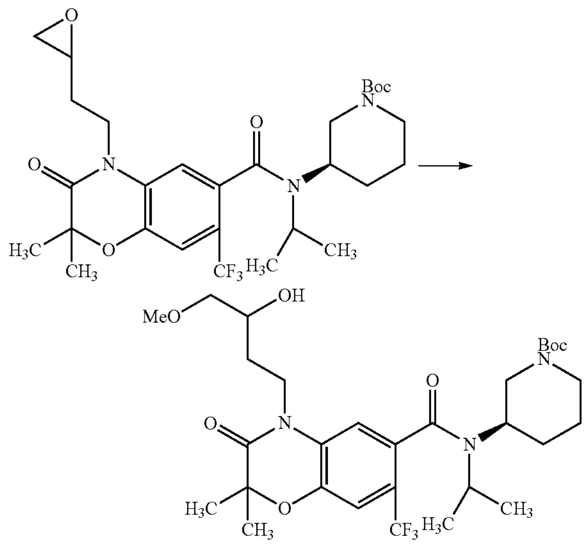

Using tert-butyl (3R)-3-[{[2,2-dimethyl-4-(2-oxiran-2-ylethyl)-3-oxo-7-(trifluoromethyl)-3,4-dihydro-2H-1,4-benzoxazin-6-yl]carbonyl}(isopropyl)amino]piperidine-1-carboxylate, the title compound was obtained in a similar manner to Reference Example 662.

MS (ESI+) 616 (M+1, 75%).

Reference Example 670 tert-Butyl (3R)-3-(isopropyl{[4-(4-methoxy-3-oxobutyl)-2,2-dimethyl-3-oxo-7-(trifluoromethyl)-3,4-dihydro-2H-1,4-benzoxazin-6-yl]carbonyl}amino)piperidine-1-carboxylate

[Chemical formula 814]

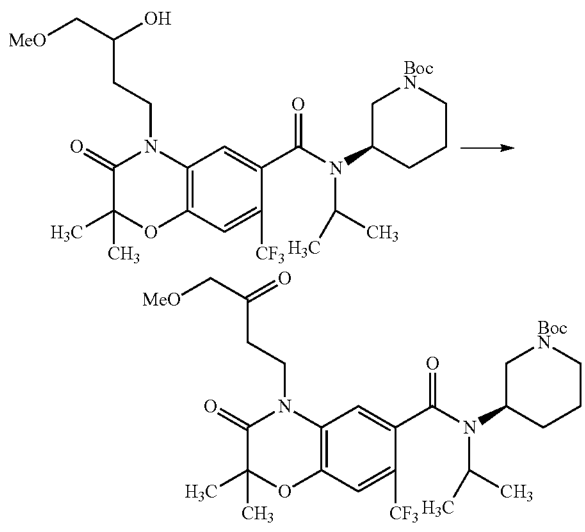

Using tert-butyl (3R)-3-[{[4-(3-hydroxy-4-methoxybutyl)-2,2-dimethyl-3-oxo-7-(trifluoro-methyl)-3,4-dihydro-2H-1,4-benzoxazin-6-yl]carbonyl}(isopropyl)amino]piperidine-1-carboxylate, the title compound was obtained in a similar manner to Reference Example 325.

MS (ESI+) 614 (M+1, 75%).

Reference Example 671

Methyl 4-(2-hydroxy-3-methoxypropyl)-2,2-dimethyl-3-oxo-7-(trifluoromethyl)-3,4-dihydro-2H-1,4-benzoxazine-6-carboxylate

[Chemical formula 815]

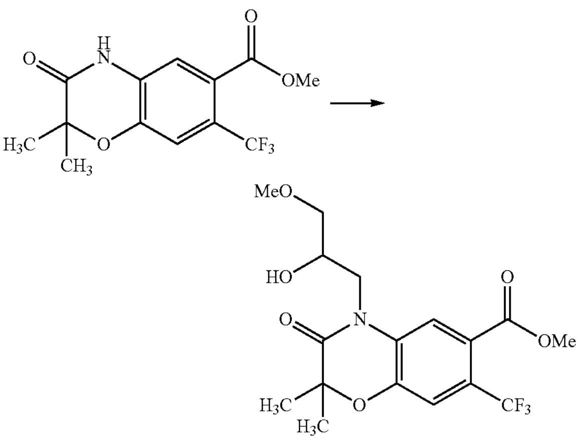

Using methyl 2,2-dimethyl-3-oxo-7-(trifluoromethyl)-3,4-dihydro-2H-1,4-benzoxazine-6-carboxylate, the title compound was obtained in a similar manner to Reference Example 3.

MS (ESI+) 392 (M+1, 100%).

Reference Example 672 tert-Butyl (3R)-3-[{[4-(2-hydroxy-3-methoxypropyl)-2,2-dimethyl-3-oxo-7-(trifluoromethyl)-3,4-dihydro-2H-1,4-benzoxazin-6-yl]carbonyl}(isopropyl)amino]piperidine-1-carboxylate

[Chemical formula 816]

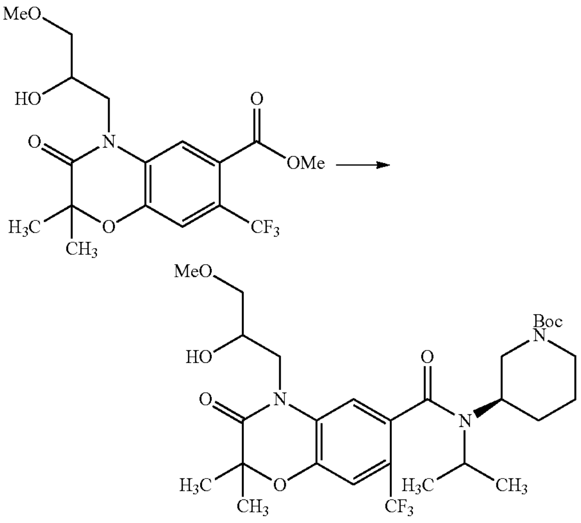

Using methyl 4-(2-hydroxy-3-methoxypropyl)-2,2-dimethyl-3-oxo-7-(trifluoromethyl)-3,4-dihydro-2H-1,4-benzoxazine-6-carboxylate, the title compound was obtained in a similar manner to Reference Example 4, 5.

MS (ESI+) 602 (M+1, 83%).

Reference Example 673

Bromo(tetrahydro-2H-pyran-4-yl)acetic acid

[Chemical formula 817]

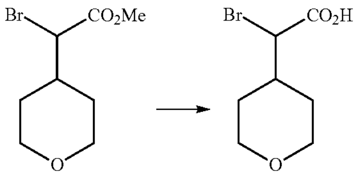

Using methyl bromo(tetrahydro-2H-pyran-4-yl)acetate [870708-17-1], the title compound was obtained in a similar manner to Reference Example 4.

MS (ESI+) 224 ($M^+$+3, 21%).

Reference Example 674 tert-Butyl (3R)-3-(isopropyl{[3-oxo-2-(tetrahydro-2H-pyran-4-yl)-7-(trifluoromethyl)-3,4-dihydro-2H-1,4-benzoxazin-6-yl]carbonyl}amino)piperidine-1-carboxylate

[Chemical formula 818]

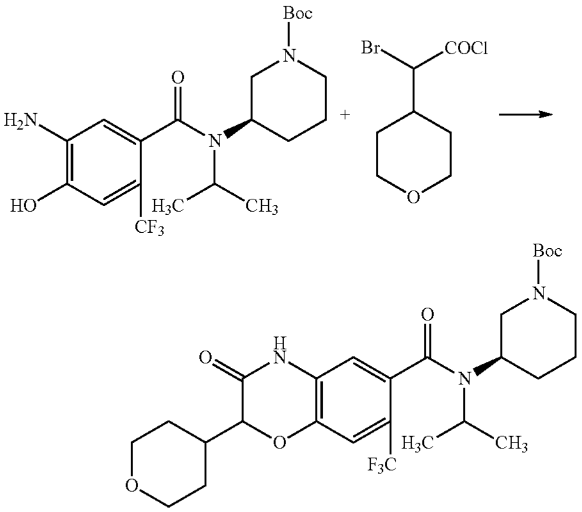

Using tert-butyl (3R)-3-[[5-amino-4-hydroxy 2-(trifluoromethyl)benzoyl](isopropyl)amino]-piperidine-1-carboxylate and bromo (tetrahydro-2H-pyran-4-yl)acetyl chloride, the title compound was obtained in a similar manner to Reference Example 55.

MS (ESI+) 570 ($M^+$+1, 77%).

Reference Example 675 tert-Butyl (3R)-3-(isopropyl{[4-(4-methoxybutyl)-3-oxo-2-(tetrahydro-2H-pyran-4-yl)-7-(trifluoro-methyl)-3,4-dihydro-2H-1,4-benzoxazin-6-yl]carbonyl}amino)piperidine-1-carboxylate

[Chemical formula 819]

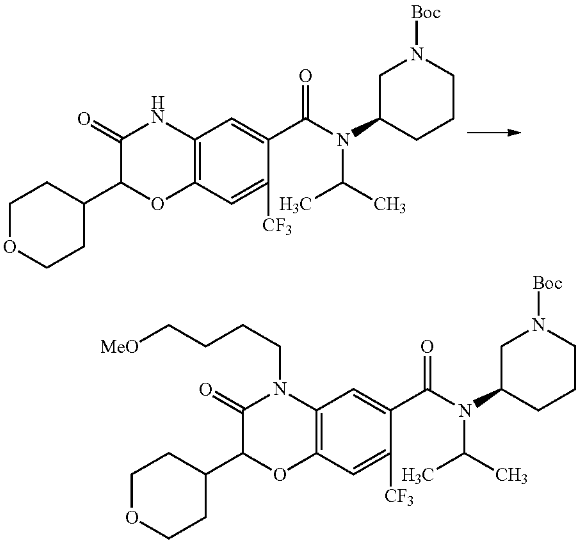

Using tert-butyl (3R)-3-(isopropyl{[3-oxo-2-(tetrahydro-2H-pyran-4-yl)-7-(trifluoromethyl)-3,4-dihydro-2H-1,4-benzoxazin-6-yl]carbonyl}amino)piperidine-1-carboxylate, the title compound was obtained in a similar manner to Reference Example 3.

MS (ESI+) 656 ($M^+$+1, 73%).

Reference Example 676 tert-Butyl (3R)-3-(isopropyl{[4-{2-[(methoxycarbonyl)amino]ethyl}-3-oxo-2-(tetrahydro-2H-pyran-4-yl)-7-(trifluoromethyl)-3,4-dihydro-2H-1,4-benzoxazin-6-yl]carbonyl}amino)piperidine-1-carboxylate

[Chemical formula 820]

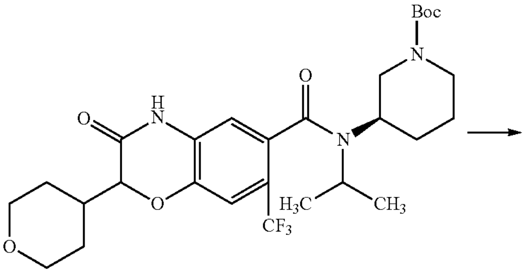

-continued

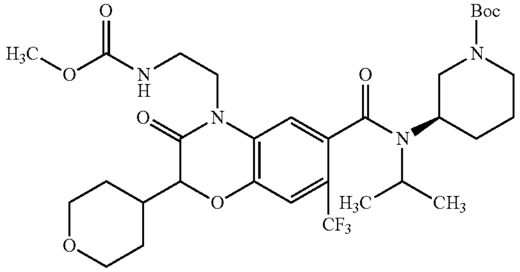

Using tert-butyl (3R)-3-(isopropyl{[3-oxo-2-(tetrahydro-2H-pyran-4-yl)-7-(trifluoromethyl)-3,4-dihydro-2H-1,4-benzoxazin-6-yl]carbonyl}amino)piperidine-1-carboxylate, the title compound was obtained in a similar manner to Reference Example 162.

MS (ESI+) 671 ($M^{+}$+1, 67%).

Reference Example 677 tert-Butyl (3R)-3-[[4-(ethylamino)-5-nitro-2-(trifluoromethyl)benzoyl](isopropyl)amino]piperidine-1-carboxylate

[Chemical formula 821]

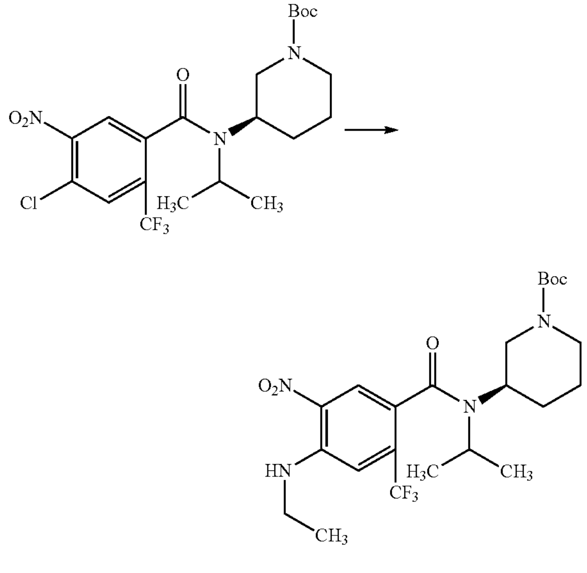

To a solution of tert-butyl (3R)-3-[[4-chloro-5-nitro-2-(trifluoromethyl)benzoyl](isopropyl)-amino]piperidine-1-carboxylate (930 mg) in ethanol (6 ml) was added ethylamine (2M methanol solution, 10 ml), and the mixture was stirred at 80° C. for 2 hours. The mixture was cooled, and the reaction solution was concentrated under reduced pressure. The obtained residue was purified by silica gel column chromatography (hexane/ethyl acetate) to give the title compound (610 mg).

MS (ESI+) 503 ($M^{+}$+1, 40%).

Reference Example 678 tert-Butyl (3R)-3-[[4-(cyclopropylamino)-5-nitro-2-(trifluoromethyl)benzoyl](isopropyl)amino]-piperidine-1-carboxylate

[Chemical formula 822]

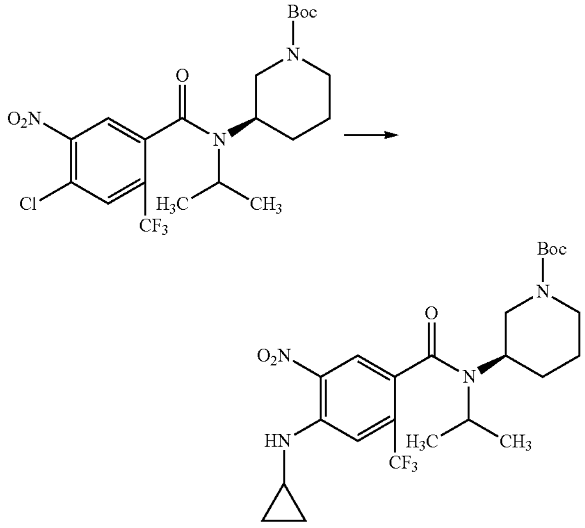

Using tert-butyl (3R)-3-[[4-chloro-5-nitro-2-(trifluoromethyl)benzoyl](isopropyl)amino]-piperidine-1-carboxylate, the title compound was obtained in a similar manner to Reference Example 677.

MS (ESI+) 515 ($M^{+}$+1, 44%).

Reference Example 679 tert-Butyl (3R)-3-[[5-amino-4-(ethylamino)-2-(trifluoromethyl)benzoyl](isopropyl)amino]piperidine-1-carboxylate

[Chemical formula 823]

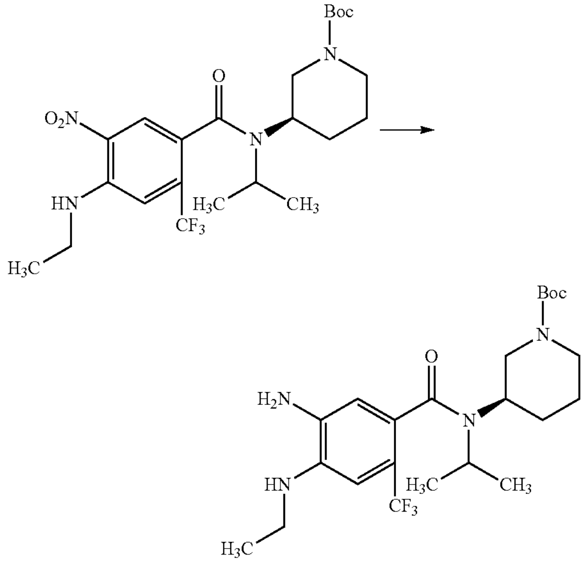

To a solution of tert-butyl (3R)-3-[[4-(ethylamino)-5-nitro-2-(trifluoromethyl)benzoyl]-(isopropyl)amino]piperidine-1-carboxylate (610 mg) in tetrahydrofuran (10 ml) was added 10% palladium-carbon (600 mg, 50% wet.), and the mixture was stirred at room temperature under hydrogen atmosphere for 3 hours. The reaction solution was filtered on celite, washed with tetrahydrofuran, and the filtrate was concentrated under reduced pressure to give the title compound (550 mg).

MS (ESI+) 473 ($M^{+}$+1, 33%).

Reference Example 680 tert-Butyl (3R)-3-[{[1-ethyl-2-oxo-6-(trifluoromethyl)-2,3-dihydro-1H-benzimidazo-5-yl]carbonyl}-(isopropyl)amino]piperidine-1-carboxylate

[Chemical formula 824]

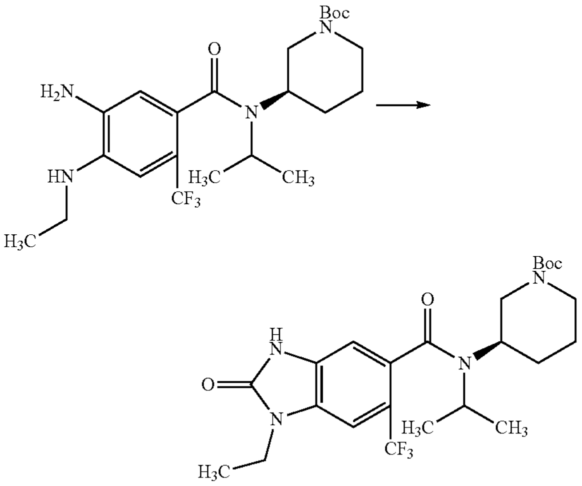

To a solution of tert-butyl (3R)-3-[[5-amino-4-(ethylamino)-2-(trifluoromethyl)benzoyl]-(isopropyl)amino]piperidine-1-carboxylate (550 mg) and triethylamine (0.33 ml) in tetrahydrofuran (10 ml) was added triphosgene (378 mg), and the mixture was stirred at room temperature overnight. To the reaction solution was added water, and the mixture was extracted with chloroform, and washed with a saturated aqueous sodium chloride solution. The resultant was dried over sodium sulfate, filtered, and concentrated under reduced pressure. The obtained residue was purified by silica gel column chromatography (hexane/ethyl acetate) to give the title compound (590 mg).

MS (ESI+) 499 ($M^{+}$+1, 48%).

Reference Example 681 tert-Butyl (3R)-3-[{[1-ethyl-3-(4-methoxybutyl)-2-oxo-6-(trifluoromethyl)-2,3-dihydro-1H-benzimidazo-5-yl]carbonyl}(isopropyl)amino]piperidine-1-carboxylate

[Chemical formula 825]

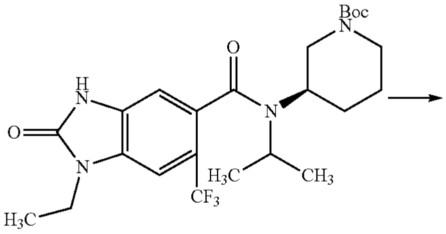

-continued

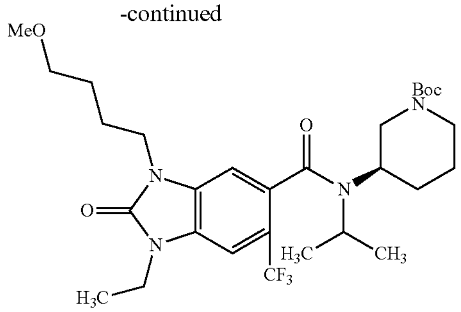

Using tert-butyl (3R)-3-[{[1-ethyl-2-oxo-6-(trifluoromethyl)-2,3-dihydro-1H-benzimidazo-5-yl]carbonyl}(isopropyl)amino]piperidine-1-carboxylate, the title compound was obtained in a similar manner to Reference Example 3.

MS (ESI+) 585 ($M^{+}$+1, 33%).

Reference Example 682 tert-Butyl (3R)-3-[{[342-(acetylamino)ethyl]-1-ethyl-2-oxo-6-(trifluoromethyl)-2,3-dihydro-1H-benzimidazo-5-yl]carbonyl}(isopropyl)amino]piperidine-1-carboxylate

[Chemical formula 826]

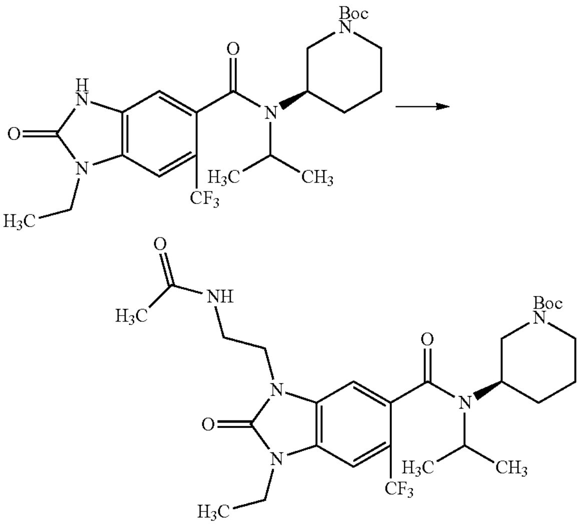

Using tert-butyl (3R)-3-[{[1-ethyl-2-oxo-6-(trifluoromethyl)-2,3-dihydro-1H-benzimidazo-5-yl]carbonyl}(isopropyl)amino]piperidine-1-carboxylate, the title compound was obtained in a similar manner to Reference Example 378, 139, 132.

MS (ESI+) 584 ($M^{+}$+1, 45%).

Reference Example 683 tert-Butyl (3R)-3-[{[1-ethyl-2-oxo-3-[2-(propionylamino)ethyl]-6-(trifluoromethyl)-2,3-dihydro-1H-benzimidazo-5-yl]carbonyl}(isopropyl)amino]piperidine-1-carboxylate

[Chemical formula 827]

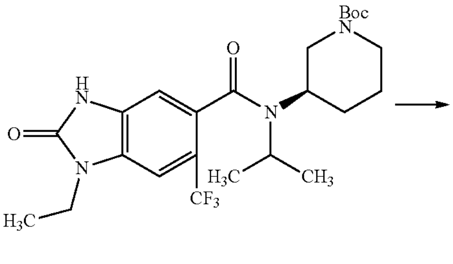

-continued

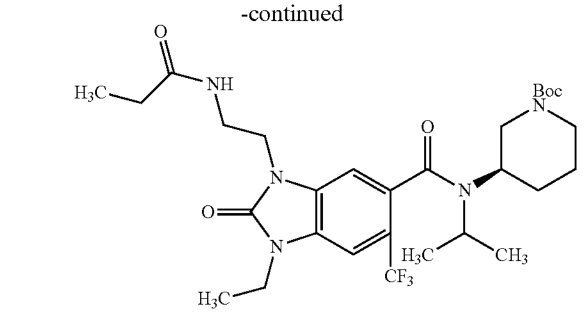

Using tert-butyl (3R)-3-[{[1-ethyl-2-oxo-6-(trifluoromethyl)-2,3-dihydro-1H-benzimidazo-5-yl]carbonyl}(isopropyl)amino]piperidine-1-carboxylate, the title compound was obtained in a similar manner to Reference Example 378, 139, 132.

MS (ESI+) 598 ($M^{+}$+1, 43%).

Reference Example 684 tert-Butyl (3R)-3-[{[1-cyclopropyl-3-(4-methoxybutyl)-2-oxo-6-(trifluoromethyl)-2,3-dihydro-1H-benzimidazo-5-yl]carbonyl}(isopropyl)amino]piperidine-1-carboxylate

[Chemical formula 828]

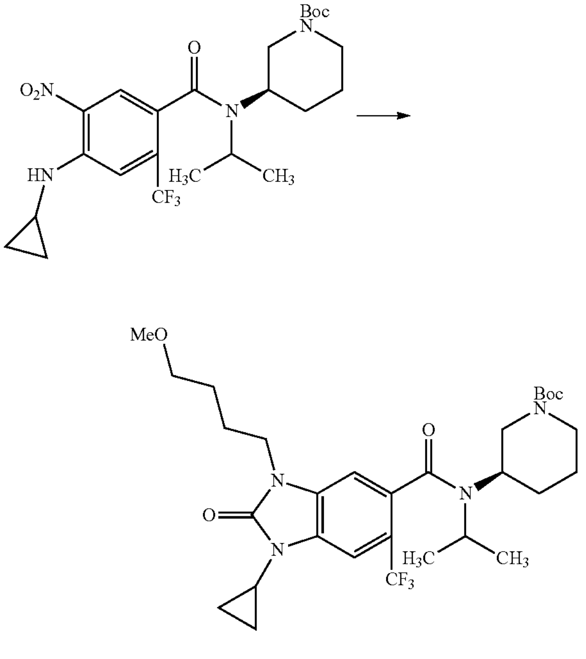

Using tert-butyl (3R)-3-[[4-(cyclopropylamino)-5-nitro-2-(trifluoromethyl)benzoyl](isopropyl)-amino]piperidine-1-carboxylate, the title compound was obtained in a similar manner to Reference Example 679, Reference Example 670, Reference Example 3.

MS (ESI+) 597 ($M^{+}$+1, 45%).

Reference Example 685

1-tert-Butyl 3-ethyl 4-[3-(benzyloxy)phenyl]-5,6-dihydropyridin-1,3(2H)-dicarboxylate

[Chemical formula 829]

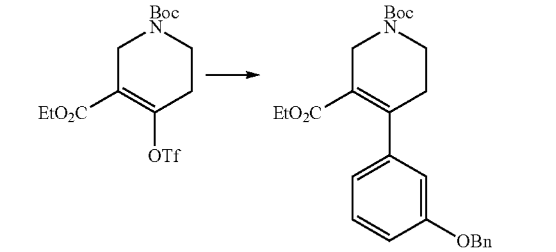

Using 1-tert-butyl 3-ethyl 4-{[(trifluoromethyl)sulfonyl]oxy}-5,6-dihydropyridin-1,3(2H)-dicarboxylate and 3-benzyloxyphenylboronic acid, the title compound was obtained in a similar manner to Reference Example 550.

MS (ESI+) 438 ($M^{+}$+1, 100%).

Reference Example 686

(rac.)-(3R,4S)-4-[3-(Benzyloxy)phenyl]-1-(tert-butoxycarbonyl)piperidine 3-carboxylic acid

[Chemical formula 830]

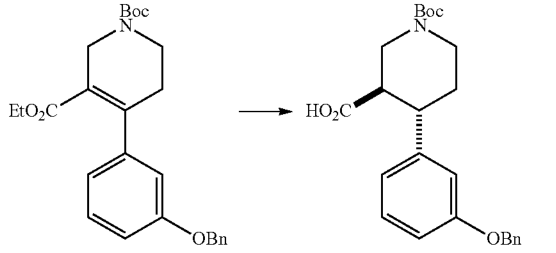

Using 1-tert-butyl 3-ethyl 4-[3-(benzyloxy)phenyl]-5,6-dihydropyridin-1,3(2H)-dicarboxylate, the title compound was obtained in a similar manner to Reference Example 580.

MS (ESI+) 412 ($M^{+}$+1, 100%).

Reference Example 687 tert-Butyl (rac.)-(3R,4R)-3-{[(benzyloxy)carbonyl]amino}-4-[3-(benzyloxy)phenyl]piperidine-1-carboxylate

[Chemical formula 831]

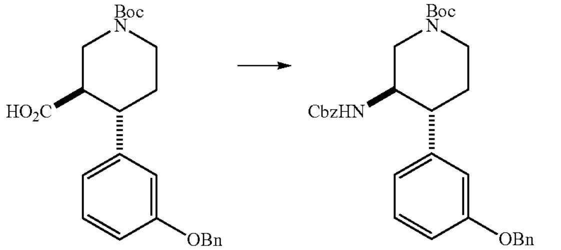

Using (rac.)-(3R,4S)-4-[3-(benzyloxy)phenyl]-1-(tert-butoxycarbonyl)piperidine-3-carboxylic acid, the title compound was obtained in a similar manner to Reference Example 523.

MS (ESI+) 517 ($M^{+}$+1, 100%).

Reference Example 688 tert-Butyl (rac.)-(3R,4R)-3-[[(benzyloxy)carbonyl](ethyl)amino]-4-[3-(benzyloxy)phenyl]piperidine-1-carboxylate

[Chemical formula 832]

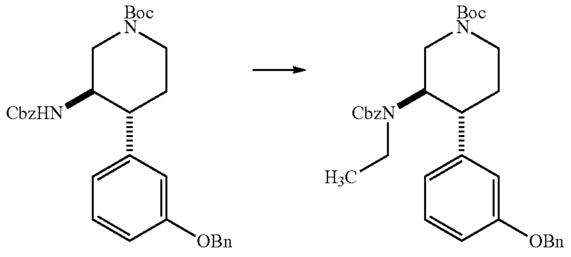

To a solution of tert-butyl (rac.)-(3R,4R)-3-{[(benzyloxy)carbonyl]amino}-4-[3-(benzyloxy)-phenyl]piperidine-1-carboxylate (3.70 g) in DMF (16 ml) was added at 0° C. sodium hydride (573 mg), and the mixture was stirred for 15 minutes. To the mixture was added ethyl iodide (1.48 ml), and the mixture was stirred at 60° C. for 5 hours. The reaction solution was cooled, and a saturated aqueous ammonium chloride solution was added thereto, and the mixture was extracted with ethyl acetate. The organic layer was washed with a saturated aqueous ammonium chloride solution (×2) and a saturated aqueous sodium chloride solution, dried over sodium sulfate, filtered, and concentrated under reduced pressure. The obtained residue was purified by silica gel column chromatography (the developing solvent: hexane/ethyl acetate=3/1) to give the title compound (2.59 g).

MS (ESI+) 545 ($M^+$+1, 100%).

Reference Example 689 tert-Butyl (rac.)-(3R,4R)-3-(ethylamino)-4-(3-hydroxyphenyl)piperidine-1-carboxylate

[Chemical formula 833]

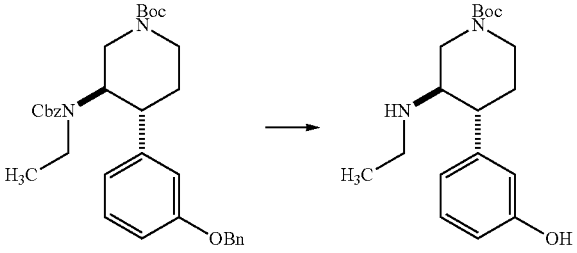

Using tert-butyl (rac.)-(3R,4R)-3-[[(benzyloxy)carbonyl](ethyl)amino]-4-[3-(benzyloxy)-phenyl]piperidine-1-carboxylate, the title compound was obtained in a similar manner to Reference Example 139.

MS (ESI+) 321 ($M^+$+1, 100%).

Reference Example 690 tert-Butyl (rac.)-(3R,4R)-4-[3-(benzoyloxy)phenyl]-3-(ethylamino)piperidine-1-carboxylate

[Chemical formula 834]

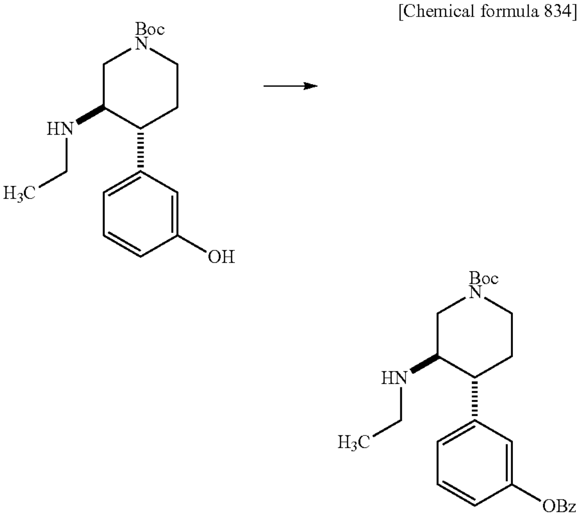

To a solution of tert-butyl (rac.)-(3R,4R)-3-(ethylamino)-4-(3-hydroxyphenyl)piperidine-1-carboxylate (1.76 g) in methylene chloride (16 ml) were added 1-(3-dimethylamino-propyl)-3-ethylcarbodiimide hydrochloride (1.37 g), N,N-dimethylaminopyridine (872 mg), triethylamine (995 μl), and benzoic acid (610 mg), and the mixture was stirred at room temperature for one hour. To the reaction mixture was added a saturated aqueous ammonium chloride solution, and the mixture was extracted with ethyl acetate. The organic layer was washed with a saturated aqueous ammonium chloride solution, a saturated aqueous sodium hydrogen carbonate solution, and a saturated aqueous sodium chloride solution, dried over magnesium sulfate, filtered, and concentrated under reduced pressure. The obtained residue was purified by silica gel column chromatography (the developing solvent: hexane/ethyl acetate=1/1) to give the title compound (968 mg).

MS (ESI+) 425 ($M^+$+1, 100%).

Reference Example 691 tert-Butyl (rac.)-(3R,4R)-4-[3-(benzoyloxy)phenyl]-3-[({442-(dibenzylamino)ethyl]-7-fluoro-2,2-dimethyl-3-oxo-3,4-dihydro-2H-1,4-benzoxazin-6-yl}carbonyl)(ethyl)amino]piperidine-1-carboxylate

[Chemical formula 835]

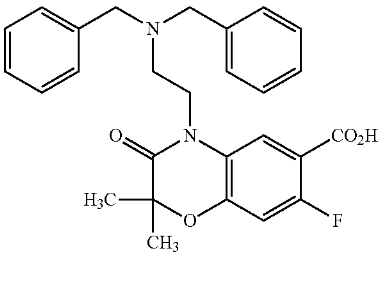

+

-continued

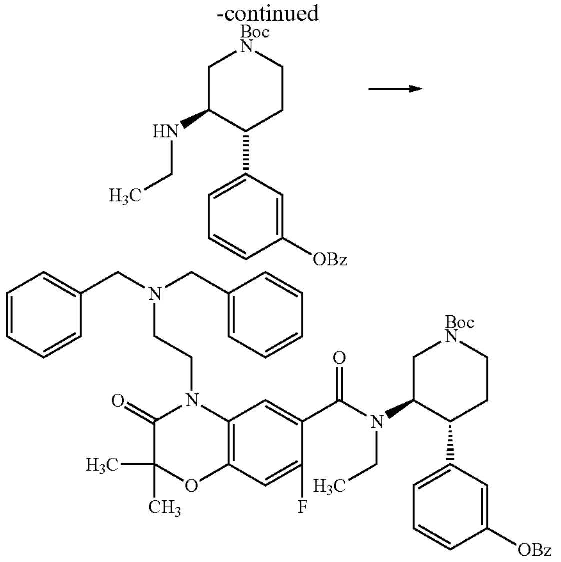

Using 4-[2-(dibenzylamino)ethyl]-7-fluoro-2,2-dimethyl-3-oxo-3,4-dihydro-2H-1,4-benzoxazine-6-carboxylic acid and tert-butyl (rac.)-(3R,4R)-4-[3-(benzoyloxy)phenyl]-3-(ethyl-amino)piperidine-1-carboxylate, the title compound was obtained in a similar manner to Reference Example 5.

MS (ESI+) 870 ($M^{+}$+1, 100%).

Reference Example 692 tert-Butyl (rac.)-(3R,4R)-3-[({4-[2-(dibenzylamino)ethyl]-7-fluoro-2,2-dimethyl-3-oxo-3,4-dihydro-2H-1,4-benzoxazin-6-yl}carbonyl)(ethyl)amino]-4-(3-hydroxyphenyl)piperidine-1-carboxylate

[Chemical formula 836]

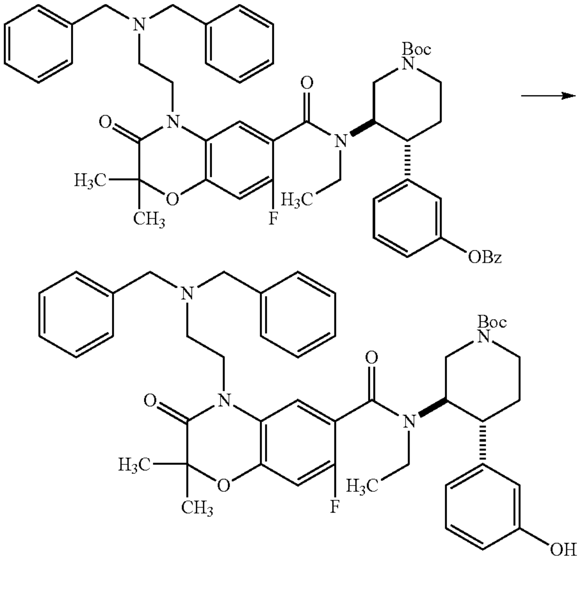

tert-Butyl (rac.)-(3R,4R)-4-[3-(benzoyloxy)phenyl]-3-[({442-(dibenzylamino)ethyl]-7-fluoro-2,2-dimethyl-3-oxo-3,4-dihydro-2H-1,4-benzoxazin-6-yl}carbonyl)(ethyl)amino]piperidine-1-carboxylate (501 mg) was dissolved in tetrahydrofuran (2 ml), and thereto was added a 1M aqueous sodium hydroxide solution (1.2 ml), and the mixture was stirred at 60° C. for 5 hours. The reaction solution was concentrated under reduced pressure, and thereto was added a 5% potassium hydrogen sulfate, and the mixture was extracted with ethyl acetate. The organic layer was washed with a saturated aqueous sodium chloride solution, dried over sodium sulfate, filtered, and concentrated under reduced pressure. The obtained residue was purified by silica gel column chromatography (the developing solvent: hexane/ethyl acetate=2/1) to give the title compound (293 mg).

MS (ESI+) 765 ($M^{+}$+1, 100%).

Reference Example 693 tert-Butyl (rac.)-(3R,4R)-3-[({4-[2-(dibenzylamino)ethyl]-7-fluoro-2,2-dimethyl-3-oxo-3,4-dihydro-2H-1,4-benzoxazin-6-yl}carbonyl)(ethyl)amino]-4-(3-methoxyphenyl)piperidine-1-carboxylate

[Chemical formula 837]

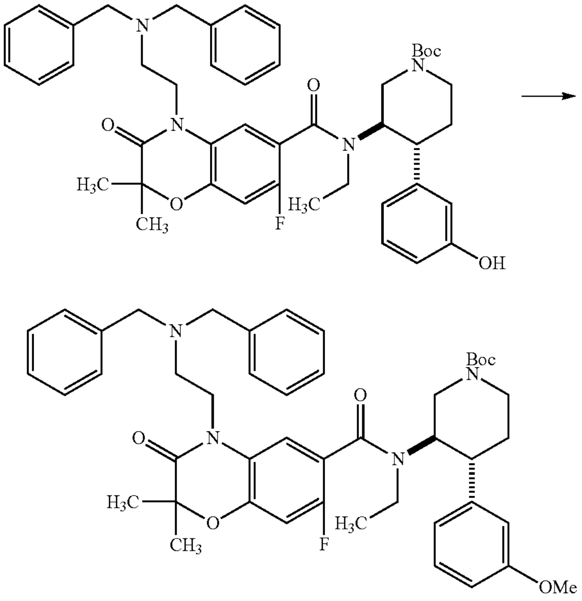

tert-Butyl (rac.)-(3R,4R)-3-[({4-[2-(dibenzylamino)ethyl]-7-fluoro-2,2-dimethyl-3-oxo-3,4-dihydro-2H-1,4-benzoxazin-6-yl}carbonyl)(ethyl)amino]-4-(3-hydroxyphenyl)piperidine-1-carboxylate (82.5 mg) was dissolved in acetonitrile (2 ml), and thereto were added potassium carbonate (29.8 mg) and methyl iodide (13.4 μl), and the mixture was refluxed for 3 hours. The reaction solution was cooled, and thereto was added a saturated aqueous ammonium chloride solution, and the mixture was extracted with ethyl acetate. The organic layer was washed with a saturated aqueous sodium chloride solution, dried over sodium sulfate, filtered, and concentrated under reduced pressure. The obtained residue was purified by silica gel column chromatography (the developing solvent: hexane/ethyl acetate=2/1) to give the title compound (68.6 mg).

MS (ESI+) 779 ($M^{+}$+1, 100%).

Reference Example 694 tert-Butyl (rac.)-(3R,4R)-3-[({4-[2-(dibenzylamino) ethyl]-7-fluoro-2,2-dimethyl-3-oxo-3,4-dihydro-2H-1,4-benzoxazin-6-yl]carbonyl)(ethyl)amino]-4-[3-(3-methoxypropoxy)phenyl]piperidine-1-carboxylate

[Chemical formula 838]

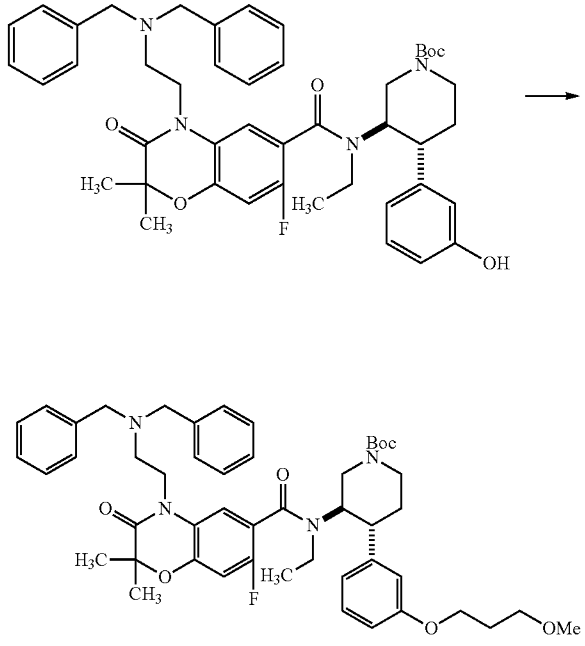

Using tert-butyl (rac.)-(3R,4R)-3-[({442-(dibenzylamino) ethyl]-7-fluoro-2,2-dimethyl-3-oxo-3,4-dihydro-2H-1,4-benzoxazin-6-yl]carbonyl)(ethyl)amino]-4-(3-hydroxyphenyl)piperidine-1-carboxylate and 3-methoxypropyl bromide, the title compound was obtained in a similar manner to Reference Example 693.

MS (ESI+) 838 ($M^+$+1, 100%).

Reference Example 695 tert-Butyl (rac.)-(3R,4R)-3-[{[4-(2-aminoethyl)-7-fluoro-2,2-dimethyl-3-oxo-3,4-dihydro-2H-1,4-benzoxazin-6-yl]carbonyl}(ethyl)amino]-4-(3-methoxyphenyl)piperidine-1-carboxylate

[Chemical formula 839]

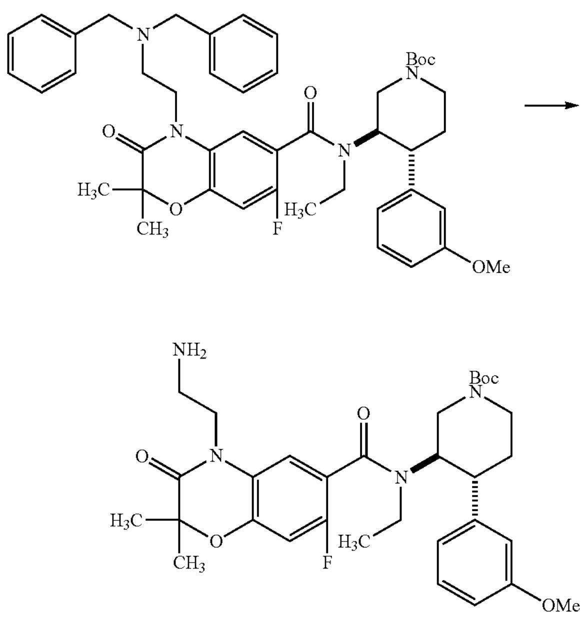

tert-Butyl (rac.)-(3R,4R)-3-[({4-[2-dibenzylamino)ethyl]-7-fluoro-2,2-dimethyl-3-oxo-3,4-dihydro-2H-1,4-benzoxazin-6-yl}carbonyl)(ethyl)amino]-4-(3-methoxyphenyl)piperidine-1-carboxylate (68.6 mg) was dissolved in tetrahydrofuran (3 ml), and thereto was added 200% palladium hydroxide-carbon (31.5 mg) at room temperature, and the mixture was stirred at room temperature for 4 hours under hydrogen atmosphere. The reaction mixture was filtered on celite, and the filtrate was concentrated under reduced pressure to give the title compound (52.0 mg).

MS (ESI+) 599 ($M^+$+1, 100%).

Reference Example 696 tert-Butyl (rac.)-(3R,4R)-3-[{[4-(2-aminoethyl)-7-fluoro-2,2-dimethyl-3-oxo-3,4-dihydro-2H-1,4-benzoxazin-6-yl]carbonyl}(ethyl)amino]-4-[3-(3-methoxypropoxy)phenyl]piperidine-1-carboxylate

[Chemical formula 840]

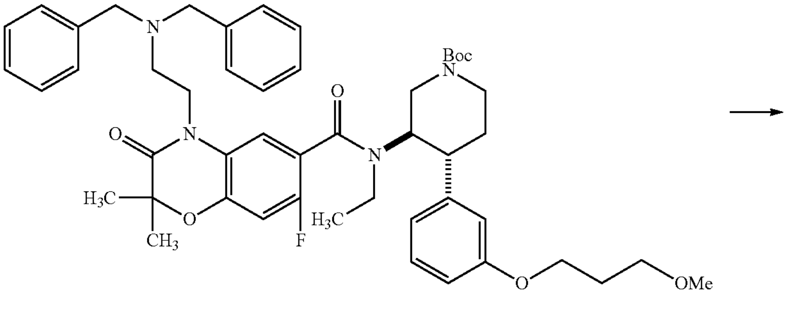

-continued

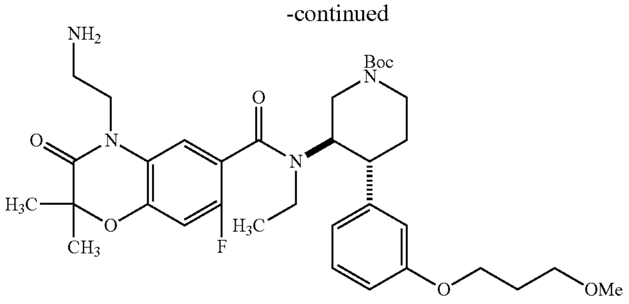

Using tert-butyl (rac.)-(3R,4R)-3-[({4-[2-(dibenzylamino)ethyl]-7-fluoro-2,2-dimethyl-3-oxo-3,4-dihydro-2H-1,4-benzoxazin-6-yl}carbonyl)(ethyl)amino]-4-[3-(3-methoxypropoxy)phenyl]-piperidine-1-carboxylate, the title compound was obtained in a similar manner to Reference Example 695.

MS (ESI+) 657 ($M^+$+1, 100%).

Reference Example 697 tert-Butyl (rac.)-(3R,4R)-3-[ethyl ({7-fluoro-2,2-dimethyl-3-oxo-4-[2-(propionylamino)ethyl]-3,4-dihydro-2H-1,4-benzoxazin-6-yl}carbonyl)amino]-4-(3-methoxyphenyl)piperidine-1-carboxylate

[Chemical formula 841]

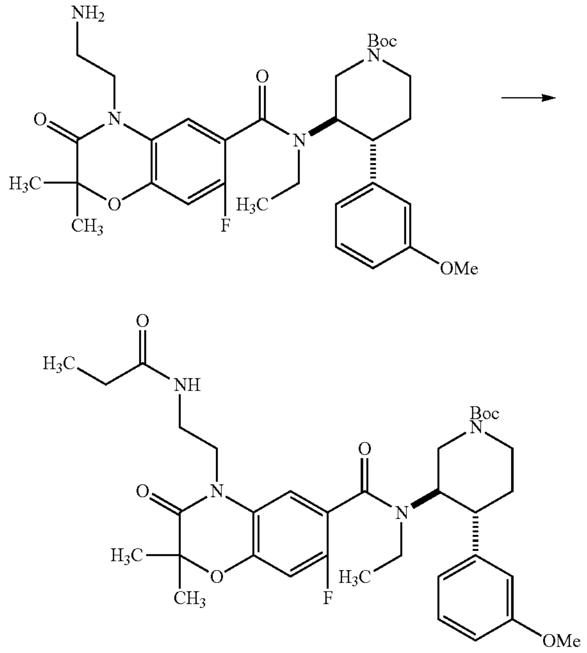

Using tert-butyl (rac.)-(3R,4R)-3-[{[4-(2-aminoethyl)-7-fluoro-2,2-dimethyl-3-oxo-3,4-dihydro-2H-1,4-benzoxazin-6-yl]carbonyl}(ethyl)amino]-4-(3-methoxyphenyl)piperidine-1-carboxylate, the title compound was obtained in a similar manner to Reference Example 132.

MS (ESI+) 655 ($M^+$+1, 100%).

Reference Example 698 tert-Butyl (rac.)-(3R,4R)-3-[ethyl({7-fluoro-2,2-dimethyl-3-oxo-4-[2-(propionylamino)ethyl]-3,4-dihydro-2H-1,4-benzoxazin-6-yl}carbonyl)amino]-4-[3-(3-methoxypropoxy)phenyl]piperidine-1-carboxylate

[Chemical formula 842]

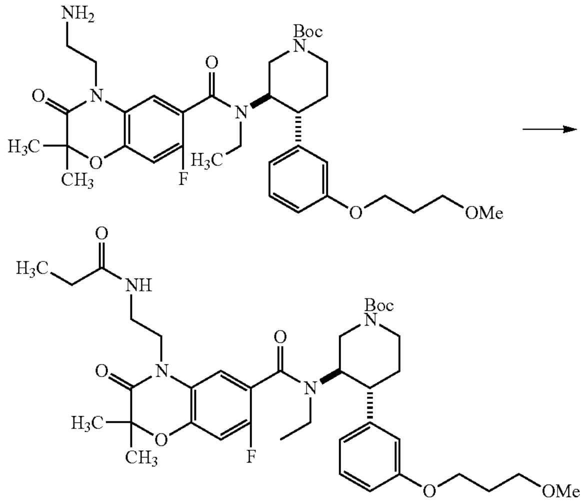

Using tert-butyl (rac.)-(3R,4R)-3-[{[4-(2-aminoethyl)-7-fluoro-2,2-dimethyl-3-oxo-3,4-dihydro-2H-1,4-benzoxazin-6-yl]carbonyl}(ethyl)amino]-4-[3-(3-methoxypropoxy)phenyl]piperidine-1-carboxylate, the title compound was obtained in a similar manner to Reference Example 132.

MS (ESI+) 713 ($M^+$+1, 100%).

Reference Example 699 tert-Butyl (3R)-3-[({7-(difluoromethyl)-2,2-dimethyl-3-oxo-4-[2-(propionylamino)ethyl]-3,4-dihydro-2H-1,4-benzoxazin-6-yl}carbonyl)(isopropyl)amino]piperidine-1-carboxylate

[Chemical formula 843]

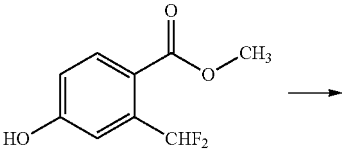

-continued

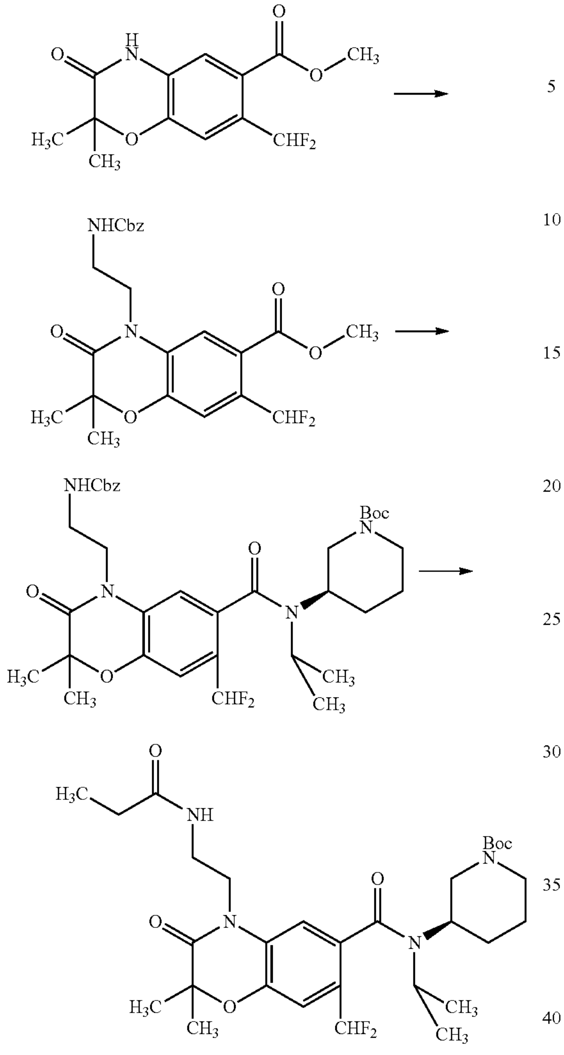

Using methyl 2-(difluoromethyl)-4-hydroxybenzoate, the title compound was obtained in a similar manner to Reference Example 55, Reference Example 3, Reference Example 5, Reference Example 139 and Reference Example 132.

MS (ESI+) 595 ($M^{+}$+1, 12%).

Reference Example 700 tert-Butyl (3R)-3-[{[4-{2-[(difluoroacetyl)amino]ethyl}-7-(difluoromethyl)-2,2-dimethyl-3-oxo-3,4-dihydro-2H-1,4-benzoxazin-6-yl]carbonyl}(isopropyl)amino]piperidine-1-carboxylate

[Chemical formula 844]

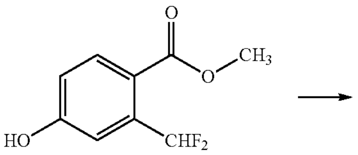

-continued

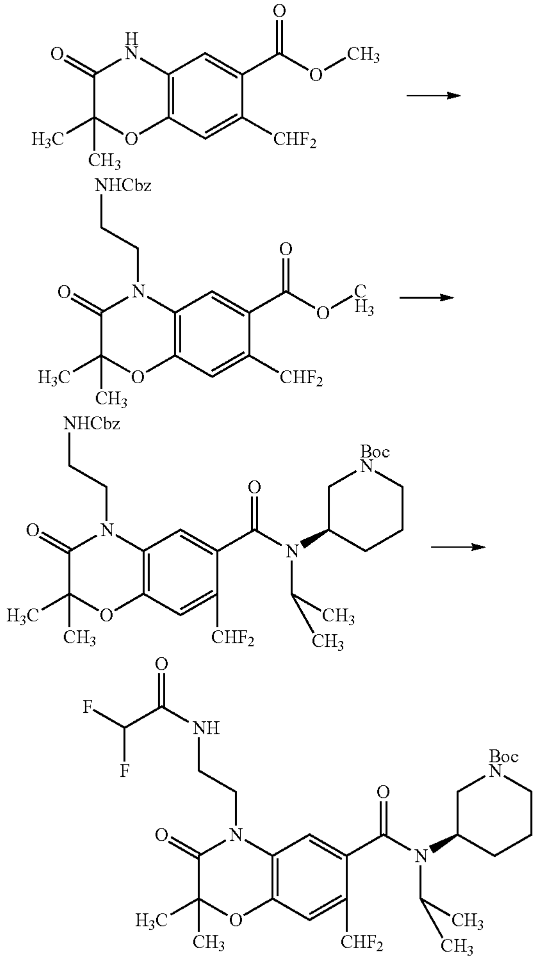

Using methyl 2-(difluoromethyl)-4-hydroxybenzoate, the title compound was obtained in a similar manner to Reference Example 55, Reference Example 3, Reference Example 5, Reference Example 139 and Reference Example 120.

MS (ESI+) 617 ($M^{+}$+1, 64%).

Reference Example 701 tert-Butyl (3R)-3-(isopropyl{[2-methyl-3-oxo-4-[2-(propynylamino)ethyl]-2-[(propynyloxy)methyl]-7-(trifluoromethyl)-3,4-dihydro-2H-1,4-benzoxazin-6-yl]carbonyl}amino)piperidine-1-carboxylate

[Chemical formula 845]

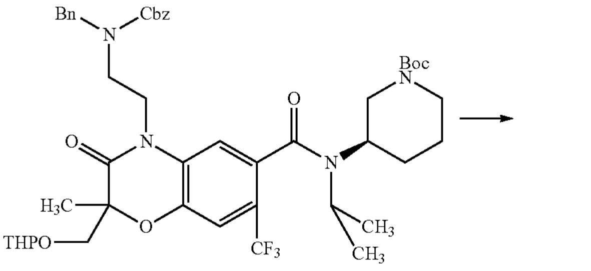

-continued

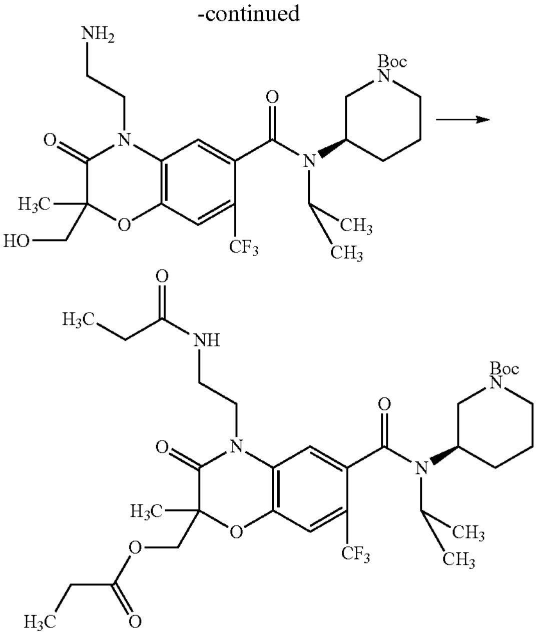

tert-Butyl (3R)-3-[{[4-(2-{benzyl[(benzyloxy)carbonyl]amino}ethyl)-2-methyl-3-oxo-2-[(tetrahydro-2H-pyran-2-yloxy)methyl]-7-(trifluoromethyl)-3,4-dihydro-2H-1,4-benzoxazin-6-yl]carbonyl}(isopropyl)amino]piperidine-1-carboxylate (24.9 g) was dissolved in methanol (300 mL), and thereto was added a 10% palladium/carbon (50% wet.: 30.0 g), and the mixture was vigorously stirred under hydrogen atmosphere at room temperature for 36 hours. After the reaction was complete, the mixture was filtered on celite, washed with ethyl acetate, and the filtrate was concentrated under reduced pressure. tert-Butyl (3R)-3-[{[4-(2-aminomethyl)-2-(hydroxymethyl)-2-methyl-3-oxo-7-(trifluoromethyl)-3,4-dihydro-2H-1,4-benzoxazin-6-yl]carbonyl}(isopropyl)amino]piperidine-1-carboxylate was dissolved in dichloromethane (300 ml), and thereto were added propionyl chloride (2.7 ml) and triethylamine (6.5 mL), and the mixture was stirred for one hour. To the reaction solution was added a saturated aqueous sodium hydrogen carbonate solution, and the mixture was extracted with chloroform. The organic layer was dried over sodium sulfate, filtered, concentrated under reduced pressure. The obtained residue was purified by column chromatography to give the title compound (5.48 g).

MS (ESI+) 685 ($M^+$+1, 12%).

Reference Example 702 tert-Butyl (3R)-3-[{[2-(hydroxymethyl)-2-methyl-3-oxo-4-[2-(propynylamino)ethyl]-7-(trifluoro-methyl)-3,4-dihydro-2H-1,4-benzoxazin-6-yl]carbonyl}(isopropyl)amino]piperidine-1-carboxylate

[Chemical formula 846]

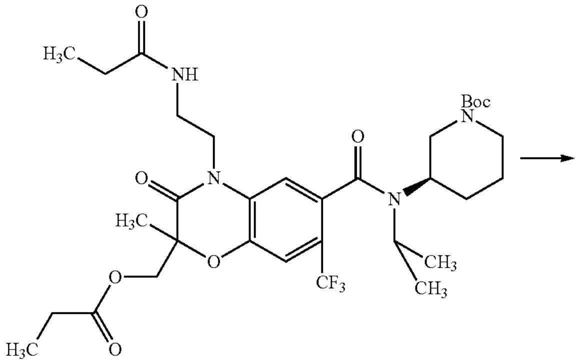

-continued

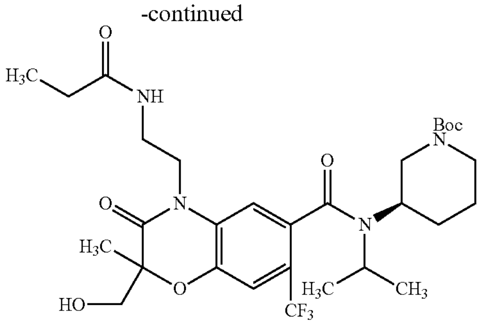

tert-Butyl (3R)-3-(isopropyl{[2-methyl-3-oxo-4-[2-(propynylamino)ethyl]-2-[(propynyl-oxy)methyl]-7-(trifluoromethyl)-3,4-dihydro-2H-1,4-benzoxazin-6-yl]carbonyl}amino)piperidine-1-carboxylate (24.9 g) was dissolved in methanol (100 mL), and thereto was added potassium carbonate (553 mg), and the mixture was stirred at 0° C. for one hour. After the reaction was complete, a saturated aqueous ammonium chloride solution was added thereto, and methanol was removed by evaporation under reduced pressure. The residue was diluted with water, and the mixture was extracted with ethyl acetate. The organic layer was dried over sodium sulfate, filtered, and concentrated under reduced pressure. The obtained residue was purified by column chromatography to give the title compound (4.92 g).

MS (ESI+) 629 ($M^+$+1, 27%).

Example 1

7-Bromo-N-isopropyl-4-(3-methoxypropyl)-2,2-dimethyl-3-oxo-N-[(3R)-piperidin-3-yl]-3,4-dihydro-2H-1,4-benzoxazine-6-carboxamide hydrochloride

[Chemical formula 847]

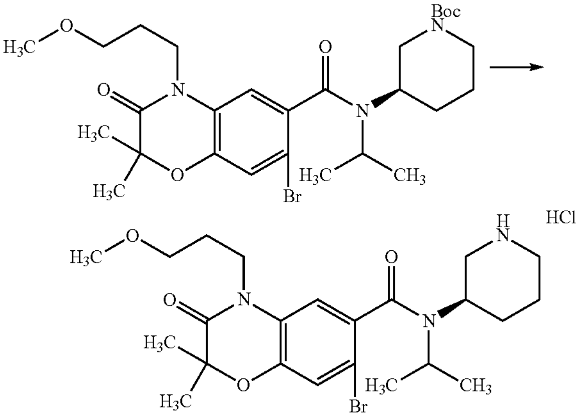

To a solution of the compound of Reference Example 6 (100 mg) in 1,4-dioxane (3 ml) was added a 4N hydrochloric acid/dioxane solution (2 ml), and the mixture was stirred at 25° C. for 2 hours. The mixture was concentrated under reduced pressure to give the title compound (90.8 mg).

$^1$H NMR (400 MHz, $CDCl_3$) δ 9.78 (br, 2H), 7.15 (s, 1H), 6.91-6.90 (m, 1H), 4.21-4.12 (m, 1H), 3.99-3.86 (m, 3H), 3.73-3.69 (m, 1H), 3.48-3.34 (m, 4H), 3.31 (s, 3H), 2.95-2.86 (m, 2H), 2.11-2.00 (m, 2H), 1.90-1.82 (m, 3H), 1.56 (s, 3H), 1.43-1.41 (m, 3H), 1.38-1.12 (m, 6H).

The compounds of Examples 2 to 26 were synthesized in a similar manner to a corresponding Reference Example and Example 1.

TABLE 1

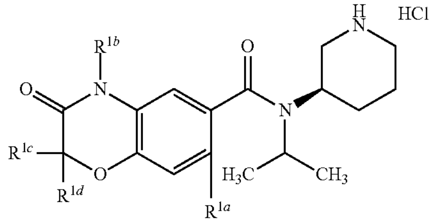

| Ex. No. | $R^{1d}$ | $R^{1c}$ | $R^{1b}$ | $R^{1a}$ |
|---|---|---|---|---|
| 2 | Me | Me | $MeO(CH_2)_3$ | Cl |
| 3 | Me | Me | $MeO(CH_2)_3$ | CN |
| 4 | Me | Me | $MeO(CH_2)_3$ | Me |
| 5 | Me | Me | $MeO(CH_2)_3$ | Et |
| 6 | Me | Me | $MeO(CH_2)_3$ | n-Pr |
| 7 | Me | Me | $MeO(CH_2)_4$ | Cl |
| 8 | Me | Me | $MeO(CH_2)_4$ | Me |
| 9 | Me | Me | $EtO(CH_2)_3$ | Cl |
| 10 | Me | Me | $MeOC(O)NH(CH_2)_2$ | Br |
| 11 | Me | Me | $MeOC(O)NH(CH_2)_2$ | Cl |
| 12 | Me | Me | $MeOC(O)NH(CH_2)_2$ | Me |
| 13 | Me | Et | $MeO(CH_2)_3$ | Cl |
| 14 | Me | Et | $MeO(CH_2)_3$ | Br |

TABLE 1-continued

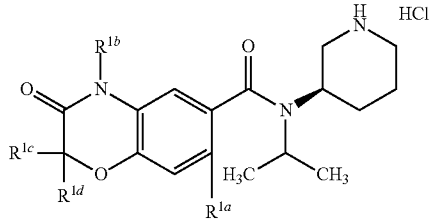

| Ex. No. | $R^{1d}$ | $R^{1c}$ | $R^{1b}$ | $R^{1a}$ |
|---|---|---|---|---|
| 15 | Me | Et | $MeO(CH_2)_3$ | CN |
| 16 | (R)-Me | H | $MeO(CH_2)_3$ | Cl |
| 17 | (R)-Me | H | $MeO(CH_2)_3$ | Br |
| 18 | (R)-Me | H | $MeO(CH_2)_3$ | Me |
| 19 | (R)-Me | H | $MeO(CH_2)_4$ | Cl |
| 20 | (R)-Me | H | $MeO(CH_2)_4$ | Br |
| 21 | (R)-Me | H | $MeO(CH_2)_4$ | Me |
| 22 | (R)-Me | H | $MeOC(O)NH(CH_2)_2$ | Cl |
| 23 | (R)-Me | H | $MeOC(O)NH(CH_2)_2$ | Br |
| 24 | (R)-Me | H | $MeOC(O)NH(CH_2)_2$ | Me |
| 25 | Et | H | $MeO(CH_2)_3$ | Cl |
| 26 | Me | $EtOCH_2$ | $MeO(CH_2)_4$ | Cl |

TABLE 2

| Ex. | $^1H$ NMR (400 MHz, $CDCl_3$) |
|---|---|
| 2 | δ 9.84 (br, 2H), 6.99 (s, 1H), 6.91 (s, 1H), 4.18 (br, 1H), 4.01-3.87 (m, 3H), 3.75-3.68 (m, 1H), 3.49-3.35 (m, 4H), 3.31 (s, 3H), 2.95-2.88 (m, 2H), 2.06-2.01 (m, 2H), 1.89-1.81 (m, 3H), 1.56 (s, 3H), 1.43-1.41 (m, 3H), 1.38-1.12 (m, 6H) |
| 3 | δ 9.83 (br, 2H), 7.22 (s, 1H), 7.06 (s, 1H), 4.18 (brs, 1H), 4.01-3.89 (m, 3H), 3.70-3.67 (m, 1H), 3.49-3.39 (m, 4H), 3.31 (s, 3H), 2.97-2.81 (m, 2H), 2.07-2.01 (m, 2H), 1.91-1.87 (m, 3H), 1.53-1.49 (m, 6H), 1.38-1.21 (m, 6H) |
| 4 | δ 9.89-9.77 (m, 2H), 6.79 (brs, 2H), 4.24-4.21 (m, 1H), 4.01-3.75 (m, 4H), 3.48-3.34 (m, 4H), 3.33-3.30 (m, 3H), 2.95-2.89 (m, 2H), 2.21-2.19 (m, 3H), 2.08-2.04 (m, 2H), 1.88-1.83 (m, 3H), 1.56 (s, 3H), 1.41-1.39 (m, 3H), 1.32-1.22 (m, 3H), 1.19-1.14 (m, 3H) |
| 5 | δ 9.81 (br, 2H), 6.86 (s, 1H), 6.78 (s, 1H), 4.22-4.19 (m, 1H), 3.99-3.78 (m, 4H), 3.42-3.36 (m, 4H), 3.33-3.30 (m, 3H), 2.93-2.89 (m, 2H), 2.56-2.47 (m, 2H), 2.02-1.87 (m, 5H), 1.56 (s, 3H), 1.42-1.40 (m, 3H), 1.31-1.15 (m, 9H) |
| 6 | δ 9.92-9.78 (m, 2H), 6.85-6.83 (m, 1H), 6.79-6.76 (m, 1H), 4.24-4.19 (m, 1H), 4.00-3.80 (m, 4H), 3.49-3.36 (m, 4H), 3.33-3.30 (m, 3H), 2.95-2.89 (m, 2H), 2.51-2.43 (m, 2H), 2.05-2.01 (m, 2H), 1.91-1.86 (m, 3H), 1.69-1.64 (m, 2H), 1.56 (s, 3H), 1.42-1.40 (m, 3H), 1.27-1.25 (m, 3H), 1.19-1.15 (m, 3H), 0.94 (t, J = 7.3 Hz, 3H) |
| 7 | δ 9.83 (br, 2H), 6.99-6.98 (m, 1H), 6.83-6.73 (m, 1H), 4.21-4.14 (m, 1H), 4.01-3.69 (m, 4H), 3.49-3.37 (m, 4H), 3.30 (s, 3H), 2.96-2.83 (m, 2H), 2.13-1.61 (m, 7H), 1.55 (s, 3H), 1.44 (s, 3H), 1.39-1.11 (m, 6H) |
| 8 | δ 9.87-9.85 (m, 2H), 6.79 (s, 1H), 6.70-6.62 (m, 1H), 4.24-4.20 (m, 1H), 3.99-3.95 (m, 1H), 3.86-3.75 (m, 3H), 3.48-3.32 (m, 4H), 3.29 (s, 3H), 2.93-2.88 (m, 2H), 2.20-2.18 (m, 3H), 2.12-1.59 (m, 7H), 1.54 (s, 3H), 1.41 (s, 3H), 1.30-1.13 (m, 6H) |
| 9 | δ 9.84-9.48 (m, 2H), 7.01 (s, 1H), 6.78-6.68 (m, 1H), 4.18-4.14 (m, 1H), 4.00-3.85 (m, 3H), 3.74-3.70 (m, 1H), 3.49-3.38 (m, 6H), 2.95-2.84 (m, 2H), 2.15-2.04 (m, 2H), 1.89-1.82 (m, 3H), 1.56 (s, 3H), 1.43-1.41 (m, 3H), 1.35-0.86 (m, 9H) |
| 10 | δ 9.75 (br, 2H), 7.21-7.13 (m, 2H), 5.75 (brs, 0.5H), 5.04 (brs, 0.5H), 4.16-4.09 (m, 2H), 3.91-3.86 (m, 2H), 3.75-3.70 (m, 2H), 3.63-3.59 (m, 3H), 3.48-3.37 (m, 3H), 2.93-2.76 (m, 2H), 2.09-1.92 (m, 3H), 1.54 (s, 3H), 1.44 (s, 3H), 1.38-1.15 (m, 6H) |
| 11 | δ 9.87 (br, 2H), 7.26-7.21 (m, 1H), 6.99-6.97 (m, 1H), 5.67 (brs, 0.5H), 4.99 (brs, 0.5H), 4.15-4.11 (m, 2H), 3.96-3.88 (m, 2H), 3.72-3.66 (m, 2H), 3.59 (s, 3H), 3.48-3.38 (m, 3H), 2.94-2.79 (m, 2H), 2.09-1.90 (m, 3H), 1.54 (s, 3H), 1.43 (s, 3H), 1.37-1.30 (m, 3H), 1.24-1.15 (m, 3H) |
| 12 | δ 9.85 (br, 2H), 7.07-7.03 (m, 1H), 6.78 (s, 1H), 5.69 (brs, 0.5H), 5.04 (brs, 0.5H), 4.19-3.70 (m, 6H), 3.62-3.60 (m, 3H), 3.48-3.39 (m, 3H), 2.94-2.83 (m, 2H), 2.21-2.18 (m, 3H), 2.09-2.02 (m, 2H), 1.89-1.86 (m, 1H), 1.53 (s, 3H), 1.41 (s, 3H), 1.36-1.30 (m, 3H), 1.20-1.16 (m, 3H) |
| 13 | δ 9.86-9.76 (m, 2H), 7.00-6.98 (m, 1H), 6.90-6.87 (m, 1H), 4.20-4.16 (m, 1H), 3.99-3.85 (m, 3H), 3.78-3.69 (m, 1H), 3.49-3.36 (m, 4H), 3.32-3.30 (m, 3H), 2.95-2.84 (m, 2H), 2.16-1.78 (m, 7H), 1.52-1.39 (m, 3H), 1.37-1.12 (m, 6H), 1.01-0.89 (m, 3H) |
| 14 | δ 9.95-9.68 (br, 2H), 7.15-7.12 (m, 1H), 6.98-6.86 (m, 1H), 4.28-4.11 (m, 1H), 4.10-3.61 (m, 4H), 3.59-3.35 (m, 4H), 3.32-3.28 (m, 3H), 3.03-2.83 (m, 2H), 2.26-1.61 (m, 7H), 1.54-1.41 (m, 3H), 1.40-1.11 (m, 6H), 1.05-0.87 (m, 3H) |

TABLE 2-continued

| Ex. | $^1$H NMR (400 MHz, $CDCl_3$) |
|---|---|
| 15 | δ 9.83-9.68 (br, 2H), 7.25-7.12 (m, 1H), 6.98-6.90 (m, 1H), 4.18-4.04 (m, 1H), 4.02-3.77 (m, 3H), 3.70-3.58 (m, 1H), 3.47-3.25 (m, 4H), 3.23-3.17 (m, 3H), 2.92-2.72 (m, 2H), 2.15-1.72 (m, 7H), 1.70-1.60 (m, 3H), 1.53-1.15 (m, 6H), 0.97-0.83 (m, 3H) |
| 16 | δ 10.0-9.60 (br, 2H), 7.05-7.01 (m, 1H), 7.00-6.92 (m, 1H), 4.74-4.55 (m, 1H), 4.39-3.65 (m, 5H), 3.55-3.33 (m, 4H), 3.32-3.28 (m, 3H), 3.03-2.80 (m, 2H), 2.21-1.68 (m, 5H), 1.63-1.50 (m, 3H), 1.40-1.12 (m, 6H) |
| 17 | δ 9.95-9.60 (br, 2H), 7.13-7.11 (m, 1H), 6.89-6.83 (m, 1H), 4.68-4.48 (m, 1H), 4.18-3.52 (m, 5H), 3.45-3.28 (m, 4H), 3.26-3.23 (m, 3H), 2.95-2.75 (m, 2H), 2.15-1.71 (m, 5H), 1.55-1.40 (m, 3H), 1.38-1.02 (m, 6H) |
| 18 | δ 9.99-9.68 (br, 2H), 6.87-6.81 (m, 2H), 4.72-4.50 (m, 1H), 4.30-3.71 (m, 5H), 3.53-3.33 (m, 4H), 3.33-3.27 (m, 3H), 3.01-2.86 (m, 2H), 2.29-2.18 (m, 3H), 2.17-1.68 (m, 5H), 1.63-1.47 (m, 3H), 1.40-1.11 (m, 6H). MS (ESI+) 418 ($M^+$ + 1, 100%). |
| 19 | δ 10.1-9.77 (br, 2H), 7.25-7.16 (m, 1H), 7.05-7.03 (m, 1H), 4.73-4.56 (m, 1H), 4.30-3.63 (m, 5H), 3.54-3.36 (m, 4H), 3.35-3.28 (m, 3H), 3.02-2.80 (m, 2H), 2.22-1.80 (m, 3H), 1.75-1.50 (m, 7H), 1.41-1.08 (m, 6H) |
| 20 | δ 10.2-9.65 (br, 2H), 7.22-7.18 (m, 1H), 7.05-6.86 (m, 1H), 4.72-4.55 (m, 1H), 4.31-3.60 (m, 5H), 3.55-3.38 (m, 4H), 3.33-3.28 (m, 3H), 3.04-2.73 (m, 2H), 2.23-1.50 (m, 10H), 1.49-1.10 (m, 6H) |
| 21 | δ 9.88-9.66 (br, 2H), 6.93-6.84 (m, 1H), 6.76-6.74 (m, 1H), 4.62-4.43 (m, 1H), 4.22-3.64 (m, 5H), 3.45-3.27 (m, 4H), 3.25-3.18 (m, 3H), 2.95-2.81 (m, 2H), 2.17-2.11 (m, 3H), 2.10-1.72 (m, 3H), 1.70-1.35 (m, 7H), 1.28-1.02 (m, 6H) |
| 22 | δ 9.95-9.58 (br, 2H), 7.26-7.17 (m, 1H), 7.04-7.01 (m, 1H), 5.83 (brs, 0.5H), 5.06 (brs, 0.5H), 4.75-4.57 (m, 1H), 4.27-4.10 (m, 2H), 4.08-3.82 (m, 2H), 3.80-3.65 (m, 2H), 3.65-3.50 (m, 3H), 3.49-3.28 (m, 3H), 3.05-2.80 (m, 2H), 2.18-1.85 (m, 3H), 1.65-1.46 (m, 3H), 1.43-1.11 (m, 6H) |
| 23 | δ 9.90-9.61 (br, 2H), 7.33-7.18 (m, 2H), 5.35 (brs, 0.5H), 5.04 (brs, 0.5H), 4.75-4.55 (m, 1H), 4.23-4.03 (m, 2H), 4.02-3.83 (m, 2H), 3.78-3.33 (m, 8H), 3.02-2.72 (m, 2H), 2.08-1.88 (m, 3H), 1.63-1.52 (m, 3H), 1.47-1.13 (m, 6H) |
| 24 | δ 9.95-9.65 (br, 2H), 7.20-7.05 (m, 1H), 6.83-6.80 (m, 1H), 5.70 (brs, 0.5H), 5.01 (brs, 0.5H), 4.71-4.53 (m, 1H), 4.32-3.71 (m, 6H), 3.70-3.51 (m, 3H), 3.50-3.28 (m, 3H), 2.98-2.75 (m, 2H), 2.28-2.12 (m, 3H), 2.10-1.88 (m, 3H), 1.64-1.45 (m, 3H), 1.43-1.10 (m, 6H) |
| 25 | δ 9.95-9.70 (br, 2H), 7.05-7.02 (m, 1H), 6.98-6.90 (m, 1H), 4.58-4.43 (m, 1H), 4.28-3.65 (m, 5H), 3.53-3.34 (m, 4H), 3.32-3.30 (m, 3H), 3.03-2.71 (m, 2H), 2.23-1.73 (m, 7H), 1.42-1.12 (m, 6H), 1.11-1.03 (m, 3H) |
| 26 | δ 9.95-9.70 (br, 2H), 7.03-6.98 (m, 1H), 6.87-6.67 (m, 1H), 4.30-3.43 (m, 10H), 3.42-3.33 (m, 3H), 3.32-3.25 (m, 3H), 3.07-2.80 (m, 2H), 2.28-1.61 (m, 7H), 1.55-1.38 (m, 3H), 1.37-1.12 (m, 6H), 1.11-1.03 (m, 3H) |

The compounds of Examples 27 to 201 were synthesized in a similar manner to a corresponding Reference Example and Example 1. Subsequently, the compounds of Examples 30, 36, 37, 49, 64, 65, 77, 78, 135 were obtained by using a corresponding compound in a similar manner to Examples 64, 65.

Example 64

(2R)—N-Isopropyl-4-(4-methoxybutyl)-2-(methoxymethyl)-2,7-dimethyl-3-oxo-N-[(3R)-piperidin-3-yl]-3,4-dihydro-2H-1,4-benzoxazine-6-carboxamide hydrochloride

Example 65

(2S)—N-Isopropyl-4-(4-methoxybutyl)-2-(methoxymethyl)-2,7-dimethyl-3-oxo-N-[(3R)-piperidin-3-yl]-3,4-dihydro-2H-1,4-benzoxazine-6-carboxamide hydrochloride

[Chemical formula 848]

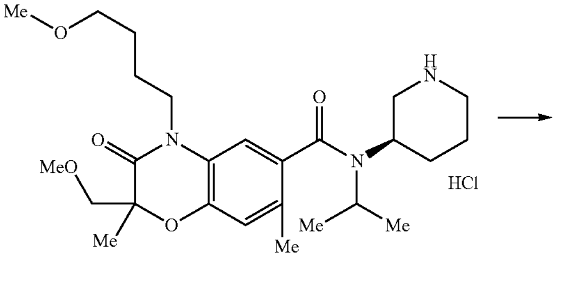

-continued

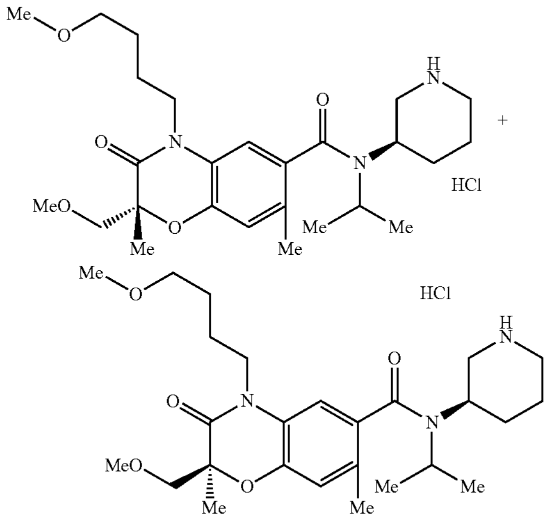

The compound of Example 58 was separated and collected by HPLC, using SUMIPAX ODS A-212 (acetonitrile/0.1% aqueous trifluoroacetic acid solution=42/58) or using Daicel chiralpak AD-H (hexane/0.3% diethylamine (2-propanol solution)=80/20) to give (2R)—N-isopropyl-4-(4-methoxybutyl)-2-(methoxymethyl)-2,7-dimethyl-3-oxo-N-[(3R)-piperidin-3-yl]-3,4-dihydro-2H-1,4-benzoxazine-6-carboxamide and (2S)—N-isopropyl-4-(4-methoxybutyl)-2-(methoxymethyl)-2,7-dimethyl-3-oxo-N-[(3R)-piperidin-3-yl]-3,4-dihydro-2H-1,4-benzoxazine-6-carboxamide, to which a 4M hydrochloric acid-dioxane solution was added individually, and concentrated under reduced pressure to give the title compounds.

The compounds of Examples 27 to 48 were synthesized in a similar manner to a corresponding Reference Example and Example 1.

TABLE 3

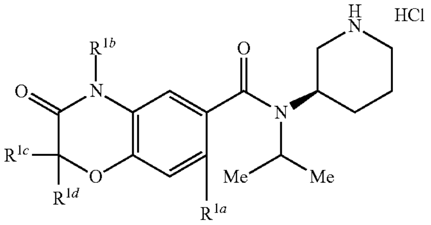

| Ex. | $R^{1d}$ | $R^{1c}$ | $R^{1b}$ | $R^{1a}$ |
| --- | --- | --- | --- | --- |
| 27 | $Me_2NC(O)$ | Me | $MeO(CH_2)_4$ | Cl |
| 28 | 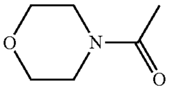 | Me | $MeO(CH_2)_4$ | Cl |
| 29 | 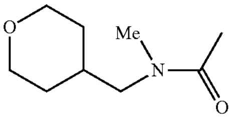 | Me | $MeO(CH_2)_4$ | Cl |
| 30 | 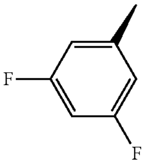 | Me | $MeOC(O)NH(CH_2)_2$ | Cl |
| 31 | $MeOCH_2$ | Me | $MeO(CH_2)_4$ | Cl |
| 32 | Me | Me | $MeO(CH_2)_3$ | $CF_3$ |
| 33 | Me | Me | $MeO(CH_2)_4$ | $CF_3$ |
| 34 | Me | Me | $MeOC(O)NH(CH_2)_2$ | $CF_3$ |
| 35 | Me | Me | $MeO(CH_2)_4$ | Br |
| 36 | 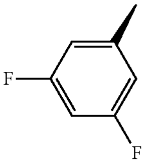 | Me | $MeOC(O)NH(CH_2)_2$ | Br |
| 37 | 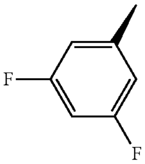 | Me | $MeOC(O)NH(CH_2)_2$ | Me |
| 38 | Me | Me | $MeO(CH_2)_4$ | OMe |
| 39 | Me | Me | $NC(CH_2)_4$ | Me |
| 40 | Me | Me | $Me_2NC(O)O(CH_2)_2$ | Me |
| 41 | $MeCH_2OCH_2$ | Me | $MeO(CH_2)_4$ | Br |
| 42 | $MeCH_2OCH_2$ | Me | $MeO(CH_2)_4$ | Me |
| 43 | 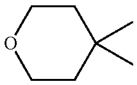 | | $MeO(CH_2)_4$ | Cl |
| 44 | Me | Me | $CH_3C(O)NH(CH_2)_2$ | Me |
| 45 | Me | Me | $CH_3S(O)_2NH(CH_2)_2$ | Me |

TABLE 3-continued

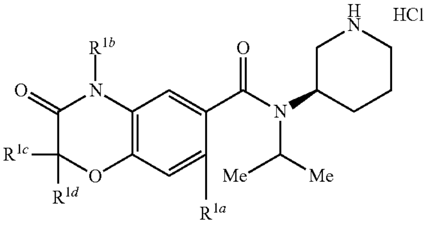

| Ex. | $R^{1d}$ | $R^{1c}$ | $R^{1b}$ | $R^{1a}$ |
|---|---|---|---|---|
| 46 | Me | Me | 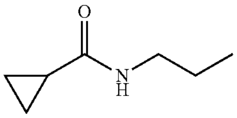 | Me |
| 47 | 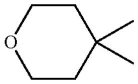 | | $MeO(CH_2)_4$ | Br |
| 48 | 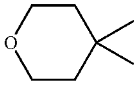 | | $MeO(CH_2)_4$ | Me |

TABLE 4

| Ex. | $^1H$ NMR (300 or 400 MHz, solvent)/MS (ESI+) |
|---|---|
| 27 | (400 MHz, DMSO-$d_6$) δ9.10-8.71 (br, 2H), 7.41-7.13 (m, 2H), 4.13-3.99 (m, 1H), 3.95-3.73 (m, 2H), 3.72-2.93 (m, 10H), 2.95-2.49 (m, 7H), 1.95-1.64 (m, 3H), 1.62-1.31 (m, 7H), 1.25-1.15 (m, 6H) |
| 28 | (400 MHz, DMSO-$d_6$) δ9.21-8.91 (br, 2H), 7.48-7.13 (m, 2H), 4.11-3.98 (m, 1H), 3.95-3.73 (m, 2H), 3.72-3.22 (m, 13H), 3.20-3.05 (m, 1H), 3.18 (s, 3H), 2.84-2.51 (m, 2H), 2.04-1.73 (m, 3H), 1.61-1.30 (m, 7H), 1.24-1.03 (m, 6H) |
| 29 | (400 MHz, $CDCl_3$) δ9.87-9.23 (br, 2H), 7.08-6.65 (m, 2H), 4.23-2.48 (m, 20H), 2.31-1.38 (m, 18H), 1.37-0.97 (m, 6H) |
| 30 | RT 3.739 min (Shim-pack XR-ODS, 0.1% trifluoroacetic acid in water/acetonitrile, acetonitrile 30-90% 5.7 min, 1.0 ml/min). MS (ESI+) 579 ($M^+$ + 1, 100%). |
| 31 | (400 MHz, $CDCl_3$) δ9.98-9.45 (br, 2H), 6.96-6.92 (m, 1H), 6.82-6.57 (m, 1H), 4.21-3.99 (m, 1H), 3.98-3.71 (m, 4H), 3.70-3.42 (m, 4H), 3.33 (s, 3H), 3.35-3.25 (m, 2H), 3.23 (s, 3H), 2.95-2.68 (m, 2H), 2.20-1.88 (m, 3H), 1.87-1.46 (m, 7H), 1.39-0.98 (m, 6H) |
| 32 | RT 3.548 min (Shim-pack XR-ODS, 0.1% trifluoroacetic acid in water/acetonitrile, acetonitrile 30-90% 5.7 min, 1.0 ml/min). MS (ESI+) 486 ($M^+$ + 1, 100%). |
| 33 | (400 MHz, DMSO-$d_6$) δ9.18-9.72 (m, 2H), 7.08-7.26 (m, 2H), 2.50-4.22 (m, 17H), 1.28-1.97 (m, 10H), 0.97-1.22 (m, 6H) |
| 34 | (400 MHz, DMSO-$d_6$) δ8.78-9.50 (m, 2H), 7.50 (brs, 1H), 7.24-7.42 (m, 2H), 2.96-3.98 (m, 12H), 2.52-2.85 (m, 2H), 1.60-1.96 (m, 3H), 1.48 (s, 3H), 1.42 (s, 3H), 0.98-1.19 (m, 6H) |
| 35 | RT 3.487 min (Shim-pack XR-ODS, 0.1% trifluoroacetic acid in water/acetonitrile, acetonitrile 30-90% 5.7 min, 1.0 ml/min). MS (ESI+) 510 ($M^+$ + 1, 100%). |
| 36 | RT 3.894 min (Shim-pack XR-ODS, 0.1% trifluoroacetic acid in water/acetonitrile, acetonitrile 30-90% 5.7 min, 1.0 ml/min). MS (ESI+) 623 ($M^+$ + 1, 100%). |
| 37 | RT 3.702 min (Shim-pack XR-ODS, 0.1% trifluoroacetic acid in water/acetonitrile, acetonitrile 30-90% 5.7 min, 1.0 ml/min). MS (ESI+) 559 ($M^+$ + 1, 100%). |
| 38 | (300 MHz, DMSO-$d_6$) δ9.39 (m, 1H), 7.00-6.89 (m, 1H), 6.78-6.75 (m, 1H), 3.95-3.60 (m, 7H), 3.38-3.02 (m, 8H), 2.73-2.51 (m, 3H), 1.91-1.65 (m, 3H), 1.49-1.37 (m, 10H), 1.16-1.01 (m, 5H) |
| 39 | (300 MHz, DMSO-$d_6$) δ9.04 (m, 1H), 7.06-6.97 (m, 1H), 6.90 (m, 1H), 4.05-3.60 (m, 5H), 3.33-3.18 (m, 4H), 2.13 (s, 3H), 1.91-1.73 (m, 3H), 1.56-0.84 (m, 18H) |
| 40 | (300 MHz, DMSO-$d_6$) δ9.23 (m, 1H), 7.10-7.03 (m, 1H), 6.90 (m, 1H), 3.84-3.59 (m, 2H), 3.34-3.05 (m, 2H), 2.75-2.70 (m, 6H), 2.51-2.50 (m, 6H), 2.13 (s, 3H), 1.91-1.76 (m, 3H), 1.44-1.25 (m, 9H), 1.15-1.05 (m, 4H) |
| 41 | (400 MHz, $CDCl_3$) δ9.95-9.36 (br, 2H), 6.77-6.75 (m, 1H), 6.64-6.50 (m, 1H), 4.32-4.04 (m, 1H), 4.01-3.61 (m, 6H), 3.59-3.15 (m, 6H), 3.22 (s, 3H), 2.97-2.65 (m, 2H), 2.18-1.48 (m, 10H), 1.39-0.90 (m, 9H) |

TABLE 4-continued

| Ex. | $^1$H NMR (300 or 400 MHz, solvent)/MS (ESI+) |
|---|---|
| 42 | (400 MHz, $CDCl_3$) δ 9.89-9.67 (br, 2H), 6.98-6.67 (m, 2H), 4.28-3.29 (m, 13H), 3.29-3.21 (m, 3H), 3.08-2.79 (m, 2H), 2.28-1.61 (m, 10H), 1.57-1.38 (m, 3H), 1.39-1.11 (m, 6H), 1.10-1.03 (m, 3H) |
| 43 | RT 2.823 min (Shim-pack XR-ODS, 0.1% trifluoroacetic acid in water/acetonitrile, acetonitrile 30-90% 5.7 min, 1.0 ml/min). MS (ESI+) 508 ($M^+$ + 1, 100%). |
| 44 | (300 MHz, DMSO-$d_6$) δ9.46-9.31 (m, 1H), 7.17-7.09 (m, 1H), 6.88 (m, 1H), 4.07-3.58 (m, 5H), 3.30-3.20 (m, 3H), 2.77-2.68 (m, 2H), 2.51-2.50 (m, 2H), 2.14 (s, 3H), 1.91-1.77 (m, 6H), 1.49-1.36 (m, 6H), 1.23-1.03 (m, 5H) |
| 45 | (300 MHz, DMSO-$d_6$) δ9.35 (m, 1H), 7.05-6.96 (m, 1H), 6.87 (m, 1H), 3.93-3.50 (m, 4H), 3.35-3.09 (m, 5H), 2.95-2.78 (m, 3H), 2.49-2.48 (m, 2H), 2.12 (s, 3H), 1.90-1.73 (m, 3H), 1.44-1.39 (m, 6H), 1.17-1.01 (m, 6H) |
| 46 | (300 MHz, DMSO-$d_6$) δ9.94-8.79 (m, 1H), 6.81-6.69 (m, 1H), 6.37 (m, 1H), 3.35-3.00 (m, 4H), 2.85-2.63 (m, 6H), 2.31-2.23 (m, 3H), 2.65 (s, 3H), 1.45-1.24 (m, 3H), 1.01-0.85 (m, 6H), 0.73-0.54 (m, 5H), 0.32-0.25 (m, 4H) |
| 47 | RT 2.995 min (Shim-pack XR-ODS, 0.1% trifluoroacetic acid in water/acetonitrile, acetonitrile 30-90% 5.7 min, 1.0 ml/min). MS (ESI+) 552 ($M^+$ + 1, 100%). |
| 48 | RT 2.730 min (Shim-pack XR-ODS, 0.1% trifluoroacetic acid in water/acetonitrile, acetonitrile 30-90% 5.7 min, 1.0 ml/min) MS (ESI+) 488 ($M^+$ + 1, 100%). |

The compounds of Examples 49 to 71 were synthesized in a similar manner to Reference Example and Example 1.

TABLE 5

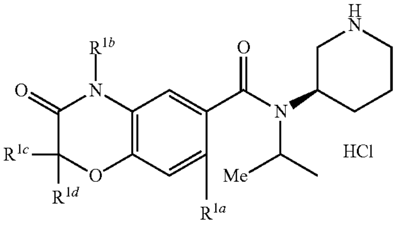

| Ex. | $R^{1d}$ | $R^{1c}$ | $R^{1b}$ | $R^{1a}$ |
|---|---|---|---|---|
| 49 | 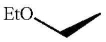 | 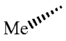 | $MeO(CH_2)_4$ | Me |
| 50 | Me | Me | $CH_3CH_2C(O)NH(CH_2)_2$ | Me |
| 51 | Me | Me | $CH_3(CH_2)_5$ | Me |
| 52 | Me | Me | 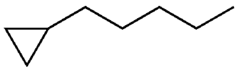 | Me |
| 53 | Me | Me | 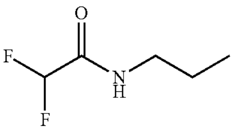 | Me |
| 54 | Me | Me | $CH_3CH_2C(O)NH(CH_2)_2$ | Cl |
| 55 | Me | Me | 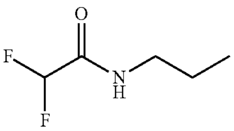 | Cl |
| 56 | Me | Me | 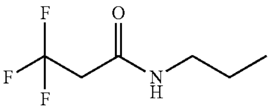 | Cl |

TABLE 5-continued

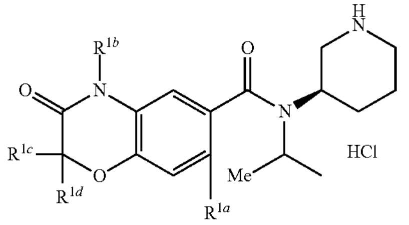

| Ex. | $R^{1d}$ | $R^{1c}$ | $R^{1b}$ | $R^{1a}$ |
|---|---|---|---|---|
| 57 | 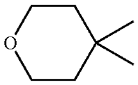 | | $CH_3OC(O)NH(CH_2)_2$ | Me |
| 58 | $MeOCH_2$ | Me | $MeO(CH_2)_4$ | Me |
| 59 | $CH_3CH_2NHC(O)OCH_2$ | Me | $MeO(CH_2)_4$ | Me |
| 60 | 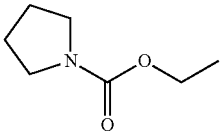 | Me | $MeO(CH_2)_4$ | Me |
| 61 | Me | Me | 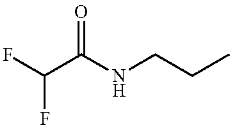 | $CF_3$ |
| 62 | 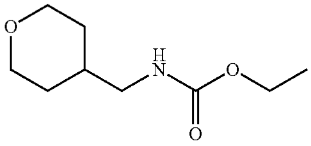 | Me | $MeO(CH_2)_4$ | Me |
| 63 | Me | Me | 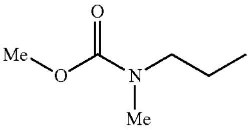 | $CF_3$ |
| 64 | 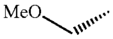 | 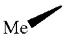 | $MeO(CH_2)_4$ | Me |
| 65 | 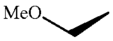 | 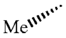 | $MeO(CH_2)_4$ | Me |
| 66 | H | 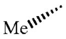 | $MeO(CH_2)_4$ | $CF_3$ |
| 67 | Me | Me | $CH_3CH_2C(O)(CH_2)_3$ | Me |
| 68 | Me | Me | $MeO(CH_2)_4$ | $CF_3$ |
| 69 | $MeOCH_2$ | Me | $MeO(CH_2)_3$ | $CF_3$ |
| 70 | Me | Me | $HO(CH_2)_4$ | Me |
| 71 | Et | Me | $MeOC(O)NH(CH_2)_2$ | $CF_3$ |

TABLE 6

| Ex. | $^1H$ NMR (300 or 400 MHz, solvent)/MS (ESI+) |
|---|---|
| 49 | RT 20.425 min (CHIRALPAK AD-H, hexane/0.1% diethylamine in 2-propanol = 80/20, 1.00 ml/min) MS (ESI+) 490 ($M^+$ + 1, 100%). |
| 50 | (300 MHz, DMSO-$d_6$) δ9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |

TABLE 6-continued

| Ex. | $^1$H NMR (300 or 400 MHz, solvent)/MS (ESI+) |
|---|---|
| 51 | (300 MHz, DMSO-$d_6$) δ9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 52 | (300 MHz, DMSO-$d_6$) δ9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 53 | (300 MHz, DMSO-$d_6$) δ9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 54 | (300 MHz, DMSO-$d_6$) δ9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 55 | (300 MHz, DMSO-$d_6$) δ9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 56 | (300 MHz, DMSO-$d_6$) δ9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 57 | (400 MHz, $CDCl_3$) δ9.83-9.38 (br, 2H), 7.12-6.73 (m, 2H), 5.61 (brs, 0.5H), 4.99 (brs, 0.5H), 4.11-3.68 (m, 6H), 3.63-3.52 (m, 4H), 3.48-3.25 (m, 3H), 2.93-2.75 (m, 2H), 2.21-1.89 (m, 10H), 1.40-1.05 (m, 9H) |
| 58 | (400 MHz, $CDCl_3$) δ9.95-9.60 (br, 2H), 6.97-6.81 (m, 2H), 4.15-3.72 (m, 6H), 3.54-3.41 (m, 2H), 3.37-3.28 (m, 2H), 3.31 (s, 3H), 3.22 (s, 3H), 2.92-2.77 (m, 2H), 2.10-1.89 (m, 2H), 1.77-1.51 (m, 6H), 1.41-1.29 (m, 6H), 1.25-1.01 (m, 6H) |
| 59 | (400 MHz, DMSO-$d_6$) δ9.45-9.09 (br, 2H), 7.15-7.05 (m, 1H), 7.03-6.87 (m, 2H), 4.39-4.10 (m, 2H), 4.07-3.95 (m, 1H), 3.89-3.68 (m, 2H), 3.66-3.45 (m, 3H), 3.40-3.08 (m, 8H), 2.98-2.88 (m, 2H), 2.80-2.58 (m, 2H), 2.13 (s, 3H), 1.97-1.67 (m, 4H), 1.61-1.23 (m, 4H), 1.19-0.98 (m, 9H) |
| 60 | (400 MHz, DMSO-$d_6$) δ9.29-8.99 (br, 2H), 7.07-6.85 (m, 2H), 4.38-4.15 (m, 2H), 4.11-3.68 (m, 3H), 3.66-3.52 (m, 3H), 3.28-2.95 (m, 7H), 2.75-2.55 (m, 3H), 2.12 (s, 3H), 1.95-1.57 (m, 7H), 1.52-1.32 (m, 9H), 1.29-1.03 (m, 6H) |
| 61 | (300 MHz, DMSO-$d_6$) δ9.00-8.61 (m, 1H), 7.37-7.31 (m, 2H), 3.95-3.86 (m, 2H), 3.62-3.17 (m, 7H), 1.91-1.63 (m, 3H), 1.63-1.42 (m, 8H), 1.23-1.03 (m, 7H) |
| 62 | (400 MHz, DMSO-$d_6$) δ9.45-9.10 (br, 2H), 7.28-7.12 (m, 1H), 7.08-6.79 (m, 2H), 4.40-4.16 (m, 2H), 4.08-3.98 (m, 1H), 3.88-3.51 (m, 7H), 3.23 (s, 3H), 3.18-3.10 (m, 5H), 2.85-2.58 (m, 4H), 2.13 (s, 3H), 1.90-1.63 (m, 3H), 1.63-1.21 (m, 12H), 1.20-1.01 (m, 6H) |
| 63 | (300 MHz, DMSO-$d_6$) δ9.12-9.01 (m, 1H), 7.45-7.36 (m, 2H), 3.98-3.74 (m, 2H), 3.65-3.10 (m, 10H), 2.79-2.54 (m, 2H), 1.95-1.80 (m, 2H), 1.51-1.38 (m, 4H), 1.19-1.05 (m, 6H), 0.92-0.84 (m, 3H) |
| 64 | RT 9.395 min (CHIRALPAK AD-H, hexane/0.3% diethylamine in 2-propanol = 80/20, 1.00 ml/min).<br>MS (ESI+) 476 ($M^+$ + 1, 100%). |
| 65 | RT 15.558 min (CHIRALPAK AD-H, hexane/0.3% diethylamine in 2-propanol = 80/20, 1.00 ml/min).<br>MS (ESI+) 476 ($M^+$ + 1, 100%). |
| 66 | (300 MHz, DMSO-$d_6$) δ9.46-9.31 (m, 1H), 7.17-7.09 (m, 1H), 6.88 (m, 1H), 4.07-3.58 (m, 5H), 3.30-3.20 (m, 3H), 2.77-2.68 (m, 2H), 2.51-2.50 (m, 2H), 2.14 (s, 3H), 1.91-1.77 (m, 6H), 1.49-1.36 (m, 6H), 1.23-1.03 (m, 5H) |
| 66 | RT 3.499 min (Shim-pack XR-ODS, 0.1% trifluoroacetic acid in water/acetonitrile, acetonitrile 30-90% 5.7 min, 1.0 ml/min).<br>MS (ESI+) 486 ($M^+$ + 1, 100%). |
| 67 | 1H NMR (300 MHz, DMSO-$d_6$) δ9.00-8.78 (m, 1H), 6.73-6.64 (m, 2H), 4.31-3.44 (m, 8H), 2.99-2.80 (m, 3H), 2.49-2.37 (m, 2H), 2.18-2.10 (m, 2H), 2.04-1.81 (m, 7H), 1.48-0.84 (m, 14H) |
| 68 | $^1$H NMR (400 MHz, $CDCl_3$) δ9.92-9.53 (br, 2H), 7.13-6.55 (m, 2H), 4.18-3.65 (m, 5H), 3.64-3.50 (m, 2H), 3.45-3.12 (m, 10H), 2.95-2.62 (m, 2H), 2.15-1.45 (m, 10H), 1.35-1.03 (m, 6H). |
| 69 | (400 MHz, DMSO-d6) δ9.70-9.23 (br, 2H), 7.32-7.08 (m, 2H), 4.21-3.86 (m, 2H), 3.85-3.62 (m, 3H), 3.60-3.42 (m, 2H), 3.40-3.23 (m, 4H), 3.21-3.05 (m, 6H), 2.83-2.47 (m, 2H), 1.93-1.57 (m, 4H), 1.52-1.38 (m, 4H), 1.28-0.98 (m, 6H) |
| 70 | (300 MHz, DMSO-$d_6$) δ9.25-9.12 (m, 1H), 6.93-6.89 (m, 2H), 4.08-4.02 (m, 1H), 3.83-3.77 (m, 2H), 3.68-3.57 (m, 4H), 2.76-2.64 (m, 2H), 2.13 (s, 3H), 1.88-1.70 (m, 3H), 1.49-1.24 (m, 10H), 1.13-1.02 (m, 8H) |
| 71 | (300 MHz, DMSO-$d_6$) δ9.09-8.94 (m, 1H), 7.40-7.33 (m, 2H), 3.98-3.74 (m, 2H), 3.60-3.04 (m, 7H), 2.79-2.58 (m, 2H), 1.99-1.60 (m, 5H), 1.49-1.36 (m, 4H), 1.17-1.01 (m, 6H), 0.92-0.84 (m, 3H) |

The compounds of Examples 72 to 89 were obtained in a similar manner to a corresponding Reference Example and Example 1.

TABLE 7

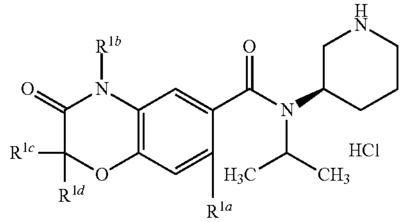

| Ex. | $R^{1d}$ | $R^{1c}$ | $R^{1b}$ | $R^{1a}$ |
|---|---|---|---|---|
| 72 | Me | Me | $CH_3CH_2C(O)NH(CH_2)_2$ | $CF_3$ |
| 73 | | 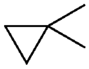 | $MeO(CH_2)_4$ | $CF_3$ |
| 74 | | 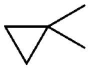 | $CH_3OC(O)NH(CH_2)_2$ | $CF_3$ |
| 75 | Me | Me | $CH_3CH_2C(S)NH(CH_2)_2$ | $CF_3$ |
| 76 | Me | Me | 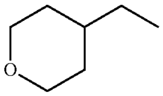 | Me |
| 77 | 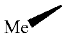 | 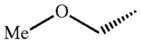 | $MeO(CH_2)_4$ | $CF_3$ |
| 78 | 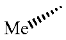 | 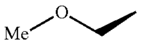 | $MeO(CH_2)_4$ | $CF_3$ |
| 79 | Me | Me | $MeO(CH_2)_4$ | Et |
| 80 | Me | Me | $CH_3OC(O)NH(CH_2)_2$ | Et |

TABLE 7-continued

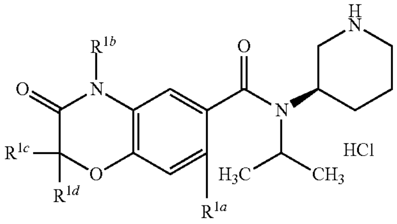

| Ex. | $R^{1d}$ | $R^{1c}$ | $R^{1b}$ | $R^{1a}$ |
|---|---|---|---|---|
| 81 | Me | Me | 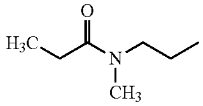 | Me |
| 82 | Me | Me | $CH_3NHC(O)(CH_2)_3$ | Me |
| 83 | Me | Me | $CH_3CH_2NHC(O)(CH_2)_3$ | Me |
| 84 | Me | Me | $CH_3(CH_2)_2NHC(O)(CH_2)_2$ | Me |
| 85 | Me | Me | 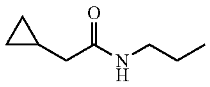 | Me |
| 86 | Me | Me | 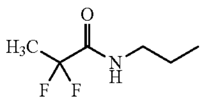 | Me |
| 87 | Me | Me | $CH_3CH_2C(O)NH(CH_2)_2$ | Et |
| 88 | Me | Me | 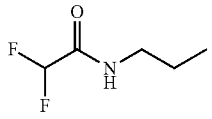 | Et |
| 89 | Me | Me | $MeO(CH_2)_4$ | $CHF_2$ |

TABLE 8

| Ex. | $^1H$ NMR (300 or 400 MHz, solvent)/MS (ESI+) |
|---|---|
| 72 | (300 MHz, DMSO-$d_6$) δ9.18-9.05 (m, 1H), 7.35-7.30 (m, 2H), 4.02-3.23 (m, 8H), 3.03-2.38 (m, 3H), 2.21-1.68 (m, 3H), 1.53-1.34 (m, 8H), 1.18-0.85 (m, 9H) |
| 73 | (400 MHz, $CD_3OD$) δ7.28 (s, 0.5H), 7.28 (s, 0.5H), 7.21 (s, 0.5H), 7.13 (s, 0.5H), 4.21-3.98 (m, 2H), 4.00-3.89 (m, 1H), 3.83-3.68 (m, 1H), 3.64-3.54 (m, 1H), 3.45-3.36 (m, 1H), 3.41 (t, J = 6.1 Hz, 2H), 3.31 (s, 3H), 3.13-2.91 (m, 1H), 2.90-2.66 (m, 1H), 2.15-2.04 (m, 1H), 2.05-1.94 (m, 2H), 1.94-1.77 (m, 2H), 1.75-1.64 (m, 2H), 1.67-1.56 (m, 2H), 1.41-1.37 (m, 2H), 1.31-1.26 (m, 2H), 1.26-1.21 (m, 3H), 1.21-1.16 (m, 3H) |
| 74 | (400 MHz, $CD_3OD$) δ7.68 (s, 0.5H), 7.60 (s, 0.5H), 7.27 (s, 0.5H), 7.26 (s, 0.5H), 4.14-3.93 (m, 3H), 3.83-3.69 (m, 1H), 3.68-3.55 (m, 2H), 3.63 (s, 1.5H), 3.60 (s, 1.5H), 3.43-3.35 (m, 1H), 3.36-3.27 (m, 1H), 3.13-2.92 (m, 1H), 2.90-2.71 (m, 1H), 2.19-2.05 (m, 2H), 1.95-1.77 (m, 2H), 1.44-1.38 (m, 2H), 1.33-1.22 (m, 5H), 1.22-1.15 (m, 3H) |
| 75 | (300 MHz, DMSO-$d_6$) δ10.33-10.25 (m, 1H), 9.03-8.83 (m, 1H), 7.58-7.54 (m, 1H), 7.35-7.34 (m, 1H), 4.11-4.06 (m, 2H), 3.83-3.57 (m, 4H), 3.43-2.53 (m, 5H), 1.90-1.56 (m, 3H), 1.50-1.36 (m, 7H), 1.19-1.01 (m, 10H) |
| 76 | (300 MHz, DMSO-$d_6$) δ9.01-8.82 (m, 1H), 7.10-7.01 (m, 1H), 6.92-6.87 (m, 1H), 4.00-3.58 (m, 6H), 3.41-3.10 (m, 6H), 2.13 (s, 3H), 1.89-1.71 (m, 3H), 1.55-1.03 (m, 18H) |
| 77 | RT 9.275 min (CHIRALPAK AD-H, hexane/0.5% diethylamine in ethanol = 90/10, 1.00 ml/min)<br>MS (ESI+) 530 ($M^+$ + 1, 100%) |
| 78 | RT 21.608 min (CHIRALPAK AD-H, hexane/0.5% diethylamine in ethanol = 90/10, 1.00 ml/min)<br>MS (ESI+) 530 ($M^+$ + 1, 100%) |
| 79 | RT 3.414 min (Shim-pack XR-ODS, 0.1% trifluoroacetic acid in water/acetonitrile, acetonitrile 30-90% 5.7 min, 1.0 ml/min).<br>MS (ESI+) 460 ($M^+$ + 1, 100%). |

TABLE 8-continued

| Ex. | $^1$H NMR (300 or 400 MHz, solvent)/MS (ESI+) |
|---|---|
| 80 | RT 3.038 min (Shim-pack XR-ODS, 0.1% trifluoroacetic acid in water/acetonitrile, acetonitrile 30-90% 5.7 min, 1.0 ml/min). MS (ESI+) 475 ($M^+$ + 1, 100%). |
| 81 | (300 MHz, DMSO-$d_6$) δ9.16-9.07 (m, 1H), 7.20-7.12 (m, 1H), 6.90-6.85 (m, 1H), 3.94-3.83 (m, 2H), 2.97-2.65 (m, 4H), 2.23-1.97 (m, 5H), 1.90-1.74 (m, 6H), 1.43-1.33 (m, 7H), 1.16-0.95 (m, 6H), 0.91-0.80 (m, 3H) |
| 82 | (300 MHz, DMSO-$d_6$) δ9.04-8.98 (m, 1H), 7.19-7.12 (m, 1H), 6.90-6.87 (m, 1H), 3.89-3.82 (m, 2H), 3.63-3.57 (m, 2H), 3.43-3.02 (m, 3H), 2.76-2.65 (m, 1H), 2.56-2.48 (m, 2H), 2.12 (s, 3H), 1.90-1.70 (m, 5H), 1.43-1.34 (m, 8H), 1.14-1.01 (m, 8H) |
| 83 | (300 MHz, DMSO-$d_6$) δ9.41-9.03 (m, 1H), 7.19-7.14 (m, 1H), 6.90-6.87 (m, 1H), 3.89-3.82 (m, 2H), 3.61-3.52 (m, 3H), 3.41-3.26 (m, 2H), 3.06-3.02 (m, 3H), 2.81-2.69 (m, 1H), 2.12 (s, 3H), 1.90-1.70 (m, 6H), 1.43-1.24 (m, 8H), 1.15-0.96 (m, 8H) |
| 84 | (300 MHz, DMSO-$d_6$) δ9.20-9.11 (m, 1H), 7.24-7.19 (m, 1H), 6.91-6.86 (m, 1H), 3.84-3.80 (m, 3H), 3.63-3.57 (m, 3H), 3.37-3.19 (m, 2H), 2.94-2.72 (m, 1H), 2.21-2.12 (m, 3H), 2.02-1.97 (m, 1H), 1.90-1.73 (m, 3H), 1.55-1.34 (m, 10H), 1.15-0.98 (m, 6H), 0.88-0.79 (m, 4H) |
| 85 | (300 MHz, DMSO-$d_6$) δ9.19-9.13 (m, 1H), 7.19-7.12 (m, 1H), 6.79-6.77 (m, 1H), 3.95-3.49 (m, 10H), 3.16-2.19 (m, 2H), 2.19-1.99 (m, 4H), 1.92-1.79 (m, 3H), 1.67-1.26 (m, 6H), 1.09-0.93 (m, 4H), 0.84-0.80 (m, 1H), 0.39-0.29 (m, 3H), 0.11-0.03 (m, 3H) |
| 86 | (300 MHz, DMSO-$d_6$) δ9.15-9.09 (m, 1H), 7.14-7.04 (m, 1H), 6.89-6.83 (m, 1H), 3.95-3.84 (m, 2H), 3.63-3.57 (m, 2H), 3.35-3.09 (m, 2H), 2.76-2.67 (m, 3H), 2.12 (s, 3H), 1.90-1.58 (m, 6H), 1.42-1.33 (m, 7H), 1.13-1.01 (m, 7H) |
| 87 | RT 2.998 min (Shim-pack XR-ODS, 0.1% trifluoroacetic acid in water/acetonitrile, acetonitrile 30-90% 5.7 min, 1.0 ml/min). MS (ESI+) 473 ($M^+$ + 1, 100%). |
| 88 | RT 3.233 min (Shim-pack XR-ODS, 0.1% trifluoroacetic acid in water/acetonitrile, acetonitrile 30-90% 5.7 min, 1.0 ml/min). MS (ESI+) 495 ($M^+$ + 1, 100%). |
| 89 | (400 MHz, $CDCl_3$) δ9.97-9.35 (br, 2H), 7.14 (s, 1H), 6.94-6.50 (m, 2H), 4.30-3.65 (m, 5H), 3.55-3.30 (m, 4H), 3.22 (s, 3H), 2.95-2.68 (m, 2H), 2.32-1.75 (m, 5H), 1.71-1.28 (m, 8H), 1.22-0.99 (m, 6H) |

The compounds of Examples 90 to 100 were synthesized in a similar manner to a corresponding Reference Example and Example 1.

TABLE 9

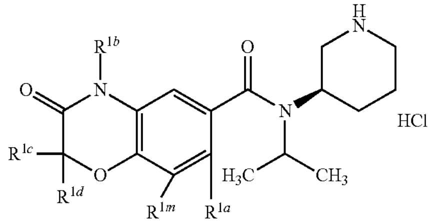

| Ex. | $R^{1m}$ | $R^{1d}$ | $R^{1c}$ | $R^{1b}$ | $R^{1a}$ |
|---|---|---|---|---|---|
| 90 | F | Me | Me | $MeO(CH_2)_4$ | $CHF_2$ |
| 91 | H | Me | Me | 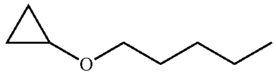 | Me |
| 92 | H | Me | Me | 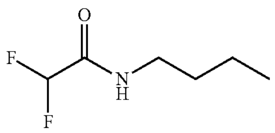 | Me |
| 93 | H | Me | Me | 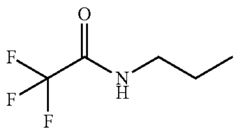 | $CF_3$ |
| 94 | H | 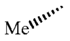 | H | $MeO(CH_2)_4$ | Et |

TABLE 9-continued

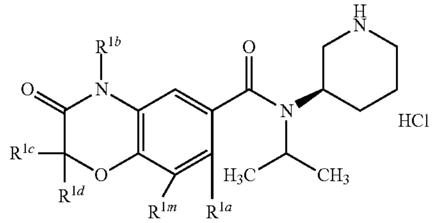

| Ex. | $R^{1m}$ | $R^{1d}$ | $R^{1c}$ | $R^{1b}$ | $R^{1a}$ |
|---|---|---|---|---|---|
| 95 | H | 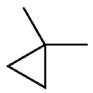 | | $CH_3CH_2C(O)NH(CH_2)_2$ | $CF_3$ |
| 96 | H | 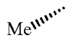 | H | $MeOC(O)NH(CH_2)_2$ | $CF_3$ |
| 97 | H | 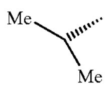 | H | $MeO(CH_2)_4$ | Me |
| 98 | H | Me | Me | 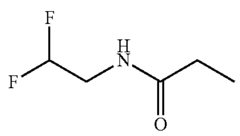 | Me |
| 99 | H | 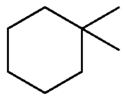 | | $CH_3CH_2C(O)NH(CH_2)_2$ | Me |
| 100 | H | Me | Me | $CH_3C(O)NH(CH_2)_3$ | Me |

TABLE 10

| Ex. | $^{1}$H NMR (300 or 400 MHz, solvent)/MS (ESI+) |
|---|---|
| 90 | (400 MHz, $CDCl_3$) δ9.95-9.38 (br, 2H), 6.89-6.47 (m, 2H), 4.24-3.45 (m, 6H), 3.33 (s, 3H), 3.26 (s, 3H), 2.95-2.61 (m, 2H), 2.19-1.75 (m, 5H), 1.68-1.38 (m, 8H), 1.32-0.94 (m, 6H) |
| 91 | (300 MHz, DMSO-$d_6$) δ8.54-8.45 (m, 1H), 6.64-6.49 (m, 2H), 3.64-2.78 (m, 6H), 1.90-1.86 (m, 1H), 1.74 (s, 3H), 1.52-1.36 (m, 2H), 1.09-0.66 (m, 21H) |
| 92 | (300 MHz, DMSO-$d_6$) δ9.10-8.84 (m, 1H), 7.00-6.89 (m, 2H), 3.99-3.84 (m, 2H), 3.63-3.52 (m, 2H), 3.14-2.99 (m, 2H), 2.82-2.62 (m, 1H), 2.12 (s, 3H), 1.90-1.69 (m, 5H), 1.43-1.34 (m, 7H), 1.11-1.01 (m, 10H) |
| 93 | (300 MHz, DMSO-$d_6$) δ9.62-9.60 (m, 1H), 9.13-8.95 (m, 1H), 7.37-7.25 (m, 2H), 4.20-4.04 (m, 2H), 3.83-3.55 (m, 3H), 3.43-2.56 (m, 3H), 1.90-1.63 (m, 3H), 1.53-1.34 (m, 8H), 1.19-1.01 (m, 7H) |
| 94 | RT 3.233 min (Shim-pack XR-ODS, 0.1% trifluoroacetic acid in water/acetonitrile, acetonitrile 30-90% 5.7 min, 1.0 ml/min). MS (ESI+) 446 ($M^+$ + 1, 100%). |
| 95 | (400 MHz, $CD_3OD$) δ7.63 (s, 0.5H), 7.50 (s, 0.5H), 7.26 (s, 1H), 4.18-3.93 (m, 3H), 3.84-3.69 (m, 1H), 3.64-3.52 (m, 1H), 3.51-3.32 (m, 3H), 3.02-2.91 (m, 1H), 2.91-2.69 (m, 1H), 2.22-2.05 (m, 4H), 1.94-1.76 (m, 2H), 1.43-1.37 (m, 2H), 1.32-1.23 (m, 5H), 1.22-1.14 (m, 3H), 1.14-1.03 (m, 3H) |
| 96 | RT 2.834 min (Shim-pack XR-ODS, 0.1% trifluoroacetic acid in water/acetonitrile, acetonitrile 30-90% 5.7 min, 1.0 ml/min). MS (ESI+) 461 ($M^+$ + 1, 100%). |
| 97 | (400 MHz, DMSO-$d_6$) δ9.40-9.15 (m, 1H), 6.97 (s, 1H), 6.91 (s, 1H), 4.39-4.35 (m, 1H), 4.15-0.91 (m, 37H) |
| 98 | (300 MHz, DMSO-$d_6$) δ9.19-9.15 (m, 1H), 6.88-6.60 (m, 2H), 4.66-4.48 (m, 2H), 3.83-3.81 (m, 1H), 3.63-3.36 (m, 5H), 3.11-3.05 (m, 2H), 2.27-2.62 (m, 2H), 2.11 (s, 3H), 1.97-1.68 (m, 3H), 1.44-1.38 (m, 6H), 1.11-0.99 (m, 6H) |
| 99 | (400 MHz, $CDCl_3$) δ10.0-9.39 (br, 2H), 7.25-6.80 (m, 2H), 6.01 (brs, 0.5H), 5.35 (brs, 0.5H), 4.31-3.99 (m, 2H), 3.95-3.23 (m, 6H), 2.97-2.73 (m, 2H), 2.43-1.97 (m, 10H), 1.89-1.45 (m, 9H), 1.42-1.05 (m, 9H) |
| 100 | (300 MHz, DMSO-$d_6$) δ9.19-9.13 (m, 1H), 6.98-6.89 (m, 2H), 3.96-3.80 (m, 2H), 3.63-2.62 (m, 5H), 2.12 (s, 3H), 1.93-1.63 (m, 9H), 1.42-1.34 (m, 6H), 1.11-1.01 (m, 6H) |

The compounds of Examples 101 to 112 were synthesized in a similar manner to a corresponding Reference Example and Example 1.

TABLE 11

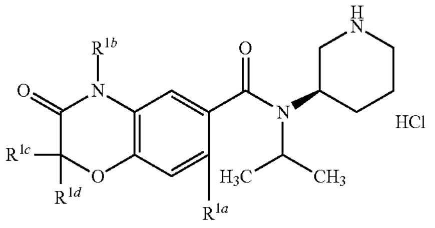

| Ex. | $R^{1d}$ | $R^{1c}$ | $R^{1b}$ | $R^{1a}$ |
|---|---|---|---|---|
| 101 | Me | Me | 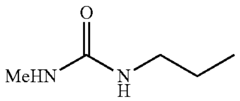 | Me |
| 102 | Me | Me | 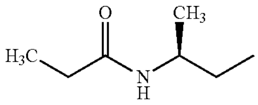 | $CF_3$ |
| 103 | 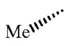 | H | $CH_3C(O)NH(CH_2)_2$ | Et |
| 104 | 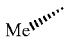 | H | $CH_3CH_2C(O)NH(CH_2)_2$ | Et |
| 105 | 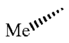 | H | $HC(O)NH(CH_2)_2$ | Et |

TABLE 11-continued

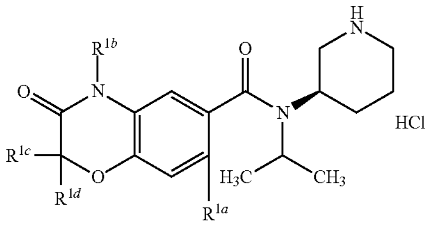

| Ex. | $R^{1d}$ | $R^{1c}$ | $R^{1b}$ | $R^{1a}$ |
|---|---|---|---|---|
| 106 | Me | Me | 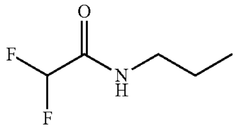 | $CF_3$ |
| 107 | Me | Me | $CF_3(CH_2)_3$ | Me |
| 108 | Me | Me | $CF_3(CH_2)_4$ | Me |
| 109 | 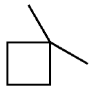 | | $CH_3CH_2C(O)NH(CH_2)_2$ | Me |
| 110 | 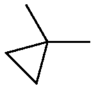 | | 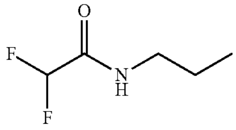 | $CF_3$ |
| 111 | Me | Me | $EtOC(O)(CH_2)_2$ | $CF_3$ |
| 112 | Me | Me | $EtNHC(O)(CH_2)_2$ | $CF_3$ |

TABLE 12

| Ex. | $^{1}$H NMR (300 or 400 MHz, solvent)/MS (ESI+) |
|---|---|
| 101 | (300 MHz, DMSO-$d_6$) δ9.19-9.14 (m, 1H), 7.42-7.38 (m, 1H), 6.88-6.86 (m, 1H), 3.89-3.45 (m, 5H), 3.29-3.13 (m, 5H), 2.77-2.53 (m, 2H), 2.12 (s, 3H), 1.97-1.74 (m, 3H), 1.43-1.22 (m, 8H), 1.11-0.95 (m, 6H) |
| 102 | (300 MHz, DMSO-$d_6$) δ9.09-8.87 (m, 1H), 8.03-7.93 (m, 1H), 7.33-7.16 (m, 1H), 4.22-4.01 (m, 1H), 3.80-3.55 (m, 2H), 3.15-2.49 (m, 4H), 2.36-2.23 (m, 2H), 2.02-1.86 (m, 2H), 1.66-1.37 (m, 6H), 1.23-0.89 (m, 16H) |
| 103 | RT 2.656 min (Shim-pack XR-ODS, 0.1% trifluoroacetic acid in water/acetonitrile, acetonitrile 30-90% 5.7 min, 1.0 ml/min). MS (ESI+) 445 ($M^{+}$ + 1, 100%). |
| 104 | RT 2.805 min (Shim-pack XR-ODS, 0.1% trifluoroacetic acid in water/acetonitrile, acetonitrile 30-90% 5.7 min, 1.0 ml/min). MS (ESI+) 459 ($M^{+}$ + 1, 100%). |
| 105 | RT 2.659 min (Shim-pack XR-ODS, 0.1% trifluoroacetic acid in water/acetonitrile, acetonitrile 30-90% 5.7 min, 1.0 ml/min). MS (ESI+) 431 ($M^{+}$ + 1, 100%). |
| 106 | (400 MHz, $CDCl_3$) δ 7.52 (s, 1H), 7.22 (s, 1H), 6.06-5.75 (m, 1H), 4.37-3.89 (m, 3H), 3.78-3.49 (m, 9H), 3.30-3.20 (br, 1H), 2.63-2.36 (m, 2H), 2.19-1.73 (m, 6H), 1.57-1.48 (m, 6H), 1.41-1.15 (m, 6H) |
| 107 | (300 MHz, DMSO-$d_6$) δ9.28-9.20 (m, 1H), 7.07-6.90 (m, 2H), 4.20-4.10 (m, 1H), 3.87-3.82 (m, 1H), 3.69-3.56 (m, 2H), 3.35-3.11 (m, 1H), 2.77-2.51 (m, 2H), 2.37-2.30 (m, 2H), 2.13 (s, 3H), 1.91-1.70 (m, 4H), 1.14-1.03 (m, 6H) |
| 108 | (300 MHz, DMSO-$d_6$) δ9.27-9.25 (m, 1H), 7.07-6.90 (m, 2H), 4.10-3.58 (m, 4H), 3.37-2.64 (m, 5H), 2.34-2.23 (m, 2H), 2.13 (s, 3H), 1.91-1.69 (m, 3H), 1.56-1.35 (m, 10H), 1.15-1.03 (m, 6H) |
| 109 | (400 MHz, $CDCl_3$) δ9.89-9.38 (br, 2H), 7.37-7.08 (m, 2H), 6.49 (br, 0.5H), 5.93 (br, 0.5H), 4.33-3.29 (m, 12H), 2.88-2.66 (m, 4H), 2.58-1.78 (m, 6H), 2.10 (s, 3H), 1.46-0.89 (m, 9H) |
| 110 | (400 MHz, $CD_3OD$) δ7.61 (s, 0.5H), 7.50 (s, 0.5H), 7.28 (s, 0.5H), 7.27 (s, 0.5H), 6.02 (t, J = 54 Hz, 0.5H), 6.00 (t, J = 54 Hz, 0.5H), 4.20-3.95 (m, 3H), 3.84-3.67 (m, 1H), 3.68-3.32 (m, 4H), 3.01-2.90 (m, 1H), 2.88-2.68 (m, 1H), 2.18-2.01 (m, 1H), 1.92-1.77 (m, 1H), 1.46-1.35 (m, 2H), 1.33-1.21 (m, 5H), 1.22-1.13 (m, 3H) |
| 111 | (300 MHz, DMSO-$d_6$) δ8.92-8.62 (m, 1H), 7.40-7.35 (m, 2H), 4.33-3.98 (m, 2H), 3.80-3.56 (m, 4H), 3.42-3.29 (m, 5H), 1.91-1.82 (m, 1H), 1.53-1.35 (m, 6H), 1.24-1.03 (m, 13H) |
| 112 | (300 MHz, DMSO-$d_6$) δ9.01-8.85 (m, 1H), 7.35-7.24 (m, 2H), 4.15-4.10 (m, 2H), 3.63-3.54 (m, 2H), 3.03-2.97 (m, 2H), 2.36-2.34 (m, 1H), 1.90-1.75 (m, 2H), 1.48-1.35 (m, 7H), 1.19-0.90 (m, 15H) |

The compounds of Examples 113 to 115 were synthesized in a similar manner to a corresponding Reference Example and Example 1.

TABLE 13

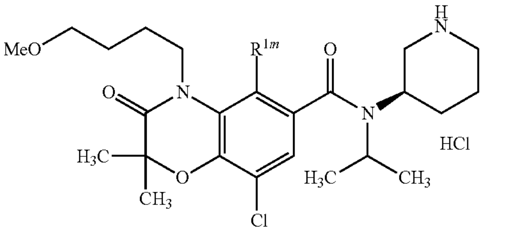

| Ex. | $R^{1m}$ |
|---|---|
| 113 | H |
| 114 | Cl |
| 115 | Br |

TABLE 14

| Ex. | $^{1}$H NMR (400 MHz, DMSO-$d_6$) |
|---|---|
| 113 | δ7.16 (s, 1H), 7.10 (s, 1H), 3.98-3.14 (m, 12H), 2.79-2.55 (m, 2H), 1.90-1.72 (m, 3H), 1.58-1.07 (m, 16H) |
| 114 | δ7.30-7.18 (m, 1H), 4.12-3.08 (m, 12H), 2.85-2.55 (m, 2H), 1.88-1.75 (m, 3H), 1.54-1.07 (m, 16H) |
| 115 | δ7.28-7.15 (m, 1H), 4.11-3.38 (m, 5H), 3.34-3.05 (m, 7H), 2.85-2.60 (m, 2H), 1.88-1.74 (m, 3H), 1.54-1.06 (m, 16H) |

The compounds of Examples 116 to 122 were synthesized in a similar manner to a corresponding Reference Example and Example 1.

TABLE 15

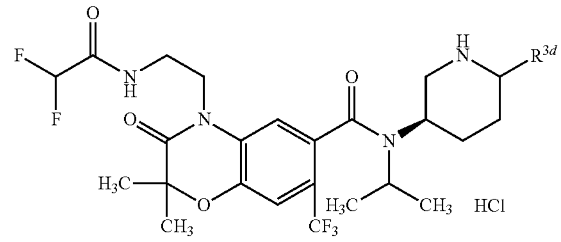

| Ex. | $R^{3d}$ |
|---|---|
| 116 | 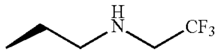 |
| 117 | 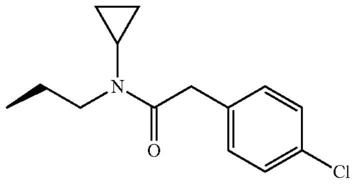 |

TABLE 15-continued

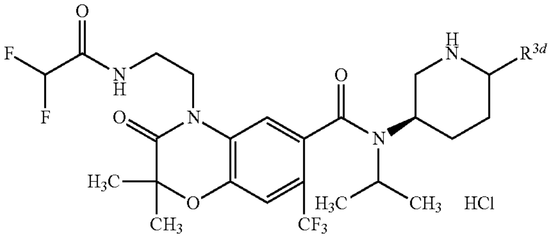

| Ex. | $R^{3d}$ |
|---|---|
| 118 | 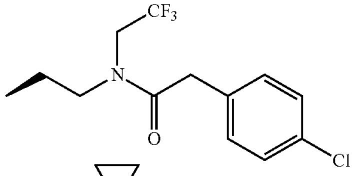 |
| 119 | 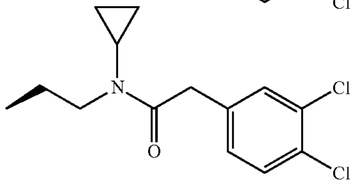 |

TABLE 15-continued

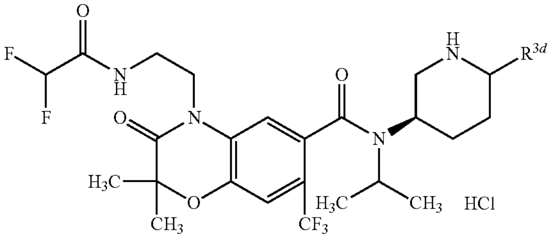

| Ex. | $R^{3d}$ |
|---|---|
| 120 | 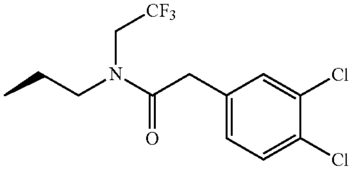 |
| 121 | 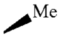 |
| 122 | 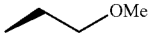 |

TABLE 16

| Ex. | $^1H$ NMR (400 MHz, solvent) |
|---|---|
| 116 | ($CDCl_3$) δ 7.70 (br, 1H), 7.23 (s, 1H), 6.08-5.81 (m, 1H), 4.28-3.17 (m, 11H), 2.82-2.60 (m, 2H), 2.30-2.18 (br, 1H), 1.88-1.72 (m, 6H), 1.57-1.48 (m, 6H), 1.33-1.13 (m, 6H) |
| 117 | ($CDCl_3$) δ 7.50 (s, 1H), 7.32-7.28 (m, 2H), 7.24-7.23 (m, 3H), 6.07-5.75 (m, 1H), 4.29-3.16 (m, 13H), 2.77 (br, 1H), 2.57-2.22 (m, 2H), 1.85-1.71 (m, 3H), 1.60-1.57 (m, 5H), 1.48 (s, 1H), 1.32-1.14 (m, 6H), 1.00-0.84 (m, 4H) |
| 118 | (3 $CDCl_3$) δ 7.53 (s, 1H), 7.40-7.16 (m, 5H), 6.08-5.75 (m, 1H), 4.35-3.23 (m, 16H), 2.77 (br, 1H), 2.55-1.84 (m, 6H), 1.58 (s, 3H), 1.48 (s, 3H), 1.24-1.13 (m, 6H) |
| 119 | ($CDCl_3$) δ 7.51-7.32 (m, 3H), 7.23-7.06 (m, 2H), 6.06-5.75 (m, 1H), 4.36-3.2 (m, 13H), 2.81 (br, 1H), 2.57 (br, 1H), 2.38-1.75 (m, 6H), 1.57 (s, 3H), 1.48 (s, 3H), 1.27-1.13 (m, 6H), 0.99-0.83 (m, 4H) |
| 120 | ($CDCl_3$) δ 7.53-7.34 (m, 3H), 7.25-6.98 (m, 2H), 6.09-5.75 (m, 1H), 4.38-3.22 (m, 14H), 2.91-1.73 (m, 7H), 1.57 (s, 3H), 1.48 (s, 3H), 1.24-1.14 (m, 6H) |
| 121 | ($CD_3OD$) δ7.58-7.48 (m, 1H), 7.34-7.33 (m, 1H), 7.22-7.08 (m, 2H), 6.00 (dt, J = 9.2 Hz, 53.9 Hz, 1H), 4.17-4.06 (m, 3H), 3.79-3.28 (m, 6H), 3.16-3.11 (m, 1H), 2.88-2.75 (m, 1H), 2.07-1.85 (m, 2H), 1.81-1.77 (m, 1H), 1.54-1.46 (m, 9H), 1.26-1.16 (m, 6H). |
| 122 | ($CD_3OD$) δ7.54-7.43 (m, 1H), 7.34-7.33 (m, 1H), 7.20-7.14 (m, 2H), 6.01 (dt, J = 11.0 Hz, 53.8 Hz, 1H), 4.16-4.07 (m, 3H), 3.85-3.28 (m, 11H), 2.90-2.79 (m, 1H), 2.21-2.05 (m, 2H), 2.01-1.88 (m, 2H), 1.79-1.47 (m, 8H), 1.28-1.17 (m, 6H). |

The compounds of Examples 123 to 132 were synthesized in a similar manner to a corresponding Reference Example and Example 1.

TABLE 17

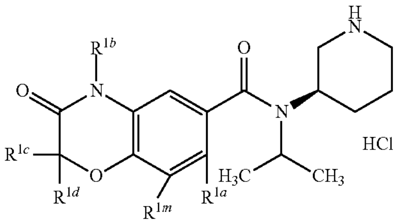

| Ex. | $R^{1m}$ | $R^{1d}$ | $R^{1c}$ | $R^{1b}$ | $R^{1a}$ |
|---|---|---|---|---|---|
| 123 | H | Me | Me | $MeNHC(O)(CH_2)_2$ | $CF_3$ |
| 124 | H | Me | Me | $FCH_2CH_2NHC(O)(CH_2)_2$ | $CF_3$ |

TABLE 17-continued

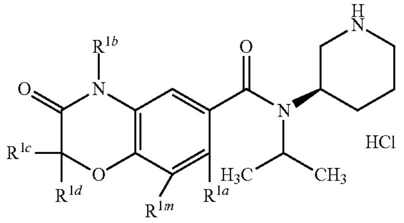

| Ex. | $R^{1m}$ | $R^{1d}$ | $R^{1c}$ | $R^{1b}$ | $R^{1a}$ |
|---|---|---|---|---|---|
| 125 | H | Me | Me | $F_2CHCH_2NHC(O)(CH_2)_2$ | $CF_3$ |
| 126 | F | Me | Me | $MeO(CH_2)_4$ | H |
| 127 | H | 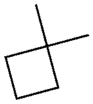 | | $CH_3CH_2C(O)NH(CH_2)_2$ | $CF_3$ |
| 129 | H | Me | Me | 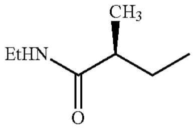 | $CF_3$ |

TABLE 17-continued

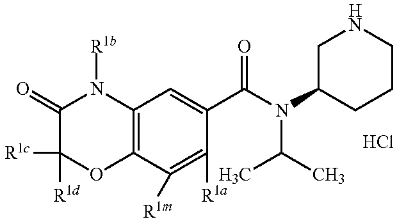

| Ex. | $R^{1m}$ | $R^{1d}$ | $R^{1c}$ | $R^{1b}$ | $R^{1a}$ |
|---|---|---|---|---|---|
| 130 | H | Me | Me | 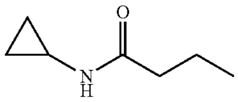 | $CF_3$ |
| 131 | H | Me | Me | $EtOC(O)NH(CH_2)_2$ | Et |
| 132 | H | Me | Me | $CH_3(CH_2)_2C(O)NH(CH_2)_2$ | Et |

TABLE 18

| Ex. | $^1H$ NMR (300 or 400 MHz, solvent)/MS (ESI+) |
|---|---|
| 123 | (300 MHz DMSO-$d_6$) δ9.26-9.08 (m, 1H), 7.36-7.21 (m, 2H), 4.17-4.07 (m, 2H), 3.85-3.57 (m, 3H), 3.36-3.00 (m, 4H), 2.80-2.76 (m, 1H), 2.39-2.35 (m, 2H), 1.93-1.85 (m, 3H), 1.54-1.32 (m, 8H), 1.27-1.03 (m, 6H) |
| 124 | (300 MHz DMSO-$d_6$) δ9.22-9.07 (m, 1H), 7.35-7.20 (m, 2H), 4.45-4.14 (m, 4H), 3.80-3.54 (m, 3H), 3.39-2.99 (m, 3H), 2.75-2.34 (m, 3H), 1.90-1.63 (m, 3H), 1.53-1.34 (m, 8H), 1.20-1.01 (m, 6H) |
| 125 | (300 MHz DMSO-$d_6$) δ9.25-9.08 (m, 1H), 7.35-7.19 (m, 2H), 3.80-3.57 (m, 2H), 3.47-3.02 (m, 4H), 2.75-2.72 (m, 1H), 2.59-2.43 (m, 6H), 1.90-1.79 (m, 2H), 1.52-1.34 (m, 8H), 1.20-1.01 (m, 6H) |
| 126 | (400 MHz, $CDCl_3$) δ9.75 (br, 2H), 6.81-6.77 (m, 2H), 4.19-4.06 (m, 1H), 4.06-3.83 (m, 4H), 3.53-3.35 (m, 4H), 3.30 (s, 3H), 2.97-2.74 (m, 2H), 2.18-1.59 (m, 7H), 1.54 (s, 6H), 1.39-1.12 (m, 6H) |
| 127 | (400 MHz, CDCl3) δ9.91-9.41 (br, 2H), 7.35-7.11 (m, 2H), 6.55 (br, 0.5H), 5.81 (br, 0.5H), 4.20-3.33 (m, 12H), 2.89-2.70 (m, 4H), 2.53-1.78 (m, 6H), 1.43-0.88 (m, 9H) |
| 129 | (300 MHz, DMSO-$d_6$) δ9.12-9.07 (m, 1H), 7.35-7.19 (m, 2H), 4.01-3.57 (m, 2H), 3.11-2.64 (m, 5H), 1.90-1.76 (m, 3H), 1.53-1.31 (m, 8H), 1.27-0.79 (m, 15H) |
| 130 | (300 MHz, DMSO-$d_6$) δ9.04-8.88 (m, 1H), 7.79-7.76 (m, 1H), 7.05-6.89 (m, 2H), 3.83-3.80 (m, 2H), 3.44-2.68 (m, 5H), 2.34-2.01 (m, 3H), 1.68-1.33 (m, 8H), 0.92-0.71 (m, 6H), 0.28-0.23 (m, 2H), 0.10-0.08 (m, 2H) |
| 131 | RT 3.316 min (Shim-pack XR-ODS, 0.1% trifluoroacetic acid in water/acetonitrile, acetonitrile 30-90% 5.7 min, 1.0 ml/min).<br>MS (ESI+) 489 ($M^+$ + 1, 100%). |
| 132 | RT 3.280 min (Shim-pack XR-ODS, 0.1% trifluoroacetic acid in water/acetonitrile, acetonitrile 30-90% 5.7 min, 1.0 ml/min).<br>MS (ESI+) 487 ($M^+$ + 1, 100%). |

The compounds of Examples 133 to 134 were synthesized in a similar manner to a corresponding Reference Example and Example 1.

TABLE 19

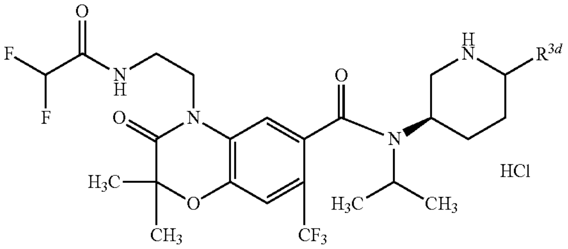

| Ex. | $R^{3d}$ |
|---|---|
| 133 | 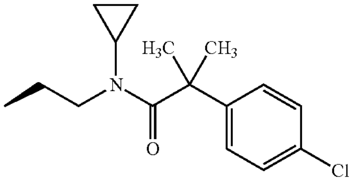 |
| 134 | 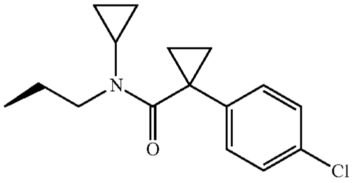 |

TABLE 20

| Ex. | $^1$H NMR (400 MHz, $CDCl_3$) |
|---|---|
| 133 | δ 7.52 (s, 1H), 7.33-7.14 (m, 5H), 6.07-5.77 (m, 1H), 4.38-2.79 (m, 14H), 2.73-1.72 (m, 7H), 1.57-1.47 (m, 8H), 1.26-1.14 (m, 8H), 0.47 (br, 4H) |
| 134 | δ 7.53 (s, 1H), 7.44-7.11 (m, 5H), 6.07-5.76 (m, 1H), 4.38-3.91 (m, 4H), 3.78-1.82 (m, 15H), 1.57-1.47 (m, 8H), 1.30-1.16 (m, 8H), 0.68-0.61 (m, 4H) |

The compounds of Examples 135 to 137 were synthesized in a similar manner to a corresponding Reference Example and Example 1.

TABLE 21

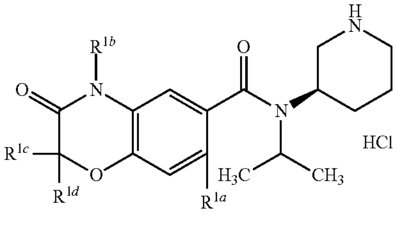

| Ex. | $R^{1d}$ | $R^{1c}$ | $R^{1b}$ | $R^{1a}$ |
|---|---|---|---|---|
| 135 | 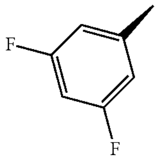 | 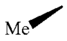 | $CH_3CH_2C(O)NH(CH_2)_2$ | Me |

TABLE 21-continued

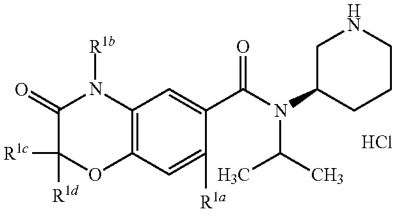

| Ex. | $R^{1d}$ | $R^{1c}$ | $R^{1b}$ | $R^{1a}$ |
|---|---|---|---|---|
| 136 | 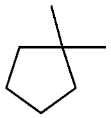 | | $CH_3CH_2C(O)NH(CH_2)_2$ | $CF_3$ |
| 137 | Me | Me | $FCH_2C(O)NH(CH_2)_2$ | $CF_3$ |

TABLE 22

| Ex. | $^1$H NMR (400 MHz, solvent) |
|---|---|
| 135 | ($CDCl_3$) δ9.90-9.48 (br, 2H), 7.12-6.53 (m, 5H), 6.42 (br, 0.5H), 5.95 (br, 0.5H), 4.21-3.24 (m, 9H), 2.85-2.52 (m, 2H), 2.17 (s, 3H), 2.17-1.75 (m, 5H), 1.75 (s, 3H), 1.45-0.92 (m, 9H). |
| 136 | (DMSO-$d_6$) δ9.06-8.72 (br, 2H), 8.14-8.03 (m, 1H), 7.60-7.25 (m, 2H), 3.97-3.72 (m, 3H), 3.62-3.49 (m, 2H), 3.28-2.97 (m, 4H), 2.85-2.51 (m, 2H), 2.28-2.17 (m, 1H), 2.08-1.93 (m, 2H), 1.92-1.61 (m, 9H), 1.53-1.30 (m, 1H), 1.19-1.01 (m, 6H), 0.99-0.90 (m, 3H) |
| 137 | (DMSO-$d_6$) δ9.02-8.94 (m, 1H), 7.39-7.32 (m, 2H), 4.01-3.88 (m, 1H), 3.80-3.55 (m, 3H), 3.04-2.60 (m, 3H), 1.90-1.63 (m, 2H), 1.54-1.36 (m, 8H), 1.17-1.01 (m, 11H) |

The compounds of Examples 138 to 140 were synthesized in a similar manner to a corresponding Reference Example and Example 1.

TABLE 23

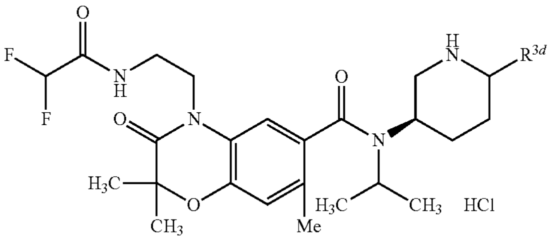

| Ex. | $R^{3d}$ |
|---|---|
| 138 | 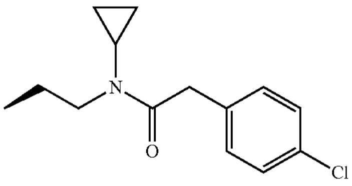 |

TABLE 23-continued

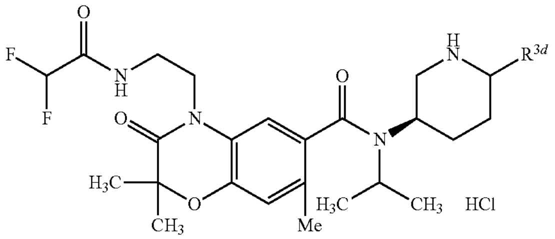

| Ex. | $R^{3d}$ |
|---|---|
| 139 | 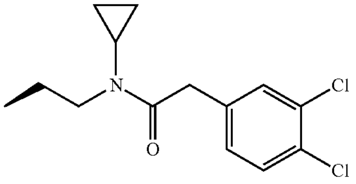 |
| 140 | 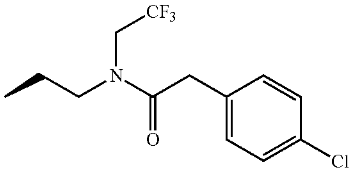 |

TABLE 24

| Ex. | $^1$H NMR (400 MHz, $CDCl_3$) |
|---|---|
| 138 | δ 7.29-7.17 (m, 5H), 6.83-6.80 (m, 1H), 6.04-5.74 (m, 1H), 4.30-3.17 (m, 13H), 2.80-2.70 (br, 2H), 2.36-2.10 (m, 6H), 1.94-1.74 (m, 3H), 1.54 (s, 3H), 1.43 (s, 3H), 1.24-1.15 (m, 6H), 0.99-0.85 (m, 4H) |
| 139 | δ 7.27-7.10 (m, 4H), 6.83-6.80 (m, 1H), 6.04-5.74 (m, 1H), 4.31-3.11 (m, 13H), 2.87-2.69 (br, 2H), 2.21 (s, 4H), 2.00-1.81 (m, 5H), 1.54 (s, 3H), 1.44 (s, 3H), 1.24-1.17 (m, 6H), 1.01-0.86 (m, 4H) |
| 140 | δ 7.27-6.97 (m, 5H), 6.83-6.80 (m, 1H), 6.04-5.74 (m, 1H), 4.30-3.01 (m, 15H), 2.89-2.64 (br, 1H), 2.36-1.69 (m, 9H), 1.53 (s, 3H), 1.44 (s, 3H), 1.24-1.17 (m, 6H) |

The compounds of Examples 141 to 148 were synthesized in a similar manner to a corresponding Reference Example and Example 1.

TABLE 25

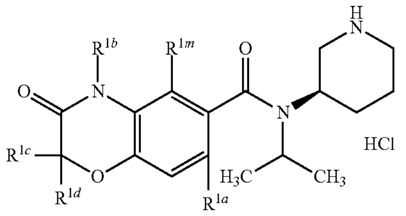

| Ex. | $R^{1m}$ | $R^{1d}$ | $R^{1c}$ | $R^{1b}$ | $R^{1a}$ |
|---|---|---|---|---|---|
| 141 | H | F | F | $CH_3CH_2C(O)NH(CH_2)_2$ | Me |
| 142 | Me | Me | Me | $CH_3CH_2C(O)NH(CH_2)_2$ | H |
| 143 | H | 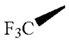 | 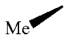 | $CH_3CH_2C(O)NH(CH_2)_2$ | $CF_3$ |
| 144 | H | 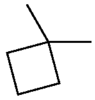 | | $MeOC(O)NH(CH_2)_2$ | $CF_3$ |
| 145 | H | Me | Me | HCl 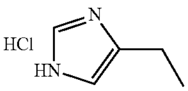 | $CF_3$ |
| 146 | H | Ph | Me | $CH_3CH_2C(O)NH(CH_2)_2$ | Cl |
| 147 | H | Ph | Me | $CH_3CH_2C(O)NH(CH_2)_2$ | Me |
| 148 | H | 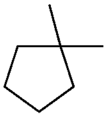 | | $MeOC(O)NH(CH_2)_2$ | $CF_3$ |

TABLE 26

| Ex. | $^1$H NMR (400 MHz, solvent) |
|---|---|
| 141 | (DMSO-$d_6$) δ9.32-9.10 (m, 1H), 8.07-7.99 (m, 1H), 7.43 (s, 1H), 7.30 (s, 1H), 4.15-0.90 (m, 28H) |
| 142 | (DMSO-$d_6$) δ6.94-6.81 (m, 2H), 4.10-3.02 (m, 5H), 2.79-2.63 (m, 2H), 2.22 (s, 3H), 1.96-1.70 (m, 5H), 1.43-0.81 (m, 15H) |
| 143 | (DMSO-$d_6$) δ9.25-8.93 (m, 1H), 8.14-8.07 (m, 1H), 7.68 (s, 1H), 7.54 (s, 1H), 4.07-0.91 (m, 28H) |
| 144 | (DMSO-$d_6$) δ9.50-9.01 (br, 2H), 7.51-7.11 (m, 3H), 3.95-3.86 (m, 2H), 3.81-3.45 (m, 8H), 3.25-3.05 (m, 2H), 2.78-2.38 (m, 4H), 2.30-2.17 (m, 2H), 1.95-1.69 (m, 5H), 1.30-1.02 (m, 6H). |
| 145 | (DMSO-$d_6$) δ9.30-9.25 (m, 1H), 8.98-8.96 (m, 1H), 7.49-7.33 (m, 2H), 5.47-5.41 (m, 1H), 5.19-5.11 (m, 1H), 3.65-3.60 (m, 3H), 3.15-2.98 (m, 1H), 2.77-2.72 (m, 1H), 1.90-1.77 (m, 3H), 1.55-1.44 (m, 8H), 1.35-1.33 (m, 1H), 1.16-1.14 (m, 1H), 1.04-0.85 (m, 6H) |
| 146 | (DMSO-$d_6$) δ9.28-9.26 (m, 1H), 9.26-9.04 (m, 1H), 8.11-8.06 (m, 1H), 7.41-7.24 (m, 7H), 4.09-3.92 (m, 2H), 3.86-3.74 (m, 1H), 3.74-3.63 (m, 1H), 3.31-3.12 (m, 4H), 3.11-3.03 (m, 1H), 2.81-2.69 (m, 1H), 2.67-2.53 (m, 1H), 2.11-2.00 (m, 2H), 2.91-2.82 (m, 3H), 2.83-2.76 (m, 3H), 1.48-1.37 (m, 1H), 1.19-1.05 (m, 4H), 1.06-0.94 (m, 4H) |
| 147 | (DMSO-$d_6$) δ9.14 (brs, 2H), 8.12-8.06 (m, 1H), 7.38-7.12 (m, 6H), 7.04-6.99 (m, 1H), 4.09-3.97 (m, 1H), 3.91-3.74 (m, 2H), 3.64-3.55 (m, 1H), 3.31-3.24 (m, 4H), 2.81-2.69 (m, 1H), 2.69-2.51 (m, 1H), 2.13-2.07 (m, 3H), 2.07-2.02 (m, 2H), 1.90-1.82 (m, 3H), 1.77 (s, 3H), 1.43-1.38 (m, 1H), 1.14-1.02 (m, 4H), 1.02-0.92 (m, 5H) |

TABLE 26-continued

| Ex. | $^1$H NMR (400 MHz, solvent) |
|---|---|
| 148 | ($CD_3OD$) δ7.62 (s, 0.5H), 7.53 (s, 0.5H), 7.31 (s, 0.5H), 7.31 (s, 0.5H), 4.12-3.90 (m, 3H), 3.82-3.68 (m, 1H), 3.66-3.50 (m, 2H), 3.62 (s, 1.5H), 3.59 (s, 1.5H), 3.44-3.33 (m, 1H), 3.03-2.91 (m, 1H), 2.88-2.70 (m, 1H), 2.30-2.18 (m, 1H), 2.18-2.02 (m, 2H), 2.06-1.73 (m, 9H), 1.30-1.22 (m, 3H), 1.23-1.14 (m, 3H) |

The compounds of Examples 149 to 169 were synthesized in a similar manner to a corresponding Reference Example and Example 1.

TABLE 27

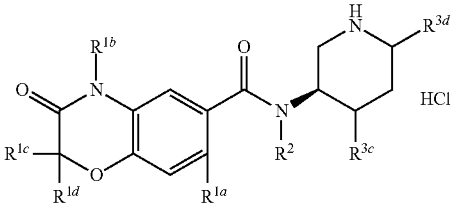

| Ex. | $R^{1d}$ | $R^{1c}$ | $R^{1b}$ | $R^{1a}$ | $R^2$ | $R^{3c}$ | $R^{3d}$ |
|---|---|---|---|---|---|---|---|
| 149 | Me | Me | $CH_3CH_2C(O)NH(CH_2)_2$ | $CF_3$ | H | H | H |
| 150 | Me | Me | $CH_3CH_2C(O)NH(CH_2)_2$ | $CF_3$ | Et | H | H |
| 151 | Me | Me | $CH_3CH_2C(O)NH(CH_2)_2$ | $CF_3$ | 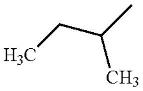 | H | H |
| 152 | Me | Me | $CH_3CH_2C(O)NH(CH_2)_2$ | $CF_3$ | Bn | H | H |
| 153 | Ph | Me | $CH_3CH_2C(O)NH(CH_2)_2$ | $CF_3$ | i-Pr | H | H |
| 154 | Me | Me | $CH_3O(CH_2)_4$ | $CF_3$ | H | H | H |
| 155 | Me | Me | $CH_3O(CH_2)_4$ | $CF_3$ | H | 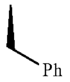 | H |
| 156 | Me | Me | $CH_3O(CH_2)_4$ | $CF_3$ | H | 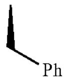 | H |
| 157 | Me | Me | $CH_3O(CH_2)_4$ | $CF_3$ | Me | H | H |
| 158 | Me | Me | $CH_3O(CH_2)_4$ | $CF_3$ | Me | 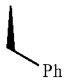 | H |
| 159 | Me | Me | $CH_3O(CH_2)_4$ | $CF_3$ | Me | 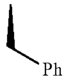 | H |
| 160 | 3-MeOPh | Me | $CH_3CH_2C(O)NH(CH_2)_2$ | $CF_3$ | i-Pr | H | H |
| 161 | 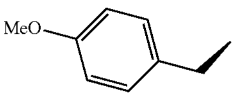 | H | $CH_3CH_2C(O)NH(CH_2)_2$ | $CF_3$ | i-Pr | H | H |
| 162 | Me | Me | $CH_3O(CH_2)_4$ | CN | i-Pr | H | H |
| 163 | 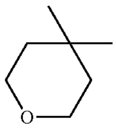 | | $CH_3O(CH_2)_4$ | Et | i-Pr | H | H |
| 164 (TFAsalt) | Me | Me | $HO_2C(CH_2)_3$ | Me | i-Pr | H | H |
| 165 | Me | Me | $CH_3(CH_2)_2O(CH_2)_2$ | Me | i-Pr | H | H |

TABLE 27-continued

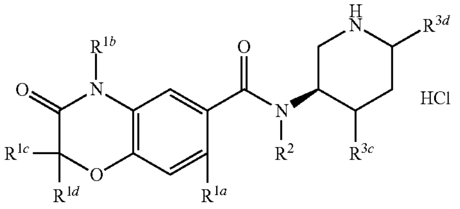

| Ex. | $R^{1d}$ | $R^{1c}$ | $R^{1b}$ | $R^{1a}$ | $R^2$ | $R^{3c}$ | $R^{3d}$ |
|---|---|---|---|---|---|---|---|
| 166 | Me | Me | $CH_3CH_2CO_2CH_2CH_2$ | Me | i-Pr | H | H |
| 167 | 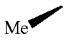 | H | $CH_3O(CH_2)_4$ | $CF_3$ | i-Pr | H | H |
| 168 | Me | Me | 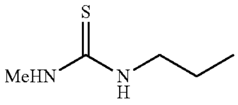 | $CF_3$ | i-Pr | H | 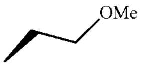 |
| 169 | 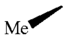 | H | $CH_3CH_2C(O)NH(CH_2)_2$ | $CF_3$ | i-Pr | H | H |

TABLE 28

| Ex. | $^1$H NMR (400 MHz, solvent)/MS (ESI+) |
|---|---|
| 149 | (DMSO-$d_6$) δ9.11-8.91 (br, 2H), 8.73-8.67 (br, 1H), 8.13-8.08 (br, 1H), 7.59 (s, 1H), 7.33 (s, 1H), 4.14-4.05 (m, 1H), 4.03-3.93 (m, 2H), 3.35-3.25 (m, 3H), 3.20-3.13 (m, 1H), 2.91-2.79 (m, 2H), 2.04 (q, J = 7.6 Hz, 2H), 1.95-1.85 (m, 2H), 1.82-1.50 (m, 2H), 1.44 (s, 6H), 0.99 (t, J = 7.6 Hz, 3H). |
| 150 | ($CDCl_3$) δ9.82-9.27 (br, 2H), 7.20-7.03 (m, 2H), 6.82 (brs, 0.5H), 6.65 (brs, 0.5H), 4.25-3.13 (m, 8H), 2.63-2.40 (m, 4H), 2.23-1.88 (m, 5H), 1.59-1.38 (m, 6H), 1.37-1.01 (m, 6H). |
| 151 | ($CDCl_3$) δ9.91-9.43 (br, 2H), 7.37-7.04 (m, 2H), 6.43 (brs, 0.5H), 5.27 (brs, 0.5H), 4.18-3.13 (m, 10H), 2.90-2.64 (m, 2H), 2.15-1.84 (m, 5H), 1.56-1.30 (m, 6H), 1.28-0.68 (m, 10H). |
| 152 | ($CDCl_3$) δ9.90-9.45 (br, 2H), 7.55-7.05 (m, 7H), 6.47 (brs, 0.5H), 6.24 (brs, 0.5H), 4.59-4.23 (m, 2H), 4.07-3.83 (m, 2H), 3.70-2.93 (m, 4H), 2.22-1.68 (m, 6H), 1.62-1.39 (m, 6H), 1.31-0.85 (m, 6H). |
| 153 | (DMSO-$d_6$) δ9.27-9.00 (m, 2H), 8.18-8.12 (m, 1H), 7.59-7.50 (m, 1.6H), 7.46 (s, 0.4H), 7.39-7.25 (m, 5H), 4.18-4.05 (m, 1H), 3.93-3.62 (m, 3H), 3.61-3.44 (m, 2H), 3.26-3.18 (m, 2H), 3.11-2.94 (m, 1H), 2.84-2.65 (m, 1H), 2.64-2.51 (m, 1H), 2.09-2.02 (m, 2H), 2.00-1.89 (m, 1H), 1.81 (s, 3H), 1.68-1.58 (m, 0.6H), 1.52-1.13 (m, 1.4H), 1.16 (d, J = 6.6 Hz, 1H), 1.12-0.92 (m, 8H) |
| 154 | (DMSO-$d_6$) δ9.05 (brs, 2H), 8.72 (d, J = 7.4 Hz, 1H), 7.34 (s, 1H), 7.33 (s, 1H), 4.10-4.08 (m, 1H), 3.98-3.95 (m, 2H), 3.37-3.28 (m, 3H), 3.20 (s, 3H), 3.17-3.14 (m, 1H), 2.86-2.80 (m, 1H), 2.76-2.71 (m, 1H), 1.91-1.85 (m, 2H), 1.72-1.68 (m, 1H), 1.61-1.45 (m, 5H), 1.42 (s, 6H). |
| 155 | (DMSO-$d_6$) δ8.99 (brs, 2H), 8.78 (d, J = 8.4 Hz, 1H), 7.52 (s, 1H), 7.37 (s, 1H), 7.31-7.27 (m, 2H), 7.21-7.17 (m, 3H), 4.39-4.36 (m, 1H), 4.08-4.05 (m, 2H), 3.37-3.27 (m, 1H), 3.22-3.14 (m, 5H), 2.88-2.82 (m, 1H), 2.79-2.75 (m, 1H), 2.53-2.45 (m, 1H), 2.15-2.13 (m, 1H), 1.75-1.61 (m, 3H), 1.57-1.52 (m, 3H), 1.49-1.43 (m, 7H). |
| 156 | (DMSO-$d_6$) δ8.90-8.27 (m, 3H), 7.38 (m, 1H), 7.31-7.27 (m, 3H), 7.21-7.18 (m, 3H), 4.00-3.91 (m, 3H), 3.39-3.35 (m, 1H), 3.26-3.23 (m, 2H), 3.19-3.16 (m, 1H), 3.12-3.08 (m, 4H), 2.78-2.72 (m, 1H), 2.67-2.61 (m, 1H), 2.29-2.23 (m, 1H), 1.90-1.85 (m, 1H), 1.63-1.56 (m, 3H), 1.51-1.35 (m, 9H). |
| 157 | (DMSO-$d_6$)δ9.03 (brs, 2H), 7.40-7.27 (m, 2H), 3.97-3.58 (m, 3H), 3.30-2.65 (m, 12H), 1.98-1.77 (m, 3H), 1.55-1.41 (m, 11H). |
| 158 | (DMSO-$d_6$)δ9.37 (brs, 2H), 7.40-7.27 (m, 4H), 7.25-7.15 (m, 3H), 4.00-3.80 (m, 3H), 3.59 (m, 1H), 3.44-3.37 (m, 1H), 3.25 (m, 1H), 3.20-3.11 (m, 4H), 3.04-2.80 (m, 6H), 2.62 (m, 1H), 1.71-1.34 (m, 13H). |
| 159 | (DMSO-$d_6$)δ 8.90 (brs, 2H), 8.17-8.09 (m, 1H), 7.64-7.46 (m, 2H), 7.28-2.22 (m, 1H), 6.95-6.81 (m, 3H), 4.16-4.07 (m, 1H), 3.89-3.72 (m, 3H), 3.69 (s, 3H), 3.64-3.51 (m, 2H), 3.28-3.16 (m, 2H), 3.09-2.95 (m, 1H), 2.83-2.71 (m, 1H), 2.62-2.50 (m, 1H), 2.12-2.04 (m, 2H), 1.97-1.61 (m, 2H), 1.80 (s, 3H), 1.48-1.34 (m, 1H), 1.17-1.09 (m, 2H), 1.07-0.90 (m, 7H) |
| 160 | (DMSO-$d_6$)δ 8.90 (brs, 2H), 8.17-8.09 (m, 1H), 7.64-7.46 (m, 2H), 7.28-2.22 (m, 1H) 6.95-6.81 (m, 3H), 4.16-4.07 (m, 1H), 3.89-3.72 (m, 3H), 3.69 (s, 3H), 3.64-3.51 (m, 2H), 3.28-3.16 (m, 2H), 3.09-2.95 (m, 1H), 2.83-2.71 (m, 1H), 2.62-2.50 (m, 1H), 2.12-2.04 (m, 2H), 1.97-1.61 (m, 2H), 1.80 (s, 3H), 1.48-1.34 (m, 1H), 1.17-1.09 (m, 2H), 1.07-0.90 (m, 7H). |
| 161 | (DMSO-$d_6$)δ9.41-9.00 (m, 1H), 8.14 (m, 1H), 7.25-7.08 (m, 4H), 6.83 (s, 1H), 6.74 (s, 1H), 5.05 (d, 2H), 4.00-0.93 (m, 29H) |

TABLE 28-continued

| Ex. | $^1$H NMR (400 MHz, solvent)/MS (ESI+) |
|---|---|
| 162 | RT 3.164 min (Shim-pack XR-ODS, 0.1% trifluoroacetic acid in water/acetonitrile, acetonitrile 30-90% 5.7 min, 1.0 ml/min). MS (ESI+) 457 ($M^+$ + 1, 100%). |
| 163 | ($CD_3OD$)) δ7.11, 7.09 (s, 1H), 7.00, 6.93 (s, 1H), 4.05-4.12 (m, 2H), 3.65-3.90 (m, 8H), 3.38-3.44 (m, 4H), 3.28-3.29 (m, 2H), 2.94-2.99 (m, 1H), 2.81-2.84 (m, 1H), 2.56-2.61 (m, 2H), 1.91-2.19 (m, 5H), 1.56-1.77 (m, 7H), 1.20-1.29 (m, 9H). |
| 164 | (DMSO-$d_6$)δ7.68-7.65 (m, 1H), 6.91-6.89 (m, 2H), 4.00-3.91 (m, 4H), 2.78-2.33 (m, 5H), 1.86-1.01 (m, 22H). |
| 165 | (DMSO-$d_6$)δ9.17-9.12 (m, 1H), 7.09-7.03 (m, 1H), 6.87 (s, 1H), 4.12-3.97 (m, 2H), 3.62-3.50 (m, 3H), 3.35-3.13 (m, 6H), 2.78-2.62 (m, 2H), 2.12 (s, 3H), 1.90-1.72 (m, 3H), 1.43-1.33 (m, 9H), 1.14-1.01 (m, 5H), 0.78-0.73 (m, 3H). |
| 166 | (DMSO-$d_6$)δ9.09-9.03 (m, 1H), 7.07-7.00 (m, 1H), 6.89-6.87 (m, 1H), 4.22-4.16 (m, 6H), 3.61-3.53 (m, 1H), 2.20-2.12 (m, 6H), 1.87-1.75 (m, 4H), 1.43-1.33 (m, 6H), 1.13-0.90 (m, 8H). |
| 167 | ($CD_3OD$)δ7.37 (d, J = 2.9 Hz, 1H), 7.23 (s, 0.5H), 7.15 (s, 0.5H), 4.81-4.75 (m, 1H), 4.23-3.94 (m, 3H), 3.76-3.63 (m, 3H), 3.44-3.39 (m, 3H), 3.31-3.29 (m, 3H), 3.03-2.70 (m, 2H), 2.11-1.86 (m, 3H), 1.70-1.48 (m, 8H), 1.26-1.16 (m, 6H). |
| 168 | ($CDCl_3$) δ 7.55 (br, 1H), 7.23 (m, 1H), 4.22-4.13 (m, 3H), 3.89 (m, 3H), 3.71-3.53 (m, 5H), 3.36 (m, 3H), 2.94-2.79 (m, 3H), 2.62 (br, 1H), 2.36-2.18 (m, 2H), 2.01-1.77 (m, 2H), 1.59 (m, 3H), 1.48 (s, 3H), 1.33-1.14 (m, 6H). |
| 169 | RT = 3.082 min (Shim-pack XR-ODS, 0.1% trifluoroacetic acid in water/acetonitrile, acetonitrile 30-90% 5.7 min, 1.0 ml/min) MS (ESI+) 499 (M+ + 1, 100%). |

The compounds of Examples 170 to 184 were synthesized in a similar manner to a corresponding Reference Example and Example 1.

TABLE 29

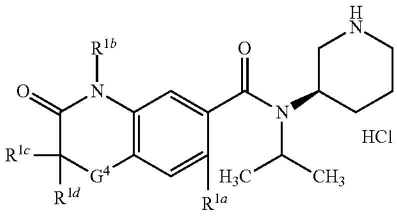

| Ex. | $G^4$ | $R^{1d}$ | $R^{1c}$ | $R^{1b}$ | $R^{1a}$ |
|---|---|---|---|---|---|
| 170 | S | Me | Me | $CH_3C(O)NH(CH_2)_2$ | Me |
| 171 | S | H | Me | $MeO(CH_2)_4$ | Me |
| 172 | S | Me | Me | $CH_3CH_2C(O)NH(CH_2)_2$ | Me |
| 173 | S | 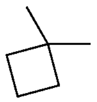 | | $MeOC(O)NH(CH_2)_2$ | $CF_3$ |
| 174 | S | 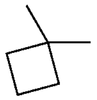 | | $CH_3CH_2C(O)NH(CH_2)_2$ | $CF_3$ |
| 175 | S | 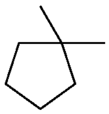 | | $MeOC(O)NH(CH_2)_2$ | $CF_3$ |

TABLE 29-continued

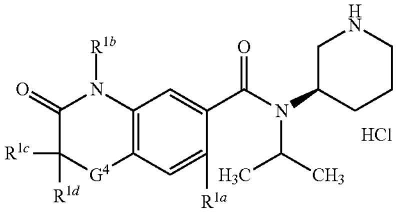

| Ex. | $G^4$ | $R^{1d}$ | $R^{1c}$ | $R^{1b}$ | $R^{1a}$ |
|---|---|---|---|---|---|
| 176 | S | 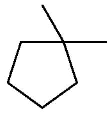 | | $CH_3CH_2C(O)NH(CH_2)_2$ | $CF_3$ |
| 177 | S | Me | $MeOCH_2$ | $MeO(CH_2)_4$ | $CF_3$ |
| 178 | S | H | Me | $MeO(CH_2)_4$ | $CF_3$ |
| 179 | S | H | Me | $MeOC(O)NH(CH_2)_2$ | Me |
| 180 | S | H | Me | $CH_3CH_2C(O)NH(CH_2)_2$ | Me |
| 181 | $SO_2$ | Me | Me | $MeO(CH_2)_4$ | Me |
| 182 | S | H | Me | $CH_3CH_2C(O)NH(CH_2)_2$ | $CF_3$ |
| 183 | S | Me | Me | $CH_3CH_2C(O)NH(CH_2)_2$ | $CF_3$ |
| 184 | S | 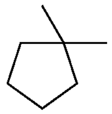 | | $MeOC(O)NH(CH_2)_2$ | Me |

TABLE 30

| Ex. | $^1$H NMR (400 MHz, solvent)/MS (ESI+) |
|---|---|
| 170 | RT 2.773 min (Shim-pack XR-ODS, 0.1% trifluoroacetic acid in water/acetonitrile, acetonitrile 30-90% 5.7 min, 1.0 ml/min). MS ($ESI^+$) 476 ($M^+$ + 1, 100%). |

TABLE 30-continued

| Ex. | $^1$H NMR (400 MHz, solvent)/MS (ESI+) |
|---|---|
| 171 | ($CD_3OD$) δ7.34 (s, 1H), 7.14, 7.09 (S x 2, 1H), 3.91-4.28 (m, 3H), 3.72-3.88 (m, 1H), 3.51-3.69 (m, 2H), 3.31-3.48 (m, 4H), 3.26 (s, 3H), 2.75-3.05 (m, 2H), 2.25 (s, 3H), 2.08 (m, 1H), 1.86-1.99 (m, 2H), 1.53-1.62 (m, 4H), 1.36-1.42 (m, 3H), 1.20-1.29 (m, 6H) |
| 172 | ($CDCl_3$) δ9.74-9.60 (brs, 2H), 7.14-7.06 (m, 2H), 5.98 (brs, 1H), 4.22-4.01 (m, 2H), 3.98-3.76 (m, 2H), 3.76-3.62 (m, 2H), 3.56-3.31 (m, 3H), 2.96-2.74 (m, 2H), 2.16 (s, 3H), 2.15-2.06 (m, 2H), 2.03-1.85 (m, 3H), 1.48-1.38 (m, 3H), 1.39-1.15 (m, 6H), 1.16-1.05 (m, 3H), 1.05-0.98 (m, 3H) |
| 173 | ($CD_3OD$) δ7.80 (s, 0.5H), 7.80 (s, 0.5H), 7.77 (s, 0.5H), 7.67 (s, 0.5H), 4.17-3.90 (m, 3H), 3.82-3.52 (m, 2H), 3.63 (s, 1.5H), 3.59 (s, 1.5H), 3.45-3.22 (m, 2H), 3.04-2.91 (m, 1H), 2.90-2.70 (m, 2H), 2.63-2.50 (m, 1H), 2.30-1.78 (m, 9H), 1.31-1.23 (m, 3H), 1.22-1.14 (m, 3H) |
| 174 | ($CD_3OD$) δ7.79 (s, 0.5H), 7.74 (s, 0.5H), 7.58 (s, 0.5H), 7.56 (s, 0.5H), 4.18-3.91 (m, 3H), 3.82-3.43 (m, 3H), 3.45-3.31 (m, 1H), 3.04-2.67 (m, 3H), 2.61-2.48 (m, 1H), 2.39-1.76 (m, 10H), 1.25 (d, J = 6.6 Hz, 1H), 1.22-1.13 (m, 3H), 1.12-1.02 (m, 3H) |
| 175 | ($CD_3OD$) δ7.82 (s, 0.5H), 7.77 (s, 1H), 7.73 (s, 0.5H), 4.18-3.90 (m, 3H), 3.82-3.67 (m, 1H), 3.68-3.52 (m, 2H), 3.64 (s, 1.5H), 3.63 (s, 1.5H), 3.45-3.34 (m, 2H), 3.04-2.91 (m, 1H), 2.89-2.70 (m, 1H), 2.58-2.37 (m, 1H), 2.16-2.04 (m, 1H), 1.94-1.60 (m, 9H), 1.35-1.22 (m, 3H), 1.25-1.13 (m, 3H) |
| 176 | ($CD_3OD$) δ7.77 (s, 0.5H), 7.75 (s, 0.5H), 7.75 (s, 0.5H), 7.63 (s, 0.5H), 4.19-3.91 (m, 3H), 3.83-3.52 (m, 3H), 3.53-3.33 (m, 2H), 3.13-2.90 (m, 1H), 2.90-2.67 (m, 1H), 2.52-2.41 (m, 1H), 2.24-2.00 (m, 4H), 1.98-1.57 (m, 9H), 1.30-1.22 (m, 3H), 1.22-1.13 (m, 3H), 1.13-1.03 (m, 3H) |
| 177 | ($CD_3OD$) δ7.79 (s, 0.5H), 7.76 (s, 0.5H), 7.26 (s, 0.5H), 7.16 (s, 0.5H), 4.31-4.13 (m, 1H), 4.14-3.96 (m, 2H), 3.81-3.68 (m, 1H), 3.70-3.20 (m, 6H), 3.39 (s, 3H), 3.27 (s, 1.5H), 3.24 (s, 1.5H), 3.03-2.90 (m, 1H), 2.90-2.66 (m, 1H), 2.15-2.04 (m, 1H), 2.05-1.95 (m, 1H), 1.95-1.70 (m, 2H), 1.73-1.50 (m, 4H), 1.49 (s, 3H), 1.27-1.12 (m, 6H) |
| 178 | ($CD_3OD$) δ7.82 (s, 0.5H), 7.82 (s, 0.5H), 7.33 (s, 0.5H), 7.26 (s, 0.5H), 4.38-4.12 (m, 1H), 4.14-3.95 (m, 2H), 3.50-3.31 (m, 4H), 3.27 (s, 1.5H), 3.26 (s, 1.5H), 3.05-2.89 (m, 1H), 2.91-2.68 (m, 1H), 2.13-2.04 (m, 1H), 2.04-1.92 (m, 1H), 1.95-1.75 (m, 2H), 1.70-1.49 (m, 4H), 1.45 (d, J = 7.0 Hz, 1.5H), 1.40 (d, J = 7.0 Hz, 1.5H), 1.27-1.13 (m, 3H) |
| 179 | ($CD_3OD$) δ7.50, 7.43 (d, J = 15 Hz, 1H), 7.30 (s, 3H), 3.87-4.16 (m, 3H), 3.72-3.85 (m, 1H), 3.51-3.67 (m, 6H), 3.32-3.43 (m, 3H), 2.95-3.05 (m, 1H), 2.79-2.91 (m, 1H), 2.25 (s, 3H), 2.09-2.12 (m, 1H), 1.88-1.96 (m, 2H), 1.55-1.62 (m, 1H), 1.44, 1.38 (d, J = 7 Hz, 3H), 1.23-1.26 (m, 6H) |
| 180 | RT 2.421 min (Shim-pack XR-ODS, 0.1% trifluoroacetic acid in water/acetonitrile, acetonitrile 30-90% 5.7 min, 1.0 ml/min). MS (ESI$^+$) 460 (M$^+$ + 1, 100%). |
| 181 | ($CD_3OD$) δ7.86 (s, 1H), 7.43, 7.37 (s, 1H), 4.22-4.31 (m, 1H), 4.02-4.17 (m, 1H), 3.61-3.77 (m, 3H), 3.32-3.48 (m, 4H), 3.27 (s, 3H), 2.96-3.04 (m, 1H), 2.77-2.86 (m, 1H), 2.36 (m, 3H), 2.09-2.13 (m, 1H), 1.85-2.02 (m, 2H), 1.62-1.69 (m, 2H), 1.58-1.60 (m, 6H), 1.45 (s, 3H), 1.21-1.27 (m, 6H) |
| 182 | ($CD_3OD$) δ7.56-7.82 (m, 2H), 4.05-4.24 (m, 3H), 3.62-3.83 (m, 5H), 3.32-3.55 (m, 3H), 2.93-3.00 (m, 1H), 2.75-2.86 (m, 1H), 2.18-2.28 (m, 3H), 1.82-1.97 (m, 2H), 1.47, 1.41 (d, J = 7 Hz, 3H), 1.05-1.27 (m, 10H) |
| 183 | ($CD_3OD$) δ7.78 (d, J = 18 Hz, 1H), 7.70 (d, J = 41 Hz, 1H), 3.92-4.22 (m, 3H), 3.57-3.82 (m, 3H), 3.25-3.48 (m, 3H), 2.91-3.05 (m, 2H), 2.71-2.90 (m, 1H), 2.08-2.22 (m, 4H), 1.89-1.99 (m, 2H), 1.51 (s, 3H), 1.37 (s, 3H), 1.26 (d, J = 6.52, 3H), 1.19 (t, J = 6.8 Hz, 3H), 1.03-1.12 (m, 3H) |
| 184 | ($CD_3OD$) δ8.18 (s, 0.5H), 7.51 (s, 0.5H), 7.25 (s, 0.5H), 7.26 (s, 0.5H), 4.18-3.82 (m, 3H), 3.85-3.13 (m, 5H), 3.62 (s, 1.5H), 3.60 (s, 1.5H), 3.03-2.75 (m, 2H), 2.50-2.31 (m, 1H), 2.06-1.51 (m, 11H), 1.37-1.10 (m, 6H) |

The compounds of Examples 185 to 200 were synthesized in a similar manner to Reference Example and Example 1.

TABLE 31

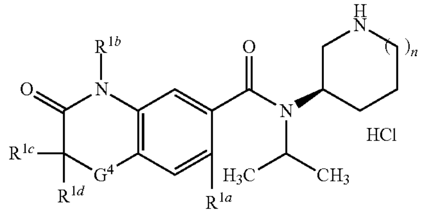

| Ex. | $G^4$ | $R^{1d}$ | $R^{1c}$ | $R^{1b}$ | $R^{1a}$ | n |
|---|---|---|---|---|---|---|
| 185 | $CH_2$ | Me | Me | $MeO(CH_2)_4$ | Cl | 1 |
| 186 | $CH_2$ | Me | Me | $MeO(CH_2)_4$ | Me | 1 |

TABLE 31-continued

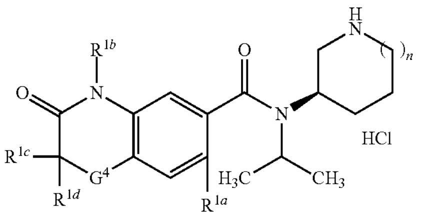

| Ex. | $G^4$ | $R^{1d}$ | $R^{1c}$ | $R^{1b}$ | $R^{1a}$ | n |
|---|---|---|---|---|---|---|
| 187 | $CH_2$ | Me | Me | $MeOC(O)NH(CH_2)_2$ | Br | 1 |
| 189 | $CH_2$ | Me | Me | $MeOC(O)NH(CH_2)_2$ | Cl | 1 |
| 190 | $CMe_2$ | H | H | $MeO(CH_2)_4$ | Me | 1 |

TABLE 31-continued

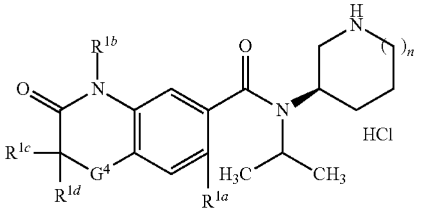

| Ex. | $G^4$ | $R^{1d}$ | $R^{1c}$ | $R^{1b}$ | $R^{1a}$ | n |
|---|---|---|---|---|---|---|
| 191 | $CH_2$ | Me | Me | $MeOC(O)NH(CH_2)_2$ | Me | 1 |
| 192 | $CH_2$ | Me | Me | $MeOC(O)NH(CH_2)_2$ | Et | 1 |
| 193 | $CH_2$ | Me | Me | $CH_3CH_2C(O)NH(CH_2)_2$ | Cl | 1 |
| 194 | $CH_2$ | Me | Me | $CH_3CH_2C(O)NH(CH_2)_2$ | Me | 1 |
| 195 | $CH_2$ | Me | Me | $CH_3CH_2C(O)NH(CH_2)_2$ | $CF_3$ | 1 |

TABLE 31-continued

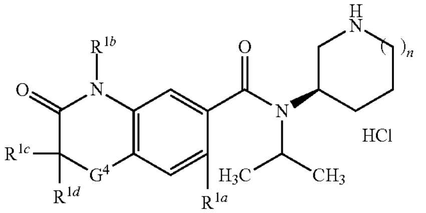

| Ex. | $G^4$ | $R^{1d}$ | $R^{1c}$ | $R^{1b}$ | $R^{1a}$ | n |
|---|---|---|---|---|---|---|
| 196 | $CH_2$ | 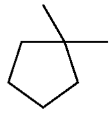 | | $CH_3CH_2C(O)NH(CH_2)_2$ | $CF_3$ | 1 |
| 200 | O | Me | Me | $MeO(CH_2)_4$ | $CF_3$ | 2 |

TABLE 32

| Ex. | $^1$H NMR (400 MHz, solvent)/MS (ESI+) |
|---|---|
| 185 | ($CDCl_3$) δ9.81-9.78 (brs 2H), 7.16 (brs, 1H), 6.92 (brs, 2H), 4.18 (brs, 1H), 4.01-3.84 (m, 4H), 3.50-3.38 (m, 4H), 3.32 (s, 3H), 3.92-2.81 (m, 2H), 2.76 (s, 2H), 2.19-2.04 (m, 2H), 1.88 (brs, 1H), 1.78 (brs, 1H), 1.67-1.61 (m, 4H), 1.32 (brs, 2H), 1.38-1.31 (m, 3H), 1.16 (d, J = 2.0 Hz, 5H) |
| 186 | ($CDCl_3$) δ9.83 (brs, 2H), 6.96 (s, 1H), 6.65 (s, 1H), 4.23 (brs, 1H), 4.03-3.75 (m, 5H), 3.52-3.45 (m, 2H), 3.45-3.39 (m, 3H), 3.27 (s, 3H), 2.93 (brs, 2H), 2.77-2.61 (m, 2H), 2.29-2.05 (m, 6H), 1.94-1.85 (m, 1H), 1.46-1.25 (m, 4H), 1.25-1.14 (m, 6H), 1.09 (d, J = 2.0 Hz, 3H) |
| 187 | ($CDCl_3$) δ7.32 (brs, 2H), 4.52-3.94 (m, 3H), 3.94-3.64 (m, 5H), 3.63-3.28 (m, 2H), 3.26-2.71 (m, 5H), 2.44-1.83 (m, 7H), 1.71-1.07 (m, 12H) |
| 189 | ($CDCl_3$) δ9.93-9.78 (m, 2H), 7.26 (d, J = 4 Hz, 1H), 7.16 (d, J = 4 Hz, 1H), 4.28-4.11 (m, 2H), 3.98-3.83 (m, 2H), 3.77-3.68 (m, 1H), 3.68-3.58 (m, 3H), 3.51-3.30 (m, 4H), 3.02-2.88 (m, 2H), 2.94-2.67 (m, 2H), 2.08-2.00 (m, 2H), 1.99-1.72 (m, 2H), 1.42-1.36 (m, 3H), 1.31-1.16 (m, 6H), 1.15-1.05 (m, 3H) |
| 190 | ($CDCl_3$) δ9.98-9.45 (brs, 2H), 7.12 (m, 1H), 6.88 (m, 1H), 4.48-4.36 (m, 1H), 4.26-4.17 (m, 1H), 4.12-3.95 (m, 2H), 3.62-3.36 (m, 4H), 3.37-3.26 (m, 6H), 2.96-2.76 (m, 2H), 2.33 (s, 3H), 2.18-1.93 (m, 4H), 1.57-1.47 (m, 3H), 1.41-1.34 (m, 3H), 1.30-1.17 (m, 6H), 1.16-1.11 (m, 3H) |
| 191 | ($CDCl_3$) δ 9.84 (brs, 2H), 7.13 (s, 0.6H), 7.09 (s, 0.4H), 6.95 (s, 1H), 5.80 (t, J = 5.4 Hz, 0.4H), 5.28 (t, J = 5.8 Hz, 0.6H), 4.25-4.12 (m, 1H), 4.08-3.82 (m, 3H), 3.78-3.69 (m, 1H), 3.68-3.55 (m, 3H), 3.55-3.27 (m, 3H), 2.99-2.81 (m, 2H), 2.81-2.53 (m, 3H), 2.23-2.17 (m, 3H), 2.18-1.99 (m, 2H), 1.96-1.82 (m, 1H), 1.41-1.24 (m, 3H), 1.24-1.11 (m, 6H), 1.07 (s, 3H) |
| 192 | ($CDCl_3$) δ9.64-9.51 (m, 2H), 7.01 (s, 0.5H), 6.98 (s, 0.5H), 6.94 (s, 1H), 5.69 (m, 0.5H), 5.19 (t, J = 5.4 Hz, 0.5H), 4.20-4.14 (m, 1H), 4.13-3.96 (m, 1H), 3.96-3.76 (m, 2H), 3.74-3.63 (m, 1H), 3.61-3.50 (m, 4H), 3.48-3.22 (m, 3H), 2.93-2.78 (m, 2H), 2.78-2.59 (m, 2H), 2.55-2.26 (m, 2H), 2.15-1.97 (m, 1H), 2.05-1.90 (m, 1H), 1.88-1.75 (m, 1H), 1.34-1.22 (m, 3H), 1.22-1.09 (m, 9H), 1.06 (s, 3H) |
| 193 | ($CDCl_3$) δ9.84-9.53 (m, 2H), 7.20 (s, 1H), 7.08 (s, 1H), 4.18-3.77 (m, 4H), 3.71-3.56 (m, 3H), 3.54-3.32 (m, 3H), 2.94-2.83 (m, 1H), 2.83-2.61 (m, 2H), 2.21-1.94 (m, 9H), 1.46-1.24 (m, 2H), 1.24-1.05 (m, 10H) |
| 194 | ($CDCl_3$) δ9.69 (brs, 2H), 7.18-6.93 (m, 2H), 4.33-4.14 (m, 1H), 4.16-3.84 (m, 3H), 3.84-3.74 (m, 2H), 3.64-3.34 (m, 3H), 3.04-2.84 (m, 2H), 2.84-2.68 (m, 2H), 2.58-2.42 (m, 3H), 2.31-2.11 (m, 6H), 1.44-1.15 (m, 7H), 1.15-1.06 (m, 8H) |
| 195 | ($DMSO-d_6$) δ9.51-9.46 (brs, 1H), 9.32-9.27 (m, 0.6H), 9.24-9.22 (m, 0.4H), 8.17-8.10 (m, 1H), 7.66-7.57 (m, 1.6H), 7.53 (s, 0.4H), 3.91-3.82 (m, 2H), 3.82-3.75 (m, 2H), 3.29-3.25 (m, 1H), 3.21-3.12 (m, 2H), 3.03-3.00 (m, 1H), 2.93-2.82 (m, 2H), 2.76-2.69 (m, 1H), 2.64-2.58 (m, 1H), 2.09-2.02 (m, 2H), 1.87 (brs, 2H), 1.69-1.64 (m, 1H), 1.52-1.50 (m, 0.6H), 1.40-1.36 (m, 0.4H), 1.20-1.12 (d, J = 6.7 Hz, 2H), 1.14-1.03 (m, 5H), 1.01-0.81 (m, 8H) |
| 196 | ($DMSO-d_6$) δ 9.18 (brs, 2H), 8.16-8.08 (m, 1H), 7.66-7.58 (m, 1.6H), 7.50 (s, 0.4H), 3.91-3.77 (m, 3H), 3.71-3.66 (m, 1H), 3.57-3.51 (m, 1H), 3.38-3.25 (m, 1H), 3.22-3.15 (m, 2H), 3.08-3.02 (m, 1H), 2.82-2.73 (m, 1H), 2.64-2.58 (m, 1H), 2.09-2.02 (m, 4H), 1.94-1.78 (m, 2H), 1.70-1.59 (m, 6H), 1.43-1.35 (m, 3H), 1.19-1.17 (d, J = 6.6 HZ, 2H), 1.14-1.09 (m, 2H), 1.00 (d, J = 2.4 Hz, 2H), 0.99-0.91 (m, 3H) |
| 200 | ($DMSO-d_6$) δ 9.41 (brs, 1H), 8.63 (brs, 1H), 7.39-7.16 (m, 2H), 4.12-4.09 (m, 1H) 3.91-3.88 (m, 1H), 3.79 (m, 1H), 3.65-3.50 (m, 2H), 3.45-3.42 (m, 1H), 3.21-3.16 (m, 5H), 3.11-3.03 (m, 1H), 2.40-2.28 (m, 1H), 1.90-1.76 (m, 4H), 1.60-1.48 (m, 9H), 1.41 (s, 3H), 1.17-1.03 (m, 6H) |

Example 201

N-Isopropyl-4-(4-methoxybutyl)-2,2-dimethyl-3-oxo-N-pyrrolidine-3-yl-7-(trifluoromethyl)-3,4-dihydro-2H-1,4-benzoxazine-6-carboxamide hydrochloride

[Chemical formula 849]

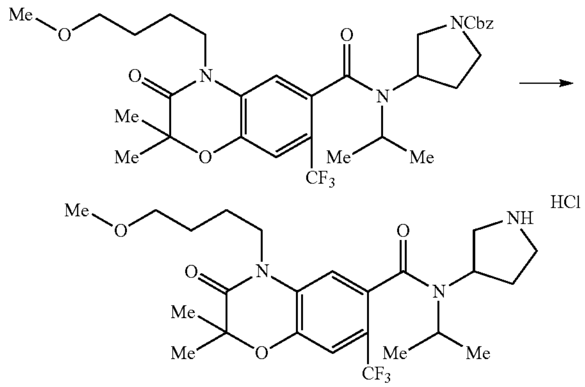

Benzyl 3-(isopropyl{[4-(4-methoxybutyl)-2,2-dimethyl-3-oxo-7-(trifluoromethyl)-3,4-dihydro-2H-1,4-benzoxazin-6-yl]carbonyl}amino)pyrrolidine-1-carboxylate (58.0 mg) was dissolved in methanol (5 ml), and thereto was added 10% palladium-carbon (106 mg), and the mixture was stirred at room temperature for 3 hours under hydrogen atmosphere. The mixture was filtered on celite, and concentrated under reduced pressure. The obtained residue was purified by silica gel column chromatography (chloroform/methanol=10/1), and the obtained compound was dissolved in dioxane (2 ml), and further thereto was added 4N hydrochloric acid-dioxane (2 ml). The mixture was concentrated to give the title compound (25.2 mg) as a white solid.

$^1$H-NMR (400 MHz, DMSO-$d_6$) δ 9.44 (m, 2H), 7.38-7.24 (m, 2H), 4.25 (m, 1H), 4.10 (m, 1H), 3.89 (m, 1H), 3.71 (m, 1H), 3.58-3.54 (m, 2H), 3.16 (s, 3H), 3.08 (m, 1H), 2.22 (m, 2H), 2.00 (m, 1H), 1.51-1.48 (m, 7H), 1.41 (s, 3H), 1.31-1.30 (m, 2H), 1.14-1.11 (m, 3H), 1.05-1.02 (m, 3H).

MS (ESI+) 486 (M+1, 100%).

The compounds of Examples 202 to 223 were synthesized in a similar manner to a corresponding Reference Example and Example 1.

TABLE 33

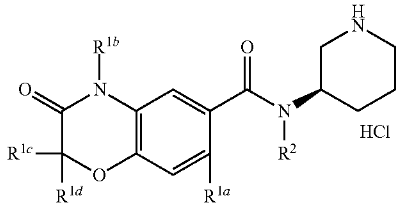

| Ex. | $R^{1d}$ | $R^{1c}$ | $R^{1b}$ | $R^{1a}$ | $R^2$ |
|---|---|---|---|---|---|
| 202 | Me | Me | $CH_3CH_2C(O)NH(CH_2)_2$ | $CF_3$ | 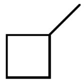 |
| 203 | Me | Me | $CH_3CH_2C(O)NH(CH_2)_2$ | $CF_3$ | 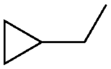 |
| 204 | Me | Me | $CH_3CH_2C(O)NH(CH_2)_2$ | $CF_3$ | 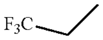 |
| 205 | 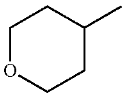 | H | $CH_3O(CH_2)_4$ | $CF_3$ | i-Pr |
| 206 | 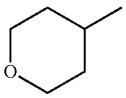 | H | $MeOC(O)NH(CH_2)_2$ | $CF_3$ | i-Pr |
| 207 | 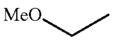 | Me | $CH_3CH_2C(O)NH(CH_2)_2$ | $CF_3$ | i-Pr |
| 208 | 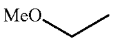 | Me | $MeOC(O)NH(CH_2)_2$ | $CF_3$ | i-Pr |
| 209 | 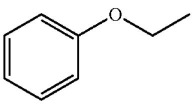 | Me | $MeOC(O)NH(CH_2)_2$ | $CF_3$ | i-Pr |

TABLE 33-continued
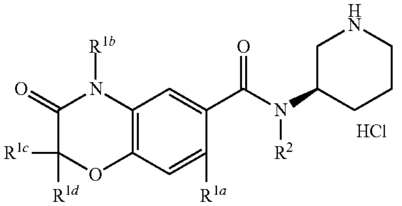
| Ex. | $R^{1d}$ | $R^{1c}$ | $R^{1b}$ | $R^{1a}$ | $R^2$ |
|---|---|---|---|---|---|
| 210 | 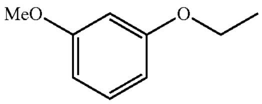 | Me | $MeOC(O)NH(CH_2)_2$ | $CF_3$ | i-Pr |
| 211 | 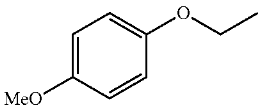 | Me | $MeOC(O)NH(CH_2)_2$ | $CF_3$ | i-Pr |
| 212 | 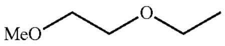 | Me | $CH_3O(CH_2)_4$ | $CF_3$ | i-Pr |
| 213 | 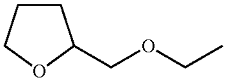 | Me | $CH_3O(CH_2)_4$ | $CF_3$ | i-Pr |
| 214 | 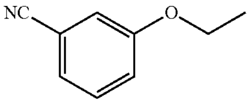 | Me | $CH_3O(CH_2)_4$ | $CF_3$ | i-Pr |
| 215 | 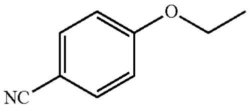 | Me | $CH_3O(CH_2)_4$ | $CF_3$ | i-Pr |
| 216 | 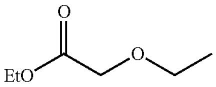 | Me | $CH_3O(CH_2)_4$ | $CF_3$ | i-Pr |
| 217 | 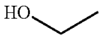 | Me | $CH_3O(CH_2)_4$ | $CF_3$ | i-Pr |
| 218 | 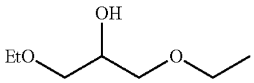 | Me | $CH_3O(CH_2)_4$ | $CF_3$ | i-Pr |
| 219 | 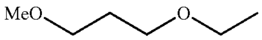 | Me | $CH_3O(CH_2)_4$ | $CF_3$ | i-Pr |
| 220 | 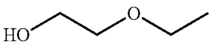 | Me | $CH_3O(CH_2)_4$ | $CF_3$ | i-Pr |
| 221 | 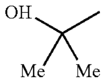 | Me | $CH_3O(CH_2)_4$ | $CF_3$ | i-Pr |
| 222 | 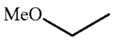 | Me | $CHF_2C(O)NH(CH_2)_2$ | $CF_3$ | i-Pr |
| 223 | 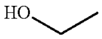 | Me | $CHF_2C(O)NH(CH_2)_2$ | $CF_3$ | i-Pr |

TABLE 34

| Ex. | $^1H$ NMR (400 MHz, solvent)/MS (ESI+) |
|---|---|
| 202 | RT 2.350 min (Shim-pack XR-ODS, 0.1% trifluoroacetic acid in water/acetonitrile, acetonitrile 30-90% 5.7 min, 1.0 ml/min). MS (ESI+) 525 ($M^+$ + 1, 100%). |
| 203 | RT 2.346 min (Shim-pack XR-ODS, 0.1% trifluoroacetic acid in water/acetonitrile, acetonitrile 30-90% 5.7 min, 1.0 ml/min). MS (ESI+) 525 ($M^+$ + 1, 100%). |
| 204 | RT 2.156 min (Shim-pack XR-ODS, 0.1% trifluoroacetic acid in water/acetonitrile, acetonitrile 30-90% 5.7 min, 1.0 ml/min). MS (ESI+) 553 ($M^+$ + 1, 100%). |
| 205 | RT 2.435 min (Shim-pack XR-ODS, 0.1% trifluoroacetic acid in water/acetonitrile, acetonitrile 30-90% 5.7 min, 1.0 ml/min). MS (ESI+) 556 ($M^+$ + 1, 100%). |
| 206 | RT 1.881 min (Shim-pack XR-ODS, 0.1% trifluoroacetic acid in water/acetonitrile, acetonitrile 30-90% 5.7 min, 1.0 ml/min). MS (ESI+) 571 ($M^+$ + 1, 100%). |
| 207 | ($CD_3OD$) δ7.56-7.43 (m, 2H), 7.29-7.27 (m, 2H), 4.25-3.99 (m, 4H), 3.88-3.61 (m, 4H), 3.68-3.52 (m, 3H), 3.44-3.29 (m, 4H), 3.01-2.71 (m, 4H), 2.20-1.85 (m, 4H), 1.52-1.44 (m, 2H), 1.28-1.15 (m, 6H), 1.11-1.02 (m, 3H) |
| 208 | ($CD_3OD$) δ7.61-7.52 (m, 2H), 7.29-7.26 (m, 2H), 4.11-3.98 (m, 4H), 3.88-3.61 (m, 4H), 3.65 (s, 3H), 3.60-3.52 (m, 1H), 3.42-3.25 (m, 4H), 3.01-2.65 (m, 4H), 2.27-1.85 (m, 4H), 1.53-1.45 (m, 2H), 1.28-1.16 (m, 6H) |
| 209 | RT 3.025 min (Shim-pack XR-ODS, 0.1% trifluoroacetic acid in water/acetonitrile, acetonitrile 30-90% 5.7 min, 1.0 ml/min). MS (ESI+) 607 ($M^+$ + 1, 100%). |
| 210 | RT 3.018 min (Shim-pack XR-ODS, 0.1% trifluoroacetic acid in water/acetonitrile, acetonitrile 30-90% 5.7 min, 1.0 ml/min). MS (ESI+) 637 ($M^+$ + 1, 100%). |
| 211 | RT 2.907 min (Shim-pack XR-ODS, 0.1% trifluoroacetic acid in water/acetonitrile, acetonitrile 30-90% 5.7 min, 1.0 ml/min). MS (ESI+) 637 ($M^+$ + 1, 100%). |
| 212 | RT 2.526 min (Shim-pack XR-ODS, 0.1% trifluoroacetic acid in water/acetonitrile, acetonitrile 30-90% 5.7 min, 1.0 ml/min). MS (ESI+) 574 ($M^+$ + 1, 100%). |
| 213 | RT 2.640 min (Shim-pack XR-ODS, 0.1% trifluoroacetic acid in water/acetonitrile, acetonitrile 30-90% 5.7 min, 1.0 ml/min). MS (ESI+) 600 ($M^+$ + 1, 100%). |
| 214 | RT 3.108 min (Shim-pack XR-ODS, 0.1% trifluoroacetic acid in water/acetonitrile, acetonitrile 30-90% 5.7 min, 1.0 ml/min). MS (ESI+) 617 ($M^+$ + 1, 100%). |
| 215 | RT 2.973 min (Shim-pack XR-ODS, 0.1% trifluoroacetic acid in water/acetonitrile, acetonitrile 30-90% 5.7 min, 1.0 ml/min). MS (ESI+) 617 ($M^+$ + 1, 100%). |
| 216 | RT 2.680 min (Shim-pack XR-ODS, 0.1% trifluoroacetic acid in water/acetonitrile, acetonitrile 30-90% 5.7 min, 1.0 ml/min). MS (ESI+) 602 ($M^+$ + 1, 100%). |
| 217 | RT 1.690 min (Shim-pack XR-ODS, 0.1% trifluoroacetic acid in water/acetonitrile, acetonitrile 30-90% 5.7 min, 1.0 ml/min). MS (ESI+) 516 ($M^+$ + 1, 100%). |
| 218 | RT 2.280 min (Shim-pack XR-ODS, 0.1% trifluoroacetic acid in water/acetonitrile, acetonitrile 30-90% 5.7 min, 1.0 ml/min). MS (ESI+) 618 ($M^+$ + 1, 100%). |
| 219 | RT 1.848 min (Shim-pack XR-ODS, 0.1% trifluoroacetic acid in water/acetonitrile, acetonitrile 30-90% 5.7 min, 1.0 ml/min). MS (ESI+) 560 ($M^+$ + 1, 100%). |
| 220 | RT 2.695 min (Shim-pack XR-ODS, 0.1% trifluoroacetic acid in water/acetonitrile, acetonitrile 30-90% 5.7 min, 1.0 ml/min). MS (ESI+) 588 ($M^+$ + 1, 100%). |
| 221 | RT 2.527 min (Shim-pack XR-ODS, 0.1% trifluoroacetic acid in water/acetonitrile, acetonitrile 30-90% 5.7 min, 1.0 ml/min). MS (ESI+) 544 ($M^+$ + 1, 100%). |
| 222 | ($CD_3OD$) δ7.53, 7.42 (s, 1H), 7.31 (s, 1H), 6.14, 6.02, 5.87 (s, 1H), 4.02-4.22 (m, 2H), 3.72-3.91 (m, 2H), 3.34-3.70 (m, 6H), 3.24 (s, 3H), 2.92-3.02 (m, 1H), 2.72-2.88 (m, 1H), 1.80-2.17 (m, 4H), 1.53-1.64 (m, 2H), 1.51, 1.46 (s, 3H), 1.16-1.33 (m, 6H). MS (ESI+) 565 (M + 1, 100%). |
| 223 | ($CD_3OD$) δ7.53, 7.42 (s, 1H), 7.33 (s, 1H), 6.15, 6.02, 5.88 (s, 1H), 4.02-4.17 (m, 2H), 3.63-3.99 (m, 3H), 3.34-3.62 (m, 5H), 3.15-3.34 (m, 1H), 2.92-3.02 (m, 1H), 2.70-2.86 (m, 1H), 1.75-2.15 (m, 4H), 1.47-1.73 (m, 2H), 1.42, 1.46 (s, 3H), 1.23-1.28 (m, 3H), 1.15-1.23 (m, 3H). MS (ESI+) 551 (M + 1, 100%). |

The compounds of Examples 224 to 237 were synthesized in a similar manner to a corresponding Reference Example and Example 1.

TABLE 35

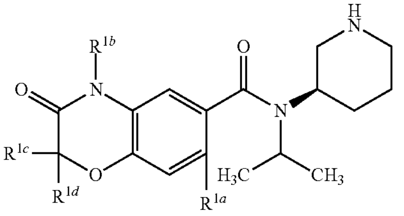

HCl

| Ex. | $R^{1d}$ | $R^{1c}$ | $R^{1b}$ | $R^{1a}$ |
|---|---|---|---|---|
| 224 | 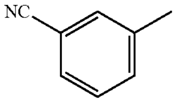 | Me | $CH_3CH_2C(O)NH(CH_2)_2$ | $CF_3$ |
| 225 | 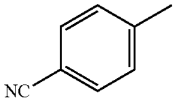 | Me | $CH_3CH_2C(O)NH(CH_2)_2$ | $CF_3$ |
| 226 | 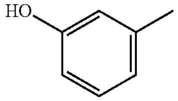 | Me | $CH_3CH_2C(O)NH(CH_2)_2$ | $CF_3$ |
| 227 | 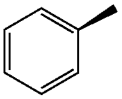 | Me | $CH_3CH_2C(O)NH(CH_2)_2$ | $CF_3$ |
| 228 | 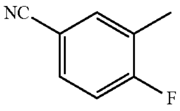 | Me | $CH_3CH_2C(O)NH(CH_2)_2$ | $CF_3$ |
| 229 | 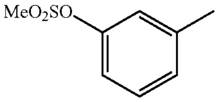 | Me | $CH_3CH_2C(O)NH(CH_2)_2$ | $CF_3$ |

TABLE 35-continued

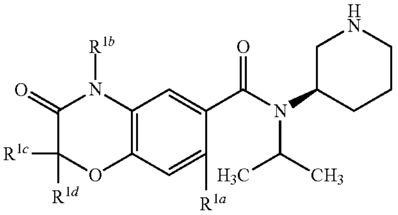

HCl

| Ex. | $R^{1d}$ | $R^{1c}$ | $R^{1b}$ | $R^{1a}$ |
|---|---|---|---|---|
| 230 | 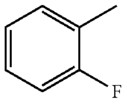 | Me | $CH_3CH_2C(O)NH(CH_2)_2$ | $CF_3$ |
| 231 | 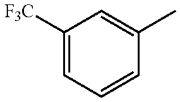 | Me | $CH_3CH_2C(O)NH(CH_2)_2$ | Me |
| 232 | 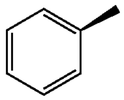 | Me | $CH_3CH_2C(O)NH(CH_2)_2$ | Cl |
| 233 | 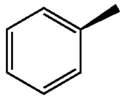 | Me | $CH_3CH_2C(O)NH(CH_2)_2$ | Me |
| 234 | 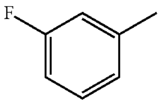 | Me | $CH_3CH_2C(O)NH(CH_2)_2$ | $CF_3$ |
| 235 | 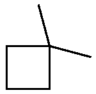 | | $CHF_2C(O)NH(CH_2)_2$ | Me |
| 236 | 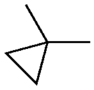 | | $CH_3CH_2C(O)NH(CH_2)_2$ | Me |
| 237 | 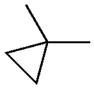 | | $CHF_2C(O)NH(CH_2)_2$ | Me |

TABLE 36

| Ex. | $^1$H NMR (400 MHz, solvent)/MS (ESI+) |
|---|---|
| 224 | (DMSO-d6) δ8.18-7.46 (m, 6H), 4.06-3.88 (m, 3H), 3.80-3.23 (m, 5H), 2.80-2.51 (m, 3H), 2.07-1.99 (m, 2H), 1.80 (s, 3H), 1.46-1.30 (m, 3H), 1.16-0.90 (m, 8H).<br>MS (ESI+) 600 (M + 1, 100%). |
| 225 | (DMSO-d6) δ8.15-7.45 (m, 6H), 4.08-3.58 (m, 3H), 3.56-3.22 (m, 5H), 2.81-2.54 (m, 3H), 2.09-1.90 (m, 2H), 1.84 (s, 3H), 1.46-1.22 (m, 3H), 1.16-0.91 (m, 8H).<br>MS (ESI+) 600 (M + 1, 100%). |
| 226 | ($CD_3OD$) δ8.13-8.04 (m, 1H), 7.55 (brs, 0.5H), 7.51-7.40 (m, 1.5H), 7.16-7.06 (m, 1H), 6.86-6.74 (m, 2H), 6.70-6.62 (m, 1H), 4.28-4.12 (m, 1.5H), 4.12-3.96 (m, 1.5H), 3.86-3.74 (m, 1H), 3.71-3.50 (m, 4H), 3.44-3.32 (m, 2H), 3.31-3.24 (m, 1H), 2.99-2.88 (m, 1H), 2.86-2.68 (m, 1H), 2.24-2.18 (m, 3H), 2.16-2.02 (m, 2H), 1.99-1.86 (m, 3H), 1.33-1.25 (m, 1.5H), 1.24-1.16 (m, 1.5H), 1.16-1.04 (m, 6H).<br>MS (ESI+) 591 (M + 1, 100%). |
| 227 | (CDCl3) δ9.86-9.52 (m, 2H), 7.38-7.15 (m, 5H), 7.14-7.01 (m, 2H), 4.24-4.05 (m, 2H), 3.93-3.80 (m, 2H), 3.81-3.75 (m, 1H), 3.74-3.67 (m, 1H), 3.63-3.37 (m, 3H), 3.41-3.28 (m, 1H), 2.92-2.81 (m, 1H), 2.84-2.69 (m, 1H), 2.26-2.19 (m, 2H), 2.04-1.83 (m, 6H), 1.32-1.23 (m, 3H), 1.24-1.23 (m, 3H), 1.16-1.00 (m, 3H).<br>MS (ESI+) 575 (M + 1, 100%). |

TABLE 36-continued

| Ex. | $^1$H NMR (400 MHz, solvent)/MS (ESI+) |
|---|---|
| 228 | ($CD_3OD$) δ8.00-7.96 (m, 0.5H), 7.88-7.76 (m, 1.5H), 7.64-7.62 (m, 0.5H), 7.54-7.48 (m, 0.5H), 7.43-7.37 (m, 2H), 4.19-4.02 (m, 3H), 3.86-.75 (m, 1H), 3.62-3.44 (m, 2H), 3.42-3.24 (m, 4H), 3.03-2.91 (m, 1H), 2.89-2.68 (m, 1H), 2.21-2.04 (m, 4H), 2.00-1.76 (m, 5H), 1.28-1.21 (m, 1.5H), 1.19-1.11 (m, 1.5H), 1.11-1.02 (m, 6H). MS (ESI+) 618 (M + 1, 100%). |
| 229 | ($CD_3OD$) δ7.58-7.54 (m, 1.5H), 7.48-7.44 (m, 3.5H), 7.24-7.20 (m, 1H), 4.28-4.11 (m, 1.5H), 4.08-3.94 (m, 1.5H), 3.82-3.63 (m, 1H), 3.62-3.50 (m, 2H), 3.46-3.21 (m, 4H), 3.21-3.14 (m, 3H), 3.02-2.89 (m, 1H), 2.84-2.67 (m, 1H), 2.23-2.04 (m, 4H), 1.94-1.71 (m, 5H), 1.27-1.25 (m, 1.5H), 1.21-1.24 (m, 1.5H), 1.14-1.04 (m, 6H). MS (ESI+) 669 (M + 1, 100%). |
| 230 | ($CD_3OD$) δ7.51-7.29 (m, 4H), 7.22-7.03 (m, 2H), 4.26-4.04 (m, 3H), 3.84-3.73 (m, 1H), 3.72-3.55 (m, 3H), 3.46-3.35 (m, 2H), 3.31-3.24 (m, 1H), 2.99-2.92 (m, 1H), 2.88-2.73 (m, 1H), 2.26-2.04 (m, 4H), 2.01-1.94 (m, 3H), 1.95-1.82 (m, 2H), 1.31-1.25 (m, 1.5H), 1.22-1.16 (m, 1.5H), 1.16-1.04 (m, 6H). MS (ESI+) 593 (M + 1, 100%). |
| 231 | (CDCl3) δ9.84-9.64 (brs, 2H), 7.68-7.36 (m, 4H), 7.03-6.84 (m, 2H), 4.20-4.04 (m, 2H), 3.94-3.74 (m, 3H), 3.58-3.31 (m, 4H), 2.94-2.71 (m, 2H), 2.21-2.02 (m, 5H), 2.01-1.94 (m, 2H), 2.93-1.82 (m, 4H), 1.34-1.00 (m, 9H). MS (ESI+) 589 (M + 1, 100%). |
| 232 | (CDCl3) δ9.84-9.54 (m, 2H), 7.36-7.17 (m, 5H), 7.16-7.04 (m, 2H), 4.20-4.04 (m, 2H), 3.91-3.81 (m, 2H), 3.80-3.74 (m, 1H), 3.71-3.64 (m, 1H), 3.60-3.36 (m, 3H), 3.39-3.28 (m, 1H), 2.91-2.81 (m, 1H), 2.81-2.68 (m, 1H), 2.24-2.21 (m, 2H), 2.02-1.84 (m, 6H), 1.34-1.26 (m, 3H), 1.26-1.22 (m, 3H), 1.14-1.01 (m, 3H). MS (ESI+) 521 (M + 1, 100%). |
| 233 | (CDCl3) δ9.77-9.50 (m, 2H), 7.29-7.11 (m, 5H), 6.87-6.79 (m, 2H), 4.16-3.89 (m, 2H), 3.84-3.74 (m, 1H), 3.69-3.53 (m, 2H), 3.52-3.24 (m, 4H), 2.84-2.68 (m, 2H), 2.48-2.31 (m, 2H), 2.12 (s, 3H), 2.08-1.94 (m, 2H), 1.93-1.73 (m, 5H), 1.31-1.18 (m, 3H), 1.21-0.96 (m, 6H). MS (ESI+) 541 (M+, 100%). |
| 234 | (DMSO-d6) δ7.66-7.11 (m, 6H), 4.11-3.75 (m, 3H), 3.60-3.22 (m, 5H), 3.10-2.52 (m, 2H), 2.30-2.03 (m, 3H), 1.83 (s, 3H), 1.56-1.38 (m, 3H), 1.19-0.92 (m, 8H). MS (ESI+) 593 (M + 1, 100%). |
| 235 | (DMSO-d6) δ7.08-6.96 (s, 1H), 6.30-6.03 (m, 1H), 4.00-3.61 (m, 4H), 3.15-3.13 (m, 1H), 2.80-2.50 (m, 4H), 2.49-2.40 (m, 1H), 2.39-2.13 (m, 3H), 2.14 (s, 3H), 1.98-1.72 (m, 6H), 1.46-1.43 (m, 1H), 1.12 (m, 6H). MS (ESI+) 493 (M + 1, 100%). |
| 236 | ($CD_3OD$) δ7.30, 7.20 (s, 1H), 6.83 (s, 1H), 4.12 (t, 2H), 3.81-4.08 (m, 2H), 3.55-3.68 (m, 1H), 3.33-3.55 (m, 4H), 2.77-3.03 (m, 2H), 2.12-2.26 (m, 6H), 1.85-2.12 (m, 4H), 1.52-1.63 (m, 1H), 1.05-1.38 (m, 12H). MS (ESI+) 457 (M + 1, 100%). |
| 237 | ($CD_3OD$) δ7.31, 7.23 (s, 1H), 6.83 (s, 1H), 6.14, 6.00, 5.87 (s, 1H), 4.08-4.14 (m, 2H), 3.98-4.02 (m, 1H), 3.82-3.86 (m, 1H), 3.3.34-3.67 (m, 3H), 2.92-3.03 (m, 1H), 2.77-2.92 (m, 1H), 2.23 (d, 4H), 1.82-2.13 (m, 6H), 1.53-1.64 (m, 1H), 1.19-1.39 (m, 9H). MS (ESI+) 479 (M + 1, 100%). |

The compounds of Examples 238 to 244 were synthesized in a similar manner to a corresponding Reference Example and Example 1.

TABLE 37

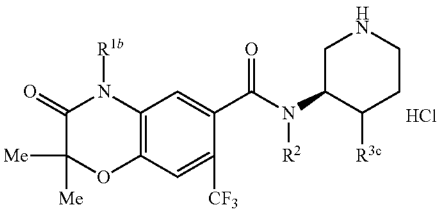

| Ex. | $R^{1b}$ | $R^2$ | $R^{1a}$ | $R^{3c}$ |
|---|---|---|---|---|
| 238 | $CH_3CH_2C(O)NH(CH_2)_2$ | i-Pr | $CF_3$ | 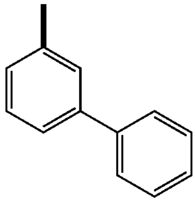 |

TABLE 37-continued

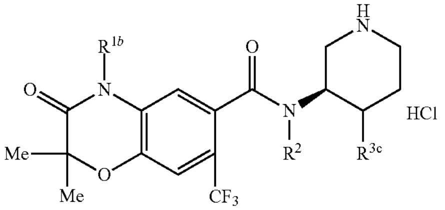

| Ex. | $R^{1b}$ | $R^2$ | $R^{1a}$ | $R^{3c}$ |
|---|---|---|---|---|
| 239 | $MeO(CH_2)_4$ | H | $CF_3$ | 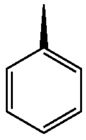 |
| 240 | $MeO(CH_2)_4$ | Et | $CF_3$ | 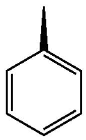 |

TABLE 37-continued

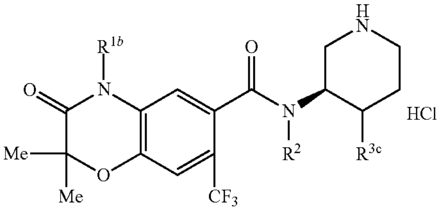

| Ex. | $R^{1b}$ | $R^2$ | $R^{1a}$ | $R^{3c}$ |
|---|---|---|---|---|
| 241 | $MeO(CH_2)_4$ | H | $CF_3$ | 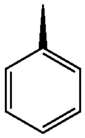 |
| 242 | $MeO(CH_2)_4$ | Et | $CF_3$ | 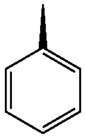 |

TABLE 37-continued

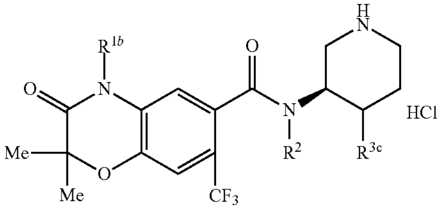

| Ex. | $R^{1b}$ | $R^2$ | $R^{1a}$ | $R^{3c}$ |
|---|---|---|---|---|
| 243 | $CH_3CH_2C(O)NH(CH_2)_2$ | Et | $CF_3$ | 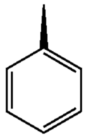 |
| 244 | $CH_3CH_2C(O)NH(CH_2)_2$ | Et | F | 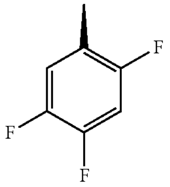 |

TABLE 38

| Ex. | $^1H$ NMR (400 MHz, solvent)/MS (ESI+) |
|---|---|
| 238 | (CDCl3) δ 7.68-7.33 (m, 11H), 4.46 (br, 1H), 4.18-3.93 (m, 3H), 3.78-3.51 (m, 4H), 3.24-2.95 (br, 2H), 2.68 (br, 1H), 2.23 (br, 1H), 2.07-2.01 (m, 2H), 1.55-1.40 (m, 7H), 1.23 (br, 4H), 1.02 (m, 3H), 0.46 (m, 3H). MS (ESI+) 665 (M + 1, 80%). |
| 239 | (DMSO-d6) δ9.07 (brs, 2H), 8.80 (d, J = 9.6 Hz, 1H), 7.30-7.19 (m, 6H), 6.99 (s, 1H), 4.75-4.73 (m, 1H), 4.06-3.93 (m, 2H), 3.45-3.25 (m, 6H), 3.21 (s, 3H), 3.09 (m, 1H), 2.58-2.49 (m, 1H), 1.92-1.89 (m, 1H), 1.67-1.53 (m, 4H), 1.42 (s, 3H), 1.39 (s, 3H). MS (ESI+) 434 (M + 1, 100%). |
| 240 | (DMSO-d6) δ9.33-9.31 (m, 2H), 8.30-6.52 (m, 7H), 4.32-3.70 (m, 3H), 3.67-3.30 (m, 8H), 3.25-3.20 (m, 2H), 3.15 (s, 3H), 2.88-2.66 (m, 2H), 2.22-1.84 (m, 2H), 1.46-0.55 (m, 12H). MS (ESI+) 462 (M + 1, 100%). |
| 241 | (DMSO-d6) δ9.07 (brs, 2H), 8.68-8.66 (m, 1H), 7.37-7.24 (m, 6H), 6.52 (s, 1H), 4.48-4.45 (m, 1H), 3.76-3.74 (m, 2H), 3.39-3.28 (m, 1H), 3.23 (s, 3H), 3.05-2.91 (m, 2H), 2.84-2.78 (m, 1H), 1.99-1.94 (m, 2H), 1.46-1.39 (m, 10H). MS (ESI+) 434 (M + 1, 100%). |
| 242 | (DMSO-d6) δ9.22 (brs, 2H), 7.45-6.14 (m, 7H), 4.03-3.86 (m, 2H), 3.73 (m, 2H), 3.56-3.54 (m, 1H), 3.43-3.17 (m, 3H), 3.12-3.06 (m, 2H), 2.85 (brs, 1H), 2.29-1.97 (m, 2H), 1.54-1.23 (m, 11H), 0.87-0.58 (m, 3H). MS (ESI+) 462 (M + 1, 100%). |
| 243 | (DMSO-d6) δ9.10 (brs, 2H), 7.76-6.15 (m, 8H), 4.01-3.68 (m, 5H), 3.38-3.07 (m, 8H), 2.08-1.90 (m, 3H), 1.57-0.73 (m, 12H). MS (ESI+) 575 (M + 1, 100%). |
| 244 | (DMSO-d6) δ9.60-9.08 (m, 2H), 8.32-6.92 (m, 5H), 4.43-4.07 (m, 1H), 3.95-3.86 (m, 3H), 3.66-3.05 (m, 9H), 2.12-1.83 (m, 4H), 1.53-0.75 (m, 9H). MS (ESI+) 579 (M + 1, 100%). |

The compounds of Examples 245 to 249 were synthesized in a similar manner to Reference Example and Example 1.

TABLE 39

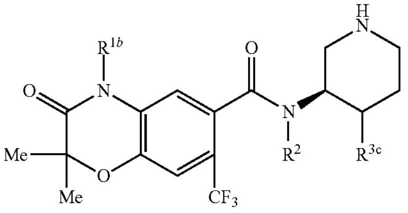

HCl

| Ex. | $R^{1b}$ | $R^2$ | $R^{3C}$ |
|---|---|---|---|
| 245 | $MeO(CH_2)_4$ | H | 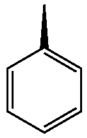 |
| 246 | $MeO(CH_2)_4$ | H | 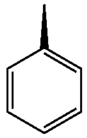 |

TABLE 39-continued

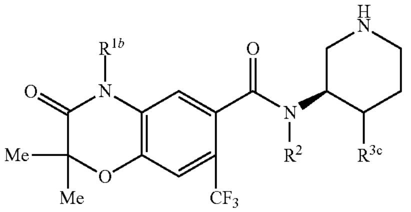

HCl

| Ex. | $R^{1b}$ | $R^2$ | $R^{3C}$ |
|---|---|---|---|
| 247 | $MeO(CH_2)_4$ | Et | 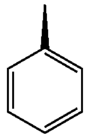 |
| 248 | $MeO(CH_2)_4$ | Et | 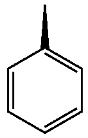 |
| 249 | $MeO(CH_2)_4$ | i-Pr | H |

TABLE 40

| Ex. | $^1$H NMR (400 MHz, solvent)/MS (ESI+) |
|---|---|
| 245 | (DMSO-d6) δ9.07 (brs, 2H), 8.68-8.66 (m, 1H), 7.37-7.24 (m, 6H), 6.52 (s, 1H), 4.48-4.45 (m, 1H), 3.76-3.74 (m, 2H), 3.39-3.28 (m, 1H), 3.23 (s, 3H), 3.05-2.91 (m, 2H), 2.84-2.78 (m, 1H), 1.99-1.94 (m, 2H), 1.46-1.39 (m, 10H). MS (ESI+) 434 (M + 1, 100%). |
| 246 | (DMSO-d6) δ9.07 (brs, 2H), 8.80 (d, J = 9.6 Hz, 1H), 7.30-7.19 (m, 6H), 6.99 (s, 1H), 4.75-4.73 (m, 1H), 4.06-3.93 (m, 2H), 3.45-3.25 (m, 6H), 3.21 (s, 3H), 3.09 (m, 1H), 2.58-2.49 (m, 1H), 1.92-1.89 (m, 1H), 1.67-1.53 (m, 4H), 1.42 (s, 3H), 1.39 (s, 3H). MS (ESI+) 434 (M + 1, 100%). |
| 247 | (DMSO-d6) δ9.22 (brs, 2H), 7.45-6.14 (m, 7H), 4.03-3.86 (m, 2H), 3.73 (m, 2H), 3.56-3.54 (m, 1H), 3.43-3.17 (m, 3H), 3.12-3.06 (m, 2H), 2.85 (brs, 1H), 2.29-1.97 (m, 2H), 1.54-1.23 (m, 11H), 0.87-0.58 (m, 3H). MS (ESI+) 462 (M + 1, 100%). |
| 248 | (DMSO-d6) δ9.33-9.31 (m, 2H), 8.30-6.52 (m, 7H), 4.32-3.70 (m, 3H), 3.67-3.30 (m, 8H), 3.25-3.20 (m, 2H), 3.15 (s, 3H), 2.88-2.66 (m, 2H), 2.22-1.84 (m, 2H), 1.46-0.55 (m, 12H). MS (ESI+) 462 (M + 1, 100%). |
| 249 | (CDCl3) δ9.92-9.53 (br, 2H), 7.13-6.55 (m, 2H), 4.18-3.65 (m, 5H), 3.64-3.50 (m, 2H), 3.45-3.12 (m, 10H), 2.95-2.62 (m, 2H), 2.15-1.45 (m, 10H), 1.35-1.03 (m, 6H). MS (ESI+) 500 (M + 1, 100%). |

The compounds of Examples 250 to 253 were synthesized in a similar manner to a corresponding Reference Example and Example 1.

TABLE 41

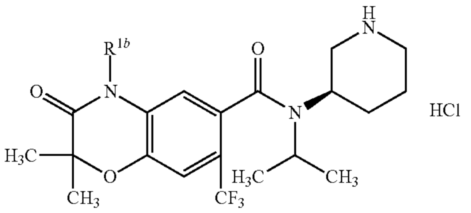

| Ex. | $R^{1b}$ |
|---|---|
| 250 | $CH_3CH_2CH(CF_3)NH(CH_2)_2$ |
| 251 | $MeOCH_2CH(OH)(CH_2)_2$ |
| 252 | $MeOCH_2C(O)(CH_2)_2$ |
| 253 | $MeOCH_2CH(OH)CH_2$ |

TABLE 42

| Ex. | $^1$H NMR (400 MHz, solvent)/MS (ESI+) |
|---|---|
| 250 | ($CDCl_3$) δ 7.91-7.35 (m, 2H), 4.46 (br, 2H), 4.06 (m, 2H), 3.75-3.57 (m, 3H), 3.38-3.31 (m, 2H), 2.98-2.70 (m, 2H), 2.11-1.85 (m, 6H), 1.55-1.51 (m, 6H) 1.33-1.13 (m, 5H). MS (ESI+) 567 (M + 1, 12%). |
| 251 | RT 2.293 min (Shim-pack XR-ODS, 0.1% trifluoroacetic acid in water/acetonitrile, acetonitrile 30-90% 5.7 min, 1.0 ml/min). MS (ESI+) 516 ($M^+$ + 1, 100%). |
| 252 | RT 2.333 min (Shim-pack XR-ODS, 0.1% trifluoroacetic acid in water/acetonitrile, acetonitrile 30-90% 5.7 min, 1.0 ml/min). MS (ESI+) 514 ($M^+$ + 1, 100%). |
| 253 | RT 2.102 min (Shim-pack XR-ODS, 0.1% trifluoroacetic acid in wate/acetonitrile, acetonitrile 30-90% 5.7 min, 1.0 ml/min). MS (ESI+) 502 ($M^+$ + 1, 100%). |

Example 254

5-Chloro-3,3-dimethyl-N-isopropyl-1-(4-methoxybutyl)-2-oxo-N-[(3R)-piperidin-3-yl] indoline-6-carboxamide hydrochloride

[Chemical formula 850]

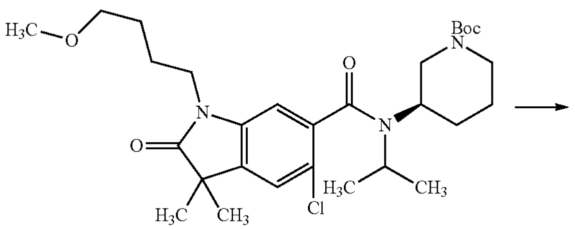

-continued

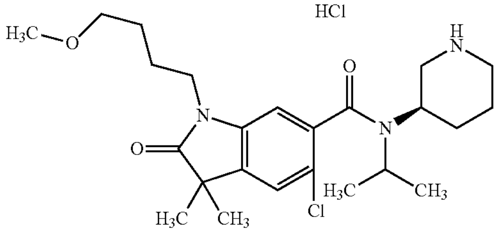

To a solution of tert-butyl (3R)-3-[{[5-chloro-1-(4-methoxybutyl)-3,3-dimethyl-2-oxo-2,3-dihydro-1H-indol-6-yl] carbonyl}(isopropyl)amino]piperidine-1-carboxylate (100 mg) in 1,4-dioxane (3 ml) was added a 4N hydrochloric acid/dioxane solution (2 ml), and the mixture was stirred at 25° C. for 2 hours, and concentrated under reduced pressure to give the title compound (70 mg).

$^1$H NMR (400 MHz, $OD_3OD$) δ 7.57-7.55 (m, 1H), 7.15-7.05 (m, 1H), 3.82-3.46 (m, 3H), 3.44-3.29 (m, 2H), 3.27-3.25 (m, 3H), 3.19-3.07 (m, 4H), 2.80-2.59 (m, 1H), 1.87-1.70 (m, 2H), 1.57-1.45 (m, 4H), 1.28-1.17 (m, 10H), 1.10-1.00 (m, 4H).

MS (ESI+) 450 (M+1, 100%).

Example 255

5-Chloro-N-isopropyl-3,3-dimethyl-2-oxo-N-[(3R)-piperidin-3-yl]-1-[2-(propionylamino)ethyl]-indoline-6-carboxamide hydrochloride

[Chemical formula 851]

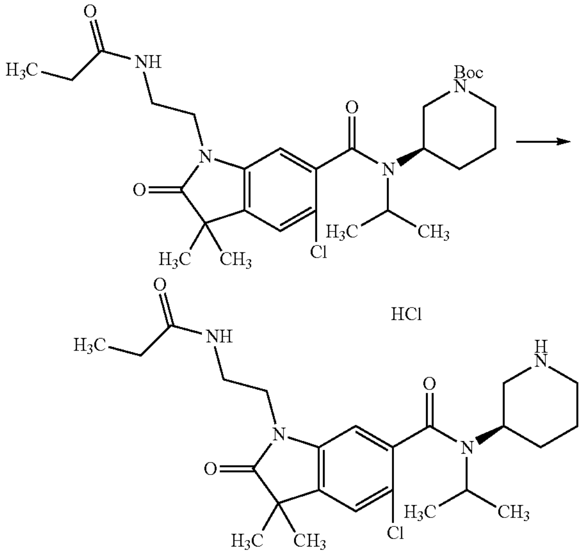

Using tert-butyl (3R)-3-[({5-chloro-3,3-dimethyl-2-oxo-1-[2-(propionylamino)ethyl]-2,3-dihydro-1H-indol-6-yl}carbonyl)(isopropyl)amino]piperidine-1-carboxylate, the title compound was obtained in a similar manner to Example 1.

$^1$H NMR (400 MHz, $OD_3OD$) δ 7.53-7.49 (m, 1H), 7.14-7.01 (m, 1H), 3.83-3.39 (m, 6H), 3.27-3.11 (m, 3H), 2.91-2.50 (m, 3H), 2.07-1.75 (m, 7H), 1.30-1.01 (m, 8H), 0.91-0.76 (m, 4H).

MS (ESI+) 463 (M+1, 100%).

Example 256

5-Chloro-1-{2-[(difluoroacetyl)amino]ethyl}-N-isopropyl-3,3-dimethyl-2-oxo-N-[(3R)-piperidin-3-yl]indoline-6-carboxamide hydrochloride

[Chemical formula 852]

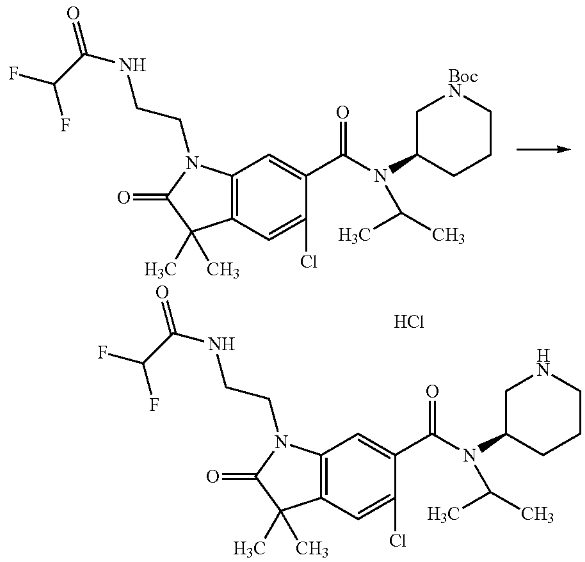

Using tert-butyl (3R)-3-[[(5-chloro-1-{2-[(difluoroacetyl) amino]ethyl}-3,3-dimethyl-2-oxo-2,3-dihydro-1H-indol-6-yl)carbonyl](isopropyl)amino]piperidine-1-carboxylate, the title compound was obtained in a similar manner to Example 1.

$^{1}$H NMR (400 MHz, $OD_3OD$) δ 7.61-7.49 (m, 1H), 7.14-7.09 (m, 1H), 3.80-3.55 (m, 5H), 3.19-3.04 (m, 2H), 2.88-2.61 (m, 2H), 1.89-1.75 (m, 3H), 1.26-1.01 (m, 15H).

MS (ESI+) 487 (M+1, 100%).

Example 257

5-Chloro-3,3diethyl-N-isopropyl-2-oxo-N-[(3R)-piperidin-3-yl]-1-[2-(propionylamino)ethyl]indoline-6-carboxamide hydrochloride

[Chemical formula 853]

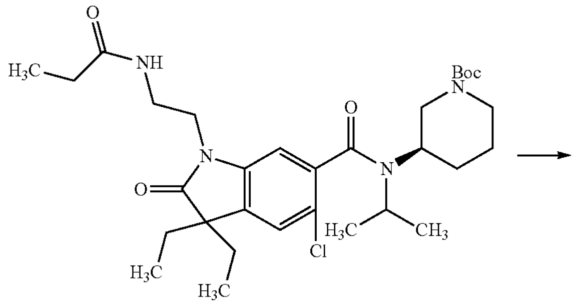

-continued

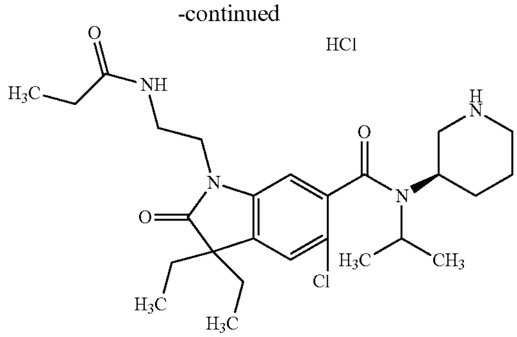

Using tert-butyl (3R)-3-[({5-chloro-3,3-diethyl-2-oxo-1-[2-(propionylamino)ethyl]-2,3-dihydro-1H-indol-6-yl}carbonyl)(isopropyl)amino]piperidine-1-carboxylate, the title compound was obtained in a similar manner to Example 1.

$^{1}$H NMR (400 MHz, $OD_3OD$) δ 7.48-7.43 (m, 1H), 7.23-7.05 (m, 1H), 3.86-3.74 (m, 4H), 3.65-3.55 (m, 2H), 3.30-3.13 (m, 3H), 2.90-2.51 (m, 2H), 2.09-1.78 (m, 6H), 1.23-1.02 (m, 9H), 0.87-0.80 (m, 3H), 0.53-0.48 (m, 6H).

MS (ESI+) 457 (M+1, 100%).

Example 258

N-Isopropyl3,6-dimethyl-2-oxo-N-[(3R)-piperidin-3-yl]-1-2-(propionylamino)ethyl]-1,2-dihydroquinoline-7-carboxamide hydrochloride

[Chemical formula 854]

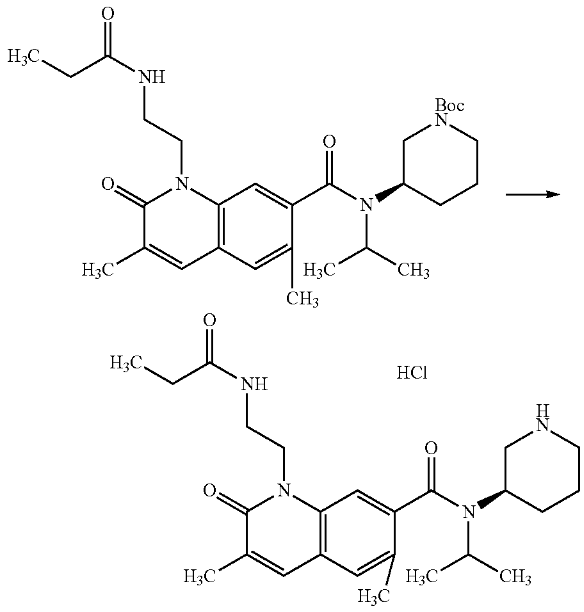

Using tert-butyl (3R)-3-[({3,6-dimethyl-2-oxo-1-[2-(propionylamino)ethyl]-1,2-dihydro-quinolin-7-yl}carbonyl)(isopropyl)amino]piperidine-1-carboxylate, the title compound was obtained in a similar manner to Example 1.

RT 2.230 min (Shim-pack XR-ODS, 0.1% trifluoroacetic acid in water/acetonitrile, acetonitrile 30-90% 5.7 min, 1.0 ml/min).

MS (ESI+) 441 ($M^{+}$+1, 100%).

Example 259

4-{2-[(Difluoroacetyl)amino]ethyl}-N-isopropyl-2,2,7-trimethyl-3-oxo-N-[(3R)-piperidin-3-yl]-3,4-dihydro-2H-1,4-benzothiazine-6-carboxamide hydrochloride

[Chemical formula 855]

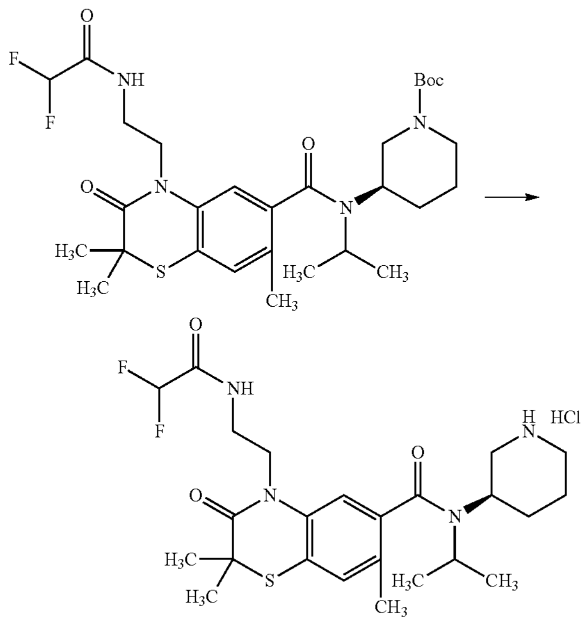

To a solution of tert-butyl (3R)-3-[[(4-{2-[(difluoroacetyl)amino]ethyl}-2,2,7-trimethyl-3-oxo-3,4-dihydro-2H-1,4-benzothiazin-6-yl)carbonyl](isopropyl)amino]piperidine-1-carboxylate (1 g) in chloroform (8 ml) was added a 4N hydrochloric acid/dioxane solution (8 ml), and the mixture was stirred at room temperature for one hour. The mixture was concentrated under reduced pressure to give the title compound (0.9 g).

$^1$H NMR (400 MHz, $OD_3OD$) δ 7.47 (s, 0.5H), 7.37 (s, 0.5H), 7.28 (s, 1H), 6.01 (t, J=54 Hz, 0.5H), 5.99 (t, J=54 Hz, 0.5H), 4.17-3.94 (m, 3H), 3.88-3.73 (m, 1H), 3.62-3.50 (m, 2H), 3.45-3.30 (m, 2H), 3.02-2.75 (m, 2H), 2.26 (s, 0.6H), 2.25 (s, 0.4H), 2.14-2.05 (m, 1H), 2.00-1.78 (m, 2H), 1.63-1.51 (m, 1H), 1.44 (s, 3H), 1.34 (s, 3H), 1.30-1.15 (m, 6H).

Example 260

N-Isopropyl-7-methyl-3-oxo-N-[(3R)-piperidin-3-yl]-4-[2-(propionylamino)ethyl]-3,4-dihydrospiro-[1,4-benzothiazine-2,1'-cyclobutane]-6-carboxamide hydrochloride

[Chemical formula 856]

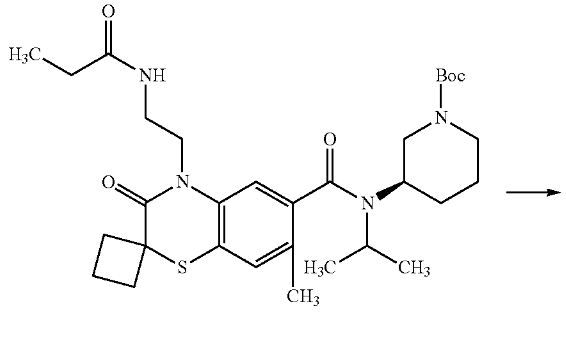

-continued

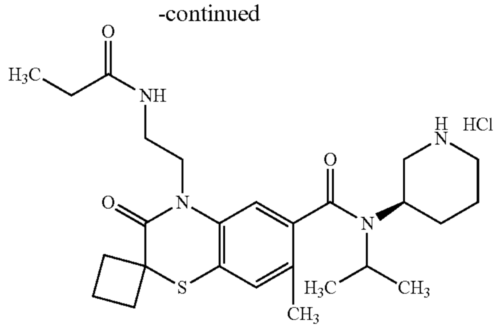

To a solution of tert-butyl (3R)-3-[isopropyl({7-methyl-3-oxo-4-[2-(propionylamino)ethyl]-3,4-dihydrospiro[1,4-benzothiazine-2,1'-cyclobutan]-6-yl}carbonyl)amino]piperidine-1-carboxylate (2.5 g) in chloroform (7 ml)-methanol (15 ml) was added a 4N hydrochloric acid/dioxane solution (21 ml), and the mixture was stirred at room temperature for one hour. The mixture was concentrated under reduced pressure to give the title compound (2.2 g).

$^1$H NMR (400 MHz, $OD_3OD$) δ 7.40 (s, 0.5H), 7.32 (s, 0.5H), 7.31 (s, 0.5H), 7.29 (s, 0.5H), 4.17-3.91 (m, 3H), 3.86-3.74 (m, 1H), 3.65-3.51 (m, 2H), 3.44-3.10 (m, 2H), 3.03-2.92 (m, 1H), 2.90-2.76 (m, 2H), 2.55-2.44 (m, 1H), 2.25 (s, 1.5H), 2.24 (s, 1.5H), 2.22-2.04 (m, 4H), 2.03-1.80 (m, 5H), 1.64-1.50 (m, 1H), 1.27-1.16 (m, 6H), 1.12-1.03 (m, 3H).

The compounds of Examples 261 to 264 were synthesized in a similar manner to a corresponding Reference Example and Example 1.

TABLE 43

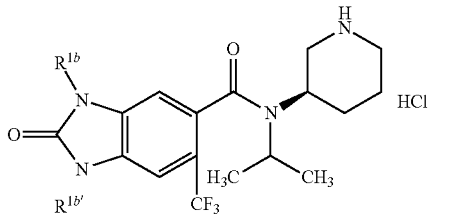

| Ex. | $R^{1b}$ | $R^{1b'}$ |
|---|---|---|
| 261 | $MeO(CH_2)_4$ | Et |
| 262 | $CH_3CH_2C(O)NH(CH_2)_2$ | Et |
| 263 | $CH_3C(O)NH(CH_2)_2$ | Et |
| 264 | $MeO(CH_2)_4$ | 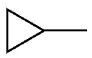 |

TABLE 44

| Ex. | $^1$H NMR (400 MHz, solvent)/MS (ESI+) |
|---|---|
| 261 | RT 1.948 min (Shim-pack XR-ODS, 0.1% trifluoroacetic acid in water/acetonitrile, acetonitrile 30-90% 5.7 min, 1.0 ml/min). MS (ESI+) 485 ($M^+$ + 1, 100%). |
| 262 | RT 1.635 min (Shim-pack XR-ODS, 0.1% trifluoroacetic acid in water/acetonitrile, acetonitrile 30-90% 5.7 min, 1.0 ml/min). MS (ESI+) 498 ($M^+$ + 1, 100%). |
| 263 | RT 1.496 min (Shim-pack XR-ODS, 0.1% trifluoroacetic acid in water/acetonitrile, acetonitrile 30-90% 5.7 min, 1.0 ml/min). MS (ESI+) 484 ($M^+$ + 1, 100%). |

TABLE 44-continued

| Ex. | $^1H$ NMR (400 MHz, solvent)/MS (ESI+) |
|---|---|
| 264 | RT 2.093 min (Shim-pack XR-ODS, 0.1% trifluoroacetic acid in water/acetonitrile, acetonitrile 30-90% 5.7 min, 1.0 ml/min). MS (ESI+) 497 ($M^+$ + 1, 100%). |

The compounds of Examples 265 and 266 were synthesized in a similar manner to a corresponding Reference Example and Example 1.

TABLE 45

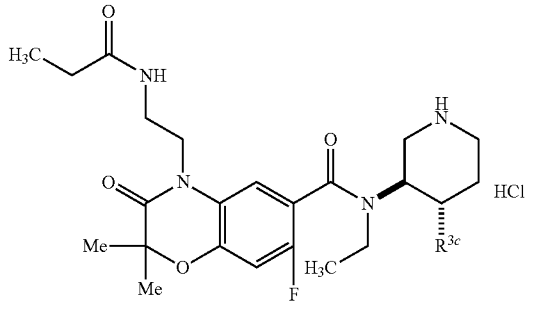

| Ex. | $R^{3c}$ |
|---|---|
| 265 | 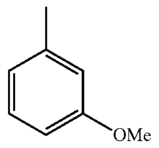 |
| 266 | 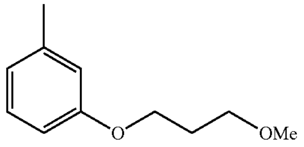 |

TABLE 46

| Ex. | $^1H$ NMR (400 MHz, solvent)/MS (ESI+) |
|---|---|
| 265 | 1H NMR (400 MHz, DMSO-d6) δ 9.11 n (brs, 2H), 8.25-5.99 (m, 7H), 4.30-3.61 (m, 8H), 3.03-2.89 (m, 3H), 2.25-1.84 (m, 6H), 1.53-0.79 (m, 14H). MS (ESI+) 555 (M + 1, 100%). |
| 266 | 1H NMR (400 MHz, DMSO-d6) δ 9.40 (m, 2H), 8.32-5.97 (m, 7H), 3.99-3.73 (m, 6H), 3.49-3.43 (m, 3H), 3.17-3.04 (m, 5H), 2.07-1.80 (m, 7H), 1.53-1.37 (m, 7H), 1.23-0.79 (m, 8H). MS (ESI+) 613 (M + 1, 100%). |

The compounds of Examples 267 to 269 were synthesized in a similar manner to a corresponding Reference Example and Example 1.

TABLE 47

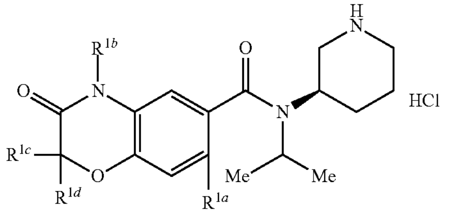

| Ex. | $R^{1d}$ | $R^{1c}$ | $R^{1b}$ | $R^{1a}$ |
|---|---|---|---|---|
| 267 | Me | Me | $CH_3CH_2C(O)NH(CH_2)_2$ | $CHF_2$ |
| 268 | Me | Me | $CHF_2C(O)NH(CH_2)_2$ | $CHF_2$ |
| 269 | 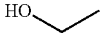 | Me | $CH_3CH_2C(O)NH(CH_2)_2$ | $CF_3$ |

TABLE 48

| Ex. | $^1H$ NMR (400 MHz, solvent)/MS (ESI+) |
|---|---|
| 267 | 1H NMR (400 MHz, DMSO-d6) δ 9.10-9.40 (br, 2H), 8.15 (brs, 1H), 6.76-7.56 (m, 3H), 2.60-3.92 (m, 12H), 1.80-2.04 (m, 2H), 1.39-1.52 (m, 8H), 0.94-1.21 (m, 9H). |
| 268 | 1H NMR (400 MHz, DMSO-d6) δ 8.90-9.20 (br, 2H), 6.70-7.31 (m, 3H), 6.17 (t, J = 53 Hz, 1H), 2.60-3.92 (m, 7H), 1.80-2.04 (m, 2H), 1.39-1.52 (m, 8H), 0.94-1.21 (m, 9H). |
| 269 | 1H NMR (400 MHz, $CD_3OD$) δ 7.30-7.34 (m, 2H), 3.91-4.16 (m, 4H), 3.65-3.75 (m, 3H), 3.30-3.35 (m, 4H), 2.93-2.96 (m, 1H), 2.70-2.82 (m, 2H), 2.13-2.17 (m, 2H), 1.73-1.82 (m, 2H), 1.57-1.58 (m, 3H), 1.39-1.40 (m, 2H), 1.28-1.31 (m, 2H), 1.20-1.24 (m, 2H), 1.12-1.15 (m, 2H), 1.04-1.08 (m, 4H). MS (ESI+) 529 (M + 100%). |

In Vitro Renin Inhibitory Activity Assay

Recombinant human renin (50 ng) was reacted in 0.1M HEPES buffer (pH 7.4) containing 0.1M NaCl, 1 mM EDTA and 0.1 mg/mL BSA together with a substrate and a test compound at 37° C. for one hour. As the substrate, Arg-Glu (EDANS)-Ile-His-Pro-Phe-His-Leu-Val-Ile-His-Thr-Lys (DABCYL)-Arg or DABCYL-γ-Abu-Ile-His-Pro-Phe-His-Leu-Val-Ile-His-Thr-EDANS was added in such an amount so that the final concentration thereof became 4 μM. The elevated fluorescence intensity at the exciting wavelength 340 nm and the fluorescence wavelength 500 nm was measured by a fluorescence plate reader. The concentration of a test compound to be needed to inhibit an enzyme activity in the presence of a test compound in plural concentrations by 50% was calculated as an $IC_{50}$ value.

TABLE 49

| Test Compound | Human renin inhibitory activity $IC_{50}$ (nM) |
|---|---|
| Example 1 | 0.7 |
| Example 2 | 2.4 |
| Example 3 | 26 |
| Example 4 | 6.1 |
| Example 5 | 10 |
| Example 6 | 4.3 |
| Example 7 | 0.1 |
| Example 8 | 5.3 |
| Example 9 | 24 |
| Example 10 | 0.1 |
| Example 11 | 3.0 |
| Example 12 | 0.6 |

TABLE 49-continued

| Test Compound | Human renin inhibitory activity $IC_{50}$ (nM) |
|---|---|
| Example 13 | 12 |
| Example 14 | 3.3 |
| Example 15 | 42 |
| Example 16 | 12 |
| Example 17 | 1.7 |
| Example 18 | 11 |
| Example 19 | 4.0 |
| Example 20 | 1.9 |
| Example 21 | 3.4 |
| Example 22 | 4.0 |
| Example 23 | 0.4 |
| Example 24 | 3.2 |
| Example 25 | 17 |
| Example 26 | 6.0 |
| Example 28 | 31 |
| Example 30 | 0.8 |
| Example 33 | 0.6 |
| Example 34 | 0.4 |
| Example 36 | 0.2 |
| Example 38 | 3.2 |
| Example 41 | 2.4 |
| Example 42 | 3.8 |
| Example 44 | 3.8 |
| Example 46 | 11.5 |
| Example 48 | 8.4 |
| Example 52 | 17.2 |
| Example 54 | 0.2 |
| Example 55 | 0.4 |
| Example 57 | 8.0 |
| Example 58 | 4.2 |
| Example 59 | 4.5 |
| Example 66 | 0.7 |
| Example 68 | 0.6 |
| Example 71 | 2.2 |
| Example 73 | 0.5 |
| Example 79 | 19.2 |
| Example 80 | 4.6 |
| Example 81 | 9.3 |
| Example 89 | 0.7 |
| Example 90 | 1.3 |
| Example 107 | 27 |
| Example 111 | 1.3 |
| Example 112 | 0.8 |
| Example 114 | 6.0 |
| Example 115 | 5.3 |
| Example 117 | 0.08 |
| Example 118 | 0.2 |
| Example 121 | 4.0 |
| Example 122 | 6.2 |
| Example 123 | 1.0 |
| Example 126 | 49 |
| Example 130 | 27 |
| Example 133 | 0.4 |
| Example 136 | 0.2 |
| Example 137 | 0.9 |
| Example 138 | 0.1 |
| Example 140 | 0.2 |
| Example 141 | 6.7 |
| Example 146 | 0.5 |
| Example 150 | 3.3 |
| Example 151 | 0.9 |
| Example 160 | 0.3 |
| Example 162 | 4.0 |
| Example 170 | 0.4 |
| Example 171 | 3.5 |
| Example 172 | 0.4 |
| Example 173 | 0.2 |
| Example 176 | 0.1 |
| Example 177 | 0.9 |
| Example 181 | 16.2 |
| Example 185 | 2.1 |
| Example 186 | 5.7 |
| Example 187 | 1.3 |
| Example 192 | 3.7 |
| Example 195 | 0.9 |
| Example 200 | 69 |
| Example 201 | 82 |
| Example 202 | 1.3 |
| Example 205 | 17.4 |
| Example 208 | 2.5 |
| Example 209 | 2.0 |
| Example 210 | 1.2 |
| Example 212 | 1.7 |
| Example 216 | 1.1 |
| Example 217 | 1.8 |
| Example 219 | 1.1 |
| Example 224 | 0.6 |
| Example 228 | 1.5 |
| Example 229 | 0.3 |
| Example 238 | 39 |
| Example 242 | 9.0 |
| Example 243 | 2.2 |
| Example 244 | 1.4 |
| Example 251 | 23.8 |
| Example 252 | 1.5 |
| Example 254 | 14 |
| Example 255 | 20 |
| Example 261 | 15 |
| Example 262 | 30 |
| Example 265 | 2.2 |

INDUSTRIAL APPLICABILITY

The compounds of the present invention are useful as a therapeutic agent for treatment of hypertension. These compounds are also useful in the control of acute and chronic congestive heart failure. These compounds can also be expected to be useful in the treatment of primary and secondary pulmonary hypertension, primary and secondary hyperaldosteronism, renovascular hypertension, primary and secondary kidney diseases such as glomerulonephritis, IgA nephropathy, diabetic nephropathy, hypertensive nephropathy (nephrosclerosis), nephrotic syndrome, kidney failure, left ventricular hypertrophy, left ventricular fibrosis, left ventricular diastolic failure, left ventrical failure, auricular fibrillation, unstable angina pectoris, cardiac infarction, cardiomyopathy, stroke, restenosis after vascular reconstruction, diabetic retinopathy, cognition disorder such as Alzheimer's disease, cerebrovascular dementia, and also useful in inhibition of angiopathy such as migraine, Raynaud's disease, and atherosclerosis process as much as possible. In addition, these compounds are useful in the treatment of diseases relating to elevated intraocular pressure such as glaucoma.

SEQUENCE LISTING FREE TEXT

The amino acid sequence disclosed in Seq ID: 1 is an amino acid sequence used in the renin inhibitory activity assay.

The amino acid sequence disclosed in Seq ID: 2 is an amino acid sequence used in the renin inhibitory activity assay.

The invention claimed is:

1. A compound of the formula (I) or a pharmaceutically acceptable salt thereof:

[Chemical formula]

(I)

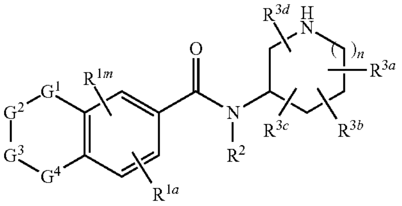

wherein $R^{1a}$ is a halogen atom, a hydroxy group, a formyl group, a carboxyl group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-6}$ cycloalkyl group, an optionally substituted $C_{5-6}$ cycloalkenyl group, an optionally substituted $C_{1-6}$ alkylthio group, an optionally substituted $C_{6-10}$ arylthio group, an optionally substituted $C_{1-6}$ alkylsulfonyl group, an optionally substituted $C_{1-6}$ alkoxy group, an optionally substituted $C_{3-6}$ cycloalkoxy group, an optionally substituted $C_{5-6}$ cycloalkenyloxy group, an optionally substituted amino group, an optionally substituted aminocarbonyl group, an optionally substituted $C_{1-4}$ alkoxycarbonyl group, an optionally substituted $C_{1-4}$ alkylcarbonyl group, an optionally substituted $C_{6-10}$ arylcarbonyl group, an optionally substituted $C_{6-10}$ aryl group, an optionally substituted $C_{6-10}$ aryloxy group, an optionally substituted $C_{7-14}$ aralkyloxy group, or an optionally substituted 5- to 10-membered monocyclic or polycyclic heteroaryl group;

$R^{1m}$ is a hydrogen atom, a halogen atom, a $C_{1-6}$ alkyl group, a $C_{3-6}$ cycloalkyl group, a $C_{1-6}$ alkoxy group, or a $C_{3-6}$ cycloalkoxy group;

$G^1$ is —N($R^{1b}$)—, $G^2$ is —CO—, $G^3$ is —C($R^{1c}$)($R^{1d}$)—, and $G^4$ is —C($R^{1x}$)($R^{1y}$)—, —$SO_2$—, an oxygen atom, a sulfur atom, or does not exist at all;

$R^{1b}$ is an optionally substituted $C_{1-6}$ alkyl group, an optionally substituted $C_{2-6}$ alkenyl group, an optionally substituted $C_{2-6}$ alkynyl group, or an optionally substituted 5- to 10-membered monocyclic or polycyclic heteroaryl-$C_{1-4}$ alkyl group;

$R^{1c}$ and $R^{1d}$ are independently a hydrogen atom, a halogen atom, a hydroxy group, a carboxyl group, an optionally substituted $C_{2-6}$ alkenyl group, an optionally substituted $C_{5-6}$ cycloalkenyl group, an optionally substituted $C_{2-6}$ alkynyl group, an optionally substituted $C_{1-6}$ alkyl group, an optionally substituted $C_{3-6}$ cycloalkyl group, an optionally substituted aminocarbonyl group, an optionally substituted saturated heterocyclic group, an optionally substituted $C_{1-6}$ alkoxy group, an optionally substituted $C_{3-6}$ cycloalkoxy group, an optionally substituted aminocarbonyl group, an optionally substituted $C_{1-4}$ alkoxycarbonyl group, an optionally substituted $C_{1-4}$ alkylcarbonyl group, an optionally substituted $C_{6-10}$ arylcarbonyl group, an optionally substituted 5- to 10-membered monocyclic or polycyclic heteroaryl group, a cyano group, an optionally substituted $C_{6-10}$ aryloxy group, an optionally substituted 5- to 10-membered monocyclic or polycyclic heteroaryloxy, an optionally substituted $C_{7-14}$ aralkyloxy group, or a group of the following formula:

[Chemical formula]

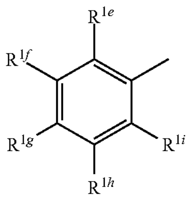

(in which $R^{1e}$, $R^{1f}$, $R^{1g}$, $R^{1h}$ and $R^{1i}$ are independently a hydrogen atom, a halogen atom, a cyano group, a $C_{1-4}$ alkyl group (said group being optionally substituted with a 5- or 6-membered saturated heterocyclyl-oxy, or a $C_{1-4}$ alkoxy (being optionally substituted with $C_{1-4}$ alkoxy or $C_{3-6}$ cycloalkoxy)), a $C_{1-4}$ alkoxy group (said group being optionally substituted with 1 to 3 halogen atom(s), $C_{1-4}$ alkoxy or $C_{1-6}$ alkylaminocarbonyl), a $C_{3-6}$ cycloalkoxy group (being optionally substituted with $C_{1-4}$ alkoxy), 5- or 6-membered saturated heterocyclyl-oxy group, or a $C_{1-6}$ alkylaminocarbonyl group, or $R^{1e}$, $R^{1h}$ and $R^{1i}$ are independently a hydrogen atom, $R^{1f}$ and $R^{1g}$ combine with each other to form a condensed ring), or $R^{1c}$ and $R^{1d}$ combine with each other to form a group of the following formula:

[Chemical formula]

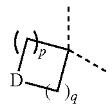

(wherein D is an oxygen atom, a sulfur atom, —$SO_2$—, —$NR^5$—, —$NR^5CO$—, —$NR^5SO_2$—, —$NR^5CONR^5$—, —$CH(R^6)$—, or —$CH(R^6)CH_2$—, $R^5$ is a hydrogen atom, an optionally substituted $C_{1-6}$ alkyl group, an optionally substituted $C_{1-4}$ alkoxycarbonyl group, an optionally substituted $C_{1-4}$ alkylsulfonyl group, or an optionally substituted $C_{6-10}$ arylsulfonyl group, $R^6$ is an hydrogen atom, an optionally substituted $C_{1-6}$ alkoxy group, an optionally substituted $C_{3-6}$ cycloalkoxy group, an optionally substituted $C_{7-14}$ aralkyloxy group, or an optionally substituted aminocarbonyloxy group, p and q are independently 0, 1 or 2);

$R^{1x}$ and $R^{1y}$ are independently a hydrogen atom, a halogen atom, or a $C_{1-4}$ alkyl group, or $R^{1x}$ and $R^{1y}$ combine with each other to form a group of the following formula:

[Chemical formula]

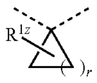

in which $R^{1z}$ is a hydrogen atom, a halogen atom, a $C_{1-4}$ alkyl group or a $C_{1-4}$ alkoxy group, and r is 1, 2, 3 or 4;

$R^2$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, or an optionally substituted 5- to 10-membered monocyclic or polycyclic heteroaryl group;

$R^{3a}$, $R^{3b}$, $R^{3c}$ and $R^{3d}$ are independently a halogen atom, a hydroxy group, a formyl group, a carboxyl group, a cyano group, or a group: -A-B (in which A is a single bond, —$(CH_2)_sO$—, —$(CH_2)_sN(R^4)$—, —$(CH_2)_sSO_2$—, —$(CH_2)_sCO$—, —$(CH_2)_sCOO$—, —$(CH_2)_sN(R^4)CO$—, —$(CH_2)_sN(R^4)SO_2$—, —$(CH_2)_sN(R^4)COO$—, —$(CH_2)_sOCON(R^4)$—, —$(CH_2)_sO$—CO—, —$(CH_2)_sCON(R^4)$—, —$(CH_2)_sN(R^4)CON(R^4)$—, or —$(CH_2)_sSO_2N(R^4)$—, B is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5- to 10-membered monocyclic or polycyclic heteroaryl group, an optionally substituted 5- to 10-membered monocyclic or polycyclic heteroaryl-$C_{1-4}$ alkyl group, or an optionally substituted saturated heterocycle group or when A is —$(CH_2)_sN(R^4)$—, or —$(CH_2)_sOCON(R^4)$—, —$(CH_2)_sCON(R^4)$—, —$(CH_2)_sN(R^4)CON(R^4)$—, or —$(CH_2)_sSO_2N(R^4)$—, then $R^4$ and B may combine with each other to form a ring, or when two of $R^{3a}$, $R^{3b}$, $R^{3c}$ and $R^{3d}$ are hydrogen atoms, the remaining 2 groups may combine with each other to form a fused ring;

$R^4$ is a hydrogen atom, an optionally substituted $C_{1-6}$ alkyl group, an optionally substituted $C_{3-10}$ cycloalkyl group, an optionally substituted $C_{6-10}$ aryl group, an optionally substituted $C_{7-14}$ aralkyl group, or an optionally substituted 5- to 10-membered monocyclic or polycyclic heteroaryl group;

s is 0, 1 or 2 provided that when A is —$(CH_2)_sN(R^4)$—, then s is 0 or 2, and provided that when A is —$(CH_2)_sCON(R^4)$—, then s is 1 or 2;

n is 0, 1 or 2.

2. The compound according to claim 1 or a pharmaceutically acceptable salt thereof, wherein $G^1$ is —$N(R^{1b})$—, $G^2$ is —CO—, $G^3$ is —$C(R^{1c})(R^{1d})$—, and $G^4$ is —$CH_2$—, —$C(CH_3)(CH_3)$—, —$SO_2$—, an oxygen atom, or a sulfur atom.

3. The compound according to claim 2 or a pharmaceutically acceptable salt thereof, wherein $G^4$ is an oxygen atom.

4. The compound according to claim 2 or a pharmaceutically acceptable salt thereof, wherein $G^4$ is a sulfur atom.

5. The compound according to claim 2 or a pharmaceutically acceptable salt thereof, wherein $G^4$ is —$CH_2$—.

6. The compound according to claim 1 or a pharmaceutically acceptable salt thereof, wherein $R^{1a}$ is one group selected from a group consisting of 1: a halogen atom;

2: a cyano group;

3: a $C_{1-6}$ alkyl group (said group being optionally substituted with (a) 1 to 3 fluorine atom(s), (b) $C_{1-4}$ alkoxy, or (c) $C_{3-6}$ cycloalkoxy);

4: a $C_{1-6}$ alkoxy group (said group being optionally substituted with (a) 1 to 3 fluorine atom(s), or (b) $C_{3-6}$ cycloalkoxy);

5: a $C_{3-6}$ cycloalkyl group;

6: a $C_{3-6}$ cycloalkoxy group (said group being optionally substituted with (a) 1 to 3 fluorine atom(s), or (b) $C_{1-4}$ alkoxy); and 7: a 5- or 6-membered heteroaryl group (said group being optionally substituted with a halogen atom or $C_{1-4}$ alkyl).

7. The compound according to claim 6 or a pharmaceutically acceptable salt thereof, wherein $R^{1a}$ is a halogen atom, a cyano group, a $C_{1-6}$ alkyl group being optionally substituted with 1 to 3 fluorine atom(s), or a $C_{1-6}$ alkoxy group.

8. The compound according to claim 7 or a pharmaceutically acceptable salt thereof, wherein $R^{1a}$ is a $C_{1-6}$ alkyl group being optionally substituted with 1 to 3 fluorine atom(s).

9. The compound according to claim 1 or a pharmaceutically acceptable salt thereof, wherein $R^{1m}$ is a hydrogen atom, a halogen atom, or a $C_{1-6}$ alkoxy group.

10. The compound according to claim 9 or a pharmaceutically acceptable salt thereof, wherein $R^{1m}$ is a hydrogen atom.

11. The compound according to claim 1 or a pharmaceutically acceptable salt thereof, wherein $R^{1b}$ is 1: a $C_{1-6}$ alkyl group (said group being optionally substituted with one group selected from a group consisting of (a) hydroxy, (b) $C_{1-4}$ alkoxy (being optionally substituted with 1 to 3 fluorine atom(s) or $C_{1-4}$ alkoxy), (c) cyano, (d) trifluoromethyl, (e) trifluoromethoxy, (f) $C_{3-6}$ cycloalkyl (being optionally substituted with 1 to 2 fluorine atom(s) or $C_{1-4}$ alkoxy), (g) $C_{3-6}$ cycloalkoxy, (h) formylamino, (i) $C_{1-4}$ alkylcarbonylamino (being optionally substituted with 1 to 3 fluorine atom(s)), (j) N—($C_{1-4}$ alkylcarbonyl)-N—($C_{1-6}$ alkyl)-amino, (k) $C_{3-6}$ cycloalkylcarbonylamino, (l) ($C_{3-6}$ cycloalkyl-$C_{1-4}$ alkyl)carbonylamino, (m) $C_{1-4}$ alkylthiocarbonylamino, (n) $C_{1-4}$ alkoxycarbonylamino (being optionally substituted with 1 to 3 fluorine atom(s)), (o)N—($C_{1-4}$ alkoxycarbonyl)-N—($C_{1-6}$ alkyl)-amino, (p) mono- or di-($C_{1-6}$ alkyl)aminocarbonyloxy, (q) $C_{1-6}$ alkylaminocarbonyl (being optionally substituted with 1 to 3 fluorine atom(s)), (r) di-($C_{1-6}$ alkyl)aminocarbonyl, (s) $C_{3-6}$ cycloalkylaminocarbonyl, (t) $C_{1-6}$ alkylaminocarbonylamino, (u) $C_{1-6}$ alkyl-aminothiocarbonylamino, (v) $C_{1-4}$ alkylcarbonyl, (w) $C_{1-4}$ alkylcarbonyloxy, (x) $C_{1-4}$ alkoxycarbonyl, (y) $C_{1-6}$ alkylsulfonyl, (z) $C_{1-4}$ alkylsulfonylamino, (aa) 5- or 6-membered saturated heterocyclic group, (ab) carboxyl, and (ac) $C_{1-6}$ alkylamino);

2: a $C_{2-6}$ alkenyl group (said group being optionally substituted with a halogen atom);

3: a $C_{2-6}$ alkynyl group (said group being optionally substituted with $C_{1-4}$ alkoxy); or 4: a 5- or 6-membered heteroaryl-$C_{1-4}$ alkyl group.

12. The compound according to claim 11 or a pharmaceutically acceptable salt thereof, wherein $R^{1b}$ is a $C_{1-6}$ alkyl group being optionally substituted with $C_{1-6}$ alkoxy, $C_{1-4}$ alkylcarbonylamino (being optionally substituted with 1 to 3 fluorine atom(s)), or $C_{1-4}$ alkoxycarbonylamino; or 5- or 6-membered heteroaryl-$C_{1-4}$ alkyl group.

13. The compound according to claim 12 or a pharmaceutically acceptable salt thereof, wherein $R^{1b}$ is a $C_{1-6}$ alkyl group being optionally substituted with $C_{1-6}$ alkoxy.

14. The compound according to claim 12 or a pharmaceutically acceptable salt thereof, wherein $R^{1b}$ is a $C_{1-6}$ alkyl group being optionally substituted with $C_{1-4}$ alkylcarbonylamino (being optionally substituted with 1 to 3 fluorine atom(s)).

15. The compound according to claim 12 or a pharmaceutically acceptable salt thereof, wherein $R^{1b}$ is a $C_{1-6}$ alkyl group being optionally substituted with $C_{1-4}$ alkoxycarbonylamino.

16. The compound according to claim 1 or a pharmaceutically acceptable salt thereof, wherein $R^{1c}$ is a hydrogen atom, a halogen atom, or a $C_{1-6}$ alkyl group being optionally substituted with $C_{1-4}$ alkoxy.

17. The compound according to claim 1 or a pharmaceutically acceptable salt thereof, wherein $R^{1d}$ is one group selected from a group consisting of 1: a hydrogen atom;

2: a halogen atom;

3: a cyano group;

4: a $C_{2-6}$ alkenyl group (said group being optionally substituted with $C_{6-10}$ aryl having optionally $C_{1-4}$ alkoxy substituent);

5: a $C_{2-6}$ alkynyl group (said group being optionally substituted with $C_{6-10}$ aryl having optionally $C_{1-4}$ alkoxy substituent);

6: a $C_{1-6}$ alkyl group (said group being optionally substituted with the same or different 1 to 2 group(s) selected from a group consisting of (a) 1 to 3 halogen atom(s), (b) cyano, (c) $C_{3-6}$ cycloalkyl group (said group being optionally substituted with a halogen atom, $C_{1-4}$ alkyl or $C_{1-4}$ alkoxy), (d) hydroxy, (e) $C_{1-4}$ alkoxy group (said group being optionally substituted with the same or different 1 to 3 group(s) selected from a group consisting of a halogen atom, cyano, $C_{3-6}$ cycloalkoxy (having optionally mono- or di-($C_{1-6}$ alkyl) aminocarbonyl substituent), mono- or di-($C_{1-6}$ alkyl) aminosulfonyl, $C_{1-6}$ alkylsulfonyl, aminocarbonyl having optionally mono- or di-($C_{1-6}$ alkyl) substituent, $C_{1-4}$ alkylcarbonyl, and 5- to 7-membered cyclic aminocarbonyl), (f) $C_{3-6}$ cycloalkoxy group (said group being optionally substituted with $C_{1-4}$ alkyl (having optionally $C_{1-4}$ alkoxy substituent)), (g) $C_{6-10}$ aryloxy group (said group being optionally substituted with the same or different 1 to 3 group(s) selected from a group consisting of a halogen atom, cyano, and $C_{1-4}$ alkoxy), (h) mono- or di-substituted amino group (said group being substituted with 1 to 2 group(s) selected from a group consisting of $C_{1-6}$ alkyl, $C_{3-6}$ cycloalkyl, $C_{3-6}$ cycloalkyl-$C_{1-4}$ alkyl (having optionally aminocarbonyl substituent), $C_{3-6}$ cycloalkyl-$C_{1-4}$ alkoxycarbonyl, $C_{1-4}$ alkylcarbonyl, $C_{3-6}$ cycloalkylcarbonyl (having optionally $C_{1-4}$ alkylsulfonylamino substituent), 5- or 6-membered saturated heterocyclyl-$C_{1-4}$ alkyl (having optionally $C_{1-4}$ alkyl substituent), 5- or 6-membered saturated heterocyclyl-carbonyl, 5- or 6-membered saturated heterocyclyl-oxycarbonyl, 5- or 6-membered saturated heterocyclyl-$C_{1-4}$ alkylcarbonyl, and $C_{1-4}$ alkylsulfonyl), (i) 5- to 7-membered cyclic amino (being optionally substituted with the same or different 1 to 4 group(s) selected from a group consisting of $C_{1-4}$ alkyl, and $C_{7-14}$ aralkyl), (j) mono- or di-($C_{1-6}$ alkyl)aminocarbonyl, (k) 4- to 7-membered cyclic aminocarbonyl (being optionally substituted with $C_{1-4}$ alkyl), (l) mono- or di-substituted aminocarbonyloxy (said amino being substituted with the same or different 1 to 2 group(s) selected from a group consisting of $C_{1-6}$ alkyl (having optionally 5- or 6-membered saturated heterocyclic substituent), $C_{3-6}$ cycloalkyl (having optionally hydroxy substituent), and 5- or 6-membered saturated heterocyclic group), (m) 5- to 7-membered cyclic aminocarbonyloxy (being optionally substituted with 1 to 2 fluorine atom(s)), (n) 5- to 7-membered cyclic aminocarbonyl-$C_{1-4}$ alkoxy, (o) mono- or di-($C_{1-6}$ alkyl)aminocarbonyl-$C_{1-4}$ alkoxy, (p) 5- or 6-membered saturated heterocyclic group (said group being optionally substituted with $C_{1-4}$ alkyl), (q) 5- or 6-membered saturated heterocyclyl-$C_{1-4}$ alkoxy (having optionally $C_{1-4}$ alkyl substituent), (r) 5- or 6-membered saturated heterocyclyl-oxy (having optionally the same or different 1 to 2 substituents selected from a group consisting of $C_{1-4}$ alkyl), (s) mono- or di-$C_{1-4}$ alkylaminosulfonyl, (t) carboxy, (u) $C_{1-4}$ alkoxycarbonyl, (v) $C_{6-10}$ arylcarbonyl group (said group having optionally $C_{1-4}$ alkoxy substituent), (w) $C_{1-4}$ alkoxycarbonylamino, (x) $C_{6-10}$ aryloxycarbonylamino (having optionally a halogen substituent), (y) 5- or 6-membered monocyclic aryloxycarbonylamino, and (z) N—($C_{1-4}$ alkylaminocarbonyl)-N—($C_{1-6}$ alkyl) amino);

7: a $C_{3-10}$ cycloalkyl group (said group being optionally substituted with (a) a halogen atom, (b) hydroxy, or (c) $C_{1-4}$ alkoxy);

8: a $C_{7-14}$ aralkyl group (said group being optionally substituted with the same or different 1 to 3 group(s) selected from a group consisting of (a) a halogen atom, (b) cyano, (c) hydroxy, (d) $C_{1-4}$ alkoxy, and (e) $C_{1-4}$ alkyl having optionally $C_{1-4}$ alkoxy substituent);

9: a $C_{1-6}$ alkoxy group (said group being optionally substituted with $C_{1-4}$ alkoxycarbonylamino;

10: a $C_{3-6}$ cycloalkoxy group;

11: a $C_{7-14}$ aralkyloxy group (having optionally $C_{1-4}$ alkoxy substituent);

12: mono- or di-substituted aminocarbonyl group (said amino being optionally substituted with $C_{1-6}$ alkyl having optionally 5- or 6-membered saturated heterocyclic substituent);

13: 5- to 7-membered cyclic aminocarbonyl group (said group being optionally substituted with a group selected from a group consisting of (a) a halogen atom, (b) $C_{1-4}$ alkoxy, and (c) $C_{6-10}$ aryl having optionally a halogen substituent);

14: a saturated heterocyclic group (said group being optionally substituted with the same or different 1 to 4 group(s) selected from a group consisting of (a) $C_{1-4}$ alkyl, and (b) $C_{6-10}$ aryl having optionally 1 to 3 halogen substituent(s);

15: a saturated heterocyclyl-oxy group (said group being optionally substituted with $C_{1-4}$ alkoxycarbonyl or $C_{1-4}$ alkylcarbonyl);

16: 5- to 10-membered monocyclic or polycyclic heteroaryl group (said group being optionally substituted with the same or different 1 to 2 group(s) selected from a group consisting of (a) a halogen atom, (b) $C_{1-4}$ alkyl having optionally 1 to 3 fluorine substituent(s), and (c) $C_{1-4}$ alkoxy (having optionally mono- or di-($C_{1-6}$ alkyl) aminocarbonyl substituent));

17: 5- to 10-membered monocyclic or polycyclic heteroaryl-$C_{1-4}$ alkyl group; and 18: a group of the following formula:

[Chemical formula]

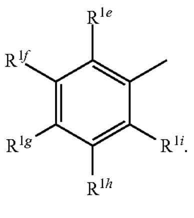

18. The compound according to claim 17 or a pharmaceutically acceptable salt thereof, wherein $R^{1d}$ is one group selected from a group consisting of 1: a hydrogen atom;

2: a halogen atom;

3: a $C_{1-6}$ alkyl group (said group being optionally substituted with (a) 1 to 3 halogen atom(s), (b) hydroxy, (c) a $C_{1-4}$ alkoxy, (d) a $C_{6-10}$ aryloxy group (said group having optionally the same or different 1 to 3 substituent(s) selected from a group consisting of cyano and $C_{1-4}$ alkoxy), (e) a $C_{1-6}$, alkylaminocarbonyloxy, (f) (5- or 6-membered saturated heterocyclyl-$C_{1-4}$ alkyl) aminocarbonyloxy, or (g) 5- to 7-membered cyclic aminocarbonyloxy);

5: a mono- or di-($C_{1-6}$ alkyl)aminocarbonyl group;

6: an N-(5- or 6-membered saturated heterocyclyl-$C_{1-4}$ alkyl)-N—($C_{1-6}$ alkyl)-aminocarbonyl group;

7: a 5- to 7-membered cyclic aminocarbonyl group;

8: a $C_{7-14}$ aralkyl group being optionally substituted with $C_{1-4}$ alkoxy;

9: a 5- or 6-membered saturated heterocyclic group;

10: a $C_{3-6}$ cycloalkyl group;

11: a $C_{3-6}$ cycloalkoxy group; and

12: a group of the following formula:

[Chemical formula]

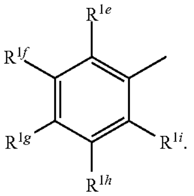

19. The compound according to claim 18 or a pharmaceutically acceptable salt thereof, wherein $R^{1d}$ is a $C_{1-6}$ alkyl group being substituted with one group selected from a group consisting of 1: halogen, 2: hydroxy, 3: $C_{1-4}$ alkoxy 4: $C_{6-10}$ aryloxy group (said group having optionally the same or different 1 to 3 substituent(s) selected from a group consisting of cyano and $C_{1-4}$ alkoxy), 5: $C_{1-6}$ alkylaminocarbonyloxy, 6: (5- or 6-membered saturated heterocyclyl-$C_{1-4}$ alkyl) aminocarbonyloxy, and 7: 5- to 7-membered cyclic aminocarbonyloxy.

20. The compound according to claim 18 or a pharmaceutically acceptable salt thereof, wherein $R^{1d}$ is a group of the following formula:

[Chemical formula]

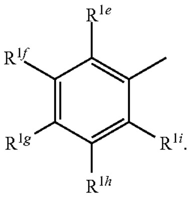

21. The compound according to claim 1 or a pharmaceutically acceptable salt thereof, wherein $R^{1e}$, $R^{1f}$, $R^{1g}$, $R^{1h}$ and $R^{1i}$ are independently 1: a hydrogen atom,
2: a halogen atom,
3: a cyano group,
4: a $C_{1-4}$ alkyl group (said group being optionally substituted with
(a) 5- or 6-membered saturated heterocyclyl-oxy, or
(b) $C_{1-4}$ alkoxy (having optionally $C_{1-4}$ alkoxy or $C_{3-6}$ cycloalkoxy substituent),
5: a $C_{1-4}$ alkoxy group (said group being optionally substituted with
(a) halogen atom,
(b) $C_{1-4}$ alkoxy, or
(c) $C_{1-6}$ alkylaminocarbonyl),
6: a $C_{3-6}$ cycloalkoxy group (said group being optionally substituted with $C_{1-4}$ alkoxy),
7: a 5- or 6-membered saturated heterocyclyl-oxy group, or
8: a $C_{1-6}$ alkylaminocarbonyl group.

22. The compound according to claim 21 or a pharmaceutically acceptable salt thereof, wherein $R^{1e}$, $R^{1f}$, $R^{1g}$, $R^{1h}$ and $R^{1i}$ are independently the same or different, and each is the same or different 1 to 3 group(s) selected from a hydrogen atom, a halogen atom, a cyano group, a $C_{1-4}$ alkyl group or a $C_{1-4}$ alkoxy group.

23. The compound according to claim 22 or a pharmaceutically acceptable salt thereof, wherein $R^{1e}$, $R^{1f}$, $R^{1g}$, $R^{1h}$ and $R^{1i}$ are independently a hydrogen atom, a halogen atom, or a $C_{1-4}$ alkoxy group.

24. The compound according to claim 1 or a pharmaceutically acceptable salt thereof, wherein $R^{1c}$ and $R^{1d}$ combine with each other to form a group of the following formula:
[Chemical formula]

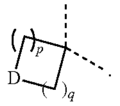

25. The compound according to claim 24 or a pharmaceutically acceptable salt thereof, wherein $R^5$ is a hydrogen atom, a $C_{1-6}$ alkyl group, a $C_{1-4}$ alkoxycarbonyl group, a $C_{1-4}$ alkylsulfonyl group, or a $C_{6-10}$ arylsulfonyl group.

26. The compound according to claim 24 or a pharmaceutically acceptable salt thereof, wherein $R^6$ is a hydrogen atom, a $C_{1-4}$ alkoxy group being optionally substituted with $C_{1-4}$ alkoxy, a $C_{7-14}$ aralkyloxy group having optionally 1 to 3 substituent(s) selected from a group consisting of fluorine atom and cyano, or an aminocarbonyloxy group being optionally substituted with mono- or di-($C_{1-6}$ alkyl).

27. The compound according to claim 24 or a pharmaceutically acceptable salt thereof, wherein D, p and q are one of the following combinations:
(i) D is an oxygen atom, and p and q are the same and each is 2,
(ii) D is $—CH_2—$, and p and q are the same and each is 1 or 2, or
(iii) D is $—CH_2CH_2—$, and p and q are the same and each is 0 or 1.

28. The compound according to claim 1 or a pharmaceutically acceptable salt thereof, wherein $R^2$ is one group selected from a group consisting of a $C_{1-6}$ alkyl group being optionally substituted with $C_{3-6}$ cycloalkyl (said $C_{3-6}$ cycloalkyl having optionally halogen substituent, $C_{1-4}$ alkyl substituent or $C_{1-4}$ alkoxy substituent); a $C_{3-6}$ cycloalkyl group being optionally substituted with halogen atom or $C_{1-4}$ alkyl, a $C_{2-6}$ alkenyl group, and a $C_{7-10}$ aralkyl group having optionally halogen substituent.

29. The compound according to claim 28 or a pharmaceutically acceptable salt thereof, wherein $R^2$ is $C_{1-6}$ alkyl.

30. The compound according to claim 29 or a pharmaceutically acceptable salt thereof, wherein $R^2$ is an isopropyl group.

31. The compound according to claim 1 or a pharmaceutically acceptable salt thereof, wherein $R^{3a}$, $R^{3b}$, $R^{3c}$ and $R^{3d}$ are independently a group: -A-B wherein A is a single bond, $—(CH_2)_sO—$, $—(CH_2)_sN(R^4)—$, $—(CH_2)_sCOO—$, $—(CH_2)_sN(R^4)CO—$, $—(CH_2)_sN(R^4)SO_2—$, $—(CH_2)_sN(R^4)COO—$, $—(CH_2)_sOCON(R^4)—$, $—(CH_2)_sCON(R^4)—$, or $—(CH_2)_sN(R^4)CON(R^4)—$, and B is one group selected from a group consisting of
1: a hydrogen atom;
2: a $C_{1-6}$ alkyl group (said group being optionally substituted with 1 to 3 group(s) selected from a group consisting of
(a) a halogen atom,
(b) $C_{3-6}$ cycloalkyl group (said group having optionally the same or different 1 to 2 substituent(s) selected from a group consisting of a halogen atom, hydroxy, $C_{1-4}$ alkoxy and $C_{3-6}$ cycloalkylcarbonylamino),
(c) hydroxy,
(d) $C_{1-4}$ alkoxy,
(e) carboxy,
(f) $C_{1-4}$ alkoxycarbonyl,
(g) saturated heterocyclic group (said group having optionally the same or different 1 to 3 substituent(s) selected from a group consisting of $C_{1-4}$ alkyl, $C_{1-4}$ alkoxy, $C_{1-4}$ alkylcarbonylamino, and oxo),
(h) aminocarbonyl (said amino having optionally $C_{1-4}$ alkyl, $C_{3-6}$ cycloalkyl, or $C_{3-6}$ cycloalkyl-$C_{1-4}$ alkyl substituent), and
(i) 5- to 7-membered cyclic amino group (said group having optionally the same or different 1 to 3 substituent(s) selected from a group consisting of a halogen atom, $C_{1-4}$ alkyl, $C_6$ aryl having optionally $C_{1-4}$ alkoxy substituent, $C_6$ aryloxy having optionally 1 to 3 halogen substituent(s), and oxo));
3: a $C_{2-6}$ alkenyl group (said group being optionally substituted with (a) fluorine substituent, or (b) $C_{1-6}$ alkyl substituent);
4: a $C_{3-10}$ cycloalkyl group (said group being optionally substituted with (a) a halogen atom, (b) $C_{1-4}$ alkyl having optionally $C_{1-4}$ alkoxy substituent, (c) hydroxy, or (d) $C_{1-4}$ alkoxy);
5: a $C_6$ aryl group (said group being optionally substituted with the same or different 1 to 4 group(s) selected from a group consisting of
(a) a halogen atom,
(b) $C_{1-4}$ alkyl (said $C_{1-4}$ alkyl having optionally one substituent selected from a group consisting of 5- to 7-membered cyclic amino (being optionally substituted with a $C_6$ aryl having optionally 1 to 3 halogen substituent(s)), mono-$C_{1-6}$ alkylamino (said $C_{1-6}$ alkyl being optionally substituted with a $C_6$ aryloxy having optionally 1 to 3 halogen substituent(s)), 5- or 6-membered saturated heterocyclic amino (said saturated heterocycle having optionally $C_6$ aryl substituent), 5- or 6-membered saturated heterocyclyl-oxy (said saturated heterocycle having optionally $C_6$ aryl or 5- to 10-membered monocyclic or polycyclic heteroaryl substituent), $C_6$ aryloxy (being optionally substituted with the same or different 1 to 3 group(s) selected from a group consisting of a halogen atom and $C_{1-4}$ alkyl), $C_{1-4}$ alkoxy, and $C_{3-6}$ cycloalkoxy), (c) $C_{1-4}$ alkoxy (said $C_{1-4}$ alkoxy being optionally substituted with one group selected from a group consisting of $C_{1-4}$ alkoxy, $C_6$ aryloxy (being optionally substituted with $C_{1-4}$ alkyl or 1 to 3 halogen atom(s)), $C_{3-6}$ cycloalkyloxy (being optionally substituted with $C_{1-4}$ alkyl), phenylamino (said phenyl being optionally substituted with 1 to 3 halogen atom(s)), and $C_{7-10}$ aralkyloxy (being optionally substituted with 1 to 3 halogen atom(s))), (d) $C_6$ aryloxy group (said group being optionally substituted with 1 to 3 group(s) selected from a group consisting of a halogen atom, cyano, $C_{1-4}$ alkyl, and $C_{1-4}$ alkoxy), (e) $C_{7-10}$ aralkyloxy (being optionally substituted with 1 to 3 group(s) selected from a group consisting of a halogen atom and $C_{1-4}$ alkoxy), (f) 5- to 7-membered cyclic amino ring (said ring being optionally substituted with ($C_{1-6}$ alkyl)(phenylcarbonyl) amino, or $C_6$ aryloxy (being optionally substituted with the same or different 1 to 3 group(s) selected from a group consisting of a halogen atom and $C_{1-4}$ alkyl having optionally hydroxy substituent)), (g) 5- or 6-membered saturated heterocyclyl-oxy ring (said ring being optionally substituted with $C_6$ aryl having optionally 1 to 3 halogen substituent(s), 5- to 10-membered monocyclic or poly cyclic heteroaryl, 5- or 6-membered saturated heterocyclyl-carbonyl, or oxo), (h) 5- or 6-membered monocyclic heteroaryloxy (being optionally substituted with $C_{1-4}$ alkyl), (i) 5- to 7-membered cyclic aminocarbonyl (being optionally substituted with $C_6$ aryloxy having optionally 1 to 3 halogen substituent(s)), and (j) 5- to 7-membered cyclic aminocarbonyloxy (being optionally substituted with $C_6$ aryl);

6: $C_{7-14}$ aralkyl group (said group being optionally substituted with the same or different 1 to 3 group(s) selected from a group consisting of (a) a halogen atom, (b) cyano, (c) $C_{1-4}$ alkyl, (d) hydroxy, (e) $C_{1-4}$ alkoxy (being optionally substituted with 1 to 3 fluorine atom(s)), (f) $C_{3-6}$ cycloalkoxy (being optionally substituted with 1 to 2 halogen atom(s)), (g) $C_{1-4}$ alkoxycarbonyl, (h) aminocarbonyl, (i) $C_{6-10}$ aryl (being optionally substituted with 1 to 3 halogen atom(s)) and (j) $C_{1-4}$ alkylsulfonyl);

7: 5- to 10-membered monocyclic or polycyclic heteroaryl group (said group being optionally substituted with a halogen atom);

8: 5- to 10-membered monocyclic or polycyclic heteroaryl-$C_{1-4}$ alkyl group (said group being optionally substituted with a halogen atom, or $C_{1-4}$ alkyl (having optionally 1 to 3 fluorine substituent(s))); and 9: saturated heterocyclic group (said group being optionally substituted with $C_{1-4}$ alkyl (having optionally $C_{1-4}$ alkoxy substituent))provided that when A is —$(CH_2)_sN(R^4)$—, —$(CH_2)_sOCON(R^4)$—, —$(CH_2)_sCON(R^4)$—, or —$(CH_2)_sN(R^4)CON(R^4)$—, then $R^4$ and B combine with each other to form a ring).

32. The compound according to claim 1 or a pharmaceutically acceptable salt thereof, wherein $R^4$ is a hydrogen atom, a $C_{1-6}$ alkyl group being substituted with 1 to 3 halogen atom(s) or $C_{3-6}$ cycloalkyl, a $C_{3-6}$ cycloalkyl group being optionally substituted with 1 to 2 halogen atom(s), or a $C_7$ aralkyl group.

33. The compound according to claim 32 or a pharmaceutically acceptable salt thereof, wherein $R^4$ is a $C_{1-6}$ alkyl group being substituted with 1 to 3 halogen atom(s), or a $C_{3-6}$ cycloalkyl group.

34. The compound according to claim 33 or a pharmaceutically acceptable salt thereof, wherein $R^4$ is a $C_{3-6}$ cycloalkyl group.

35. The compound according to claim 1 or a pharmaceutically acceptable salt thereof, wherein $R^{3a}$, $R^{3b}$, $R^{3c}$ and $R^{3d}$ are each a group: -A-B (in which A is a single bond, B is a hydrogen atom).

36. The compound according to claim 1 or a pharmaceutically acceptable salt thereof, wherein n is 1.

37. A pharmaceutical composition, which comprises as the active ingredient a compound as set forth in claim 1 or a pharmaceutically acceptable salt thereof.

38. A method for treatment of hypertension, which comprises administering an effective amount of a compound as set forth in claim 1 or a pharmaceutically acceptable salt thereof to a patient in need.

* * * * *

SEQUENCE LISTING

<160> NUMBER OF SEQ ID NOS: 2

<210> SEQ ID NO 1
<211> LENGTH: 14
<212> TYPE: PRT
<213> ORGANISM: Artificial
<220> FEATURE:
<223> OTHER INFORMATION: 2-Glu is designed by EDANS. 13-Lys is designed by DABCYL.

<400> SEQUENCE: 1

Arg Glu Ile His Pro Phe His Leu Val Ile His Thr Lys Arg
1 5 10

<210> SEQ ID NO 2
<211> LENGTH: 10
<212> TYPE: PRT
<213> ORGANISM: Artificial
<220> FEATURE:
<223> OTHER INFORMATION: 1-Ile is designed by (DABCYL--Abu). 10-Thr is designed by EDANS.

<400> SEQUENCE: 2

Ile His Pro Phe His Leu Val Ile His Thr
1 5 10